(12) United States Patent
Arasappan et al.

(10) Patent No.: US 8,697,694 B2
(45) Date of Patent: Apr. 15, 2014

(54) SUBSTITUTED PYRIDINE AND PYRIMIDINE DERIVATIVES AND THEIR USE IN TREATING VIRAL INFECTIONS

(75) Inventors: Ashok Arasappan, Bridgewater, NJ (US); F. George Njoroge, Warren, NJ (US); Cecil D. Kwong, Birmingham, AL (US); Subramaniam Ananthan, Birmingham, AL (US); Frank Bennett, Cranford, NJ (US); Jeremy Clark, Birmingham, AL (US); Hollis S. Kezar, III, Hoover, AL (US); Vinay M. Girijavallabhan, Denville, NJ (US); Yuhua Huang, Westfield, NJ (US); Regina Huelgas, New York, NY (US); Joseph A. Maddry, Birmingham, AL (US); John J. Piwinski, Lebanon, NJ (US); Robert C. Reynolds, Birmingham, AL (US); Abhijit Roychowdhury, Birmingham, AL (US); Anita T. Fowler, Irondale, AL (US); Feng Geng, Piscataway, NJ (US); John A. Secrist, III, Birmingham, AL (US); Neng-Yang Shih, Lexington, MA (US); Vishal Verma, Jersey City, NJ (US); Francisco Velazquez, Clinton, NJ (US); Srikanth Venkatraman, Edison, NJ (US)

(73) Assignees: Merck Sharp & Dohme Corp., Rahway, NJ (US); Southern Research Institute, Birmingham, AL (US)

( * ) Notice: Subject to any disclaimer, the term of this patent is extended or adjusted under 35 U.S.C. 154(b) by 255 days.

(21) Appl. No.: 13/059,193

(22) PCT Filed: Aug. 19, 2009

(86) PCT No.: PCT/US2009/054264
§ 371 (c)(1),
(2), (4) Date: Aug. 5, 2011

(87) PCT Pub. No.: WO2010/022121
PCT Pub. Date: Feb. 25, 2010

(65) Prior Publication Data
US 2011/0318305 A1    Dec. 29, 2011

Related U.S. Application Data

(60) Provisional application No. 61/090,442, filed on Aug. 20, 2008.

(51) Int. Cl.
*C07D 239/48*    (2006.01)
*C07D 491/04*    (2006.01)
*A61K 31/506*    (2006.01)

(52) U.S. Cl.
USPC ............... 514/235.8; 514/255.05; 514/275; 544/122; 544/295; 544/296; 544/323; 544/324

(58) Field of Classification Search
USPC ................ 544/122, 295, 296, 323, 324; 514/235.8, 255.05, 275
See application file for complete search history.

(56) References Cited

U.S. PATENT DOCUMENTS

| | | | |
|---|---|---|---|
| 4,535,080 A * | 8/1985 | Audiau et al. | 514/252.14 |
| 4,634,697 A | 1/1987 | Hamashima | |
| 4,812,561 A | 3/1989 | Hamashima et al. | |
| 4,933,443 A | 6/1990 | Hamashima et al. | |
| 5,017,380 A | 5/1991 | Hamashima et al. | |
| 5,153,352 A * | 10/1992 | Norbeck et al. | 560/17 |

(Continued)

FOREIGN PATENT DOCUMENTS

| | | |
|---|---|---|
| DE | 10212098 A1 | 10/2003 |
| EP | 0215759 A1 | 5/1987 |

(Continued)

OTHER PUBLICATIONS

Goldberg, CAPLUS Abstract 47:23589 (1953).*

(Continued)

*Primary Examiner* — Deepak Rao
(74) *Attorney, Agent, or Firm* — Carol S. Quagliato; Sheldon O. Heber

(57) ABSTRACT

The present invention provides compounds of Formula (I): and tautomers, isomers, and esters of said compounds, and pharmaceutically acceptable salts, solvates, and prodrugs of said compounds, wherein each of R, $R^1$, X, Y, Z, $R^2$, $R^3$, $R^4$, $R^5$, $R^6$, $R^7$, $R^8$, $R^9$, $R^{18}$, $R^{19}$ and n is selected independently and as defined herein. Compositions comprising such compounds are also provided. The compounds of the invention are effective as inhibitors of HCV, and are useful, alone and together with other therapeutic agents, in treating or preventing diseases or disorders such as viral infections and virus-related disorders.

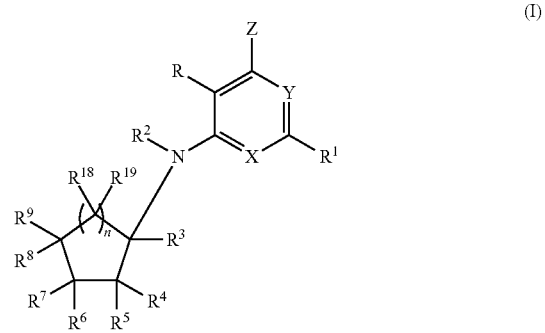

(I)

7 Claims, No Drawings

(56) References Cited

U.S. PATENT DOCUMENTS

| | | | |
|---|---|---|---|
| 6,498,163 | B1 | 12/2002 | Boschelli et al. |
| 6,800,434 | B2 | 10/2004 | Saksena et al. |
| 6,838,475 | B2 | 1/2005 | Arasappan et al. |
| 6,846,802 | B2 | 1/2005 | Chen et al. |
| 6,911,428 | B2 | 6/2005 | Zhu et al. |
| 6,914,122 | B2 | 7/2005 | Venkatraman et al. |
| 7,012,066 | B2 | 3/2006 | Saksena et al. |
| 2002/0160962 | A1 | 10/2002 | Saksena et al. |
| 2005/0176648 | A1 | 8/2005 | Saksena et al. |
| 2005/0249702 | A1 | 11/2005 | Njoroge et al. |

FOREIGN PATENT DOCUMENTS

| | | | |
|---|---|---|---|
| FR | 2574407 | A1 | 6/1986 |
| GB | 731956 | * | 6/1955 |
| WO | 93/17020 | A2 | 9/1993 |
| WO | 98/14181 | A1 | 4/1998 |
| WO | 98/17679 | A1 | 4/1998 |
| WO | 98/22496 | A2 | 5/1998 |
| WO | 99/07734 | A2 | 2/1999 |
| WO | 00/07998 | A1 | 2/2000 |
| WO | 01/07027 | A2 | 2/2001 |
| WO | 02/08205 | A1 | 1/2002 |
| WO | 03/084953 | A1 | 10/2003 |
| WO | 2004/037166 | A2 | 5/2004 |
| WO | 2006/065590 | A2 | 6/2006 |
| WO | WO 2006/079556 | * | 8/2006 |
| WO | 2006/136442 | A1 | 12/2006 |
| WO | 2007/003596 | A1 | 1/2007 |
| WO | 2008/032162 | A1 | 3/2008 |
| WO | 2008/040778 | A2 | 4/2008 |
| WO | 2008/124161 | A1 | 10/2008 |

OTHER PUBLICATIONS

Tsatsaronis et al., CAPLUS Abstract 85:78077 (1976).*
Mittelbach, CAPLUS Abstract 94:139730 (1981).*
Legraverend et al., CAPLUS Abstract 100:7033 (1984).*
Secrist et al., CAPLUS Abstract 100:121523 (1984).*
Goff, PubMed Abstract (J Gene Med 3(6):517-28), Nov.-Dec. 2001.*
Bosseray et al., PubMed Abstract (Pathol Biol (Paris) 50(8):483-92), Oct. 2002.*
Razonable et al., PubMed Abstract (Herpes 10(3):60-5), Dec. 2003.*
Douglas, Jr. Introduction to Viral Diseases, Cecil Textbook of Medicine, 20th Edition, vol. 2, pp. 1739-1747, 1996.*
Legraverend et al., CAPLUS Abstract 103:160792 (1985).*
Anderson et al., The Practice of Medicinal Chemistry (1996), Academic Press, New York.
Beaulieu et al., "Inhibitors of the HCV NS5B polymerase New hope for the treatment of hepatitis C infections", Current Opinion in Investigational Drugs, 2004. p. 838-850, vol. 5, No. 8.
S. Berge et al., Journal of Pharmaceutical Sciences (1977) 66 (1), p. 1-19.
A.L. Bingham et al., "Over one hundred solvates of sulfathiazole", Chem. Commun., 603-604 (2001).
BioWorld Today 9(217) 4 (Nov. 10, 1998).
Burgess, K., Ke, Chun-Yen, "Large Scale Syntheses of N-Protected 2,3-Methanomethionine Stereoisomers", Synthesis, 1996, p. 1463-1467.
M. Caira et al., "Preparation and Crystal Characterization of a Polymorph, a Monohydrate, and an Ethyl Acetate Solvate of the Antifungal Fluconazole", Journal of Pharmaceutical Sciences, 2004, P. 601-611, vol. 93, No. 3.
Davey, D.D. et al., "Design, Synthesis, and Activity of 2-Imidazol-1-ylpyrimidine Derived Inducible Nitric Oxide Synthase Dimenzation Inhibitors", J. Med. Chem. 2007, p. 1146-1157, vol. 50, No. 6.
Dimasi et al., "Characterization of Engineered Hepatitis C Virus NS3 Protease Inhibitors Affinity Selected from Human Pancreatic Secretory Trypsin Inhibitor and Minibody Repertoires", Journal of Virology, 1997, p. 7461-7469, vol. 71, No. 10.
Elzouki, et al., "Senne protease inhibitors in patients with chronic viral hepatitis", Journal of Hepatology, 1997, p. 42-48, vol. 27.
Gould, Philip L., "Salt selection for basic drugs", International Journal of Pharmaceutics, 1986, p. 201-217, vol. 33.
T.W. Green et al., Protective Groups in Organic Synthesis (1991), Wiley, New York.
T.Higuchi and V. Stella, Pro-drugs as Novel Delivery Systems (1987) 14 of the A.C.S. Symposium Series.
Holland et al., "Hepatitis C Genotyping by Direct Sequencing of the Product from the Roche Amplicor Test; Methodology and Application to a South Australian Population", Pathology, 1998, p. 192-195, vol. 30.
Ingallinella et al., "Potent Peptide Inhibitors of Human Hepatitis C Virus NS3 Protease Are Obtained by Optimizing the Cleavage Products", Biochemistry, 1998, p. 8906-8914, vol. 37, No. 25.
Koga, M. et al., "C-2 Arylamino Substituted Purine ara-Carbocyclic Nucleosides as Potential Anti-Cytomegalovirus Agents", Journal of Heterocyclic Chemistry, 1992, vol. 29, pp. 1741-1747, No. 7.
Lamballerie et al., "Classification of hepatitis C virus variants in six major types based on analysis of the envelope 1 and nonstructural 5B genome regions and complete polyprotein sequences", Journal of General Virology, 1997, pp. 45-51, vol. 78 (PT1).
Landro et al., "Mechanistic Role of an NS4A Peptide Cofactor with the Truncated NS3 Protease of Hepatitis C Virus Elucidation of the NS4A Stimulatory Effect via Kinetic Analysis and Inhibitor Mapping", Biochemistry, 1997, p. 9340-9348, vol. 36, No. 31.
Legraverend, et al., "(+)-2-Amino-3,4-dihydro-7-[2,3-dihydroxy-4(hydroxymethyl)-1-cyclopentyl]-7H-pyrrolo[2,3-d]pyrimidin-4-ones New Carbocyclic Analogues of 7-Deazaquanosine with Antiviral Activity", J. Med. Chem., 1985, p. 1477-1480, vol. 28, No. 10.
Liu, et al., "Synthesis of Enantiomerically Pure N-tert Butanesulfinyl Imines (tert-Butanesulfinimines) by the Direct Condensation of tert-Butanesulfinamide with Aldehydes and Ketones", J. Org Chem., 1999, pp. 1278-1284, vol. 64, No. 4.
Llinas-Brunet et al., "Peptide-Based Inhibitors of the Hepatitis C Virus Serine Protease", Bioorganic & Medicinal Chemistry Letters, 1998, p. 1713-1718, vol. 8.
Malcolm, et al., "SCH 503034, a Mechanism-Based Inhibitor of Hepatitis C Virus NS3 Protease, Suppresses Polyprotein Maturation and Enhances the Antiviral Activity of Alpha Interferon in Replicon Cells", Antimicrobial Agents and Chemotherapy, 2006, p. 1013-1920, vol. 50, No. 3.
Martin, F., et al., "Affinity selection of a camelized VH domain antibody inhibitor of hepatitis C virus NS3 protease", Protein Engineering, 1997, p. 607-614, vol. 10, No. 5.
Martin. F., et al., "Design-of-Selective Eglin Inhibitora of HCV NS3 Proteinase", Biochemistry, 1998, p. 11459-11468, vol. 37, No. 33.
Ni, Z-J., et al., "Progress and development of small molecule HCV antivirals", Current Opinion in Drug Discovery & Development, 2004, p. 446-459, vol. 7, No. 4.
Prakash, et al., "Stereoselective Nucleophilic Trifluoromethylation of N-(tert-Bulylsulfinyl)-imines by Using Trimethyl (trifluoromethyl)-silane", Angew. Chem. Int. Ed., 2001, p. 589-590, vol. 40, No. 3.
Roche, E.B., "Bioreversible Carriers in Drug Design", 1987.
Sakamoto, T. et al., "Condensed Heteroaromatic Ring Systems. VII. Synthesis of Thienopyridines, Thienopyrimidines, and Furopyridines from o-Substituted N-Heteroarylacetylenes", Chem. Pharm. Bull., 1986, p. 2719-2724, vol. 34, No. 7.
Simmonds, P., et al., "Classification of hepatitis C virus into six major genotypes and a series of subtypes by phylogenetic analysis of the NS-5 region", Jouranl of General Virology, 1993. p. 2391-2399, vol. 74.
Simmonds, P., et al., "Identification of genotypes of hepatitis C virus by sequence comparisons in the core, E1 and NS-5 regions", Journal of General Virology, 1994, p. 1053-1061, vol. 75.
Stahl, P., et al., "Handbook of Pharmaceutical Salts. Properties, Selection and Use", 2002. Zurich: Wiley-VCH.
Tan, S-L., et al., "Hepatitis C Therapeutics: Current Status and Emerging Strategies", Nature Reviews, 2002. p. 867-881, vol. 1.
Van Tonder, E.C., et al., "Preparation and Physicochemical Characterization of 5 Niclosamide Solvates and 1 Hemisolvate", AAPS PharmSciTech, 2004, p. 1-10, vol. 5, No. 1, Article 12.

(56) References Cited

OTHER PUBLICATIONS

Moriarty, K.J., et al., "The synthesis and SAR of 2-amino-pyrrolo[2,3-d]pyrimidines: A new class of Aurora-A kinase inhibitors", Bioorganic & Medicinal Chemistry Letters, 2006, vol. 16, pp. 5778-5783.

Patil, S., et al., "Synthesis and Antiviral Properties of (±)-5'-Noraristeromycin and Related Purine Carbocyclic Nucleosides. A New Lead for Anti-Human Cytomegalovirus Agent Design", J. Med. Chem., 1992, vol. 35, pp. 3372-3377, No. 18.

Shealy, Y.F., et al., "Carboyclic Analogs of Guanosine and 8-Azaguanosine", Journal of Pharmaceutical Sciences, 1973, vol. 62, pp. 1432-1434, No. 9.

Shealy, Y.F., et al., "Synthesis and Antiviral Evaluation of Carbocyclic Analogues of 2-Amino-6-substituted-purine 3'-Deoxyribofuranosides", J. Med. Chem., 1987, vol. 30, pp. 1090-1094, No. 6.

Sheldon, J. et al., "Novel protease and polymerase inhibitors for the treatment of hepatitis C virus infection", Expert Opinion Investig. Drugs, 2007, vol. 16, pp. 1171-1181, No. 8.

Toogood, P.L., et al., "Discovery of a Potent and Selective Inhibitor of Cyclin-Dependent Kinase", J. Med. Chem., 2005, vol. 48, pp. 2388-2406, No. 7.

International Search Report for PCT/US2009/054264, mailed Feb. 8, 2010, (4 pages).

Written Opinion of The International Searching Authority for PCT/US2009/054264, (8, pages), (2010).

International Search Report for PCT/US2009/054268, mailed Feb. 1, 2010, (7 pages).

Written Opinion of The International Searching Authority for PCT/US2009/054268, (5 pages), (2010).

International Search Report for PCT/US2009/054269, mailed Dec. 15, 2009, (4 pages).

Written Opinion of The International Search Authority for PCT/US2009/054269, (7 pages), (2010).

International Search Report for PCT/US2009/054271, mailed Jan. 19, 2010, (4 pages).

Written Opinion of The International Search Authority for PCT/US2009/054271, (6 pages), (2010).

Bhushan, R.G., et al., "Synthesis of Conformationally Restricted 2',3'-exo-Methylene Carbocyclic Nucleosides Built on a Bicyclo[3.1.0]hexane Template", Bioorganic & Medicinal Chemistry, 2002, vol. 10, pp. 2325-2333.

Nishio, M., et al., "Antiviral effect of 6-diazo-5-oxo-L-norleucine, antagonist of γ-glutamyl transpeptidase, on replication of human parainfluenza virus type 2", Jouranl of General Virology, 1990, vol. 71, pp. 61-67.

\* cited by examiner

SUBSTITUTED PYRIDINE AND PYRIMIDINE DERIVATIVES AND THEIR USE IN TREATING VIRAL INFECTIONS

CROSS-REFERENCE TO RELATED APPLICATION

This application is a 371 of PCT application no. US2009/054264, filed Aug. 19, 2009, which claims benefit of provisional application U.S. Ser. No. 61/090,442, filed Aug. 20, 2008, incorporated by reference.

REFERENCE TO SEQUENCE LISTING SUBMITTED ELECTRONICALLY

The sequence listing of the present application is submitted electronically via EFS-Web as an ASCII formatted sequence listing with a file name "IN06869-SEQLIST-27JAN2014.txt", having a creation date of Jan. 27, 2014, and a size of 1.39 KB. This sequence listing submitted via EFS-Web is part of the specification and is herein incorporated by reference in its entirety.

FIELD OF THE INVENTION

The present invention relates to certain substituted pyridine and pyrimidine derivatives, to compositions comprising them, and to methods for their use as inhibitors of HCV and in treating or preventing viral infections or virus-related disorders.

BACKGROUND OF THE INVENTION

HCV is a (+)-sense single-stranded RNA virus that has been implicated as the major causative agent in non-A, non-B hepatitis (NANBH). NANBH is distinguished from other types of viral-induced liver disease, such as hepatitis A virus (HAV), hepatitis B virus (HBV), hepatitis delta virus (HDV), as well as from other forms of liver disease such as alcoholism and primary biliary cirrhosis.

Hepatitis C virus is a member of the hepacivirus genus in the family Flaviviridae. It is the major causative agent of non-A, non-B viral hepatitis and is the major cause of transfusion-associated hepatitis and accounts for a significant proportion of hepatitis cases worldwide. Although acute HCV infection is often asymptomatic, nearly 80% of cases resolve to chronic hepatitis. About 60% of patients develop liver disease with various clinical outcomes ranging from an asymptomatic carrier state to chronic active hepatitis and liver cirrhosis (occurring in about 20% of patients), which is strongly associated with the development of hepatocellular carcinoma (occurring in about 1-5% of patients). The World Health Organization estimates that 170 million people are chronically infected with HCV, with an estimated 4 million living in the United States.

HCV has been implicated in cirrhosis of the liver and in induction of hepatocellular carcinoma. The prognosis for patients suffering from HCV infection remains poor as HCV infection is more difficult to treat than other forms of hepatitis. Current data indicates a four-year survival rate of below 50% for patients suffering from cirrhosis and a five-year survival rate of below 30% for patients diagnosed with localized resectable hepatocellular carcinoma. Patients diagnosed with localized unresectable hepatocellular carcinoma fare even worse, having a five-year survival rate of less than 1%.

HCV is an enveloped RNA virus containing a single-stranded positive-sense RNA genome approximately 9.5 kd in length. The RNA genome contains a 5'-nontranslated region (5' NTR) of 341 nucleotides, a large open reading frame (ORF) encoding a single polypeptide of 3,010 to 3,040 amino acids, and a 3'-nontranslated region (3'-NTR) of variable length of about 230 nucleotides. HCV is similar in amino acid sequence and genome organization to flaviviruses and pestiviruses, and therefore HCV has been classified as a third genus of the family Flaviviridae.

The 5' NTR, one of the most conserved regions of the viral genome, contains an internal ribosome entry site (IRES) which plays a pivotal role in the initiation of translation of the viral polyprotein. A single long open reading frame encodes a polyprotein, which is co- or post-translationally processed into structural (core, E1, E2 and p7) and nonstructural (NS2, NS3, NS4A, NS4B, NS5A, and NS5B) viral proteins by either cellular or viral proteinases. The 3' NTR consists of three distinct regions: a variable region of about 38 nucleotides following the stop codon of the polyprotein, a polyuridine tract of variable length with interspersed substitutions of cytidines, and 98 nucleotides (nt) at the very 3' end which are highly conserved among various HCV isolates. By analogy to other plus-strand RNA viruses, the 3'-NTR is thought to play an important role in viral RNA synthesis. The order of the genes within the genome is: $NH_2$—C-E1-E2-p7-NS2-NS3-NS4A-NS4B-NS5A-NS5B-COOH.

Processing of the structural proteins core (C), envelope protein 1 and (E1, E2), and the p7 region is mediated by host signal peptidases. In contrast, maturation of the nonstructural (NS) region is accomplished by two viral enzymes. The HCV polyprotein is first cleaved by a host signal peptidase generating the structural proteins C/E1, E1/E2, E2/p7, and p7/NS2. The NS2-3 proteinase, which is a metalloprotease, then cleaves at the NS2/NS3 junction. The NS3/4A proteinase complex (NS3 being a serine protease and NS4A acting as a cofactor of the NS3 protease), is then responsible for processing all the remaining cleavage junctions. RNA helicase and NTPase activities have also been identified in the NS3 protein. One-third of the NS3 protein functions as a protease, and the remaining two-thirds of the molecule acts as the helicase/ATPase that is thought to be involved in HCV replication. NS5A may be phosphorylated and acts as a putative cofactor of NS5B. The fourth viral enzyme, NS5B, is a membrane-associated RNA-dependent RNA polymerase (RdRp) and a key component responsible for replication of the viral RNA genome. NS5B contains the "GDD" sequence motif, which is highly conserved among all RdRps characterized to date.

Replication of HCV is thought to occur in membrane-associated replication complexes. Within these, the genomic plus-strand RNA is transcribed into minus-strand RNA, which in turn can be used as a template for synthesis of progeny genomic plus-strands. At least two viral enzymes appear to be involved in this reaction: the NS3 helicase/NTPase, and the NS5B RNA-dependent RNA polymerase. While the role of NS3 in RNA replication is less clear, NS5B is the key enzyme responsible for synthesis of progeny RNA strands. Using recombinant baculoviruses to express NS5B in insect cells and a synthetic nonviral RNA as a substrate, two enzymatic activities have been identified as being associated with it: a primer-dependent RdRp and a terminal transferase (TNTase) activity. It was subsequently confirmed and further characterized through the use of the HCV RNA genome as a substrate. Other studies have shown that NS5B with a C-terminal 21 amino-acid truncation expressed in *Escherichia coli* is also active for in vitro RNA synthesis. On certain RNA templates, NS5B has been shown to catalyze RNA synthesis via a de novo initiation mechanism, which has been postulated to be the mode of viral replication in viva Templates with single-stranded 3' termini, especially those containing a 3'-terminal cytidylate moiety, have been found to direct de novo synthesis efficiently. There has also been evidence for NS5B to utilize di- or tri-nucleotides as short primers to initiate replication.

It is well-established that persistent infection of HCV is related to chronic hepatitis, and as such, inhibition of HCV replication is a viable strategy for the prevention of hepatocellular carcinoma. Present treatment approaches for HCV infection suffer from poor efficacy and unfavorable side-effects and there is currently a strong effort directed to the discovery of HCV replication inhibitors that are useful for the treatment and prevention of HCV related disorders. New approaches currently under investigation include the development of prophylactic and therapeutic vaccines, the identification of interferons with improved pharmacokinetic characteristics, and the discovery of agents designed to inhibit the function of three major viral proteins: protease, helicase and polymerase. In addition, the HCV RNA genome itself, particularly the IRES element, is being actively exploited as an antiviral target using antisense molecules and catalytic ribozymes.

Particular therapies for HCV infection include α-interferon monotherapy and combination therapy comprising α-interferon and ribavirin. These therapies have been shown to be effective in some patients with chronic HCV infection. The use of antisense oligonucleotides for treatment of HCV infection has also been proposed as has the use of free bile acids, such as ursodeoxycholic acid and chenodeoxycholic acid, and conjugated bile acids, such as tauroursodeoxycholic acid. Phosphonoformic acid esters have also been proposed as potentially for the treatment of various viral infections including HCV. Vaccine development, however, has been hampered by the high degree of viral strain heterogeneity and immune evasion and the lack of protection against reinfection, even with the same inoculum.

The development of small-molecule inhibitors directed against specific viral targets has become a major focus of anti-HCV research. The determination of crystal structures for NS3 protease, NS3 RNA helicase, and NS5B polymerase has provided important structural insights that should assist in the rational design of specific inhibitors.

NS5B, the RNA-dependent RNA polymerase, is an important and attractive target for small-molecule inhibitors. Studies with pestiviruses have shown that the small molecule compound VP32947 (3-[((2-dipropylamino)ethyl)thio]-5H-1,2,4-triazino[5,6-b]indole) is a potent inhibitor of pestivirus replication and most likely inhibits the NS5B enzyme since resistant strains are mutated in this gene. Inhibition of RdRp activity by (−)β-L-2',3'-dideoxy-3'-thiacytidine 5'-triphosphate (3TC; lamivudine triphosphate) and phosphonoacetic acid also has been observed. Despite the intensive effort directed at the treatment and prevention of HCV and related viral infections, there exists a need in the art for non-peptide, small-molecule compounds having desirable or improved physicochemical properties that are useful for inhibiting viruses and treating viral infections and virus-related disorders.

SUMMARY OF THE INVENTION

The present invention provides certain substituted pyridine and pyrimidine derivatives (collectively referred to herein as "compounds of the invention"), compositions comprising such compounds, and methods for their use as HCV inhibitors and for treating viral infections and disorders related thereto.

In one embodiment, the compounds of the invention have a general structure shown in Formula (I):

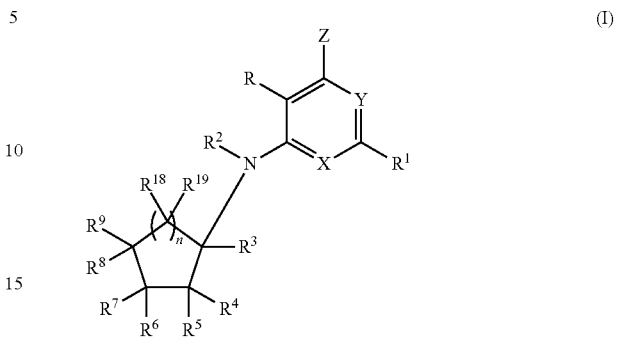

and include tautomers, isomers, and esters of said compounds, and pharmaceutically acceptable salts, solvates, and prodrugs of said compounds, tautomers, isomers, and esters, wherein each of R, $R^1$, X, Y, Z, $R^2$, $R^3$, $R^4$, $R^5$, $R^6$, $R^7$, $R^8$, $R^9$, $R^{18}$, $R^{19}$ and n are selected independently and wherein:

R is selected from alkyl, aryl, heteroaryl, cycloalkyl, aryl-fused cycloalkyl, heteroaryl-fused cycloalkyl, cycloalkenyl, aryl-fused cycloalkenyl, heteroaryl-fused cycloalkenyl, heterocycloalkyl, aryl-fused heterocycloalkyl, and heteroaryl-fused heterocycloalkyl, wherein each of said alkyl, said aryl, said heteroaryl, said cycloalkyl, said aryl-fused cycloalkyl, said heteroaryl-fused cycloalkyl, said cycloalkenyl, said aryl-fused cycloalkenyl, said heteroaryl-fused cycloalkenyl, said heterocycloalkyl, said aryl-fused heterocycloalkyl, and said heteroaryl-fused heterocycloalkyl, is unsubstituted or optionally independently substituted with from one to five substituents, which are the same or different, each substituent being independently selected from halo, —OH, —CN, oxo, alkyl, cycloalkyl, alkenyl, alkynyl, haloalkyl, heteroalkyl, heterohaloalkyl, -alkyl-OH, —O-alkyl, —O-haloalkyl, —O-alkyl-OH, aryl, —O-aryl, —S-aryl, —O-alkyl-aryl, —S-alkyl-aryl, heteroaryl, heteroarylalkyl-, —O-heteroaryl, —S-heteroaryl, —O-alkyl-heteroaryl, —S-alkyl-heteroaryl, heterocycloalkyl, heterocycloalkylalkyl-, —C(O)-alkyl, —C(O)-haloalkyl, —C(O)-cycloalkyl, —C(O)-heterocycloalkyl, —C(O)H, —C(O)OH, —C(O)O-alkyl, —C(O)O-haloalkyl, —C(O)O-cycloalkyl, —C(O)O-heterocycloalkyl, —OC(O)-alkyl, —OC(O)-haloalkyl, —OC(O)-cycloalkyl, —OC(O)-heterocycloalkyl, —C(O)NH$_2$, —C(O)NHR$^{10}$, —C(O)NR$^{10}$R$^{11}$, —OC(O)NH$_2$, —CO(O)NHR$^{10}$, —CO(O)NR$^{10}$R$^{11}$, —NH$_2$, —NHR$^{10}$, —NR$^{10}$R$^{11}$, —NO$_2$, —S(O)NHR$^{10}$, —S(O)NR$^{10}$R$^{11}$, —S(O)R$^{10}$, —S(O)$_2$NH$_2$, —S(O)$_2$NHR$^{10}$, —S(O)$_2$NR$^{10}$R$^{11}$, —S(O)$_2$R$^{10}$, substituted aryl, and substituted heteroaryl, wherein each of said substituted aryl and said substituted heteroaryl independently contains from one to three substituents, which may be the same or different, each substituent being independently selected from halo, alkyl, —O-alkyl, and —C(O)Oalkyl;

X and Y are each independently selected from N and CH, with the proviso that at least one of X or Y is N;

Z=H, halo, —OH, —SH, —CN, alkyl, alkenyl, alkynyl, heteroalkyl, haloalkyl, heterohaloalkyl, —S-alkyl, —O-alkyl, —O-aryl, —O-heteroaryl, cycloalkyl, aryl, heteroaryl, —NH$_2$, —NHR$^{12}$, and —NR$^{12}$R$^{13}$;

$R^1$ is selected from H, halo, alkyl, haloalkyl, heteroalkyl, heterohaloalkyl, heteroaryl, —OH, —O-alkyl, —O-aryl, —O-heteroalkyl, —O-heteroaryl, —SH, —S-alkyl, —S-aryl, —S-heteroalkyl, —S-heteroaryl, —NH$_2$, —NHR$^{14}$, —NR$^{14}$R$^{15}$, —NO$_2$, —S(O)NHR$^{10}$, —S(O)NR$^{10}$R$^{11}$, —S(O)R$^{10}$, —S(O)$_2$NHR$^{10}$, —S(O)$_2$NR$^{10}$R$^{11}$, and —S(O)$_2$R$^{10}$;

$R^2$ (when $R^2$ is not joined with $R^9$) is selected from H and alkyl;

n=0, 1, or 2;

$R^3$ is selected from H, -alkyl, alkenyl, alkynyl, aryl, heteroaryl, and cycloalkyl,
  wherein each of said -alkyl, said -alkenyl, said alkynyl, said aryl, said heteroaryl, and said cycloalkyl, is unsubstituted or optionally independently substituted with from one to three substituents, which can be the same or different, each substituent being independently selected from halo, —OH, alkyl, —O-alkyl, —O-alkenyl, —O-haloalkyl, —O-haloalkenyl, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, aryl, heteroaryl, cycloalkyl, cycloalkenyl, heterocycloalkyl, and heterocycloalkenyl;

$R^4$ is selected from H, —OH, halo, -alkyl, -alkenyl, alkynyl, azido, aryl, heteroaryl, —O-alkyl, —O-alkenyl, —OC(O)-alkyl, —SH, —S-alkyl, —NH$_2$, —NO$_2$, —NHR$^{10}$, —NR$^{10}$R$^{11}$, —C(O)OH, —C(O)OR$^{10}$, —C(O)NH$_2$, —C(O)NHR$^{10}$, —C(O)NR$^{10}$R$^{11}$, —S(O)NHR$^{10}$, —S(O)NR$^{10}$R$^{11}$, —S(O)R$^{10}$, —S(O)$_2$NHR$^{10}$, —S(O)$_2$NR$^{10}$R$^{11}$, and —S(O)$_2$R$^{10}$,
  wherein each of said -alkyl, said -alkenyl, said alkynyl, said aryl, said heteroaryl, said —O-alkyl, said —O-alkenyl, said —OC(O)-alkyl, and said —S-alkyl is unsubstituted or optionally independently substituted with from one to three substituents, which can be the same or different, each substituent being independently selected from halo, —OH, alkyl, haloalkyl, heteroalkyl, heterohaloalkyl, —O-alkyl, —O-alkenyl, —O-haloalkyl, —O-haloalkenyl, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, aryl, heteroaryl, cycloalkyl, cycloalkenyl, heterocycloalkyl, and heterocycloalkenyl;

$R^5$ is selected from H, —OH, halo, -alkyl, -alkenyl, alkynyl, azido, aryl, heteroaryl, —O-alkyl, —O-alkenyl, —OC(O)-alkyl, —SH, —S-alkyl, —NH$_2$, —NO$_2$, —NHR$^{10}$, —NR$^{10}$R$^{11}$, —C(O)OH, —C(O)OR$^{10}$, —C(O)NH$_2$, —C(O)NHR$^{10}$, —C(O)NR$^{10}$R$^{11}$, —S(O)NHR$^{10}$, —S(O)NR$^{10}$R$^{11}$, —S(O)R$^{10}$, —S(O)$_2$NHR$^{10}$, —S(O)$_2$NR$^{10}$R$^{11}$, and —S(O)$_2$R$^{10}$,
  wherein each of said -alkyl, said -alkenyl, said alkynyl, said aryl, said heteroaryl, said —O-alkyl, said —O-alkenyl, said —OC(O)-alkyl, and said —S-alkyl is unsubstituted or optionally independently substituted with from one to three substituents, which can be the same or different, each substituent being independently selected from halo, —OH, alkyl, haloalkyl, heteroalkyl, heterohaloalkyl, —O-alkyl, —O-alkenyl, —O-haloalkyl, —O-haloalkenyl, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, aryl, heteroaryl, cycloalkyl, cycloalkenyl, heterocycloalkyl, and heterocycloalkenyl;
  or, alternatively, $R^4$ and $R^5$ are taken together with the carbon atom to which they are shown attached to form a 3- to 7-membered, saturated or partially unsaturated, spirocycloalkyl ring containing from 0 to 3 spiro ring heteroatoms selected from O, N, and S;

$R^6$ is selected from H, —OH, halo, -alkyl, -alkenyl, alkynyl, azido, aryl, heteroaryl, —O-alkyl, —O-alkenyl, —OC(O)-alkyl, —SH, —S-alkyl, —NH$_2$, —NO$_2$, —NHR$^{10}$, —NR$^{10}$R$^{11}$, —C(O)OH, —C(O)OR$^{10}$, —C(O)NH$_2$, —C(O)NHR$^{10}$, —C(O)NR$^{10}$R$^{11}$, —S(O)NHR$^{10}$, —S(O)NR$^{10}$R$^{11}$, —S(O)R$^{10}$, —S(O)$_2$NHR$^{10}$, —S(O)$_2$NR$^{10}$R$^{11}$, and —S(O)$_2$R$^{10}$,
  wherein each of said -alkyl, said -alkenyl, said alkynyl, said aryl, said heteroaryl, said —O-alkyl, said —O-alkenyl, said —OC(O)-alkyl, and said —S-alkyl is unsubstituted or optionally independently substituted with from one to three substituents, which can be the same or different, each substituent being independently selected from halo, —OH, alkyl, haloalkyl, heteroalkyl, heterohaloalkyl, —O-alkyl, —O-alkenyl, —O-haloalkyl, —O-haloalkenyl, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, aryl, heteroaryl, cycloalkyl, cycloalkenyl, heterocycloalkyl, and heterocycloalkenyl;
  or, alternatively, $R^5$ and $R^6$ are taken together to form a double bond;

$R^7$ is selected from H, —OH, halo, -alkyl, -alkenyl, alkynyl, azido, aryl, heteroaryl, —O-alkyl, —O-alkenyl, —OC(O)-alkyl, —SH, —S-alkyl, —NH$_2$, —NO$_2$, —NHR$^{10}$, —NR$^{10}$R$^{11}$, —C(O)OH, —C(O)OR$^{10}$, —C(O)NH$_2$, —C(O)NHR$^{10}$, —C(O)NR$^{10}$R$^{11}$, —S(O)NHR$^{10}$, —S(O)NR$^{10}$R$^{11}$, —S(O)R$^{10}$, —S(O)$_2$NHR$^{10}$, —S(O)$_2$NR$^{10}$R$^{11}$, and —S(O)$_2$R$^{10}$,
  wherein each of said -alkyl, said -alkenyl, said alkynyl, said aryl, said heteroaryl, said —O-alkyl, said —O-alkenyl, said —OC(O)-alkyl, and said —S-alkyl is unsubstituted or optionally independently substituted with from one to three substituents, which can be the same or different, each substituent being independently selected from halo, —OH, alkyl, haloalkyl, heteroalkyl, heterohaloalkyl, —O-alkyl, —O-alkenyl, —O-haloalkyl, —O-haloalkenyl, —OC(O)-alkyl, —CO)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, aryl, heteroaryl, cycloalkyl, cycloalkenyl, heterocycloalkyl, and heterocycloalkenyl;
  or, alternatively, $R^6$ and $R^7$ are taken together with the carbon atom to which they are shown attached to form a 3- to 7-membered, saturated or partially unsaturated, spirocycloalkyl ring containing from 0 to 3 spiro ring heteroatoms selected from O, N, and S;

$R^8$ is selected from H, —OH, halo, -alkyl, -alkenyl, alkynyl, azido, aryl, heteroaryl, —O-alkyl, —O-alkenyl, —OC(O)-alkyl, —SH, —S-alkyl, —NH$_2$, —NO$_2$, —NHR$^{10}$, —NR$^{10}$R$^{11}$, —C(O)OH, —C(O)OR$^{10}$, —C(O)NH$_2$, —C(O)NHR$^{10}$, —C(O)NR$^{10}$R$^{11}$, —S(O)NHR$^{10}$, —S(O)NR$^{10}$R$^{11}$, —S(O)R$^{10}$, —S(O)$_2$NHR$^{10}$, —S(O)$_2$NR$^{10}$R$^{11}$, and —S(O)$_2$R$^{10}$,
  wherein each of said -alkyl, said -alkenyl, said alkynyl, said aryl, said heteroaryl, said —O-alkyl, said —O-alkenyl, said —CO(O)-alkyl, and said —S-alkyl is unsubstituted or optionally independently substituted with from one to five substituents, which can be the same or different, each substituent being independently selected from halo, —OH, alkyl, haloalkyl, heteroalkyl, heterohaloalkyl, —O-alkyl, —O-cycloalkyl, —O-alkenyl, —O-haloalkyl, —O-haloalkenyl, —O(C)O—N(R$^{10}$)R$^{11}$, —O(C)O—NHR$^{11}$, —O(C)O—NH$_2$, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, —S(O)₂R¹⁰, —SR¹⁰, —S(O)₂NHR¹⁰, —S(O)₂NR¹⁰R¹¹, —CN, —NH₂, —NHR¹⁶, and —NR¹⁶R¹⁷, —N(R¹⁰)S(O)₂R¹⁰, —NHS(O)₂R¹⁰, aryl, heteroaryl, cycloalkyl, cycloalkenyl, heterocycloalkyl, and heterocycloalkenyl;

R⁹ is selected from H, —OH, halo, -alkyl, -alkenyl, alkynyl, azido, aryl, heteroaryl, —O-alkyl, —O-alkenyl, —OC(O)-alkyl, —SH, —S-alkyl, —NH₂, —NO₂, —NHR¹⁰, —NR¹⁰R¹¹, —C(O)OH, —C(O)OR¹⁰, —C(O)NH₂, —C(O)NHR¹⁰, —C(O)NR¹⁰R¹¹, —S(O)NHR¹⁰, —S(O)NR¹⁰R¹¹, —S(O)R¹⁰, —S(O)₂NHR¹⁰, —S(O)₂NR¹⁰R¹¹, and —S(O)₂R¹⁰, wherein each of said -alkyl, said -alkenyl, said alkynyl, said aryl, said heteroaryl, said —O-alkyl, said —O-alkenyl, said —OC(O)-alkyl, and said —S-alkyl is unsubstituted or optionally independently substituted with from one to five substituents, which can be the same or different, each substituent being independently selected from halo, —OH, alkyl, haloalkyl, heteroalkyl, heterohaloalkyl, —O-alkyl, —O-cycloalkyl, —O-alkenyl, —O-haloalkyl, —O-haloalkenyl, —O(C)O—N(R¹⁰)R¹¹, —O(C)O—NHR¹¹, —O(C)O—NH₂, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, —S(O)₂R¹⁰, —SR¹⁰, —S(O)₂NHR¹⁰, —S(O)₂NR¹⁰R¹¹, —CN, —NH₂, —NHR¹⁶, and —NR¹⁸R¹⁷, —N(R¹⁰)S(O)₂R¹⁰, —NHS(O)₂R¹⁰, aryl, heteroaryl, cycloalkyl, cycloalkenyl, heterocycloalkyl, and heterocycloalkenyl;

or, alternatively, R⁸ and R⁹ are taken together with the carbon atom to which they are shown attached to form a 3- to 7-membered, saturated or partially unsaturated, spirocycloalkyl ring containing from 0 to 3 spiro ring heteroatoms selected from O, N, and S;

each R¹⁸ (when present) is selected from H, —OH, halo, -alkyl, -alkenyl, alkynyl, azido, aryl, heteroaryl, —O-alkyl, —O-alkenyl, —OC(O)-alkyl, —SH, —S-alkyl, —NH₂, —NO₂, —NHR¹⁰, —NR¹⁰R¹¹, —C(O)OH, —C(O)OR¹⁰, —C(O)NH₂, —C(O)NHR¹⁰, —C(O)NR¹⁰R¹¹, —S(O)NHR¹⁰, —S(O)NR¹⁰R¹¹, —S(O)R¹⁰, —S(O)₂NHR¹⁰, —S(O)₂NR¹⁰R¹¹, and —S(O)₂R¹⁰, wherein each of said -alkyl, said -alkenyl, said alkynyl, said aryl, said heteroaryl, said —O-alkyl, said —O-alkenyl, said —OC(O)-alkyl, and said —S-alkyl is unsubstituted or optionally independently substituted with from one to three substituents, which can be the same or different, each substituent being independently selected from halo, —OH, alkyl, haloalkyl, heteroalkyl, heterohaloalkyl, —O-alkyl, —O-alkenyl, —O-haloalkyl, —O-haloalkenyl, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, aryl, heteroaryl, cycloalkyl, cycloalkenyl, heterocycloalkyl, and heterocycloalkenyl;

each R¹⁹ (when present) is selected from H, —OH, halo, -alkyl, -alkenyl, alkynyl, azido, aryl, heteroaryl, —O-alkyl, —O-alkenyl, —OC(O)-alkyl, —SH, —S-alkyl, —NH₂, —NO₂, —NHR¹⁰, —NR¹⁰R¹¹, —C(O)OH, —C(O)OR¹⁰, —C(O)NH₂, —C(O)NHR¹⁰, —C(O)NR¹⁰R¹¹, —S(O)NHR¹⁰, —S(O)NR¹⁰R¹¹, —S(O)R¹⁰, —S(O)₂NHR¹⁰, —S(O)₂NR¹⁰R¹¹, and —S(O)₂R¹⁰, wherein each of said -alkyl, said -alkenyl, said alkynyl, said aryl, said heteroaryl, said —O-alkyl, said —O-alkenyl, said —OC(O)-alkyl, and said —S-alkyl is unsubstituted or optionally independently substituted with from one to three substituents, which can be the same or different, each substituent being independently selected from halo, —OH, alkyl, haloalkyl, heteroalkyl, heterohaloalkyl, —O-alkyl, —O-alkenyl, —O-haloalkyl, —O-haloalkenyl, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, aryl, heteroaryl, cycloalkyl, cycloalkenyl, heterocycloalkyl, and heterocycloalkenyl;

or, alternatively, n is 1 and R¹⁸ and R¹⁹ are taken together with the carbon atom to which they are attached to form a 3- to 7-membered, saturated or partially unsaturated, spirocycloalkyl ring containing from 0 to 3 spiro ring heteroatoms selected from O, N, and S;

or, alternatively, R⁴ and R⁷, together with the carbon atoms to which they are shown attached, form a moiety (1C):

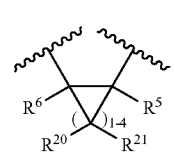

wherein R²⁰ and R²¹ are each independently selected from H, alkyl, and heteroalkyl and wherein R⁵ and R⁶ are defined above, with the proviso that when R⁴ and R⁷ form a moiety (1C), then R⁵ and R⁶ are not taken together to form a double bond;

or, alternatively, R⁴ and R⁷, together with the carbon atoms to which they are shown attached, form a moiety (1D):

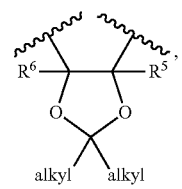

wherein R⁵ and R⁶ are as defined above;

or, alternatively, R⁴ and R⁷, together with the carbon atoms to which they are shown attached, form a moiety (1E):

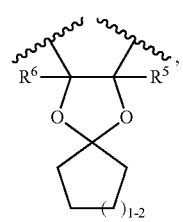

wherein R⁵ and R⁶ are as defined above;

each R¹⁰ is independently selected from alkyl, alkenyl, haloalkyl, heteroalkyl, heterohaloalkyl, —S(O)₂-alkyl, -alkyl-OH, —C(O)Oalkyl, —C(O)alkyl, —C(O)NHalkyl, —C(O)N(alkyl)₂, cycloalkyl, heterocycloalkyl, heterocycloalkenyl, aryl, and heteroaryl;

each R¹¹ is independently selected from alkyl, alkenyl, haloalkyl, heteroalkyl, heterohaloalkyl, —S(O)₂-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;

or, alternatively, R$^{10}$ and R$^{11}$ are linked together with the nitrogen to which they are attached to form an unsubstituted or substituted 4- or 6-membered heterocycloalkyl;

each R$^{12}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;

each R$^{13}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;

or, alternatively, R$^{12}$ and R$^{13}$ are linked together with the nitrogen to which they are attached to form an unsubstituted or substituted 4- to 6-membered heterocycloalkyl;

each R$^{14}$ is independently selected from alkyl, alkoxy, alkenyl, haloalkyl, heteroalkyl, heterohaloalkyl, alkylamino, alkylthio, heteroalkenyl, haloalkenyl, —S(O)$_2$-alkyl, -alkyl-OH, -alkyl-O-Acyl, —C(O)Oalkyl, —C(O)alkyl, cycloalkyl, cycloalkyl-alkyl-, heterocycloalkyl, heterocycloalkyl-alkyl-, heterocycloalkenyl, heterocycloalkenyl-alkyl-, aryl, arylalkyl-, heteroaryl, and heteroaryl-alkyl-, wherein each said alkyl, each said alkoxy, each said alkenyl, each said haloalkyl, each said heteroalkyl, each said heterohaloalkyl, each said alkylamino, each said alkylthio, each said heteroalkenyl, each said haloalkenyl, each said —S(O)$_2$-alkyl, each said -alkyl-OH, each said -alkyl-O-Acyl, each said —C(O)Oalkyl, each said —C(O)alkyl, each said cycloalkyl, each said cycloalkyl-alkyl-, each said heterocycloalkyl, each said heterocycloalkyl-alkyl-, each said heterocycloalkenyl, each said heterocycloalkenyl-alkyl-, each said aryl, each said aryl-alkyl-, each said heteroaryl, and each said heteroaryl-alkyl-, is unsubstituted or optionally independently substituted with from one to five substituent, which can be the same or different, each substitutent being independently selected from —OH, halo, —NH$_2$, —NHR$^{10}$, —NR$^{10}$R$^{11}$, —C(O)OH, —C(O)OR$^{10}$, —C(O)NH$_2$, —C(O)NHR$^{10}$, —C(O)NR$^{10}$R$^{11}$, —S(O)$_2$alkyl, —S(O)$_2$aryl, alkyl, alkoxy, haloalkyl, heteroalkyl, haloalkoxy, heteroaryl, heterohaloalkyl, aryl, cycloalkyl, and heterocycloalkyl;

each R$^{15}$ is independently selected from alkyl, alkoxy, alkenyl, haloalkyl, heteroalkyl, heterohaloalkyl, alkylamino, alkylthio, heteroalkenyl, haloalkenyl, —S(O)$_2$-alkyl, -alkyl-OH, -alkyl-O-Acyl, —C(O)Oalkyl, —C(O)alkyl, cycloalkyl, cycloalkyl-alkyl-, heterocycloalkyl, heterocycloalkyl-alkyl-, heterocycloalkenyl, heterocycloalkenyl-alkyl-, aryl, arylalkyl-, heteroaryl, and heteroaryl-alkyl-, wherein each said alkyl, each said alkoxy, each said alkenyl, each said haloalkyl, each said heteroalkyl, each said heterohaloalkyl, each said alkylamino, each said alkylthio, each said heteroalkenyl, each said haloalkenyl, each said —S(O)$_2$-alkyl, each said -alkyl-OH, each said -alkyl-O-Acyl, each said —C(O)Oalkyl, each said —C(O)alkyl, each said cycloalkyl, each said cycloalkyl-alkyl-, each said heterocycloalkyl, each said heterocycloalkyl-alkyl-, each said heterocycloalkenyl, each said heterocycloalkenyl-alkyl-, each said aryl, each said aryl-alkyl-, each said heteroaryl, and each said heteroaryl-alkyl-, is unsubstituted or optionally independently substituted with from one to five substituent, which can be the same or different, each substitutent being independently selected from —OH, halo, —NH$_2$, —NHR$^{10}$, —NR$^{10}$R$^{11}$, —C(O)OH, —C(O)OR$^{10}$, —C(O)NH$_2$, —C(O)NHR$^{10}$, —C(O)NR$^{10}$R$^{11}$, —S(O)$_2$alkyl, —S(O)$_2$aryl, alkyl, alkoxy, haloalkyl, haloalkoxy, heteroaryl, heteroalkyl, heterohaloalkyl, aryl, cycloalkyl, and heterocycloalkyl;

or, alternatively, R$^{14}$ and R$^{15}$ are linked together with the nitrogen to which they are attached to form an unsubstituted or substituted 4- to 6-membered heterocycloalkyl;

each R$^{16}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl; and each R$^{17}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;

or, alternatively, R$^{16}$ and R$^{17}$ are linked together with the nitrogen to which they are attached to form an unsubstituted or substituted 4- or 6-membered heterocycloalkyl.

In another embodiment, the invention provides compositions, including pharmaceutical compositions, comprising one or more compounds of the invention (e.g., one compound of the invention), or a pharmaceutically acceptable salt, solvate, ester, or prodrug thereof, and a pharmaceutically acceptable carrier or diluent. In one embodiment, said compound or compounds of the invention are present in the composition in an amount effective for inhibiting HCV, and/or for treating or preventing a viral infection or a virus-related disorder in a patient in need thereof.

In another embodiment, the invention provides a pharmaceutical composition comprising one or more compounds of the invention, or a pharmaceutically acceptable salt, solvate, ester, or prodrug thereof, together with one or more additional therapeutic agents, optionally further comprising a pharmaceutically effective carrier or diluent. Non-limiting examples of such additional therapeutic agents include one or more of any of the following: HCV polymerase inhibitors, HCV protease inhibitors, HCV replicase inhibitors, nucleosides, Interferon, and/or ribavirin (or Levovirin or Viramidine). Non-limiting examples of interferon include PEG-interferon, PEG interferon alpha conjugate, alpha-interferon, and pegylated interferon. These and other examples are known to those of ordinary skill in the art.

In another embodiment, the present invention provides for the use of one or more compounds of the invention, or a pharmaceutically acceptable salt, solvate, ester, and/or prodrug thereof, alone or in combination with one or more additional therapeutic agents such as those described above, for inhibiting HCV and/or for treating or preventing a viral infection or a virus-related disorder in a patient in need thereof.

In another embodiment, the invention provides a method of inhibiting HCV in vivo, ex vivo, or in vitro, comprising exposing a population of cells comprising HCV to an effective amount of at least one compound of the invention, or a pharmaceutically acceptable salt, solvate, ester, or prodrug thereof, alone or in combination with one or more additional therapeutic agents such as those described above. In one such embodiment, the compound or compounds of the invention are used as the neat chemical. In another such embodiment, the compounds of the invention are used in the form of a pharmaceutically acceptable composition.

In another embodiment, the invention provides a method for treating or preventing a viral infection or a virus-related disorder in a patient, comprising administering to the patient an effective amount of at least one compound of the invention, or a pharmaceutically acceptable salt, solvate, ester, or prodrug thereof, alone or in combination with one or more additional therapeutic agents such as those described above. In one such embodiment, the compound or compounds of the invention are used as the neat chemical. In another such embodiment, the compounds of the invention are used in the form of a pharmaceutically acceptable composition.

The details of the invention are set forth in the accompanying detailed description below. Although any methods and materials similar to those described herein can be used in the practice or testing of the present invention, illustrative methods and materials are described herein. Other features, objects, and advantages of the invention will be apparent from the description and the claims. All patents and publications cited in this specification are incorporated herein by reference.

DETAILED DESCRIPTION OF THE INVENTION

In one embodiment, the compounds of the invention have the structural Formula (I) as described above, and include pharmaceutically acceptable salts, esters, prodrugs, tautomers, and isomers of said compounds.

In one embodiment, in Formula (I), each of $R^3$, $R^5$, $R^6$, and $R^8$ is H.

In one embodiment, in Formula (I), n is 1; each of $R^2$, $R^3$, $R^5$, $R^6$, $R^8$, $R^{18}$ and $R^{19}$ is H; $R^4$ and $R^7$ are OH; and $R^9$ is alkyl, wherein said alkyl is unsubstituted or substituted with from one to five substituents, which can be the same or different, each substituent being independently selected from halo, —OH, alkyl, haloalkyl, heteroalkyl, heterohaloalkyl, —O-alkyl, —O-cycloalkyl, —O-alkenyl, —O-haloalkyl, —O-haloalkenyl, —OC(O)-alkyl, —OC(O)-alkenyl, —OC(O)-haloalkyl, —OC(O)-haloalkenyl, —O(C)O—NHR$^{10}$, —O(C)O—N(R$^{10}$)R$^{11}$, —C(O)O-alkyl, —C(O)O-alkenyl, —C(O)O-haloalkyl, —C(O)O-haloalkenyl, —S(O)$_2$R$^{10}$, —SR$^{10}$, —S(O)$_2$NHR$^{10}$, —S(O)$_2$NR$^{10}$R$^{11}$, —CN, —NH$_2$, —NHR$^{16}$, and —NR$^{16}$R$^{17}$, —NHS(O)$_2$R$^{10}$, —N(R$^{10}$)S(O)$_2$R$^{10}$, aryl, heteroaryl, cycloalkyl, cycloalkenyl, heterocycloalkyl, and heterocycloalkenyl.

In one embodiment, in Formula (I), n is 1; each of $R^2$, $R^3$, $R^5$, $R^6$, $R^8$, $R^{18}$ and $R^{19}$ is H; $R^4$ and $R^7$ are OH; and $R^9$ is alkyl, wherein said alkyl is unsubstituted or substituted with from one to five groups independently selected from —OH, halo, —CN, —NH$_2$, —NHR$^{16}$, —NR$^{16}$R$^{17}$, —NHS(O)$_2$R$^{10}$, —N(R$^{10}$)S(O)$_2$R$^{10}$, —Oalkyl, —Ocycloalkyl, —O-alkyl-cycloalkyl, —OC(O)-alkyl, —O(C)O—NHR$^{10}$, —O(C)O—N(R$^{10}$)R$^{11}$, —C(O)O-alkyl, —S(O)$_2$R$^{10}$, —SR$^{10}$, —S(O)$_2$NHR$^{10}$, and —S(O)$_2$NR$^{10}$R$^{11}$.

In one embodiment, in Formula (I), n is 1; each $R^2$, $R^3$, $R^5$, $R^6$, $R^8$, $R^{18}$ and $R^{19}$ is H; $R^4$ and $R^7$ are OH; and $R^9$ is methyl, wherein said methyl is unsubstituted or substituted with from one to three groups independently selected from —OH, halo, alkyl, —CN, —NH$_2$, —NHR$^{16}$, —NR$^{16}$R$^{17}$, —NHS(O)$_2$R$^{10}$, —N(R$^{10}$)S(O)$_2$R$^{10}$, —Oalkyl, —Ocycloalkyl, —O-alkyl-cycloalkyl, —OC(O)-alkyl, —O(C)O—NHR$^{10}$, —O(C)O—N(R$^{10}$)R$^{11}$, —C(O)O-alkyl, —S(O)$_2$R$^{10}$, —SR$^{10}$, —S(O)$_2$NHR$^{10}$, and —S(O)$_2$NR$^{10}$R$^{11}$.

In some embodiments, $R^9$ is -alkyl-NHS(O)$_2$R$^{10}$, wherein $R^{10}$ is selected from methyl, ethyl, and cyclopropyl.

In some embodiments, $R^9$ is selected from -alkyl—N(CH$_3$)S(O)$_2$R$^{10}$ and -alkyl-N(CH$_2$CH$_3$)S(O)$_2$R$^{10}$, wherein $R^{10}$ is selected from methyl, ethyl, and cyclopropyl.

In some embodiments, $R^9$ is -alkyl-O(C)O—NHR$^{10}$, wherein $R^{10}$ is selected from methyl, ethyl, and cyclopropyl.

In some embodiments, $R^9$ is selected from $R^9$-alkyl-O(C)O—N(CH$_3$)R$^{10}$ and —O(C)O—N(CH$_2$CH$_3$)R$^{10}$, wherein $R^{10}$ is selected from methyl, ethyl, and cyclopropyl.

In one embodiment, in Formula (I), n is 1; each of $R^2$, $R^3$, $R^5$, $R^6$, $R^8$, $R^{18}$ and $R^{19}$ is H; $R^4$ and $R^7$ are OH; and $R^9$ is selected from —CH$_2$—O-alkyl, —CH$_2$—OH, —CH$_3$, H, —CH$_2$—CH$_3$, —CH$_2$—OC(O)CF$_3$, —CH$_2$—NH$_2$, —CH$_2$—NHR$^{16}$, and —CH$_2$—NR$^{16}$R$^{17}$.

In one embodiment, in Formula (I), each of $R^3$, $R^5$, $R^6$, and $R^8$ is H and each of $R^4$ and $R^7$ is —OH.

In one embodiment, in Formula (I), each of $R^3$, $R^5$, $R^6$, and $R^8$ is H; each of $R^4$ and $R^7$ is —OH; and $R^9$ is —O-alkyl.

In one embodiment, in Formula (I), each of $R^3$, $R^5$, $R^6$, and $R^8$ is H; each of $R^4$ and $R^7$ is —OH; and $R^9$ is —O—CH$_3$.

In one embodiment, in Formula (I), each of $R^3$, $R^5$, $R^6$, and $R^8$ is H; each of $R^4$ and $R^7$ is —OH; $R^9$ is —O—CH$_3$, and n is 1.

In one embodiment, in Formula (I), each of $R^3$, $R^5$, $R^6$, and $R^8$ is H; each of $R^4$ and $R^7$ is —OH; $R^9$ is —O—CH$_3$, and n is 2.

In one embodiment, the compounds of the invention have the structural Formula (I.A):

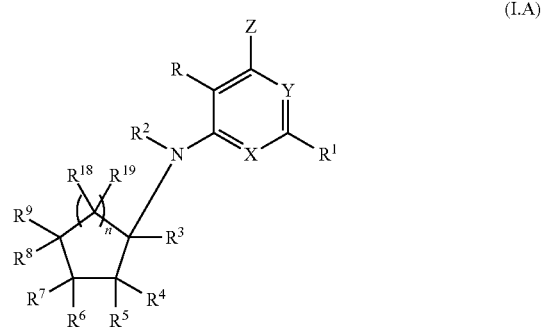

(I.A)

and includes tautomers, isomers, and esters of such compounds, and pharmaceutically acceptable salts, solvates, and prodrugs of said compounds, tautomers, isomers, and esters, wherein each of R, R$^1$, X, Y, Z, R$^2$, R$^3$, R$^4$, R$^5$, R$^6$, R$^7$, R$^8$, R$^9$, R$^{18}$, R$^{19}$ and n are selected independently and wherein:

R, R$^1$, R$^2$, X, Y, Z, and n are as defined in Formula (I);

R$^3$ is selected from H, -alkyl, -alkenyl, alkynyl, aryl, heteroaryl, and cycloalkyl,
  wherein each of said -alkyl, said -alkenyl, said alkynyl, said aryl, said heteroaryl, and said cycloalkyl, is unsubstituted or optionally independently substituted with from one to three substituents, which can be the same or different, each substituent being independently selected from halo, —OH, alkyl, —O-alkyl, —O-alkenyl, —O-haloalkyl, —O-haloalkenyl, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, aryl, heteroaryl, cycloalkyl, cycloalkenyl, heterocycloalkyl, and heterocycloalkenyl;

R$^4$ is selected from H, —OH, halo, -alkyl, -alkenyl, alkynyl, azido, aryl, heteroaryl, —O-alkyl, —O-alkenyl, —OC(O)-alkyl, —SH, —S-alkyl, —NH$_2$, —NHalkyl, and —N(alkyl)$_2$,
  wherein each of said -alkyl, said -alkenyl, said alkynyl, said aryl, said heteroaryl, said —O-alkyl, said —O-alkenyl, said —OC(O)-alkyl, and said —S-alkyl, is unsubstituted or optionally independently substituted with from one to three substituents, which can be the same or different, each substituent being independently selected from halo, —OH, alkyl, —O-alkyl, —O-alkenyl, —O-haloalkyl, —O-haloalkenyl, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, aryl, heteroaryl, cycloalkyl, cycloalkenyl, heterocycloalkyl, and heterocycloalkenyl;

$R^5$ is selected from H, —OH, halo, -alkyl, -alkenyl, alkynyl, azido, aryl, heteroaryl, —O-alkyl, —O-alkenyl, —OC(O)-alkyl, —SH, —S-alkyl, —NH$_2$, —NHalkyl, and —N(alkyl)$_2$, wherein each of said -alkyl, said -alkenyl, said alkynyl, said aryl, said heteroaryl, said —O-alkyl, said —O-alkenyl, said —OC(O)-alkyl, and said —S-alkyl, is unsubstituted or optionally independently substituted with from one to three substituents, which can be the same or different, each substituent being independently selected from halo, —OH, alkyl, —O-alkyl, —O-alkenyl, —O-haloalkyl, —O-haloalkenyl, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, aryl, heteroaryl, cycloalkyl, cycloalkenyl, heterocycloalkyl, and heterocycloalkenyl;

$R^6$ is selected from H, —OH, halo, -alkyl, -alkenyl, alkynyl, azido, aryl, heteroaryl, —O-alkyl, —O-alkenyl, —OC(O)-alkyl, —SH, —S-alkyl, —NH$_2$, —NHalkyl, and —N(alkyl)$_2$, wherein each of said -alkyl, said -alkenyl, said alkynyl, said aryl, said heteroaryl, said —O-alkyl, said —O-alkenyl, said —OC(O)-alkyl, and said —S-alkyl, is unsubstituted or optionally independently substituted with from one to three substituents, which can be the same or different, each substituent being independently selected from halo, —OH, alkyl, —O-alkyl, —O-alkenyl, —O-haloalkyl, —O-haloalkenyl, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, aryl, heteroaryl, cycloalkyl, cycloalkenyl, heterocycloalkyl, and heterocycloalkenyl;

$R^7$ is selected from H, —OH, halo, -alkyl, -alkenyl, alkynyl, azido, aryl, heteroaryl, —O-alkyl, —O-alkenyl, —OC(O)-alkyl, —SH, —S-alkyl, —NH$_2$, —NHalkyl, and —N(alkyl)$_2$, wherein each of said -alkyl, said -alkenyl, said alkynyl, said aryl, said heteroaryl, said —O-alkyl, said —O-alkenyl, said —OC(O)-alkyl, and said —S-alkyl, is unsubstituted or optionally independently substituted with from one to three substituents, which can be the same or different, each substituent being independently selected from halo, —OH, alkyl, —O-alkyl, —O-alkenyl, —O-haloalkyl, —O-haloalkenyl, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, aryl, heteroaryl, cycloalkyl, cycloalkenyl, heterocycloalkyl, and heterocycloalkenyl;

or, alternatively, $R^6$ and $R^7$ are taken together with the carbon atom to which they are shown attached to form a 3- to 7-membered, saturated or partially unsaturated, spirocycloalkyl ring containing from 0 to 3 spiro ring heteroatoms selected from O, N, and S;

$R^8$ is selected from is selected from H, —OH, halo, -alkyl, -alkenyl, alkynyl, azido, aryl, heteroaryl, —O-alkyl, —O-alkenyl, —OC(O)-alkyl, —SH, —S-alkyl, —NH$_2$, —NHalkyl, and —N(alkyl)$_2$, wherein each of said -alkyl, said -alkenyl, said alkynyl, said aryl, said heteroaryl, said —O-alkyl, said —O-alkenyl, said —OC(O)-alkyl, and said —S-alkyl, is unsubstituted or optionally independently substituted with from one to five substituents, which can be the same or different, each substituent being independently selected from halo, —OH, —NH$_2$, —NHR$^{16}$, —NR$^{16}$R$^{17}$, —NHS(O)$_2$R$^{10}$, —N(R$^{10}$)S(O)$_2$R$^{10}$, alkyl, —O-alkyl, —S-alkyl, —S(O)$_2$-alkyl, —S(O)$_2$NH$_2$, —S(O)$_2$NHalkyl, —S(O)$_2$N(alkyl)$_2$, —O-alkenyl, —O-haloalkyl, —O-haloalkenyl, —OC(O)-alkyl, —O(C)O—NHR$^{10}$, —O(C)O—N(R$^{10}$)R$^{11}$, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, —S(O)$_2$R$^{10}$, —SR$^{10}$, —S(O)$_2$NHR$^{10}$, —S(O)$_2$NR$^{10}$R$^{11}$, —CN, —NH$_2$, —NHR$^{16}$, and —NR$^{16}$R$^{17}$, aryl, heteroaryl, cycloalkyl, cycloalkenyl, heterocycloalkyl, and heterocycloalkenyl;

$R^9$ is selected from H, —OH, halo, -alkyl, -alkenyl, alkynyl, azido, aryl, heteroaryl, —O-alkyl, —O-alkenyl, —OC(O)-alkyl, —SH, —S-alkyl, —NH$_2$, —NHalkyl, and —N(alkyl)$_2$, wherein each of said -alkyl, said -alkenyl, said alkynyl, said aryl, said heteroaryl, said —O-alkyl, said —O-alkenyl, said —OC(O)-alkyl, and said —S-alkyl, is unsubstituted or optionally independently substituted with from one to five substituents, which can be the same or different, each substituent being independently selected from halo, —OH, —NH$_2$, —NHR$^{16}$, —NR$^{16}$R$^{17}$, —NHS(O)$_2$R$^{10}$, —N(R$^{10}$)S(O)$_2$R$^{10}$, alkyl, —O-alkyl, —S-alkyl, —S(O)$_2$-alkyl, —S(O)$_2$NH$_2$, —S(O)$_2$NHalkyl, —S(O)$_2$N(alkyl)$_2$, —O-alkenyl, —O-haloalkyl, —O-haloalkenyl, —OC(O)-alkyl, —O(C)O—NHR$^{10}$, —O(C)O—N(R$^{10}$)R$^{11}$, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, —S(O)$_2$R$^{10}$, —SR$^{10}$, —S(O)$_2$NHR$^{10}$, —S(O)$_2$NR$^{10}$R$^{11}$, —CN, —NH$_2$, —NHR$^{16}$, and —NR$^{16}$R$^{17}$, aryl, heteroaryl, cycloalkyl, cycloalkenyl, heterocycloalkyl, and heterocycloalkenyl;

each $R^{18}$ (when present) is independently selected from H, —OH, halo, -alkyl, -alkenyl, alkynyl, azido, aryl, heteroaryl, —O-alkyl, —O-alkenyl, —OC(O)-alkyl, —SH, —S-alkyl, —NH$_2$, —NHalkyl, and —N(alkyl)$_2$, wherein each of said -alkyl, said -alkenyl, said alkynyl, said aryl, said heteroaryl, said —O-alkyl, said —O-alkenyl, said —OC(O)-alkyl, and said —S-alkyl, is unsubstituted or optionally independently substituted with from one to three substituents, which can be the same or different, each substituent being independently selected from halo, —OH, alkyl, —O-alkyl, —O-alkenyl, —O-haloalkyl, —O-haloalkenyl, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, aryl, heteroaryl, cycloalkyl, cycloalkenyl, heterocycloalkyl, and heterocycloalkenyl;

each $R^{19}$ (when present) is independently selected from H, —OH, halo, -alkyl, -alkenyl, alkynyl, azido, aryl, heteroaryl, —O-alkyl, —O-alkenyl, —OC(O)-alkyl, —SH, —S-alkyl, —NH$_2$, —NHalkyl, and —N(alkyl)$_2$, wherein each of said -alkyl, said -alkenyl, said alkynyl, said aryl, said heteroaryl, said —O-alkyl, said —O-alkenyl, said —OC(O)-alkyl, and said —S-alkyl, is unsubstituted or optionally independently substituted with from one to three substituents, which can be the same or different, each substituent being independently selected from halo, —OH, alkyl, —O-alkyl, —O-alkenyl, —O-haloalkyl, —O-haloalkenyl, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, aryl, heteroaryl, cycloalkyl, cycloalkenyl, heterocycloalkyl, and heterocycloalkenyl;

each $R^{10}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)(alkyl)$_2$, cycloalkyl, heterocycloalkyl, heterocycloalkenyl, aryl, and heteroaryl;

each $R^{11}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)(alkyl)$_2$, cycloalkyl, heterocycloalkyl, heterocycloalkenyl, aryl, and heteroaryl;

or, alternatively, $R^{10}$ and $R^{11}$ are linked together with the nitrogen to which they are attached to form an unsubstituted or substituted 4- or 6-membered heterocycloalkyl;

each $R^{12}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, cycloalkyl, heterocycloalkyl, heterocycloalkenyl, aryl, and heteroaryl;

each $R^{13}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, cycloalkyl, heterocycloalkyl, heterocycloalkenyl, aryl, and heteroaryl;

or, alternatively, $R^{12}$ and $R^{13}$ are linked together with the nitrogen to which they are attached to form an unsubstituted or substituted 4- to 6-membered heterocycloalkyl;

each $R^{14}$ is independently selected from alkyl, alkoxy, alkenyl, haloalkyl, heteroalkyl, heterohaloalkyl, alkylamino, heteroalkenyl, haloalkenyl, —S(O)$_2$-alkyl, -alkyl-OH, -alkyl-O-Acyl, —C(O)Oalkyl, —C(O)alkyl, cycloalkyl, cycloalkyl-alkyl-, heterocycloalkyl, heterocycloalkyl-alkyl-, heterocycloalkenyl, heterocycloalkenyl-alkyl-, aryl, arylalkyl-, heteroaryl, and heteroaryl-alkyl-, wherein each said alkyl, each said alkoxy, each said alkenyl, each said haloalkyl, each said heteroalkyl, each said heterohaloalkyl, each said alkylamino, each said heteroalkenyl, each said haloalkenyl, each said —S(O)$_2$-alkyl, each said -alkyl-OH, each said -alkyl-O-Acyl, each said —C(O)Oalkyl, each said —C(O)alkyl, each said cycloalkyl, each said cycloalkyl-alkyl-, each said heterocycloalkyl, each said heterocycloalkyl-alkyl-, each said heterocycloalkenyl, each said heterocycloalkenyl-alkyl-, each said aryl, each said aryl-alkyl-, each said heteroaryl, and each said heteroaryl-alkyl-, is unsubstituted or optionally independently substituted with from one to three substituent, which can be the same or different, each substitutent being independently selected from halo, —OH, —NH$_2$, —NHalkyl, —N(alkyl)$_2$, alkyl, alkoxy, haloalkyl, haloalkoxy, heteroaryl, heteroalkyl, and heterohaloalkyl;

each $R^{15}$ is independently selected from alkyl, alkoxy, alkenyl, haloalkyl, heteroalkyl, heterohaloalkyl, alkylamino, heteroalkenyl, haloalkenyl, —S(O)$_2$-alkyl, -alkyl-OH, -alkyl-O-Acyl, —C(O)Oalkyl, —C(O)alkyl, cycloalkyl, cycloalkyl-alkyl-, heterocycloalkyl, heterocycloalkyl-alkyl-, heterocycloalkenyl, heterocycloalkenyl-alkyl-, aryl, arylalkyl-, heteroaryl, and heteroaryl-alkyl-, wherein each said alkyl, each said alkoxy, each said alkenyl, each said haloalkyl, each said heteroalkyl, each said heterohaloalkyl, each said alkylamino, each said heteroalkenyl, each said haloalkenyl, each said —S(O)$_2$-alkyl, each said -alkyl-OH, each said -alkyl-O-Acyl, each said —C(O)Oalkyl, each said —C(O)alkyl, each said cycloalkyl, each said cycloalkyl-alkyl-, each said heterocycloalkyl, each said heterocycloalkyl-alkyl-, each said heterocycloalkenyl, each said heterocycloalkenyl-alkyl-, each said aryl, each said aryl-alkyl-, each said heteroaryl, and each said heteroaryl-alkyl-, is unsubstituted or optionally independently substituted with from one to three substituent, which can be the same or different, each substitutent being independently selected from halo, —OH, —NH$_2$, —NHalkyl, —N(alkyl)$_2$, alkyl, alkoxy, haloalkyl, haloalkoxy, heteroaryl, heteroalkyl, and heterohaloalkyl;

or, alternatively, $R^{14}$ and $R^{15}$ are linked together with the nitrogen to which they are attached to form an unsubstituted or substituted 4- to 6-membered heterocycloalkyl;

each $R^{16}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, cycloalkyl, heterocycloalkyl, heterocycloalkenyl, aryl, and heteroaryl; and each $R^{17}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, cycloalkyl, heterocycloalkyl, heterocycloalkenyl, aryl, and heteroaryl;

or, alternatively, $R^{16}$ and $R^{17}$ are linked together with the nitrogen to which they are attached to form an unsubstituted or substituted 4- or 6-membered heterocycloalkyl.

In one embodiment, the compounds of the invention have the structural Formula (I.a):

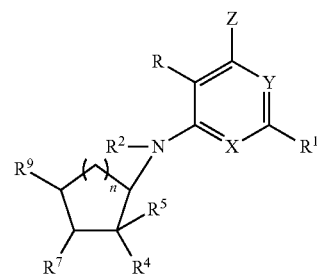

(I.a)

and includes pharmaceutically acceptable salts, esters, prodrugs, or isomers of said compounds, wherein each of R, $R^1$, X, Y, Z, $R^2$, $R^4$, $R^5$, $R^7$, and $R^9$ is selected independently and defined in Formula (I).

In one embodiment, in Formula (I.a), n is 1; $R^2$ is H; $R^4$ and $R^7$ are each independently selected from H and OH; $R^5$ is selected from H, halo, and alkyl; and $R^9$ is alkyl, wherein said alkyl is unsubstituted or substituted with from one to five substituents, which can be the same or different, each substituent being independently selected from halo, —OH, alkyl, haloalkyl, heteroalkyl, heterohaloalkyl, —O-alkyl, —O-cycloalkyl, —O-alkenyl, —O-haloalkyl, —O-haloalkenyl, —OC(O)-alkyl, —OC(O)-alkenyl, —OC(O)-haloalkyl, —OC(O)-haloalkenyl, —O(C)O—NHR$^{10}$, —O(C)O—N(R$^{10}$)R$^{11}$, —C(O)O-alkyl, —C(O)O-alkenyl, —C(O)O-haloalkyl, —C(O)O-haloalkenyl, —S(O)$_2$R$^{10}$, —SR$^{10}$, —S(O)$_2$NHR$^{10}$, —S(O)$_2$NR$^{10}$R$^{11}$, —CN, —NH$_2$, —NHR$^{16}$, and —NR$^{16}$R$^{17}$, —NHS(O)$_2$R$^{10}$, —N(R$^{10}$)S(O)$_2$R$^{10}$, aryl, heteroaryl, cycloalkyl, cycloalkenyl, heterocycloalkyl, and heterocycloalkenyl.

In one embodiment, in Formula (I.a), n is 1; $R^2$ is H; $R^4$ and $R^7$ are each independently selected from H and OH; $R^5$ is selected from H, halo, and alkyl; and $R^9$ is alkyl, wherein said alkyl is unsubstituted or substituted with from one to five groups independently selected from —OH, halo, —ON, —NH$_2$, —NHR$^{16}$, —NR$^{16}$R$^{17}$, —NHS(O)$_2$R$^{10}$, —N(R$^{10}$)S(O)$_2$R$^{10}$, —Oalkyl, —Ocycloalkyl, —O-alkyl-cycloalkyl, —OC(O)-alkyl, —O(C)O—NHR$^{10}$, —O(C)O—N(R$^{10}$)R$^{11}$, —C(O)O-alkyl, —S(O)$_2$R$^{10}$, —SR$^{10}$, —S(O)$_2$NHR$^{10}$, and —S(O)$_2$NR$^{10}$R$^{11}$.

In one embodiment, in Formula (I.a), n is 1; $R^2$ is H; $R^4$ and $R^7$ are each independently selected from H and OH; $R^5$ is selected from H, halo, and alkyl; and $R^9$ is methyl, wherein said methyl is unsubstituted or substituted with from one to three groups independently selected from —OH, halo, alkyl, —CN, —NH$_2$, —NHR$^{16}$, —NR$^{16}$R$^{17}$, —NHS(O)$_2$R$^{10}$, —N(R$^{10}$)S(O)$_2$R$^{10}$, —Oalkyl, —Ocycloalkyl, —O-alkyl-cycloalkyl, —OC(O)-alkyl, —O(C)O—NHR$^{10}$, —O(C)O—N(R$^{10}$)R$^{11}$, —C(O)O-alkyl, —S(O)$_2$R$^{10}$, —SR$^{10}$, —S(O)$_2$NHR$^{10}$, and —S(O)$_2$NR$^{10}$R$^{11}$.

In some embodiments, in Formula (I.a), $R^9$ is -alkyl-NHS(O)$_2$R$^{10}$, wherein $R^{10}$ is selected from methyl, ethyl, and cyclopropyl.

In some embodiments, in Formula (I.a), $R^9$ is selected from -alkyl-N(CH$_3$)S(O)$_2$R$^{10}$ and -alky—N(CH$_2$CH$_3$)S(O)$_2$R$^{10}$, wherein $R^{10}$ is selected from methyl, ethyl, and cyclopropyl.

In some embodiments, in Formula (I.a), $R^9$ is -alkyl-O(C)O—NHR$^{10}$, wherein $R^{10}$ is selected from methyl, ethyl, and cyclopropyl.

In some embodiments, in Formula (I.a), $R^9$ is selected from $R^9$-alkyl-O(C)O—N(CH$_3$)R$^{10}$ and -alkyl-O(C)O—N(CH$_2$CH$_3$)R$^{10}$, wherein $R^{10}$ is selected from methyl, ethyl, and cyclopropyl.

In one embodiment, in Formula (I.a), n is 1; $R^2$ is H; $R^4$ and $R^7$ are each independently selected from H and OH; $R^5$ is selected from H, halo, and alkyl; and In one embodiment, in Formula (I.a), n is 1; $R^2$ is H; $R^4$ and $R^7$ are each independently selected from H and OH; $R^5$ is selected from H, halo, and alkyl; and $R^9$ is selected from H, —COOH, —C(O)O-alkyl, —OC(O)-alkyl, —C(O)O-aryl, —OC(O)-aryl, —C(O)O-alkyl-aryl, —OC(O)-alkyl-aryl, —C(O)O-alkyl-heteroaryl, —OC(O)-alkyl-heteroaryl, alkyl, —O-alkyl, heteroalkyl, haloalkyl, heterohaloalkyl, —O-heteroalkyl, —O-haloalkyl, —O-heterohaloalkyl, -alkyl-OH, -alkyl-OC(O)-alkyl, -alkyl-OC(O)-haloalkyl, -alkyl-NH$_2$, -alkyl-NHR$^{16}$, and -alkyl-NR$^{16}$R$^{17}$.

In one embodiment, in Formula (I.a), n is 1; $R^2$ is H; $R^4$ and $R^7$ are each independently selected from H and OH; $R^5$ is selected from H, halo, and alkyl; and $R^9$ is selected from H, —CH$_3$, —CH$_2$—CH$_3$, —CH$_2$—OH, —CH$_2$—O-alkyl, —CH$_2$—OC(O)-alkyl, —CH$_2$—OC(O)-haloalkyl, —CH$_2$—NH$_2$, —CH$_2$—NHR$^{16}$, and —CH$_2$—NR$^{16}$R$^{17}$.

In one embodiment, in Formula (I.a), n is 1, $R^2$ is H, $R^5$ is —CH$_3$, and $R^9$ is selected from H, —CH$_3$, —CH$_2$—CH$_3$, —CH$_2$—OH, —CH$_2$—O-alkyl, —CH$_2$—OC(O)CF$_3$, —CH$_2$—NH$_2$, —CH$_2$—NHR$^{16}$, and —CH$_2$—NR$^{16}$R$^{17}$.

In one embodiment, in Formula (I.a), n is 1; $R^2$ is H; $R^4$ and $R^7$ are each —OH, $R^5$ is —CH$_3$, and $R^9$ is H.

In one embodiment, in Formula (I.a), n is 1; $R^2$ is H; $R^4$ and $R^7$ are each —OH, $R^5$ is selected from H and —CH$_3$, and $R^9$ is selected from H, —OH, halo, -alkyl, -alkenyl, alkynyl, azido, aryl, heteroaryl, —O-alkyl, —O-alkenyl, —OC(O)-alkyl, —SH, —S-alkyl, —NH$_2$, —NO$_2$, —NHR$^{10}$, —NR$^{10}$R$^{11}$, —C(O)OH, —C(O)OH, —C(O)OR$^{10}$, —C(O)NH$_2$, —C(O)NHR$^{10}$, —C(O)NR$^{10}$R$^{11}$, —S(O)NHR$^{10}$, —S(O)NR$^{10}$R$^{11}$, —S(O)R$^{10}$, —S(O)$_2$NHR$^{10}$, —S(O)$_2$NR$^{10}$R$^{11}$, and —S(O)$_2$R$^{10}$, wherein each of said -alkyl, said -alkenyl, said alkynyl, said aryl, said heteroaryl, said —O-alkyl, said —O-alkenyl, said —OC(O)-alkyl, and said —S-alkyl is unsubstituted or optionally independently substituted with from one to three substituents, which can be the same or different, each substituent being independently selected from halo, —OH, alkyl, haloalkyl, heteroalkyl, heterohaloalkyl, —O-alkyl, —O-alkenyl, —O-haloalkyl, —O-haloalkenyl, —OC(O)-alkyl, —OC(O)-alkenyl, —OC(O)-haloalkyl, —OC(O)-haloalkenyl, —C(O)O-alkyl, —C(O)O-alkenyl, —C(O)O-haloalkyl, —C(O)O-haloalkenyl, aryl, heteroaryl, cycloalkyl, cycloalkenyl, heterocycloalkyl, and heterocycloalkenyl.

In one embodiment, in Formula (I.a), X is N, Y is N, n is 1; $R^2$ is H; $R^4$ and $R^7$ are each —OH, $R^5$ is selected from H and —CH$_3$, and $R^9$ is selected from H —-alkyl, -alkyl-OH, -alkyl-S(O)$_2$alkyl, -alkyl-5-alkyl, haloalkyl, heteroalkyl, -alkyl-CN, -alkyl-NH$_2$, -alkyl-NHR$^{16}$, and -alkyl-N(alkyl)$_2$. In one such embodiment, each said alkyl is selected from straight or branched lower alkyl.

In one embodiment, the compounds of the invention have the structural Formula (I.a.1):

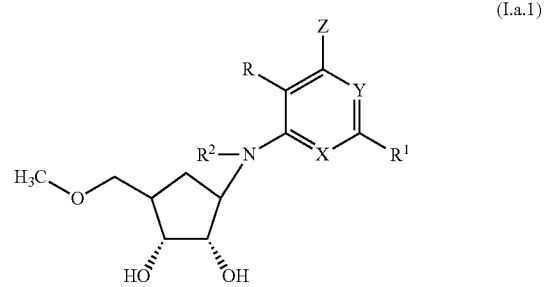

(I.a.1)

and include pharmaceutically acceptable salts, esters, prodrugs, or isomers of said compounds, wherein each of R, R$^1$, X, Y, Z, and R$^2$ is selected independently and defined in Formula (I).

In one embodiment, the compounds of the invention have the structural Formula (I.a.1.i):

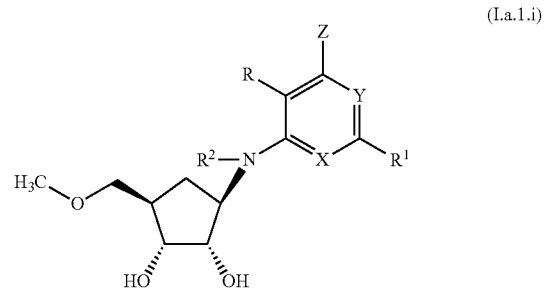

(I.a.1.i)

and include pharmaceutically acceptable salts, esters, prodrugs, or isomers of said compounds, wherein each of R, R$^1$, X, Y, Z, and R$^2$ is selected independently and defined in Formula (I).

In one embodiment, the compounds of the invention have the structural Formula (I.a.2):

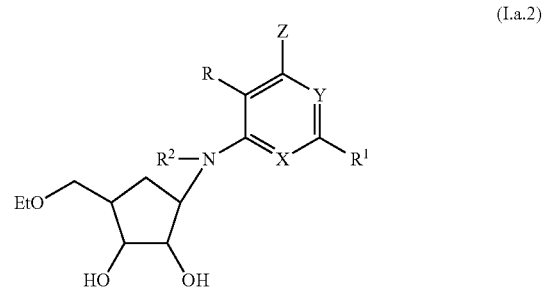

(I.a.2)

and include pharmaceutically acceptable salts, esters, prodrugs, or isomers of said compounds, wherein each of R, R$^1$, X, Y, Z, and R$^2$ is selected independently and defined in Formula (I).

In one embodiment, the compounds of the invention have the structural Formula (I.a.2.i):

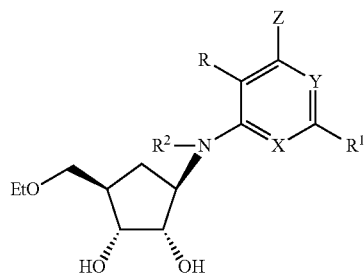
(I.a.2.i)

and include pharmaceutically acceptable salts, esters, prodrugs, or isomers of said compounds, wherein each of R, R¹, X, Y, Z, and R² is selected independently and defined in Formula (I).

In one embodiment, the compounds of the invention have the structural Formula (I.a.3):

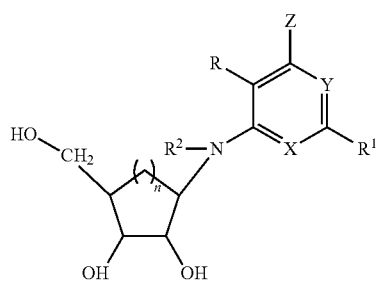
(I.a.3)

and include pharmaceutically acceptable salts, esters, prodrugs, or isomers of said compounds, wherein each of R, R¹, X, Y, Z, R², and n is selected independently and defined in Formula (I).

In one embodiment, the compounds of the invention have the structural Formula (I.a.3.i)

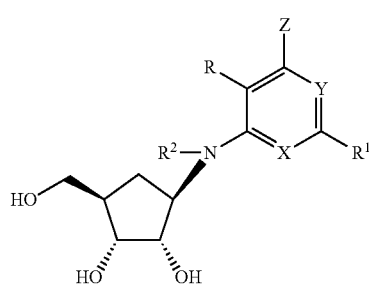
(I.a.3.i)

and include pharmaceutically acceptable salts, esters, prodrugs, or isomers of said compounds, wherein each of R, R¹, X, Y, Z, and R² is selected independently and defined in Formula (I).

In one embodiment, the compounds of the invention have the structural Formula (I.a.4):

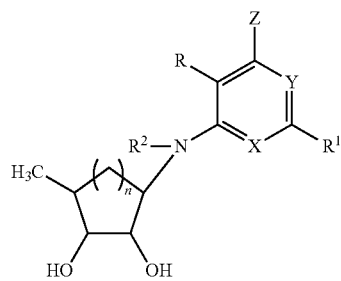
(I.a.4)

and include pharmaceutically acceptable salts, esters, prodrugs, or isomers of said compounds, wherein each of R, R¹, X, Y, Z, R², and n is selected independently and defined in Formula (I).

In one embodiment, the compounds of the invention have the structural Formula (I.a.4.i):

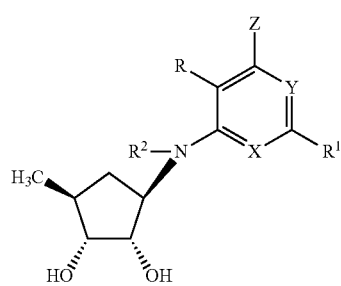
(I.a.4.i)

and include pharmaceutically acceptable salts, esters, prodrugs, or isomers of said compounds, wherein each of R, R¹, X, Y, Z, and R² is selected independently and defined in Formula (I).

In one embodiment, the compounds of the invention have the structural Formula (I.a.5):

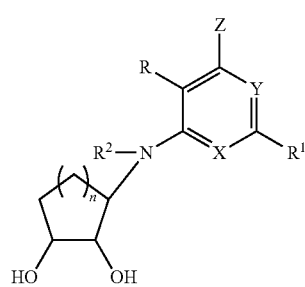
(I.a.5)

and include pharmaceutically acceptable salts, esters, prodrugs, or isomers of said compounds, wherein each of R, R¹, X, Y, Z, R², and n is selected independently and defined in Formula (I).

In one embodiment, the compounds of the invention have the structural Formula (I.a.5.i):

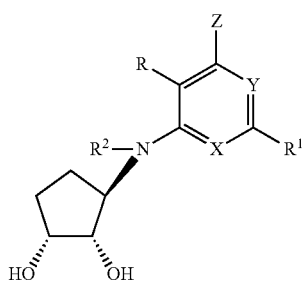
(I.a.5.i)

and include pharmaceutically acceptable salts, esters, prodrugs, or isomers of said compounds, wherein each of R, R¹, X, Y, Z, and R² is selected independently and defined in Formula (I).

In one embodiment, the compounds of the invention have the structural Formula (I.a.6):

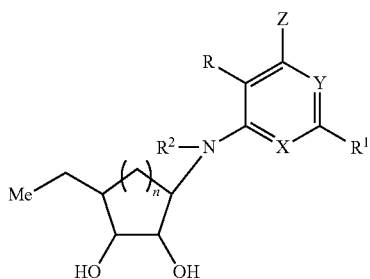
(I.a.6)

and include pharmaceutically acceptable salts, esters, prodrugs, or isomers of said compounds, wherein each of R, R¹, X, Y, Z, R², and n is selected independently defined in Formula (I).

In one embodiment, the compounds of the invention have the structural Formula (I.a.6.i):

(I.a.6.i)

and include pharmaceutically acceptable salts, esters, prodrugs, or isomers of said compounds, wherein each of R, R¹, X, Y, Z, and R² is selected independently and defined in Formula (I).

In one embodiment, the compounds of the invention have the structural Formula (I.a.7):

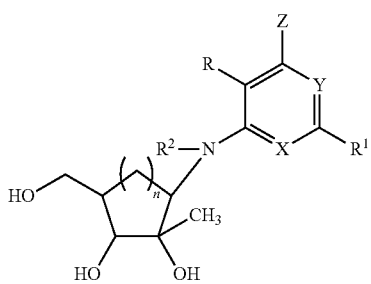
(I.a.7)

and include pharmaceutically acceptable salts, esters, prodrugs, or isomers of said compounds, wherein each of R, R¹, X, Y, Z, R², and n is selected independently and defined in Formula (I).

In one embodiment, the compounds of the invention have the structural Formula (I.a.7.i):

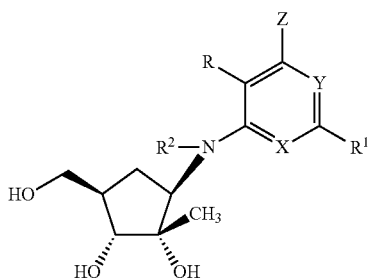
(I.a.7.i)

and include pharmaceutically acceptable salts, esters, prodrugs, or isomers of said compounds, wherein each of R, R¹, X, Y, Z, and R² is selected independently and defined in Formula (I).

In one embodiment, the compounds of the invention have the structural Formula (I.a.8):

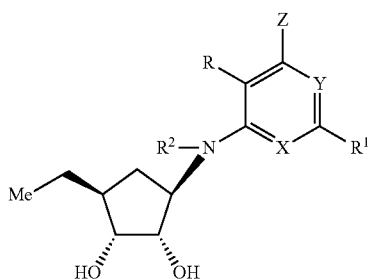
(I.a.8)

and include pharmaceutically acceptable salts, esters, prodrugs, or isomers of said compounds, wherein each of R, R¹, X, Y, Z, R², and n is selected independently defined in Formula (I).

In one embodiment, the compounds of the invention have the structural Formula (I.a.8.i):

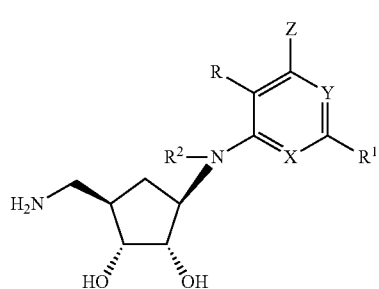

(I.a.8.i)

and include pharmaceutically acceptable salts, esters, prodrugs, or isomers of said compounds, wherein each of R, R¹, X, Y, Z, and R² is selected independently and defined in Formula (I).

In one embodiment, the compounds of the invention have the structural Formula (I.a.9):

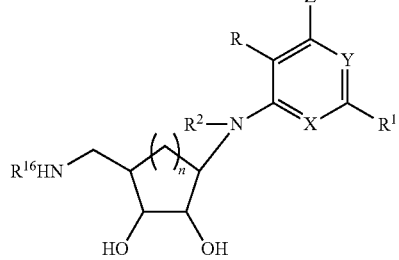

(I.a.9)

and include pharmaceutically acceptable salts, esters, prodrugs, or isomers of said compounds, wherein each of R, R¹, X, Y, Z, R², n, and R¹⁶ is selected independently defined in Formula (I).

In one embodiment, the compounds of the invention have the structural Formula (I.a.9.i):

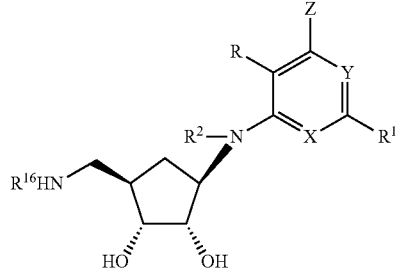

(I.a.9.i)

and include pharmaceutically acceptable salts, esters, prodrugs, or isomers of said compounds, wherein each of R, R¹, X, Y, Z, R², and R¹⁶ is selected independently and defined in Formula (I).

In one embodiment, the compounds of the invention have the structural Formula (I.a.10):

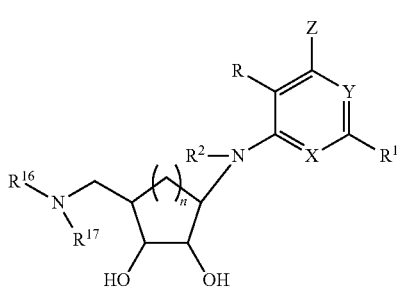

(I.a.10)

and include pharmaceutically acceptable salts, esters, prodrugs, or isomers of said compounds, wherein each of R, R¹, X, Y, Z, R², n, R¹⁶, and R¹⁷ is selected independently and defined in Formula (I).

In one embodiment, the compounds of the invention have the structural Formula (I.a.10.i):

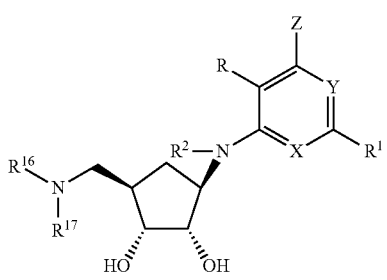

(I.a.10.i)

and include pharmaceutically acceptable salts, esters, prodrugs, or isomers of said compounds, wherein each of R, R¹, X, Y, Z, R², R¹⁶, and R¹⁷ is selected independently and defined in Formula (I).

In one embodiment, the compounds of the invention have the structural Formula (I.a.10.j):

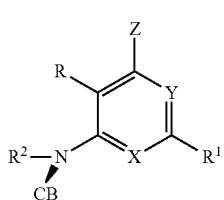

(I.a.10.j)

and include pharmaceutically acceptable salts, esters, prodrugs, or isomers of said compounds, wherein each of R, R¹, X, Y, Z, and is selected independently and defined in Formula (I), and wherein CB is a moiety selected from the group consisting of:

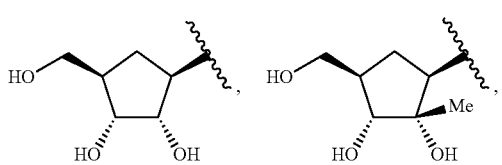

-continued
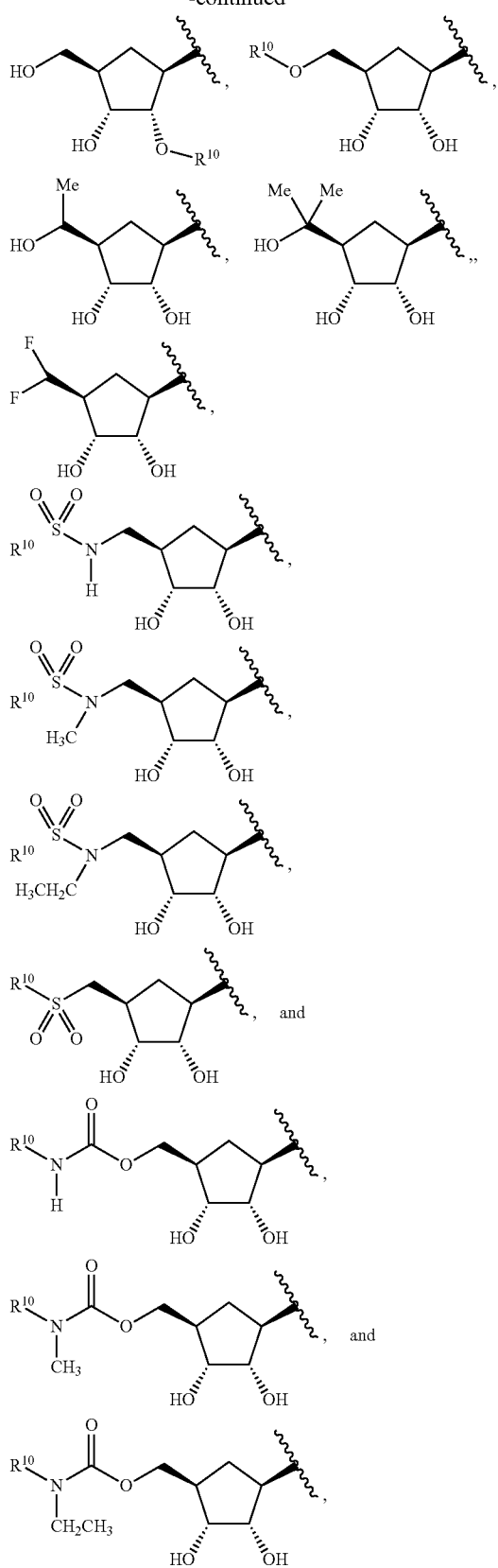
wherein each $R^{10}$ is independently selected from the group consisting of methyl, ethyl, and cyclopropyl.
In one embodiment, in Formula (I.a.10.j):
X is N;
Y is N;
$R^2$ is H;
Z is selected from the group consisting of H, methyl, and chloro;
R is a moiety selected from the group consisting of:
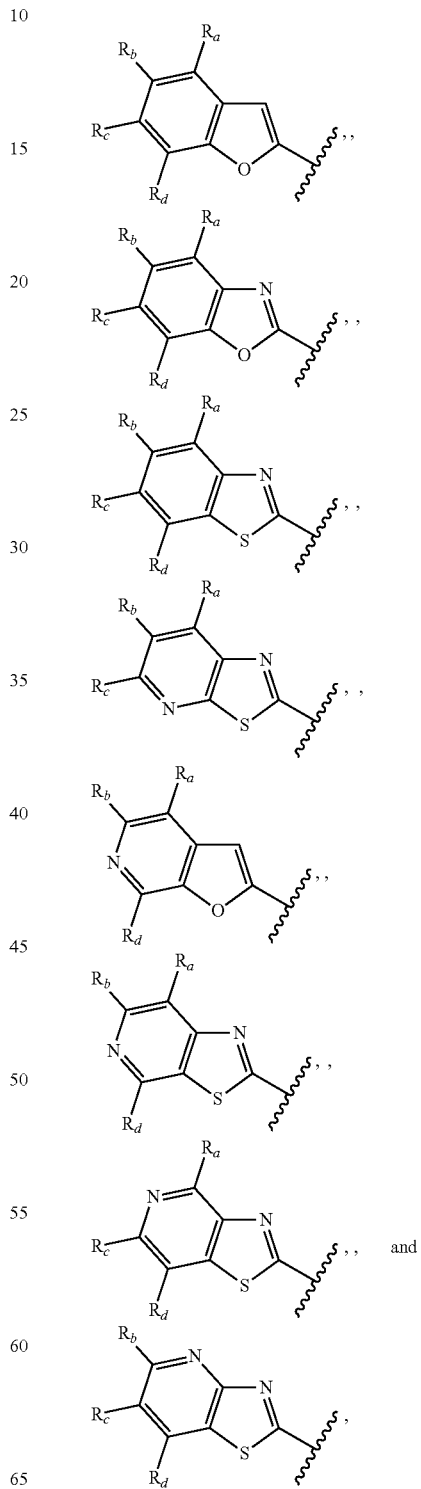

wherein the wavy line represents the point of attachment of R to the rest of the molecule, and wherein each of $R_a$, $R_b$, $R_c$, and $R_d$ is independently selected from H, halo, —OH, —CN, alkyl, cycloalkyl, haloalkyl, -alkyl-OH, heteroalkyl, heterohaloalkyl, —O-alkyl, —O-haloalkyl, —O-alkyl-OH, aryl, —O-aryl, —S-aryl, —O-alkyl-aryl, —S-alkyl-aryl, heteroaryl, —O-heteroaryl, —S-heteroaryl, —O-alkyl-heteroaryl, —S-alkyl-heteroaryl, heterocycloalkyl, —C(O)-alkyl, —C(O)-haloalkyl, —C(O)H, —C(O)OH, —C(O)O-alkyl, —OC(O)-alkyl, —C(O)NH$_2$, —C(O)NHR$^{10}$, —C(O)NR$^{10}$R$^{11}$, —C(O)ONH$_2$, —C(O)ONHR$^{10}$, —C(O)ONR$^{10}$R$^{11}$, —NH$_2$, —NHR$^{10}$, —NR$^{10}$R$^{11}$, —NO$_2$, substituted aryl, and substituted heteroaryl, wherein each of said substituted aryl and said substituted heteroaryl independently contains from one to three substituents, which may be the same or different, each substituent being independently selected from halo, alkyl, —O-alkyl, and —C(O)Oalkyl; and R$^1$ is as defined in Formula (I), or, alternatively, as in the various other embodiments described herein, or, alternatively, as in the examples. In one such embodiment, R$^1$ is selected from the group consisting of —NH$_2$, —NHR$^{14}$, and —NR$^{14}$R$^{15}$.

In one embodiment, the compounds of the invention have the structural Formula (I.B):

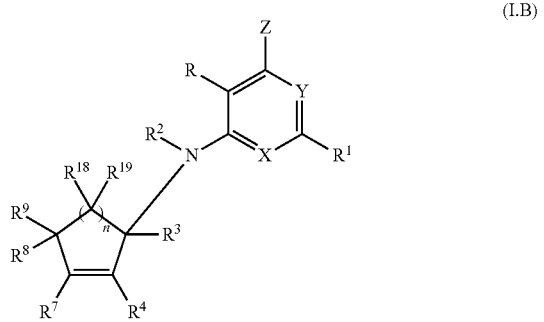

(I.B)

and includes pharmaceutically acceptable salts, esters, prodrugs, or isomers of said compounds, wherein each of R, R$^1$, X, Y, Z, R$^2$, R$^3$, R$^4$, R$^7$, R$^8$, R$^9$, R$^{18}$, R$^{19}$, and n is selected independently and defined in Formula (I).

In one embodiment, the compounds of the invention have the structural Formula (I.b):

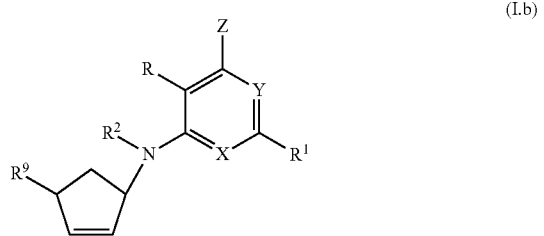

(I.b)

and includes pharmaceutically acceptable salts, esters, prodrugs, or isomers of said compounds, wherein each of R, R$^1$, X, Y, Z, R$^2$, and R$^9$ is selected independently and defined in Formula (I).

In one embodiment, in Formula (I.b), R$^2$ is H, and R$^9$ is selected from H, —CH$_3$, —CH$_2$—O-alkyl, —CH$_2$—OH, —CH$_2$—OC(O)-alkyl, —CH$_2$—OC(O)-haloalkyl, —CH$_2$—CH$_3$,—CH$_2$—NH$_2$, —CH$_2$—NHR$^{16}$, and —CH$_2$—NR$^{16}$R$^{17}$.

In one embodiment, in Formula (I.b), R$^2$ is H, and R$^9$ is selected from —CH$_2$—O-alkyl, and —CH$_2$—OH.

In one embodiment, the compounds of the invention have the structural Formula (I.b.1):

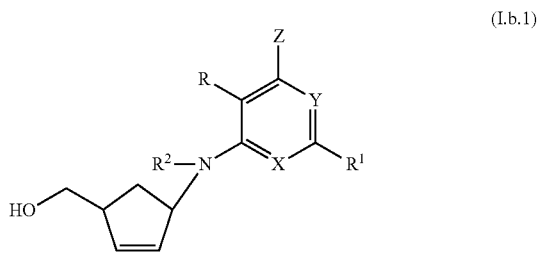

(I.b.1)

and include pharmaceutically acceptable salts, esters, prodrugs, or isomers of said compounds, wherein each of R, R$^1$, X, Y, Z, and R$^2$ is selected independently and defined in Formula (I).

In one embodiment, the compounds of the invention have the structural Formula (I.b.1.i):

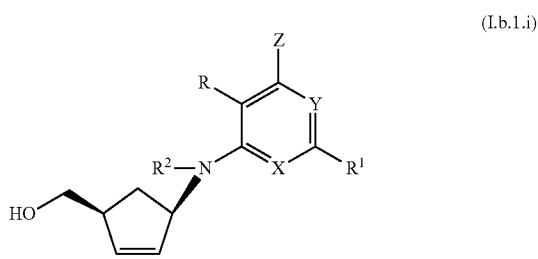

(I.b.1.i)

and include pharmaceutically acceptable salts, esters, prodrugs, or isomers of said compounds, wherein each of R, R$^1$, X, Y, Z, and R$^2$ is selected independently and defined in Formula (I).

In one embodiment, the compounds of the invention have the structural Formula (I.b.2):

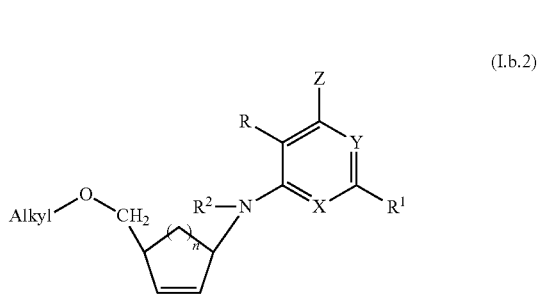

(I.b.2)

and include pharmaceutically acceptable salts, esters, prodrugs, or isomers of said compounds, wherein each of R, R$^1$, X, Y, Z, R$^2$, and n is selected independently and defined in Formula (I).

In one embodiment, the compounds of the invention have the Formula (I.b.2.i):

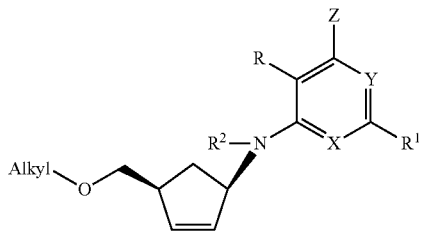
(I.b.2.i)

and include pharmaceutically acceptable salts, esters, prodrugs, or isomers of said compounds, wherein each of R, R¹, X, Y, Z, and R² is selected independently and defined in Formula (I).

In one embodiment, the compounds of the invention have the structural Formula (I.C):

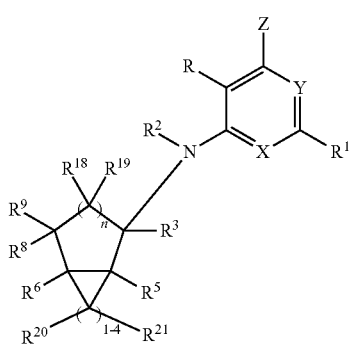
(I.C)

and includes pharmaceutically acceptable salts, esters, prodrugs, or isomers of said compounds, wherein each of R, R¹, X, Y, Z, R², R³, R⁵, R⁶, R⁸, R⁹, R¹⁸, R¹⁹, R²⁰, R²¹, and n is selected independently and defined in Formula (I), with the proviso that R⁵ and R⁶ are not taken together to form a double bond.

In one embodiment, the compounds of the invention have the structural Formula (I.c):

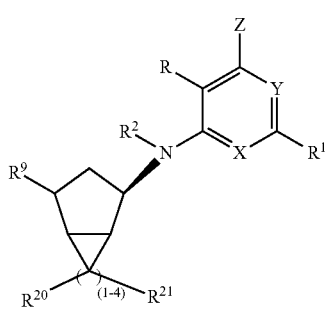
(I.c)

and include pharmaceutically acceptable salts, esters, prodrugs, or isomers of said compounds, wherein each of R, R¹, X, Y, Z, R², R⁹, R²⁰, and R²¹ is selected independently and defined in Formula (I).

In one embodiment, in Formula (I.c), R² is H; R⁹ is selected from H, —CH₃, —CH₂—O-alkyl, —CH₂—OH, —CH₂— OC(O)-alkyl, —CH₂—OC(O)-haloalkyl, —CH₂—CH₃,—CH₂—NH₂, —CH₂—NHR¹⁶, and —CH₂—NR¹⁶R¹⁷; and each of R²⁰ and R²¹ is independently selected from H and —CH₃.

In one embodiment, the compounds of the invention have the structural Formula (I.c.1):

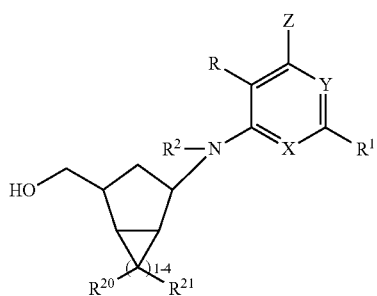
(I.c.1)

and include pharmaceutically acceptable salts, esters, prodrugs, or isomers of said compounds, wherein each of R, R¹, X, Y, Z, and R² is selected independently and defined in Formula (I).

In one embodiment, the compounds of the invention have the structural Formula (I.c.1.i):

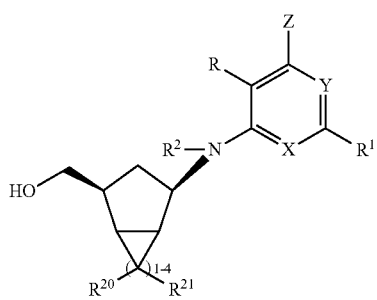
(I.c.1.i)

and include pharmaceutically acceptable salts, esters, prodrugs, or isomers of said compounds, wherein each of R, R¹, X, Y, Z, and R² is selected independently and defined in Formula (I).

In one embodiment, the compounds of the invention have the structural Formula (I.c.2):

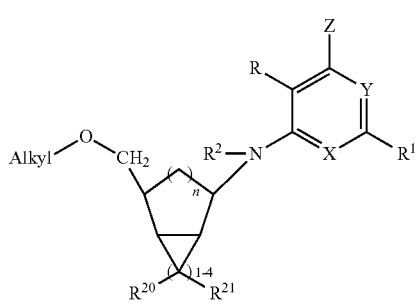
(I.c.2)

and include pharmaceutically acceptable salts, esters, prodrugs, or isomers of said compounds, wherein each of R, R¹, X, Y, Z, R², and n is selected independently and defined in Formula (I).

In one embodiment, the compounds of the invention have the structural Formula (I.c.2.i):

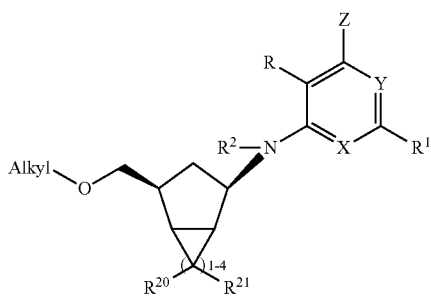

(I.c.2.i)

and include pharmaceutically acceptable salts, esters, prodrugs, or isomers of said compounds, wherein each of R, R¹, X, Y, Z, and R² is selected independently defined in Formula (I).

In one embodiment, the compounds of the invention have the structural Formula (I.D):

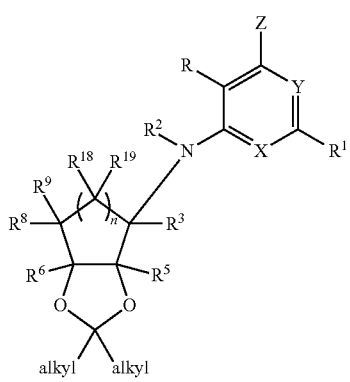

(I.D)

and includes pharmaceutically acceptable salts, esters, prodrugs, or isomers of said compounds, wherein each of R, R¹, X, Y, Z, R², R³, R⁵, R⁶, R⁸, R⁹, R¹⁸, and R¹⁹, and n is selected independently and defined in Formula (I).

In one embodiment, the compounds of the invention have the structural Formula (I.d):

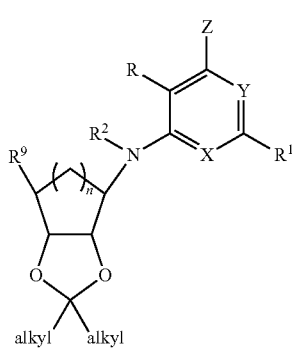

(I.d)

and includes pharmaceutically acceptable salts, esters, prodrugs, or isomers of said compounds, wherein each of R, R¹, X, Y, Z, R², R⁹, and n is selected independently and defined in Formula (I).

In one embodiment, in Formula (I.d), n is 1 and R⁹ is selected from H, —CH₃, —CH₂—O-alkyl, —CH₂—OH, —CH₂—OC(O)-alkyl, —CH₂—OC(O)-haloalkyl, —CH₂—CH₃, —CH₂—NH₂, —CH₂—NHR¹⁶, and —CH₂—NR¹⁶R¹⁷.

In one embodiment, in Formula (I.d), n is 1 and R⁹ is selected from —CH₂—O-alkyl, and —CH₂—OH.

In one embodiment, the compounds of the invention have the structural Formula (I.d.1):

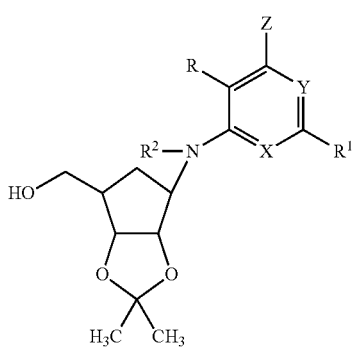

(I.d.1)

and include pharmaceutically acceptable salts, esters, prodrugs, or isomers of said compounds, wherein each of R, R¹, X, Y, Z, and R² is selected independently and defined in Formula (I).

In one embodiment, the compounds of the invention have the structural Formula (I.d.1.i):

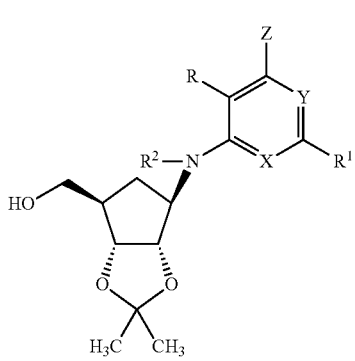

(I.d.1.i)

and include pharmaceutically acceptable salts, esters, prodrugs, or isomers of said compounds, wherein each of R, R¹, X, Y, Z, and R² is selected independently and defined in Formula (I).

In one embodiment, the compounds of the invention have the structural Formula (I.E):

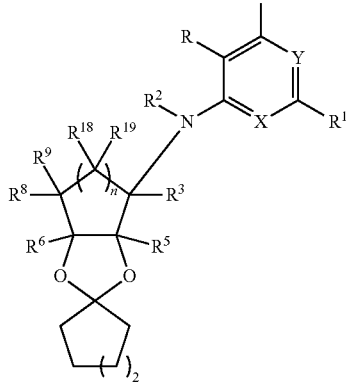

(I.E)

and includes pharmaceutically acceptable salts, esters, prodrugs, or isomers of said compounds, wherein each of R, R¹, X, Y, Z, R², R³, R⁵, R⁶, R⁸, R⁹, R¹⁸, and R¹⁹, and n is selected independently and defined in Formula (I).

In one embodiment, the compounds of the invention have the structural Formula (II):

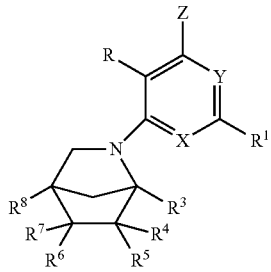

(II)

and include pharmaceutically acceptable salts, esters, prodrugs, or isomers of said compounds, wherein each of R, R¹, X, Y, Z, R³, R⁴, R⁵, R⁶, R⁷, and R⁸ is selected independently and defined in Formula (I).

In one embodiment, the compounds of the invention have the structural Formula (II):

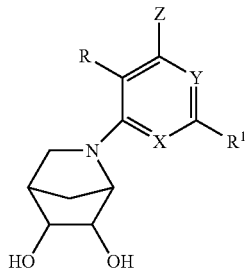

(II.A)

and include pharmaceutically acceptable salts, esters, prodrugs, or isomers of said compounds, wherein each of R, R¹, X, Y, and Z is selected independently and wherein R, R¹, X, Y, and Z are defined in Formula (I).

In one embodiment, in Formula (I), the compounds of the invention have the structural Formula (II.a.1):

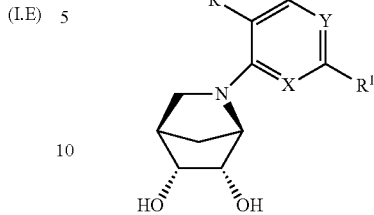

(II.A.1)

and include pharmaceutically acceptable salts, prodrugs, or isomers of said compounds, wherein each of R, R¹, X, Y, and Z is selected independently and wherein R, R¹, X, Y, and Z are defined in Formula (I).

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), X is N and Y is N.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), X is N and Y is CH.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), X is CH and Y is N.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), R is selected from aryl, heteroaryl, benzo-fused heteroaryl, cycloalkyl, cycloalkenyl, benzo-fused cycloalkyl, benzo-fused cycloalkenyl, heterocycloalkyl, and benzo-fused heterocycloalkyl, wherein each of said alkyl, said aryl, said heteroaryl, said benzo-fused heteroaryl, said cycloalkyl, said cycloalkenyl, said heterocycloalkyl, said heterocycloaklenyl, and said benzo-fused heterocycloalkyl is unsubstituted or optionally independently substituted with from one to three substituents, which are the same or different, each substituent being independently selected from halo, —OH, —CN, alkyl, alkenyl, alkynyl, haloalkyl, heteroalkyl, heterohaloalkyl, -alkyl-OH, —O-alkyl, —O-haloalkyl, —O-alkyl-OH, aryl, —O-aryl, —S-aryl, -alkyl-aryl, —S-alkyl-aryl, heteroaryl, —O-heteroaryl, —S-heteroaryl, —O-alkyl-heteroaryl, —S-alkyl-heteroaryl, heterocycloalkyl, —C(O)-alkyl, —C(O)-haloalkyl, —C(O)H, —C(O)OH, —C(O)O-alkyl, —OC(O)-alkyl, —C(O)NH₂, —C(O)NHR¹⁰, —C(O)NR¹⁰R¹¹, —C(O)ONH₂, —C(O)ONHR¹⁰, —C(O)ONR¹⁰R¹¹, —NH₂, —NHR¹⁰, —NR¹⁰R¹¹, —NO₂, substituted aryl, and substituted heteroaryl, wherein each of said substituted aryl and said substituted heteroaryl independently contains from one to three substituents, which may be the same or different, each substituent being independently selected from halo, alkyl, —O-alkyl, and —C(O)Oalkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), R is selected from the group consisting of substituted or unsubstituted aryl, substituted or unsubstituted heteroaryl, and substituted or unsubstituted benzo-fused heteroaryl, each of said substituents being independently selected from the group consisting of alkyl and —O-alkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), R is selected from substituted alkynyl, substituted alkynyl, unsubstituted aryl, substituted aryl, unsubstituted cycloalkyl, substituted cycloalkyl, unsubstituted benzo-fused cycloalkyl, substituted benzo-fused cycloalkyl, unsubstituted cycloalkenyl, and substituted cycloalkenyl, which substituents, when present, are as defined in Formula (I).

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), R is unsubstituted aryl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), R is substituted aryl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), R is unsubstituted cycloalkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), R is unsubstituted benzo-fused cycloalkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), R is substituted benzo-fused cycloalkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), R is substituted cycloalkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), R is unsubstituted cycloalkenyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), R is substituted cycloalkenyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), R is selected from unsubstituted heteroaryl, substituted heteroaryl, unsubstituted benzo-fused heteroaryl, substituted benzo-fused heteroaryl, unsubstituted heterocycloalkyl, substituted heterocycloalkyl, unsubstituted benzo-fused heterocycloalkyl, substituted benzo-fused heterocycloalkyl, unsubstituted heterocycloalkenyl, and unsubstituted heterocycloalkenyl, which substituents, when present, are as defined in Formula (I).

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2),
(I.b.2.i), (I.C), (I.c), (I.c.1), (I.c.1.i), (I.c.2), (I.c.2.i), (I.d), (I.d.1), (I.d.1.i), (I.E), (II), (II.A), and (II.A.1), R is unsubstituted heteroaryl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), R is substituted heteroaryl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), R is unsubstituted benzo-fused heteroaryl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), R is substituted benzo-fused heteroaryl.

In other embodiments, in each of Formulas (I), (I.A), (I.a), (I.a.1), (I.a.1.i), (I.a.2), (I.a.2.i), (I.a.3), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), R is unsubstituted heterocycloalkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), R is substituted heterocycloalkyl.

In other embodiments, in each of Formulas (I), (I.A), (I.a), (I.a.1), (I.a.1.i), (I.a.2), (I.a.2.i), (I.a.3), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), R is unsubstituted benzo-fused heterocycloalkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.D), (I.d), (I.d.1), (I.d.1.i), (I.E), (II), (II.A), and (II.A.1), R is substituted benzo-fused heterocycloalkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), R is unsubstituted heterocycloalkenyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), R is substituted heterocycloalkenyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), R is an unsubstituted or substituted monocyclic aryl moiety or an unsubstituted or substituted heteroaryl moiety. Non-limiting examples of such unsubstituted or substituted monocyclic aryl moiety or unsubstituted or substituted heteroaryl moiety include:

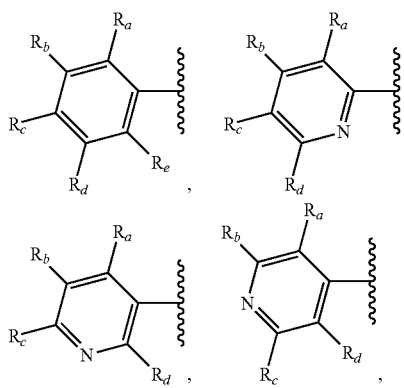

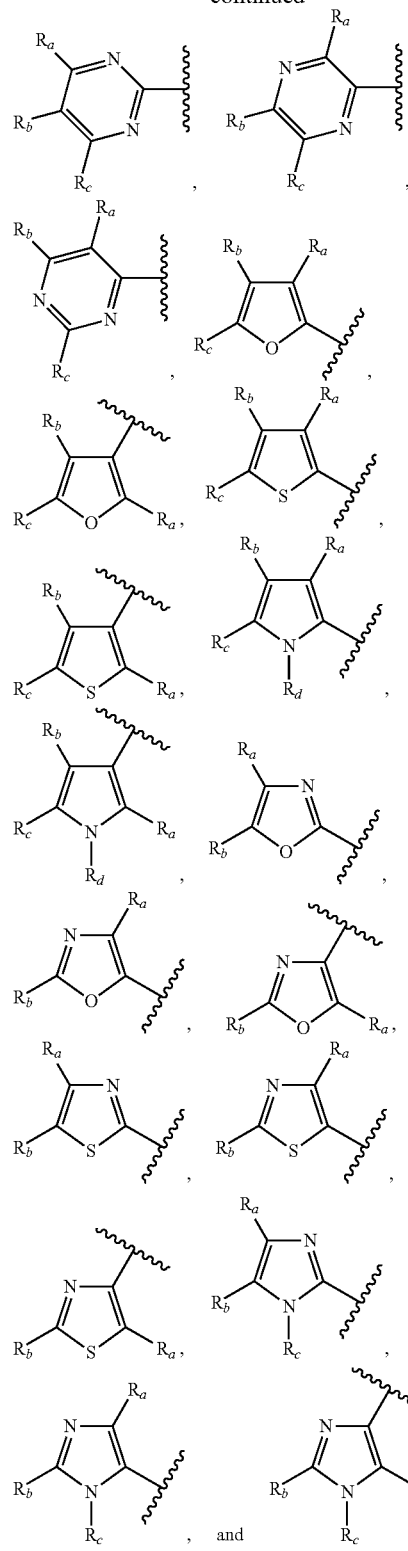

wherein the wavy line represents the point of attachment of R to the rest of the molecule, and wherein each of $R_a$, $R_b$, $R_c$, $R_d$, and $R_e$, is independently selected from H, halo, —OH, —CN, alkyl, haloalkyl, -alkyl-OH, heteroalkyl, heterohaloalkyl, —O-alkyl, —O-haloalkyl, —O-alkyl-OH, aryl, —O-aryl, —S-aryl, —O-alkyl-aryl, —S-alkyl-aryl, heteroaryl, —O- heteroaryl, —S-heteroaryl, —O-alkyl-heteroaryl, —S-alkyl-heteroaryl, heterocycloalkyl, —C(O)-alkyl, —C(O)-haloalkyl, —C(O)H, —C(O)OH, —C(O)O-alkyl, —OC(O)-alkyl, —C(O)NH$_2$, —C(O)NHR$^{10}$, —C(O)NR$^{10}$R$^{11}$, —C(O)ONH$_2$, —C(O)ONHR$^{10}$, —C(O)ONR$^{10}$R$^{11}$, —NH$_2$, —NHR$^{10}$, —NR$^{10}$R$^{11}$, —NO$_2$, substituted aryl, and substituted heteroaryl, wherein each of said substituted aryl and said substituted heteroaryl independently contains from one to three substituents, which may be the same or different, each substituent being independently selected from halo, alkyl, —O-alkyl, and —C(O)Oalkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), R is an unsubstituted or an substituted bicyclic heteroaryl moiety. Non-limiting examples of such unsubstituted or substituted bicyclic heteroaryl moieties include:

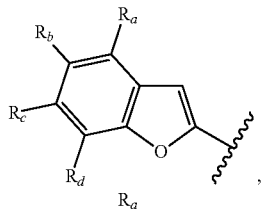

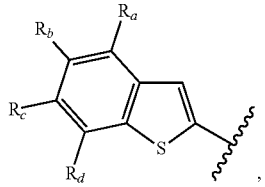

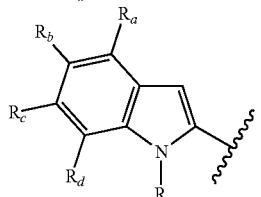

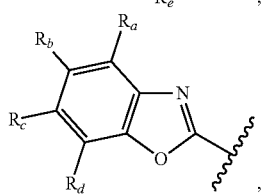

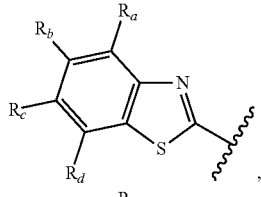

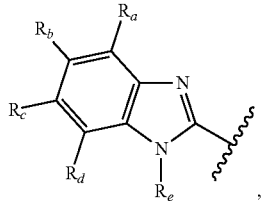

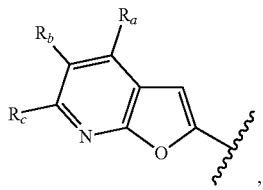

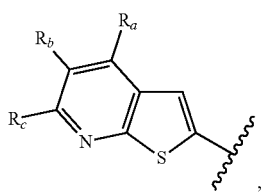

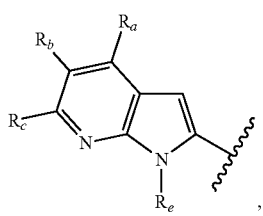

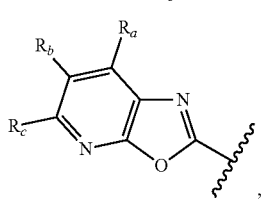

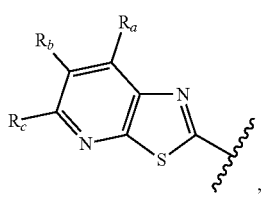


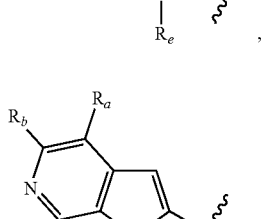

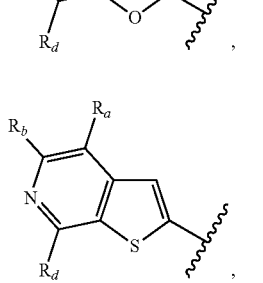

-continued

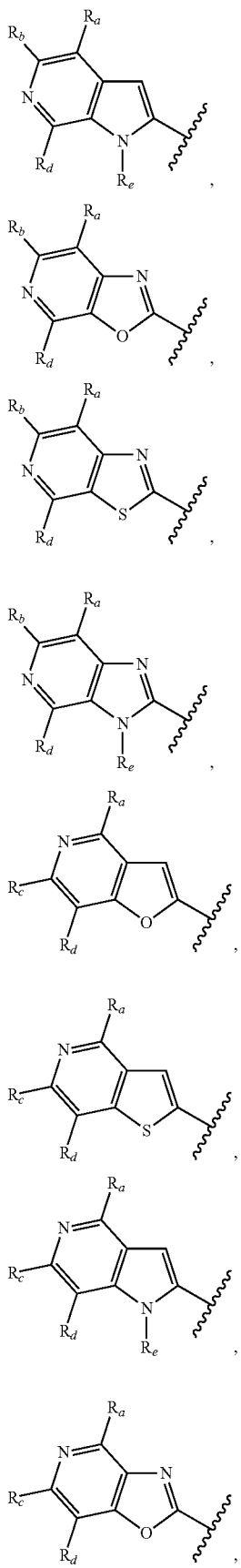

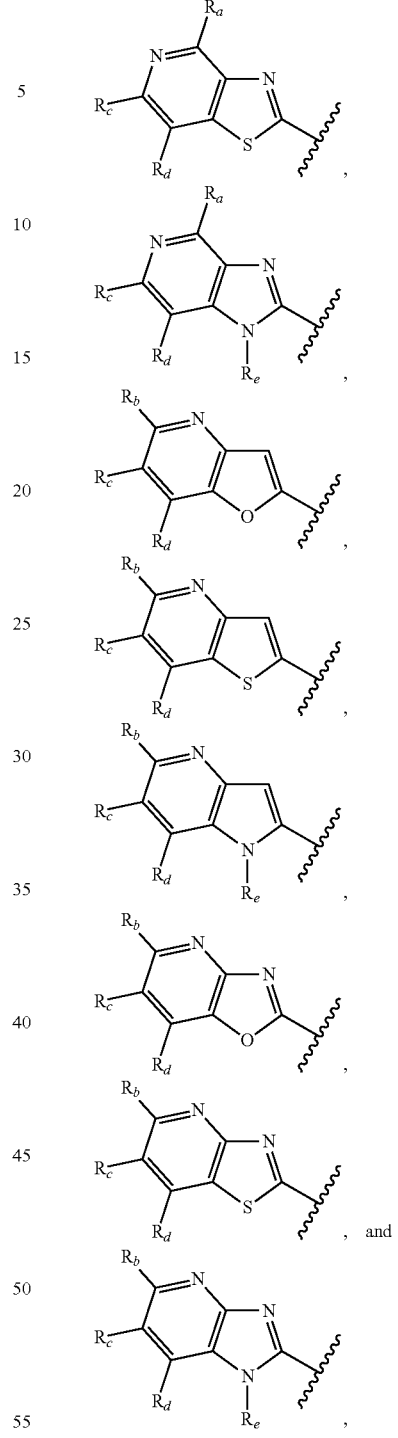

wherein the wavy line represents the point of attachment of R to the rest of the molecule, and wherein each of $R_a$, $R_b$, $R_c$, $R_d$, and $R_e$, is independently selected from H, halo, —OH, —ON, alkyl, cycloalkyl, haloalkyl, -alkyl-OH, heteroalkyl, heterohaloalkyl, —O-alkyl, —O-haloalkyl, —O-alkyl-OH, aryl, —O-aryl, —S-aryl, —O-alkyl-aryl, —S-alkyl-aryl, heteroaryl, —O-heteroaryl, —S-heteroaryl, —O-alkyl-heteroaryl, —S-alkyl-heteroaryl, heterocycloalkyl, —C(O)-alkyl, —C(O)-haloalkyl, —C(O)H, —C(O)OH, —C(O)O-alkyl, —OC(O)-alkyl, —C(O)NH$_2$, —C(O)NHR$^{10}$, —C(O)

NR$^{10}$R$^{11}$, —C(O)ONH$_2$, —C(O)ONHR$^{10}$, —C(O)ONR$^{10}$R$^{11}$, —NH$_2$, —NHR$^{10}$, —NR$^{10}$R$^{11}$, —NO$_2$, substituted aryl, and substituted heteroaryl, wherein each of said substituted aryl and said substituted heteroaryl independently contains from one to three substituents, which may be the same or different, each substituent being independently selected from halo, alkyl, —O-alkyl, and —C(O)Oalkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), R is a moiety selected from the group consisting of:

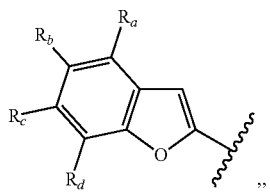

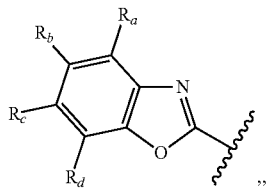

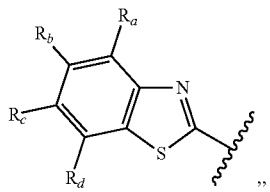

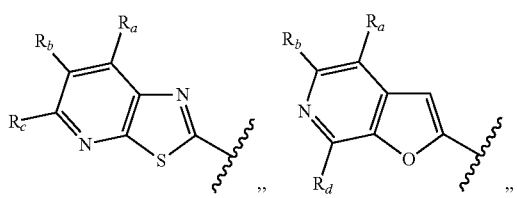

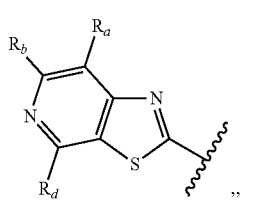

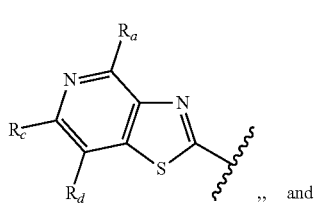
, and

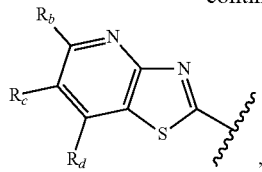
, wherein the wavy line represents the point of attachment of R to the rest of the molecule, and wherein each of R$_a$, R$_b$, R$_c$, R$_d$, and R$_e$, is independently selected from H, halo, —OH, —CN, alkyl, cycloalkyl, haloalkyl, -alkyl-OH, heteroalkyl, heterohaloalkyl, —O-alkyl, —O-haloalkyl, —O-alkyl-OH, aryl, —O-aryl, —S-aryl, —O-alkyl-aryl, —S-alkyl-aryl, heteroaryl, —O-heteroaryl, —S-heteroaryl, —O-alkyl-heteroaryl, —S-alkyl-heteroaryl, heterocycloalkyl, —C(O)-alkyl, —C(O)-haloalkyl, —C(O)H, —C(O)OH, —C(O)O-alkyl, —OC(O)-alkyl, —C(O)NH$_2$, —C(O)NHR$^{10}$, —C(O)NR$^{10}$R$^{11}$, —C(O)ONH$_2$, —C(O)ONHR$^{10}$, —C(O)ONR$^{10}$R$^{11}$, —NH$_2$, —NHR$^{10}$, —NR$^{10}$R$^{11}$, —NO$_2$, substituted aryl, and substituted heteroaryl, wherein each of said substituted aryl and said substituted heteroaryl independently contains from one to three substituents, which may be the same or different, each substituent being independently selected from halo, alkyl, —O-alkyl, and —C(O)Oalkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), R is a moiety selected from the group consisting of:

,

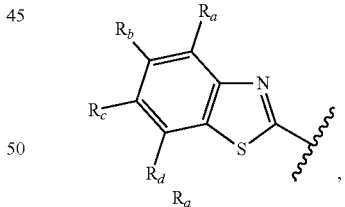
,

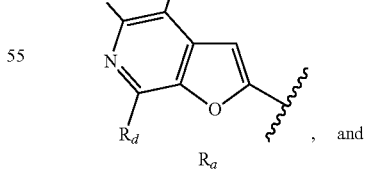
, and

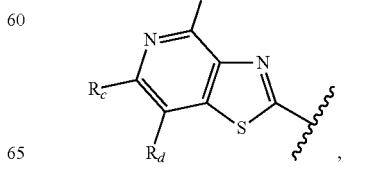
, wherein the wavy line represents the point of attachment of R to the rest of the molecule, and wherein each of $R_a$, $R_b$, $R_c$, $R_d$, and $R_e$, is independently selected from H, halo, —OH, —CN, alkyl, cycloalkyl, haloalkyl, -alkyl-OH, heteroalkyl, heterohaloalkyl, —O-alkyl, —O-haloalkyl, —O-alkyl-OH, aryl, —O-aryl, —S-aryl, —O-alkyl-aryl, —S-alkyl-aryl, heteroaryl, —O-heteroaryl, —S-heteroaryl, —O-alkyl-heteroaryl, —S-alkyl-heteroaryl, heterocycloalkyl, —C(O)-alkyl, —C(O)-haloalkyl, —C(O)H, —C(O)OH, —C(O)O-alkyl, —OC(O)-alkyl, —C(O)NH$_2$, —C(O)NHR$^{10}$, —C(O)NR$^{10}$R$^{11}$, —C(O)ONH$_2$, —C(O)ONHR$^{10}$, —C(O)ONR$^{10}$R$^{11}$, —NH$_2$, —NHR$^{10}$, —NR$^{10}$R$^{11}$, —NO$_2$, substituted aryl, and substituted heteroaryl, wherein each of said substituted aryl and said substituted heteroaryl independently contains from one to three substituents, which may be the same or different, each substituent being independently selected from halo, alkyl, —O-alkyl, and —C(O)Oalkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), R is a moiety selected from the group consisting of:

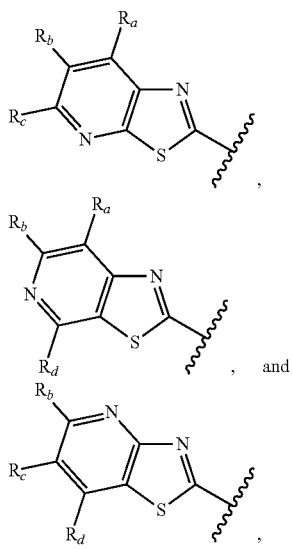

wherein the wavy line represents the point of attachment of R to the rest of the molecule, and wherein each of $R_a$, $R_b$, $R_c$, $R_d$, and $R_e$, is independently selected from H, halo, —OH, —ON, alkyl, cycloalkyl, haloalkyl, -alkyl-OH, heteroalkyl, heterohaloalkyl, —O-alkyl, —O-haloalkyl, —O-alkyl-OH, aryl, —O-aryl, —S-aryl, —O-alkyl-aryl, —S-alkyl-aryl, heteroaryl, —O-heteroaryl, —S-heteroaryl, —O-alkyl-heteroaryl, —S-alkyl-heteroaryl, heterocycloalkyl, —C(O)-alkyl, —C(O)-haloalkyl, —C(O)H, —C(O)OH, —C(O)O-alkyl, —OC(O)-alkyl, —C(O)NH$_2$, —C(O)NHR$^{10}$, —C(O)NR$^{10}$R$^{11}$, —C(O)ONH$_2$, —C(O)ONHR$^{10}$, —C(O)ONR$^{10}$R$^{11}$, —NH$_2$, —NHR$^{10}$, —NR$^{10}$R$^{11}$, —NO$_2$, substituted aryl, and substituted heteroaryl, wherein each of said substituted aryl and said substituted heteroaryl independently contains from one to three substituents, which may be the same or different, each substituent being independently selected from halo, alkyl, —O-alkyl, and —C(O)Oalkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), R is a moiety selected from the group consisting of:

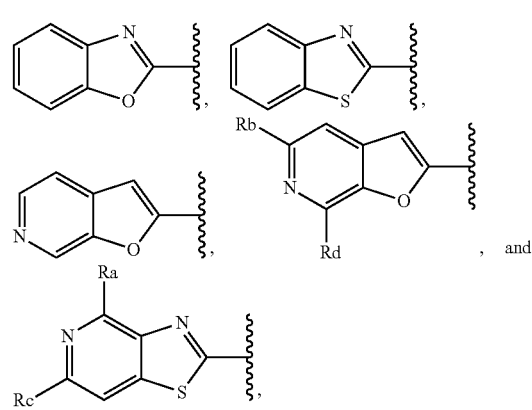

wherein the wavy line represents the point of attachment of R to the rest of the molecule, and wherein:

Ra is selected from the group consisting of H, methyl, ethyl, n-propyl, cyclopropyl, and cyclobutyl;

Rb is selected from the group consisting of methyl, ethyl, n-propyl, —O-methyl, and —O-ethyl;

Rc is selected from the group consisting of H, methyl, ethyl, and cyclopropyl; and Rd is selected from the group consisting of H, methyl, and ethyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is selected from the group consisting of halo, alkyl, haloalkyl, cycloalkyl, and —NH$_2$. Non-limiting examples of Z when Z is cycloalkyl include cyclopropyl. Non-limiting examples of Z when Z is haloalkyl include fluoroalkyl (up to perfluoroalkyl).

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is selected from the group consisting of halo, alkyl, and cycloalkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is selected from the group consisting of H, alkyl, halo, and cyclopropyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is selected from the group consisting of H, methyl, and chloro.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is H.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is halo.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is —CL In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is —F.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is —OH.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is —SH.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is —Salkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is —S—CH$_3$.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is -alkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is —CH$_3$.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is —CH$_2$CH$_3$.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is —Oalkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is —OCH$_3$.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is -haloalkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is —CF$_3$.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is —CHF$_2$.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is —CH$_2$F.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is cycloalkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is cyclopropyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is aryl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is phenyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is heteroaryl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is 2-thiophenyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is 3-thiophenyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is 2-thiazolyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is 2-oxazolyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is 2-pyrimidinyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is 2-pyridyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is 2-pyrazinyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is 2-imidazolyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is —NH$_2$.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is —NHR$^{12}$.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is —NR$^{12}$R$^{13}$.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is selected from the group consisting of Cl and methyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), R$^1$ is selected from the group consisting of —NH$_2$, —NHR$^{14}$, and —NR$^{14}$R$^{15}$.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), R$^1$ is selected from the group consisting of —NH$_2$ and —NHR$^{14}$.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), $R^1$ is H.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), $R^1$ is halo.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), $R^1$ is Cl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), $R^1$ is F.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), $R^1$ is alkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), $R^1$ is —$CH_3$.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), $R^1$ is —$CH_2CH_3$.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), $R^1$ is heteroalkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), $R^1$ is heteroaryl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), $R^1$ is —OH.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), $R^1$ is —O-alkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), $R^1$ is —O-aryl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), $R^1$ is —O-heteroalkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), $R^1$ is —O-heteroaryl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), $R^1$ is —SH.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), $R^1$ is —S-alkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), $R^1$ is —S-aryl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), $R^1$ is —S-heteroalkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.0, (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), $R^1$ is —S-heteroaryl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), $R^1$ is $-NH_2$.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), $R^1$ is $-NHR^{14}$. Non-limiting examples of $R^1$ when $R^1$ is $-NHR^{14}$ include:

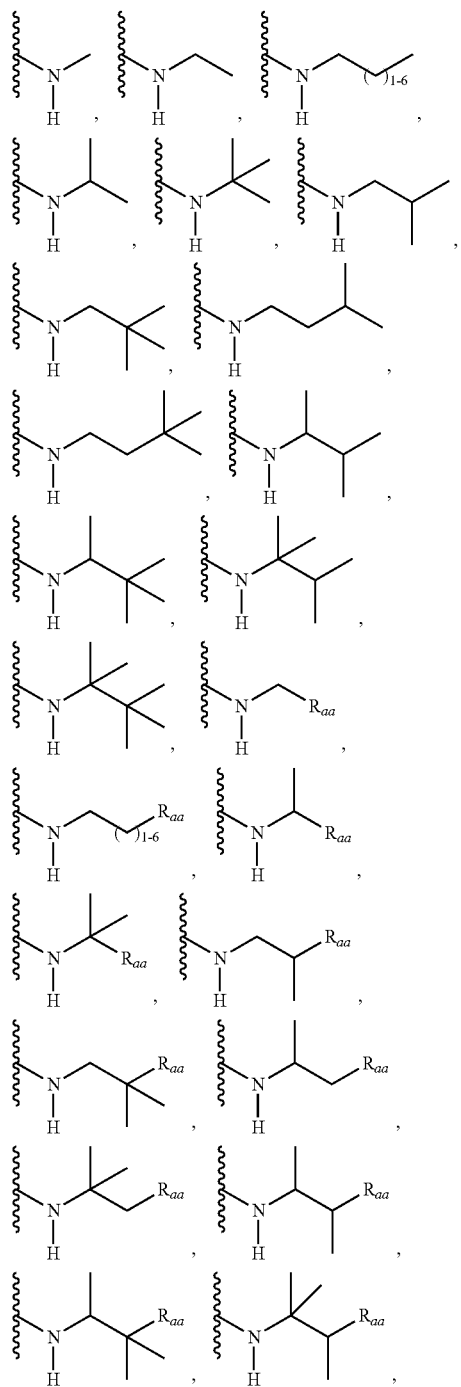

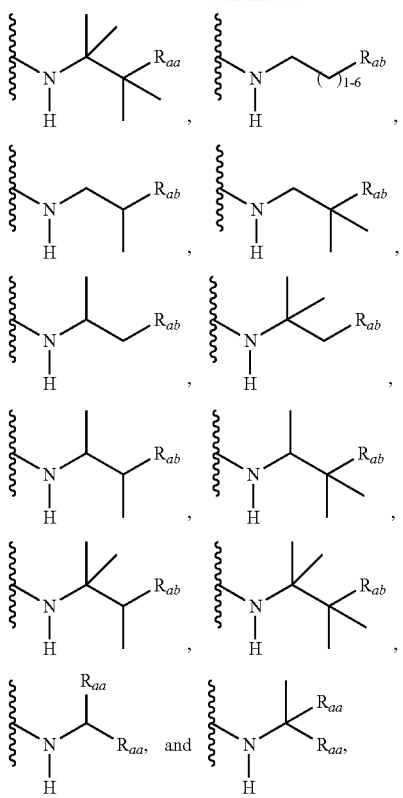

wherein the wavy line represents the point of attachment of $R^1$ to the rest of the molecule, and wherein each $R_{aa}$ is independently selected from haloalkyl (non-limiting examples of which include $-CH_2F$, $-CHF_2$, $-CF_3$, etc.), $R_{ab}$ is selected from OH, OAc, and $-O$-alkyl (non-limiting examples of which include $-O$-Me, $-O$-Et, $-O$-n-Pr, $-O$-i-Pr, $-O$-n-Bu, $-O$-i-Bu, and $-O$-t-Bu), $-O$-haloalkyl (non-limiting examples of which include $-O-CH_2F$, $-O-CHF_2$, and $-O-CF_3$), $-NH_2$, $-NH$alkyl, and $-N$(alkyl)$_2$.

Additional non-limiting examples of $R^1$ when $R^1$ is $-NHR^{14}$ include:

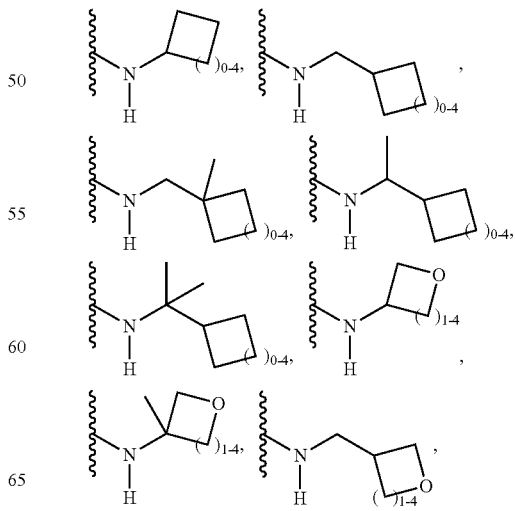

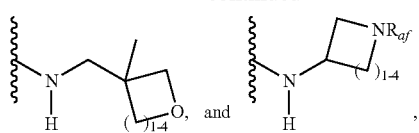

wherein the wavy line represents the point of attachment of R¹ to the rest of the molecule, and wherein $R_{af}$ is selected from H and acetyl. It shall be understood that positional isomers of the heteroatoms shown in the moieties above are also contemplated. Such positional isomers include semmetric positional isomers such as

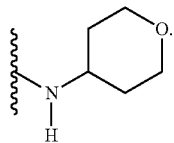

Additional non-limiting examples of R¹ when R¹ is —NHR¹⁴ include:

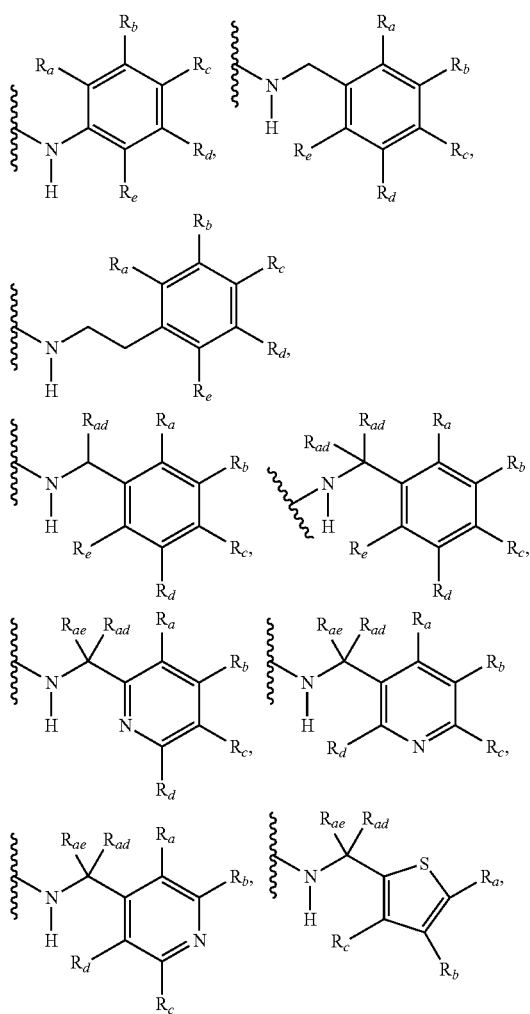

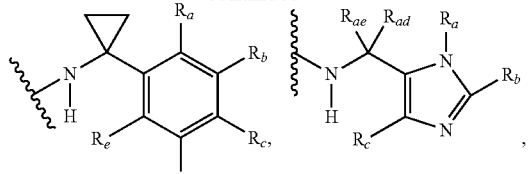

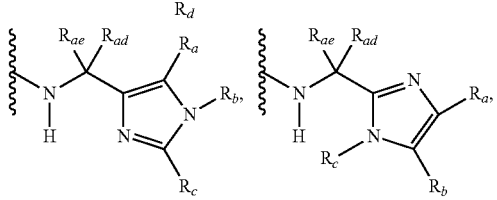

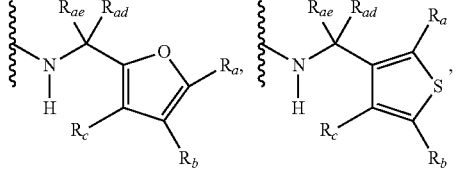

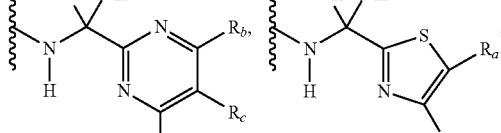

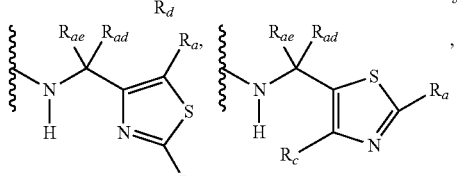

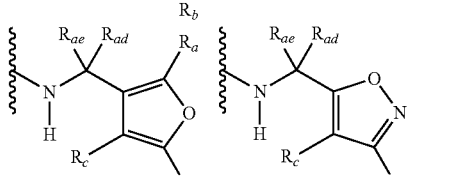

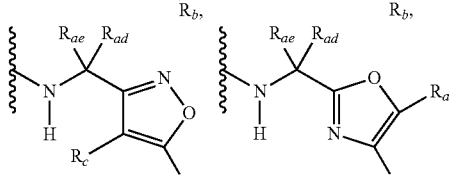

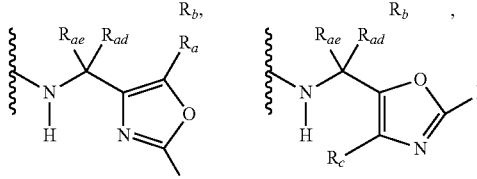

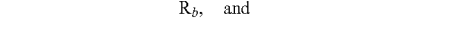

and wherein the wavy line represents the point of attachment of R¹ to the rest of the molecule, and wherein each of $R_a$, $R_b$, $R_c$, $R_d$, and $R_e$, is independently selected from H, halo, —OH, —CN, alkyl, haloalkyl, -alkyl-OH, heteroalkyl, heterohaloalkyl, —O-alkyl, —O-haloalkyl, —O-alkyl-OH, aryl, —O-aryl, —S-aryl, —O-alkyl-aryl, —S-alkyl-aryl, heteroaryl, —O-heteroaryl, —S-heteroaryl, —O-alkyl-heteroaryl, —S-alkyl-heteroaryl, heterocycloalkyl, —C(O)-alkyl, —C(O)-haloalkyl, —C(O)H, —C(O)OH, —C(O)O-alkyl, —OC(O)-alkyl, —C(O)NH₂, —C(O)NHR¹⁰, —C(O)NR¹⁰R¹¹, —C(O)ONH$_2$, —C(O)ONHR$^{10}$, —C(O)ONR$^{10}$R$^{11}$, —NH$_2$, —NHR$^{10}$, —NR$^{10}$R$^{11}$, —NO$_2$, substituted aryl, and substituted heteroaryl, wherein each of said substituted aryl and said substituted heteroaryl independently contains from one to three substituents, which may be the same or different, each substituent being independently selected from halo, alkyl, —O-alkyl, and —C(O)Oalkyl, and wherein each R$_{ad}$ and each R$_{ae}$ is independently selected from alkyl and haloalkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), R$^1$ is —NR$^{14}$R$^{15}$. Non-limiting examples of R$^1$ when R$^1$ is —NR$^{14}$R$^{15}$ include:

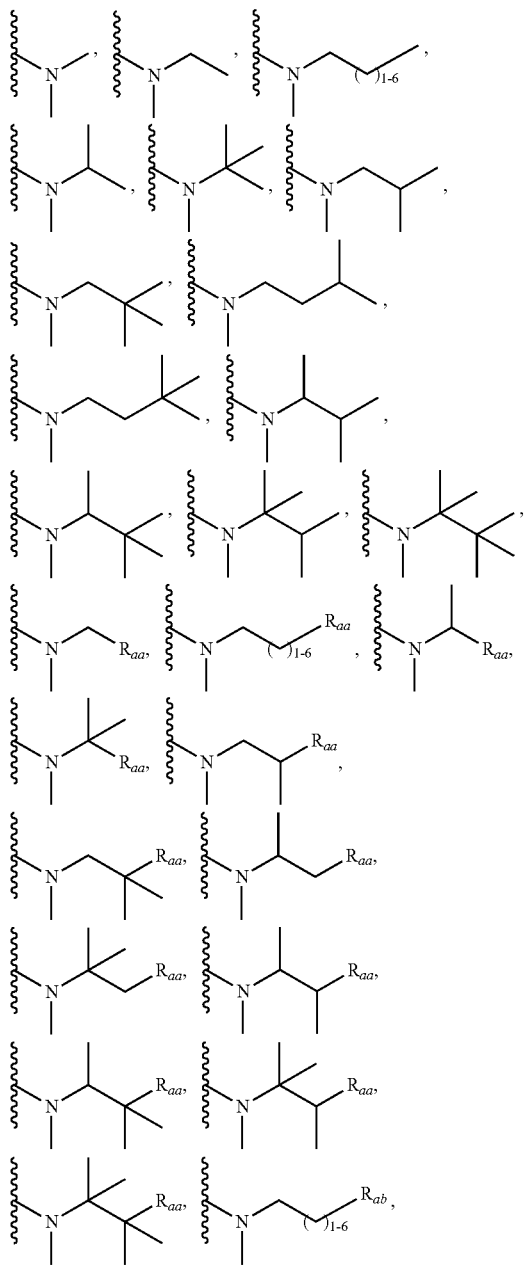

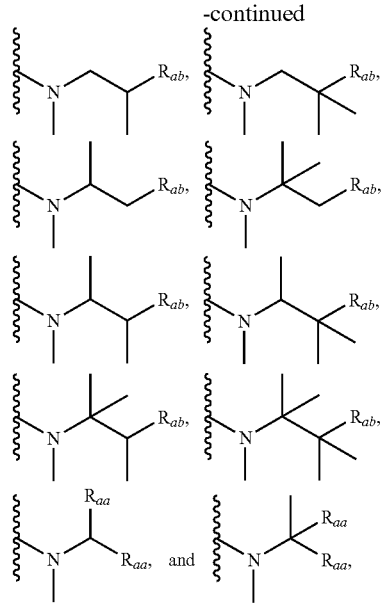

wherein the wavy line represents the point of attachment of R$^1$ to the rest of the molecule, and wherein each R$_{aa}$ is independently selected from haloalkyl (non-limiting examples of which include —CH$_2$F, —CHF$_2$, —CF$_3$, etc.), R$_{ab}$ is selected from OH, OAc, and —O-alkyl (non-limiting examples of which include —O-Me, —O-Et, —O-n-Pr, —O-i-Pr, —O-n-Bu, —O-i-Bu, and —O-t-Bu), —O-haloalkyl (non-limiting examples of which include —O—CH$_2$F, —O—CHF$_2$, and —O—CF$_3$), —NH$_2$, —NHalkyl, and —N(alkyl)$_2$.

Additional non-limiting examples of R$^1$ when R$^1$ is —NR$^{14}$R$^{15}$ include:

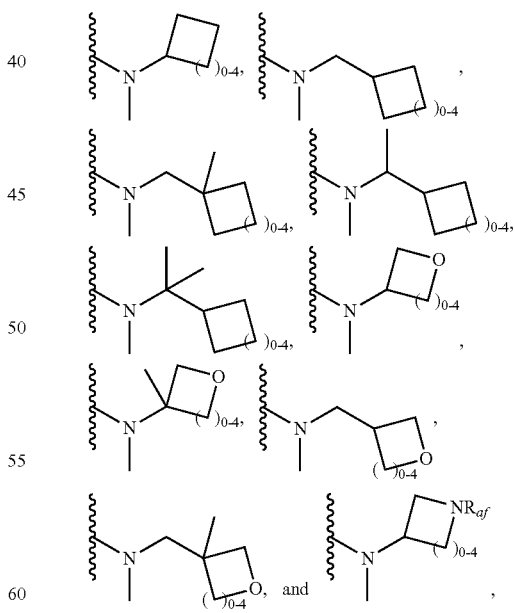

wherein the wavy line represents the point of attachment of R$^1$ to the rest of the molecule, and wherein R$_{af}$ is selected from H and acetyl.

Additional non-limiting examples of R$^1$ when R$^1$ is —NR$^{14}$R$^{15}$ include:

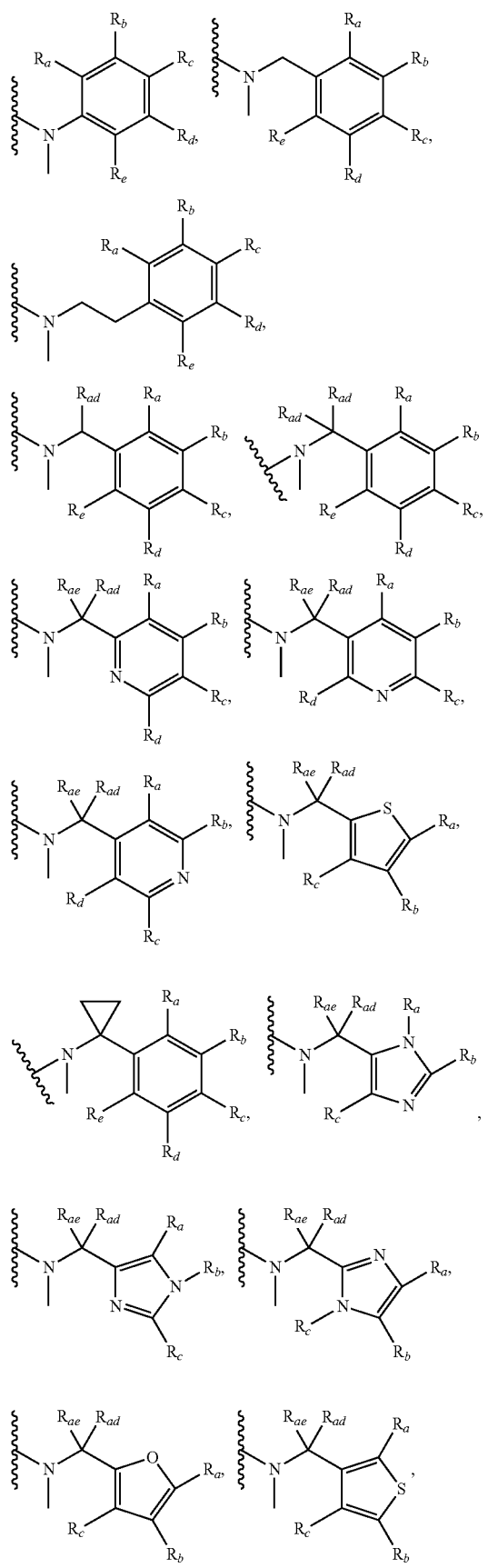
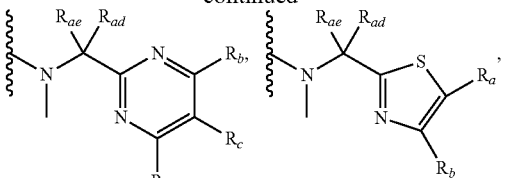
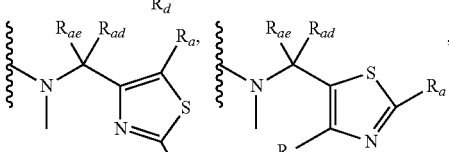
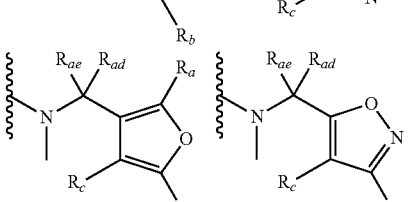
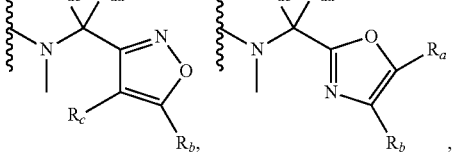
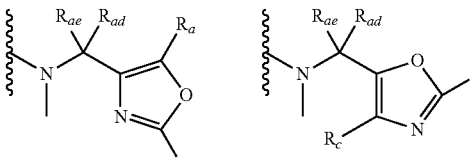
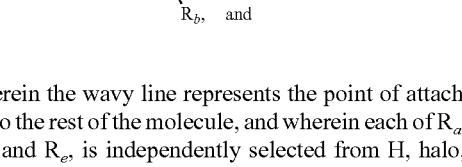

wherein the wavy line represents the point of attachment of $R^1$ to the rest of the molecule, and wherein each of $R_a$, $R_b$, $R_c$, $R_d$, and $R_e$, is independently selected from H, halo, —OH, —CN, alkyl, haloalkyl, -alkyl-OH, heteroalkyl, heterohaloalkyl, —O-alkyl, —O-haloalkyl, —O-alkyl-OH, aryl, —O-aryl, —S-aryl, —O-alkyl-aryl, —S-alkyl-aryl, heteroaryl, —O-heteroaryl, —S-heteroaryl, —O-alkyl-heteroaryl, —S-alkyl-heteroaryl, heterocycloalkyl, —C(O)-alkyl, —C(O)-haloalkyl, —C(O)H, —C(O)OH, —C(O)O-alkyl, —OC(O)-alkyl, —C(O)NH$_2$, —C(O)NHR$^{10}$, —C(O)NR$^{10}$R$^{11}$, —C(O)ONH$_2$, —C(O)ONHR$^{10}$, —C(O)ONR$^{10}$R$^{11}$, —NH$_2$, —NHR$^{10}$, —NR$^{10}$R$^{11}$, —NO$_2$, substituted aryl, and substituted heteroaryl, wherein each of said substituted aryl and said substituted heteroaryl independently contains from one to three substituents, which may be the same or different, each substituent being independently selected from halo, alkyl, —O-alkyl, and —C(O)Oalkyl, and wherein each $R_{ad}$ and each $R_{ae}$ is independently selected from alkyl and haloalkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), $R^1$ is —NR$^{14}$R$^{15}$, wherein R$^{14}$ and R$^{15}$ are linked together with the nitrogen to which they are attached to form an unsubstituted or substituted 4- to 6-membered heterocycloalkyl. Non-limiting examples of R$^1$ when R$^1$ is —NR$^{14}$R$^{15}$ and R$^{14}$ and R$^{15}$ are so linked include:

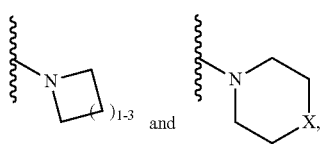

wherein X is selected from O, NH, and NMe.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.0), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is halo; $R^1$ is selected from $—NH_2$, $—NHR^{14}$, and $—NR^{14}R^{15}$; and R is as defined in claim 1.

In other embodiments, in each of Formulas (I), (I.A), (I.a), (I.a.1), (I.a.1.0), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is heteroaryl; $R^1$ is selected from $—NH_2$, $—NHR^{14}$, and $—NR^{14}R^{15}$; and R is as defined in claim 1.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is H; $R^1$ is selected from $—NH_2$, $—NHR^{14}$, and $—NR^{14}R^{15}$; and R is as defined in claim 1.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is alkyl; $R^1$ is selected from $—NH_2$, $—NHR^{14}$, and $—NR^{14}R^{15}$; and R is as defined in claim 1.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is halo; $R^1$ is selected from $—NH_2$, $—NHR^{14}$, and $—NR^{14}R^{15}$; and R is heteroaryl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is heteroaryl; $R^1$ is selected from $—NH_2$, $—NHR^{14}$, and $—NR^{14}R^{15}$; and R is heteroaryl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is H; $R^1$ is selected from $—NH_2$, $—NHR^{14}$, and $—NR^{14}R^{15}$; and R is heteroaryl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), Z is alkyl; $R^1$ is selected from $—NH_2$, $—NHR^{14}$, and $—NR^{14}R^{15}$; and R is heteroaryl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1), X and Y are each N; R is selected from unsubstituted aryl, substituted aryl, unsubstituted heteroaryl, and substituted heteroaryl, wherein said substituents, when present, are defined in Formula (I); Z is selected from halo, —OH, —SH, alkyl, $—NH_2$, $—NHR^{12}$, and $—NR^{12}R^{13}$; $R^1$ is selected from $—NH_2$, $—NHR^{14}$, and $—NR^{14}R^{15}$; and $R^2$ is selected from H and alkyl.

In other embodiments, in each of Formulas (I), (I.A), (I.a), (I.a.1), (I.a.1.i), (I.a.2), (I.a.2.i), (I.a.3), (I.a.3.i), (I.a.4), (I.a.4.i), (I.a.5), (I.a.5.i), (I.a.6), (I.a.6.i), (I.a.7), (I.a.7.i), (I.a.8), (I.a.8.i), (I.a.10), (I.a.10.i), (I.a.10.j), (I.B), (I.b), (I.b.1), (I.b.1.i), (I.b.2), (I.b.2.i), (I.C), (I.c), (I.c.1), (I.c.1.i), (I.c.2), (I.c.2.i), (I.D), (I.d), (I.d.1), (I.d.1.i), (I.E), (II), (II.A), and (II.A.1):

X is N;

Y is N;

R is selected from the group consisting of:

(a) an unsubstituted or substituted monocyclic aryl moiety or an unsubstituted or substituted heteroaryl moiety selected from the group consisting of:

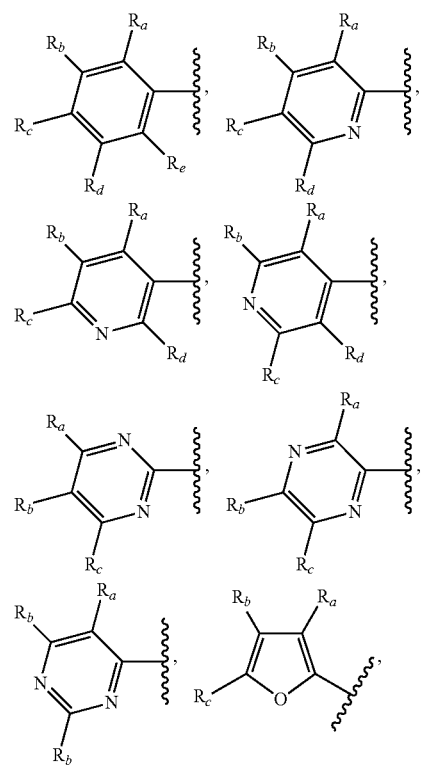

-continued

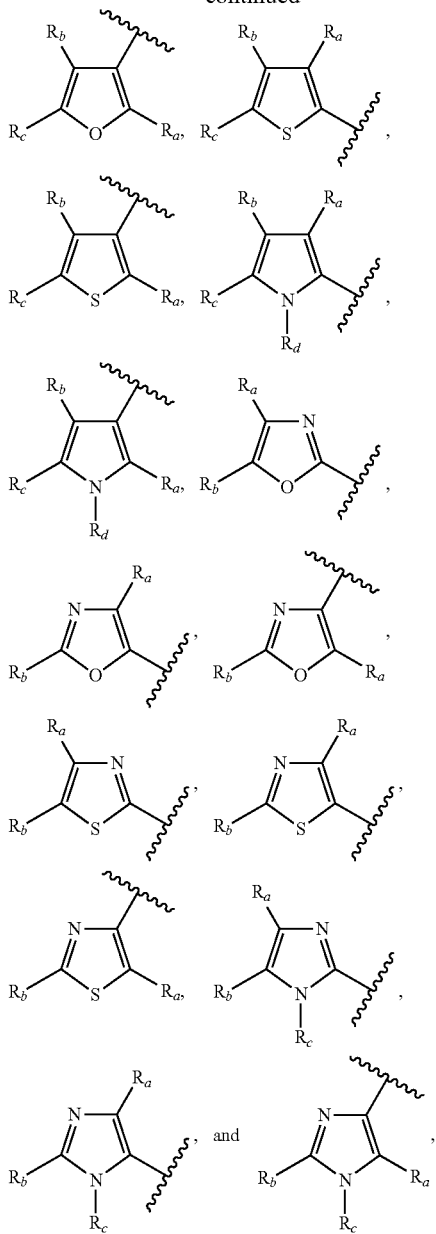

wherein the wavy line represents the point of attachment of R to the rest of the molecule, and wherein each of $R_a$, $R_b$, $R_c$, $R_d$, and $R_e$, is independently selected from H, halo, —OH, —CN, alkyl, haloalkyl, -alkyl-OH, heteroalkyl, heterohaloalkyl, —O-alkyl, —O-haloalkyl, —O-alkyl-OH, aryl, —O-aryl, —S-aryl, —O-alkyl-aryl, —S-alkyl-aryl, heteroaryl, —O-heteroaryl, —S-heteroaryl, —O-alkyl-heteroaryl, —S-alkyl-heteroaryl, heterocycloalkyl, —C(O)-alkyl, —C(O)-haloalkyl, —C(O)H, —C(O)OH, —C(O)O-alkyl, —OC(O)-alkyl, —C(O)NH$_2$, —C(O)NHR$^{10}$, —C(O)NR$^{10}$R$^{11}$, —C(O)ONH$_2$, —C(O)ONHR$^{10}$, —C(O)ONR$^{10}$R$^{11}$, —NH$_2$, —NHR$^{10}$, —NR$^{10}$R$^{11}$, —NO$_2$, substituted aryl, and substituted heteroaryl, wherein each of said substituted aryl and said substituted heteroaryl independently contains from one to three substituents, which may be the same or different, each substituent being independently selected from halo, alkyl, —O-alkyl, and —C(O)Oalkyl, and (b) an unsubstituted or an substituted bicyclic heteroaryl moiety selected from the group consisting of:

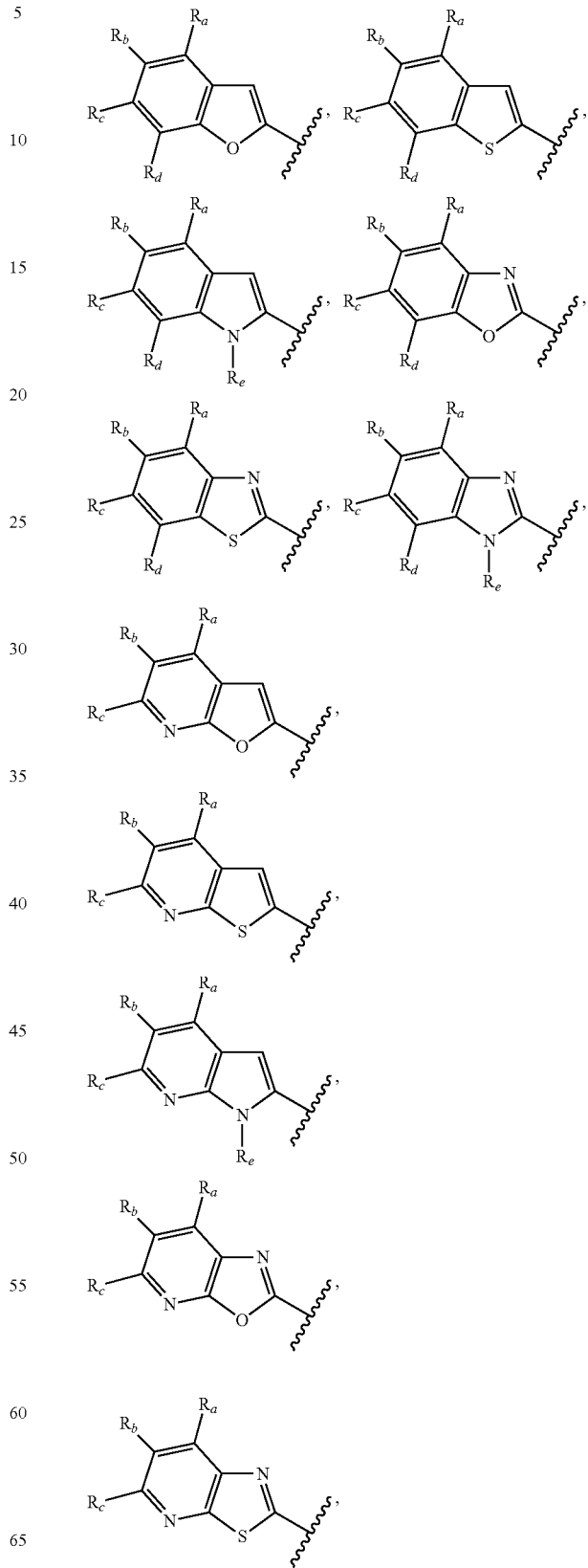

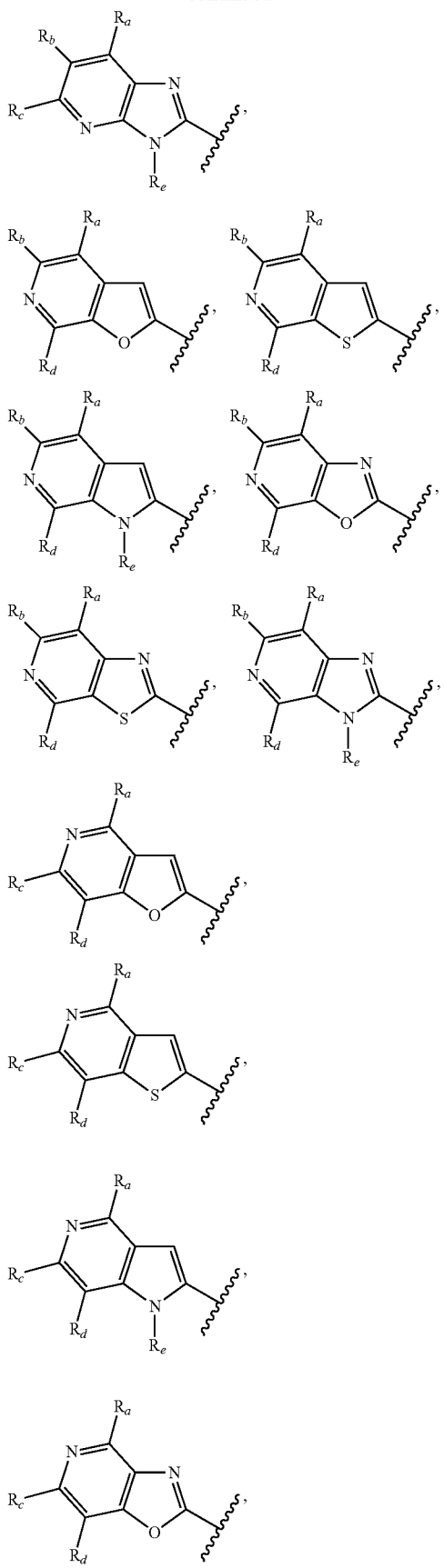

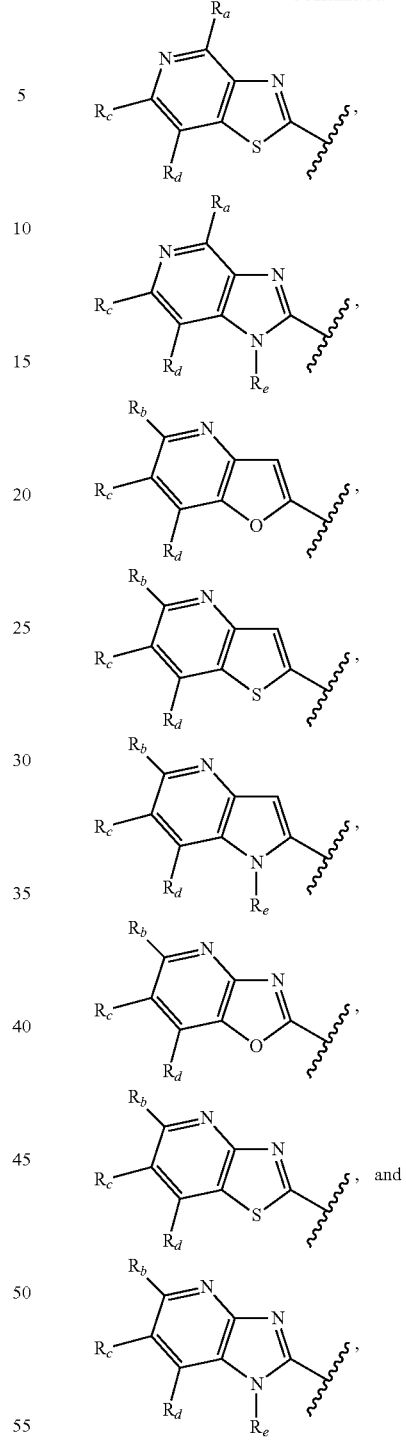

wherein the wavy line represents the point of attachment of R to the rest of the molecule, and wherein each of $R_a$, $R_b$, $R_c$, $R_d$, and $R_e$, is independently selected from H, halo, —OH, —CN, alkyl, haloalkyl, -alkyl-OH, heteroalkyl, heterohaloalkyl, —O-alkyl, —O-haloalkyl, —O-alkyl-OH, aryl, —O-aryl, —S-aryl, —O-alkyl-aryl, —S-alkyl-aryl, heteroaryl, —O-heteroaryl, —S-heteroaryl, —O-alkyl-heteroaryl, —S-alkyl-heteroaryl, heterocycloalkyl, —C(O)-alkyl, —C(O)-haloalkyl, —C(O)H, —C(O)OH, —C(O)O-alkyl, —OC(O)-alkyl, —C(O)NH$_2$, —C(O)NHR$^{10}$, —C(O)NR$^{10}$R$^{11}$, —C(O)ONH$_2$, —C(O)ONHR$^{10}$, —C(O)ONR$^{10}$R$^{11}$, —NH$_2$, —NHR$^{10}$, —NR$^{10}$R$^{11}$, —NO$_2$, substituted aryl, and substituted heteroaryl, wherein each of said substituted aryl and said substituted heteroaryl independently contains from one to three substituents, which may be the same or different, each substituent being independently selected from halo, alkyl, —O-alkyl, and —C(O)Oalkyl;

R$^1$ is selected from the group consisting of:

(a)
—NH$_2$, (b)

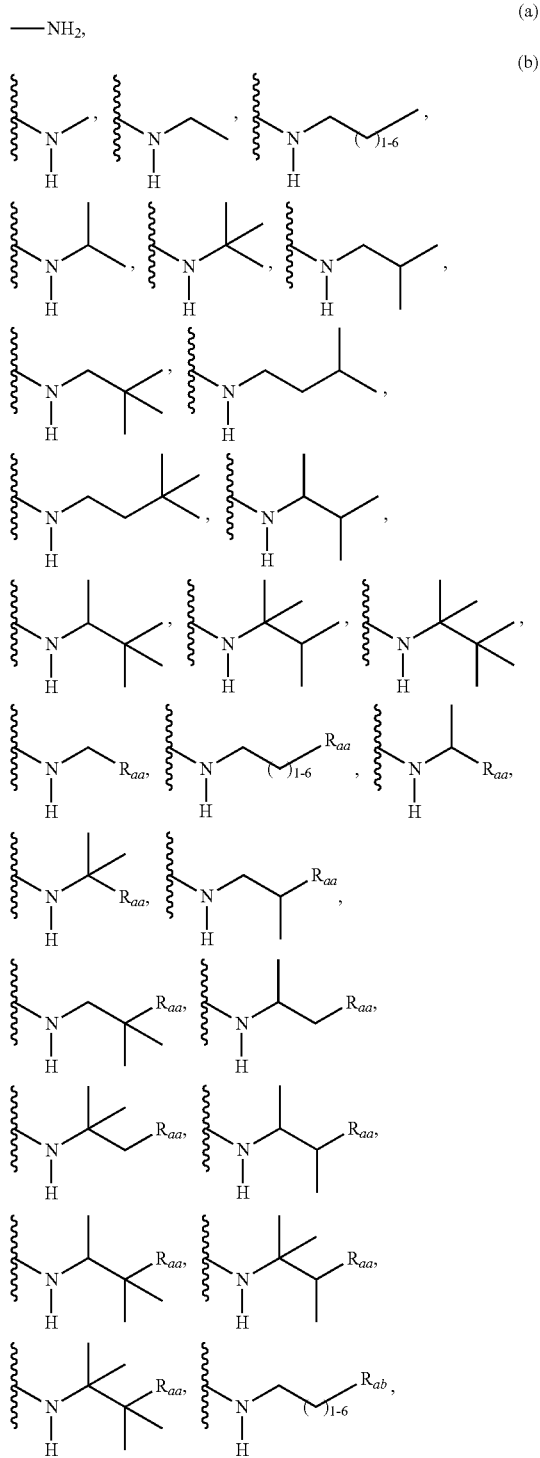

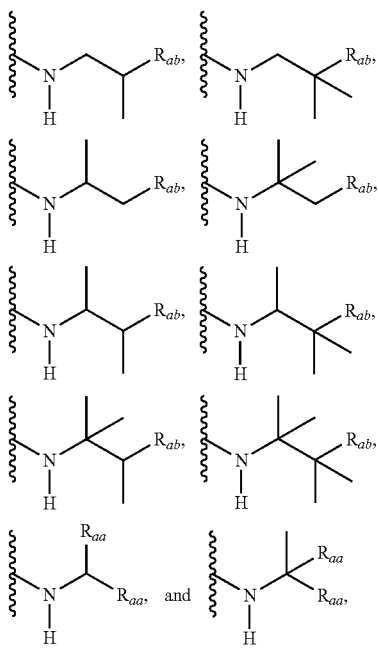

wherein the wavy line represents the point of attachment of R$^1$ to the rest of the molecule, and wherein each R$_{aa}$ is independently selected from haloalkyl (non-limiting examples of which include —CH$_2$F, —CHF$_2$, —CF$_3$, etc.), R$_{ab}$ is selected from OH, OAc, and —O-alkyl (non-limiting examples of which include —O-Me, —O-Et, —O-n-Pr, —O-i-Pr, —O-n-Bu, —O-i-Bu, and —O-t-Bu), —O-haloalkyl (non-limiting examples of which include —O—CH$_2$F, —O—CHF$_2$, and —O—CF$_3$), —NH$_2$, —NHalkyl, and —N(alkyl)$_2$,

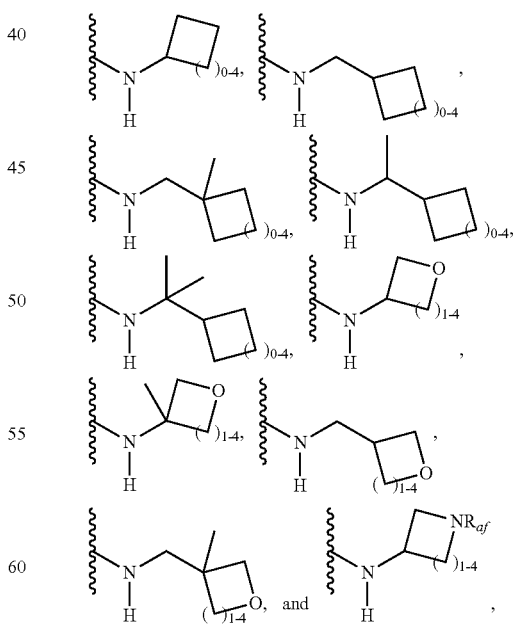

wherein the wavy line represents the point of attachment of R$^1$ to the rest of the molecule, and wherein R$_{af}$ is selected from H and acetyl, (d)

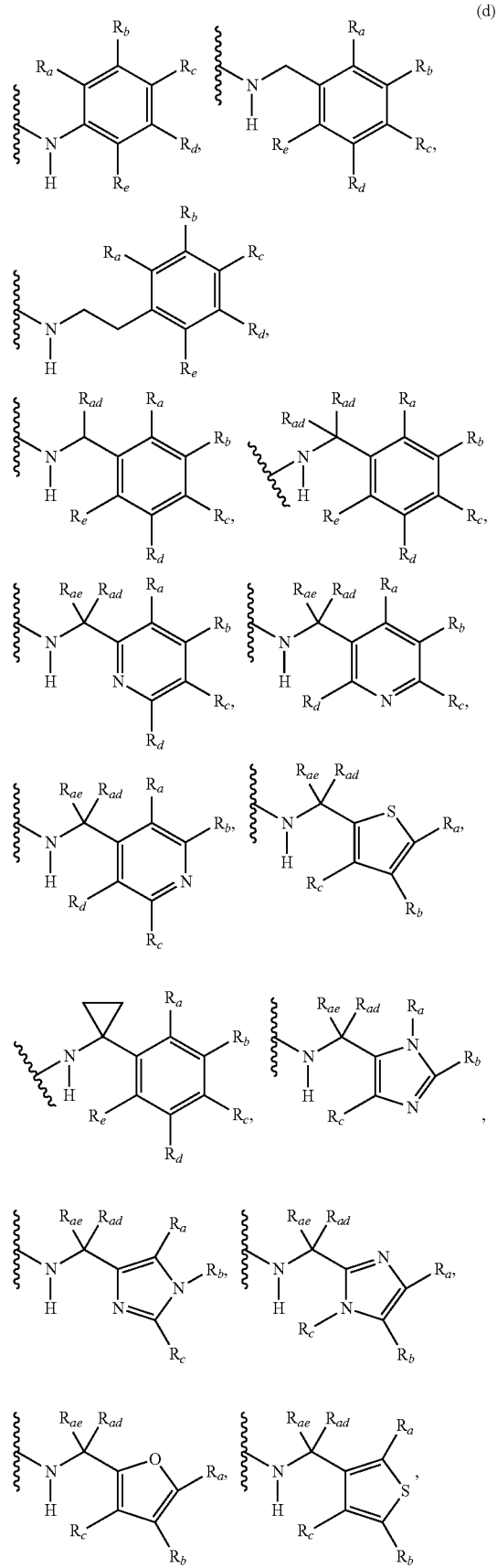

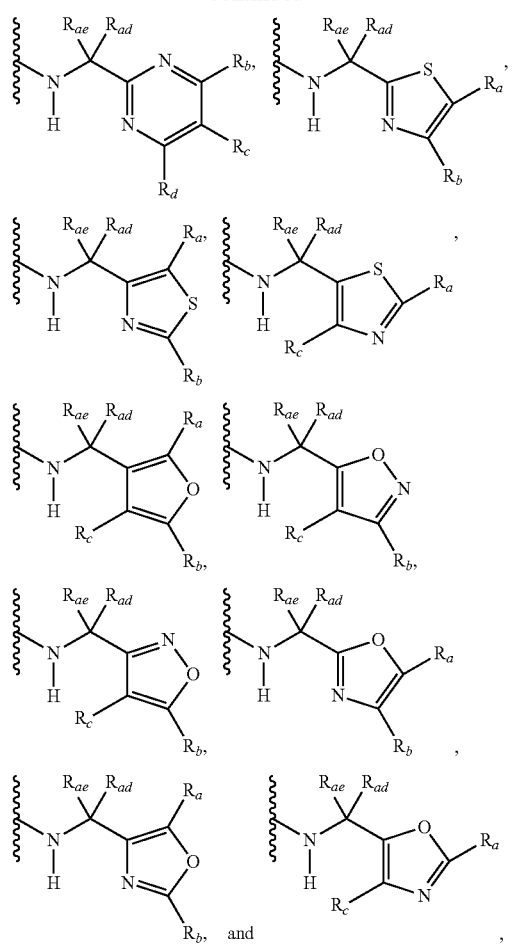

wherein the wavy line represents the point of attachment of $R^1$ to the rest of the molecule, and wherein each of $R_a$, $R_b$, $R_c$, $R_d$, and $R_e$, is independently selected from H, halo, —OH, —CN, alkyl, cycloalkyl, haloalkyl, -alkyl-OH, heteroalkyl, heterohaloalkyl, —O-alkyl, —O-haloalkyl, —O-alkyl-OH, aryl, —O-aryl, —S-aryl, —O-alkyl-aryl, —S-alkyl-aryl, heteroaryl, —O-heteroaryl, —S-heteroaryl, —O-alkyl-heteroaryl, —S-alkyl-heteroaryl, heterocycloalkyl, —C(O)-alkyl, —C(O)-haloalkyl, —C(O)H, —C(O)OH, —C(O)O-alkyl, —OC(O)-alkyl, —C(O)NH$_2$, —C(O)NHR$^{10}$, —C(O)NR$^{10}$R$^{11}$, —C(O)ONH$_2$, —C(O)ONHR$^{10}$, —C(O)ONR$^{10}$R$^{11}$, —NH$_2$, —NHR$^{10}$, —NR$^{10}$R$^{11}$, —NO$_2$, substituted aryl, and substituted heteroaryl, wherein each of said substituted aryl and said substituted heteroaryl independently contains from one to three substituents, which may be the same or different, each substituent being independently selected from halo, alkyl, —O-alkyl, and —C(O)Oalkyl, and wherein each $R_{ad}$ is independently selected from alkyl and haloalkyl, (e)

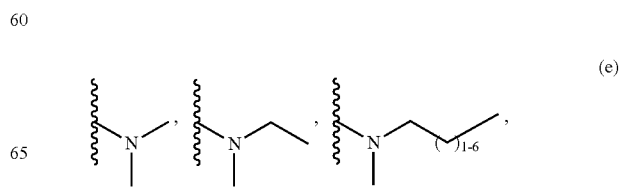

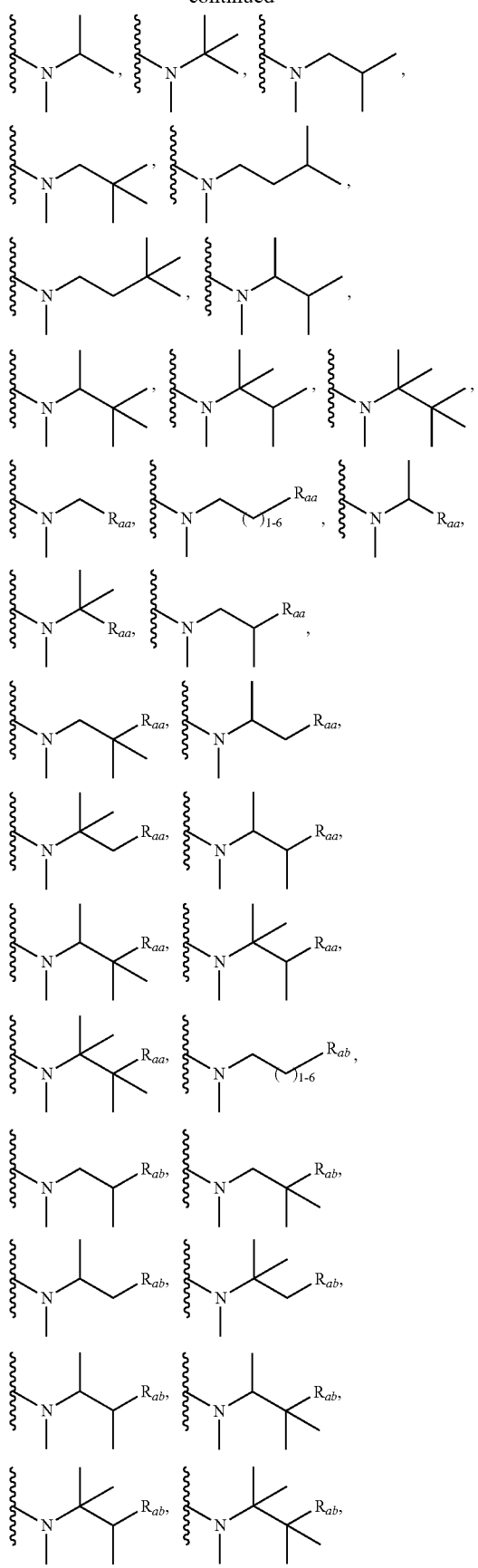
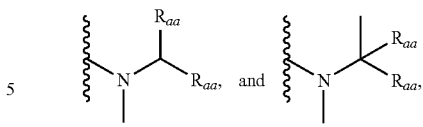

wherein the wavy line represents the point of attachment of $R^1$ to the rest of the molecule, and wherein each $R_{aa}$ is independently selected from haloalkyl (non-limiting examples of which include —$CH_2F$, —$CHF_2$, —$CF_3$, etc.), $R_{ab}$ is selected from OH, OAc, and —O-alkyl (non-limiting examples of which include —O-Me, —O-Et, —O-n-Pr, —O-i-Pr, —O-n-Bu, —O-i-Bu, and —O-t-Bu), —O-haloalkyl (non-limiting examples of which include —O—$CH_2F$, —O—$CHF_2$, and —O—$CF_3$), —$NH_2$, —NHalkyl, and —N(alkyl)$_2$, (f)

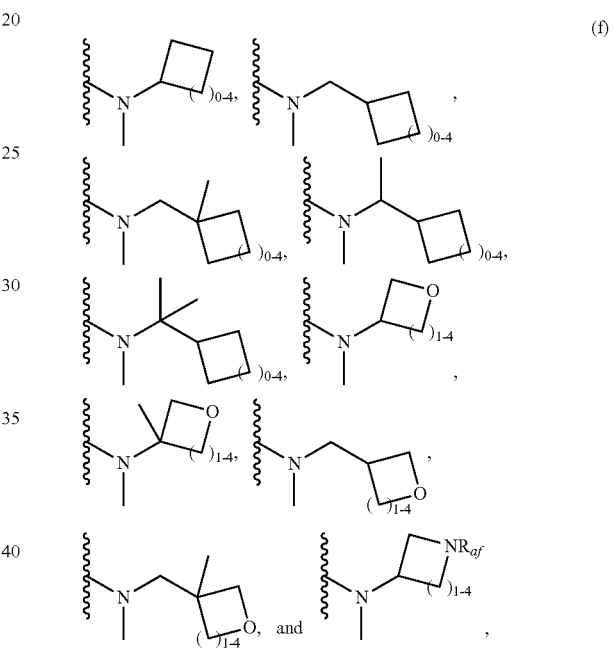

wherein the wavy line represents the point of attachment of $R^1$ to the rest of the molecule, and wherein $R_{af}$ is selected from H and acetyl, (g)

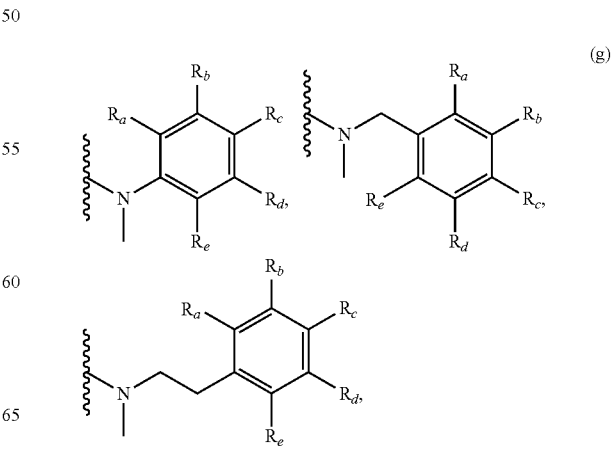

-continued

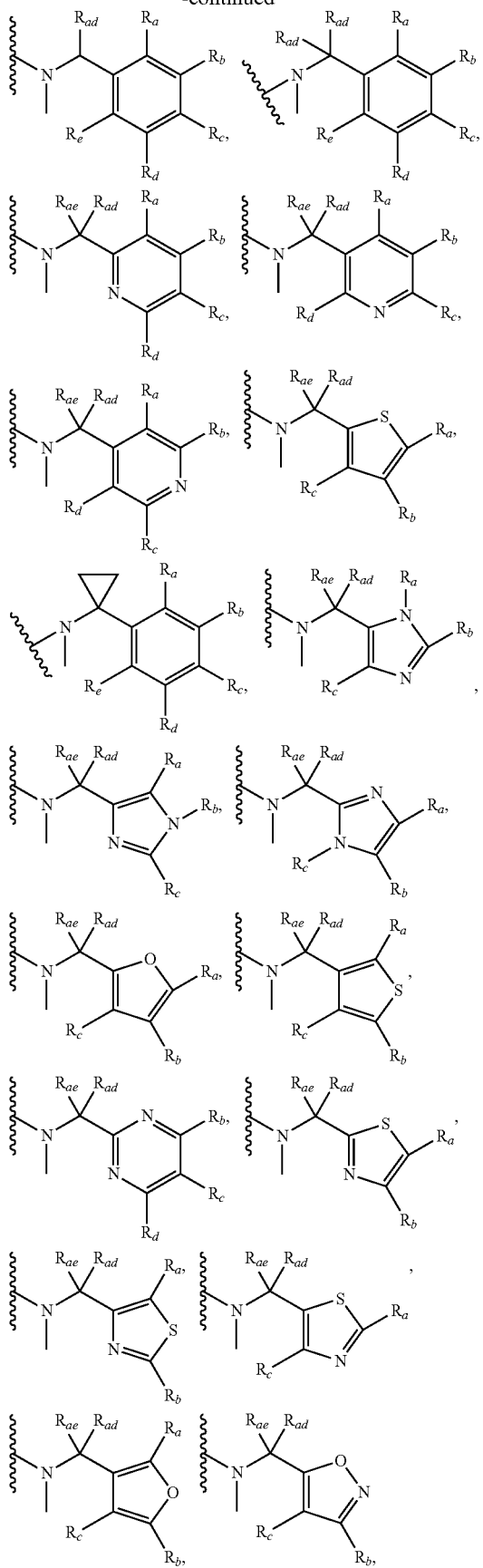

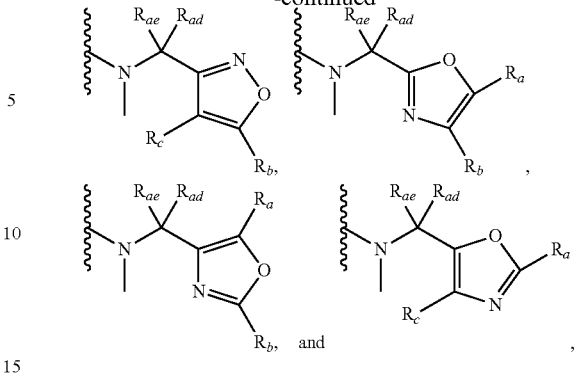

wherein the wavy line represents the point of attachment of $R^1$ to the rest of the molecule, and wherein each of $R_a$, $R_b$, $R_c$, $R_d$, and $R_e$, is independently selected from H, halo, —OH, —CN, alkyl, haloalkyl, -alkyl-OH, heteroalkyl, heterohaloalkyl, —O-alkyl, —O-haloalkyl, —O-alkyl-OH, aryl, —O-aryl, —S-aryl, —O-alkyl-aryl, —S-alkyl-aryl, heteroaryl, —O-heteroaryl, —S-heteroaryl, —O-alkyl-heteroaryl, —S-alkyl-heteroaryl, heterocycloalkyl, —C(O)-alkyl, —C(O)-haloalkyl, —C(O)H, —C(O)OH, —C(O)O-alkyl, —OC(O)-alkyl, —C(O)NH$_2$, —C(O)NHR$^{10}$, —C(O)NR$^{10}$R$^{11}$, —C(O)ONH$_2$, —C(O)ONHR$^{10}$, —C(O)ONR$^{10}$R$^{11}$, —NH$_2$, —NHR$^{10}$, —NR$^{10}$R$^{11}$, —NO$_2$, substituted aryl, and substituted heteroaryl, wherein each of said substituted aryl and said substituted heteroaryl independently contains from one to three substituents, which may be the same or different, each substituent being independently selected from halo, alkyl, —O-alkyl, and —C(O)Oalkyl, and wherein each $R_{ad}$ is independently selected from alkyl and haloalkyl, and (h)

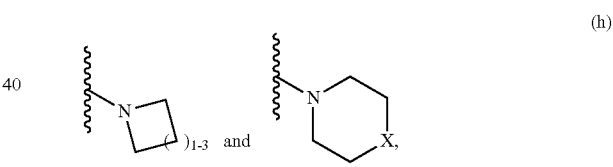

wherein X is selected from O, NH, and NMe; and

Z is selected from the group consisting of H, halo, —OH, —SH, —CN, alkyl, alkenyl, alkynyl, heteroalkyl, haloalkyl, heterohaloalkyl, —S-alkyl, —O-alkyl, —O-aryl, —O-heteroaryl, cycloalkyl, aryl, heteroaryl, —NH$_2$, —NHR$^{12}$, and —NR$^{12}$R$^{13}$.

In other embodiments, the compounds of the invention have a structural formula as depicted in Table I below and include tautomers, and pharmaceutically acceptable salts, esters, prodrugs, isomers, and solvates of such compounds and such tautomers.

DEFINITIONS

The terms used herein have their ordinary meaning and the meaning of such terms is independent at each occurrence thereof. That notwithstanding and except where stated otherwise, the following definitions apply throughout the specification and claims. Chemical names, common names and chemical structures may be used interchangeably to describe that same structure. These definitions apply regardless of whether a term is used by itself or in combination with other terms, unless otherwise indicated. Hence the definition of "alkyl" applies to "alkyl" as well as the "alkyl" protion of "hydroxyalkyl", "haloalkyl", arylalkyl-, alkylaryl-, "alkoxy" etc.

"At least one" means one or more than one, for example, 1, 2, or 3, or in another example, 1 or 2, or in another example 1.

"One or more" means one or more than one, for example, 1, 2, or 3, or in another example, 1 or 2, or in another example 1.

"Patient" includes both human and non-human animals. Non-human animals include research animals, farm animals, and companion animals such as mice, primates, monkeys, great apes, cows, sheep, horse, canine (e.g., dogs), and feline (e.g., house cats), etc.

"Composition" includes "pharmaceutical composition" and other compositions not suitable for pharmaceutical use but which may be suitable for other uses such as research or other uses.

"Pharmaceutical composition" (or "pharmaceutically acceptable composition") means a composition suitable for administration to a patient. Such compositions may contain the neat compound (or compounds) of the invention or mixtures thereof, or salts, solvates, prodrugs, isomers, or tautomers thereof, or they may contain one or more pharmaceutically acceptable carriers or diluents. The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the aforesaid "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the aforesaid bulk composition and individual dosage units.

"Halogen" means fluorine, chlorine, bromine, or iodine. Preferred are fluorine, chlorine and bromine.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being as described herein or independently selected from the group consisting of halo, alkyl, haloalkyl, spirocycloalkyl, aryl, cycloalkyl, cyano, hydroxy, alkoxy, alkylthio, amino, —NH(alkyl), —NH(cycloalkyl), —N(alkyl)$_2$, —O—C(O)-alkyl, —O—C(O)-aryl, —O—C(O)-cycloalkyl, carboxy and —C(O)O-alkyl. Non-limiting examples of suitable alkyl groups include methyl, ethyl, n-propyl, isopropyl and t-butyl.

"Haloalkyl" means an alkyl as defined above wherein one or more hydrogen atoms on the alkyl is replaced by a halo group defined above.

"Aminoalkyl" means an alkyl which has been substituted at one or more available carbon atoms by one or more amino group(s). Non-limiting examples of such amino groups include those described herein, such as —NH$_2$, —NHR$^{12}$, —NR$^{12}$R$^{13}$, —NHR$^{14}$, and —NHR$^{15}$.

"Heteroalkyl" means an alkyl moiety as defined above, having one or more carbon atoms, for example one, two or three carbon atoms, including a terminal carbon atom, replaced with one or more heteroatoms, which may be the same or different, where the point of attachment to the remainder of the molecule is through a carbon atom of the heteroalkyl radical. Suitable such heteroatoms include O, S, S(O), S(O)$_2$, —NH—, —N(alkyl)-, and —N(alkyl)$_2$. Non-limiting examples include ethers, thioethers, amines, hydroxymethyl, 3-hydroxypropyl, 1,2-dihydroxyethyl, 2-methoxyethyl, 2-aminoethyl, 2-dimethylaminoethyl, and the like. Additional non-limiting examples include -alkyl-NHalkyl and -alkyl-N(alkyl)$_2$. A non-limiting example of heteroalkyl wherein a terminal carbon atom is replaced with a heteroatom includes -alkyl-NH$_2$.

"Heterohaloalkyl" means an haloalkyl moiety as defined above, having one or more, for example one, two, or three carbon atoms, including a terminal carbon atom, replaced with one or more heteroatoms, which may be the same or different, where the point of attachment to the remainder of the molecule is through a carbon atom of the heterohaloalkyl radical.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene. More generally, the suffix "ene" on alkyl, aryl, heterocycloalkyl, etc. indicates a divalent moiety, e.g., —CH$_2$CH$_2$— is ethylene, and

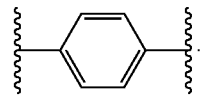

is para-phenylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Alkenylene" means a difunctional group obtained by removal of a hydrogen from an alkenyl group that is defined above. Non-limiting examples of alkenylene include —CH=CH—, —C(CH$_3$)=CH—, and —CH=CHCH$_2$—.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined herein. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like. Further non-limiting examples of cycloalkyl include the following:

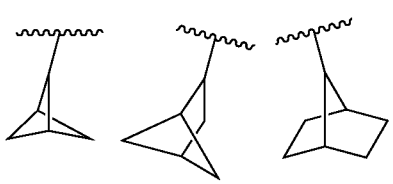

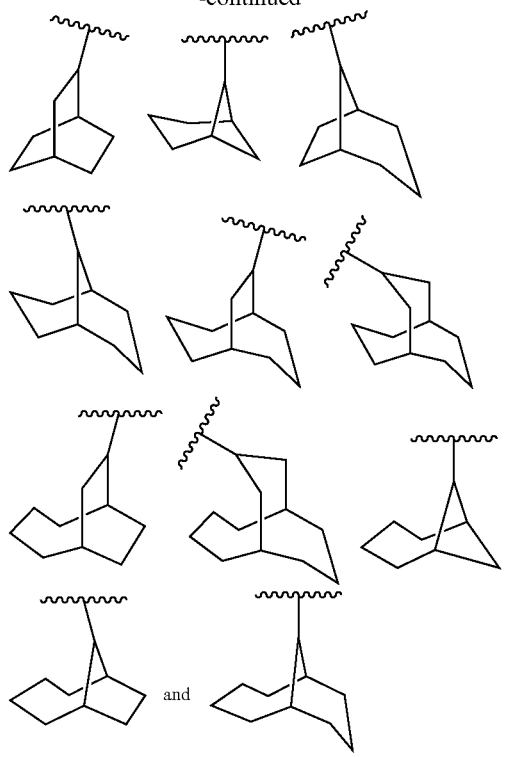

"Spirocycloalkyl" means a cycloalkyl moiety in which two available hydrogen atoms attached to the same carbon atom are replaced to form a cycloalkyl group.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Heterocycloalkyl" (or "heterocyclyl") means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Thus, the term "oxide," when it appears in a definition of a variable in a general structure described herein, refers to the corresponding N-oxide, S-oxide, or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" also includes rings wherein =O replaces two available hydrogens on the same carbon atom (i.e., heterocyclyl includes rings having a carbonyl group in the ring). Such =O groups may be referred to herein as "oxo." An example of such a moiety is pyrrolidinone (or pyrrolidone):

"Heterocycloalkenyl" (or "heterocyclenyl") means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" also includes rings wherein =O replaces two available hydrogens on the same carbon atom (i.e., heterocyclyl includes rings having a carbonyl group in the ring). Example of such moiety is pyrrolidenone (or pyrrolone):

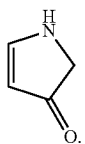

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

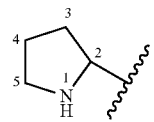

there is no —OH attached directly to carbons marked 2 and 5.

It should also be noted that tautomeric forms of the compounds of the invention are also contemplated as being within the scope of the invention.

"Arylcycloalkyl" (or "arylfused cycloalkyl") means a group derived from a fused aryl and cycloalkyl as defined herein. Preferred arylcycloalkyls are those wherein aryl is phenyl (which may be referred to as "benzofused") and cycloalkyl consists of about 5 to about 6 ring atoms. The arylcycloalkyl can be optionally substituted as described herein. Non-limiting examples of suitable arylcycloalkyls include indanyl (a benzofused cycloalkyl) and 1,2,3,4-tetrahydronaphthyl and the like. The bond to the parent moiety is through a non-aromatic carbon atom.

"Arylheterocycloalkyl" (or "arylfused heterocycloalkyl") means a group derived from a fused aryl and heterocycloalkyl as defined herein. Preferred arylheterocycloalkyls are those wherein aryl is phenyl (which may be referred to as "benzofused") and heterocycloalkyl consists of about 5 to about 6 ring atoms. The arylheterocycloalkyl can be optionally substituted, and/or contain the oxide or oxo, as described herein. Non-limiting examples of suitable arylfused heterocycloalkyls include:

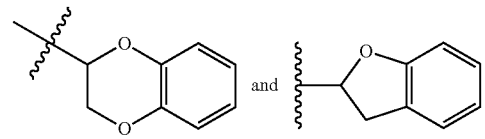 [SMILES: *C1COc2ccccc2O1 ; *C1Cc2ccccc2O1]

The bond to the parent moiety is through a non-aromatic carbon atom.

It is also understood that the terms "arylfused aryl", "arylfused cycloalkyl", "arylfused cycloalkenyl", "arylfused heterocycloalkyl", "arylfused heterocycloalkenyl", "arylfused heteroaryl", "cycloalkylfused aryl", "cycloalkylfused cycloalkyl", "cycloalkylfused cycloalkenyl", "cycloalkylfused heterocycloalkyl", "cycloalkylfused heterocycloalkenyl", "cycloalkylfused heteroaryl, "cycloalkenylfused aryl", "cycloalkenylfused cycloalkyl", "cycloalkenylfused cycloalkenyl", "cycloalkenylfused heterocycloalkyl", "cycloalkenylfused heterocycloalkenyl", "cycloalkenylfused heteroaryl", "heterocycloalkylfused aryl", "heterocycloalkylfused cycloalkyl", "heterocycloalkylfused cycloalkenyl", "heterocycloalkylfused heterocycloalkyl", "heterocycloalkylfused heterocycloalkenyl", "heterocycloalkylfused heteroaryl", "heterocycloalkenylfused aryl", "heterocycloalkenylfused cycloalkyl", "heterocycloalkenylfused cycloalkenyl", "heterocycloalkenylfused heterocycloalkyl", "heterocycloalkenylfused heterocycloalkenyl", "heterocycloalkenylfused heteroaryl", "heteroarylfused aryl", "heteroarylfused cycloalkyl", "heteroarylfused cycloalkenyl", "heteroarylfused heterocycloalkyl", "heteroarylfused heterocycloalkenyl", and "heteroarylfused heteroaryl" are similarly represented by the combination of the groups aryl, cycloalkyl, cycloalkenyl, heterocycloalkyl, heterocycloalkenyl, and heteroaryl, as previously described. Any such groups may be unsubstituted or substituted with one or more ring system substituents at any available position as described herein.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl. The term (and similar terms) may be written as "arylalkyl-" to indicate the point of attachment to the parent moiety.

Similarly, "heteroarylalkyl", "cycloalkylalkyl", "cycloalkenylalkyl", "heterocycloalkylalkyl", "heterocycloalkenylalkyl", etc., mean a heteroaryl, cycloalkyl, cycloalkenyl, heterocycloalkyl, heterocycloalkenyl, etc. as described herein bound to a parent moiety through an alkyl group. Preferred groups contain a lower alkyl group. Such alkyl groups may be straight or branched, unsubstituted and/or substituted as described herein.

Similarly, "arylfused arylalkyl-", arylfused cycloalkylalkyl-, etc., means an arylfused aryl group, arylfused cycloalkyl group, etc. linked to a parent moiety through an alkyl group. Preferred groups contain a lower alkyl group. Such alkyl groups may be straight or branched, unsubstituted and/or substituted as described herein.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkylether" means a non-aromatic ring of 3 to 7 members comprising an oxygen atom and 2 to 7 carbon atoms. Ring carbon atoms can be substituted, provided that substituents adjacent to the ring oxygen do not include halo or substituents joined to the ring through an oxygen, nitrogen or sulfur atom.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl, adamantylpropyl, and the like.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclylalkyl" (or "heterocycloalkylalkyl") means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenylalkyl" means a heterocyclenyl moiety as defined above linked via an alkyl moiety (defined above) to a parent core.

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Cyanoalkyl" means a NC-alkyl-group in which alkyl is as previously defined. Preferred cyanoalkyls contain lower alkyl. Non-limiting examples of suitable cyanoalkyl groups include cyanomethyl and 2-cyanoethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Heteroaroyl" means an heteroaryl-C(O)— group in which the heteroaryl group is as previously described. The bond to the parent moiety is through the carbonyl. Non-limiting examples of suitable groups include pyridoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Alkyoxyalkyl" means a group derived from an alkoxy and alkyl as defined herein. The bond to the parent moiety is through the alkyl.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" (or "arylalkyloxy") means an aralkyl-O— group (an arylaklyl-O -group) in which the aralkyl group is as previously described. Non-limiting examples of suitable aralkyloxy groups include benzyloxy and 1- or 2-naphthalenemethoxy. The bond to the parent moiety is through the ether oxygen.

"Arylalkenyl" means a group derived from an aryl and alkenyl as defined herein. Preferred arylalkenyls are those wherein aryl is phenyl and the alkenyl consists of about 3 to about 6 atoms. The arylalkenyl can be optionally substituted by one or more substituents. The bond to the parent moiety is through a non-aromatic carbon atom.

"Arylalkynyl" means a group derived from a aryl and alkenyl as defined herein. Preferred arylalkynyls are those wherein aryl is phenyl and the alkynyl consists of about 3 to about 6 atoms. The arylalkynyl can be optionally substituted by one or more substituents. The bond to the parent moiety is through a non-aromatic carbon atom.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-$S(O_2)$— group. Preferred groups are those in which the alkyl group is lower alkyl. The bond to the parent moiety is through the sulfonyl.

"Arylsulfonyl" means an aryl-$S(O_2)$— group. The bond to the parent moiety is through the sulfonyl.

"Spirocycloalkyl" means a cycloalkyl group attached to a parent moiety at a single carbon atom. Non-limiting examples of spirocycloalkyl wherein the parent moiety is a cycloalkyl include Spiro[2.5] octane, Spiro[2.4] heptane, etc. Non-limiting examples of spirocycloalkyl wherein the parent moiety is an The alkyl moiety linking fused ring systems (such as the alkyl moiety in heteroarylfused heteroarylalkyl-) may optionally be substituted with spirocycloalkyl or other groups as described herein. Non-limiting spirocycloalkyl groups include spirocyclopropyl, spriorcyclobutyl, spirocycloheptyl, and spirocyclohexyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

Substitution on a cycloalkylalkyl, heterocycloalkylalkyl, arylalkyl, heteroarylalkyl, arylfused cycloalkylalkyl-moiety or the like includes substitution on any ring portion and/or on the alkyl portion of the group.

When a variable appears more than once in a group, e.g., $R^8$ in —$N(R^8)_2$, or a variable appears more than once in a structure presented herein such as Formula (I), the variables can be the same or different.

With reference to the number of moieties (e.g., substituents, groups or rings) in a compound, unless otherwise defined, the phrases "one or more" and "at least one" mean that there can be as many moieties as chemically permitted, and the determination of the maximum number of such moieties is well within the knowledge of those skilled in the art. With respect to the compositions and methods comprising the use of "at least one compound of the invention, e.g., of Formula (I)," one to three compounds of the invention, e.g., of Formula (I) can be administered at the same time, preferably one.

Compounds of the invention may contain one or more rings having one or more ring system substituents. "Ring system substituent" means a substituent attached to an aromatic or non-aromatic ring system which, for example, replaces an available hydrogen on the ring system. Ring system substituents may be the same or different, each being as described herein or independently selected from the group consisting of alkyl, alkenyl, alkynyl, haloalkyl, heteroalkyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —O—C(O)-alkyl, —O—C(O)-aryl, —O—C(O)-cycloalkyl, —C(=N—CN)—$NH_2$, —C(=NH)—$NH_2$, —C(=NH)—NH(alkyl), $Y_1Y_2N$—, $Y_1Y_2$N-alkyl-, $Y_1Y_2$NC(O)—, $Y_1Y_2NSO_2$— and —$SO_2NY_1Y_2$, wherein $Y_1$ and $Y_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moieties are rings such as heteroaryl, cycloalkyl, cycloalkenyl, heterocycloalkyl, and heterocycloalkenyl rings. Additional non-limiting examples include methylene dioxy, ethylenedioxy, —$C(CH_3)_2$— and the like which form moieties such as, for example:

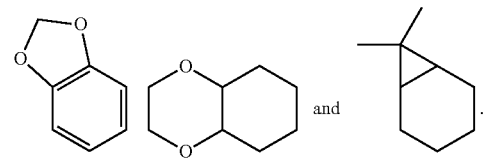

As used herein, the term "composition" is intended to encompass a product comprising the specified ingredients in the specified amounts, as well as any product which results, directly or indirectly, from combination of the specified ingredients in the specified amounts.

The line - - - -, as a bond generally indicates a mixture of, or either of, the possible isomers, e.g., containing (R)- and (S)-stereochemistry. For example:

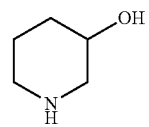

means containing both

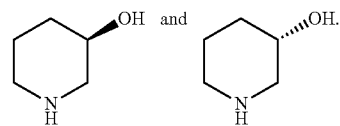

The wavy line ~~~, as used herein, indicates a point of attachment to the rest of the compound. For example, each wavy line in the following structure:

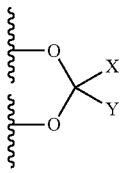

indicates a point of attachment to the core structure, as described herein.

Lines drawn into the ring systems, such as, for example:

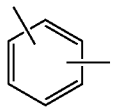

indicate that the indicated line (bond) may be attached to any of the substitutable ring carbon atoms.

"Oxo" is defined as a oxygen atom that is double bonded to a ring carbon in a cycloalkyl, cycloalkenyl, heterocyclyl, heterocyclenyl, or other ring described herein, e.g.,

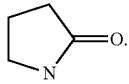

In this specification, where there are multiple oxygen and/or sulfur atoms in a ring system, there cannot be any adjacent oxygen and/or sulfur present in said ring system.

It is noted that the carbon atoms for compounds of the invention may be replaced with 1 to 3 silicon atoms so long as all valency requirements are satisfied.

As well known in the art, a bond drawn from a particular atom wherein no moiety is depicted at the terminal end of the bond indicates a methyl group bound through that bond to the atom, unless stated otherwise. For example:

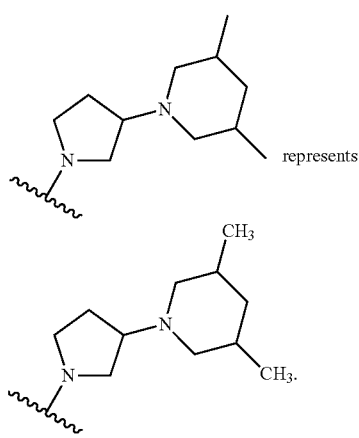

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon (or other atom or heteroatom) with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of the invention or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of the invention or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di(($C_1$-$C_2$)alkylcarbamoyl-(C1-C2)alkyl and piperidino-, pyrrolidino- or morpholino($C_2$-$C_3$) alkyl, and the like.

Similarly, if a compound of the invention contains an alcohol functional group, a prodrug can be formed by the replacement of the hydrogen atom of the alcohol group with a group such as, for example, $(C_1-C_6)$alkanoyloxymethyl, $1-((C_1-C_6)$alkanoyloxy)ethyl, $1$-methyl-$1-((C_1-C_6)$alkanoyloxy)ethyl, $(C_1-C_6)$alkoxycarbonyloxymethyl, $N-(C_1-C_6)$alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, $P(O)(OH)_2$, $-P(O)(O(C_1-C_6)$alkyl$)_2$ or glycosyl (the radical resulting from the removal of a hydroxyl group of the hemiacetal form of a carbohydrate), and the like.

If a compound of the invention incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$ cycloalkyl, benzyl, or R-carbonyl is a natural α-aminoacyl or natural α-aminoacyl, $-C(OH)C(O)OY^1$ wherein $Y^1$ is H, $(C_1-C_6)$alkyl or benzyl, $-C(OY^2)Y^3$ wherein $Y^2$ is $(C_1-C_4)$ alkyl and $Y^3$ is $(C_1-C_6)$alkyl, carboxy$(C_1-C_6)$alkyl, amino$(C_1-C_4)$alkyl or mono-N— or di-N,N—$(C_1-C_6)$alkylaminoalkyl, $-C(Y^4)Y^5$ wherein $Y^4$ is H or methyl and $Y^5$ is mono-N— or di-N,N—$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al., *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example IR spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of the invention can form salts which are also within the scope of this invention. Reference to a compound of the invention herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of the invention contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the invention may be formed, for example, by reacting a compound of the invention with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

Compounds of the invention, and salts, solvates, esters and prodrugs thereof, may exist in their tautomeric form (for example, as an amide or imino ether). All such tautomeric forms are contemplated herein as part of the present invention.

The compounds of the invention may contain asymmetric or chiral centers, and, therefore, exist in different stereoisomeric forms. It is intended that all stereoisomeric forms of the compounds of the invention as well as mixtures thereof, including racemic mixtures, form part of the present invention. In addition, the present invention embraces all geometric and positional isomers. For example, if a compound of the invention incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of chiral HPLC column.

It is also possible that the compounds of the invention may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of the invention incorporates a double bond or a fused ring, both the cis- and trans-forms, as well as mixtures, are embraced within the scope of the invention. Also, for example, all keto-enol and imine-enamine forms of the compounds are included in the invention).

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively.

Certain isotopically-labelled compounds of the invention (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labelled compounds of the invention can generally be prepared by following procedures analogous to those disclosed in the Schemes and/or in the Examples hereinbelow, by substituting an appropriate isotopically labelled reagent for a non-isotopically labelled reagent.

Polymorphic forms of the compounds of the invention, and of the salts, solvates, esters and prodrugs of the compounds of the invention, are intended to be included in the present invention.

Suitable doses for administering compounds of the invention to patients may readily be determined by those skilled in the art, e.g., by an attending physician, pharmacist, or other skilled worker, and may vary according to patient health, age, weight, frequency of administration, use with other active ingredients, and/or indication for which the compounds are administered. Doses may range from about 0.001 to 500 mg/kg of body weight/day of the compound of the invention. In one embodiment, the dosage is from about 0.01 to about 25 mg/kg of body weight/day of a compound of the invention, or a pharmaceutically acceptable salt or solvate of said compound. In another embodiment, the quantity of active compound in a unit dose of preparation may be varied or adjusted from about 1 mg to about 100 mg, preferably from about 1 mg to about 50 mg, more preferably from about 1 mg to about 25 mg, according to the particular application. In another embodiment, a typical recommended daily dosage regimen for oral administration can range from about 1 mg/day to about 500 mg/day, preferably 1 mg/day to 200 mg/day, in two to four divided doses.

As discussed above, the amount and frequency of administration of the compounds of the invention and/or the pharmaceutically acceptable salts thereof will be regulated according to the judgment of the attending clinician considering such factors as age, condition and size of the patient as well as severity of the symptoms being treated.

When used in combination with one or more additional therapeutic agents, the compounds of this invention may be administered together or sequentially. When administered sequentially, compounds of the invention may be administered before or after the one or more additional therapeutic agents, as determined by those skilled in the art or patient preference.

If formulated as a fixed dose, such combination products employ the compounds of this invention within the dosage range described herein and the other pharmaceutically active agent or treatment within its dosage range.

Accordingly, in an aspect, this invention includes combinations comprising an amount of at least one compound of the invention, or a pharmaceutically acceptable salt, solvate, ester or prodrug thereof, and an effective amount of one or more additional agents described above.

The pharmacological properties of the compounds of this invention may be confirmed by a number of pharmacological assays. Certain assays are exemplified elsewhere in this document.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

In one embodiment, the compound is administered orally.

In some embodiments, it may be advantageous for the pharmaceutical preparation comprising one or more compounds of the invention be prepared in a unit dosage form. In such forms, the preparation is subdivided into suitably sized unit doses containing appropriate quantities of the active component, e.g., an effective amount to achieve the desired purpose.

PREPARATIVE EXAMPLES

Compounds of the invention can be made using procedures known in the art.

The following reaction schemes show typical procedures, but those skilled in the art will recognize that other procedures can also be suitable.

Techniques, solvents and reagents may be referred to by their following abbreviations:
Thin layer chromatography: TLC
High performance liquid chromatography: HPLC
ethyl acetate: AcOEt or EtOAc
methanol: MeOH
ether: Et$_2$O
tetrahydrofuran: THF
Acetonitrile: MeCN
1,2-dimethoxyethane: DME
Trifluoroacetic acid: TFA
Dimethylacetamide: DMA
Dimethylformamide: DMF
Dimethylsulfoxide: DMSO
triethylamine: Et$_3$N or TEA
tert-Butoxycarbonyl: t-Boc or Boc
2-(Trimethylsilyl)ethoxycarbonyl: Teoc
nuclear magnetic resonance spectroscopy: NMR
liquid chromatography mass spectrometry: LCMS
high resolution mass spectrometry: HRMS
milliliters: mL
millimoles: mmol
microliters: µl
grams: g
milligrams: mg
centimeters: cm
room temperature (ambient, about 25° C.): rt
Retention time: tR
N-bromosuccinimide: NBS
N-chlorosuccinimide: NCS
Methyl magnesium bromide: MeMgBr
iron(III) acetylacetonate: Fe(acac)$_3$
Diphenylphosphoryl azide: DPPA
1-(3-Dimethylaminopropyl)-3-ethylcarbodiimide hydrochloride: EDCl
Diisopropylethylamine: DIEA or i-Pr$_2$NEt or DIPEA
Diisopropylamine: i-Pr$_2$NH
2-(Trimethylsilyl)ethanol: TMSethanol
3-Chloroperoxybenzoic acid: mCPBA
n-Butyllithium: nBuLi
lithium diisopropylamide: LDA
[1,1'-Bis(diphenylphosphino)ferrocene]dichloropalladium (II): PdCl$_2$dppf
Palladium(II) acetate: Pd(OAc)$_2$
Methanesulfonyl chloride: MeSO$_2$Cl
Triphenyl phosphine: TPP or Ph$_3$P
General Method I:

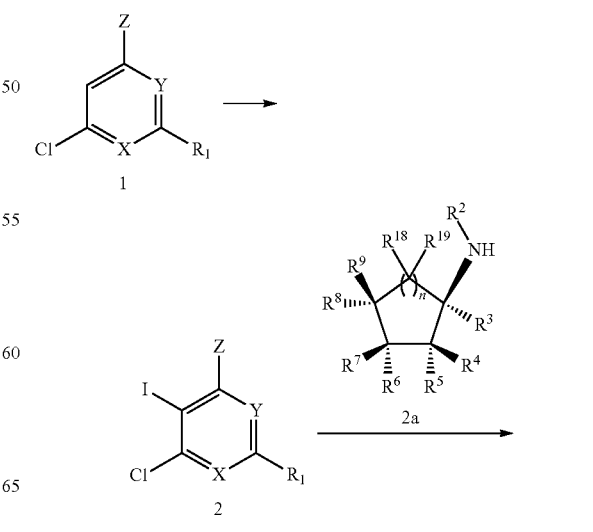

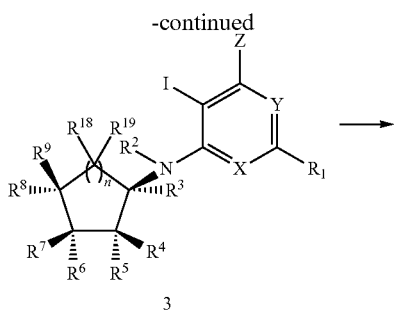

3

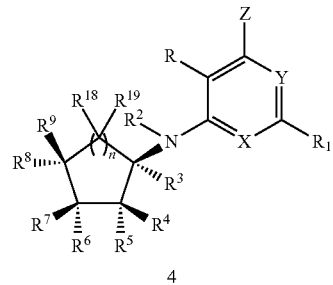

4 wherein X, Y, Z, R, $R^1$, $R^2$, $R^3$, $R^4$, $R^5$, $R^6$, $R^7$, $R^8$, $R^9$, $R^{18}$, $R^{19}$, and n are all variables as defined herein.

Example 5

Procedure A-1

To a stirred mixture of 2-amino-4,6-dichloropyrimidine (1, X, Y=N, Z=Cl, 5.0 g, 30.5 mmol) in glacial acetic acid (120 mL) was added dropwise a solution of ICl (5.01 mL, 100 mmol) in glacial acetic acid (120 mL). After 5 h, the mixture was filtered, and the collected solids were washed with glacial acetic acid and then azeotroped with toluene (2×), giving 2.78 g of 2 as a white solid. After 7 days, more solid was visible in the filtrate, and thus, it was again filtered, the collected solids washed with glacial acetic acid and azeotroped with toluene (2×), giving another 4.22 g of 2, with TLC and MS data that matched the first batch.

MS m/z (M+H)$^+$ 289.93 (2 Cl pattern);

A mixture of 2 (58.0 g, 0.20 mol), the cyclopentylamine sugar (1R,2S,3R,4R)-2,3-dihydroxy-4-(hydroxymethyl)-1-aminocyclopentane hydrochloride 2a, (40.4 g, 0.22 mol) in ethanol (800 ml) and triethylamine (92 ml, 0.66 mol) was refluxed for 18 h, during which time complete dissolution occurred. After concentrating and adsorbing the residue onto silica gel, the crude was purified by chromatography, eluting with a gradient of EtOAc/MeOH (97.5/2.5→95/5). The desired product 3 (X, Y=N, Z=Cl, $R^1$=NH$_2$, $R^2$, $R^3$, $R^4$, $R^7$, $R^8$=H, $R^5$, $R^6$=OH, $R^9$=CH$_2$OH) was obtained as a white solid (67 g).

MS m/z (M+H)$^+$ 401.00 (Cl pattern);

$^1$H NMR (300 MHz, DMSO-d6) δ 6.61 (s, 2H, 2H D$_2$O exchangeable), 6.22 (d, 1H, J=7.7 Hz, D$_2$O exchangeable), 4.75 (dd, 1H, J=4.8, 4.8 Hz, D$_2$O exchangeable), 4.60 (d, 1H, J=5.2 Hz, D$_2$O exchangeable), 4.41 (d, 1H, J=4.5 Hz, D$_2$O exchangeable), 4.30-4.18 (m, 1H; upon D$_2$O exchange collapses to 4.22, dd, J=7.4, 12.9 Hz), 3.77-3.70 (m, 2H), 3.39 (dd, 2H, J=5.1, 5.1 Hz; upon D$_2$O exchange collapses to 3.43, d, J=5.3 Hz), 2.24-2.14 (m, 1H), 1.93-1.83 (m, 1H), 1.15-1.06 (m, 1H).

Analysis calculated for C$_{16}$H$_{18}$Cl$_2$N$_6$O$_3$: C, 46.50; H, 4.39; N, 20.34. Found: C, 46.25; H, 4.26; N, 20.09

Example 5

(1R,2S,3R,5R)-3[(2-amino-6-chloro-5-phenyl-4-pyrimidinyl)amino]-5-hydroxymethyl)-1,2-cyclopentanol To a stirring solution of compound 3 (X, Y=N, Z=Cl, $R^1$=NH$_2$, $R^2$, $R^3$, $R^4$, $R^7$, $R^8$=H, $R^5$, $R^6$=OH, $R^9$=CH$_2$OH, 0.1 g; 0.25 mmol) (under Ar at room temperature) and phenylboronic acid (0.04 g; 0.3 mmol) in anhydrous DMF (5.0 mL) was added anhydrous K$_2$CO$_3$ (0.17 g; 1.25 mmol). After 5.0 min, tetrakis(triphenylphosphine)-palladium (0) (0.014 g; 0.012 mmol) was added. The reaction vessel (RB flask) was then covered with aluminum foil and stirred at 90° C. for 24 h. Then, the reaction mixture was cooled to room temperature (22° C.), and the solvent was removed in vacuo and then co-evaporated with MeOH. The obtained brown residue was purified by column chromatography, eluting with 94:6 CHCl$_3$/MeOH (V/V) (Fisher), giving the pure product 5 (Structure 4, General Method I, R=phenyl, X, Y=N, Z=Cl, $R^1$=NH$_2$, $R^2$, $R^3$, $R^4$, $R^7$, $R^8$=H, $R^5$, $R^6$=OH, $R^9$=CH$_2$OH) as an off-white solid (0.045 g).

General Method II:

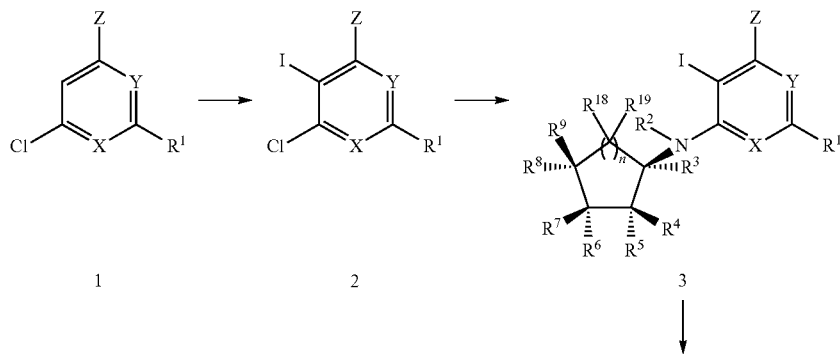

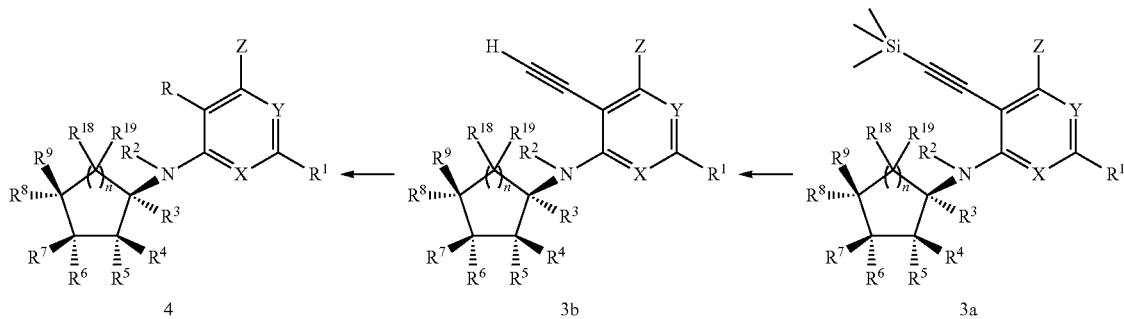

Wherein X, Y, Z, R, $R^1$, $R^2$, $R^3$, $R^4$, $R^5$, $R^6$, $R^7$, $R^8$, $R^9$, $R^{18}$, $R^{19}$, and n are all variables as defined herein.

Example 9

Procedure A-2

To a degassed solution of 3 (synthesis previously described, X, Y=N, Z=Cl, $R^1$=$NH_2$, $R^2$, $R^3$, $R^4$, $R^7$, $R^8$=H, $R^5$, $R^6$=OH, $R^9$=$CH_2OH$, 5.0 g, 12.5 mmol) in DMF (50 ml) was added (with protection from light) triethylamine (7.0 mL, 50 mmol) dropwise over 10 min, followed by CuI (952 mg, 5.0 mmol) and then tetrakis(triphenylphosphine)palladium (2.9 g, 2.5 mmol). After degassing with Ar for 10 min, the addition of TMS acetylene (5.3 mL, 37.5 mmol) was followed by sealing the reaction vessel with a rubber septum. Then, while still protecting the sealed flask from light, the reaction mixture was heated in an oil bath at 55° C. for 18 h. After concentrating, the methanol extract was filtered, and the filtrate concentrated onto silica. Chromatography on silica (eluting gradient of $CHCl_3$/MeOH (95/5→90/10) gave 2.62 g of a brown foam that contained triethylamine salts. A second chromatography (eluting with EtOAc/MeOH, 95/5) gave 2.55 g of 3a (X, Y=N, Z=Cl, $R^1$=$NH_2$, $R^2$, $R^3$, $R^4$, $R^7$, $R^8$=H, $R^5$, $R^6$=OH, $R^9$=$CH_2OH$) as a reddish brown solid. (Even after the 2 chromatographic isolations, the obtained 3a still contained impurities, by TLC, that was used as is in the next reaction.)

$^1$H NMR (300 MHz, DMSO-d6) δ 6.94 (s, 2H), 6.10 (d, 1H, J=7.7 Hz), 4.68-4.62 (m, 2H), 4.45 (d, 1H, J=4.5 Hz), 4.27-4.17 (m, 1H), 3.76-3.65 (m, 2H), 3.40 (dd, 2H, J=5.1, 5.1 Hz), 2.26-2.16 (m, 1H), 1.93-1.83 (m, 1H), 1.16-1.07 (m, 1H), 0.23 (s, 3H).

To a solution of 3a (X, Y=N, Z=Cl, $R^1$=$NH_2$, $R^2$, $R^3$, $R^4$, $R^7$, $R^8$=H, $R^5$, $R^6$=OH, $R^9$=$CH_2OH$) 4.17 g, 11.2 mmol) in acetonitrile (100 ml) was added tetraethylammonium fluoride dihydrate (1.04 g, 5.62 mmol). After 2 h, MeOH was added to dissolve precipitated material, and the resulting solution was concentrated onto silica gel. Chromatography on silica (eluting gradient of $CHCl_3$/MeOH, 95/5→92.5/7.5) followed by chromatography eluting with EtOAc/MeOH (95/5) resulted in the recovery of 3.06 g of 3b (X, Y=N, Z=Cl, $R^1$=$NH_2$, $R^2$, $R^3$, $R^4$, $R^7$, $R^8$=H, $R^5$, $R^6$=OH, $R^9$=$CH_2OH$) as a light tan solid.

$^1$H NMR (DMSOd$_6$): δ1.10 (m, 1H), 1.89 (m, 1H), 2.15 (m, 1H), 3.38 (t, J=5.1 Hz, 2H), 3.73 (m, 2H), 4.28 (m, 1H), 4.40 (d, 1H, J=3.9 Hz), 4.58 (d, 1H, J=5.1 Hz), 4.71 (t, 1H, J=5.1 Hz), 6.58 (d, 1H, J=8.1 Hz), 6.87 (s, 2H)

MS m/z (M+H)$^+$: 299.15 (Cl pattern);

Example 9

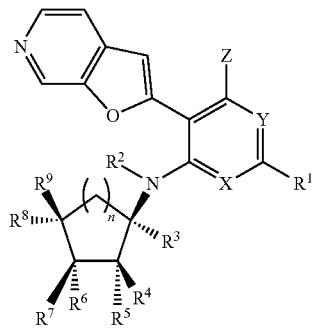

To a degassed solution of 3b (150 mg, 0.50 mmol) and a 1-halo, 2-hydroxy or thio-aryl compound (e.g., 4-iodo-3-pyridinol, 261 mg, 1.5 mmol) in DMF (5 ml) was added (with protection from light) triethylamine (0.28 ml, 2.0 mmol), followed by CuI (38 mg, 0.2 mmol) and then tetrakis(triphenylphosphine)palladium (116 mg, 0.1 mmol). After sealing the reaction vessel with a rubber septum, the reaction mixture was heated in an oil bath at 40° C. for 18 h. After concentrating, the methanol extract was filtered and the filtrate chromatographed, using an elution gradient of $CHCl_3$/MeOH (95/5→90/10). Example 9 (X, Y=N, Z=Cl, $R^1$=$NH_2$, $R^2$, $R^3$, $R^4$, $R^7$, $R^8$=H, $R^5$, $R^6$=OH, $R^9$=$CH_2OH$, 24 mg) was recovered as yellow crystals after recrystallizing from MeOH.

Analysis calculated for $C_{17}H_{18}ClN_5O_4$ 0.1 MeOH 1.1SiO$_2$: C, 44.70; H, 4.04; N, 15.24.

Found: C, 44.72; H, 4.20; N, 15.24.

Example 21

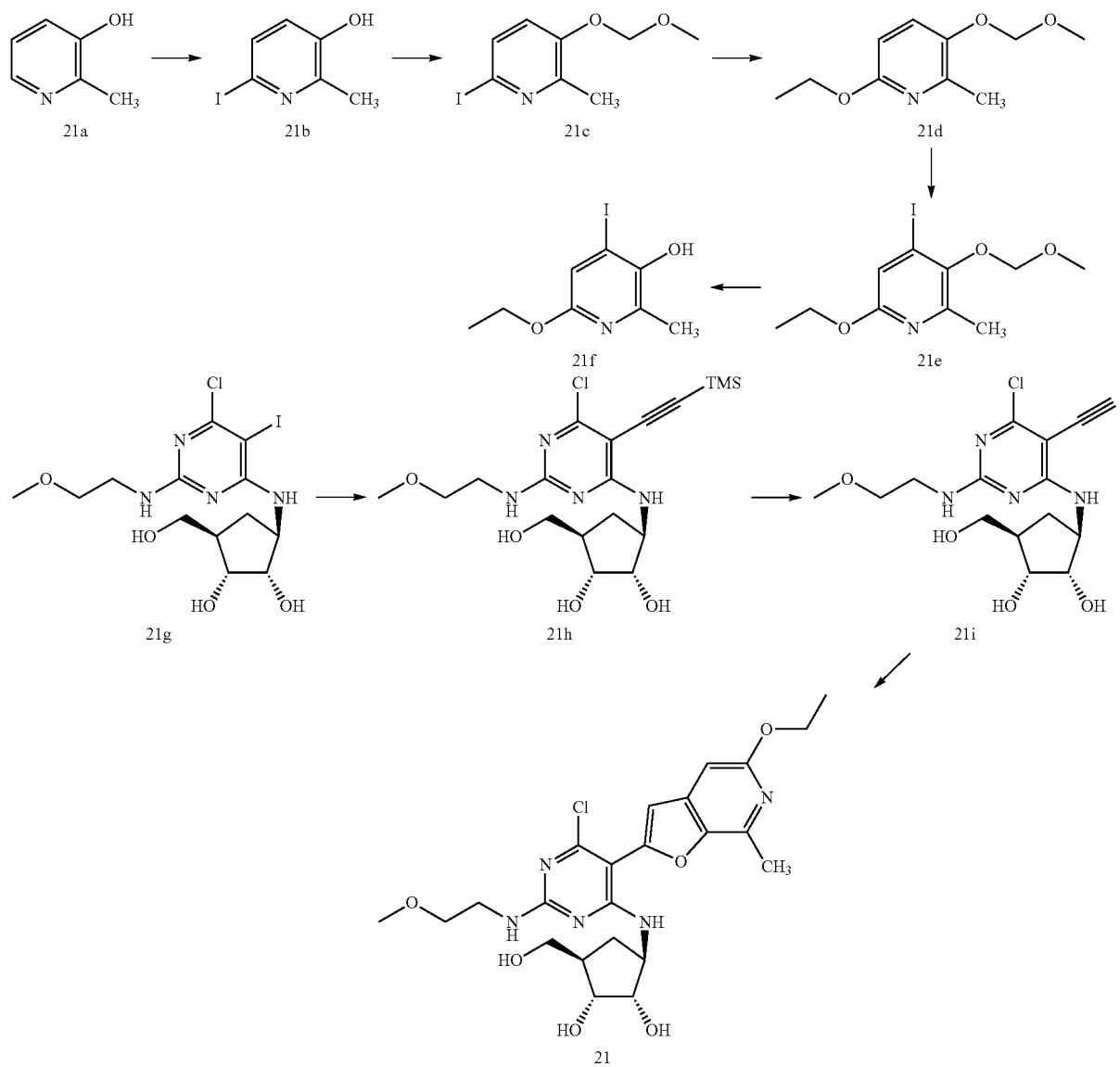

To a stirred solution of potassium carbonate (111 g, 0.80 mol) in water (350 ml) at room temperature under Ar was added 3-hydroxy-2-methylpyridine (21a, 25.6 g, 0.23 mol). After cooling in an ice bath, iodine (70.0 g, 0.28 mol) was added, and the reaction was allowed to warm to room temperature overnight. After adding saturated aqueous sodium thiosulfate, the reaction mixture was acidified with conc. aqueous HCl to a pH of 2, followed by extraction with ethyl acetate (3×). The combined organic extract was washed with water, saturated brine, dried with sodium sulfate, and then concentrated. Recovered 55.5 g of crude product that was chromatographed on silica, eluting with a EtOAc/hexanes gradient (0/100→75/25). Recovered 21b (33.7 g) as a slightly yellow solid.

To a stirred mixture of 21b (33.7 g, 0.143 mol) in methylene chloride (400 ml) under Ar and cooled in a dry ice/acetone bath was added chloromethyl methyl ether (12.5 ml, 0.165 mol). After 15 min, diisopropylethyl amine (37.4 ml, 0.215 mol) was added dropwise over 30 min. The resulting mixture was then allowed to slowly warm to room temperature overnight. The reaction solution was washed with water (2×), saturated brine, dried with sodium sulfate, and concentrated. Recovered 37.4 g of crude product that was chromatographed on silica, eluting with a EtOAc/hexanes gradient (0/100→90/10). Recovered 21c (36.0 g) as a slightly colored oil.

To a solution of 21c (2.5 g, 8.96 mmol) in absolute ethanol (25 ml) was added sodium ethoxide (3.8 g, 44.8 mmol) followed by sonication to give an orange solution. After adding copper (I) bromide (262 mg, 1.79 mmol), the resulting mixture was placed in a preheated oil bath at 95° C. After 4.5 h, the reaction was cooled to room temperature and then filtered through a short pad of celite, washing with ethanol. Combined filtrate was concentrated, followed by partitioning with ethyl acetate and water. The separated aqueous layer was further extracted with ethyl acetate. The combined organic extract was washed saturated brine, dried (MgSO$_4$), and concentrated. Recovered 1.72 g of crude product that was chromatographed on silica, eluting with a EtOAc/hexanes gradient (0/100→90/10). Recovered 21d (1.60 g) as a slightly yellow oil.

To a solution of 21d (1.20 g, 6.1 mmol) in THF under Ar, a solution of 1.6M nBuLi in hexanes (4.2 ml, 6.7 mmol) was added dropwise at a rate to keep the reaction temperature <−70° C. After 1 h, a solution of iodine (1.85 g, 7.3 mmol) in THF (25 ml) was added dropwise again at a rate to keep the reaction temperature <−70° C. After 2 h, dilute aqueous ammonium chloride was added, and the reaction was allowed to warm to room temperature. After partitioning between ethyl acetate and water, the organic extract was washed saturated aqueous sodium thiosulfate, water, saturated brine, dried with sodium sulfate, and concentrated. Recovered 2.07 g of crude product that was then chromatographed on silica eluting with EtOAc/hexanes (25/75). Recovered 21e (1.77 g) as a slightly yellow oil that contained (by NMR) 10% starting material.

To a solution of 21e (1.77 g, 5.48 mmol) in methylene chloride (50 ml) under Ar cooled in an ice/water bath was added trifluoroacetic acid (10.2 ml, 137 mmol). After allowing to warm room temperature while stirring overnight, the solution was diluted with methylene chloride and carefully washed saturated aqueous sodium bicarbonate until the aqueous layer was basic. The organic extract was washed water, saturated brine, dried with sodium sulfate, and concentrated, giving 21f (1.16 g) of 2,4,6-trichloropyrimidine as a yellow solid that was used as is.

Compound 21 g was prepared from 2,4,6-trichloropyrimidine in a fashion similar to 124e.

To a degassed solution of 21 g (2.64 g, 5.75 mmol) in dioxane (50 ml) was added triethylamine (3.2 ml, 23 mmol) followed by CuI (219 mg, 1.15 mmol) and then dichlorobis(triphenylphosphine) palladium (404 mg, 0.575 mmol). After degassing with Ar for 10 min, the addition of TMS acetylene (2.44 ml, 17.3 mmol) was followed by sealing of the reaction vessel with a rubber septum. While protecting from light, the sealed flask was heated in an oil bath at 50° C. for 20 h. After concentrating onto silica, the residue was chromatographed on silica, eluting with a CHCl$_3$/MeOH gradient (100/0→90/10). Recovered a product that contained triethylamine salts. After chromatography on silica eluting with EtOAc/MeOH (100/0→90/10), recovered 1.71 g of 21 h as a purple foam.

To a solution of 21 h (1.7 g, 3.96 mmol) in acetonitrile (25 ml) was added tetraethylammonium fluoride dihydrate (367 mg, 1.98 mmol). After stirring overnight, the reaction mixture was concentrated onto silica gel and chromatographed on silica, eluting with a CHCl$_3$/MeOH gradient (100/0→95/5). Recovered 1.32 g of 21i as a light brown crystalline solid.

To a degassed solution of 21i (178 mg, 0.50 mmol) and 21f (167 mg, 0.60 mmol) in DMF (5 ml) was added triethylamine (0.35 ml, 2.5 mmol) followed by CuI (19 mg, 0.1 mmol) and then tetrakistriphenylphosphine palladium (58 mg, 0.05 mmol). After sealing, the reaction vial was microwaved (300W) at 90° C. for 10 min. After concentrating, the methanol extract was concentrated onto silica and chromatographed eluting with a CHCl$_3$/MeOH gradient (100/0→90/10). Recovered 236 mg of a yellow solid that was purified by reverse phase HPLC (Phenomenex Luna C-18 column) using water/MeCN (containing 0.1% TFA) gradient. Recovered 104 mg of 21 as a yellow solid.

Example 101

Procedure A

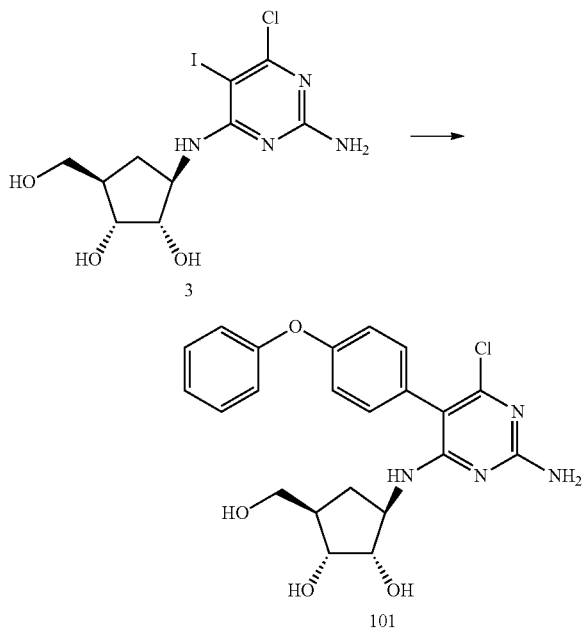

A mixture of 3 (previously described, 40 mg, 0.1 mmol), 4-phenoxyphenyl boronic acid (63 mg, 0.3 mmol), potassium carbonate (69 mg, 0.5 mmol) and (1,1'-bis(diphenyl)phosphino)ferrocene) dichloropalladium (II) (16 mg, 0.02 mmol) in dimethoxyethane (2 ml)/water (1 ml) was heated to 90° C. for 1.5 hr. The reaction mixture was cooled to room temperature, filtered and concentrated. The dark residue was purified by silica gel (50 g prepacked cartridge) using 0/100 to 8/92 MeOH/chloroform to provide 101 (12 mg).

Example 102

Procedure B

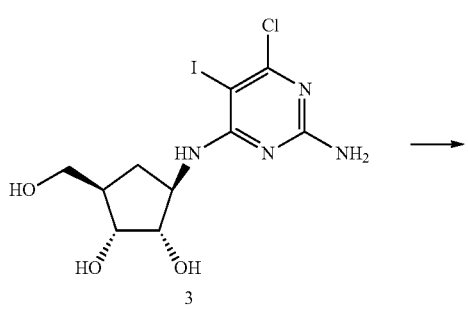

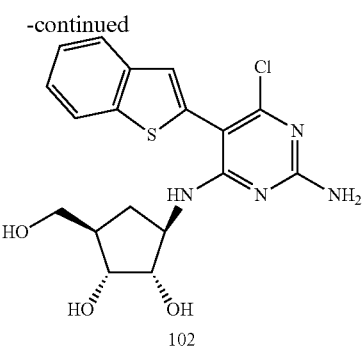

To a 0.5-2 ml microwave vial containing stir bar was added intermediate 3 (previously described, 40 mg, 0.1 mmol), thiophene-2-boronic acid (55 mg, 0.3 mmol), potassium carbonate (69 mg, 0.5 mmol) and (1,1'-bis(diphenylphosphino)ferrocene) dichloropalladium (II) (10 mg, 0.01 mmol) and dimethoxyethane (1 ml)/water (0.5 ml). The vial was sealed and subjected to microwave reaction at 120° C. for 15 min. Then the solvent was removed in vacuo, and the residue dissolved in chloroform/MeOH and flushed through a silicycle Si-carbonate cartridge (2 g). The cartridge was flushed with MeOH (~15 ml) and the filtrate was combined and concentrated. The crude residue was purified by reverse phase HPLC (Phenomenex Luna C-18 column) using water/MeCN (containing 0.1% formic acid) gradient which resulted in 16 mg of 102.

Example 105

Procedure C

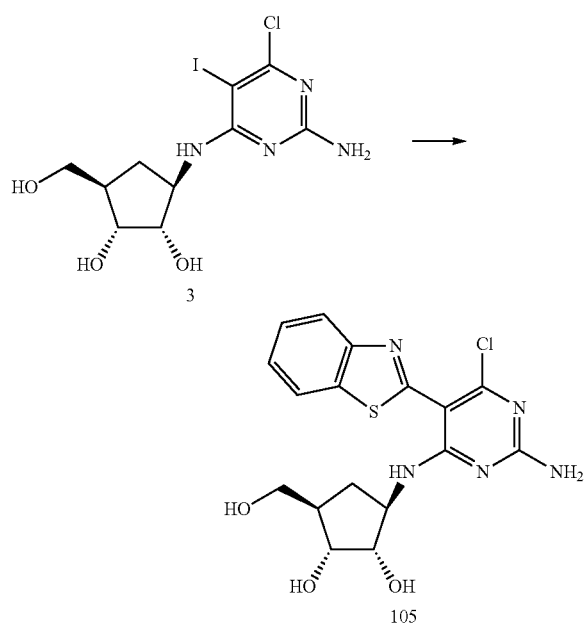

To a 0.5-2 ml microwave vial containing stir bar was added intermediate 3 (previously described, 60 mg, 0.15 mmol), tri-n-butylstannyl benzothiazole (128 mg, 0.3 mmol), copper iodide (12 mg, 0.06 mmol), dichlorobis(triphenylphosphine) palladium(II) (21 mg, 0.03 mmol), triethylamine (0.09 ml, 0.6 mmol) and DMF (1.5 ml). The vial was sealed and subjected to microwave reaction at 120° C. for 15 min. Then the solvent was removed in vacuo, and the residue dissolved in MeOH (~15 ml) and flushed through a silicycle Si-carbonate cartridge (2 g). The cartridge was flushed with MeOH (~15 ml) and the filtrate was combined and concentrated. The crude residue was purified by reverse phase HPLC (Phenomenex Luna C-18 column) using water/MeCN (containing 0.1% formic acid) gradient which resulted in 18 mg of 105 as a pale yellow solid.

Note: Tetrakis(triphenylphosphine) palladium(0) can be used, instead of dichlorobis(triphenylphosphine) palladium (II), as the catalyst with similar results.

Example 108

Procedure D

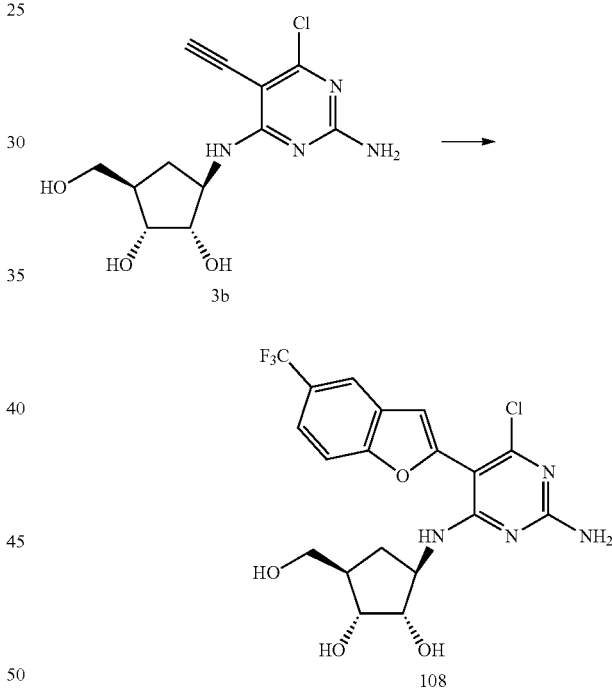

To a 0.5-2 ml microwave vial containing stir bar was added intermediate 3b (previously described by, 100 mg, 0.335 mmol), 2-bromo-4-trifluoromethyl phenol (121 mg, 0.5 mmol), copper iodide (26 mg, 0.134 mmol), tetrakis(triphenylphosphine) palladium(0) (77 mg, 0.07 mmol), triethylamine (0.19 ml, 1.34 mmol) and DMF (1.6 ml). The vial was sealed and subjected to microwave reaction at 120° C. for 10 min. Then the solvent was removed in vacuo, and the residue dissolved in MeOH (~15 ml). The solid was filtered off and the filtrate was flushed through a silicycle Si-carbonate cartridge (2 g). The cartridge was flushed with MeOH (~5 ml) and the filtrate was combined and concentrated. The crude residue was purified by reverse phase HPLC (Phenomenex Luna C-18 column) using water/MeCN (containing 0.1% formic acid) gradient which resulted in 41 mg of 108 as a pale yellow solid.

Example 110

Procedure E

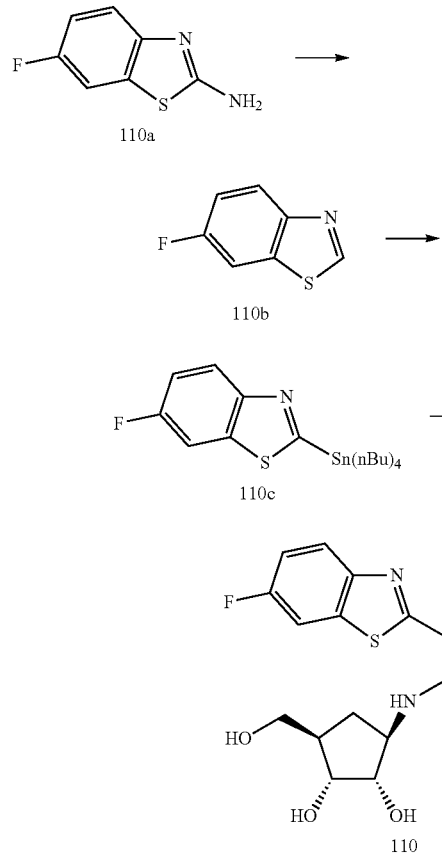

Step 1: Compound 110a was converted to compound 110b using literature described procedure (Chem. Pharm. Bull., 1998, 46 (4), 623-630.

Step 2: Compound 110b thus obtained (765 mg, 5 mmol) was dissolved in THF (10 ml) and cooled to −78° C. BuLi (1.6 M in hexanes, 3.15 ml, 5 mmol) was added dropwise over 15-20 minute period. Maintained reaction temperature at −78° C. for 1 hr and then added a solution of tri-n-butylstannyl chloride (1.63 g, 5 mmol) in THF (5 ml) over 15-20 min period. The reaction was warmed to −10° C. over 3 hrs. Then the reaction mixture was concentrated in vacuo. The crude material was dissolved in diethyl ether (~20 ml) and filtered. The filtrate was concentrated to provide 110c (2.16 g), which was used without any purification.

Step 3: Treatment of 110c with 3 (0.15 mmol) followed procedures described above (Procedure C). After the reaction the residue was dissolved in MeOH and filtered thru 0.2 uM polypropylene filter cartridge. The filtrate was concentrated and the residue was purified as described above (see Procedure A) using reverse phase HPLC to obtain 37 mg of solid material. This solid was washed with acetone few times (4-5 ml each time) to provide 23 mg of 110.

Example 115

Procedure F

-continued

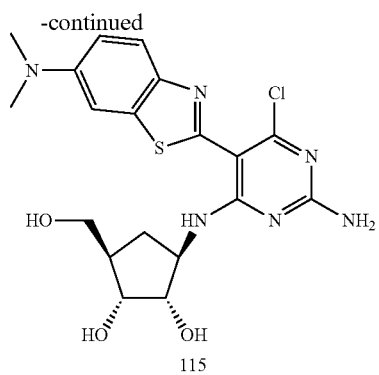

115

Step 1: To a slurry of 3 (4.8 g, 12 mmol) in acetone at 0° C. was added 2,2-dimethoxypropane (2.97 ml, 24 mmol) followed by methanesulfonic acid (0.78 ml, 12 mmol). The reaction mixture was warmed to room temperature, overnight. Then the solvent was concentrated. To the residue was added saturated sodium bicarbonate solution (150 ml) and extracted with chloroform (2×100 ml). The organic layers were combined, washed with saturated sodium bicarbonate solution (150 ml), brine (200 ml), dried ($Na_2SO_4$), filtered and concentrated to afford 114a (5.48 g) which was taken further without any purification.

Step 2: To a 5 ml microwave vial containing stir bar were added intermediate 114a (180 mg, 0.41 mmol), benzothiazole derivative 114b (140 mg, 0.79 mmol, 114b was prepared as described in literature; Synthesis, 2005, 4, 600-604), copper iodide (20 mg, 0.1 mmol), tetrakis(triphenylphosphine) palladium(0) (75 mg, 0.065 mmol), cesium carbonate (650 mg, 2 mmol) and DMF (4 ml). The vial was sealed and subjected to microwave reaction at 100° C. for 30 min. Then the reaction mixture was filtered thru 0.2 uM polypropylene filter cartridge and rinsed with EtOAc. Added water to the filtrate (50 ml) and extracted with EtOAc (2×50 ml). The organic layers were combined, washed with water (50 ml), brine (50 ml), dried ($Na_2SO_4$), filtered and concentrated. The residue was purified by silica gel (40 g prepacked cartridge) using 10/90 to 70/30 EtOAc/hexanes to provide 114 as a solid (26 mg). Some amounts of both the starting materials (114a and 114b) were also recovered.

Step 3: The material obtained above, 114 (26 mg) was taken in MeOH (2 ml) and treated with aq 1N HCl (2 ml) at room temperature, overnight. The solvent was concentrated and the residue was dried under vacuum to provide 115 (26 mg, HCl salt).

Examples 120 and 121

Procedure G

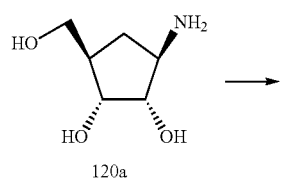

120a

-continued

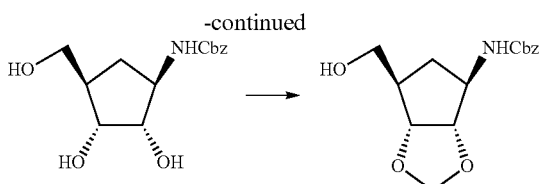

120b         120c

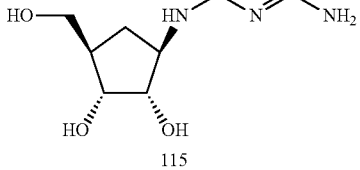

120d

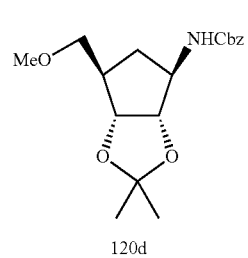 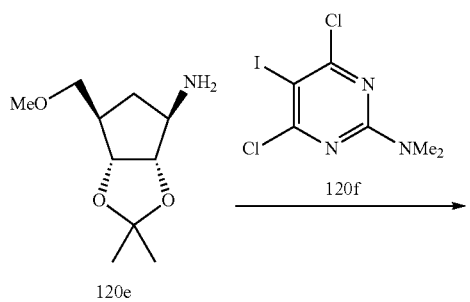

120e         120f

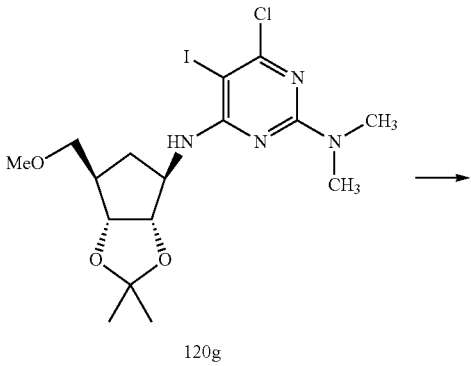

120g

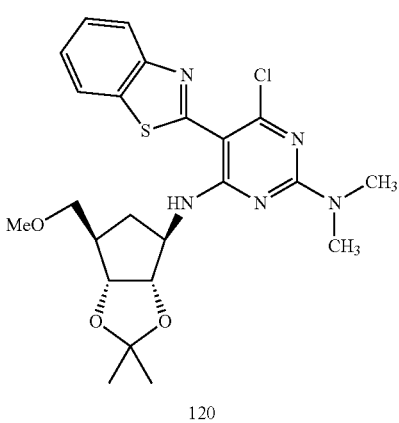

120

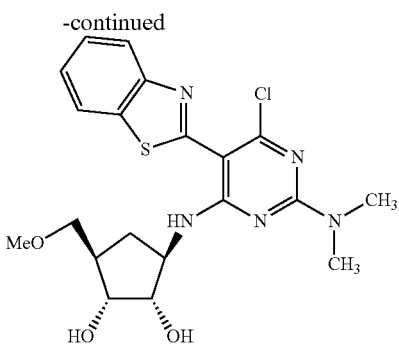

121

Step 1: To the carbasugar 120a (same as 2a, 1 g, 5.45 mmol) in dioxane (10 ml) and aq 1M sodium carbonate solution (15 ml) at room temperature was added Cbz-Cl (0.78 ml, 5.45 mmol). Stirred at room temperature for 5 hrs. Then concentrated the solvent. To the residue was added water (250 ml) and dichloromethane (150 ml). The org layer was separated and the aq layer was extracted with EtOAc (150 ml). The combined org layer was concentrated to approx half it volume and stored at 0 C overnight. The precipitated solid was filtered off. The filtrate was concentrated and the residue was combined with the solid to provide 120b (610 mg).

Step 2: To a slurry of 120b (590 mg, 2.1 mmol) in acetone (20 ml) at 0° C. was added 2,2-dimethoxy propane (0.52 ml, 4.2 mmol) and methanesulfonic acid (4 drops). The reaction mixture was warmed to room temperature, overnight. Then the solvent was concentrated. To the residue was added saturated sodium bicarbonate solution (75 ml) and extracted with EtOAc (75 ml). The organic layer was separated, washed with brine (50 ml), dried (Na$_2$SO$_4$), filtered and concentrated to afford 120c (680 mg) which was taken further without any purification.

Step 3: To a solution of 120c (640 mg, 2 mmol) in acetonitrile (20 ml) was added iodomethane (2.1 ml, 34 mmol) and silver oxide (740 mg, 3.2 mmol). The reaction flask was covered with aluminum foil and refluxed overnight. The reaction mixture was cooled to room temperature, filtered through a pad of celite and rinsed with EtOAc. The combined filtrate was concentrated. The residue was purified by silica gel (80 g prepacked cartridge) using 10/90 to 60/40 EtOAc/hexanes to provide 120d (380 mg, white solid).

Step 4: To a solution of 120d (370 mg, 1.12 mmol) in MeOH (20 ml) was added 10% palladium on carbon (catalytic amount) and the mixture was hydrogenated (using a balloon filled with hydrogen gas) at room temperature for 3 hrs. The reaction mixture was filtered through a pad of celite and the filtrate was concentrated to provide 120e (200 mg).

Step 5: To 120e (190 mg, 1 mmol) and 120f (318 mg, 1 mmol, prepared as described below for 124d from appropriate starting material) in ethanol (10 ml) was added triethylamine (0.5 ml, 3.5 mmol) and heated to reflux, overnight. The reaction mixture was concentrated and purified by silica gel (40 g prepacked cartridge) using 25/75 to 75/25 of dichloromethane/hexanes to provide 120 g (205 mg).

Step 6: To 120 g (200 mg, 0.42 mmol) in dioxane (7 ml) was added a solution of tri-n-butylstannyl benzothiazole (350 mg, 0.84 mmol) in dioxane (3 ml). Then tetrakis(triphenylphosphine) palladium (0) (100 mg, 0.084 mmol), copper iodide (16 mg, 0.084 mmol) and triethylamine (0.24 ml, 1.68 mmol) were added and the mixture was heated to 100° C. for 1 hr. The reaction mixture was cooled to room temperature, filtered through 0.2 micron syringe filter and concentrated.

The residue was purified by silica gel (40 g prepacked cartridge) using 0/100 to 50/50 EtOAc/hexanes to provide 120 as a solid (150 mg) which was slightly impure. This material was washed with MeOH (3×5-10 ml) to provide pure 120 (100 mg).

Step 7: To 120 (95 mg, 0.194 mmol) in MeOH (6 ml) was added aq 1N HCl (9 ml) and dioxane (9 ml) and stirred at room temperature, overnight. The mixture was concentrated to give a solid residue that was washed with diethyl ether (2×10 ml). The resultant solid was dried to provide 121 (75 mg) as HCl salt.

Example 124

Procedure H

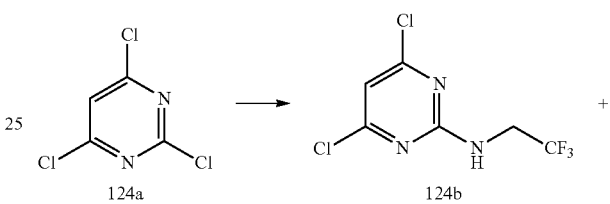

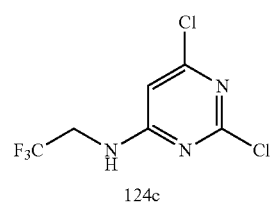

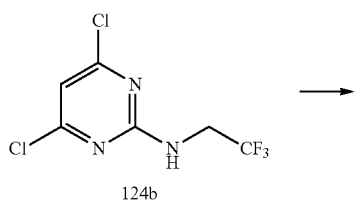

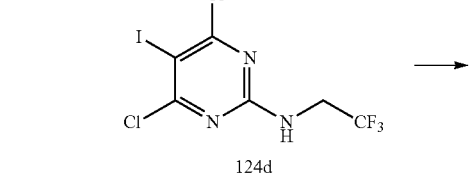

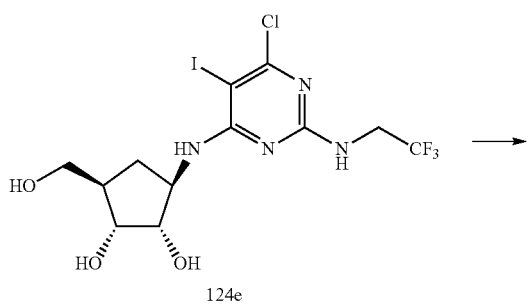

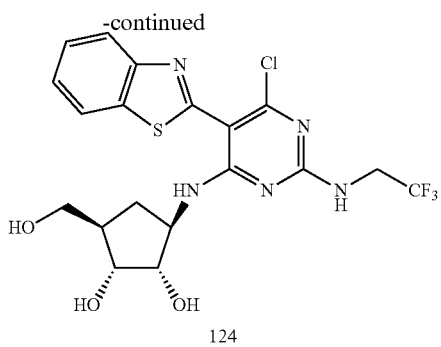

124

Step 1: To trichloropyrimidine 124a (2.9 ml, 25 mmol) in THF (25) at −15 C was added a solution of trifluoroethylamine (3.74 ml, 47.5 mmol) in THF (25 ml) over 1 hr. The reaction was warmed to 10 C over 4 hrs and stored at 8 C for approximately 48 hrs. Then water (150 ml) was added and extracted with EtOAc (2×150 ml). The combined organic layer was washed with brine (150 ml), dried (Na₂SO₄), filtered and concentrated. The residue (white solid, ~7 g, 124b and 124c) was stirred in heptane (100 ml) for 30 min at room temperature. The solid was filtered off, the filtrate was concentrated and purified by silica gel (120 g prepacked cartridge) using 0/100 to 50/50 EtOAc/hexanes to provide only 124b (1.04 g, white solid).

Step 2: To 124b (1 g, 4.07 mmol) in acetic acid (10 ml) was added a solution of ICl (1.98 g, 12.2 mmol) in acetic acid (10 ml) over 30 minutes at room temperature. The mixture was stirred at room temperature, overnight. Added more ICl (2×~2 g) in acetic acid (5 ml) for complete conversion of starting material. The reaction was quenched by dropwise addition of ice cold saturated sodium bicarbonate solution (200 ml). Then added EtOAc (150 ml) and the mixture was stirred overnight. The organic layer was separated and the aqueous layer was extracted with EtOAc (100 ml). The combined organic layer was washed with saturated sodium bicarbonate (200 ml), 10% aq. sodium bisulfite (2×200 ml), brine (150 ml), dried (Na₂SO₄), filtered and concentrated to afford 124d (1.68 g) as a white solid.

Step 3: The above obtained intermediate 124d (1.65 g, 4.44 mmol) in EtOH (25 ml) was treated with carbasugar 120a (4.40 mmol) and triethylamine (2.2 ml, 15.54 mmol). The mixture was refluxed, overnight. Then solvent was evaporated, and the residue was washed with water several times to afford 124e (1.88 g) as a solid.

Step 4: To a mixture of 124e (482 mg, 1 mmol), tetrakis(triphenylphosphine) palladium (0) (231 mg, 0.2 mmol), copper iodide (38 mg, 0.2 mmol), triethylamine (0.56 ml, 4 mmol) and tri-n-butylstannyl benzothiazole (848 mg, 2 mmol) in dioxane (20 ml) were added and the mixture was heated to 100 C for 1 hr. The reaction mixture was cooled (RT to 50 C), diluted with EtOAc and filtered thorough a pad of celite. The filtrate was concentrated. The solid residue was washed with dichloromethane/MeOH (minimum amount) and the filtrate was discarded. The solid was then washed with 1:1 dichloromethane/MeOH (few times) and filtered. The solid (258 mg) was essentially product, 124 (by mass spectral analysis). The filtrate was concentrated and purified by silica gel (50 g prepacked cartridge) using 0/100 to 12/88 MeOH/dichloromethane to afford a yellow-brown solid (42 mg) that was washed with cold acetone (3×~2 ml) to provide additional 124 (21 mg, pale yellow solid).

Example 125

Procedure I

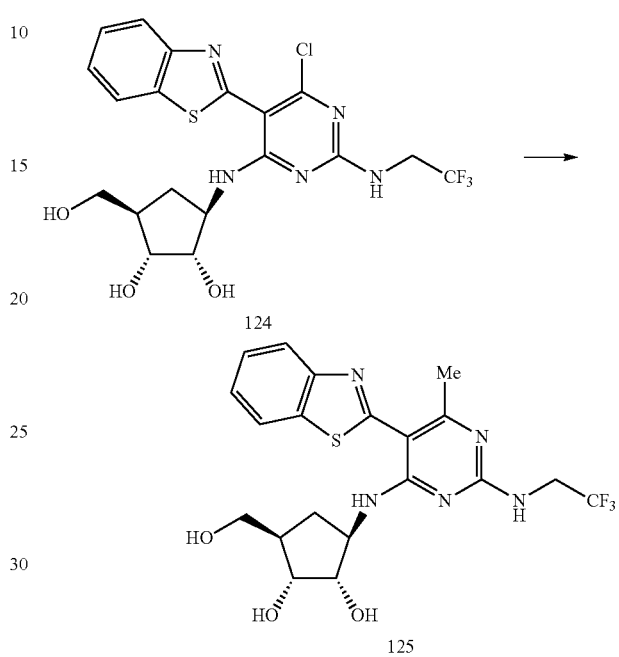

A mixture of 124 (122 mg, 0.25 mmol), methyl boronic acid (45 mg, 0.75 mmol), potassium carbonate (173 mg) and dichloro(bis-triphenylphosphine)palladium II (35 mg, 0.05 mmol) in dioxane (6 ml)/water (3 ml) was heated to 100-110 C for 2 hr. The solvent was evaporated and the residue was washed with water. The remaining black residue was purified by silica gel (50 g prepacked cartridge) using 0/100 to 12/88 MeOH/dichloromethane to provide 125 (31 mg) as an off-white solid.

(Note: Tetrakis(triphenylphosphine) palladium (0) can be used instead of dichloro(bis-triphenylphosphine)palladium II with similar results).

Example 112

Procedure J

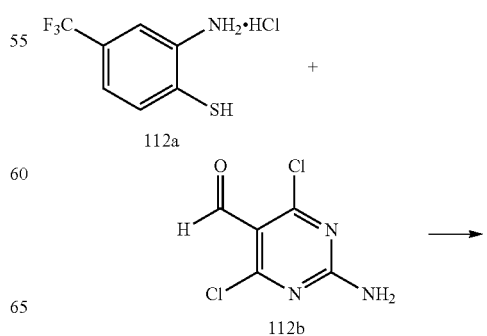

111

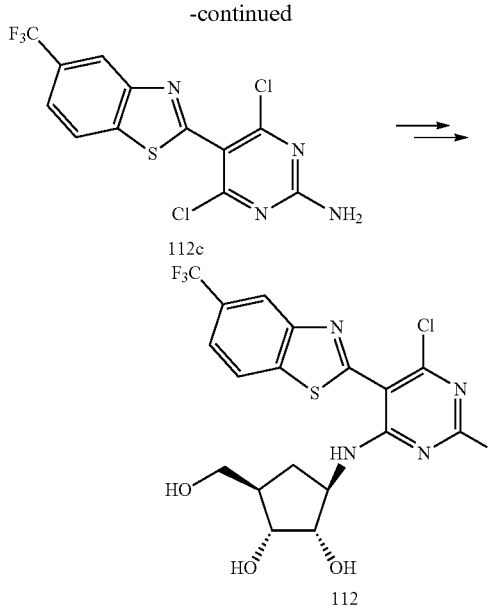

To a mixture of 112a (253 mg, 1.1 mmol) and 112b (192 mg, 1.0 mmol) was added DMF (20 ml) and the reaction mixture was stirred at room temperature overnight. Then poured the mixture into ice/saturated sodium bicarbonate solution (40 ml). The precipitated solid was collected by filtration and washed with water. The solid was taken in DMF (10 ml) and added gl. acetic acid (10 drops). The reaction mixture was stirred at room temperature overnight and processed as above. The solid thus obtained (223 mg) was taken in dichloromethane (10 ml) and treated with DDQ (138 mg, 0.6 mmol) at room temperature for 1 hr. The reaction mixture was diluted with chloroform (30 ml) and washed with saturated sodium bicarbonate solution (50 ml). Separated the organic layer, and the aqueous layer was extracted with EtOAc (50 ml). Combined the organic layers, dried ($Na_2SO_4$), filtered and concentrated to provide 112c which was taken further without any purification.

Conversion of 112c (0.6 mmol) to required product 112 followed procedures described above (Procedure H, Step 3). Crude 112 thus obtained was treated with excess di-tert-butyl dicarbonate (440 mg), catalytic DMAP (10 mg) in THF (8 ml) at room temperature, overnight. The reaction mixture was processed using EtOAc (50 ml) and brine (50 ml). The organic layer was separated, dried ($Na_2SO_4$), filtered and concentrated. The residue was purified using silica gel (prepacked, 40 g cartridge) with 20/80 to 70/30 of EtOAc/hexanes. This resulted in 32 mg of product containing two t-boc groups. This material was deprotected with 4M HCl in dioxane (5 ml) at room temperature, overnight. The reaction mixture was concentrated, and the residue purified using silica gel (prepacked, 12 g cartridge) with 1/99 to 12/88 of MeOH/chloroform to provide 6 mg of 112 as a light brown solid.

Example 403 and 404

Procedure K

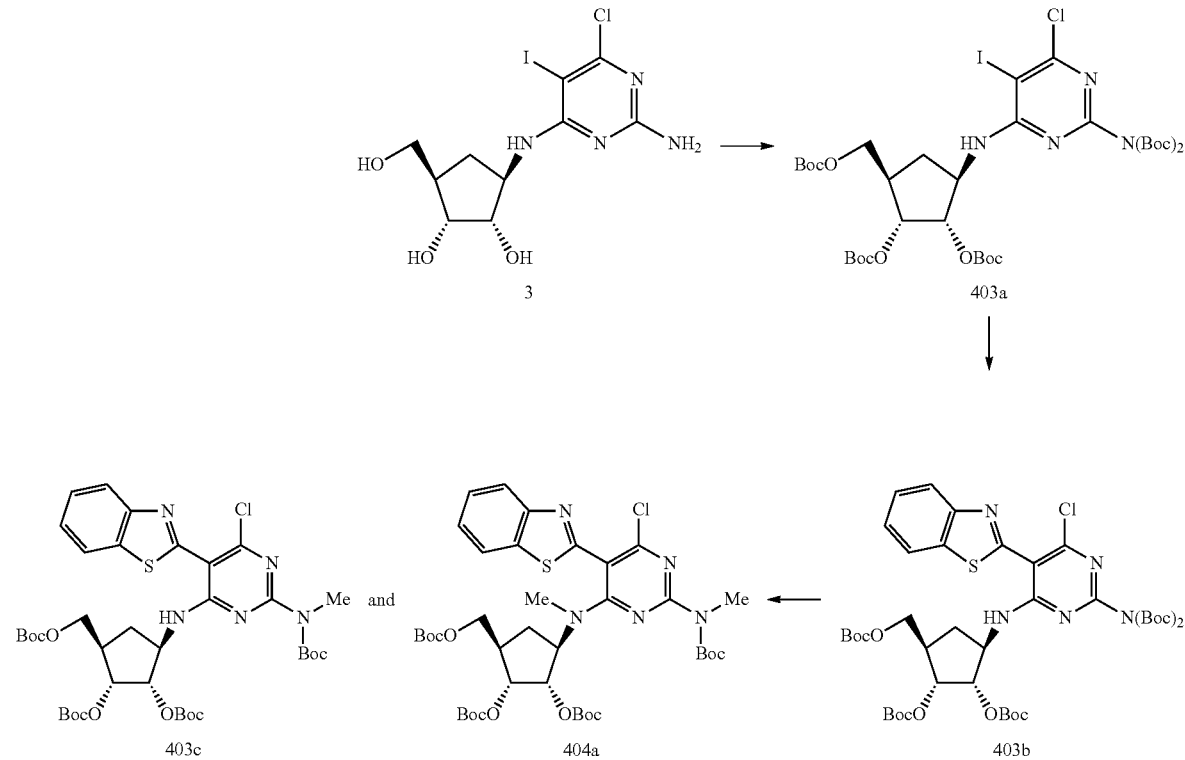

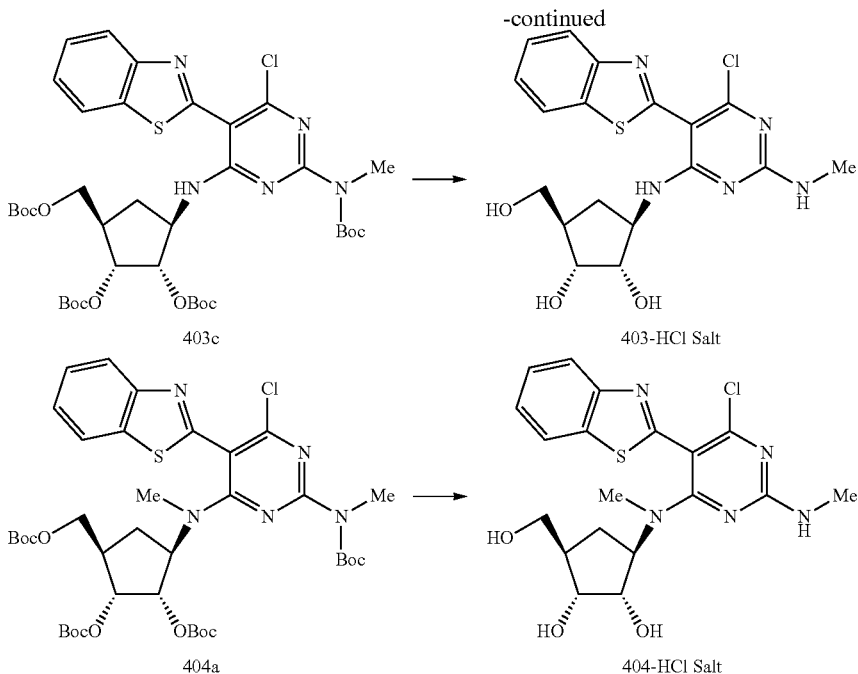

403c

403-HCl Salt

404a

404-HCl Salt

Di-tert-butyl dicarbonate (0.474 g) was added to a stirred mixture of the triol (3; 0.134 g) and DMAP (0.08 g) in THF (5 ml) and the resulting reaction mixture was stirred at room temperature overnight. The reaction was partitioned between EtOAc and 10% aq. HCl. The organic phase was separated, washed with sat. aq. NaHCO3, water, dried (MgSO4). The volatiles were removed under reduced pressure and the residue purified by silica gel column chromatography using hexanes: EtOAc; 5:1 as eluent to provide the desired penta-Boc derivative (403a; 0.226 g) as a white solid.

Triethylamine (0.124 ml) was added to a mixture of 2-tributylstannylbenzothiazole (0.200 g), the iodide (403a; 0.200 g), dichlorobis(triphenylphosphine)palladium(II) (0.032 g), copper(I) iodide (0.016 g) in dioxane (3 ml) and the resulting reaction mixture was heated to 100 C (oil bath temp.) for a period of 1 h. After cooling, EtOAc was added and the suspension was filtered through a pad of celite and the solid was thoroughly washed with EtOAc. The filtrate was washed with water, dried (MgSO4) and the volatiles were removed under reduced pressure. The residue was purified by silica gel column chromatography using hexanes: EtOAc; 5:1 as eluent to provide the desired benzthiazole (403b; 0.201 g) as a light-brown solid.

Sodium hydride (0.008 g of a 60% dispersion in mineral oil), followed by iodomethane (0.047 g) were added to a stirred solution of 403b (0.200 g) in anhydrous THF (3 ml). The resulting mixture was stirred for 2 h., and additional portions of sodium hydride (0.008 g) and iodomethane (0.047 g) were added and the reaction was stirred overnight. The reaction mixture was partitioned between EtOAc and water and AcOH (~1 ml) was added. The organic phase was separated, dried (MgSO4) and the volatiles were removed under reduced pressure. The residue was purified by silica gel column chromatography to give 403c (0.007 g); 1H NMR (CDCl$_3$) δ1.43 (s, 9H), 1.46 (s, 9H), 1.49 (s, 9H), 1.50-1.55 (m, 1H), 1.56 (s, 9H), 2.62-2.76 (m, 2H), 3.40 (s, 3H), 4.20 (d, 2H, J=5.3 Hz), 4.60-4.66 (m, 1H), 5.02-5.06 (m, 1H), 5.23-5.27 (m, 1H), 7.39-7.44 (m, 1H), 7.47-7.52 (m, 1H), 7.92 (d, 1H, J=8.0 Hz), 8.09 (d, 1H, J=8.0 Hz) and 11.22 (d, NH, J=5.8 Hz), MH+, 822.28 and 404a (0.038 g); $^1$H NMR (CDCl$_3$) δ1.44 (s, 9H), 1.46 (s, 9H), 1.47-1.49 (m, 1H), 1.48 (s, 9H), 1.55 (s, 9H), 2.12-2.22 (m, 1H), 2.36-2.46 (m, 2H), 2.58 (s, 3H), 3.41 (s, 3H), 4.01-4.11 (m, 2H), 4.84-4.90 (m, 1H), 5.02-5.11 (m, 2H), 7.41-7.46 (m, 1H), 7.50-7.55 (m, 1H), 7.89 (d, 1H, J=8.1 Hz), and 8.10 (d, 1H, J=8.1 Hz), MH+, 836.30.

2N HCl in ether (2 ml) was added to 403c (0.007 g) and the mixture was stirred at room temperature overnight. The volatiles were removed under reduced pressure to give 403-HCl salt (0.006 g).

2N HCl in ether (2 ml) was added to 404a (0.038 g) and the mixture was stirred at room temperature overnight. The volatiles were removed under reduced pressure to give 404-HCl salt (0.022 g).

Example 308

Procedure L

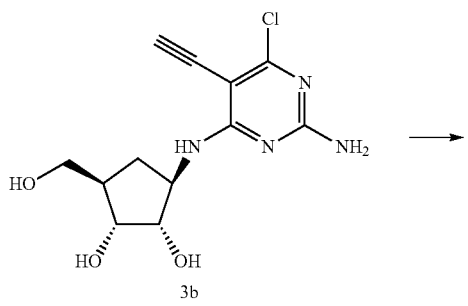

3b

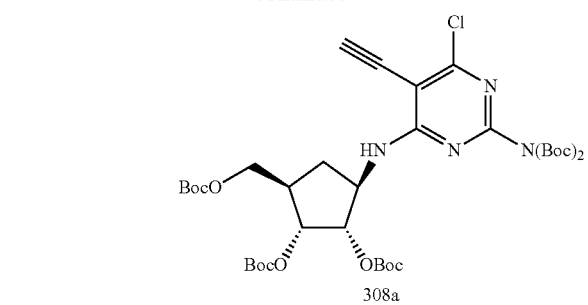

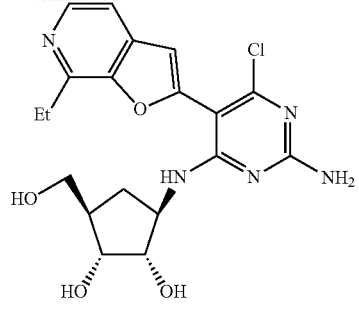

308-HCl salt

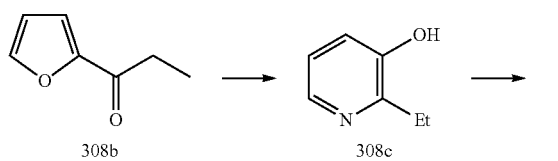

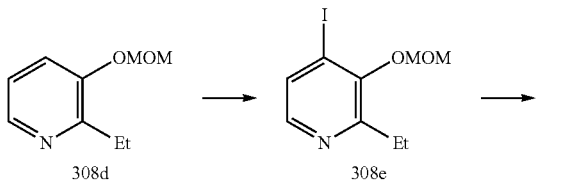

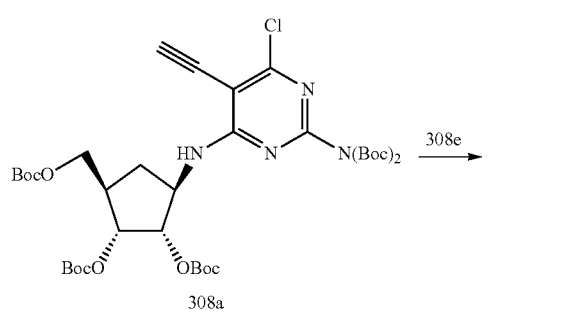

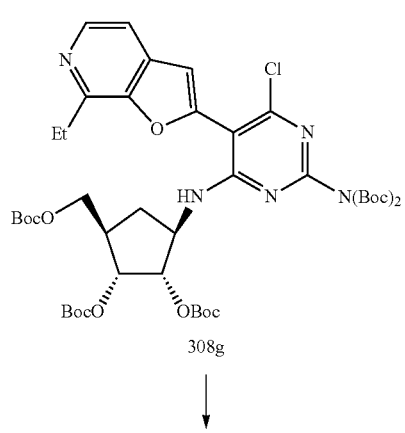

Di-tert-butyl dicarbonate (0.474 g) was added to a stirred mixture of the triol (3b; 0.100 g) and DMAP (0.08 g) in THF (5 ml) and the resulting reaction mixture was stirred at room temperature overnight. The reaction was partitioned between EtOAc and 10% aq. HCl. The organic phase was separated, washed with sat. aq. NaHCO3, water, dried (MgSO4). The volatiles were removed under reduced pressure and the residue purified by silica gel column chromatography using hexanes; EtOAc; 10:3 as eluent to provide the desired penta-Boc derivative (308a; 0.210 g) as a white solid.

Ammonia was bubbled into a suspension of ammonium chloride (3.00 g) and the ketone (308b; 6.20 g) in ethanol (15 ml) in a pressure bottle for 10 min. The bottle was sealed and heated in an oil bath at 200 C overnight. After cooling, the volatiles were removed under reduced pressure and the residue partitioned between methylene chloride and continuously extracted overnight. The volatiles were removed under reduced pressure and the crude reaction product was purified by silica gel column chromatography using hexanes; EtOAc (5:1) to give the desired pyridol (308c; 0.701 g) as a brown solid.

Chloromethyl methyl ether (0.46 ml) was added dropwise to a stirred mixture of 308c (0.65 g), Hunigs base (1.41 ml) in anhydrous dichloromethane (10 ml), while cooled in an ice bath, under an atmosphere of nitrogen. The resulting mixture was allowed to reach room temperature, overnight. Solid sodium bicarbonate was added and the suspension was partitioned between methylene chloride and water. the organic phase was separated, dried (MgSO4) and the volatiles removed under reduced pressure. The residue was purified by silica gel column chromatography using hexanes; EtOAc (1:10) as eluent to give the desired ether 308d (0.59 g) as a yellow oil.

To a solution of the ether (308d; 0.55 g) in anhydrous THF (10 ml) at −78 C, under an atmosphere of nitrogen was added n-Butyl lithium (1.5 ml of a 2.5M solution in hexanes). The resulting mixture was stirred at this temperature for 1 h. and a solution of iodine (0.92 g) in anhydrous THF (5 ml) was added. After stirring for a further 1 h., a 1M aq. solution of NH4Cl was added and the suspension was allowed to warm to room temperature before partitioning between EtOAc and water. The organic phase was separated, washed with 10% aq. sodium thiosulfate, water, dried (MgSO4) and the volatiles were removed under reduced pressure. The solid was subjected to silica gel column chromatography (hexanes; EtOAc; 1:10) to provide the desired iodide 308e (0.926 g) as a white solid.

To a solution of the acetal (308e; 0.900 g) in dichloromethane (8 ml) was added TFA (2 ml) at room temperature under an atmosphere of nitrogen. The resulting mixture was stirred overnight before removing the volatiles under reduced pressure to give the salt 308f (1.09 g) as a light-brown oil.

To the acetylene (308a 0.114 g), the iodide (308f; 0.077 g), Tetrakis(triphenylphosphine) palladium (0) (0.040 g), copper (I) iodide (0.013 g) in dioxane (3 ml) was added triethylamine (0.100 ml) and the resulting mixture was heated to 100 C (oil bath temp.), under an atmosphere of nitrogen, for a period of 1 h. After cooling, EtOAc was added and the mixture was filtered through a pad of celite and the solid was thoroughly washed with EtOAc. The combined filtrate was washed with 10% aq. HCl, water, dried (MgSO4) and the volatiles removed under reduced pressure. The crude reaction product was purified by silica gel using hexanes:EtOAc (10:3) as eluent to give the desired azabenzofuran (308 g; 0.091 g) as a white solid.

To the pyridylfuran (308 g; 0.080 g) was added 4M HCl in dioxane (3 ml) and the resulting solution was allowed to stand at room temperature overnight. the volatiles were removed under reduced pressure to give the triol (308).

Example 310

Procedure M silica gel column chromatography using hexanes; EtOAc (1:10) as eluent to give the desired ether 310b (0.44 g) as a yellow oil.

MCPBA (0.515 g of 77% pure material) was added to the ether (310b; 0.32 g) and sodium bicarbonate (0.528 g) in dichloromethane (5 ml) while cooled in an ice bath. the resulting mixture was stirred for 1.5 h. and 5% aq. sodium carbonate was added and the mixture partitioned between methylene chloride and water. The organic phase was separated and the aqueous phase further extracted with methylene chloride. The combined organic phases was dried (MgSO4) and the volatiles were removed under reduced pressure to give the N-oxide (310c) used in the next step without purification.

Acetic anhydride (0.237 ml) was added to a mixture of the N-oxide (310c; all material from the previous step) Hunigs base (0.474 ml) in dioxane and the resulting mixture was heated to reflux, overnight, under an atmosphere of nitrogen. After cooling, the reaction was partitioned between methylene chloride and water. The organic phase was separated, dried (MgSO4) and the volatiles removed under reduced pressure. The residue was purified by silica gel column chromatography to give the desired ester (310d; 0.340 g) as a colourless oil.

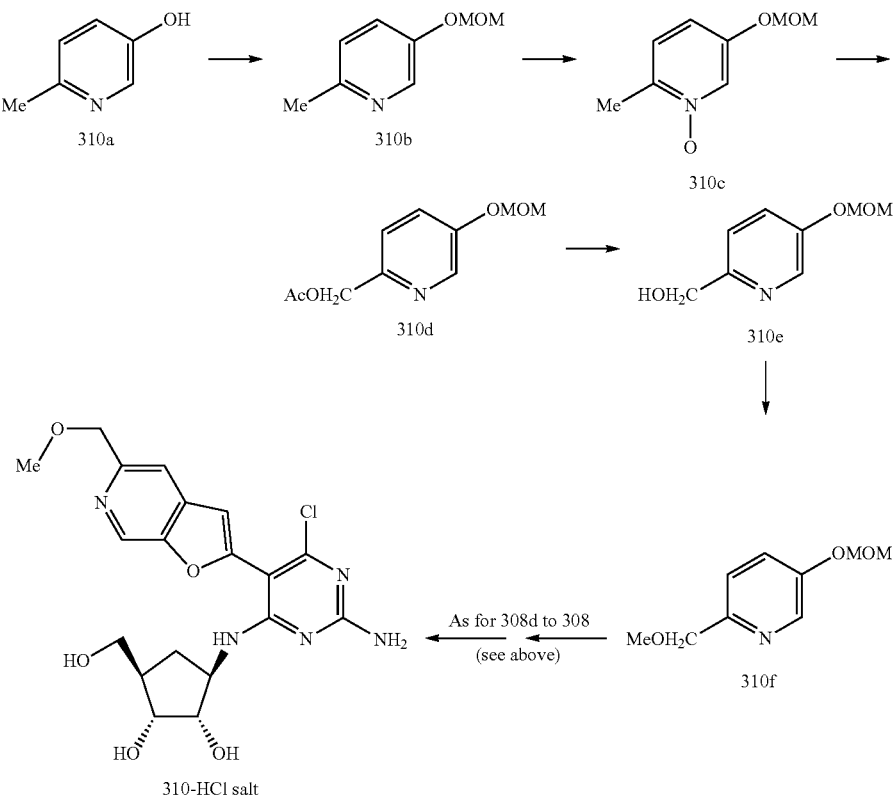

Chloromethyl methyl ether (0.78 ml) was added dropwise to a stirred mixture of 310a (1.00 g), Hunigs base (2.41 ml) in anhydrous dichloromethane (30 ml), while cooled in an ice bath, under an atmosphere of nitrogen. The resulting mixture was allowed to reach room temperature, overnight. Solid sodium bicarbonate was added and the suspension was partitioned between methylene chloride and water. The organic phase was separated, dried (MgSO4) and the volatiles removed under reduced pressure. The residue was purified by Potassium carbonate (0.050 g) was added to a solution of the ester (310d; 0.34 g) in methanol (5 ml) at room temperature and the resulting mixture was stirred for a period of 4 h. The volatiles were removed under reduced pressure and the residue partitioned between methylene chloride and water. The organic phase was separated and the aqueous phase further extracted with methylene. The organic phases were combined, dried (MgSO4) and concentrated. Gave the alcohol (310e; 0.229 g).

Iodomethane (0.101 ml) was added dropwise to a stirred suspension of the alcohol (310e; 0.229 g) and sodium hydride (0.081 g of a 60% dispersion in mineral oil) in anhydrous THF (5 ml) while cooled in an ice bath under an atmosphere of nitrogen and the resulting mixture was allowed to warm to room temperature over a period of 3 days. The reaction mixture was partitioned between methylene chloride and water. The organic phase was separated, dried (MgSO4). The residue was purified by silica gel column chromatography to give the desired ether (310f; 0.201 g) as a yellow oil.

Using the same series of transformations as described above for the conversion of 308d to 308, 310f was used for the preparation of 310.

Example 312

Procedure N

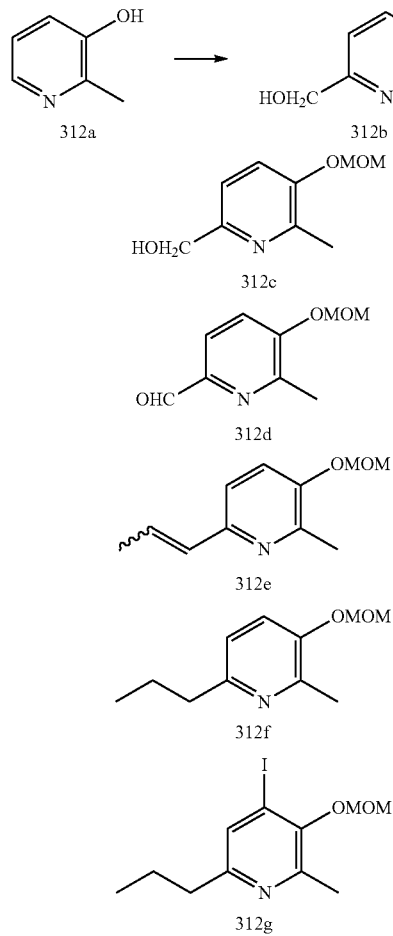

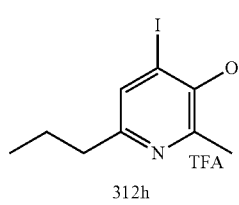

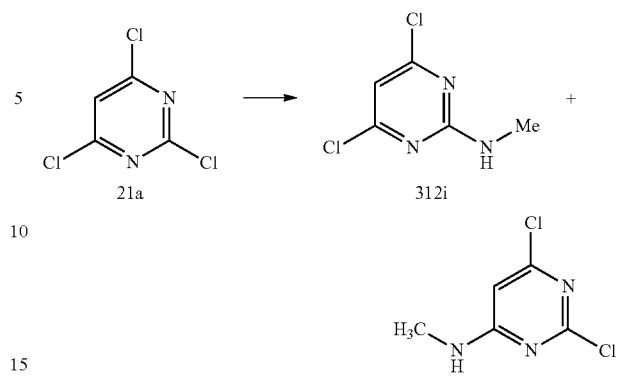

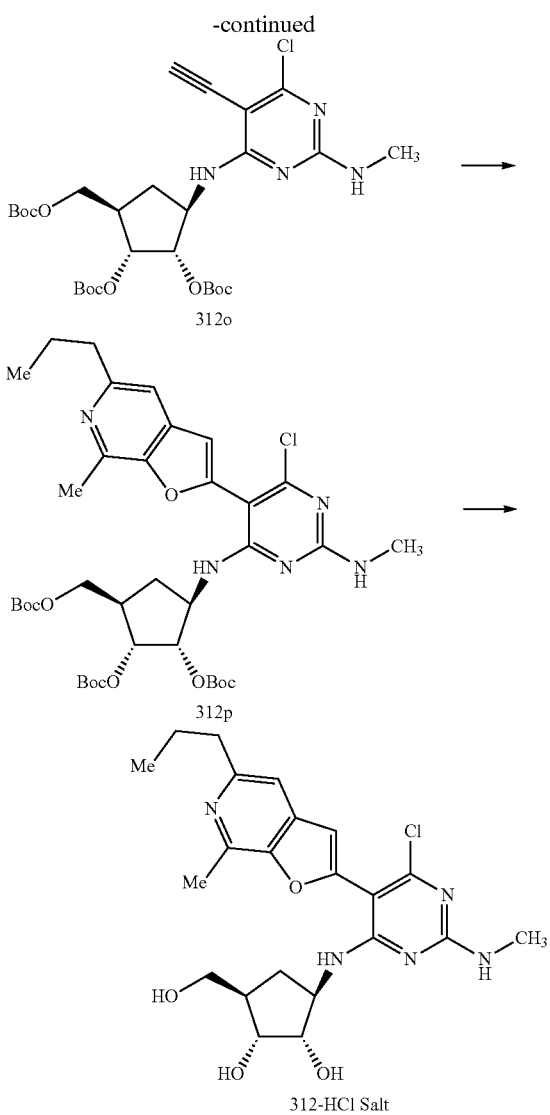

A mixture of 3-hydroxy-2-methylpyridine (21a; 3.64 g), 10% aq. NaOH (13 ml) and 40% formalin (3 ml) in water (10 ml) was refluxed for 2 h. An additional portion of formalin (3 ml) was added and the resulting mixture was heated to reflux for an additional 2 h. The reaction mixture is acidified with acetic acid, filtered and the filtrate evaporated to dryness. The residue was purified by silica gel column chromatography using methylene chloride: MeOH (20:1) as eluent to give the desired diol (312b; 3.00 g).

To the diol (312b; 1.00 g) and potassium t-butoxide (0.888 g) in anhydrous THF (20 ml) was added chloromethyl methyl ether (0.65 ml) and the resulting mixture stirred at room temperature overnight. The volatiles were removed under reduced pressure and to the residue was added methylene chloride followed by sodium bicarbonate. The suspension was filtered and the filtrate concentrated under reduced pressure. The crude reaction product was purified by silica gel column chromatography using methylene chloride: MeOH (48:1) to give the desired acetal (312c; 0.87 g).

The Dess-Martin periodinane (0.76 g) was added to a stirred solution of the alcohol (312c; 0.30 g) and the resulting mixture was stirred at room temperature for 3 h. The reaction was diluted with EtOAc and washed with 5% aq. sodium sulfite, sat aq. sodium bicarbonate, dried (MgSO4) and the volatiles removed under reduced pressure. The crude aldehyde (312d) was used in the next step without purification.

KHMDS (6.6 ml of a 0.5M solution in toluene) was added to a suspension of ethyltriphenylphosphonium bromide (1.23 g) in anhydrous THF (10 ml) at room temperature, under an atmosphere of nitrogen. After stirring for 0.5 h, the orange suspension was cooled to −78 C before the addition of the aldehyde (312d; all material from the previous step) in anhydrous THF (@2 ml). The reaction was maintained at this temperature for 0.5 h., and allowed to warm to room temperature and stirred for a further 0.5 h. The reaction was partitioned between EtOAc and sat. aq. sodium bicarbonate. The organic phase was separated, dried (MgSO4) and concentrated. The residue was purified by silica gel column chromatography using EtOAc:hexanes (1:20) to give the alkenes (312e; 0.095 g).

10% Pd/C was added to a ethanol (3 ml) solution of the alkenes (312e; 0.095 g) and the black suspension was placed under an atmosphere of hydrogen (balloon), overnight. The reaction was filtered through a pad of celite and the solid was washed thoroughly with methanol. The combined filtrate was concentrated under reduced pressure. The residue was purified by silica gel column chromatography to give the dialkylpyridine (312f; 0.071 g).

The pyridine (312f; 0.064 g) was dissolved in anhydrous THF (1 ml) was cooled to −78 C, under an atmosphere of nitrogen and a solution of nBuLi (0.16 ml of a 2.5M solution in hexanes) was added and the resulting reaction mixture maintained at this temperature for 1 h. Iodine (0.108 g) in anhydrous THF (1 ml) was added and the reaction was stirred for a further 1 h, before 1M aq. ammonium chloride. After warming to room temperature the mixture was partitioned between EtOAc and 10% aq. sodium thiosulfate. The organic phase was separated, washed with sat. aq. sodium bicarbonate, water, dried (MgSO4) and the volatiles removed under reduced pressure. The residue was purified by silica gel column chromatography using EtOAc:hexanes (1:10) as eluent to give the iodide (312 g; 0.0806 g), containing a small amount of starting material.

To the iodide from the previous step (312 g; 0.080 g) in dichloromethane (5 ml) was added TFA (1 ml) and the mixture left to stand a room temperature overnight. The volatiles were removed under reduced pressure to give the salt (312 h).

A solution of methylamine (57 ml of a 2M solution in THF) was added dropwise to a stirred solution of trichloropyrimidine (124a; 10.00 g) in anhydrous THF (80 ml) at −20 C, under an atmosphere of nitrogen and the reaction was maintained at this temperature for 0.5 h. The volatiles were removed under reduced pressure and the residue partitioned between methylene chloride and 10% aq. NaOH. The organic phase was separated, washed with water, dried (MgSO4), and concentrated under reduced pressure. The residue was purified by silica gel column chromatography using EtOAc; hexanes (1:20) as eluent to give the desired product (312i; 4.05 g) as a white solid. The relatively more polar isomer (312j) was set aside at this time.

Iodine monochloride (12.08 g) was dissolved in acetic acid and added dropwise to the aminopyrimidine (312i; 4.00 g) and the resulting mixture was stirred overnight at room temperature. EtOAc and sat aq. sodium bicarbonate was added. Additional excess sodium bicarbonate was added and the mixture was poured in to a mixture of 10% aq. sodium thiosulfate and EtOAc. The organic phase was separated, washed with water, dried (MgSO4) and concentrated under reduced pressure. Gave the desired iodopyrimidine (312 k; 5.97 g) as a white solid.

Triethylamine (1.61 ml) was added to a mixture of the 'carbasugar hydrochloride' (120a; 0.606 g) and pyrimidine (312 k; 1.00 g) in ethanol (50 ml) and the resulting mixture was heated to reflux overnight, under an atmosphere of nitrogen. After cooling, the volatiles were removed under reduced pressure and the residue was purified by silica gel column chromatography using methylene chloride; methanol (20:1) as eluent to give the desired product (3121; 1.32 g) as a white sold.

To the triol (3121; 0.56 g) in anhydrous THF (25 ml) was added di-tert-butyl dicarbonate (1.42 g) followed by DMAP (0.040 g). the resulting mixture was stirred at room temperature, under an atmosphere of nitrogen overnight. The reaction was partitioned between EtOAc and 10% aq. HCl. The organic phase was separated, washed with sat. aq. sodium bicarbonate, water, dried (MgSO4) and the volatiles were removed under reduced pressure. The residue was purified by silica gel column chromatography to give the tri-Boc (312m; 0.79 g) as a white solid.

Copper(I) iodide (0.014 g) followed by dichlorobis(triphenylphosphine)palladium(II) (0.026 g) were added to a stirred mixture of the tri-Boc (312m; 0.261 g), triethylamine (0.203 ml) and trimethylsilylacetylene (0.152 ml) in anhydrous dioxane (4 ml) and the resulting mixture was heated to 50 C, under an atmosphere of nitrogen, overnight. After cooling, further portion of the palladium catalyst (0.026 g), copper (I) iodide (0.014 g) and the mixture heated for a further period of 1 h. The volatiles were removed under reduced pressure and EtOAc was added. The suspension was filtered through a pad of celite and the solid was washed thoroughly with EtOAc. The combined filtrate was washed with 10% aq. HCl, water, dried (MgSo4) and the volatiles removed under reduced pressure. The residue was purified by silica gel column chromatography to give the desired acetylene (312n; 0.0201 g) as a white solid. To the silane (312n; 0.181 g) in acetonitrile (3 ml) was added tetraethylammonium fluoride hydrate and the resulting mixture was stirred at room temperature for 2 h. The volatiles were removed under reduced pressure and the residue was purified by silica gel column chromatography using EtOAc:hexanes (15:85) to give the desired product (312o; 0.121 g) as a white solid.

Copper(I) iodide (0.013 g) followed by tetrakis(triphenylphosphine) palladium (0) (0.040 g) were added to a mixture of the phenol (312 h; all the material derived from 312o described above) triethylamine (0.113 ml) and the acetylene (213o; 0.100 g) in dioxane (3 ml) and the resulting mixture was heated to 100 C (oil bath temp.), under an atmosphere of nitrogen for 1 h. After cooling, EtOAc was added and the suspension was filtered through a pad of celite and the solid was washed thoroughly with EtOAc. The combined filtrate was washed with 10% Aq. HCl, water, dried (MgSO4) and the volatiles were removed under reduced pressure. The residue was purified by silica gel column chromatography using EtOAc; hexanes (1:5) as eluent to give the desired azabenzofuran (312p; 0.0623 g) as a white solid.

To the tri-Boc (312p; 0.060 g) was added 4M HCl in dioxane and the resulting solution was allowed to stand at room temperature overnight. The volatiles were removed under reduced pressure to give the triol (312; 0.036 g) as a light-brown solid.

Example 418

Procedure O

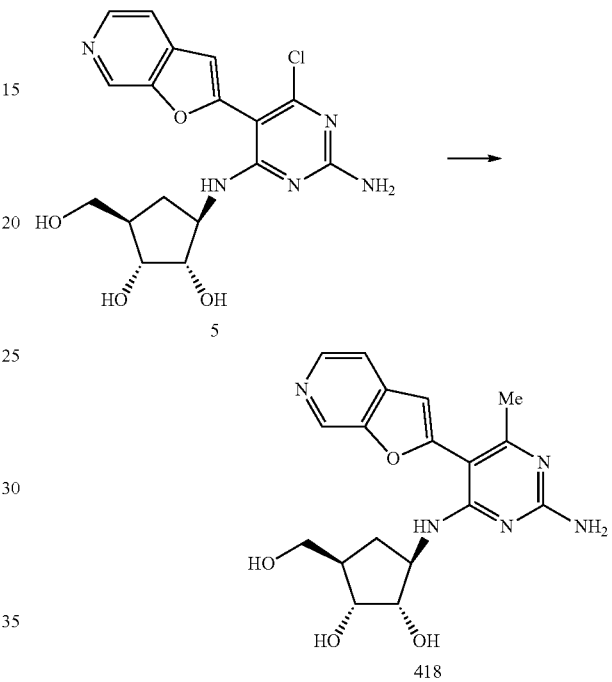

418

Dichlorobis(triphenylphosphine)palladium(II) (0.018 g) was added to a mixture of the chloride (5; 0.050 g) methylboronic acid (0.022 g) and potassium carbonate (0.088 g) in a mixture of dioxane (2 ml) and water. The resulting mixture was heated to 120 C, for 2 h., under an atmosphere of nitrogen. After cooling, methanol was added and the suspension was filtered through a pad of celite and the solid was washed thoroughly with methanol. The combined filtrate was concentrated under reduced pressure. The residue was purified by silica gel plate chromatography using methylene chloride: methanol (5:1) as eluent to give the desired alkylated product (418; 0.006 g). Some impure material was also obtained but was not pursued at this time, Intermediate 516

Procedure P

310e

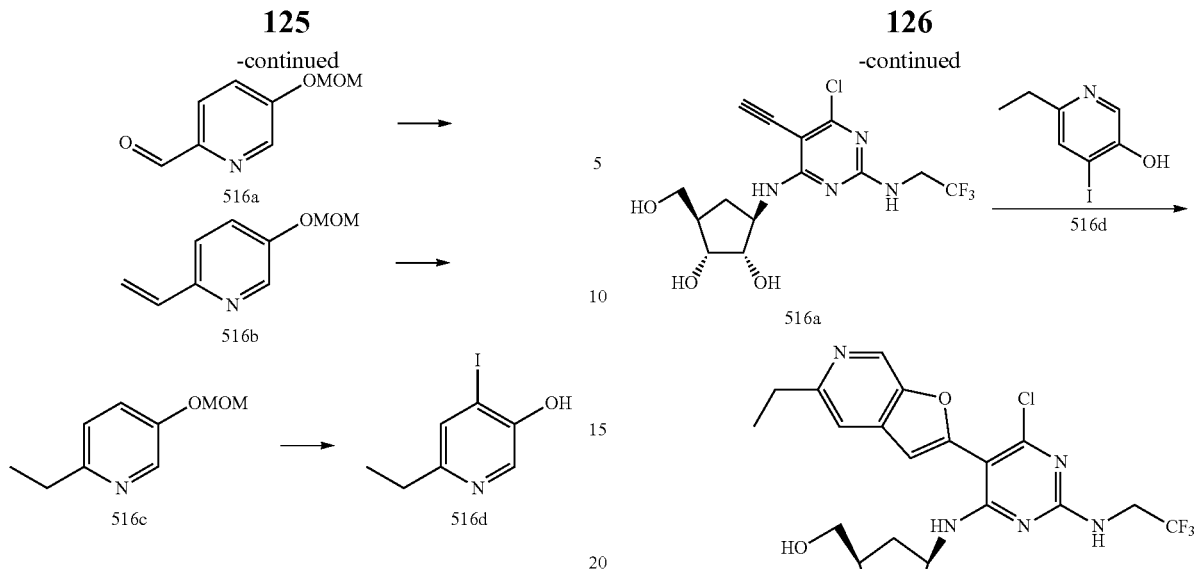

Step 1: Compound 310e (synthesis described in Procedure M, 1.4 g, 8.38 mmol) was dissolved in methylene chloride (20 mL) and Dess Martin Periodinane (3.9 g, 9.2 mmol) was added. The reaction was stirred for 2 hours and then quenched with water. The aqueous layer was extracted with ethyl acetate. The combined organic layers were dried over sodium sulfate and evaporated under reduced pressure to provide the aldehyde 516a (1.4 g) that was used without purification.

Step 2: Methylphosphonium bromide (6.0 g, 16.76 mmol) was suspended in THF (20 mL) and a 0.5M solution of KHMDS in toluene (33 mL, 16.5 mmol) was added. The reaction mixture was stirred for twenty minutes and then cooled in an ice bath. The aldehyde 516a (1.4 g, 8.38 mmol) from step 1 was added dropwide in THF (10 mL) and the reaction was stirred for 1 hour and then quenched with water. The aqueous layer was extracted with ethyl acetate. The combined organic layers were dried over sodium sulfate and evaporated under reduced pressure. The resulting residue was purified by column chromatography (80% hexanes/ethyl acetate) to provide the desired alkene 516b (1.2 g).

Step 3: The alkene 516b from Step 2 (1.2 g, 7.36 mmol) was dissolved in methanol (15 mL). 10% Pd—C was added under an inert atmosphere. The reaction mixture was purged with hydrogen and stirred under a hydrogen atmosphere (1 atm) for 12 hours. The reaction mixture was filtered over celite and the solvent was removed under reduced pressure to provide the desired product 516c (1.0 g) that was used without purification.

Step 4: Compound 516d was prepared from 516c using procedures similar to those described in Procedure L.

Example 516

Procedure Q

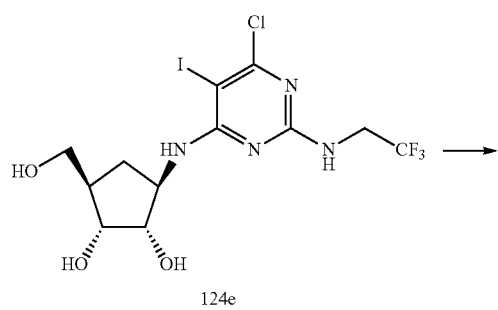

Step 1: Compound 516a was prepared from 124e as described in general procedure A2.

Step 2: Compound 516a and 516d were reacted using chemistry described in general procedure A2 (example 5) to provide compound 516.

Procedure R

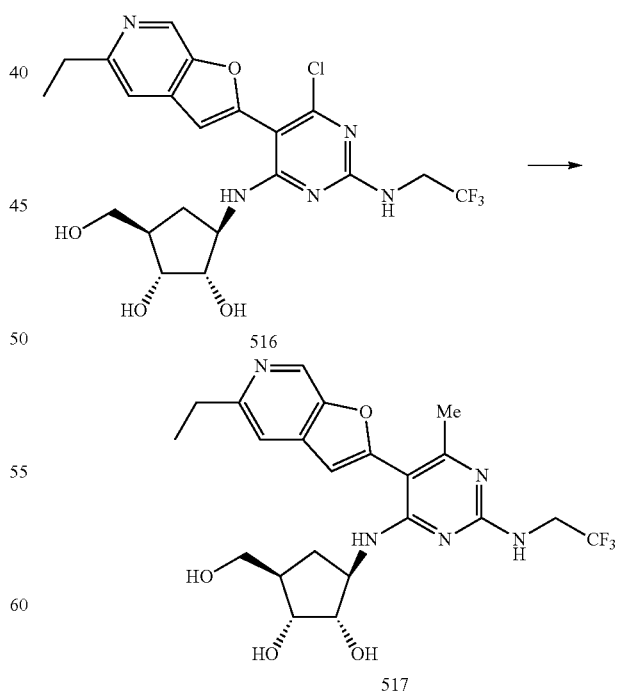

Compound 517 was prepared from compound 516 using chemistry described in Procedure O.

Example 321

Procedure S

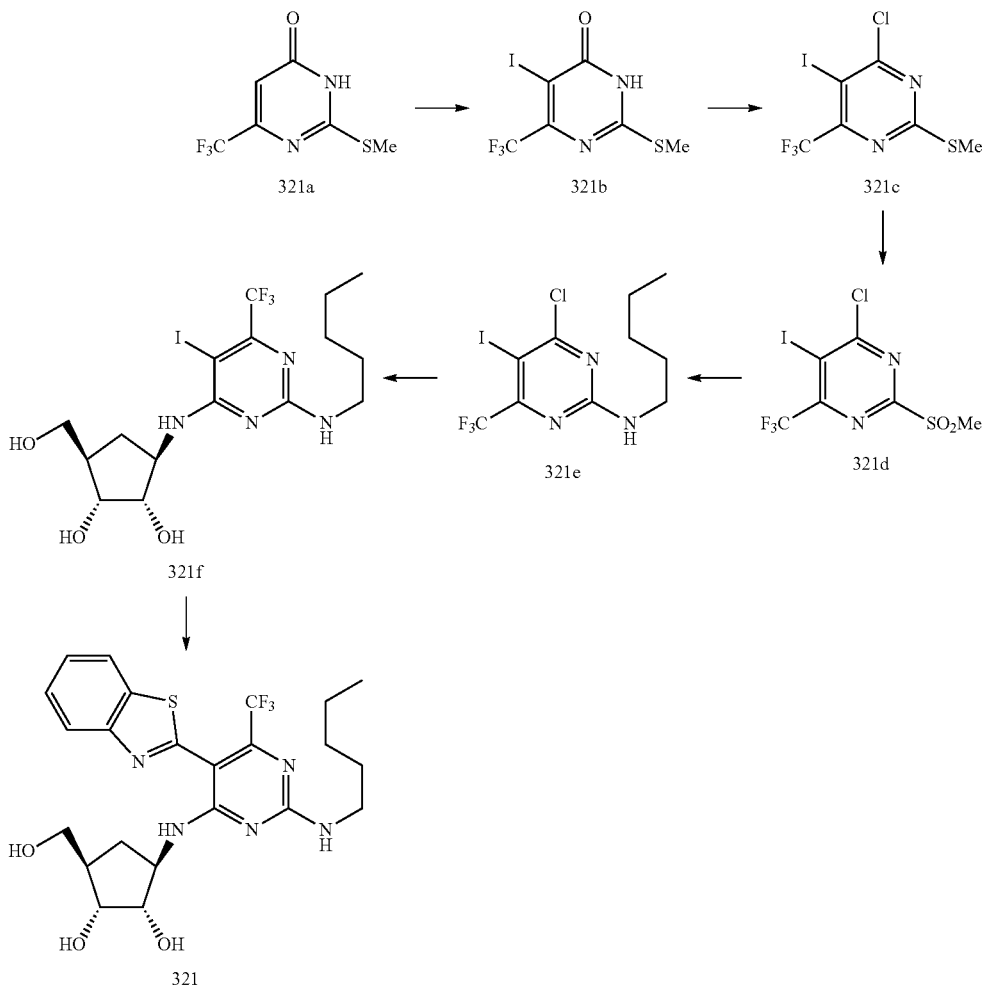

N-Iodosuccinimide (5.92 g; 26 mmol) was added to a stirred solution of the pyrimidone (321a; 5.00 g; 24 mmol; Aldrich) in acetonitrile (50 ml) and the resulting mixture was heated to reflux, under an atmosphere of nitrogen, for 4 h. After cooling, the volatiles were removed under reduced pressure. The residue was partitioned ethyl acetate and 10% aq. sodium thiosulfate. The organic phase was separated, washed with water, dried (MgSO4) and the volatiles were removed under reduced pressure to provide the iodide (321b; 5.56 g) as a yellow solid which was used without purification.

Phosphorous pentachloride (3.61 g) was added to a solution of the iodopyrimidone (321b; 5.30 g) in phosphorous oxychloride (18 ml). The mixture was refluxed for 3 h and the volatiles were removed under reduced pressure. Ice followed by methylene chloride were added to the residue. The organic phase was separated, washed with water and dried (MgSO4). The solvent was removed under reduced pressure to provide the chloride (321c; 4.96 g) as a light-brown sold, which was used without purification.

A mixture of MCPBA (1.46 g of 77% pure material) and the sulfide (321c; 1.0 g) in dichloromethane (15 ml) was stirred at 0 C for 30 min. and allowed to warm to room temperature overnight. The reaction mixture was filtered and the filtrate washed with 10% aq. potassium carbonate, dried (MgSO4) and concentrated under reduced pressure to give the desired sulfone (321d; 0.89 g) as a white solid.

Amylamine (0.54 ml; 2 eq.) was added dropwise to a stirred solution of the sulfone (321d; 0.89 g) in anhydrous DMF (10 ml), under an atmosphere of nitrogen. The resulting mixture was stirred at room temperature, overnight. The reaction was partitioned between EtOAc and water. The organic phase was separated, washed with water (×3), dried (MgSO4) and concentrated under reduced pressure. The residue was purified by silica gel column chromatography to yield the 2-aminopyrimidine (321e; 0.181 g).

A mixture of the pyrimidine (321e; 0.1 g), carbasugar (2a; 0.047 g) and triethylamine (0.18 ml) in ethanol (5 ml) was refluxed overnight. After cooling, the volatiles were removed under reduced pressure and the residue was purified by silica gel column chromatography using methylene chloride: methanol (20:1) as eluent to give the desired product (321f; 0.055 g).

A mixture of tri-n-butylstannyl benzothiazole (186 mg), iodide (321f; 55 mg), dichlorobis(triphenylphosphine)palladium(II) (30 mg), copper(I) Iodide (16 mg) and triethylamine (0.12 ml) in dioxane (3 ml) was heated to 100 C for 10 h. After cooling the volatiles were removed under reduced pressure and the residue was purified by silica gel column chromatography using methylene chloride:methanol (20:1) as eluent to give the desired product (321; 11 mgs). A considerable amount of impure product was also obtained but was not pursued at this time.

Example 324

Procedure T

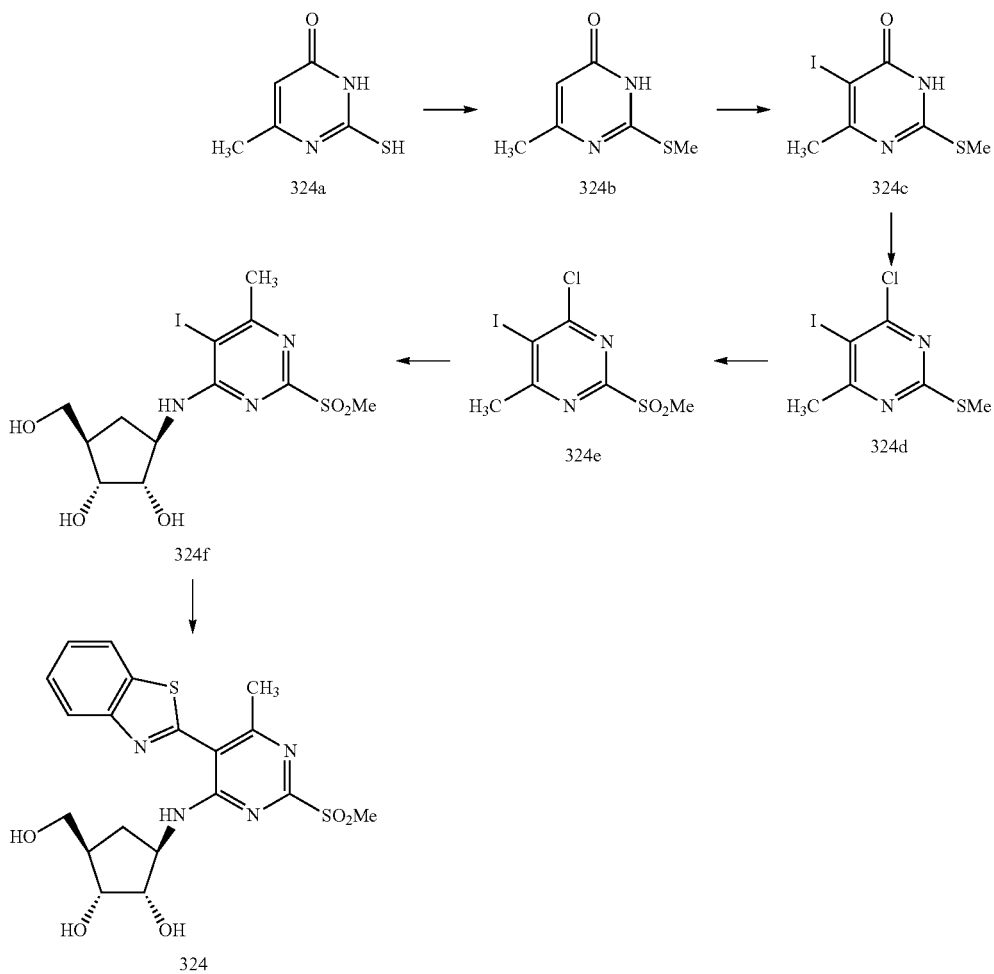

To a solution of the pyrimidine (324a; 522.3 g) in DMSO (5 L), potassium carbonate (535.6 g) followed by iodomethane (245 ml) were added while maintaining a reaction temperature of 22-25 C (dry ice/acetone bath). When the addition was complete the reaction was allowed to stir at room temperature overnight. Ice (7 L) and water (13 L) were added to the reaction. After 0.5 h., the mixture was filtered and the solid washed with cold water, cold acetonitrile and cold ether to give the methyl sulfide (324b; 95.7 g).

To the filtrate was added 50% aq. HCl (300 ml) while cooled in a dry ice/acetone bath. After stirring for 5 min., the white solid was collected. After washing with cold water, acetonitrile and ether a further portion of the methylsulfide (324b; 361.2 g) was recovered.

A mixture of the pyrimidone (324b; 437 g), iodine (852.6 g) and sodium hydroxide (134.2 g) in water (2 L) was heated to 80 C for 15 h. After cooling the reaction was neutralized with acetic acid and the solid collected to give the iodide (324c; 656 g) as a light-brown solid. Used in the next step without purification.

The iodide (324c; 500 g) was added to phosphorous oxychloride (1 L) and heated to reflux for 1 h. After cooling, the volatiles were removed under reduced pressure. The resulting solid was portioned between chloroform and ice. Potassium carbonate was added (to pH=7-8). The aqueous layer was further extracted with chloroform (total 8 L). The combined organic phases were washed with 2 L of 1N NaOH. The organic phase was dried (MgSO4) and concentrated to give the chloride (324d; 470 g) as a yellow solid.

To the sulfide (324d; 2.00 g) in dichloromethane (50 ml) was added MCPBA (3.50 g of 77% pure material) while cooled in an ice bath and the resulting reaction was allowed to warm to room temperature overnight. The reaction was filtered and the filtrate was washed with 10% aq. NaOH. The organic phase was separated, dried (MgSO4), and concentrated under reduced pressure to give the desired sulfone (324e; 2.06 g) as a white solid. Used without purification.

A mixture of the sulfone (324e; 1.213 g), the carbasugar (2a; 0.736 g) and triethylamine (1.12 ml) in acetonitrile (25 ml) was heated to 60 C for 4 h, under an atmosphere of nitrogen. After cooling, the volatiles were removed under reduced pressure and the residue purified by silica gel column chromatography using dichloromethane; methanol (10:1) as eluent. Gave the desired adduct (324f; 0.968 g).

A mixture of tri-n-butylstannyl benzothiazole (191 mg), iodide (324f; 100 mg), dichlorobis(triphenylphosphine)palladium(II) (32 mg), copper(I) Iodide (17 mg) and triethylamine (0.125 ml) in dioxane (3 ml) was heated to 100 C for 2 h. After cooling the reaction was filtered through a pad of celite and the volatiles were removed under reduced pressure. The residue was purified by silica gel column chromatography using methylene chloride:methanol (10:1) as eluent to give the desired product (324; 17.6 mgs). A considerable amount of impure product was also obtained but was not pursued at this time.

Example 328 and 329

Procedure U

Triethylamine (111.0 g) was added to a mixture of the pyrimidine (324d; 72.3 g) and carbasugar (2a; 40.0 g) and the resulting reaction heated to 70 C, overnight. After cooling, the volatiles were removed under reduced pressure to give the crude adduct (329a; used without purification).

To the crude triol (329a; above) was added acetone (2 L) followed by 2,2-dimethoxypropane (55 ml) and methanesulfonic acid (15 ml) while cooled in an ice bath. When the addition was complete the reaction was allowed to warm to room temperature overnight. The reaction mixture was partitioned between EtOAc (4 L), water (1 L) and brine (200 ml). The organic phase was separated, washed with brine, dried (MgSO4) and concentrated. The residue was purified by column chromatography to give the desired primary alcohol (329b; 78.2 g) as a yellow solid.

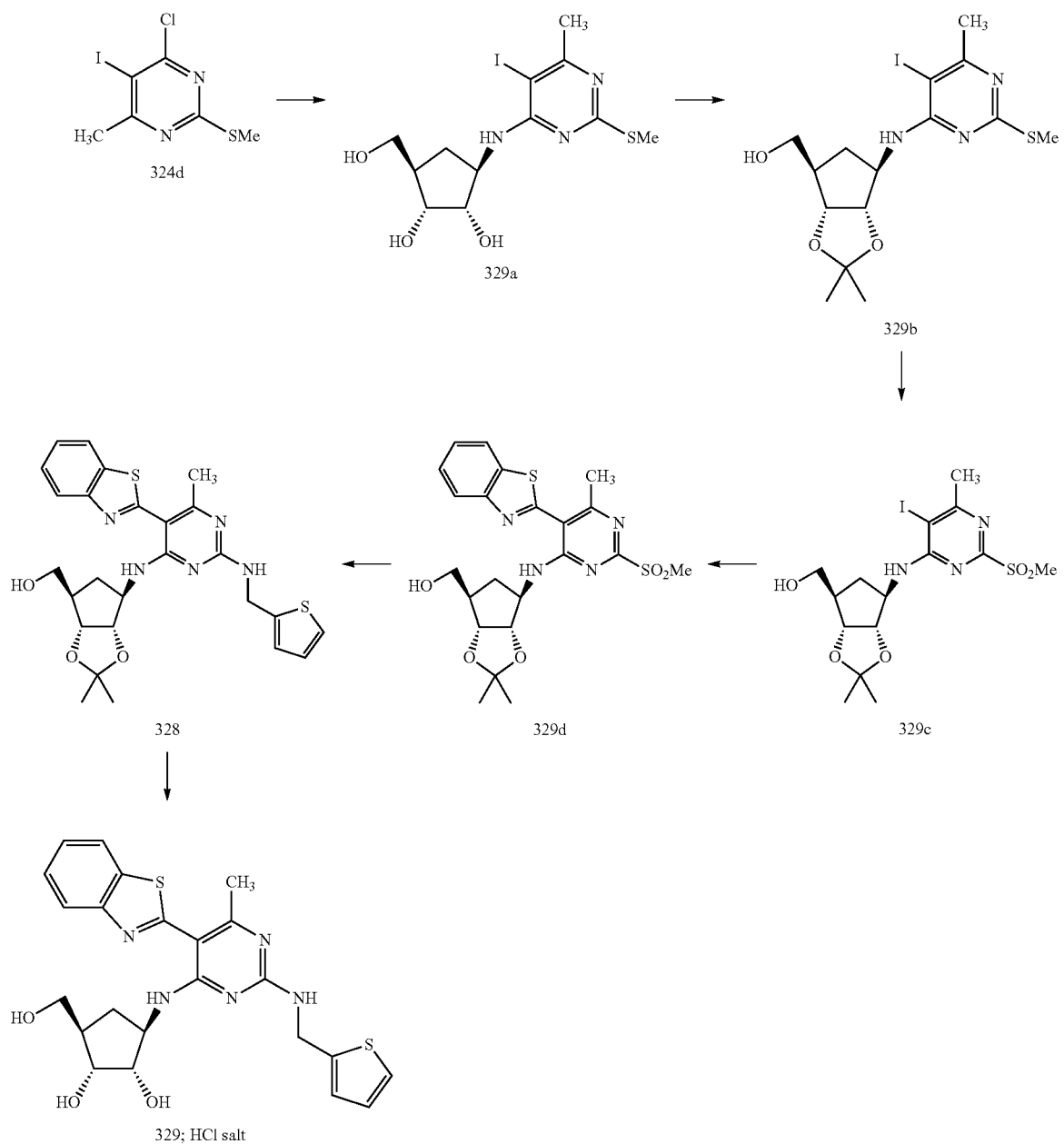

MCPBA (1.096 g of 77% pure material) was added to a dichloromethane (15 ml) solution of the sulfide (329b; 0.932 g) while cooled in an ice bath, under an atmosphere of nitrogen. The resulting mixture was allowed to warm to room temperature overnight. The suspension was filtered and the filtrate washed with 10% aq. sodium thiosulfate followed by 10% aq. potassium carbonate, dried (MgSO4) and concentrated under reduced pressure to give the desired sulfone (329c; 0.698 g) as a white solid. This material was used without purification.

A mixture of tri-n-butylstannyl benzothiazole (1.23 g), iodide (329c; 698 mg), dichlorobis(triphenylphosphine)palladium(II) (197 mg), copper(I) Iodide (98 mg) and triethylamine (0.763 ml) in dioxane (20 ml) was heated to 100 C for 1 h. After cooling the reaction was filtered through a pad of celite and the solid was washed thoroughly with EtOAc. The filtrate was washed with 10% aq. HCl, water, dried (MgSO4) and the volatiles were removed under reduced pressure. The residue was purified by silica gel column chromatography using methylene chloride:methanol (97:3) as eluent to give the desired product (329d; 422 mgs), as a light-brown solid.

2-Thiophenemethylamine (0.042 ml) was added dropwise to a solution of the sulfone (329d; 0.100 g) in acetonitrile (3 ml) and the resulting mixture was heated to reflux, under an atmosphere of nitrogen, overnight. After cooling, the reaction mixture was partitioned between EtOAc and 10% aq. HCl. The organic phase was separated, dried (MgSO4) and concentrated under reduced pressure. Upon concentration the 2-aminopyrimidine (328; 0.042 g) was collected as a yellow solid. A considerable amount of product remained in the filtrate but was not pursued at this time. In most examples the desired product was purified and obtained via silica gel column chromatography.

1N aq. HCl (5 ml) was added dropwise to a solution of the dimethyl acetal (328; 36 mg) in dioxane (5 ml) and water (5 ml) and the resulting mixture was stirred at room temperature overnight. The volatiles were removed under reduced pressure and the solid washed with diethyl ether. Gave the desired triol (329; 27.6 mgs), as the hydrochloride salt, a light-brown solid.

Example 332 and 327

Procedure V

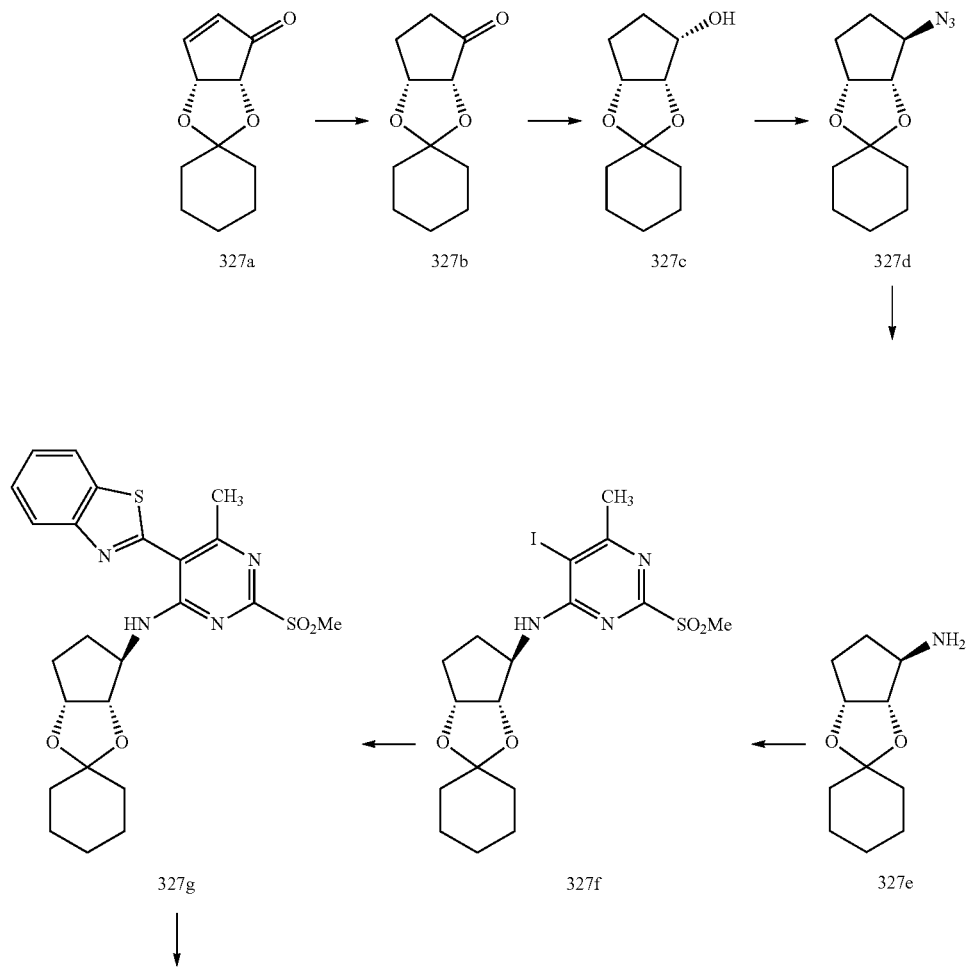

-continued

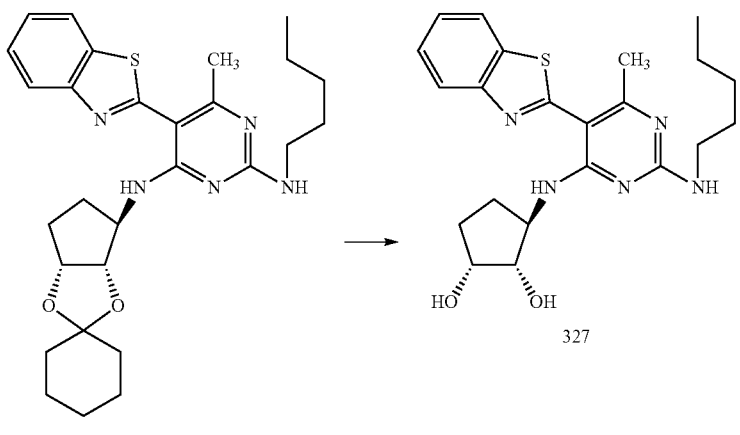

10% Pd/C (0.5 g) was added to a solution of the enone (327a; 1.0 g; prepared according to the procedures set forth in Helvetica Chimica Acta 1982, vol 65, page 2570 and patent U.S. Pat. No. 4,859,677) in ethanol (10 ml) and the resulting suspension was placed under an atmosphere of hydrogen overnight. The reaction was filtered through a pad of celite and the solid was washed thoroughly with ethanol. The filtrate was concentrated under reduced pressure to give the ketone (327b; 0.98 g), used without purification.

Sodium borohydride (0.281 g) was added to a stirred solution of the ketone (327b; 0.98 g) in methanol (50 ml) while cooled in an ice bath. The resulting mixture was stirred for 1 h. and water was added. Most of the methanol was removed under reduced pressure and the remaining residue extracted with dichloromethane (×3). The combined organic phases were dried (MgSO4) and concentrated. The residue was purified by silica gel column chromatography to yield the alcohol (327c; 0.895 g), as a colourless oil.

To a solution of the alcohol (327c; 0.895 g) in dichloromethane (25 ml) was added triethylamine (0.945 ml) followed by methanesulfonyl chloride (0.42 ml) and the resulting mixture stirred for 2 h. The reaction was partitioned between dichloromethane and dil. aq. HCl. The organic phase was separated, washed with water, dried (MgSO4) and concentrated to give the crude, intermediate, mesylate. The mesylate was dissolved in DMF (30 ml) and sodium azide (0.352 g) was added and the resulting mixture was heated to 100 C, under an atmosphere of nitrogen, overnight. After cooling, the reaction mixture was partitioned between EtOAc and water. The organic phase was separated, washed with water (×3), dried (MgSO4) and concentrated under reduced pressure. The residue was purified by silica gel column chromatography to give the desired azide (327d; 0.48 g). $^1$H NMR (CDCl3) δ 1.34-1.42 (m, 2H), 1.49-1.64 (m, 8H), 1.70-1.74 (m, 1H), 1.76-1.83 (m, 1H), 1.86-1.91 (s, 1H), 1.98-2.05 (m, 1H), 3.96 (d, 1H, J=4.6 Hz), 4.38 (dd, 1H, J=5.5 and 1.2 Hz) and 4.70 (app. t, 1H, J=5.3 Hz). $^{13}$C NMR (CDCl$_3$) δ 23.58, 23.99, 25.15, 27.65, 30.64, 33.28, 35.86, 66.69, 79.66, 83.97 and 110.90.

10% Pd/C (0.25 g) was added to a solution of the azide (327d; 0.48 g) in ethanol (5 ml) and the resulting suspension was placed under an atmosphere of hydrogen overnight. The reaction was filtered through a pad of celite and the solid was washed thoroughly with ethanol. The filtrate was concentrated under reduced pressure to give the amine (327e; 0.98 g), used without purification.

A mixture of the sulfone (324e; 0.89 g), the amine (327e; 0.44 g) and triethylamine (1.56 ml) in acetonitrile (15 ml) was heated to reflux, under an atmosphere of nitrogen, overnight. After cooling, the reaction was partitioned between EtOAc and 10% aq. HCl. The organic phase was separated, dried (MgSO4) and the volatiles were removed under reduced pressure. The residue purified by silica gel column chromatography using EtOAc; hexanes (3:10) as eluent. Gave the desired adduct (327f; 0.968 g).

A mixture of tri-n-butylstannyl benzothiazole (0.816 g), iodide (327f; 475 mg), dichlorobis(triphenylphosphine)palladium(II) (137 mg), copper(I) Iodide (74 mg) and triethylamine (0.55 ml) in dioxane (15 ml) was heated to 100 C for 1 h. After cooling the reaction was filtered through a pad of celite and the solid was washed thoroughly with EtOAc. The filtrate was washed with 10% aq. HCl, water, dried (MgSO4) and the volatiles were removed under reduced pressure. The residue was purified by silica gel column chromatography to give the desired product (327 g), as a light-brown solid.

Amylamine (0.22 g) was added dropwise to a solution of the sulfone (327 g; 0.25 g) in acetonitrile (5 ml) and the resulting mixture was heated to reflux, under an atmosphere of nitrogen, overnight. After cooling, the reaction mixture was partitioned between EtOAc and 10% aq. HCl. The organic phase was separated, dried (MgSO4) and concentrated under reduced pressure. The crude reaction mixture was purified by silica gel column chromatography to give the desired product (332; 0.196 g), as a white solid.

4N HCl in dioxane (5 ml) was added dropwise to a solution of the cyclohexyl acetal (332; 36 mg) in dioxane (3 ml) and water (5 ml) and the resulting mixture was stirred at room temperature for 2 h. The volatiles were removed under reduced pressure. To the residue was added methanol followed by triethylamine and the mixture concentrated to dryness. The residue was purified by silica gel column chroma- Example 335
Procedure W
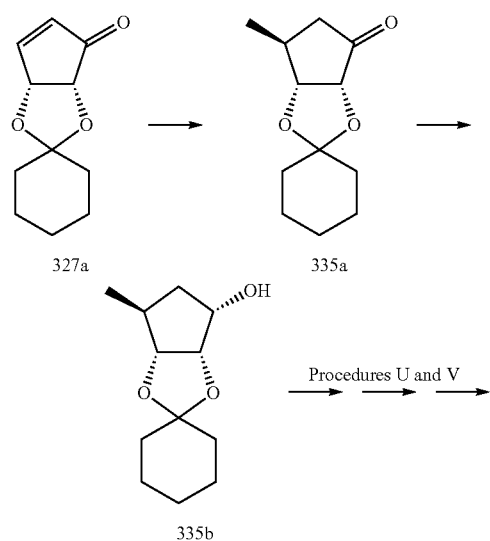
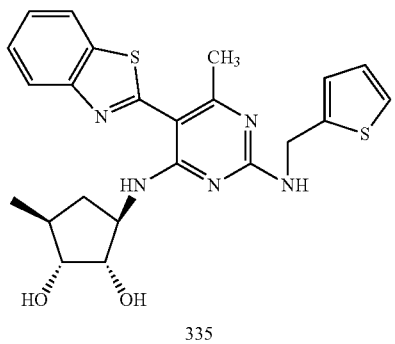
335
Using the procedure set forth in Journal of Medicinal Chemistry, 1992, vol 35, page 1787, 1.0 g of enone (327a) was transformed into the ketone (335a: 0.502 g).
Using the same reference 0.50 g of the ketone (335a) was converted into the alcohol (335b; 0.496 g).
Using the chemistries set forth in procedures U and V, alcohol (335b) was converted into diol (335).
Example 333 and 338
Procedure X
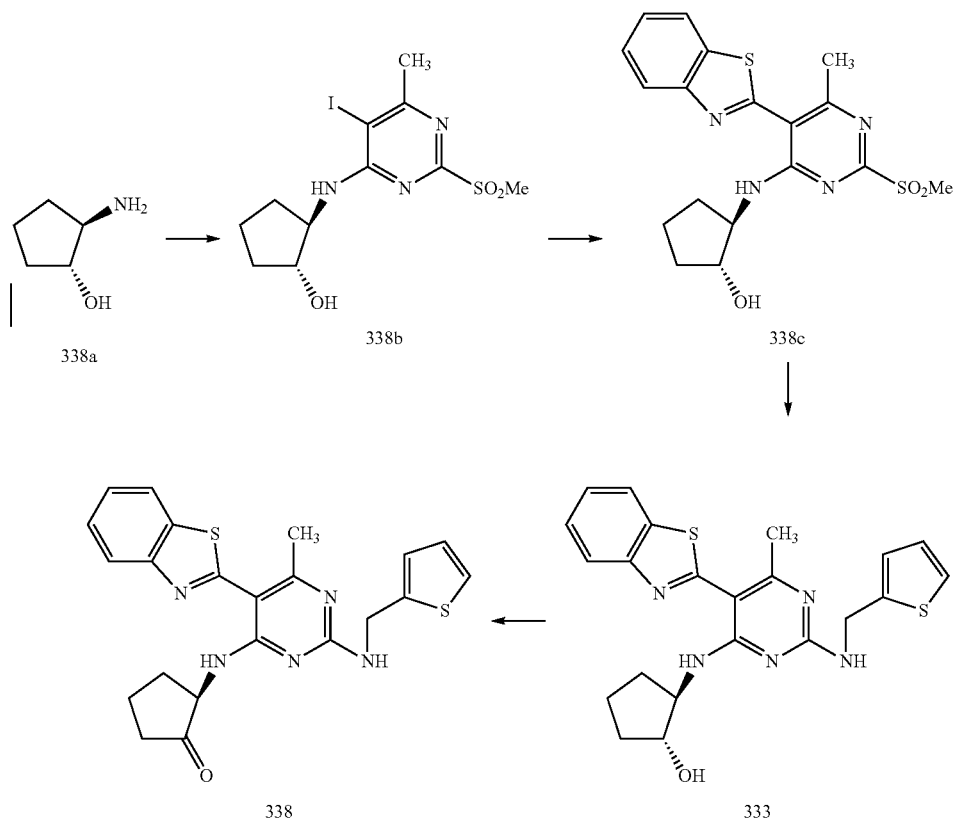

A mixture of the sulfone (324e; 0.60 g), the racemic amine (338a; 0.2 g; Aldrich) and triethylamine (1.01 ml) in acetonitrile (15 ml) was heated to reflux, under an atmosphere of nitrogen, overnight. After cooling, the reaction was partitioned between EtOAc and 10% aq. HCl. The organic phase was separated, dried (MgSO4) and the volatiles were removed under reduced pressure. The residue purified by silica gel column chromatography using EtOAc; hexanes (1:1) as eluent. Gave the desired adduct (338b; 0.252 g), as a white solid.

A mixture of tri-n-butylstannyl benzothiazole (0.538 g), iodide (338b; 252 mg), dichlorobis(triphenylphosphine)palladium(II) (91 mg), copper(I) Iodide (48 mg) and triethylamine (0.36 ml) in dioxane (10 ml) was heated to 100 C for 1 h. After cooling the reaction was filtered through a pad of celite and the solid was washed thoroughly with EtOAc. The filtrate was washed with 10% aq. HCl, water, dried (MgSO4) and the volatiles were removed under reduced pressure. EtOAc was added to the residue and the desired benzthiazole (338c; 0.152 g) was collected as a light-brown solid.

2-Thiophenemethylamine (0.19 ml) was added dropwise to a solution of the sulfone (338c; 0.150 g) in acetonitrile (12 ml) and the resulting mixture was heated to reflux, under an atmosphere of nitrogen, overnight. After cooling, the reaction mixture was concentrated under reduced pressure from which the desired alcohol (333) was collected as a white solid. This solid was washed with water to give 0.154 g.

To the alcohol (333; 0.05 g) in dichloromethane (3 ml) was added the Dess-Martin periodinane (0.049 g) and the resulting mixture heated to 70 C for 6 h. A further portion of the periodinane (0.049 g) was added and heating was continued for a further 2 h. After cooling, the reaction mixture was partitioned between EtOAc and 10% aq. sodium thiosulfate. The organic phase was separated, washed with sat. aq. sodium bicarbonate, dried (MgSO4) and concentrated. The residue was purified by silica gel plate chromatography to give the ketone (338; 0.004 g), as a white solid.

Example 524

Procedure Y

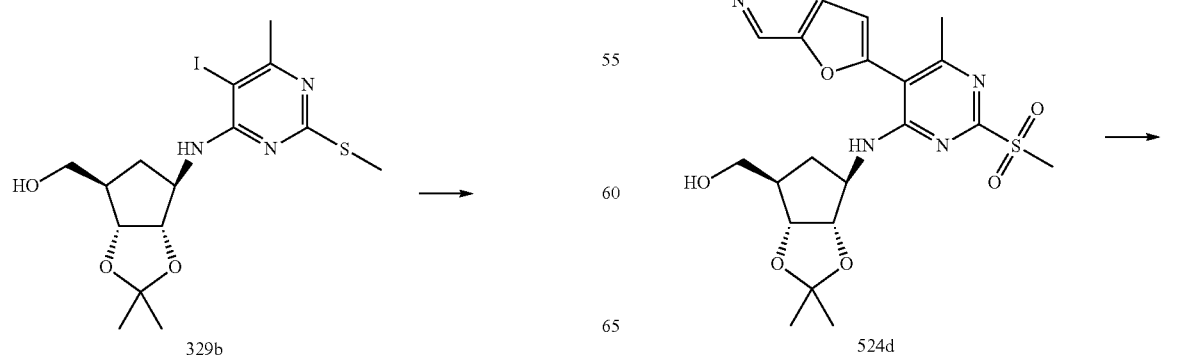

141
-continued

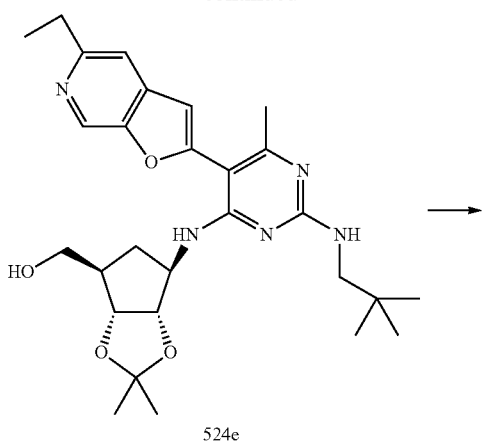

524e

524

Step 1:

The starting iodide (329b, 500 mg, 1.1 mmol) was dissolved in methylene chloride (20 mL) and 77% m-CPBA (543 mg, 2.43 mmol) was added. The reaction was stirred at room temperature for 1 hour and then quenched with aqueous potassium carbonate. The organic layer was dried over sodium sulfate and concentrated under reduced pressure to provide the desired product (540 mg). [M+H]=484.13.

Step 2:

Compound 524a (540 mg, 1.1 mmol), TMS-acetylene (437 mg, 4.46 mmol), Pd(PPh$_3$)$_4$(254 mg, 0.22 mmol), CuI (80 mg), triethylamine (0.61 mL, 4.4 mmol) were dissolved in dioxane and stirred at 60 C for 2 hours and room temperature overnight. The reaction was quenched with water and the product was extracted with ethyl acetate. The organic layer was dried over sodium sulfate and concentrated under reduced pressure. Column chromatography (1:1 Hexanes/ethyl acetate) provided the desired product (410 mg). [M+H]=454.34

Step 3:

Compound 524b (400 mg, 0.88 mmol) was dissolved in THF (15 mL) and cooled in an ice bath. Tetramethylammonium fluoride (50 mg) was added to the reaction and stirred for 2 hours. The reaction was quenched with water and extracted with ethyl acetate. The combined organic layers were dried over sodium sulfate and concentrated under reduced pressure to provide the desired product that was used without further purification (290 mg). [M+H]=382.29

142

Step 4:

Compound 524c (250 mg, 0.65 mmol), compound 516b (163 mg, 0.65 mmol), Pd(PPh$_3$)$_4$ (150 mg), CuI (70 mg), and triethylamine (0.36 mL) were dissolved in dioxane and stirred at 80 C for 2 hours. The reaction was quenched with brine and extracted with ethyl acetate. The organic layers were dried over sodium sulfate and concentrated under reduced pressure. The residue was purified by column chromatography (EtOAc—>5% MeOH/EtOAc) to provide the desired product (200 mg). [M+H]=503.3

Step 5:

Compound 524d (50 mg, 0.099 mol) and neopentylamine (0.2 mL) were dissolved in acetonitrile (2 mL) and stirred in a pressure bottle at 80 C overnight. The reaction was cooled to room temperature and the solid were filtered to provide the desired product (50 mg). [M+H]=510.4

Step 6:

Compound 524e (50 mg, 0.093 mmol) was dissolved in a mixture of 4M HCl dioxane (1 mL), MeOH (3 mL) and water (0.2 mL). The reaction was stirred at room temperature for 2 hours and then all solvents were removed under reduced pressure. The residue was triturated with methylene chloride to provide the desired product (35 mg). [M+H]=470.4

1H NMR (DMSO-d6) 0.9 (s, 9H), 1.0-1.1 (m, 1H), 1.2-1.3 (m, 3H), 1.9-2.0 (m, 1H), 2.0-2.2 (m, 1H), 2.4 (m, 3H), 3.0-3.2 (m, 2H), 3.2-3.4 (m, 4H), 3.6-3.8 (m, 2H), 4.4-4.5 (m, 2H), 7.4 (s, 1H), 8.0 (m, 1H), 8.15 (m, 1H), 8.2 (m, 1H) 9.3 (s, 1H).

Example 523

Procedure Z

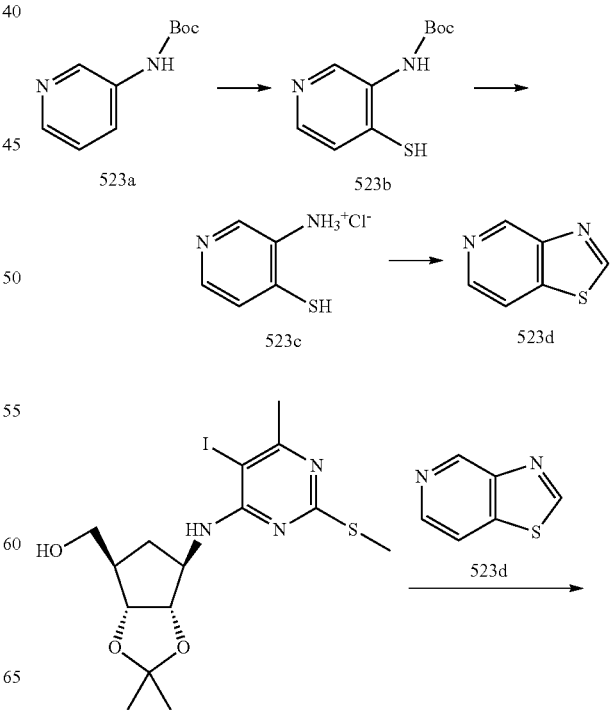


523e

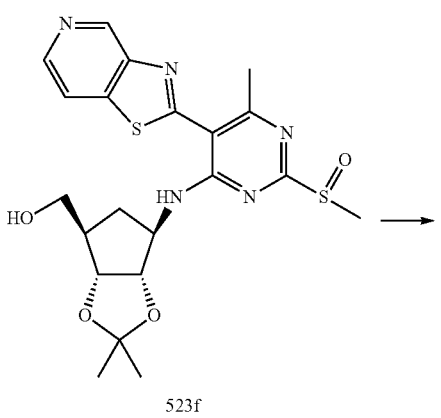

523f

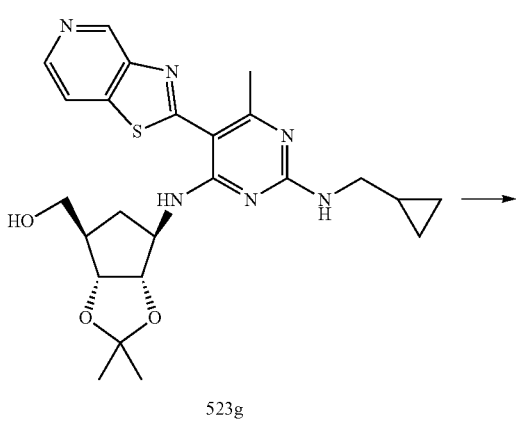

523g

Step 1:

The reaction to form 523b from 523a was performed in the same manner as U.S. Pat. No. 5,077,287, 31 Dec. 1991.

Step 2:

The reaction to form 523c from 523b was performed in the same manner as U.S. Pat. No. 5,077,287, 31 Dec. 1991.

Step 3:

Compound 523c (1.42 g, 8.8 mmol) was dissolved in formic acid (15 mL) and refluxed overnight. The solvent was removed under reduced pressure and the residue was dissolved in ethyl acetate and 1N NaOH solution. The aqueous layer was extracted with ethyl acetate several times. The combined organic layers were dried over sodium sulfate and concentrated under reduced pressure to provide the desired product (1.0 g) that was used without further purification. [M+H]=137.25.

Step 4:

See procedure F (Step 2) for the experimental conditions for the synthesis of 523e.

Step 5:

Compound 523e (75 mg, 0.163 mmol) was dissolved in methylene chloride (6 mL) and cooled in an ice bath. 77% m-CPBA (55 mg, 0.244 mmol) was added and the reaction was stirred for 1 hour at the same temperature and then quenched with aqueous potassium carbonate. The organic layer was dried over sodium sulfate and concentrated under reduced pressure to provide the desired product (75 mg). [M+H]=476.2

Step 6:

Compound 523f (75 mg, 0.15 mmol) was dissolved in acetonitrile (2 mL) and cyclopropylamine (0.1 mL) was added. The reaction was stirred at 80 C for 1 hour and then cooled to room temperature. The solids were filtered to provide the desired product (55 mg). [M+H]=483.2

Step 7:

Compound 523 g (53 mg, 0.109 mmol) was dissolved in a mixture of 4 M HCl dioxane (1 mL), MeOH (3 mL) and water (0.1 mL) and stirred at room temperature for 2 hours. The solvents were removed and the residue was triturated with diethyl ether to provide the desired product (46 mg). [M+H]=443.2

Example 535

Procedure Z1

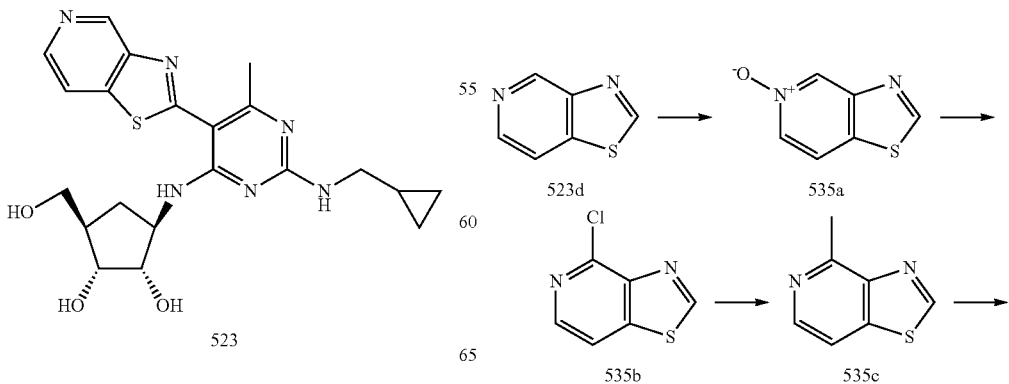

523d    535a 535b    535c

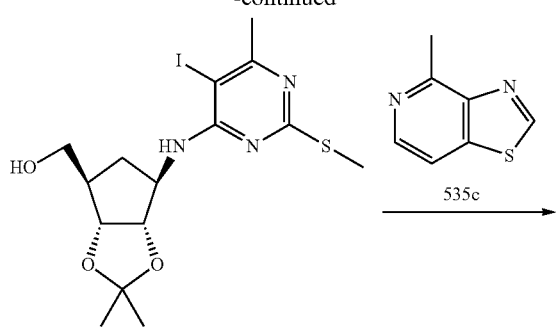
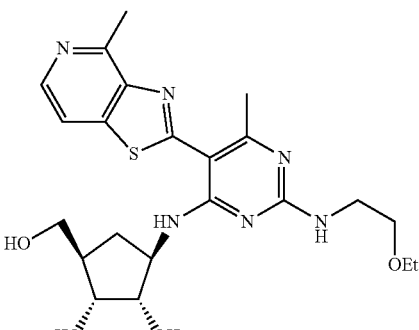

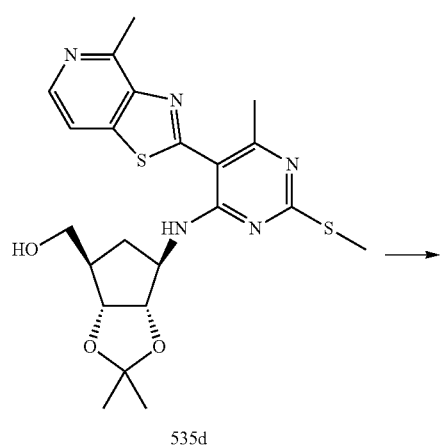

535d

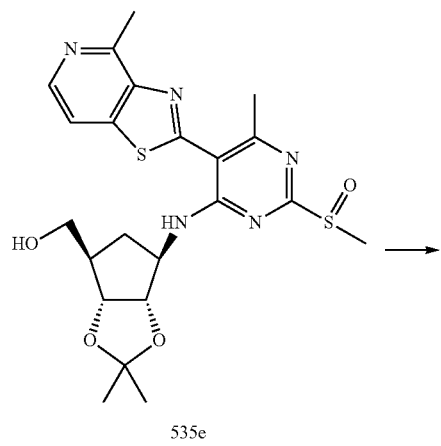

535e

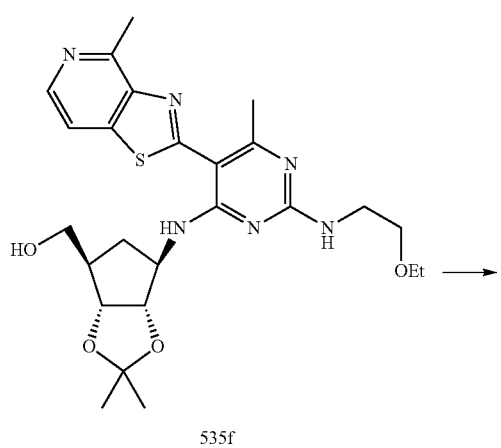

535f

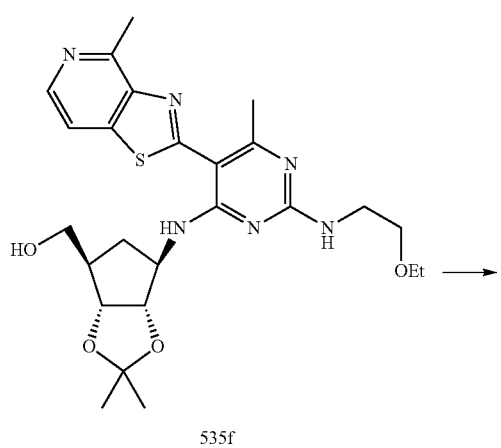

535

Step 1:

Compound 523d (670 mg, 4.9 mmol) was dissolved in methylene chloride (20 mL) and m-CPBA (1.65 g, 7.38 mmol) was added. The reaction was stirred for 2 hours and then quenched with a solution of 1M potassium carbonate. The organic layer was dried over sodium sulfate and concentrated to provide compound 535a (450 mg). [M+H]=153.2

Step 2:

Compound 535a (400 mg, 2.61 mmol) was dissolved in phosphorus oxychloride (5 mL) and refluxed for 2 hours. The reaction was concentrated under reduced pressure and then quenched with saturated sodium bicarbonate solution and extracted with ethyl acetate. The combined organic layers were dried over sodium sulfate and concentrated to provide the desired product (180 mg). [M+H]=171.1

Step 3:

Compound 535b (180 mg, 1.05 mmol), methylboronic acid (200 mg), Pd(PPh₃)₄ (100 mg), and potassium carbonate (500 mg) were dissolved in dioxane (10 mL) and water (3 mL) and stirred at reflux for 4 hours. The reaction was quenched with water and extracted with ethyl acetate. The organic layer was dried over sodium sulfate and concentrated. Column chromatography (2:1 ethyl acetate/hexanes) provided the desired product (70 mg). [M+H]=151.1

Step 4:

Reaction was performed in the same manner as procedure F (Step 2). [M+H]=474.4

Step 5:

Reaction was performed in the same manner as procedure U (Step 5). [M+H]=490.3

Step 6:

Reaction was performed in the same manner as procedure U (Step 6). [M+H]=515.5

Step 7:

Reaction was performed in the same manner as procedure U (Step 7). [M+H]=475.2

Example 542

Procedure Z2

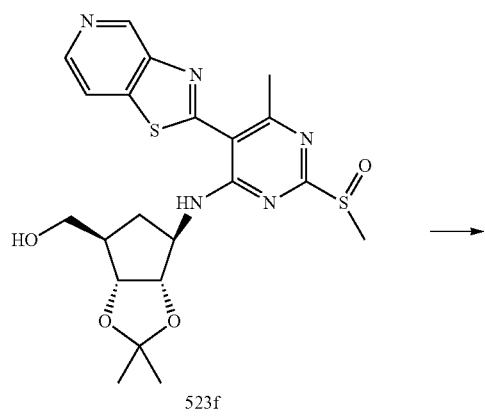
523f

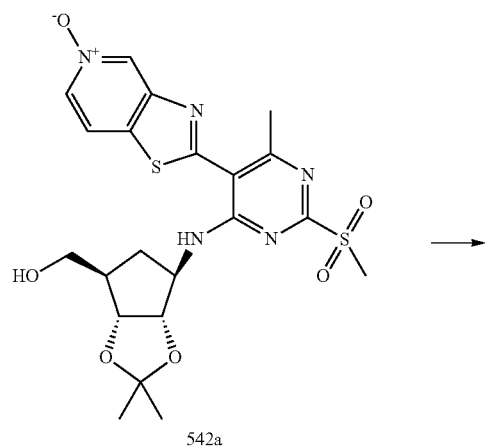
542a

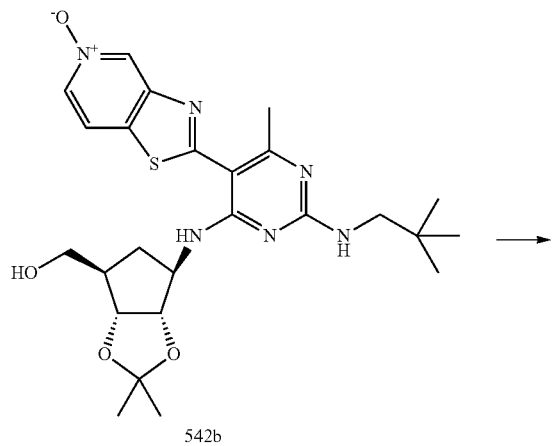
542b

-continued

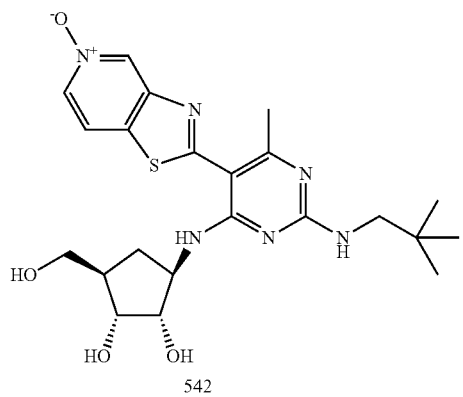
542

Step 1:

Compound 523f (100 mg, 0.21 mmol), m-CPBA (100 mg), and potassium carbonate (100 mg) were dissolved in methylene chloride (5 mL) and stirred at room temperature for 2 hours. The reaction was quenched with water and extracted with methylene chloride. The combined organic layers were dried over sodium sulfate and concentrated under reduced pressure to provide the desired product (100 mg).

Step 2:

Compound 542a (100 mg, 0.2 mmol) and neopentylamine (0.2 mL) were dissolved in acetonitrile (2 mL) and stirred at 100 C for 3 hours. The solvent was removed under reduced pressure and the solids were triturated with diethyl ether to provide the desired product (30 mg)

Step 3:

Reaction was performed in the same manner as procedure U (Step 7). [M+H]=475.4

Examples 248 and 252

Procedure Z3

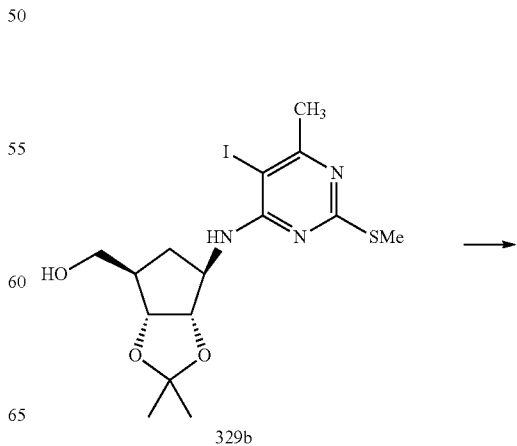
329b

-continued
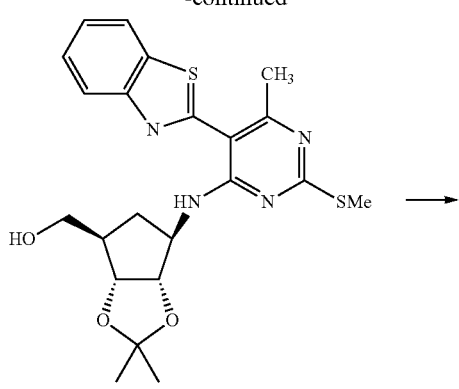
252a
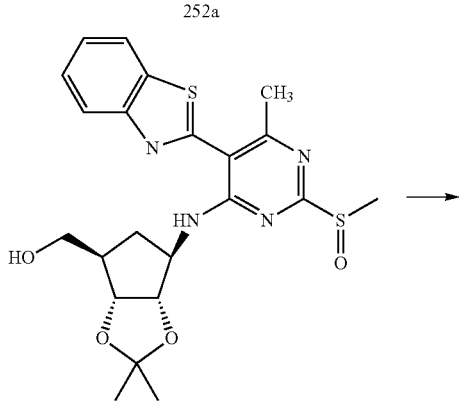
252b
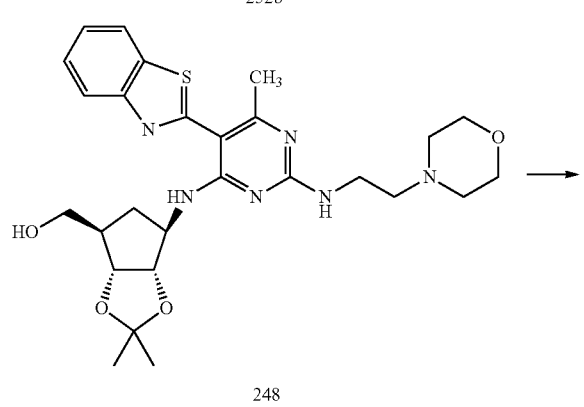
248
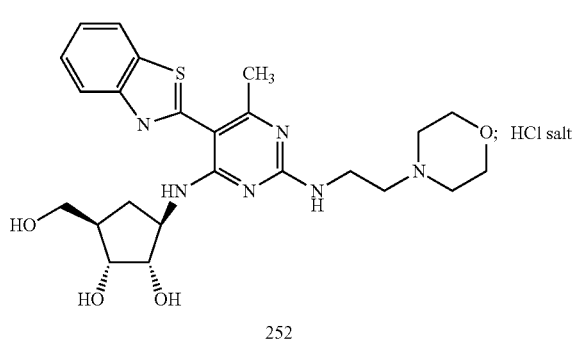
252
Step 1: Compound 329b was converted to 252a using procedure U, step 4 (conversion of 329b to 329c)
Step 2: Compound 252a was converted to 252b using Procedure Z, step 5.
Step 3: Compound 252b was converted to 248 using Procedure Z, step 6 (longer reaction time, 4-16 hrs)
Step 4: Compound 248 was converted to 252 using Procedure Z, step 7 (longer reaction time, 4-16 hrs).
Example 1015
Procedure Z10
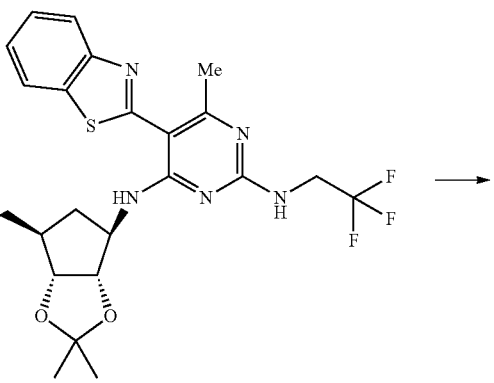
1015a
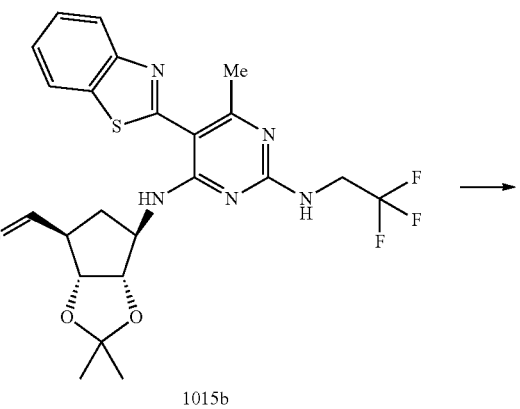
1015b
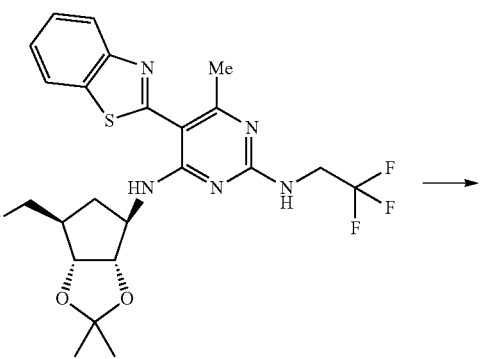
1015c

151

-continued

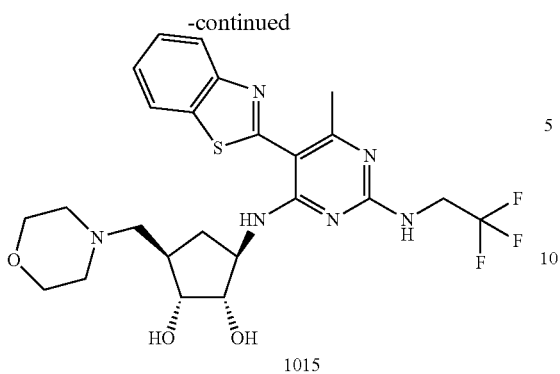
1015

To the SM, 1015a (prepared as in procedure U, 1 g, 2.0 mmol) in CH2Cl2/THF (50/25 ml) at 0° was added Dess-Martins periodinane (1.27 g, 3.0 mmol). 0°-10° C., 2 hrs. TLC (50/50 EtOAc/hexanes) indicated product and SM. So added more oxidant (~650 mg) and kept at that temp for additional 2 hrs. Then stored in the refrigerator (<5° C.), overnight. Then quenched with 10% sodium thiosulfate solution (50 ml)/satd bicarbonate (50 ml). Diluted with CH$_2$Cl$_2$ (100 ml). Stirred vigorously for 5 min. The org layer was separated and washed with 10% sodium thiosulfate solution (50 ml)/satd bicarbonate (50 ml), brine (100 ml), dried (Na2SO4), filtered and concentrated. The crude material was purified by flash silica chromatography using 0/100 to 60/40 of EtOAc/hexanes to give 1015b, wt=740 mg (white solid).

To 1015b (140 mg, 0.276 mmol) in dichloroethane (5 ml) at room temperature was added morpholine (0.025 ml, 0276 mmol) and sodium triacetoxy borohydride (77 mg, 0.359 mmol). Stirred at room temp for 1.5 hr. TLC (5/95 MeOH/CH2Cl2) indicated reaction completion. Cooled reaction mixture in an ice bath, and quenched with addition of satd NaHCO3, dropwise. Diluted with CH2Cl2 (50 ml), washed with satd NaHCO3 solution (50 ml), dried (Na2SO4), filtered and concentrated. The crude material was purified by flash silica chromatography using 0/100 to 5/95 of MeOH/CH$_2$Cl$_2$ to give 1015c, wt=83 mg.

1015c was converted to product 1015 using procedures described earlier (Z3, last step).

Example 1019

Procedure Z11

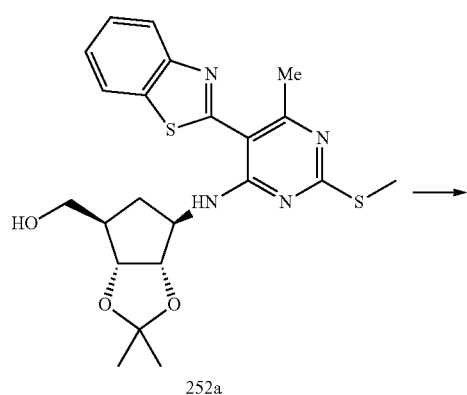
252a

152

-continued

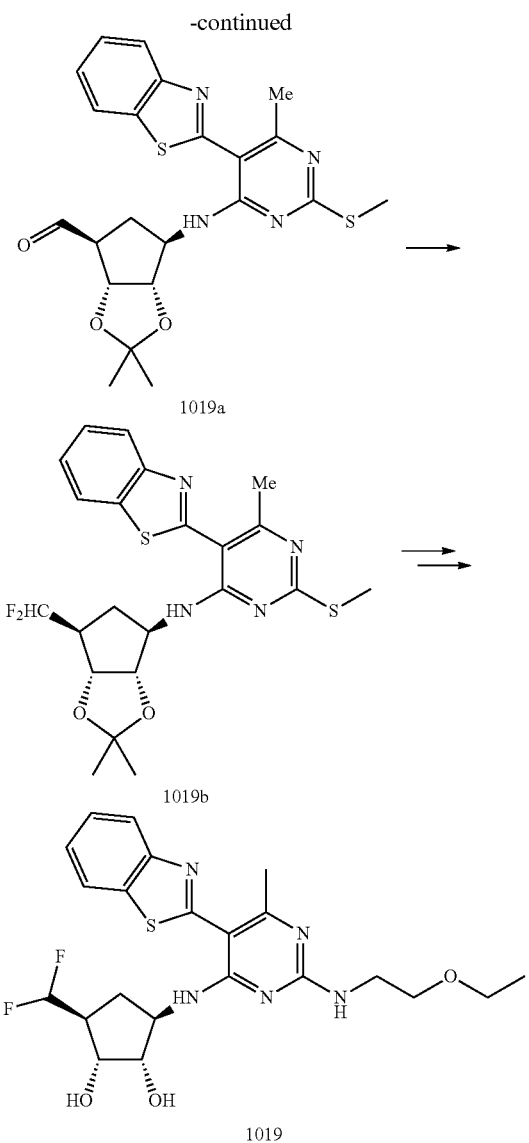
1019a

1019b

1019

To the 252a (100 mg, 0.22 mmol) in CH$_2$Cl$_2$ (5 ml) at 0° was added DM periodinane (112 mg, 0.26 mmol, 12 equiv). 0°-10° C., 1 hr. TLC (50/50 EtOAc/hexanes) showed reaction completion. Quenched with 10% sodium thiosulfate solution (25 ml)/satd bicarbonate (25 ml). Diluted with EtOAc (50 ml). Stirred vigorously for 5 min. The org layer was separated and washed with 10% sodium thiosulfate solution (25 ml)/satd bicarbonate (25 ml), brine (50 ml), dried (Na2SO4), filtered and concentrated. The crude material was purified by flash silica chromatography using 0/100 to 60/40 of EtOAc/hexanes to give 1019a, wt=81 mg (white solid).

To the aldehyde, 1019a (81 mg, 0.18 mmol) in CH$_2$Cl$_2$ (3 ml) at RT was added Deoxo-Fluor, Bis(2-methoxyethyl)aminosulfur trifluoride (50% in THF, 1 ml).

Maintained at room temp for 1 hr to two days (till reaction completion by TLC). Then quenched by pouring (DROPWISE) into ice cold satd NaHCO3, with vigorous stirring (~25 ml). Added CH2Cl2 (25 ml) and stirred for 10 min. Then poured into step funnel, and separated the org layer. Extracted the aq layer with CH2Cl2 (25 ml). The combined org layer was dried (Na2SO4), filtered and concentrated. The crude material was purified by flash silica chromatography using 0/100 to 50/50 of EtOAc/hexanes to give 1019b, wt=31 mg (white solid).

1019b was converted to product 1019 using procedures described earlier (Z3).

Example 1057

Procedure Z13

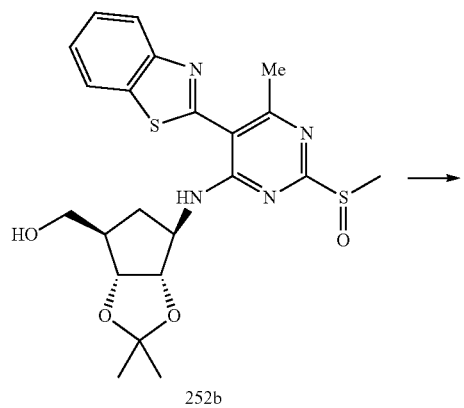
252b

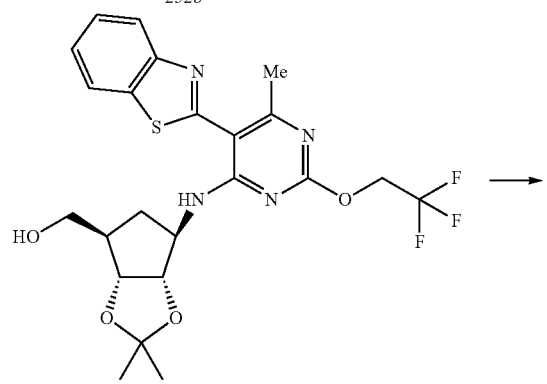
1057a

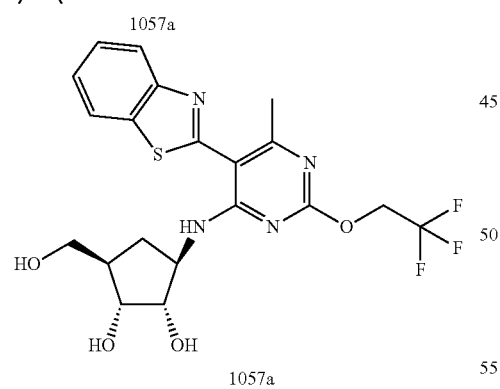
1057a

To a solution of trifluoroethanol (0.03 ml) in dry THF (3 ml) was added sodium hydride (60% dispersion in oil, 16 mg). Stirred at room temp for 15 min. Then added a solution of 252b (200 mg) in dry THF (3 ml). Heated to 100° C. and monitored by TLC till completion of reaction. Reaction was quenched by addition od saturated NH4Cl solution. Extracted organics into EtoAc (50 ml), washed with water (50 ml), brine (50 ml), dried (Na2SO4), filtered and concentrated. The crude material was purified by flash silica chromatography using EtOAc/hexanes to give 1057a.

1057a was converted to product 1057 using procedures described earlier (Z3, last step).

(Note: Rxn had to be heated to 45° C. for complete deprotection).

Example 1058

Procedure Z14

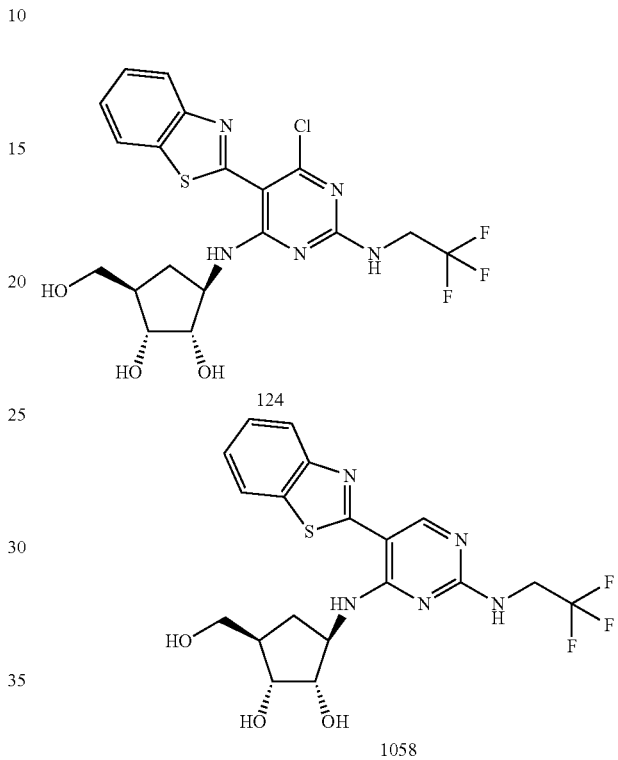

Compound 124 (100 mg) was taken in gl AcOH (10 ml) and MeOH (10 ml). Added spatula tip of 20% Pd(OH)$_2$/C (wet) and hydrogenated at ~40-50 psi of H2 using the Parr shaker, overnight. Then filtered thru celite, rinsed with MeOH and concentrated. The crude residue was purified by reverse phase HPLC, as described in Procedure C, to provide pure 1058.

Example 1104

Procedure Z-15

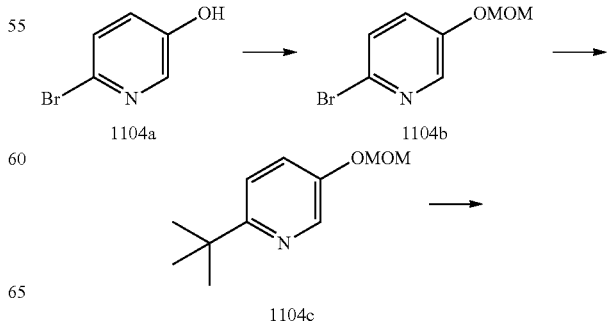

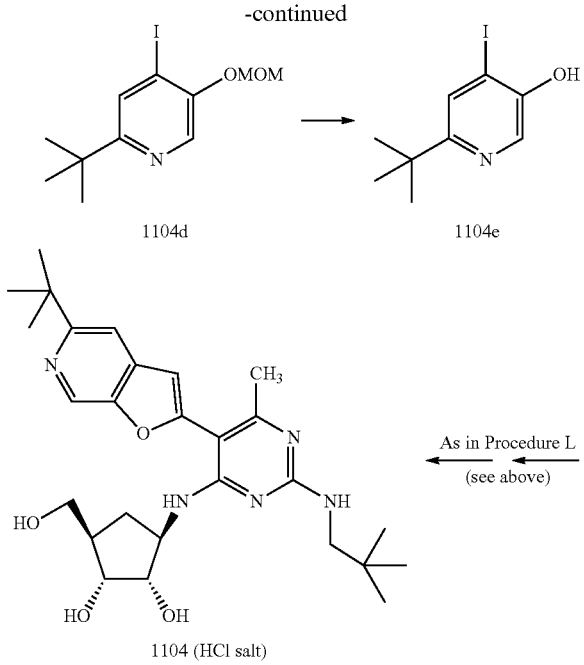

Chloromethylmethyl ether (2.11 ml) in DMF (15 ml) was added to an ice bath cooled solution of the pyridol (1104a; 4.86 g; 28 mmol) in DMF (70 ml) under an atmosphere of nitrogen. The resulting mixture was allowed to attain room temperature overnight. Aqueous work-up and silica gel column chromatography gave the desired methoxymethyl ether (1104b; 3.86 g) as a pale-yellow oil. MH+, 218, 220.17 tert-Butylmagnesium chloride (Aldrich; 27.5 ml of a 2.0M solution in diethyl ether) was added to a stirred suspension of cuprous cyanide (1.232 g; 13.8 mmol) in anhydrous THF (60 ml) at −78 C, under an atmosphere of nitrogen. After 0.5 h., the bromide (1104b; 0.75 g; 3.4 mmol) in THF (2 ml) was added and after ~2 h. at −78 C, the resulting reaction mixture was allowed to reach room temperature, overnight. sat. aq. sodium bicarbonate was added and the mixture was partitioned between EtOAc and water. The organic phase was separated, dried (MgSO4) and concentrated. The residue was purified by silica gel column chromatography on silica gel using EtOAc:hexanes (1:20) as eluent to give the desired alkylpyridine (1104c; 0.303 g) as a colourless oil. MH+, 196.25.

n-Butyl lithium (1.2 ml of a 1.6M solution in hexanes; Aldrich) was added dropwise to a stirred solution of the pyridine (1104c; 0.282 g; 1.46 mmol) in anhydrous THF (5 ml) at −78 C, under an atmosphere of nitrogen. after stirring for 1 h., iodine (0.441 g; 1.7 mmol) in THF (1 ml) was added and the temperature was maintained at −78 C for a further 2 h before the addition of sat. aq. NH4Cl. aqueous work-up and silica gel column chromatography using EtOAc-hexanes (1:10) gave the desired aryl iodide (1104d; 0.332 g) as a colourless oil. MH+, 322.17

TFA (1 ml) was added to a stirred solution of the ether (1104d; 0.320 g) in dichloromethane (4 ml) while cooled in an ice bath, under an atmosphere of nitrogen. When the addition was complete the reaction mixture was stirred at room temperature, overnight. The volatiles were removed under reduced pressure and the residue partitioned between EtOAc and sat. aq. sodium bicarbonate. The aqueous phase was separated and further extracted with EtOAc. The combined organic phases were dried (MgSO4) and concentrated to give the desired pyridol (1104e; 0.252 g) as a white solid. MH+, 278.17

Using the procedures set forth in procedure Y, 1104e was transformed into 1103 (MH+, 538.3) and 1104 (498.3)

Example 1120

Procedure Z16

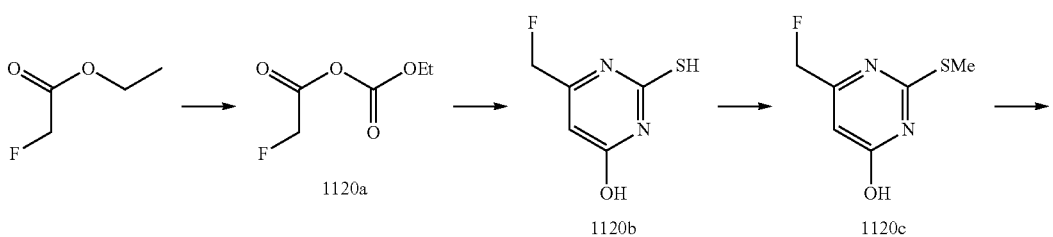

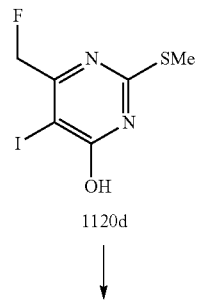

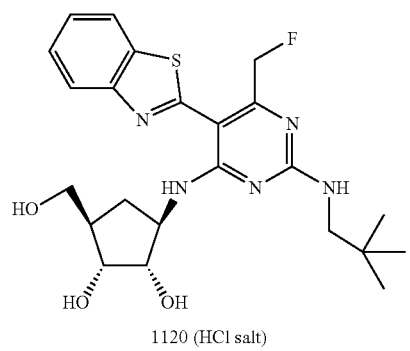

1120 (HCl salt)

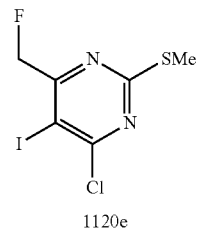

1120e

As in Procedure U
(see above)

LDA (59 ml of a 2.0M solution in heptane/THF/ethylbenzene) was added to a solution of ethylacetate (9.7 ml; 109 mmol) in ether (100 ml) at −78 C under an atmosphere of nitrogen. After stirring for 0.5 h ethyl fluoroacetate (10.5 g; 99 mmol) was added and the resulting reaction mixture was allowed to reach room temperature overnight. The reaction was partitioned between EtOAc and 10% aq. HCl. Aqueous work-up gave a residue that was purified by vacuum distillation to give the desired fluoroacetylacetate (1120a; 4.26 g), as a colourless oil.

A mixture of the fluoroacetylacetate (1120a; 4.24 g), thiourea (2.3 g) and 2M methanolic NaOMe (15 ml) were left to stand at room temperature for 48 h. The volatiles were removed under reduced pressure and the residue was dissolved in water. Acetic acid was added and the mixture was left at room temperature overnight. The desired pyrimidine (1120b; 1.26 g) was collected. a considerable amount of product remained in the mother liquor but was not pursued at this time.

Methyl iodide (0.398 g) was added dropwise to a stirred mixture of the pyrimidine (0.831 g) and potassium carbonate (0.870 g) while cooled in an ice bath. the resulting reaction mixture was allowed to reach room temperature overnight. water (40 ml) was added and the solid was collected (1120c; 0.262 g). A second crop precipitated but was set aside.

The methyl sulfide (1120c; 0.189 g), NIS (0.268 g) in acetonitrile was heated to reflux for 2.5 h. The volatiles were removed under reduced pressure and the residue partitioned between EtOAc and 10% aq. sodium thiosulfate. The organic phase was separated, washed with water, dried (MgSO4) and concentrated to give the pyrimidyl iodide (1120d) used without purification in the next step.

To the crude product (1120d) from the previous step was added phosphoryl chloride (2 ml) and the mixture was heated to reflux for 1 h. After cooling ice was added and the mixture partitioned between methylene chloride and water. The aqueous phase was made alkaline with the addition of potassium carbonate. The organic phase was separated, dried (MgSO4) and concentrated. Silica gel column chromatography using EtOAc:hexanes (1:20) gave the chloropyrimidine (1120e; 0.196 g). MH+, 319.6

Using chloropyrimidine (1120e;) and the chemistry described in general method U or (procedure U), 1120 and 1121 were prepared.

Example 1132

Procedure Z17

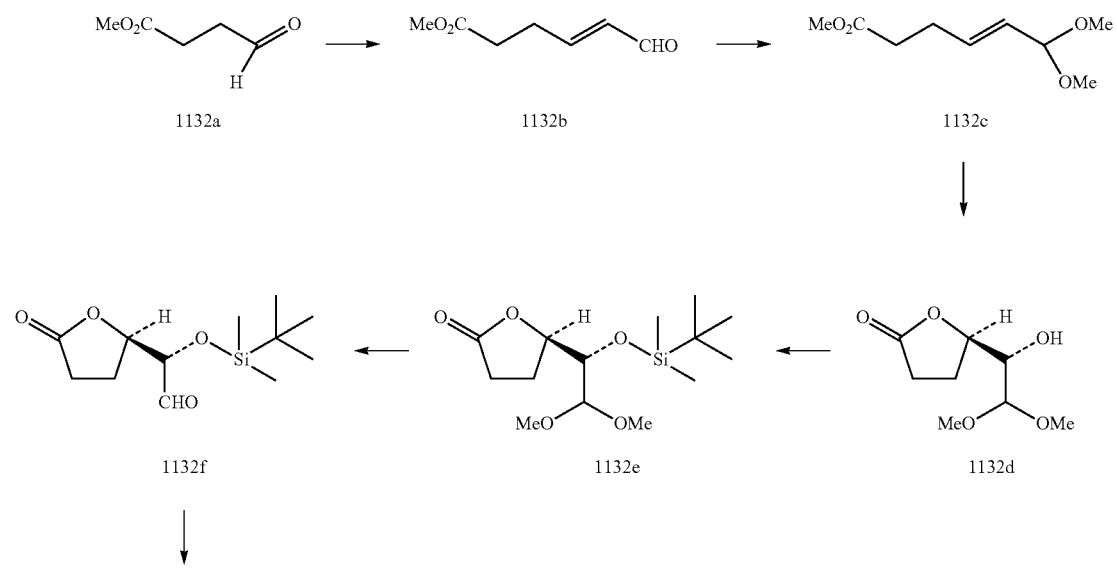

-continued

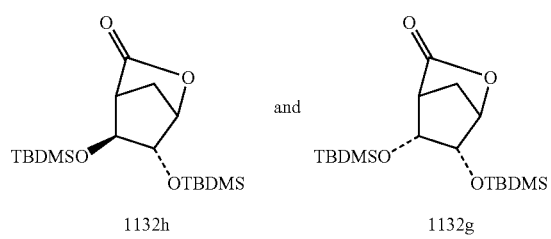

1132h and 1132g

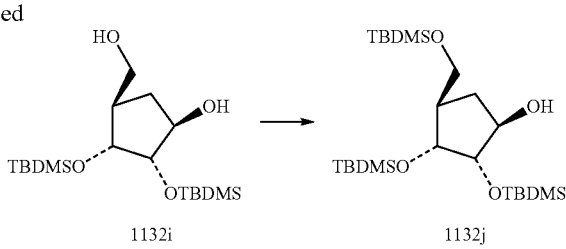

1132i    1132j

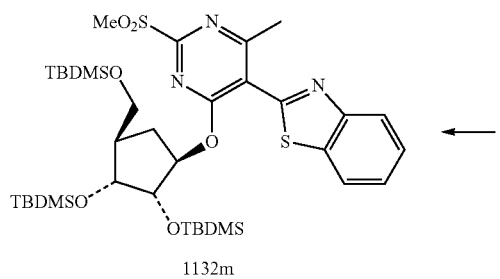

1132m    1132l

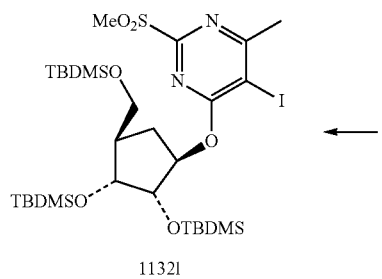

1132k

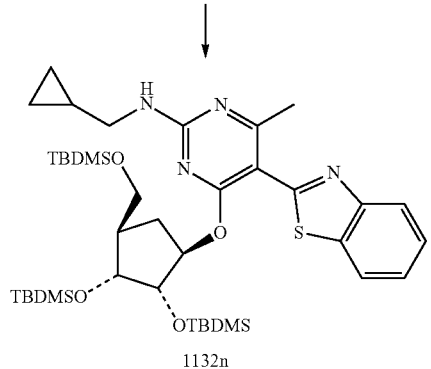

1132n

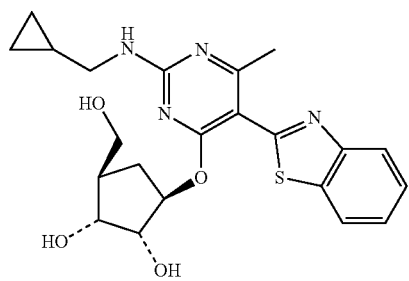

1132 (HCl salt)

(Formylmethylene)triphenylphosphorane (8.26 g; 1.05 eq.) was added to a stirred solution of the aldehyde (1132a) at room temperature and the resulting mixture was stirred overnight. The volatiles were removed under reduced pressure and the residue was purified by silica gel column using EtOAc:hexanes;1:5 as eluent to provide the desired unsaturated aldehyde (1132b; 2.11 g) as a yellow oil.

Ammonium nitrate (36 mgs) was added to a stirred solution of the aldehyde (1132b; 1.525 g) and trimethylorthoformate (1.368 g) in anhydrous methanol in an ice bath, under an atmosphere of nitrogen. The resulting mixture was allowed to warm to room temperature overnight, Sodium bicarbonate was added and the volatiles were removed under reduced pressure. The residue was partitioned between EtOAc and sat. aq. sodium bicarbonate. The organic phase was separated, washed with water, dried (MgSO4) and concentrated under reduced pressure to give the desired acetal (1132c; 1.976 g) as an orange oil, which was used without purification.

AD-mix-☐ (6.30 g) was added to the dimethylacetal (1132c; 0.846 g) in tert-butanol (22.5 ml) and water (22.5 ml) followed by additional portions of (DHQD)$_2$PHAL (31.5 mgs) and potassium osmate (31.5 mgs) and the resulting mixture stirred at room temperature for 3 h., before adding sodium sulfite (6.8 g). Aqueous work-up gave the crude lactone (1132d; 0.692 g), used without purification.

TBDMSOTf (1.54 ml) was added dropwise to a stirred solution of the alcohol (1132d; 1.167 g) and 2,6-lutidine (2.13 ml) in methylene chloride (15 ml) at room temperature, under an atmosphere of nitrogen. After 5 h., 5% aq. citric acid was added. Aqueous work-up and purification by silica gel column chromatography gave the desired silyl ether (1132e; 0.962 g) as a pale-yellow oil.

Lithium tetrafluoroborate (0.199 g) was added to the aqueous (2%) acetonitrile (18 ml) solution of the acetal (1132e; 0.585 g) and the resulting mixture was heated to 100 C. (oil bath temp.) for 12 h. After cooling, sat. aq. sodium bicarbonate was added. Aqueous work-up gave the desired aldehyde (1132f; 0.376 g).

TBDMSOTf (0.243 ml) was added dropwise to a stirred solution diisopropylethylamine (0.184 ml) in dichloromethane (4 ml) at room temperature under an atmosphere of nitrogen. The mixture was stirred at room temperature for 10 min., before the addition of the aldehyde (1132f; 0.100 g) in dichloromethane (2 ml). The reaction was stirred overnight and sat. aq. ammonium chloride was added. The aqueous phase was separated and further extracted with methylene chloride. The combined organic phases were dried (MgSO4) and concentrated. The residue was purified by silica gel column chromatography using EtOAc:hexanes (1:50) to give the lactone (1132 g; 0.033 g) followed by the isomer (1132 h; 0.072 g). Both were obtained as colourless oils.

A THF solution of lithium tetraborohydride (0.7 ml Of a 2.0M) was added to a THF (3 ml) solution of the lactone (1132 g; 0.100 g) while cooled in an ice bath, under an atmosphere of nitrogen and the resulting mixture was stirred at room temperature for a period of 6 h., before the addition of sat. aq. ammonium chloride. The mixture was partitioned between water and methylene chloride. The aqueous phase was separated and further extracted with methylene chloride (×2). The combined organic phases were dried (MgSO4) and concentrated to provide the diol (1132i; 0.071 g).

DMAP (0.062 g) was added to a stirred mixture of the diol (1132i; 0.062 g) and TBDMSCl (0.028 g) and the resulting mixture was stirred overnight at room temperature. The reaction mixture was partitioned between methylene chloride and 10% aq. HCl. The organic phase was separated washed with sat. aq. sodium bicarbonate, water, dried (MgSO4) and concentrated under reduced pressure. The crude reaction product was purified by silica gel column chromatography to give the secondary alcohol (1132j; 0.052 g).

NaH (0.011 g of a 60% dispersion in mineral oil) followed by the pyrimidine (324d; 0.0425 g) were added to a THF solution of the alcohol (1132j; 0.046 g) at room temperature and the resulting mixture was stirred overnight. Additional portions of NaH (0.011 g) and pyrimidine (0.0425 g) were added and the reaction was stirred for a further 24 h. Sat. aq. ammonium chloride was added and the organics were extracted into methylene chloride, dried (MgSO4) and concentrated. The residue was purified by silica gel column chromatography using EtOAc:hexanes:1:99 to give the desired ether (1132 k; 0.062 g), containing a small quantity of an impurity.

MCPBA (0.034 g of 77% pure material) was added to a stirred solution of the sulfide (1132 k; 0.062) and sodium bicarbonate (0.069 g) in dichloromethane (3 ml) and the mixture was stirred at room temperature overnight. A further portion of MCPBA (0.034 g) and the mixture was stirred for a further 24 h. The reaction mixture was partitioned between EtOAc and 10% sodium thiosulfate. The organic phase was separated, washed with 10% aq. sodium carbonate solution, dried (MgSO4) and concentrated under reduced pressure. The residue was purified by silica gel column chromatography using EtOAc:Hexanes 1:20 to give the desired sulfone (11321).

Triethylamine (0.022 ml) was added to a mixture of the iodide (11321; 0.034 g), (2-tributylstannylbenzothiazole (0.037 g), copper(1) iodide (0.003 g) and PdCl$_2$(PPh$_3$)$_2$ (0.006 g) in dioxane (2 ml) and the reaction mixture was heated to 100 C, under an atmosphere of nitrogen for 1 h. After cooling, additional portions of the stannane, copper iodide, palladium catalyst and triethylamine were added and the mixture heated for a further 1 h. after cooling, the reaction was partitioned between EtOAc and 10% aq. HCl. The organic phase was separated, washed with water, dried (MgSO4) and concentrated under reduced pressure. The residue was purified by silica gel column chromatography using EtOAc-hexanes (1:10) to give the benzthiazole (1132m; 0.012 g) as a white solid.

Cyclopropylmethylamine (0.050 ml) was added to a solution of the sulfone (1132m; 0.012 g) and the mixture was heated to 110 C (oil bath temp.) for a period of 4 h., under an atmosphere of nitrogen. The volatiles were removed under reduced pressure to provide the desired amine (1132n) used without purification in the next step.

To all the material (1132n) from the previous step was added THF (1 ml), MeOH (1 ml) and 6N aq. HCl (0.5 ml). The resulting mixture was allowed to stand at room temperature for 2 h. The volatiles were removed under reduced pressure and the solid was washed with ether to provide the triol (1132, HCl salt; 0.0047 g) as a white solid.

Example 1133

Procedure Z18

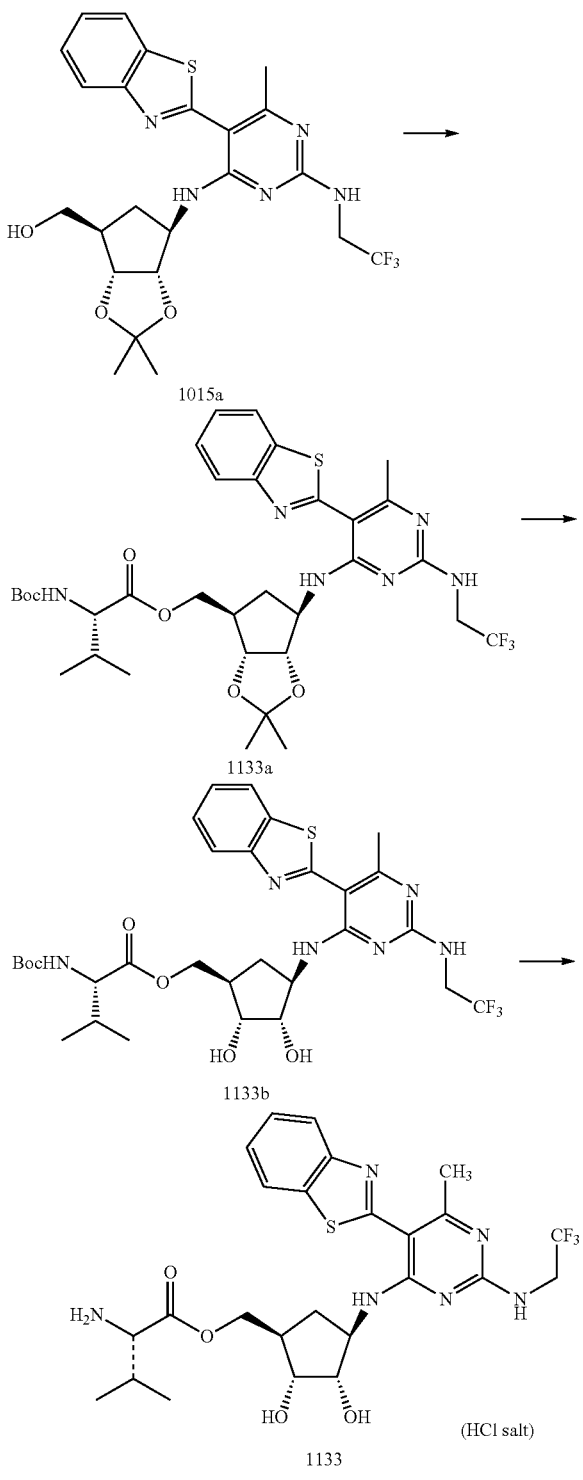

Triethylamine (0.082 ml) was added to a stirred mixture of the primary alcohol (1015a; 0.08 g), Boc-L-Val-OH (0.0423 g) and BOP reagent (0.086 g) in dichloromethane (3 ml) and the resulting mixture was stirred at room temperature overnight. The reaction was partitioned between EtOAc and 10% aq. HCl. the organic phase was separated, washed with sat. aq. sodium bicarbonate, water, dried and the volatiles were removed under reduced pressure. the residue was purified by silica gel column chromatography to give the desired ester (1133a; 0.046 g) as a white solid.

4M HCl in dioxane (5 ml) was added dropwise to a stirred solution of the dimethylketal (1133a; 0.040 g) in methanol (3 ml) and water (5 ml) while cooled in an ice bath. The resulting mixture was stirred for 2.5 h and solid sodium bicarbonate was added. aqueous work-up and silica gel column chromatography gave the desired diol (1133b; 0.0361 g) as a white solid.

To the protected amino acid ester (1133b; 0.035 g) in a mixture of methanol (3 ml) and water (5 ml) was added 4M HCl in dioxane (5 ml) while cooled in an ice bath. The resulting mixture was allowed to warm to room temperature overnight. The volatiles were removed under a stream of nitrogen to give the desired HCl salt (1133; 0.0286 g) as white solid.

Example 1134

Procedure Z19

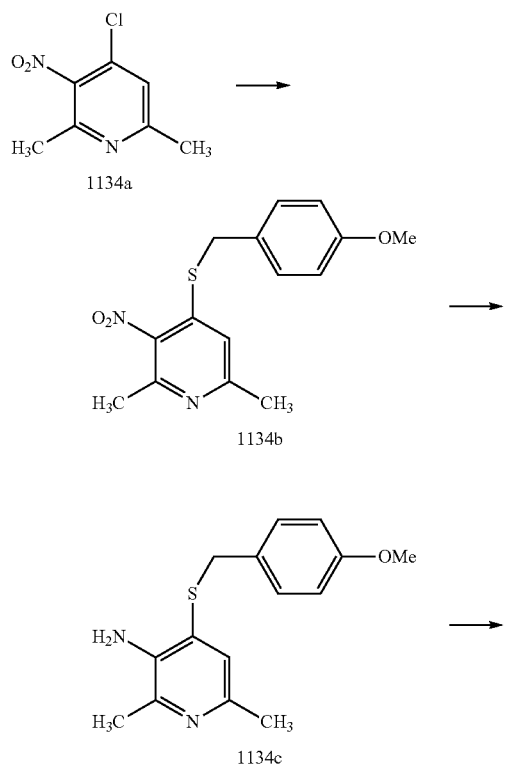

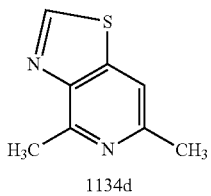

1134d

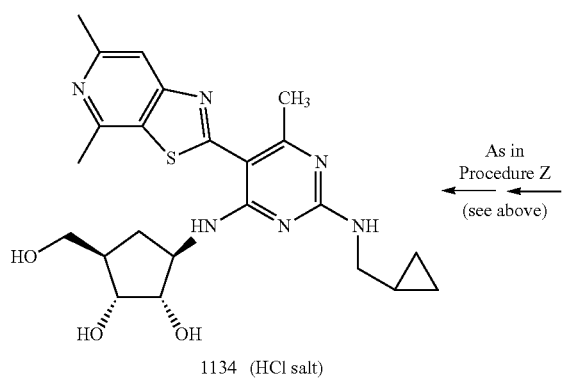

1134 (HCl salt)

Sodium hydride (0.223 g of a 60% dispersion in mineral oil) was added to a mixture of the chloride (as prepared according to J. Med. Chem. 1998, vol 41(22), pp. 4408-4420; 1134a; 0.691 g) and 4-methoxybenzylthiol (0.860 g) in anhydrous THF (10 ml) and the resulting mixture was stirred at room temperature for a period of 1 h. Saturated aq. sodium bicarbonate was added and the organics were extracted into methylene chloride (×3). The combined organic phases were dried (MgSO$_4$) and concentrated under reduced pressure to give the desired sulfide (1134b; 1.019 g) as a pale-yellow solid.

To the nitro compound (1134b, 1.06 g) was added ethanol (10 ml) and 10% Pd—C (0.50 g) was added and the resulting suspension was stirred under an atmosphere of hydrogen (balloon) at room temperature overnight. The reaction was filtered through a pad of celite and the solid was washed thoroughly with methanol. The filtrate was concentrated under reduced pressure to provide the desired amine (1134c) used in the next step without purification.

Formic acid (10 ml) was added to the amine (1134c) and the resulting mixture was heated (1500; oil bath temp.) for a period of 3 h. After cooling, TFA (30 ml) was added and the mixture heated (150; oil bath temperature) overnight. After cooling, the volatiles were removed under reduced pressure and the residue was partitioned between methylene chloride and sat. aq. sodium bicarbonate. The organic phase was separated, dried (MgSO4) and concentrated. The residue was purified by silica gel column chromatography to give the pyridylthiazole (1134d; 0.201 g).

Using the procedures set forth in procedure Z above 1134d was transformed into 1134.

Example 1136

Procedure Z20

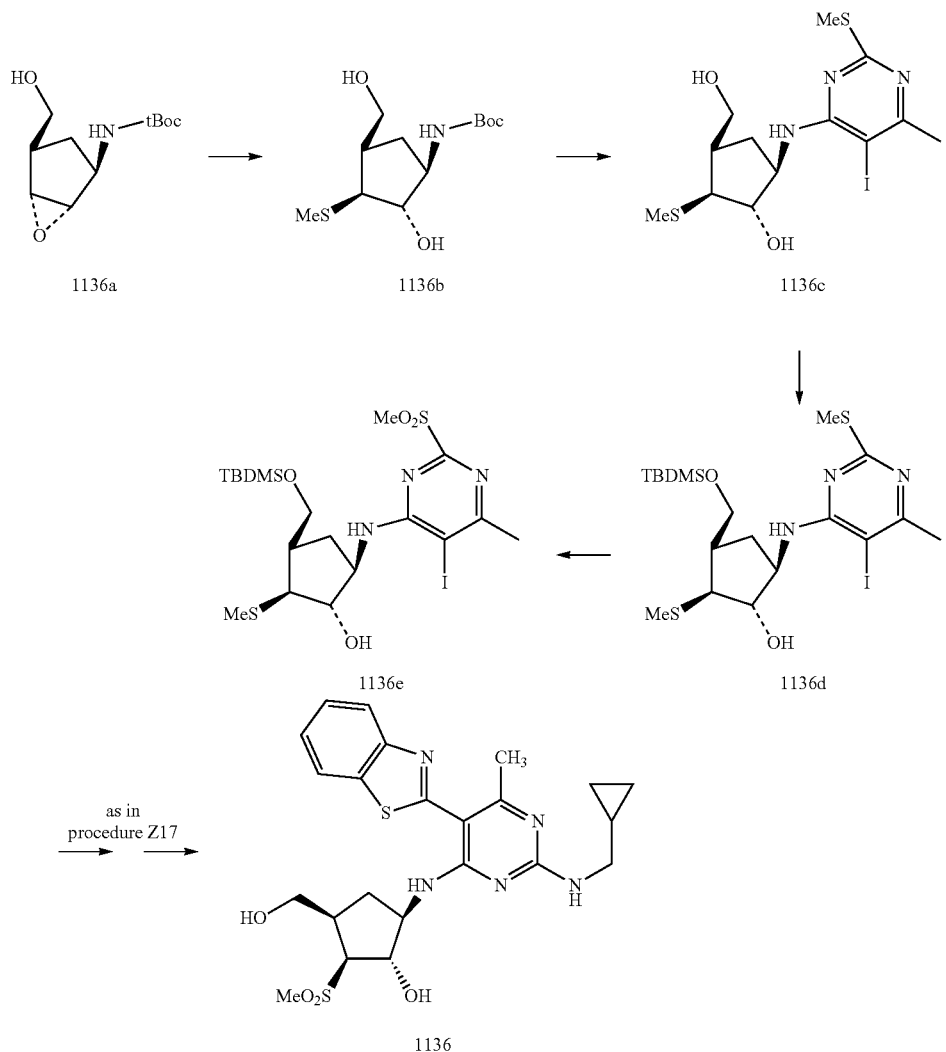

To the epoxide (prepared according to J.A.C.S. 2005, 127 (51), pp. 18143-18149; 1136a; 1.00 g) in ethanol was added NaSMe (0.379 g) and the resulting mixture was stirres at room temperature overnight, under an atmosphere of nitrogen. The volatiles were removed under reduced pressure and the residue partitioned between EtOAc and water. the organic phase was separated, dried (MgSO4) and concentrated. The residue was purified by silica gel column chromatography to give the diol (1136b; 0.421 g) as a white solid.

4M HCl in dioxane (5 ml) was added to the carbamate (1136b; 0.400 g) and the mixture was allowed to stand at room temperature for 2 h. the volatiles were removed under reduced pressure and ethanol (7 ml), the pyrimidine (324d; 0.535 g) and triethylamine (1.04 ml) were added and the resulting mixture was heated to reflux overnight. After cooling, the volatiles were removed under reduced pressure and the residue was purified by silica gel column chromatography to give the desired adduct (1136c; 0.409 g)

DMAP (0.011 g) was added to a mixture of the diol (1136c; 0.400 g), TBDMSCl (0.150 g), and triethylamine (0.151 ml) in dichloromethane (10 ml) and the resulting mixture was stirred at room temperature overnight. The reaction was partitioned between EtOAc and 10% aq. HCl. The organic phase was separated, washed with sat. aq. sodium bicarbonate, water, dried (MgSO4) and concentrated under reduced pressure. The residue was purified by silica gel column chromatography to give the silyl ether (1136d; 0.362 g).

To the di-methylsulfide (1136d; 0.195 g) and sodium bicarbonate (0.295 g) in dichloromethane was added MCPBA (0.394 g of 77% pure material) and the resulting suspension was stirred at room temperature overnight. The reaction was partitioned between EtOAc and 10% sodium thiosulfate. The organic phase was separated, dried (MgSO4) and concentrated under reduced pressure to give the di-sulfone (1136e; 0.184 g).

PdCl$_2$(PPh$_3$)$_2$ (0.0403 g) followed by CuI (0.020 g) were added to mixture of the iodide (1136e; 0.184 g), 2-tributylstannylbenzothiazole (0.252 g) and triethylamine (0.156 ml) in dioaxane (3 ml). The resulting mixture was heated to 100 C for 2 h. After cooling, aqueous work-up and silica gel column chromatography gave the desired adduct (1136f; 0.096 g).

Using the benzthiazole (1136f) and the procedures set forth in general procedure Z17, 1136 was obtained.

Example 1211

Procedure Z21

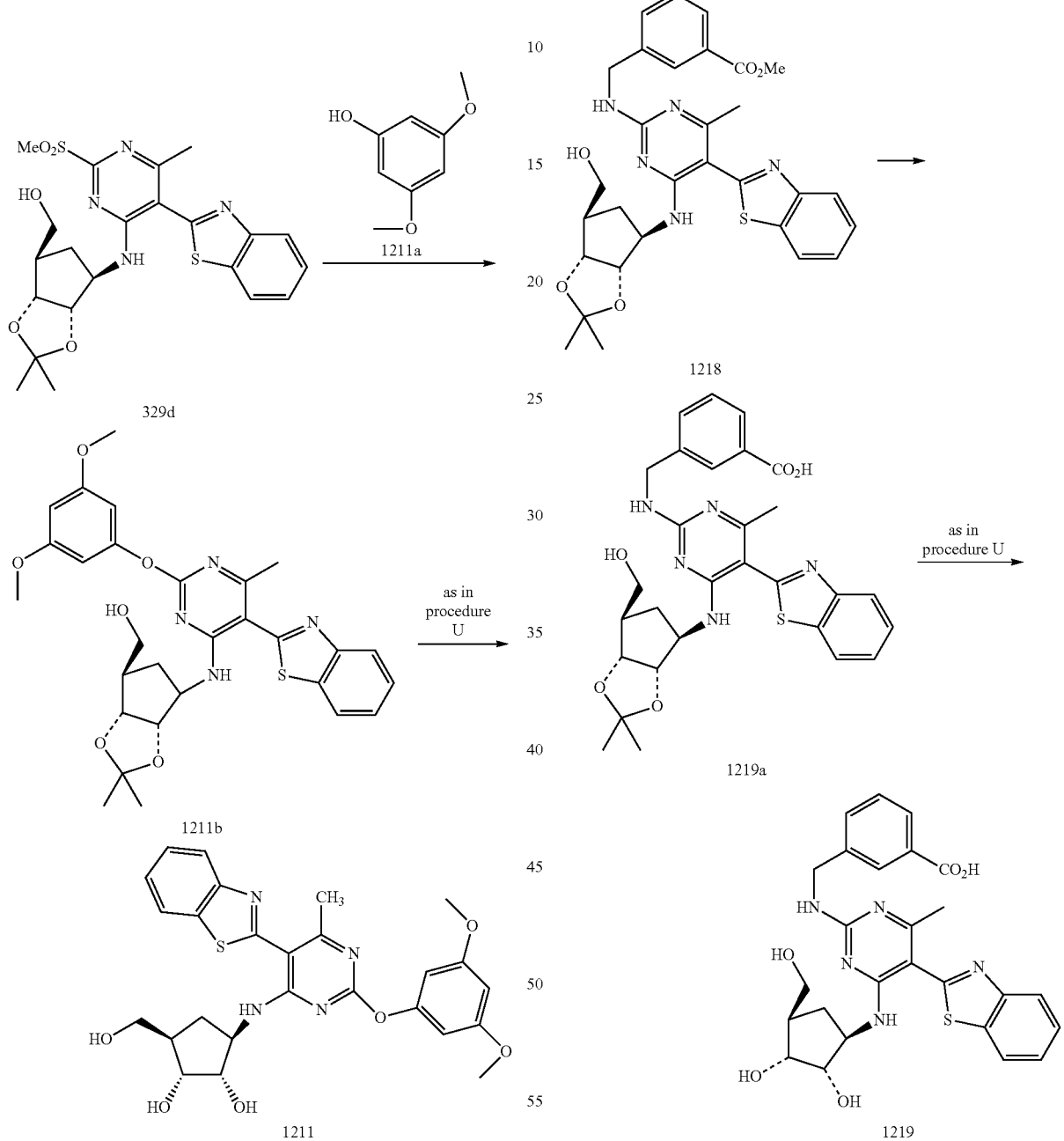

A mixture of sulfone (329d; 0.100 g) and the phenol (1211a; 0.157) in acetonitrile (5 ml) was heated to 100 C (oil bath temperature) under an atmosphere of nitrogen, overnight. After cooling, the volatiles were removed under reduced pressure. The residue was purified by silica gel plate chromatography to give the desired ether (1211b; 0.045 g).

1211b was transformed into 1211 as carried out for the conversion of 328 to 329 in procedure U.

Example 1219

Procedure Z21

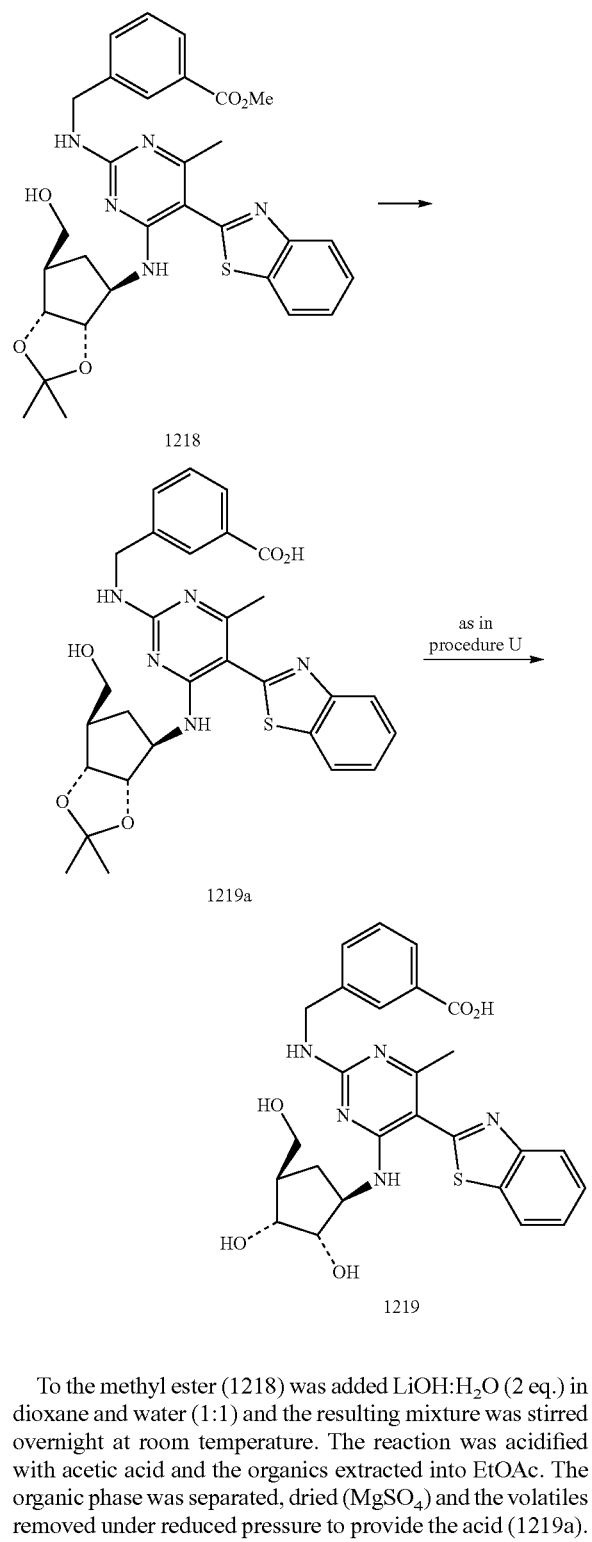

To the methyl ester (1218) was added $LiOH:H_2O$ (2 eq.) in dioxane and water (1:1) and the resulting mixture was stirred overnight at room temperature. The reaction was acidified with acetic acid and the organics extracted into EtOAc. The organic phase was separated, dried ($MgSO_4$) and the volatiles removed under reduced pressure to provide the acid (1219a).

1219a was transformed into 1219 as carried our for the conversion of 328 to 329 in procedure U.

Example 1223

Procedure Z22

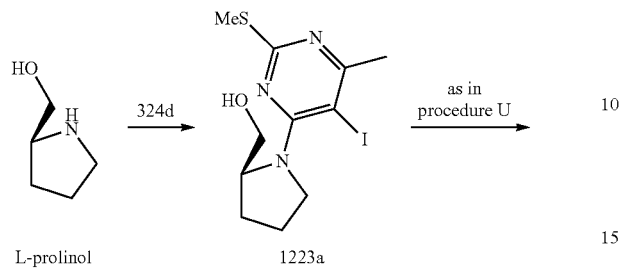

Using L-prolinol rather than the carbasugar, 1223 was produced via procedure U.

Example 1227

Procedure Z23

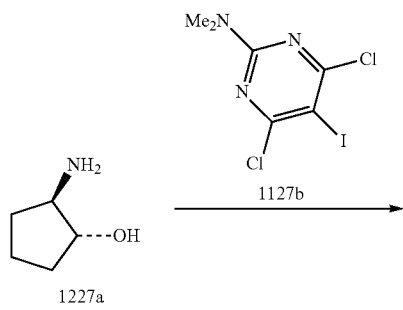

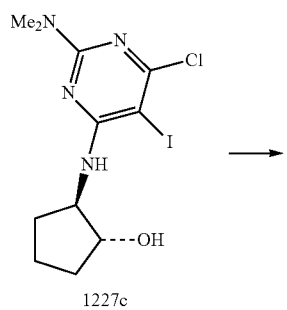

A mixture of the amino alcohol (rac-1227a; 0.477 g), pyrimidine (1227b; 1.00 g) and triethylamine (1.54 ml) in ethanol (20 ml) was refluxed under an atmosphere of nitrogen, overnight. The volatiles were removed under reduced pressure and the residue was purified by silica gel column chromatography to give the adduct (1227c).

Triethylamine (0.292 ml) was added to a mixture of the iodide (1227c; 0.200 g), 2-tributylstannylbenzothiazole (0.444 g), copper iodide (0.040 g) and $PdCl_2(PPh_3)_2$ in dioxane (20 ml) and the mixture was heated to 110 C under an atmosphere of nitrogen for 2 h. After cooling, the mixture was filtered through a pad of celite and the solid was washed thoroughly with EtOAc. The filtrate was concentrated and the residue was purified by silica gel column chromatography to give the benzthiazole (1227; 0.090 g).

Example 1238

Procedure Z24

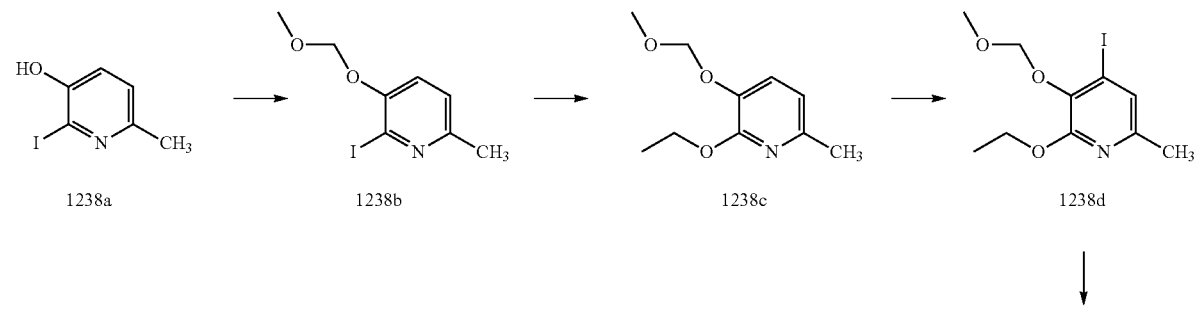

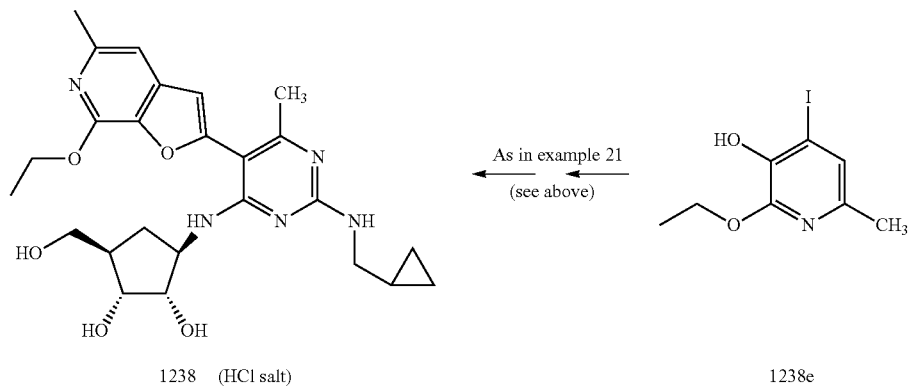

1238 (HCl salt)   1238e

To a mixture of the phenol (1238a; 2.00 g) and Hunigs base (2.2 ml) in dichloromethane (20 ml) was added chloromethylmethyl ether (1.29 ml) while cooled in an ice bath, under an atmosphere of nitrogen. The reaction mixture was allowed to reach room temperature, overnight. Solid sodium bicarbonate is added and the suspension is partitioned between methylene chloride and water. the organic phase was separated, dried (MgSO4) and concentrated under reduced pressure. The residue was purified by silica gel column chromatography to give the desired ether (1238b; 7.30 g)

Sodium ethoxide (1.48 g) was added to anhydrous ethanol (30 ml) and stirred for 10 min. at room temperature before the addition of the iodide (1238b; 1.22 g) and copper(I) bromide (0.125 g). The resulting mixture was heated to 900 for 2.5 h. The solvent was removed under reduced pressure and the residue purified by silica gel column chromatography to provide the desired adduct (1238c; 0.69 g).

n-BuLi (2.9 ml of a 2.5M solution in hexanes) was added dropwise to a stirred solution (THF; 20 ml) of the MOM ether (1238c; 1.20 g) at −78 C, under an atmosphere of nitrogen. The resulting mixture was stirred at this temperature for a period of 1 h., before the addition of iodine (1.70 g) in THF (10 ml). After stirring for a further 1 h., 1M aq. ammonium chloride and the mixture was allowed to warm to room temperature then partitioned between EtOAc and 10% aq. sodium thiosulfate. The organic phase was separated, washed with sat. aq. sodium bicarbonate, dried (MgSO4) and the volatiles were removed under reduced pressure. The residue was purified by silica gel column chromatography to give the desired iodide (1238d; 1.763 g).

TFA (4 ml) was added to a dichloromethane (16 ml) solution of the acetal (1238d; 1.60 g) while cooled in an ice bath, under an atmosphere of nitrogen. The resulting mixture was stirred at room temperature overnight and the volatiles were removed under reduced pressure and the residue partitioned between dichloromethane ans sat. aq. sodium bicarbonate. The organic phase was separated, dried (MgSO4) and concentrated under reduced pressure to give the desired pyridol (1238e; 1.292 g)

The iodopyridol (1238e) was transformed into 1238 using the chemistry set forth in example 21, above.

Example 1240

Procedure Z25

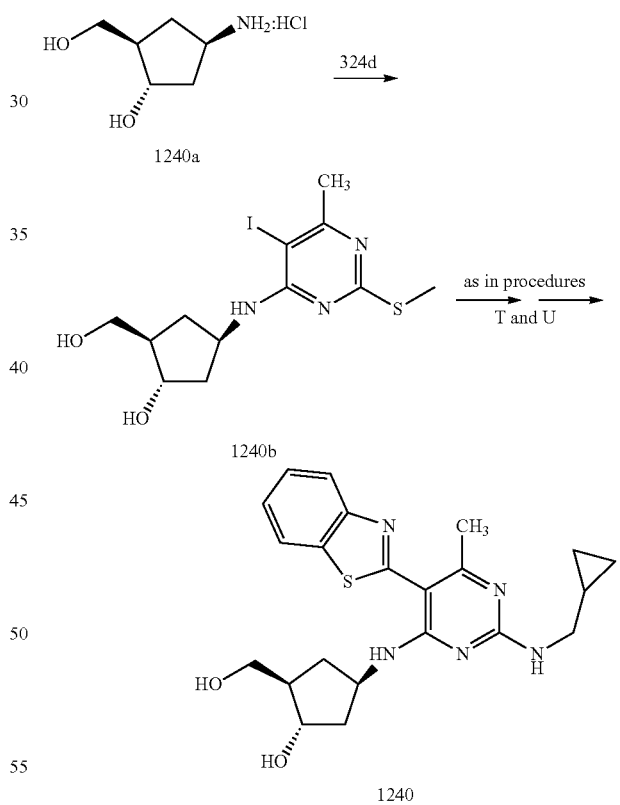

A mixture of the hydrochloride salt (1240a; 2.6 mmol; prepared as in J.A.C.S., 2005, 127(51), p18143), pyrimidine (324d; 0.937 g) and triethylamine (1.81 ml) in ethanol (10 ml) was refluxed under an atmosphere of nitrogen for a period of 12 h. After cooling, the volatiles were removed under reduced pressure and the residue was purified by silica gel column chromatograpghy to give the desired adduct (1240b; 0.844 g).

Using the chemistries outlined in procedures T and U above the diol (1240) was transformed into 1240.

Example 1244

Procedure Z26

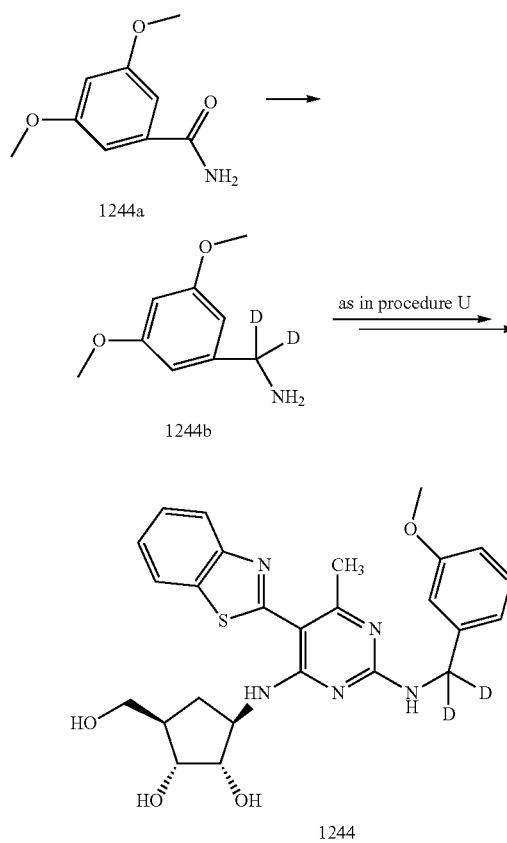

Lithium aluminium deuteride (0.42 g) was added in portions to a THF (20 ml) solution of the carboxamide (1244a; 1.63 g) at room temperature, under an atmosphere of nitrogen. 10% aq. NaOH followed by water and dichloromethane were added and the mixture was filtered through a pad of celite. The solid was washed thoroughly with THF and methanol. The filtrate was concentrated. Toluene was added (×3) and concentrated to give the amine (1244b)

The amine (1244b) was converted into 1244 using the chemistry described in procedure U.

Example 1251

Procedure Z27

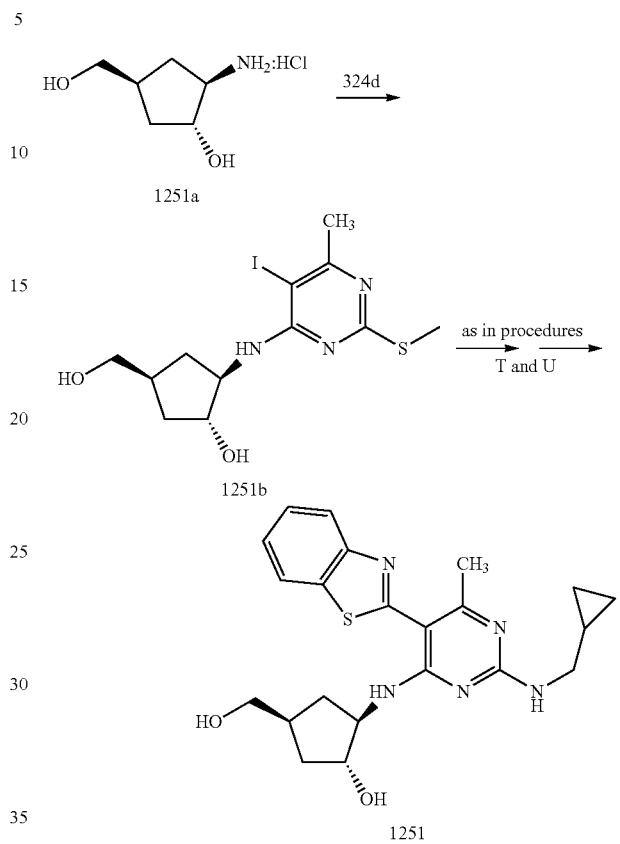

A mixture of the hydrochloride salt (1251a; 1 equivalent with respect to 324d; prepared as in J.A.C.S., 2005, 127(24), p8846), pyrimidine (324d; 0.288 g) and triethylamine (0.61 ml) in ethanol (8 ml) was refluxed under an atmosphere of nitrogen for a period of 12 h. After cooling, the volatiles were removed under reduced pressure and the residue was purified by silica gel column chromatograpghy to give the desired adduct (1251b; 0.200 g).

Using the chemistries outlined in procedures T and U above the diol (1251b) was transformed into 1251.

Example 1252

Procedure Z28

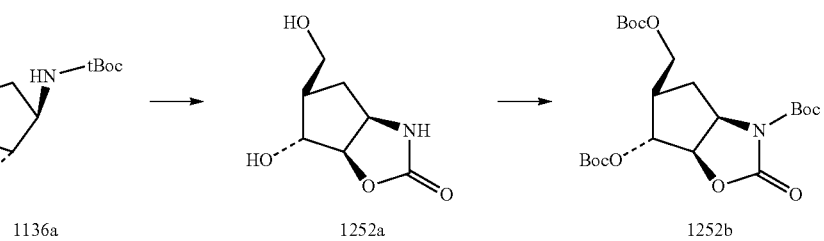

-continued

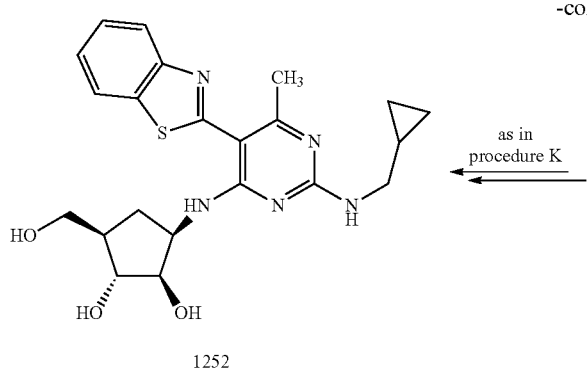

1252

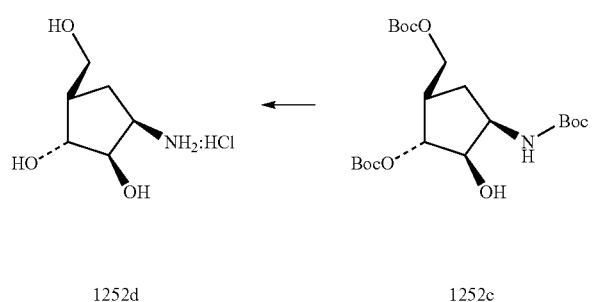

1252d                                      1252c

To the epoxide (1136a; 1.00 g) in methylene chloride (15 ml) was added (1S)-(+)-10-camphorsulfonic acid (0.101 g; 0.18q.) and the resulting mixture was stirred at room temperature for 12 h. Sat. aq. sodium bicarbonate was added and the organics were extracted into methylene chloride (×3). The combine organic phases were dried (MgSO4) and concentrated under reduced pressure. The residue was purified by silica gel column chromatography to provide the diol (1252a; 0.494 g).

Triethylamine (1.2 ml) followed by DMAP (0.068 g) were added to the dial (0.494 g) in THF (40 ml) and the resulting mixture was stirred at room temperature overnight. The volatiles were removed under reduced pressure and the residue was purified by silica gel column chromatography to give the desired adduct (1252b; 1.08 g).

Caesium carbonate (0.17 g) was added to the oxazolidinone (1252b; 1.08 g) in methanol (25 ml) and the resulting mixture was stirred at room temperature overnight. Sat. aq. ammonium chloride was added and the organics were extracted into methylene chloride. The organic phase was dried (MgSO4), and concentrated under reduced pressure. The residue was purified by silica gel column chromatograpghy to give the alcohol (1252c; 0.67 g)

The alcohol (1252c) was converted to the triol (1252d) with 4M HCl in dioxane and further converted into 1252 using the appropriate steps outlined in general procedure K.

Example 1301

Procedure Z29

-continued

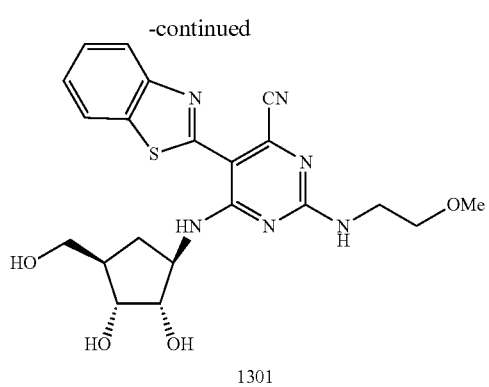

1301

Compound 201 (100 mg, 0.21 mmol) was combined with Zn(CN)$_2$ (300 mg), Pd(PPh3)$_4$ (50 mg), and NMP (2 mL). The reaction was stirred at 100 C overnight. The reaction was poured into water and filtered. The solids were washed with water and methylene chloride. After drying the solids were stirred in MeOH (2 mL) and then filtered. The methanol was concentrated to provide the product, 1301 (100 mg). [M+H] =457.3.

Example 1302

Procedure Z30

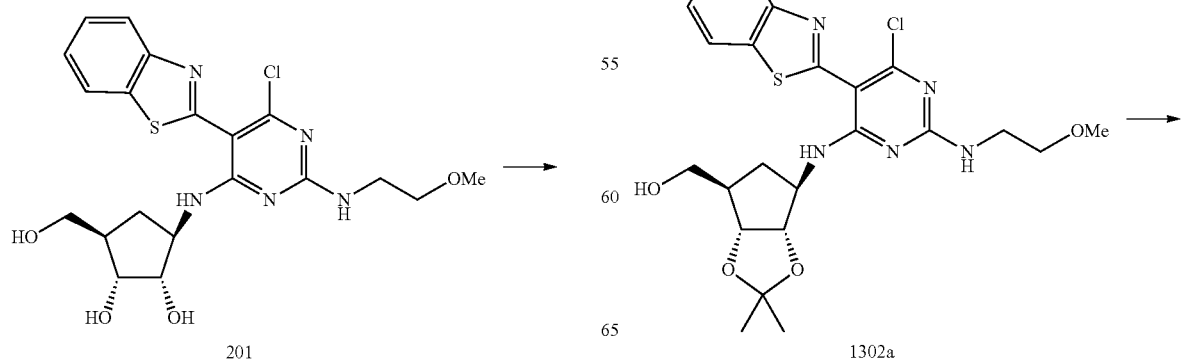

201                                      1302a

-continued

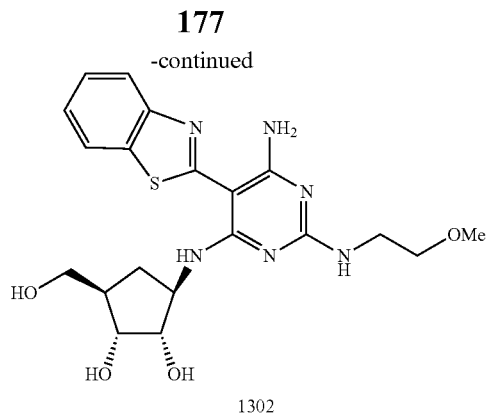

1302

Compound 1302a (100 mg, 0.197 mmol) was dissolved in ammonium hydroxide (3 mL) and dioxane (3 mL) and refluxed for 48 hrs. The reaction was quenched with water and extracted with ethyl acetate. The combined organic layers were dried over sodium sulfate and concentrated to provide 40 mg of the acetonide protected material [M+H]=487.4. This material was dissolved in MeOH (3 mL), 4M HCl dioxane (1 mL) and water (0.1 mL) and stirred for 3 hours at room temperature. The reaction was concentrated to provide the desired product 1302 (40 mg). [M+H]=447.2

Example 1315

Procedure Z31

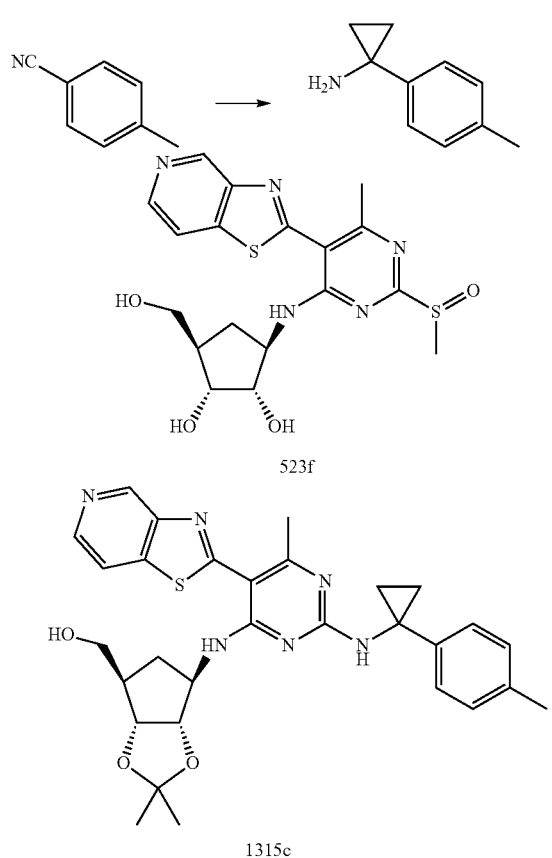

-continued

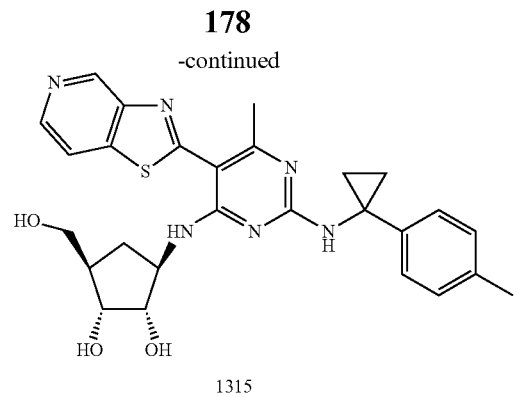

1315

Step 1:
See *Journal of Organic Chemistry*, 2003, 68, 7133 for the synthesis of similar derivatives from corresponding benzonitriles. [M+H]=148.2

Step 2:
See Procedure Z for similar experimental.

Step 3:
See Procedure Z for similar experimental.

Example 1318

Procedure Z32

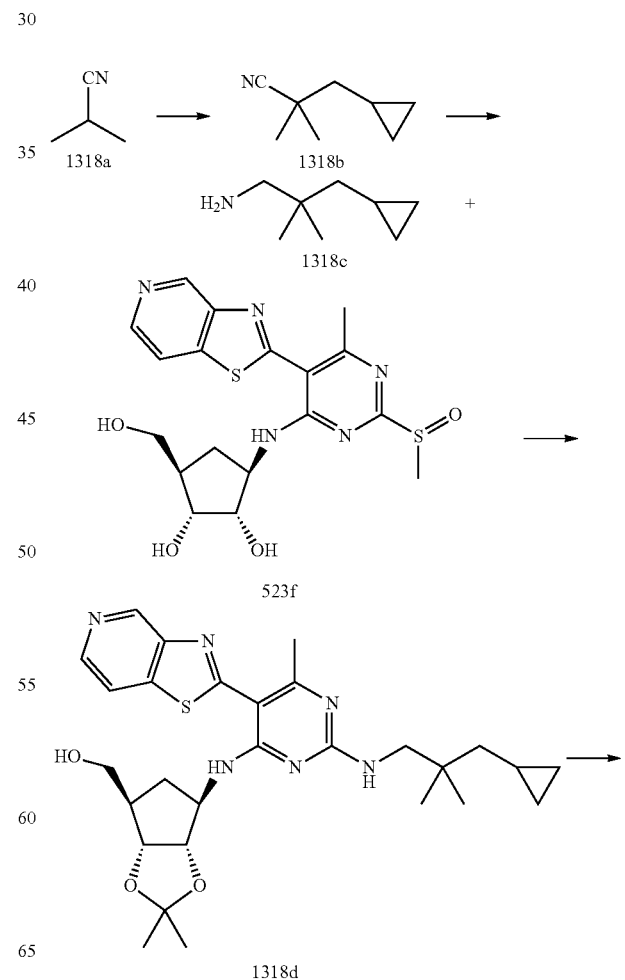

-continued

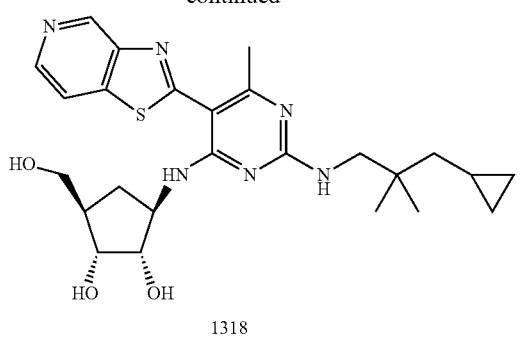

1318

Step 1:

A solution of 2M LDA (17 mL, 35 mmol) was cooled to −78 C and isobutyronitrile (1318a, 2.0 g, 30 mmol) was added dropwise in THF (20 mL). After the reaction was stirred for 1 hr at −78 C and 1 hr at 0 C, a solution of cyclopropylmethyl bromide (4.69 g, 35 mmol) was added dropwise in THF (15 mL). The resulting solution was stirred overnight at room temperature and then quenched with saturated ammonium chloride and extracted with diethyl ether. The organic layer was dried over sodium sulfate and concentrated. The residue was purified by column chromatography (hexanes→20% Et2O/hexanes) to provide 2.1 g of the product 1318b.

Step 2:

Compound 1318b (900 mg, 7.31 mmol) was dissolved in diethyl ether (10 mL) and treated with lithium aluminum hydride (300 mg). The mixture was refluxed overnight and then slowly quenched with 1N NaOH. The solids were filtered and washed with ether. The combined ether layers were dried over sodium sulfate and concentrated to provide the desired product 1318c (700 mg).

Step 3:

See Procedure Z for similar experimental.

Step 4:

See Procedure Z for similar experimental.

Example 1321

Procedure Z33

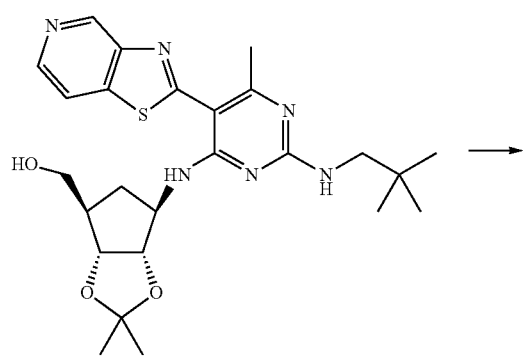

536

-continued

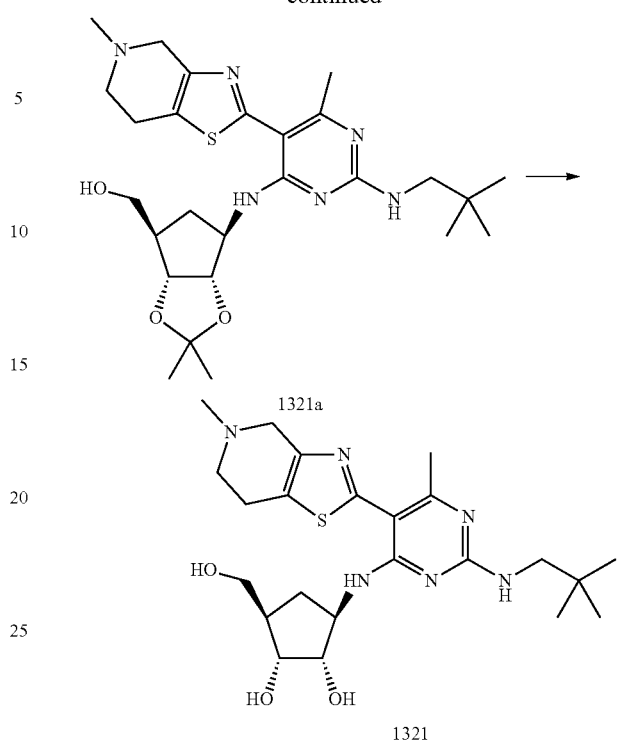

1321

Step 1:

Compound 536 (60 mg, 0.120 mmol) was dissolved in acetone (3 mL) and is iodomethane (0.3 mL). The solution was stirred at 80 C for 2 hours. The solvent was evaporated and the product was used without purification (~65 mg). [M+H]=513.5. The residue was dissolved in THF (5 mL) and water (5 mL) and treated with sodium borohydride (0.2 g). The reaction was stirred overnight and then quenched with saturated sodium bicarbonate and extracted with ethyl acetate. The combined organic layers were dried over sodium sulfate and concentrated to provide 1321a (60 mg). [M+H]=517.6

Step 2:

See Procedure Z for similar experimental.

Example 1327

Procedure Z34

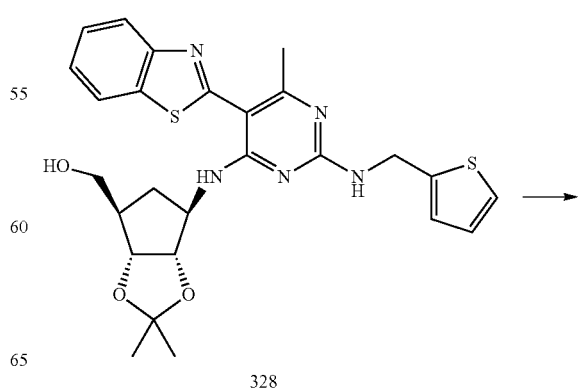

328

-continued

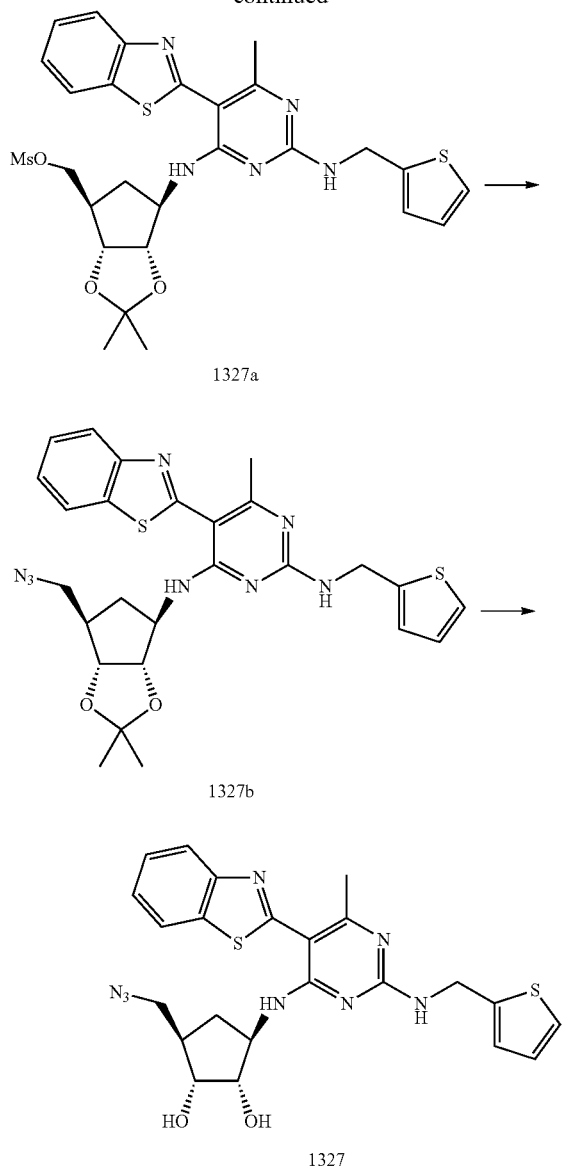

1327a

1327b

1327

Compound 328 was synthesized using procedure U.

Step 1:

Compound 328 (370 mg, 0.707 mmol) was dissolved in methylene chloride (10 mL) and triethylamine (0.1 mL) and cooled to 0 C. Methanesulfonyl chloride (89 mg, 0.78 mmol) was added dropwise in methylene chloride (1 mL) and the reaction was stirred for 1 hour at room temperature. The reaction was treated with water and the organic layer was dried over sodium sulfate and concentrated to provide the desired product 1327a (380 mg). [M+H]=602.5

Step 2:

Compound 1327a (380 mg, 0.62 mmol) was dissolved in DMF (5 mL) and treated with sodium azide (500 mg). The reaction was stirred at 90 C for 3 hours and then quenched with water and extracted with ethyl acetate. The combined organic layers were washed with water, brine, dried over sodium sulfate, and concentrated to provide compound 1327b (350 mg). [M+H]=549.48

Step 3:

See Procedure Z for similar experimental.

Example 1328

Procedure Z35

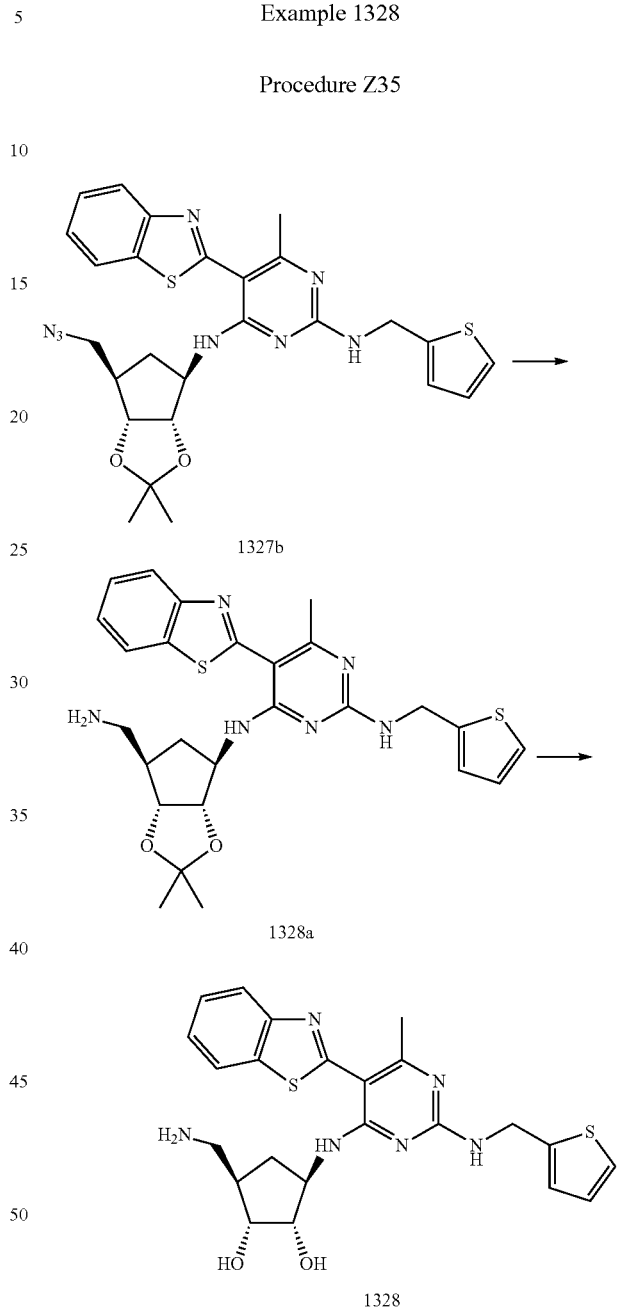

1327b

1328a

1328

Step 1:

Compound 1327b (100 mg, 0.182 mmol) was dissolved in THF (3 mL) and treated with triphenylphosphine (95 mg, 0.36 mmol). The reaction was stirred for 15 minutes and then treated with ammonium hydroxide (0.5 mL) and refluxed for 2 hours. The reaction was quenched with water and extracted with ethyl acetate. The combined organic layers were dried over sodium sulfate and concentrated. The residue was treated with 4M HCl dioxane (0.5 mL). The solids were filtered to provide the desired product 1328a (75 mg). [M+H]=523.5

Step 2:
See Procedure Z for similar experimental.

Example 1330

Procedure Z36

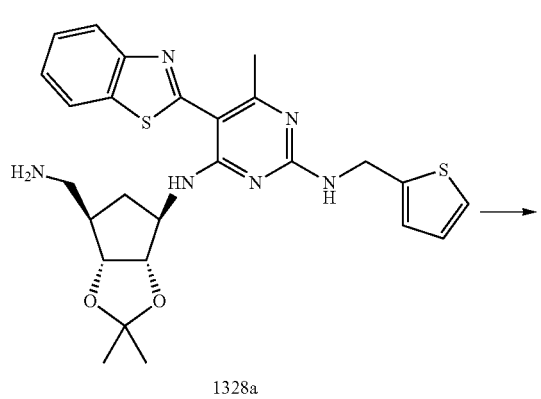

1328a

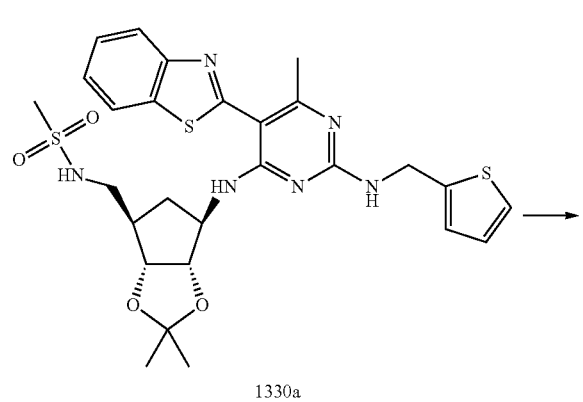

1330a

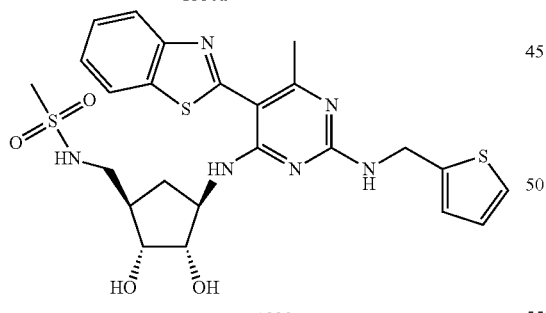

1330

Step 2:
See Procedure Z for similar experimental.

Example 1331

Procedure Z37

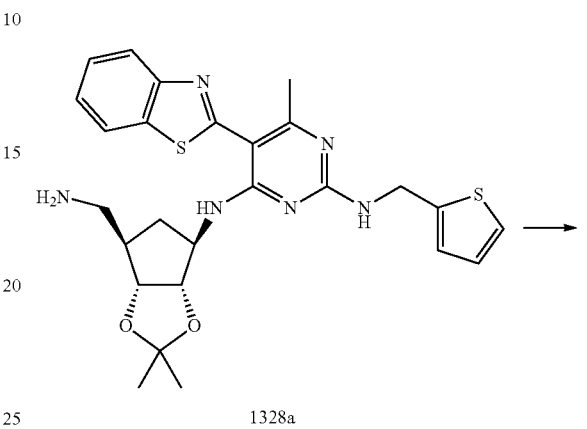

1328a

1331a

1331

Step 1:
Compound 1328a (65 mg, 0.124 mmol) was dissolved in methylene chloride (5 mL) and treated with triethylamine (13 mg, 0.124 mmol) and methanesulfonyl chloride (15 mg, 0.124 mmol). The reaction was stirred for 2 hours at room temperature and then quenched with water. The organic layer was dried over sodium sulfate and concentrated. The residue was purified by column chromatography (1:1 hexane/ethyl acetate→ethyl acetate). Isolated 45 mg of product, 1330a. [M+H]=601.5

Step 1:
Compound 1328a (65 mg, 0.124 mmol) was dissolved in THF (5 mL) and 1M NaOH (3 mL) and treated with acetic anhydride (0.1 mL). After 2 hours the reaction was quenched with water and extracted with ethyl acetate. The combined organic layers were dried over sodium sulfate and concentrated. The residue was purified by column chromatography (ethyl acetate) to provide 45 mg of compound 1331a. [M+H]=565.5

Step 2:
  See Procedure Z for similar experimental.

Example 1343

Procedure Z38

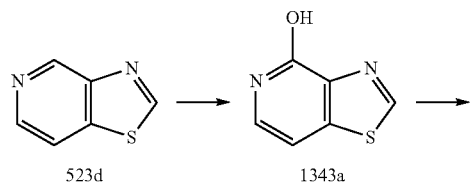

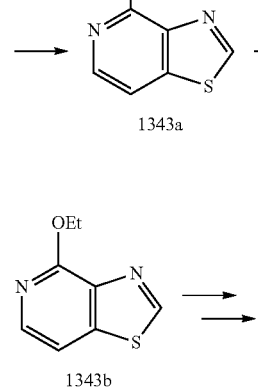

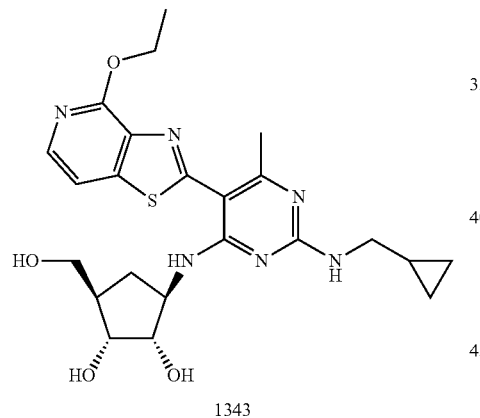

1343

Step 1:
  Compound 523d (1.5 g, 10.94 mmol) was suspended in methylene chloride (50 mL) and 77% mCPBA (3.77 g, 16.4 mmol) was added. The reaction was stirred for 2 hours and then the solvent was removed. The solids were washed with methylene chloride (2×). The solids were triturated with ethyl acetate to provide 700 mg of clean product 1343a and 700 mg with slight mCPBA impurities. [M+H]=153.16

Step 2:
  Compound 1343a (400 mg, 2.61 mmol) was dissolved in chloroform (15 mL) and treated with EtI (2 mL) and silver carbonate (1.0 g, 3.63 mmol) at reflux. After 3 hours the reaction was filtered and concentrated. The residue was purified by column chromatography (30% ethyl acetate/hexanes) to provide 140 mg of compound 1343b.

Step 3:
  The product 1343 was synthesized from 1343b using chemistry similar to that found in procedure Z.

Example 1350

Procedure Z39

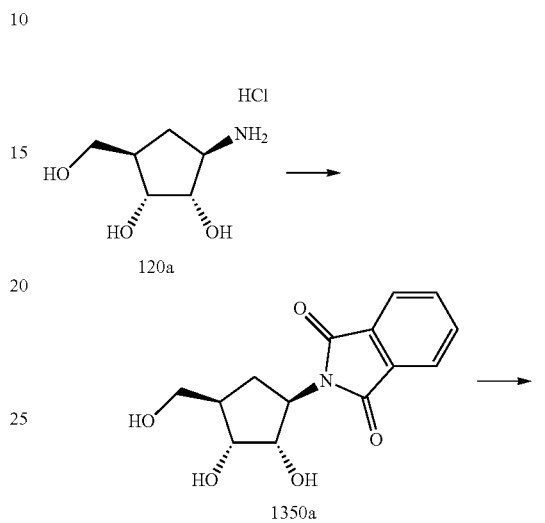

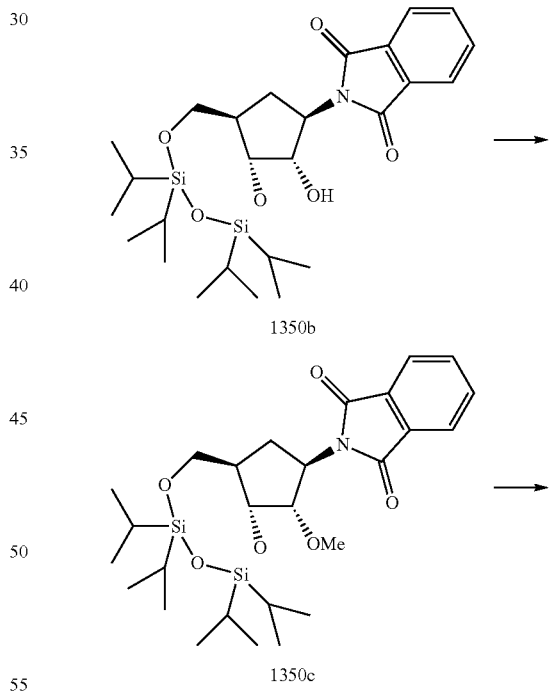

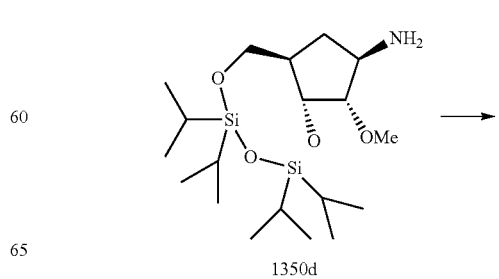

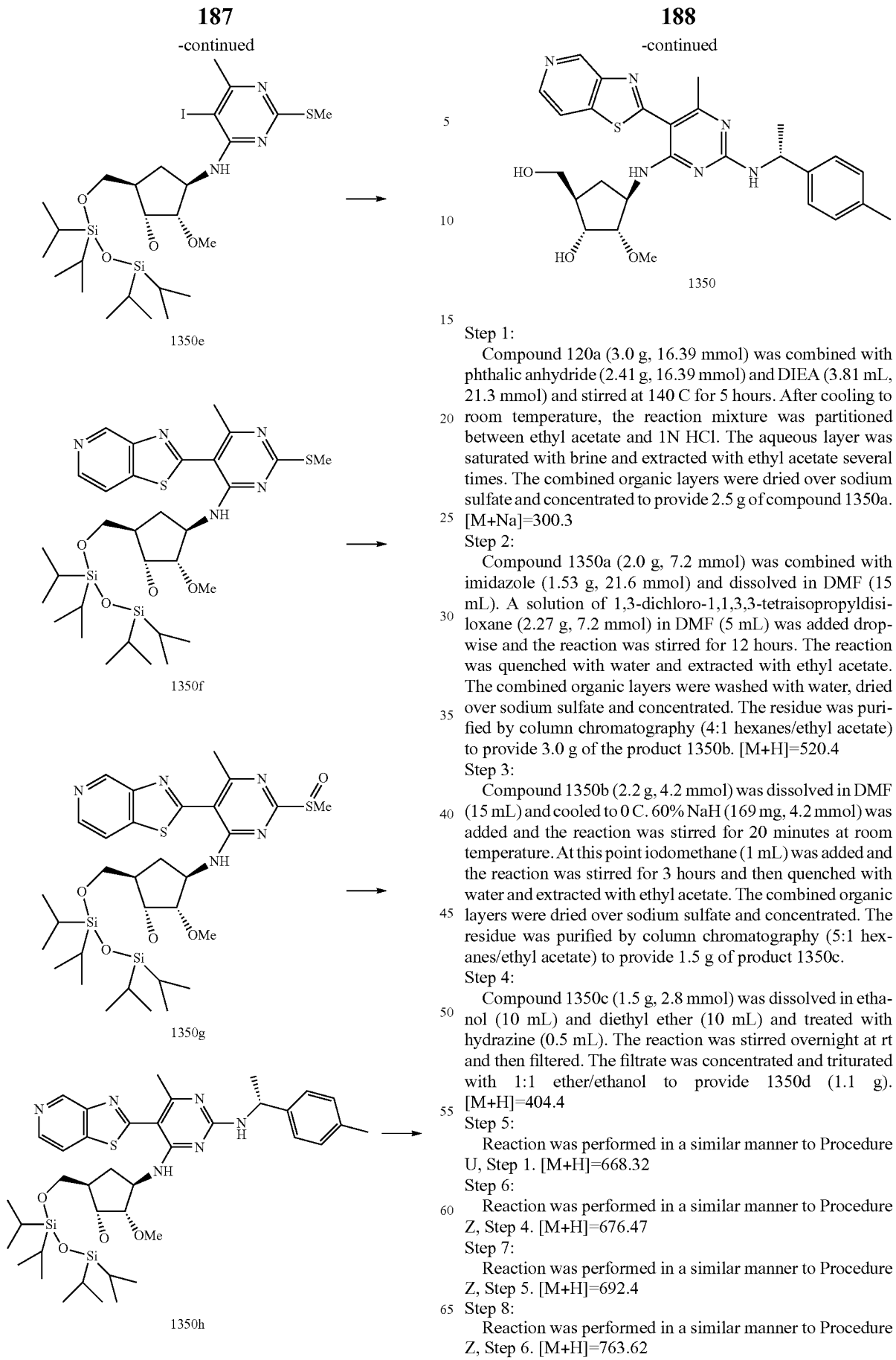

Step 1:
Compound 120a (3.0 g, 16.39 mmol) was combined with phthalic anhydride (2.41 g, 16.39 mmol) and DIEA (3.81 mL, 21.3 mmol) and stirred at 140 C for 5 hours. After cooling to room temperature, the reaction mixture was partitioned between ethyl acetate and 1N HCl. The aqueous layer was saturated with brine and extracted with ethyl acetate several times. The combined organic layers were dried over sodium sulfate and concentrated to provide 2.5 g of compound 1350a. [M+Na]=300.3

Step 2:
Compound 1350a (2.0 g, 7.2 mmol) was combined with imidazole (1.53 g, 21.6 mmol) and dissolved in DMF (15 mL). A solution of 1,3-dichloro-1,1,3,3-tetraisopropyldisiloxane (2.27 g, 7.2 mmol) in DMF (5 mL) was added dropwise and the reaction was stirred for 12 hours. The reaction was quenched with water and extracted with ethyl acetate. The combined organic layers were washed with water, dried over sodium sulfate and concentrated. The residue was purified by column chromatography (4:1 hexanes/ethyl acetate) to provide 3.0 g of the product 1350b. [M+H]=520.4

Step 3:
Compound 1350b (2.2 g, 4.2 mmol) was dissolved in DMF (15 mL) and cooled to 0 C. 60% NaH (169 mg, 4.2 mmol) was added and the reaction was stirred for 20 minutes at room temperature. At this point iodomethane (1 mL) was added and the reaction was stirred for 3 hours and then quenched with water and extracted with ethyl acetate. The combined organic layers were dried over sodium sulfate and concentrated. The residue was purified by column chromatography (5:1 hexanes/ethyl acetate) to provide 1.5 g of product 1350c.

Step 4:
Compound 1350c (1.5 g, 2.8 mmol) was dissolved in ethanol (10 mL) and diethyl ether (10 mL) and treated with hydrazine (0.5 mL). The reaction was stirred overnight at rt and then filtered. The filtrate was concentrated and triturated with 1:1 ether/ethanol to provide 1350d (1.1 g). [M+H]=404.4

Step 5:
Reaction was performed in a similar manner to Procedure U, Step 1. [M+H]=668.32

Step 6:
Reaction was performed in a similar manner to Procedure Z, Step 4. [M+H]=676.47

Step 7:
Reaction was performed in a similar manner to Procedure Z, Step 5. [M+H]=692.4

Step 8:
Reaction was performed in a similar manner to Procedure Z, Step 6. [M+H]=763.62

Step 9:

Compound 1350 h (75 mg, 0.098 mmol) was dissolved in THF (5 mL) and treated with TBAF (26 mg, 0.098 mmol). After 2 hours the reaction was quenched with saturated ammonium chloride and extracted with ethyl acetate. The combined organic layers were dried over sodium sulfate and concentrated. The residue was purified by column chromatography (10:1 ethyl acetate/methanol) to provide the desired product 1350 (28 mg). [M+H]=521.37

Example 1367

Procedure Z40

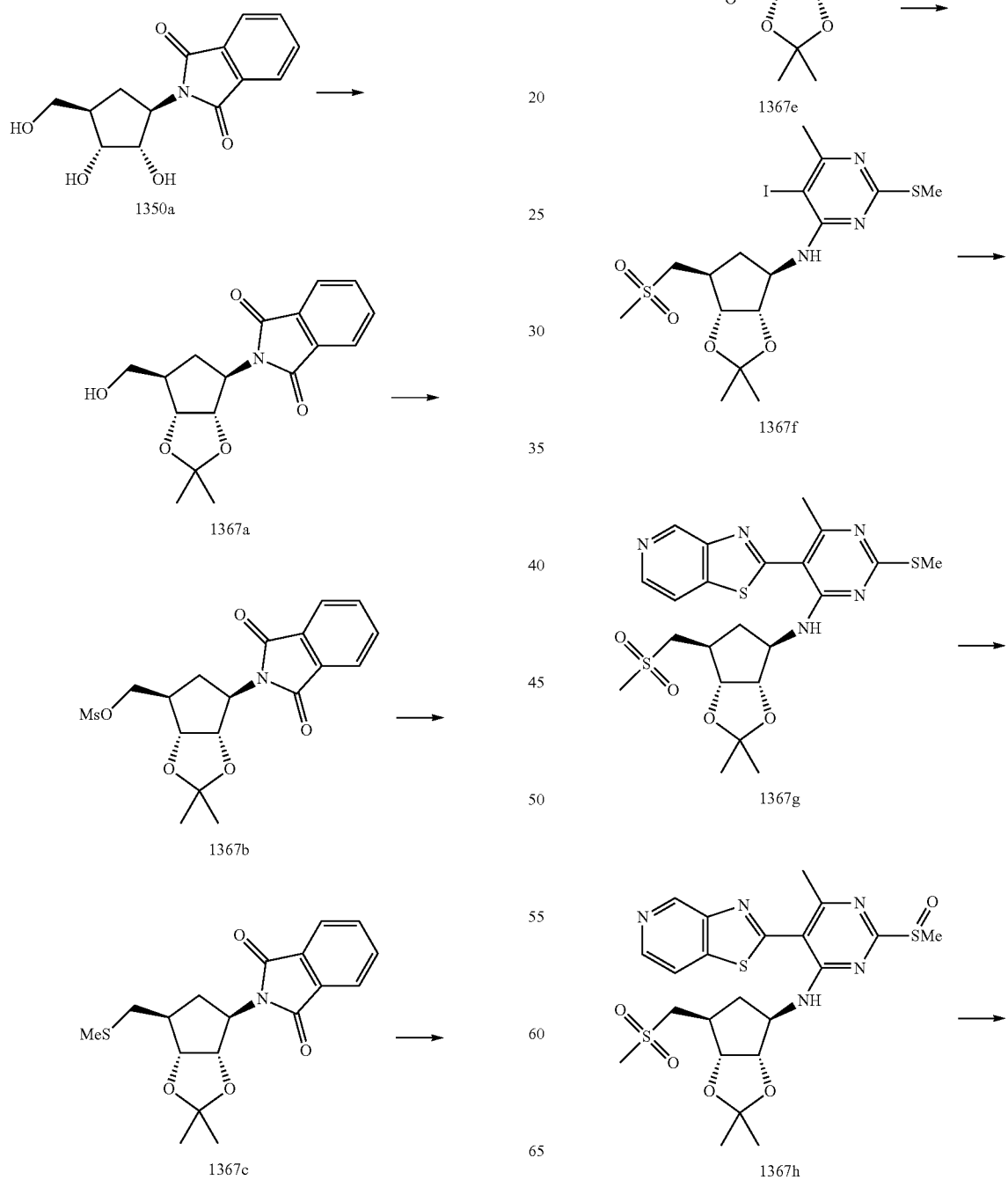

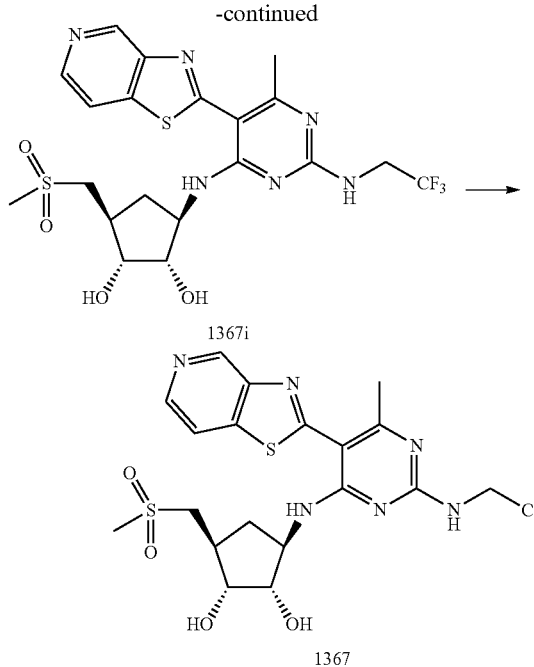

Step 1:
Compound 1350a (1.3 g, 4.6 mmol) was dissolved in acetone (30 mL) and treated with 2,2-dimethoxypropane (2 mL) and methanesulfonic acid (1 mL). After 5 hours the reaction was quenched with water and extracted with ethyl acetate. The combined organic layers were dried over sodium sulfate and concentrated. The residue was purified by column chromatography (1:1 hexanes/ethyl acetate) to provide 1.2 g of compound 1367a. [M+Na]=340.2

Step 3:
Compound 1367a (1.2 g, 3.77 mmol) was dissolved in methylene chloride (40 mL) and triethylamine (0.7 mL, 5 mmol). The reaction was cooled to 0 C and then methanesulfonyl chloride (517 mg, 4.5 mmol) was added dropwise in methylene chloride (5 mL). After stirring overnight the reaction was quenched with water. The organic layer was dried over sodium sulfate and concentrated. The residue was purified by column chromatography (1:1 hexanes/ethyl acetate) to provide 1.25 g of compound 1367b. [M+Na]=418.21

Step 4:
Compound 1367b (1.1 g, mmol) was dissolved in DMA (10 mL) and was treated with sodium thiomethoxide (290 mg, 4.15 mmol). The reaction was stirred for 5 hours and then quenched with water and extracted with ethyl acetate. The combined organic layers were washed with water, dried over sodium sulfate and concentrated to provide 1.0 g of compound 1367c that was used without purification.

Step 5:
Compound 1367c (1.0 g, 2.8 mmol) was dissolved in methylene chloride (20 mL) and treated with 77% mCPBA (3.2 g, 14.4 mmol). After stirring overnight the reaction was quenched with 1M potassium carbonate and extracted with methylene chloride. The organic layers were dried over sodium sulfate and concentrated to provide compound 1367d that was used without purification (550 mg).

Step 6:
Compound 1367d (550 mg, 1.45 mmol) was suspended in ethanol (10 mL) and treated with hydrazine monohydrate (0.5 mL). After stirring at 70 C for 30 minutes (to solubilize the reaction), the temperature was reduced to rt and the reaction was stirred overnight. The reaction was filtered and the filtrate was concentrated to provide compound 1367e (330 mg). [M+H]=250.18

Step 7:
Reaction was performed in a similar manner to Procedure U, Step 1. [M+H]=514.14

Step 8:
Reaction was performed in a similar manner to Procedure F, Step 2. [M+H]=522.20

Step 9:
Reaction was performed in a similar manner to Procedure Z, Step 5. [M+H]=538.23

Step 10:
Reaction was performed in a similar manner to Procedure Z, Step 6. [M+H]=573

Step 11:
The product 1367 was synthesized from 1367i using chemistry similar to that found in procedure Z.

Example 1366

Procedure Z41

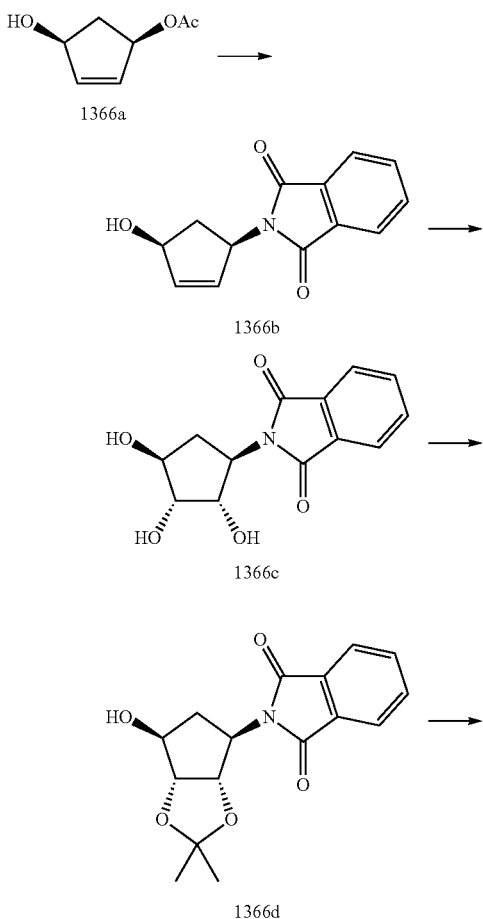

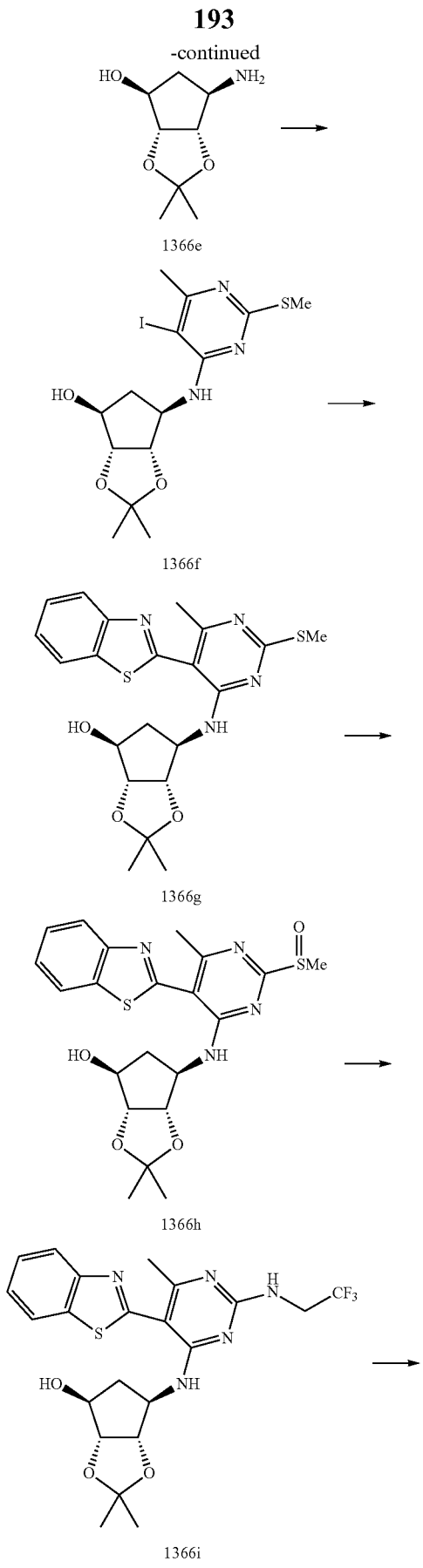

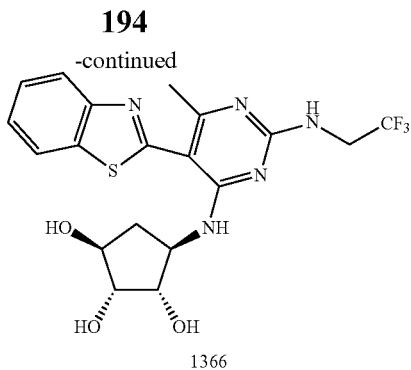

1366

Step 1:

Compound 1366a (429 mg, 3 mmol), potassium phthalimide (613 mg, 3.3 mmol), and Pd(PPh3)4 (300 mg) were dissolved in DMF (20 mL) and stirred at 90 C for 5 hours and then room temperature overnight. The reaction was quenched with water and extracted with ethyl acetate. The combined organic layers were washed with water, dried over sodium sulfate and concentrated. The residue was purified by column chromatography (2:1 hexanes/ethyl acetate→1:1 hexanes/ethyl acetate) to provide compound 1366b (400 mg). [M+H]=212.11.

Step 2:

Compound 1366b (400 mg, 1.88 mmol) was dissolved in THF (20 mL) and water (2 mL) and treated with NMO (448 mg, 3.76 mmol) and osmium tetroxide (50 mg). After stirring for 12 hours the reaction was quenched with water and extracted with ethyl acetate. The combined organic layers were dried over sodium sulfate and concentrated. The residue was triturated with methylene chloride to provide 300 mg of compound 1366c.

Step 3:

Compound 1366c (300 mg, 1.13 mmol) was dissolved in acetone (15 mL) and 2,2-dimethoxypropane (1 mL) and treated with methanesulfonic acid (0.4 mL). After stirring for 3 hours the reaction was quenched with water and extracted with ethyl acetate. The combined organic layers were dried over sodium sulfate and concentrated to provide compound 1366d (300 mg). [M+H]=304.22

Step 4:

Compound 1366d (300 mg, 0.98 mmol) was dissolved in ethanol (5 mL) and treated with hydrazine monohydrate (0.5 mL). The reaction was stirred at 70 C for 2 hours. After cooling to rt, the solids were filtered and the filtrate was concentrated to provide 170 mg of compound 1366e. [M+H]=174.17

Step 5:

Reaction was performed in a similar manner to Procedure U, Step 1. [M+H]=438.09

Step 6:

Reaction was performed in a similar manner to Procedure Z, Step 4. [M+H]=445.20

Step 7:

Reaction was performed in a similar manner to Procedure Z, Step 5. [M+H]=461.20

Step 8:

Reaction was performed in a similar manner to Procedure Z, Step 6. [M+H]=496.11

Step 9:
Reaction was performed in a similar manner to Procedure Z, Step 7. [M+H]=456

Example 1374

Procedure Z42

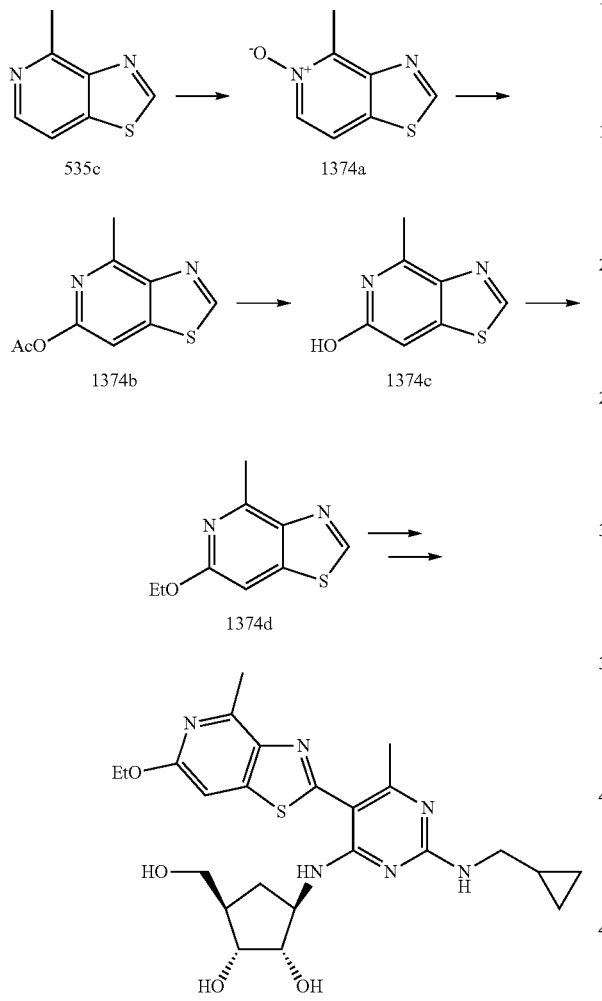

Step 1:
Compound 535c (1.4 g, 9.27 mmol) was dissolved in methylene chloride (20 mL) and treated with 77% mCPBA (2.48 g, 11.1 mmol). After 2 hours the reaction was quenched with 1M potassium carbonate and extracted with methylene chloride. The combined organic layers were dried over sodium sulfate and concentrated to provide 1.2 g of compound 1374a.

Step 2:
Compound 1374a (1.2 g, 7.18 mmol) was dissolved in acetic anhydride (10 ml) and stirred at 120 C for 3 hours. The acetic anhydride was removed under reduced pressure and the residue was dissolved in ethyl acetate. The organic layer was washed with water, dried over sodium sulfate, and concentrated. The residue was purified by column chromatography (1:1 hexanes/ethyl acetate) to provide the desired product 1374b (300 mg). Also recovered 600 mg of the 6-membered rearrangement product.

Step 3:
Compound 1374b (300 mg, 1.44 mmol) was dissolved in 7M NH3 in methanol (5 mL) and stirred at rt for 2 hours. The solvent was removed under reduced pressure. The residue was triturated with diethyl ether to provide the desired product 1374c (150 mg). [M+H]=167.13

Step 4:
Compound 1374c (150 mg, 0.89 mmol) was dissolved in chloroform (15 mL) and treated with silver carbonate (0.5 g) and iodoethane (2 mL). The mixture was stirred at 90 C in a sealed vial. After 2 hours the reaction was filtered over celite and washed with water, dried over sodium sulfate and concentrated. The residue was purified by column chromatography (1:1 hexanes/ethyl acetate) to provide compound 1374d (125 mg). [M+H]=195.11

Step 5:
Compound 1374 was synthesized from 1374d using chemistry from Procedure Z.

Example 1383

Procedure Z43

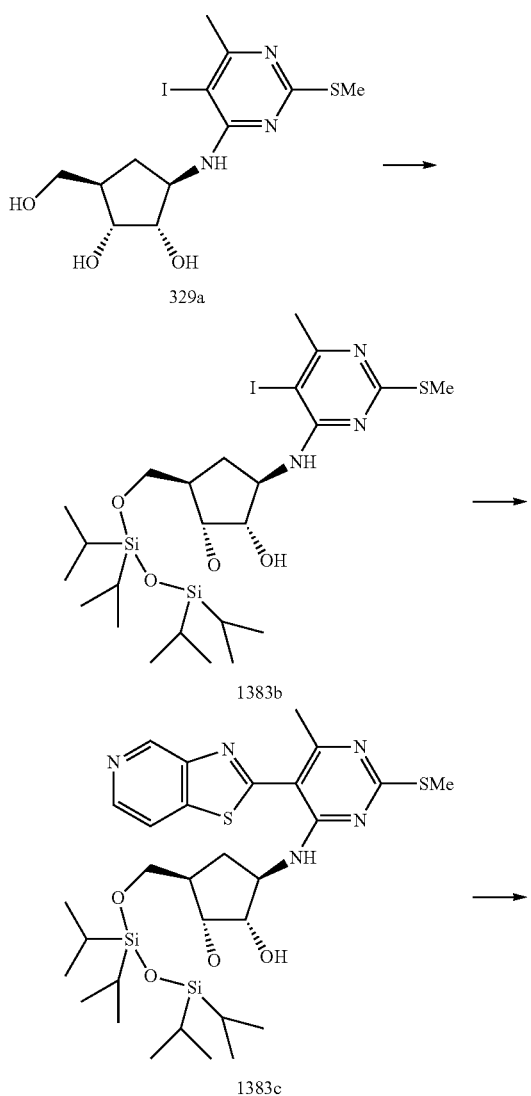

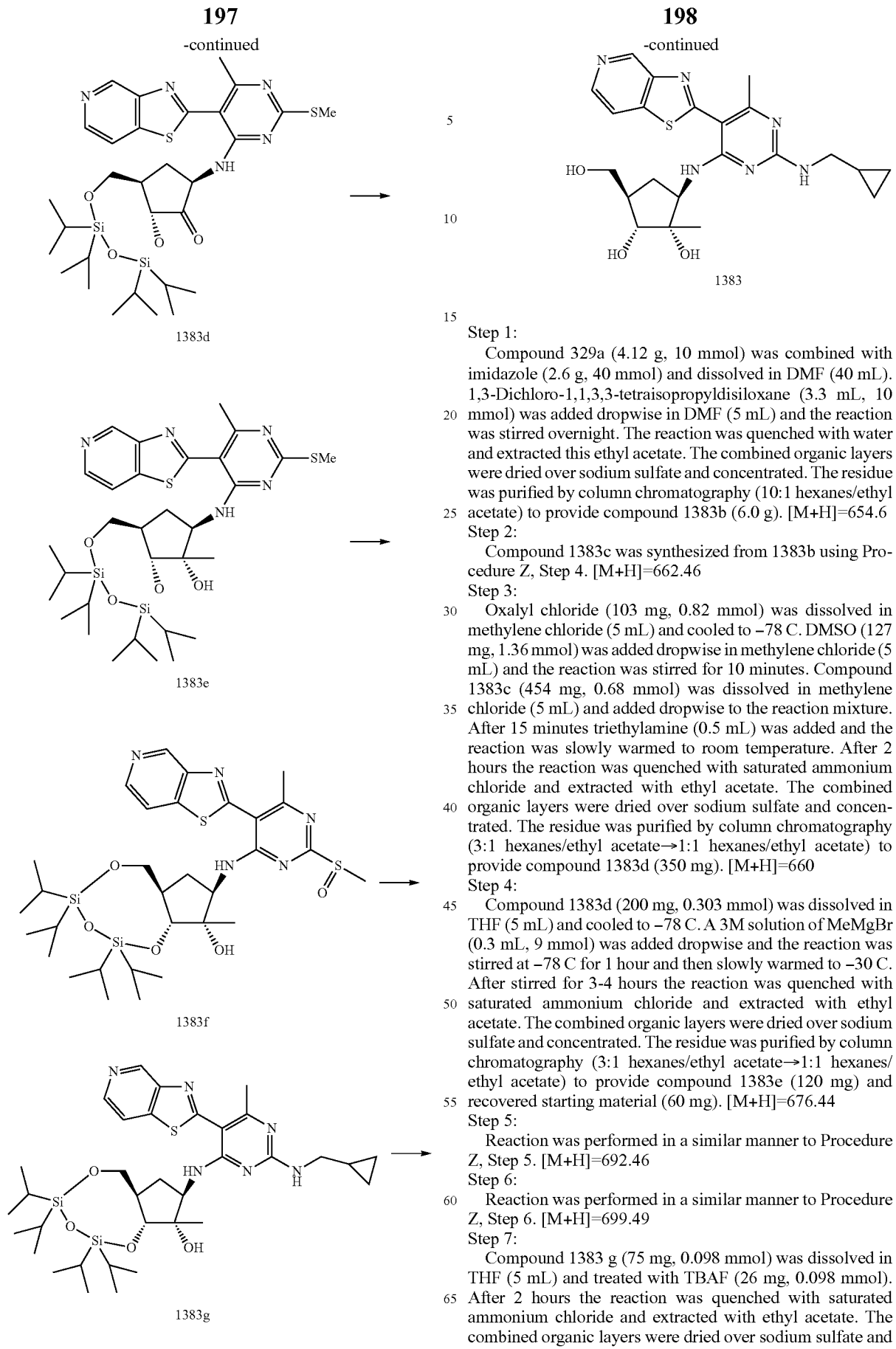

Step 1:
Compound 329a (4.12 g, 10 mmol) was combined with imidazole (2.6 g, 40 mmol) and dissolved in DMF (40 mL). 1,3-Dichloro-1,1,3,3-tetraisopropyldisiloxane (3.3 mL, 10 mmol) was added dropwise in DMF (5 mL) and the reaction was stirred overnight. The reaction was quenched with water and extracted this ethyl acetate. The combined organic layers were dried over sodium sulfate and concentrated. The residue was purified by column chromatography (10:1 hexanes/ethyl acetate) to provide compound 1383b (6.0 g). [M+H]=654.6

Step 2:
Compound 1383c was synthesized from 1383b using Procedure Z, Step 4. [M+H]=662.46

Step 3:
Oxalyl chloride (103 mg, 0.82 mmol) was dissolved in methylene chloride (5 mL) and cooled to −78 C. DMSO (127 mg, 1.36 mmol) was added dropwise in methylene chloride (5 mL) and the reaction was stirred for 10 minutes. Compound 1383c (454 mg, 0.68 mmol) was dissolved in methylene chloride (5 mL) and added dropwise to the reaction mixture. After 15 minutes triethylamine (0.5 mL) was added and the reaction was slowly warmed to room temperature. After 2 hours the reaction was quenched with saturated ammonium chloride and extracted with ethyl acetate. The combined organic layers were dried over sodium sulfate and concentrated. The residue was purified by column chromatography (3:1 hexanes/ethyl acetate→1:1 hexanes/ethyl acetate) to provide compound 1383d (350 mg). [M+H]=660

Step 4:
Compound 1383d (200 mg, 0.303 mmol) was dissolved in THF (5 mL) and cooled to −78 C. A 3M solution of MeMgBr (0.3 mL, 9 mmol) was added dropwise and the reaction was stirred at −78 C for 1 hour and then slowly warmed to −30 C. After stirred for 3-4 hours the reaction was quenched with saturated ammonium chloride and extracted with ethyl acetate. The combined organic layers were dried over sodium sulfate and concentrated. The residue was purified by column chromatography (3:1 hexanes/ethyl acetate→1:1 hexanes/ethyl acetate) to provide compound 1383e (120 mg) and recovered starting material (60 mg). [M+H]=676.44

Step 5:
Reaction was performed in a similar manner to Procedure Z, Step 5. [M+H]=692.46

Step 6:
Reaction was performed in a similar manner to Procedure Z, Step 6. [M+H]=699.49

Step 7:
Compound 1383 g (75 mg, 0.098 mmol) was dissolved in THF (5 mL) and treated with TBAF (26 mg, 0.098 mmol). After 2 hours the reaction was quenched with saturated ammonium chloride and extracted with ethyl acetate. The combined organic layers were dried over sodium sulfate and concentrated. The residue was purified by column chromatography (10:1 ethyl acetate/methanol) to provide the desired product 1383 (28 mg). [M+H]=457.30

Example 1396

Procedure Z44

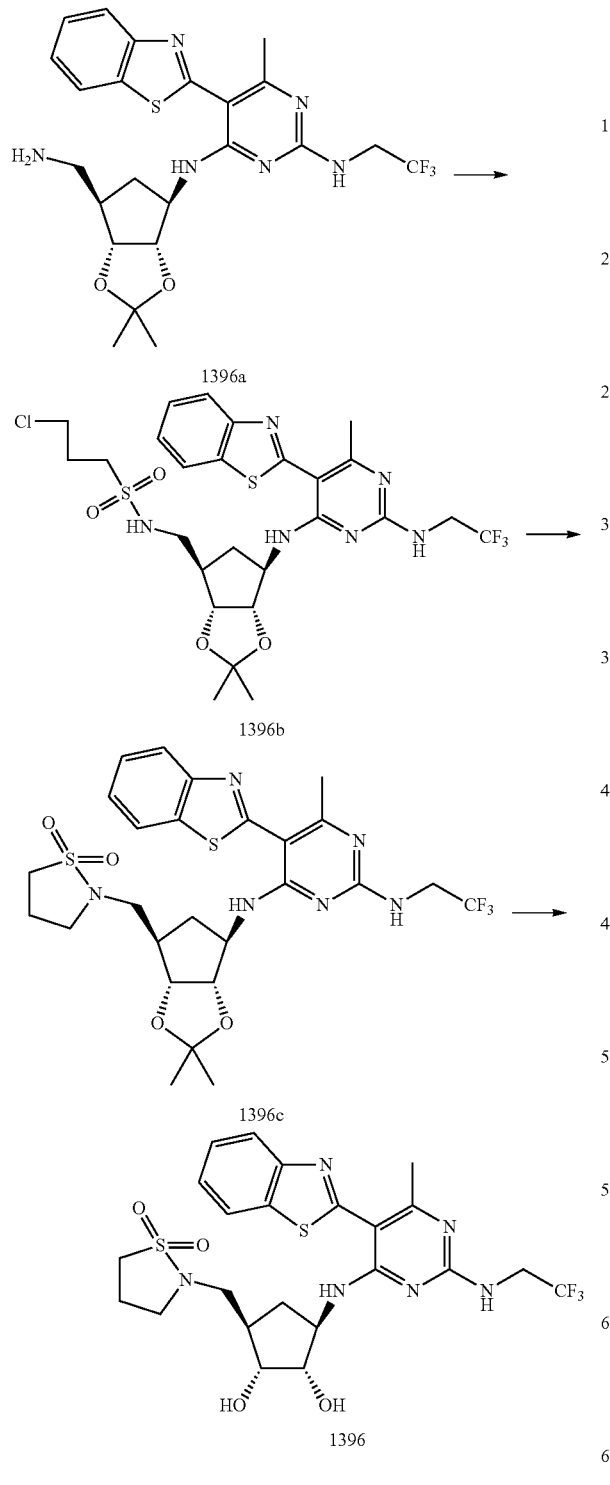

Step 1:

Compound 1396a (60 mg, 0.118 mmol) was suspended in methylene chloride (8 mL) and triethylamine (0.041 mL, 0.295 mmol) and sonicated to make a solution. After cooling to 0 C, 3-chloropropane-1-sulfonyl chloride (25 mg, 0.14 mmol) was added dropwise in methylene chloride (2 mL). After stirring for 1 hour the reaction was quenched with water and extracted with methylene chloride. The combined organic layers were dried over sodium sulfate and concentrated. The residue was purified by column chromatography (1:1 hexanes/ethyl acetate→ethyl acetate) to provide product 1396b (65 mg). [M+H]=649.

Step 2:

Compound 1396b (65 mg, 0.1 mmol) was dissolved in DMF (5 mL) and treated with NaI (0.2 g) and cesium carbonate (0.5 g). The mixture was heated at 110 C for 1 hour and then quenched with water and extracted with ethyl acetate. The organic layer was washed with water, dried over sodium sulfate and concentrated. The residue was purified by column chromatography (1:1 hexanes/ethyl acetate→ethyl acetate) to provide product 1396c (60 mg). [M+H]=613.37

Step 3:

Reaction was performed in a similar manner to Procedure Z. Step 7. [M+H]=573.29

Example 1400

Procedure Z45

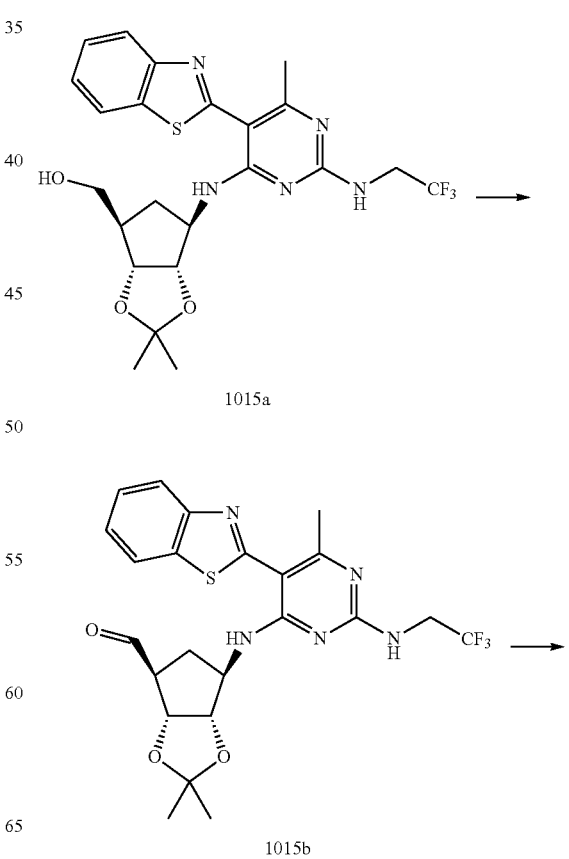

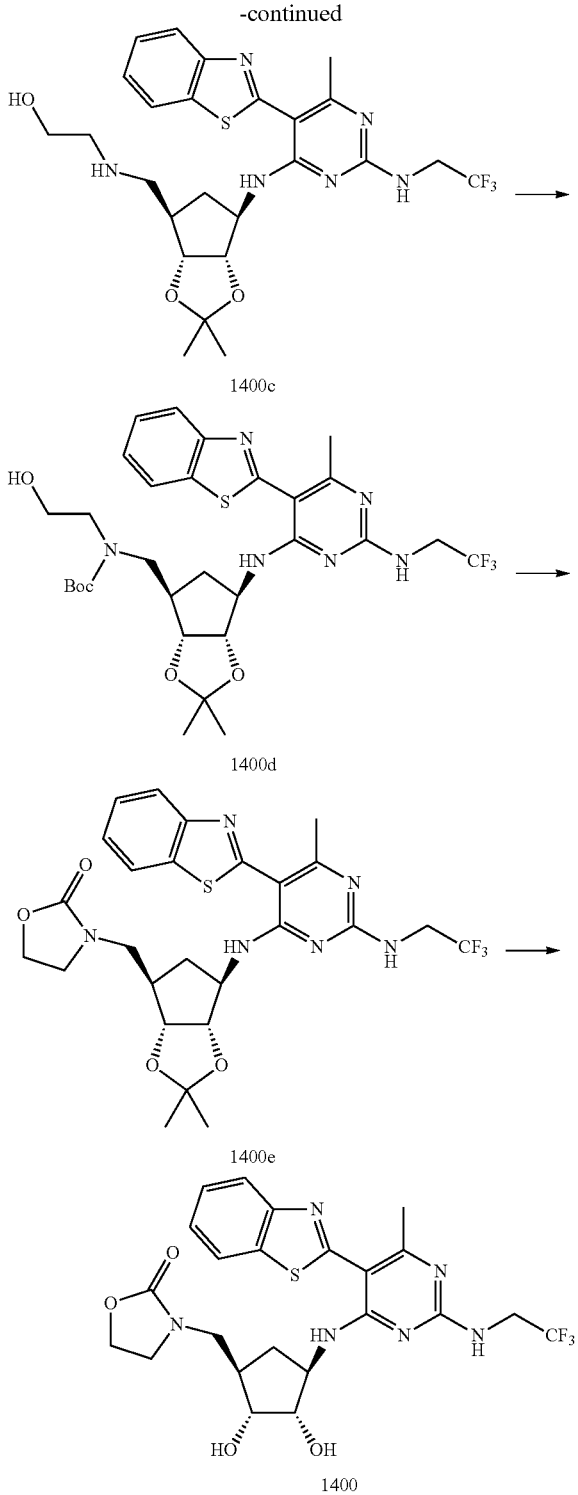

sodium sulfate and concentrated. The residue was purified by column chromatography (1:1 hexanes/ethyl acetate) to provide 1015b (320 mg).

Step 2:

Compound 1015b (150 mg, 0.295 mmol) was dissolved in THF (5 mL) and treated with ethanolamine (72 mg, 1.18 mmol). The solution was stirred for 10 minutes and then sodiumtriacetoxyborohydride (0.6 g) was added and the reaction was stirred for 4 hours. The reaction was quenched with water and extracted with ethyl acetate. The combined organic layers were dried over sodium sulfate and concentrated to provide compound 1400c (160 mg). [M+H]=553

Step 3:

Compound 1400c (45 mg, 0.081 mmol) was dissolved in diethylcarbonate (1 mL) and treated with triethylamine (0.1 mL) and BOC2O (18 mg, 0.081 mmol). All were stirred at room temperature for 10 minutes and then 100 C for 6 hours. Removed solvent under reduced pressure and purified residue by column chromatography (1:1 hexanes/ethyl acetate) to provide compound 1400d (55 mg). [M+H]=653

Step 4

Compound 1400d (55 mg, 0.08 mmol) was dissolved in DMF (2 mL) and treated with 60% NaH (15 mg). The mixture was stirred at 100 C for 1 hour and then quenched with water and extracted with ethyl acetate. The combined organic layers were dried over sodium sulfate and concentrated. The residue was purified by column chromatography (2:1 ethyl acetate/hexanes) to provide 1400e (25 mg).

Step 5:

Reaction was performed in a similar manner to Procedure Z, Step 7. [M+H]=539.33

Example 1402

Procedure Z46

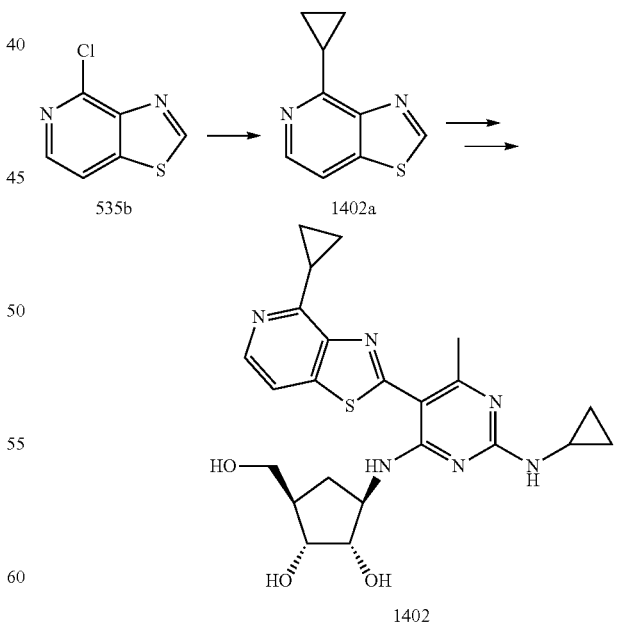

Step 1:

Compound 1015a (350 mg, 0.687 mmol) was dissolved in methylene chloride (10 mL) and cooled to 0 C. Dess Martin Periodinane (437 mg, 1.03 mmol) and a drop of water were added and the reaction was stirred for 3 hours and then quenched with sodium thiosulfate solution and saturated sodium bicarbonate. The mixture was extracted with methylene chloride. The combined organic layers were dried over Step 1:

Compound 535b (200 mg, 1.17 mmol) and Pd(PPh3)4 (50 mg) were dissolved in 0.5M cyclopropylzinc bromide (4.6 mL, 2.33 mmol) and stirred at 70 C overnight. The reaction was quenched with water and extracted with ethyl acetate. The combined organic layers were dried over sodium sulfate and concentrated. The residue was purified by column chromatography (2:1 hexanes/ethyl acetate) to provide 1402a (125 mg). [M+H]=177.11

Step 2:

See procedure Z1 for similar experimental procedures.

Example 1398

Procedure Z47

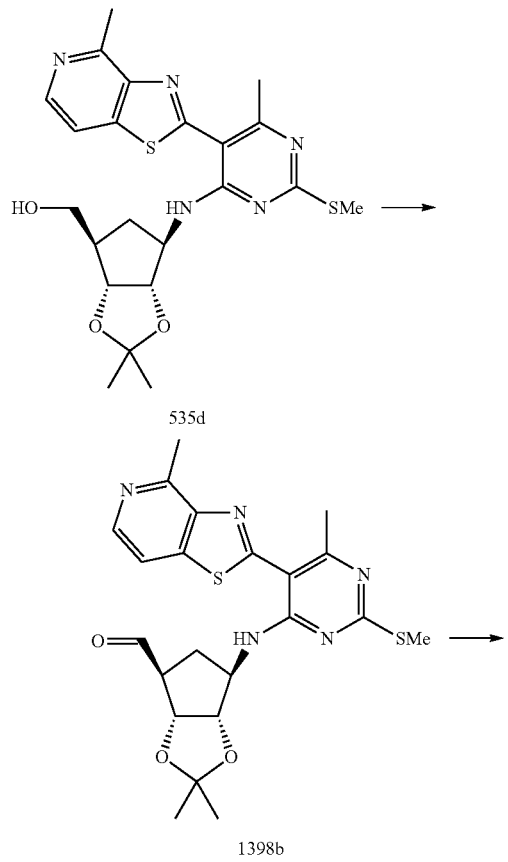

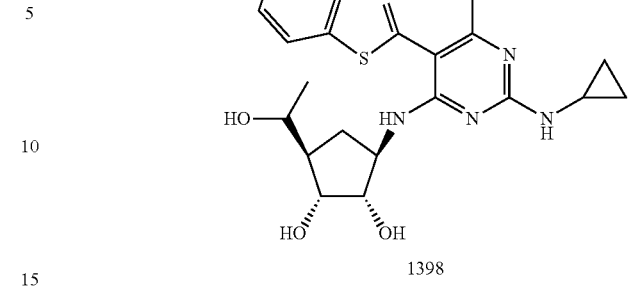

Step 1:

Compound 535d (200 mg, 0.42 mmol) was dissolved in methylene chloride (20 mL) and 2 drops of water. Dess Martin Periodinane (356 mg, 0.84 mmol) was added at 0 C and the solution was stirred for 2 hours at 0 C and then overnight in a refrigerator. The reaction was quenched with quenched with sodium thiosulfate solution and saturated sodium bicarbonate. The mixture was extracted with methylene chloride. The combined organic layers were dried over sodium sulfate and concentrated. The residue was purified by column chromatography (ethyl acetate) to provide 1398b (130 mg). [M+H]=472.25

Step 2:

Compound 1398b (130 mg, 0.275 mmol) was dissolved in THF (5 mL) and cooled to 0 C. A solution of 3M MeMgBr in diethylether (0.91 mmol, 2.75 mmol) was added dropwise and the solution was stirred for 1 hr at 0 C and then quenched with saturated ammonium chloride. The aqueous layer was extracted with ethyl acetate and the combined organic layers were dried over sodium sulfate and concentrated.

The residue was purified by column chromatography (ethyl acetate→10% MeOH) to provide compound 1398c (100 mg). [M+H]=488

Step 3:

Compound 1398 was synthesized from 1398c using chemistry in Procedure Z1.

Examples 1392 and 1393

Procedure Z48

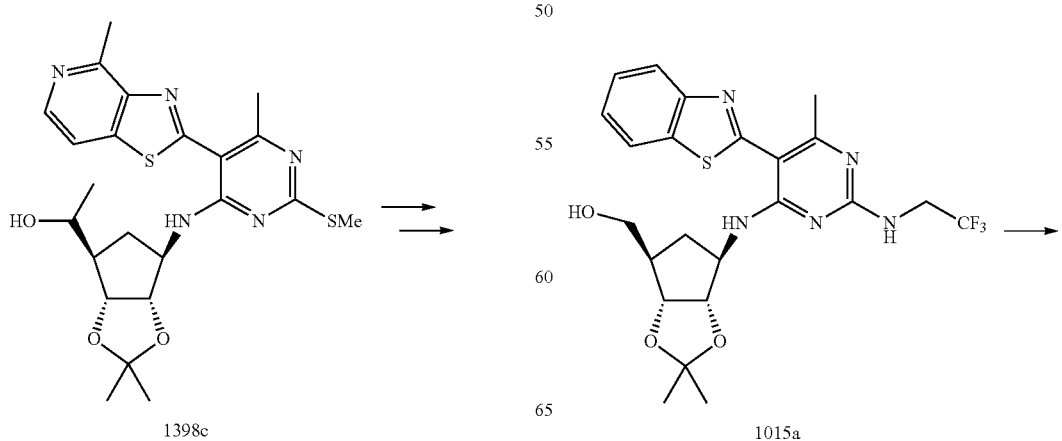

-continued

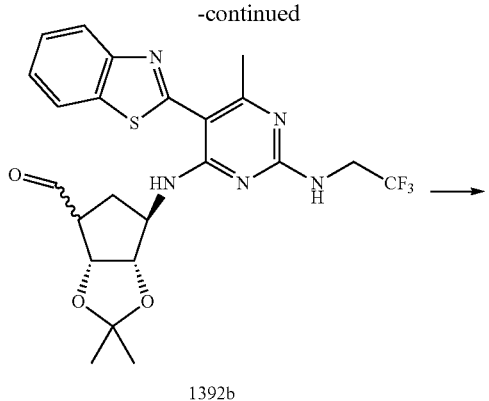

1392b

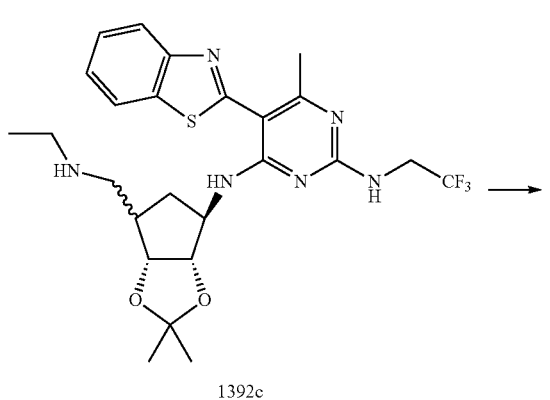

1392c

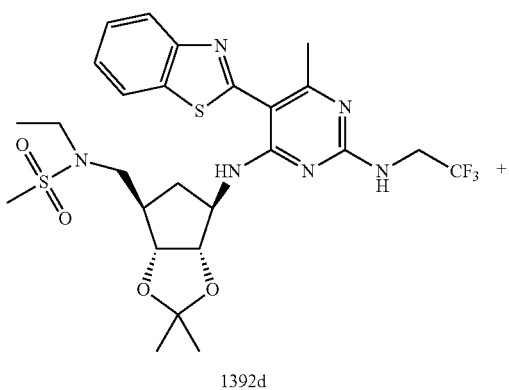

1392d

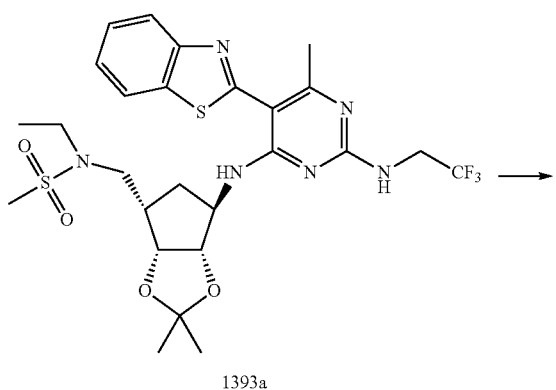

1393a

-continued

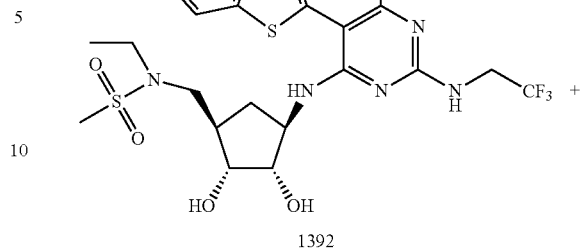

1392

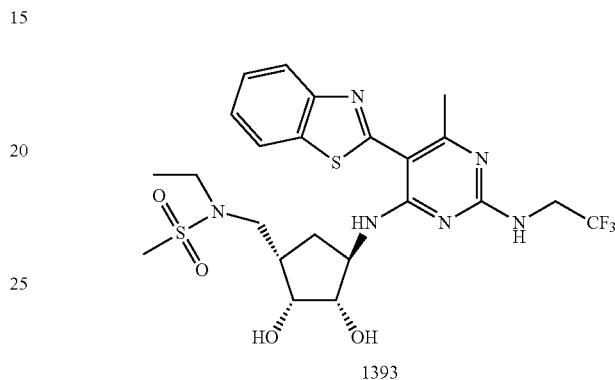

1393

Step 1:

Compound 1015a (350 mg, 0.687 mmol) was dissolved in methylene chloride (10 mL) and cooled to 0 C. Dess Martin Periodinane (437 mg, 1.03 mmol) and a drop of water were added and the reaction was stirred for 3 hours at room temperature and then quenched with sodium thiosulfate solution and saturated sodium bicarbonate. The mixture was extracted with methylene chloride. The combined organic layers were dried over sodium sulfate and concentrated. The residue was purified by column chromatography (1:1 hexanes/ethyl acetate) to provide 1392b as a mixture of epimers (320 mg).

Step 2:

Compound 1392b (70 mg, 0.13 mmol) was dissolved in THF (5 mL) and treated with 2 Methylamine (0.138 mmol, 0.27 mmol). The solution was stirred for 10 minutes and then sodiumtriacetoxyborohydride (0.4 g) was added and the reaction was stirred for 4 hours. The reaction was quenched with water and extracted with ethyl acetate. The combined organic layers were dried over sodium sulfate and concentrated to provide compound 13920 (60 mg).

Step 3:

Compound 1392c (60 mg, 0.11 mmol) was dissolved in methylene chloride (5 mL) and triethylamine (0.1 mL) and cooled to 0 C. Methanesulfonyl chloride (13 mg, 0.11 mmol) was added in methylene chloride (1 mL) dropwise. After 1 hour the reaction was quenched with water and extracted with methylene chloride. The combined organic layers were dried over sodium sulfate and concentrated. The residue was purified by column chromatography to provide two products, compound 1392d (30 mg) and compound 1393a (30 mg).

Step 4:

The two compounds 1392 and 1393 were synthesized using Procedure Z, Step 7.

Example 1528

Procedure Z49

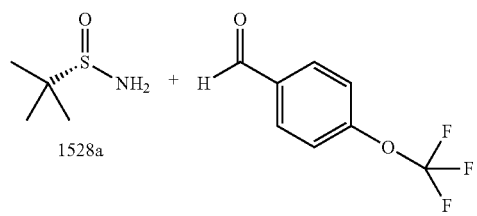

1528a + 1528b

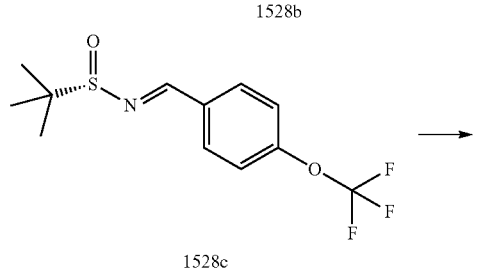

1528c

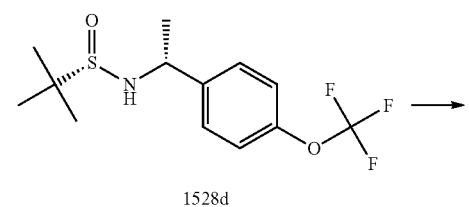

1528d

1528e

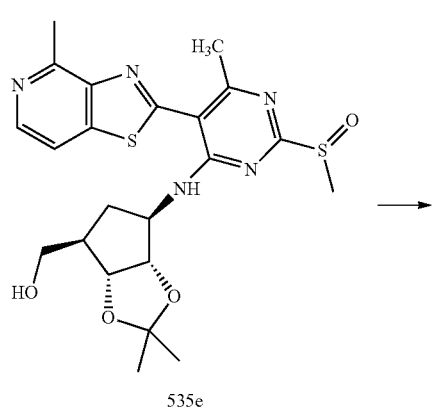

535e

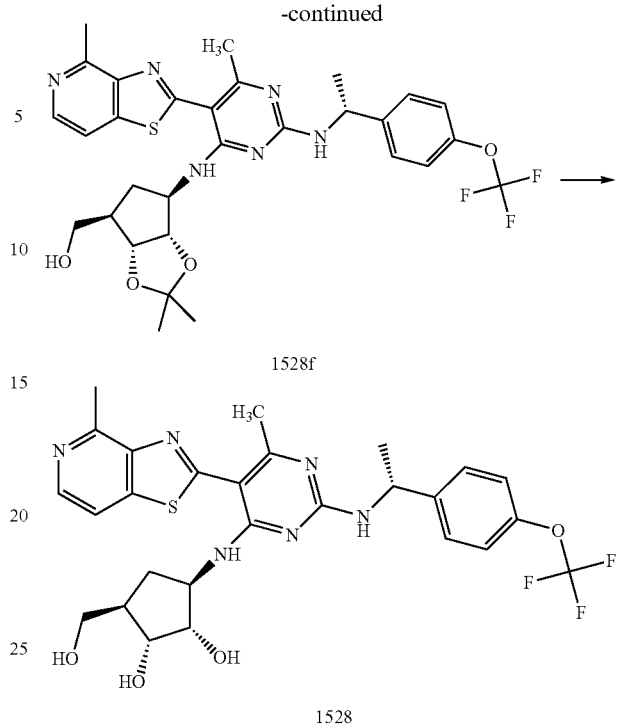

1528f

1528

Step 1:
Compound 1528a (2.54 g, 21.0393 mmol) and 1528b (4-(Trifluoromethoxy)benzaldehyde, 4.0 g, 21.0393 mmol) were stirred in 40.0 ml of THF and treated with Titanium isopropoxide (14.95 g, 15.7 ml, 52.598 mmol.). All were stirred at 70° C. for 6 h then allowed to stir at rt overnight. The reaction was diluted with water, then added ethyl acetate and filtered through a celite pad, rinsed with ethyl acetate. separate layers and extracted aqueous once more with ethyl acetate. The combined organic layers were washed with water, brine, dried over sodium sulfate, and concentrated to provide compound 1528c (4.85 g). [M+H]=294.16

Step 2:
Compound 1528c (4.85 g, 16.535 mmol) was dissolved in Anhydrous THF (104 ml) and cooled t—−30° to −40°. Added 3M (16.54 mL) of MeMgBr (dropwise) via an addition funnel. Stirred at −30° to −40° C. for 1 to 2 h. The reaction was monitored by TLC and MS [M+H]=310.21. The reaction was treated very slowly added with 150 mL of water at −45° C.−−50° C., then added 150 mL ethyl acetate, stirred and extracted 2-3 times, combined organics, dried over Na2SO4, filtered, concentrated, to obtain 1528d (3.51 g). [M+H]=310.28.

Step 3:
Compound 1528d (3.51 g, 11.34463 mmol) was stirred in anhydrous Methanol (30 ml) and at rt under N2, then added 4M HCl in 1-4 Dioxane (9.75 mL). Reaction was Allowed to stir for 2-3 hours at rt under N2. The reaction was monitored by TLC and MS [M+H]=206.14. Reaction was concentrated to dryness. An oily syrup residue obtain. Residue was treated with Diethyl Ether, stirred and a white solid formed. Mixture was filtered and white solid rinsed with ether. Isolated a white solid, dried under vacuum.

Afforded Compound 1528e (2.52 g). [M+H]=206.16. as an HCl Salt.

Step 4:
Compound 535e (620 mg, 1.2663 mmol) was dissolved in (3.5 mL) of 1,4-Dioxane art rt under N2, then added Compound 1528e (612 mg, 2.533 mmol) and (0.961 g, 1.324 ml, 9.497 mmol,) of Triethylamine. Reaction mixture was heated to 120° C. The reaction was monitored by TLC and MS [M+H]=631.40. Reaction was concentrated to give a crude product. Purification by column chromatography (hexanes/Ethyl acetate→20% Methanol) to provide g of the product 1528f (0.575 g). [M+H]=631.48.

Step 5:

Compound 1528f (0.575 g, 0.9117 mmol) was stirred in Methanol (6.5 ml), followed by addition of 4M HCl in 1-4 Dioxane (3.5 ml) and water (0.3 mL). Allow reaction to stir at rt for 2-4 hours. Reaction monitored by MS [M+H]=591.41. Concentrate rxn to dryness. a syrup obtain. Dry product under vacuum to obtain an ivory solid. Afforded Compound 1528. (0.62 g) HCl Salt. LC MS [M+H]=591.2.

Example 1538

Procedure Z50

Compound 1538a was synthesized using procedure Z34.

Step 1:

Compound 1538a (50 mg, 0.0935 mmol) and vinyl acetate (1 mL) were stirred in a pressure bottle at 120 C overnight. The reaction was diluted with water and extracted with ethyl acetate. The combined organic layers were washed with water, brine, dried over sodium sulfate, and concentrated to provide compound 1538b (33 mg). [M+H]=560.59

Step 2:

1538 was synthesized from 1538b using procedure Z, Step 7.

Example 1539

Procedure Z51

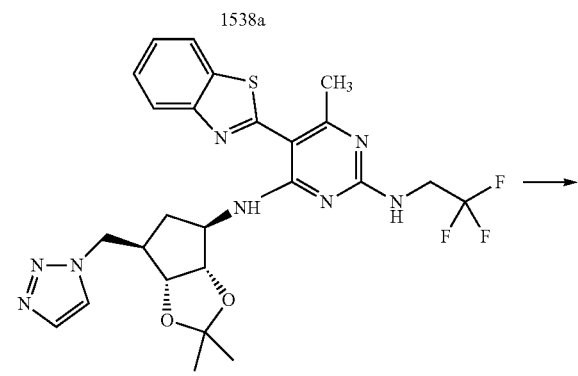
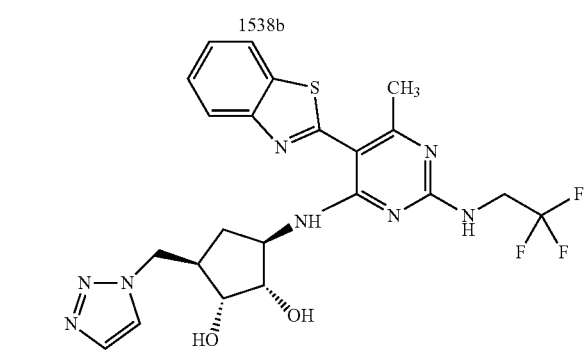
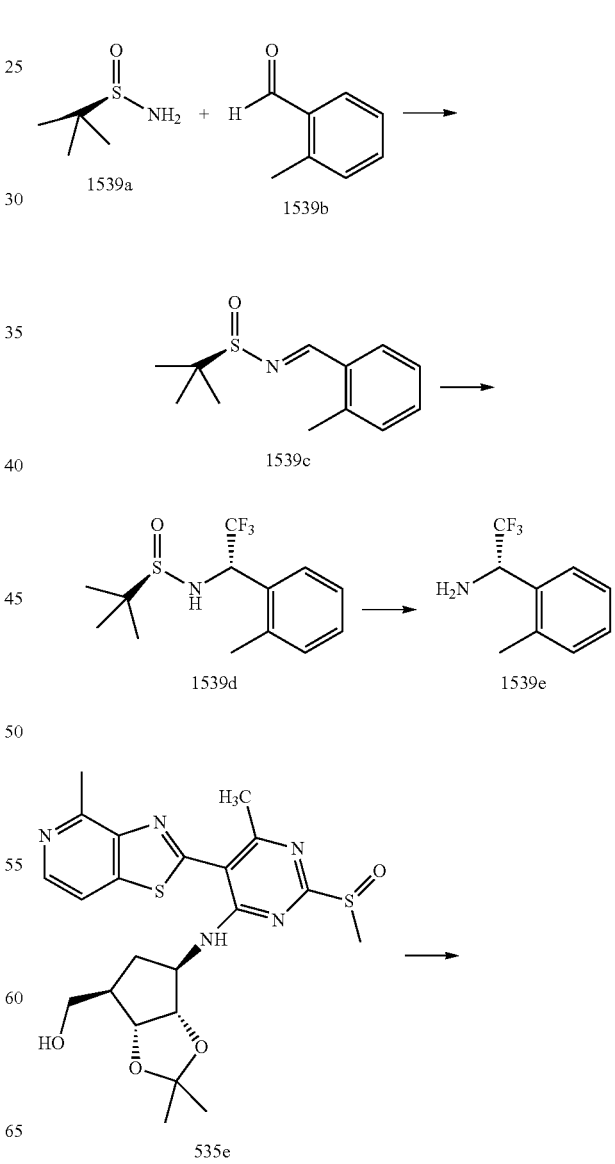

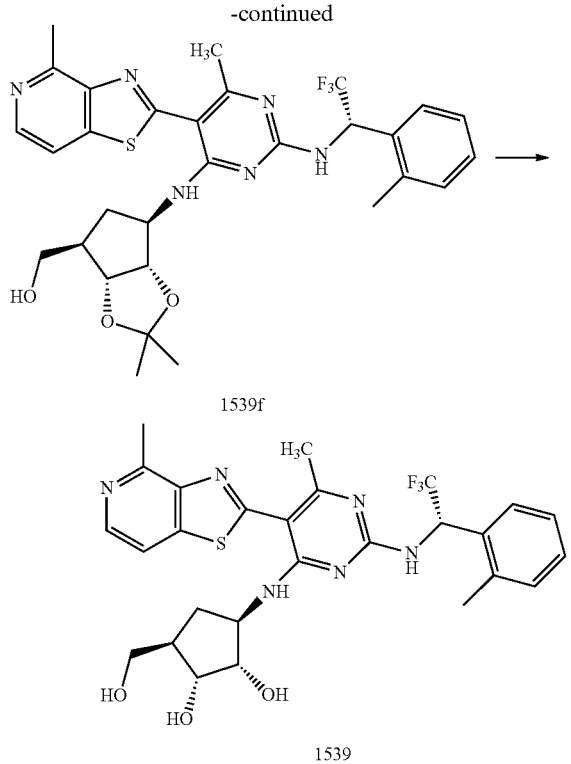

1539f

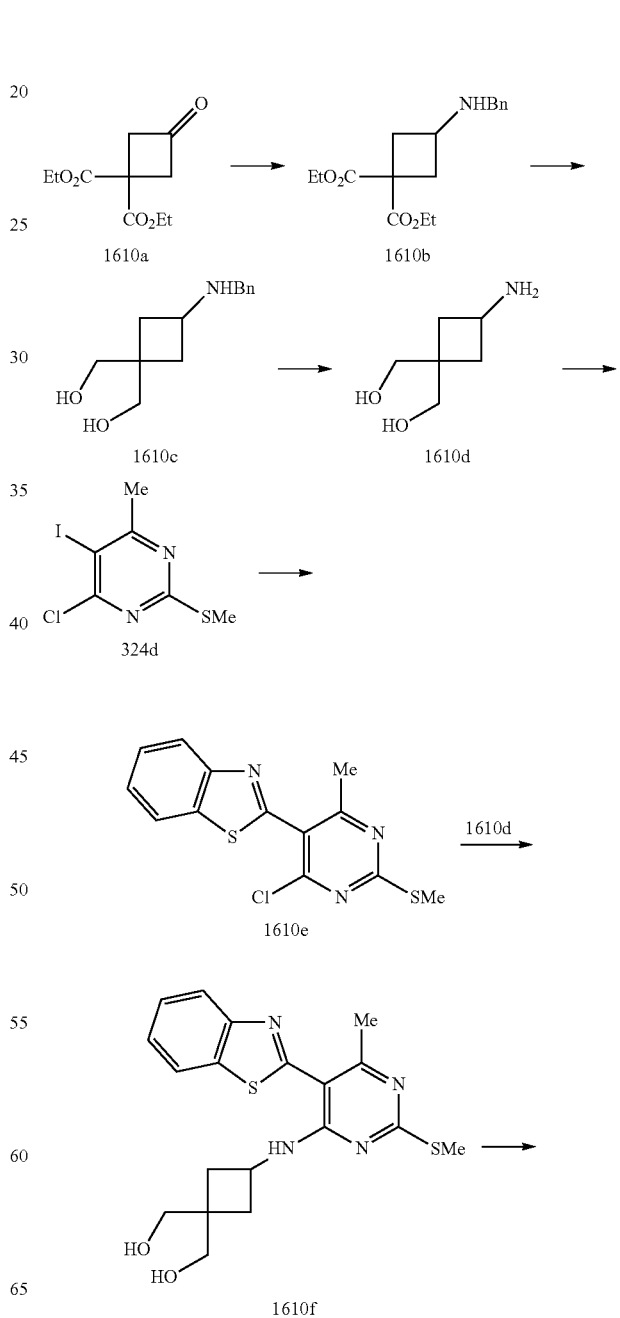

Ethyl acetate→45% Methanol) to provide g of the product 1539f (26.9 mg). [M+H]=631.48.

Step 5:

Compound 1539f 23 mg, 0.0374 mmol) was stirred in Methanol (3.0 ml), followed by addition of 4M HCl in 1-4 Dioxane (1 ml) and water (0.2 mL). Allow reaction to stir at rt for 2-4 hours. Reaction monitored by MS [M+H]=575.39. Concentrate rxn to dryness. Dried product under vacuum to obtain an ivory solid. Afforded Compound 1539. (0.24 mg) HCl Salt. LC MS [M+H]=575.39.

Example 1610

Procedure Z56

1539

Step 1: Compound 1539c was synthesized from 1539a and 1539b using Procedure Z49.

Step 2:

Combined in a flame-dried round-bottom flask Compound 1539c (0.6 g, 2.687 mmol) and Tetrabutyl ammonium difluorotriphenylsilicate (2.176 g, 4.0305 mmol) and dissolved and stir in Anhydrous THF (13.3 ml); and cooled t—−78° C., then Added TMS-CF3 (0.573 g, 0.595 ml, 4.0305 mmol.) in 13.3 ml of anhydrous THF)(dropwise) via an addition funnel for a period of 10 minutes. Then allow to stir for 2 hours at 0 degrees C. Quench reaction mixture at 0 degrees C. with saturated Ammonium Chloride; Extracted ethyl acetate 2-3 times, combined organics, dried over Na2SO4, filtered, concentrated, to obtain crude product. [M+H]=294.25. Purification by column chromatography afforded 1539d (0.46 g). [M+H]=294.19.

Step 3:

Compound 1539d (0.46 g, 1.568 mmol) was stirred in anhydrous Methanol (3 ml) and at rt under N2, then added 4M HCl in 1-4 Dioxane (1.0 mL). Reaction was Allowed to stir for 2-3 hours at rt under N2. The reaction was monitored by TLC and MS [M+H]=190.14. Reaction was concentrated to dryness. An oily residue obtain. Residue was treated with ethyl acetate (1 ml) and Diethyl Ether (5 ml), stirred and a white solid formed. Mixture was filtered and white solid rinsed with ether. Isolated a white solid, dried under vacuum. Afforded Compound 1539e (0.3 g) as an HCl Salt. [M+H]=206.16.

Step 4:

Compound 535e (50 mg, 0.102 mmol) was dissolved in (1.0 mL) of 1,4-Dioxane art rt under N2, then added Compound 1539e (159 mg, 0.71 mmol) and (0.132 ml, 1.02 mmol,) of diipropylethylamine. Reaction mixture was heated to 130° C. The reaction was monitored by TLC and MS [M+H]=615.42. Reaction was concentrated to give a crude product. Purification by column chromatography (hexanes/

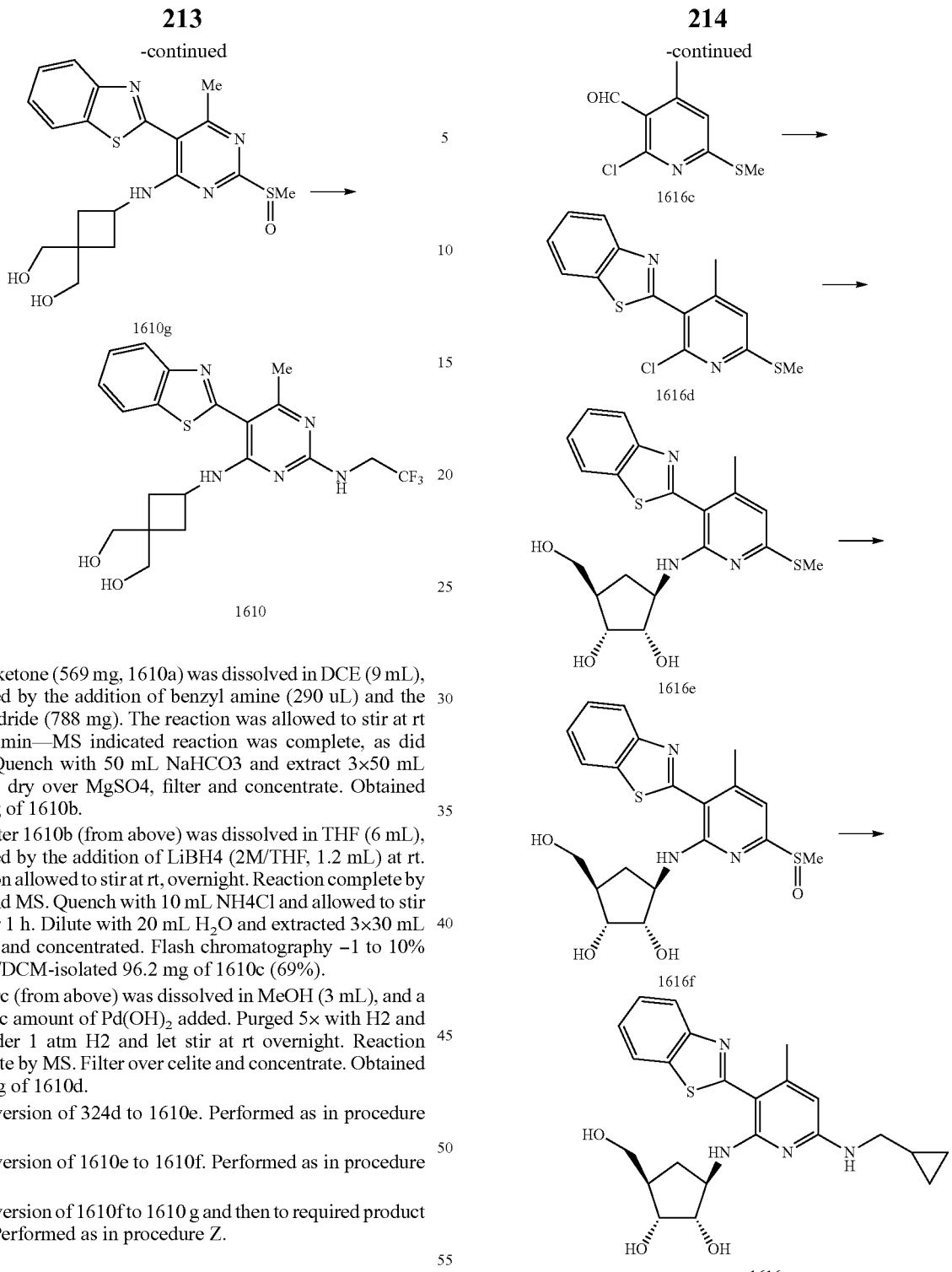

The ketone (569 mg, 1610a) was dissolved in DCE (9 mL), followed by the addition of benzyl amine (290 uL) and the borohydride (788 mg). The reaction was allowed to stir at rt for 45 min—MS indicated reaction was complete, as did TLC. Quench with 50 mL NaHCO3 and extract 3×50 mL EtOAc, dry over MgSO4, filter and concentrate. Obtained 690 mg of 1610b.

Diester 1610b (from above) was dissolved in THF (6 mL), followed by the addition of LiBH4 (2M/THF, 1.2 mL) at rt. Reaction allowed to stir at rt, overnight. Reaction complete by TLC and MS. Quench with 10 mL NH4Cl and allowed to stir at rt for 1 h. Dilute with 20 mL $H_2O$ and extracted 3×30 mL EtOAc and concentrated. Flash chromatography −1 to 10% MeOH/DCM-isolated 96.2 mg of 1610c (69%).

1610c (from above) was dissolved in MeOH (3 mL), and a catalytic amount of $Pd(OH)_2$ added. Purged 5× with H2 and put under 1 atm H2 and let stir at rt overnight. Reaction complete by MS. Filter over celite and concentrate. Obtained 57.5 mg of 1610d.

Conversion of 324d to 1610e. Performed as in procedure U.

Conversion of 1610e to 1610f. Performed as in procedure U.

Conversion of 1610f to 1610g and then to required product 1610. Performed as in procedure Z.

Example 1616

Procedure Z57

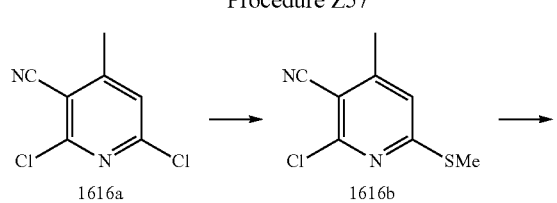

Step 1: SM, 1616a (4.8 g) dissolved in THF (100 mL). NaSMe (2 g), followed immediately by CuBr (220 mg) was added and reaction heated from rt to 60° C. for 5 h. Quench with 100 mL NaHCO3 and 100 mL $H_2O$ and extract 3×100 mL EtOAc and concentrate. Flash chromatography −1 to 5% EtOAc/hexanes to 1 to 5% EtOAc/DCM. 3.06 g of desired, 1616b (61%) and 998 mg of undesired regioisomer obtained.

Step 2: 1616b (694 mg) dissolved in CH2Cl2 (20 mL) and cooled to −78° C. DIBAL (1M/hexanes, 3.8 mL) added dropwise over 1 min and let stir at −78° C. for 2 h. then warmed to rt. After 15 min quench with 30 mL NH₄Cl and acidify with 30 mL 3N HCl. Extract 3×40 mL EtOAc, dry over MgSO₄, filter and concentrate. Flash chromatography −5 to 15 to 20% EtOAc/hexanes, gave 459.8 mg of 1616c (65%).

Step 3: Aminothiophenol (100 uL) added to aldehyde 1616c (156 mg) dissolved in MeOH/DMF (5/0.5 mL), followed by AcOH (100 uL) and let stir overnight. Reaction complete to the thiazoline by MS and LCMS. H₂O added to the reaction and filtered through a glass frit. Washed 5× with H₂O, then dissolved in CDCl3 and 262.2 mg DDQ added and let stir at rt. Reaction complete within 10 min. Add 20 mL 10% K2CO3 and extract 2×40 mL CHCl3, dry over MgSO4, filter and concentrate to give 1616d.

Step 4: 1616d, (178 mg) dissolved in NMP (2 mL) in a microwave vial and carbasugar, 120a (323 mg) followed by DBU (350 uL) added. Microwave for 30 min at 200° C. Reaction complete by MS. Dilute with 40 mL H2O and extract 2×30 mL EtOAc and concentrate. Dissolve in DCM, gave lots of insoluble material. Filter through a frit funnel—MS and NMR indicates solid is clean product. Take filtrate and concentrate. Redissolve in DCM and filter. Combined solid material to give 1616e, 94.1 mg (39%).

Step 5 & 6: Conversion of 1616e to 1616f and further to 1616, as in procedure Z.

Example 1617

Procedure Z58

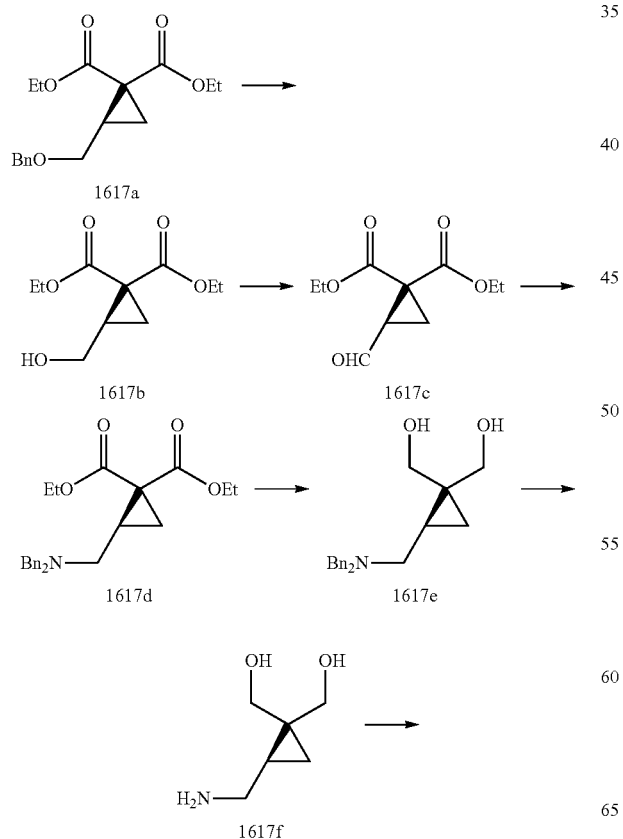

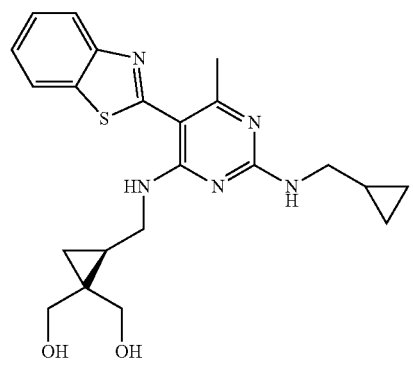

1617

1617a was synthesized by the method of: Burgess, K.; Ye, C-Y. *Synthesis* 1996, 1463.

Step 1: Hydrogenation of 1617a to give 1617b, as in procedure Z56.

Step 2: 1617b, (538 mg) dissolved in CH₂Cl₂ (3 mL). NaHCO3 (660 mg), then Dess-Martin's periodinane (2 g) was added and let stir at rt. Add 4 mL (total of 7 mL) CH₂Cl₂ and let stir. After 45 min, TLC indicates reaction is complete. Quench with 5 mL 1M Na2SO3 and let stir till organic layer is clear. Dilute with 20 mL H₂O and extract with 3×30 mL EtOac, dry over MgSO₄, filter and concentrate. Obtained 506.6 mg of 1617c, 95%.

Steps 3, 4 & 5: As in procedure Z56.

Step 6: Conversion of 1617f to 1617, as in procedure Z.

Example 1628

Procedure Z59

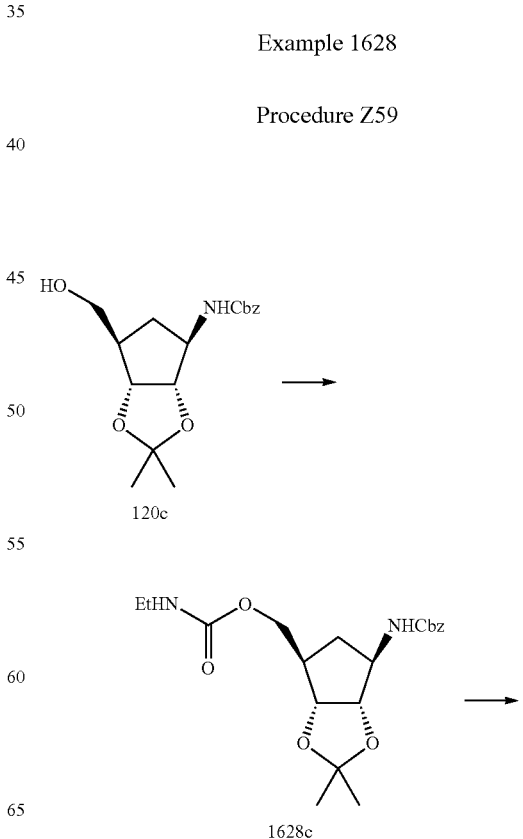

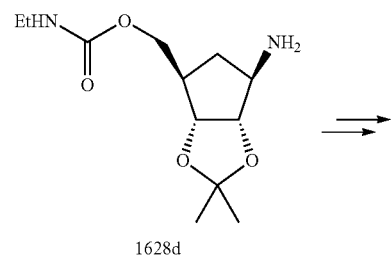

1628d

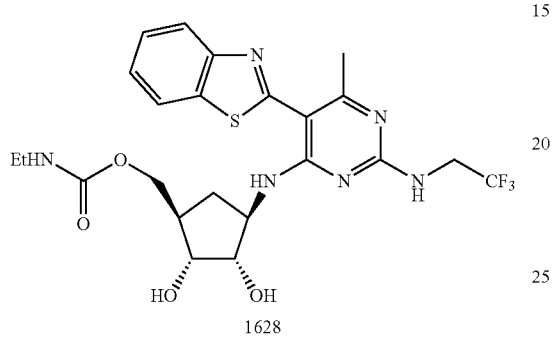

1628

Step 1: SM, 120c (630 mg) dissolved in DMF (13 mL), then ethylisocyanate (170 mg) followed by CuCl (160 mg) added to flask. Let stir at RT, overnight. 80 mg isocyanate and 79.0 mg CuCl were added. Heated to 60° C. Stopped reaction and purified via flash chromatography to give 69.8 mg of 1628c.

Step 4: 1628c (70 mg) dissolved in EtOH (5 mL) and scoop of 10% Pd/C added. Fitted with a H2 balloon and flushed 5×, then let stir at rt for 2 h. Complete by MS. Filter over celite and concentrate to give 46.0 mg of 1628d.

Conversion of 1628d to 1628, as in procedures U & Z.

Example 1630

Procedure Z60

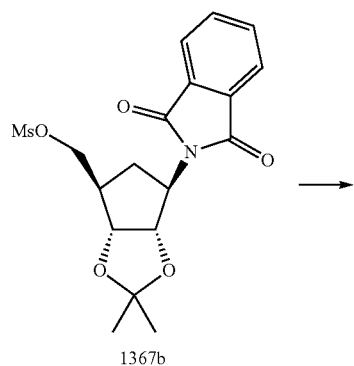

1367b

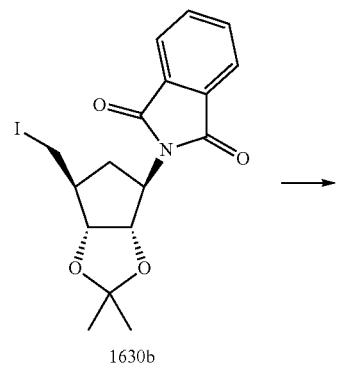

1630b

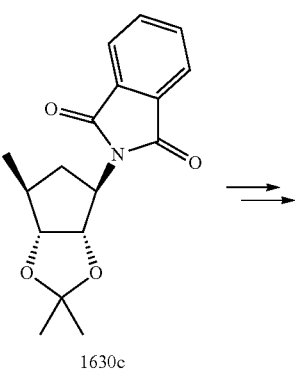

1630c

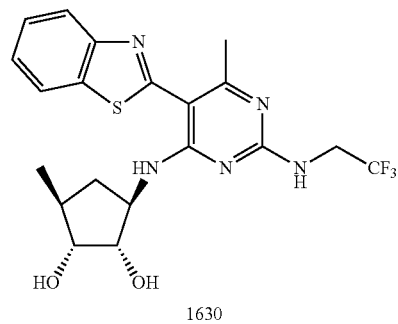

1630

Step 1: SM, 1367b (20 mg) dissolved in acetone (300 uL) and NaI (75 mg) added. Let stir at rt for 2 h. Heated to 50° C. Reaction essentially complete by TLC. Dilute with 1 mL H2O and extract 2×2 mL EtOAc, dry over MgSO4, filter and concentrate. Isolated 18.7 mg of 1630b (88% crude yield).

Step 2: SM, 1630b (19 mg) dissolved in EtOH (1.5 mL). Et3N (15 uL) added, followed by scoop of 10% Pd/C. Hydrogenated with a balloon of H2, flushed 5×, and let stir overnight. Filter over celite and concentrate. 18.4 mg of 1630c was isolated. Conversion of 1630c to 1630, as in Z40 and Z56.

Example 1632

Procedure Z61

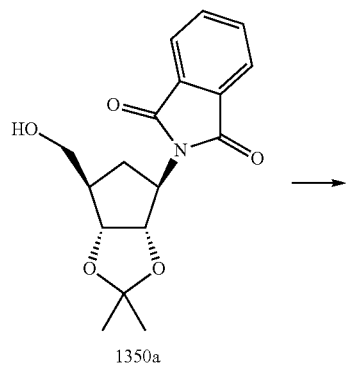
1350a

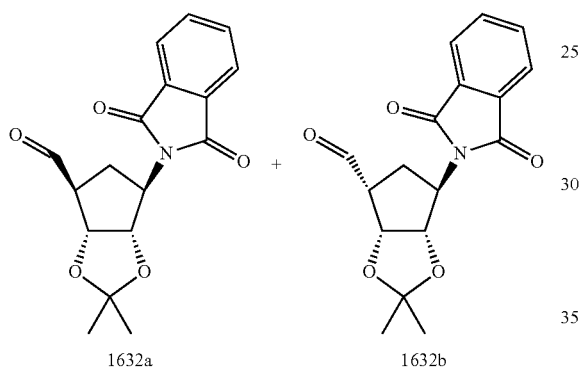
1632a      1632b

1632a →

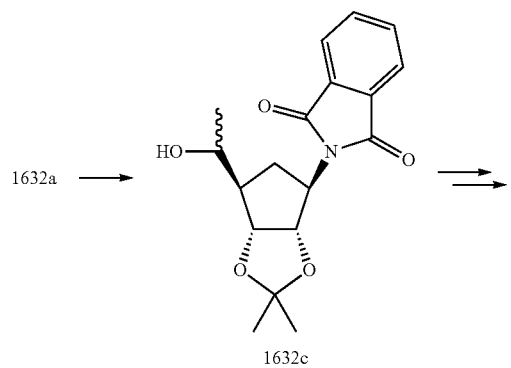
1632c

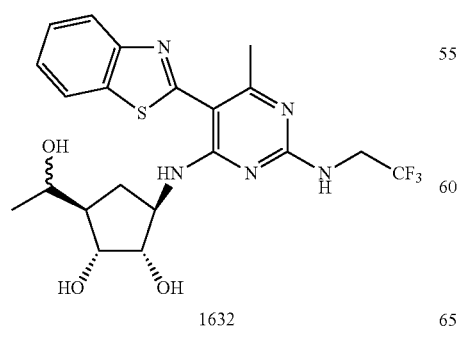
1632

Step 1: (COCl)$_2$ (1 mL) dissolved in 30 mL DCM and cooled to −78° C. DMSO (1.8 mL) added dropwise and let stir 10 min. SM, 1350a (2.2 g) added in 20 mL DCM. Stir for 1 h. Et3N added and let stir at rt. Quench after 2 h with 60 mL H2O and diluted with 250 mL DCM. Organic layer washed with H2O (60 mL), NH4Cl (2×60 mL), NaHCO3, (60 mL) and brine (60 mL). Organic layer dried over MgSO4, filtered and concentrated. Flash chromatography—10 to 60% EtOAc/hexanes gave 1.71 g of product—NMR indicates approximately 1:1 ratio of epimerized aldehydes. Flash chromatography—EtOAc/DCM/hexanes resulted in separate isomers, 1632a and 1632b.

Step 2: SM, 1632a (100 mg) dissolved in THF and cooled to −78° C. MeMgBr (3M, 110 uL) added dropwise and let stir at −78° C. for 1 h. Reaction complete by TLC. Quench with 5 mL NH4Cl and let stir at rt. Dilute with 25 mL H2O and extract 2×35 mL EtOAc, dry over MgSO4, filter and concentrate. Flash chromatography −30 to 60% EtOAc/hexanes gave 60.6 mg of a ~1:1 mixture of diastereomers, 1632c (57%).

Remaining steps: Conversion of 1632c to 1632, as in Z40.

Example 1637

Procedure Z62

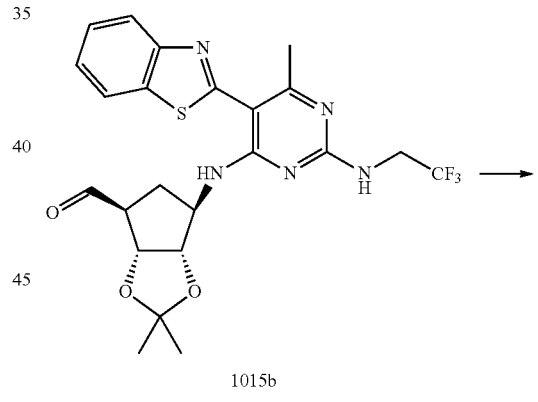
1015b

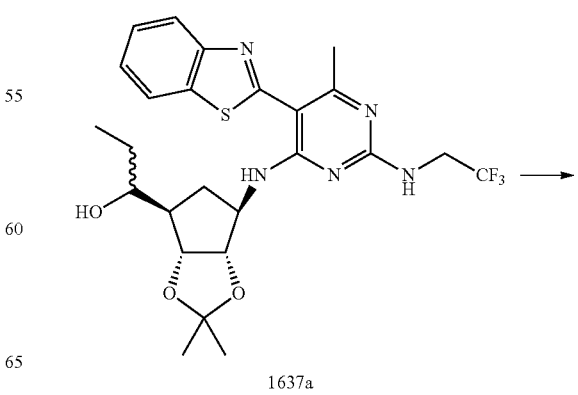
1637a

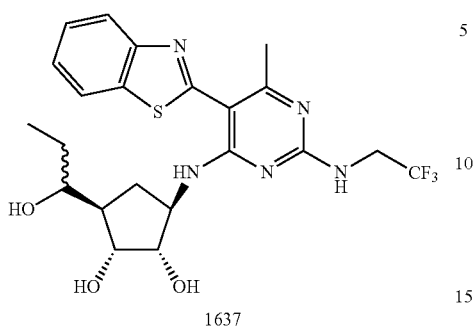
1637

Step 1: SM, 1015b (48 mg) dissolved in THF (3 mL) and cooled to −78° C. EtMgBr (3M, 100 uL) added dropwise and let stir at −78° C. for 2 h. One eq of EtMgBr added. Almost complete by TLC and MS. After 2 h, quench with 5 mL NH4Cl and let stir at rt. Dilute with 25 mL H2O and extract 3×30 mL EtOAc, dry over Na2SO4, filter and concentrate. Flash chromatography—5 to 50% EtOAc/hexanes gave 23.7 mg of 1637a (44%).

Step 2: Conversion of 1637a to 1637, as in procedure Z.

Examples 1636 and 1640

Procedure Z63

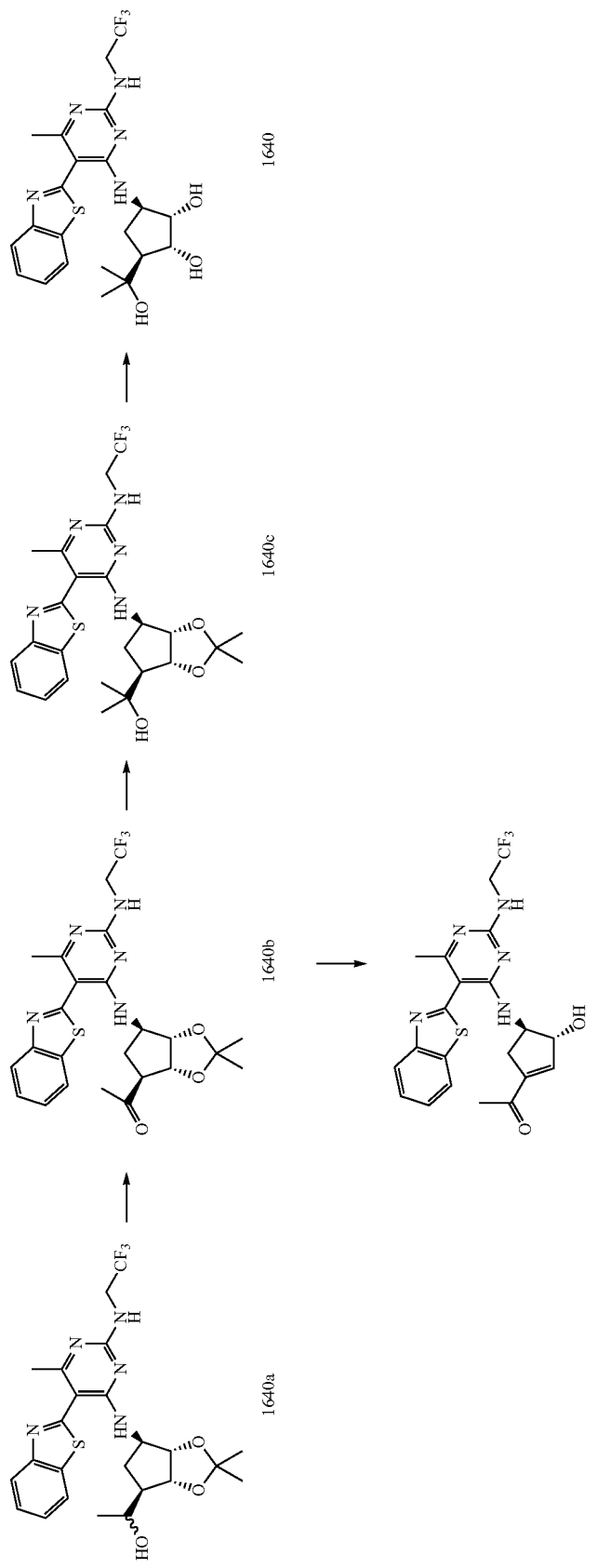

Step 1: SM, 1640a (102 mg, obtained as in procedure Z62, step 1) dissolved in CH$_2$Cl$_2$ (4 mL). NaHCO3 (51 mg), then Dess-Martin's periodinane (164 mg) added and let stir at rt for 4.5 h. TLC and MS indicates reaction is complete. Quench with 5 mL 10% Na2S2O3 and let stir till organic layer is clear. Dilute 20 mL H2O and extract 3×30 mL EtOac, dry over MgSO4, filter and concentrate. Obtained 110.0 mg of 1640b.

Step 2: Conversion of 1640b to 1640c, as in procedure Z62.

Remaining steps: Conversion of 1640b to 1636, and 1640c to 1640, as in procedure Z, with modifications.

Example 1643

Procedure Z64

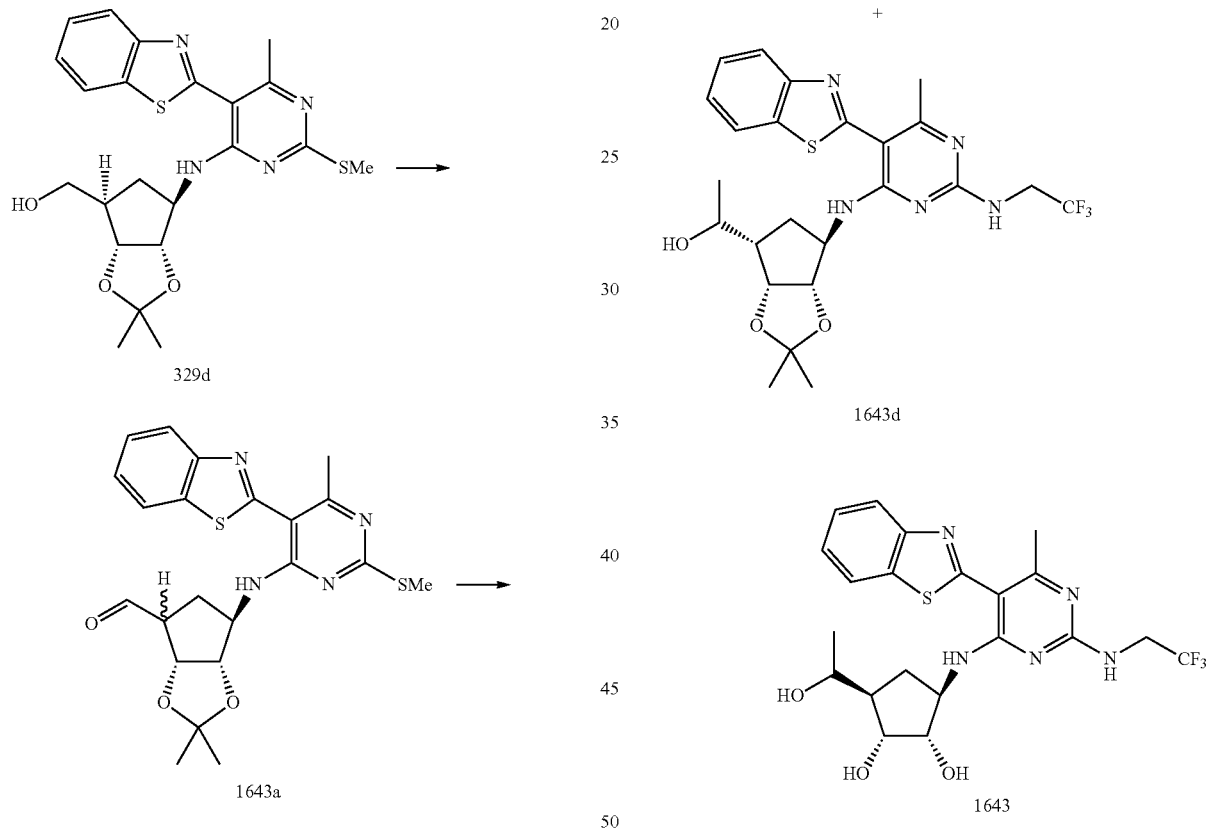

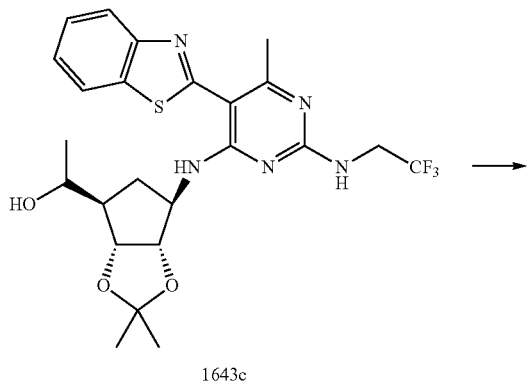

Step 1: SM, 329d (2.2 g) dissolved in CH2Cl2 (40 mL), cooled to 0° C., then Dess-Martin's periodinane (DMP, 2.5 g) added and let stir at rt 3 h. Add 2.5 g DMP. After 30 min, complete by TLC. Quench with 25 mL 10% Na2S2O3 and let stir till organic layer is clear. Dilute 100 mL H2O and extract 3×80 mL EtOac, dry over Na2SO4, filter and concentrate to give 2.66 g of 1643a.

Step 2: SM, 1643a (390 mg) dissolved in THF (20 mL) and cooled to −78° C. MeMgBr (3M, 1.7 mL) added dropwise and let stir at −78° C. for 2 h. Quench with 20 mL NH4Cl and let stir at rt. Dilute with 75 mL H2O and extract 3×50 mL EtOAc, dry over Na2SO4, filter and concentrate. Flash 20 to 40% EtOAc/hexanes to give 1643b (102.3 mg of isomer 1 and 151.2 mg of isomer 2 at the newly created stereocenter).

Remaining steps: As in procedure Z (single isomers 1643c and 1643d were separated at amine displacement of sulfoxide stage). 1643c was carried forward to 1643.

Example 1653

Procedure Z66

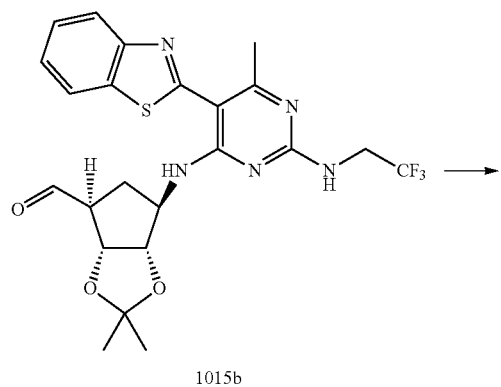

1015b

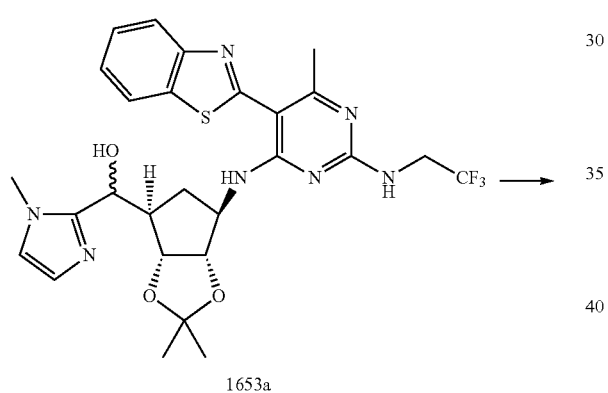

1653a

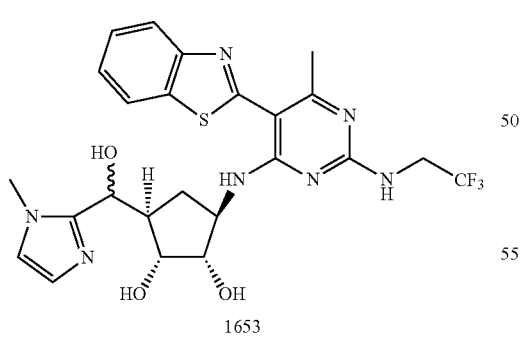

1653

Step 1: Imidazole (17 uL) dissolved in THF (2 mL) and cooled to −78° C. n-BuLi (1.6M, 130 uL) added and let stir 15 min, then aldehyde, 1015b (0.2 mmol) added. After 30 min, add 10 eq. imidazole/n-BuLi mixture (pre-formed at rt) to reaction. Quench with 10 mL NH4Cl, dilute with 50 mL H2O and extract 2×50 mL EtOAc. Dry Na2SO4, filter and concentrate. Flash chromatography gave 49.0 mg of 1653a.

Step 2: Conversion of 1653a to 1653, as in procedure Z.

Example 1701

Procedure Z67

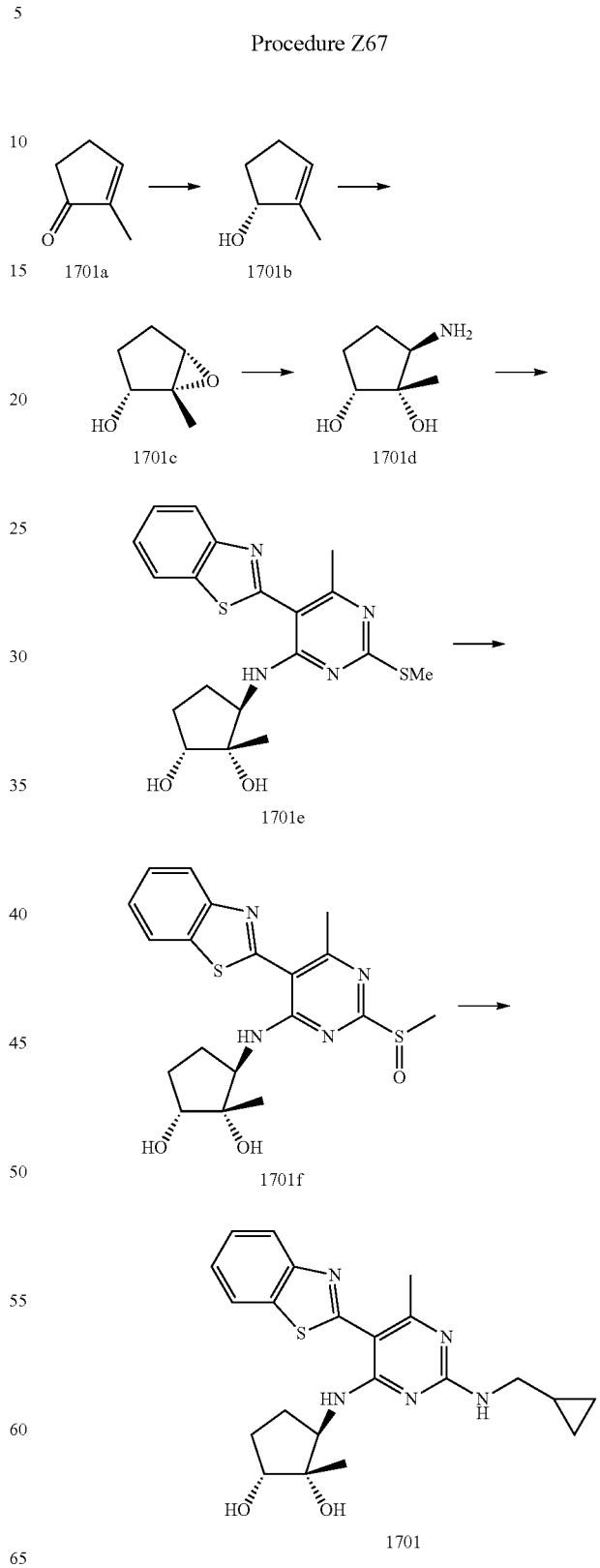

Step 1:

A solution of 2-methyl-cyclohex-2-en-1-one (1701a) (4.0 g, 41.61 mmol, 4.08 mL, d 0.979) in dry dichloromethane (80 mL) was slowly added (over 30 min) to an ice-cooled solution of (R)-1-methyl-3,3-diphenylhexahydropyrrolo[1,2-c][1,3,2]oxazaborole (Corey's Me-CBS, 10 mol %, 4.2 mL of 1 M solution in toluene) and borane-dimethylsulfide complex (1.0 eq, 4.16 mL) in dichloromethane (20 mL). After addition was completed the mixture was stirred for further 15 min. The reaction was quenched by careful and slow addition of methanol (20 mL). The mixture was concentrated in rotavap and the residue was diluted with aqueous saturated sodium bicarbonate (100 mL), the product was extracted into ethyl acetate (4×100 mL). The combined organic extracts were washed with aqueous saturated sodium bicarbonate (50 mL), aqueous saturated ammonium chloride (50 mL) and brine (50 mL). The organic layer was dried over magnesium sulfate, filtered and concentrated in rotavap. The residue was purified on a Redisep (120 g) silica gel column (gradient: 0 to 50% ethyl acetate in hexanes) to give the product 1701b (2.7 g, 67%) as a colorless oil.

Step 2:

A solution of (R)-2-methylcyclopent-2-enol (1701b) (300 mg, 3.056 mmol) in 30 mL of benzene was cooled in an ice-water bath and treated with VO(acac)$_2$ (5 mol %, 219 mg) and tert-butylhydroperoxide (1.0 eq, 2.13 mL of 70 wt % in water). The reaction mixture was stirred for 10 min and a second equivalent of t-butylhydroperoxide was added. The reaction was stirred for further 20 min at room temp. The mixture was cooled again and a third equivalent of t-butylhydroperoxide was added. The reaction was stirred for further 20 min at room temp and TLC (30% ethyl acetate in hexanes) showed complete conversion. The mixture was treated with aqueous 10% sodium thiosulfate (50 mL) and vigorously stirred for 10 min. The product was extracted into ethyl acetate (1×100 mL, 2×50 mL). The combined extracts were washed with brine, dried over magnesium sulfate, filtered and concentrated in rotavap. The residue was purified on a Redisep (120 g) silica gel column (0 to 70% ethyl acetate in hexanes) to give the product 1701c (1.0 g, 54%) as a colorless oil.

Step 3:

A microwave reaction tube was charged with a solution of (1R,2R,5S)-1-methyl-6-oxabicyclo[3.1.0]hexan-2-ol (1701c) (90 mg, 0.788 mmol) in 1 mL of dioxane. Concentrated ammonium hydroxide was added (2 mL) and the tube was sealed. The reaction was carried out in microwave at 135° C. for 30 min. TLC (50% ethyl acetate in hexanes) showed complete conversion. The mixture was concentrated in rotavap and the residual water was co-evaporated with benzene to give the crude product 1701d (ca 99%, 102 mg) as a slightly yellow oil.

Step 4:

A solution of (1S,2R,5R)-5-amino-1-methylcyclopentane-1,2-diol (1701d) (1.1 eq, 117 mg) in ethanol (8 mL) was treated with 2-(4-chloro-6-methyl-2-(methylthio)pyrimidin-5-yl)benzo[d]thiazole (250 mg, 0.812 mmol) and triethylamine (4.0 eq, 0.456 mL, d 0.720). The mixture was heated in an oil bath at 80° C. for 20 h. LCMS showed partial conversion (approx 20% SM left). All the volatiles were removed in rotavap and the residue was dried under vacuum. The crude product was purified on a Redisep (24 g) silica gel column (gradient: 0 to 40% ethyl acetate in dichloromethane) to give the product 1701e (214 mg, 60%) as a white solid.

Step 5:

A solution of (1S,2R,5R)-5-(5-(benzo[d]thiazol-2-yl)-6-methyl-2-(methylthio)-pyrimidin-4-ylamino)-1-methylcyclopentane-1,2-diol (1701e) (200 mg, 0.496 mmol) in 10 mL of dichloromethane was placed in an ice-water bath and treated with m-CPBA (1.3 eq, 148 mg of 75% m-CPBA). The reaction mixture was stirred for 5 min and TLC (30% ethyl acetate in dichloromethane) showed complete consumption of the starting material. The reaction was treated with aqueous saturated sodium bicarbonate soln (10 mL) and the product was taken into ethyl acetate (50 mL). The layers were separated and the organic layer was washed with aqueous saturated sodium thiosulfate (10 mL) and brine (10 mL). The organic layer was dried over magnesium sulfate, filtered and concentrated in rotavap to give the crude product 1701f (207 mg, 100%) as a white solid which was used without further purification. LCMS showed 80:20 distribution between sulfoxide/sulfone products.

Step 6:

The (1S,2R,5R)-5-(5-(benzo[d]thiazol-2-yl)-6-methyl-2-(methylsulfinyl)pyrimidin-4-ylamino)-1-methylcyclopentane-1,2-diol (1701f) (0.248 mmol, 104 mg) was dissolved in cyclopropylmethanamine (2 mL, by 83-85° C.) and heated in a sealed tube (oil bath 100° C.) for 17 h. LCMS showed complete conversion into product. The volatiles were removed in rotavap and the residue was dissolved in DCM (5 mL) and purified on a Redisep (24 g) silica gel column (gradient: 0 to 60% ethyl acetate in hexanes) to give the product 1701 (90 mg, 88%) as a white solid.

Example 1702

Procedure Z68

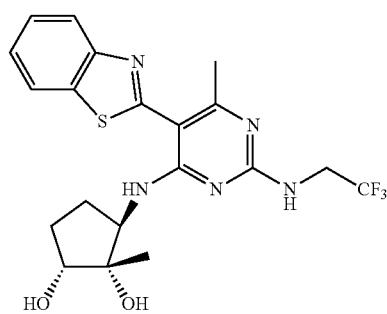

1702

Step 1:

Synthesized from 1701f (104 mg) and 2,2,2-trifluoroethanamine following the procedure Z67, step 6 to give 1702. Purified in semiprep-HPLC and isolated as HCl salt (60 mg, 51%)

Example 1703

Procedure Z69

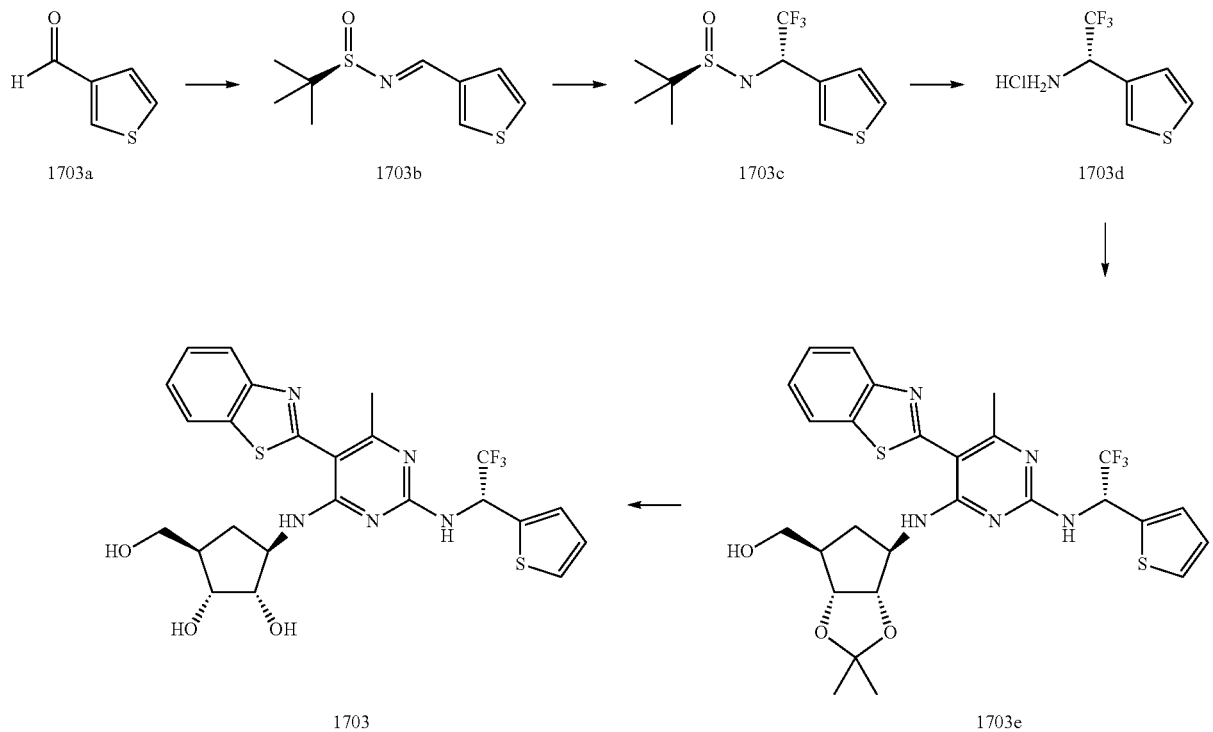

Step 1:

Intermediate 1703b (3.15 g, 81%) was synthesized from thiopehe-3-carboxaldehyde (1703a, 2.03 g, Aldrich) following the procedure described in *J. Org. Chem.* 1999, 64, 1278-1284.

Step 2:

Intermediate 1703c (1.1 g, 42%) was synthesized from 1703b (2.0 g) following the procedure described in *Angew. Chem. Int Ed.* 2001, 40, 589-590.

Step 3:

A solution of (R)-2-methyl-N-((S)-2,2,2-trifluoro-1-(thiophen-3-yl)ethyl)propane-2-sulfinamide 1703c (1.1 g, 3.85 mmol) in 40 mL of methanol was treated with 4 M HCl in dioxane (8 mL). The mixture was stirred for 10 min and TLC (30% ethyl acetate in hexanes) showed complete consumption of the starting material. All the volatiles were removed in rotavap and the residue was treated with dichloromethane to make a homogeneous solution. Hexanes (50 mL) was added and the mixture was concentrated in rotavap to half its volume. More hexanes (50 mL) was added to the resulting slurry and the mixture was concentrated to half its volume again. The solids were recovered by filtration (whatman #1) to give the product 1703d (780 mg, 95%) as a white solid.

Step 4:

1703e was obtained from 1703d in 62% yield (110 mg) as described in Procedure U, step 5 using dioxane as solvent and purification was done by chromatography on silica gel.

Step 5:

1703 was obtained from 1703e (90 mg) as the hydrochloric salt (80 mg, 97%) as described in Procedure U, step 6.

Example 1901

Procedure Z70

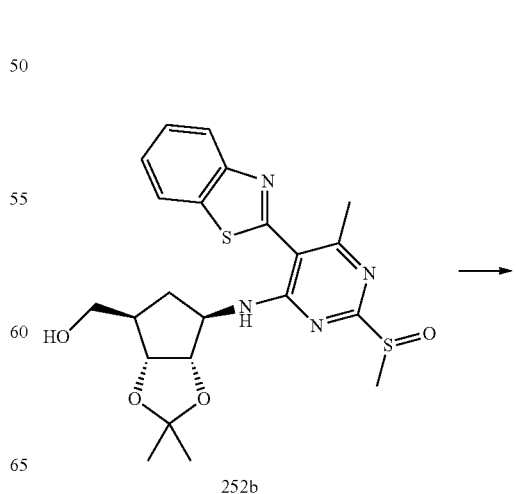

252b

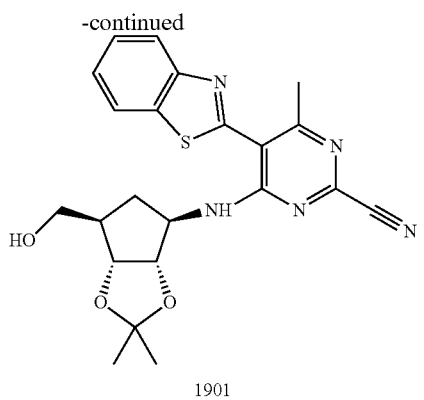

1901

A solution of sulfoxide 252b (333 mg, 0.678 mmol) in anhydrous Dichloromethane (5 ml) was treated with tetrabutylammonium cyanide (182 mg, 0.678 mmol) at room temperature for 4 hours. The solvent was evaporated and the mixture was purified on a silica gel column with 0-80% EtOAc/Hexanes to give a light yellow solid 1901 (243 mg).

Example 1902

Procedure Z71

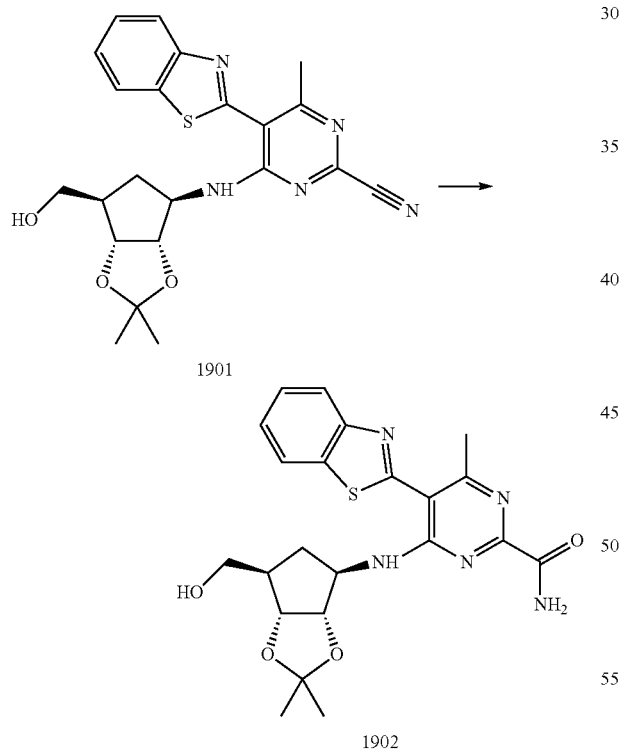

1901

1902

A solution of nitrile compound 1901 (100 mg, 0.2285 mmol) in Tetrahydrofuran (2 ml) and Methanol (2 ml) was cooled to 0° C. and treated with potassium carbonate (47.3 mg, 0.3427 mmol) and hydrogen peroxide (0.7 ml) and allowed to warm to room temperature. The reaction was stirred for 1 hour. TLC #1 with 70% EtOAc/Hexanes shows all starting material was consumed. The THF was removed by evaporation and DCM was added. The DCM was washed with 50% sodium thiosulfate/sodium bicarbonate solution. The DCM layer was dried and evaporated to give a pale yellow solid 1902, (94 mg).

Example 1905

Procedure Z72

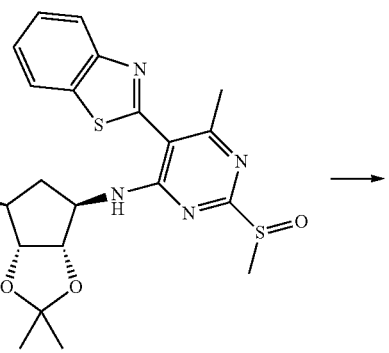

252b

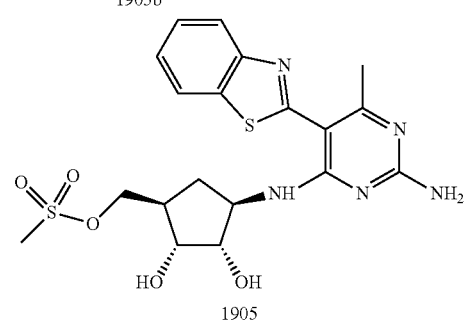

1905a

1905b

1905

Step A: A solution of sulfoxide 252b (~500 mg, 1.053 mmol) in tetrahydrofuran (10 ml) was treated with ammonium hydroxide (2.5 ml) in a sealed flask and heated to 50° C. for 5 hours. The solvent was removed and the crude was purified on a silica gel column with 0-70% Acetone/Hexanes to give a white solid 1905a (225 mg).

Step B: A solution of amine 1905a (50 mg, 0.1169 mmol) in chloroform (1.5 ml) was treated with triethyl amine (24.4 ul, 0.1753 mmol) and mesyl chloride (9.05 ul, 0.1169 mmol) and stirred at rt for 16 hours. A second equivalent of reagents were added and the reaction was stirred for an additional 2 hours. The solvent was removed and the product was purified on 1000 um silica gel prep plates with 2 elutions of 50% Acetone/Hexanes to give 1905b (24 mg).

Step C: Compound 1905b was converted to 1905HCl salt using Procedure F, step 3.

Example 1907

Procedure Z73

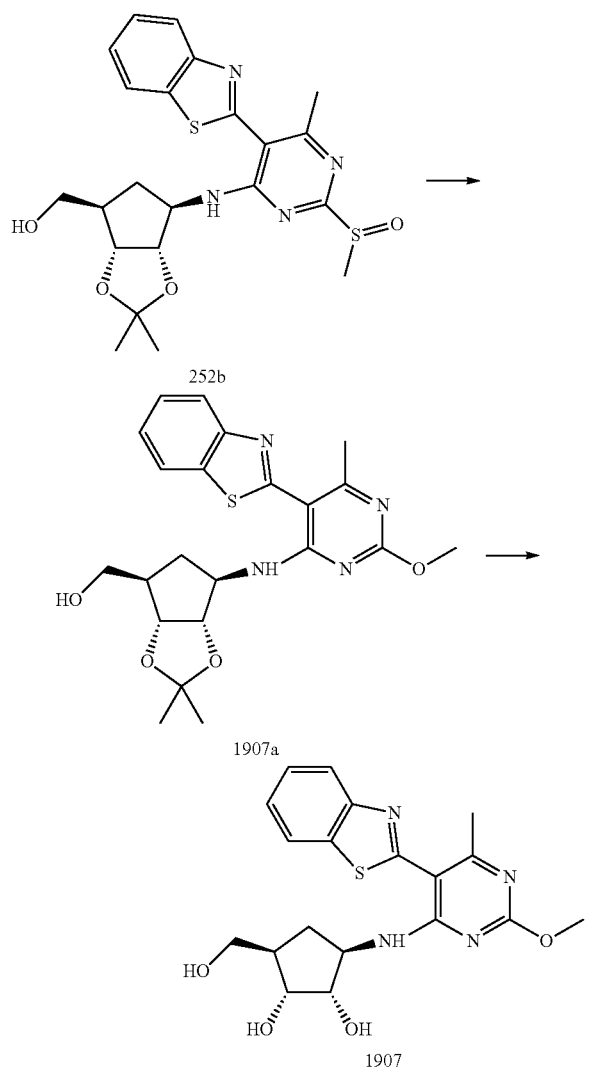

Step A: A solution of sulfoxide 252b (100 mg, 0.2107 mmol) in Methanol (2 ml) was treated with potassium carbonate (1.0 mmol) at room temperature for 72 hours. The methanol was removed by evaporation, ethyl acetate was added, washed with water and dried over sodium sulfate. The mixture was filtered and solvent removed to give crude product. The residue was purified on a silica gel column with 0-100% Ethyl acetate/Hexanes to give a white solid 1907a (40 mg).

Step B: Compound 1907a was converted to 1907HCl salt using Procedure F, step 3.

Example 1915

Procedure Z74

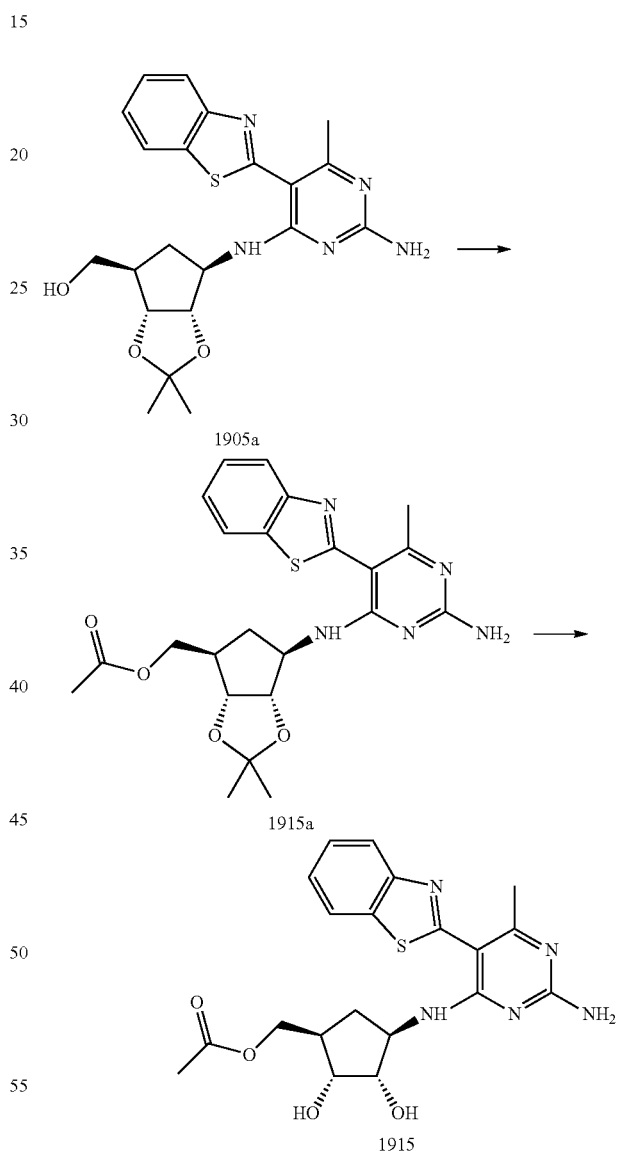

Step A: A solution of amine 1905a (50 mg, 0.1169 mmol) in chloroform (1.5 ml) was treated with triethyl amine (24.4 ul, 0.1753 mmol) and acetyl chloride (8.31 ul, 0.1169 mmol) and stirred at rt for 3 hours. A second equivalent of reagents were added and the reaction was stirred for an additional 3 hours. The solvent was removed and the product was purified on a silica gel column with 0-100% EtOAc/Hexanes to give a white solid 1915a (31 mg).

Step B: Compound 1915a was converted to 1915HCl salt using Procedure F, step 3, then purified on C18 reverse phase column eluting with 10-70% THF/Water/TFA to give 1915 TFA salt.

Example 1916

Procedure Z75

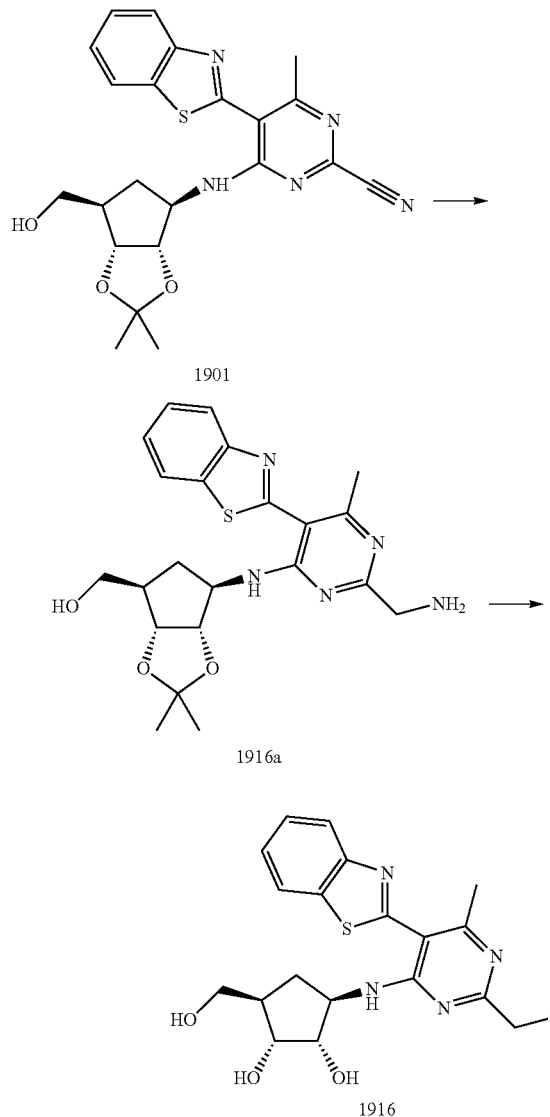

1901

1916a

1916

Step A: A solution of Nitrile compound 1901 (125 mg, 0.2857 mmol) was dissolved in Tetrahydrofuran (4.5 ml) and Methanol (0.5 ml), cooled to 0° C. in ice bath and treated with cobalt chloride (74.2 mg, 0.5714 mmol) then portion by portion with the sodium borohydride (108 mg, 2.857 mmol) over 30 minutes and stirred at 0° C. for 1 hour. The solvent was removed by evaporation. EtOAc was added to residue and washed with sat. sodium bicarbonate solution and brine. The EtOAc layer was dried and evaporated to give crude 1916a (71 mg).

Step B: Compound 1916a was converted to crude 1916 using Procedure F, step 3, then purified on C18 reverse phase column eluting with 10-70% THF/Water/TFA to give 1916 TFA salt (21 mg).

Example 1917

Procedure Z76

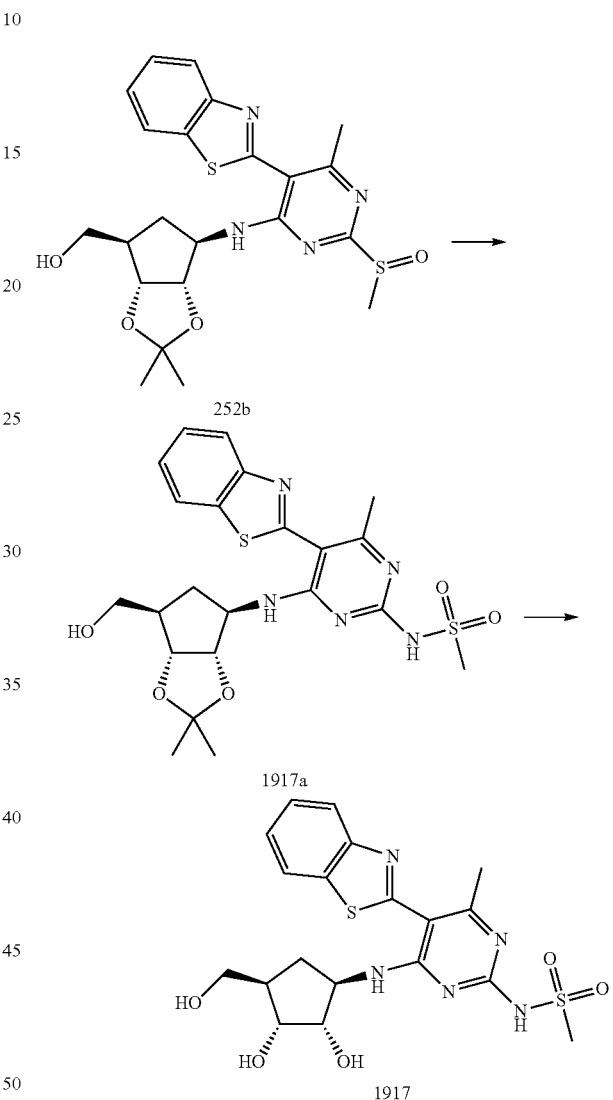

252b

1917a

1917

Step A: A solution of methanesulfonamide (1142 mg, 1.201 mmol) in anhydrous THF (1.5 ml) was cooled to 0° C. and treated with NaH (48 mg, 60% in oil) in one portion. The reaction was allowed to warm to room temperature then stirred for 30 minutes. The reaction was again cooled to 0° C., the sulfoxide 252b (57 mg, 0.1201 mmol) was added and stirred for 0.25 hours again allowing to warm to room temperature then stirred 16 hours. The reaction was made acidic with 1N HCl. EtOAc was added then washed with sat. sodium bicarbonate, 2× with water, brine and filtered through sodium sulfate. The solvent was removed and the residue was purified on a silica gel column with 0-60% THF/Hexanes to give a white solid 1917a (17 mg).

Step B: Compound 1917a was converted to crude 1917HCl salt using Procedure F, step 3, then purified on C18 reverse phase column eluting with 10-90% Acetonitrile/Water/TFA to give 1917 TFA salt (12 mg).
Example 31
Procedure A-3
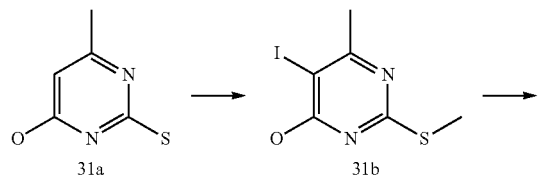
31a → 31b
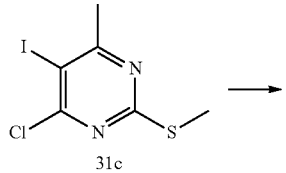
31c
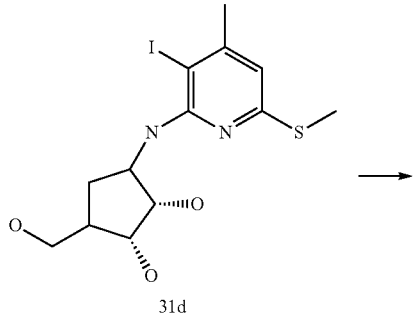
31d
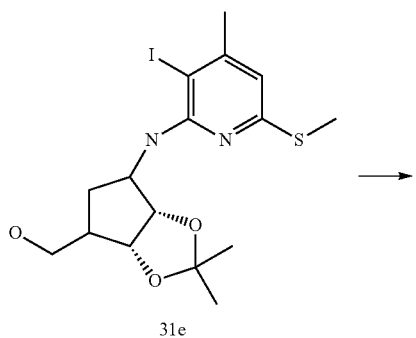
31e
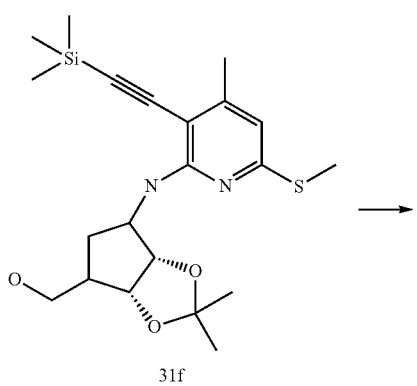
31f
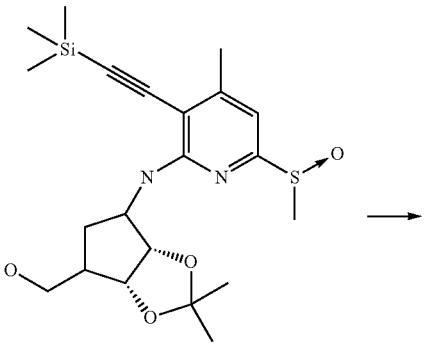
31g
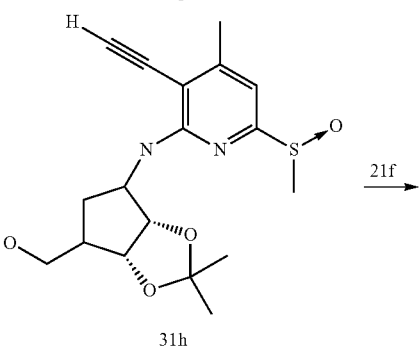
31h
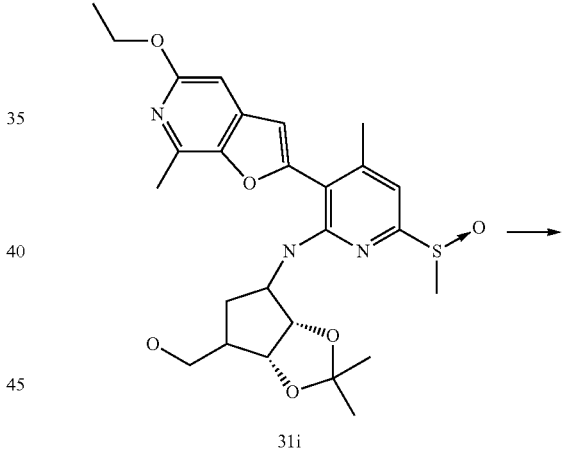
31i
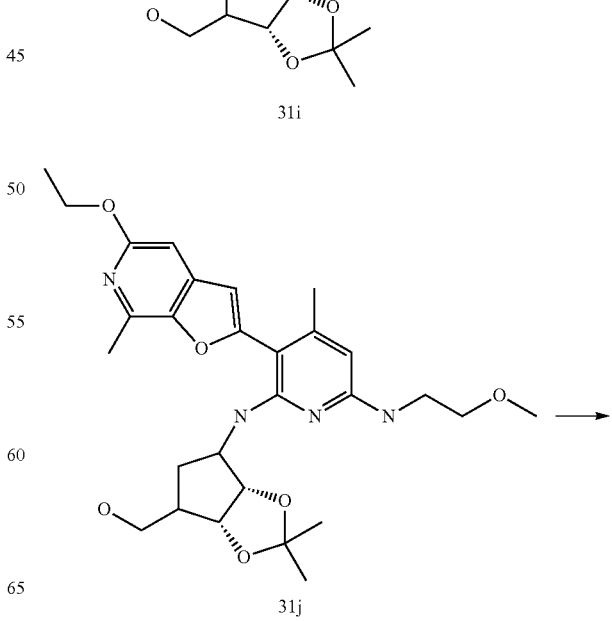
31j

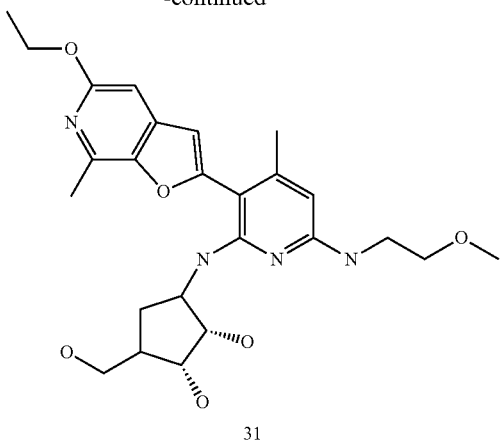

31

2-Methylthio-4-methyl-6-hydroxypyrimidine 31a was prepared according to the method in (*J. Med. Chem.*, 2007, 50, 1146-57).

2-Methylthio-4-methyl-5-iodo-6-hydroxypyrimidine 31b was prepared from 31a according to the method in *Chem. Pharm. Bull.*, 1986, 34, 2719.

2-Methylthio-4-methyl-5-iodo-6-chloropyrimidine 31c was prepared from 31b according to the method in *Chem. Pharm. Bull.*, 1986, 34, 2719.

Step 1: To a stirred mixture of the chloropyrimidine (2-methylthio-4-Me-5-iodo-6-chloropyrimidine, 51.6 g, 0.172 mol) and the cyclopentylamine carbasugar (34.6 g, 0.189 mol) in EtOH was added diisopropylethylamine (100 mL, 0.566 mol). The resulting mixture was refluxed overnight, becoming a solution after ~1 h of heating. After TLC showed that a small amount of the starting chloropyrimidine present, another 0.1 eq of the cyclopentylamine carbasugar (3.46 g) and more diisopropylethylamine (10 mL) were added and while heating a mixture was formed. After refluxing overnight, the reaction was allowed to cool to room temperature and to set for ~2 h. The resulting precipitated solid was filtered and collected, washed with EtOH, and dried under high vacuum to give a 79% yield of the desired adduct as an off-white solid. The filtrate was chromatographed on silica gel eluting with a chloroform/methanol (grad. 0 to 10% MeOH) to give more of the desired adduct 31d as a slightly impure solid product (total yield was ess. quantitative).

Step 2: Carbasugar adduct 31d (ess. 14.1 g, 35 mmol) was suspended in acetone (200 mL), and dimethoxypropane (8.6 mL, 7.3 g, 70 mmol) was added, followed by methanesulfonic acid (2.3 mL, 3.4 g, 35 mmol). The reaction was allowed to stir overnight becoming a solution over time. After concentrating the reaction mixture, the residue was taken up in methylene chloride and washed with saturated aqueous NaHCO$_3$, dried over sodium sulfate, and concentrated. After silica gel chromatographing eluting with chloroform/methanol (grd. 0 to 5%), the desired product 31e (11.99 g, 75.7% yield) was isolated as a white foam.

Step 3: Argon was bubbled through a stirred mixture of carbasugar protected 31e (11.99 g, 26.5 mmol) in anhydrous dioxane (175 mL), and then, Et$_3$N (14.8 mL, 106 mmol) was added, followed by CuI (1.01 mg, 5.3 mmol) and (Ph$_3$P)$_2$PdCl$_2$ (1.86 g, 2.65 mmol). The reaction vessel was sealed with a rubber septum equipped with an outlet needle, and the deoxygenation of the vessel with bubbling argon was continued for another ~10 min, TMS acetylene (11.2 mL, 79.5 mmol) was added, and the reaction sealed and protected from light. The reaction was then heated on a 50° oil bath for ~20 h. The reaction mixture was concentrated under vacuum and then partitioned with methylene chloride and water. The organic extract was washed with water, dried over Na$_2$SO$_4$, and concentrated. The crude product was chromatographed on silica gel eluting with chloroform/methanol (grad. 0 to 2% MeOH) to giving 31f (10.47 g, 93.6%) as a dark, highly colored foam or viscous glass.

Step 4: To a stirred methylene chloride (40 mL) solution of 31f (1.0 g, 2.4 mmol), cooled in an ice/water bath, was added mCPBA (655 mg, 2.8 mmol) in one aliquot. After ~1 h saturated aq. Na$_2$S$_2$O$_3$ was then added, and the mixture was diluted with methylene chloride and water. The organic extract was washed with water, saturated brine, dried over Na$_2$SO$_4$, and concentrated. The residue was chromatographed on silica gel eluting with chloroform/methanol (grd. 0 to 5% MeOH). Sulfoxide 31 g (747 mg, 71.1%) was isolated as a mixture of diastereomers (by NMR). A small amount (146 mg) of the sulfone corresponding to 31 g was also isolated.

Step 5: To a solution of sulfoxide 31 g (747 mg, 1.71 mmol) in CH$_3$CN under argon with stirring was added Et$_4$NF.2H$_2$O (106 mg, 0.57 mmol). The reaction was allowed to stir overnight then chromatographed on silica gel eluting with chloroform/methanol (grad. 0 to 4% MeOH). Product 31 h was isolated as a slightly colored foam (515 mg, 82A % yield).

Step 6: While bubbling argon through a solution of 31 h (183 mg, 0.5 mmol) and 21f (167 mg, 0.6 mmol) in DMF (3 mL), Et$_3$N (0.35 mL, 2.5 mmol) was added, followed by CuI (19 mg, 0.1 mmol). After 10 min stirring, (Ph$_3$P)$_4$Pd (58 mg, 0.05 mmol) was added, and after another ~2 min of argon bubbling, the reaction tube was capped and microwaved at 300 W at 90° C. for 10 min. The reaction mixture was then concentrated, taken up in MeOH, and filtered. The filtrate was chromatographed on silica gel eluting with chloroform/methanol (grad. 0 to 5% MeOH). The desired product 31i was isolated as a yellow foam (232 mg, 89.8% yield).

Step 7: To a solution of sulfoxide 31i (100 mg, 0.194 mmol) in acetonitrile (5 mL) was added methoxyethylamine (0.17 ml, 1.94 mmol). The resulting solution was refluxed overnight. After cooling to room temperature, a solid formed which was isolated by filtration, collected, washed with acetonitrile, and then dried under vacuum. The obtained grayish solid was the desired product 31j (42 mg, 41.2% yield).

Step 8: To a solution of isopropylidene 31j (40 mg, 0.076 mmol) in MeOH (3 mL) was added aqueous 1N HCl and stirred overnight. The reaction was then filtered and concentrated to give the desired product 31 as a yellow solid as its HCl salt (48 mg, product contains 0.5 eq of MeOH).

Example 48

Procedure A-4

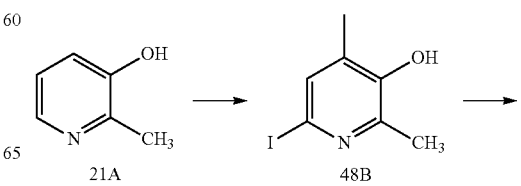

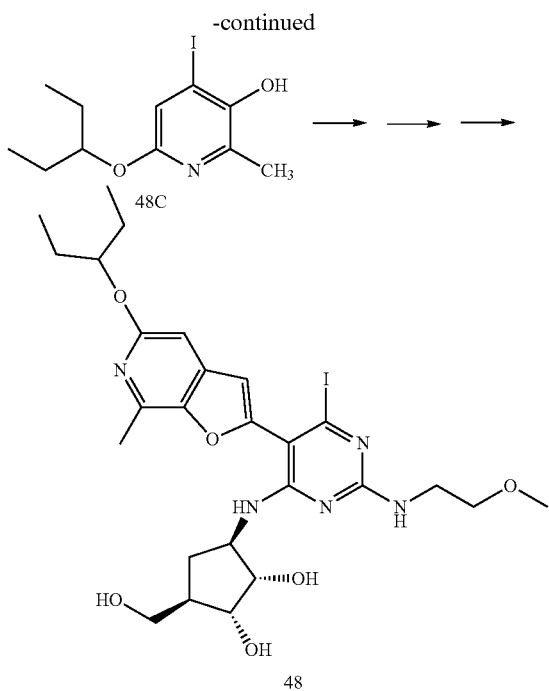

After a solution of aqueous K₂CO₃ (106.4 g in 350 mL) was cooled to room temp, compound 21A (24.0 g, 0.22 mol) was added, and the resulting solution was placed in an ice bath and stirred for ~25 min. Then, solid I₂ (112.0 g (0.44 mol) was added in one portion, and the resulting suspension was left to warm to room temp overnight with stirring. The suspension was then treated with a concentrated sodium thiosulfate solution (~60 mL), and then conc. HCl (~115 ml) was added dropwise with via an addition funnel at a rate that avoided clumping. (The addition of a little EtOAc helped to separate any clumps that formed. The pH of the resulting suspension is about 2-3 by pH paper.) The resulting mixture was then extracted with EtOAc (3×150 mL) and the combined organic layers washed with brine (1×400 mL), dried (Na₂SO₄), filtered, and concentrated to dryness. Flash chromatography eluting with a stepwise gradient of 0 to 25% EtOAc in hexanes afforded compound 48B (TLC in 1:4 EtOAc/hexane, R_f 48B=~0.4).

A mixture of 3-pentanol (1.5 mL, 0.013 mol) and 4 Å molecular sieves (~0.7 g, crushed and activated) in THF (50 mL) was stirred for ~10 min at room temp under argon). NaH was then added in portions over ~5 min, and the mixture was allowed to stir until H, evolution ceased (~5 min). To this mixture was added 48B (2.5 g, 6.9 mmol) followed by CuBr (0.2 g, 0.0013 mol), and the mixture was placed in an oil bath maintained at 85-90° C. After 2 h, TLC showed that the starting material was essentially consumed, and the mixture was filtered through Celite and washed with a minimal amount of CH₂Cl₂. The solvent was then removed in vacuo, and the residue was partitioned between EtOAc and ~0.5 M HCl (15 mL each). The organic layer was separated and washed with sodium thiosulfate (1×15 mL), brine (1×15 mL) and concentrated to dryness. The residue was then preadsorbed onto silica gel (coarse, ~8.0 g) and purified by flash chromatography, eluting with a stepwise gradient of 0 to 25% EtOAc in hexanes, affording compound 48C (1.5 g).

48C was then used in place of 21f in Procedure A-3, and following the same essential procedure, target 48 was obtained.

Example 53

Procedure A-5

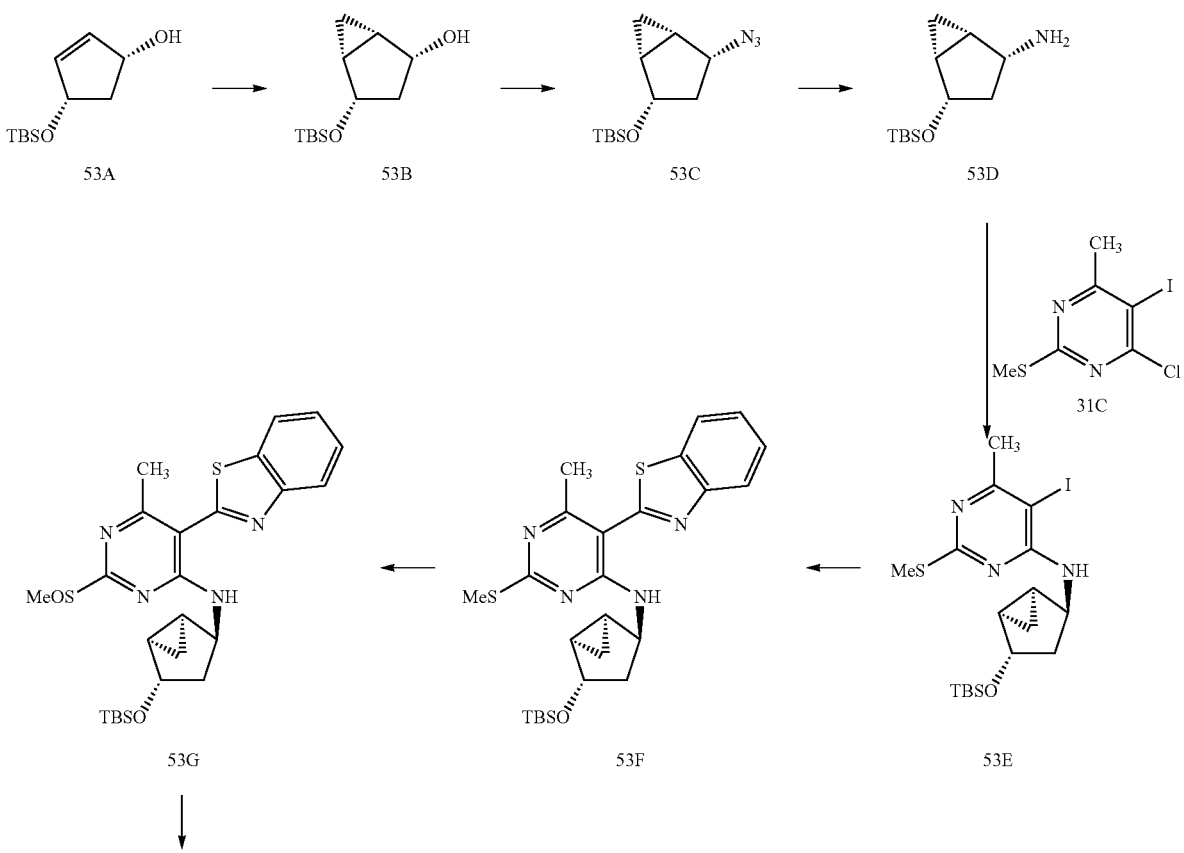

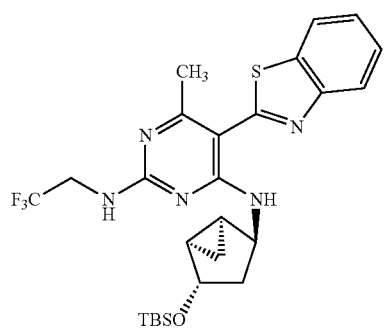 53H

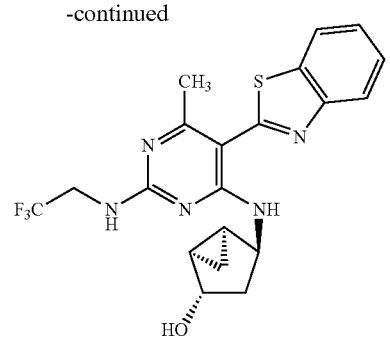 53

To a solution of 53A (1.0 g, 4.66 mmol) in methylene chloride (30 ml) was added diethyl zinc solution (5.4 ml, 1M hexanes, 5.36 mmol) at a rate to keep the temperature at <2° C. After the addition was complete, a solution of diiodomethane (0.43 ml, 5.36 mmol) in methylene chloride (2.3 ml) was added in one portion. After 15 min, another portion of diethyl zinc solution (5.4 ml, 1M hexanes, 5.36 mmol) was added at a rate to keep the temperature at <2° C., and then after 15 min, another solution of diiodomethane (0.43 ml, 5.36 mmol) in methylene chloride (2.3 ml) was added in one portion. After 15 min, the resulting mixture was allowed to warm to room temperature, and then, after 4 h, the reaction was quenched with saturated ammonium chloride and diluted with methylene chloride and saturated ammonium chloride. After separating the layers, the aqueous layer was further extracted with methylene chloride (3×), and the combined organic extracts were dried with sodium sulfate and then concentrated. Compound 53B (1.02 g) was obtained as a slightly yellow crystalline solid.

To a solution of 53B (988 mg, 4.32 mmol) and triphenyl phosphine (2.84 g, 10.8 mmol) in tetrahydrofuran (25 ml), diisopropyl azodicarboxylate (1.70 ml, 8.65 mmol) was added at a rate to keep the temperature between −20° C. and −18° C. After the addition was complete, diphenylphosphoryl azide (0.93 ml, 4.32 mmol) was added dropwise. The resulting mixture was then allowed to warm to room temperature and left overnight. The reaction was partitioned between ethyl ether and saturated brine, the aqueous layer was further extracted with ethyl ether (2×), and the combined organic extracts were dried sodium sulfate and concentrated. The recovered 5.3 g of crude product was chromatographed on silica, eluting with EtOAc/hexanes (gradient 0/100→10/90). Compound 53C (637 mg) was obtained as a clear oil.

To a stirred solution of 53C (278 mg, 1.1 mmol) and triphenyl phosphine (360 mg, 1.37 mmol) in tetrahydrofuran (5 ml) was added water (0.5 ml). After 3 days, the resulting mixture was concentrated and coevaporated with ethanol (3×). The crude reaction mixture containing 53D was combined with chloropyrimidine 31C (413 mg, 1.38 mmol) in ethanol, and diisopropylethyl amine (0.72 ml, 3.75 mmol) was added. The resulting mixture was then refluxed for 2 days and then concentrated and chromatographed on silica, eluting with a gradient of methylene chloride/methanol (100/0, then gradient 100/0→98/2). Compound 53E (344 mg) was obtained as a clear oil.

To an argon-flushed flask containing 53E (344 mg, 0.70 mmol) was added copper(I) iodide (33 mg, 0.17 mmol) followed by tetrakistriphenylphosphine palladium (121 mg, 0.10 mmol), cesium carbonate (1.14 g, 3.5 mmol), benzothiazole (0.15 ml, 1.4 mmol) and DMF (10 ml), sequentially. After degassing with Ar for 10 min, the flask was by sealed with a rubber septum and was heated in a preheated oil bath at 100° C. for 4 h. After diluting with ethyl acetate, the mixture was filtered through a celite pad, washing with ethyl acetate. The filtrate was diluted with ethyl acetate and combined organic extract washed with water (2×) and saturated brine, dried with sodium sulfate and concentrated. After chromatography on silica eluting with chloroform/methanol (100/0, then gradient 100/0→98/2), compound 53F (178 mg) was recovered as a slightly yellow solid.

To an ice water bath-cooled solution of sulfide 53F (178 mg, 0.36 mmol) in methylene chloride (10 ml) was added MCPBA (82 mg, ~75% purity, 0.36 mmol). After 1 h, more MCPBA (8 mg) was added. The reaction was then quenched a few minutes later with saturated sodium thiosulfate. After diluting with methylene chloride, the separated combined organic extract was washed with a sodium thiosulfate solution and saturated sodium bicarbonate, then dried with sodium sulfate and concentrated. The resulting residue was chromatographed on silica eluting chloroform/methanol (100/0, then gradient 100/0→98/2). Compound 53G (154 mg) was obtained as a slightly yellow solid.

To a microwave reaction vial containing sulfoxide 53G (145 mg, 0.282 mmol) was added trifluoroethylamine (3 ml). The sealed vial was then heated in the microwave at 100° C. for 2 h, then at 125° C. for another 2 h. After concentrating, the resulting residue was chromatographed on silica, eluting with chloroform/methanol (100/0, then gradient 100/0→99/1). Compound 53H (140 mg) was obtained as a slightly yellow solid.

To a solution of 53H (124 mg, 0.23 mmol) in acetonitrile (5 ml) and tetrahydrofuran (5 ml) was added tetraethylammonium fluoride dihydrate (42 mg, 0.23 mmol), and the whole was stirred overnight. Another 42 mg of tetraethylammonium fluoride dihydrate was then added, and stirring was continued for another 24 h. After concentrating, the residue was chromatographed on silica, eluting with chloroform/methanol (gradient 100/0→94/4) giving the free base of 53 (66 mg) as a slightly colored solid. This solid was then suspended in methanol (20 ml) and 1N HCl (3 ml) was added. After concentrating and azeotroping with methanol (3×), compound 53 (66 mg) was obtained as a white solid.

Example 54

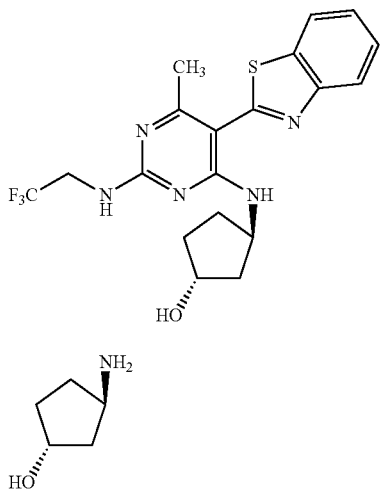

Compound 54 was also prepared by essentially the above procedure A-5, using the required hydroxycyclopentylamine 54A (WO 077551, 2008) instead of cyclopentylamine 53D.

Example 55

Procedure A-6

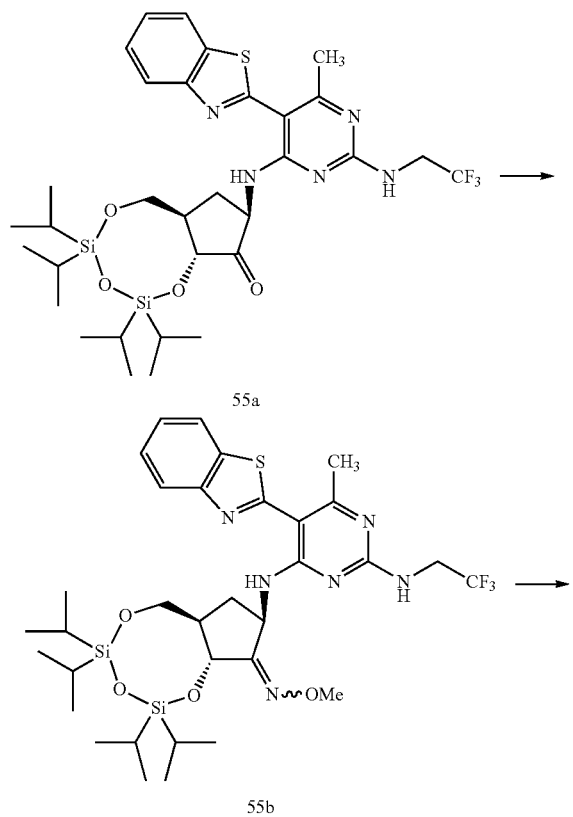

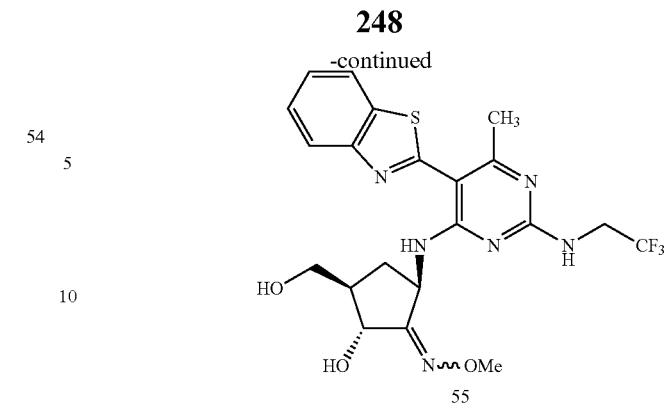

To a solution of 55a (prepared in a similar manner to 1383d, procedure Z43, 94 mg, 0.13 mmol) in pyridine (5 ml), diethyl O-methylhydroxylamine hydrochloride (13 mg, 0.16 mmol) was added. After stirring overnight and concentrating, the residue was partitioned with chloroform and saturated aqueous sodium bicarbonate. The organic extract was dried over sodium sulfate and then concentrated. Chromatography of the residue on silica gel, eluting with a gradient of EtOAc/hexanes (0/100→20/80) gave 55b (86 mg) as a solid.

To a solution of 55b (85 mg, 0.115 mmol) in acetonitrile (8 ml) was added tetraethyl-ammonium fluoride dihydrate (21 mg, 0.115 mmol), and the mixture was stirred overnight. After concentrating, the residue was chromatographed on silica gel, eluting with a gradient of chloroform/methanol (100/0→95/5), giving 55 (49 mg) as a slightly colored solid that was a mixture of oxime isomers.

Example 43

Procedure A-7

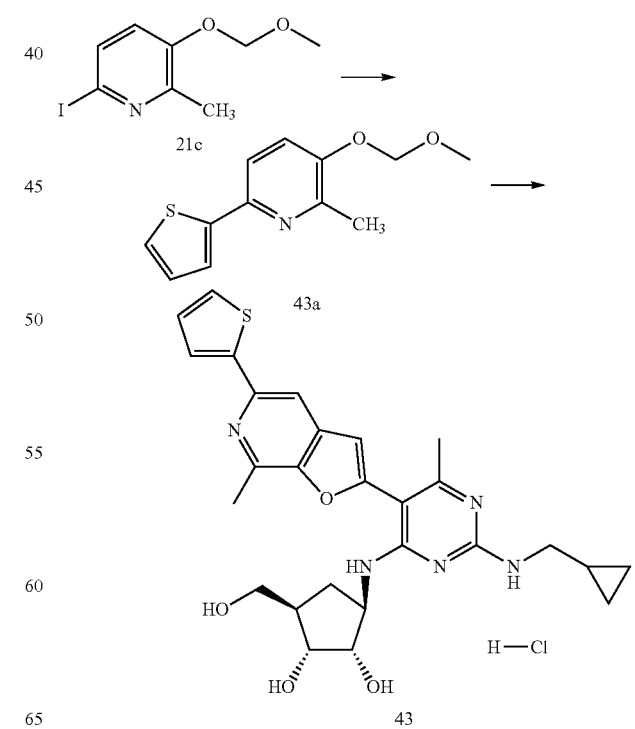

To a solution of [1,3-bis(2,6-diisopropylphenyl)imidazol-2-ylidene](3-chloropyridyl)palladium(II) dichloride (31 mg, 0.045 mmol) and lithium bromide (780 g, 8.99 mmol) in tetrahydrofuran (10 ml) and 1,3-dimethyl-2-imidazolidinone (10 ml), was added a solution of thienylzinc bromide (9.0 ml, 0.5M THF, 4.5 mmol). A solution of 21c (783 mg, 2.80 mmol) in 1,3-dimethyl-2-imidazolidinone (5 ml) was then cannulated into the reaction, followed by tetrahydrofuran (10 ml). After 3 h, the mixture was diluted with ethyl ether (50 ml) and washed with 1M ethylenediaminetetraacetic acid trisodium salt solution, followed by washing with water and brine, then dried with sodium sulfate and concentrated. Chromatography on silica gel, eluting with a gradient of EtOAc/hexanes (0/100→15/85), gave an oil comprised of a 3:1 ratio of 21c:43a, (637 mg). Then, to a solution of [1,3-bis(2,6-diisopropylphenyl)imidazol-2-ylidene](3-chloropyridyl)palladium (II) dichloride (31 mg, 0.045 mmol) and lithium bromide (780 mg, 8.99 mmol) in tetrahydrofuran (10 ml) and 1,3-dimethyl-2-imidazolidinone (10 ml) was cannulated a solution of the above mixture of 21c:43a (664 mg) in 1,3-dimethyl-2-imidazolidinone (5 ml), followed by tetrahydrofuran (10 ml). A solution of thienylzinc bromide (9.0 ml, 0.5M THF, 4.5 mmol) was added, and this solution was refluxed overnight. After diluting with ethyl ether (50 ml), the mixture was washed with 1M ethylenediaminetetraacetic acid trisodium salt solution, water, and brine, and then dried over sodium sulfate and concentrated. Chromatography on silica gel eluting gradient of EtOAc/hexanes (0/100→20/80) yielded 43a (478 mg) as a yellow oil.

Subsequent conversion of 43a to compound 43 followed appropriate reaction sequences from procedures A-2 and A-3.

In other embodiments, the compounds of the invention have a structural formula as depicted in Table I below and include tautomers, and pharmaceutically acceptable salts, esters, prodrugs, isomers, and solvates of such compounds and such tautomers.

TABLE I

| Compd # | Structure | EC90 (µM) range | NMR data | LC-MS (M + H)+ | Procedure |
|---|---|---|---|---|---|
| 5 | 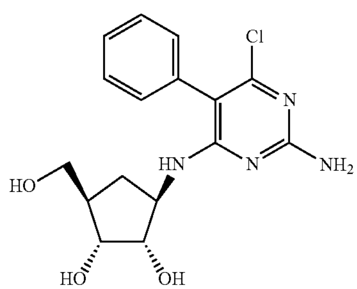 [SMILES: Nc1nc(Cl)c(-c2ccccc2)c(N[C@@H]2C[C@H](CO)[C@@H](O)[C@H]2O)n1] | C | (DMSO-$d_6$): δ 0.91 (m, 1H), 1.82 (m, 1H), 2.18 (m, 1H), 3.26 (t, 2H, J = 4.8 Hz), 3.55 (m, 2H), 4.37 (m, 2H), 4.51 (d, 1H, J = 4.0 Hz), 5.37 (d, 1H, J = 7.8 Hz), 6.48 (bs, 2H), 7.21 (d, 2H, J = 8.1), 7.43 (m, 3H). | 351.1 | A-1 |
| 6 | 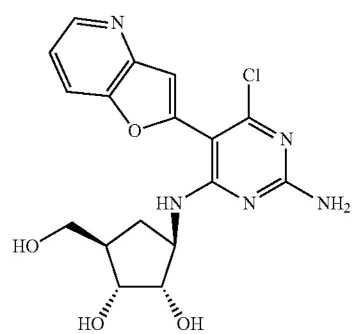 [SMILES: Nc1nc(Cl)c(-c2cc3ncccc3o2)c(N[C@@H]2C[C@H](CO)[C@@H](O)[C@H]2O)n1] | — | (DMSO-$d_6$): δ 1.02 (dt, 1H, J = 8.5, 13.0 Hz), 1.77-1.90 (m, 1H), 2.00-2.12 (m, 1H), 3.22-3.39 (m, 2H + $H_2O$), 2.59-2.72 (m, 2H), 4.30-4.43 (m, 2H), 4.47-4.57 (m (app quart), 2H, OHs), 6.61 (d, 1H, J = 7.9 Hz, NH), 6.87 (hr s, 2H, $NH_2$), 7.12 (d, 1H, J = 1.0 Hz), 7.33 (dd, 1H, J = 4.8, 8.3 Hz), 7.99 (dm, 1H, J = 8.3 Hz), 8.51 (dd, 1H, J = 1.3, 4.7 Hz). | 392.2 (Cl pattern) | A-2 |
| 7 | 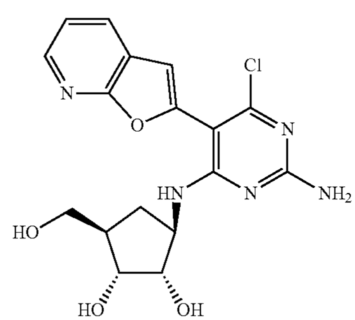 [SMILES: Nc1nc(Cl)c(-c2cc3cccnc3o2)c(N[C@@H]2C[C@H](CO)[C@@H](O)[C@H]2O)n1] | — | (DMSO-$d_6$): δ 1.01 (dt, 1H, J = 8.9, 13.0 Hz), 1.77-1.89 (m, 1H), 2.00-2.12 (m, 1H), 3.22-3.39 (m, 2H), 2.59-2.71 (m, 2H), 4.30-4.43 (m, 2H), 4.46-4.55 (m, 72H, OHs), 6.58 (d, 1H, J = 7.9 Hz, NH), 6.86 (br s, 2H, $NH_2$), 6.99 (s, 1H), 7.35 (dd, 1H, J = 4.8, 7.6 Hz), 8.10 (dd, 1H, J = 1.6, 7.6 Hz), 8.29 (dd, 1H, J = 1.7, 4.8 Hz). | 392.1 (Cl pattern) | A-2 |

| | | | | | |
|---|---|---|---|---|---|
| 8 | 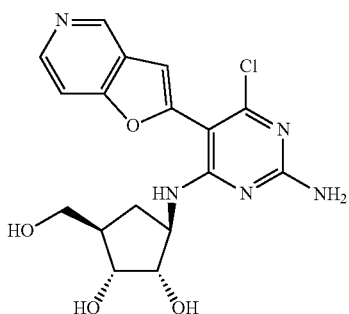 [SMILES: Nc1nc(Cl)c(-c2cc3cnccc3o2)c(N[C@@H]2C[C@H](CO)[C@@H](O)[C@H]2O)n1] | B | (DMSO-d6) δ 0.96-1.05 (m, 1H), 1.78-1.87 (m, 1H), 2.01-2.11 (m, 1H), 3.27-3.34 (m, 2H coincident with $H_2O$), 3.59-3.68 (m, 2H), 4.30-4.40 (m, 2H), 4.48-4.53 (m, 2H), 6.56 (d, 1 H, J = 7.8 Hz), 6.87 (s, 2 H), 7.08 (d, 1 H, J = 0.7 Hz), 7.65 (d, 1 H, J = 5.6 Hz). | 392.16 | A-2 |
| 9 | 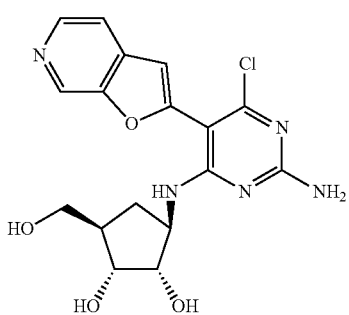 [SMILES: Nc1nc(Cl)c(-c2cc3ccncc3o2)c(N[C@@H]2C[C@H](CO)[C@@H](O)[C@H]2O)n1] | A | (DMSO-d6) δ 0.98-1.08 (m, 1H), 1.75-1.95 (m, 1H), 2.04-2.14 (m, 1H), 3.27-3.35 (m, 2H), 3.62-3.68 (m, 2H), 4.30-4.40 (m, 1H), 6.72 (d, 1 H, J = 7.8 Hz), 7.02 (s, 2 H), 7.27 (d, 1 H, J = 20.66 Hz), 7.65 (dd, 1 H, J = 0.4, 5.6 Hz), 8.52 (d, 1 H, J = 25.7 Hz), 9.20 (s, 1 H). | 392.20 | A-2 |
| 10 | 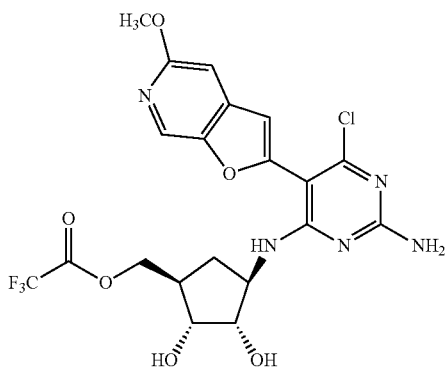 [SMILES: COc1cc2cc(-c3c(Cl)nc(N)nc3N[C@@H]3C[C@H](COC(=O)C(F)(F)F)[C@@H](O)[C@H]3O)oc2cn1] | A | (DMSO-d6) δ 0.98-1.08 (m. 1H), 1.78-1.90 (m, 1H), 2.04-2.14 (m, 1H), 3.26-3.36 (m, 2H), 3.62-3.69 (m, 2H), 3.87 (s, 3H), 4.30-4.37 (m, 1H, coincident with $H_2O$), 6.58 (d, 1 H, J = 7.9 Hz, $D_2O$ exchangeable), 6.84-6.94 (br s, 2 H, $D_2O$ exchangeable), 6.93 (s, 1 H), 7.01 (s, 1 H), 8.56 (s, 1H). | 518.11 | A-2 |
| 11 | 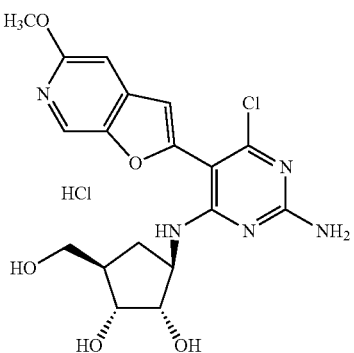 [SMILES: COc1cc2cc(-c3c(Cl)nc(N)nc3N[C@@H]3C[C@H](CO)[C@@H](O)[C@H]3O)oc2cn1 ; Cl] | A | (DMSO-d6) δ 1.00-1.07 (m, 1H), 1.78-1.90 (m, 1H), 2.02-2.14 (m, 1H), 3.28-3.50 (m, 2H), 3.63-3.70 (m, 2H), 3.93 (s, 3H), 4.30-4.37 (m, 1H, coincident with $H_2O$), 6.84 (d, 1 H, J = 7.6 Hz, $D_2O$ exchangeable), 7.04 (s, 1 H), 7.16 (s, 1 H), 8.61 (s, 1 H). | 422.14 | A-2 |

TABLE I-continued

| | | | | | |
|---|---|---|---|---|---|
| 12 | (structure) | B | (DMSO-d6) δ 1.05-1.12 (m, 1H), 1.84-1.93 (m, 1H), 2.14-2.24 (m, 1H), 2.56 (s, 3H), 3.11 (s, 6H), 3.34-3.38 (m, 2H, coincident with HDO), 3.63-3.76 (m, 2H), 3.85 (s, 3H), 4.24-4.30 (m, 1H), 4.40 (d, 1H, J = 5.2 Hz, D$_2$O exchangeable), 4.49-4.53 (m, 2H, D$_2$O exchangeable), 6.70 (d, 1 H, J = 7.1 Hz, D$_2$O exchangeable), 6.80 (d, 1 H, J = 0.6 Hz), 6.89 (s, 1 H). | 464.22 | A-2 |
| 13 | (structure) •HCl | C | (DMSO-d6) δ 1.06-1.16 (m, 1H), 1.85-1.95 (m, 1H), 2.16-2.26 (m, 1H), 2.64 (s, 3H), 3.12 (s, 6H), 3.31-3.37 (m, 2H), 3.66-3.75 (m, 2H), 3.95 (s, 3H), 4.25-4.30 (m, 1H), 6.80 (d, 1 H, J = 7.0 Hz, D$_2$O exchangeable), 7.03-7.10 (m, 2H). | | A-2 |
| 14 | (structure) CF$_3$CO$_2$H• | A | (DMSO-d6) δ 0.98-1.09 (m, 1H), 1.80-1.89 (m, 1H), 2.05-2.17 (m, 1H), 2.58 (s, 3H), 3.29-3.35 (m, 2H), 3.62-3.70 (m, 2H), 3.87 (s, 3H), 4.29-4.37 (m, 1H), 6.66 (d, 1 H, J = 7.6 H), 6.73-7.07 (br s, 2H), 6.87 (s, 1H), 6.93 (s, 1H). | 436.1 | A-2 |
| 15 | (structure) •CF$_3$CO$_2$H | A | (DMSO-d6) δ 0.98-1.15 (m, 1H), 1.82-1.93 (m, 1H), 2.10-2.25 (m, 1H), 2.59 (s, 3H), 2.80 (s, 3H), 3.28-3.38 (m, 2H), 3.63-3.76 (m, 2H), 3.88 (s, 3H), 4.27-4.34 (m, 1H), 6.62-6.82 (m, 1 H, D$_2$O exchangeable), 6.89 (s, 1H), 6.94 (s, 1H), 7.24-7.46 (br s, 1H, D$_2$O exchangeable). | 450.21 | A-2 |

TABLE I-continued

| | | | | | |
|---|---|---|---|---|---|
| 16 | 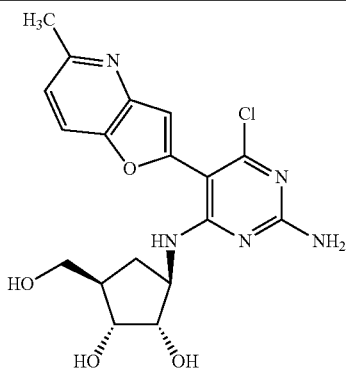 | B | (CD3OD) δ 1.18-1.27 (m, 1H), 2.01-2.10 (m, 1H), 2.30-2.40 (m, 1H), 2.62 (s, 3H), 3.42-3.56 (m, 2H), 3.80-3.89 (m, 2H), 4.38-4.48 (m, 1H), 6.98 (br s, 1H), 7.20 (d, 1H, J = 8.4 Hz), 7.81 (d, 1H, J = 8.8 Hz). | 406.1 | A-2 |
| 17 | 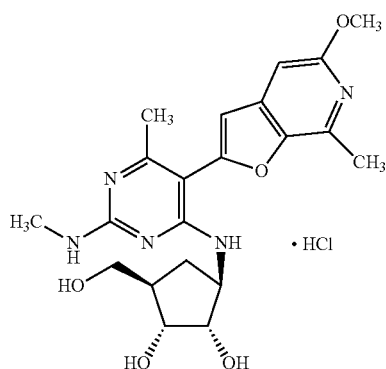 | A | (DMSO-d6) δ 1.05-1.12 (m, 1H), 1.82-1.94 (m, 1H), 2.12 (s, 3H), 2.10-2.28 (m, 1H), 2.56 (s, 3H), 2.80 (d, 3H, J = 4.7 Hz), 3.34-3.39 (m, 2H, coincident with H₂O), 3.64-3.72 (m, 2H), 3.84 (s, 3H), 4.24-4.30 (m, 1H), 4.33-4.36 (m, 1H, D₂O exchangeable), 4.48-4.52 (m, 1H, D₂O exchangeable), 4.55-4.60 (m, 1H, D₂O exchangeable), 6.20-6.31 (br s, 1H, D₂O exchangeable), 6.76 (s, 1H), 6.77 (s, 1H), 6.75-6.88 (br s, 1H, D₂O exchangeable). | 430.2 | A-2 |
| 18 | 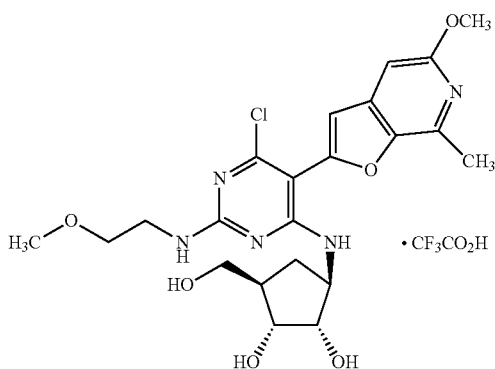 | A | (DMSO-d6) δ 1.02-1.16 (m, 1H), 1.81-1.93 (m, 1H), 2.09-2.25 (m, 1H), 2.58 (s, 3H), 3.27 (s, 3H), 3.31-3.45 (m, 2H), 3.40-3.53 (m, 4H), 3.64-3.77 (m, 2H), 3.88 (s, 3H), 4.24-4.37 (m, 1H), 4.47-4.9 (br s, H2O under which are the hydroxyls), 6.61-6.85 (m, 1H, D₂O exchangeable), 6.88 (s, 1 H), 6.94 (s, 1H), 7.29-7.57 (m, 1H, D₂O exchangeable). | 494.2 | A-2 |
| 19 | 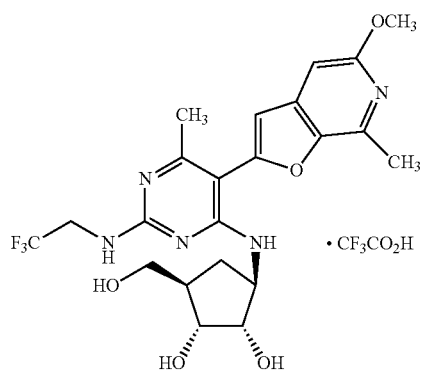 [SMILES: COc1cc2cc(-c3c(C)nc(NCC(F)(F)F)nc3N[C@@H]3C[C@H](CO)[C@@H](O)[C@H]3O)oc2c(C)n1 ; "· CF3CO2H"] | A | (DMSO-d6): δ 1.02-1.18 (m, 1H), 1.81-1.95 (m, 1H), 2.03-2.23 (m, 1H), 2.57 (s, 3H), 3.27-3.42 (m, 2H), 3.61-3.78 (m, 2H), 3.86 (s, 3H), 4.03-4.17 m, 1H), 4.20-4.37 (m, 2H, visible upon D₂O exchange), 6.84 (s, 1H), 6.80-6.95 (m, 1H, D₂O exchangeable), 6.95 (s, 1H), 7.92-8.13 (m, 1H, D₂O exchangeable). | 518.2 | A-2 |

| | | | | | |
|---|---|---|---|---|---|
| 20 | 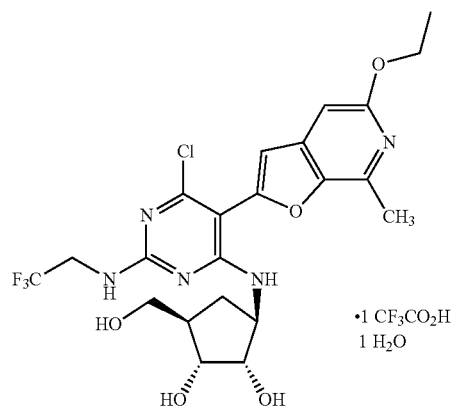 [SMILES: CCOc1cc2cc(-c3c(Cl)nc(NCC(F)(F)F)nc3N[C@@H]3C[C@H](CO)[C@@H](O)[C@H]3O)oc2c(C)n1]
•1 CF$_3$CO$_2$H
1 H$_2$O | | A | (DMSO-d6) δ 1.02-1.17 (m, 1H), 1.32 (t, 3H, J = 6.9 Hz), 1.83-1.94 (m, 1H), 2.07-2.22 (m, 1H), 2.55 (s, 3H), 3.33-3.4 (m, 2H, visible upon D$_2$O exchange), 3.69-3.83 (m, 2H, 2H visible upon D$_2$O exchange), 4.16-4.15 (m, 1H), 4.20-4.31 (m, 2H), 4.28 (q, 2H, J = 7.0 Hz), 6.80 (s, 1H), 6.83-6.93 (m, 1H, D$_2$O exchangeable), 6.93 (s, 1H), 7.92-8.12 (m, 1H, D$_2$O exchangeable). | 532.2 | A-2 |
| 21 | 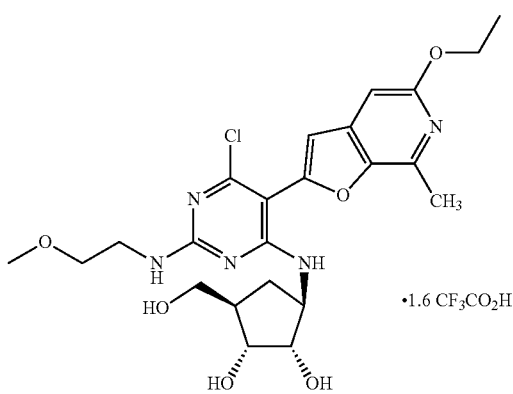 [SMILES: CCOc1cc2cc(-c3c(Cl)nc(NCCOC)nc3N[C@@H]3C[C@H](CO)[C@@H](O)[C@H]3O)oc2c(C)n1]
•1.6 CF$_3$CO$_2$H | | A | (DMSO-d6) δ 1.02-1.16 (m, 1H), 1.33 (t, 3H, J = 7.1 Hz), 1.81-1.93 (m, 1H), 2.09-2.25 (m, 1H), 2.56 (s, 3H), 3.27 (s, 3H), 3.30-3.37 (m, 2H), 3.39-3.50 (m, 4H), 3.64-3.77 (m, 2H), 3.88 (s, 3H), 4.24-4.35 (m, 3H), 4.58-5.6 (hr s, H$_2$O under which are the hydroxyls), 6.60-6.81 (m, 1H, D$_2$O exchangeable), 6.84 (s, 1H), 6.92 (s, 1H), 7.25-7.55 (m, 1H, D$_2$O exchangeable). | 508.2 | A-2 |
| 22 | 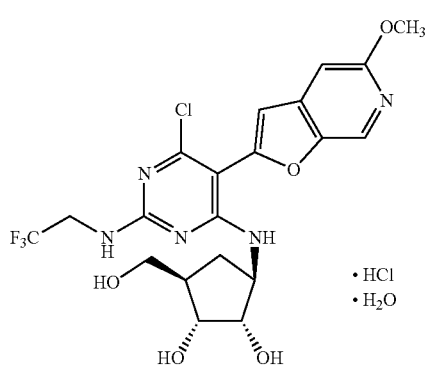 [SMILES: COc1cc2cc(-c3c(Cl)nc(NCC(F)(F)F)nc3N[C@@H]3C[C@H](CO)[C@@H](O)[C@H]3O)oc2cn1]
• HCl
• H$_2$O | | A | (DMSO-d6) δ 1.05-1.18 (m, 1H), 1.84-1.98 (m, 1H), 2.12-2.28 (m, 1H), 3.33-3.43 (m, 2H), 3.63-3.80 (m, 2H), 3.88 (s, 3H), 4.02-4.16 (hr s, 1H), 4.20-4.31 (hr s, 2H), 4.34-4.43 (m, 1H, D$_2$O exchangeable), 4.48-4.56 (m, 2H D$_2$O exchangeable), 6.78-6.90 (m, 1H, D$_2$O exchangeable), 6.97 (s, 1 H), 7.01 (s, 1 H), 7.90-8.12 (m, 1H, D$_2$O exchangeable), 8.49 (s, 1 H). | 504.1 | A-2 |

| | | | | | |
|---|---|---|---|---|---|
| 24 | 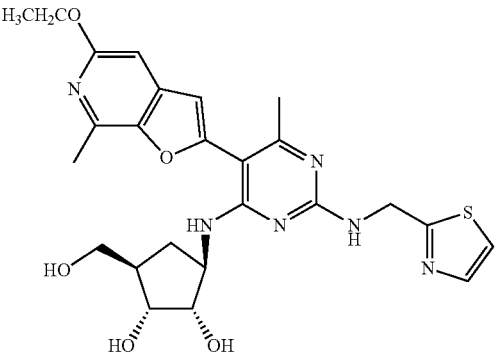 | 0.02 | (DMSO-d6) δ 1.00-1.15 (m, 1H), 1.19-1.34 (m, 1H), 1.35 (t, 3H, J = 7.0 Hz), 1.80-1.98 (m, 2H), 2.31 (br s, 3H), 2.61 (s, 3H), 3.17 (s, 1H), 3.25-3.39 (m, 2H), 3.58-3.69 (m, 1H), 3.76 (app t, 1H, J = 5.9 Hz), 4.28-4.40 (m, 2Hz), 7.02 (s, 1H), 7.13 (s, 1H), 7.70 (d, 1H, J = 3.1 Hz), 7.79 (d, 1H, J = 3.1 Hz) 8.09 (app d, 1H, J = 2.9 Hz), 8.60-8.72 (br s, 1H). | 527.2 | A-2 |
| 25 | 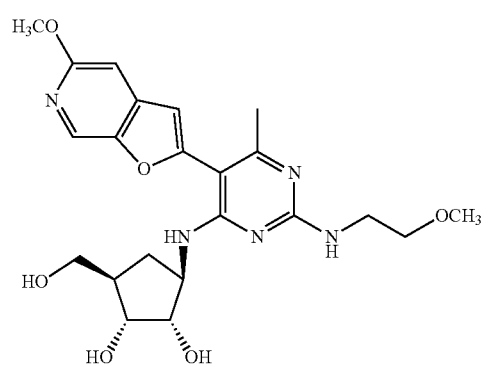 [SMILES: COCCNc1nc(C)c(-c2cc3cc(OC)ncc3o2)c(N[C@@H]2C[C@H](CO)[C@@H](O)[C@H]2O)n1] | 0.8 | (DMSO-d6) δ 1.10-1.26 (m, 1H), 1.84-1.97 (m, 1H), 2.04-2.18 (m, 1H), 2.24 (s, 3H), 3.31 (s, 3H), 3.25-3.39 (m, 2H), 3.49-3.58 (m, 2H), 3.56-3.70 (m, 3H), 3.79 (app t, 1H, J = 5.9 Hz), 3.90 (s, 3H), 4.35-4.49 (m, 1H), 7.11 (s, 1H), 7.13 (s, 1H), 7.91-8.04 (m, 2H), 8.59 (s, 1H), 13.43 (br s, 1H). | 460.2 | A-2 |
| 26 | 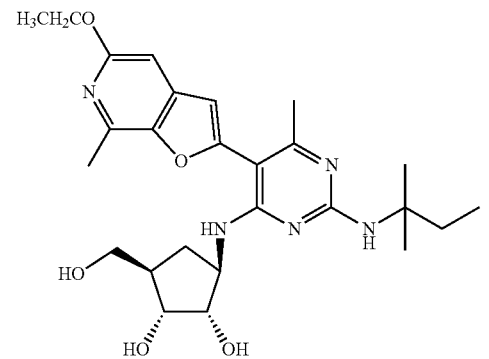 | 0.5 | (DMSO-d6) δ 0.89 (t, 3H, J = 7.4 Hz), 1.11-1.26 (m, 2H), 1.36 (t, 3H, J = 7.0 Hz), 1.41 (s, 6H), 1.82 (app q, 2H, J = 7.6 Hz), 1.84-1.97 (m, 1H), 2.08-2.21 (m, 1H), 2.26 (s, 3H), 2.62 (s, 3H), 3.29-3.40 (m, 2H), 3.69 (app t, 1H, J = 5.0 Hz), 3.81 (app t, 1H, J = 5.6 Hz), 4.28-4.42 (m, 3H), 7.02 (s, 1H), 7.12 (s, 1H), 7.98 (d, 1H, J = 7.8 Hz), 8.01 (s, 1H), 13.37 (br s, 1H). | 500.3 | A-2 |
| 27 | 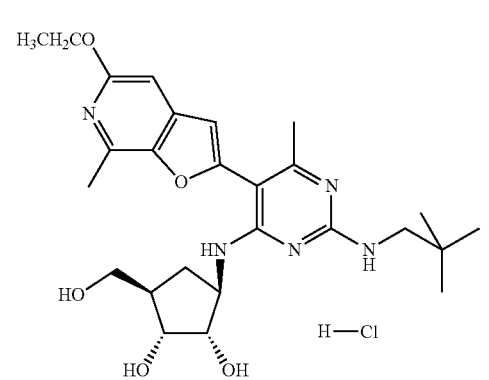 | 0.35 | (DMSO-d6) δ 0.95 (s, 9H), 1.12-1.28 (m, 1H), 1.34 (t, 3H, J = 7.0 Hz), 1.86-1.98 (m, 1H), 2.07-2.20 (m, 1H), 2.27 (s, 3H), 2.59 (s, 3H), 3.24-3.41 (m, 4H), 3.67 (app t, 1H, J = 5.0 Hz), 3.80 (app t, 1H, J = 5.8 Hz), 4.31 (q, 2H, J = 7.0 Hz), 4.30-4.44 (m, 2H), 6.94 (s, 1H), 7.08 (s, 1H), 7.96 (d, 1H, J = 7.3 Hz), 8.18-8.28 (m, 1H), 13.33 (br s, 1H). | 500.3 | A-2 |

TABLE I-continued
| | | | | | |
|---|---|---|---|---|---|
| 28 | 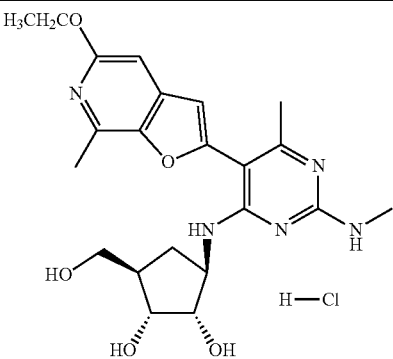 | 0.45 | (DMSO-d6) δ 1.09-1.27 (m, 1H), 1.34 (t, 3H, J = 7.0 Hz), 1.85-1.98 (m, 1H), 2.07-2.20 (m, 1H), 2.27 (s, 3H), 2.60 (s, 3H), 2.97 (d, 3H, J = 4.5 Hz), 3.27-3.41 (m, 2H), 3.67 (app t, 1H, J = 5.0 Hz), 3.80 (app t, 1H, J = 5.8 Hz), 6.96 (s, 1H), 7.08 (s, 1H), 7.78-7.88 (m, 1H), 7.93-8.03 (m, 1H), 13.30 (br s, 1H). | 444.2 | A-2 |
| 29 | 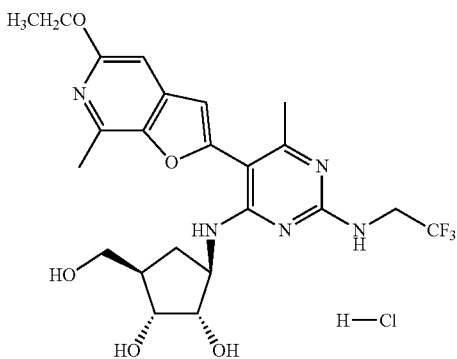 | 0.1 | (DMSO-d6) δ 1.11-1.28 (m, 1H), 1.34 (t, 3H, J = 7.0 Hz), (m, 1H), 2.05-2.20 (m, 1H), 2.31 (s, 3H), 2.60 (s, 3H), 3.27-3.41 (m, 2H), 3.66 (app t, 1H, J = 5.0 Hz), 3.79 (app t, 1H, J = 5.8 Hz), 6.97 (s, 1H), 7.12 (s, 1H), 8.12-8.22 (m, 1H), 8.41-8.54 (m, 1H). | 512.2 | A-2 |
| 30 | 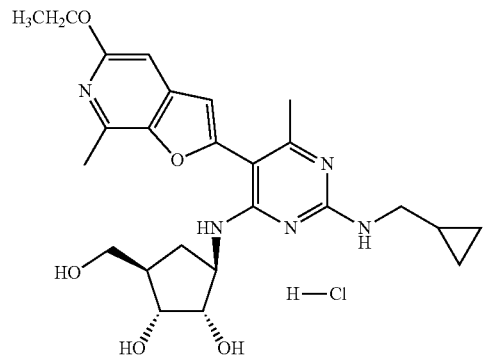 | 0.14 | (DMSO-d6) δ 0.28-0.34 (m, 2H), 0.46-0.55 (m, 2H), 1.08-1.26 (m, 2H), 1.34 (t, 3H, J = 7.0 Hz), 1.85-1.98 (m, 1H), 2.05-2.20 (m, 1H), 2.27 (s, 3H), 2.59 (s, 3H), 3.27-3.40 (m, 5H), 4.31 (q, 3H, J = 7.0 Hz), 4.35-4.48 (m, 1H), 6.96 (s, 1H), 7.08 (s, 1H), 7.93-8.02 (m, 1H), 7.96-8.08 (m, 1H), 13.18 (br s, 1H). | 484.3 | A-2 |
| 31 | 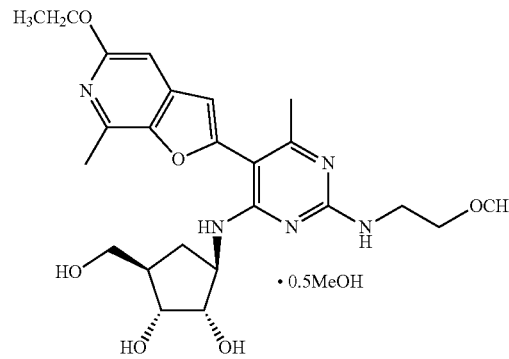 | A | (DMSO-d6) δ 1.10-1.25 (m, 1H), 1.35 (t, 3H, J = 7.0 Hz), 1.84-1.98 (m, 1H), 2.05-2.18 (m, 1H), 2.27 (br s, 3H), 2.60 (s, 3H), 3.17 (s, 1H), 3.25-3.40 (6H), 3.48-3.71 (m, 6H), 3.79 (app t, 1H, J = 5.9 Hz), 4.32 (q, 2H, J = 7.0 Hz), 4.37-4.50 (m, 1H), 6.98 (s, 1H), 7.10 (s, 1H), 7.90-8.07 (m, 2H, D$_2$O exchangeable). | 488.2 | A-3 |

TABLE I-continued

| | | | | | |
|---|---|---|---|---|---|
| 32 | [structure] | 0.95 | (DMSO-d6) δ 1.10-1.25 (m, 1H), 1.23 (d, 3H, J = 2.3 Hz), 1.26 (d, 3H, J = 2.3 Hz), 1.35 (t, 3H, J = 7.0 Hz), 1.85-1.98 (m, 1H), 2.07-2.21 (m, 1H), 2.26 (s, 3H), 2.60 (s, 3H), 3.27-3.40 (m, 2H), 3.68 (app t. 1H, J = 4.9 Hz), 3.82 (app t, 1H, J = 6.0 Hz), 4.10-4.24 (m, 1H), 4.32 (q, 3H, J = 7.0 Hz), 4.32-4.48 (m, 1H), 6.98 (s, 1H), 7.09 (s, 1H), 7.93-8.09 (m, 2H), 13.21 (brs, 1H). | 472.3 | A-2 |
| 33 | [structure] | C | (DMSO-d6) δ 1.13-1.28 (m, 1H), 1.34 (t, 3H, J = 7.0 Hz), 1.86-1.98 (m, 1H), 2.04-2.18 (m, 1H), 2.33 (s, 3H), 2.60 (s, 3H), 3.28-3.40 (m, 2H), 3.69 (app t, 1H, J = 4.9 Hz). 3.82 (app t, 1H, J = 5.9 Hz), 6.96 (s, 1H), 7.13 (s, 1H), 7.19 (t, 1H, J = 7.4 Hz), 7.42 (t, 2H, J = 7.9 Hz), 7.67 (d, 2H, J = 7.6 Hz), 8.21 (app d, 1H, J = 7.6 Hz), 10.52 (s, 1H). | 506.3 | A-2 |
| 34 | [structure] | 0.1 | (DMSO-d6) δ 0.99 (t, 3H, J = 7.4 Hz), 1.12-1.25 (m, 1H), 1.75 (hex, 2H, J = 7.3 Hz), 1.86-1.99 (m, 1H), 2.07-2.20 (m, 1H), 2.31 (s, 3H), 2.60 (s, 3H), 3.28-3.40 (m, 2H), 3.67 (app t, 1H, J = 5.0 Hz), 3.79 (app t, 1H, J = 5.9 Hz), 6.99 (s, 1H), 7.12 (s, 1H), 8.12-8.22 (m, 1H), 8.42-8.54 (m, 1H), 13.63 (br s, 1H). | 526.2 | A-2 |
| 35 | [structure] | 0.1 | (DMSO-d6) δ 0.99) t, 3H, J = 7.4 Hz), 1.12-1.24 (m, 1H), 1.78 (hex, 2H, J = 7.2 Hz), 1.87-1.99 (m, 1H), 2.07-2.30 (m, 1H), 2.28 (s, 3H), 2.60 (s, 3H), 3.31 (s, 3H), 3.28-3.40 (m. 2H), 3.51-3.60 (m, 1H), 3.58-3.66 (m, 1H), 3.68 (app t, 1H, J = 4.8 Hz), 4.24 (app t, 2H, J = 6.4 Hz), 4.38-4.48 (m, 1H), 6.99 (s, 1H), 7.10 (s, 1H), 7.89-8.04 (m, 2H), 13.34 (br s, 1H). | 502.3 | A-2 |

| | | | | | |
|---|---|---|---|---|---|
| 36 | (structure) | 0.01 | (DMSO-d6) δ 1.04-1.14 (m, 1H), 1.34 (t, 3H, J = 7.0 Hz), 1.84-2.01 (m, 1H), 2.28 (s, 3H), 2.59 (s, 3H), 3.31-3.40 (app d, 2H, J = 4.7 Hz), 3.66 (app t, 1H, J = 4.8 Hz), 3.74 (s, 6H), 3.78 (app t, 1H, J = 5.7 Hz), 6.40-6.43 (m, 1H), 6.57 (s, 1H), 6.58 (s, 1H), 6.96 (s, 1H), 7.08 (s, 1H), 7.99 (app d, 1H, J = 7.2 Hz), 8.44-8.53 (m, 1H), 13.39 (br s, 1H). | 580.3 | A-2 |
| 37 | (structure) | 0.3 | (DMSO-d6) δ 1.08-1.24 (m, 1H), 1.30 (s, 3H) 1.32 (s, 3H), 1.85-1.96 (m, 1H), 2.06-2.20 (m 1H), 2.28 (s, 3H), 2.60 (s, 3H), 3.28-3.40 (m, 2H), 3.31 (s, 3H), 3.50-3.58 (m, 2H), 3.58-3.65 (m, 2H), 3.67 (app t, 1H, J = 4.8 Hz), 3.80 (app t, 1H, J = 5.7 Hz), 4.35-3.48 (m, 1H), 5.22 (quint, 1H, J = 6.1 Hz), 6.97 (s, 1H), 7.09 (s, 1H), 7.89-8.04 (m, 2H), 13.35 (br s, 1H). | 502.3 | A-2 |
| 38 | (structure) | 0.25 | (DMSO-d6) δ 0.28-0.35 (m, 2H), 0.47-0.55 (m, 2H), 0.99 (t, 3H, J = 7.4 Hz), 1.06-1.26 (m, 2H), 1.75 (hex, 2H, J = 1.3 Hz), 1.85-1.97 (m, 1H), 2.06-2.20 (m, 1H), 2.27 (s, 3H), 2.60 (s, 3H), 3.28-3.41 (m, 4H), 3.67 (app t, 1H, J = 4.9 Hz), 3.80 (app t, 1H, J = 5.6 Hz), 4.22 (t, 2H, J = 6.7 Hz), 4.36-4.47 (m, 1H), 6.97 (s, 1H), 7.08 (s, 1H), 7.91-8.01 (m, 1H), 8.03-8.12 (m, 1H), 13.30 (br s, 1H). | 498.3 | A-2 |
| 39 | (structure) | 0.1 | (DMSO-d6) δ 0.29-0.36 (m, 2H), 0.48-0.57 (m, 2H), 1.08-1.26 (m, 2H), 1.31 (s, 3H), 1.33 (s, 3H), 1.87-1.99 (m, 1H), 2.07-2.20 (m, 1H), 2.28 (s, 3H), 2.61 (s, 3H), 3.28-3.41 (m, 4H), 3.68 (app t, 1H, J = 4.9 Hz), 3.80 (app t, 1H, J = 5.8 Hz), 5.20 (quint, 1H, J = 6.1 Hz), 6.99 (s, 1H), 7.09 (s, 1H), 7.91-8.01 (m, 1H), 8.04-8.15 (m, 1H), 13.40 (br s, 1H). | 498.3 | A-2 |

TABLE I-continued
| 40 | 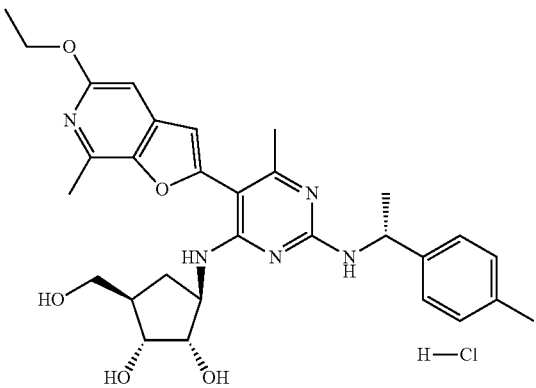 | 0.15 | (DMSO-d6) δ 0.90-1.02 (m, 1H), 1.33 (t, 3H, J = 7.0 Hz), 1.50 (d, 3H, J = 6.9 Hz), 1.60-1.74 (m, 1H), 1.81-1.95 (m, 1H), 2.25 (s, 3H), 2.28 (s, 3H), 2.57 (s, 3H), 3.31 (d, 2H, J = 5.3 Hz), 3.65 (app t, 1H, J = 4.8 Hz), 3.76 (app t, 1H, J = 5.7 Hz), 5.01-5.14 (m, 1H), 6.95 (s, 1H), 7.05 (s, 1H), 7.17 (d, 2H, J = 7.9 Hz), 7.31 (d, 2H, J = 8.0 Hz), 7.98 (app d, 1H, J = 7.6 Hz), 8.63-8.72 (m, 1H), 13.24 (br s, 1H). | 548.3 | A-2 |
|---|---|---|---|---|---|
| 41 | 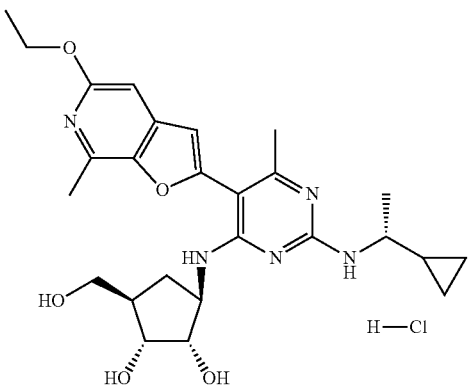 | 0.2 | (DMSO-d6) δ 0.23-0.59 (m, 4H), 0.99-1.13 (m, 1H), 1.12-1.28 (m, 1H), 1.29 (d, 3H, J = 6.6 Hz), 1.34 (t, 3H, J = 7.0 Hz), 1.84-1.97 (m, 1H), 2.02-2.18 (m, 1H), 2.26 (s, 3H), 2.60 (s, 3H), 3.28-3.40 (m, 2H), 3.55-3.67 (m, 1H), 3.66 (app t, 1H, J = 4.9 Hz), 3.79 (app t, 1H, J = 5.9 Hz), 6.96 (s, 1H), 7.08 (s, 1H), 7.90-7.99 (m, 1H), 8.06-8.16 (m, 1H), 13.17 (br s, 1H). | 499.3 | A-2 |
| 42 | 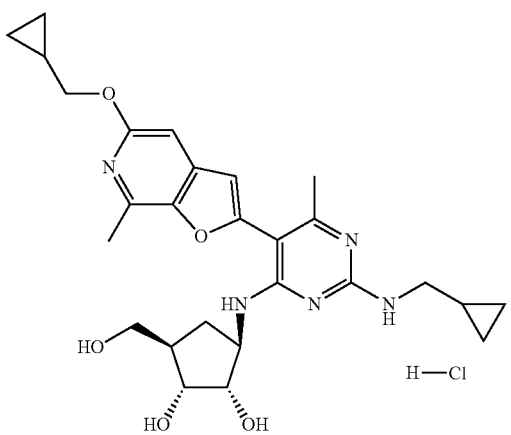 | 0.3 | (DMSO-d6) δ 0.28-0.39 (m, 4H), 0.47-0.61 (m, 4H), 1.08-1.32 (m, 3H), 1.85-1.98 (m, 1H), 2.05-2.20 (m, 1H), 2.27 (s, 3H), 2.59 (s, 3H), 3.28-3.40 (m, 4H), 3.67 (app t, 1H, J = 4.9 Hz), 3.79 (app t, 1H, J = 5.8 Hz), 4.12 (d, 2H, J = 7.0 Hz), 6.98 (s, 1H), 7.09 (s, 1H), 7.92-8.01 (m, 1H), 8.03-8.13 (m, 1H), 13.35 (br s, 1H). | 510.2 | A-2 |
| 43 | 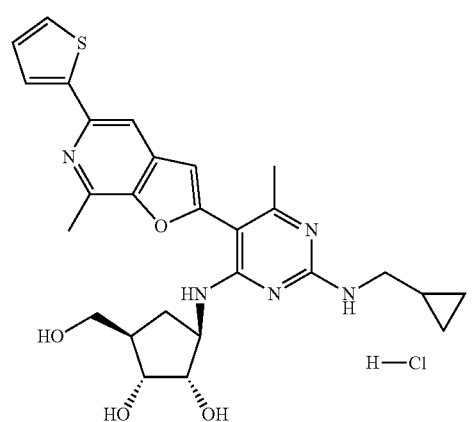 | C | (DMSO-d6) δ 0.29-0.36 (m, 2H), 0.48-0.56 (m, 2H), 1.08-1.30 (m, 2H), 1.86-1.99 (m, 1H), 2.06-2.21 (m, 1H), 2.30 (s, 3H), 2.71 (s, 3H), 3.28-3.41 (m, 4H), 3.68 (app t, 1H, J = 4.9 Hz), 3.80 (app t, 1H, J = 5.9 Hz), 7.15-7.20 (m, 1H), 7.21 (s, 1H), 7.60 (dd, 1H, J = 0.9, 5.1 Hz), 7.78-7.82 (m, 1H), 7.96-8.05 (m, 1H), 8.03-8.13 (m, 2H), 8.10 (s, 1H), 13.31 (br s, 1H). | 522.2 | A-7 |

TABLE I-continued

| | | | | |
|---|---|---|---|---|
| 44 | (structure) | >25 | (DMSO-d$_6$) δ 0.29-0.33 (m, 2H), 0.47-0.53 (m, 2H), 0.91 (t, 6H, J = 7.4 Hz), 1.08-1.40 (m, 2H), 1.59-1.74 (m, 4H), 1.90-2.00 (m, 1H), 2.08-2.18 (m, 1H), 2.27 (s, 3H), 2.59 (s, 3H), 3.27-3.39 (m, 4H), 3.61-3.72 (m, 1H), 4.37-4.44 (m, 1H), 4.90-4.95 (m, 1H), 6.99 (s, 1H), 7.07 (s, 1H), 7.90-8.07 (m, 2H, D$_2$O exchangeable). | A-3, A-4 |
| 45 | (structure) | >25 | (DMSO-d$_6$) δ 0.21-0.22 (m, 2H), 0.39-0.41 (m, 2H), 1.00 (s, 9H), 1.86-1.95 (m, 1H), 2.11 (s, 3H), 3.10-3.19 (m, 2H), 3.61-3.72 (m, 2H), 4.27-4.44 (m, 2H), 4.51-4.52 (m, 2H), 6.10-6.29 (bs, 1H), 6.76 (s, 2H), 6.86-7.04 (m, 3H). | A-3, A-4 |
| 46 | (structure) | 0.85 | (CD$_3$OD) δ 1.03 (s, 9H), 1.22-1.35 (m, 1H), 2.05-2.15 (m, 1H), 2.32 (s, 3H), 2.35-2.46 (m, 1H), 2.65 (s, 3H), 3.40-3.47 (m, 2H), 3.49-3.53 (m, 2H), 3.87-3.89 (m, 2H), 4.56-4.59 (m, 1H), 6.98 (s, 1H), 7.03 (s, 1H). | 555.3 A-3, A-4 |
| 47 | (structure) | 0.4 | (CD$_3$OD) δ 0.35-0.40 (m, 2H), 0.50-0.65 (m, 2H), 1.22-1.35 (m, 1H), 2.05-2.15 (m, 2H), 2.05-2.18 (m, 1H), 2.36 (s, 3H), 2.75 (s, 3H), 3.40-3.57 (m, 4H), 3.89-3.99 (m, 2H), 4.55-4.65 (m, 1H), 7.21 (s, 1H), 7.80 (s, 1H). | 538.2 A-3, A-4 |

TABLE I-continued

| | | | | | |
|---|---|---|---|---|---|
| 48 | [structure] | >25 | (DMSO-d₆) δ 0.91 (t, 6H, J = 7.5 Hz), 1.10-1.20 (m, 1H), 1.59-1.74 (m, 4H), 1.87-2.00 (m, 1H), 2.08-2.18 (m, 1H), 2.26 (s, 3H), 2.58 (s, 3H), 3.30 (s, 3H), 3.50-3.79 (m, 4H), 4.90-4.95 (m, 1H), 6.92 (s, 1H), 7.04 (s, 1H), 7.85-7.99 (m, 2H, D₂O exchangeable). | 530.3 | A-3, A-4 |
| 49 | [structure] | >25 | (DMSO-d₆) δ 1.11 (s, 9H), 1.28-1.36 (m, 1H), 1.10-1.20 (m, 1H), 2.05-2.15 (m, 1H), 2.35 (s, 3H), 2.77 (s, 3H), 3.41 (s, 1H), 3.51 (m, 1H), 3.60-3.65 (m, 3H), 3.71-3.80 (m, 1H), 3.90 (m, 2H), 4.55-4.62 (m, 1H), 7.23 (s, 1H), 7.28 (s, 1H). | | A-3, A-4 |
| 50 | [structure] | 0.05 | (DMSO-d6) δ 1.40.-1.12 (m, 1H), 1.33 (t, 3H, J = 7.0 Hz), 1.90-1.99 (m, 1H), 1.97-2.07 (m, 1H), 2.25 (s, 3H), 3.30-3.40 (m, 2H), 3.67 (t, 1H, J = 5.1 Hz), 3.81 (app t, 1H, J = 6.4 Hz), 4.31 (q, 2H, J = 7.0 Hz), 4.64-4.72 (m, 1H), 4.78-4.85 (m, 1H), 6.93 (s, 1H), 7.05 (s, 1H). 7.10-7.19 (m, 2H), 7.40-7.48 (m, 1H), 8.03 (br d, 1H, J = 7.6 Hz), 8.42 (br s. 1H). | 556.3 | A-2 |
| 51 | [structure] | 0.08 | (DMSO-d6) δ 1.22.-1.29 (m, 1H), 1.34 (t, 3H, J = 7.0 Hz), 1.90-1.99 (m, 1H), 2.10-2.22 (m, 1H), 2.26 (s, 3H), 2.60 (s, 3H), 2.86 (app t, 2, J = 7.2 Hz), 3.55-3.67 (m, 2H), 3.70 app (t, 1H, J = 4.9 Hz), 3.79-3.84 (m, 1H), 3.83 (s, 3H), 4.33 (q, 2H, J = 7.0 Hz), 4.46-4.52 (m, 1H), 6.99 (s, 1H), 7.09 (d, 1H, J = 4.5 Hz), 7.10 (d, 1H, J = 3.9 Hz), 7.27 (dd, 1H, J = 2.0 Hz, 8.4 Hz), 7.26-7.38 (m, 1H). | 598.2 | A-2 |

TABLE I-continued
| | | | | | |
|---|---|---|---|---|---|
| 52 | 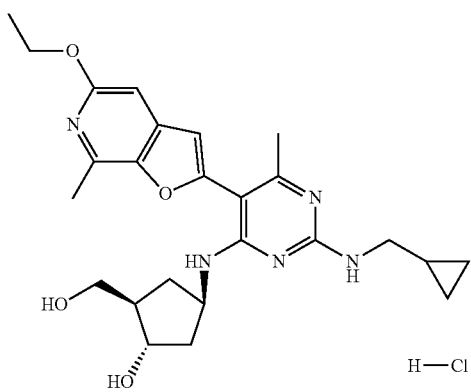 [SMILES: CCOc1cc2cc(-c3c(C)nc(NCC4CC4)nc3N[C@@H]3C[C@H](CO)[C@@H](O)C3)oc2c(C)n1 ; Cl] | 0.3 | 0.28-0.35 (m, 2H), 0.47-0.55 (m, 2H), 1.07-1.20 (m, 1H), 1.34 (t, 3H, J = 7.0 Hz), 1.76-1.91 (m, 3H), 2.08-2.21 (m, 1H), 2.27 (s, 3H), 2.59 (s, 3H), 3.28-3.46 (m, 4H), 3.87-3.95 (m, 1H), 4.32 (q, 2H, J = 7.1 Hz), 6.95 (s, 1H), 7.07 (s, 1H), 7.95-8.04 (m, 1H), 7.99-8.12 (m, 1H), 13.27 (br s, 1H). | 468.2 | A-2 |
| 53 | 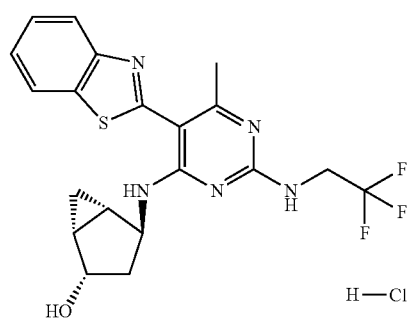 [SMILES: Cc1nc(NCC(F)(F)F)nc(N[C@H]2C[C@H](O)[C@@H]3C[C@@H]32)c1-c1nc2ccccc2s1 ; Cl] | 2.1 | (DMSO-d6) δ 0.42-0.53 (m, 1H), 0.60-0.68 (m, 1H), 1.38-1.50 (m, 2H), 1.50-1.60 (m, 1H), 1.81 (dd, 1H, J = 7.5, 14.5 Hz), 2.58 (s, 3H), 4.28-4.45 (m, 2H), 4.48-4.62 (m, 2H), 7.50-7.68 (m, 2H), 8.09 (d, 1H, J = 7.9 Hz), 8.22 (d, 1H, J = 7.8 Hz), 8.34-8.45 (m, 1H), 10.00 (br s, 1H). | 436.1 | A-5 |
| 54 | 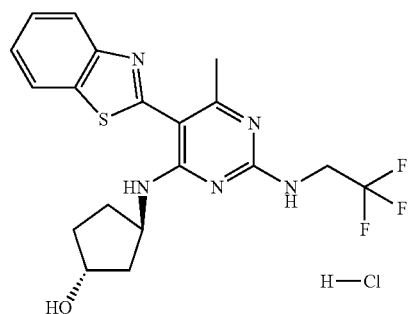 | 1.0 | (DMSO-d6) δ 1.48-1.59 (m, 2H), 1.69-1.77 (m, 1H), 1.83-2.00 (m, 2H), 2.12-2.23 (m, 1H), 2.47 (s, 3H), 4.18-4.25 (m, 2H), 4.35 (q, 1H, J = 9.4 Hz), 4.62-4.73 (m, 1H), 7.52-7.66 (m, 2H), 8.13 (d, 1H, J = 8.0 Hz), 8.21 (d, 1H, J = 8.0 Hz). | 419.2 | A-5 |
| 55 | 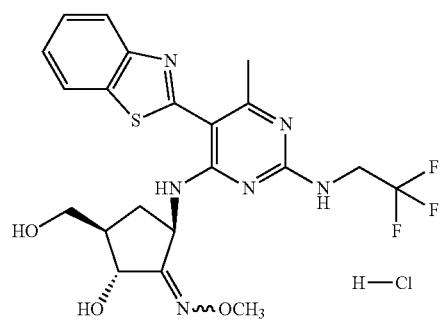 | 3.4 | (DMSO-d6, 2 isomers) δ 1.10-1.25 and 1.40-1.50 (m, 1H), 1.66-1.82 and 1.72-1.85 (m, 1H), 2.36-2.50 (m, 1H), 2.45 and 2.62 (s, 3H), 3.42-3.62 (m, 2H), 3.70 and 3.87 (s, 2H), 4.00-4.48 (m, 3H), 4..50-4.66 (m 1H), 4.80-5.04 (m 1H), 5.20 and 5.26 (d, 1H, J = 6.2 Hz), 7.44 (app t, 1H, J = 7.5 Hz), 7.55 (app t, 1H, J = 8.0 Hz), 7.64-7.92 (m, 1H), 7.92 (m, 1H), 8.12 (d, 1H, J = 7.8 Hz), 9.3, 9.7, and 10.0 (3 br s, 1H). | 4.97 | A-6 |

TABLE I-continued
| 56 | 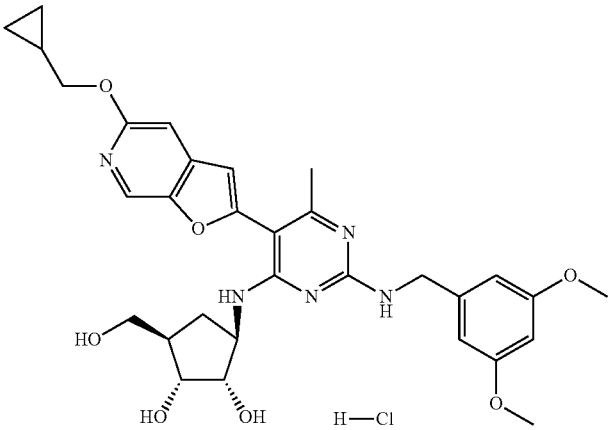 [SMILES: COc1cc(CNc2nc(C)c(-c3cc4cc(OCC5CC5)ncc4o3)c(N[C@@H]3C[C@H](CO)[C@@H](O)[C@H]3O)n2)cc(OC)c1 ; Cl] | 0.06 | (DMSO-d6) δ 0.31-0.39 (m, 2H), 0.59-0.63 (m, 2H), 1.10-1.18 (m, 1H), 1.25-1.31 (m, 1H), 2.00-2.09 (m, 1H), 2.18 (s, 3H), 2.25-2.31 (m, 2H), 3.45-3.55 (m, 2H, CH$_2$), 3.75 (s, 6H, 2 × OCH$_3$), 3.78-3.88 (m, 2H), 4.19 (t, 1H, J = 6.3 Hz), 4.33-4.41 (m, 1H), 4.49-4.62 (m, 1H), 6.33 (t, 1H, J = 2.1 Hz), 6.53 (d, 1H, J = 2.4 Hz), 6.78-6.80 (m, 1H), 6.95-6.99 (m, 1H), 8.30 (s, 1H). | 592.3 | A-3, A-4 |
| 57 | 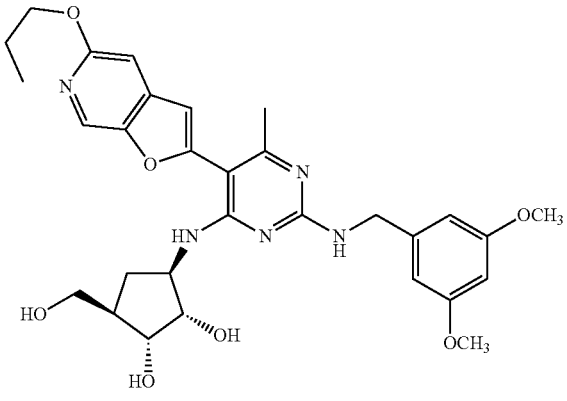 [SMILES: CCCOc1cc2cc(-c3c(C)nc(NCc4cc(OC)cc(OC)c4)nc3N[C@@H]3C[C@H](CO)[C@@H](O)[C@H]3O)oc2cn1] | 0.1 | (DMSO-d6) δ 1.02 (t, 1H, J = 7.2 Hz), 1.10-1.18 (m, 1H), 1.78-1.83 (m, 1H), 2.00-2.09 (m, 1H), 2.19 (s, 3H), 2.24-2.31 (m, 1H), 3.44-3.51 (m, 2H, CH$_2$), 3.75 (s, 6H, 2 × OCH$_3$), 3.78-3.88 (m, 2H), 4.07 (d, 1H, J = 6.9 Hz), 4.37 (q, 1H, J = 6 Hz), 4.49-4.62 (m, 1H), 6.34 (t, 1H, J = 2.1 Hz), 6.55 (d, 1H, J = 2.4 Hz), 6.78-6.80 (m, 1H), 6.95-6.99 (m, 1H), 8.32 (s, 1H). | 488.2 | A-3, A-4 |
| 58 | 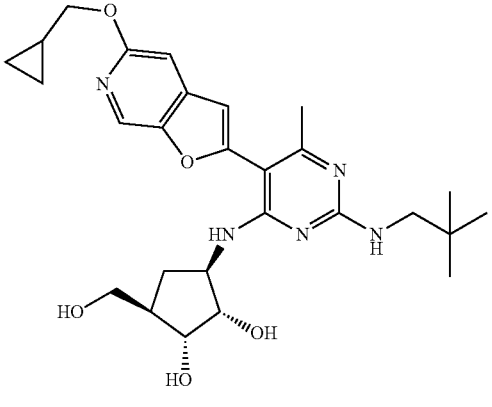 [SMILES: Cc1nc(NCC(C)(C)C)nc(N[C@@H]2C[C@H](CO)[C@@H](O)[C@H]2O)c1-c1cc2cc(OCC3CC3)ncc2o1] | 1.0 | (DMSO-d6) δ 0.50-0.58 (m, 2H), 0.75-0.79 (m, 2H), 1.03 (s, 9H), 1.30-1.45 (m, 2H), 2.00-2.09 (m, 1H), 2.36-2.42 (m, 4H), 3.45-3.55 (m, 4H, CH2), 3.87-3.95 (m, 2H), 4.29-4.35 (m, 2H), 4.59 (bs, 1H), 7.35-7.45 (m, 1H), 7.68-7.75 (m, 1H), 8.86 (s, 1H). | 512.3 | A-3, A-4 |
| 59 | 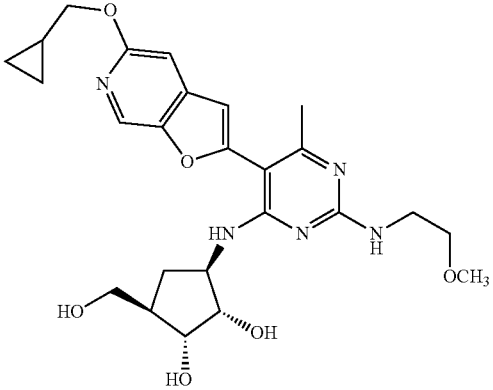 [SMILES: COCCNc1nc(C)c(-c2cc3cc(OCC4CC4)ncc3o2)c(N[C@@H]2C[C@H](CO)[C@@H](O)[C@H]2O)n1] | 2.0 | (DMSO-d6) δ 0.34-0.39 (m, 2H), 0.58-0.62 (m, 2H), 1.20-1.31 (m, 2H), 2.06-3.0 (m, 1H), 2.17 (s, 3H), 2.38-2.42 (m, 1H), 3.50-3.56 (m, 2H, CH$_3$), 3.59-3.62 (m, 2H), 4.09-4.11 (m, 2H), 4.37-4.42 (m, 1H), 6.78-6.8 (m, 1H), 6.95-6.99 (m, 1H), 8.32 (s, 1H). | 500.02 | A-3, A-4 |

TABLE I-continued
| # | Structure | IC50 | NMR | MS | Method |
|---|---|---|---|---|---|
| 60 | 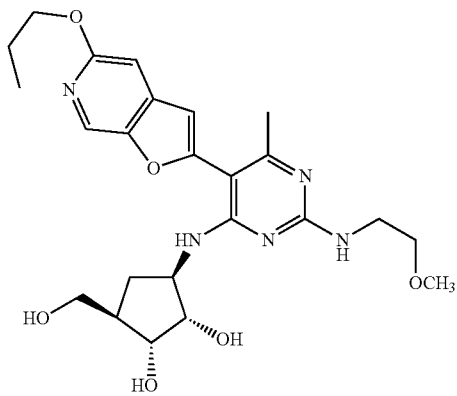 [SMILES: CCCOc1cc2cc(-c3c(C)nc(NCCOC)nc3N[C@@H]3C[C@H](CO)[C@@H](O)[C@H]3O)oc2cn1] | C | (DMSO-d6) δ 1.05 (t, 3H, J = 7.2 Hz), 1.20-1.31 (m, 2H), 2.04-2.1 (m, 1H), 2.17 (s, 3H), 2.35-2.41 (m, 1H), 3.39 (s, 3H), 3.54-3.56 (m, 4H, CH₂), 3.59-3.62 (m, 2H), 4.09-4.11 (m, 2H), 4.37-4.42 (m, 1H), 6.78-6.8 (m, 1H), 6.95-6.99 (m, 1H), 8.32 (s, 1H). | 488.2 | A-3, A-4 |
| 61 | 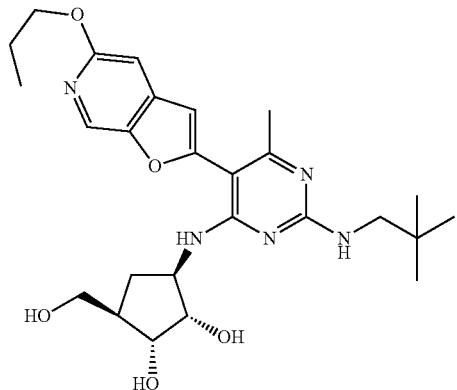 [SMILES: CCCOc1cc2cc(-c3c(C)nc(NCC(C)(C)C)nc3N[C@@H]3C[C@H](CO)[C@@H](O)[C@H]3O)oc2cn1] | >1 | (DMSO-d6) δ 1.03 (s, 9H), 1.12 (t, 3H, J = 7.2 Hz), 1.32-1.38 (m, 2H), 1.89-1.98 (m, 1H), 2.08-2.14 (m, 1H), 2.18 (s, 3H), 2.38-2.44 (m, 1H), 3.29-3.34 (m, 2H), 3.5-3.57 (m, 2H), 3.82-3.91 (m, 2H), 4.19 (t, 3H, J = 6.3 Hz), 4.39-4.42 (m, 1H), 6.78-6.8 (m, 1H), 6.95-6.99 (s, 1H), 8.32 (s, 1H). | 500.2 | A-3, A-4 |
| 62 | 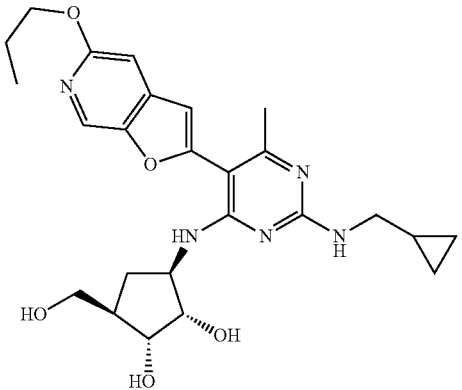 [SMILES: CCCOc1cc2cc(-c3c(C)nc(NCC4CC4)nc3N[C@@H]3C[C@H](CO)[C@@H](O)[C@H]3O)oc2cn1] | 0.7 | (DMSO-d6) δ 0.29-0.30 (m, 2H), 0.48-0.52 (m, 2H), 1.05 (t, 3H, J = 7.2 Hz), 1.20-1.35 (m, 2H), 1.89-1.96 (m, 1H), 2.06-2.10 (m, 1H), 2.32-2.41 (m + s, 4H), 3.41-3.47 (m, 2H, CH₂), 3.49-3.56 (m, 2H), 4.87-4.92 (m, 2H), 4.38 (t, 3H, J = 6.3 Hz), 4.59 (bs, 1H), 7.34 (s, 1H), 7.61 (s, 1H), 8.79 (s, 1H). | 484.5 | A-3, A-4 |
| 63 | 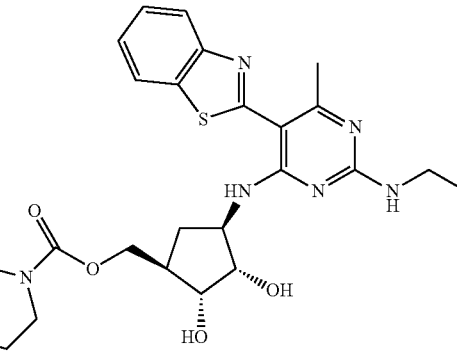 | 0.45 | (DMSO-d6) δ 1.10 1.19 (m, 1H), 2.16-2.20 (m, 1H), 2.37-2.42 (m, 1H), 2.55 (s, 3H), 3.23-3.32 (m, 4H), 3.39-3.48 (m, 4H), 3.73-3.79 (m, 1H), 3.79-3.89 (m, 1H), 3.9-4.08 (m, 1H), 4.19-4.31 (m, 2H), 4.70-4.81 (bs, 2H), 7.40-7.50 (m, 1H), 7.52-7.60 (m, 1H), 7.90-8.05 (m, 1H), 8.12 (t, 3H, J = 7.8 Hz), 9.68 (bs, 1H). | 583.2 | Similar to procedure Z59 with modifications |

| | | | | | |
|---|---|---|---|---|---|
| 64 | 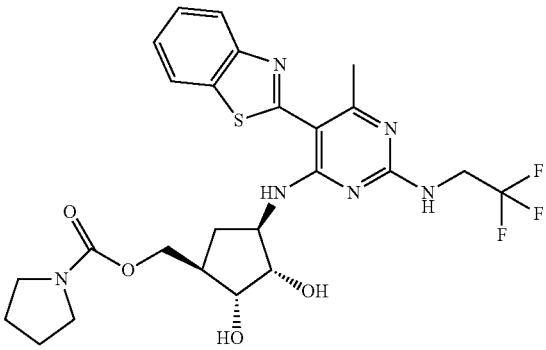 [SMILES: Cc1nc(NCC(F)(F)F)nc(N[C@@H]2C[C@H](COC(=O)N3CCCC3)[C@@H](O)[C@H]2O)c1-c1nc2ccccc2s1] | 0.8 | (DMSO-d6) δ 1.30-1.39 (m, 1H), 1.65-1.78 (m, 4H), 2.30-2.40 (m, 1H), 2.50-2.60 (m, 1H), 2.60 (s, 3H), 3.22-3.34 (m, 4H), 3.95-3.98 (m, 2H), 4.13-4.17 (m, 4H), 4.31 (bs, 1H), 4.42-4.41 (m, 1H), 7.41 (t, 1H, J = 5.7 Hz), 7.52 (t, 1H, J = 5.7 Hz), 7.97 (t, 1H, J = 5.1 Hz), 8.12 (t, 3H, J = 7.8 Hz), 9.68 (bs, 1H). | 567.2 | Similar to procedure Z59 with modifications |
| 65 | 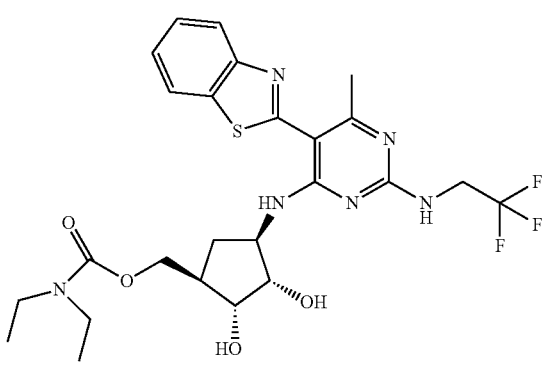 [SMILES: CCN(CC)C(=O)OC[C@H]1C[C@@H](Nc2nc(NCC(F)(F)F)nc(C)c2-c2nc3ccccc3s2)[C@H](O)[C@@H]1O] | 1.0 | (DMSO-d6) δ 1.0-1.06 (m, 6H), 1.27-1.33 (m, 1H), 2.30-2.38 (m, 1H), 2.50-2.54 (m, 1H), 2.57 (s, 3H), 3.15-3.24 (m, 4H), 3.89-3.95 (m, 2H), 4.09-4.19 (m, 2H), 4.28 (bs, 1H), 4.38-4.45 (m, 1H), 7.35-7.39 (m, 1H), 7.45-7.49 (m, 1H), 7.92-7.95 (m, 2H). | 569.2 | Similar to procedure Z59 with modifications |
| 66 | 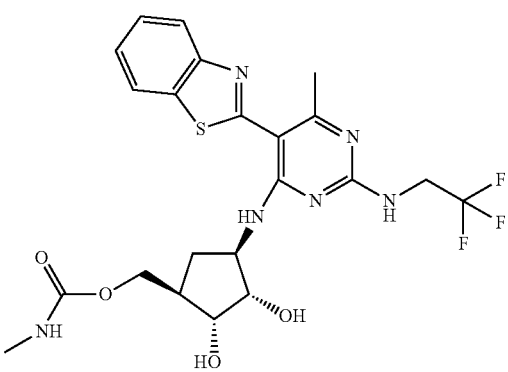 [SMILES: CNC(=O)OC[C@H]1C[C@@H](Nc2nc(NCC(F)(F)F)nc(C)c2-c2nc3ccccc3s2)[C@H](O)[C@@H]1O] | 0.85 | (DMSO-d6) δ 1.25-1.35 (m, 1H), 2.24-2.35 (m, 1H), 2.40-2.50 (m, 1H), 2.63-2.68 (m, 6H), 3.84-3.88 (m, 1H), 3.96-4.0 (m, 1H), 4.02-4.12 (m, 2H), 4.23-4.27 (m, 1H), 4.58-4.64 (m, 1H), 7.52-7.58 (m, 1H), 7.60-7.65 (m, 1H), 8.09-8.16 (m, 2H). | 527.2 | Similar to procedure Z59 with modifications |
| 101 | 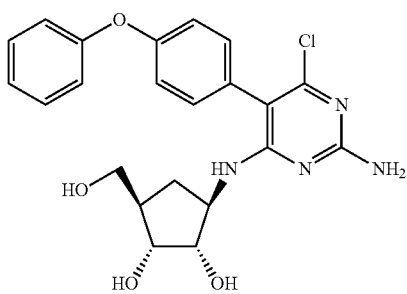 [SMILES: Nc1nc(Cl)c(-c2ccc(Oc3ccccc3)cc2)c(N[C@@H]2C[C@H](CO)[C@@H](O)[C@H]2O)n1] | C | — | 443.2 | A |

TABLE I-continued
| | | | | | |
|---|---|---|---|---|---|
| 102 | 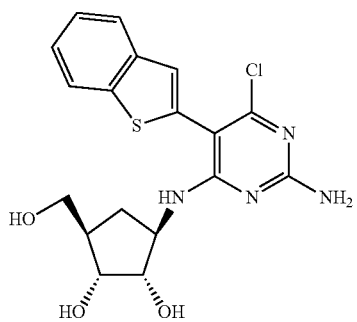 [SMILES: Nc1nc(Cl)c(-c2cc3ccccc3s2)c(N[C@@H]2C[C@H](CO)[C@@H](O)[C@H]2O)n1] | C | — | 407.2 | B |
| 103 | 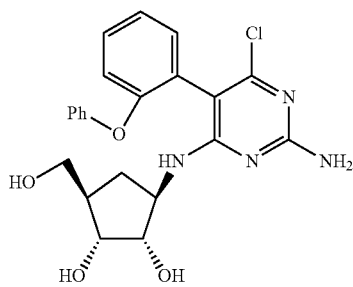 [SMILES: Nc1nc(Cl)c(-c2ccccc2Oc2ccccc2)c(N[C@@H]2C[C@H](CO)[C@@H](O)[C@H]2O)n1] | C | — | 443.2 | B |
| 104 | 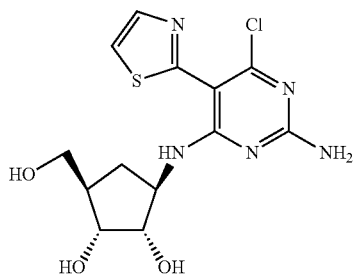 | C | — | 358.2 | C |
| 105 | 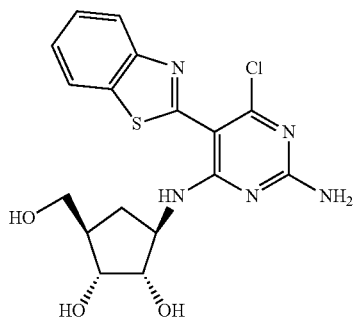 [SMILES: Nc1nc(Cl)c(-c2nc3ccccc3s2)c(N[C@@H]2C[C@H](CO)[C@@H](O)[C@H]2O)n1] | A | 1H NMR (CD$_3$OD + DMSO-d$_6$, 3 drops) δ 1.38-1.45 (m, 1H), 2.14-2.20 (m, 1H), 2.47-2.55 (m, 1H), 3.62-3.70 (m, 2H), 3.92-3.96 (m, 2H), 4.44-4.51 (m, 1H), 7.43 (t, 1H, J = 8.1 Hz), 7.52 (t, 1H, J = 8.5 Hz), 8.00 (t, 2H, J = 8.5 Hz), 10.66 (d, 1H, J = 5.5 Hz). | 408.2 | C |
| 106 | 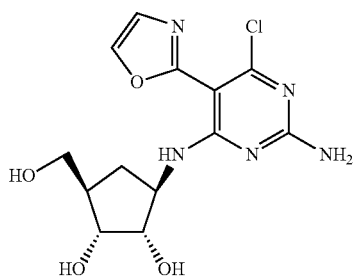 [SMILES: Nc1nc(Cl)c(-c2ncco2)c(N[C@@H]2C[C@H](CO)[C@@H](O)[C@H]2O)n1] | C | — | 342.2 | C |

TABLE I-continued
| | | | | | |
|---|---|---|---|---|---|
| 107 | 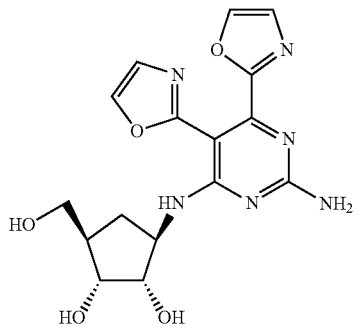 [SMILES: Nc1nc(N[C@@H]2C[C@H](CO)[C@@H](O)[C@H]2O)c(-c2ncco2)c(-c2ncco2)n1] | C | — | 375.2 | C |
| 108 | 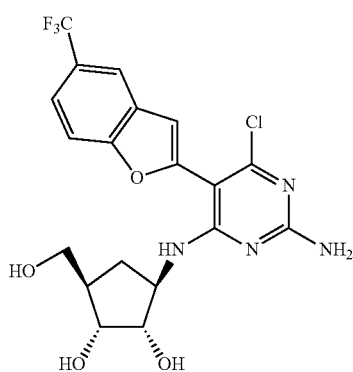 [SMILES: Nc1nc(Cl)c(-c2cc3cc(C(F)(F)F)ccc3o2)c(N[C@@H]2C[C@H](CO)[C@@H](O)[C@H]2O)n1] | C | 1H NMR (CD₃OD) δ 1.17-1.24 (m, 1H), 2.01-2.09 (m, 1H), 2.3l-2.39 (m, 1H), 3.49-3.51 (m, 2H), 3.80 (t, 1H, J = 5.2 Hz), 3.85 (t, 1H, J = 5.1 Hz), 4.37-4.42 (m, 1H), 7.05 (s, 1H), 7.60 (d, 1H, J = 8.9 Hz), 7.68 (d, 1H, J = 8.7 Hz), 7.98 (s, 1H). | — | C |
| 109 | 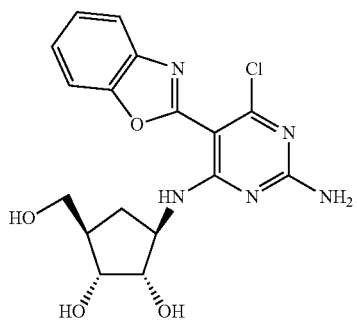 [SMILES: Nc1nc(Cl)c(-c2nc3ccccc3o2)c(N[C@@H]2C[C@H](CO)[C@@H](O)[C@H]2O)n1] | A | 1H NMR (CD₃OD) δ 1.34-1.41 (m, 1H), 2.11-2.20 (m, 1H), 2.44-2.52 (m, 1H), 3.61-3.69 (m, 2H), 3.89-3.94 (m, 2H), 4.43-4.50 (m, 1H), 7.35-7.40 (m, 2H), 7.60-7.64 (m, 1H), 7.68-7.72 (m, 1H), 9.45 (d, 1H, J = 6.4 Hz). | — | C |
| 110 | 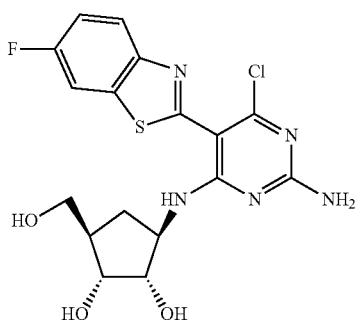 [SMILES: Nc1nc(Cl)c(-c2nc3ccc(F)cc3s2)c(N[C@@H]2C[C@H](CO)[C@@H](O)[C@H]2O)n1] | B | 1H NMR (CD₃OD + DMSO-d6, 3 drops) δ 1.37-1.4 (m, 1H), 2.12-2.19 (m, 1H), 2.46-2.54 (m, 1H), 3.62-3.68 (br. s, 2H), 3.92-3.96 (br. s, 2H), 4.30-4.50 (m, 1H), 7.27-731 (m, 1H), 7.75-7.79 (m, 1H), 7.98-8.02 (m, 1H), 10.52-10.54 (m, 1H). | 426.2 | E |

TABLE I-continued
| | | | | | |
|---|---|---|---|---|---|
| 111 | 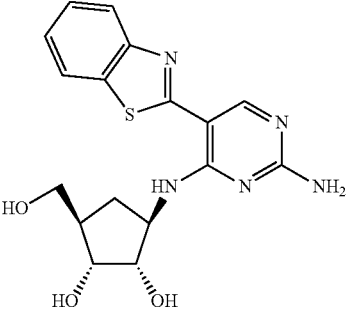 [SMILES: Nc1ncc(-c2nc3ccccc3s2)c(N[C@@H]2C[C@H](CO)[C@@H](O)[C@H]2O)n1] | A | — | 476.3 | Prepared via hydrogenation of 105 (H₂, 20% Pd(OH)₂, MeOH/ AcOH, 50 psi). |
| 112 | 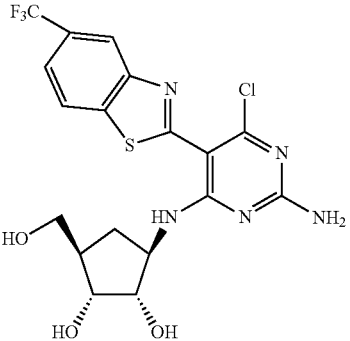 [SMILES: Nc1nc(Cl)c(-c2nc3cc(C(F)(F)F)ccc3s2)c(N[C@@H]2C[C@H](CO)[C@@H](O)[C@H]2O)n1] | B | — | 476.3 | J |
| 113 | 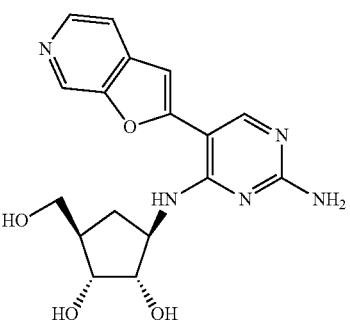 [SMILES: Nc1ncc(-c2cc3ccncc3o2)c(N[C@@H]2C[C@H](CO)[C@@H](O)[C@H]2O)n1] | B | — | 358.2 | Prepared via hydrogenation of 4 (H2, 10% Pd/C, MeOH/ THF). |
| 114 | 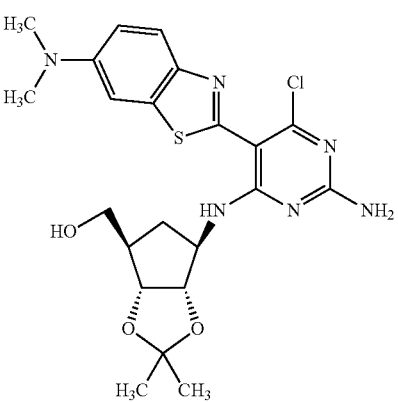 [SMILES: CN(C)c1ccc2nc(-c3c(Cl)nc(N)nc3N[C@@H]3C[C@H](CO)[C@H]4OC(C)(C)O[C@H]43)sc2c1] | — | 1H NMR(CDCl3) δ 1.34 (s, 3H), 1.51 (s, 3H), 1.71-1.75 (m, 1H), 2.41-2.45 (m, 1H), 2.53-2.60 (m, 1H), 3.04 (s, 6H), 3.78-3.82 (m, 2H), 4.51-4.56 (m, 1H), 4.58-4.62 (m, 2H), 5.12 (s, 2H), 6.95 (dd, 1H, J = 9.6, 2.5 Hz), 7.09 (d, 1H, J = 2.1 Hz), 7.79 (d, 1H, J = 8.7 Hz), 10.44 (d, 1H, J = 6.4 Hz). | 491.3 | F |

| 115 | 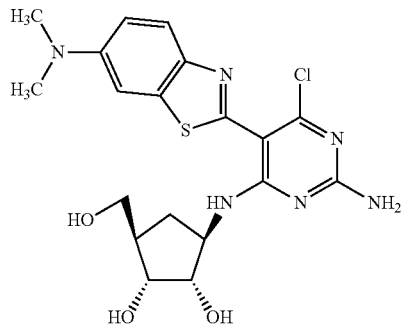 [SMILES: CN(C)c1ccc2nc(-c3c(Cl)nc(N)nc3N[C@@H]3C[C@H](CO)[C@@H](O)[C@H]3O)sc2c1] | C | — | 451.2 | F |
| 116 | 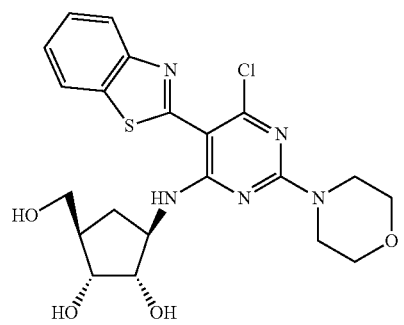 [SMILES: OC[C@H]1C[C@@H](Nc2nc(N3CCOCC3)nc(Cl)c2-c2nc3ccccc3s2)[C@H](O)[C@@H]1O] | B | 1H NMR (DMSO-d$_6$) δ 1.21-1.32 (m, 1H), 1.96-2.01 (m, 1H), 2.32-2.39 (m, 1H), 3.40-3.48 (m, 2H), 3.66-3.84 (m, 10H), 4.30-4.35 (m, 1H), 4.51 (d, 1H, J = 5.1 Hz), 4.66 (t, 1H, J = 5.1 Hz), 4.73 (d, 1H, J = 6.0 Hz), 7.43 (t, 1H, J = 7.4 Hz), 7.53 (t, 1H, J = 7.7 Hz), 8.02 (d, 1H, J = 8.0 Hz), 8.10 (d, 1H, J = 8.1 Hz), 10.51 (d, 1H, J = 6.6 Hz). | 478.3 | H |
| 117 | 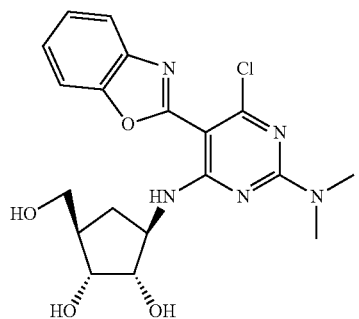 [SMILES: CN(C)c1nc(Cl)c(-c2nc3ccccc3o2)c(N[C@@H]2C[C@H](CO)[C@@H](O)[C@H]2O)n1] | B |  | 420.2 | C |
| 118 | 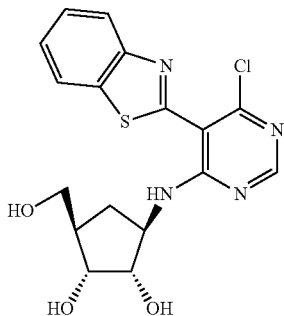 [SMILES: OC[C@H]1C[C@@H](Nc2ncnc(Cl)c2-c2nc3ccccc3s2)[C@H](O)[C@@H]1O] | C |  | 393.2 | H (Step 4) |

TABLE I-continued
| | | | | | |
|---|---|---|---|---|---|
| 119 | 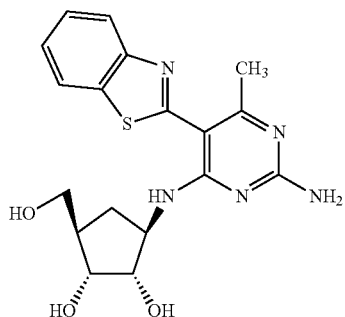 [SMILES: Cc1nc(N)nc(N[C@@H]2C[C@H](CO)[C@@H](O)[C@H]2O)c1-c1nc2ccccc2s1] | A | | 388.2 | I |
| 120 | 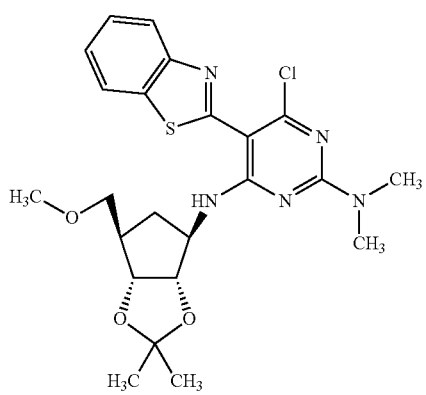 | C | 1H NMR(CDC₃) δ 1.31 (s, 3H), 1.52 (s, 3H), 1.71-1.77 (m, 1H), 2.45-2.51 (m, 1H), 2.52-2.59 (m, 1H), 3.23 (s, 6H), 3.29 (s, 3H), 3.51 (d, 2H, J = 5.7 Hz), 4.49-4.55 (m, 2H), 4.63-4.65 (m, 1H), 7.34 (t, 1H, J = 8.2 Hz), 7.45 (t, 1H, J = 7.7 Hz), 7.86 (d, 1H, J = 7.4 Hz), 7.92 (d, 1H, J = 8.1), 10.61 (d, 1H, J = 6.1 Hz). | 490.3 | G |
| 121 | 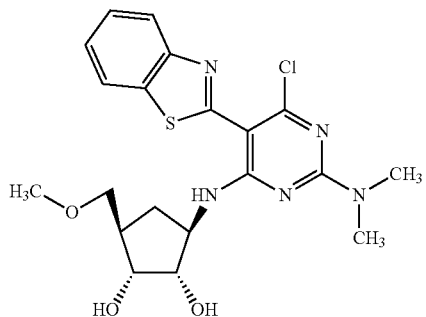 | A | — | 450.2 | G (Step 7) (Obtained from 120) |
| 122 | 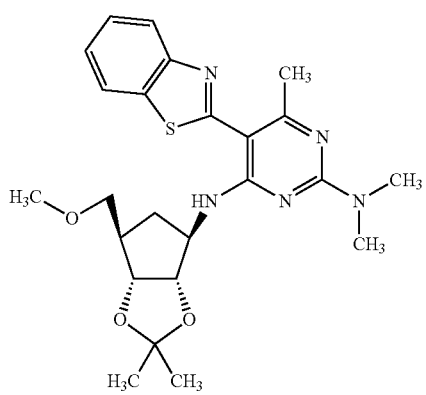 | — | 1H NMR (CDCl₃) δ 1.30 (s, 3H), 1.52 (s, 3H), 1.66-1.73 (m, 1H), 2.42-2.47 (m, 1H), 2.50-2.58 (m, 1H), 2.69 (s, 3H), 3.24 (s, 9H), 3.48 (d, 2H, J = 6.6 Hz), 4.50-4.55 (m, 2H), 4.63-4.65 (m, 1H), 7.33 (t, 1H, J = 7.7 Hz), 7.45 (t, 1H, J = 7.7 Hz), 7.85 (d, 1H, J = 8.2 Hz), 7.94 (d, 1H, J = 8.1 Hz), 9.62 (d, 1H, J = 6.0 Hz). | 470.12 | I |

TABLE I-continued
| 123 | 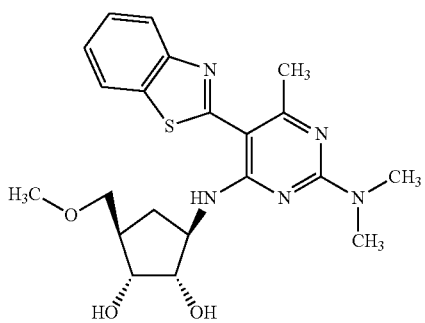 | C | — | 430.2 | G (Step 7) (Obtained from 122) |
| --- | --- | --- | --- | --- | --- |
| 124 | 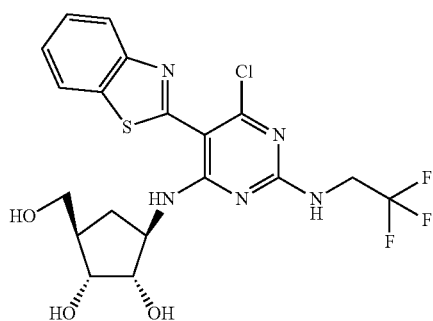 [SMILES: OC[C@H]1C[C@@H](Nc2nc(NCC(F)(F)F)nc(Cl)c2-c2nc3ccccc3s2)[C@H](O)[C@@H]1O] | A | 1H NMR (DMSO-$d_6$) δ 1.20-1.29 (m, 1H), 1.93-2.01 (m, 1H), 2.31-2.39 (m, 1H), 3.39-3.48 (m, 2H), 3.75 (q, 1H, J = 10.2, 5.1 Hz), 3.79-3.83 (m, 1H), 4.05-4.16 (m, 1H), 4.23-4.40 (m, 2H), 4.53 (d, 1H, J = 5.2 Hz), 4.64 (t, 1H, J = 5.1 Hz), 4.69 (d, 1H, J = 5.2 Hz), 7.45 (t, 1H, J = 7.3 Hz), 7.54 (t, 1H, J = 7.3 Hz), 8.03 (d, 1H, J = 8.1 Hz), 8.11 (d, 1H, J = 8.0 Hz), 8.28-8.32 (m, 1H), 10.53 (d, 1H, J = 5.8 Hz). | 490.3 | H |
| 125 | 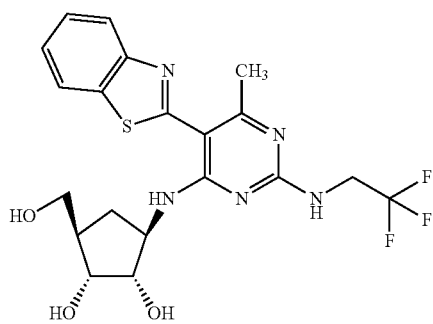 [SMILES: Cc1nc(NCC(F)(F)F)nc(N[C@@H]2C[C@H](CO)[C@@H](O)[C@H]2O)c1-c1nc2ccccc2s1] | A | 1H NMR (DMSO-$d_6$) δ 1.13-1.25 (m, 1H), 1.93-2.01 (m, 1H), 2.28-2.37 (m, 1H), 2.55 (s, 3H), 3.37-3.49 (m, 2H), 3.71-3.79 (m, 2H), 4.06-4.17 (m, 1H), 4.19-4.32 (m, 2H), 4.42-4.50 (m, 1H), 4.58-4.61 (m, 2H), 7.43 (t, 1H, J = 7.2 Hz), 7.54 (t, 1H, J = 7.7 Hz), 7.61 and 7.62-7.79 (br. s and m, 1H) 8.02 (d, 1H, J = 8.1 Hz), 8.11 (d, 1H, J = 7.8 Hz), 9.33 and 9.59-9.65 (br. s and m, 1H) | 470.3 | I |
| 126 |  | A | 1H NMR (DMSO-$d_6$) δ 1.12-1.29 (m, 1H), 1.89-2.01 (m, 3H), 2.31-2.42 (m, 1H), 3.36-3.50 (m, 4H), 3.76-3.82 (m, 2H), 4.27-4.33 (m, 1H), 4.45-4.51 (m, 2H), 4.56-4.68 (m, 3H), REDO this proton, 7.52 (t, 1H, J = 7.5 Hz), 7.80-7.86 (br. s, 1H), 7.99 (d, 1H, J = 8.3 Hz), 8.08 (d, 1H, J = 7.2 Hz), 10.59 (d, 1H, J = 5.7 Hz). | 468.3 | H |

TABLE I-continued
| | | | | | |
|---|---|---|---|---|---|
| 127 | 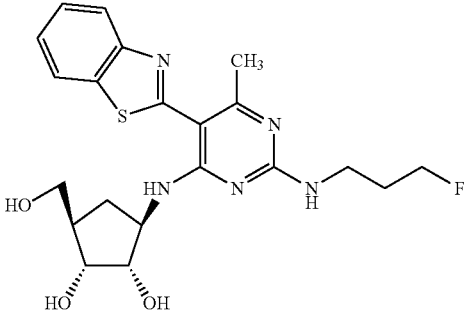 [SMILES: Cc1nc(NCCCF)nc(N[C@@H]2C[C@H](CO)[C@@H](O)[C@H]2O)c1-c1nc2ccccc2s1] | 0.7 | 1H NMR (DMSO-d$_6$) δ 1.14-1.25 (m, 1H), 1.88-1.98 (m, 3H), 2.30-2.38 (m, 1H), 2.55 (s, 3H), 3.38-3.46 (m, 4H), 3.71-3.78 (m, 2H), 4.27-4.33 (m, 1H), 4.45-4.65 (m, 5H), 7.26-7.30 (br. s, 1H), 7.39 (t, 1H, J = 7.5 Hz), 7.50 (t, 1H, J = 7.7 Hz), 7.97 (d, 1H, J = 8.0 Hz), 8.07 (d, 1H, J = 8.3 Hz), 9.78-9.80 (br. s, 1H). | 448.2 | I |
| 151 | 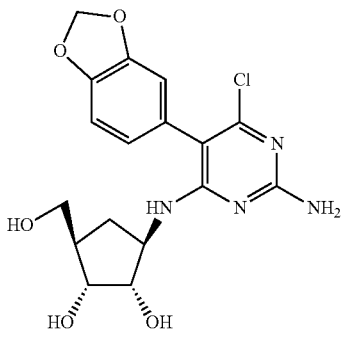 [SMILES: Nc1nc(Cl)c(-c2ccc3c(c2)OCO3)c(N[C@@H]2C[C@H](CO)[C@@H](O)[C@H]2O)n1] | C | | 395.2 | A |
| 152 | 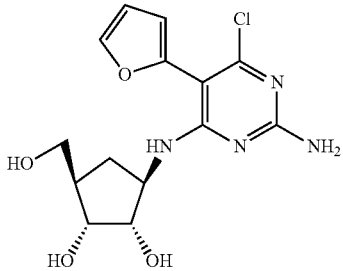 [SMILES: Nc1nc(Cl)c(-c2ccco2)c(N[C@@H]2C[C@H](CO)[C@@H](O)[C@H]2O)n1] | C | | 341.2 | B |
| 153 | 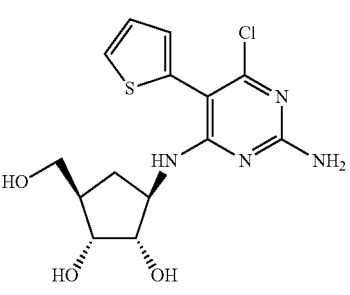 [SMILES: Nc1nc(Cl)c(-c2cccs2)c(N[C@@H]2C[C@H](CO)[C@@H](O)[C@H]2O)n1] | C | | 357.2 | B |
| 154 | 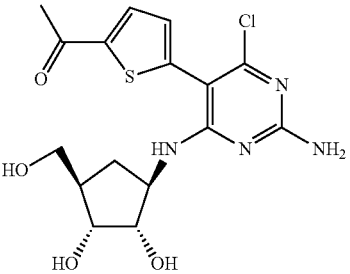 [SMILES: CC(=O)c1ccc(-c2c(Cl)nc(N)nc2N[C@@H]2C[C@H](CO)[C@@H](O)[C@H]2O)s1] | C | | 399.2 | B |

TABLE I-continued

| | | | | |
|---|---|---|---|---|
| 155 | (structure) | C | 385.2 | B |
| 156 | (structure) | C | 369.2 | B |
| 157 | (structure) | C | 352.2 | C |
| 158 | (structure) | C | 437.2 | C |
| 159 | (structure) | C | 353.2 | C |

TABLE I-continued

| | | | | |
|---|---|---|---|---|
| 160 | (structure) | C | NA | C |
| 161 | (structure) | C | 358.2 | C |
| 162 | (structure) | C | 395.2 | C |
| 163 | (structure) | C | 358.2 | C |
| 164 | (structure) | C | 409.2 | D |

TABLE I-continued
| | | | | |
|---|---|---|---|---|
| 165 | 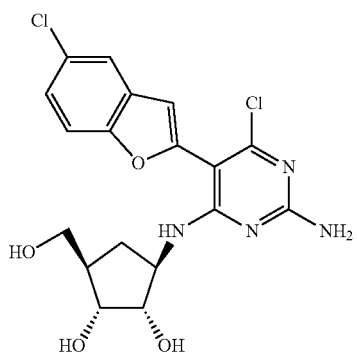 [SMILES: Nc1nc(Cl)c(-c2cc3cc(Cl)ccc3o2)c(N[C@@H]2C[C@H](CO)[C@@H](O)[C@H]2O)n1] | C | 425.2 | D |
| 166 | 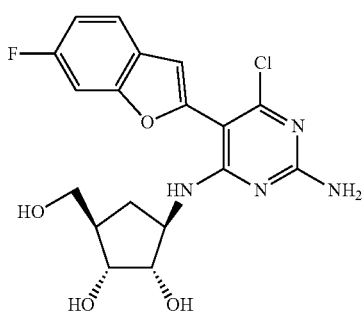 [SMILES: Nc1nc(Cl)c(-c2cc3ccc(F)cc3o2)c(N[C@@H]2C[C@H](CO)[C@@H](O)[C@H]2O)n1] | B | 462.3 | D |
| 167 | 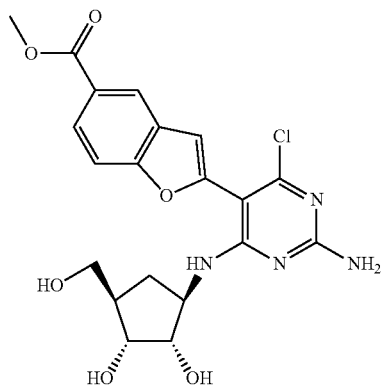 [SMILES: COC(=O)c1ccc2oc(-c3c(Cl)nc(N)nc3N[C@@H]3C[C@H](CO)[C@@H](O)[C@H]3O)cc2c1] | C | 409.2 | D |
| 168 | 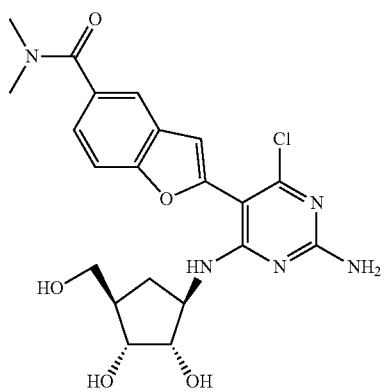 [SMILES: CN(C)C(=O)c1ccc2oc(-c3c(Cl)nc(N)nc3N[C@@H]3C[C@H](CO)[C@@H](O)[C@H]3O)cc2c1] | C | 462.3 | D |

TABLE I-continued
| 169 | 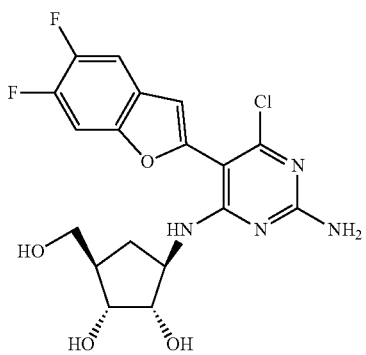 [SMILES: Nc1nc(Cl)c(-c2cc3cc(F)c(F)cc3o2)c(N[C@@H]2C[C@H](CO)[C@@H](O)[C@H]2O)n1] | C | 427.2 | D |
| 170 | 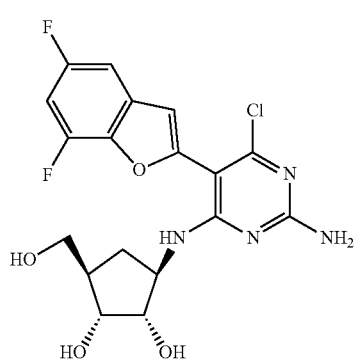 [SMILES: Nc1nc(Cl)c(-c2cc3cc(F)cc(F)c3o2)c(N[C@@H]2C[C@H](CO)[C@@H](O)[C@H]2O)n1] | C | 427.2 | D |
| 171 | 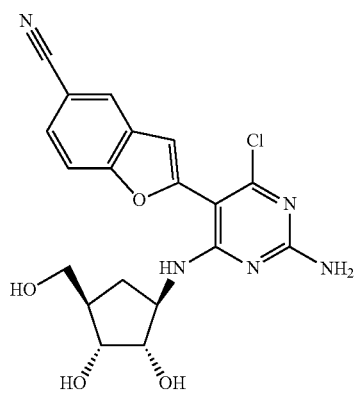 [SMILES: N#Cc1ccc2oc(-c3c(Cl)nc(N)nc3N[C@@H]3C[C@H](CO)[C@@H](O)[C@H]3O)cc2c1] | C | 416.2 | D |
| 172 | 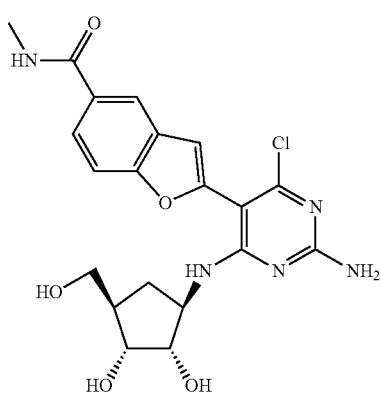 [SMILES: CNC(=O)c1ccc2oc(-c3c(Cl)nc(N)nc3N[C@@H]3C[C@H](CO)[C@@H](O)[C@H]3O)cc2c1] | C | 448.2 | D |

TABLE I-continued
| | | | | |
|---|---|---|---|---|
| 173 | 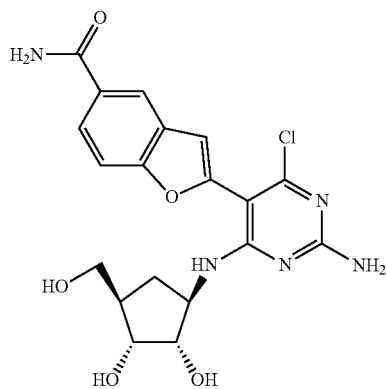 [SMILES: NC(=O)c1ccc2oc(-c3c(Cl)nc(N)nc3N[C@@H]3C[C@H](CO)[C@@H](O)[C@H]3O)cc2c1] | C | 434.2 | D |
| 174 | 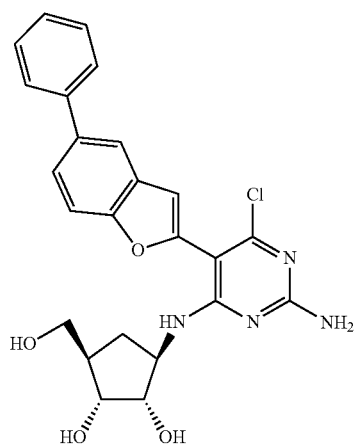 [SMILES: Nc1nc(Cl)c(-c2cc3cc(-c4ccccc4)ccc3o2)c(N[C@@H]2C[C@H](CO)[C@@H](O)[C@H]2O)n1] | C | 467.3 | D |
| 175 | 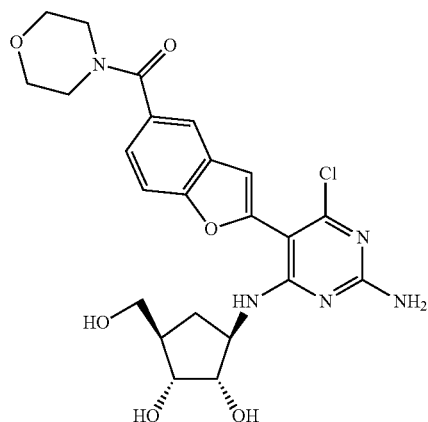 [SMILES: Nc1nc(Cl)c(-c2cc3cc(C(=O)N4CCOCC4)ccc3o2)c(N[C@@H]2C[C@H](CO)[C@@H](O)[C@H]2O)n1] | C | 504.3 | D |
| 176 | 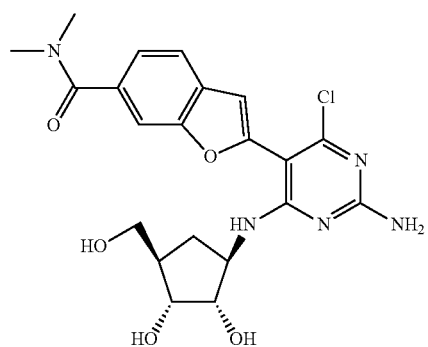 [SMILES: CN(C)C(=O)c1ccc2cc(-c3c(Cl)nc(N)nc3N[C@@H]3C[C@H](CO)[C@@H](O)[C@H]3O)oc2c1] | C | 461.99 | D |

TABLE I-continued
| | | | | |
|---|---|---|---|---|
| 177 | 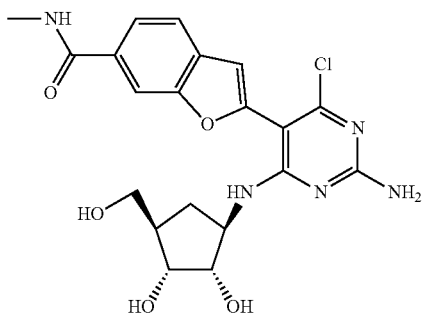 [SMILES: CNC(=O)c1ccc2cc(-c3c(Cl)nc(N)nc3N[C@@H]3C[C@H](CO)[C@@H](O)[C@H]3O)oc2c1] | C | NA | D |
| 178 | 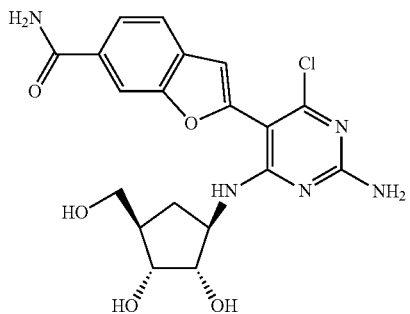 [SMILES: NC(=O)c1ccc2cc(-c3c(Cl)nc(N)nc3N[C@@H]3C[C@H](CO)[C@@H](O)[C@H]3O)oc2c1] | C | 433.95 | D |
| 179 | 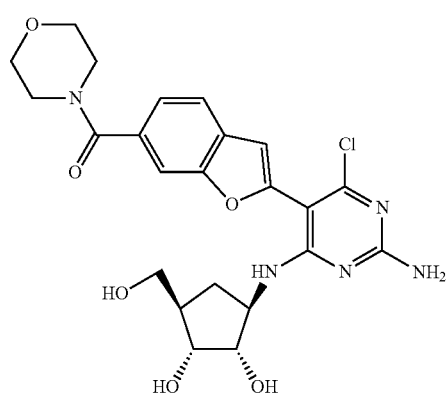 [SMILES: Nc1nc(Cl)c(-c2cc3ccc(C(=O)N4CCOCC4)cc3o2)c(N[C@@H]2C[C@H](CO)[C@@H](O)[C@H]2O)n1] | C | 504.3 | D |
| 180 | 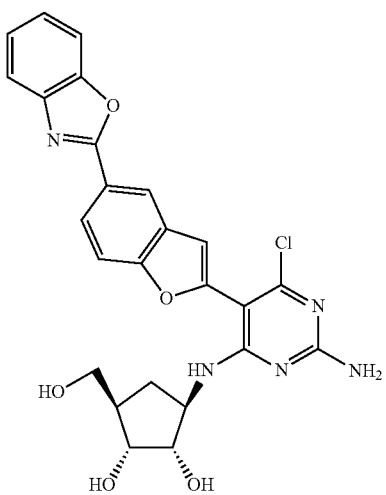 [SMILES: Nc1nc(Cl)c(-c2cc3cc(-c4nc5ccccc5o4)ccc3o2)c(N[C@@H]2C[C@H](CO)[C@@H](O)[C@H]2O)n1] | C | 508.3 | D |

TABLE I-continued
| | | | | | |
|---|---|---|---|---|---|
| 181 | 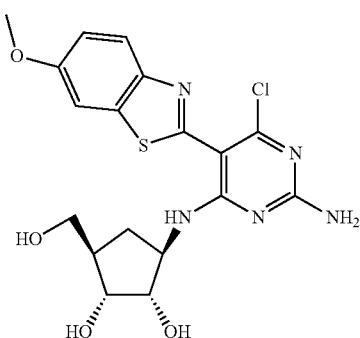 [SMILES: COc1ccc2nc(-c3c(Cl)nc(N)nc3N[C@@H]3C[C@H](CO)[C@@H](O)[C@H]3O)sc2c1] | A | | 438.2 | E |
| 182 | 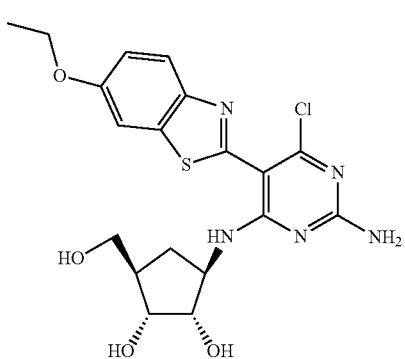 [SMILES: CCOc1ccc2nc(-c3c(Cl)nc(N)nc3N[C@@H]3C[C@H](CO)[C@@H](O)[C@H]3O)sc2c1] | A | | 452.2 | E |
| 183 | 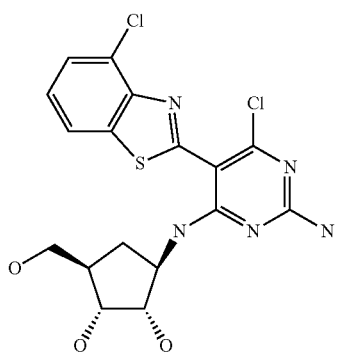 [SMILES: Nc1nc(Cl)c(-c2nc3c(Cl)cccc3s2)c(N[C@@H]2C[C@H](CO)[C@@H](O)[C@H]2O)n1] | B | 1H NMR (CD3OD) δ 1.10-1.20 (,, 31H), 2.01-2.09 (m, 1H), 2.22-2.34 (m, 1H), 3.47-3.60 (m, 2H), 3.69-3.77 (m, 2H), 3.85 (s, 2H), 4.20-4.29 (m, 1H), 6.63-6.67 (m, 1H), 6.70-6.73 (m, 1H), 6.75-6.79 (m, 1H). | 442.2 | E |
| 184 | 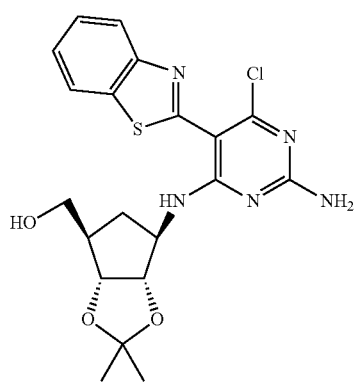 [SMILES: CC1(C)O[C@@H]2[C@@H](CO)C[C@@H](Nc3nc(N)nc(Cl)c3-c3nc4ccccc4s3)[C@@H]2O1] | A | 1H NMR (CD3OD + DMSO-d6, 3 drops) δ 1.33 (s, 3H), 1.50 (s, 3H) 1.67-1.77 (m, 1H), 2.31-2.42 (m, 1H), 2.48-2.58 (m, 1H), 2.61-2.64 (m, 1H), 3.68-3.73 (m, 2H), 4.46-4.54 (m, 1H), 4.60-4.64 (m, 2H), 7.41 (t, 1 H, J = 7.7 Hz), 7.51 (t, 1 H, J = 7.3 Hz), 7.97 (d, 1 H, J = 8.0 Hz), 10.57 (d, 1 H, J = 5.9 Hz). | 448.2 | Prepared from 105 using Procedure F, Step 1. |

| | | | | | |
|---|---|---|---|---|---|
| 185 | 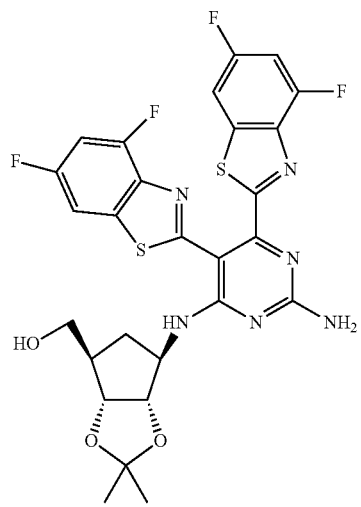 [SMILES: CC1(C)O[C@@H]2[C@@H](CO)C[C@@H](Nc3nc(N)nc(-c4nc5c(F)cc(F)cc5s4)c3-c3nc4c(F)cc(F)cc4s3)[C@@H]2O1] | C | | 619.3 | F |
| 186 | 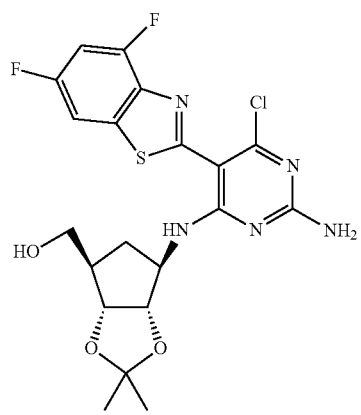 [SMILES: CC1(C)O[C@@H]2[C@@H](CO)C[C@@H](Nc3nc(N)nc(Cl)c3-c3nc4c(F)cc(F)cc4s3)[C@@H]2O1] | B | | 484.6 | F |
| 187 | 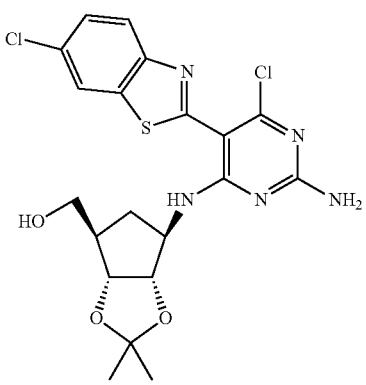 [SMILES: CC1(C)O[C@@H]2[C@@H](CO)C[C@@H](Nc3nc(N)nc(Cl)c3-c3nc4ccc(Cl)cc4s3)[C@@H]2O1] | C | 1H NMR (CDCl3) δ 1.33 (s, 3H), 1.54 (s, 3H), 1.70-1.78 (m, 1H), 2.40-2.47 (m, 1H), 2.52-2.64 (m, 1H), 3.78-3.83 (m, 1H), 4.51-4.64 (m, 2H), 5.19-5.25 (m, 1H), 7.40-7.45 (m, 1H), 7.83-7.91 (m, 2H), 10.55-10.62 (m, 1H). | 615.3 | F |
| 188 | 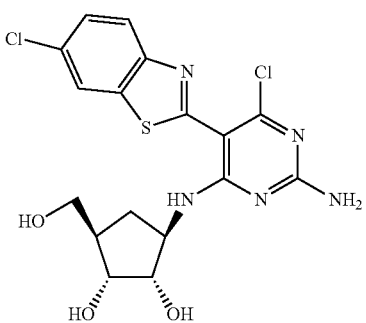 [SMILES: Nc1nc(Cl)c(-c2nc3ccc(Cl)cc3s2)c(N[C@@H]2C[C@H](CO)[C@@H](O)[C@H]2O)n1] | C | 1H NMR (CD3OD + DMSO-d6, 3 drops) δ 1.40-1.53 (m, 1H), 2.17-2.25 (m, 1H), 2.48-2.61 (m, 1H), 3.51-3.56 (m, 2H), 3.65-3.73 (m, 2H), 3.96-4.03 (m, 1H), 4.49-4.57 (m, 1H), 7.43 (t, 1 H, J = 8.1 Hz), 7.56-7.63 (m, 1 H), 8.05-8.09 (m, 1H), 8.14-8.16 (m, 1H). | 442.2 | F |

TABLE I-continued
| 189 | 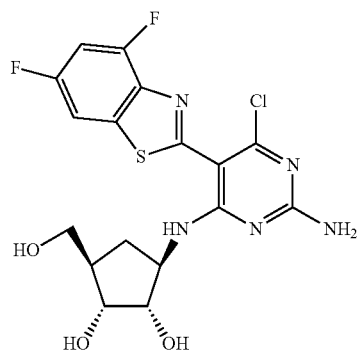 [SMILES: Nc1nc(Cl)c(-c2nc3c(F)cc(F)cc3s2)c(N[C@@H]2C[C@H](CO)[C@@H](O)[C@H]2O)n1] | B | 1H NMR (CD3OD + DMSO-d6, 3 drops) δ 1.28-1.41 (m, 1H), 2.11-2.22 (m, 1H), 2.45-2.57 (m, 1H), 3.55-3.69 (m, 2H), 3.87-3.96 (m, 2H), 4.45-4.53 (m, 1H), 7.23-7.31 (m, 1 H), 7.68-7.74 (m, 1 H). | 444.2 | F |
| 190 | 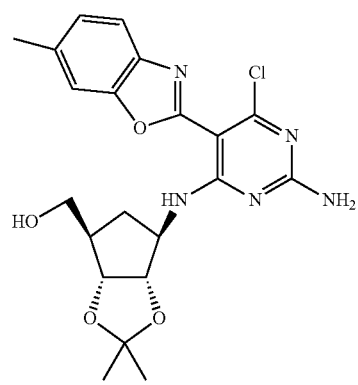 [SMILES: Cc1ccc2nc(-c3c(Cl)nc(N)nc3N[C@@H]3C[C@H](CO)[C@H]4OC(C)(C)O[C@H]43)oc2c1] | C | | 446.2 | F |
| 191 | 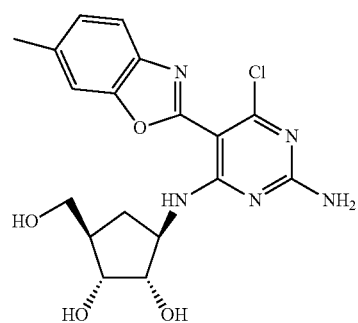 [SMILES: Cc1ccc2nc(-c3c(Cl)nc(N)nc3N[C@@H]3C[C@H](CO)[C@@H](O)[C@H]3O)oc2c1] | B | 1H NMR (CD3OD + DMS0-d6, 3 drops) 51.43-1.51 (m, 1H), 2.17-2.54 (m, 1H), 2.48-2.61 (m, 4H), 3.67-3.70 (m, 2H), 3.96-4.06 (m, 2H), 4.52-4.61 (m, 1H), 7.33-7.39 (m, 1 H), 7.59-7.66 (m, 1 H), 7.70-7.76 (m, 1H). | 406.2 | F |
| 192 | 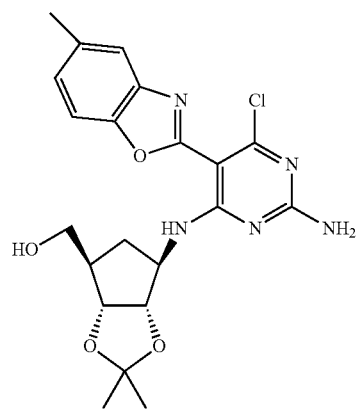 [SMILES: Cc1ccc2oc(-c3c(Cl)nc(N)nc3N[C@@H]3C[C@H](CO)[C@H]4OC(C)(C)O[C@H]43)nc2c1] | C | | 446.2 | F |

TABLE I-continued
| 193 | 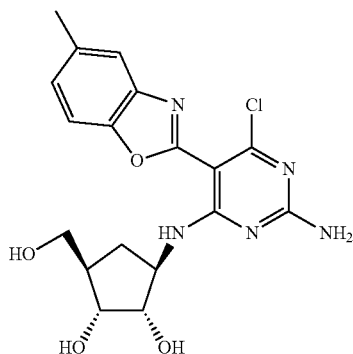 [SMILES: Cc1ccc2oc(-c3c(Cl)nc(N)nc3N[C@@H]3C[C@H](CO)[C@@H](O)[C@H]3O)nc2c1] | C | 1H NMR (CD3OD) δ 1.29-1.37 (m, 1H), 2.04-2.13 (m, 1H), 2.36-2.46 (m, 4H), 3.51-3.58 (m, 2H), 3.81-3.93 (m, 2H), 4.39-4.66 (m, 2H), 7.18-7.24 (mm 1H), 7.46-7.55 (mm 1H). | 406.2 | F |
|---|---|---|---|---|---|
| 194 | 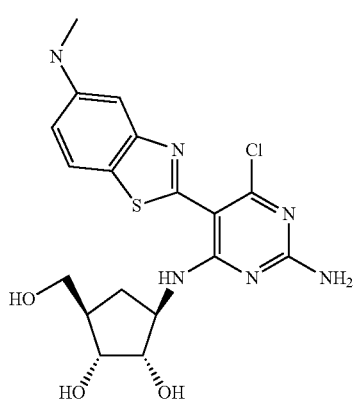 [SMILES: CNc1ccc2sc(-c3c(Cl)nc(N)nc3N[C@@H]3C[C@H](CO)[C@@H](O)[C@H]3O)nc2c1] | A | 1H NMR (CD3OD + DMSO-d6, 3 drops) δ 1.41-1.51 (m, 1H), 2.15-2.24 (m, 1H), 2.49-2.58 (m, 1H), 3.18 (s, 3H), 3.65-3.71 (m, 2H), 3.94-4.01 (m, 2H), 4.47-4.55 (m, 1H), 7.54-7.61 (m, 1H), 7.65-7.71 (m, 1 H), 8.17-8.19 (m, 1 H), 8.24 (d, 1H, J = 9.0 Hz). | 437.2 | F |
| 195 | 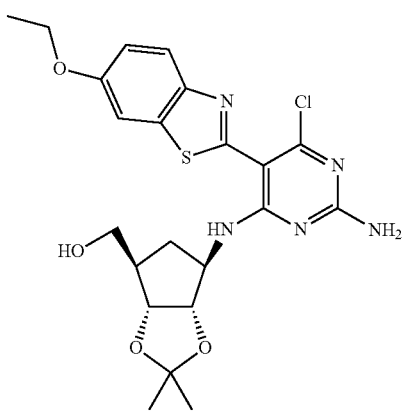 [SMILES: CCOc1ccc2nc(-c3c(Cl)nc(N)nc3N[C@@H]3C[C@H](CO)[C@H]4OC(C)(C)O[C@H]43)sc2c1] | A |  | 492.3 | E |
| 196 | 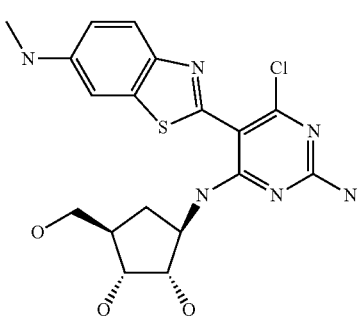 [SMILES: CNc1ccc2nc(-c3c(Cl)nc(N)nc3N[C@@H]3C[C@H](CO)[C@@H](O)[C@H]3O)sc2c1] | A | 1H NMR (CD3OD + DMSO-d6, 3 drops) δ 1.37-1.48 (m, 1H), 2.11-2.20 (m, 1H), 2.44-2.54 (m, 1H), 3.09-3.16 (m, 3H), 3.52-3.74 (m, 4H), 3.89-4.11 (m, 2H), 4.42-4.51 (m, 1H), 7.47-7.52 (m, 1H), 7.98-8.03 (m, 1 H), 8.10-8.15 (m, 1 H). | 437.2 | F |

TABLE I-continued
| | | | | | |
|---|---|---|---|---|---|
| 197 | 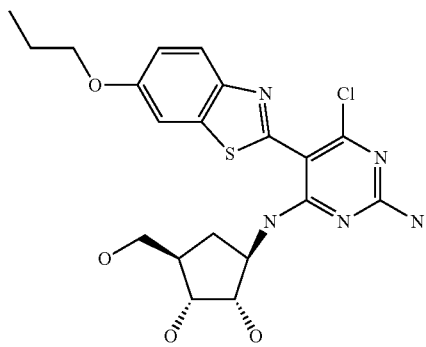 [SMILES: CCCOc1ccc2nc(-c3c(Cl)nc(N)nc3N[C@@H]3C[C@H](CO)[C@@H](O)[C@H]3O)sc2c1] | A | 1H NMR(CDCl3) δ 1.07 (t, 3H, J = 7.3 Hz), 1.25 (s, 1H), 1.32 (s, 3H), 1.53 (s, 1H), 1.69-1.78 (m, 1H), 1.81-1.90 (m, 2H), 2.38-2.48 (m, 1H), 2.51-2.61 (m, 1H), 3.75-3.86 (m, 1H), 3.99 (t, 1H, J = 6.6 Hz), 4.50-4.55 (m, 1H), 4.58-4.64 (m, 1H), 5.22 (s, 1H), 7.04-7.10 (m, 1H), 7.31-7.34 (m, 1 H), 7.84 (d, 1H, J = 8.9 Hz), 10.50 (d, 1H, J = 6.4 Hz). | 466.3 | F |
| 198 | 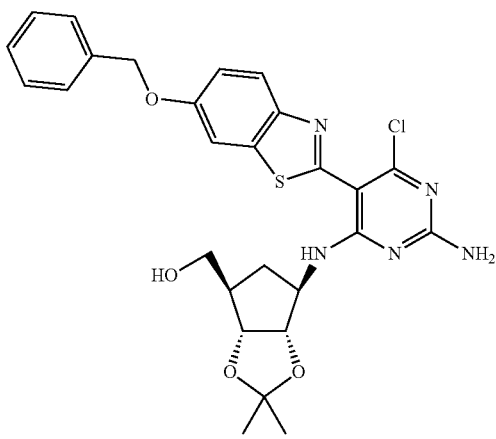 [SMILES: CC1(C)O[C@@H]2[C@@H](CO)C[C@@H](Nc3nc(N)nc(Cl)c3-c3nc4ccc(OCc5ccccc5)cc4s3)[C@@H]2O1] | C | 1H NMR (CDCl3) δ 1.32 (s, 3H), 1.52 (s, 3H), 1.69-1.80 (m, 1H), 2.38-2.48 (m, 1H), 2.51-2.61 (m, 1H), 3.76-3.84 (m, 1H), 4.52-4.56 (m, 1H), 4.58-4.65 (m, 1H), 5.14-5.19 (m, 2H), 7.12-7.17 (m, 1H), 7.35-7.39 (m, 1 H), 7.39-7.50 (m, 1H), 7.83-7.89 (m, 1H), 10.49-10.54 (m, 1H). | 554.3 | F |
| 199 | 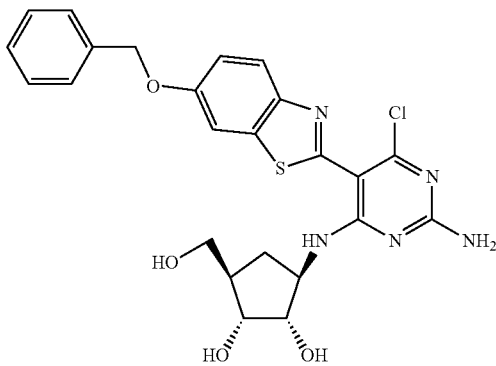 [SMILES: Nc1nc(Cl)c(-c2nc3ccc(OCc4ccccc4)cc3s2)c(N[C@@H]2C[C@H](CO)[C@@H](O)[C@H]2O)n1] | C | | 514.3 | F |
| 200 | 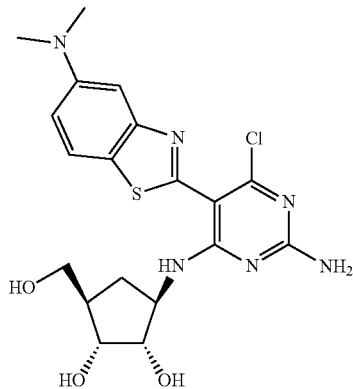 [SMILES: CN(C)c1ccc2sc(-c3c(Cl)nc(N)nc3N[C@@H]3C[C@H](CO)[C@@H](O)[C@H]3O)nc2c1] | A | | 451.2 | F (from starting material 403a) |

TABLE I-continued
| | | | | | |
|---|---|---|---|---|---|
| 201 | 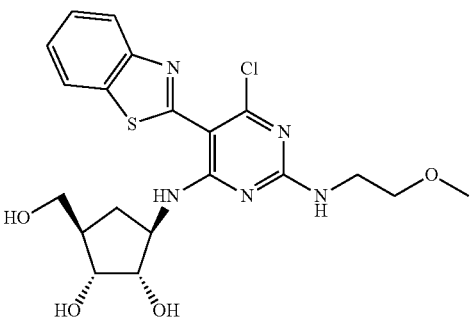 [SMILES: COCCNc1nc(Cl)c(-c2nc3ccccc3s2)c(N[C@@H]2C[C@H](CO)[C@@H](O)[C@H]2O)n1] | A | | 466.3 | H |
| 202 | 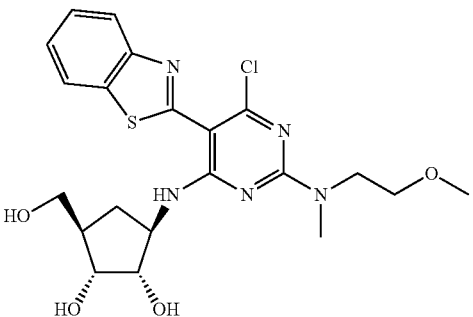 [SMILES: COCCN(C)c1nc(Cl)c(-c2nc3ccccc3s2)c(N[C@@H]2C[C@H](CO)[C@@H](O)[C@H]2O)n1] | B | | 480.3 | H |
| 203 | 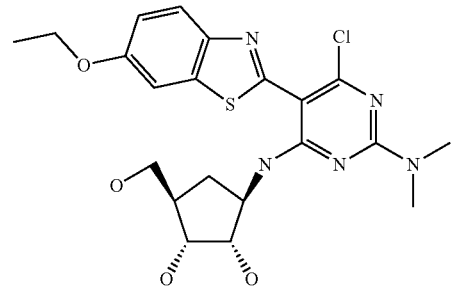 [SMILES: CCOc1ccc2nc(-c3c(Cl)nc(N(C)C)nc3N[C@@H]3C[C@H](CO)[C@@H](O)[C@H]3O)sc2c1] | C | 1.36-1.50 (m, 4H), 2.13-2.24 (m, 1H), 2.52-2.63 (m, 1H), 3.23 (s, 3H), 3.61-3.72 (m, 2H), 3.92-4.01 (m, 2H), 4.11-4.19 (m, 2H), 4.37-4.12 (m, 1H), 4.43-4.52 (m, 1H), 7.09-7.15 (m, 1H), 7.15-7.53 (m, 1 H), 7.52 (t, 1 H, J = 8.5 Hz), 7.90 (6, 1 H, J = 8.8 Hz), 10.57 (d, 1 H, J = 6.8 Hz). | 480.3 | E |
| 204 | 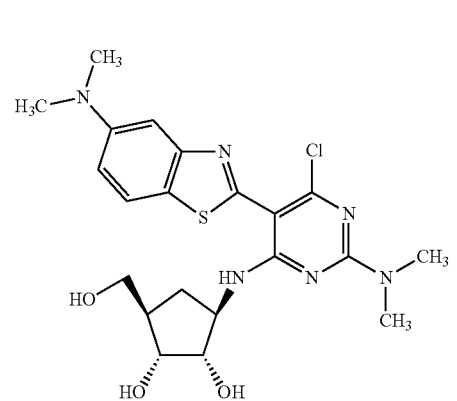 | C | 1H NMR (CD3OD + DMSO-d6, 3 drops) δ 1.38-1.47 (m, 1H), 2.18-2.33 (m, 1H), 2.55-2.61 (m, 1H), 3.064 (s, 1H) 3.65-3.71 (m, 2H), 3.92-3.99 (m, 2H), 4.37 (s, 1H) 4.44-4.53 (m, 1H), 7.02-7.05 (m, 1H), 7.33 (d, 1 H, J = 2.0 Hz), 7.56 (d, 1 H, J = 8.8 Hz), 10.77 (d, 1 H, J = 5.5 Hz). | 479.3 | E (Steps 2 and 3) |
| 205 | 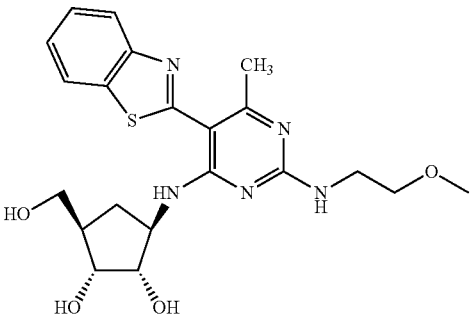 | A | | 446.2 | I |

TABLE I-continued
| | | | | | | |
|---|---|---|---|---|---|---|
| 206 | 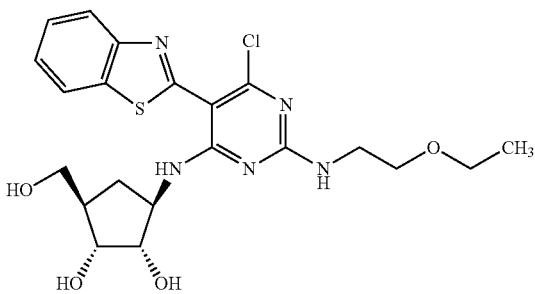 [SMILES: CCOCCNc1nc(Cl)c(-c2nc3ccccc3s2)c(N[C@@H]2C[C@H](CO)[C@@H](O)[C@H]2O)n1] | | A | 1H NMR (DMSO) δ 1.17-1.28 (m, 1H), 1.91-2.02 (m, 1H), 2.27-2.41 (m, 1H), 3.39-3.52 (m, 4H) 3.72-3.84 (m, 2H), 4.26-4.34 (m, 1H) 4.52-4.53 (m, 1H), 4.61-4.67 (m, 1H), 4.68-4.74 (m, 1H), 7.38-7.46 (m, 1H), 7.48-7.56 (m, 1 H). 7.70-7.77 (m, 1 H), 7.99 (d, 1H, J = 8.0 Hz), 8.07 (d, 1H, J = 8.2 Hz) 10.58-10.59 (m, 1 H). | 480.3 | H |
| 207 | 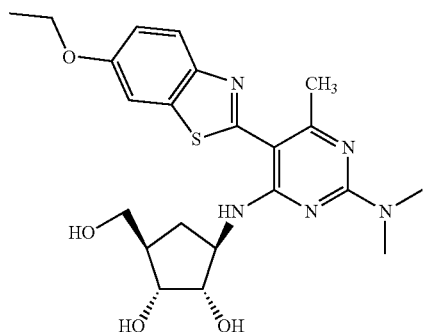 [SMILES: CCOc1ccc2nc(-c3c(C)nc(N(C)C)nc3N[C@@H]3C[C@H](CO)[C@@H](O)[C@H]3O)sc2c1] | | C | | 460.3 | I |
| 208 | 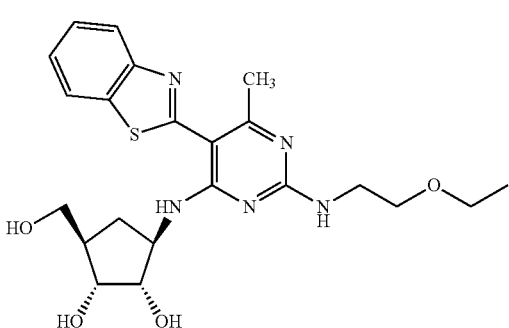 [SMILES: CCOCCNc1nc(C)c(-c2nc3ccccc3s2)c(N[C@@H]2C[C@H](CO)[C@@H](O)[C@H]2O)n1] | | A | | 460.3 | I |
| 209 | 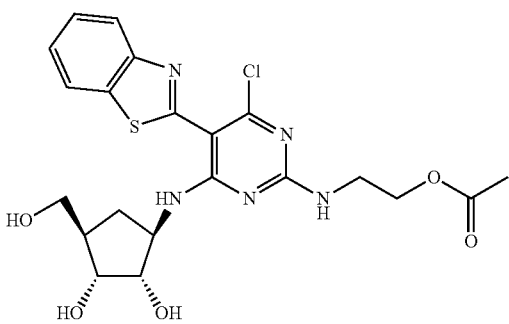 [SMILES: CC(=O)OCCNc1nc(Cl)c(-c2nc3ccccc3s2)c(N[C@@H]2C[C@H](CO)[C@@H](O)[C@H]2O)n1] | | A | 1H NMR (DMSO)-d6) δ 1.21-1.29 (m, 1H), 1.90-1.98 (m, 1H), 2.00 (s, 3H), 2.29-2.41 (m, 1H), 3.32 (s, 3H), 3.40-3.47 (m, 2H) 3.52-3.57 (m, 2H) 3.74-3.74 (m, 1H), 3.79-3.83 (m, 1H) 4.13-4.17 (m, 1H), 4.25-4.30 (m, 1H), 4.52 (d, 1H J = 5.1 Hz), 4.65 (t, 1H J = 4.8 Hz), 4.70 (d, 1H, J = 5.1 Hz), 7.38-7.46 (m, 1H), 7.52 (t, 1H, J = 7.3 Hz), 7.83-7.89 (m, 1H), 7.99-8.03 (m, 1H), 8.06-8.11 (m, 1H), 10.58 (d, 1H, J = 5.9 Hz) | 494.3 | H |

| | | | | |
|---|---|---|---|---|
| 210 | 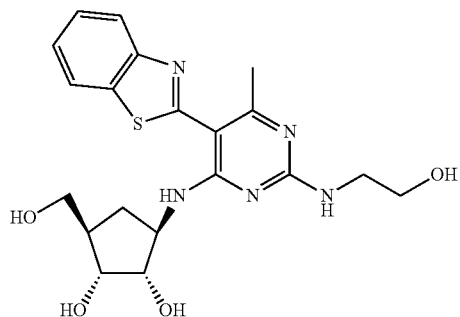 [SMILES: Cc1nc(NCCO)nc(N[C@@H]2C[C@H](CO)[C@@H](O)[C@H]2O)c1-c1nc2ccccc2s1] | A | | 432.2 | I |
| 211 | 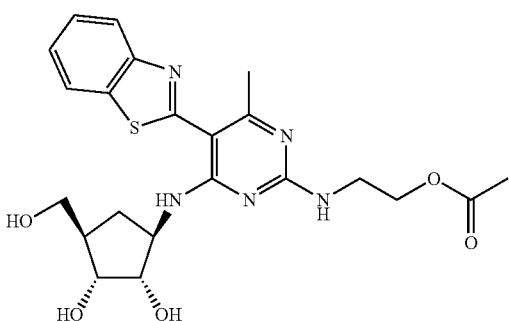 [SMILES: CC(=O)OCCNc1nc(C)c(-c2nc3ccccc3s2)c(N[C@@H]2C[C@H](CO)[C@@H](O)[C@H]2O)n1] | A | 1H NMR (DMSO)-D6) δ 1.08-1.30 (m, 1H), 1.88-1.99 (m, 1H), 2.00 (s, 3H), 2.28-2.40 (m, 1H), 2.54 (s, 3H), 3.38-3.48 (m, 2H) 3.50-3.56 (m, 3H), 3.69-3.79 (m, 1H), 4.10-4.18 (m, 1H), 4.22-4.37 (m, 1H), 4.57-4.68 (m, 1H), 7.39 (t, 1H, J = 7.0 Hz), 7.50 (t, 1H, J = 7.8 Hz), 7.97 (d, 1H, J = 7.3 Hz), 8.07 (d, 1H, J = 8.3 Hz) | 474.3 | I |
| 212 | 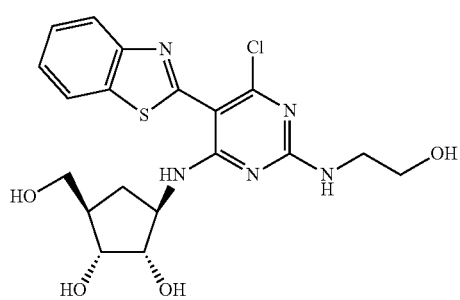 [SMILES: OCCNc1nc(Cl)c(-c2nc3ccccc3s2)c(N[C@@H]2C[C@H](CO)[C@@H](O)[C@H]2O)n1] | A | 1H NMR (DMSO)-d6) δ 1.20-1.30 (m, 1H), 1.91-2.03 (m, 1H), 2.28-2.44 (m, 1H), 3.36-3.56 (m, 4H). 3.72-3.84 (m, 2H), 4.25-4.37 (m, 1H), 4.50-4.51 (m, 1H), 4.62-4.74 (m, 3H), 7.39-7.46 (m, 1H), 7.47-7.49 (m, 1H), 7.59-7.65 (m, 1H), 7.98 (d, 1H, J = 8.3 Hz), 8.07 (d, 1H, J = 7.1 Hz), 10.58 (d, 1H, J = 5.9 Hz). | 452.2 | Prepared via treatment of 209 with aqueous potassium carbonate and dioxane. |
| 213 | 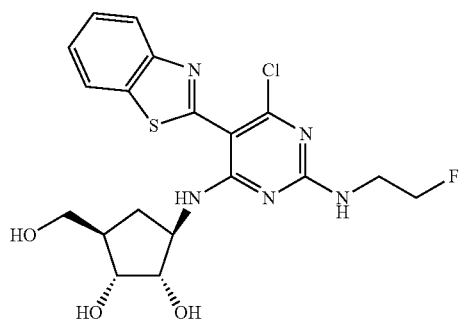 [SMILES: OC[C@H]1C[C@@H](Nc2nc(NCCF)nc(Cl)c2-c2nc3ccccc3s2)[C@H](O)[C@@H]1O] | A | 1H NMR (DMSO)-d6) δ 1.22-1.32 (m, 1H), 1.92-2.03 (m, 1H), 2.29-2.40 (m, 1H), 3.39-3.49 (m, 2H), 3.54-3.67 (m, 2H) 3.74-3.82 (m, 2H), 4.24-4.35 (m, 1H), 4.44-4.55 (m, 1H), 4.60-4.72 (m, 1H), 7.39-7.46 (m, 1H), 7.50-7.55 (m, 1H), 7.91-7.95 (m, 1H), 8.08-8.11 (m, 1H), 10.53-10.60 (m, 1H) | 454.2 | H |

TABLE I-continued
| | | | | | |
|---|---|---|---|---|---|
| 214 | 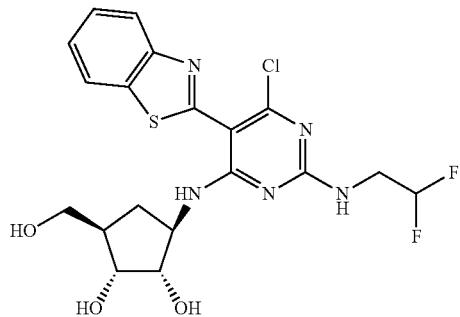 [SMILES: OC[C@H]1C[C@@H](Nc2nc(NCC(F)F)nc(Cl)c2-c2nc3ccccc3s2)[C@H](O)[C@@H]1O] | A | 1H NMR (DMSO)-d6) δ 1.22-1.32 (m, 1H), 1.92-2.04 (m, 1H), 2.29-2.39 (m, 1H), 3.40-3.51 (m, 2H), 3.64-3.83 (m, 4H) 4.25-4.37 (m, 1H), 4.43-4.55 (m, 1H), 4.57-4.72 (m, 2H), 4.63-4.72 (m, 2H) 6.03-6.31 (m, 1H), 7.41-7.47 (m, 1H), 7.51-7.56 (m, 1H), 7.84-7.89 (m, 1H), 8.04-8.10 (m, 1H), 8.09 (d, 1H J = 8.3 Hz), 10.54 (d, 1H J = 5.2 Hz) | 472.3 | H |
| 215 | 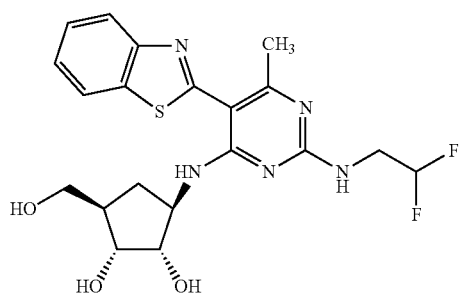 [SMILES: Cc1nc(NCC(F)F)nc(N[C@@H]2C[C@H](CO)[C@@H](O)[C@H]2O)c1-c1nc2ccccc2s1] | A | 1H NMR (DMSO)-d6) δ 1.08-1.31 (m, 1H), 1.91-2.05 (m, 1H), 2.25-2.39 (m, 1H) 2.53 (s, 3H), 3.37-3.53 (m, 3H), 3.63-3.81 (m, 4H) 4.23-4.36 (m, 1H), 4.41-4.52 (m, 1H), 4.57-4.72 (m, 2H) 6.00-6.29 (m, 1H), 7.34-7.44 (m, 1H), 7.45-7.56 (m, 1H), 7.99 (d, 1H, J = 1H, Hz), 8.10 (d, 1H, J = 7.8 Hz), 9.52-9.65 (m, 1H) | 452.2 | I |
| 216 | 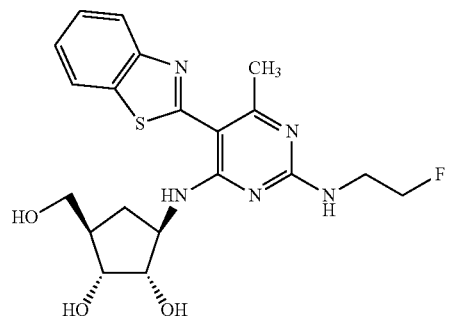 [SMILES: Cc1nc(NCCF)nc(N[C@@H]2C[C@H](CO)[C@@H](O)[C@H]2O)c1-c1nc2ccccc2s1] | B | | 434.2 | I |
| 217 | 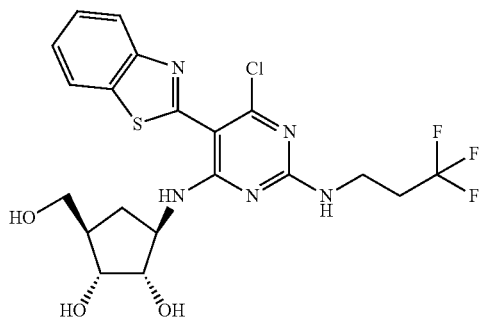 [SMILES: OC[C@H]1C[C@@H](Nc2nc(NCCC(F)(F)F)nc(Cl)c2-c2nc3ccccc3s2)[C@H](O)[C@@H]1O] | A | 1H NMR (DMSO) δ 1.12-1.33 (m, 1H), 1.91-2.05 (m, 1H), 2.29-2.43 (m, 1H), 2.54-3.39 (m, 2H), 3.38-3.63 (m, 4H) 3.71-3.88 (m, 2H), 4.23-4.39 (m, 1H) 4.47-4.57 (m, 1H), 4.62-4.76 (m, 1H), 7.39-7.61 (m, 2H), 7.86-7.95 (m, 1 H), 8.01-8.15 (m, 2H), 10.54-10.67 (m, 1 H). | 504.3 | H |

TABLE I-continued
| | | | | | |
|---|---|---|---|---|---|
| 218 | 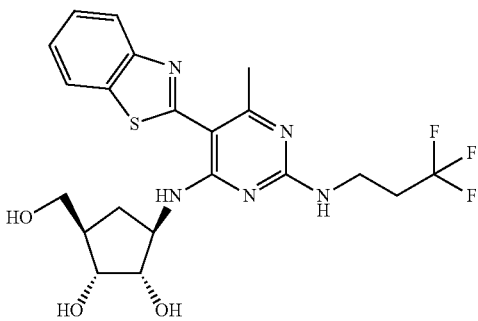 [SMILES: Cc1nc(NCCC(F)(F)F)nc(N[C@@H]2C[C@H](CO)[C@@H](O)[C@H]2O)c1-c1nc2ccccc2s1] | A | | 484.3 | I |
| 219 | 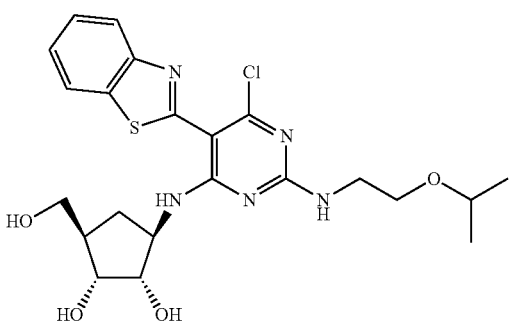 [SMILES: CC(C)OCCNc1nc(Cl)c(-c2nc3ccccc3s2)c(N[C@@H]2C[C@H](CO)[C@@H](O)[C@H]2O)n1] | A | 1H NMR (DMSO) δ 1.08 (d, 6H J = 5.9), 1.16-1.29 (m, 1H), 1.90-2.02 (m, 1H), 2.28-2.42 (m, 1H), 3.24-3.62 (m, 4H) 3.72-3.85 (m, 2H), 3.99-4.16 (m, 1H), 4.25-4.36 (m, 1H), 4.43-4.74 (m, 3H), 7.38-7.46 (m, 1H), 7.51 (t, 1 H J = ), 8.01-8.15 (m, 2H), 10.54-10.67 (m, 1 H). | 494.3 | H |
| 220 | 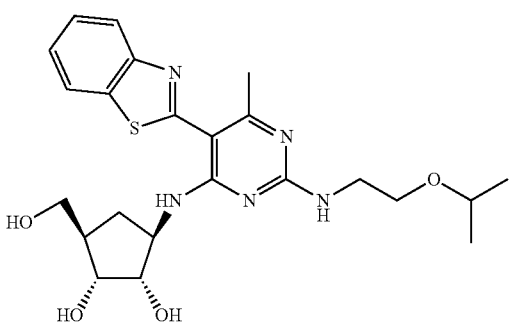 [SMILES: Cc1nc(NCCOC(C)C)nc(N[C@@H]2C[C@H](CO)[C@@H](O)[C@H]2O)c1-c1nc2ccccc2s1] | A | — | 474.3 | I |
| 222 | 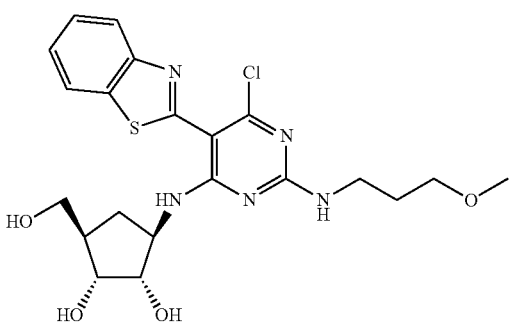 [SMILES: COCCCNc1nc(Cl)c(-c2nc3ccccc3s2)c(N[C@@H]2C[C@H](CO)[C@@H](O)[C@H]2O)n1] | A | — | 480.3 | H |
| 223 | 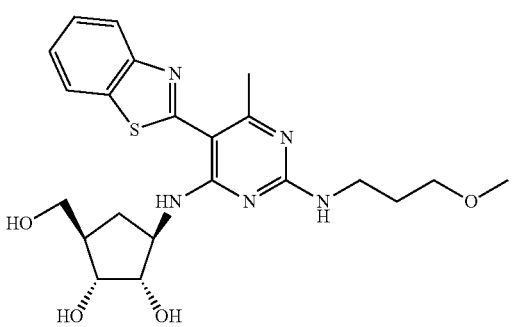 [SMILES: COCCCNc1nc(C)c(-c2nc3ccccc3s2)c(N[C@@H]2C[C@H](CO)[C@@H](O)[C@H]2O)n1] | A | — | 460.3 | I |

TABLE I-continued

| # | Structure | | | |
|---|---|---|---|---|
| 224 | (structure) | A | 518.3 | H |
| 225 | (structure) | A — | 498.3 | I |
| 226 | (structure) | A — | 494.3 | H |
| 227 | (structure) | A — | 474.3 | I |
| 228 | (structure) | A | 480.3 | H |

TABLE I-continued

| | | | | | |
|---|---|---|---|---|---|
| 229 | | A | | 460.3 | I |
| 302 | | B | 1H NMR (DMSO)-d6) δ 0.98-1.06 (m, 1H), 1.78-1.87 (m, 1H), 2.04-2.12 (m, 1H), 3.24-3.35 (m, 2H), 3.60-3.67 (m, 2H), 4.31-4.38 (m, 2H), 4.48-4.53 (m, 2H), 6.69 (d, 1 H, J = 6.69 Hz), 6.96 (br. s, 2 H), 7.22 (s, 1 H), 8.97 (d, 1 H, J = 2.6 Hz) and 9.19 (d, 1 H, J = 2.6 Hz). 13C NMR(DMSO-d6) δ 29.90, 44.92, 55.67, 62.50, 71.81, 75.29, 93.69, 109.30, 121.30, 126.11, 140.13, 141.65, 153.08, 158.59, 161.80, 162.35 and 163.63 | 437.2 | A-2 |
| 303 | | B | 1H NMR (CD3OD) δ 0.80-1.00 (m, 1H), 1.99-2.08 (m, 1H), 2.22-2.40 (m, 1H), 3.41-3.55 (m, 2H), 3.72-3.80 (m, 2H), 4.35-4.49 (m, 1H), 7.18 (s, 1H), 8.28 (br. s, 1 H) and 8.75 (br. s, 1 H). | 410.2 | L |
| 304 | | C | 1H NMR (CD3OD) δ 1.18-1.26 (m, 1H), 2.00-2.09 (m, 1H), 2.30-2.39 (m, 1H), 2.55 (s, 3H), 3.48-3.54 (m, 2H), 3.78-3.83 (m, 1H), 3.83-3.88 (m, 1H), 4.38-4.45 (m, 1H), 7.10 (s, 1 H), 8.16 (br. s, 1H) and 8.64 (br. s, 1 H), 13C NMR (CD3OD) δ15.71, 30.79, 46.28, 57.45. 63.81, 74.20, 78.12, 97.03, 107.90. 128.12, 131.59, 137.19, 142.35, 153.12, 154.67, 160.05, 163.32 and 163.69. | 406.2 | L |

TABLE I-continued
| | | | | | |
|---|---|---|---|---|---|
| 306 | 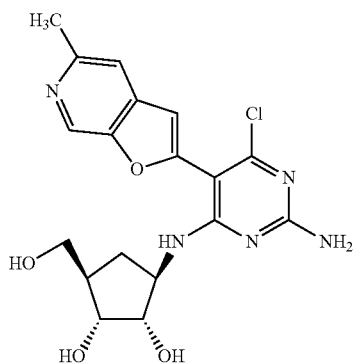 [SMILES: Cc1cc2cc(-c3c(Cl)nc(N)nc3N[C@@H]3C[C@H](CO)[C@@H](O)[C@H]3O)oc2cn1] | A | 1H NMR (CD3OD) δ 1.17-1.23 (m, 1H), 2.00-2.09 (m, 1H), 2.31-2.39 (m, 1H), 2.60 (s, 3H), 3.48-3.54 (m, 2H), 3.78-3.83 (m, 1H), 3.83-3.88 (m, 1H), 4.38-4.43 (m, 1H), 6.96 (d, 1 H,), 7.52 (br. s, 1H) and 8.66 (br. s, 1 H). 13C NMR (CD3OD) δ 23.45, 30.82, 46.25, 57.44, 63.74, 74.22, 78.14, 97.01, 108.84, 116.24, 132.67, 138.23, 151.71, 152.14, 155.44, 159.97, 163.22 and 163.66. | 406.2 | L |
| 305 | 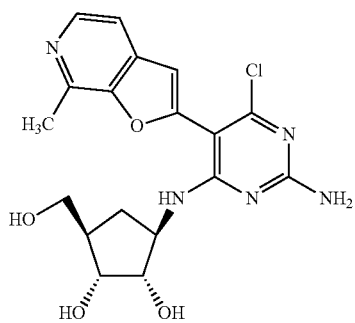 [SMILES: Cc1nccc2cc(-c3c(Cl)nc(N)nc3N[C@@H]3C[C@H](CO)[C@@H](O)[C@H]3O)oc12] | A | 1H NMR (CD3OD) δ 1.18-1.23 (m, 1H), 2.00-2.10 (m, 1H), 2.31-2.40 (m, 1H), 2.72 (s, 3H), 3.46-3.53 (m, 2H), 3.78-3.83 (m, 1H), 3.83-3.88 (m, 1H), 4.38-4.44 (m, 1H), 7.02 (s, 1 H,), 7.52 (d, 1H, J = 5.6 Hz) and 8.19 (d, 1 H, J = 5.6 Hz). 13C NMR (CD3OD) δ 17.99, 30.87, 46.25, 57.41. 63.78, 74.26, 78.22, 97.05, 109.42, 115.64, 136.64, 141.99, 143.51, 152.00, 154.59, 159.97, 163.28 and 163.69. | 406.2 | L |
| 307 | 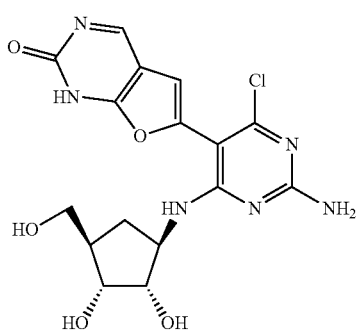 [SMILES: Nc1nc(Cl)c(-c2cc3cnc(=O)[nH]c3o2)c(N[C@@H]2C[C@H](CO)[C@@H](O)[C@H]2O)n1] | C | 1H NMR (CD3OD) δ 1.23-1.38 (m, 1H), 2.00-2.11 (m, 1H), 2.27-2.38 (m, 1H), 3.42-3.56 (m, 2H), 3.80-3.92 (m, 2H), 4.48-4.59 (m, 1H), 7.03 (s, 1 H,) and 8.43 (s, 1 H). | 409.0 | L |

TABLE I-continued
| | | | | | |
|---|---|---|---|---|---|
| 308 | 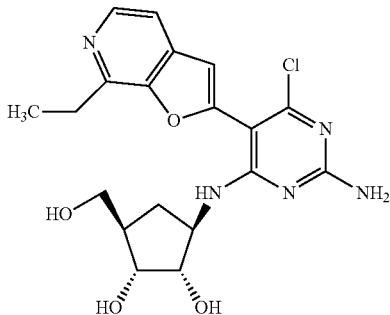 [SMILES: CCc1nccc2cc(-c3c(Cl)nc(N)nc3N[C@@H]3C[C@H](CO)[C@@H](O)[C@H]3O)oc12] | A | 1H NMR (DMSO-d6) δ 0.99-1.08 (m, 1H), 1.46 (t, 3H, J = 7.4 Hz), 1.82-1.90 (m, 1H), 2.10-2.19 (m, 1H), 3.22-3.34 (m, 4H), 3.62-3.72 (m, 2H), 4.31-4.41 (m, 1H), 6.92 (d, N<u>H</u>, J = 7.6 Hz), 7.12 (br. s, N<u>H2</u>) 7.43 (s, 1 H), 8.08 (d, 1H, J@ 5 Hz) and 8.50 (br. s, 1H). 13C NMR (DMSO-d6) δ 12.37, 21.97, 29.86, 44.79, 55.67, 62.34, 71.80, 75.38, 93.10, 108.88, 116.13, 133.84, 140.83, 142.82, 148.80, 158.27, 159.95, 161.13 and 162.07. | 420.2 | L |
| 309 | 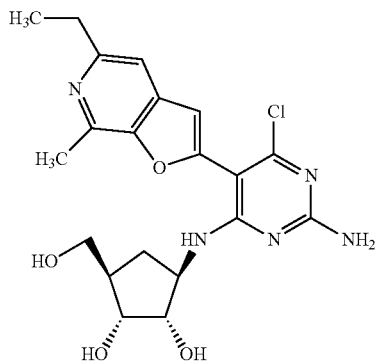 [SMILES: CCc1cc2cc(-c3c(Cl)nc(N)nc3N[C@@H]3C[C@H](CO)[C@@H](O)[C@H]3O)oc2c(C)n1] | A | 1H NMR (CD3OD) δ 1.20-1.26 (m, 1H), 1.32 (t, 3H, J = 7.6 Hz), 2.01-2.09 (m, 1H), 2.32-2.40 (m, 1H), 2.71 (s, 3H), 2.86 (q, 2H, J = 7.6 Hz), 3.47-3.53 (m, 2H), 3.77-3.81 (m, 1H), 3.83-3.87 (m, 1H), 4.38-4.43 (m, 1H), 6.94 (s, 1 H,) and 7.36 (s, 1 H). 13C NMR (CD3OD) δ 15.40, 17.78, 30.88, 31.49, 46.24, 57.40, 63.77, 74.26, 78.24, 97.23, 109.28, 112.97, 137.51, 142.37, 150.62, 154.64, 156.84, 159.87, 163.25 and 163.61. | 434.2 | N |
| 403 | 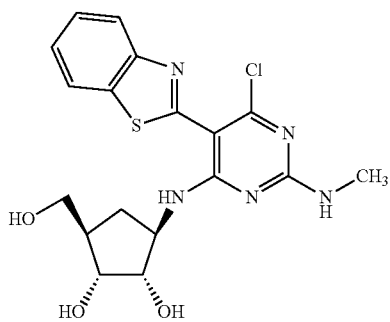 [SMILES: CNc1nc(Cl)c(-c2nc3ccccc3s2)c(N[C@@H]2C[C@H](CO)[C@@H](O)[C@H]2O)n1] | A | 1H NMR (DMSO-d6) 1.13-1.30 (m, 1H), 1.11-2.04 (m, 1H), 2.28-2.47 (m, 1H), 2.78-2.92 (m, NHC<u>H3</u>), 3.39-3.52 (m, 2H), 3.72-3.80 (m, 1H), 3.80-3.87 (m, 1H), 4.27-4.40 (m, 1H), 4.43-4.52 (m, 1H), 4.60-4.69 (m, O<u>H</u>), 4.69-4.76 (m, O<u>H</u>), 7.37-7.47 (m, 1H), 7.47-7.55 (m, 1H), @7.50, 7.64 and 7.77 (br. s., N<u>H</u>CH3), 7.96-8.02 (m, 1H), 8.03-8.12 (m, 1H) and 10.30, 10.47 and 10.56 (d, 1 H, all J = 6.2). | 422.2 | K |

TABLE I-continued
| | | | | | |
|---|---|---|---|---|---|
| 310 | 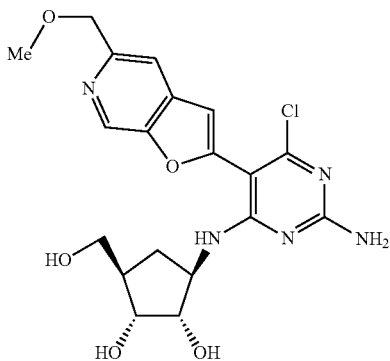 [SMILES: COCc1cc2cc(-c3c(Cl)nc(N)nc3N[C@@H]3C[C@H](CO)[C@@H](O)[C@H]3O)oc2cn1] | A | | 436.1 | Combination of M and N |
| 311 | 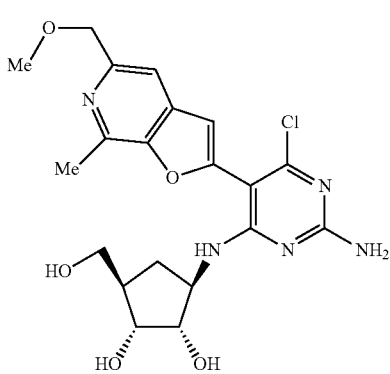 [SMILES: COCc1cc2cc(-c3c(Cl)nc(N)nc3N[C@@H]3C[C@H](CO)[C@@H](O)[C@H]3O)oc2c(C)n1] | A | 1H NMR (DMSO-d6 + CD3OD) δ 1.04-1.10 (m, 1H), 1.83-1.92 (m, 1H), 2.12-2.20 (m, 1H), 2.86 (s, 3H) 3.30-3.35 (m, 2H), 3.43 (s, 3H), 3.66-3.70 (m, 2H), 4.33-4.40 (m, 1H), 4.73 (s, 2H), 7.38 (s, 1H) and 8.02 (s, 1H). | 450.16 | Combination of M and N |
| 408 | 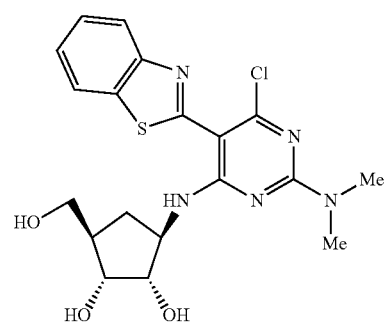 [SMILES: CN(C)c1nc(Cl)c(-c2nc3ccccc3s2)c(N[C@@H]2C[C@H](CO)[C@@H](O)[C@H]2O)n1] | A | 1H NMR (DMSO-d6) δ 1.22-1.30 (m, 1H), 1.97-2.05 (m, 1H), 2.36-2.46 (m, 1H), 3.17 (s, 6H, 2xNCH3) 3.42-3.52 (m, 2H), 3.75-3.79 (m, 1H), 3.82-3.86 (m, 1H), 4.28-4.35 (m, 1H), 4.51 (d, 1 OH, J = 5.2 Hz), 4.65 (t, 1 OH, J = 5.2 Hz), 4.71 (d, 1 OH, J = 5.4 Hz), 7.42-7.60 (m, 1 H), 7.51-7.60 (m, 1 H), 8.02 (d, 1 H, J = 8.0 Hz), 8.10 (d, 1H, J = 7.8 Hz) and 10.51 (d, 1H, J = 6.5 Hz). 13C NMR (DMSO-d6) δ 30.36, 36.36 (2xC), 44.85, 56.03, 62.44, 72.50, 76.56, 96.81, 121.16, 121.56, 124.99, 126.31, 132.80, 150.27, 157.76, 158.09, 159.83 and 162.96. | 436.05 | C |

TABLE I-continued
| 312 | 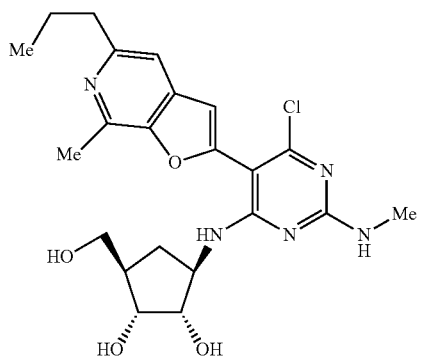 [SMILES: CCCc1cc2cc(-c3c(Cl)nc(NC)nc3N[C@@H]3C[C@H](CO)[C@@H](O)[C@H]3O)oc2c(C)n1] | A | 1H NMR (DMSO-d6) δ 0.93 (t, CH3CH2, J = 7.4 Hz), 0.97-1.14 (m, 1H), 1.67-1.75 (m, 2H), 1.81-1.92 (m, 1H), 2.06-2.23 (m, 1H), 2.65 (s, CH3), 2.72-2.80 (m, 2H), 2.83 (br.s, NHCH3), 3.27-3.41 (m, 2H), 3.61-3.78 (m, 2H), 4.27-4.36 (m, 1H), 4.44 (br. s, OH), 4.55 (br. s, 2x OH), 6.61 and 6.76 (br. s, NH), 6.99 (s, 1H), 7.29 and 7.37 (br. s, NH) and 7.37 (s, 1H). | 462.3 | N |
| --- | --- | --- | --- | --- | --- |
| 313 | 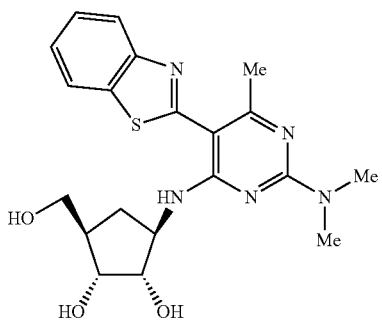 [SMILES: Cc1nc(N(C)C)nc(N[C@@H]2C[C@H](CO)[C@@H](O)[C@H]2O)c1-c1nc2ccccc2s1] | A | 1H NMR (DMSO-d6) δ 1.18-1.26 (m, 1H), 1.96-2.03 (m, 1H), 2.35-2.43 (m, 1H), 2.60 (s, 3H, CH3), 3.17 (s, 6H, 2xNCH3) 3.40-3.52 (m, 2H), 3.73-3.81 (m, 2H), 4.27-4.33 (m, 1H), 4.48 (d, 1 OH, J = 5.0 Hz), 4.61 (t, 1 OH, J = 5.2 Hz), 4.65 (d, 1 OH, J = 5.2 Hz), 7.38-7.42 (m, 1 H), 7.50-7.54 (m, 1 H), 7.99 (d, 1 H, J = 8.0 Hz), 8.09 (d, 1H, J = 8.0 Hz) and 9.70 (d, 1H, J = 6.4 Hz). 13C NMR (DMSO-d6) δ25.89, 30.67, 36.24 (2xC), 44.95, 55.57, 62.67, 72.58, 76.70, 98.77, 121.22, 121.49, 124.49, 126.26, 133.06, 151.11, 159.32, 159.47, 164.62 and 164.81. | 416.2 | O |
| 314 | 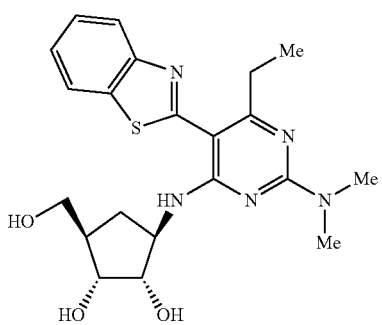 [SMILES: CCc1nc(N(C)C)nc(N[C@@H]2C[C@H](CO)[C@@H](O)[C@H]2O)c1-c1nc2ccccc2s1] | C | 1H NMR (CD3OD) δ 1.27 (t, 3H, J = 7.5 Hz), 1.30-1.35 (m, 1H), 2.09-2.18 (m, 1H), 2.44-2.51 (m, 1H), 2.84 (q, 2H, J = 7.5 Hz), 3.22 (s, 6H, 2xNCH3) 3.54-3.62 (m, 2H), 3.87-3.90 (m, 2H), 4.41-4.48 (m, 1H), 7.38-7.42 (m, 1H), 7.48-7.52 (m, 1H) and 7.94-7.98 (s, 2H). | 430.1 | O |

TABLE I-continued
| | | | | | |
|---|---|---|---|---|---|
| 412 | 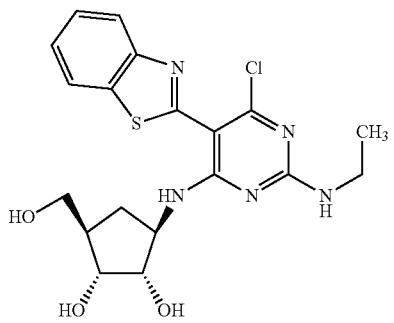 [SMILES: CCNc1nc(Cl)c(-c2nc3ccccc3s2)c(N[C@@H]2C[C@H](CO)[C@@H](O)[C@H]2O)n1] | A | 1H NMR (DMSO-d6 + DCl) δ 1.12 (t, 3H, J = 7.5 Hz), 1.15-1.25 (m, 1H), 1.92-2.01 (m, 1H), 2.28-2.38 (m, 1H), 3.32 (q, 2H, J = 7.5 Hz), 3.36-3.46 (m, 2H), 3.71-3.76 (m, 1H), 3.78-3.82 (m, 1H), 4.23-4.31 (m, 1H), 7.37-7.44 (m, 1 H), 7.46-7.53 (m, 1 H), 7.99 (d, 1 H, J = 8.0 Hz), 8.05 (d, 1H, J = 8.0 Hz) and 10.60 (br. s, NH). | 436.2 | H |
| 317 | 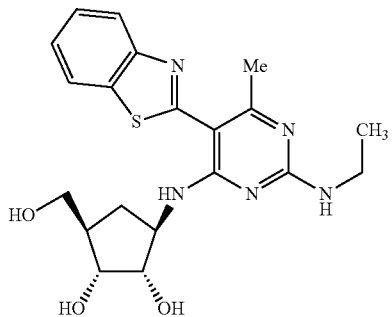 [SMILES: CCNc1nc(C)c(-c2nc3ccccc3s2)c(N[C@@H]2C[C@H](CO)[C@@H](O)[C@H]2O)n1] | | 1H NMR (DMSO-d6) δ 1.14 (t, 3H, CH3, J = 7.1 Hz), 1.14-1.27 (m, 1H), 1.89-2.04 (m, 1H), 2.29-2.41 (m, 1H), 2.56 (s, 3H, CH3), 3.35 (q, 2H) 3.38-3.51 (m, 2H), 3.69-3.87 (m, 2H), 4.27-4.35 (m, 1H), 4.45 (br. s, 1 OH), 4.60 (t, 1 OH, J = 5.2 Hz), 4.68 (d, 1 OH, J = 5.2 Hz), 7.20 (br. s, 1H, NH), 7.32-7.41 (m, 1 H), 7.46-7.53 (m, 1 H), 7.99 (d, 1 H, J = 8.0 Hz), 8.08 (d, 1 H, J = 8.0 Hz) and 9.82 (br. s, 1H, NH). 13C NMR (DMSO-d6) δ 14.84, 25.42, 30.80, 35.22, 45.01, 55.54, 62.76, 72.55, 76.74, 98.77, 121.21, 121.42, 124.42, 126.23, 133.00, 151.10, 159.73, 159.89, 164.87 and 164.96. | 416.06 | O |
| 318 | 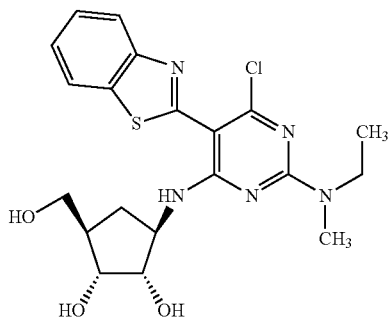 [SMILES: CCN(C)c1nc(Cl)c(-c2nc3ccccc3s2)c(N[C@@H]2C[C@H](CO)[C@@H](O)[C@H]2O)n1] | A | | 450.2 | H |

TABLE I-continued
| | | | | | | |
|---|---|---|---|---|---|---|
| 319 | 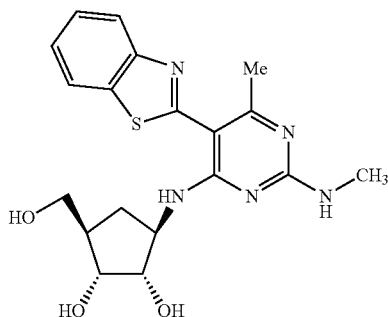 | | A | 1H NMR (DMSO-d6 + DCl) δ 1.12-1.25 (m, 1H), 1.90-2.04 (m, 1H), 2.26-2.42 (m, 1H), 2.55 (s, 3H, CH3), 2.82 (s, 3H, NHCH3), 3.37-3.51 (m, 2H), 3.68-3.86 (m, 2H), 4.26-4.39 (m, 1H), 7.30-7.58 m, 2 H), 7.99 (d, 1 H, J = 7.9 Hz) and 8.09 (d, 1H, J = 7.9 Hz). | 402.2 | O |
| 321 | 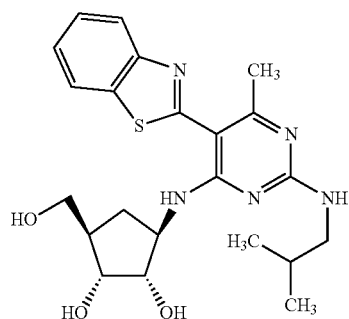 [SMILES: Cc1nc(NCC(C)C)nc(N[C@@H]2C[C@H](CO)[C@@H](O)[C@H]2O)c1-c1nc2ccccc2s1] | | A | 1H NMR (DMSO-d6 + DCl) δ 0.93 (d, 6H, 2xCH3, J = 7.6 Hz), 1.16-1.27 (m, 1H), 1.86-1.99 (m, 2H), 2.18-2.27 (m, 1H), 2.48 (s, 3H, CH3), 3.22-3.41 (m, 4H), 3.66-3.70 (m, 1H), 3.77-3.82 (m, 1H), 4.31-4.38 (m, 1H), 7.49-7.52 (m, 1 H), 7.56-7.61 (m, 1H), 8.13 (d, 1 H, J = 8.0 Hz) and 8.19 (d, 1H, J = 8.0 Hz). | 444.2 | O |
| 320 | 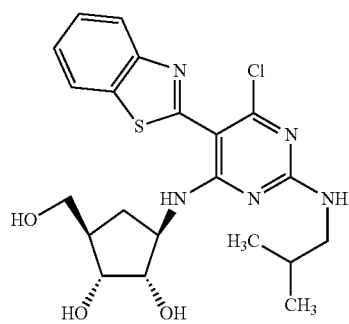 [SMILES: CC(C)CNc1nc(Cl)c(-c2nc3ccccc3s2)c(N[C@@H]2C[C@H](CO)[C@@H](O)[C@H]2O)n1] | | A | 1H NMR (DMSO-d6 + DCl) δ 0.88 (d, 6H, 2xCH3, J = 7.6 Hz), 1.19-1.27 (m, 1H), 1.80-1.90 (m, 1H), 1.93-2.01 (m, 1H), 2.30-2.39 (m, 1H), 3.08-3.22 (m, 2H), 3.36-3.46 (m, 2H), 3.72-3.75 (m, 1H), 3.79-3.82 (m, 1H), 4.24-4.30 (m, 1H), 7.40-7.44 (m, 1 H), 7.49-7.54 (m, 1H), 8.02 (d, 1 H, J = 8.0 Hz) and 8.08 (d, 1H, J = 8.0 Hz). | 464.3 | H |
| 401 | 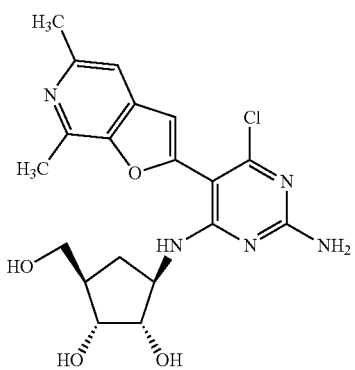 [SMILES: Cc1cc2cc(-c3c(Cl)nc(N)nc3N[C@@H]3C[C@H](CO)[C@@H](O)[C@H]3O)oc2c(C)n1] | | A | 1H NMR (DMSO-d6) δ 1.10-1.02 (m, 1H), 1.82-1.91 (m, 1H), 2.10-2.20 (m, 1H), 2.74 (s, 3H), 2.89 (s, 3H), 3.28-3.35 (m, 2H), 3.66-3.72 (m, 2H), 4.30-4.39 (m, 1H), 6.86 (d, 1 H, J = Hz), 7.10 (br. s, NH2), 7.34 (s, 1H) and 7.86 (s, 1H). | 420.1 | L |

TABLE I-continued

| | | | | | |
|---|---|---|---|---|---|
| 402 | (structure) | C | | 393.1 | L |
| 404 | (structure) | C | | 436.1 | K |
| 406 | (structure) | A | 1H NMR (DMSO-d6) δ 1.01-1.08 (m, 1H), 1.33 (t, 3H, J = 7.6 Hz), 1.80-1.88 (m, 1H), 2.07-2.15 (m, 1H), 3.05-3.12 (m, 2H), 3.28-3.34 (m, 2H), 3.63-3.69 (m, 2H), 4.30-4.38 (m, 1H), 6.84 (d, 1 NH, J = 7.2 Hz), 7.40 (s, 1 H), 8.11 (s, 1H) and 9.34 (s, 1 H). | 420.05 | Combination of M and N. |
| 407 | (structure) | A | 1H NMR (DMSO-d6) δ 0.98-1.06 (m, 1H), 1.33 (t, 3H, J = 7.2 Hz), 1.41 (t, 3H, J = 7.4 Hz), 1.80-1.89 (m, 1H), 2.07-2.16 (m, 1H), 3.08 (q, 2H, J = 7.2 Hz), 3.24-3.34 (m, 4H), 3.62-3.67 (m, 2H), 4.30-4.39 (m, 1H), 6.90 (d, 1 NH, J = 7.5 Hz), 7.34 (s, 1 H) and 7.91 (s, 1 H). | 448.2 | L |

| | | | | | |
|---|---|---|---|---|---|
| 410 | 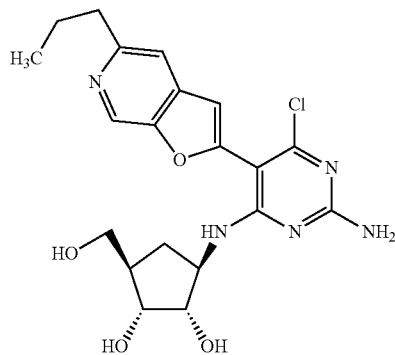 [SMILES: CCCc1cc2cc(-c3c(Cl)nc(N)nc3N[C@@H]3C[C@H](CO)[C@@H](O)[C@H]3O)oc2cn1] | A | | 434.2 | Combination of M and N. |
| 411 | 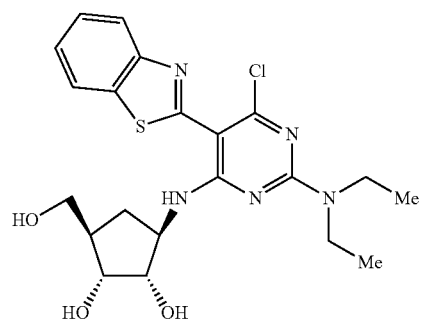 [SMILES: CCN(CC)c1nc(Cl)c(-c2nc3ccccc3s2)c(N[C@@H]2C[C@H](CO)[C@@H](O)[C@H]2O)n1] | B | 1H NMR (DMSO-d6) δ 1.10-1.22 (m, 2xCH3), 1.22-1.32 (m, 1H), 1.97-2.05 (m, 1H), 2.33-2.42 (m, 1H), 3.40-3.52 (m, 2H), 3.52-3.71 (m, 4H), 3.76-3.87 (m, 2H), 4.23-4.31 (m, 1H), 4.54 (br. s, 1 OH), 4.61-4.72 (m, 2x OH), 7.39-7.47 (m, 1 H), 7.50-7.57 (m, 1 H), 8.00 (d, 1 H, J = 7.7 Hz), 8.08 (d, 1H, J = 7.7 Hz) and 10.49 (d, 1H, J = 5.8 Hz). | 464.3 | H |
| 413 | 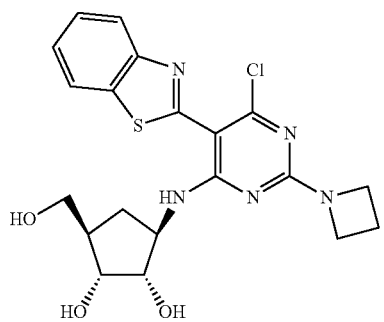 [SMILES: OC[C@H]1C[C@@H](Nc2nc(N3CCC3)nc(Cl)c2-c2nc3ccccc3s2)[C@H](O)[C@@H]1O] | B | 1H NMR (DMSO-d6) δ 1.19-1.27 (m, 1H). 1.94-2.02 (m, 1H), 2.26-2.40 (m, 3H), 3.38-3.49 (m, 2H), 3.74-3.78 (m, 1H), 3.79-3.84 (m, 1H), 4.05-4.14 (m, 4H), 4.23-4.30 (m, 1H), 4.49 (d, 1 OH, J = 4.6 Hz), 4.63 (t, 1 OH, J = 5.0 Hz), 4.74 (d, 1 OH, J = 5.0 Hz), 7.40-7.45 (m, 1 H), 7.50-7.55 (m, 1 H), 8.01 (d, 1 H, J = 7.9 Hz), 8.09 (d, 1H, J = 7.9 Hz) and 10.48 (d, 1H, J = 6.5 Hz). | 448.2 | H |
| 414 | 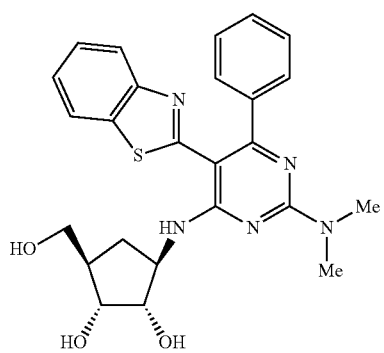 [SMILES: CN(C)c1nc(N[C@@H]2C[C@H](CO)[C@@H](O)[C@H]2O)c(-c2nc3ccccc3s2)c(-c2ccccc2)n1] | C | | 478.3 | O |

TABLE I-continued
| | | | | | |
|---|---|---|---|---|---|
| 415 | 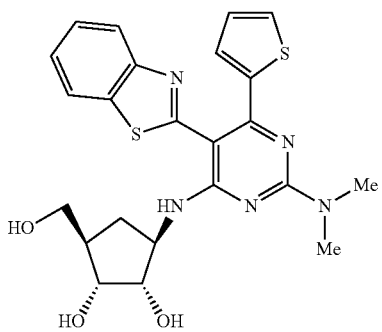 [SMILES: CN(C)c1nc(N[C@@H]2C[C@H](CO)[C@@H](O)[C@H]2O)c(-c2nc3ccccc3s2)c(-c2cccs2)n1] | C | 1H NMR (DMSO-d6) δ 1.10-1.17 (m, 1H), 1.96-2.04 (m, 1H), 2.36-2.43 (m, 1H), 3.33 (s, 6H, 2xNCH3) 3.39-3.50 (m, 2H), 3.73-3.76 (m, 2H), 4.28-4.34 (m, 1H), 4.99 (d, OH, J = 5.1 Hz), 4.62 (t, 1 OH, J = 5.2 Hz), 4.68 (d, OH, J = 5.2 Hz), 7.08-7.13 (m, 1 H), 7.26-7.34 (m, 1H), 7.41-7.47 (m, 1 H), 7.57-7.62 (m, 1H), 7.70-7.74 (m, 1H), 7.84 (d, 1 H, J = 8.0 Hz), 8.94 (d, 1H, J = 8.0 Hz) and 9.49 (d, 1H, J = 6.7 Hz). 13C NMR (DMSO-d6) δ 30.61, 36.37 (2xC), 44.96, 55.63, 62.63, 72.57, 76.72, 98.48, 121.05, 121.56, 124.61, 125.91, 126.68, 127.87, 128.70, 133.94, 139.97, 151.01, 159.21, 159.68, 161.57 and 165.70. | 484.3 | O |
| 416 | 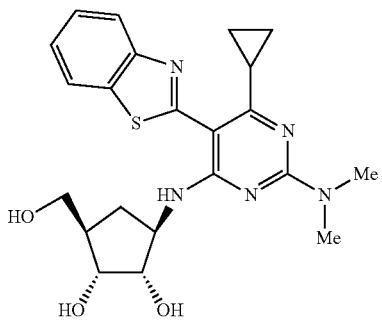 [SMILES: CN(C)c1nc(N[C@@H]2C[C@H](CO)[C@@H](O)[C@H]2O)c(-c2nc3ccccc3s2)c(C2CC2)n1] | B | 1H NMR (DMSO-d6) δ 0.97-1.03 (m, 2H), 1.13-1.22 (m, 3H), 1.92-2.00 (m, 1H), 2.30-2.44 (m, 2H), 3.02 (s, 6H, 2xNCH3) 3.35-3.49 (m, 2H), 3.68-3.77 (m, 2H), 4.22-4.28 (m, 1H), 4.45 (br. s, 1 OH), 4.58 (br. s, 1 OH), 4.64 (br. s, 1 OH), 7.38-7.43 (m, 1 H), 7.49-7.54 (m, 1 H), 8.00 (d, 1 H, J = 8.0 Hz), 8.07 (d, 1H, J = 8.0 Hz) and 9.04 (d, 1H, J = 6.6 Hz). 13C NMR (DMSO-d6) δ 9.91 (2xC), 15.57, 30.55. 36.05 (2xC), 44.88, 55.51, 62.60, 72.42, 76.56, 98.78, 121.24, 121.59, 124.53, 126.05, 133.58, 151.47, 159.08, 159.62, 164.65 and 167.40. | 442.2 | O |
| 418 | 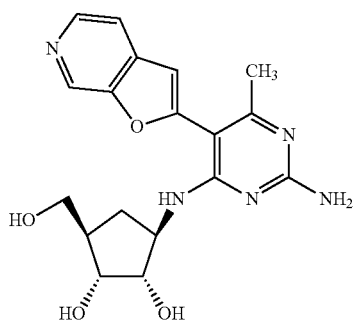 [SMILES: Cc1nc(N)nc(N[C@@H]2C[C@H](CO)[C@@H](O)[C@H]2O)c1-c1cc2ccncc2o1] | — | | 372.2 | O |

| | | | | | |
|---|---|---|---|---|---|
| 420 | 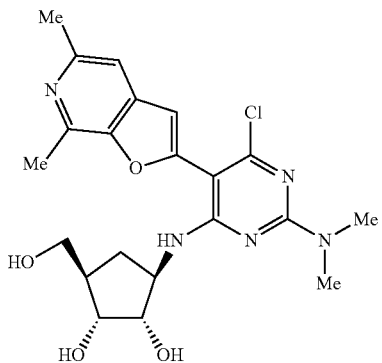 [SMILES: Cc1cc2cc(-c3c(Cl)nc(N(C)C)nc3N[C@@H]3C[C@H](CO)[C@@H](O)[C@H]3O)oc2c(C)n1] | C | 1H NMR (DMSO-d6) δ 1.07-1.17 (m, 1H), 1.85-1.94 (m, 1H), 2.17-2.27 (m, 1H), 2.68 (s, 3H), 2.72 (s, 3H), @ 3.05 (s, 6H), @3.40 (m, 2H), 3.65-3.77 (m, 2H), 4.24-4.32 (m, 1H), 4.53 (br. s, 3x OH), 6.80 (d, NH, J = 6.0 Hz), 7.12 (s, 1H) and 7.57 (s, 1H). | 448.2 | L |
| 419 | 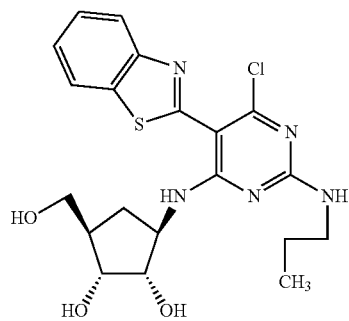 [SMILES: CCCNc1nc(Cl)c(-c2nc3ccccc3s2)c(N[C@@H]2C[C@H](CO)[C@@H](O)[C@H]2O)n1] | A | 1H NMR (DMSO-d6) δ 0.92 (t, 3H, CH3, J = 7.3 Hz), 1.26-1.33 (m, 1H), 1.52-1.60 (m, 2H), 1.93-2.05 (m, 1H), 2.33-2.43 (m, 1H), 3.20-3.30 (m, 2H), 3.39-3.51 (m, 2H), 3.72-3.80 (m, 1H), 3.81-3.87 (m, 1H), 4.26-4.33 (m, 1H), 4.54 (br. s, OH), 4.64 (br. s, OH), 4.70 (br. s, OH), 7.40-7.49 (m, 1 H), 7.57-7.60 (m, 1H), 7.80 (t, NH, J = 4.6 Hz), 8.00 (d, 1 H, J = 7.9 Hz), 8.10 (d, 1H, J = 7.9 Hz), and 10.60 (d, 1H, J = 6.4 Hz).<br>13C NMR (DMSO-d6) δ 11.37, 22.06, 30.47, 42.39, 44.90, 56.03, 62.46, 72.44, 76.53, 96.71, 121.09, 121.43, 124.84, 126.25, 131.50, 150.22, 158.70, 160.28, 163.01 and 166.88. | 450.2 | H |
| 422 | 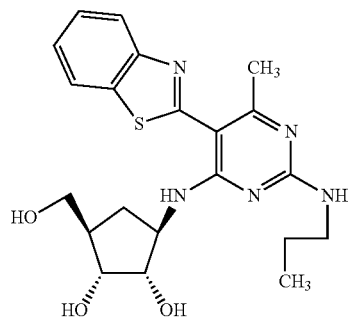 [SMILES: CCCNc1nc(C)c(-c2nc3ccccc3s2)c(N[C@@H]2C[C@H](CO)[C@@H](O)[C@H]2O)n1] | A | | 430.2 | O |

TABLE I-continued

| | | | | | |
|---|---|---|---|---|---|
| 423 | (structure) | C | 1H NMR (CD3OD + DCl) δ 1.28-1.39 (m, 1H), 2.06-2.14 (m, 1H), 2.33-2.42 (m, 1H), 2.85 (s, 3H), 3.30 (s, 6H), 3.50-3.56 (m, 2H), 3.87-3.92 (m, 1H), 3.99-4.02 (m, 1H), 4.49-4.57 (m, 1H), 7.77 (s, 1 H), 8.06 (m, 1H) and 9.06 (s, 1H). | 428.2 | L |
| 424 | (structure) | A | 1H NMR (DMSO-d6) δ 1.25-1.34 (m, 1H), 1.44-1.58 (m, 2H), 1.83-2.04 (m, 3H), 2.30-2.40 (m, 1H), 3.29-3.52 (m, 4H), 3.72-3.79 (m, 1H), 3.80-3.90 (m, 3H), 3.91-4.01 (m, 1H), 4.20-4.28 (m, 1H), 4.53 (br. s, OH), 4.60-4.73 (m, 2xOH), 7.38-7.46 (m, 1 H), 7.50-7.60 (m, 1H), 7.80 (d, NH, J = 7.3 Hz), 8.00 (d, 1 H, J = 8.0 Hz), 8.10 (d, 1H, J = 8.0 Hz), and 10.55 (d, 1H, J = 6.3 Hz). | 492.3 | H |
| 425 | (structure) | A | 1H NMR (DMSO-d6 + DCl) δ 1.19-1.32 (m, 1H), 1.50-1.64 (m, 2H), 1.87-2.02 (m, 3H), 2.13-2.25 (m, 1H), 2.49 (s, 3H), 3.29-3.53 (m, 4H), 3.64-3.72 (m, 1H), 3.77-3.92 (m, 3H), 4.05-4.16 (m, 1H), 7.47-7.62 (m, 2 H), 8.12 (d, 1 H, J = 8.0 Hz), and 8.19 (d, 1H, J = 8.0 Hz). | 472.3 | O |
| 426 | (structure) | A | 1H NMR (DMSO-d6 + CD3OD) δ 1.15 (d, 3H, J = 6.5 Hz), 1.16 (d, 3H, J = 6.5 Hz), 1.12-1.26 (m, 1H), 1.93-2.04 (m, 1H), 2.30-2.40 (m, 1H), 3.37-3.48 (m, 2H), 3.72-3.76 (m, 1H), 3.77-3.84 (m, 1H), 4.24-4.31 (m, 1H), 7.38-7.44 (m, 1H), 7.48-7.54 (m, 1H), 7.99 (d, 1 H, J = 8.0 Hz), and 8.05 (d, 1H, J = 8.0 Hz). | 450.2 | H |

TABLE I-continued
| | | | | | |
|---|---|---|---|---|---|
| 427 | 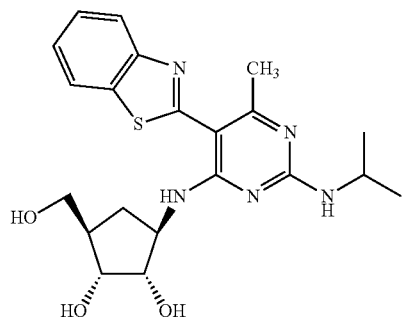 [SMILES: Cc1nc(NC(C)C)nc(N[C@@H]2C[C@H](CO)[C@@H](O)[C@H]2O)c1-c1nc2ccccc2s1] | A | | 430.2 | O |
| 428 | 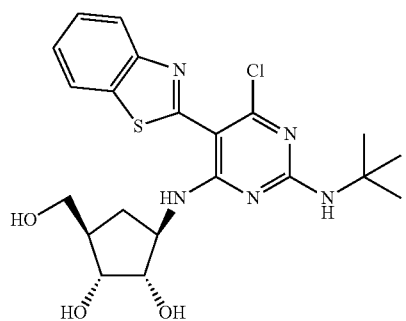 [SMILES: CC(C)(C)Nc1nc(Cl)c(-c2nc3ccccc3s2)c(N[C@@H]2C[C@H](CO)[C@@H](O)[C@H]2O)n1] | A | 1H NMR (DMSO-d6) δ 1.24-1.33 (m, 1H), 1.43 (s, 9H), 1.96-2.04 (m, 1H), 2.34-2.42 (m, 1H), 3.40-3.53 (m, 2H), 3.76-3.87 (m, 2H), 4.30-4.37 (m, 1H), 4.56 (br. s, OH), 4.62-4.67 (m, 2x OH), 7.38-7.46 (m, 2 H), 7.50-7.56 (m, 1H), 8.00 (d, 1 H, J = 8.0 Hz), 8.08 (d, 1H, J = 8.0 Hz), and 10.61 (d, 1H, J = 5.7 Hz). 13C NMR (DMSO-d6) δ28.72 (3xC), 30.94, 44.90, 50.59, 56.03, 62.49, 72.63, 76.78, 96.30, 121.17, 121.53, 124.92, 126.31, 131.82, 150.30, 157.46, 158.19, 159.94 and 163.11. | 464.3 | H |
| 429 | 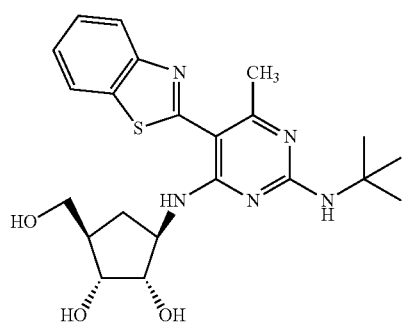 [SMILES: Cc1nc(NC(C)(C)C)nc(N[C@@H]2C[C@H](CO)[C@@H](O)[C@H]2O)c1-c1nc2ccccc2s1] | A | 1H NMR (DMSO-d6) δ 1.23-1.30 (m, 1H), 1.41 (s, 9H), 1.93-2.00 (m, 1H), 2.30-2.38 (m, 1H), 2.53 (s, 3H), 3.37-3.50 (m, 2H), 3.73-3.78 (m, 2H), 4.26-4.32 (m, 1H), 4.49 (br. s, OH), 4.65 (br. s, OH), 4.59 (t, OH, J = 5.1 Hz), 6.71 (br. s, NH), 7.34-7.40 (m, 1 H), 7.46-7.51 (m, 1H), 7.96 (d, 1 H, J = 8.0 Hz), 8.05 (d, 1H, J = 8.0 Hz), and 9.77 (br. s, NH). | 444.2 | O |

| | | | | | |
|---|---|---|---|---|---|
| 430 | 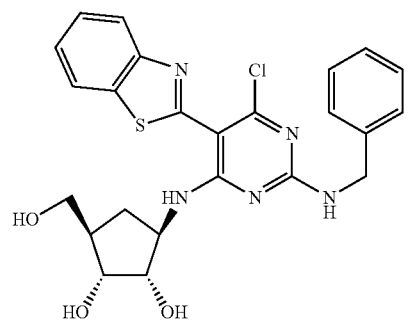 | A | 1H NMR (DMSO-d6) δ 1.12-1.22 (m, 1H), 1.93-2.01 (m, 1H), 2.19-2.26 (m, 1H), 3.40-3.50 (m, 2H), 3.73-3.83 (m, 2H), 4.28-4.34 (m, 1H), 4.45-4.59 (m, 3H), 4.63 (t, OH, J = 5.2 Hz), 4.67 (d, OH, J = 5.3 Hz), 7.19-7.26 (m, 1H), 7.29-7.45 (m, 5H), 7.49-7.55 (m, 1H), 8.00 (d, 1 H, J = 8.0 Hz), 8.08 (d, 1H, J = 8.0 Hz), 8.31 (t, NH, J = 6.0 Hz) and 10.53 (d, NH, J = 6.5 Hz). 13C NMR (DMSO-d6) δ 30.32, 44.23, 44.99, 55.97, 62.42, 72.37, 76.51, 97.20, 121.17, 121.57, 124.97, 126.31, 126.70, 127.53 (2xC), 128.19 (2xC), 132.81, 139.85, 150.28, 157.88, 158.69, 160.32 and 162.94. | 498.3 | H |
| 431 | 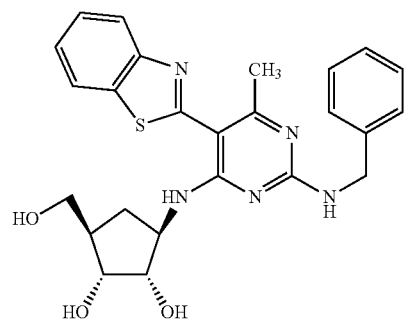 [SMILES: Cc1nc(NCc2ccccc2)nc(N[C@@H]2C[C@H](CO)[C@@H](O)[C@H]2O)c1-c1nc2ccccc2s1] | A | | 478.3 | O |

| | | | | | |
|---|---|---|---|---|---|
| 432 | 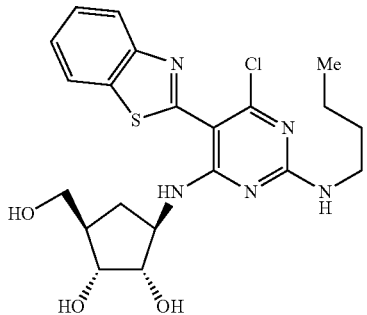 [SMILES: CCCCNc1nc(Cl)c(-c2nc3ccccc3s2)c(N[C@@H]2C[C@H](CO)[C@@H](O)[C@H]2O)n1] | A | 1H NMR (DMSO-d6) δ 0.91 (t, 3H, J = 7.3 Hz), 1.22-1.28 (m, 1H), 1.30-1.39 (m, 2H), 1.48-1.58 (m, 2H), 1.93-2.03 (m, 1H), 2.31-2.43 (m, 1H), 3.25-3.37 (m, 2H), 3.40-3.51 (m, 2H), 3.74-3.80 (m, 1H), 3.82-3.86 (m, 1H), 4.28-4.38 (m, 1H), 4.52 (d, OH, J = 4.8 Hz), 4.64 (t, OH, J = 5.1 Hz), 4.69 (d, OH, J = 5.4 Hz), 7.40-7.46 (m, 1H), 7.50-7.56 (m, 1H), 7.77 (d, NH, J = 5.4 Hz), 8.00 (d, 1 H, J = 8.0 Hz), 8.08 (d, 1H, J = 8.0 Hz), and 10.60 (d, NH, J = 6.3 Hz). 13C NMR (DMSO-d6) δ13.63, 19.52, 30.48, 30.87, 40.25, 44.94, 56.03, 62.48, 72.38, 76.50, 96.69, 121.09, 121.42, 124.83, 126.24, 132.69, 150.22, 157.68, 158.65, 160.31 and 163.02. | 464.3 | H |
| 433 | 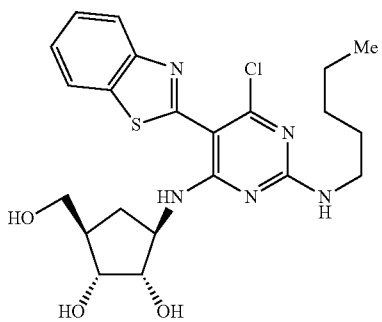 [SMILES: CCCCCNc1nc(Cl)c(-c2nc3ccccc3s2)c(N[C@@H]2C[C@H](CO)[C@@H](O)[C@H]2O)n1] | A | 1H NMR (DMSO-d6) δ 0.87 (t, 3H, J = 6.5 Hz), 1.21-1.37 (m, 5H), 1.49-1.60 (m, 2H), 1.93-2.03 (m, 1H), 2.30-2.43 (m, 1H), 3.25-3.39 (m, 2H), 3.40-3.50 (m, 2H), 3.74-3.80 (m, 1H), 3.82-3.86 (m, 1H), 4.28-4.38 (m, 1H), 4.52 (d, OH, J = 4.9 Hz), 4.65 (t, OH, J = 5.3 Hz), 4.69 (d, OH, J = 5.4 Hz), 7.40-7.46 (m, 1H), 7.50-7.55 (m, 1H), 7.78 (d, NH, J = 5.7 Hz), 8.00 (d, 1 H, J = 8.0 Hz), 8.08 (d, 1H, J = 8.0 Hz), and 10.60 (d, NH, J = 6.3 Hz). | 478.3 | H |
| 434 | 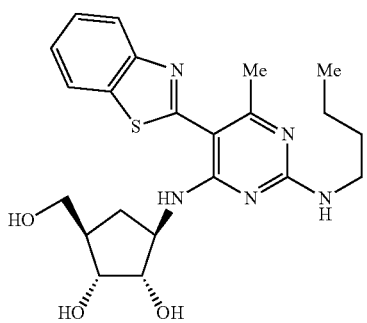 | A | | 444.2 | O |

TABLE I-continued
| 435 | 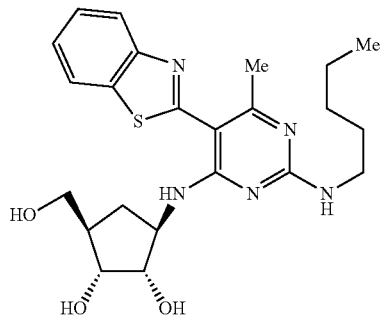 [SMILES: CCCCCNc1nc(C)c(-c2nc3ccccc3s2)c(N[C@@H]2C[C@H](CO)[C@@H](O)[C@H]2O)n1] | A | | 458.3 | O |
|---|---|---|---|---|---|
| 436 | | A | 1H NMR (DMSO-d6) δ 0.92 (s, 9H), 1.24-1.32 (m, 1H), 1.93-2.05 (m, 1H), 2.33-2.44 (m, 1H), 3.17-3.28 (m, 2H), 3.40-3.53 (m, 2H), 3.74-3.86 (m, 2H), 4.26-4.32 (m, 1H), 4.54 (d, OH, J = 5.1 Hz), 4.60-4.67 (m, 2x OH), 7.39-7.40 (m, 1H), 7.49-7.56 (m, 1H), 7.80 (t, NH, J = 6.4 Hz), 7.99 (d, 1 H, J = 8.0 Hz), 8.08 (d, 1H, J = 8.0 Hz), and 10.57 (d, 1H, J = 6.3 Hz). 13C NMR (DMSO-d6) 827.36 (3xC), 30.56, 32.51, 44.84, 51.61, 55.96, 62.31, 72.47, 76.56, 96.77, 121.09, 121.42, 124.83, 126.24, 132.66, 150.22, 157.67, 159.36, 160.11 and 162.97. | 478.3 | H |
| 437 | 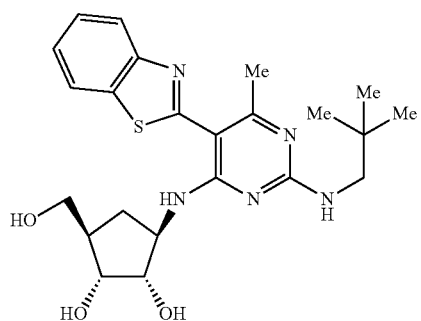 [SMILES: Cc1nc(NCC(C)(C)C)nc(N[C@@H]2C[C@H](CO)[C@@H](O)[C@H]2O)c1-c1nc2ccccc2s1] | A | 1H NMR (DMSO-d6) δ 0.90 (s, 9H), 1.16-1.31 (m, 1H), 1.93-2.04 (m, 1H), 2.32-2.45 (m, 1H), 2.56 (s, 3H), 3.16-3.30 (m, 2H), 3.38-3.54 (m, 2H), 3.70-3.86 (m, 2H), 4.22-4.33 (m, 1H), 4.51-4.73 (m, 3x OH), 7.24 (br. s, NH), 7.36-7.42 (m, 1H), 7.49-7.54 (m, 1H), 7.98 (d, 1 H, J = 8.0 Hz), 8.07 (d, 1H, J = 8.0 Hz), and 9.82 (d, 1H, J = 5.0 Hz). | 458.3 | O |

| | | | | | |
|---|---|---|---|---|---|
| 438 | 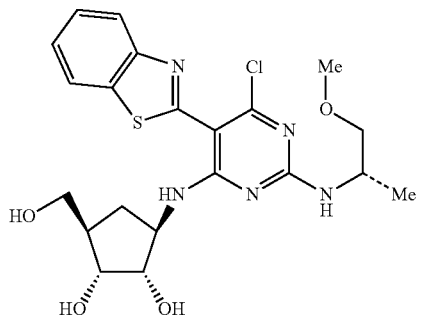 [SMILES: COC[C@H](C)Nc1nc(Cl)c(-c2nc3ccccc3s2)c(N[C@@H]2C[C@H](CO)[C@@H](O)[C@H]2O)n1] | A | 1H NMR (DMSO-d6) δ 1.15 (d, 3H, J = 6.6 Hz), 1.20-1.29 (m, 1H), 1.93-2.03 (m, 1H), 2.31-2.43 (m, 1H), 3.29 (s, 3H), @3.30 (m, 1H), 3.41-3.51 (m, 3H), 3.73-3.79 (m, 1H), 3.81 (m, 1H), 4.16-4.24 (m, 1H), 4.26-4.33 (m, 1H), 4.52 (d, OH, J = 4.1 Hz), 4.65 (t, OH, J = 4.3 Hz), 4.68 (d, OH, J = 4.3 Hz), 7.40-7.46 (m, 1H), 7.50-7.56 (m, 1H), 7.65 (d, NH, J = 7.8 Hz), 8.01 (d, 1 H, J = 8.0 Hz), 8.09 (d, 1H, J = 8.0 Hz), and 10.6 (d, 1H, J = 6.2 Hz). | 480.3 | H |
| 439 | 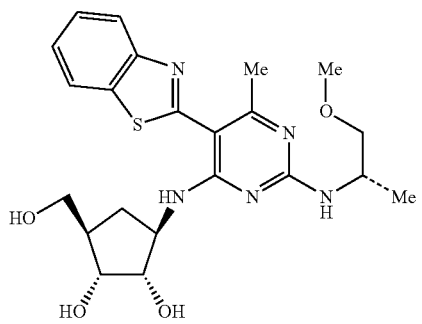 [SMILES: COC[C@H](C)Nc1nc(C)c(-c2nc3ccccc3s2)c(N[C@@H]2C[C@H](CO)[C@@H](O)[C@H]2O)n1] | A | 1H NMR (DMSO-d6) δ 1.14 (d, 3H, J = 6.7 Hz), @ 1.20 (m, 1H), 1.92-2.01 (m, 1H), 2.28-2.41 (m, H), 2.56 (s, 3H), 3.23-3.30 (m, 1H), 3.28 (s, 3H), 3.37-3.51 (m, 3H), 3.70-3.81 (m, 2H), 4.17-4.33 (m, 2H), 4.46 (br. s, OH), 4.57-4.63 (m, 2x OH), 7.03 (br. s, NH), 7.37-7.42 (m, 1H), 7.49-7.54 (m, 1H), 7.98 (d, 1 H, J = 7.9 Hz), 8.07 (d, 1H, J = 7.9 Hz), and 9.79 (br. s, NH). | 460.3 | O |
| 440 | 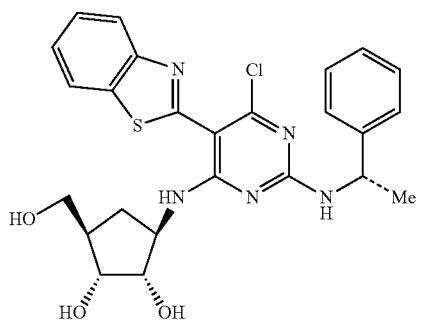 [SMILES: C[C@H](Nc1nc(Cl)c(-c2nc3ccccc3s2)c(N[C@@H]2C[C@H](CO)[C@@H](O)[C@H]2O)n1)c1ccccc1] | B | 1H NMR (DMSO-d6) δ 1.22-1.29 (m, 1H), 1.46 (d, 3H, J = 7.0 Hz), 2.00-2.09 (m, 1H), 2.44-2.53 (m, 1H), 3.40-3.54 (m, 2H), 3.71-3.80 (m, 2H), 4.20-4.28 (m, 1H), 4.52 (d, OH, J = 4.6 Hz), 4.55 (d, OH, J = 4.6 Hz), 4.67 (t, OH, J = 5.0 Hz), 5.08-5.18 (m, 1H), 7.17-7.24 (m, 1H), 7.28-7.37 (m, 2H), 7.39-7.47 (m, 3H), 7.49-7.55 (m, 1H), 8.00 (d, 1 H, J = 8.0 Hz), 8.08 (d, 1H, J = 8.0 Hz), 8.35 (d, NH, J = 8.0 Hz) and 10.6 (d, 1H, J = 6.2 Hz). | 512.3 | H |

TABLE I-continued
| | | | | | |
|---|---|---|---|---|---|
| 441 | 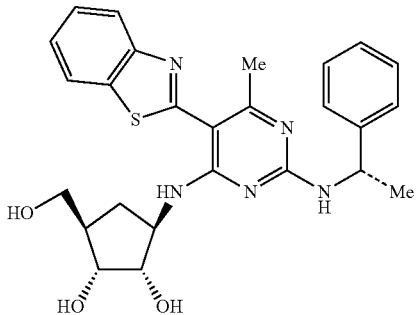 [SMILES: Cc1nc(N[C@@H](C)c2ccccc2)nc(N[C@@H]2C[C@H](CO)[C@@H](O)[C@H]2O)c1-c1nc2ccccc2s1] | — | 1H NMR (DMSO-d6) δ 1.22-1.28 (m, 1H), 1.45 (d, 3H, J = 7.0 Hz), 1.99-2.08 (m, 1H), 2.42-2.51 (m, 1H), 2.52 (s, 3H), 3.39-3.57 (m, 2H), 3.67-3.76 (m, 2H), 4.19-4.28 (m, 1H), 4.42 (br. s, OH), 4.50 (br. s, OH), 4.61 (br. s, OH), 5.10-5.19 (m, 1H), 7.16-7.22 (m, 1H), 7.25-7.33 (m, 2H), 7.36-7.54 (m, 4H), 7.79 (d, NH, J = 8.0 Hz), 7.97 (d, 1 H, J = 7.8 Hz), 8.06 (d, 1H, J = 7.9 Hz) and 9.69 (d, 1H, J = 4.5 Hz). | 492.3 | O |
| 501 | 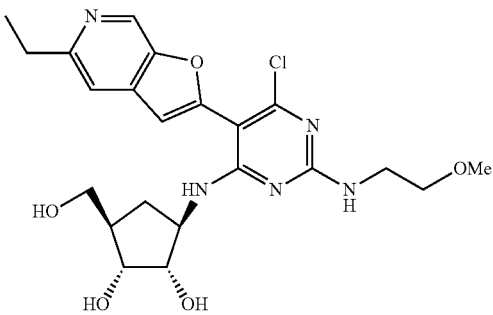 [SMILES: CCc1cc2cc(-c3c(Cl)nc(NCCOC)nc3N[C@@H]3C[C@H](CO)[C@@H](O)[C@H]3O)oc2cn1] | A | 1H NMR (DMSO-d6) δ 0.98-1.06 (m, 1H), 1.2-1.3 (t, 3H), 1.78-1.87 (m, 1H), 2.04- 2.2 (m, 1H), 2.79- 2.84 (m, 2H), 3.22-3.25 (s, 3H), 3.40-3.50 (m, 4H), 3.60-3.70 (m, 2H), 4.20-4.38 (m, 2H), 4.45-4.50 (m, 2H), 6.50-6.7 (m, 1 H), 6.95-6.97 (s, 1 H), 7.25-7.45 (m, 1 H), 7.5- 7.7 (m, 1 H) and 8.78-8.8 (m, 1H). | 478.3 | Q |
| 502 | 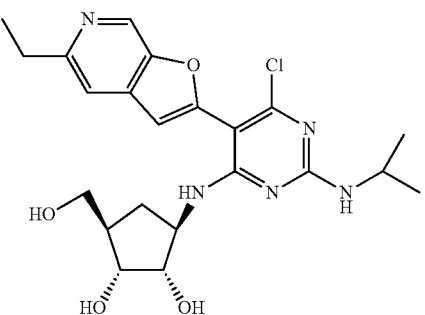 [SMILES: CCc1cc2cc(-c3c(Cl)nc(NC(C)C)nc3N[C@@H]3C[C@H](CO)[C@@H](O)[C@H]3O)oc2cn1] | A | 1H NMR (DMSO-d6) δ 0.98-1.06 (m, 7H), 1.2-1.3 (t, 3H), 1.78- 1.87 (m, 1H), 2.04- 2.2 (m, 1H), 2.79- 2.84 (m, 2H), 3.0-3.1 (m, 1H), 3.59-3.65 (m, 2H), 3.70-3.80 (m, 2H), 4.20-4.4 (m, 2H), 4.45-4.60 (m, 2H), 6.60- 6.7 (m, 1 H), 6.95-6.97 (s, 1 H), 7.35-7.45 (m, 1 H), 7.5- 7.6 (m, 1 H) and 8.78-8.8 (m, 1H). | 462.3 | Q |
| 503 | 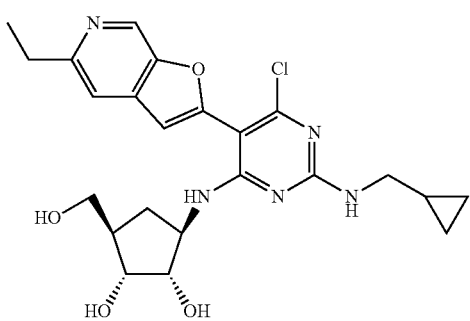 [SMILES: CCc1cc2cc(-c3c(Cl)nc(NCC4CC4)nc3N[C@@H]3C[C@H](CO)[C@@H](O)[C@H]3O)oc2cn1] | A | 1H NMR (DMSO-d6) δ 0.19-0.22 (m, 2H), 0.38-0.44 (m, 2H), 1.0-1.1 (m, 1H), 1.2-1.3 (t, 3H), 1.32-1.36 (m, 1H), 1.78-1.87 (m, 1H), 2.04- 2.2 (m, 1H), 2.75-2.85 (m, 2H), 3.1-3.2 (m, 2H), 3.59-3.75 (m, 2H), 4.20-4.4 (m, 2H), 4.45-4.55 (m, 2H), 6.50-6.65 (m, 1 H), 6.95-7.0 (s, 1 H), 7.40-7.58 (m, 1 H), 7.5- 7.6 (m, 1 H) and 8.75-8.8 (m, 1H). | 474.3 | Q |

| | | | | | |
|---|---|---|---|---|---|
| 504 | 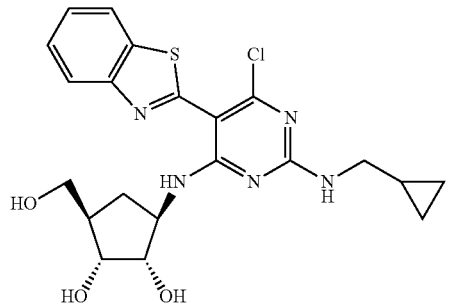 [SMILES: OC[C@H]1C[C@@H](Nc2nc(NCC3CC3)nc(Cl)c2-c2nc3ccccc3s2)[C@H](O)[C@@H]1O] | A | 1H NMR (DMSO-d6) δ 0.2-0.25 (m, 2H), 0.4-0.45 (m, 2H), 1.0-1.15 (m, 1H), 1.15-1.3 (m, 1H), 1.9-2.05 (m, 1H), 2.3-2.42 (m, 1H), 3.1-3.25 (m, 2H), 3.40-3.5 (m, 2H), 3.72-3.85 (m, 2H), 4.25-4.4 (m, 1H), 4.4-4.5 (m, 1H), 4.6-4.7 (m, 2H), 7.4-7.55 (m, 2 H), @7.6, 7.8 and 8.2 (m, NHCH2cyclopropyl), 7.95-8.1 (m, 2H), 10.55-10.6 (m, 1H). | 462.3 | H |
| 505 | 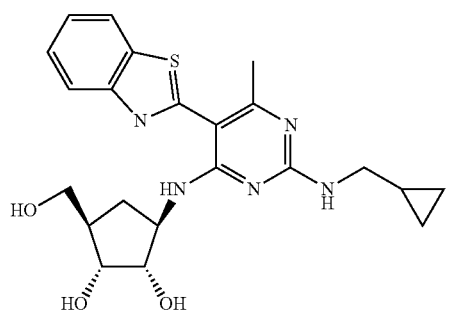 | A | 1H NMR (DMSO-d6) δ 0.2-0.25 (m, 2H), 0.4-0.45 (m, 2H), 1-0-1.15 (m, 1H), 1.15-1.3 (m, 1H), 1.9-2.05 (m, 1H), 2.3-2.42 (m, 1H), 2.55 (s, 3H), 3.1-3.25 (m, 2H), 3.40-3.5 (m, 2H), 3.72-3.85 (m, 2H), 4.25-4.4 (m, 1H), 4.4-4.5 (m, 1H), 4.6-4.7 (m, 2H), 7.25-7.55 (m, 2 H), 7.85-8.0 (m, NHCH2cyclopropyl), 8.0-8.1 (m, 2H), 9.4-9.8 (m, 1H). | 442.2 | I |
| 506 | 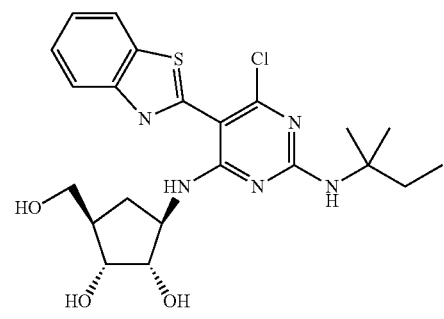 | A | 1H NMR (DMSO-d6) δ 0.79-0.80 (t, 3H), 1.0-1.15 (m, 2H), 1.35 (s, 6H), 1.8-2.05 (m, 2H), 2.3- 2.42 (m, 1H), 3.4-3.5 (m, 3H), 3.75-3.85 (m, 2H), 4.2-4.6 (m, 1H), 4.6-4.7 (m, 2H), 7.25 (bs, 1H), 7.39-7.55 (m, 2H), 7.95-8.1 (m, 2H), 10.6 (bs, 1H) | 478.3 | H |
| 507 | 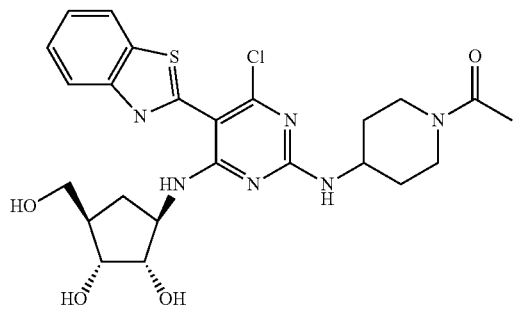 | A | 1H NMR (DMSO-d6) δ 1.25-1.45 (m, 2H), 1.8-2.0 (m, 4 H), 2.0 (s, 3H), 2.3-2.4 (m, 1H), 2.6-2.8 (m, 1H), 3.0-3.2 (m, 1H), 3.4-3.55 (m, 2H), 3.75-3.85 (m, 4H), 3.9-4.0 (m, 1H), 4.2-4.5 (m, 3H), 4.6-4.7 (m, 2H), 7.4-7.6 (m, 2H), 7.8-7.82 (m, 1H), 8.0-8.1 (m, 2H), 10.2-10.6 (m, 1H). | 533.3 | H |

TABLE I-continued
| | | | | | |
|---|---|---|---|---|---|
| 508 | 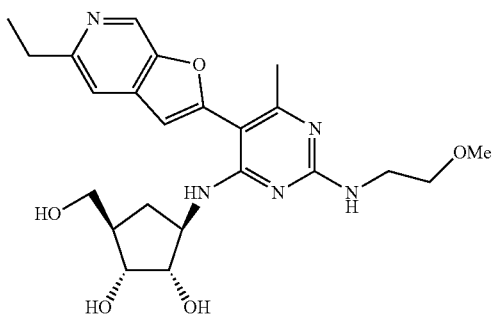 [SMILES: CCc1cc2cc(-c3c(C)nc(NCCOC)nc3N[C@@H]3C[C@H](CO)[C@@H](O)[C@H]3O)oc2cn1] | A | 1H NMR (DMSO-d6) δ 1.0-1.1 (m, 1H), 1.2-1.3 (t, 3H), 1.78-1.87 (m, 1H), 2.05 (s, 3H), 2.04-2.2 (m, 1H), 2.79-2.84 (m, 2H), 3.22-3.25 (s, 3H), 3.40-3.50 (m, 4H), 3.60-3.70 (m, 2H), 4.20-4.38 (m, 2H), 4.45-4.50 (m, 2H), 6.20-6.25 (m, 1 H), 6.85-6.90 (s, 1 H), 7.45-7.5 (m, 1H), 7.5-7.7 (m, 2 H) and 8.78-8.8 (m, 1H). | 458.3 | R |
| 509 | 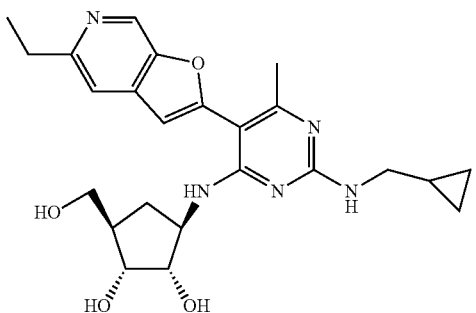 [SMILES: CCc1cc2cc(-c3c(C)nc(NCC4CC4)nc3N[C@@H]3C[C@H](CO)[C@@H](O)[C@H]3O)oc2cn1] | A | 1H NMR (DMSO-d6) δ 0.19-0.22 (m, 2H), 0.38-0.44 (m, 2H), 1.0-1.1 (m, 1H), 1.25 (m, 1H), 1.2-1.3 (t, 3H), 1.78-1.87 (m, 1H), 2.04-2.2 (m, 1H), 2.05 (s, 3H), 2.75-2.85 (m, 2H), 3.1-3.2 (m, 2H), 3.59-3.75 (m, 2H), 4.20-4.4 (m, 2H), 4.45-4.55 (m, 2H), 6.10-6.20 (m, 1 H), 6.85-6.9 (s, 1 H), 7.45-7.6 (m, 1 H), 7.5-7.6 (m, 1 H) and 8.75-8.8 (m, 1H). | 454.2 | R |
| 510 | 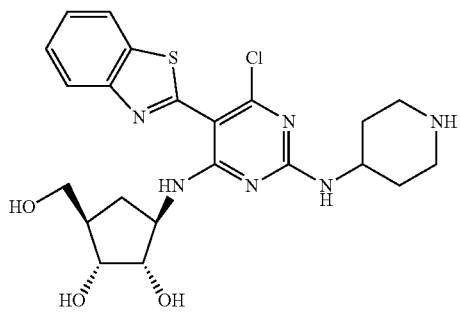 [SMILES: OC[C@H]1C[C@@H](Nc2nc(NC3CCNCC3)nc(Cl)c2-c2nc3ccccc3s2)[C@H](O)[C@@H]1O] | C | 1H NMR (DMSO-d6) δ 1.25-1.45 (m, 1H), 1.8-2.0 (m, 2 H), 2.0-2.2 (m, 2H), 2.3-2.4 (m, 1H), 3.0-3.2 (m, 2H), 3.4-3.55 (m, 4H), 3.75-3.85 (m, 2H), 3.9-4.0 (m, 1H), 4.2-4.5 (m, 2H), 7.4- 7.6 (m, 2H), 7.8-7.82 (m, 1H), 8.0-8.1 (m, 2H), 8.4-8.5 (bs, 1H), 8.6-8.8 (bs, 1H), 10.2-10.6 (m, 1H). | 491.3 | H |
| 511 | 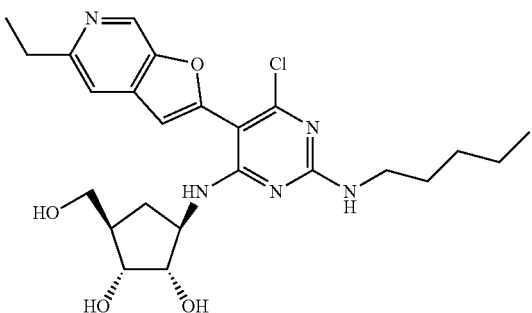 [SMILES: CCCCCNc1nc(Cl)c(-c2cc3cc(CC)ncc3o2)c(N[C@@H]2C[C@H](CO)[C@@H](O)[C@H]2O)n1] | A | 1H NMR (DMSO-d6) δ 0.8-0.9 (m, 3H), 1.0-1.1 (m, 1H), 1.2-1.4 (m, 7H), 1.4-1.6 (m, 2H), 1.8-2.2 (m, 2H), 2.75-2.85 (m, 2H), 3.2-3.25 (m, 2H), 3.6-3.8 (m, 2H), 4.2-4.4 (m, 2H), 4.45-4.55 (m, 2H), 6.5-6.65 (m, 1H), 6.95 (s, 1H), 7.45-7.5 (m, 2H), 8.75-8.8 (m, 1H). | 490.4 | Q |

| | | | | | |
|---|---|---|---|---|---|
| 512 | 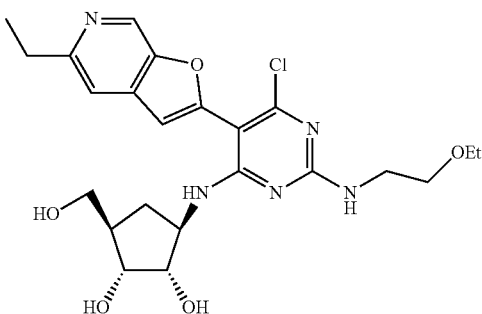 [SMILES: CCOCCNc1nc(Cl)c(-c2cc3cc(CC)ncc3o2)c(N[C@@H]2C[C@H](CO)[C@@H](O)[C@H]2O)n1] | A | 1H NMR (DMSO-d6) δ 1.0-1.1 (m, 4H), 1.1-1.15 (t, 3H), 1.2-1.25 (t, 3H), 1.8-1.85 (m, 1H), 2.0-2.2 (m, 1H), 2.8-2.85 (m, 2H), 3.35-3.5 (m, 5H), 3.6-3.75 (m, 2H), 4.2-4.4 (m, 2H), 4.45-4.55 (m, 2H), 6.5-6.7 (m, 1H), 6.95 (s, 1H), 7.2-7.4 (m, 1H), 7.5-7.55 (m, 1H), 8.8-8.85 (m, 1H). | 492.3 | Q |
| 513 | 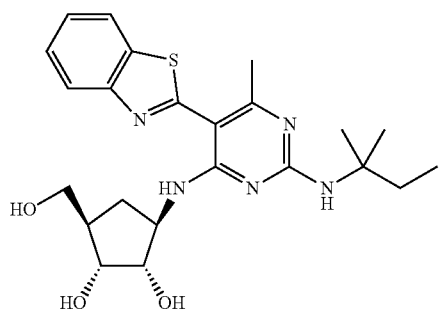 [SMILES: CCC(C)(C)Nc1nc(C)c(-c2nc3ccccc3s2)c(N[C@@H]2C[C@H](CO)[C@@H](O)[C@H]2O)n1] | A | 1H NMR (DMSO-d6) δ 0.79-0.80 (t, 3H), 1.1-1.25 (m, 1H), 1.35-1.4 (m, 7H), 1.8-1.9 (m, 1H), 1.9-2.0 (m, 1H), 2.3-2.42 (m, 1H), 2.5-2.55 (s, 3H), 3.34-3.5 (m, 2H), 3.75-3.8 (m, 2H), 4.2-4.3 (m, 1H), 4.45-4.65 (m, 3H), 7.35-7.4 (m, 1H), 7.45-7.5 (m, 1H), 7.55-7.65 (m, 1H), 7.95-8.1 (m, 2H), 8.2-8.25 and 9.8 (m, 1H) | 458.2 | I |
| 514 | 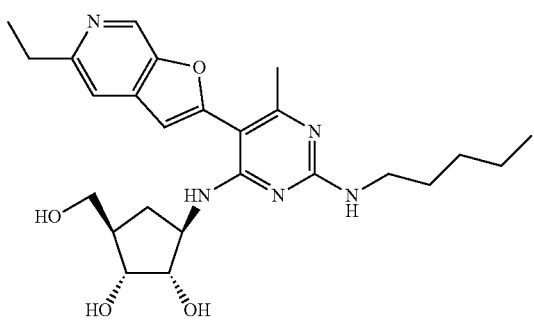 [SMILES: CCCCCNc1nc(C)c(-c2cc3cc(CC)ncc3o2)c(N[C@@H]2C[C@H](CO)[C@@H](O)[C@H]2O)n1] | A | 1H NMR (DMSO-d6) δ 0.8-0.9 (m, 3H), 1.0-1.1 (m, 1H), 1.2-1.4 (m, 7H), 1.4-1.6 (m, 2H), 1.8-1.9 (m, 1H), 2.05 (s, 3H), 2.1-2.2 (m, 1H), 2.75-2.85 (m, 2H), 3.2-3.25 (m, 2H), 3.6-3.7 (m, 2H), 4.2-4.35 (m, 2H), 4.45-4.55 (m, 2H), 6.2-6.3 (m, 1H), 6.85 (s, 1H), 7.45-7.5 (m, 2H), 8.75-8.8 (m, 1H). | 470.3 | R |
| 515 | 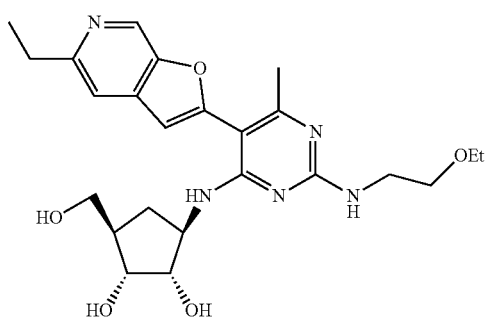 [SMILES: CCOCCNc1nc(C)c(-c2cc3cc(CC)ncc3o2)c(N[C@@H]2C[C@H](CO)[C@@H](O)[C@H]2O)n1] | A | 1H NMR (DMSO-d6) δ 1.0-1.1 (m, 1H), 1.1-1.15 (t, 3H), 1.2-1.25 (t, 3H), 1.8-1.85 (m, 1H), 2.0 (s, 3H), 2.0-2.2 (m, 1H), 2.8-2.85 (m, 2H), 3.35-3.5 (m, 6H), 3.6-3.75 (m, 2H), 4.2-4.4 (m, 1H), 4.45-4.55 (m, 2H), 6.2-6.3 (bs, 1H), 6.95 (s, 1H), 7.45-7.5 (m, 1H), 7.5-7.55 (m, 1H), 8.8-8.85 (m, 1H). | 472.3 | R |

TABLE I-continued

| | | | | | |
|---|---|---|---|---|---|
| 516 | (structure) | A | 1H NMR (DMSO-d6) δ 0.8-1.1 (m, 1H), 1.2-1.3 (m, 3H), 1.8-1.9 (m, 1H), 2.0-2.2 (m, 1H), 2.8-2.85 (m, 2H), 3.6-3.8 (m, 2H), 4.0-4.15 (m, 1H), 4.2-4.4 (m, 2H), 4.4-4.5 (m, 2H), 6.8-6.85 (bs, 1H), 7.0 (s, 1H), 7.2-7.4 (m, 1H), 7.5-7.55 (m, 1H), 8.8-8.85 (s, 1H). | 502.3 | Q |
| 517 | (structure) | A | 1H NMR (DMSO-d6) δ 1.0-1.1 (m, 1H), 1.2-1.3 (m, 3H), 1.8-1.9 (m, 1H), 2.05-2.1 (s, 3H), 2.1-2.35 (m, 1H), 2.8-2.85 (m, 2H), 3.3-3.4 (m, 2H), 3.6-3.8 (m, 2H), 4.0-4.25 (m, 2H), 4.2-4.5 (m, 2H), 4.4-4.5 (m, 2H), 6.3-6.4 (bs, 1H), 6.9 (s, 1H), 7.5 (m, 1H), 7.5-7.65 (m, 1H), 8.7-8.75 (s, 1H). | 482.3 | R |
| 518 | (structure) | A | | 476.3 | Q |
| 519 | (structure) | A | | 456.3 | R |
| 520 | (structure) | A | | 516.3 | Q |

TABLE I-continued

| | | | | |
|---|---|---|---|---|
| 521 | (structure) | A | 496.3 | R |
| 128 | (structure) | C | 496.3 | I |
| 129 | (structure) | A | 486.3 | H |
| 130 | (structure) | C | 466.3 | I |
| 131 | (structure) | A | 504.3 | H |

TABLE I-continued
| | | | | |
|---|---|---|---|---|
| 132 | 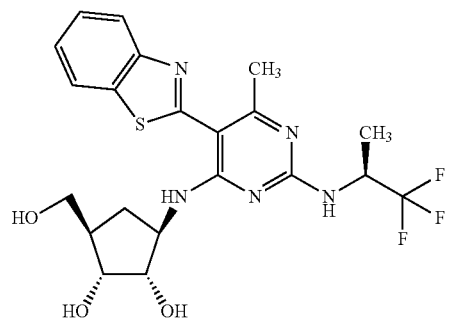 [SMILES: Cc1nc(N[C@@H](C)C(F)(F)F)nc(N[C@@H]2C[C@H](CO)[C@@H](O)[C@H]2O)c1-c1nc2ccccc2s1] | B | 484.3 | I |
| 133 | 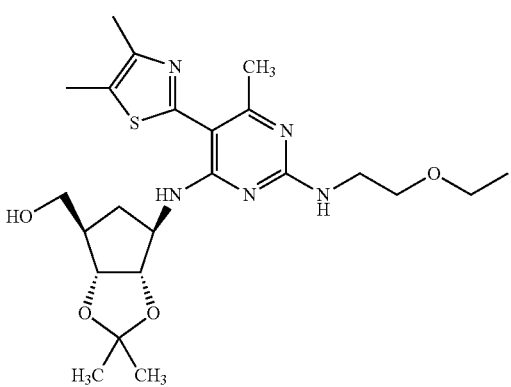 [SMILES: CCOCCNc1nc(C)c(-c2nc(C)c(C)s2)c(N[C@@H]2C[C@H](CO)[C@H]3OC(C)(C)O[C@H]32)n1] | C | 478.3 | Z (steps 4-6) |
| 134 | 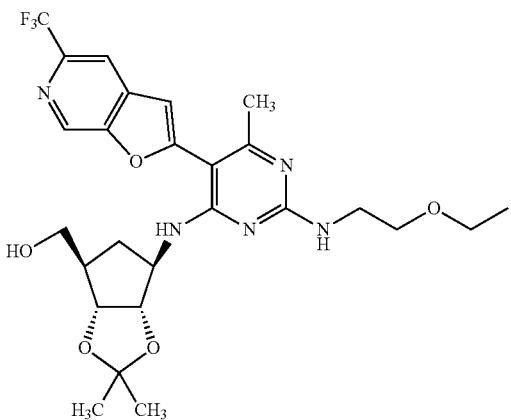 [SMILES: CCOCCNc1nc(C)c(-c2cc3cc(C(F)(F)F)ncc3o2)c(N[C@@H]2C[C@H](CO)[C@H]3OC(C)(C)O[C@H]32)n1] | C | 552.3 | Y |
| 135 | 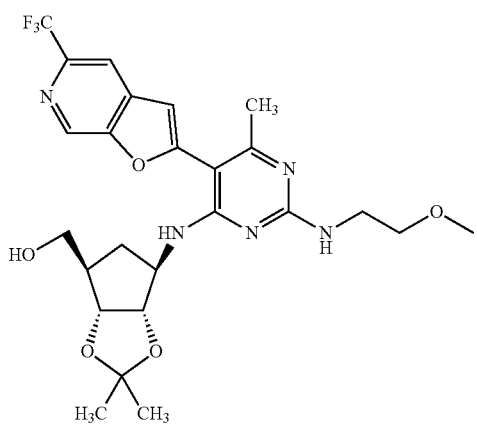 [SMILES: COCCNc1nc(C)c(-c2cc3cc(C(F)(F)F)ncc3o2)c(N[C@@H]2C[C@H](CO)[C@H]3OC(C)(C)O[C@H]32)n1] | C | 538.3 | Y |

TABLE I-continued
| | | | | |
|---|---|---|---|---|
| 136 | 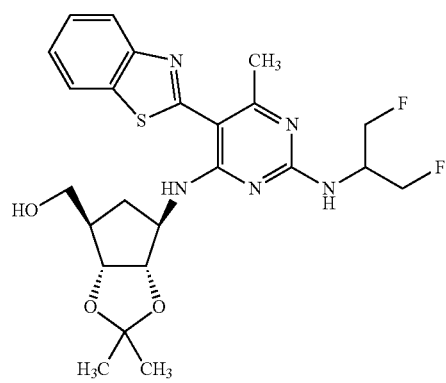 [SMILES: Cc1nc(NC(CF)CF)nc(N[C@@H]2C[C@H](CO)[C@H]3OC(C)(C)O[C@H]32)c1-c1nc2ccccc2s1] | B | 506.3 | Z3 |
| 137 | 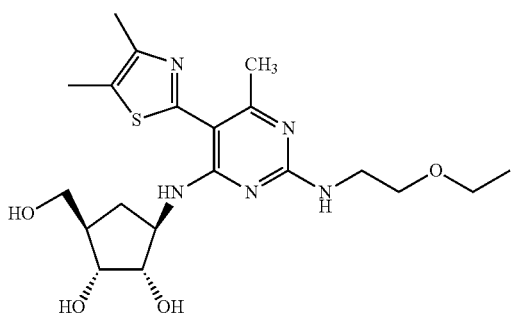 [SMILES: CCOCCNc1nc(C)c(-c2nc(C)c(C)s2)c(N[C@@H]2C[C@H](CO)[C@@H](O)[C@H]2O)n1] | B | 438.2 | Z (steps 4-7) |
| 138 | 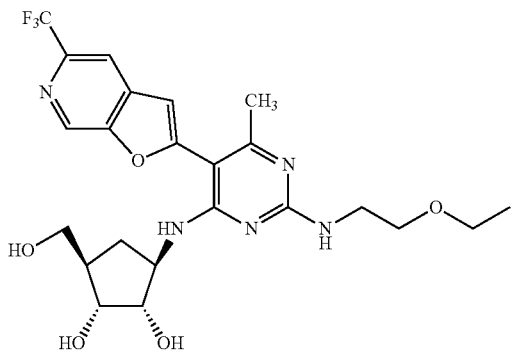 [SMILES: CCOCCNc1nc(C)c(-c2cc3cc(C(F)(F)F)ncc3o2)c(N[C@@H]2C[C@H](CO)[C@@H](O)[C@H]2O)n1] | A | 512.3 | Y |
| 139 | 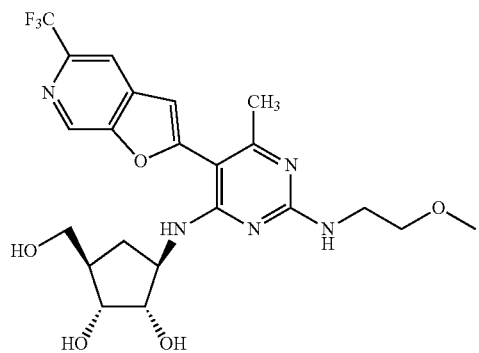 [SMILES: COCCNc1nc(C)c(-c2cc3cc(C(F)(F)F)ncc3o2)c(N[C@@H]2C[C@H](CO)[C@@H](O)[C@H]2O)n1] | B | 498.3 | Y |

TABLE I-continued
| | | | | |
|---|---|---|---|---|
| 140 | 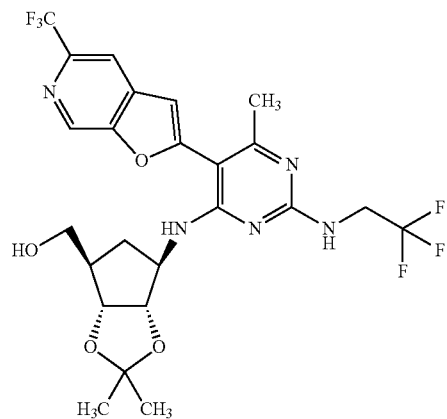 [SMILES: Cc1nc(NCC(F)(F)F)nc(N[C@@H]2C[C@H](CO)[C@H]3OC(C)(C)O[C@H]32)c1-c1cc2cc(C(F)(F)F)ncc2o1] | B | 562.3 | Y |
| 141 | 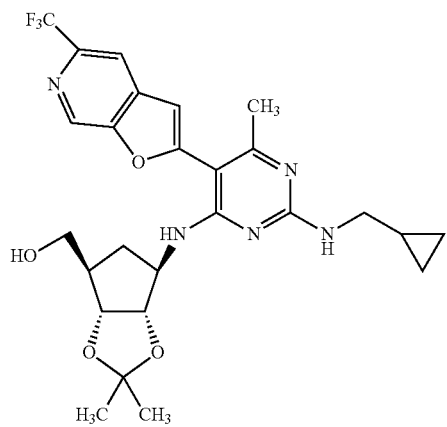 [SMILES: Cc1nc(NCC2CC2)nc(N[C@@H]2C[C@H](CO)[C@H]3OC(C)(C)O[C@H]32)c1-c1cc2cc(C(F)(F)F)ncc2o1] | B | 534.3 | Y |
| 142 | 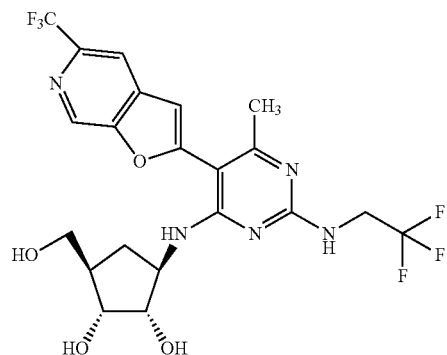 [SMILES: Cc1nc(NCC(F)(F)F)nc(N[C@@H]2C[C@H](CO)[C@@H](O)[C@H]2O)c1-c1cc2cc(C(F)(F)F)ncc2o1] | B | 522.3 | Y |
| 143 | 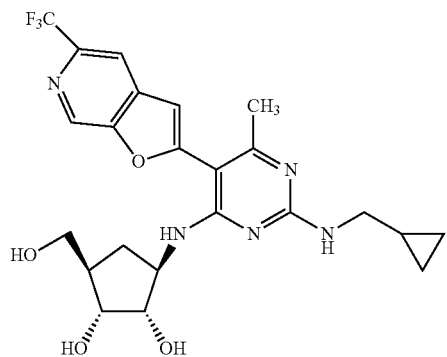 [SMILES: Cc1nc(NCC2CC2)nc(N[C@@H]2C[C@H](CO)[C@@H](O)[C@H]2O)c1-c1cc2cc(C(F)(F)F)ncc2o1] | B | 494.3 | Y |

TABLE I-continued
| | | | | | |
|---|---|---|---|---|---|
| 230 | 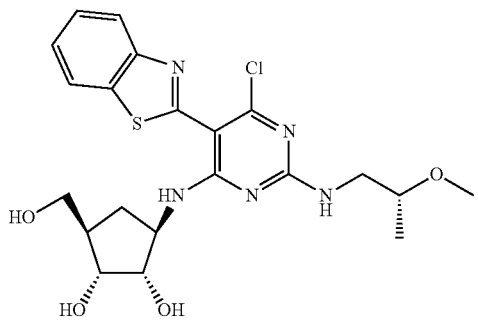 [SMILES: CO[C@H](C)CNc1nc(Cl)c(-c2nc3ccccc3s2)c(N[C@@H]2C[C@H](CO)[C@@H](O)[C@H]2O)n1] | | A | 480.3 | H |
| 231 | 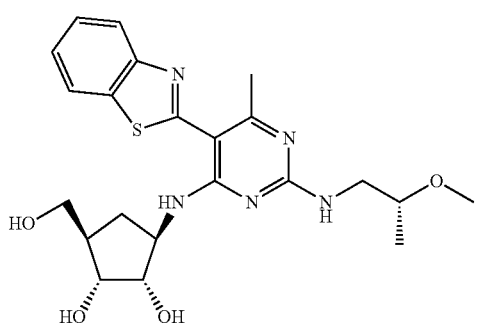 [SMILES: CO[C@H](C)CNc1nc(C)c(-c2nc3ccccc3s2)c(N[C@@H]2C[C@H](CO)[C@@H](O)[C@H]2O)n1] | | A | 460.3 | I |
| 232 | 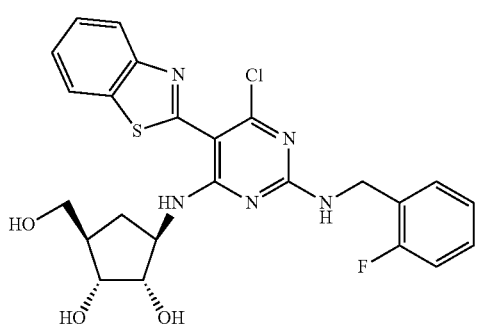 [SMILES: OC[C@H]1C[C@@H](Nc2nc(NCc3ccccc3F)nc(Cl)c2-c2nc3ccccc3s2)[C@H](O)[C@@H]1O] | | A | 1H NMR (DMSO) δ 1.04-1.22 (m, 1H), 1.88-2.00 (m, 1H), 2.11-2.20 (m, 1H), 3.40-3.48 (m, 1H), 3.72-3.81 (m, 1H), 4.22-4.38 (m, 1H), 4.47-4.57 (m, 2H), 4.60-4.75 (m, 2H), 7.13-7.22 (m, 2H), 7.25- 7.32 (m, 1 H), 7.39-7.57 (m, 2H), 7.95-8.04 (m, 1H), 8.06-8.13 (m, 1H), 8.26- 8.32 (m, 1H) 10.32-10.36 (m, 1 H). | | H |
| 233 | 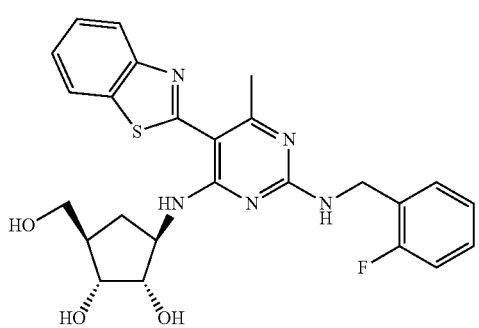 [SMILES: Cc1nc(NCc2ccccc2F)nc(N[C@@H]2C[C@H](CO)[C@@H](O)[C@H]2O)c1-c1nc2ccccc2s1] | | A | 1H NMR (DMSO) δ 0.98-1.23 (m, 1H), 1.89-1.99 (m, 1H), 2.07-2.24 (m, 1H), 2.49 (s, 3H), 3.38- 3.47 (m, 1H) 3.72- 3.81 (m, 1H), 4.18- 4.33 (m, 1H) 4.36- 4.53 (m, 1H), 4.53- 4.71 (m, 2H), 7.10- 7.18 (m, 1H), 7.20- 7.29 (m, 2H), 7.31- 7.44 (m, 2H), 7.46- 7.54 (m, 1H), 7.83- 7.93 (m, 1H), 7.93- 8.03 (m, 1H) 8.06 (d, 1H, J = 8.0 Hz) 9.65- 9.74 (m, 1 H). | 496.4 | I |

TABLE I-continued
| | | | | | |
|---|---|---|---|---|---|
| 234 | 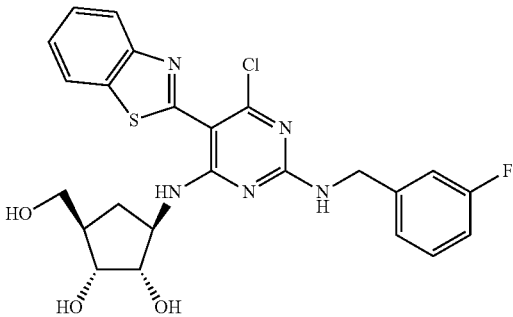 [SMILES: OC[C@H]1C[C@@H](Nc2nc(NCc3cccc(F)c3)nc(Cl)c2-c2nc3ccccc3s2)[C@H](O)[C@@H]1O] | A | 1H NMR (DMSO) δ 1.08-1.22 (m, 1H), 1.88-1.99 (m, 1H), 2.09-2.22 (m, 1H), 3.47-3.70 (m, 2H), 3.82-4.21 (m, 2H), 4.21-4.30 (m, 1H), 4.32-4.40 (m, 1H), 4.46-4.70 (m, 4H), 7.00-7.08 (m, 1H), 7.11-7.24 (m, 2H), 7.31-7.46 (m, 2H), 7.49-7.55 (m, 1H), 8.04-8.06 (m, 1H), 8.28-8.35 (m, 1H) 10.47-10.54 (m, 1 H). | 516.3 | H |
| 235 | 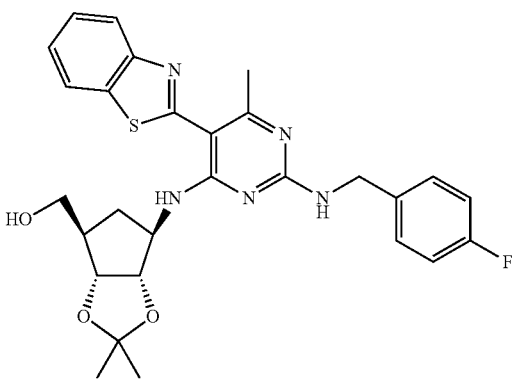 [SMILES: Cc1nc(NCc2ccc(F)cc2)nc(N[C@@H]2C[C@H](CO)[C@H]3OC(C)(C)O[C@H]32)c1-c1nc2ccccc2s1] | A | | 536.3 | Z3 |
| 236 | 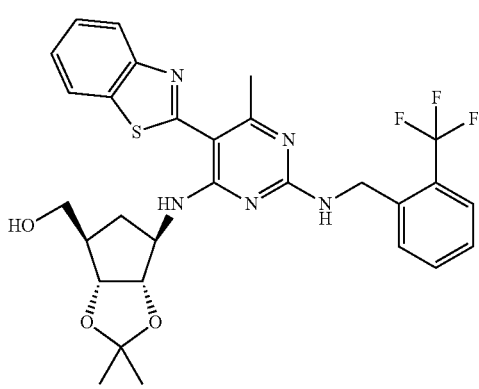 [SMILES: Cc1nc(NCc2ccccc2C(F)(F)F)nc(N[C@@H]2C[C@H](CO)[C@H]3OC(C)(C)O[C@H]32)c1-c1nc2ccccc2s1] | C | 1H NMR (CDCl3) δ 1.22 (s, 3H), 1.44 (s, 3H), 1.60-1.66 (m, 1H), 2.27-2.44 (m, 1H), 2.67 (s, 3H), 3.68-3.79 (m, 2H), 4.47-4.54 (m, 2H), 4.56-4.60 (m, 1H), 4.89-5.00 (m, 2H), 5.47-5.56 (m, 1H), 7.31-7.39 (m, 2H), 7.44-7.51 (m, 2H), 7.64-7.72 (m, 2H), 7.87 (d, 1H J = 8.0 Hz), 7.96 (d, 1H J = 8.0 Hz) 9.66-9.79 (m, 1H). | 586.3 | Z3 |
| 237 | 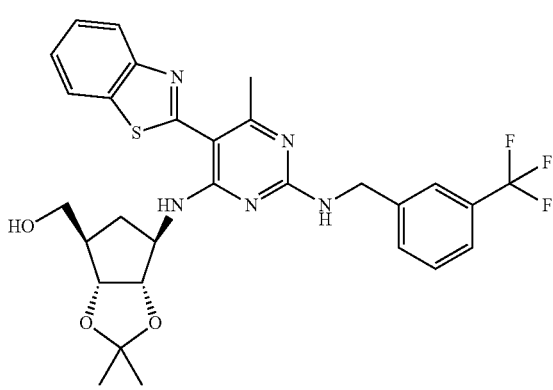 [SMILES: Cc1nc(NCc2cccc(C(F)(F)F)c2)nc(N[C@@H]2C[C@H](CO)[C@H]3OC(C)(C)O[C@H]32)c1-c1nc2ccccc2s1] | B | 1H NMR(CDCl3) δ 1.22 (s, 3H), 1.47 (s, 3H), 1.61-1.71 (m, 1H), 2.32-2.54 (m, 1H), 2.66 (s, 3H), 3.71-3.81 (m, 2H), 4.42-4.50 (m, 1H), 4.51-4.56 (m, 1H), 4.57-4.62 (m, 1H), 4.77-4.83 (m, 1H), 5.51-5.62 (m, 1H), 7.34-7.356 (m, 4H), 7.57-7.63 (m, 1H), 7.69-7.73 (m, 1H), 7.87 (m, 1H J = 8.0 Hz), 7.96 (d, 1H J = 8.0 Hz) 9.61-9.80 (m, 1H). | 586.3 | Z3 |

TABLE I-continued
| 238 | 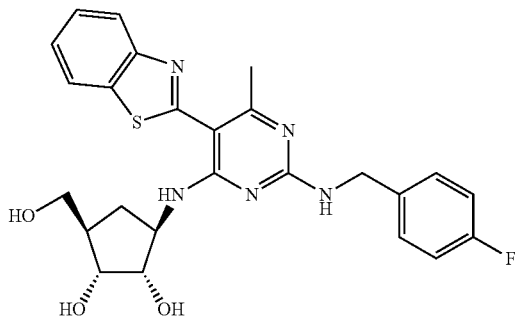 [SMILES: Cc1nc(NCc2ccc(F)cc2)nc(N[C@@H]2C[C@H](CO)[C@@H](O)[C@H]2O)c1-c1nc2ccccc2s1] | A | | 496.3 | Z3 |
| --- | --- | --- | --- | --- | --- |
| 239 | 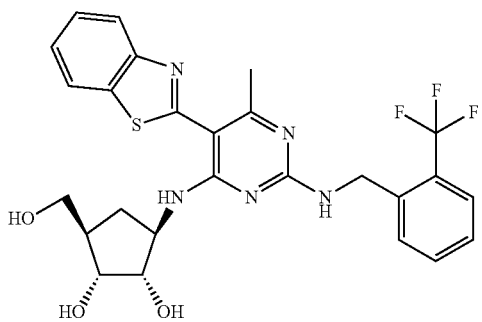 [SMILES: Cc1nc(NCc2ccccc2C(F)(F)F)nc(N[C@@H]2C[C@H](CO)[C@@H](O)[C@H]2O)c1-c1nc2ccccc2s1] | B | | 546.3 | Z3 |
| 240 | 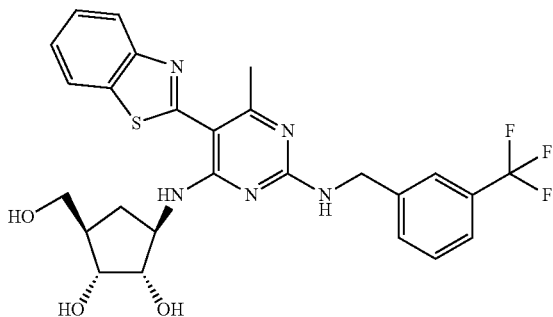 [SMILES: Cc1nc(NCc2cccc(C(F)(F)F)c2)nc(N[C@@H]2C[C@H](CO)[C@@H](O)[C@H]2O)c1-c1nc2ccccc2s1] | A | | 546.3 | Z3 |
| 241 | 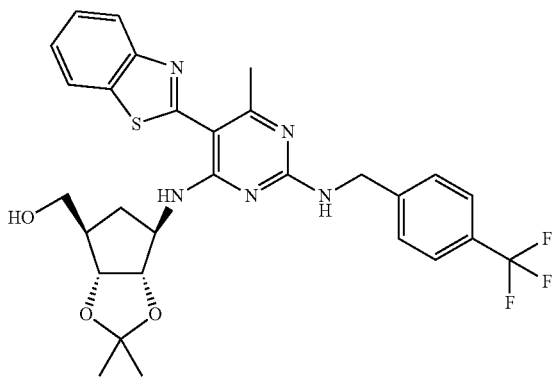 [SMILES: Cc1nc(NCc2ccc(C(F)(F)F)cc2)nc(N[C@@H]2C[C@H](CO)[C@H]3OC(C)(C)O[C@H]32)c1-c1nc2ccccc2s1] | B | 1H NMR (CDCl3) δ 1.22 (s, 3H), 1.46 (s, 3H), 1.62-1.68 (m, 1H), 2.29-2.47 (m, 1H), 2.67 (s, 3H), 3.70-3.80 (m, 2H), 4.40-4.60 (m, 3H), 4.73-4.86 (m, 2H), 5.42-5.66 (m, 1H), 7.33-7.40 (m, 1H), 7.44-7.60 (m, 5H), 7.87 (d, 1H J = 8.0 Hz), 7.96 (d, 1H J = 8.0 Hz) 9.59-9.76 (m, 1H). | 586.3 | Z3 |

| | | | | |
|---|---|---|---|---|
| 242 | 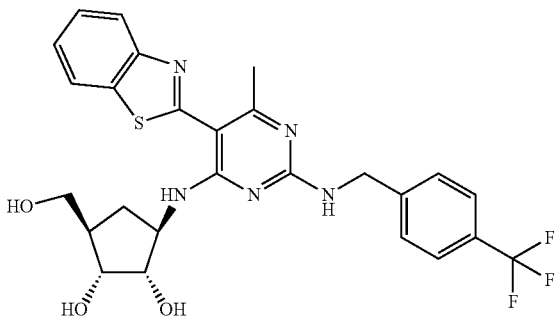 [SMILES: Cc1nc(NCc2ccc(C(F)(F)F)cc2)nc(N[C@@H]2C[C@H](CO)[C@@H](O)[C@H]2O)c1-c1nc2ccccc2s1] | A | | 546.3 | Z3 |
| 243 | 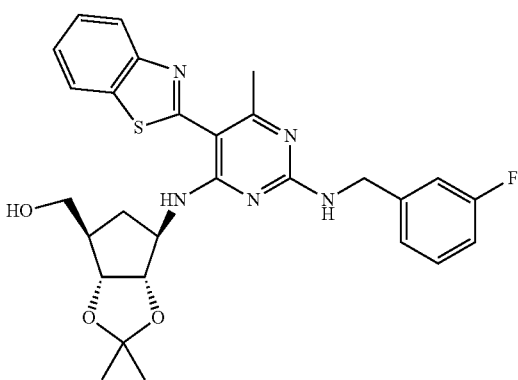 [SMILES: Cc1nc(NCc2cccc(F)c2)nc(N[C@@H]2C[C@H](CO)[C@H]3OC(C)(C)O[C@H]32)c1-c1nc2ccccc2s1] | A | 1H NMR (CDCl3) δ 1.24 (s, 3H), 1.48 (s, 3H), 1.59-1.72 (m, 1H), 2.31-2.50 (m, 2H), 2.66 (s, 3H), 3.70-3.80 (m, 2H), 4.44-4.56 (m, 2H), 4.56-4.61 (m, 1H), 4.65-4.81 (m, 2H), 5.51-5.62 (m, 1H), 6.89-6.97 (m, 1H), 7.09-7.19 (m, 2H), 7.32-7.33 (m, 1H), 7.39-7.45 (m, 1H), 7.69 (d, 1H J = 8.0 Hz), 7.93 (d, 1H J = 8.0 Hz), 9.62-9.77 (m, 1H). | 536.3 | Z3 |
| 244 | 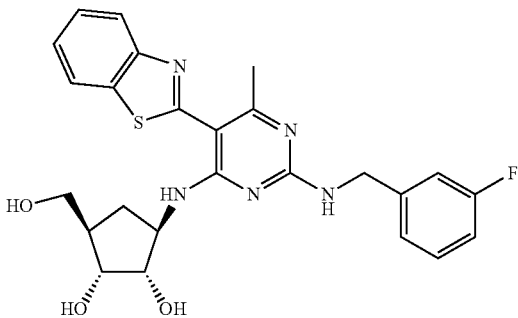 [SMILES: Cc1nc(NCc2cccc(F)c2)nc(N[C@@H]2C[C@H](CO)[C@@H](O)[C@H]2O)c1-c1nc2ccccc2s1] | A | | 496.3 | Z3 |
| 245 | 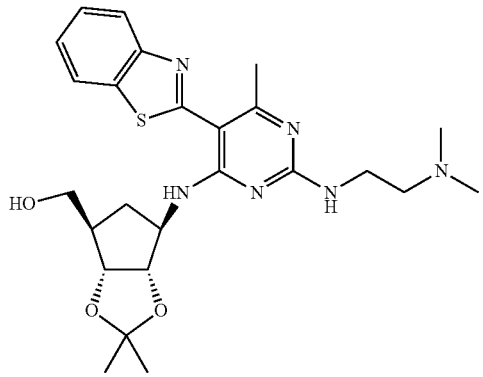 [SMILES: Cc1nc(NCCN(C)C)nc(N[C@@H]2C[C@H](CO)[C@H]3OC(C)(C)O[C@H]32)c1-c1nc2ccccc2s1] | C | | 499.3 | Z3 |

TABLE I-continued
| | | | | |
|---|---|---|---|---|
| 246 | 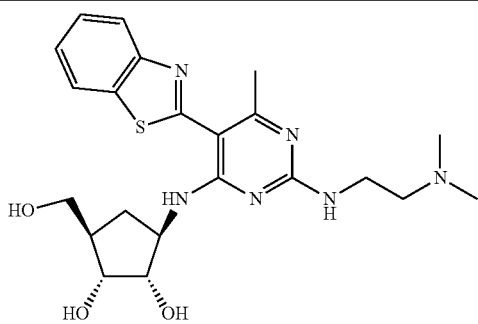 | C | 459.3 | Z3 |
| 247 | 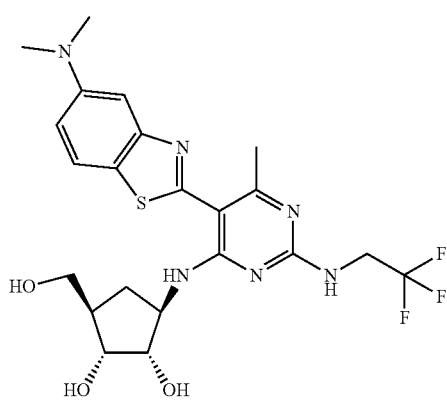 [SMILES: Cc1nc(NCC(F)(F)F)nc(N[C@@H]2C[C@H](CO)[C@@H](O)[C@H]2O)c1-c1nc2cc(N(C)C)ccc2s1] | A | 513.3 | Z (steps 4-7) |
| 248 | 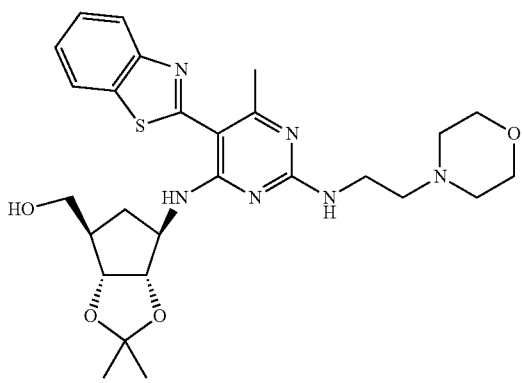 [SMILES: Cc1nc(NCCN2CCOCC2)nc(N[C@@H]2C[C@H](CO)[C@H]3OC(C)(C)O[C@H]32)c1-c1nc2ccccc2s1] | A | 541.3 | Z3 |
| 249 | 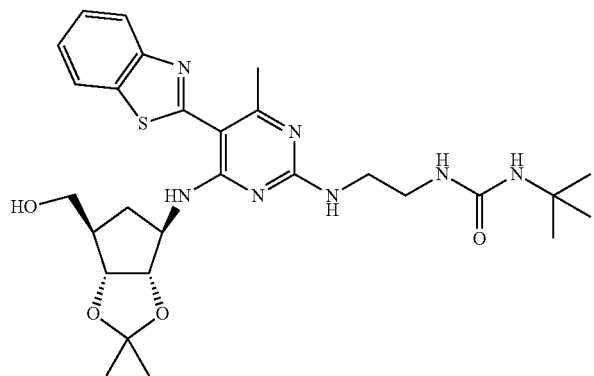 [SMILES: Cc1nc(NCCNC(=O)NC(C)(C)C)nc(N[C@@H]2C[C@H](CO)[C@H]3OC(C)(C)O[C@H]32)c1-c1nc2ccccc2s1] | C | 570.3 | Z3 |

| | | | | |
|---|---|---|---|---|
| 250 | 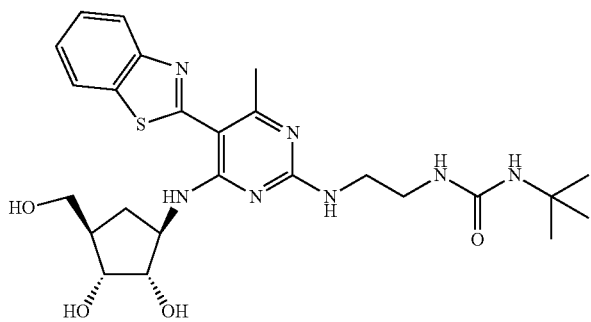 [SMILES: Cc1nc(NCCNC(=O)NC(C)(C)C)nc(N[C@@H]2C[C@H](CO)[C@@H](O)[C@H]2O)c1-c1nc2ccccc2s1] | B | | 530.3 | Z3 |
| 251 | 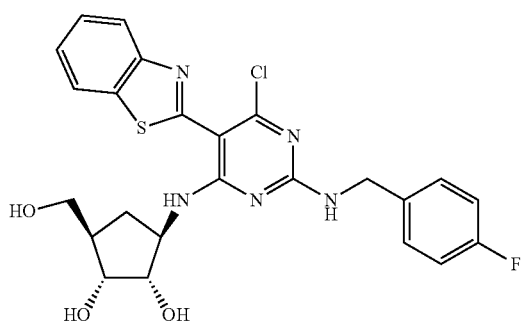 [SMILES: OC[C@H]1C[C@@H](Nc2nc(NCc3ccc(F)cc3)nc(Cl)c2-c2nc3ccccc3s2)[C@H](O)[C@@H]1O] | A | | 5156.3 | H |
| 252 | 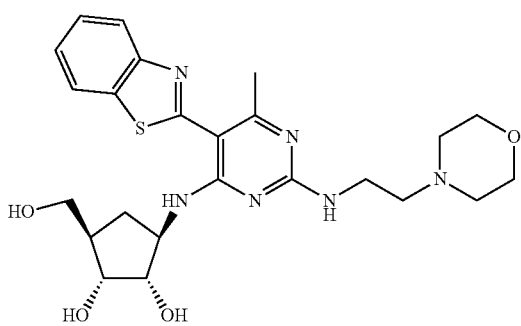 [SMILES: Cc1nc(NCCN2CCOCC2)nc(N[C@@H]2C[C@H](CO)[C@@H](O)[C@H]2O)c1-c1nc2ccccc2s1] | A | | 501.3 | Z3 |
| 253 | 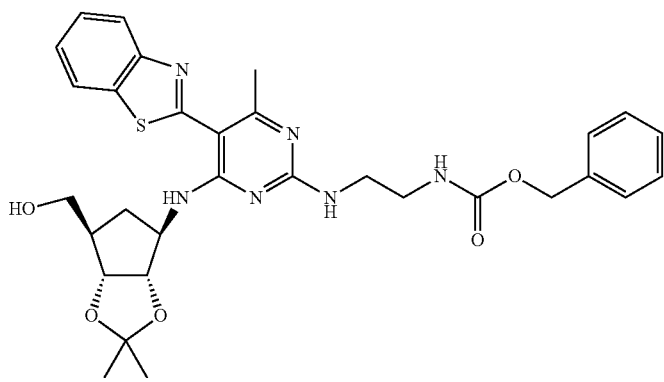 [SMILES: Cc1nc(NCCNC(=O)OCc2ccccc2)nc(N[C@@H]2C[C@H](CO)[C@H]3OC(C)(C)O[C@H]32)c1-c1nc2ccccc2s1] | B | 1H NMR (CDCl3) 1.26 (s, 3H), 1.47 (s, 3H), 1.63-1.81 (m, 1H), 2.33-2.46 (m, 2H), 2.46-2.56 (m, 1H), 2.65 (s, 3H), 3.42-3.48 (m, 2H), 3.49-3.57 (m, 1H), 3.62-3.72 (m, 2H), 4.40-4.54 (m, 2H), 4.57-4.64 (m, 1H), 4.65-4.81 (m, 2H), 5.00-5.14 (m, 2H), 5.36-5.45 (m, 1H), 5.79-6.04 (m, 1H), 7.29-7.34 (m, 6H), 7.34-7.40 (m, 3H). 7.45-7.50 (m, 2H), 7.87 (d, 1H J = 8.0 Hz), 7.96 (d, 1H J = 8.0 Hz), 9.71-9.86 (m, 1H). | 605.3 | Z3 |

TABLE I-continued
| | | | | |
|---|---|---|---|---|
| 254 | 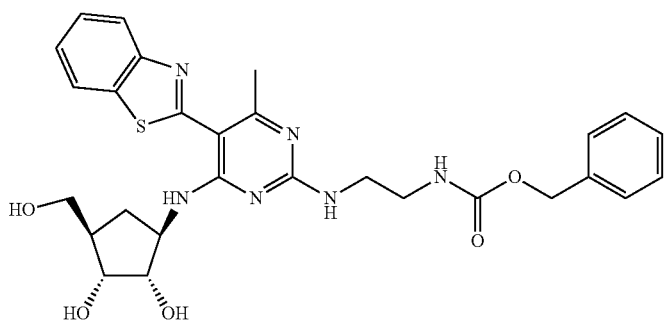 [SMILES: Cc1nc(NCCNC(=O)OCc2ccccc2)nc(N[C@@H]2C[C@H](CO)[C@@H](O)[C@H]2O)c1-c1nc2ccccc2s1] | B | 565.3 | Z3 |
| 255 | 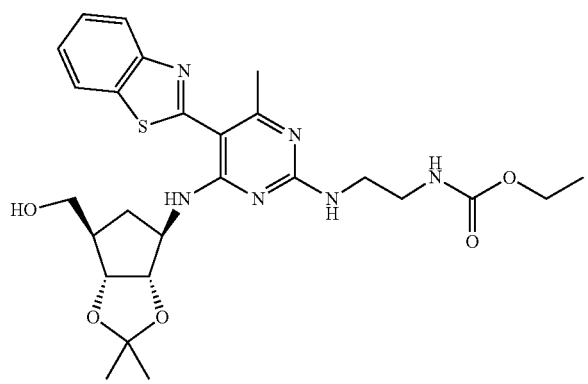 [SMILES: CCOC(=O)NCCNc1nc(C)c(-c2nc3ccccc3s2)c(N[C@@H]2C[C@H](CO)[C@H]3OC(C)(C)O[C@H]32)n1] | A | 543.3 | Z3 |
| 256 | 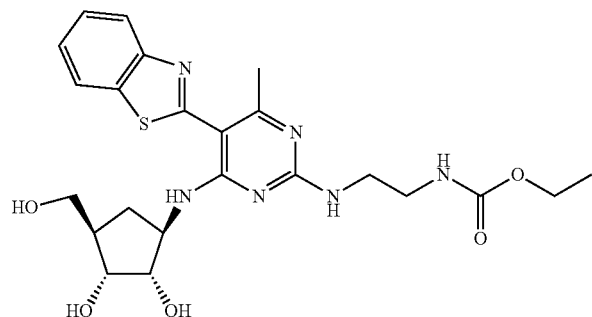 [SMILES: CCOC(=O)NCCNc1nc(C)c(-c2nc3ccccc3s2)c(N[C@@H]2C[C@H](CO)[C@@H](O)[C@H]2O)n1] | A | 503.3 | Z3 |
| 257 | 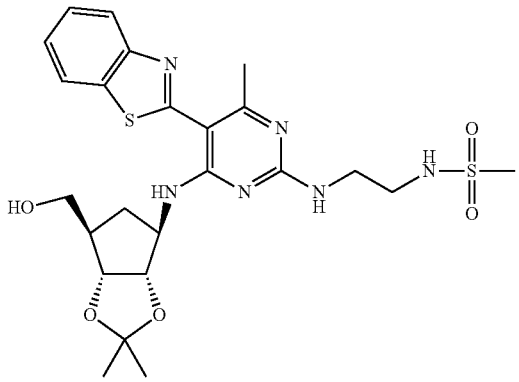 [SMILES: Cc1nc(NCCNS(C)(=O)=O)nc(N[C@@H]2C[C@H](CO)[C@H]3OC(C)(C)O[C@H]32)c1-c1nc2ccccc2s1] | A | 549.3 | Z3 |

TABLE I-continued
| | | | | | |
|---|---|---|---|---|---|
| 258 | 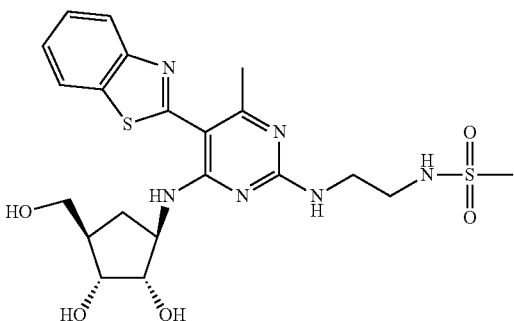 [SMILES: Cc1nc(NCCNS(C)(=O)=O)nc(N[C@@H]2C[C@H](CO)[C@@H](O)[C@H]2O)c1-c1nc2ccccc2s1] | B | | 509.3 | Z3 |
| 259 | 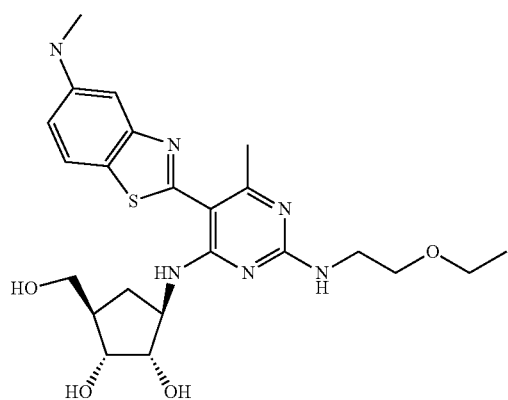 [SMILES: CCOCCNc1nc(C)c(-c2nc3cc(NC)ccc3s2)c(N[C@@H]2C[C@H](CO)[C@@H](O)[C@H]2O)n1] | A | | 489.4 | Z (steps 4-7) |
| 260 | 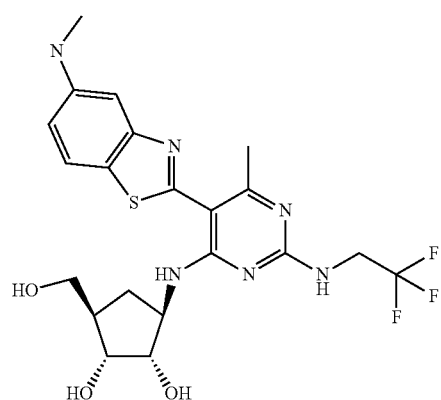 [SMILES: CNc1ccc2sc(-c3c(C)nc(NCC(F)(F)F)nc3N[C@@H]3C[C@H](CO)[C@@H](O)[C@H]3O)nc2c1] | A | | 499.4 | Z (steps 4-7) |
| 321 | 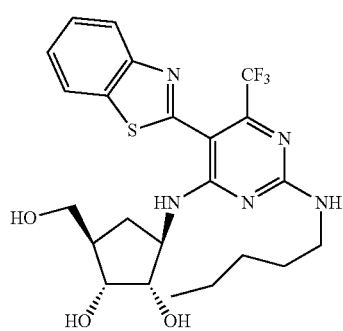 [SMILES: CCCCCNc1nc(N[C@@H]2C[C@H](CO)[C@@H](O)[C@H]2O)c(-c2nc3ccccc3s2)c(C(F)(F)F)n1] | C | 1H NMR (DMSO-d6) δ 0.84-0.92 (m, 3H, CH3), 1.00-1.09 (m, 1H), 1.26-1.38 (m, 4H), 1.50-1.63 (m, 2H), 1.79-1.91 (m, 1H), 2.04-2.19 (m, 1H), 3.21-3.39 (m, 4H), 3.56-3.73 (m, 2H), 4.27-4.5 l (m, 4H, including 3xOH), {6.73 (d, J = 6.9 Hz) and 6.94 (d, J = 6.9 Hz, 1NH)}, {7.42 (br. s) and 7.66 (t, J = 5.5 Hz, 1NH)}, 7.47-7.52 (m, 1 H), 7.54-7.58 (m, 1H), 8.09 (d, 1 H, J = 7.9 Hz) and 8.14 (d, 1H, J = 7.9 Hz), 19F NMR (DMSO-d6) δ-62.55 and -62.96. | 512.3 | S |

TABLE I-continued
| | | | | |
|---|---|---|---|---|
| 322 | 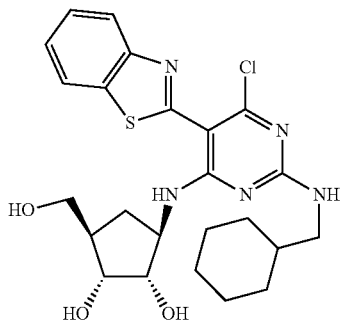 [SMILES: OC[C@H]1C[C@@H](Nc2nc(NCC3CCCCC3)nc(Cl)c2-c2nc3ccccc3s2)[C@H](O)[C@@H]1O] | A | 504.3 | H |
| 323 | 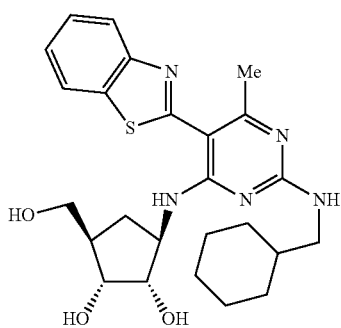 [SMILES: Cc1nc(NCC2CCCCC2)nc(N[C@@H]2C[C@H](CO)[C@@H](O)[C@H]2O)c1-c1nc2ccccc2s1] | A | 484.3 | O |
| 324 | 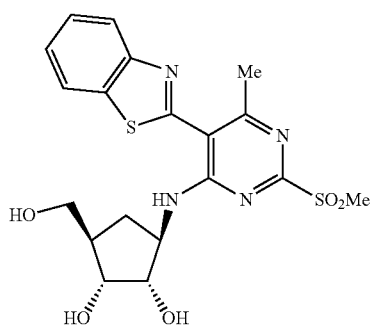 [SMILES: Cc1nc(S(C)(=O)=O)nc(N[C@@H]2C[C@H](CO)[C@@H](O)[C@H]2O)c1-c1nc2ccccc2s1] | C | 1H NMR (DMSO-d6) δ 1.13-1.21 (m, 1H), 1.89-1.98 (m, 1H), 2.18-2.26 (m, 1H), 2.51 (s, CH$_3$), 3.31-3.43 (m, 2H), 3.36 (s, CH$_3$), 3.66-3.70 (m, 1H), 3.75-3.80 (m, 1H), 4.33-4.41 (m, 1H), 4.49 (d, J = 5.2 Hz, 1xO<u>H</u>), 4.57 (t, J = 5.0 Hz, 1xO<u>H</u>), 4.65 (d, J = 5.8 Hz, 1xO<u>H</u>), 7.54-7.59 (m, 1H) 7.60-7.66 (m, 1H), 8.18 (d, 1 H, J = 8.1 Hz), 8.24 (d, 1H, J = 8.1 Hz) and 8.76 (d, J = 8.1 Hz, N<u>H</u>). | 451.2 | T |
| 325 | 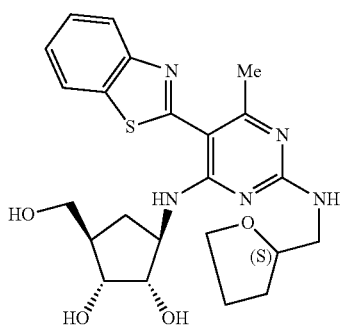 | A | 472.3 | U |

TABLE I-continued

| | | | | | |
|---|---|---|---|---|---|
| 326 | 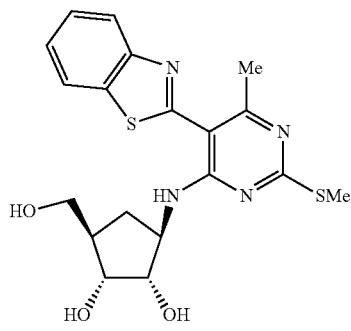 [SMILES: CSc1nc(C)c(-c2nc3ccccc3s2)c(N[C@@H]2C[C@H](CO)[C@@H](O)[C@H]2O)n1] | B | 1H NMR (DMSO-d6) δ 1.14-1.21 (m, 1H), 1.92-2.00 (m, 1H), 2.25-2.33 (m, 1H), 2.51 (s, CH$_3$), 2.52 (s, CH$_3$), 3.35-3.46 (m, 2H), 3.70-3.80 (m, 2H), 4.34-4.42 (m, 1H), 4.48 (d, J = 5.0 Hz, 1xOH), 4.60 (t, J = 5.2 Hz, 1xOH), 4.64 (d, J = 5.6 Hz, 1xOH), 7.48-7.53 (m, 1H) 7.56-7.61 (m, 1H), 8.12 (d, 1 H, J = 7.8 Hz), 8.18 (d, 1H, J = 7.8 Hz) and 9.08 (d, J = 7.1 Hz, NH). | 419.2 | From removal of dimethyl-ketal on 252a as described in pro-cedure U |
| 327 | 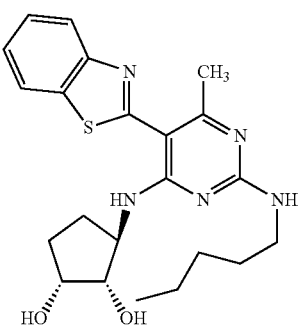 [SMILES: CCCCCNc1nc(C)c(-c2nc3ccccc3s2)c(N[C@@H]2CC[C@@H](O)[C@H]2O)n1] | A | 1H NMR (DMSO-d6) δ 0.89 (s, 3H, CH$_3$), 1.25-1.40 (m, 5H), 1.49-1.61 (m, 3H), 1.87-1.97 (m, 1H), 2.21-2.38 (m, 1H), 2.55 (s, 3H, CH$_3$), 3.19-3.38 (m, 2H), 3.72-3.87 (m, 1H), 3.90-3.99 (m, 1H), 4.22- 4.33 (m, 1H), 4.37-4.52 (m, 1xOH), 4.77 (d, J = 5.6 Hz, 1xOH), {7.12 (br. s) and 7.24 (br. s), NH}, {7.36-7.44 (m) and 7.58-7.63 (m), 1H}, {7.48-7.54 (m) and 7.63-7.68 (m), 1H}, {7.96 (d, J = 7.9 Hz) and 8.21 (d, J = 7.9 Hz), 1H}, {8.08 (d, J = 7.9 Hz) and 8.27 (d, J = 7.9 Hz), 1H} and {9.46 (br. s) and 9.88 (br. s), NH}. | 428.3 | V |
| 328 | 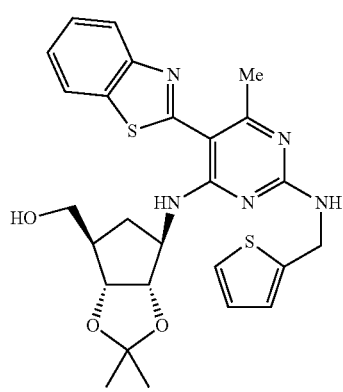 [SMILES: Cc1nc(NCc2cccs2)nc(N[C@@H]2C[C@H](CO)[C@H]3OC(C)(C)O[C@H]32)c1-c1nc2ccccc2s1] | A | 1H NMR (DMSO-d6) δ 1.20 (s, CH$_3$), 1.30 (s, CH$_3$), 1.54-1.64 (m, 1H), 2.11-2.20 (m, 1H), 2.25-2.36 (m, 1H), 2.53 (s, CH$_3$), 3.45-3.54 (m, 2H), 3.41-4.57 (m, 3H, including 2xOH), 4.65-4.82 (m, 3H, including 1xOH), 7.14 (dd, 1H, J = 5.0 and 3.4 Hz), 7.06 (br. s, 1H), 7.36 (dd, 1H, J = 5.0 and 1 Hz), 7.41-7.46 (m, 1H) 7.51-7.56 (m, 1H), 8.02 (br. s, 1H), 8.07 (d, 1 H, J = 8.0 Hz), 8.11 (d, 1 H, J = 8.0 Hz), and 9.62 (br. s, NH). | 524.3 | U |

TABLE I-continued
| | | | | |
|---|---|---|---|---|
| 329 | 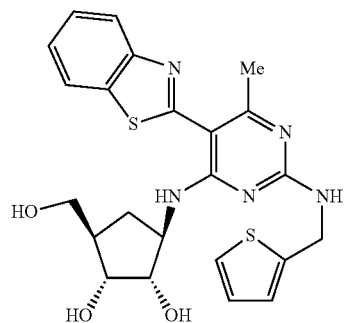 [SMILES: Cc1nc(NCc2cccs2)nc(N[C@@H]2C[C@H](CO)[C@@H](O)[C@H]2O)c1-c1nc2ccccc2s1] | A | 484.3 | U |
| 330 | 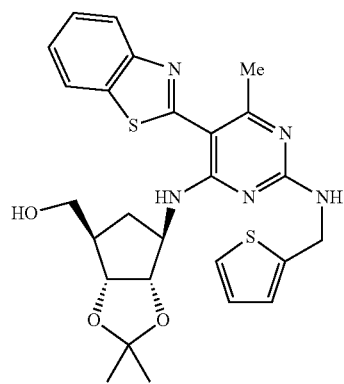 [SMILES: Cc1nc(NCc2cccs2)nc(N[C@@H]2C[C@H](CO)[C@H]3OC(C)(C)O[C@H]32)c1-c1nc2ccccc2s1] | A | 524.3 | U |
| 331 | 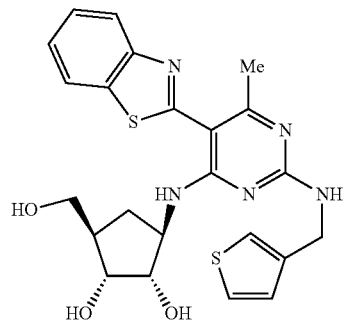 [SMILES: Cc1nc(NCc2ccsc2)nc(N[C@@H]2C[C@H](CO)[C@@H](O)[C@H]2O)c1-c1nc2ccccc2s1] | A | 484.3 | U |
| 332 | 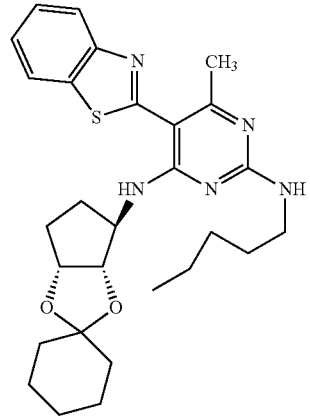 [SMILES: CCCCCNc1nc(C)c(-c2nc3ccccc3s2)c(N[C@@H]2CC[C@H]3OC4(CCCCC4)O[C@@H]23)n1] | C | 508.3 | V |

TABLE I-continued
| | | | | | |
|---|---|---|---|---|---|
| 333 | 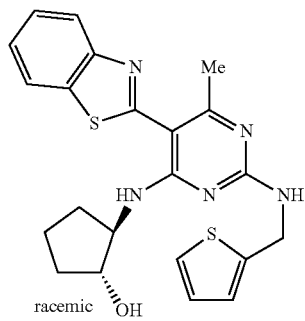 [SMILES: Cc1nc(NCc2cccs2)nc(N[C@@H]2CCC[C@H]2O)c1-c1nc2ccccc2s1] | A | 1H NMR (CDCl3 and CD3OD) δ 1.53-1.66 (m, 2H), 1.67-1.83 (m, 2H), 1.91-2.01 (m, 1H), 2.14-2.23 (m, 1H), 2.62 (s, 3H, CH₃), 3.98-4.07 (m, 1H), 4.12-4.20 (m, 1H), 4.65-4.79 (m, 2H), 6.86 (dd, 1H, J = 5.1 and 3.4 Hz), 6.95-6.98 (m, 1H), 7.10 (dd, 1H, J = 5.1 and 1.2 Hz), 7.27-7.32 (m, 1H) 7.38-7.42 (m, 1H), 7.79-7.81 (m, 1H), 7.82-7.83 (m, 1H) and 7.84 (app. d, 1 H, J = 8.1 Hz). | 438.2 | X |
| 334 | 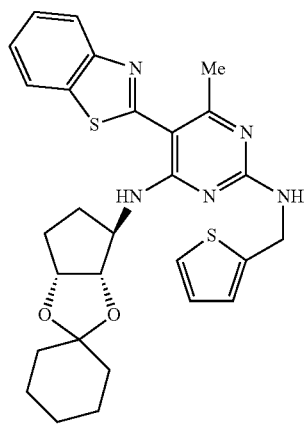 [SMILES: Cc1nc(NCc2cccs2)nc(N[C@@H]2CC[C@H]3OC4(CCCCC4)O[C@@H]23)c1-c1nc2ccccc2s1] | C | | 534.3 | V |
| 335 | 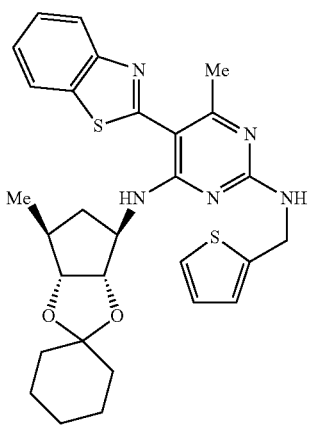 [SMILES: Cc1nc(NCc2cccs2)nc(N[C@@H]2C[C@H](C)[C@H]3OC4(CCCCC4)O[C@H]32)c1-c1nc2ccccc2s1] | C | | 548.3 | W |
| 336 | 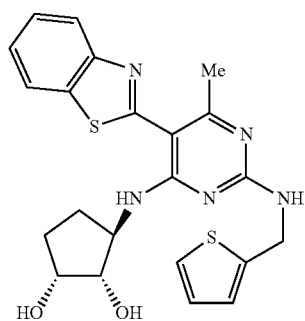 [SMILES: Cc1nc(NCc2cccs2)nc(N[C@@H]2CC[C@@H](O)[C@H]2O)c1-c1nc2ccccc2s1] | A | | 454.2 | V |

TABLE I-continued
| # | Structure | | NMR | MS | Notes |
|---|---|---|---|---|---|
| 337 | 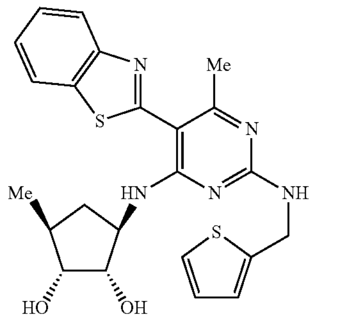 [SMILES: Cc1nc(NCc2cccs2)nc(N[C@@H]2C[C@H](C)[C@@H](O)[C@H]2O)c1-c1nc2ccccc2s1] | A | 1H NMR (DMSO-d6) δ 0.92-1.01 (m, 1H), 1.00 (d, 3H, CH$_3$, J = 6.9), 1.81-1.90 (m, 1H), 2.16-2.25 (m, 1H), 2.45 (s, 3H, CH$_3$), 3.40 (app. t, 1H, J = 6 Hz), 3.87 (app. t, 1H, J = 6 Hz), 4.40-4.49 (m, 1H), 4.74-4.92 (m, 2H), 7.00 (dd, 1H, J = 5.1 and 3.4 Hz), 7.16 (dd, 1H, J = 3.4 and 1 Hz), 7.46 (dd, 1H, J = 5.1 and 1.1 Hz), 7.51-7.56 (m, 1H) 7.59-7.64 (m, 1H), 8.14 (d, 1H, J = 8.0 Hz), 8.22 (d, 1 H, J = 8.0 Hz), 8.44 (br. s, NH), and 9.37 (br. s, NH). | 468.3 | W |
| 338 |  racemic | A | 1H NMR(CDCl3) δ 1.73-1.83 (m, 1H), 1.86-1.98 (m, 1H), 2.04-2.12 (m, 1H), 2.21-2.31 (m, 1H), 2.42-2.51 (m, 1H), 2.66-2.75 (m, 1H), 2.70 (s, 3H, CH$_3$), 4.43-4.52 (m, 1H), 4.74-4.84 (m, 2H), 5.50 (br. s, 1H, NH), 6.95 (dd, 1H, J = 5.1 and 3.5 Hz), 6.99-7.02 (m, 1H), 7.20 (dd, 1H, J = 5.1 and 1.2 Hz), 7.34-7.38 (m, 1H) 7.46-7.50 (m, 1H), 7.87 (d, 1H, J = 8.1 Hz), 8.02 (d, 1 H, J = 8.1 Hz) and 10.20 (br. s, 1H, NH). | 468.3 | X |
| 339 | 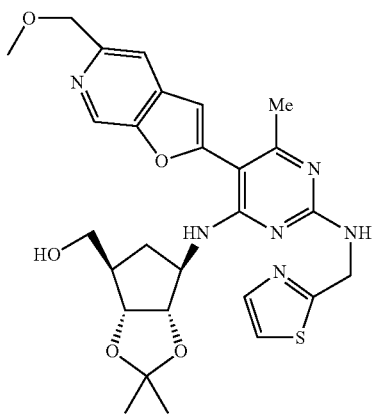 [SMILES: COCc1cc2cc(-c3c(C)nc(NCc4nccs4)nc3N[C@@H]3C[C@H](CO)[C@H]4OC(C)(C)O[C@H]43)oc2cn1] | A | | 553.3 | Combination of M and Y |

TABLE I-continued
| | | | | |
|---|---|---|---|---|
| 340 | 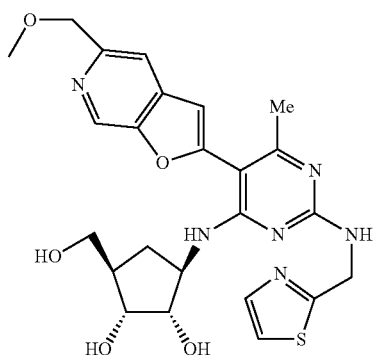 [SMILES: COCc1cc2cc(-c3c(C)nc(NCc4nccs4)nc3N[C@@H]3C[C@H](CO)[C@@H](O)[C@H]3O)oc2cn1] | A | 513.3 | Combination of M and Y |
| 341 | 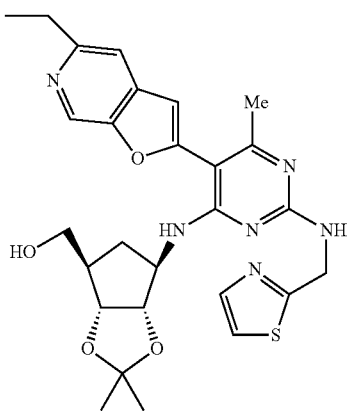 [SMILES: CCc1cc2cc(-c3c(C)nc(NCc4nccs4)nc3N[C@@H]3C[C@H](CO)[C@H]4OC(C)(C)O[C@H]43)oc2cn1] | A | 5374.3 | Y |
| 342 | 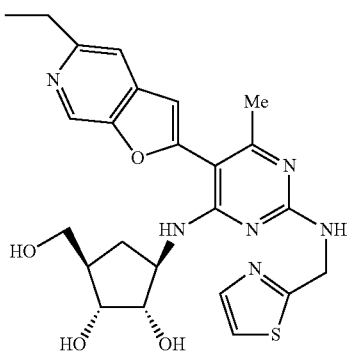 [SMILES: CCc1cc2cc(-c3c(C)nc(NCc4nccs4)nc3N[C@@H]3C[C@H](CO)[C@@H](O)[C@H]3O)oc2cn1] | A | 497.3 | Y |
| 343 | 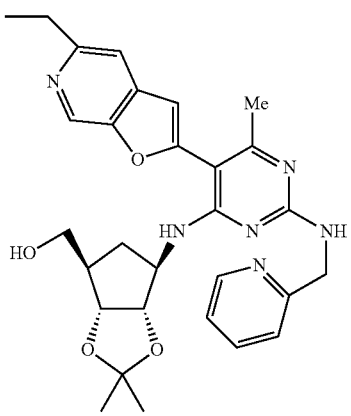 [SMILES: CCc1cc2cc(-c3c(C)nc(NCc4ccccn4)nc3N[C@@H]3C[C@H](CO)[C@H]4OC(C)(C)O[C@H]43)oc2cn1] | C | 531.3 | Y |

TABLE I-continued
| | | | | |
|---|---|---|---|---|
| 344 | 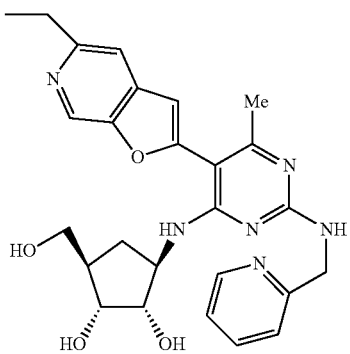 [SMILES: CCc1cc2cc(-c3c(C)nc(NCc4ccccn4)nc3N[C@@H]3C[C@H](CO)[C@@H](O)[C@H]3O)oc2cn1] | A | 491.3 | Y |
| 345 | 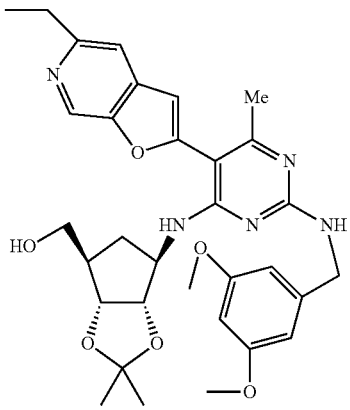 [SMILES: CCc1cc2cc(-c3c(C)nc(NCc4cc(OC)cc(OC)c4)nc3N[C@@H]3C[C@H](CO)[C@H]4OC(C)(C)O[C@H]43)oc2cn1] | A | 590.6 | Y |
| 346 | 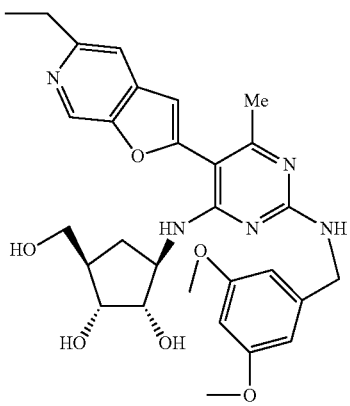 [SMILES: CCc1cc2cc(-c3c(C)nc(NCc4cc(OC)cc(OC)c4)nc3N[C@@H]3C[C@H](CO)[C@@H](O)[C@H]3O)oc2cn1] | A | 550.3 | Y |
| 347 | 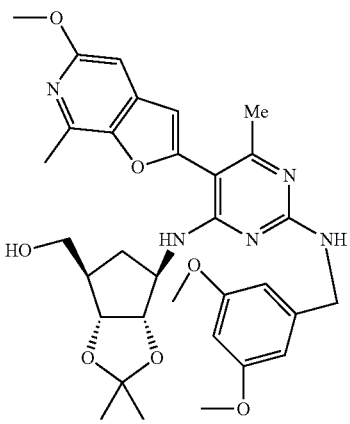 [SMILES: COc1cc(CNc2nc(C)c(-c3cc4cc(OC)nc(C)c4o3)c(N[C@@H]3C[C@H](CO)[C@H]4OC(C)(C)O[C@H]43)n2)cc(OC)c1] | A | 606.3 | Combination of A-2 and Y |

TABLE I-continued
| | | | | |
|---|---|---|---|---|
| 348 | 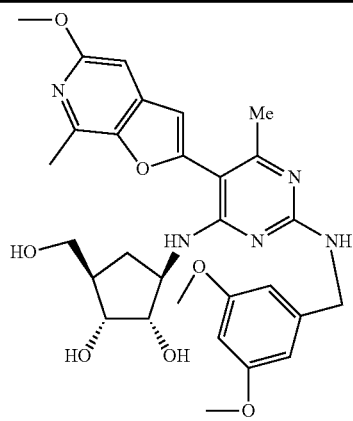 | A | 566.3 | Combination of A-2 and Y |
| 349 | 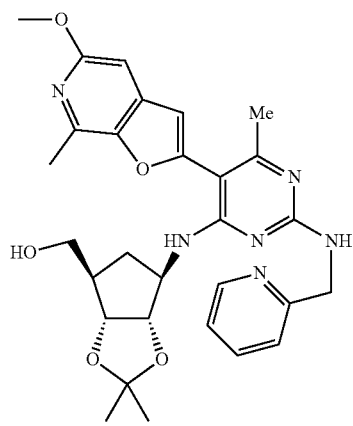 [SMILES: COc1cc2cc(-c3c(C)nc(NCc4ccccn4)nc3N[C@@H]3C[C@H](CO)[C@H]4OC(C)(C)O[C@H]43)oc2c(C)n1] | B | 547.3 | Combination of A-2 and Y |
| 350 | 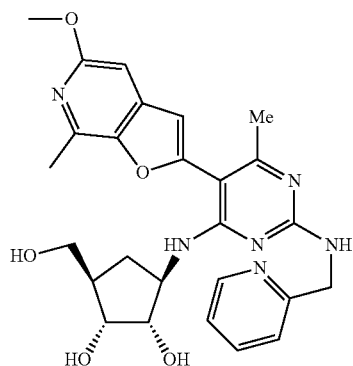 [SMILES: COc1cc2cc(-c3c(C)nc(NCc4ccccn4)nc3N[C@@H]3C[C@H](CO)[C@@H](O)[C@H]3O)oc2c(C)n1] | — | 507.3 | Combination of A-2 and Y |
| 351 | 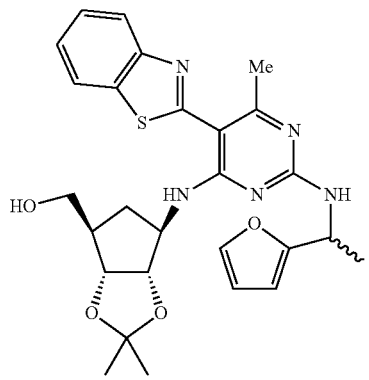 | — | 522.3 | U |
mixture of 2 diastereomers TABLE I-continued
| | | | | | |
|---|---|---|---|---|---|
| 442 | 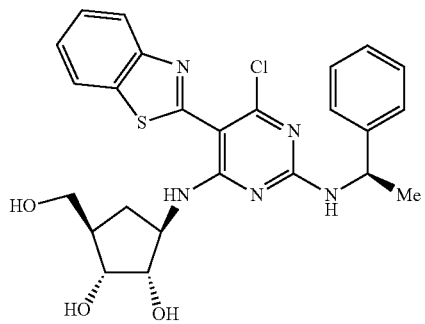 [SMILES: C[C@@H](Nc1nc(Cl)c(-c2nc3ccccc3s2)c(N[C@@H]2C[C@H](CO)[C@@H](O)[C@H]2O)n1)c1ccccc1] | — | 512.4 | H |
| 443 | 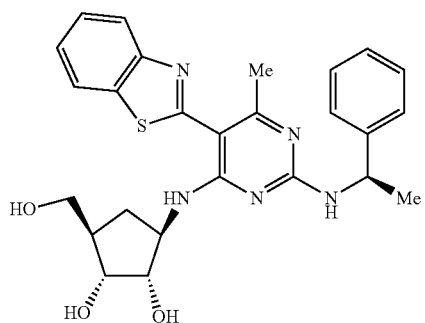 [SMILES: Cc1nc(N[C@H](C)c2ccccc2)nc(N[C@@H]2C[C@H](CO)[C@@H](O)[C@H]2O)c1-c1nc2ccccc2s1] | — | 492.3 | O |
| 444 | 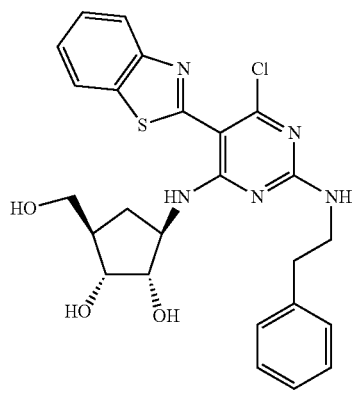 | A | 512.3 | H |
| 445 | 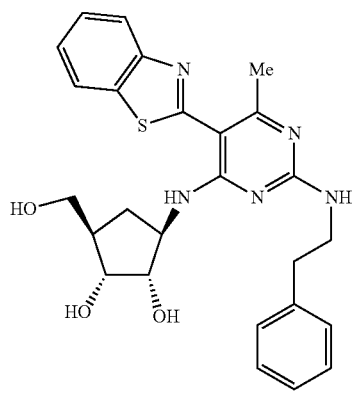 [SMILES: Cc1nc(NCCc2ccccc2)nc(N[C@@H]2C[C@H](CO)[C@@H](O)[C@H]2O)c1-c1nc2ccccc2s1] | A | 492.3 | O |

TABLE I-continued
| | | | | |
|---|---|---|---|---|
| 446 | 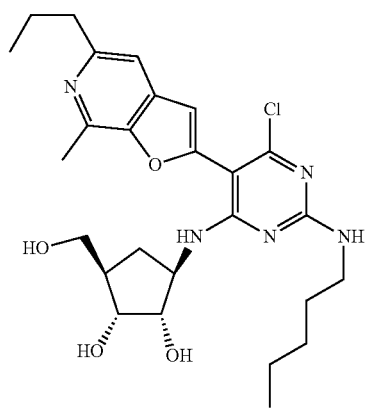 [SMILES: CCCCCNc1nc(Cl)c(-c2cc3cc(CCC)nc(C)c3o2)c(N[C@@H]2C[C@H](CO)[C@@H](O)[C@H]2O)n1] | A | 518.3 | N |
| 447 | 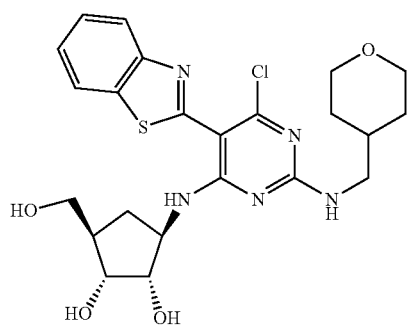 [SMILES: OC[C@H]1C[C@@H](Nc2nc(NCC3CCOCC3)nc(Cl)c2-c2nc3ccccc3s2)[C@H](O)[C@@H]1O] | A | 506.3 | H |
| 448 | 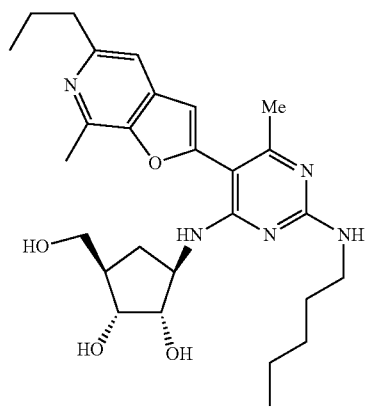 [SMILES: CCCCCNc1nc(C)c(-c2cc3cc(CCC)nc(C)c3o2)c(N[C@@H]2C[C@H](CO)[C@@H](O)[C@H]2O)n1] | A | 498.3 | O |
| 449 | 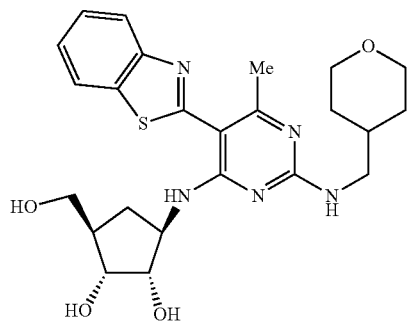 [SMILES: Cc1nc(NCC2CCOCC2)nc(N[C@@H]2C[C@H](CO)[C@@H](O)[C@H]2O)c1-c1nc2ccccc2s1] | A | 486.3 | O |

TABLE I-continued
| | | | | |
|---|---|---|---|---|
| 450 | 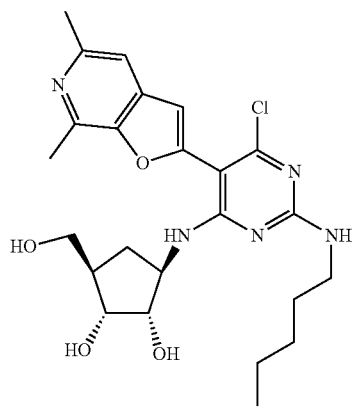 [SMILES: CCCCCNc1nc(Cl)c(-c2cc3cc(C)nc(C)c3o2)c(N[C@@H]2C[C@H](CO)[C@@H](O)[C@H]2O)n1] | A | 490.3 | L |
| 451 | 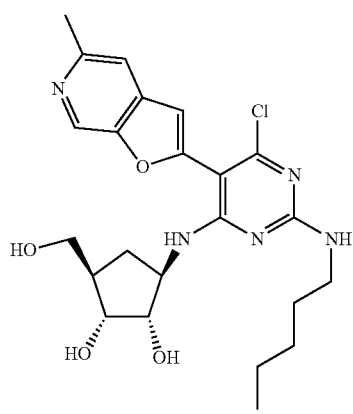 [SMILES: CCCCCNc1nc(Cl)c(-c2cc3cc(C)ncc3o2)c(N[C@@H]2C[C@H](CO)[C@@H](O)[C@H]2O)n1] | A | 476.3 | L |
| 452 | 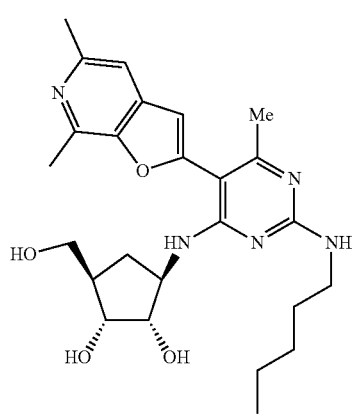 [SMILES: CCCCCNc1nc(C)c(-c2cc3cc(C)nc(C)c3o2)c(N[C@@H]2C[C@H](CO)[C@@H](O)[C@H]2O)n1] | A | 470.3 | O |
| 453 | 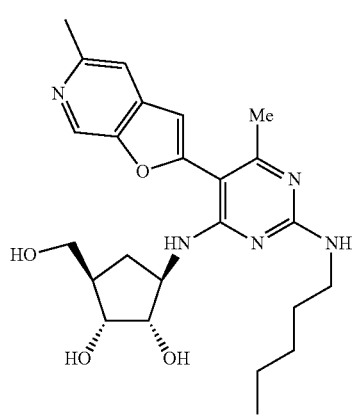 [SMILES: CCCCCNc1nc(C)c(-c2cc3cc(C)ncc3o2)c(N[C@@H]2C[C@H](CO)[C@@H](O)[C@H]2O)n1] | A | 456.3 | O |

TABLE I-continued
| | | | | |
|---|---|---|---|---|
| 454 | 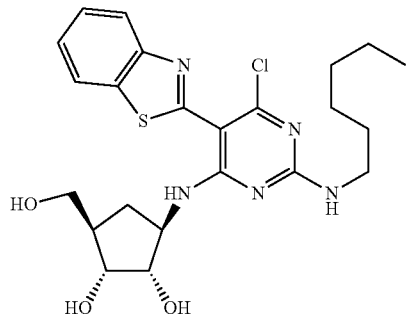 [SMILES: CCCCCCNc1nc(C)c(-c2nc3ccccc3s2)c(N[C@@H]2C[C@H](CO)[C@@H](O)[C@H]2O)n1] | A | 492.3 | H |
| 455 | 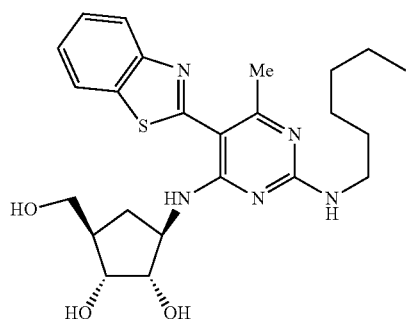 | A | 472.3 | O |
| 456 | 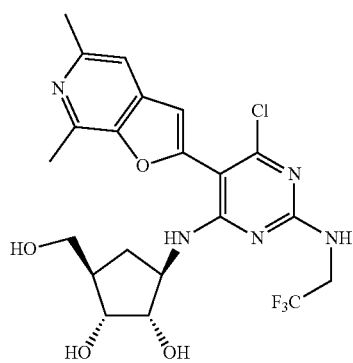 [SMILES: Cc1cc2cc(-c3c(Cl)nc(NCC(F)(F)F)nc3N[C@@H]3C[C@H](CO)[C@@H](O)[C@H]3O)oc2c(C)n1] | A | 502.3 | L |
| 457 | 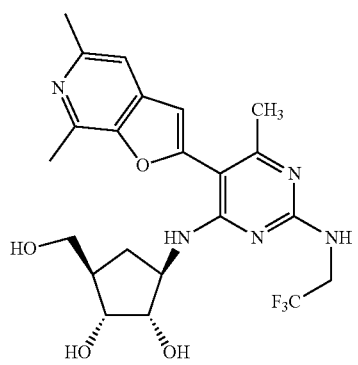 [SMILES: Cc1cc2cc(-c3c(C)nc(NCC(F)(F)F)nc3N[C@@H]3C[C@H](CO)[C@@H](O)[C@H]3O)oc2c(C)n1] | A | 482.3 | O |

421 422
TABLE I-continued
| 458 | 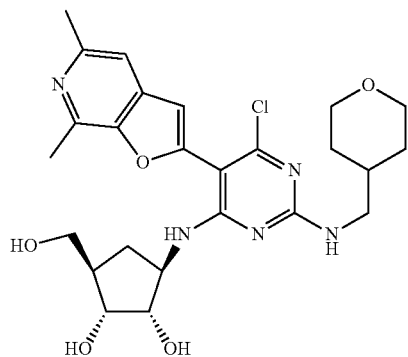 [SMILES: Cc1cc2cc(-c3c(Cl)nc(NCC4CCOCC4)nc3N[C@@H]3C[C@H](CO)[C@@H](O)[C@H]3O)oc2c(C)n1] | A | 518.3 | L |
| 459 | 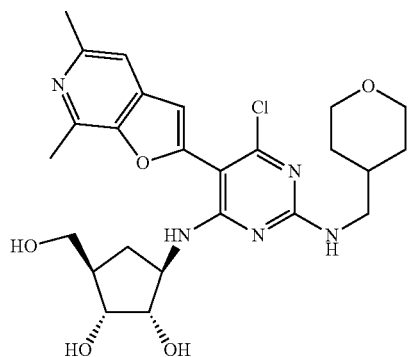 [SMILES: Cc1cc2cc(-c3c(Cl)nc(NCC4CCOCC4)nc3N[C@@H]3C[C@H](CO)[C@@H](O)[C@H]3O)oc2c(C)n1] | A | 498.3 | O |
| 460 | 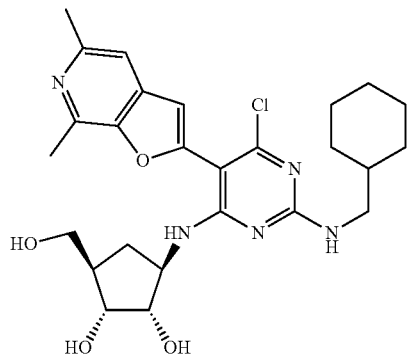 [SMILES: Cc1cc2cc(-c3c(Cl)nc(NCC4CCCCC4)nc3N[C@@H]3C[C@H](CO)[C@@H](O)[C@H]3O)oc2c(C)n1] | A | 516.3 | L |
| 461 | 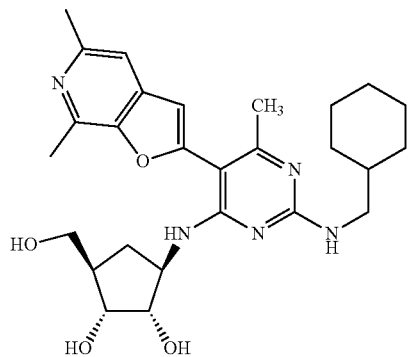 [SMILES: Cc1cc2cc(-c3c(C)nc(NCC4CCCCC4)nc3N[C@@H]3C[C@H](CO)[C@@H](O)[C@H]3O)oc2c(C)n1] | A | 496.3 | O |

TABLE I-continued
| | | | | |
|---|---|---|---|---|
| 462 | 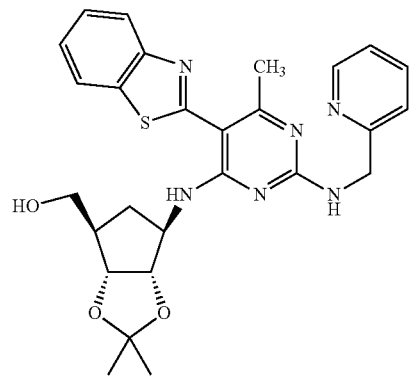 [SMILES: Cc1nc(NCc2ccccn2)nc(N[C@@H]2C[C@H](CO)[C@H]3OC(C)(C)O[C@H]32)c1-c1nc2ccccc2s1] | B | 519.3 | U |
| 463 | 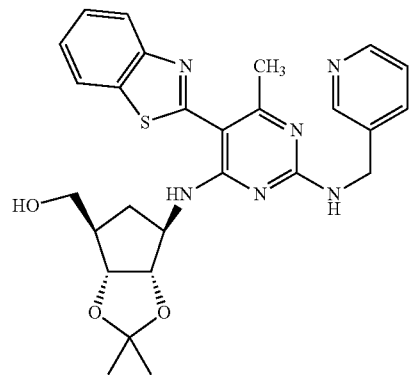 [SMILES: Cc1nc(NCc2cccnc2)nc(N[C@@H]2C[C@H](CO)[C@H]3OC(C)(C)O[C@H]32)c1-c1nc2ccccc2s1] | A | 519.3 | U |
| 464 | 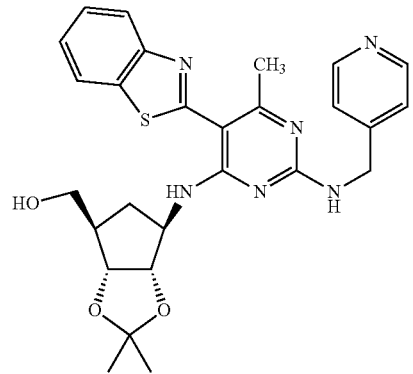 [SMILES: Cc1nc(NCc2ccncc2)nc(N[C@@H]2C[C@H](CO)[C@H]3OC(C)(C)O[C@H]32)c1-c1nc2ccccc2s1] | A | 519.3 | U |
| 465 | 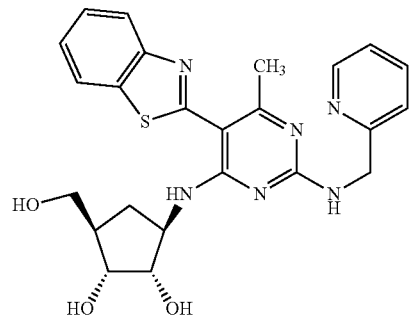 [SMILES: Cc1nc(NCc2ccccn2)nc(N[C@@H]2C[C@H](CO)[C@@H](O)[C@H]2O)c1-c1nc2ccccc2s1] | A | 479.3 | U |

| | | | | |
|---|---|---|---|---|
| 466 | 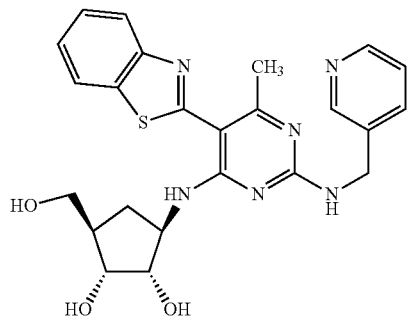 [SMILES: Cc1nc(NCc2cccnc2)nc(N[C@@H]2C[C@H](CO)[C@@H](O)[C@H]2O)c1-c1nc2ccccc2s1] | A | 479.3 | U |
| 467 | 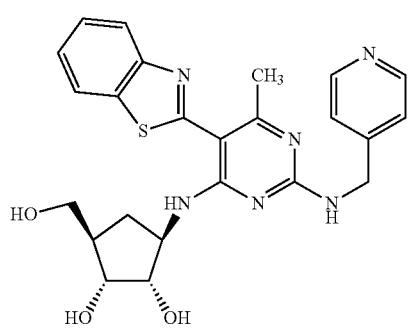 [SMILES: Cc1nc(NCc2ccncc2)nc(N[C@@H]2C[C@H](CO)[C@@H](O)[C@H]2O)c1-c1nc2ccccc2s1] | — | 479.3 | U |
| 468 | 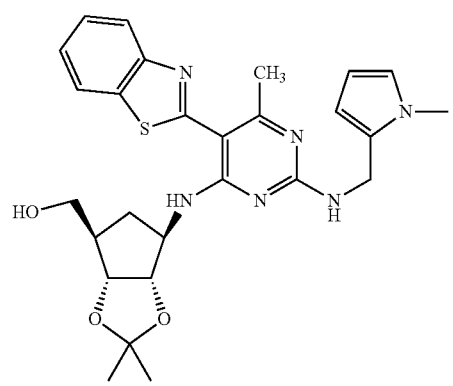 [SMILES: Cc1nc(NCc2cccn2C)nc(N[C@@H]2C[C@H](CO)[C@H]3OC(C)(C)O[C@H]32)c1-c1nc2ccccc2s1] | A | 521.2 | U |
| 469 | 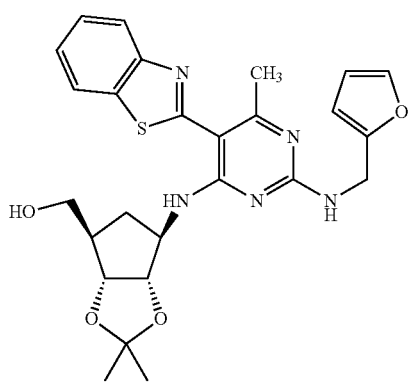 [SMILES: Cc1nc(NCc2ccco2)nc(N[C@@H]2C[C@H](CO)[C@H]3OC(C)(C)O[C@H]32)c1-c1nc2ccccc2s1] | A | 508.3 | O |

TABLE I-continued
| | | | | |
|---|---|---|---|---|
| 470 | 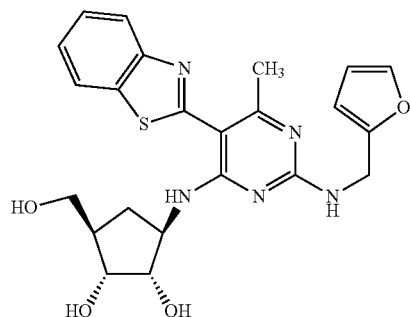 | A | 468.3 | U |
| 471 | 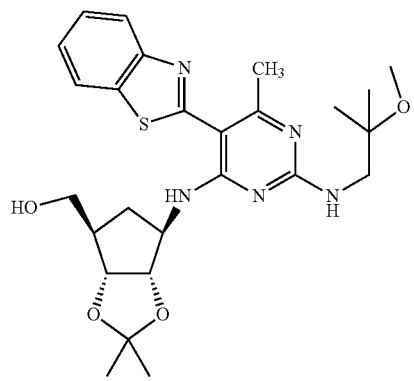 [SMILES: COC(C)(C)CNc1nc(C)c(-c2nc3ccccc3s2)c(N[C@@H]2C[C@H](CO)[C@H]3OC(C)(C)O[C@H]32)n1] | A | 514.2 | U |
| 472 | 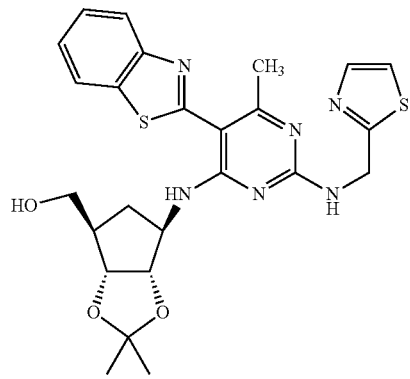 | A | 525.4 | U |
| 473 | 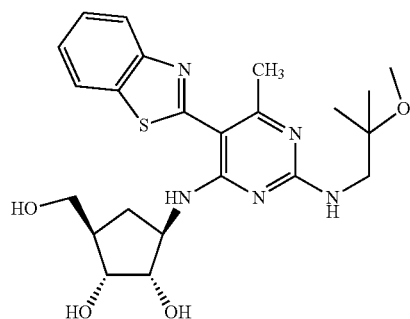 [SMILES: COC(C)(C)CNc1nc(C)c(-c2nc3ccccc3s2)c(N[C@@H]2C[C@H](CO)[C@@H](O)[C@H]2O)n1] | A | 474.2 | U |

TABLE I-continued
| | | | | |
|---|---|---|---|---|
| 474 | 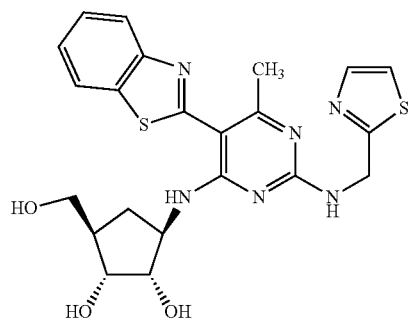 | A | 485.4 | U |
| 475 | 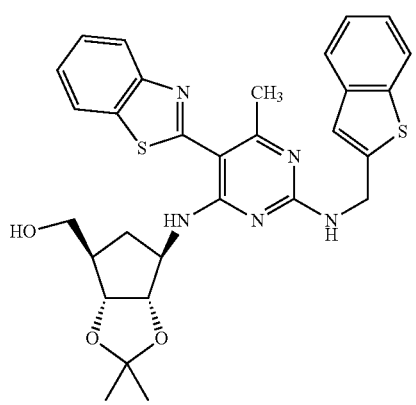 [SMILES: Cc1nc(NCc2cc3ccccc3s2)nc(N[C@@H]2C[C@H](CO)[C@H]3OC(C)(C)O[C@H]32)c1-c1nc2ccccc2s1] | B | 574.5 | U |
| 476 | 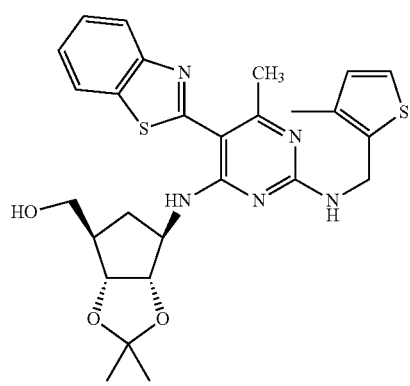 [SMILES: Cc1ccsc1CNc1nc(C)c(-c2nc3ccccc3s2)c(N[C@@H]2C[C@H](CO)[C@H]3OC(C)(C)O[C@H]32)n1] | A | 538.5 | U |
| 477 | 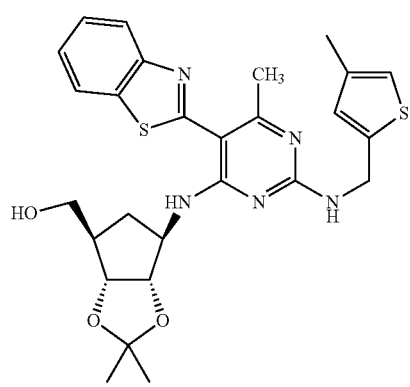 | A | 538.5 | U |

TABLE I-continued
| | | | | |
|---|---|---|---|---|
| 478 | 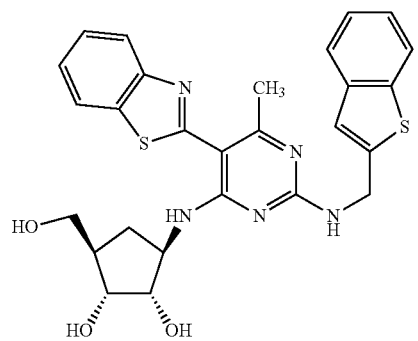 [SMILES: Cc1nc(NCc2cc3ccccc3s2)nc(N[C@@H]2C[C@H](CO)[C@@H](O)[C@H]2O)c1-c1nc2ccccc2s1] | A | 534.5 | U |
| 479 | 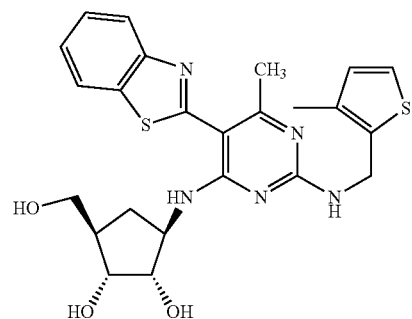 | A | 498.5 | U |
| 480 | 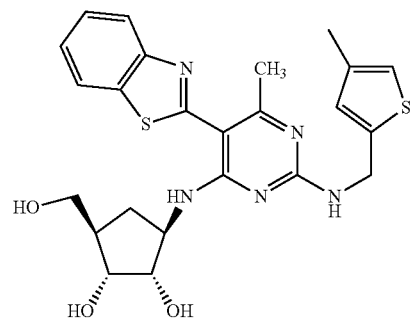 | A | 498.2 | U |
| 481 | 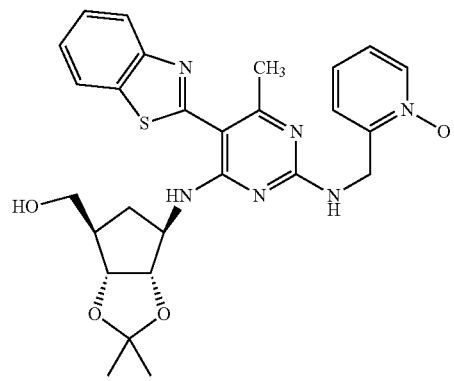 | C | 535.5 | U |

TABLE I-continued
| | | | | |
|---|---|---|---|---|
| 482 | 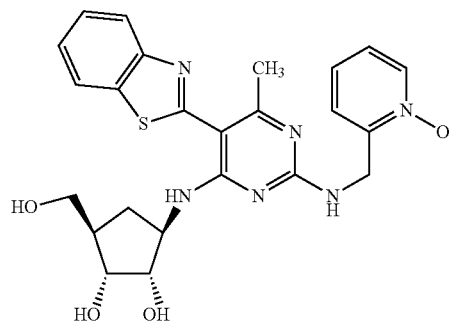 | B | 495.2 | U |
| 483 | 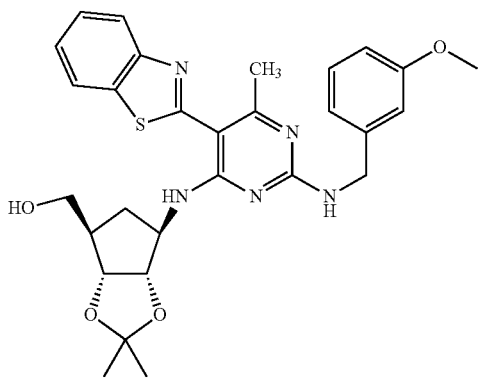 [SMILES: COc1cccc(CNc2nc(C)c(-c3nc4ccccc4s3)c(N[C@@H]3C[C@H](CO)[C@H]4OC(C)(C)O[C@H]43)n2)c1] | B | 548.2 | U |
| 484 | 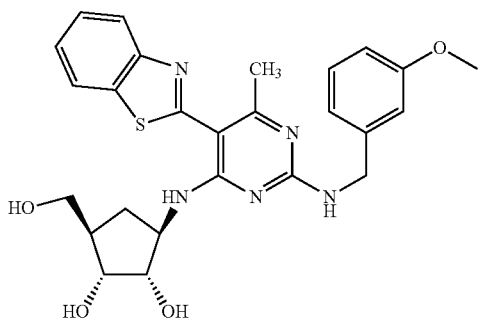 [SMILES: COc1cccc(CNc2nc(C)c(-c3nc4ccccc4s3)c(N[C@@H]3C[C@H](CO)[C@@H](O)[C@H]3O)n2)c1] | A | 495.2 | U |
| 485 | 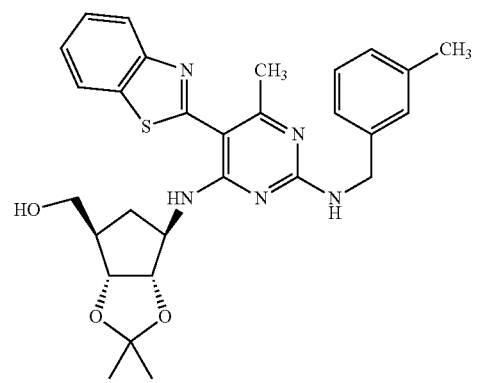 [SMILES: Cc1cccc(CNc2nc(C)c(-c3nc4ccccc4s3)c(N[C@@H]3C[C@H](CO)[C@H]4OC(C)(C)O[C@H]43)n2)c1] | B | 532.2 | U |

TABLE I-continued
| | | | | |
|---|---|---|---|---|
| 486 | 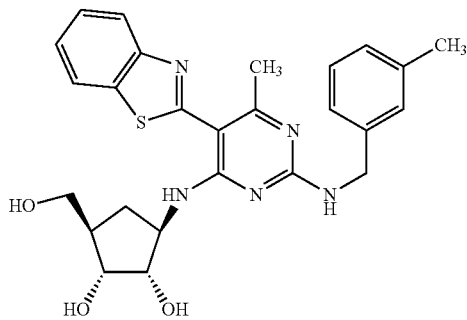 [SMILES: Cc1cccc(CNc2nc(C)c(-c3nc4ccccc4s3)c(N[C@@H]3C[C@H](CO)[C@@H](O)[C@H]3O)n2)c1] | A | 492.2 | U |
| 487 | 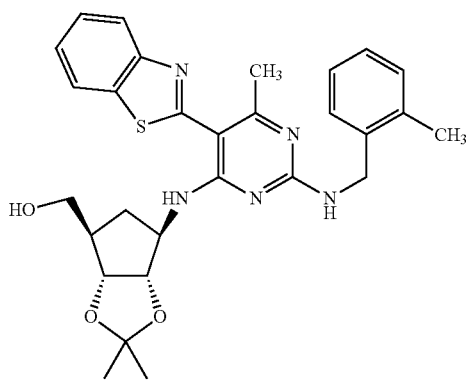 [SMILES: Cc1ccccc1CNc1nc(C)c(-c2nc3ccccc3s2)c(N[C@@H]2C[C@H](CO)[C@H]3OC(C)(C)O[C@H]32)n1] | C | 532.2 | U |
| 488 | 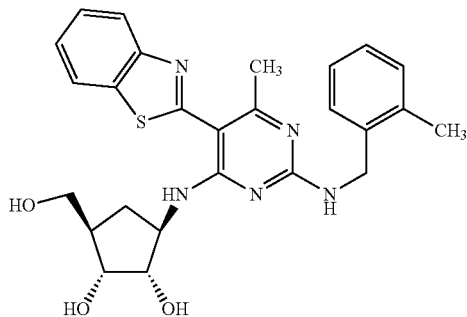 [SMILES: Cc1ccccc1CNc1nc(C)c(-c2nc3ccccc3s2)c(N[C@@H]2C[C@H](CO)[C@@H](O)[C@H]2O)n1] | A | 492.2 | U |
| 489 | 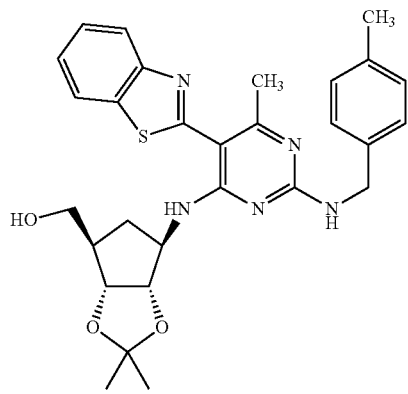 [SMILES: Cc1ccc(CNc2nc(C)c(-c3nc4ccccc4s3)c(N[C@@H]3C[C@H](CO)[C@H]4OC(C)(C)O[C@H]43)n2)cc1] | B | 532.2 | U |

| | | | | |
|---|---|---|---|---|
| 490 | 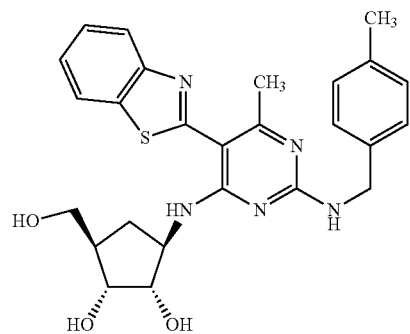 [SMILES: Cc1ccc(CNc2nc(C)c(-c3nc4ccccc4s3)c(N[C@@H]3C[C@H](CO)[C@@H](O)[C@H]3O)n2)cc1] | A | 492.2 | U |
| 491 | 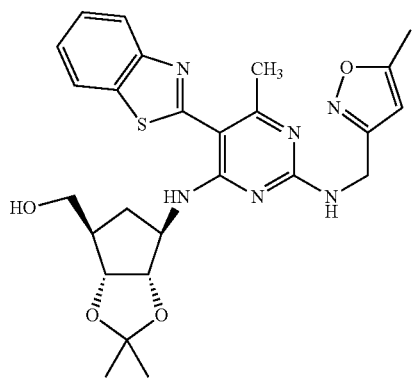 [SMILES: Cc1cc(CNc2nc(C)c(-c3nc4ccccc4s3)c(N[C@@H]3C[C@H](CO)[C@H]4OC(C)(C)O[C@H]43)n2)no1] | B | 523.2 | U |
| 492 | 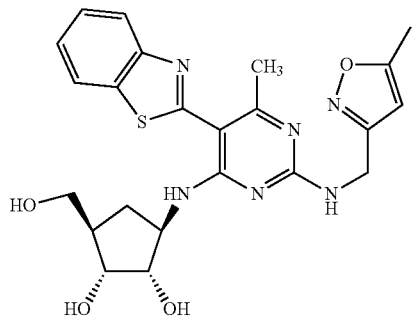 [SMILES: Cc1cc(CNc2nc(C)c(-c3nc4ccccc4s3)c(N[C@@H]3C[C@H](CO)[C@@H](O)[C@H]3O)n2)no1] | A | 483.2 | U |
| 493 | 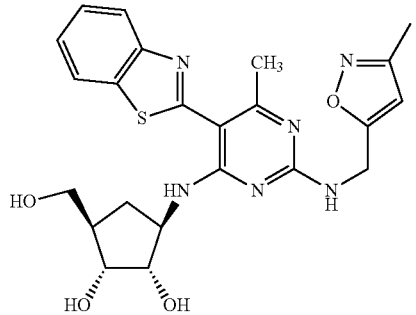 [SMILES: Cc1cc(CNc2nc(C)c(-c3nc4ccccc4s3)c(N[C@@H]3C[C@H](CO)[C@@H](O)[C@H]3O)n2)on1] | A | 483.2 | U |

TABLE I-continued
| 494 | 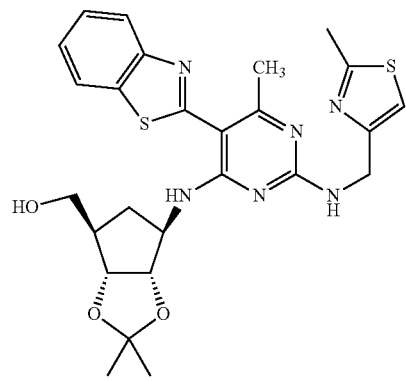 [SMILES: Cc1nc(CNc2nc(C)c(-c3nc4ccccc4s3)c(N[C@@H]3C[C@H](CO)[C@H]4OC(C)(C)O[C@H]43)n2)cs1] | C | 539.2 | U |
| 495 | 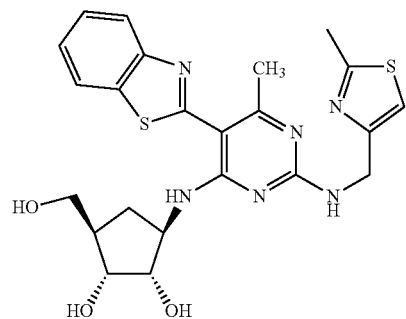 [SMILES: Cc1nc(CNc2nc(C)c(-c3nc4ccccc4s3)c(N[C@@H]3C[C@H](CO)[C@@H](O)[C@H]3O)n2)cs1] | A | 499.2 | U |
| 496 | 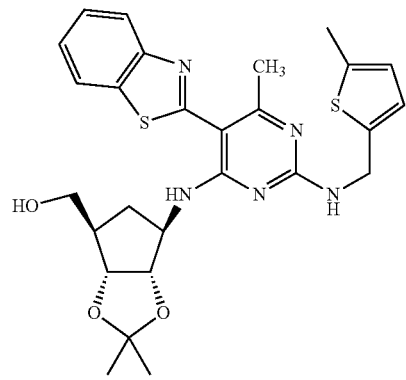 [SMILES: Cc1ccc(CNc2nc(C)c(-c3nc4ccccc4s3)c(N[C@@H]3C[C@H](CO)[C@H]4OC(C)(C)O[C@H]43)n2)s1] | A | 538.2 | U |
| 497 | 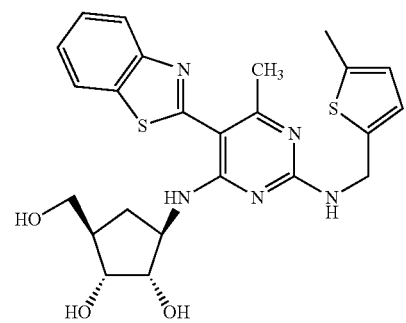 [SMILES: Cc1ccc(CNc2nc(C)c(-c3nc4ccccc4s3)c(N[C@@H]3C[C@H](CO)[C@@H](O)[C@H]3O)n2)s1] | A | 498.2 | U |

TABLE I-continued
| | | | | |
|---|---|---|---|---|
| 498 | 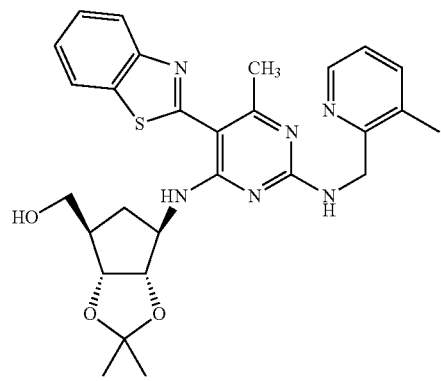 [SMILES: Cc1cccnc1CNc1nc(C)c(-c2nc3ccccc3s2)c(N[C@@H]2C[C@H](CO)[C@H]3OC(C)(C)O[C@H]32)n1] | C | 533.2 | U |
| 499 | 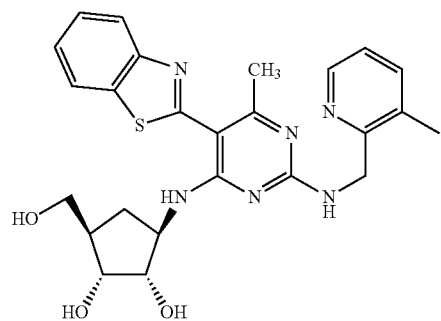 [SMILES: Cc1cccnc1CNc1nc(C)c(-c2nc3ccccc3s2)c(N[C@@H]2C[C@H](CO)[C@@H](O)[C@H]2O)n1] | A | 493.2 | U |
| 500 | 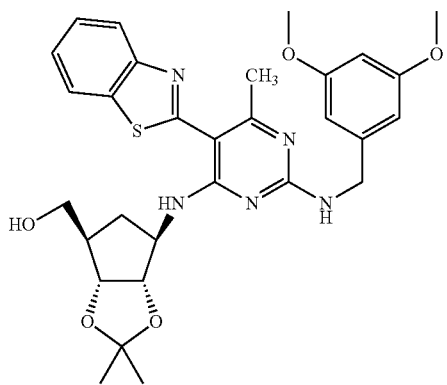 [SMILES: COc1cc(CNc2nc(C)c(-c3nc4ccccc4s3)c(N[C@@H]3C[C@H](CO)[C@H]4OC(C)(C)O[C@H]43)n2)cc(OC)c1] | A | 578.2 | U |
| 701 | 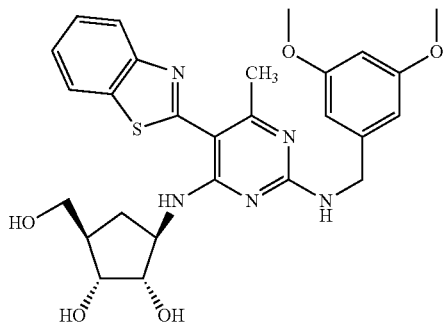 [SMILES: COc1cc(CNc2nc(C)c(-c3nc4ccccc4s3)c(N[C@@H]3C[C@H](CO)[C@@H](O)[C@H]3O)n2)cc(OC)c1] | A | 538.2 | U |

TABLE I-continued
| | | | | |
|---|---|---|---|---|
| 702 | 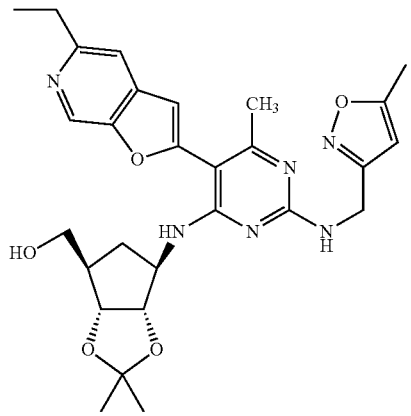 [SMILES: CCc1cc2cc(-c3c(C)nc(NCc4cc(C)on4)nc3N[C@@H]3C[C@H](CO)[C@H]4OC(C)(C)O[C@H]43)oc2cn1] | A | 535.5 | U |
| 703 | 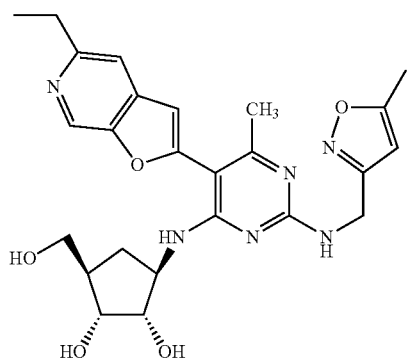 [SMILES: CCc1cc2cc(-c3c(C)nc(NCc4cc(C)on4)nc3N[C@@H]3C[C@H](CO)[C@@H](O)[C@H]3O)oc2cn1] | A | 495.2 | U |
| 704 | 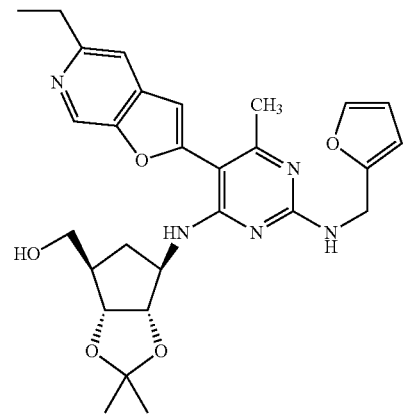 [SMILES: CCc1cc2cc(-c3c(C)nc(NCc4ccco4)nc3N[C@@H]3C[C@H](CO)[C@H]4OC(C)(C)O[C@H]43)oc2cn1] | A | 520.2 | U |
| 705 | 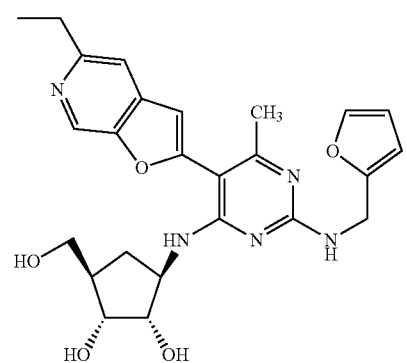 [SMILES: CCc1cc2cc(-c3c(C)nc(NCc4ccco4)nc3N[C@@H]3C[C@H](CO)[C@@H](O)[C@H]3O)oc2cn1] | A | 480.2 | U |

TABLE I-continued
| | | | | |
|---|---|---|---|---|
| 706 | 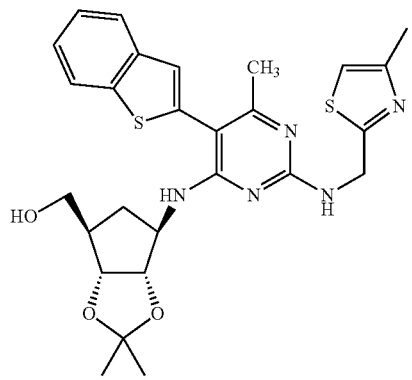 [SMILES: Cc1csc(CNc2nc(C)c(-c3cc4ccccc4s3)c(N[C@@H]3C[C@H](CO)[C@H]4OC(C)(C)O[C@H]43)n2)n1] | B | 539.2 | U |
| 707 | 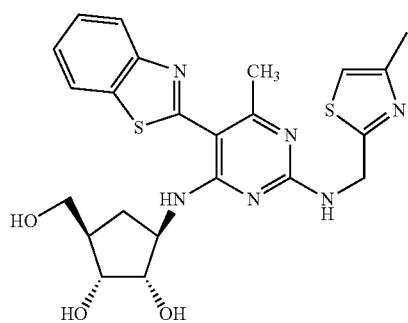 [SMILES: Cc1csc(CNc2nc(C)c(-c3nc4ccccc4s3)c(N[C@@H]3C[C@H](CO)[C@@H](O)[C@H]3O)n2)n1] | A | 499.2 | U |
| 708 | 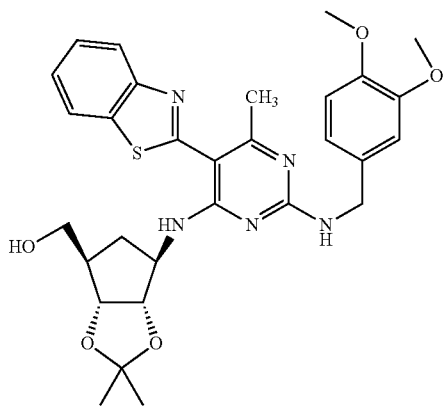 [SMILES: COc1ccc(CNc2nc(C)c(-c3nc4ccccc4s3)c(N[C@@H]3C[C@H](CO)[C@H]4OC(C)(C)O[C@H]43)n2)cc1OC] | A | 578.2 | U |
| 709 | 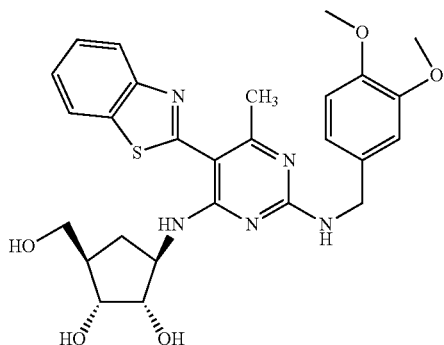 [SMILES: COc1ccc(CNc2nc(C)c(-c3nc4ccccc4s3)c(N[C@@H]3C[C@H](CO)[C@@H](O)[C@H]3O)n2)cc1OC] | A | 538.2 | U |

TABLE I-continued
| | | | | |
|---|---|---|---|---|
| 710 | 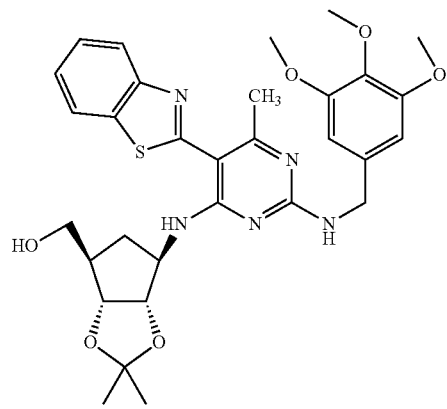 [SMILES: COc1cc(CNc2nc(C)c(-c3nc4ccccc4s3)c(N[C@@H]3C[C@H](CO)[C@H]4OC(C)(C)O[C@H]43)n2)cc(OC)c1OC] | A | 608.2 | U |
| 711 | 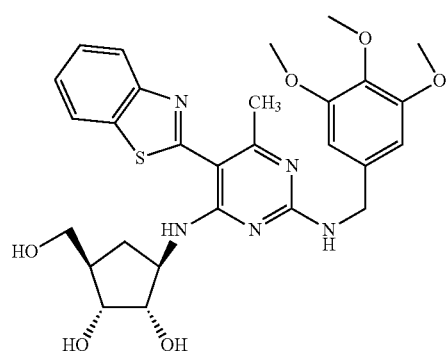 [SMILES: COc1cc(CNc2nc(C)c(-c3nc4ccccc4s3)c(N[C@@H]3C[C@H](CO)[C@@H](O)[C@H]3O)n2)cc(OC)c1OC] | A | 568.2 | U |
| 712 | 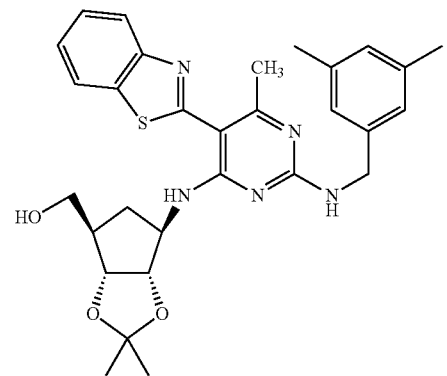 [SMILES: Cc1cc(C)cc(CNc2nc(C)c(-c3nc4ccccc4s3)c(N[C@@H]3C[C@H](CO)[C@H]4OC(C)(C)O[C@H]43)n2)c1] | A | 546.2 | U |
| 713 | 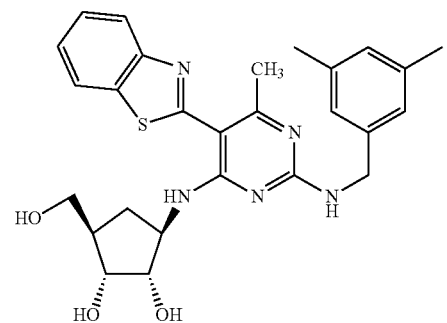 [SMILES: Cc1cc(C)cc(CNc2nc(C)c(-c3nc4ccccc4s3)c(N[C@@H]3C[C@H](CO)[C@@H](O)[C@H]3O)n2)c1] | A | 506.2 | U |

| | | | | |
|---|---|---|---|---|
| 714 | 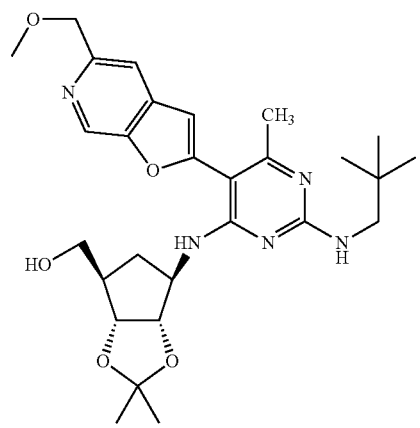 [SMILES: COCc1cc2cc(-c3c(C)nc(NCC(C)(C)C)nc3N[C@@H]3C[C@H](CO)[C@H]4OC(C)(C)O[C@H]43)oc2cn1] | B | 526.2 | Combination of M and Y |
| 715 | 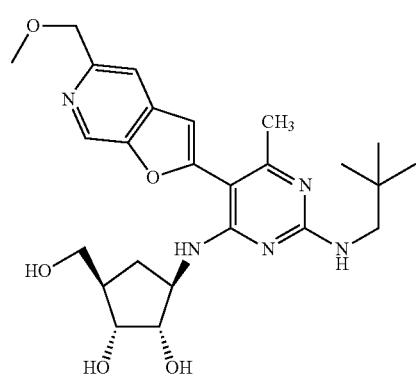 [SMILES: COCc1cc2cc(-c3c(C)nc(NCC(C)(C)C)nc3N[C@@H]3C[C@H](CO)[C@@H](O)[C@H]3O)oc2cn1] | A | 486.2 | Combination of M and Y |
| 716 | 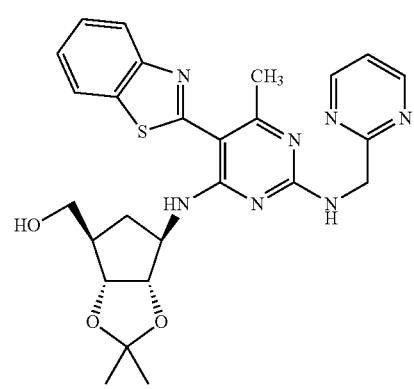 [SMILES: Cc1nc(NCc2ncccn2)nc(N[C@@H]2C[C@H](CO)[C@H]3OC(C)(C)O[C@H]32)c1-c1nc2ccccc2s1] | B | 502.2 | U |
| 717 | 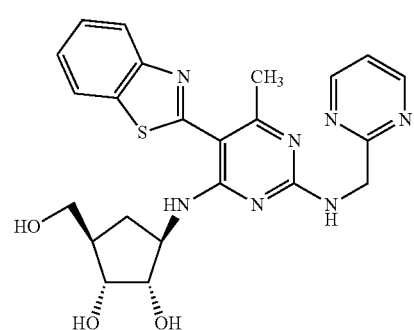 [SMILES: Cc1nc(NCc2ncccn2)nc(N[C@@H]2C[C@H](CO)[C@@H](O)[C@H]2O)c1-c1nc2ccccc2s1] | A | 480.2 | U |

TABLE I-continued
| | | | | | |
|---|---|---|---|---|---|
| 522 | 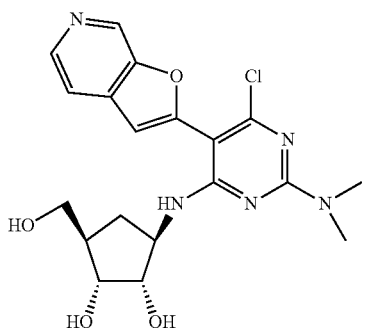 [SMILES: CN(C)c1nc(Cl)c(-c2cc3ccncc3o2)c(N[C@@H]2C[C@H](CO)[C@@H](O)[C@H]2O)n1] | B | | 420.2 | Q |
| 523 | 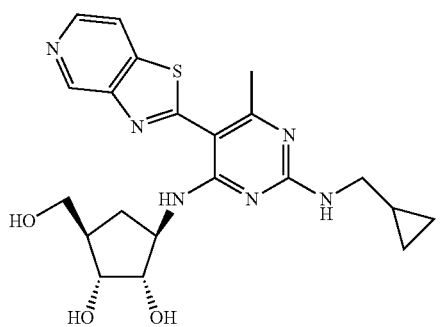 [SMILES: Cc1nc(NCC2CC2)nc(N[C@@H]2C[C@H](CO)[C@@H](O)[C@H]2O)c1-c1nc2cnccc2s1] | A | 1H NMR (DMSO-d6) 0.25 (m, 2H), 0.5 (m, 2H), 1.0-1.1 (m, 1H), 1.9-2.0 (m, 1H), 2.0-2.2 (m, 1H), 2.4 (s, 3H), 3.2-3.4 (m, 4H), 3.6-3.8 (m, 2H), 4.2-4.4 (m, 2H), 4.4-4.5 (m, 2H), 8.0 (m, 1H), 8.4 (m, 1H), 8.6 (m, 1H), 8.95 (m, 1H), 9.5 (s, 1H). | 443.3 | Z |
| 524 | 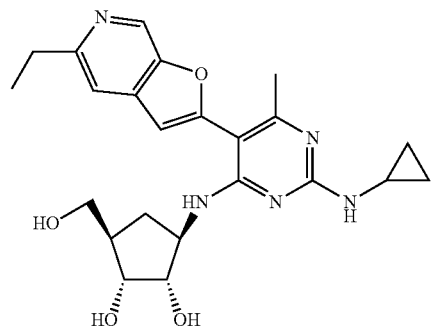 [SMILES: CCc1cc2cc(-c3c(C)nc(NC4CC4)nc3N[C@@H]3C[C@H](CO)[C@@H](O)[C@H]3O)oc2cn1] | A | | 440.3 | Y |
| 524 | 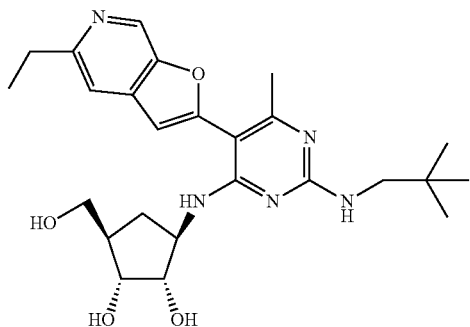 [SMILES: CCc1cc2cc(-c3c(C)nc(NCC(C)(C)C)nc3N[C@@H]3C[C@H](CO)[C@@H](O)[C@H]3O)oc2cn1] | A | 1H NMR (DMSO-d6) 0.9 (s, 9H), 1.0-1.1 (m, 1H), 1.2-1.3 (m, 3H), 1.9-2.0 (m, 1H), 2.0-2.2 (m, 1H), 2.4 (m, 3H), 3.0-3.2 (m, 2H), 3.2-3.4 (m, 4H), 3.6-3.8 (m, 2H), 4.4-4.5 (m, 2H), 7.4 (s, 1H), 8.0 (m, 1H), 8.15 (m, 1H), 8.2 (m, 1H) 9.3 (s, 1H). | 470.4 | Y |
| 525 | 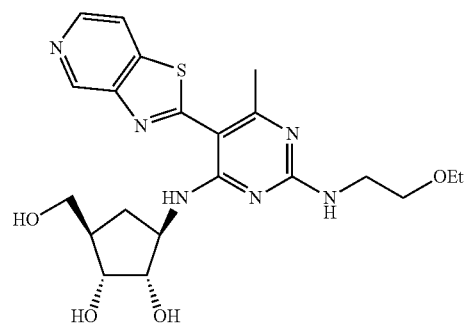 [SMILES: CCOCCNc1nc(C)c(-c2nc3cnccc3s2)c(N[C@@H]2C[C@H](CO)[C@@H](O)[C@H]2O)n1] | A | 1H NMR (DMSO-d6) 1.0 (t, 3H), 1.0-1.1 (m, 1H), 1.9-2.0 (m, 1H), 2.0-2.2 (m, 1H), 2.4 (s, 3H), 3.4 (m, 3H), 3.6-3.7 (m, 6H), 3.7-3.8 (m, 2H), 4.4-4.5 (m, 2H), 7.8 (m, 1H), 8.4 (m, 1H), 8.6 (m, 1H), 8.95 (m, 1H), 9.5 (s, 1H). | 461.5 | Z |

TABLE I-continued
| | | | | | | |
|---|---|---|---|---|---|---|
| 526 | 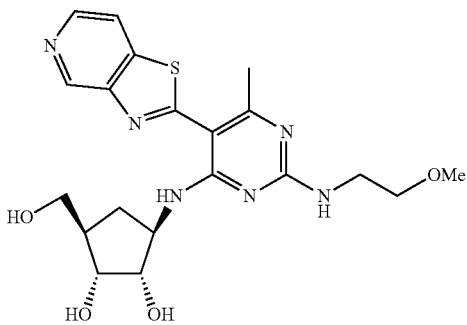 [SMILES: COCCNc1nc(C)c(-c2nc3cnccc3s2)c(N[C@@H]2C[C@H](CO)[C@@H](O)[C@H]2O)n1] | | A | 1H NMR (DMSO-d6) 1.0-1.1 (m, 1H), 1.9-2.0 (m, 1H), 2.0-2.2 (m, 1H), 2.4 (s, 3H), 3.3-3.4 (m, 6H), 3.6-3.7 (m, 4H), 3.7-3.8 (m, 2H), 4.4-4.5 (m, 2H), 7.8 (m, 1H), 8.4 (m, 1H), 8.6 (m, 1H), 8.95 (m, 1H), 9.5 (s, 1H). | 447.4 | Z |
| 527 | 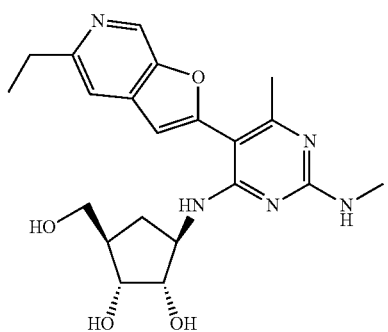 [SMILES: CCc1cc2cc(-c3c(C)nc(NC)nc3N[C@@H]3C[C@H](CO)[C@@H](O)[C@H]3O)oc2cn1] | | A | 1H NMR (DMSO-d6) δ 1.0-1.1 (m, 1H), 1.2-1.3 (m, 3H), 1.8-1.9 (m, 1H), 2.1-2.35 (m, 1H), 2.4 (s, 3H), 3.0 (s, 3H), 3.0-3.2 (m, 2H), 3.4-3.5 (m, 2H), 3.6-3.8 (m, 3H), 4.4-4.5 (m, 2H), 7.4 (s, 1H), 7.5-8.0 (m, 3H), 9.3 (s, 1H). | 414.5 | Y |
| 528 | 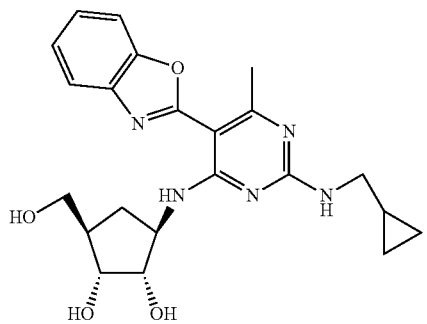 [SMILES: Cc1nc(NCC2CC2)nc(N[C@@H]2C[C@H](CO)[C@@H](O)[C@H]2O)c1-c1nc2ccccc2o1] | | B | 1H NMR (DMSO-d6) 0.25 (m, 2H), 0.5 (m, 2H), 1.0-1.1 (m, 1H), 1.2 (m, 1H), 1.9-2.0 (m, 1H), 2.25-2.3 (m, 1H), 2.7 (s, 3H), 3.2-3.5 (m, 4H), 3.8-3.95 (m, 4H), 4.4-4.5 (m, 1H), 7.4 (m, 2H), 7.8 (m, 2H), 8.1 (m, 1H), 10.0 (s, 1H). | 426.4 | Z |
| 529 | 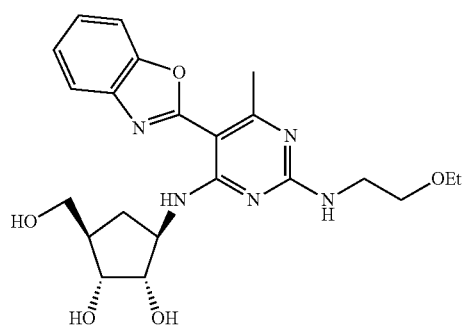 [SMILES: CCOCCNc1nc(C)c(-c2nc3ccccc3o2)c(N[C@@H]2C[C@H](CO)[C@@H](O)[C@H]2O)n1] | | A | 1H NMR (DMSO-d6 1.0 (t, 3H), 1.1-1.2 (m, 1H), 1.2 (m, 1H), 1.9-2.0 (m, 1H), 2.25-2.3 (m, 1H), 2.7 (s, 3H), 3.2-3.5 (m, 7H), 3.8-3.95 (m, 4H), 4.4-4.5 (m, 2H), 7.4 (m, 2H), 7.8 (m, 3H), 10.0 (s, 1H). | 444.4 | Z |
| 530 | 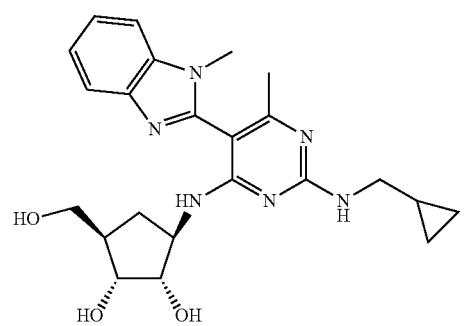 [SMILES: Cc1nc(NCC2CC2)nc(N[C@@H]2C[C@H](CO)[C@@H](O)[C@H]2O)c1-c1nc2ccccc2n1C] | | C | 1H NMR (DMSO-d6) 0.25 (m, 2H), 0.5 (m, 2H), 1.0-1.1 (m, 2H), 1.9-2.0 (m, 1H), 2.25-2.3 (m, 2H), 2.5-2.7 (m, 3H), 3.2-3.4 (m, 2H), 3.6-4.0 (m, 9H), 4.4-4.5 (m, 1H), 7.4 (m, 2H), 7.8 (m, 4H), 7.9-8.0 (m, 2H). | 439.4 | Z |

TABLE I-continued
| | | | | | |
|---|---|---|---|---|---|
| 531 | 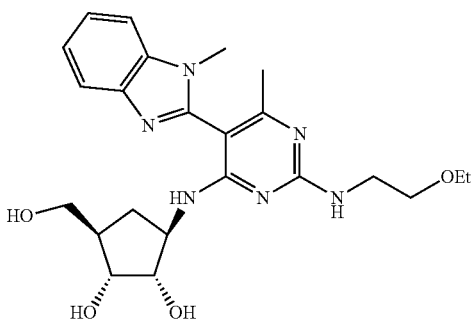 [SMILES: CCOCCNc1nc(C)c(-c2nc3ccccc3n2C)c(N[C@@H]2C[C@H](CO)[C@@H](O)[C@H]2O)n1] | C | 1H NMR (DMSO-d6) 0.095-1.1 (m, 5H), 1.9-2.0 (m, 1H), 2.0 (m, 3H), 2.25-2.3 (m, 2H), 3.0-3.1 (m, 1H), 3.6-4.0 (m, 14H), 4.4-4.5 (m, 1H), 7.4 (m, 2H), 7.8 (m, 4H), 7.9-8.0 (m, 2H). | 457.4 | Z |
| 532 | 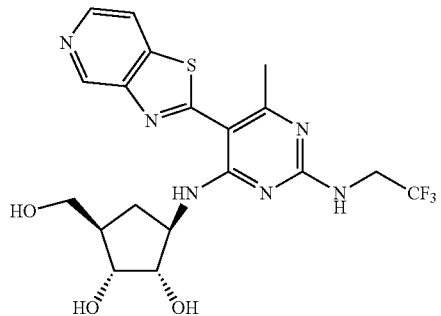 [SMILES: Cc1nc(NCC(F)(F)F)nc(N[C@@H]2C[C@H](CO)[C@@H](O)[C@H]2O)c1-c1nc2cnccc2s1] | A | 1H NMR (DMSO-d6) 1.0-1.1 (m, 1H), 1.9-2.0 (m, 1H), 2.0-2.2 (m, 1H), 2.4 (s, 3H), 3.3-3.4 (m, 2H), 3.6-3.7 (m, 2H), 4.2-4.5 (m, 5H), 8.4 (m, 1H), 8.6 (m, 1H), 8.8 (m, 1H), 8.95 (m, 1H), 9.5 (s, 1H). | 471.3 | Z |
| 533 | 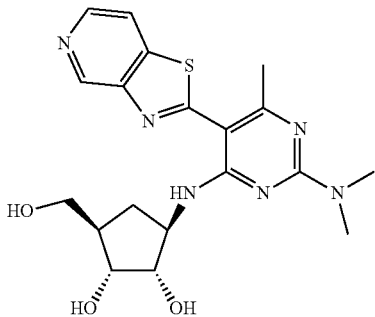 [SMILES: Cc1nc(N(C)C)nc(N[C@@H]2C[C@H](CO)[C@@H](O)[C@H]2O)c1-c1nc2cnccc2s1] | C | | 416.2 | Z |
| 534 | 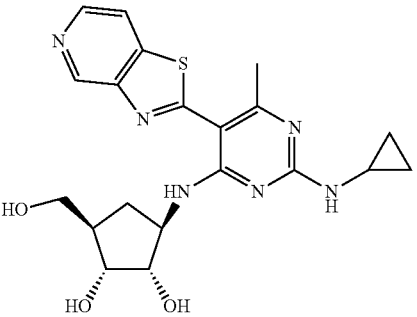 [SMILES: Cc1nc(NC2CC2)nc(N[C@@H]2C[C@H](CO)[C@@H](O)[C@H]2O)c1-c1nc2cnccc2s1] | A | | 429.4 | Z |
| 535 | 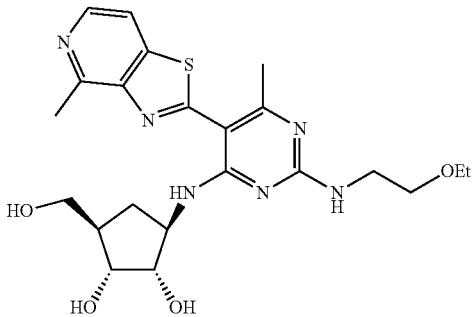 [SMILES: CCOCCNc1nc(C)c(-c2nc3c(C)nccc3s2)c(N[C@@H]2C[C@H](CO)[C@@H](O)[C@H]2O)n1] | A | | 475.2 | Z1 |

TABLE I-continued
| | | | | |
|---|---|---|---|---|
| 536 | 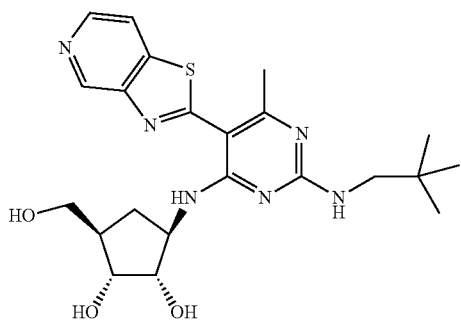 [SMILES: Cc1nc(NCC(C)(C)C)nc(N[C@@H]2C[C@H](CO)[C@@H](O)[C@H]2O)c1-c1nc2cnccc2s1] | A | 459.4 | Z |
| 537 | 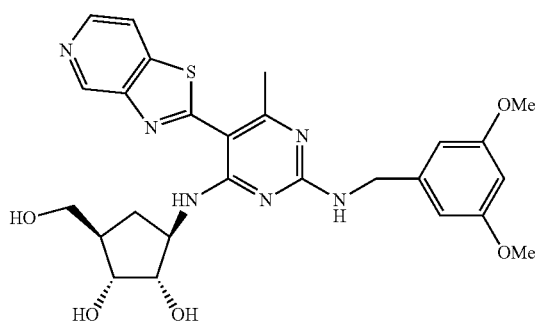 [SMILES: COc1cc(CNc2nc(C)c(-c3nc4cnccc4s3)c(N[C@@H]3C[C@H](CO)[C@@H](O)[C@H]3O)n2)cc(OC)c1] | A | 539.5 | Z |
| 538 | 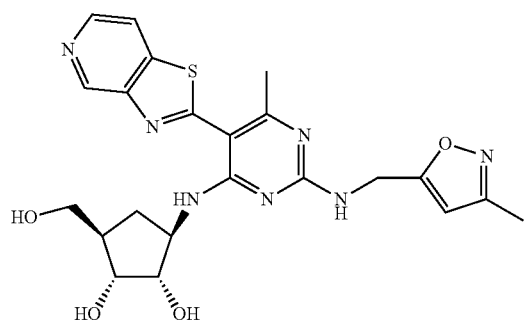 [SMILES: Cc1cc(CNc2nc(C)c(-c3nc4cnccc4s3)c(N[C@@H]3C[C@H](CO)[C@@H](O)[C@H]3O)n2)on1] | A | 484.4 | Z |
| 539 | 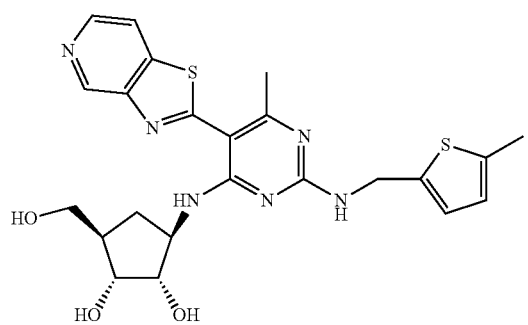 [SMILES: Cc1ccc(CNc2nc(C)c(-c3nc4cnccc4s3)c(N[C@@H]3C[C@H](CO)[C@@H](O)[C@H]3O)n2)s1] | A | 499.4 | Z |
| 540 | 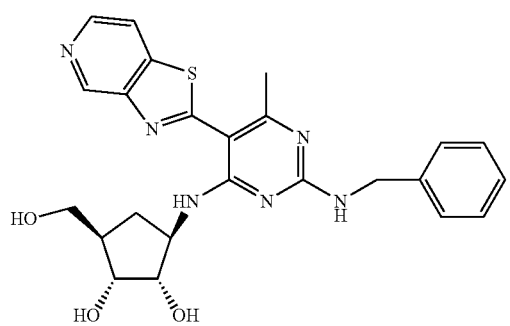 [SMILES: Cc1nc(NCc2ccccc2)nc(N[C@@H]2C[C@H](CO)[C@@H](O)[C@H]2O)c1-c1nc2cnccc2s1] | A | 479.4 | Z |

TABLE I-continued
| | | | | |
|---|---|---|---|---|
| 541 | 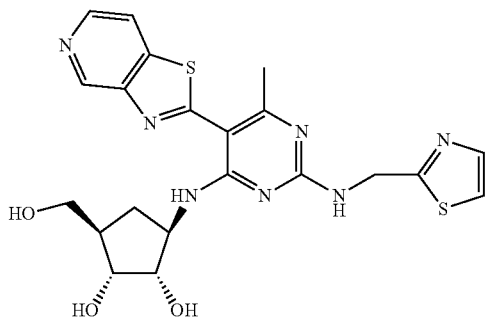 [SMILES: Cc1nc(NCc2nccs2)nc(N[C@@H]2C[C@H](CO)[C@@H](O)[C@H]2O)c1-c1nc2cnccc2s1] | A | 486.3 | Z |
| 542 | 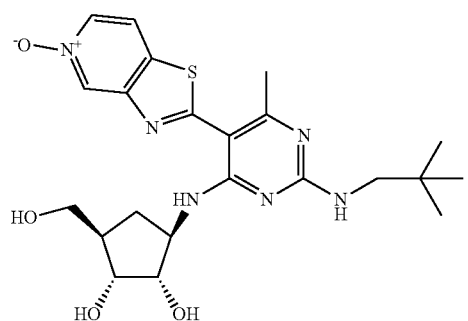 | B | 475.4 | Z2 |
| 543 | 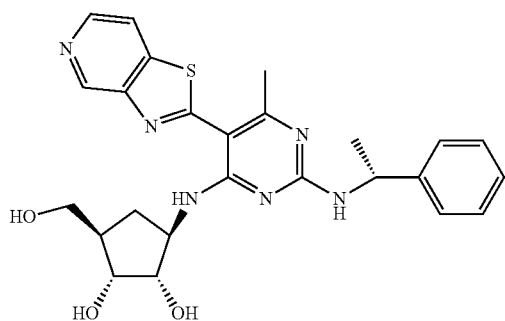 [SMILES: Cc1nc(N[C@H](C)c2ccccc2)nc(N[C@@H]2C[C@H](CO)[C@@H](O)[C@H]2O)c1-c1nc2cnccc2s1] | A | 493.2 | Z |
| 544 | 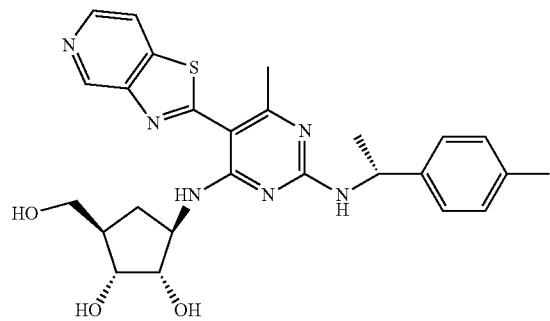 [SMILES: Cc1ccc([C@@H](C)Nc2nc(C)c(-c3nc4cnccc4s3)c(N[C@@H]3C[C@H](CO)[C@@H](O)[C@H]3O)n2)cc1] | A | 507.2 | Z |

TABLE I-continued

| Compd # | Structure | EC90 (uM) | NMR data | LC-MS (M + H)+ | Procedure |
|---|---|---|---|---|---|
| 1001 | 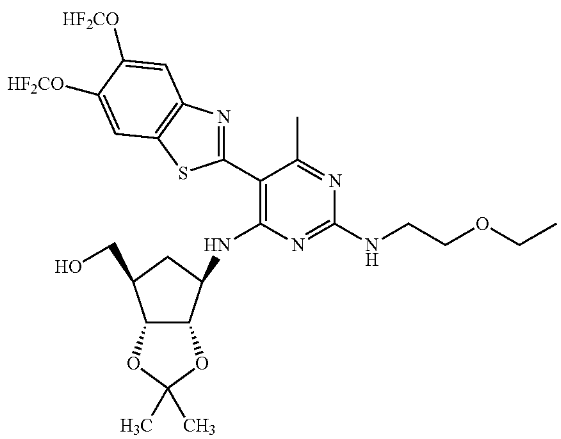 | C | | 632.3 | Combination of E and Z |
| 1002 | 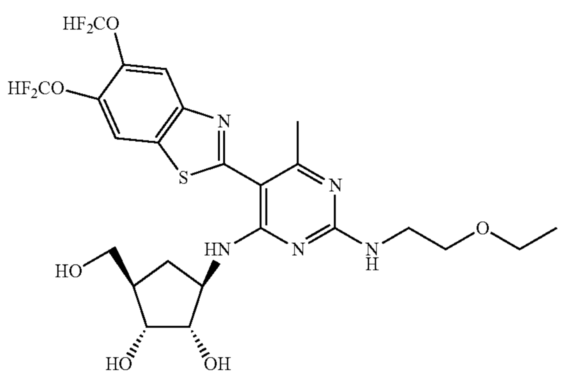 | B | | 592.3 | U (last step) |
| 1003 | 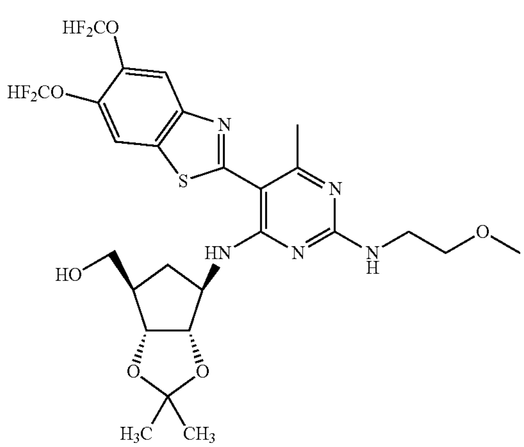 | C | | 618.3 | Combination of E and Z |

TABLE I-continued
| | | | | | |
|---|---|---|---|---|---|
| 1004 | 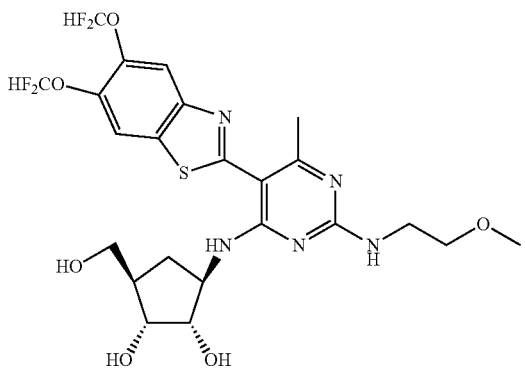 | B | 578.3 | U (last step) | |
| 1005 | 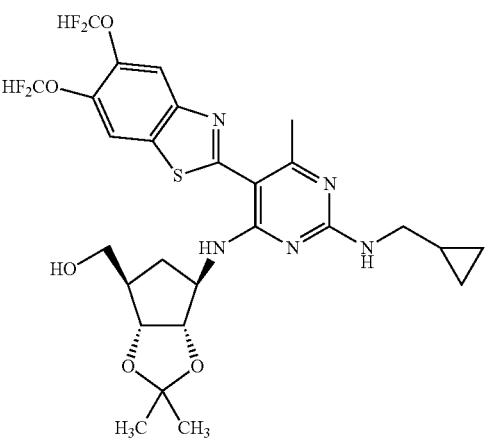 | C | 614.3 | Combination of E and Z | |
| 1006 | 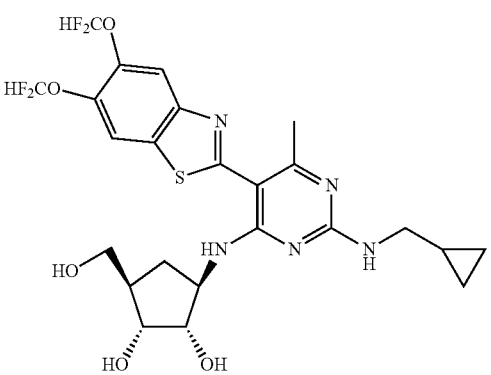 | B | 574.3 | U (last step) | |
| 1007 | 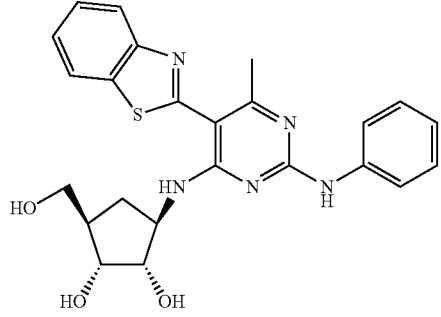 [SMILES: Cc1nc(Nc2ccccc2)nc(N[C@@H]2C[C@H](CO)[C@@H](O)[C@H]2O)c1-c1nc2ccccc2s1] | B | 464.3 | Z3 | |

TABLE I-continued
| | | | | |
|---|---|---|---|---|
| 1008 | 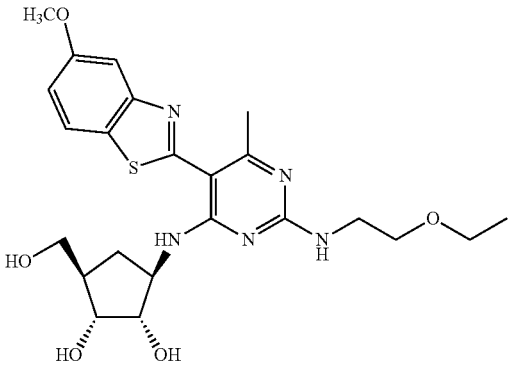 [SMILES: CCOCCNc1nc(C)c(-c2nc3cc(OC)ccc3s2)c(N[C@@H]2C[C@H](CO)[C@@H](O)[C@H]2O)n1] | B | 490.3 | Combination of E and Z |
| 1009 | 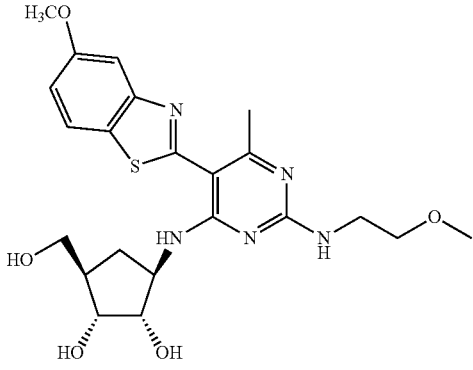 [SMILES: COCCNc1nc(C)c(-c2nc3cc(OC)ccc3s2)c(N[C@@H]2C[C@H](CO)[C@@H](O)[C@H]2O)n1] | B | 476.3 | Combination of E and Z |
| 1010 | 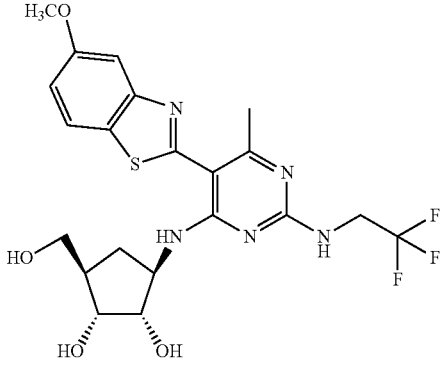 [SMILES: COc1ccc2sc(-c3c(C)nc(NCC(F)(F)F)nc3N[C@@H]3C[C@H](CO)[C@@H](O)[C@H]3O)nc2c1] | B | 500.3 | Combination of E and Z |
| 1011 | 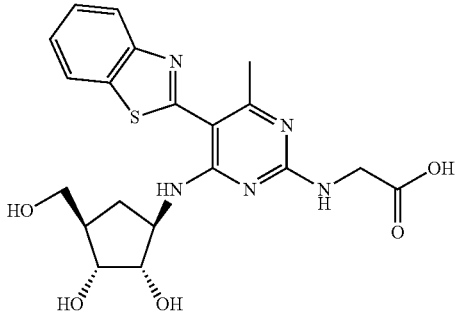 [SMILES: Cc1nc(NCC(=O)O)nc(N[C@@H]2C[C@H](CO)[C@@H](O)[C@H]2O)c1-c1nc2ccccc2s1] | B | 446.2 | Z3 |

TABLE I-continued
| | | | | |
|---|---|---|---|---|
| 1012 | 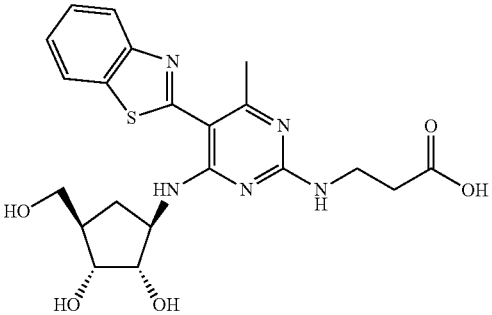 [SMILES: Cc1nc(NCCC(=O)O)nc(N[C@@H]2C[C@H](CO)[C@@H](O)[C@H]2O)c1-c1nc2ccccc2s1] | C | 460.3 | Z3 |
| 1013 | 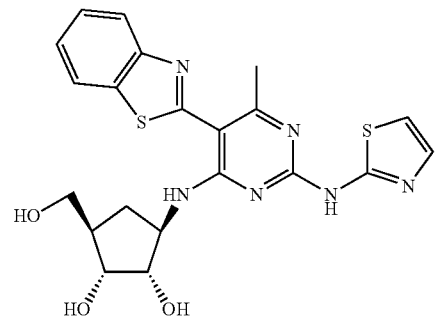 [SMILES: Cc1nc(Nc2nccs2)nc(N[C@@H]2C[C@H](CO)[C@@H](O)[C@H]2O)c1-c1nc2ccccc2s1] | B | 471.3 | Z3 |
| 1014 | 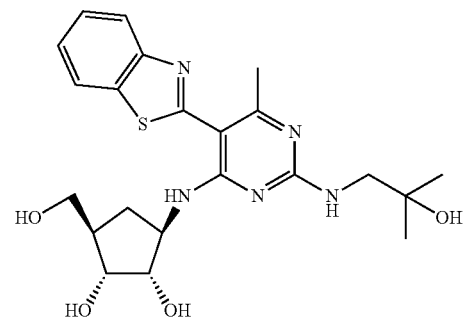 [SMILES: Cc1nc(NCC(C)(C)O)nc(N[C@@H]2C[C@H](CO)[C@@H](O)[C@H]2O)c1-c1nc2ccccc2s1] | A | 460.3 | Z3 |
| 1015 | 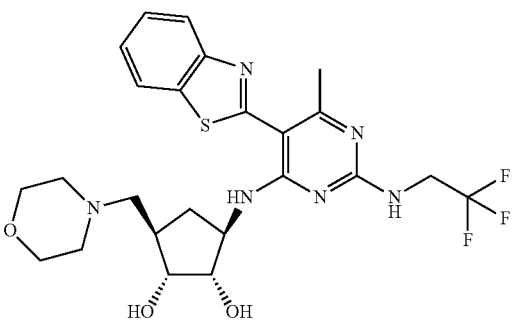 [SMILES: Cc1nc(NCC(F)(F)F)nc(N[C@@H]2C[C@H](CN3CCOCC3)[C@@H](O)[C@H]2O)c1-c1nc2ccccc2s1] | B | 539.3 | Z10 |
| 1016 | 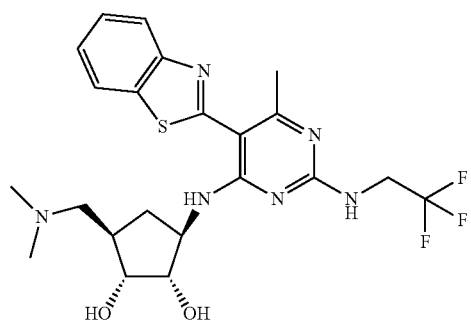 [SMILES: Cc1nc(NCC(F)(F)F)nc(N[C@@H]2C[C@H](CN(C)C)[C@@H](O)[C@H]2O)c1-c1nc2ccccc2s1] | B | 497.3 | Z10 |

TABLE I-continued
| | | | | |
|---|---|---|---|---|
| 1017 | 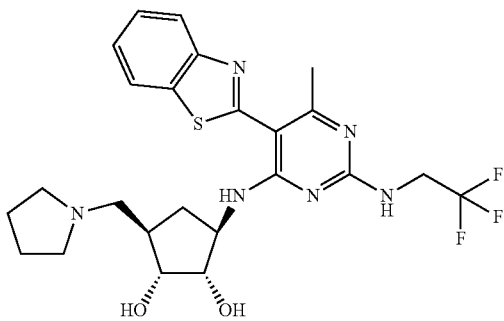 [SMILES: Cc1nc(NCC(F)(F)F)nc(N[C@@H]2C[C@H](CN3CCCC3)[C@@H](O)[C@H]2O)c1-c1nc2ccccc2s1] | B | 523.3 | Z10 |
| 1018 | 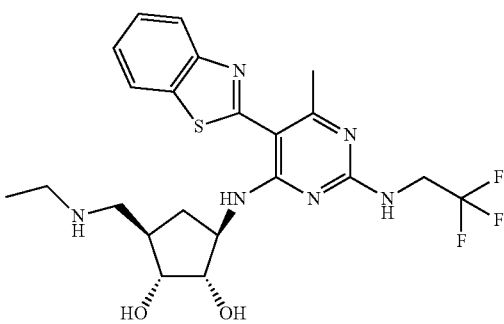 [SMILES: CCNC[C@H]1C[C@@H](Nc2nc(NCC(F)(F)F)nc(C)c2-c2nc3ccccc3s2)[C@H](O)[C@@H]1O] | B | 497.3 | Z10 |
| 1019 | 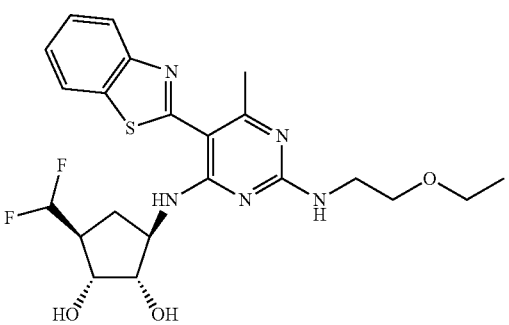 [SMILES: CCOCCNc1nc(C)c(-c2nc3ccccc3s2)c(N[C@@H]2C[C@H](C(F)F)[C@@H](O)[C@H]2O)n1] | A | 480.3 | Z11 |
| 1041 | 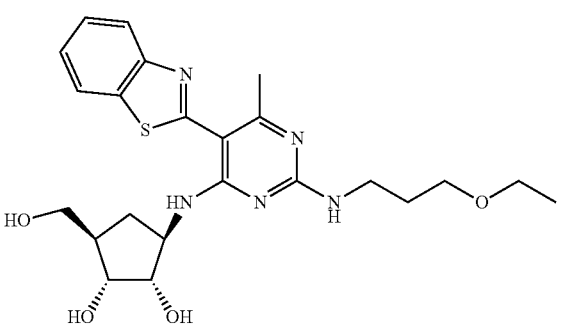 | B | 474.3 | Z3 |
| 1042 | 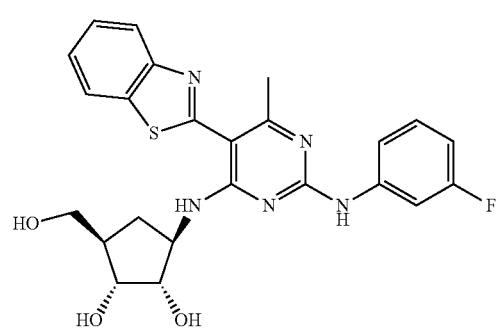 [SMILES: Cc1nc(Nc2cccc(F)c2)nc(N[C@@H]2C[C@H](CO)[C@@H](O)[C@H]2O)c1-c1nc2ccccc2s1] | C | 482.3 | Z3 |

TABLE I-continued
| | | | | |
|---|---|---|---|---|
| 1043 | 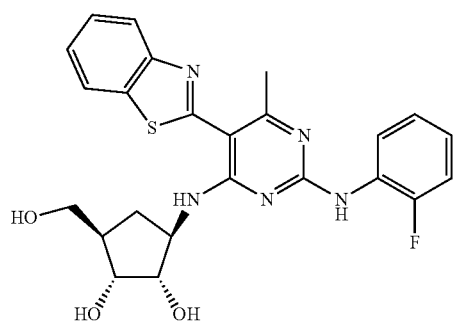 | C | 482.3 | Z3 |
| 1044 | 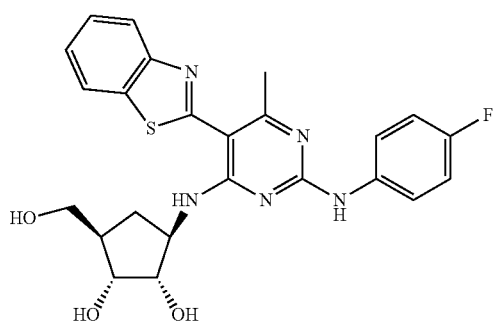 [SMILES: Cc1nc(Nc2ccc(F)cc2)nc(N[C@@H]2C[C@H](CO)[C@@H](O)[C@H]2O)c1-c1nc2ccccc2s1] | B | 482.3 | Z3 |
| 1045 | 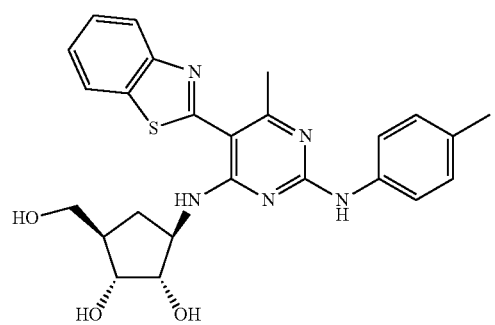 [SMILES: Cc1ccc(Nc2nc(C)c(-c3nc4ccccc4s3)c(N[C@@H]3C[C@H](CO)[C@@H](O)[C@H]3O)n2)cc1] | C | 478.3 | Z3 |
| 1046 | 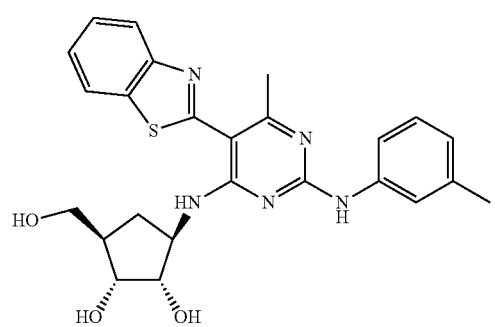 [SMILES: Cc1cccc(Nc2nc(C)c(-c3nc4ccccc4s3)c(N[C@@H]3C[C@H](CO)[C@@H](O)[C@H]3O)n2)c1] | B | 478.3 | Z3 |
| 1047 | 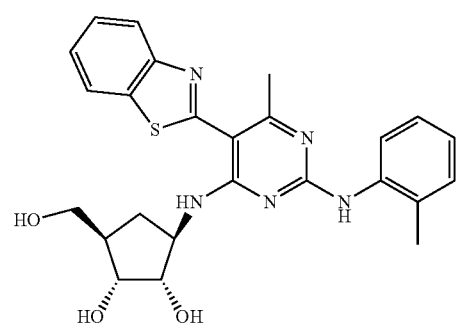 | B | 478.3 | Z3 |

TABLE I-continued

| | | | | |
|---|---|---|---|---|
| 1048 | (structure) | A | 474.3 | Z3 |
| 1050 | (structure) | A | 475.3 | Z |
| 1051 | (structure) | B | 465.3 | Z3 |
| 1052 | (structure) | A | 488.3 | Z3 |
| 1053 | (structure) | A | 483.3 | Z |

US 8,697,694 B2
475 476
TABLE I-continued
| # | Structure | | | |
|---|---|---|---|---|
| 1054 | 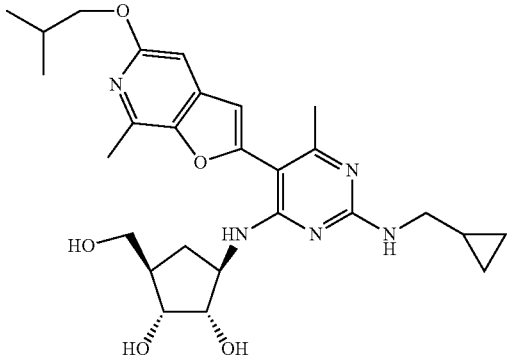 [SMILES: Cc1nc(NCC2CC2)nc(N[C@@H]2C[C@H](CO)[C@@H](O)[C@H]2O)c1-c1cc2cc(OCC(C)C)nc(C)c2o1] | B | 512.3 | Combination of A-2 and Z3 |
| 1055 | 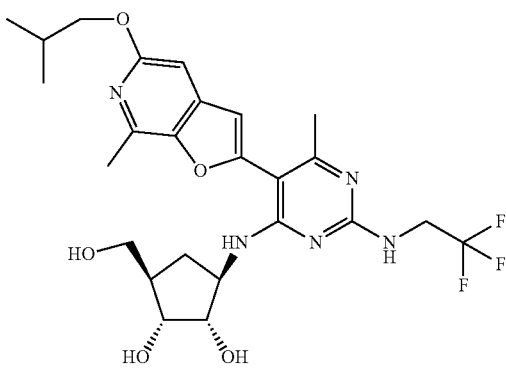 [SMILES: Cc1nc(NCC(F)(F)F)nc(N[C@@H]2C[C@H](CO)[C@@H](O)[C@H]2O)c1-c1cc2cc(OCC(C)C)nc(C)c2o1] | B | 540.3 | Combination of A-2 and Z3 |
| 1056 | 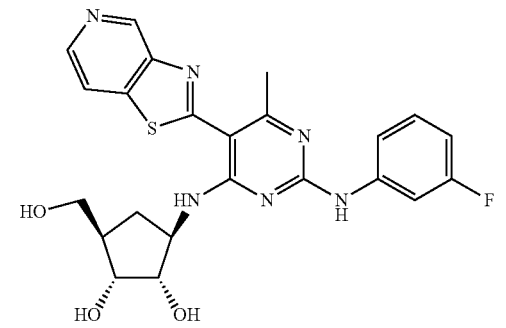 [SMILES: Cc1nc(Nc2cccc(F)c2)nc(N[C@@H]2C[C@H](CO)[C@@H](O)[C@H]2O)c1-c1nc2cnccc2s1] | A | 483.3 | Z |
| 1057 | 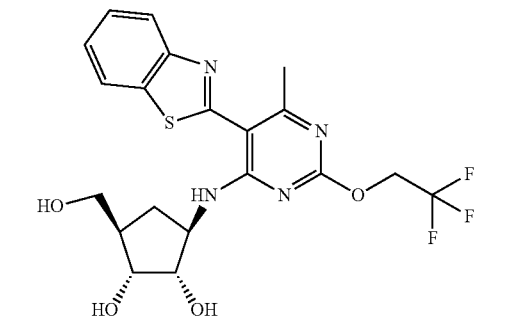 [SMILES: Cc1nc(OCC(F)(F)F)nc(N[C@@H]2C[C@H](CO)[C@@H](O)[C@H]2O)c1-c1nc2ccccc2s1] | C | 471.3 | Z13 |

TABLE I-continued
| | | | | |
|---|---|---|---|---|
| 1058 | 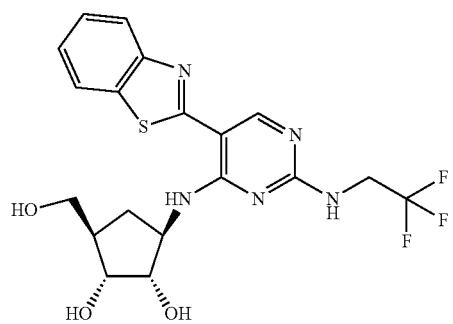 [SMILES: OC[C@H]1C[C@@H](Nc2nc(NCC(F)(F)F)ncc2-c2nc3ccccc3s2)[C@H](O)[C@@H]1O] | B | 456.3 | Z14 |
| 1059 | 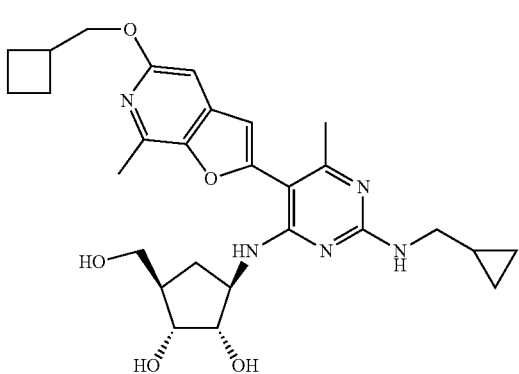 [SMILES: Cc1nc(NCC2CC2)nc(N[C@@H]2C[C@H](CO)[C@@H](O)[C@H]2O)c1-c1cc2cc(OCC3CCC3)nc(C)c2o1] | C | 524.3 | Combination of A-2 and Z3 |
| 1060 | 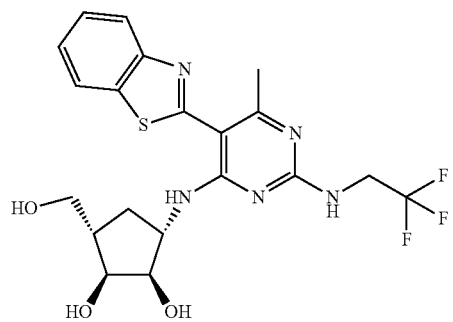 [SMILES: Cc1nc(NCC(F)(F)F)nc(N[C@H]2C[C@@H](CO)[C@H](O)[C@@H]2O)c1-c1nc2ccccc2s1] | C | 470.3 | U |
| 1061 | 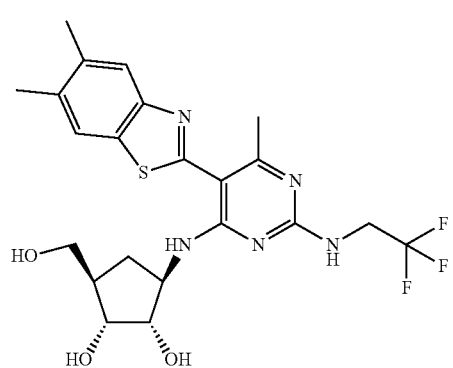 [SMILES: Cc1cc2nc(-c3c(C)nc(NCC(F)(F)F)nc3N[C@@H]3C[C@H](CO)[C@@H](O)[C@H]3O)sc2cc1C] | B | 498.3 | Combination of E and Z |

TABLE I-continued

| | | | | |
|---|---|---|---|---|
| 1062 | | C | 476.3 | Z3 |
| 1063 | | B | 484.3 | Combination of E and Z |
| 1064 | | C | 483.3 | Z (steps 4-7) |
| 1065 | | B | 455.3 | Z (steps 4-7) |

TABLE I-continued
| | | | | |
|---|---|---|---|---|
| 1066 | 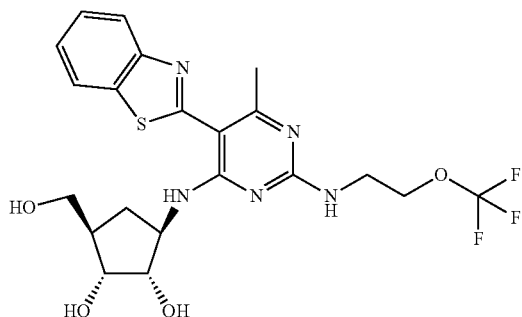 [SMILES: Cc1nc(NCCOC(F)(F)F)nc(N[C@@H]2C[C@H](CO)[C@@H](O)[C@H]2O)c1-c1nc2ccccc2s1] | A | 500.3 | Z3 |
| 1067 | 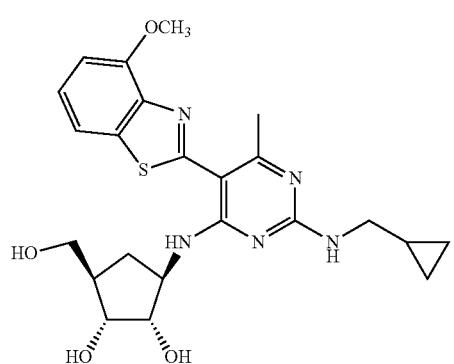 [SMILES: COc1cccc2sc(-c3c(C)nc(NCC4CC4)nc3N[C@@H]3C[C@H](CO)[C@@H](O)[C@H]3O)nc12] | A | 472.3 | Combination of E and Z |
| 1068 | 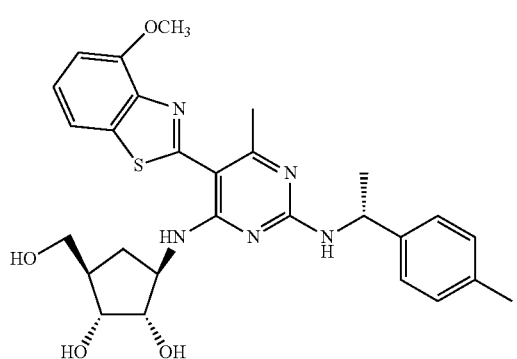 [SMILES: COc1cccc2sc(-c3c(C)nc(N[C@H](C)c4ccc(C)cc4)nc3N[C@@H]3C[C@H](CO)[C@@H](O)[C@H]3O)nc12] | B | 536.3 | Combination of E and Z |
| 1069 | 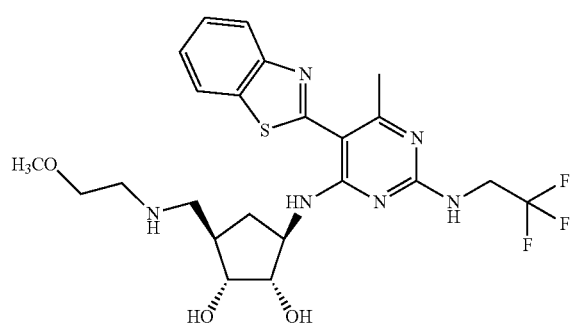 [SMILES: COCCNC[C@H]1C[C@@H](Nc2nc(NCC(F)(F)F)nc(C)c2-c2nc3ccccc3s2)[C@H](O)[C@@H]1O] | B | 527.3 | Z10 |

TABLE I-continued

| | | | | |
|---|---|---|---|---|
| 1070 | | B | 500.2 | Combination of E and Z |
| 1071 | | B | 483.3 | Z10 |
| 1072 | | B | 514.3 | new |
| 1073 | | B | 486.3 | new |

TABLE I-continued
| | | | | |
|---|---|---|---|---|
| 1074 | 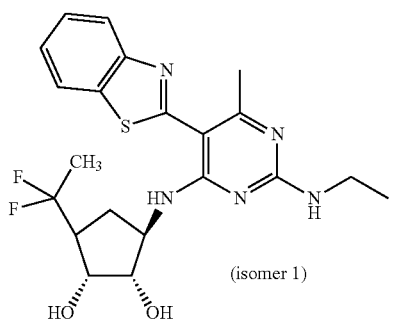 [SMILES: CCNc1nc(C)c(-c2nc3ccccc3s2)c(N[C@@H]2CC(C(C)(F)F)[C@@H](O)[C@H]2O)n1] (isomer 1) | B | 450.2 | Z11 |
| 1101 | 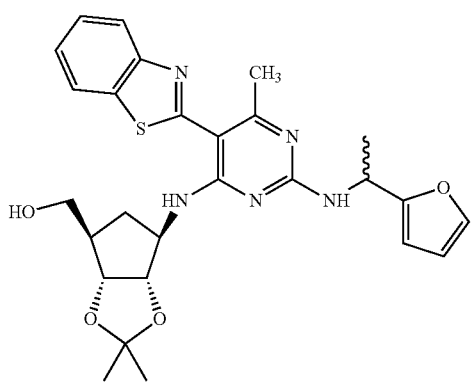 [SMILES: Cc1nc(NC(C)c2ccco2)nc(N[C@@H]2C[C@H](CO)[C@H]3OC(C)(C)O[C@H]32)c1-c1nc2ccccc2s1] | C | 522.3 | Combination of T and U |
| 1102 | 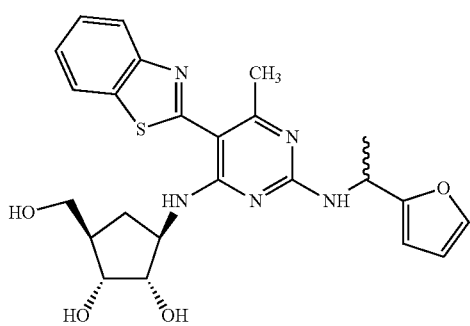 [SMILES: Cc1nc(NC(C)c2ccco2)nc(N[C@@H]2C[C@H](CO)[C@@H](O)[C@H]2O)c1-c1nc2ccccc2s1] | B | 482.3 | Combination of T and U |
| 1103 | 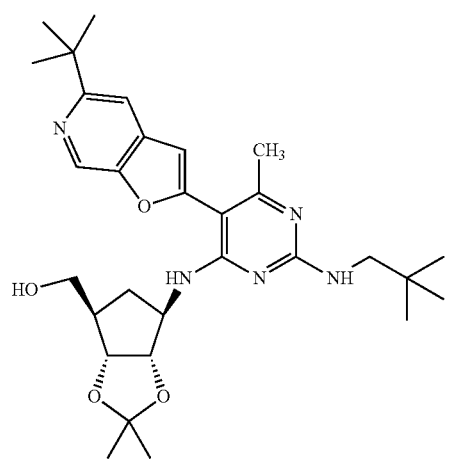 [SMILES: Cc1nc(NCC(C)(C)C)nc(N[C@@H]2C[C@H](CO)[C@H]3OC(C)(C)O[C@H]32)c1-c1cc2cc(C(C)(C)C)ncc2o1] | C | 538.3 | Z15 |

TABLE I-continued

| | | | | |
|---|---|---|---|---|
| 1104 | | C | 498.3 | Z15 |
| 1105 | | B | 561.3 | Combination of T and U. |
| 1106 | | A | 521.3 | Combination of T and U |
| 1107 | | B | 536.3 | Combination of M and Y |

TABLE I-continued
| 1108 | 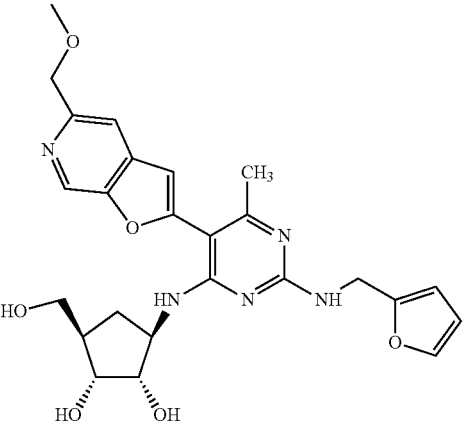 [SMILES: COCc1cc2cc(-c3c(C)nc(NCc4ccco4)nc3N[C@@H]3C[C@H](CO)[C@@H](O)[C@H]3O)oc2cn1] | A | 496.2 | Combination of M and Y. |
| 1109 | 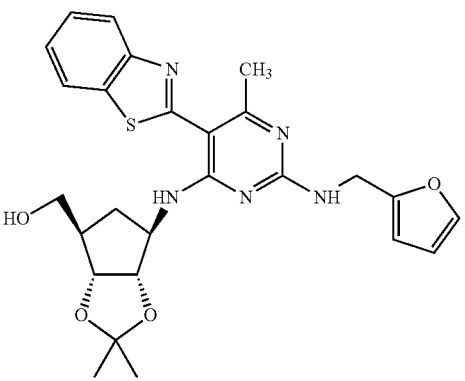 [SMILES: Cc1nc(NCc2ccco2)nc(N[C@@H]2C[C@H](CO)[C@H]3OC(C)(C)O[C@H]32)c1-c1nc2ccccc2s1] | B | 508.3 | U |
| 1110 | 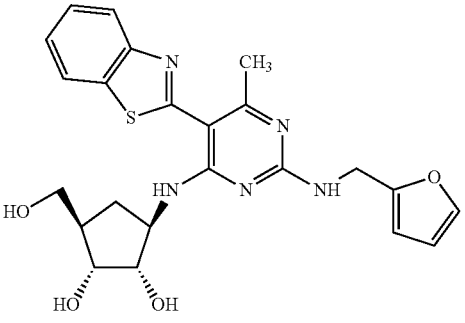 [SMILES: Cc1nc(NCc2ccco2)nc(N[C@@H]2C[C@H](CO)[C@@H](O)[C@H]2O)c1-c1nc2ccccc2s1] | A | 468.3 | U |
| 1111 | 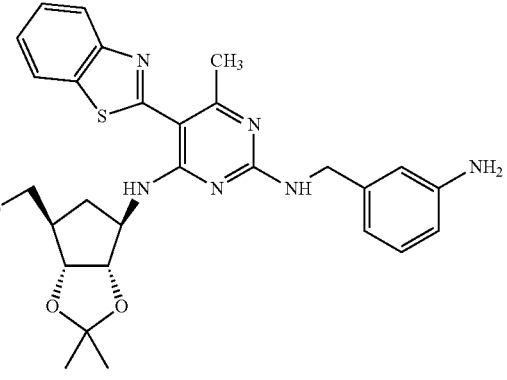 | B | 533.3 | U |

TABLE I-continued
| | | | | |
|---|---|---|---|---|
| 1112 | 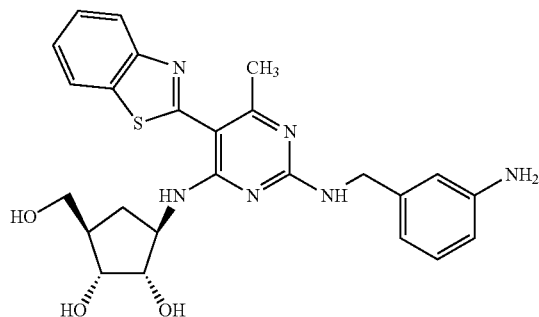 [SMILES: Cc1nc(NCc2cccc(N)c2)nc(N[C@@H]2C[C@H](CO)[C@@H](O)[C@H]2O)c1-c1nc2ccccc2s1] | B | 493.3 | U |
| 1113 | 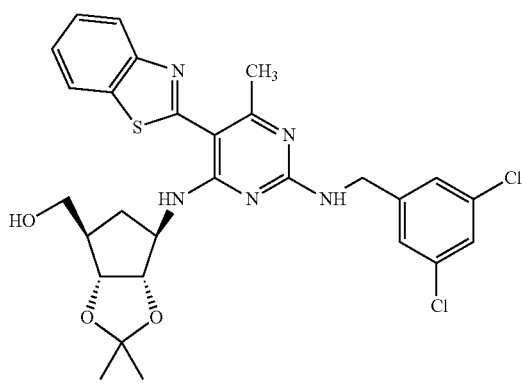 [SMILES: Cc1nc(NCc2cc(Cl)cc(Cl)c2)nc(N[C@@H]2C[C@H](CO)[C@H]3OC(C)(C)O[C@H]32)c1-c1nc2ccccc2s1] | B | 586.3 | U |
| 1114 | 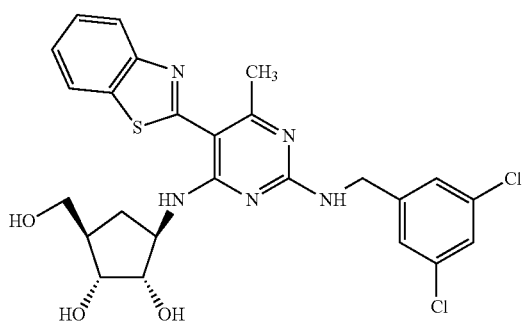 [SMILES: Cc1nc(NCc2cc(Cl)cc(Cl)c2)nc(N[C@@H]2C[C@H](CO)[C@@H](O)[C@H]2O)c1-c1nc2ccccc2s1] | B | 546.3 | U |
| 1115 | 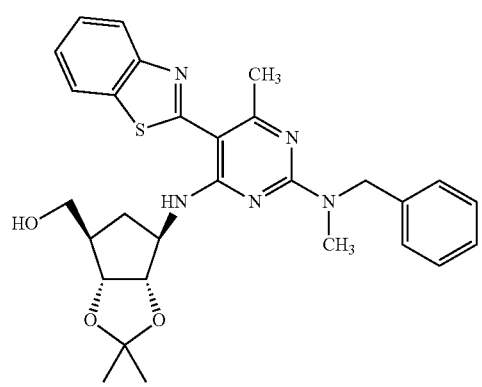 [SMILES: Cc1nc(N(C)Cc2ccccc2)nc(N[C@@H]2C[C@H](CO)[C@H]3OC(C)(C)O[C@H]32)c1-c1nc2ccccc2s1] | C | 532.3 | U |

TABLE I-continued
| | | | | |
|---|---|---|---|---|
| 1116 | 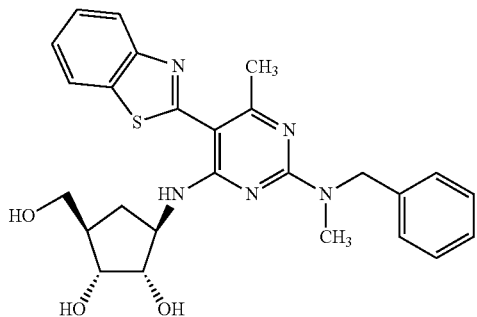 [SMILES: Cc1nc(N(C)Cc2ccccc2)nc(N[C@@H]2C[C@H](CO)[C@@H](O)[C@H]2O)c1-c1nc2ccccc2s1] | C | 492.3 | U |
| 1117 | 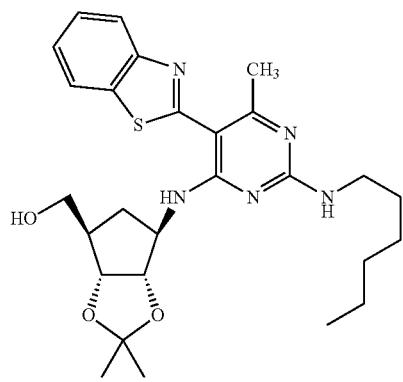 [SMILES: CCCCCCNc1nc(C)c(-c2nc3ccccc3s2)c(N[C@@H]2C[C@H](CO)[C@H]3OC(C)(C)O[C@H]32)n1] | C | 512.3 | U |
| 1118 | 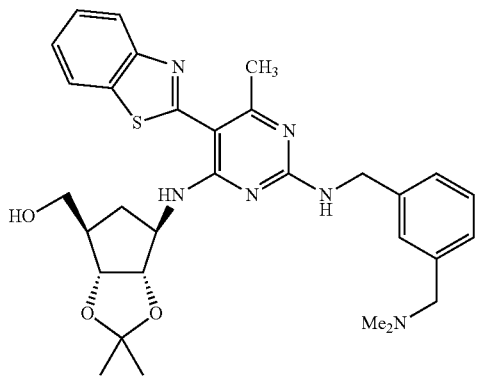 [SMILES: Cc1nc(NCc2cccc(CN(C)C)c2)nc(N[C@@H]2C[C@H](CO)[C@H]3OC(C)(C)O[C@H]32)c1-c1nc2ccccc2s1] | C | 575.3 | U |
| 1119 | 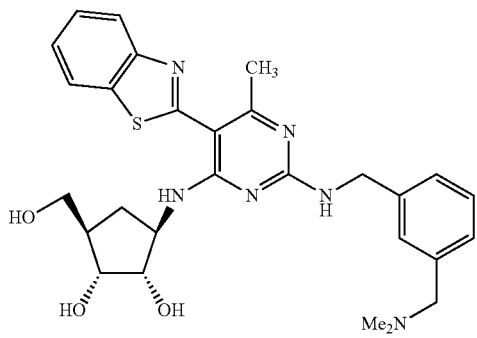 [SMILES: Cc1nc(NCc2cccc(CN(C)C)c2)nc(N[C@@H]2C[C@H](CO)[C@@H](O)[C@H]2O)c1-c1nc2ccccc2s1] | B | 535.3 | U |

| | | | | |
|---|---|---|---|---|
| 1120 | 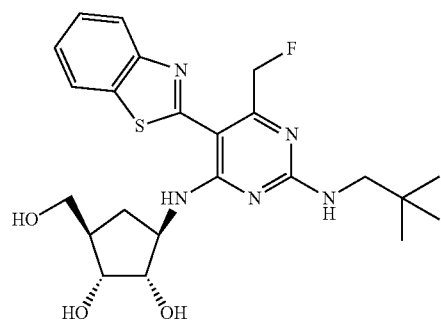 [SMILES: CC(C)(C)CNc1nc(CF)c(-c2nc3ccccc3s2)c(N[C@@H]2C[C@H](CO)[C@@H](O)[C@H]2O)n1] | C | 476.28 | Z16 |
| 1121 | 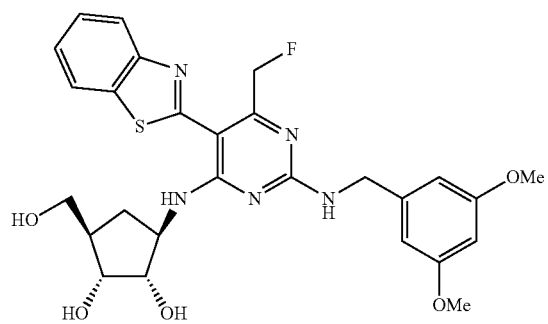 [SMILES: COc1cc(CNc2nc(CF)c(-c3nc4ccccc4s3)c(N[C@@H]3C[C@H](CO)[C@@H](O)[C@H]3O)n2)cc(OC)c1] | B | 556.3 | Z16 |
| 1122 | 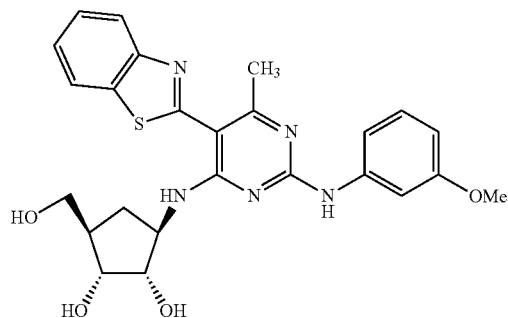 [SMILES: COc1cccc(Nc2nc(C)c(-c3nc4ccccc4s3)c(N[C@@H]3C[C@H](CO)[C@@H](O)[C@H]3O)n2)c1] | B | 494.3 | U |
| 1123 | 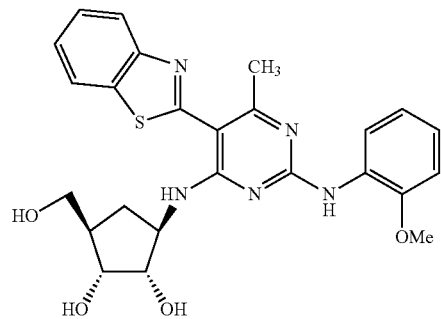 [SMILES: COc1ccccc1Nc1nc(C)c(-c2nc3ccccc3s2)c(N[C@@H]2C[C@H](CO)[C@@H](O)[C@H]2O)n1] | B | 494.3 | U |

TABLE I-continued
| | | | | |
|---|---|---|---|---|
| 1124 | 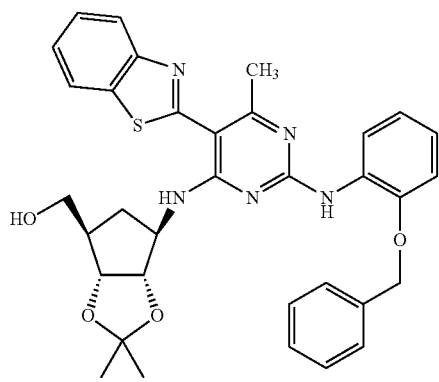 [SMILES: Cc1nc(Nc2ccccc2OCc2ccccc2)nc(N[C@@H]2C[C@H](CO)[C@H]3OC(C)(C)O[C@H]32)c1-c1nc2ccccc2s1] | C | 610.3 | U |
| 1125 | 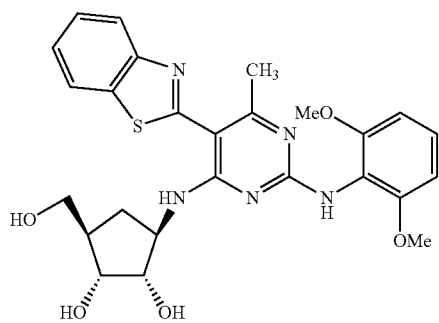 [SMILES: COc1cccc(OC)c1Nc1nc(C)c(-c2nc3ccccc3s2)c(N[C@@H]2C[C@H](CO)[C@@H](O)[C@H]2O)n1] | C | 524.3 | U |
| 1126 | 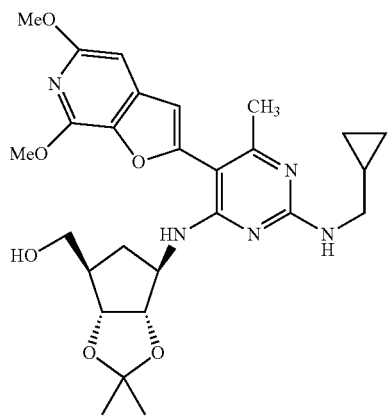 [SMILES: COc1cc2cc(-c3c(C)nc(NCC4CC4)nc3N[C@@H]3C[C@H](CO)[C@H]4OC(C)(C)O[C@H]43)oc2c(OC)n1] | B | 526.3 | Y |
| 1127 | 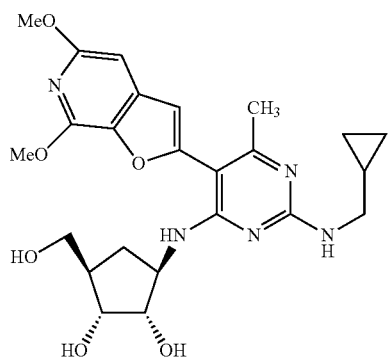 [SMILES: COc1cc2cc(-c3c(C)nc(NCC4CC4)nc3N[C@@H]3C[C@H](CO)[C@@H](O)[C@H]3O)oc2c(OC)n1] | A | 486.3 | Y |

| | | | | |
|---|---|---|---|---|
| 1128 | 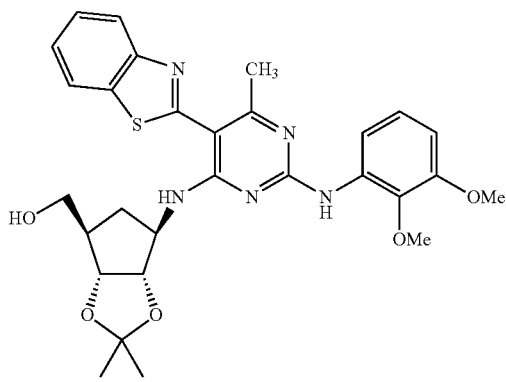 [SMILES: COc1cccc(Nc2nc(C)c(-c3nc4ccccc4s3)c(N[C@@H]3C[C@H](CO)[C@H]4OC(C)(C)O[C@H]43)n2)c1OC] | C | 564.3 | U |
| 1129 | 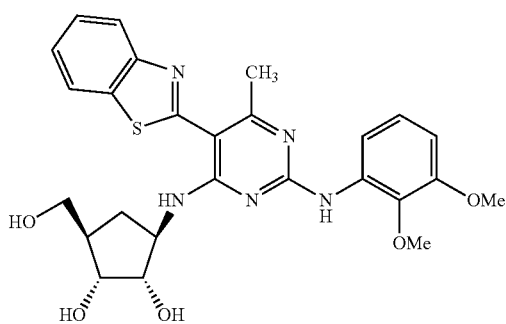 [SMILES: COc1cccc(Nc2nc(C)c(-c3nc4ccccc4s3)c(N[C@@H]3C[C@H](CO)[C@@H](O)[C@H]3O)n2)c1OC] | C | 524.3 | U |
| 1130 | 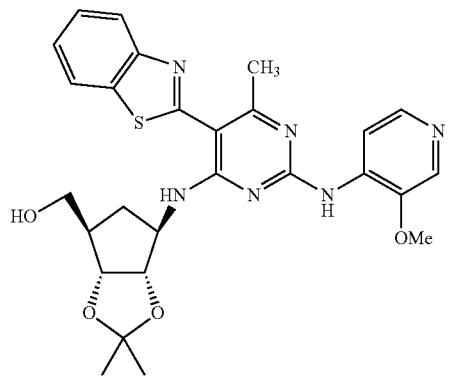 [SMILES: COc1cnccc1Nc1nc(C)c(-c2nc3ccccc3s2)c(N[C@@H]2C[C@H](CO)[C@H]3OC(C)(C)O[C@H]32)n1] | C | 535.3 | U |
| 1131 | 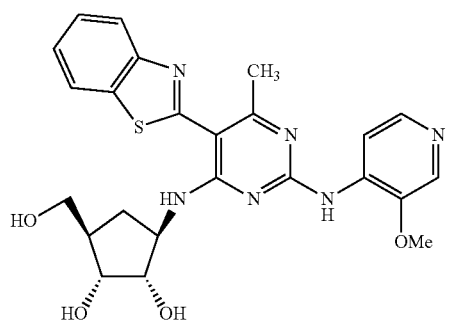 [SMILES: COc1cnccc1Nc1nc(C)c(-c2nc3ccccc3s2)c(N[C@@H]2C[C@H](CO)[C@@H](O)[C@H]2O)n1] | C | 495.3 | U |

TABLE I-continued
| | | | | |
|---|---|---|---|---|
| 1132 | 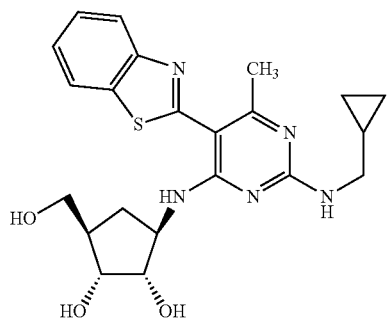 [SMILES: Cc1nc(NCC2CC2)nc(N[C@@H]2C[C@H](CO)[C@@H](O)[C@H]2O)c1-c1nc2ccccc2s1] | C | 443.2 | Z17 |
| 1133 | 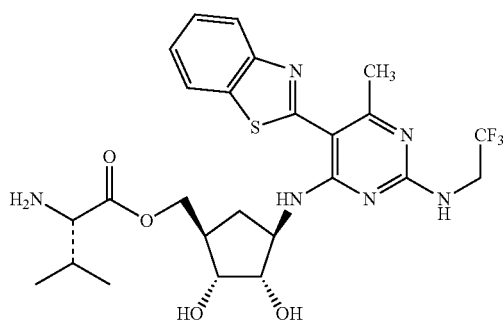 [SMILES: Cc1nc(NCC(F)(F)F)nc(N[C@@H]2C[C@H](COC(=O)[C@@H](N)C(C)C)[C@@H](O)[C@H]2O)c1-c1nc2ccccc2s1] | B | 569.3 | Z18 |
| 1134 | 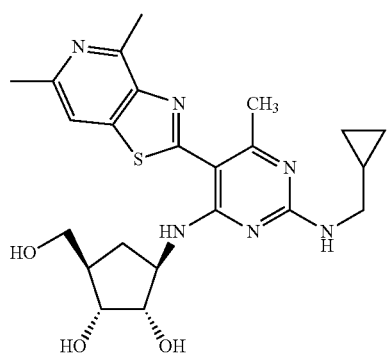 [SMILES: Cc1cc2sc(-c3c(C)nc(NCC4CC4)nc3N[C@@H]3C[C@H](CO)[C@@H](O)[C@H]3O)nc2c(C)n1] | A | 471 | Z19 |
| 1135 | 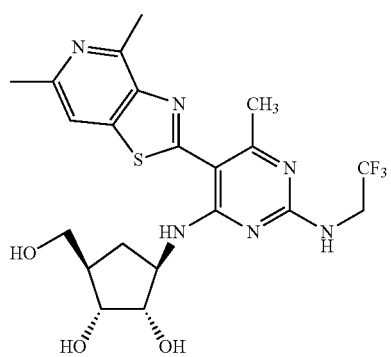 [SMILES: Cc1cc2sc(-c3c(C)nc(NCC(F)(F)F)nc3N[C@@H]3C[C@H](CO)[C@@H](O)[C@H]3O)nc2c(C)n1] | A | 499.34 | Z19 |

TABLE I-continued
| | | | | |
|---|---|---|---|---|
| 1136 | 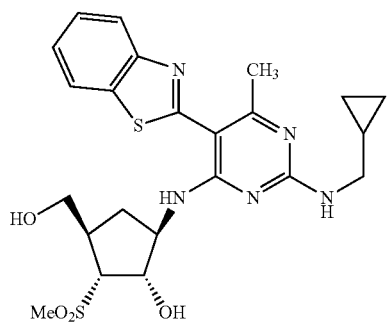 [SMILES: Cc1nc(NCC2CC2)nc(N[C@@H]2C[C@H](CO)[C@@H](S(C)(=O)=O)[C@H]2O)c1-c1nc2ccccc2s1] | B | 504.4 | Z20 |
| 1137 | 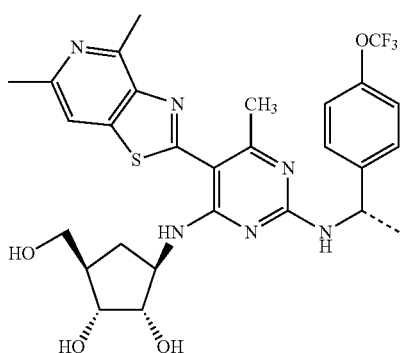 [SMILES: Cc1cc2sc(-c3c(C)nc(N[C@@H](C)c4ccc(OC(F)(F)F)cc4)nc3N[C@@H]3C[C@H](CO)[C@@H](O)[C@H]3O)nc2c(C)n1] | A | 605 | Z19 |
| 1201 | 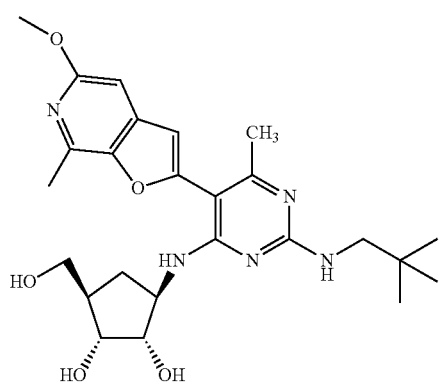 [SMILES: COc1cc2cc(-c3c(C)nc(NCC(C)(C)C)nc3N[C@@H]3C[C@H](CO)[C@@H](O)[C@H]3O)oc2c(C)n1] | B | 486.2 | General Method II |
| 1202 | 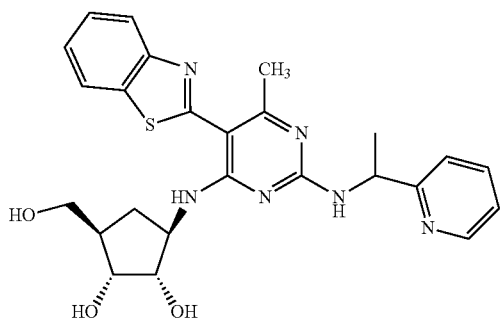 [SMILES: Cc1nc(NC(C)c2ccccn2)nc(N[C@@H]2C[C@H](CO)[C@@H](O)[C@H]2O)c1-c1nc2ccccc2s1] | B | 493.2 | U |

TABLE I-continued
| | | | | |
|---|---|---|---|---|
| 1203 | 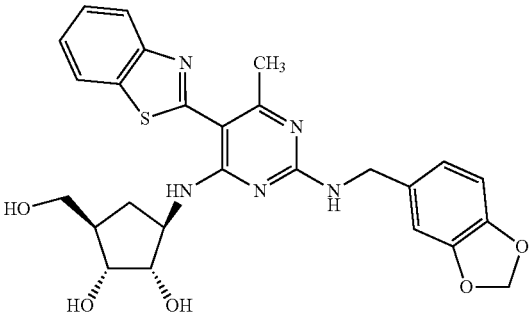 [SMILES: Cc1nc(NCc2ccc3c(c2)OCO3)nc(N[C@@H]2C[C@H](CO)[C@@H](O)[C@H]2O)c1-c1nc2ccccc2s1] | B | 522.2 | U |
| 1204 | 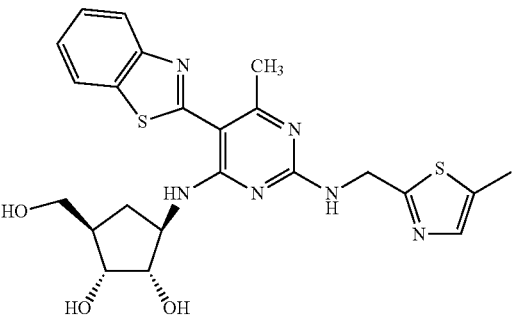 [SMILES: Cc1cnc(CNc2nc(C)c(-c3nc4ccccc4s3)c(N[C@@H]3C[C@H](CO)[C@@H](O)[C@H]3O)n2)s1] | A | 499.3 | U |
| 1205 | 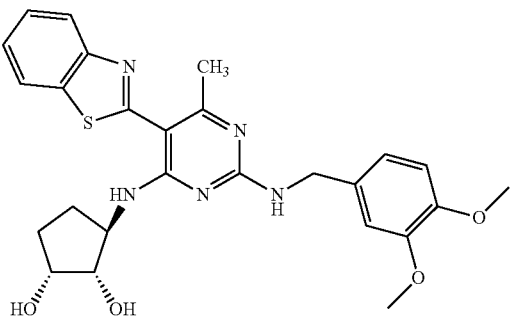 [SMILES: COc1ccc(CNc2nc(C)c(-c3nc4ccccc4s3)c(N[C@@H]3CC[C@@H](O)[C@H]3O)n2)cc1OC] | B | 508.2 | V |
| 1206 | 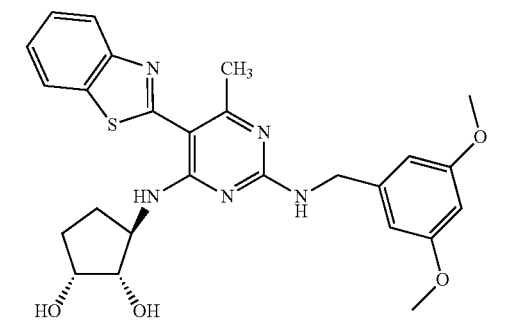 [SMILES: COc1cc(CNc2nc(C)c(-c3nc4ccccc4s3)c(N[C@@H]3CC[C@@H](O)[C@H]3O)n2)cc(OC)c1] | B | 508.0 | V |
| 1207 | 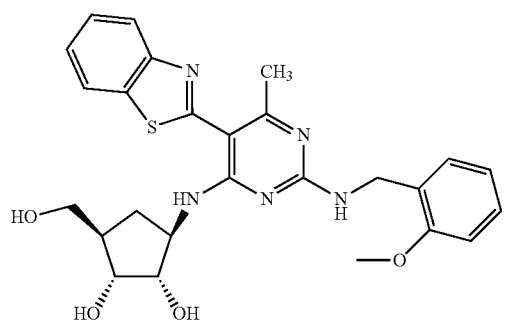 [SMILES: COc1ccccc1CNc1nc(C)c(-c2nc3ccccc3s2)c(N[C@@H]2C[C@H](CO)[C@@H](O)[C@H]2O)n1] | B | 508.2 | U |

TABLE I-continued
| | | | | |
|---|---|---|---|---|
| 1208 | 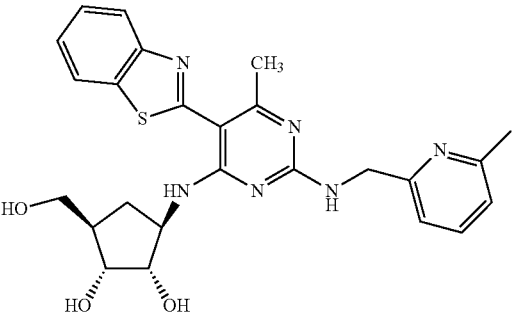 [SMILES: Cc1cccc(CNc2nc(C)c(-c3nc4ccccc4s3)c(N[C@@H]3C[C@H](CO)[C@@H](O)[C@H]3O)n2)n1] | B | 493.2 | U |
| 1209 | 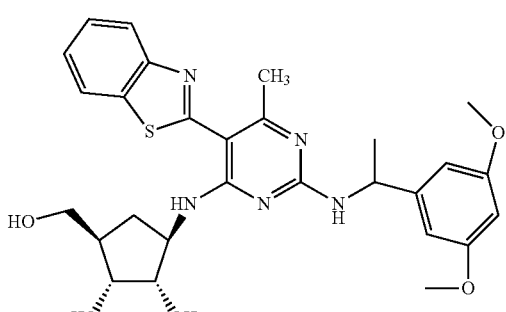 | B | 552.2 | U |
| 1210 | 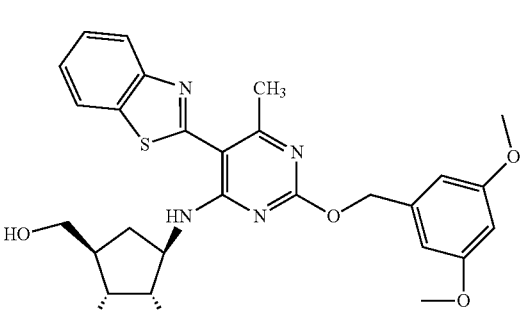 | C | 539.2 | Z21 |
| 1211 | 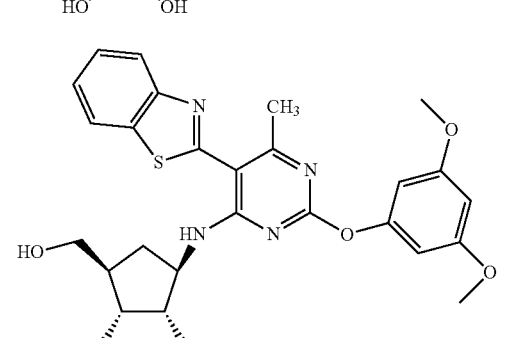 | C | 524.2 | Z21 |
| 1212 | 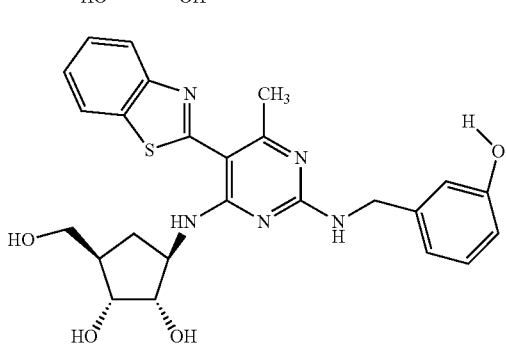 | A | 493.8 | U |

TABLE I-continued

| | | | | |
|---|---|---|---|---|
| 1213 | (structure) | C | 429.0 | Combination of V and Z |
| 1214 | (structure) | A | 454.8 | Combination of V and Z |
| 1215 | (structure) | A | 468.8 | Z |
| 1216 | (structure) | B | 465.2 | Z |
| 1217 | (structure) | C | 479.2 | Z |

TABLE I-continued
| | | | | |
|---|---|---|---|---|
| 1218 | 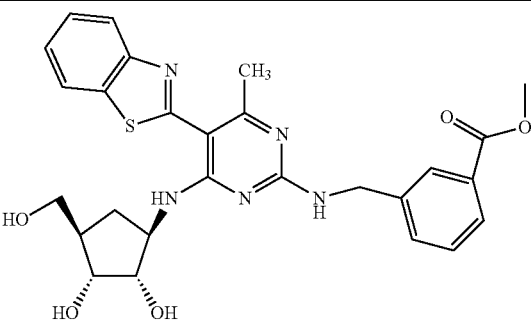 | B | 536.2 | U |
| 1219 | 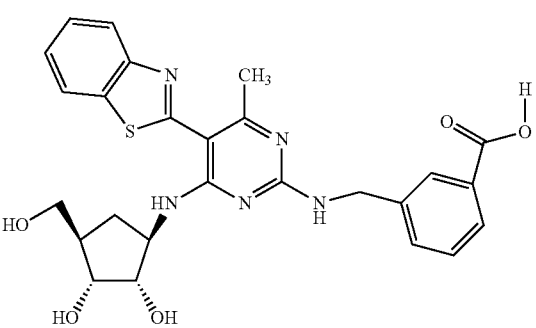 [SMILES: Cc1nc(NCc2cccc(C(=O)O)c2)nc(N[C@@H]2C[C@H](CO)[C@@H](O)[C@H]2O)c1-c1nc2ccccc2s1] | C | 522.2 | Z21 |
| 1220 | 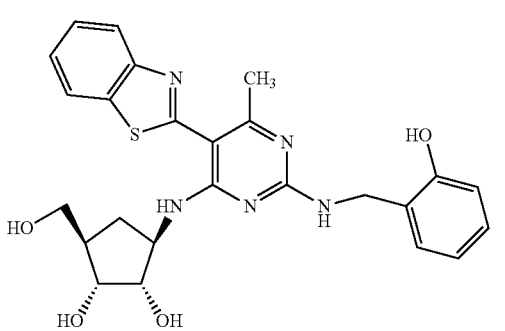 [SMILES: Cc1nc(NCc2ccccc2O)nc(N[C@@H]2C[C@H](CO)[C@@H](O)[C@H]2O)c1-c1nc2ccccc2s1] | A | 494.2 | U |
| 1221 | 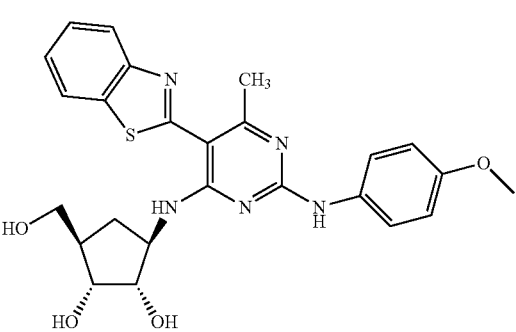 [SMILES: COc1ccc(Nc2nc(C)c(-c3nc4ccccc4s3)c(N[C@@H]3C[C@H](CO)[C@@H](O)[C@H]3O)n2)cc1] | B | 494.2 | U |
| 1222 | 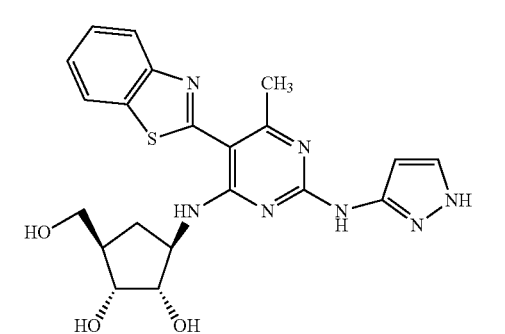 [SMILES: Cc1nc(Nc2cc[nH]n2)nc(N[C@@H]2C[C@H](CO)[C@@H](O)[C@H]2O)c1-c1nc2ccccc2s1] | C | 454.2 | U |

TABLE I-continued

| | | | | |
|---|---|---|---|---|
| 1223 | | C | 412.2 | Z22 |
| 1224 | | C | 438.2 | Z22 |
| 1225 | | B | 556.2 | U |
| 1226 | | C | 455.2 | U |
| 1227 | | | 390.2 | Z23 |

TABLE I-continued
| | | | | |
|---|---|---|---|---|
| 1228 | 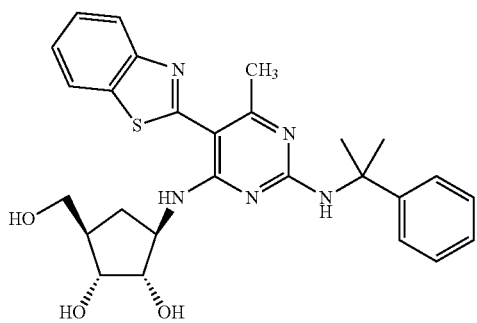 [SMILES: Cc1nc(NC(C)(C)c2ccccc2)nc(N[C@@H]2C[C@H](CO)[C@@H](O)[C@H]2O)c1-c1nc2ccccc2s1] | B | 506.5 | U |
| 1229 | 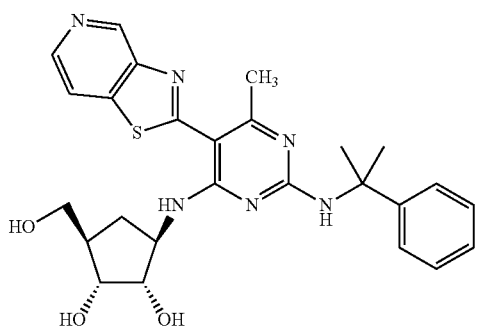 [SMILES: Cc1nc(NC(C)(C)c2ccccc2)nc(N[C@@H]2C[C@H](CO)[C@@H](O)[C@H]2O)c1-c1nc2cnccc2s1] | B | 507.2 | Z |
| 1230 | 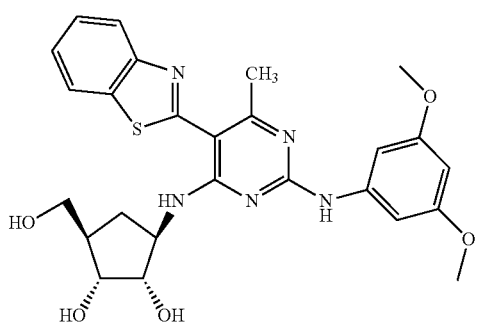 [SMILES: COc1cc(Nc2nc(C)c(-c3nc4ccccc4s3)c(N[C@@H]3C[C@H](CO)[C@@H](O)[C@H]3O)n2)cc(OC)c1] | C | 524.2 | U |
| 1231 | 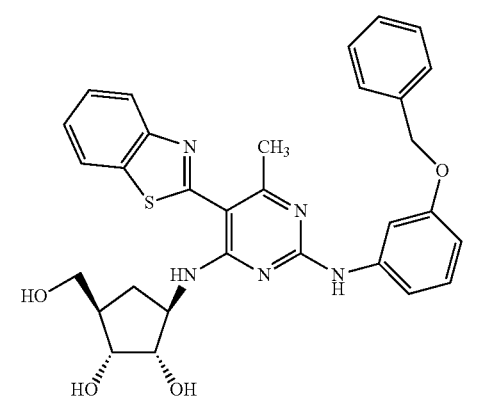 [SMILES: Cc1nc(Nc2cccc(OCc3ccccc3)c2)nc(N[C@@H]2C[C@H](CO)[C@@H](O)[C@H]2O)c1-c1nc2ccccc2s1] | B | | U |

TABLE I-continued
| | | | | |
|---|---|---|---|---|
| 1232 | 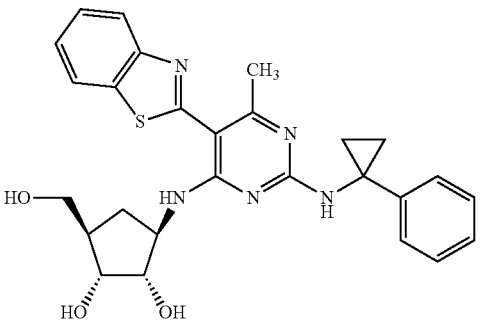 [SMILES: Cc1nc(NC2(c3ccccc3)CC2)nc(N[C@@H]2C[C@H](CO)[C@@H](O)[C@H]2O)c1-c1nc2ccccc2s1] | B | 504.2 | U |
| 1233 | 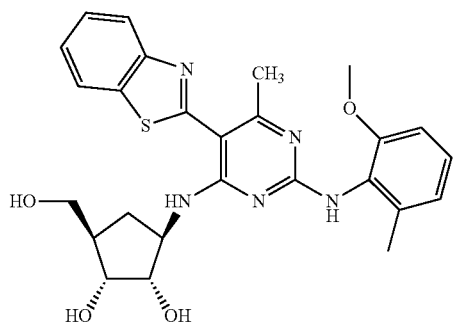 [SMILES: COc1cccc(C)c1Nc1nc(C)c(-c2nc3ccccc3s2)c(N[C@@H]2C[C@H](CO)[C@@H](O)[C@H]2O)n1] | B | 508.2 | U |
| 1234 | 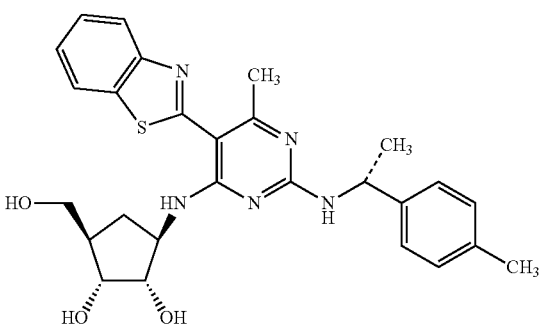 [SMILES: Cc1ccc([C@@H](C)Nc2nc(C)c(-c3nc4ccccc4s3)c(N[C@@H]3C[C@H](CO)[C@@H](O)[C@H]3O)n2)cc1] | C | 506.2 | U |
| 1235 | 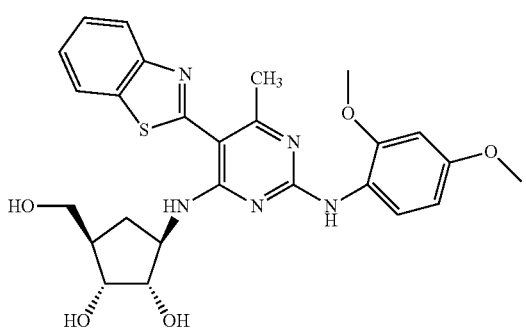 [SMILES: COc1ccc(Nc2nc(C)c(-c3nc4ccccc4s3)c(N[C@@H]3C[C@H](CO)[C@@H](O)[C@H]3O)n2)c(OC)c1] | B | 524.2 | U |
| 1236 | 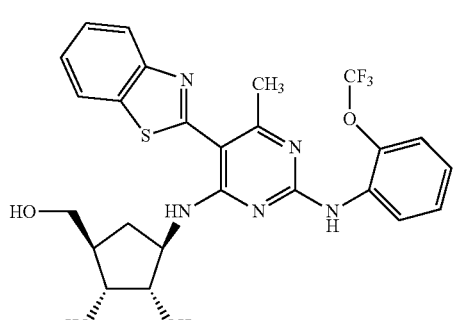 | C | 548.1 | U |

TABLE I-continued
| | | | | |
|---|---|---|---|---|
| 1237 | 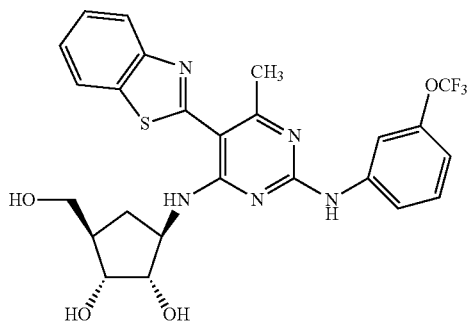 [SMILES: Cc1nc(Nc2cccc(OC(F)(F)F)c2)nc(N[C@@H]2C[C@H](CO)[C@@H](O)[C@H]2O)c1-c1nc2ccccc2s1] | C | 548.1 | U |
| 1238 | 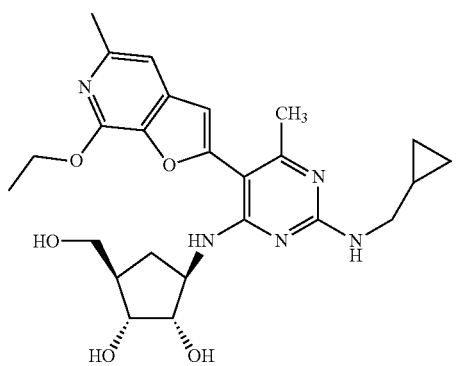 [SMILES: CCOc1nc(C)cc2cc(-c3c(C)nc(NCC4CC4)nc3N[C@@H]3C[C@H](CO)[C@@H](O)[C@H]3O)oc12] | B | 484.2 | Z24 |
| 1239 | 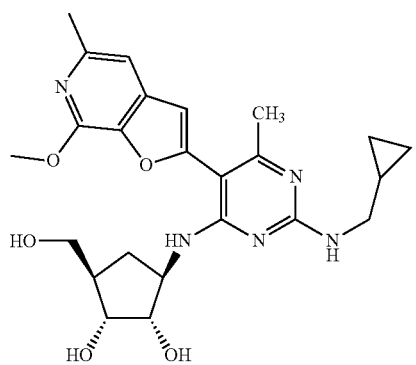 [SMILES: COc1nc(C)cc2cc(-c3c(C)nc(NCC4CC4)nc3N[C@@H]3C[C@H](CO)[C@@H](O)[C@H]3O)oc12] | B | 470.2 | Z24 |
| 1240 | 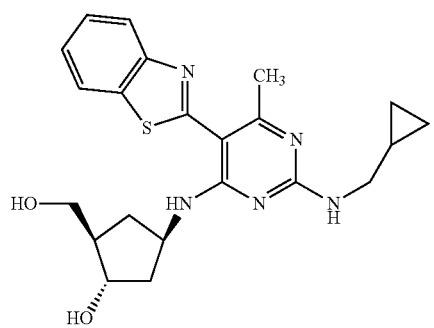 [SMILES: Cc1nc(NCC2CC2)nc(N[C@@H]2C[C@H](CO)[C@@H](O)C2)c1-c1nc2ccccc2s1] | B | 426.0 | Z25 |

TABLE I-continued
| | | | | |
|---|---|---|---|---|
| 1241 | 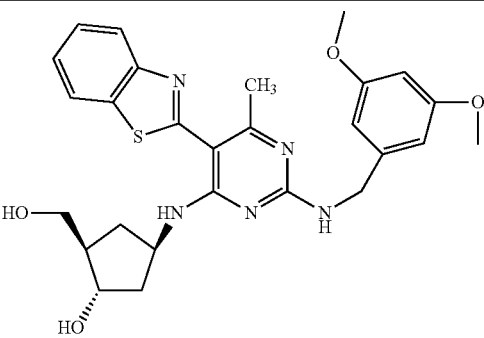 | A | 522.0 | Z25 |
| 1242 | 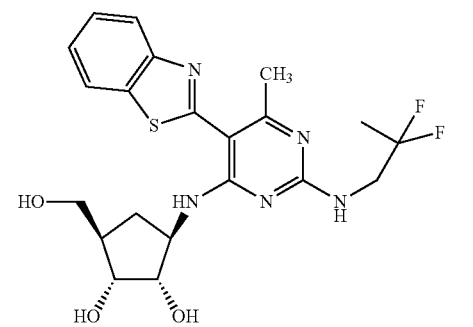 [SMILES: Cc1nc(NCC(C)(F)F)nc(N[C@@H]2C[C@H](CO)[C@@H](O)[C@H]2O)c1-c1nc2ccccc2s1] | B | 466.2 | U |
| 1243 | 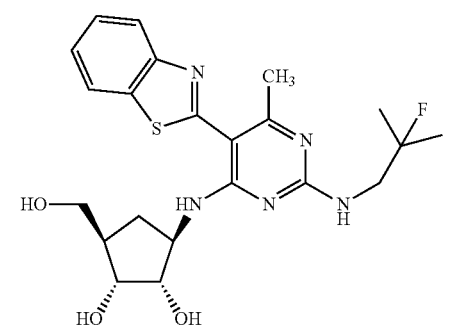 [SMILES: Cc1nc(NCC(C)(C)F)nc(N[C@@H]2C[C@H](CO)[C@@H](O)[C@H]2O)c1-c1nc2ccccc2s1] | B | 462.2 | U |
| 1244 | 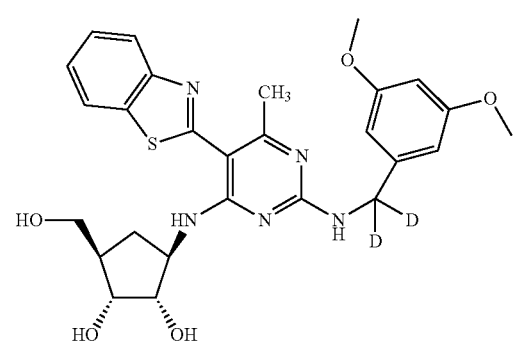 [SMILES: [2H]C([2H])(Nc1nc(C)c(-c2nc3ccccc3s2)c(N[C@@H]2C[C@H](CO)[C@@H](O)[C@H]2O)n1)c1cc(OC)cc(OC)c1] | A | 540.2 | Z26 |
| 1245 | 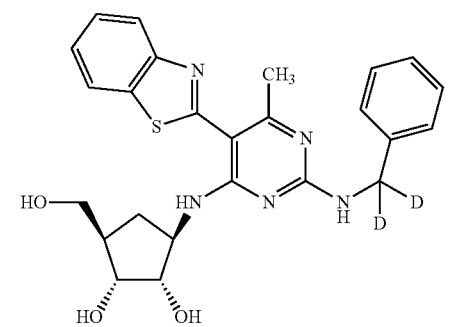 [SMILES: [2H]C([2H])(Nc1nc(C)c(-c2nc3ccccc3s2)c(N[C@@H]2C[C@H](CO)[C@@H](O)[C@H]2O)n1)c1ccccc1] | A | 480.2 | U |

TABLE I-continued
| 1246 | 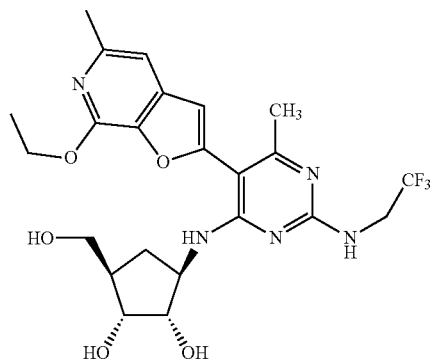 [SMILES: CCOc1nc(C)cc2cc(-c3c(C)nc(NCC(F)(F)F)nc3N[C@@H]3C[C@H](CO)[C@@H](O)[C@H]3O)oc12] | A | 512.2 | Z24 |
| 1247 | 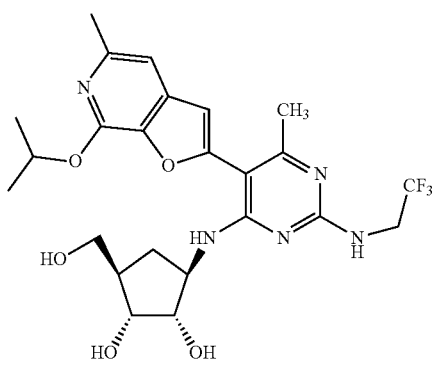 [SMILES: Cc1cc2cc(-c3c(C)nc(NCC(F)(F)F)nc3N[C@@H]3C[C@H](CO)[C@@H](O)[C@H]3O)oc2c(OC(C)C)n1] | A | 526.2 | Z24 |
| 1248 | 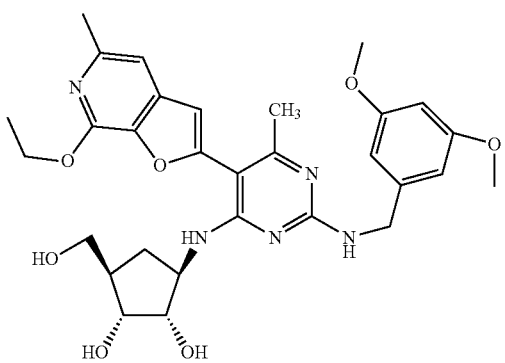 [SMILES: CCOc1nc(C)cc2cc(-c3c(C)nc(NCc4cc(OC)cc(OC)c4)nc3N[C@@H]3C[C@H](CO)[C@@H](O)[C@H]3O)oc12] | B | 580.2 | Z24 |
| 1249 | 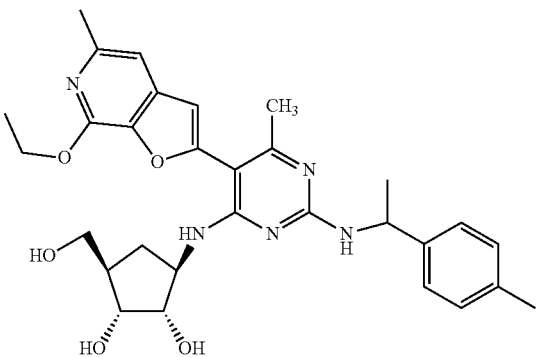 [SMILES: CCOc1nc(C)cc2cc(-c3c(C)nc(NC(C)c4ccc(C)cc4)nc3N[C@@H]3C[C@H](CO)[C@@H](O)[C@H]3O)oc12] | B | 548.2 | Z24 |

TABLE I-continued

| | | | | |
|---|---|---|---|---|
| 1250 | (structure) | B | 472.2 | Z26 |
| 1251 | (structure) | B | 426.2 | Z27 |
| 1252 | (structure) | C | 442.2 | Z28 |
| 1253 | (structure) | B | 470.0 | Z28 |
| 1301 | (structure) | C | 457.3 | Z29 |

TABLE I-continued

| | | | | |
|---|---|---|---|---|
| 1302 | (structure) | B | 447.2 | Z30 |
| 1303 | (structure) | B | 401.39 | Y |
| 1304 | (structure) | S | 527.4 | Z |
| 1305 | (structure) | B | 493.4 | Z |
| 1306 | (structure) | A | 553.3 | Z |

TABLE I-continued

| | | | | |
|---|---|---|---|---|
| 1307 | | A | 553.3 | Z |
| 1308 | | B | 473.3 | Z |
| 1309 | | A | 515.3 | Z |
| 1310 | | B | 473.5 | Z |
| 1311 | | A | 511.48 | Z |

TABLE I-continued

| | | | | |
|---|---|---|---|---|
| 1312 | [structure] | B | 505.49 | Z |
| 1313 | [structure] | B | 493.43 | Z |
| 1314 | [structure] | B | 507.4 | Z |
| 1315 | [structure] | B | 519.5 | Z, Z31 |
| 1316 | [structure] | A | 445.4 | Z |

TABLE I-continued

| | | | | |
|---|---|---|---|---|
| 1317 | (structure) | A | 475.5 | Z |
| 1318 | (structure) | A | 499.5 | Z, Z32 |
| 1319 | (structure) | A | 473.5 | Z1 |
| 1320 | (structure) | A | 521.5 | Z1 |
| 1321 | (structure) | B | 477.5 | Z, Z33 |

TABLE I-continued
| | | | | |
|---|---|---|---|---|
| 1322 | 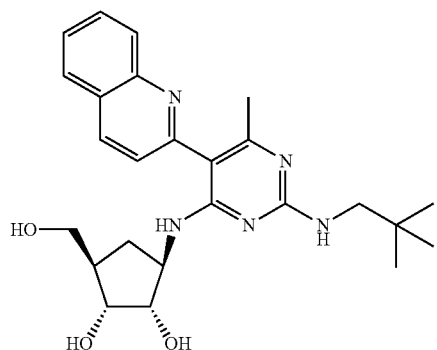 [SMILES: Cc1nc(NCC(C)(C)C)nc(N[C@@H]2C[C@H](CO)[C@@H](O)[C@H]2O)c1-c1ccc2ccccc2n1] | C | 452.5 | F |
| 1323 | 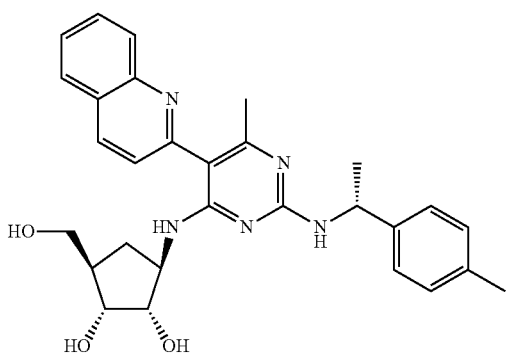 [SMILES: Cc1ccc([C@@H](C)Nc2nc(C)c(-c3ccc4ccccc4n3)c(N[C@@H]3C[C@H](CO)[C@@H](O)[C@H]3O)n2)cc1] | C | 500.5 | F |
| 1324 | 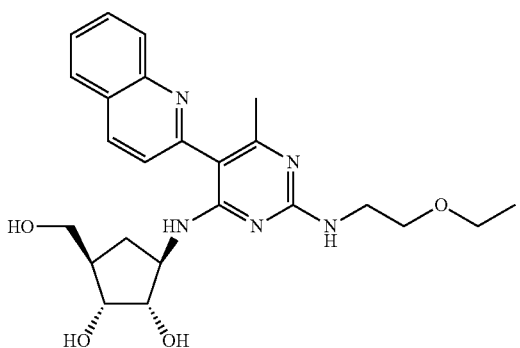 [SMILES: CCOCCNc1nc(C)c(-c2ccc3ccccc3n2)c(N[C@@H]2C[C@H](CO)[C@@H](O)[C@H]2O)n1] | C | 454.5 | F |
| 1325 | 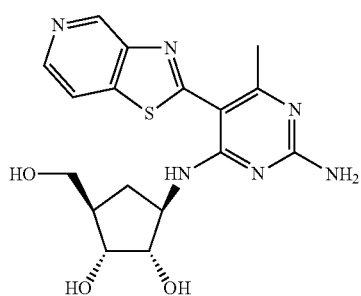 [SMILES: Cc1nc(N)nc(N[C@@H]2C[C@H](CO)[C@@H](O)[C@H]2O)c1-c1nc2cnccc2s1] | B | 389.3 | Z |
| 1326 | 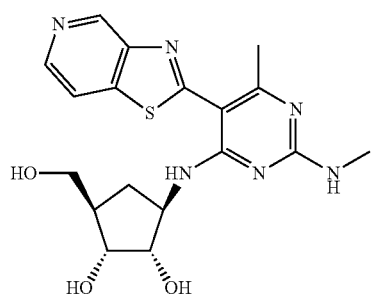 [SMILES: CNc1nc(C)c(-c2nc3cnccc3s2)c(N[C@@H]2C[C@H](CO)[C@@H](O)[C@H]2O)n1] | A | 403.3 | Z |

TABLE I-continued
| | | | | |
|---|---|---|---|---|
| 1327 | 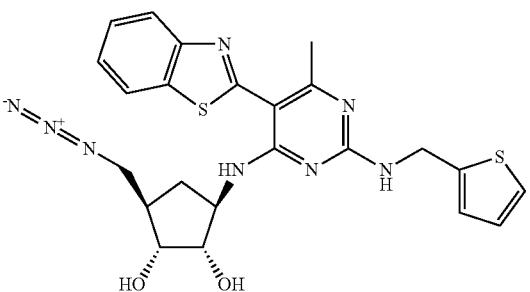 | A | 509.49 | U, Z34 |
| 1328 | 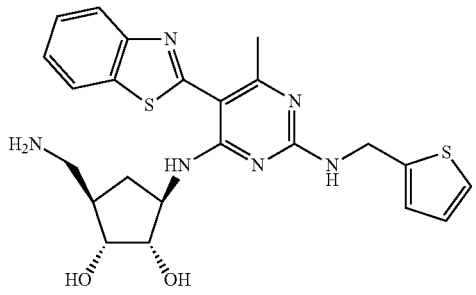 [SMILES: Cc1nc(NCc2cccs2)nc(N[C@@H]2C[C@H](CN)[C@@H](O)[C@H]2O)c1-c1nc2ccccc2s1] | A | 483.49 | U, Z35 |
| 1330 | 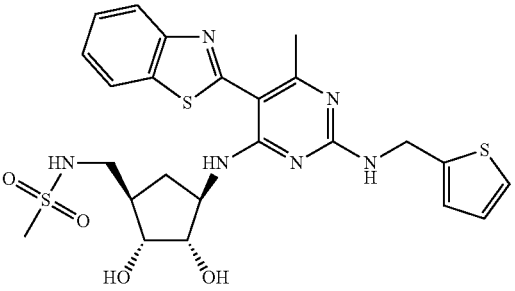 [SMILES: Cc1nc(NCc2cccs2)nc(N[C@@H]2C[C@H](CNS(C)(=O)=O)[C@@H](O)[C@H]2O)c1-c1nc2ccccc2s1] | A | 561.5 | U, Z36 |
| 1331 | 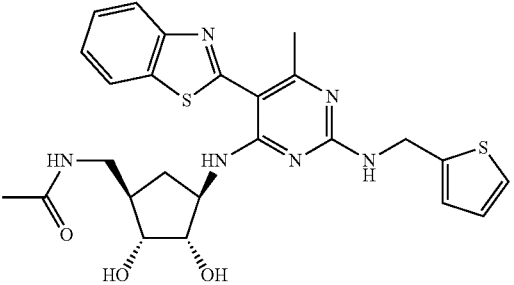 [SMILES: CC(=O)NC[C@H]1C[C@@H](Nc2nc(NCc3cccs3)nc(C)c2-c2nc3ccccc3s2)[C@H](O)[C@@H]1O] | A | 525.5 | U, Z37 |
| 1333 | 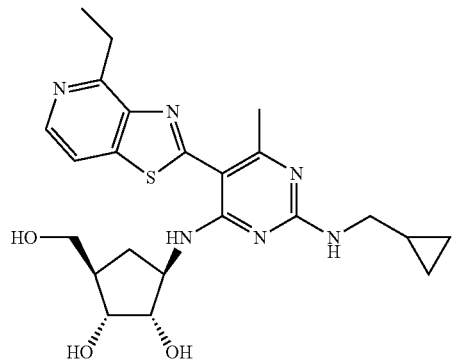 [SMILES: CCc1nccc2sc(-c3c(C)nc(NCC4CC4)nc3N[C@@H]3C[C@H](CO)[C@@H](O)[C@H]3O)nc12] | A | 471.51 | Z1 |

TABLE I-continued
| | | | | |
|---|---|---|---|---|
| 1334 | 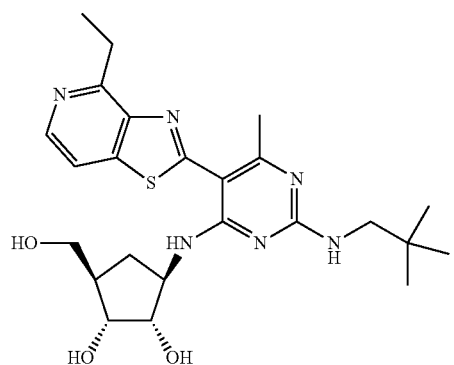 [SMILES: CCc1nccc2sc(-c3c(C)nc(NCC(C)(C)C)nc3N[C@@H]3C[C@H](CO)[C@@H](O)[C@H]3O)nc12] | A | 487.5 | Z1 |
| 1335 | 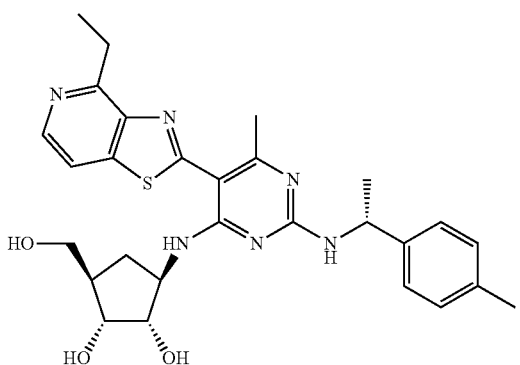 [SMILES: CCc1nccc2sc(-c3c(C)nc(N[C@H](C)c4ccc(C)cc4)nc3N[C@@H]3C[C@H](CO)[C@@H](O)[C@H]3O)nc12] | A | 535.6 | Z1 |
| 1336 | 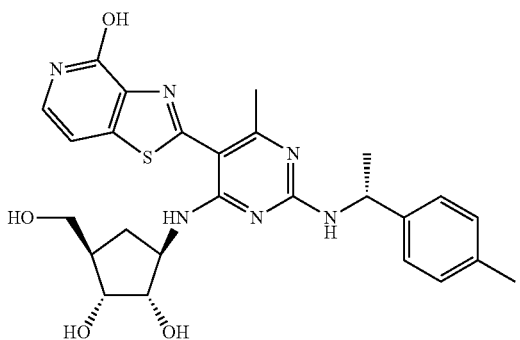 [SMILES: Cc1ccc([C@@H](C)Nc2nc(C)c(-c3nc4c(O)nccc4s3)c(N[C@@H]3C[C@H](CO)[C@@H](O)[C@H]3O)n2)cc1] | A | 537.5 | Z, Z38 |
| 1337 | 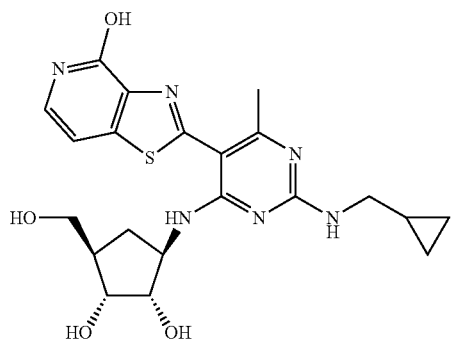 [SMILES: Cc1nc(NCC2CC2)nc(N[C@@H]2C[C@H](CO)[C@@H](O)[C@H]2O)c1-c1nc2c(O)nccc2s1] | B | 473.4 | Z, Z38 |

TABLE I-continued
| | | | | |
|---|---|---|---|---|
| 1338 | 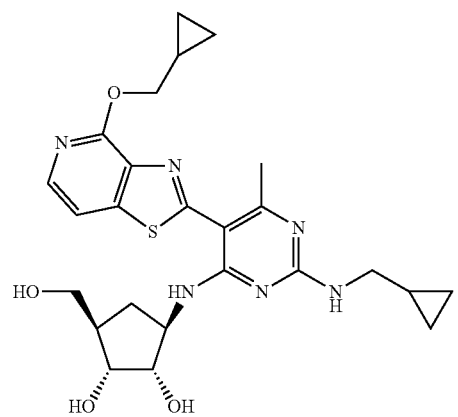 [SMILES: Cc1nc(NCC2CC2)nc(N[C@@H]2C[C@H](CO)[C@@H](O)[C@H]2O)c1-c1nc2c(OCC3CC3)nccc2s1] | A | 513.5 | Z, Z38 |
| 1339 | 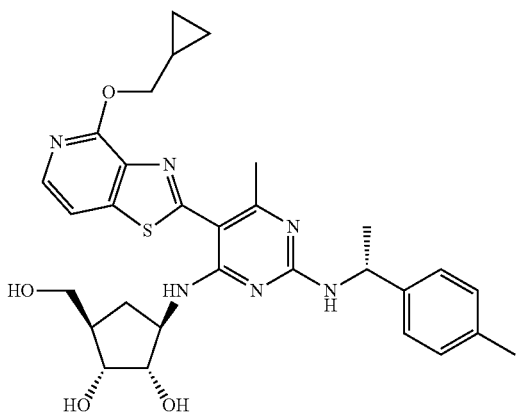 [SMILES: Cc1ccc([C@@H](C)Nc2nc(C)c(-c3nc4c(OCC5CC5)nccc4s3)c(N[C@@H]3C[C@H](CO)[C@@H](O)[C@H]3O)n2)cc1] | A | 577.57 | Z, Z38 |
| 1340 | 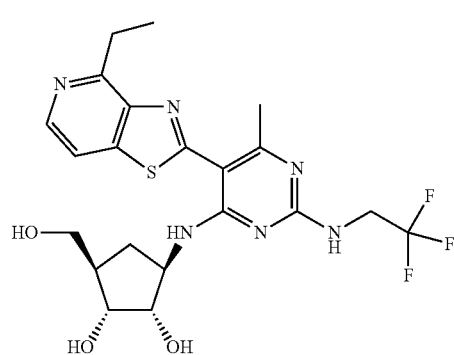 [SMILES: CCc1nccc2sc(-c3c(C)nc(NCC(F)(F)F)nc3N[C@@H]3C[C@H](CO)[C@@H](O)[C@H]3O)nc12] | A | 499.3 | Z1 |
| 1341 | 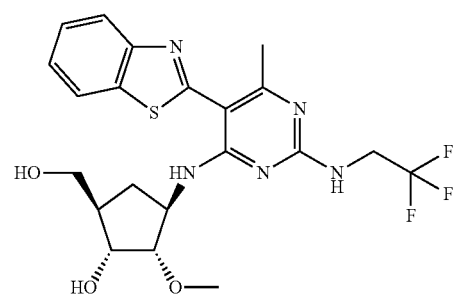 [SMILES: CO[C@@H]1[C@H](O)[C@@H](CO)C[C@H]1Nc1nc(NCC(F)(F)F)nc(C)c1-c1nc2ccccc2s1] | A | 484.2 | Z39, U |

TABLE I-continued
| | | | | |
|---|---|---|---|---|
| 1342 | 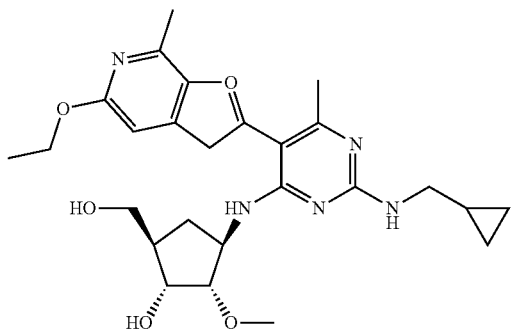 | A | 498.4 | Z39, U |
| 1343 | 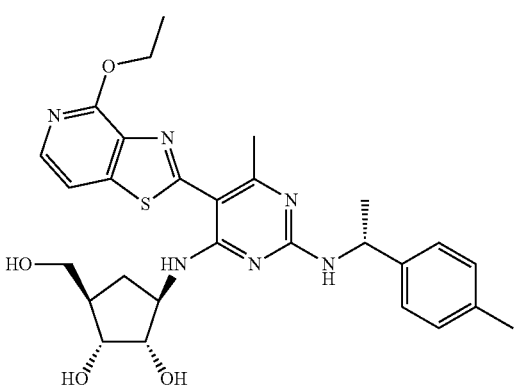 [SMILES: CCOc1nccc2sc(-c3c(C)nc(N[C@H](C)c4ccc(C)cc4)nc3N[C@@H]3C[C@H](CO)[C@@H](O)[C@H]3O)nc12] | A | 551.48 | Z, Z38 |
| 1344 | 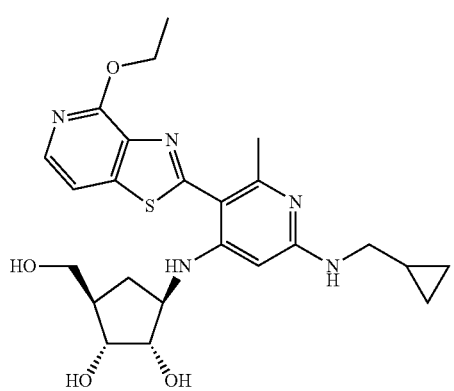 [SMILES: CCOc1nccc2sc(-c3c(N[C@@H]4C[C@H](CO)[C@@H](O)[C@H]4O)cc(NCC4CC4)nc3C)nc12] | A | 487.4 | Z, Z38 |
| 1347 | 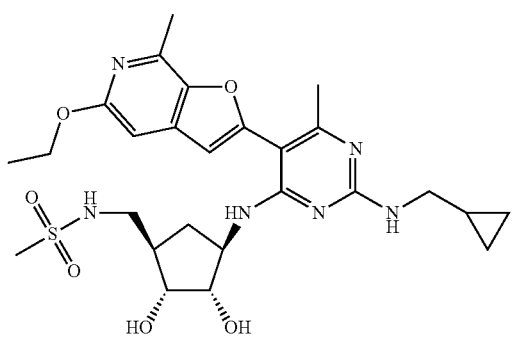 [SMILES: CCOc1cc2cc(-c3c(C)nc(NCC4CC4)nc3N[C@@H]3C[C@H](CNS(C)(=O)=O)[C@@H](O)[C@H]3O)oc2c(C)n1] | A | 561.4 | Y, Z34, Z35, Z36 |

TABLE I-continued

| | | | | |
|---|---|---|---|---|
| 1348 | (structure) | C | 539.37 | U |
| 1349 | (structure) | C | 439.28 | U |
| 1350 | (structure) | A | 521.37 | Z, Z39 |
| 1351 | (structure) | A | 499.31 | Z1 |
| 1352 | (structure) | A | 498.2 | Z, Z39 |

TABLE I-continued
| | | | | |
|---|---|---|---|---|
| 1353 | 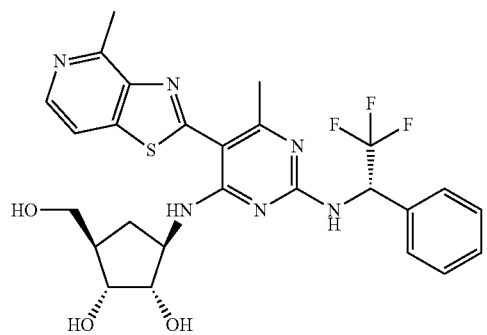 [SMILES: Cc1nc(N[C@@H](c2ccccc2)C(F)(F)F)nc(N[C@@H]2C[C@H](CO)[C@@H](O)[C@H]2O)c1-c1nc2c(C)nccc2s1] | A | 561.43 | Z1 |
| 1354 | 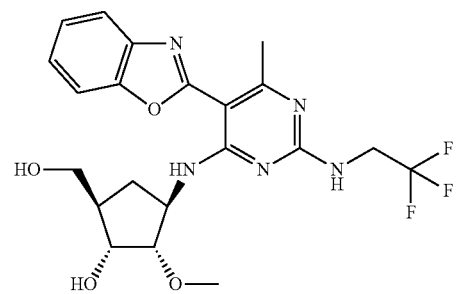 [SMILES: CO[C@@H]1[C@H](O)[C@@H](CO)C[C@H]1Nc1nc(NCC(F)(F)F)nc(C)c1-c1nc2ccccc2o1] | A | 468.27 | Z, Z39 |
| 1355 | 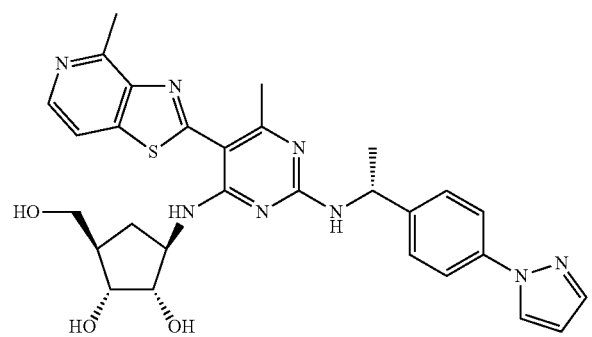 [SMILES: Cc1nc(N[C@H](C)c2ccc(-n3cccn3)cc2)nc(N[C@@H]2C[C@H](CO)[C@@H](O)[C@H]2O)c1-c1nc2c(C)nccc2s1] | A | 573.2 | Z1, |
| 1356 | 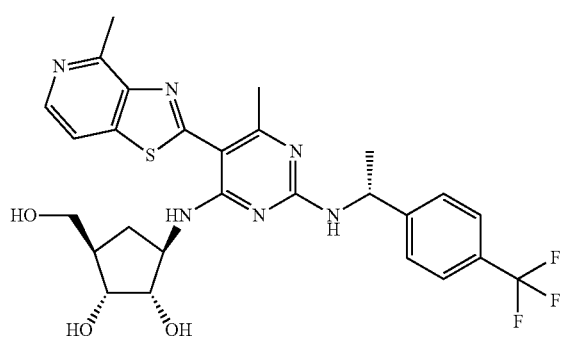 [SMILES: Cc1nc(N[C@H](C)c2ccc(C(F)(F)F)cc2)nc(N[C@@H]2C[C@H](CO)[C@@H](O)[C@H]2O)c1-c1nc2c(C)nccc2s1] | A | 575.41 | Z1 |
| 1357 | 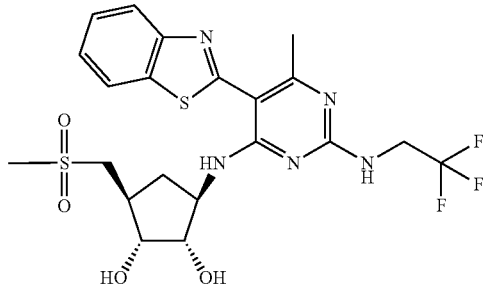 [SMILES: Cc1nc(NCC(F)(F)F)nc(N[C@@H]2C[C@H](CS(C)(=O)=O)[C@@H](O)[C@H]2O)c1-c1nc2ccccc2s1] | A | 532.27 | U, Z40 |

TABLE I-continued
| | | | | |
|---|---|---|---|---|
| 1358 | 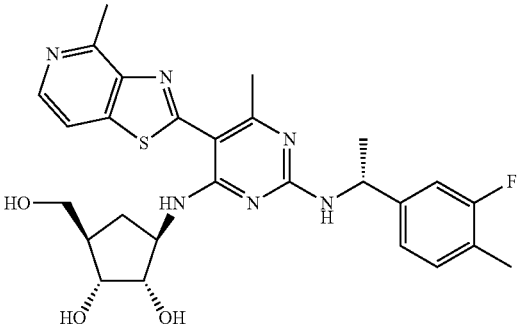 [SMILES: Cc1ccc([C@@H](C)Nc2nc(C)c(-c3nc4c(C)nccc4s3)c(N[C@@H]3C[C@H](CO)[C@@H](O)[C@H]3O)n2)cc1F] | A | 539.3 | V |
| 1359 | 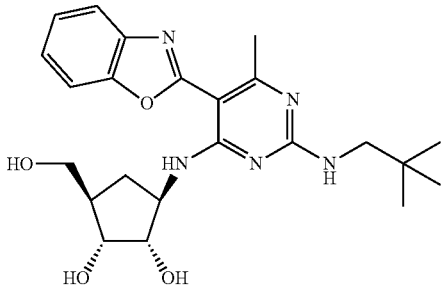 [SMILES: Cc1nc(NCC(C)(C)C)nc(N[C@@H]2C[C@H](CO)[C@@H](O)[C@H]2O)c1-c1nc2ccccc2o1] | A | 442.31 | Z |
| 1360 | 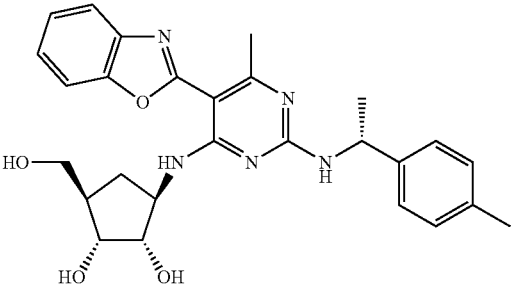 [SMILES: Cc1ccc([C@@H](C)Nc2nc(C)c(-c3nc4ccccc4o3)c(N[C@@H]3C[C@H](CO)[C@@H](O)[C@H]3O)n2)cc1] | B | 490.31 | Z |
| 1361 | 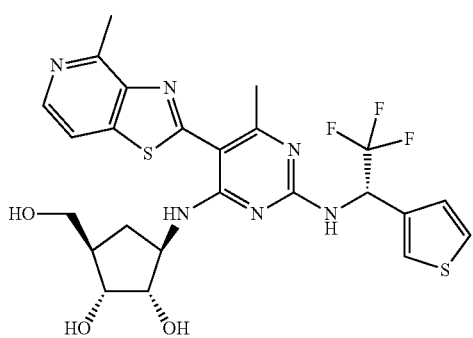 [SMILES: Cc1nc(N[C@@H](c2ccsc2)C(F)(F)F)nc(N[C@@H]2C[C@H](CO)[C@@H](O)[C@H]2O)c1-c1nc2c(C)nccc2s1] | A | 567.28 | Z1, |
| 1362 | 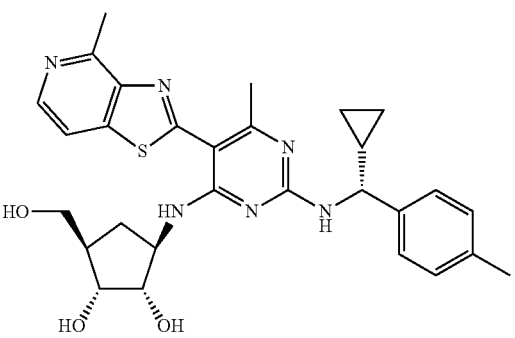 [SMILES: Cc1ccc([C@H](Nc2nc(C)c(-c3nc4c(C)nccc4s3)c(N[C@@H]3C[C@H](CO)[C@@H](O)[C@H]3O)n2)C2CC2)cc1] | A | 547.38 | Z1, |

TABLE I-continued
| | | | | |
|---|---|---|---|---|
| 1363 | 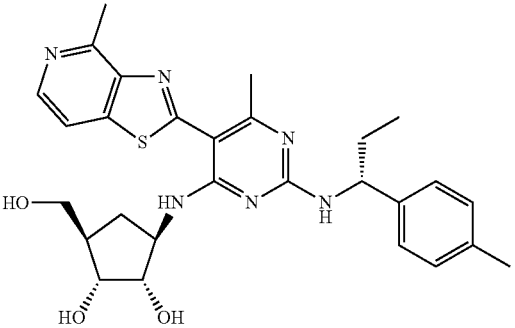 [SMILES: CC[C@@H](Nc1nc(C)c(-c2nc3c(C)nccc3s2)c(N[C@@H]2C[C@H](CO)[C@@H](O)[C@H]2O)n1)c1ccc(C)cc1] | A | 535.37 | Z1, |
| 1364 | 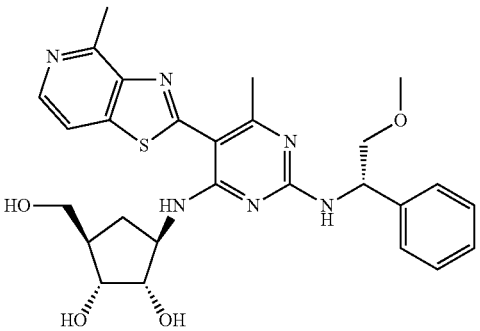 [SMILES: COC[C@@H](Nc1nc(C)c(-c2nc3c(C)nccc3s2)c(N[C@@H]2C[C@H](CO)[C@@H](O)[C@H]2O)n1)c1ccccc1] | B | 537.34 | Z1 |
| 1365 | 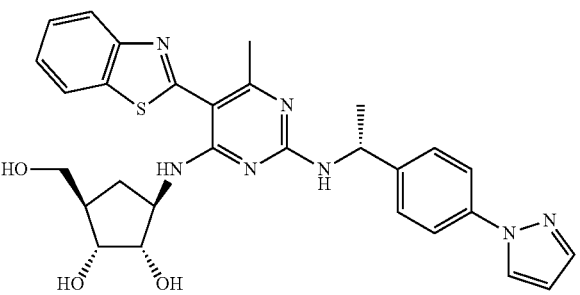 [SMILES: Cc1nc(N[C@H](C)c2ccc(-n3cccn3)cc2)nc(N[C@@H]2C[C@H](CO)[C@@H](O)[C@H]2O)c1-c1nc2ccccc2s1] | A | 558.34 | T |
| 1366 | 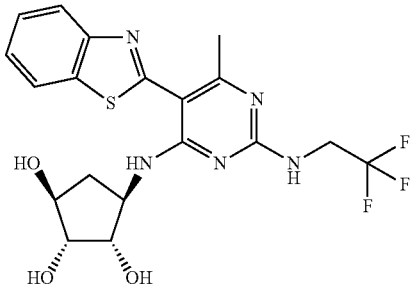 [SMILES: Cc1nc(NCC(F)(F)F)nc(N[C@@H]2C[C@H](O)[C@@H](O)[C@H]2O)c1-c1nc2ccccc2s1] | B | 456.2 | Z41 |
| 1367 | 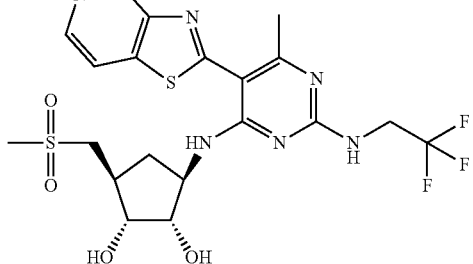 | A | 533.34 | Z, Z40 |

TABLE I-continued
| | | | | |
|---|---|---|---|---|
| 1368 | 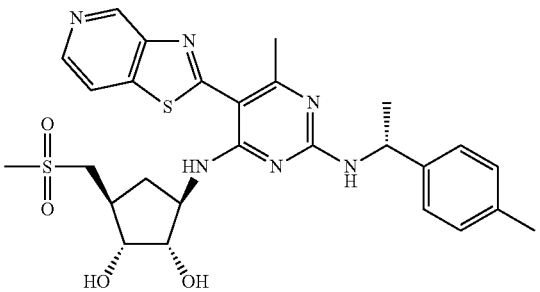 | A | 569.34 | Z, Z40 |
| 1369 | 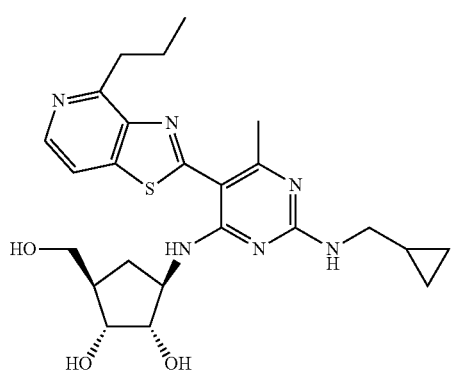 [SMILES: CCCc1nccc2sc(-c3c(C)nc(NCC4CC4)nc3N[C@@H]3C[C@H](CO)[C@@H](O)[C@H]3O)nc12] | A | 485.31 | Z1 |
| 1370 | 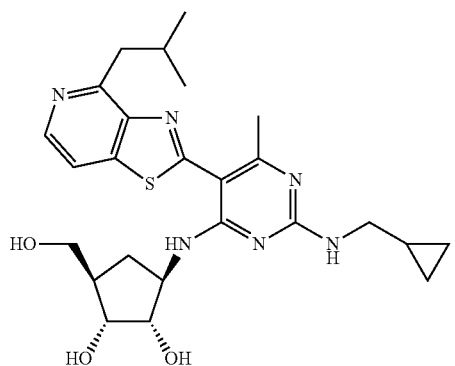 [SMILES: Cc1nc(NCC2CC2)nc(N[C@@H]2C[C@H](CO)[C@@H](O)[C@H]2O)c1-c1nc2c(CC(C)C)nccc2s1] | A | 499.34 | Z1 |
| 1371 | 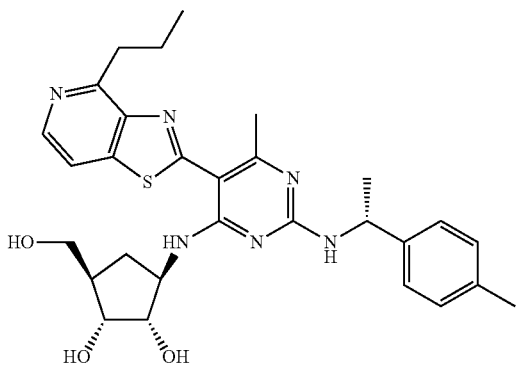 [SMILES: CCCc1nccc2sc(-c3c(C)nc(N[C@H](C)c4ccc(C)cc4)nc3N[C@@H]3C[C@H](CO)[C@@H](O)[C@H]3O)nc12] | A | 549.40 | Z1 |

TABLE I-continued
| | | | | |
|---|---|---|---|---|
| 1346 | 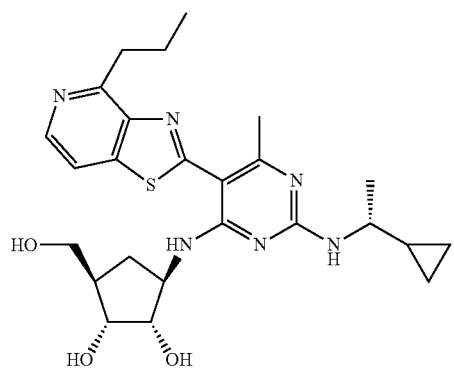 [SMILES: CCCc1nccc2sc(-c3c(C)nc(N[C@H](C)C4CC4)nc3N[C@@H]3C[C@H](CO)[C@@H](O)[C@H]3O)nc12] | A | 499.34 | Z1 |
| 1372 | 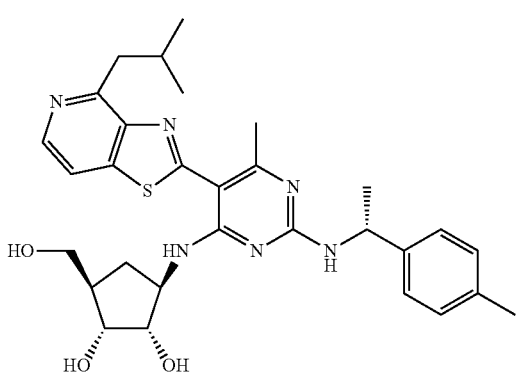 [SMILES: Cc1ccc([C@@H](C)Nc2nc(C)c(-c3nc4c(CC(C)C)nccc4s3)c(N[C@@H]3C[C@H](CO)[C@@H](O)[C@H]3O)n2)cc1] | A | 563.45 | Z1 |
| 1373 | 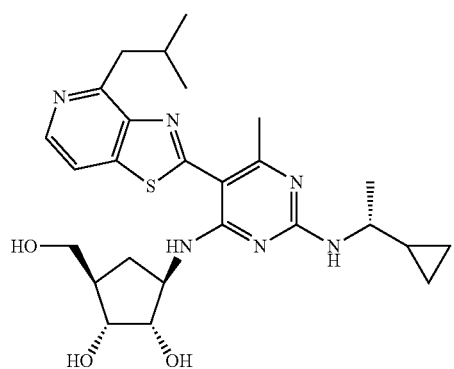 [SMILES: Cc1nc(N[C@H](C)C2CC2)nc(N[C@@H]2C[C@H](CO)[C@@H](O)[C@H]2O)c1-c1nc2c(CC(C)C)nccc2s1] | A | 513.36 | Z1 |
| 1374 | 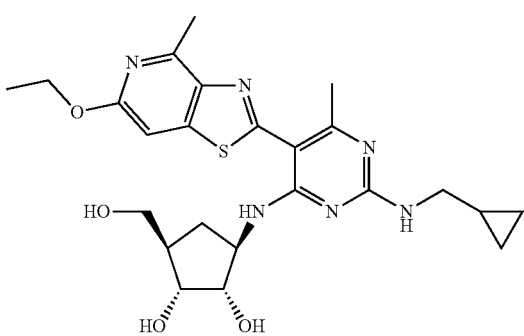 [SMILES: CCOc1cc2sc(-c3c(C)nc(NCC4CC4)nc3N[C@@H]3C[C@H](CO)[C@@H](O)[C@H]3O)nc2c(C)n1] | B | 501.31 | Z, Z42 |

TABLE I-continued

| | | | | |
|---|---|---|---|---|
| 1375 | (structure) | A | 565.6 | Z, Z42 |
| 1376 | (structure) | A | 519.6 | Z, Z42 |
| 1377 | (structure) | B | 540.6 | T, Z37 |
| 1378 | (structure) | C | 575.5 | T, Z48 |
| 1379 | (structure) | A | 561.5 | T, Z48 |

| | | | | |
|---|---|---|---|---|
| 1380 | 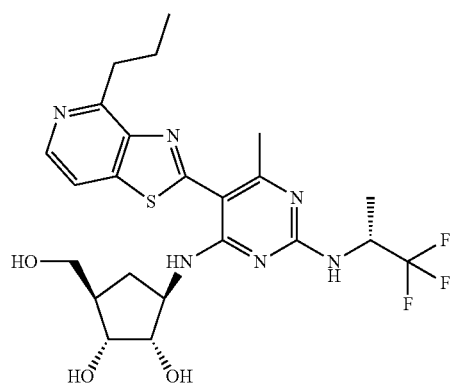 [SMILES: CCCc1nccc2sc(-c3c(C)nc(N[C@H](C)C(F)(F)F)nc3N[C@@H]3C[C@H](CO)[C@@H](O)[C@H]3O)nc12] | A | 527.31 | Z1 |
| 1381 | 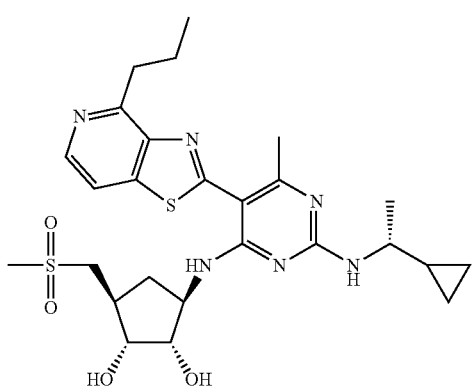 [SMILES: CCCc1nccc2sc(-c3c(C)nc(N[C@H](C)C4CC4)nc3N[C@@H]3C[C@H](CS(C)(=O)=O)[C@@H](O)[C@H]3O)nc12] | A | 561.37 | Z1, Z40 |
| 1382 | 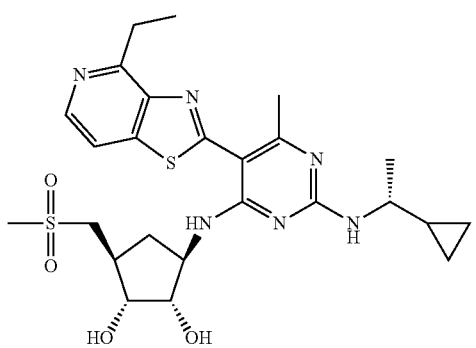 [SMILES: CCc1nccc2sc(-c3c(C)nc(N[C@H](C)C4CC4)nc3N[C@@H]3C[C@H](CS(C)(=O)=O)[C@@H](O)[C@H]3O)nc12] | A | 547.33 | Z1, Z40 |
| 1383 | 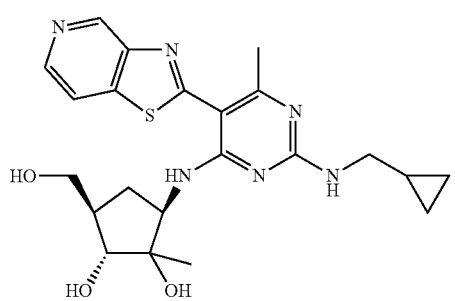 [SMILES: Cc1nc(NCC2CC2)nc(N[C@@H]2C[C@H](CO)[C@@H](O)C2(C)O)c1-c1nc2cnccc2s1] | A | 457.30 | Z43 |

TABLE I-continued
| | | | | |
|---|---|---|---|---|
| 1384 | 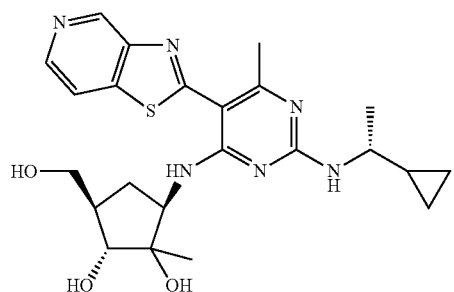 [SMILES: Cc1nc(N[C@H](C)C2CC2)nc(N[C@@H]2C[C@H](CO)[C@@H](O)C2(C)O)c1-c1nc2cnccc2s1] | A | 471.30 | Z43 |
| 1385 | 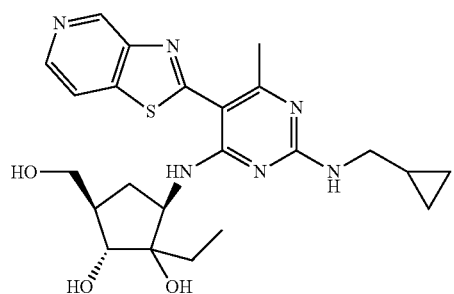 [SMILES: CCC1(O)[C@H](O)[C@@H](CO)C[C@H]1Nc1nc(NCC2CC2)nc(C)c1-c1nc2cnccc2s1] | A | 471.3 | Z43 |
| 1386 | 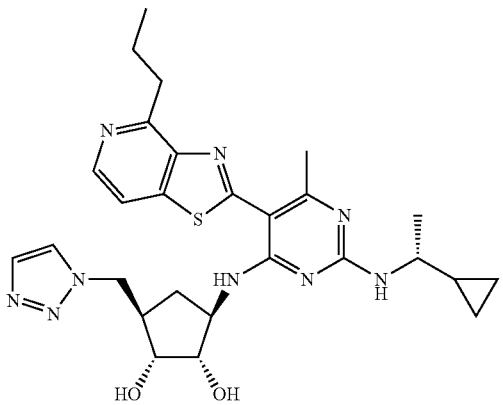 [SMILES: CCCc1nccc2sc(-c3c(C)nc(N[C@H](C)C4CC4)nc3N[C@@H]3C[C@H](Cn4ccnn4)[C@@H](O)[C@H]3O)nc12] | A | 550.45 | Z1 |
| 1387 | 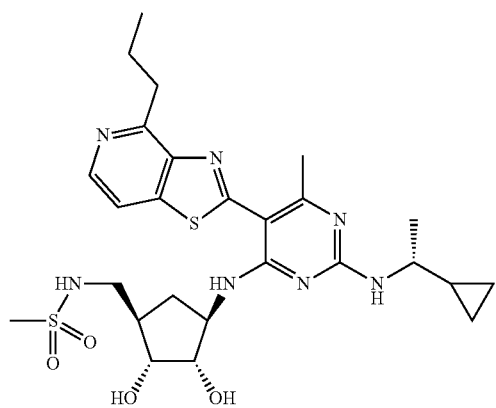 [SMILES: CCCc1nccc2sc(-c3c(C)nc(N[C@H](C)C4CC4)nc3N[C@@H]3C[C@H](CNS(C)(=O)=O)[C@@H](O)[C@H]3O)nc12] | A | 576.41 | Z1, Z36 |

TABLE I-continued
| 1388 | 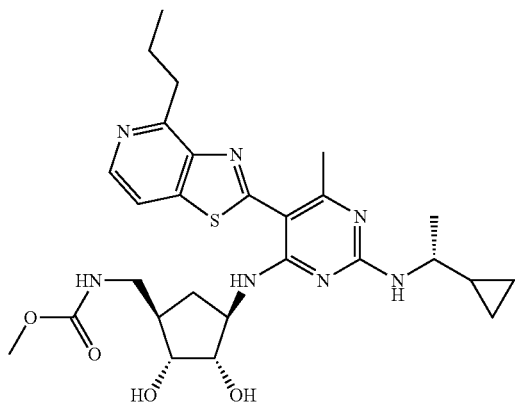 [SMILES: CCCc1nccc2sc(-c3c(C)nc(N[C@H](C)C4CC4)nc3N[C@@H]3C[C@H](CNC(=O)OC)[C@@H](O)[C@H]3O)nc12] | A | 556.41 | Z1, Z36 |
| 1389 | 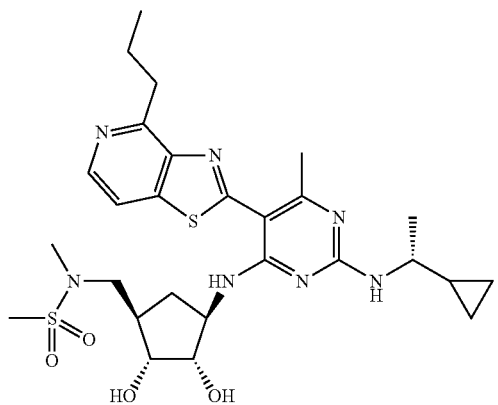 [SMILES: CCCc1nccc2sc(-c3c(C)nc(N[C@H](C)C4CC4)nc3N[C@@H]3C[C@H](CN(C)S(C)(=O)=O)[C@@H](O)[C@H]3O)nc12] | A | 590.48 | Z1, Z48 |
| 1390 | 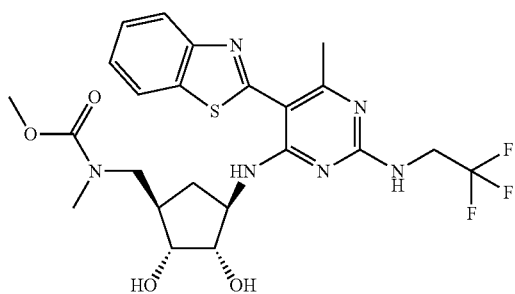 [SMILES: COC(=O)N(C)C[C@H]1C[C@@H](Nc2nc(NCC(F)(F)F)nc(C)c2-c2nc3ccccc3s2)[C@H](O)[C@@H]1O] | B | 541.34 | T, Z48 |
| 1391 | 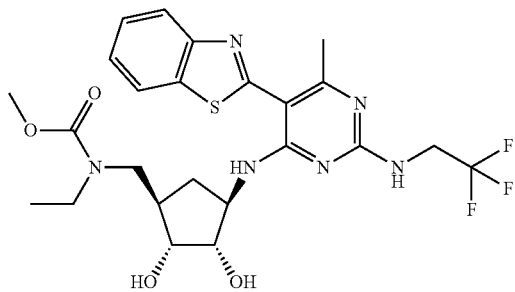 [SMILES: CCN(C[C@H]1C[C@@H](Nc2nc(NCC(F)(F)F)nc(C)c2-c2nc3ccccc3s2)[C@H](O)[C@@H]1O)C(=O)OC] | A | 555.37 | T, Z48 |

| | | | | |
|---|---|---|---|---|
| 1393 | 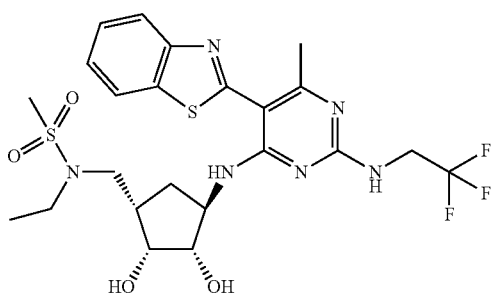 [SMILES: CCN(C[C@@H]1C[C@@H](Nc2nc(NCC(F)(F)F)nc(C)c2-c2nc3ccccc3s2)[C@H](O)[C@@H]1O)S(C)(=O)=O] | B | 575.39 | T, Z48 |
| 1392 | 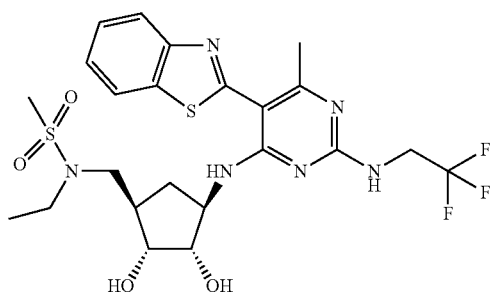 [SMILES: CCN(C[C@H]1C[C@@H](Nc2nc(NCC(F)(F)F)nc(C)c2-c2nc3ccccc3s2)[C@H](O)[C@@H]1O)S(C)(=O)=O] | A | 575.39 | T, Z48 |
| 1394 | 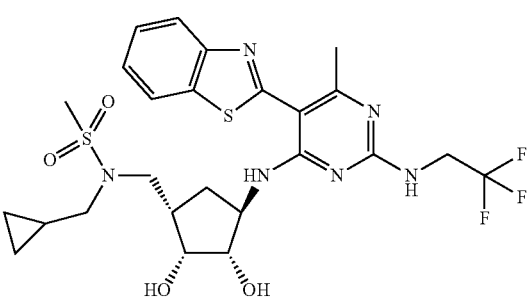 [SMILES: Cc1nc(NCC(F)(F)F)nc(N[C@@H]2C[C@@H](CN(CC3CC3)S(C)(=O)=O)[C@@H](O)[C@H]2O)c1-c1nc2ccccc2s1] | B | 601.42 | T, Z48 |
| 1395 | 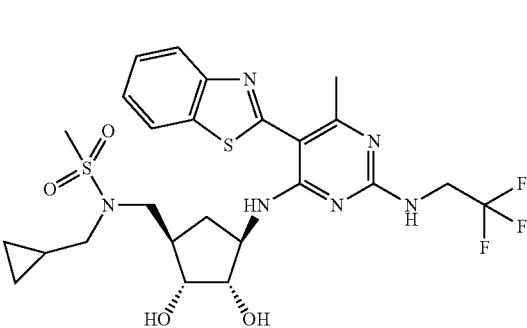 [SMILES: Cc1nc(NCC(F)(F)F)nc(N[C@@H]2C[C@H](CN(CC3CC3)S(C)(=O)=O)[C@@H](O)[C@H]2O)c1-c1nc2ccccc2s1] | A | 601.41 | T, Z48 |
| 1396 | 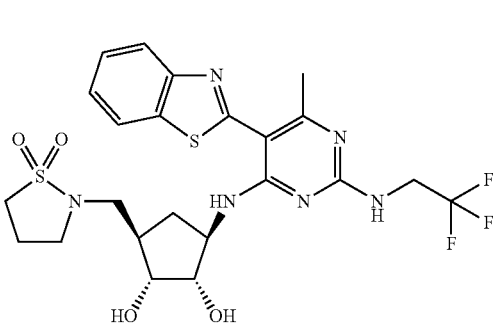 [SMILES: Cc1nc(NCC(F)(F)F)nc(N[C@@H]2C[C@H](CN3CCCS3(=O)=O)[C@@H](O)[C@H]2O)c1-c1nc2ccccc2s1] | A | 573.29 | T, Z44 |

| | | | |
|---|---|---|---|
| 1397 | 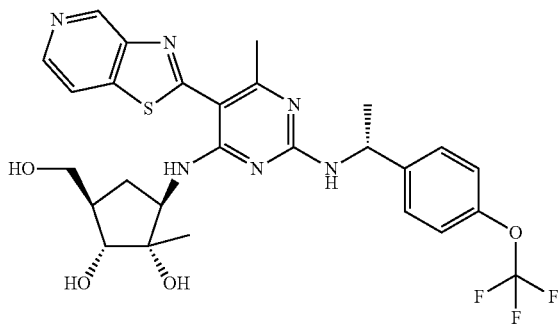 [SMILES: Cc1nc(N[C@H](C)c2ccc(OC(F)(F)F)cc2)nc(N[C@@H]2C[C@H](CO)[C@@H](O)[C@@]2(C)O)c1-c1nc2cnccc2s1] | A | 591.38 | Z43 |
| 1398 | 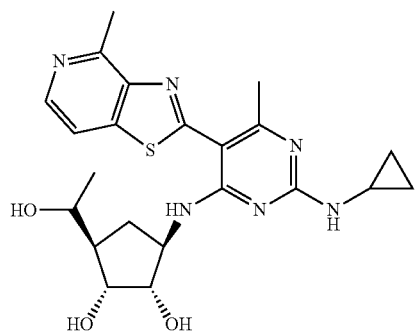 [SMILES: Cc1nc(NC2CC2)nc(N[C@@H]2C[C@H](C(C)O)[C@@H](O)[C@H]2O)c1-c1nc2c(C)nccc2s1] | A | 457.2 | Z1, Z47 |
| 1399 | 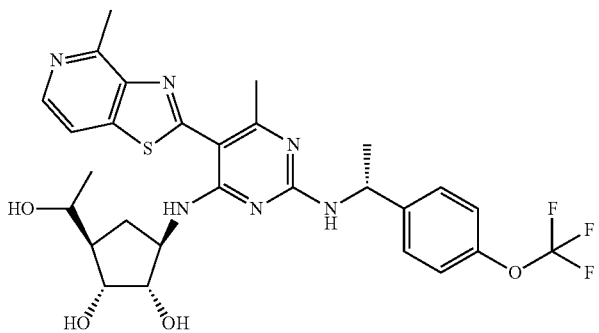 [SMILES: Cc1nc(N[C@H](C)c2ccc(OC(F)(F)F)cc2)nc(N[C@@H]2C[C@H](C(C)O)[C@@H](O)[C@H]2O)c1-c1nc2c(C)nccc2s1] | A | 605.5 | Z1, Z47 |
| 1400 | 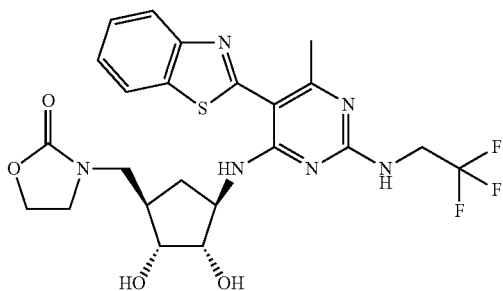 [SMILES: Cc1nc(NCC(F)(F)F)nc(N[C@@H]2C[C@H](CN3CCOC3=O)[C@@H](O)[C@H]2O)c1-c1nc2ccccc2s1] | A | 539.33 | T, Z45 |

TABLE I-continued
| | | | | |
|---|---|---|---|---|
| 1401 | 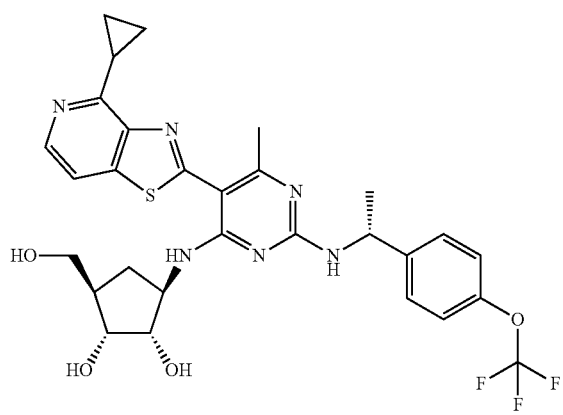 [SMILES: Cc1nc(N[C@H](C)c2ccc(OC(F)(F)F)cc2)nc(N[C@@H]2C[C@H](CO)[C@@H](O)[C@H]2O)c1-c1nc2c(C3CC3)nccc2s1] | A | 617.3 | Z46 |
| 1402 | 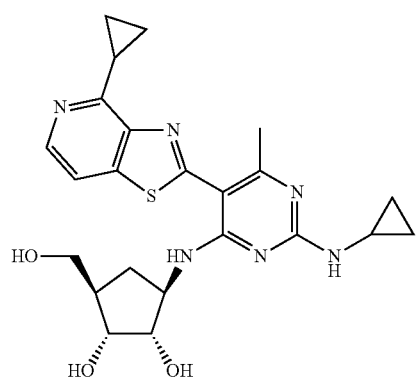 [SMILES: Cc1nc(NC2CC2)nc(N[C@@H]2C[C@H](CO)[C@@H](O)[C@H]2O)c1-c1nc2c(C3CC3)nccc2s1] | A | 469.29 | Z46 |
| 1501 | 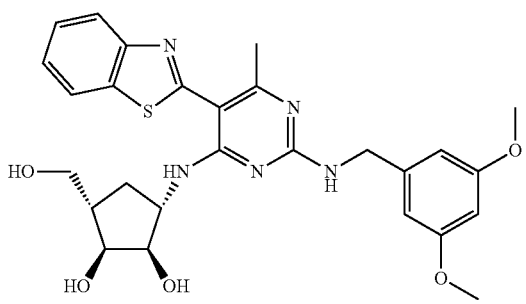 [SMILES: COc1cc(CNc2nc(C)c(-c3nc4ccccc4s3)c(N[C@H]3C[C@@H](CO)[C@H](O)[C@@H]3O)n2)cc(OC)c1] | B | 538.56 | U |
| 1502 | 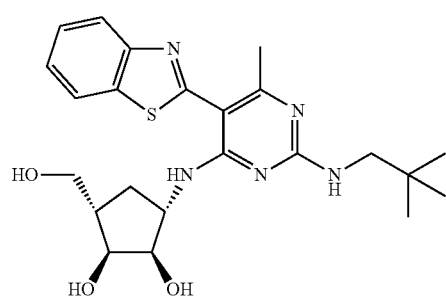 [SMILES: Cc1nc(NCC(C)(C)C)nc(N[C@H]2C[C@@H](CO)[C@H](O)[C@@H]2O)c1-c1nc2ccccc2s1] | C | 458.53 | U |

TABLE I-continued
| | | | | |
|---|---|---|---|---|
| 1503 | 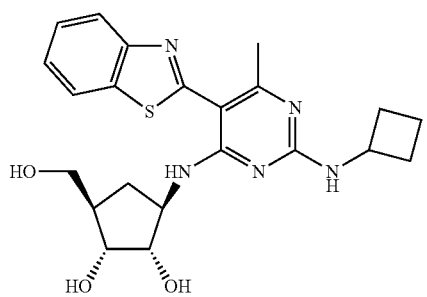 [SMILES: Cc1nc(NC2CCC2)nc(N[C@@H]2C[C@H](CO)[C@@H](O)[C@H]2O)c1-c1nc2ccccc2s1] | B | 442.45 | U |
| 1504 | 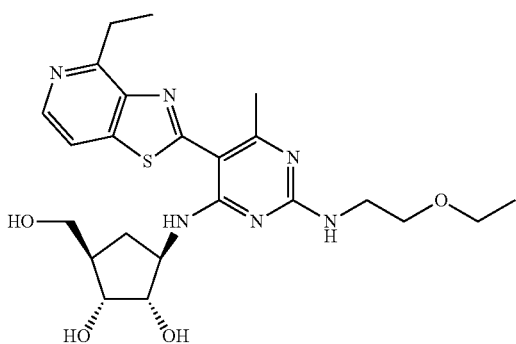 [SMILES: CCOCCNc1nc(C)c(-c2nc3c(CC)nccc3s2)c(N[C@@H]2C[C@H](CO)[C@@H](O)[C@H]2O)n1] | A | 489.3 | Z1 |
| 1505 | 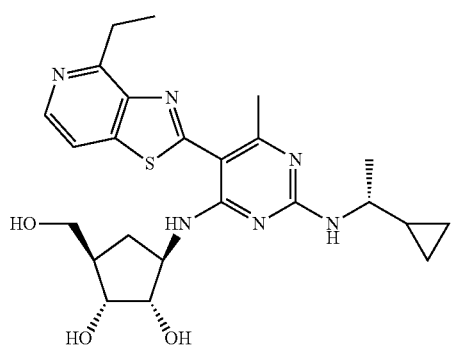 [SMILES: CCc1nccc2sc(-c3c(C)nc(N[C@H](C)C4CC4)nc3N[C@@H]3C[C@H](CO)[C@@H](O)[C@H]3O)nc12] | A | 485.3 | Z1 |
| 1506 | 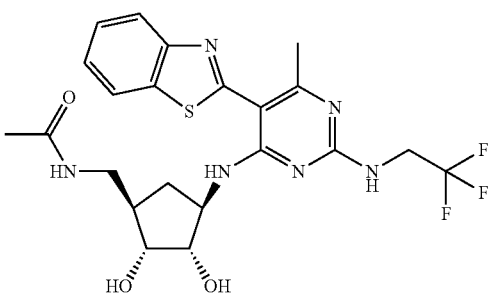 [SMILES: CC(=O)NC[C@H]1C[C@@H](Nc2nc(NCC(F)(F)F)nc(C)c2-c2nc3ccccc3s2)[C@H](O)[C@@H]1O] | B | 511.3 | U, Z37 |
| 1507 | 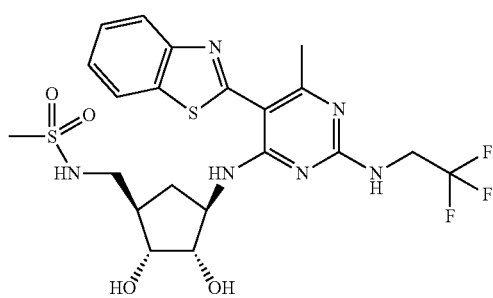 [SMILES: Cc1nc(NCC(F)(F)F)nc(N[C@@H]2C[C@H](CNS(C)(=O)=O)[C@@H](O)[C@H]2O)c1-c1nc2ccccc2s1] | A | 547.4 | U, Z36 |

TABLE I-continued
| | | | | |
|---|---|---|---|---|
| 1508 | 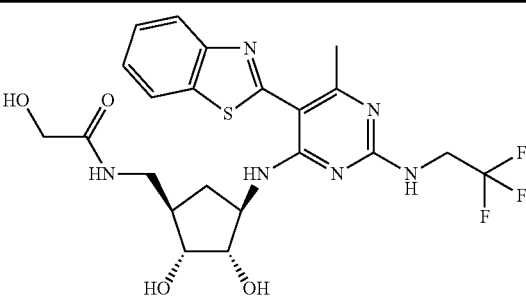 | B | 527.3 | U, Z37 |
| 1509 | 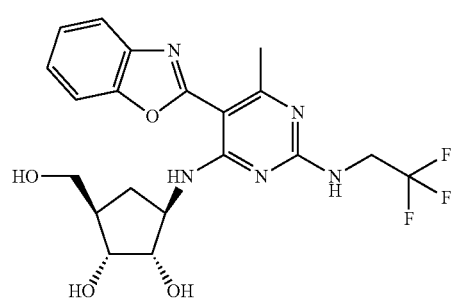 [SMILES: Cc1nc(NCC(F)(F)F)nc(N[C@@H]2C[C@H](CO)[C@@H](O)[C@H]2O)c1-c1nc2ccccc2o1] | A | 454.4 | F |
| 1510 | 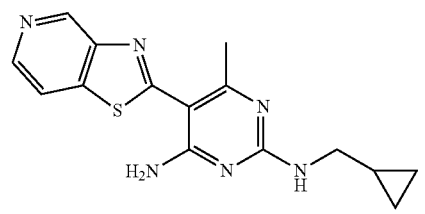 [SMILES: Cc1nc(NCC2CC2)nc(N)c1-c1nc2cnccc2s1] | B | 313.25 | Z |
| 1511 | 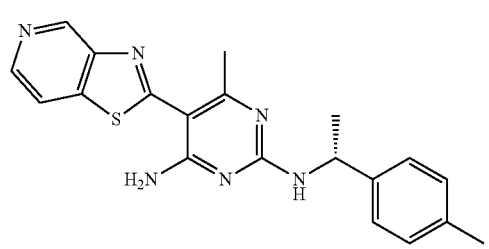 [SMILES: Cc1ccc([C@@H](C)Nc2nc(C)c(-c3nc4cnccc4s3)c(N)n2)cc1] | A | 377.28 | Z |
| 1512 | 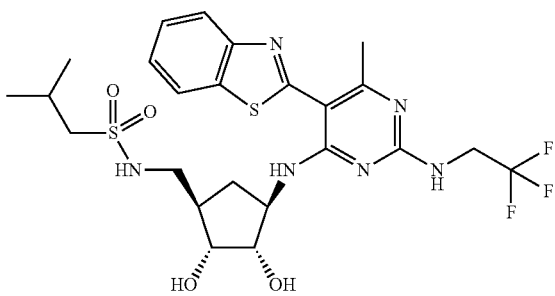 [SMILES: Cc1nc(NCC(F)(F)F)nc(N[C@@H]2C[C@H](CNS(=O)(=O)CC(C)C)[C@@H](O)[C@H]2O)c1-c1nc2ccccc2s1] | B | 589.3 | U, Z36 |
| 1513 | 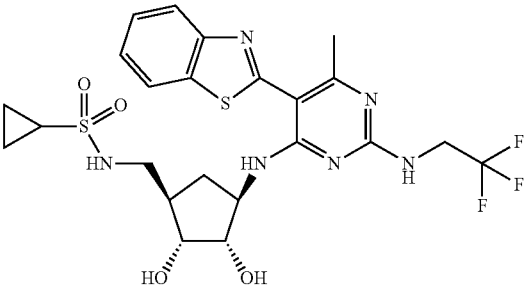 [SMILES: Cc1nc(NCC(F)(F)F)nc(N[C@@H]2C[C@H](CNS(=O)(=O)C3CC3)[C@@H](O)[C@H]2O)c1-c1nc2ccccc2s1] | B | 573.42 | U, Z36 |

TABLE I-continued
| | | | | |
|---|---|---|---|---|
| 1514 | 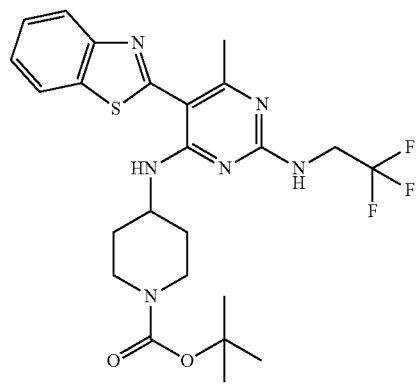 [SMILES: Cc1nc(NCC(F)(F)F)nc(NC2CCN(C(=O)OC(C)(C)C)CC2)c1-c1nc2ccccc2s1] | C | 523.37 | U |
| 1515 | 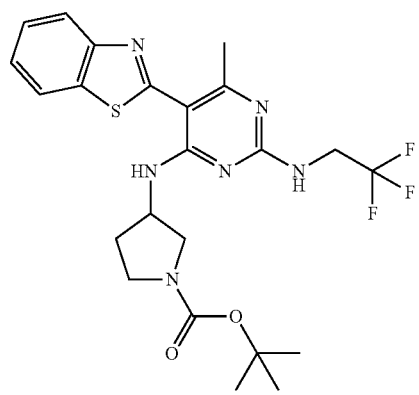 [SMILES: Cc1nc(NCC(F)(F)F)nc(NC2CCN(C(=O)OC(C)(C)C)C2)c1-c1nc2ccccc2s1] | B | 509.43 | U |
| 1516 | 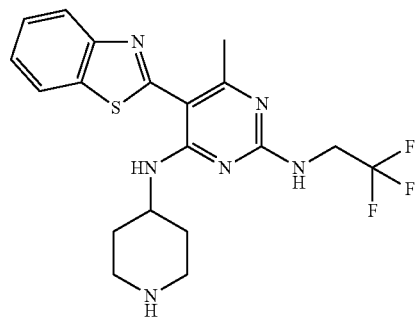 [SMILES: Cc1nc(NCC(F)(F)F)nc(NC2CCNCC2)c1-c1nc2ccccc2s1] | B | 423.26 | U |
| 1517 | 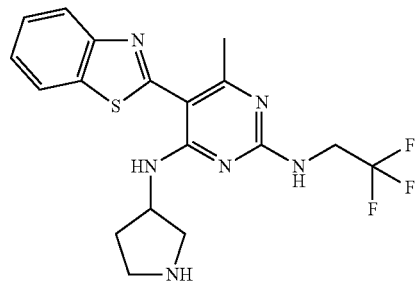 [SMILES: Cc1nc(NCC(F)(F)F)nc(NC2CCNC2)c1-c1nc2ccccc2s1] | C | 409.2 | U |

TABLE I-continued

| | | | | |
|---|---|---|---|---|
| 1518 | | C | 576.3 | Z36, U |
| 1519 | | B | 469.29 | U, Z35 |
| 1520 | | B | 615.3 | U, Z36 |
| 1521 | | B | 561.3 | U, Z36 |
| 1522 | | B | 527.31 | U, Z36 |

TABLE I-continued
| | | | | |
|---|---|---|---|---|
| 1523 | 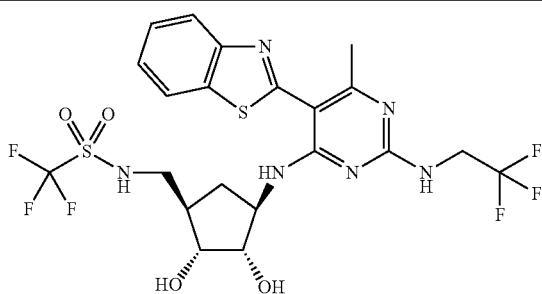 | B | 601.28 | U, Z36 |
| 1524 | 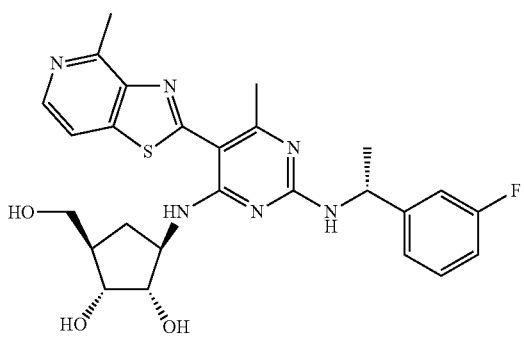 [SMILES: Cc1nc(N[C@H](C)c2cccc(F)c2)nc(N[C@@H]2C[C@H](CO)[C@@H](O)[C@H]2O)c1-c1nc2c(C)nccc2s1] | A | 525.33 | Z1 |
| 1525 | 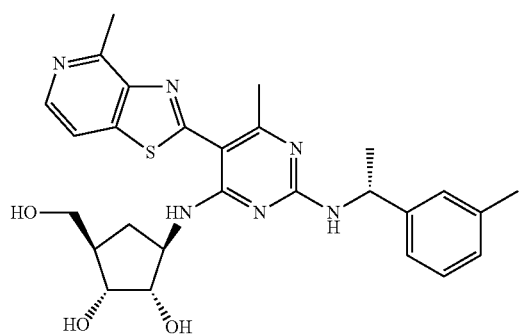 [SMILES: Cc1cccc([C@@H](C)Nc2nc(C)c(-c3nc4c(C)nccc4s3)c(N[C@@H]3C[C@H](CO)[C@@H](O)[C@H]3O)n2)c1] | A | 521.3 | Z1, Z49 |
| 1526 | 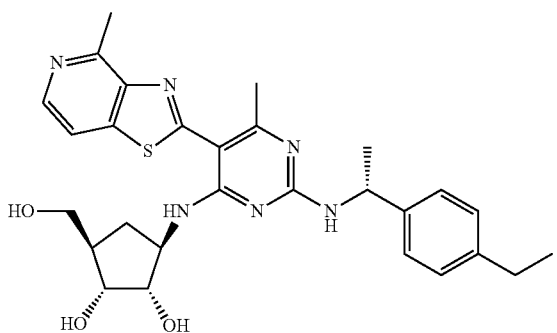 | A | 535.35 | Z1, Z49 |
| 1527 | 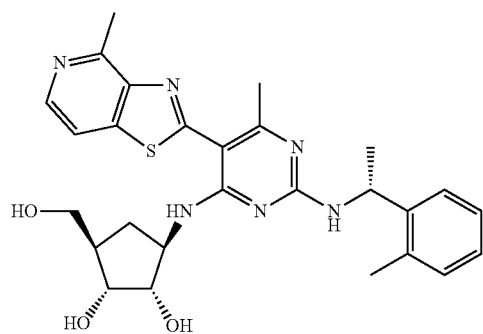 [SMILES: Cc1ccccc1[C@@H](C)Nc1nc(C)c(-c2nc3c(C)nccc3s2)c(N[C@@H]2C[C@H](CO)[C@@H](O)[C@H]2O)n1] | A | 521.36 | Z1, Z49 |

TABLE I-continued
| | | | | |
|---|---|---|---|---|
| 1528 | 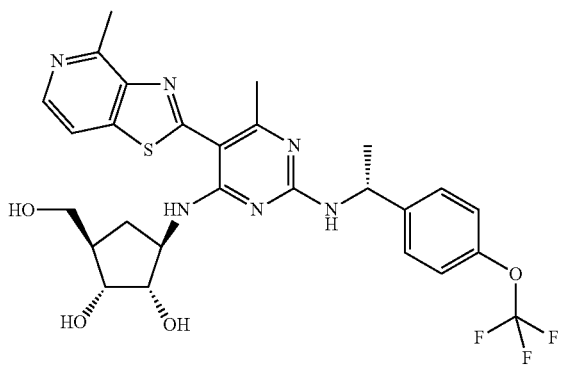 [SMILES: Cc1nc(N[C@H](C)c2ccc(OC(F)(F)F)cc2)nc(N[C@@H]2C[C@H](CO)[C@@H](O)[C@H]2O)c1-c1nc2c(C)nccc2s1] | A | 591.37 | Z1, Z49 |
| 1529 | 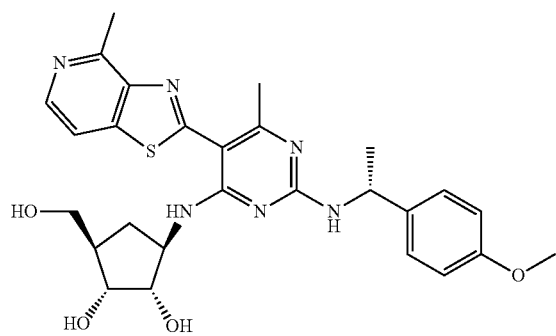 [SMILES: COc1ccc([C@@H](C)Nc2nc(C)c(-c3nc4c(C)nccc4s3)c(N[C@@H]3C[C@H](CO)[C@@H](O)[C@H]3O)n2)cc1] | A | 537.36 | Z1, Z49 |
| 1530 | 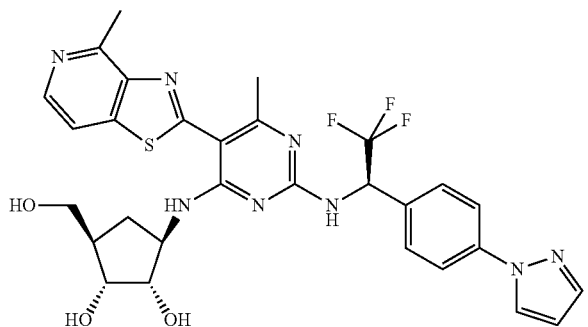 [SMILES: Cc1nc(N[C@H](c2ccc(-n3cccn3)cc2)C(F)(F)F)nc(N[C@@H]2C[C@H](CO)[C@@H](O)[C@H]2O)c1-c1nc2c(C)nccc2s1] | C | 627.36 | Z1, Z51 |
| 1531 | 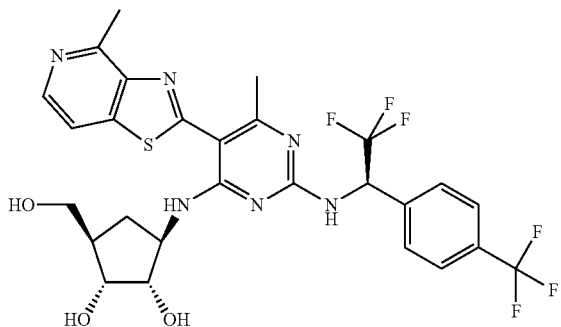 [SMILES: Cc1nc(N[C@H](c2ccc(C(F)(F)F)cc2)C(F)(F)F)nc(N[C@@H]2C[C@H](CO)[C@@H](O)[C@H]2O)c1-c1nc2c(C)nccc2s1] | C | 629.33 | Z1, Z51 |

TABLE I-continued

| | | | | |
|---|---|---|---|---|
| 1532 | | C | 537.31 | Z2, Z49 |
| 1533 | | C | 607.36 | Z2, Z49 |
| 1534 | | C | 403.2 | Z1 |
| 1535 | | A | 471.2 | Z1 |

TABLE I-continued
| | | | | |
|---|---|---|---|---|
| 1536 | 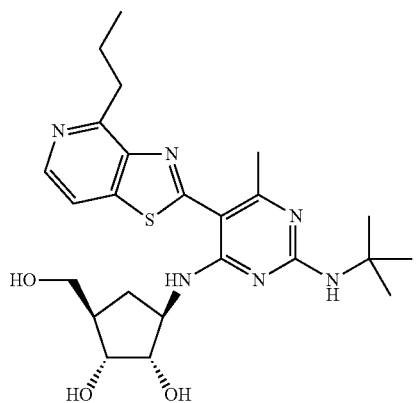 [SMILES: CCCc1nccc2sc(-c3c(C)nc(NC(C)(C)C)nc3N[C@@H]3C[C@H](CO)[C@@H](O)[C@H]3O)nc12] | A | 501.41 | Z1 |
| 1537 | 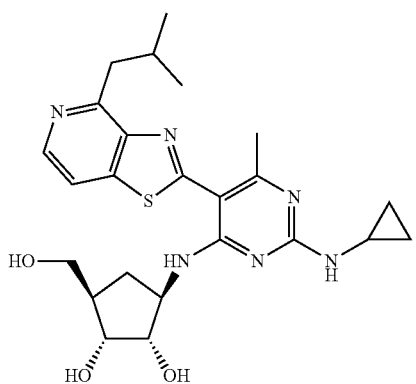 [SMILES: Cc1nc(NC2CC2)nc(N[C@@H]2C[C@H](CO)[C@@H](O)[C@H]2O)c1-c1nc2c(CC(C)C)nccc2s1] | A | 485.2 | Z1 |
| 1538 | 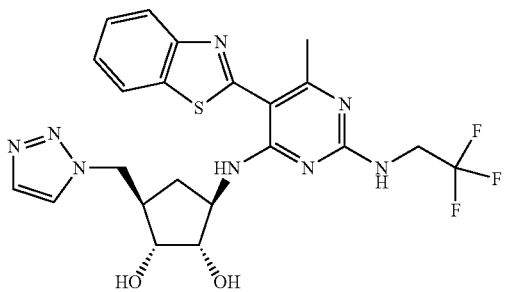 [SMILES: Cc1nc(NCC(F)(F)F)nc(N[C@@H]2C[C@H](Cn3ccnn3)[C@@H](O)[C@H]2O)c1-c1nc2ccccc2s1] | A | 521.25 | Z50 |
| 1539 | 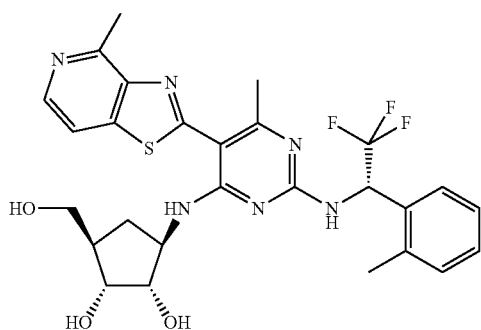 [SMILES: Cc1ccccc1[C@H](Nc1nc(C)c(-c2nc3c(C)nccc3s2)c(N[C@@H]2C[C@H](CO)[C@@H](O)[C@H]2O)n1)C(F)(F)F] | A | 575.39 | Z1, Z51 |

TABLE I-continued

| # | Structure | | | |
|---|---|---|---|---|
| 1540 | (structure) | A | 591.37 | Z1, Z51 |
| 1541 | (structure) | A | 627.40 | Z1, Z51 |
| 1542 | (structure) | B | 561.2 | Z, Z50 |
| 1543 | (structure) | A | 443.2 | Z1 |
| 1544 | (structure) | A | 457.29 | Z1 |

TABLE I-continued

| | | | | |
|---|---|---|---|---|
| 1545 | (structure) | A | 573.38 | Z1, Z50 |
| 1546 | (structure) | A | 645.36 | Z1, Z51 |
| 1601 | (structure) | C | 445.2 | B, Z |
| 1602 | (structure) | C | 483.2 | B, Z |
| 1603 | (structure) | C | 441.2 | B, Z |

TABLE I-continued
| | | | | |
|---|---|---|---|---|
| 1604 | 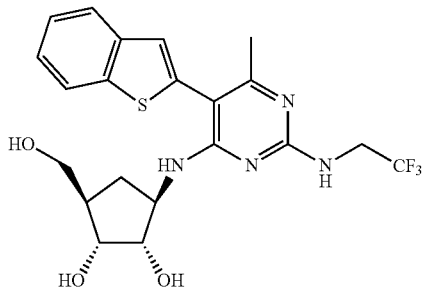 | C | 469.3 | B, Z |
| 1605 | 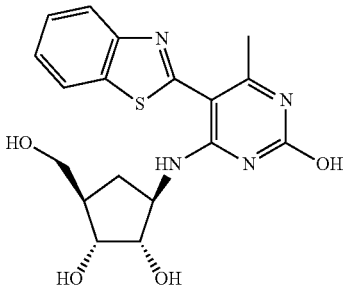 [SMILES: Cc1nc(O)nc(N[C@@H]2C[C@H](CO)[C@@H](O)[C@H]2O)c1-c1nc2ccccc2s1] | C | 388.2 | B, Z |
| 1610 | 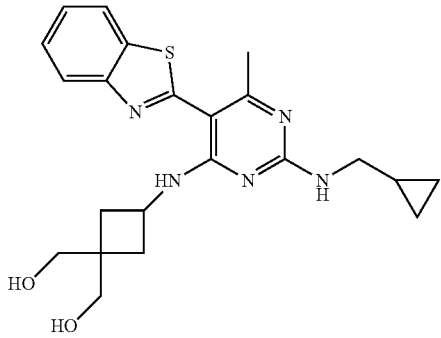 [SMILES: Cc1nc(NCC2CC2)nc(NC2CC(CO)(CO)C2)c1-c1nc2ccccc2s1] | B | 426.2 | Z56 |
| 1611 | 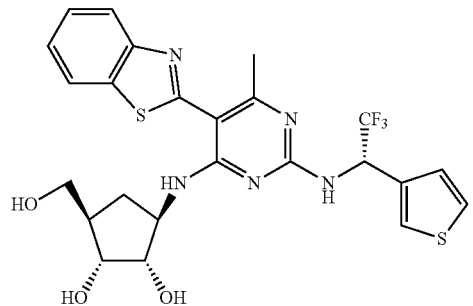 [SMILES: Cc1nc(N[C@@H](c2ccsc2)C(F)(F)F)nc(N[C@@H]2C[C@H](CO)[C@@H](O)[C@H]2O)c1-c1nc2ccccc2s1] | B | 454.2 | Z56 |
| 1616 | 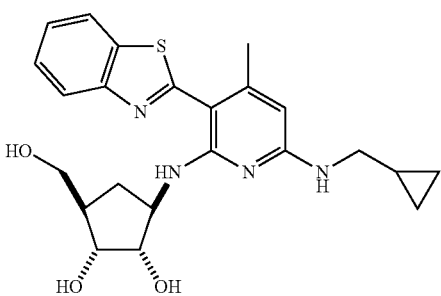 [SMILES: Cc1cc(NCC2CC2)nc(N[C@@H]2C[C@H](CO)[C@@H](O)[C@H]2O)c1-c1nc2ccccc2s1] | C | 441.0 | Z57 |

TABLE I-continued
| | | | | |
|---|---|---|---|---|
| 1617 | 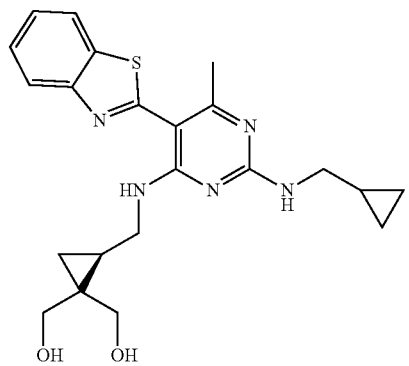 [SMILES: Cc1nc(NCC2CC2)nc(NC[C@@H]2CC2(CO)CO)c1-c1nc2ccccc2s1] | C | 426.2 | Z58 |
| 1618 | 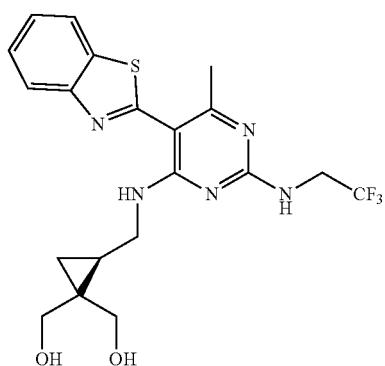 [SMILES: Cc1nc(NCC(F)(F)F)nc(NC[C@@H]2CC2(CO)CO)c1-c1nc2ccccc2s1] | B | 454.2 | Z58 |
| 1619 | 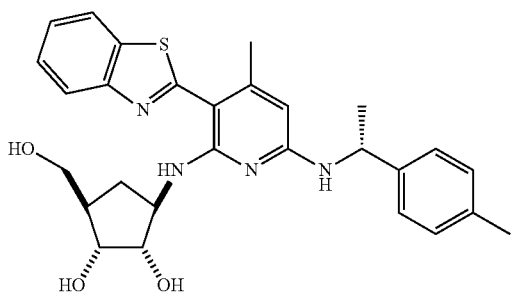 [SMILES: Cc1ccc([C@@H](C)Nc2cc(C)c(-c3nc4ccccc4s3)c(N[C@@H]3C[C@H](CO)[C@@H](O)[C@H]3O)n2)cc1] | C | 505.3 | Z57 |
| 1620 | 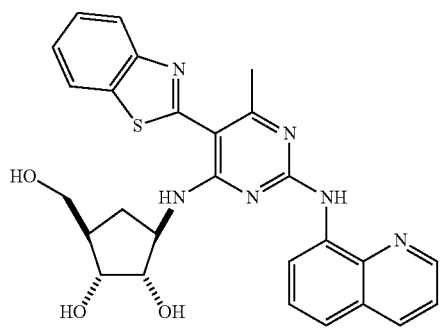 [SMILES: Cc1nc(Nc2cccc3cccnc23)nc(N[C@@H]2C[C@H](CO)[C@@H](O)[C@H]2O)c1-c1nc2ccccc2s1] | C | 515.3 | Z |

TABLE I-continued
| | | | | |
|---|---|---|---|---|
| 1623 | 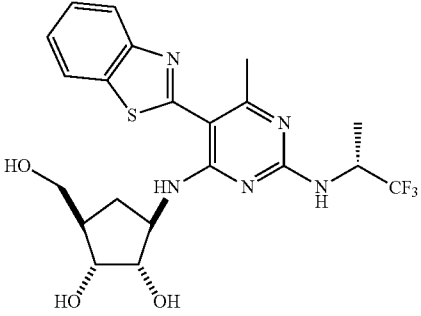 [SMILES: Cc1nc(N[C@H](C)C(F)(F)F)nc(N[C@@H]2C[C@H](CO)[C@@H](O)[C@H]2O)c1-c1nc2ccccc2s1] | B | 484.3 | Z |
| 1625 | 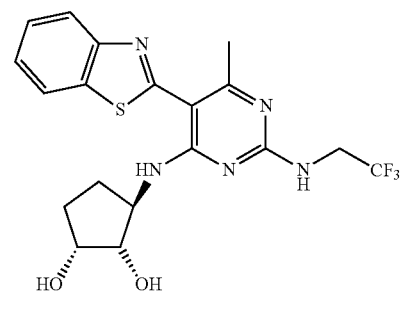 | B | 440.2 | Z67 |
| 1626 | 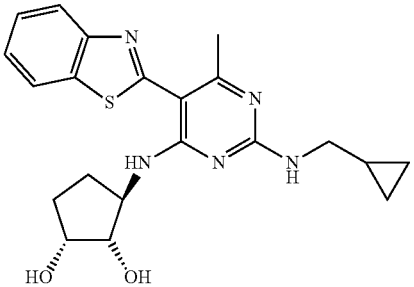 | B | 412.2 | Z67 |
| 1627 | 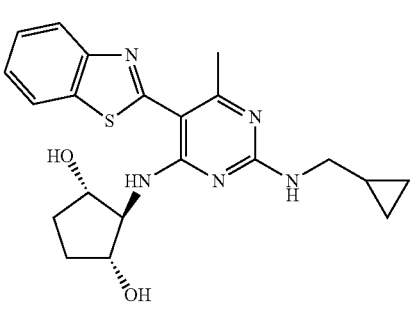 [SMILES: Cc1nc(NCC2CC2)nc(N[C@H]2[C@H](O)CC[C@@H]2O)c1-c1nc2ccccc2s1] | C | 412.2 | Z67 |
| 1628 | 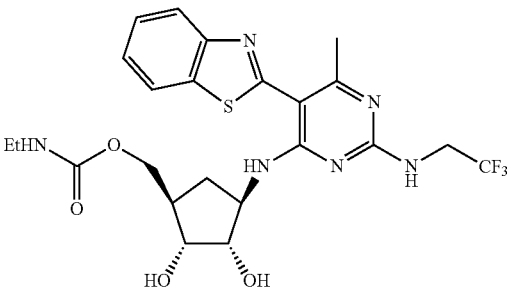 | A | 541.25 | Z59 |

TABLE I-continued
| | | | | |
|---|---|---|---|---|
| 1629 | 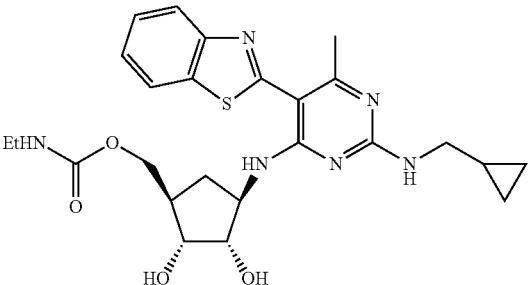 | B | 513.2 | Z59 |
| 1630 | 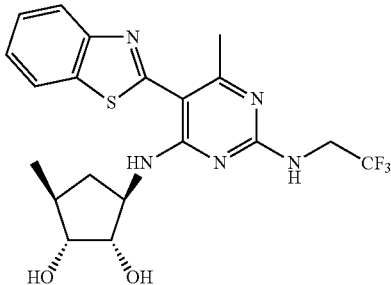 [SMILES: Cc1nc(NCC(F)(F)F)nc(N[C@@H]2C[C@H](C)[C@@H](O)[C@H]2O)c1-c1nc2ccccc2s1] | A | 454.2 | Z60 |
| 1632 | 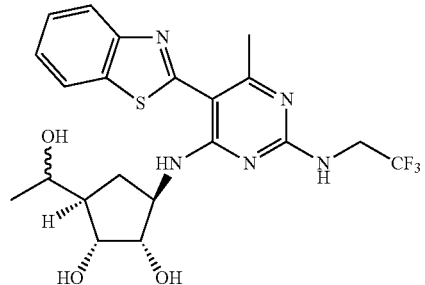 [SMILES: Cc1nc(NCC(F)(F)F)nc(N[C@@H]2C[C@H](C(C)O)[C@@H](O)[C@H]2O)c1-c1nc2ccccc2s1] | A | 484.2 | Z61 |
| 1633 | 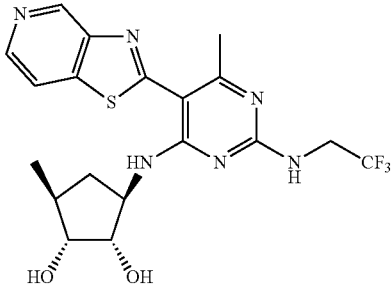 | A | 455.2 | Z60 |
| 1634 | 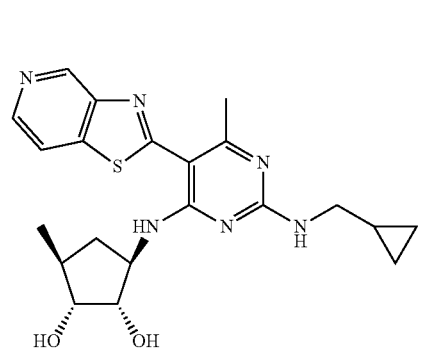 [SMILES: Cc1nc(NCC2CC2)nc(N[C@@H]2C[C@H](C)[C@@H](O)[C@H]2O)c1-c1nc2cnccc2s1] | A | 427.2 | Z60 |

TABLE I-continued

| | | | | |
|---|---|---|---|---|
| 1635 | (structure) | A | 479.2 | Z40, repalce NaSMe with NaCN |
| 1636 | (structure) | A | 464.2 | Z63 |
| 1637 | (structure) | B | 498.2 | Z62 |
| 1638 | (structure) | B | 512.2 | Z62 |
| 1639 | (structure) | A | 553.0 | Z66 |

TABLE I-continued

| | | | | |
|---|---|---|---|---|
| 1640 | (structure) | B | 498.2 | Z63 |
| 1641 | (structure) | A | 457.2 | Z62 |
| 1642 | (structure) | A | 471.2 | Z62 |
| 1643 | (structure) isomer 1 | A | 484.2 | Z64 |
| 1644 | (structure) isomer 1 | A | 456.2 | Z64 |

TABLE I-continued

| | | | | | |
|---|---|---|---|---|---|
| 1645 | (structure, isomer 1) | B | 590.2 | Z64 | |
| 1646 | (structure, isomer 2) | B | 590.2 | Z64 | |
| 1647 | (structure, isomer 2) | B | 456.2 | Z64 | |
| 1648 | (structure, isomer 2) | B | 484.2 | Z64 | |
| 1649 | (structure) | A | 591.2 | Z64 | |

TABLE I-continued
| 1650 | 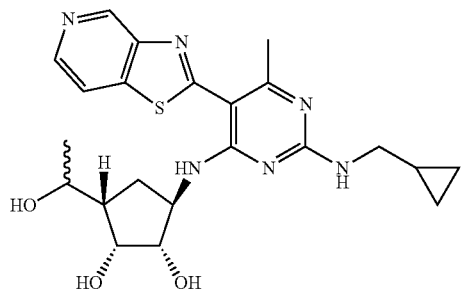 [SMILES: Cc1nc(NCC2CC2)nc(N[C@@H]2C[C@@H](C(C)O)[C@@H](O)[C@H]2O)c1-c1nc2cnccc2s1] | A | 457.2 | Z64 |
| 1651 | 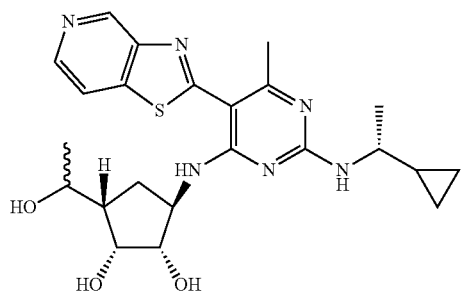 [SMILES: Cc1nc(N[C@H](C)C2CC2)nc(N[C@@H]2C[C@@H](C(C)O)[C@@H](O)[C@H]2O)c1-c1nc2cnccc2s1] | A | 471.2 | Z64 |
| 1652 | 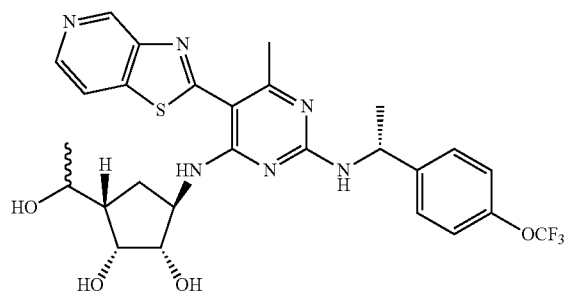 [SMILES: Cc1nc(N[C@H](C)c2ccc(OC(F)(F)F)cc2)nc(N[C@@H]2C[C@@H](C(C)O)[C@@H](O)[C@H]2O)c1-c1nc2cnccc2s1] | A | 591.2 | Z64 |
| 1653 | 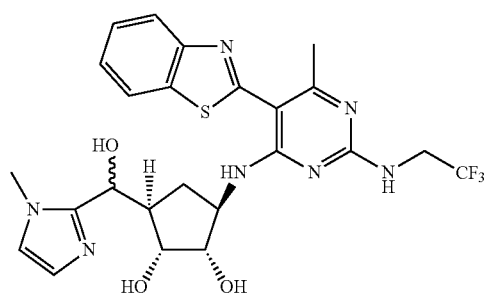 [SMILES: Cc1nc(NCC(F)(F)F)nc(N[C@@H]2C[C@H](C(O)c3nccn3C)[C@@H](O)[C@H]2O)c1-c1nc2ccccc2s1] | A | 550.2 | Z66 |

| | | | | |
|---|---|---|---|---|
| 1654 | 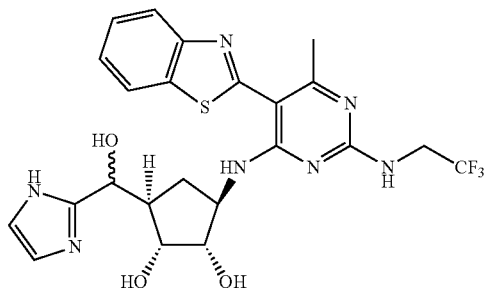 [SMILES: Cc1nc(NCC(F)(F)F)nc(N[C@@H]2C[C@H](C(O)c3ncc[nH]3)[C@@H](O)[C@H]2O)c1-c1nc2ccccc2s1] | B | | 536.2 | Z66 |
| 1701 | 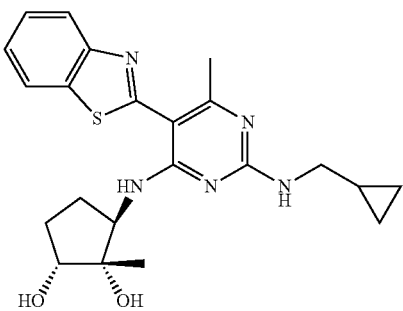 [SMILES: Cc1nc(NCC2CC2)nc(N[C@@H]2CC[C@@H](O)[C@@]2(C)O)c1-c1nc2ccccc2s1] | B | $^1$H NMR (CDCl$_3$, 400 MHz): δ 10.24 (1H, broad s), 7.92 (1H, d, J = 8.54 Hz), 7.88 (1H, d, J = 7.93 Hz), 7.48 (1H, ddd, J = 1.22, 7.93, 8.54 Hz), 7.37 (1H, t, J = 7.93 Hz), 5.26 (1H, broad s), 4.57 (1H, broad s), 3.84 (1H, d, J = 4.88 Hz), 3.40 (1H, s), 3.36 (1H, m), 3.11 (1H, broad s), 2.70 (3H, s), 2.37 (1H, ddt, J = 4.27, 9.76, 13.42 Hz), 2.08 (1H, ddt, J = 4.88, 10.98, 15.25 Hz), 1.87 (1H, m), 1.65 (2H, m), 1.12 (3H, s), 1.09 (1H, m), 0.56 (2H, dd, J = 1.22, 7.93 Hz), 0.28 (2H, m) | 426.27 | Z67 |
| 1702 | 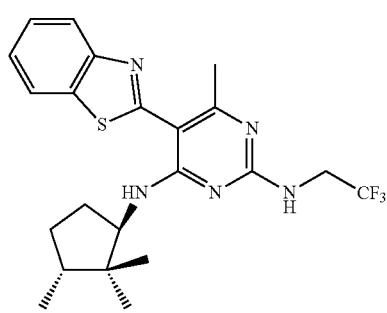 | B | $^1$H NMR (dmso-d6, 400 MHz): δ 10.32 (1H, broad s), 8.38 (1H, broad s), 8.24 (1H, d, J = 7.93 Hz), 8.07 (1H, d, J = 8.54 Hz), 7.63 (1H, dd, J = 7.32, 7.93 Hz), 7.55 (1H, t, J = 7.32 Hz), 4.54 (1H, dd, J = 7.93, 16.47 Hz), 4.36 (2H, m), 3.62 (1H, dd, J = 5.49, 6.10 Hz), 2.65 (3H, s), 2.21 (1H, ddt, J = 3.05, 9.50, 12.81 Hz), 1.91 (1H, m), 1.56 (1H, m), 1.38 (1H, m), 1.19 (3H, s) | 454.24 | Z68 |

| | | | | | |
|---|---|---|---|---|---|
| 1703 | 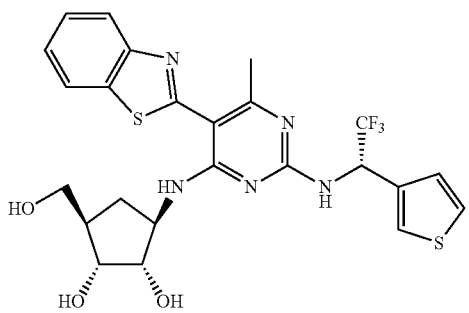 [SMILES: Cc1nc(N[C@@H](c2ccsc2)C(F)(F)F)nc(N[C@@H]2C[C@H](CO)[C@@H](O)[C@H]2O)c1-c1nc2ccccc2s1] | B | ¹H NMR (dmso-d6, 400 MHz): δ 9.61 (1H, d, J = 4.88 Hz), 9.44 (1H, broad s), 8.20 (1H, d, J = 7.93 Hz), 8.13 (1H, d, J = 8.54 Hz), 7.85 (1H, s), 7.69 (1H, s), 7.60 (1H, dd, J = 7.32, 7.93 Hz), 7.53 (1H, dd, J = 7.32, 7.93 Hz), 7.35 (1H, d, J = 3.66 Hz), 6.26 (1H, broad s), 4.41 (1H, dd, J = 6.10, 7.32 Hz), 3.81 (1H, broad s), 3.71 (1H, dd, J = 4.88, 5.49 Hz), 3.40 (2H, m), 2.48 (3H, s), 2.14 (1H, m), 2.01 (1H, m), 1.20 (1H, m) | 552.0 | Z69 |
| 1704 | 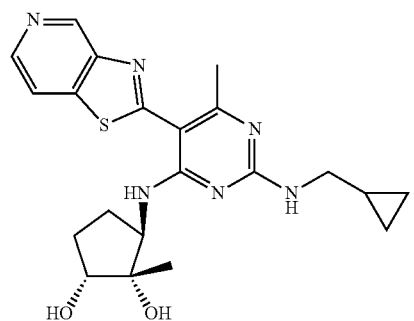 [SMILES: Cc1nc(NCC2CC2)nc(N[C@@H]2CC[C@@H](O)[C@@]2(C)O)c1-c1nc2cnccc2s1] | A | ¹H NMR (dmso-d6, 400 MHz): δ 10.05 (1H, d, J = 6.71 Hz), 9.12 (1H, s), 8.45 (1H, d, J = 5.49 Hz), 8.14 (1H, d, J = 5.49 Hz), 7.46 (1H, broad s), 4.69 (1H, d, J = 3.05 Hz), 4.44 (2H, m), 3.63 (1H, broad s), 3.18 (2H, m), 2.59 (3H, s), 2.27 (1H, m), 1.92 (1H, m), 1.53 (1H, m), 1.30 (1H, m), 1.20 (3H, s), 1.06 (1H, m), 0.39 (2H, dd, J = 1.83, 7.93 Hz), 0.19 (2H, dd, J = 4.88, 9.76 Hz) | 427.28 | Z67 |

TABLE I-continued

| | | | | |
|---|---|---|---|---|
| 1705 | | A | ¹H NMR (dmso-d6, 400 MHz): δ 13.20-13.70 (1H, broad s), 9.66 (1H, s), 8.96 (1H, d, J = 6.71 Hz), 8.74 (1H, d, J = 5.49 Hz), 8.62 (1H, d, J = 5.49 Hz), 8.09 (1H, broad s), 7.23 (2H, d, J = 7.93 Hz), 6.87 (2H, d, J = 7.93 Hz), 4.51 (1H, dd, J = 6.71, 7.93 Hz), 3.99 (2H, q, J = 6.71 Hz), 3.82 (1H, m), 3.71 (1H, m), 3.61 (2H, m), 3.37 (2H, d, J = 3.66 Hz), 2.85 (2H, t, J = 7.32 Hz), 2.42 (3H, s), 2.25 (1H, m), 1.97 (1H, m), 1.31 (3H, t, J = 6.71 Hz), 1.18 (1H, m) | 537.2 | U |
| 1706 | | B | ¹H NMR (dmso-d6, 400 MHz): δ 7.33 (1H, d, J = 8.54 Hz), 7.28 (1H, d, J = 7.32 Hz), 6.81 (1H, ddd, J = 1.22, 7.32, 7.93 Hz), 6.73 (1H, ddd, J = 1.22, 7.32, 7.93 Hz), 6.33 (1H, d, J = 4.88 Hz), 6.01 (1H, d, J = 5.49 Hz), 3.83 (1H, q, J = 7.32 Hz), 3.15 (1H, dd, J = 5.49, 6.10 Hz), 3.10 (1H, t, J = 4.88 Hz), 3.01 (1H, m), 2.91 (1H, dd, J = 6.71, 7.32 Hz), 2.77 (2H, d, J = 5.49 Hz), 2.34 (2H, dd, J = 6.71, 7.32 Hz), 1.77 (3H, s), 1.67 (1H, m), 1.42 (3H, s), 1.37 (1H, m), 0.53 (1H, dt, J = 7.93, 13.42 Hz) | 512.2 | U |

| | | | | |
|---|---|---|---|---|
| 1707 | 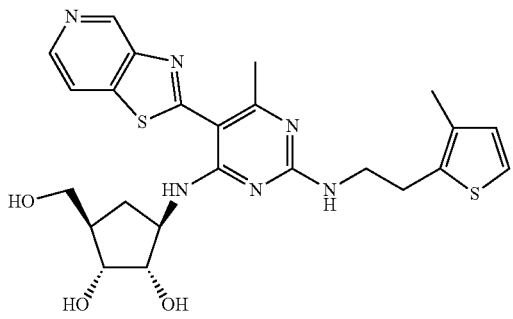 [SMILES: Cc1ccsc1CCNc1nc(C)c(-c2nc3cnccc3s2)c(N[C@@H]2C[C@H](CO)[C@@H](O)[C@H]2O)n1] | A | $^1$H NMR (CD$_3$OD), 400 MHz): δ 9.74 (1H, s), 8.78 (2H, s), 7.09 (1H, d, J = 4.88 Hz), 6.78 (1H, d, J = 5.49 Hz), 4.60 (1H, m), 3.90 (2H, m), 3.83 (1H, dd, J = 7.32, 14.03 Hz), 3.71 (1H, dt, J = 6.10, 7.32 Hz), 3.57 (2H, dd, J = 4.88, 6.71 Hz), 3.12 (2H, t, J = 6.71 Hz), 2.59 (3H, s), 2.44 (1H, m), 2.20 (3H, s), 2.13 (1H, m), 1.33 (1H, m) | 513.2 U |
| 1708 | 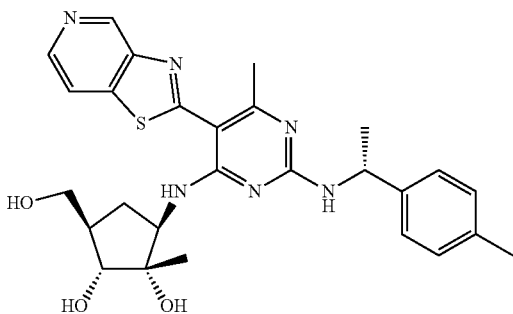 [SMILES: Cc1ccc([C@@H](C)Nc2nc(C)c(-c3nc4cnccc4s3)c(N[C@@H]3C[C@H](CO)[C@@H](O)[C@@]3(C)O)n2)cc1] | A | $^1$H NMR (CD$_3$OD), 400 MHz): δ 9.70 (1H, s), 8.81 (1H, d, J = 6.25 Hz), 8.79 (1H, d, J = 6.25 Hz), 7.37 (2H, d, J = 8.59 Hz), 7.19 (2H, d, J = 7.81 Hz), 5.28 (1H, q, J = 7.03 Hz), 4.63 (1H, dd, J = 4.68, 7.03 Hz), 3.64 (1H, d, J = 7.81 Hz), 3.60 (1H, dd, J = 3.90, 10.94 Hz), 3.53 (1H, dd, J = 3.90, 10.94 Hz), 3.24 (1H, m), 2.65 (3H, s), 2.32 (3H, s), 2.24 (1H, m), 2.09 (1H, m), 1.63 (3H, d, J = 7.03 Hz), 1.29 (3H, s) | 521.2 |
| 1709 | 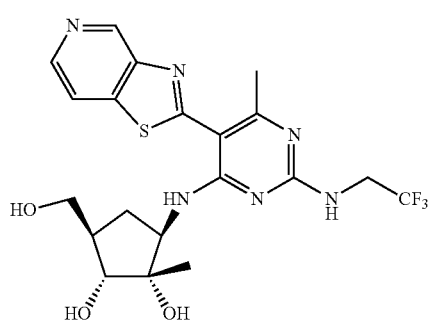 [SMILES: Cc1nc(NCC(F)(F)F)nc(N[C@@H]2C[C@H](CO)[C@@H](O)[C@@]2(C)O)c1-c1nc2cnccc2s1] | A | $^1$H NMR (CD$_3$OD), 400 MHz): δ 9.75 (1H, s), 8.82 (2H, m), 4.70 (1H, m), 4.41 (2H, m), 3.66 (1H, d, J = 7.81 Hz), 3 60 (1H, dd, J = 3.12, 10.94 Hz), 3.53 (1H, dd, J = 3.12, 10.94 Hz), 3.24 (1H, m), 2.64 (3H, S), 2.52 (1H, m), 2.12 (1H, m), 1.66 (1H, m), 1.24 (3H, s) | |

TABLE I-continued
| 1801 | 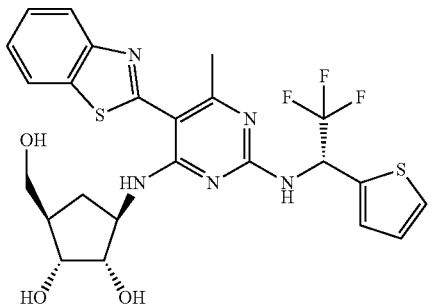 [SMILES: Cc1nc(N[C@@H](c2cccs2)C(F)(F)F)nc(N[C@@H]2C[C@H](CO)[C@@H](O)[C@H]2O)c1-c1nc2ccccc2s1] | A | 1H NMR (DMSO-d6, 400 MHz) δ 1.67 (m, 1H), 1.98 (m, 1H), 2.11 (m, 1H), 2.25 (m, 1H), 3.65 (m, 2H), 3.68 (m, 2H). 4.33 (m, 1H), 4.40 (m, 1H), (4.44 (m, 1H), 6.58 (m, 1H), 7.11 (m, 1H), 7.39 (dd, 1H, J = 3.13, 7.82 Hz), 7.50 (dd, 1H, J = 7.03, 7.03 Hz), 7.57 (dd, 1H, J = 7.03, 7.82 Hz), 7.64 (dd, 1H, J = 4.69, 6.25 Hz), 8.11 (dd, 1H, J = 3.91, 8.60 Hz), 8.17 (dd, 1H, J = 7.03, 7.03 Hz), 9.29 (broad s, 1H), 9.61 (broad s, 1H). | | Z69 |
| --- | --- | --- | --- | --- | --- |
| 1802 | 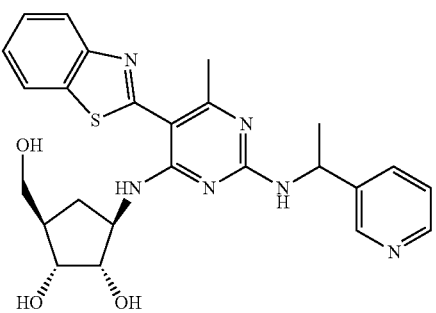 [SMILES: Cc1nc(NC(C)c2cccnc2)nc(N[C@@H]2C[C@H](CO)[C@@H](O)[C@H]2O)c1-c1nc2ccccc2s1] | B | | 493.20 | Z3 |
| 1803 | 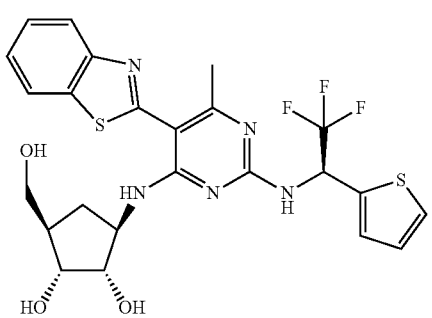 [SMILES: Cc1nc(N[C@H](c2cccs2)C(F)(F)F)nc(N[C@@H]2C[C@H](CO)[C@@H](O)[C@H]2O)c1-c1nc2ccccc2s1] | C | 1H NMR (DMSO-d6, 400 MHz) δ 1.28 (m, 1H), 1.99 (m, 1H), 2.25 (m, 1H), 3.35 (m, 1H), 3.40 (m, 1H), 3.68 (m. 1H), 3.75 (m, 1H), 4.43 (m, 1H), 6.52 (m, 1H), 7.11 (dd, 1H, J = 4.40, 4.40 Hz), 7.44 (d, 1H, J = 2.93 Hz), 7.50 (dd, 1H, J = 7.32, 7.32 Hz), 7.58 (dd, 1H, J = 7.32, 7.81 Hz), 7.66 (d, 1H, J = 3.91 Hz), 8.11 (d, 1H, J = 7.81 Hz), 8.17 (d, 1H, J = 7.81 Hz), 9.58 (broad s, 1H). | 552.26 | Z69 |

TABLE I-continued
| | | | | | |
|---|---|---|---|---|---|
| 1804 | 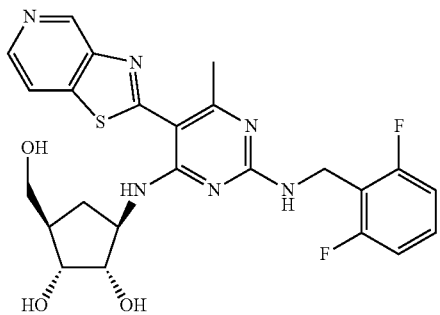 [SMILES: Cc1nc(NCc2c(F)cccc2F)nc(N[C@@H]2C[C@H](CO)[C@@H](O)[C@H]2O)c1-c1nc2cnccc2s1] | A | 1H NMR (DMSO-d6, 400 MHz) δ 1.06 (m, 1H), 1.95 (broad s, 1H), 2.07 (m, 1H), 2.36 (s, 3H), 3.35 (s, 3H), 3.76 (m, 2H), 4.45 (m, 1H), 4.67 (dd, 1H, J = 4.69, 14.07 Hz), 4.80 (dd, 1H, J = 5.47, 14.85 Hz), 7.12 (dd, 2H, J = 7.03, 7.82 Hz), 7.42 (m, 1H), 8.43 (broad s, 1H), 8.49 (broad s), 8.68 (broad s, 1H), 8.89 (d, 1H, J = 6.25 Hz), 9.56 (broad s, 1H). | 515.30 | U |
| 1805 | 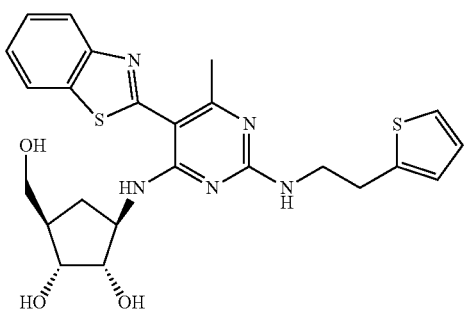 [SMILES: Cc1nc(NCCc2cccs2)nc(N[C@@H]2C[C@H](CO)[C@@H](O)[C@H]2O)c1-c1nc2ccccc2s1] | A | 1H NMR (DMSO-d6, 400 MHz) δ 1.18 (m, 1H), 1.96 (m, 1H), 2.24 (m, 1H), 2.45 (s, 3H), 3.13 (m, 2H), 3.36 (m, 2H), 3.66 (m, 4H), 3.80 (dd, 1H, J = 5.47, 6.25 Hz), 4.43 (dt, 1H, J = 7.82, 10.94 Hz), 6.97 (m, 2H), 7.36 (dd, 1H, J = 1.56, 6.25 Hz), 7.52 (dd, 1H, J = 7.03, 8.60 Hz), 7.59 (dd, 1H, J = 7.03, 8.60 Hz), 7.94 (broad s, 1H), 8.12 (d, 1H, J = 7.82 Hz), 8.19 (d, 1H, J = 7.82 Hz), 9.50 (d, 1H, J = 6.25 Hz). | 498.27 | U |
| 1806 | 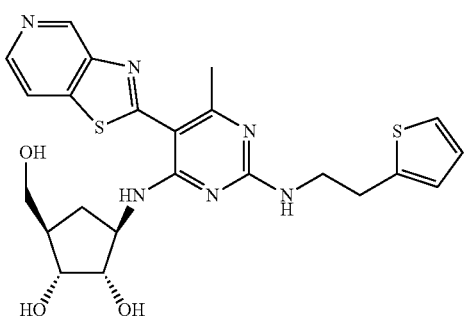 [SMILES: Cc1nc(NCCc2cccs2)nc(N[C@@H]2C[C@H](CO)[C@@H](O)[C@H]2O)c1-c1nc2cnccc2s1] | C | 1H NMR (CD3OD, 400 Hz) δ 1.38 (m, 1H), 2.17 (m, 1H), 2.49 (m, 1H), 2.61 (s, 3H), 3.25 (dd, 1H, J = 6.25, 7.03 Hz), 3.57 (m, 1H), 3.57 (dd, 1H, J = 4.69, 6.25 Hz), 3.82 (m, 1H), 3.87 (dd, 1H, J = 6.25, 7.03 Hz), 3.92 (dd, 1H, J = 4.69, 4.69 Hz), 3.97 (dd, 1H, J = 4.69, 6.25 Hz), 4.63 (m, 1H), 6.97 (m, 2H), 7.25 (d, 1H, J = 6.25 Hz), 8.77 (s, 2H), 9.73 (broad s, 1H). | | U |

TABLE I-continued
| 1808 | 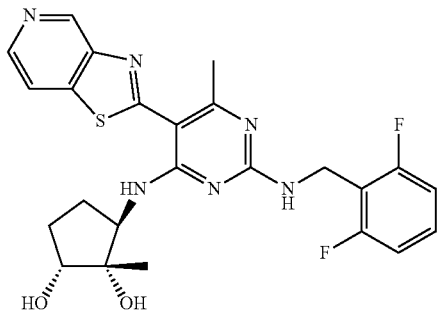 [SMILES: Cc1nc(NCc2c(F)cccc2F)nc(N[C@@H]2CC[C@@H](O)[C@@]2(C)O)c1-c1nc2cnccc2s1] | A | 1H NMR (DMSO-d6, 400 Hz) δ 1.16 (m, 1H), 1.22 (s, 3H), 1.54 (m, 1H), 1.91 (m, 1H), 2.21 (m, 1H), 2.59 (s, 3H), 3.64 (broad s, 1H), 4.28-4.76 (m, 5H), 7.04 (m, 2H), 7.34 (m, 1H), 7.75 (broad s, 1H), 8.14 (d, 1H, J = 5.37 Hz), 8.45 (d, 1H, J = 5.37 Hz), 9.13 (s, 1H), 10.06 (d, 1H, 5.86 Hz). | 499.28 | Z67 |
| --- | --- | --- | --- | --- | --- |
| 1809 | 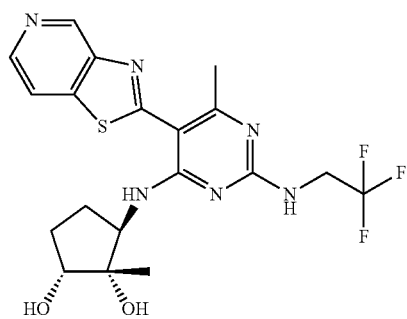 [SMILES: Cc1nc(NCC(F)(F)F)nc(N[C@@H]2CC[C@@H](O)[C@@]2(C)O)c1-c1nc2cnccc2s1] | B | 1H NMR (DMSO-d6, 400 Hz) δ 1.28 (s, 3H), 1.54 (m, 1H), 1.72 (m, 1H), 2.07 (m, 1H), 2.32 (m, 1H), 2.74 (s, 3H), 3.74 (t, 1H, J = 5.47 Hz), 4.27 (m, 1H), 4.51 (m, 1H), 8.72 (d, 1H, J = 6.25 Hz), 8.77 (d, 1H, J = 6.25 Hz), 9.69 (s, 1H). | 455.22 | Z67 |
| 1810 | 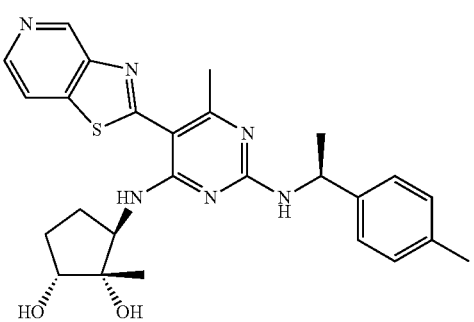 [SMILES: Cc1ccc([C@H](C)Nc2nc(C)c(-c3nc4cnccc4s3)c(N[C@@H]3CC[C@@H](O)[C@@]3(C)O)n2)cc1] | A | 1H NMR (CD3OD, 400 Hz) δ 1.21 (s, 3H), 1.51 (d, 3H, J = 6.84 Hz), 1.74 (m, 1H), 2.10 (m, 1H), 2.29 (s, 3H), 2.42 (broad s, 1H), 2.64 (s, 3H), 3.77 (dd, 1H, J = 3.42, 5.86 Hz), 4.64 (dd, 1H, J = 8.3, 8.79 Hz), 5.19 (broad s, 1H), 7.13 (d, 2H, J = 7.81 Hz), 7.30 (d, 2H, J = 7.81 Hz), 8.03 (d, 1H, J = 5.37 Hz), 8.38 (d, 1H, J = 5.86 Hz), 9.09 (s, 1H). | 491.40 | Z67 |

TABLE I-continued
| | | | | | |
|---|---|---|---|---|---|
| 1811 | 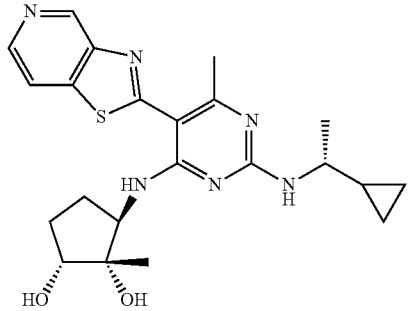 [SMILES: Cc1nc(N[C@H](C)C2CC2)nc(N[C@@H]2CC[C@@H](O)[C@@]2(C)O)c1-c1nc2cnccc2s1] | A | 1H NMR (CD3OD, 400 Hz) δ 0.28 (m, 1H), 0.39 (m, 1H), 0.47 (m, 1H), 0.53 (m, 1H), 0.99 (m, 1H), 1.27 (broad s, 2H), 1.29 (s, 2H), 1.31 (s, 2H), 1.53 (m, 1H), 1.72 (m, 1H), 2.09 (m, 1H), 2.38 (m, 1H), 2.66 (s, 1H), 3.60 (m, 1H), 3.80 (dd, 1H, J = 3.91, 6.35 Hz), 4.63 (dd, 1H, J = 8.39, 8.79 Hz), 8.06 (dd, 1H, J = 0.98, 5.37 Hz), 8.41 (d, 1H, J = 5.86 Hz), 9.11 (s, 1H). | 441.32 | Z67 |
| 1812 | 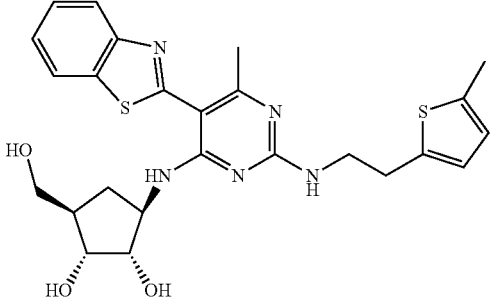 [SMILES: Cc1ccc(CCNc2nc(C)c(-c3nc4ccccc4s3)c(N[C@@H]3C[C@H](CO)[C@@H](O)[C@H]3O)n2)s1] | B | 1H NMR (DMSO-d6, 400 Hz) δ 1.16 (m, 1H), 1.94 (m, 1H), 2.22 (m, 1H), 2.37 (s, 3H), 2.44 (s, 3H), 3.03 (dd, 2H, J = 7.32, 7.32 Hz), 3.61 (m, 2H), 3.68 (dd, 1H, J = 4.40, 4.88 Hz), 3.79 (dd, 1H, J = 5.86, 5.86 Hz), 4.42 (dt, 1H, J = 7.32, 15.14 Hz), 6.62 (dd, 1H, J = 0.97, 3.42 Hz), 6.73 (d, 1H, J = 3.42 Hz), 7.52 (dd, 1H, J = 6.84, 7.32 Hz), 7.59 (dd, 1H, J = 6.84, 7.32 Hz), 7.86 (broad s, 1H), 8.12 (d, 1H, J = 7.81 Hz), 8.19 (d, 1H, J = 7.81 Hz), 9.47 (d, 1H, J = 7.81 Hz). | 512.33 | U |
| 1813 | 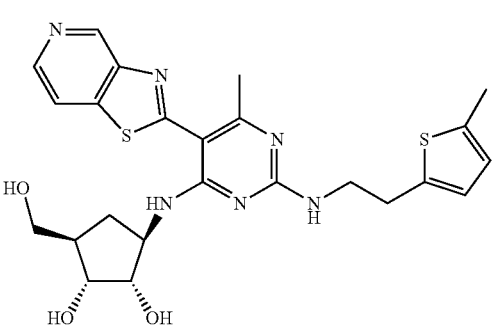 [SMILES: Cc1ccc(CCNc2nc(C)c(-c3nc4cnccc4s3)c(N[C@@H]3C[C@H](CO)[C@@H](O)[C@H]3O)n2)s1] | A | 1H NMR (DMSO-d6, 400 Hz) δ 1.15 (m, 1H), 1.94 (m, 1H), 1.97 (s, 1H), 2.21 (m, 1H), 2.37 (s, 3H), 2.41 (s, 3H), 3.03 (m, 2H), 3.34 (d, 1H, J = 5.47 Hz), 3.65 (m, 2H), 3.68 (dd, 1H, J = 4.69, 4.69 Hz), 3.79 (dd, 1H, J = 5.47, 6.25 Hz), 4.42 (dt, 1H, J = 7.82, 14.85 Hz), 5.45 (broad s, 3H), 6.62 (d, 1H, J = 2.35 Hz), 6.75 (d, 1H, J = 3.13 | 513.36 | U |

TABLE I-continued
| | | | | | |
|---|---|---|---|---|---|
| 1814 | 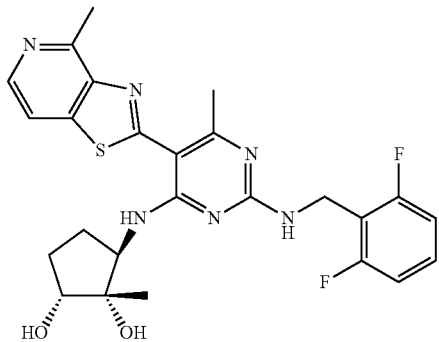 [SMILES: Cc1nc(NCc2c(F)cccc2F)nc(N[C@@H]2CC[C@@H](O)[C@@]2(C)O)c1-c1nc2c(C)nccc2s1] | A | 1H NMR (DMSO-d6, 400 Hz) δ 1.09 (broad s, 3H), 1.30 (m, 1H), 1.56 (m, 1H), 1.92 (m, 1H), 2.22 (m, 1H), 2.58 (s, 3H), 2.84 (s, 3H), 3.64 (broad s, 1H), 4.23-4.74 (m, 5H), 7.04 (dd, 2H, J = 6.84, 7.32 Hz), 7.35 (m, 1H), 7.70 (broad s, 1H), 7.95 (d, 1H, J = 5.37 Hz), 8.30 (d, 1H, J = 5.37 Hz), 9.69 (broad s, 1H). | 513.40 | Z67 |
| 1815 | 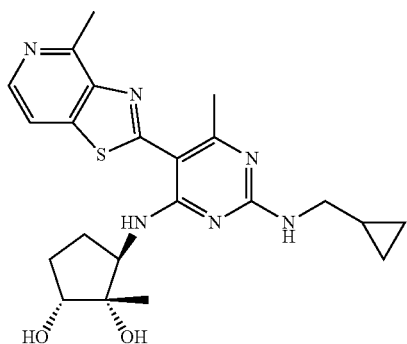 [SMILES: Cc1nc(NCC2CC2)nc(N[C@@H]2CC[C@@H](O)[C@@]2(C)O)c1-c1nc2c(C)nccc2s1] | A | 1H NMR (DMSO-d6, 400 Hz) δ 0.22 (dd, 2H, J = 4.88, 9.77 Hz), 0.39 (m, 2H), 1.09 (s, 4H), 1.34 (m, 1H), 1.55 (m, 1H), 1.93 (m, 1H), 2.25 (m, 1H), 2.59 (s, 3H), 2.84 (s, 3H), 3.18 (dd, 2H, J = 6.35, 12.70 Hz), 3.64 (m, 1H), 4.39-4.70 (m, 3H), 7.45 (dd, 1H, J = 4.40, 5.37 Hz), 7.95 (d, 1H, J = 5.37 Hz), 8.30 (d, 1H, J = 5.37 Hz), 9.79 (d, 1H, J = 7.32 Hz). | 441.37 | Z67 |
| 1816 | 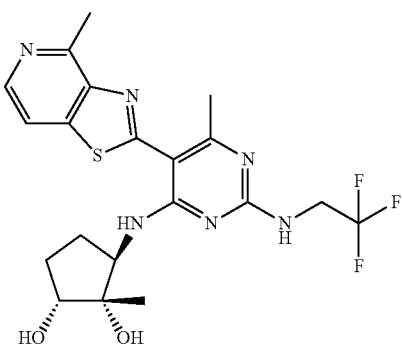 [SMILES: Cc1nc(NCC(F)(F)F)nc(N[C@@H]2CC[C@@H](O)[C@@]2(C)O)c1-c1nc2c(C)nccc2s1] | A | 1H NMR (CD3OD, 400 Hz) δ 1.20 (m, 4H), 1.53 (m, 1H), 1.74 (m, 1H), 2.10 (m, 1H), 2.39 (m, 1H), 2.70 (s, 3H), 2.94 (s, 3H), 3.79 (m, 1H), 4.19 (m, 1H), 4.28 (m, 1H), 7.91 (d, 1H, J = 5.37 Hz), 8.29 (d, 1H, J = 5.86 Hz). | 469.30 | Z67 |

TABLE I-continued
| | | | | | | |
|---|---|---|---|---|---|---|
| 1817 | 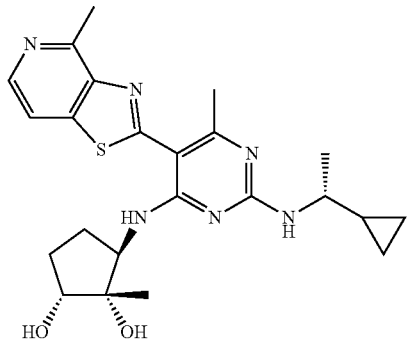 [SMILES: Cc1nc(N[C@H](C)C2CC2)nc(N[C@@H]2CC[C@@H](O)[C@@]2(C)O)c1-c1nc2c(C)nccc2s1] | | A | 1H NMR (DMSO-d6, 400 Hz) δ 0.01 (m, 1H), 0.14-0.32 (m, 3H), 0.82 (m, 1H), 0.94 (s, 3H), 1.04 (d, 3H, J = 7.03 Hz), 1.19 (m, 1H), 1.41 (m, 1H), 1.78 (m, 1H), 2.09 (m, 1H), 2.44 (s, 3H), 2.69 (s, 3H), 3.41 (m, 1H), 3.49 (m, 1H), 4.12-4.55 (m, 3H), 7.18 (d, 1H, J = 7.82 Hz), 7.80 (d, 1H, J = 5.47 Hz), 8.15 (d, 1H, J = 5.47 Hz), 9.63 (d, 1H, J = 7.03 Hz). | 455.36 | Z67 |
| 1818 | 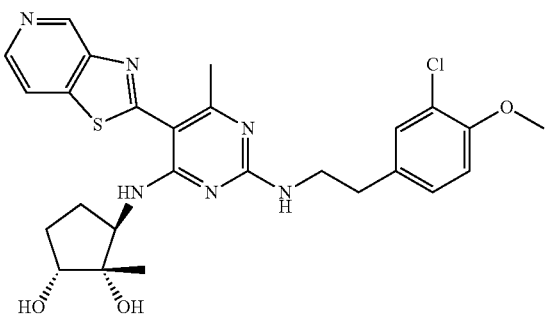 [SMILES: COc1ccc(CCNc2nc(C)c(-c3nc4cnccc4s3)c(N[C@@H]3CC[C@@H](O)[C@@]3(C)O)n2)cc1Cl] | | B | 1H NMR (DMSO-d6, 400 Hz) δ 1.18 (broad s, 1H), 1.23 (s, 2H), 1.33 (m, 1H), 1.55 (m, 1H), 1.93 (m, 1H), 2.32 (m, 1H), 2.58 (s, 3H), 2.79 (m, 2H), 3.44 (m, 2H), 3.65 (m, 1H), 3.79 (s, 3H), 4.38-4.77 (m, 3H), 7.04 (d, 1H, J = 8.30 Hz), 7.19 (m, 1H), 7.30 (d, 1H, J = 1.95 Hz), 8.14 (d, 1H, J = 4.88 Hz), 8.45 (d, 1H, J = 5.37 Hz), 9.13 (s, 1H), 10.06 (d, 1H, J = 7.32 Hz) | 541.34 | Z67 |
| 1819 | 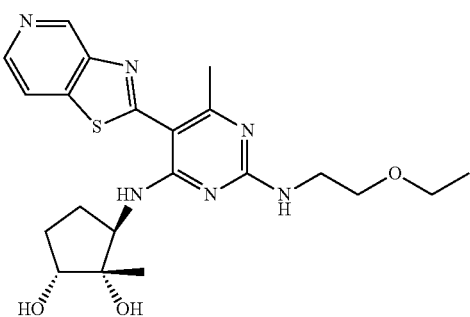 [SMILES: CCOCCNc1nc(C)c(-c2nc3cnccc3s2)c(N[C@@H]2CC[C@@H](O)[C@@]2(C)O)n1] | | A | 1H NMR (CD3OD, 400 Hz) δ 1.21 (t, 3H, J = 7.03 Hz), 1.29 (broad s, 2H), 1.53 (m, 1H), 1.72 (m, 1H), 2.10 (m, 1H), 2.93 (broad s, 1H), 2.64 (s, 3H), 3.56 (q, 2H, J = 7.03 Hz), 3.62 (s, 3H), 3.79 (dd, 1H, J = 3.91, 6.25 Hz), 4.67 (m, 1H), 8.04 (d, 1H, J = 5.47 Hz), 8.40 (d, 1H, J = 5.47 Hz), 9.11 (s, 1H). | 446.30 | Z67 |

TABLE I-continued
| | | | | | |
|---|---|---|---|---|---|
| 1820 | 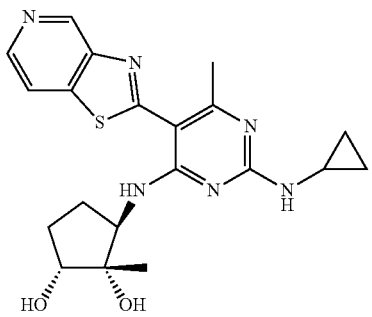 [SMILES: Cc1nc(NC2CC2)nc(N[C@@H]2CC[C@@H](O)[C@@]2(C)O)c1-c1nc2cnccc2s1] | B | 1H NMR (DMSO-d6, 400 Hz) δ 0.49 (m, 2H), 0.67 (d, 2H, J = 3.13 Hz), 1.17 (s, 3H), 1.38 (m, 1H), 1.54 (m, 1H), 1.92 (m, 1H), 2.30 (m, 1H), 2.59 (s, 3H), 2.67 (m, 1H), 3.63 (m, 1H), 4.49 (m, 1H), 4.55 (m, 1H), 4.87 (broad s, 1H), 7.61 (broad s, 1H), 8.15 (d, J = 4.69 Hz), 8.46 (d, 1H, J = 5.47 Hz), 9.15 (s, 1H), 9.92 (broad s, 1H). | 413.32 | Z67 |
| 1821 | 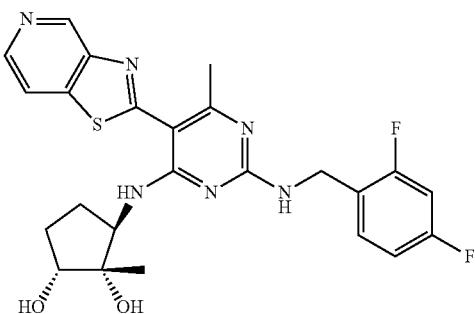 [SMILES: Cc1nc(NCc2ccc(F)cc2F)nc(N[C@@H]2CC[C@@H](O)[C@@]2(C)O)c1-c1nc2cnccc2s1] | A | 1H NMR (DMSO-d6, 400 Hz) δ 1.18 (s, 4H), 1.49 (m, 1H), 1.89 (m, 1H), 2.05 (m, 1H), 2.59 (s, 3H), 3.62 (s, 1H), 4.27 (s, 1H), 4.34-477 (m, 4H), 7.02 (dd, 1H, J = 7.03, 7.03 Hz), 7.16 (dd, 1H, J = 7.82, 10.16 Hz), 7.44 (dd, 1H, J = 8.60, 15.63 Hz), 7.91 (broad s, 1H), 8.14 (d, 1H, J = 4.69 Hz), 8.45 (d, 1H, J = 4.69 Hz), 9.12 (s, 1H), 9.99 (d, 1H, J = 4.69 Hz). | 499.37 | Z67 |
| 1901 | 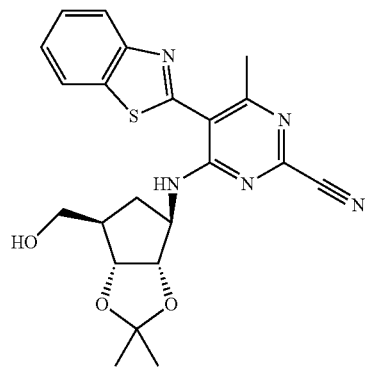 [SMILES: Cc1nc(C#N)nc(N[C@@H]2C[C@H](CO)[C@H]3OC(C)(C)O[C@H]32)c1-c1nc2ccccc2s1] | C | | 438.7 | Z70 |

TABLE I-continued

| | | | | |
|---|---|---|---|---|
| 1902 | (structure) | C | 456.7 | Z71 |
| 1903 | (structure) | C | 416.7 | Compound 1902 was converted to 1903 HCl salt using Procedure F, step 3 |
| 1904 | (structure) | C | 398.7 | Compound 1901 was converted to 1904 HCl salt using Procedure F, step 3 |
| 1905 | (structure) | B | 466.7 | Z72 |
| 1906 | (structure) | B | 428.7 | Z3 |

TABLE I-continued
| | | | | |
|---|---|---|---|---|
| 1907 | 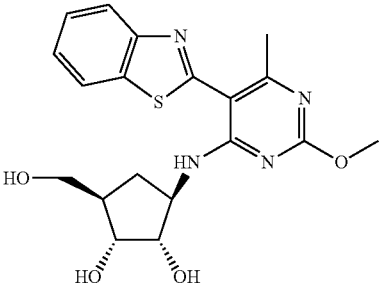 [SMILES: COc1nc(C)c(-c2nc3ccccc3s2)c(N[C@@H]2C[C@H](CO)[C@@H](O)[C@H]2O)n1] | B | 403.7 | Z73 |
| 1908 | 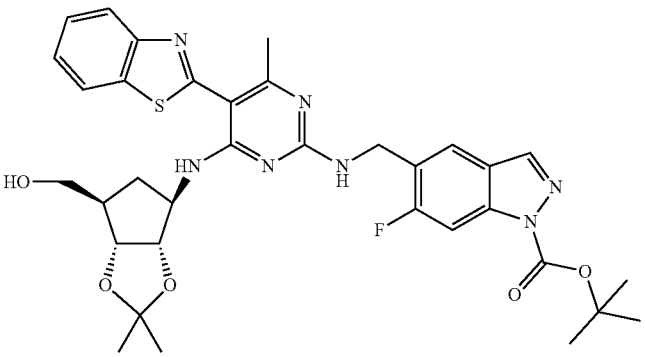 [SMILES: Cc1nc(NCc2cc3cnn(C(=O)OC(C)(C)C)c3cc2F)nc(N[C@@H]2C[C@H](CO)[C@H]3OC(C)(C)O[C@H]32)c1-c1nc2ccccc2s1] | B | 676.7 | Z3 |
| 1909 | 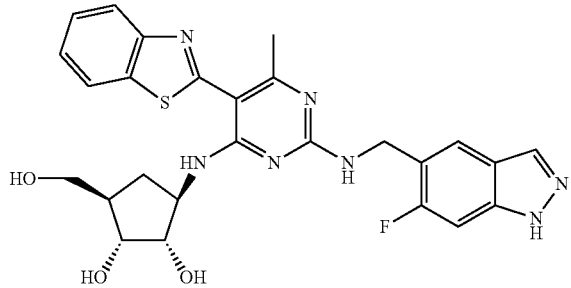 | A | 536.7 | Compound 1908 was converted to 1909 HCl salt using Procedure G, step 7 |
| 1910 | 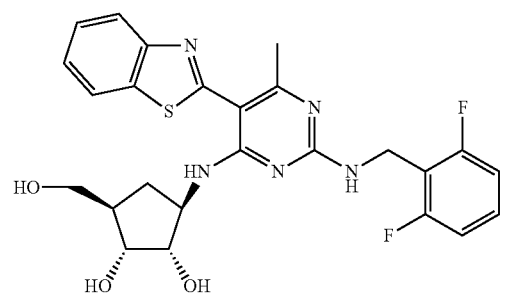 [SMILES: Cc1nc(NCc2c(F)cccc2F)nc(N[C@@H]2C[C@H](CO)[C@@H](O)[C@H]2O)c1-c1nc2ccccc2s1] | A | 514.7 | Z3 |
| 1911 | 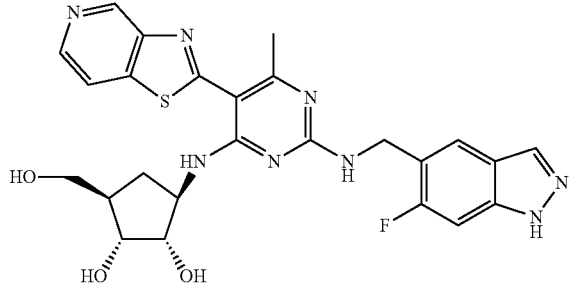 [SMILES: Cc1nc(NCc2cc3cn[nH]c3cc2F)nc(N[C@@H]2C[C@H](CO)[C@@H](O)[C@H]2O)c1-c1nc2cnccc2s1] | A | 537.3 | Z |

TABLE I-continued
| | | | | |
|---|---|---|---|---|
| 1912 | 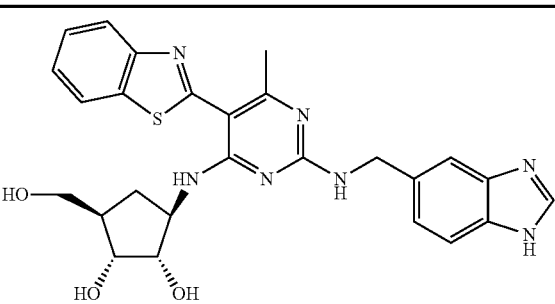 | A | 518.7 | Z3 |
| 1913 | 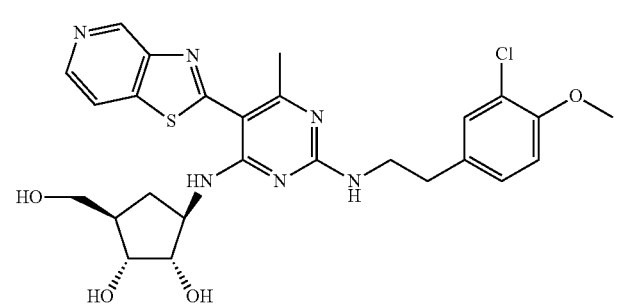 [SMILES: COc1ccc(CCNc2nc(C)c(-c3nc4cnccc4s3)c(N[C@@H]3C[C@H](CO)[C@@H](O)[C@H]3O)n2)cc1Cl] | B | 558.7 | Z |
| 1914 | 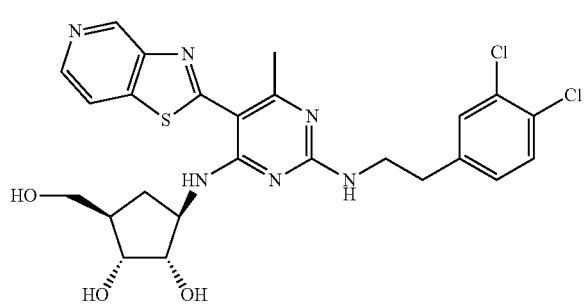 [SMILES: Cc1nc(NCCc2ccc(Cl)c(Cl)c2)nc(N[C@@H]2C[C@H](CO)[C@@H](O)[C@H]2O)c1-c1nc2cnccc2s1] | A | 561.7 | Z |
| 1915 | 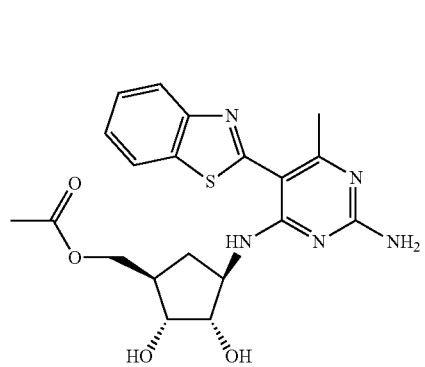 [SMILES: CC(=O)OC[C@H]1C[C@@H](Nc2nc(N)nc(C)c2-c2nc3ccccc3s2)[C@H](O)[C@@H]1O] | C | 430.7 | Z74 |
| 1916 | 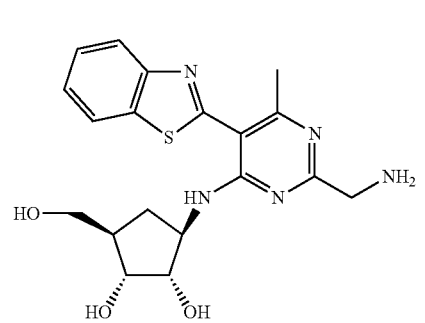 [SMILES: Cc1nc(CN)nc(N[C@@H]2C[C@H](CO)[C@@H](O)[C@H]2O)c1-c1nc2ccccc2s1] | C | 402.7 | Z75 |

| | | | | |
|---|---|---|---|---|
| 1917 | 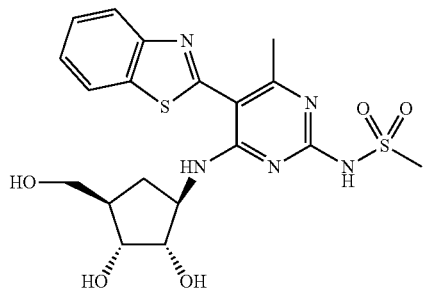 [SMILES: Cc1nc(NS(C)(=O)=O)nc(N[C@@H]2C[C@H](CO)[C@@H](O)[C@H]2O)c1-c1nc2ccccc2s1] | C | | 466.7 Z76 |
| 1918 | 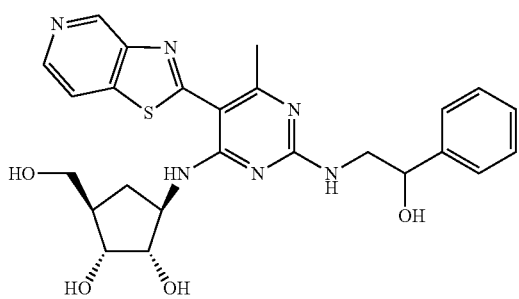 [SMILES: Cc1nc(NCC(O)c2ccccc2)nc(N[C@@H]2C[C@H](CO)[C@@H](O)[C@H]2O)c1-c1nc2cnccc2s1] | A | | 509.7 Z |
| 1919 | 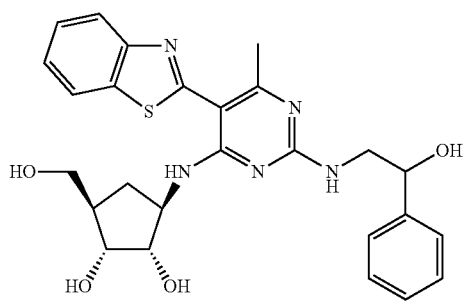 [SMILES: Cc1nc(NCC(O)c2ccccc2)nc(N[C@@H]2C[C@H](CO)[C@@H](O)[C@H]2O)c1-c1nc2ccccc2s1] | B | | 508.7 Z3 |
| 2001 | 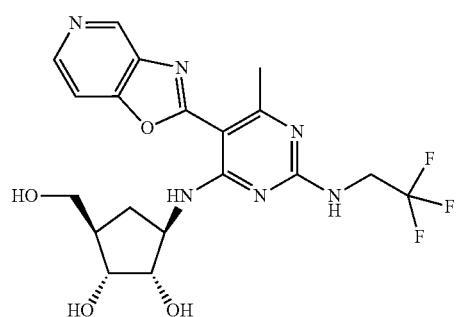 [SMILES: Cc1nc(NCC(F)(F)F)nc(N[C@@H]2C[C@H](CO)[C@@H](O)[C@H]2O)c1-c1nc2cnccc2o1] | B | ¹H NMR (400 MHz. CD₃OD), δ, 9.57 (s, 1 H), 8.96 (s, 1 H), 8.48 (d, 1 H, J = 5.6 Hz), 4.70–4.63 (m, 1 H), 4.57–4.49 (m, 1 H), 4.37–4.26 (m, 1 H), 4.06 (bt, 1 H, J = 4.0 Hz), 4.00 (bt, 1 H, J = 4.0 Hz), 3.75–3.55 (m, 2 H), 2.95 (s, 3 H), 2.59–2.53 (m, 1 H), 2.27–2.17 (m, 1 H), 1.55–1.48 (m, 1 H). | 455 Z |

TABLE I-continued
| | | | | | |
|---|---|---|---|---|---|
| 2002 | 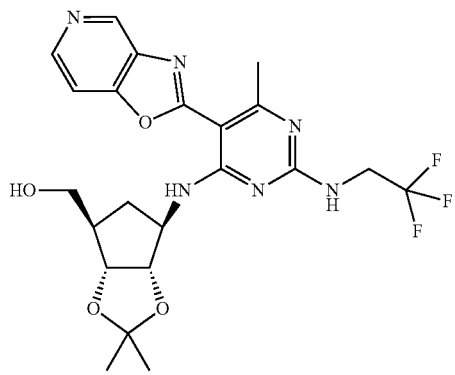 [SMILES: Cc1nc(NCC(F)(F)F)nc(N[C@@H]2C[C@H](CO)[C@H]3OC(C)(C)O[C@H]32)c1-c1nc2cnccc2o1] | C | | 495 | Z |
| 2003 | 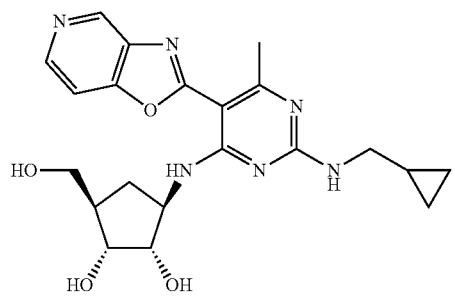 [SMILES: Cc1nc(NCC2CC2)nc(N[C@@H]2C[C@H](CO)[C@@H](O)[C@H]2O)c1-c1nc2cnccc2o1] | B | ¹H NMR (400 MHz, CD₃OD), δ, 9.54 (s, 1 H), 8.95 (s, 1 H), 8.47 (d, 1 H, J = 6.0 Hz), 4.67-4.62 (m, 1 H), 4.05-3.97 (m, 2 H), 3.69-3.63 (m, 2 H), 3.48-3.46 (m, 2 H), 2.91 (s, 3 H), 2.59-2.52 (m, 1 H), 2.21-2.17 (m, 2 H), 1.53-1.45 (m, 1 H), 1.26-1.91 (m, 1 H), 0.60 (d, 2 H, J = 7.6 Hz), 0.38 (d, 2 H, J = 4.4 Hz) | 427 | Z |
| 2004 | 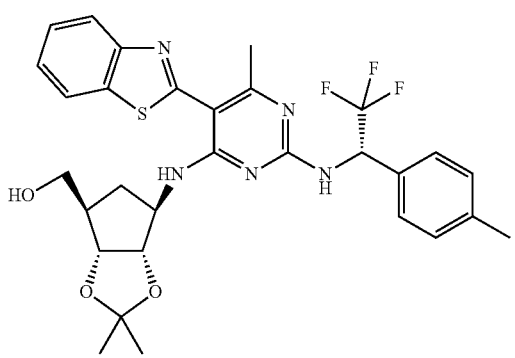 [SMILES: Cc1ccc([C@H](Nc2nc(C)c(-c3nc4ccccc4s3)c(N[C@@H]3C[C@H](CO)[C@H]4OC(C)(C)O[C@H]43)n2)C(F)(F)F)cc1] | B | | 600 | U |
| 2005 | 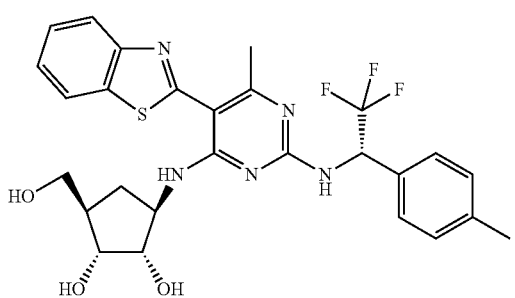 [SMILES: Cc1ccc([C@H](Nc2nc(C)c(-c3nc4ccccc4s3)c(N[C@@H]3C[C@H](CO)[C@@H](O)[C@H]3O)n2)C(F)(F)F)cc1] | B | ¹H NMR (400 MHz, CD₃OD), δ, 7.98 (d, 1 H, J = 8.4 Hz), 7.94 (d, 1 H, J = 7.6 Hz), 7.50-7.46 (m, 3 H), 7.37 (dt, 1 H, J = 0.8 & 8.0 Hz), 7.23 (d, 2 H, J = 8.0 Hz), 4.62-4.52 (m, 2 H), 4.36-4.28 (m, 1 H), 2.59 (s, 3 H), 2.35 (s, 3 H), 1.71-1.65 (m, 1 H), 1.35-1.27 (m, 1 H), 0.92-0.83 (m, 1 H). | 560 | U |

TABLE I-continued
| | | | | |
|---|---|---|---|---|
| 2006 | 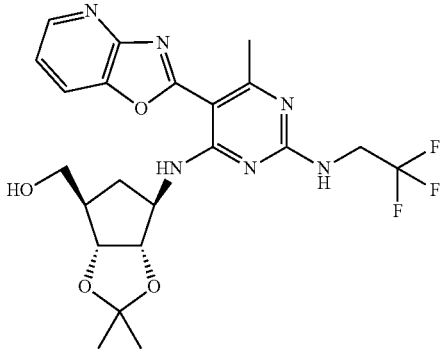 [SMILES: Cc1nc(NCC(F)(F)F)nc(N[C@@H]2C[C@H](CO)[C@H]3OC(C)(C)O[C@H]32)c1-c1nc2ncccc2o1] | B | ¹H NMR (400 MHz, D$_6$-dmso), δ, 9.23 (d, 1 H, J = 5.6 Hz), 8.45 (d, 1 H, J = 4.8 Hz), 8.13 (d, 1 H, J = 8.0 Hz), 8.07 (t, 1 H, J = 6.4 Hz), 7.38-7.35 (m, 1 H), 4.72 (t, 1 H, J = 5.2 Hz), 4.52-4.21 (m, 2 H), 4.35-4.12 (m, 3 H), 3.48 (t, 2 H, J = 5.6 Hz), 2.64 (s, 3 H), 2.40-2.33 (m, 1 H), 2.17-2.12 (m, 1 H), 1.65-1.57 (m, 1 H), 1.39 (s, 3H), 1.22 (b. 1 H), 1.20 (s, 3 H). | 495 Z |
| 2007 | 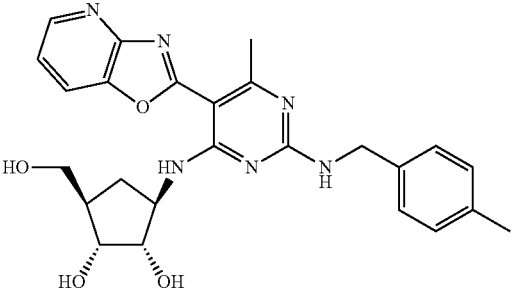 [SMILES: Cc1ccc(CNc2nc(C)c(-c3nc4ncccc4o3)c(N[C@@H]3C[C@H](CO)[C@@H](O)[C@H]3O)n2)cc1] | A | | 477 Z |
| 2008 | 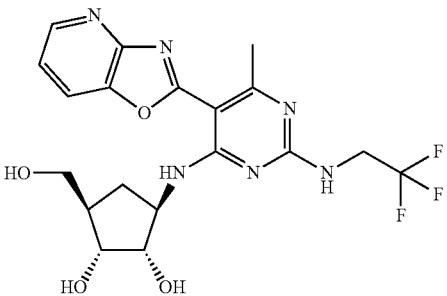 [SMILES: Cc1nc(NCC(F)(F)F)nc(N[C@@H]2C[C@H](CO)[C@@H](O)[C@H]2O)c1-c1nc2ncccc2o1] | B | | 455 Z |
| 2009 | 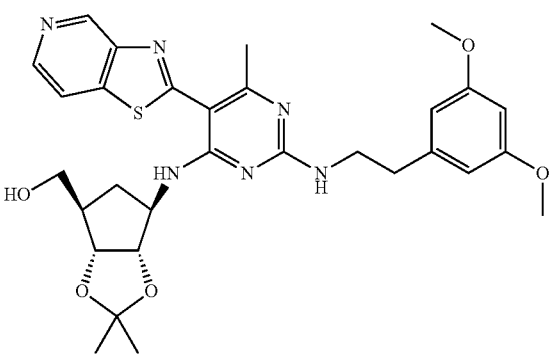 [SMILES: COc1cc(CCNc2nc(C)c(-c3nc4cnccc4s3)c(N[C@@H]3C[C@H](CO)[C@H]4OC(C)(C)O[C@H]43)n2)cc(OC)c1] | A | | 593 Z |

TABLE I-continued

| | | | | | |
|---|---|---|---|---|---|
| 2010 | [structure] | A | | 553 | Z |
| 2011 | [structure] | C | | 589 | Z |
| 2012 | [structure] | A | | 549 | Z |
| 2013 | [structure] | B | ¹H NMR (400 MHz, CD₃OD), δ, 8.15 (d, 1 H, J = 8.0 Hz), 8.10 (d, 1 H, J = 8.0 Hz), 7.62 (d, 1 H, J = 7.6 Hz), 7.55 (t, 1 H, J = 7.6 Hz), 4.52-4.47 (m, 2 H), 3.94 (t, 1 H, J = 5.2 Hz), 3.89 (t, 1 H, J = 4.8 Hz), 3.57 (d, 2H, J = 4.8 Hz), 2.61 (s, 3 H), 2.45-2.37 (m, 1 H), 2.19-2.11 (m, 1 H), 1.43-1.27 (m, 2 H), 0.89-0.66 (m, 3 H), 0.55-0.49 (m, 1 H). | 510 | U |

Assays

Cell-Based HCV Replicon Assay

To measure cell-based anti-HCV activity of the compounds of the present invention, replicon cells were seeded at 5000 cells/well in 96-well collagen I-coated Nunc plates in the presence of the compound of the invention. Various concentrations of a compound of the invention, typically in 10 serial 2-fold dilutions, were added to the assay mixture, the starting concentration of the compound ranging from 25 µM to 1 µM. The final concentration of DMSO was 0.5%, fetal bovine serum was 10%, in the assay media. Cells were harvested on day 3 by the addition of 1× cell lysis buffer (Ambion cat #8721). The replicon RNA level was measured using real time PCR (Taqman assay). The amplicon was located in 5B. The PCR primers were: 5B.2F, ATGGACAGGCGCCCTGA (SEQ. ID NO. 1); 5B.2R, TTGATGGGCAGCTTGGTTTC (SEQ. ID NO. 2); the probe sequence was FAM-labeled CACGCCATGCGCTGCGG (SEQ. ID NO. 3). GAPDH RNA was used as endogenous control and was amplified in the same reaction as NS5B (multiplex PCR) using primers and VIC-labeled probe recommended by the manufacturer (PE Applied Biosystem). The real-time RT-PCR reactions were run on ABI PRISM 7900HT Sequence Detection System using the following program: 48'C for 30 min, 95° C. for 10 min, 40 cycles of 95° C. for 15 sec, 60° C. for 1 min. The ΔCT values ($CT_{5B}$-$CT_{GAPDH}$) were plotted against the concentration of test compound and fitted to the sigmoid dose-response model using GraphPad PRISM software. $EC_{50}$ was defined as the concentration of inhibitor necessary to achieve ΔCT=1 over the projected baseline; $EC_{90}$ the concentration necessary to achieve ΔCT=3.2 over the baseline. Alternatively, to quantitate the absolute amount of replicon RNA, a standard curve was established by including serially diluted T7 transcripts of replicon RNA in the Taqman assay. All Taqman reagents were from PE Applied Biosystems. Such an assay procedure was described in detail in e.g. Malcolm et al., *Antimicrobial Agents and Chemotherapy* 50: 1013-1020 (2006).

HCV Replicon assay data for compounds of the invention that were tested was obtained using the above method. Calculated $EC_{90}$ values are reported for each compound in Table I as a falling within the following ranges:

"A"—less than or equal to about 0.5 μM

"B"—greater than about 0.5 μM to less than or equal to about 5.0 μM

"C"—greater than about 5.0 μM

Methods of Use

The compounds of the invention are useful in human and veterinary medicine for treating or preventing a viral infection or a virus-related disorder in a patient. In accordance with the invention, the compounds of the invention can be administered to a patient in need of treatment or prevention of a viral infection or a virus-related disorder.

Accordingly, in one embodiment, the invention provides methods for treating a viral infection in a patient comprising administering to the patient an effective amount of at least one compounds of the invention or a pharmaceutically acceptable salt, ester, prodrug, isomer, tautomer, or solvate thereof. In another embodiment, the invention provides methods for treating a virus-related disorder in a patient comprising administering to the patient an effective amount of at least one compounds of the invention or a pharmaceutically acceptable salt, ester, prodrug, isomer, tautomer, or solvate thereof.

Treatment or Prevention of a Viral Infection

The compounds of the invention can be used to treat or prevent a viral infection. In one embodiment, the compounds of the invention can be used to inhibit viral replication. In a specific embodiment, the compounds of the invention can be inhibitors of HCV replication. Accordingly, the compounds of the invention are useful for treating viral diseases and disorders related to the activity of a virus, such as HCV polymerase.

Such uses as are described herein may be performed in a patient in need thereof, although in vitro and ex vivo uses, such as in diagnostic and research contexts, are also contemplated. References made herein to the use of compounds of the invention also refers to uses of compositions comprising compounds of the invention.

Examples of viral infections that can be treated or prevented using the present methods, include but are not limited to, hepatitis A infection, hepatitis B infection and hepatitis C infection.

In one embodiment, the viral infection is hepatitis C infection.

In one embodiment, the hepatitis C infection is acute hepatitis C. In another embodiment, the hepatitis C infection is chronic hepatitis C.

The compositions and combinations of the present invention can be useful for treating a patient suffering from infection related to any HCV genotype. HCV types and subtypes may differ in their antigenicity, level of viremia, severity of disease produced, and response to interferon therapy as described in Holland et al., *J Pathology*, 30(2):192-195 (1998). The nomenclature set forth in Simmonds et al., *J Gen Virol*, 74(Pt11):2391-2399 (1993) is widely used and classifies isolates into six major genotypes, 1 through 6, with two or more related subtypes, e.g., 1a, 1b. Additional genotypes 7-10 and 11 have been proposed, however the phylogenetic basis on which this classification is based has been questioned, and thus types 7, 8, 9 and 11 isolates have been reassigned as type 6, and type 10 isolates as type 3 (see Lamballerie et al, *J Gen Virol*, 78(Pt1):45-51 (1997)). The major genotypes have been defined as having sequence similarities of between 55 and 72% (mean 64.5%), and subtypes within types as having 75%-86% similarity (mean 80%) when sequenced in the NS-5 region (see Simmonds et al., *J Gen Virol*, 75(Pt 5):1053-1061 (1994)).

Treatment or Prevention of a Virus-Related Disorder

The compounds of the invention can be used to treat or prevent a virus-related disorder. Accordingly, the compounds of the invention are useful for treating disorders related to the activity of a virus, such as liver inflammation or cirrhosis. Virus-related disorders include, but are not limited to, RNA-dependent polymerase-related disorders and disorders related to HCV infection.

Treatment or Prevention of a RNA-Dependent Polymerase-Related Disorder

The compounds of the invention are useful for treating or preventing a RNA dependent polymerase (RdRp) related disorder in a patient. Such disorders include viral infections wherein the infective virus contain a RdRp enzyme.

Accordingly, in one embodiment, the present invention provides a method for treating a RNA dependent polymerase-related disorder in a patient, comprising administering to the patient an effective amount of at least one compounds of the invention or a pharmaceutically acceptable salt, solvate, ester or prodrug thereof.

Treatment or Prevention of a Disorder Related to HCV Infection

The compounds of the invention can also be useful for treating or preventing a disorder related to an HCV infection. Examples of such disorders include, but are not limited to, cirrhosis, portal hypertension, ascites, bone pain, varies, jaundice, hepatic encephalopathy, thyroiditis, porphyria cutanea tarda, cryoglobulinemia, glomerulonephritis, sicca syndrome, thrombocytopenia, lichen planus and diabetes mellitus.

Accordingly, in one embodiment, the invention provides methods for treating an HCV-related disorder in a patient, wherein the method comprises administering to the patient a therapeutically effective amount of at least one compound of the invention, or a pharmaceutically acceptable salt, solvate, ester or prodrug thereof.

Combination Therapy

In another embodiment, the present methods for treating or preventing a viral infection can further comprise the administration of one or more additional therapeutic agents. In one embodiment, such one or more additional therapeutic agent may be one or more additional compounds of the invention. In another embodiment, such one or more additional therapeutic agent is an agent other than a compound of the invention.

In one embodiment, the additional therapeutic agent is an antiviral agent. Non-limiting examples of antiviral agents are as described herein and include, e.g., interferon.

In another embodiment, the additional therapeutic agent is an immunomodulatory agent, such as an immunosuppressive agent.

Accordingly, in one embodiment, the present invention provides methods for treating a viral infection in a patient, the method comprising administering to the patient: (i) at least one compound of the invention, or a pharmaceutically acceptable salt, solvate, ester or prodrug thereof, and (ii) at least one antiviral agent other than a compound of the invention, wherein the amounts administered are together effective to treat or prevent a viral infection.

When administering such a combination to a patient, the therapeutic agents in the combination, or a pharmaceutical composition or compositions comprising the therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a compound of the invention and an additional therapeutic agent may be present in fixed amounts (dosage amounts) in a single dosage unit (e.g., a capsule, a tablet and the like). (A commercial example of such single dosage unit containing fixed amounts of two different active compounds is VYTORIN® (available from Merck Schering-Plough Pharmaceuticals, Kenilworth, N.J.)).

In one embodiment, the at least one compound of the invention is administered at time when the additional antiviral agent(s) exert their prophylactic or therapeutic effect, or vice versa.

In another embodiment, the at least one compound of the invention and the additional antiviral agent(s) are administered in doses commonly employed when such agents are used as monotherapy for treating a viral infection.

In another embodiment, the at least one compound of the invention and the additional antiviral agent(s) are administered in doses lower than the doses commonly employed when such agents are used as monotherapy for treating a viral infection.

In another embodiment, the at least one compound of the invention and the additional antiviral agent(s) act synergistically and are administered in doses lower than the doses commonly employed when such agents are used as monotherapy for treating a viral infection.

In one embodiment, the at least one compound of the invention and the additional antiviral agent(s) are present in the same composition. In one embodiment, this composition is suitable for oral administration. In another embodiment, this composition is suitable for intravenous administration.

Viral infections and virus-related disorders that can be treated or prevented using the combination therapy methods of the present invention include, but are not limited to, those listed above.

In one embodiment, the viral infection is HCV infection.

The at least one compound of the invention and the additional antiviral agent(s) can act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

In one embodiment, the administration of at least one compound of the invention and the additional antiviral agent(s) may inhibit the resistance of a viral infection to these agents.

Non-limiting examples of other therapeutic agents useful in the present compositions and methods include an an viral (e.g., HCV) polymerase inhibitor, a viral (e.g., HCV) protease inhibitor, an interferon, a viral replication inhibitor, an antisense agent, a therapeutic vaccine, a viral protease inhibitor, a virion production inhibitor, an immunosuppressive agent, an antiviral antibody, a CYP-450 inhibitor, an antiviral booster, and an antiviral sensitizer, and any agent useful for treating an RNA-dependent polymerase-related disorder.

In one embodiment, the at least one additional antiviral agent is a viral polymerase inhibitor.

In another embodiment, the at least one additional antiviral agent is an HCV polymerase inhibitor.

In one embodiment, the at least one additional antiviral agent is a viral protease inhibitor.

In another embodiment, the at least one additional antiviral agent is an HCV protease inhibitor.

In another embodiment, the at least one additional antiviral agent is an interferon.

In still another embodiment, the at least one additional antiviral agent is a viral replication inhibitor.

In another embodiment, the at least one additional antiviral agent is an antisense agent.

In another embodiment, the at least one additional antiviral agent is a therapeutic vaccine.

In a further embodiment, the at least one additional antiviral agent is an virion production inhibitor.

In another embodiment, the at least one additional antiviral agent is an antibody.

In another embodiment, the at least one additional antiviral agents comprise a protease inhibitor and a polymerase inhibitor.

In still another embodiment, the at least one additional antiviral agents comprise a protease inhibitor and an immunosuppressive agent.

In yet another embodiment, the at least one additional antiviral agents comprise a polymerase inhibitor and an immunosuppressive agent.

In a further embodiment, the at least one additional antiviral agents comprise a protease inhibitor, a polymerase inhibitor and an immunosuppressive agent.

In another embodiment the at least one additional agent is ribavirin, Levovirin, or Viramidine.

In other embodiments, pharmaceutical compositions according to the invention comprise at least one compound of the invention and a CYP-450 inhibitor. Non-limiting examples of suitable CYP-450 inhibitors include ritonavir.

In other embodiments, pharmaceutical compositions according to the invention comprise at least one compound of the invention and an interferon. Non-limiting examples of such interferon are as described herein and include alpha interferon, pegylated interferon and conjugates thereof. Additional non-limiting examples of interferon include PEG-intron™ brand pegylated interferon, Pegasys™ brand pegylated interferon, Infergen™ brand interferon, and Alferon™ brand pegylated interferon.

In other embodiments, pharmaceutical compositions according to the invention comprise at least one compound of the invention and an interferon. Further comprising ribavirin, Levovirin, or Viramidine.

In other embodiments, pharmaceutical compositions according to the invention comprise at least one compound of the invention and a protease inhibitor.

In other embodiments, pharmaceutical compositions according to the invention comprise at least one compound of the invention, a protease inhibitor, and an interferon.

In other embodiments, pharmaceutical compositions according to the invention comprise at least one compound of the invention, a protease inhibitor, an interferon, and ribavirin.

In other embodiments, pharmaceutical compositions according to the invention comprise at least one compound of the invention, a polymerase inhibitor, and an interferon.

In other embodiments, pharmaceutical compositions according to the invention comprise at least one compound of the invention, a polymerase inhibitor, an interferon, and ribavirin.

In other embodiments, pharmaceutical compositions according to the invention comprise at least one compound of the invention, a protease inhibitor, polymerase inhibitor, and an interferon.

In other embodiments, pharmaceutical compositions according to the invention comprise at least one compound of the invention, a protease inhibitor, a polymerase inhibitor, an interferon, and ribavirin.

HCV polymerase inhibitors useful in the present methods and compositions include, but are not limited to VP-19744 (Wyeth/ViroPharma), HCV-796 (Wyeth/ViroPharma), NM-283 (Idenix/Novartis), R-1626 (Roche), MK-0608 (Merck), A848837 (Abbott), GSK-71185 (Glaxo SmithKline), XTL-2125 (XTL Biopharmaceuticals), and those disclosed in Ni et al., *Current Opinion in Drug Discovery and Development*, 7(4):446 (2004); Tan et al., *Nature Reviews*, 1:867 (2002); and Beaulieu et al., *Current Opinion in Investigational Drugs*, 5:838 (2004).

Additional non-limiting examples of HCV polymerase inhibitors useful in the present methods and compositions include: MK00608, NM283, HCV796, R1626, A848837, GSK71185, R7128, VCH759, GS9190, VP19744, and XTL2125.

Additional non-limiting examples of HCV polymerase inhibitors and HCV protease inhibitors useful in the present methods and compositions include: ANA598 (Anadys Pharmaceuticals), ABT-333, (Abbott), VCH-916, (Virochem), MK7009, (Merck), PF-00868554, (Pfizer) VX-500, (Vertex) GS9190, (Gilead) GSK625433, (GlazoSmithKline) ITMN-191 (R-7227), (Intermune), R7128, (Pharmasset/Roche), VCH-759 (Virochem), R1626, (Roche), TMC435350, (Medivir/Tibotec), SCH 503034 (Boceprevir) (Schering), SCH900518(Schering), and VX 950 (telaprevir) (Vertex). Additional non-limiting examples of HCV polymerase inhibitors include MK-3281 (Merck), PSI-7851 (Pharmasset), IDX184 (Indenix), ANA598 (Anadys), ABT-333 (Abbott), VCH-916 (Vertex), PF-0086554 (Pfizer), R7128 (Pharmasset/Roche), GS 9190 (Gilead), and VCH-759 (Vertex).

Additional non-limiting examples of agents useful in the present methods and compositions include: SPC3649 (LNA-antimi®-122), microRNA, Santaris Pharma, CF102, (A3AR AGONISTS) (CAN-FITE), IMO-2125, TLR9 agonist, (Idera Pharmaceuticals), PYN17, Botanical, (Phynova), Bavituximab (formerly Tarvacin), Anti-Phospholipid Therapy, (Peregrine), A-831 and/or A-832 (each of which are listed as NS5A Inhibitors from ArrowTherapeutics Ltd.), BMS-790052 (NS5A inhibitors from BMS), NOV-205, Immunomodulator, (Novelos Therapeutics), CTS-1027, Anti-inflammatory, (Conatus), Oglufanide disodium, Immunomodulator, (Implicit Bioscience), Alinia (nitazoxanide), Thiazolides, (Romark Laboratories), SCV-07, Broad spectrum immune stimulator, (SciClone), MitoQ (mitoquinone), Inflammation/Fibrosis Inhibitor, (Antipodean Pharmaceuticals), DEB10-025, Cyclophilin inhibitor, (Debio Pharm Group), SCY-635, cyclophilin inhibitor (SCYNEXIS), PF-03491390 (Formerly IDN-6556), Pancaspase Inhibitor, (Pfizer Pharmaceuticals), Civacir, HCV Immune Globulin, NABI, MX-3253 (celgosivir), Glucosidase I Inhibitor, (MIGENIX), VGX-410C (Mifepristone), IRES Inhibitor, (VGX Pharmaceuticals), Viramidine (Taribavirin), Nucleoside Analogue, (Valeant Pharmaceuticals), and ZADAXIN® (thymalfasin or thymosin alpha 1), Immunomodulator, (SciClone/Sigma-Tau).

Additional non-limiting examples of agents useful in the present methods and compositions include: TLR agonists (e.g., ANA773, Anadys Pharmaceuticals), immunomodulators (e.g., CYT107, Cytheris; oglufanide disodium, Implicit Bioscience), microRNA (e.g., SPC3649 (LNA-antimiR™-122, Santaris Pharma), A3AR agonists (e.g., CF102, CAN-FITE), TLR9 agonists (e.g., Idera Pharmaceuticals), anti-phospholipid therapeutics (e.g., bavituximab (formerly Tarvacin), Peregrine), immunomodulators (e.g., NOV-205, Novelos Therapeutics), caspase inhibitors (e.g., GS-9450, Gilead), anti-inflammatories (e.g., CTS-1027, Conatus), thiazolides (e.g., alinia (nitazoxanide), Romark Laboratories), broad spectrim immune stimulators (e.g., SCV-07, SciClone), inflammation/fibrosis inhibitors (e.g., MitoQ (mitoquinone), Antipodean Pharmaceuticals, cyclophilin inhibitors (e.g., DEBIO-025, Debio Pharm Group), pancaspase inhibitors (e.g., PF-03491390 (formerly IDN-6556, Pfizer Pharmaceuticals), and nucleoside analogues (e.g., Viramidine (Taribavirin), Valeant Pharmaceuticals).

Interferons useful in the present methods and compositions include, but are not limited to, interferon alfa-2a, interferon alfa-2b, interferon alfacon-1 and PEG-interferon alpha conjugates. "PEG-interferon alpha conjugates" are interferon alpha molecules covalently attached to a PEG molecule. Illustrative PEG-interferon alpha conjugates include interferon alpha-2a (Roferon™, Hoffman La-Roche, Nutley, N.J.) in the form of pegylated interferon alpha-2a (e.g., as sold under the trade name Pegasys™), interferon alpha-2b (Intron™, from Schering-Plough Corporation) in the form of pegylated interferon alpha-2b (e.g., as sold under the trade name PEG-Intron™), interferon alpha-2c (Berofor Alpha™, Boehringer Ingelheim, Ingelheim, Germany), interferon alpha fusion polypeptides, or consensus interferon as defined by determination of a consensus sequence of naturally occurring interferon alphas (Infergen™, Amgen, Thousand Oaks, Calif.).

Additional examples of Interferons useful in the present methods and compositions include, but are not limited to: IL-29 (PEG-Interferon Lambda), Long acting Interferon, ZymoGenetics, Oral Interferon alpha, Oral Interferon, (Amarillo Biosciences), Belerofon (oral), Oral interferon, (Nautilus Biotech), BLX-883 (Locteron), Long Acting Interferon, (Biolex Therapeutics/OctoPlus), Omega Interferon, Interferon, (Intarcia Therapeutics), Albuferon, Long Acting Interferon (injections every two weeks), (Human Genome Sciences), Consensus interferon (Infergen), and Interferon, (Three Rivers Pharma).

Antiviral antibodies (antibody therapy agents) useful in the present methods and compositions include, but are not limited to, antibodies specific to IL-10 (such as those disclosed in US Patent Publication No. US2005/0101770, humanized 12G8, a humanized monoclonal antibody against human IL-10, plasmids containing the nucleic acids encoding the humanized 12G8 light and heavy chains were deposited with the American Type Culture Collection (ATCC) as deposit numbers PTA-5923 and PTA-5922, respectively), and the like). Viral protease inhibitors useful in the present methods and compositions include, but are not limited to, NS3 serine protease inhibitors (including, but are not limited to, those disclosed in U.S. Pat. Nos. 7,012,066, 6,914,122, 6,911,428, 6,846,802, 6,838,475, 6,800,434, 5,017,380, 4,933,443, 4,812,561 and 4,634,697; and U.S. Patent Publication Nos. US20020160962, US20050176648 and US20050249702), HCV protease inhibitors (e.g., SCH503034 (Schering-Plough), VX-950 (Vertex), GS-9132 (Gilead/Achillion), ITMN-191 (InterMune/Roche)), and HIV protease inhibitors (e.g., amprenavir, atazanavir, fosemprenavir, indinavir, lopinavir, ritonavir, nelfinavir, saquinavir, tipranavir and TMC114).

Viral replication inhibitors useful in the present methods and compositions include, but are not limited to, NS3 helicase inhibitors, NS5A inhibitors, ribavirin, viramidine, A-831 (Arrow Therapeutics); an antisense agent or a therapeutic vaccine.

In one embodiment, viral replication inhibitors useful in the present methods and compositions include, but are not limited to, NS3 helicase inhibitors or NS5A inhibitors.

Examples of protease inhibitors useful in the present methods include, but are not limited to, an HCV protease inhibitor and a NS-3 serine protease inhibitor.

Examples of NS-3 serine protease inhibitors include, but are not limited to, SCH 503034 (Boceprevir) (Schering), SCH900518 (Schering), Telaprevir (VX950), ITMN-191, TMC435350, GS9132, MK7009, and BILN2061.

Examples of HCV protease inhibitors useful in the present methods include, but are not limited to, those disclosed in Landro et al., *Biochemistry,* 36(31):9340-9348 (1997); Ingallinella et al., *Biochemistry,* 37(25):8906-8914 (1998); Llinas-Brunet et al., *Bioorg Med Chem Lett,* 8(13):1713-1718 (1998); Martin et al., *Biochemistry,* 37(33) 11459-11468 (1998); Dimasi et al., *J Viral,* 71(10):7461-7469 (1997); Martin et al., *Protein Eng,* 10(5):607-614 (1997); Elzouki et al., *J Hepat,* 27(1):42-48 (1997); *BioWorld Today,* 9(217):4 (Nov. 10, 1998); and International Publication Nos. WO 98/14181; WO 98/17679, WO 98/17679, WO 98/22496 and WO 99/07734. Additional non-limiting examples of protease inhibitors include ACH-1625 (Achillion), ABT-450 (Abbott/Enanta), B1201335 (Boehringer Ingelheim Pharma), VX-813 (Vertex), PHX1766 (Phenomix), VX-500 (Vertex), ITMN-191 (R-7227) (InterMune), MK7009 (Merck), B1207127 (Boerhinger Ingelheim), SCH 503034 (Boceprevir) (Schering), SCH900518 (Schering), TMC435 (Medivir/Tibotec), Telapravir (V)(950) and (Vertex), XTL-2125 (XTL Biopharmaceuticals).

Additional examples of other therapeutic agents useful in the present methods and compositions include vaccines. Non-limiting examples of antiviral vaccines include: ChronVac-C, DNA-based Therapeutic Vaccine, (Inovio/Tripep), TG4040, Therapeutic Vaccine, (Transgene), PeviPRO™, Therapeutic vaccine, (Pevion Biotect), HCV/MF59, Vaccine(s), (Chiron/Novartis), G1-5005, Therapeutic Vaccine, (Globe Immune), IC41, Therapeutic Vaccine, (Intercell), HCV/MF59 (Chiron/Novartis), GI-5005 (Globe Immune), and Civacir (NABI).

Additional examples of other therapeutic agents useful in the present methods and compositions include anti-cancer agents. Non-limiting examples of antiviral anti-cancer agents include: Z10-101, Anti-Liver Cancer (Arsenic), (Ziopharm Oncology), GV1001 (Heptovax), Anti-Liver Cancer, (Pha (mexa), PI-88, Anti-liver cancer, (Progen Industries), Nexavar (sorafenib), Anti-liver cancer, (Onyx Pharmaceuticals), and ThermoDox (doxorubicin), Anti-liver cancer, (Celsion). Additional non-limiting examples of viral anticancer agents include CF102 (Can-Fite BioPharma), ZIO-101 (Ziopharm Oncology), GV1001 (Heptovax) (Pharmexa), PI-88 (Progen Industries), ThermoDox (doxorubicin) (Celsion), and Nexavar (sorafenib) (Onyx Pharmaceuticals).

Additional examples of other therapeutic agents useful in the present compositions and methods include, but are not limited to, Levovirin™ (ICN Pharmaceuticals, Costa Mesa, Calif.), VP 50406™ (Viropharma, Incorporated, Exton, Pa.), ISIS14803™ (ISIS Pharmaceuticals, Carlsbad, Calif.), Heptazyme™ (Ribozyme Pharmaceuticals, Boulder, Colo.), VX-950™ (Vertex Pharmaceuticals, Cambridge, Mass.), Thymosin™ (SciClone Pharmaceuticals, San Mateo, Calif.), Maxamine™ (Maxim Pharmaceuticals, San Diego, Calif.), NKB-122 (JenKen Bioscience Inc., N.C.), mycophenolate mofetil (Hoffman-LaRoche, Nutley, N.J.).

Additional examples of other therapeutic agents useful in the present methods and compositions include adjunct therapeutics such as thrombopoeitin receptor antagonists (e.g., LGD-4665, Ligand Pharmaceuticals Inc., and eltromobopag (Promacta), GlaxoSmithKline).

Additional examples of other therapeutic agents useful in the present compositions and methods include, but are not limited to: HCV/MF59, Oral Interferon alpha, Viramidine, Infergen/,Consensus, JBK-122, Bavituximab (Tarvacin), Civacir, Albuferon, IL-29 (PEG-Interferon lambda), Omega Interferon, ZADAXIN® (thymalfasin or thymosin alpha 1), NOV-205, PF-03491390 (formerly IDN-6556), Nexavar, ITMN-191, IC41, VX 950 (telaprevir), R1656, MX-3253 (Celgosivir), SCH 503034 (Boceprevir) (Schering), SCH900518 (Schering), Belerofon (oral), VGX-410C, ThermoDox (doxorubicin), R7128, R1626, A-831, DEB10-025, PeviPRO™, GV1001, PYN17, PI-88, TG4040, BLX-883 (Locteron), ChronVac-R, MitoQ, GSK625433, SOV-07, IMO-2125, Alinia (nitazoxanide), LGD-4665, Z10-101, CF102 VCH-759, VCH-916, Oglufanide disodium, VX-500, TMC435350, PF-00868554, GGI-5005 (Tarmogen), SPC3649 (LNA-antimiR™-122), CTS-1027, ABT-333, Eltrombopag, and ANA598.

Additional examples of other therapeutic agents useful in the present compositions and methods include, but are not limited to adjunct therapeutics. Non-limiting examples include: LGD-4665, Thrombopoeitin Receptor Agonist, (Ligand Pharmaceuticals Inc.), and Eltrombopag (Promacta), Thrombopoeitin Receptor Agonist, (GlaxcoSmithKline).

The doses and dosage regimen of the other agents used in the combination therapies of the present invention for the treatment or prevention of a viral infection can be determined by the attending clinician, taking into consideration the approved doses and dosage regimen in the package insert; the age, sex and general health of the patient; and the type and severity of the viral infection or related disease or disorder. When administered in combination, the compound(s) of the invention and the other agent(s) for treating diseases or conditions listed above can be administered simultaneously (i.e., in the same composition or in separate compositions one right after the other) or sequentially. This is particularly useful when the components of the combination are given on different dosing schedules, e.g., one component is administered once daily and another every six hours, or when the preferred pharmaceutical compositions are different, e.g. one is a tablet and one is a capsule. A kit comprising the separate dosage forms is therefore advantageous.

Generally, a total daily dosage of the at least one compound of the invention and the additional antiviral agent(s), when administered as combination therapy, can range from about 0.1 to about 2000 mg per day, although variations will necessarily occur depending on the target of the therapy, the patient and the route of administration. In one embodiment, the dosage is from about 10 to about 500 mg/day, administered in a single dose or in 2-4 divided doses. In another embodiment, the dosage is from about 1 to about 200 mg/day, administered in a single dose or in 2-4 divided doses. In still another embodiment, the dosage is from about 1 to about 100 mg/day, administered in a single dose or in 2-4 divided doses. In yet another embodiment, the dosage is from about 1 to about 50 mg/day, administered in a single dose or in 2-4 divided doses. In a further embodiment, the dosage is from about 1 to about 20 mg/day, administered in a single dose or in 2-4 divided doses. In another embodiment, the dosage is from about 500 to about 1500 mg/day, administered in a single dose or in 2-4 divided doses. In still another embodiment, the dosage is from about 500 to about 1000 mg/day, administered in a single dose or in 2-4 divided doses. In yet another embodiment, the dosage is from about 100 to about 500 mg/day, administered in a single dose or in 2-4 divided doses.

In one embodiment, when the other therapeutic agent is INTRON-A interferon alpha 2b (commercially available from Schering-Plough Corp.), this agent is administered by subcutaneous injection at 3MIU (12 mcg)/0.5 mL/TIW is for 24 weeks or 48 weeks for first time treatment.

In another embodiment, when the other therapeutic agent is PEG-INTRON interferon alpha 2b pegylated (commercially available from Schering-Plough Corp.), this agent is administered by subcutaneous injection at 1.5 mcg/kg/week, within a range of 40 to 150 mcg/week, for at least 24 weeks.

In another embodiment, when the other therapeutic agent is ROFERON A inteferon alpha 2a (commercially available from Hoffmann-La Roche), this agent is administered by subcutaneous or intramuscular injection at 3MIU (11.1 mcg/mL)/TIW for at least 48 to 52 weeks, or alternatively 6MIU/TIW for 12 weeks followed by 3MIU/TIW for 36 weeks.

In another embodiment, when the other therapeutic agent is PEGASUS interferon alpha 2a pegylated (commercially available from Hoffmann-La Roche), this agent is administered by subcutaneous injection at 180 mcg/1 mL or 180 mcg/0.5 mL, once a week for at least 24 weeks.

In another embodiment, when the other therapeutic agent is INFERGEN interferon alphacon-1 (commercially available from Amgen), this agent is administered by subcutaneous injection at 9 mcg/TIW is 24 weeks for first time treatment and up to 15 mcg/TIW for 24 weeks for non-responsive or relapse treatment.

In another embodiment, when the other therapeutic agent is Ribavirin (commercially available as REBETOL ribavirin from Schering-Plough or COPEGUS ribavirin from Hoffmann-La Roche), this agent is administered at a daily dosage of from about 600 to about 1400 mg/day for at least 24 weeks.

Compositions and Administration

The compounds of the invention may be used as the neat chemical or as part of a composition, such as a pharmaceutical composition. For example, when administered to a patient, the compounds of the invention can be administered as a component of a composition that comprises a pharmaceutically acceptable carrier or vehicle. The present invention provides pharmaceutical compositions comprising an effective amount of at least one compound of the invention and a pharmaceutically acceptable carrier. In the pharmaceutical compositions and methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Additionally, the compositions of the present invention may be formulated in sustained release form to provide the rate controlled release of any one or more of the components or active ingredients to optimize the therapeutic effects, i.e. anti-inflammatory activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more compounds of the invention are in a form suitable for oral administration.

In another embodiment, the one or more compounds of the invention are in a form suitable for intravenous administration.

In another embodiment, the one or more compounds of the invention are in a form suitable for topical administration.

In another embodiment, the one or more compounds of the invention are in a form suitable for sublingual administration.

In one embodiment, a pharmaceutical preparation comprising at least one compound of the invention is formulated in a unit dosage form. In such form, the preparation is subdivided into unit doses containing appropriate quantities of the active component, e.g., an effective amount to achieve the desired purpose.

Compositions can be prepared according to conventional mixing, granulating or coating methods, respectively, and the present compositions can contain, in one embodiment, from about 0.1% to about 99% of the compound(s) of the invention by weight or volume. In various embodiments, the present compositions can contain, in one embodiment, from about 1% to about 70% or from about 5% to about 60% of the compound(s) of the invention by weight or volume.

The quantity of compound(s) of the invention in a unit dose of preparation may be varied or adjusted from about 0.1 mg to about 2000 mg. In various embodiment, the quantity is from about 1 mg to about 2000 mg, 100 mg to about 200 mg, 500 mg to about 2000 mg, 100 mg to about 1000 mg, and 1 mg to about 500 mg.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The amount and frequency of administration of the compound(s) of the invention will be determined according to the judgment of the attending clinician considering such factors as age, condition and size of the patient as well as severity of the symptoms being treated. Generally, a total daily dosage of the compound(s) of the invention range from about 0.1 to about 2000 mg per day, although variations will necessarily occur depending on the target of the therapy, the patient and the route of administration. In one embodiment, the dosage is from about 1 to about 200 mg/day, administered in a single dose or in 2-4 divided doses. In another embodiment, the dosage is from about 10 to about 2000 mg/day, administered in a single dose or in 2-4 divided doses. In another embodiment, the dosage is from about 100 to about 2000 mg/day, administered in a single dose or in 2-4 divided doses. In still another embodiment, the dosage is from about 500 to about 2000 mg/day, administered in a single dose or in 2-4 divided doses.

The compositions of the invention can further comprise one or more additional therapeutic agents, selected from those described above. Accordingly, in one embodiment, the present invention provides compositions comprising: (i) at least one compound of the invention or a pharmaceutically acceptable salt, solvate, ester or prodrug thereof; (ii) one or more additional therapeutic agents that are not a compound of the invention; and (iii) a pharmaceutically acceptable carrier, wherein the amounts in the composition are together effective to treat a viral infection or a virus-related disorder.

Kits

In another embodiment, the present invention provides a kit comprising a therapeutically effective amount of at least one compound of the invention, or a pharmaceutically acceptable salt, solvate, ester, isomer, tautomer, or prodrug of said compound and a pharmaceutically acceptable carrier, vehicle or diluent.

In another aspect the present invention provides a kit comprising an amount of at least one compound of the invention, or a pharmaceutically acceptable salt, solvate, ester, isomer, tautomer, or prodrug of said compound and an amount of at least one additional therapeutic agent listed above, wherein the amounts of the two or more ingredients result in a desired therapeutic effect.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparant to those skilled in the art and are intended to fall within the scope of the appended claims.

A number of references have been cited herein. The entire disclosures of such references are incorporated herein by reference.

Therefore, we claim:

1. A compound having the general structure shown in Formula (I.a.10.j):

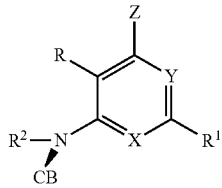

(I.a.10.j)

or a pharmaceutically acceptable salt thereof, wherein:

CB is a moiety selected from the group consisting of:

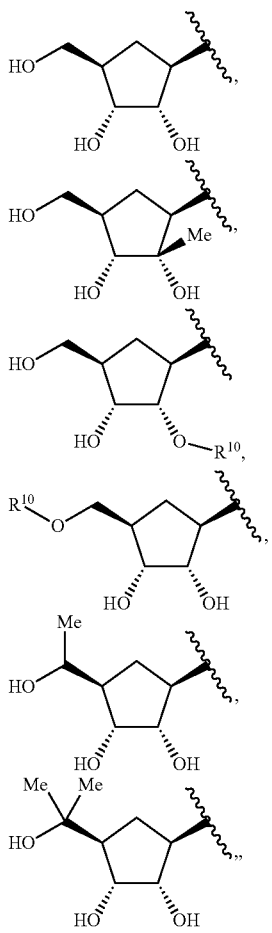

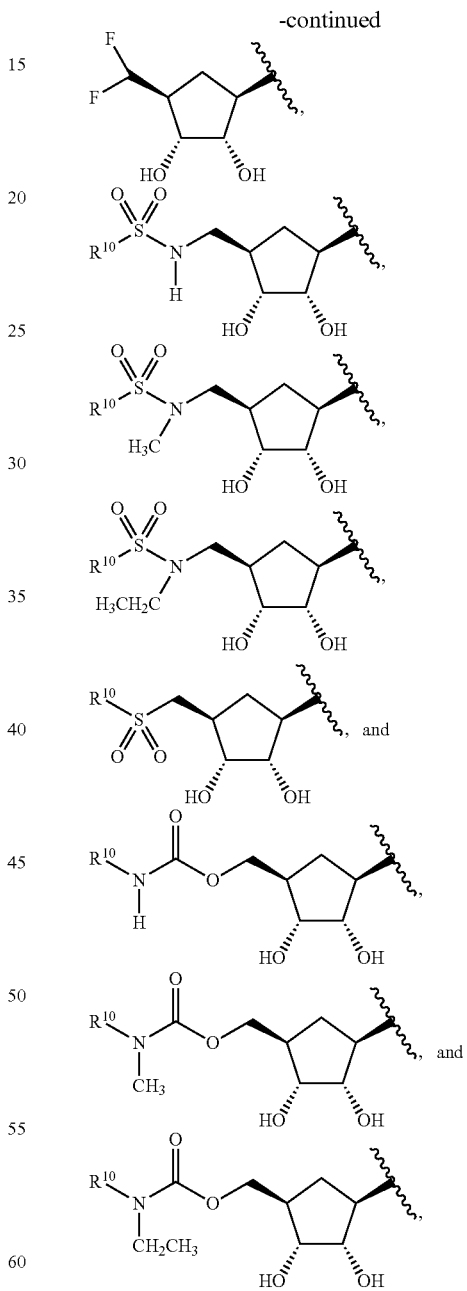

each $R^{10}$ is independently selected from the group consisting of methyl, ethyl, and cyclopropyl;
X is N;
Y is N;
$R^2$ is H;

Z is selected from the group consisting of H, methyl, and chloro;

R is a moiety selected from the group consisting of:

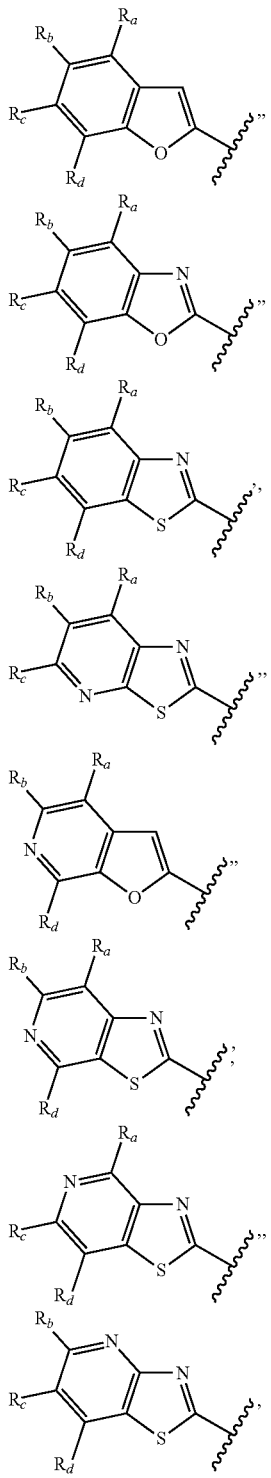

wherein the wavy line represents the point of attachment of R to the rest of the molecule, and wherein each of $R_a$, $R_b$, $R_c$, and $R_d$ is independently selected from H, halo, —OH, —CN, alkyl, cycloalkyl, haloalkyl, -alkyl-OH, heteroalkyl, heterohaloalkyl, —O-alkyl, —O-haloalkyl, —O-alkyl-OH, aryl, —O-aryl, —S-aryl, —O-alkyl-aryl, —S-alkyl-aryl, heteroaryl, —O-heteroaryl, —S-heteroaryl, —O-alkyl-heteroaryl, —S-alkyl-heteroaryl, heterocycloalkyl, —C(O)-alkyl, —C(O)-haloalkyl, —C(O)H, —C(O)OH, —C(O)O-alkyl, —OC(O)-alkyl, —C(O)NH$_2$, —C(O)NHR$^{10}$, —C(O)NR$^{10}$R$^{11}$, —C(O)ONH$_2$, —C(O)ONHR$^{10}$, —C(O)ONR$^{10}$R$^{11}$, —NH$_2$, —NHR$^{10}$, —NR$^{10}$R$^{11}$, —NO$_2$, substituted aryl, and substituted heteroaryl, wherein each of said substituted aryl and said substituted heteroaryl independently contains from one to three substituents, which may be the same or different, each substituent being independently selected from halo, alkyl, —O-alkyl, and —C(O)Oalkyl;

R$^1$ is selected from H, halo, alkyl, haloalkyl, heteroalkyl, heterohaloalkyl, heteroaryl, —OH, —O-alkyl, —O-aryl, —O-heteroalkyl, —O-heteroaryl, —SH, —S-alkyl, —S-aryl, —S-heteroalkyl, —S-heteroaryl, —NH$_2$, —NHR$^{14}$, —NR$^{14}$R$^{15}$, —NO$_2$, —S(O)NHR$^{10}$, —S(O)NR$^{10}$R$^{11}$, —S(O)R$^{10}$, —S(O)$_2$NHR$^{10}$, —S(O)$_2$NR$^{10}$R$^{11}$, and —S(O)$_2$R$^{10}$;

each R$^{11}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;

each R$^{14}$ is independently selected from alkyl, alkoxy, alkenyl, haloalkyl, heteroalkyl, heterohaloalkyl, alkylamino, alkylthio, heteroalkenyl, haloalkenyl, —S(O)$_2$-alkyl, -alkyl-OH, -alkyl-O-Acyl, —C(O)Oalkyl, —C(O)alkyl, cycloalkyl, cycloalkyl-alkyl-, heterocycloalkyl, heterocycloalkyl-alkyl-, heterocycloalkenyl, heterocycloalkenyl-alkyl-, aryl, arylalkyl-, heteroaryl, and heteroaryl-alkyl-, wherein each said alkyl, each said alkoxy, each said alkenyl, each said haloalkyl, each said heteroalkyl, each said heterohaloalkyl, each said alkylamino, each said alkylthio, each said heteroalkenyl, each said haloalkenyl, each said —S(O)$_2$-alkyl, each said -alkyl-OH, each said -alkyl-O-Acyl, each said —C(O)Oalkyl, each said —C(O)alkyl, each said cycloalkyl, each said cycloalkyl-alkyl-, each said heterocycloalkyl, each said heterocycloalkyl-alkyl-, each said heterocycloalkenyl, each said heterocycloalkenyl-alkyl-, each said aryl, each said arylalkyl-, each said heteroaryl, and each said heteroarylalkyl-, is unsubstituted or optionally independently substituted with from one to five substituent, which can be the same or different, each substitutent being independently selected from —OH, halo, —NH$_2$, —NHR$^{10}$, —NR$^{10}$R$^{11}$, —C(O)OH, C(O)OH, —C(O)OR$^{10}$, —C(O)NH$_2$, —C(O)NHR$^{10}$, —C(O)NR$^{10}$R$^{11}$, —S(O)$_2$alkyl, —S(O)$_2$aryl, alkyl, alkoxy, haloalkyl, haloalkoxy, heteroaryl, heteroalkyl, heterohaloalkyl, aryl, cycloalkyl, and heterocycloalkyl;

each R$^{15}$ is independently selected from alkyl, alkoxy, alkenyl, haloalkyl, heteroalkyl, heterohaloalkyl, alkylamino, alkylthio, heteroalkenyl, haloalkenyl, —S(O)$_2$-alkyl, -alkyl-OH, -alkyl-O-Acyl, —C(O)Oalkyl, —C(O)alkyl, cycloalkyl, cycloalkyl-alkyl-, heterocycloalkyl, heterocycloalkyl-alkyl-, heterocycloalkenyl, heterocycloalkenyl-alkyl-, aryl, arylalkyl-, heteroaryl, and heteroaryl-alkyl-, wherein each said alkyl, each said alkoxy, each said alkenyl, each said haloalkyl, each said heteroalkyl, each said heterohaloalkyl, each said alkylamino, each said alkylthio, each said heteroalkenyl, each said haloalkenyl, each said —S(O)₂-alkyl, each said -alkyl-OH, each said -alkyl-O-Acyl, each said —C(O)Oalkyl, each said —C(O)alkyl, each said cycloalkyl, each said cycloalkyl-alkyl-, each said heterocycloalkyl, each said heterocycloalkyl-alkyl-, each said heterocycloalkenyl, each said heterocycloalkenyl-alkyl-, each said aryl, each said aryl-alkyl-, each said heteroaryl, and each said heteroaryl-alkyl-, is unsubstituted or optionally independently substituted with from one to five substituent, which can be the same or different, each substitutent being independently selected from —OH, halo, —NH₂, —NHR¹⁰, —NR¹⁰R¹¹, —C(O)OH, C(O)OH, —C(O)OR¹⁰, —C(O)NH₂, —C(O)NHR¹⁰, —C(O)NR¹⁰R¹¹, —S(O)₂alkyl, —S(O)₂aryl, alkyl, alkoxy, haloalkyl, haloalkoxy, heteroaryl, heteroalkyl, heterohaloalkyl, aryl, cycloalkyl, and heterocycloalkyl;

or, alternatively, R¹⁴ and R¹⁵ are linked together with the nitrogen to which they are attached to form an unsubstituted or substituted 4- to 6-membered heterocycloalkyl.

2. A according to claim 1, or a pharmaceutically acceptable salt thereof, wherein:

R¹ is selected from the group consisting of —NH₂, —NHR¹⁴, and —NR¹⁴R¹⁵.

3. A compound having the general structure shown in Formula (I.D):

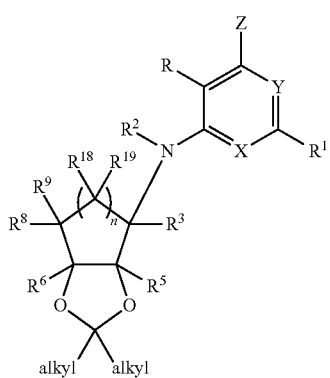

(I.D)

or a pharmaceutically acceptable salt thereof, wherein

X is N;
Y is N;
n is 1;
R², R³, R⁵, R⁶, R⁸, R¹⁸ and R¹⁹ are H;
R⁹ is methyl, wherein said methyl is unsubstituted or substituted with from one to three groups independently selected from —OH, halo, alkyl, —CN, —NH₂, —NHR¹⁶, —NR¹⁶R¹⁷, —NHS(O)₂R¹⁰, —N(R¹⁰)S(O)₂R¹⁰, —Oalkyl, —Ocycloalkyl, —O-alkyl-cycloalkyl, —OC(O)-alkyl, —O(C)O—NHR¹⁰, —O(C)O—N(R¹⁰)R¹¹, —C(O)O-alkyl, —S(O)₂R¹⁰, —SR¹⁰, —S(O)₂NHR¹⁰ and —S(O)₂NR¹⁰R¹¹;

Z is selected from the group consisting of H, methyl, and chloro;

R is a moiety selected from the group consisting of:

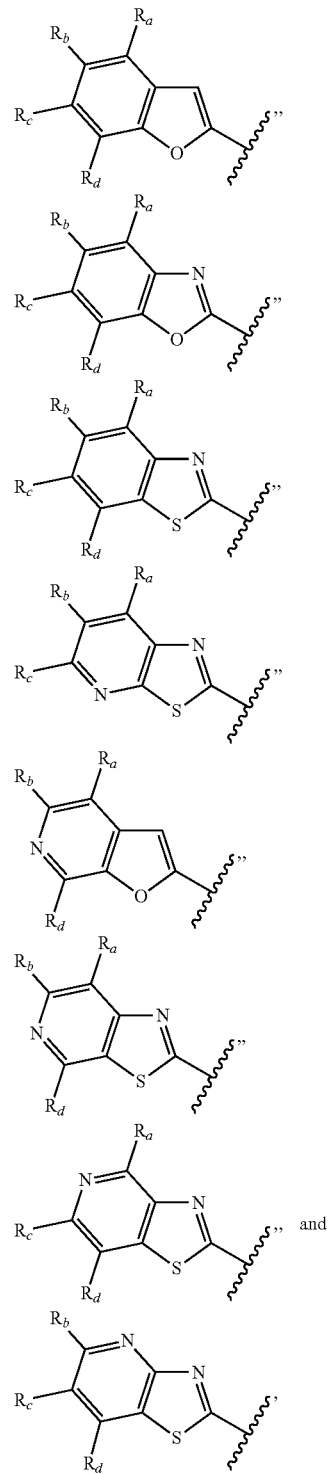

wherein the wavy line represents the point of attachment of R to the rest of the molecule, and wherein each of Rₐ, R_b, R_c, and R_d is independently selected from H, halo, —OH, —CN, alkyl, cycloalkyl, haloalkyl, -alkyl-OH, heteroalkyl, heterohaloalkyl, —O-alkyl, —O-haloalkyl, —O-alkyl-OH, aryl, —O-aryl, —S-aryl, —O-alkyl-aryl, —S-alkyl-aryl, heteroaryl, —O-heteroaryl, —S- heteroaryl, —O-alkyl-heteroaryl, —S-alkyl-heteroaryl, heterocycloalkyl, —C(O)-alkyl, —C(O)-haloalkyl, —C(O)H, —C(O)OH, —C(O)O-alkyl, —OC(O)-alkyl, —C(O)NH$_2$, —C(O)NHR$^{10}$, —C(O)NR$^{10}$R$^{11}$, —C(O)ONH$_2$, —C(O)ONHR$^{10}$, —C(O)ONR$^{10}$R$^{11}$, —NH$_2$, —NHR$^{10}$, —NR$^{10}$R$^{11}$, —NO$_2$, substituted aryl, and substituted heteroaryl, wherein each of said substituted aryl and said substituted heteroaryl independently contains from one to three substituents, which may be the same or different, each substituent being independently selected from halo, alkyl, —O-alkyl, and —C(O)Oalkyl;

R$^1$ is selected from H, halo, alkyl, haloalkyl, heteroalkyl, heterohaloalkyl, heteroaryl, —OH, —O-alkyl, —O-aryl, —O-heteroalkyl, —O-heteroaryl, —SH, —S-alkyl, —S-aryl, —S-heteroalkyl, —S-heteroaryl, —NH$_2$, —NHR$^{14}$, —NR$^{14}$R$^{15}$, —NO$_2$, —S(O)NHR$^{10}$, —S(O)NR$^{10}$R$^{11}$, —S(O)R$^{10}$, —S(O)$_2$NHR$^{10}$, —S(O)$_2$NR$^{10}$R$^{11}$, and —S(O)$_2$R$^{10}$;

each R$^{10}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;

each R$^{11}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;

each R$^{14}$ is independently selected from alkyl, alkoxy, alkenyl, haloalkyl, heteroalkyl, heterohaloalkyl, alkylamino, alkylthio, heteroalkenyl, haloalkenyl, —S(O)$_2$-alkyl, -alkyl-OH, -alkyl-O-Acyl, —C(O)Oalkyl, —C(O)alkyl, cycloalkyl, cycloalkyl-alkyl-, heterocycloalkyl, heterocycloalkyl-alkyl-, heterocycloalkenyl, heterocycloalkenyl-alkyl-, aryl, arylalkyl-, heteroaryl, and heteroaryl-alkyl-, wherein each said alkyl, each said alkoxy, each said alkenyl, each said haloalkyl, each said heteroalkyl, each said heterohaloalkyl, each said alkylamino, each said alkylthio, each said heteroalkenyl, each said haloalkenyl, each said —S(O)$_2$-alkyl, each said -alkyl-OH, each said -alkyl-O-Acyl, each said —C(O)Oalkyl, each said —C(O)alkyl, each said cycloalkyl, each said cycloalkyl-alkyl-, each said heterocycloalkyl, each said heterocycloalkyl-alkyl-, each said heterocycloalkenyl, each said heterocycloalkenyl-alkyl-, each said aryl, each said arylalkyl-, each said heteroaryl, and each said heteroaryl-alkyl-, is unsubstituted or optionally independently substituted with from one to five substituent, which can be the same or different, each substitutent being independently selected from —OH, halo, —NH$_2$, —NHR$^{10}$, —NR$^{10}$R$^{11}$, —C(O)OH, —C(O)OR$^{10}$, —C(O)NH$_2$, —C(O)NHR$^{10}$, —C(O)NR$^{10}$R$^{11}$, —S(O)$_2$alkyl, —S(O)$_2$aryl, alkyl, alkoxy, haloalkyl, haloalkoxy, heteroaryl, heteroalkyl, heterohaloalkyl, aryl, cycloalkyl, and heterocycloalkyl;

each R$^{15}$ is independently selected from alkyl, alkoxy, alkenyl, haloalkyl, heteroalkyl, heterohaloalkyl, alkylamino, alkylthio, heteroalkenyl, haloalkenyl, —S(O)$_2$-alkyl, -alkyl-OH, -alkyl-O-Acyl, —C(O)Oalkyl, —C(O)alkyl, cycloalkyl, cycloalkyl-alkyl-, heterocycloalkyl, heterocycloalkyl-alkyl-, heterocycloalkenyl, heterocycloalkenyl-alkyl-, aryl, arylalkyl-, heteroaryl, and heteroaryl-alkyl-, wherein each said alkyl, each said alkoxy, each said alkenyl, each said haloalkyl, each said heteroalkyl, each said heterohaloalkyl, each said alkylamino, each said alkylthio, each said heteroalkenyl, each said haloalkenyl, each said —S(O)$_2$-alkyl, each said -alkyl-OH, each said -alkyl-O-Acyl, each said —C(O)Oalkyl, each said —C(O)alkyl, each said cycloalkyl, each said cycloalkyl-alkyl-, each said heterocycloalkyl, each said heterocycloalkyl-alkyl-, each said heterocycloalkenyl, each said heterocycloalkenyl-alkyl-, each said aryl, each said arylalkyl-, each said heteroaryl, and each said heteroaryl-alkyl-, is unsubstituted or optionally independently substituted with from one to five substituent, which can be the same or different, each substitutent being independently selected from —OH, halo, —NH$_2$, —NHR$^{10}$, —NR$^{10}$R$^{11}$, —C(O)OH, —C(O)OR$^{10}$, —C(O)NH$_2$, —C(O)NHR$^{10}$, —C(O)NR$^{10}$R$^{11}$, —S(O)$_2$alkyl, —S(O)$_2$aryl, alkyl, alkoxy, haloalkyl, haloalkoxy, heteroaryl, heteroalkyl, heterohaloalkyl, aryl, cycloalkyl, and heterocycloalkyl;

or, alternatively, R$^{14}$ and R$^{15}$ are linked together with the nitrogen to which they are attached to form an unsubstituted or substituted 4- to 6-membered heterocycloalkyl.

4. A compound having the general structure shown in Formula (I.E):

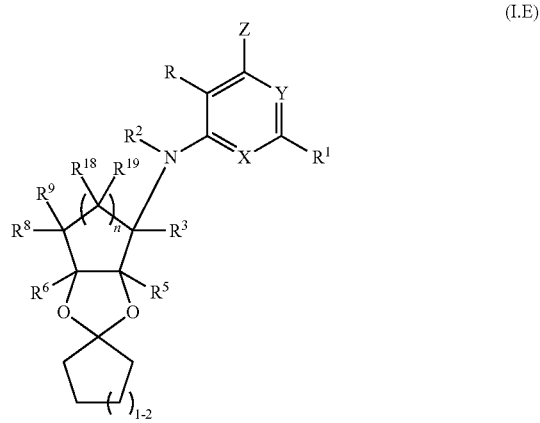

(I.E)

or a pharmaceutically acceptable salt thereof, wherein

X is N;

Y is N;

n is 1;

R$^2$, R$^3$, R$^5$, R$^6$, R$^8$, R$^{18}$ and R$^{19}$ are H;

R$^9$ is methyl, wherein said methyl is unsubstituted or substituted with from one to three groups independently selected from —OH, halo, alkyl, —CN, —NH$_2$, —NHR$^{16}$, —NR$^{16}$R$^{17}$, —NHS(O)$_2$R$^{10}$, —N(R$^{10}$)S(O)$_2$R$^{10}$, —Oalkyl, —Ocycloalkyl, —O-alkyl-cycloalkyl, —OC(O)-alkyl, —O(C)O—NHR$^{10}$, —O(C)O—N(R$^{10}$)R$^{11}$, —C(O)O-alkyl, —S(O)$_2$R$^{10}$, —SR$^{10}$, —S(O)$_2$NHR$^{10}$, and —S(O)$_2$NR$^{10}$R$^{11}$;

Z is selected from the group consisting of H, methyl, and chloro;

R is a moiety selected from the group consisting of:

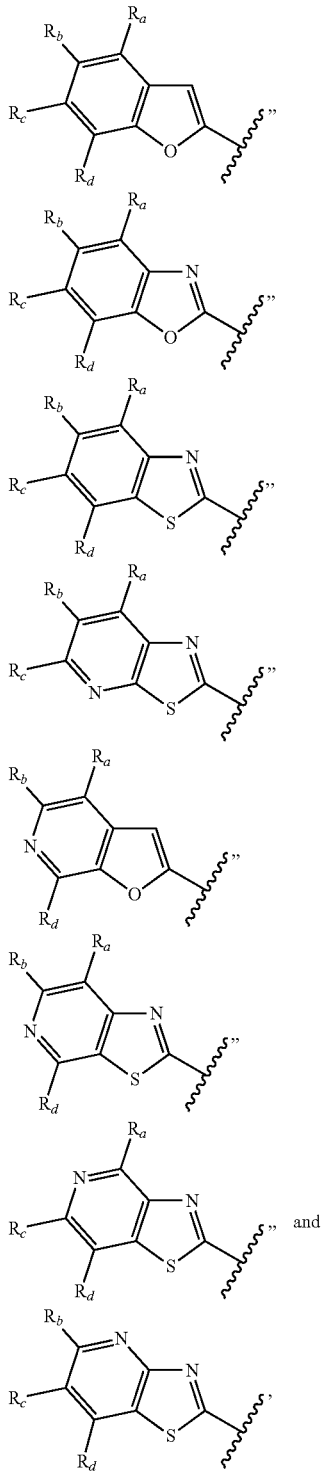

wherein the wavy line represents the point of attachment of R to the rest of the molecule, and wherein each of $R_a$, $R_b$, $R_c$, and $R_d$ is independently selected from H, halo, —OH, —CN, alkyl, cycloalkyl, haloalkyl, -alkyl-OH, heteroalkyl, heterohaloalkyl, —O-alkyl, —O-haloalkyl, —O-alkyl-OH, aryl, —O-aryl, —S-aryl, —O-alkyl-aryl, —S-alkyl-aryl, heteroaryl, —O-heteroaryl, —S-heteroaryl, —O-alkyl-heteroaryl, —S-alkyl-heteroaryl, heterocycloalkyl, —C(O)-alkyl, —C(O)-haloalkyl, —C(O)H, —C(O)OH, —C(O)O-alkyl, —OC(O)-alkyl, —C(O)NH$_2$, —C(O)NHR$^{10}$, —C(O)NR$^{10}$R$^{11}$, —C(O)ONH$_2$, —C(O)ONHR$^{10}$, —C(O)ONR$^{10}$R$^{11}$, —NH$_2$, —NHR$^{10}$, —NR$^{10}$R$^{11}$, —NO$_2$, substituted aryl, and substituted heteroaryl, wherein each of said substituted aryl and said substituted heteroaryl independently contains from one to three substituents, which may be the same or different, each substituent being independently selected from halo, alkyl, —O-alkyl, and —C(O)Oalkyl;

R$^1$ is selected from H, halo, alkyl, haloalkyl, heteroalkyl, heterohaloalkyl, heteroaryl, —OH, —O-alkyl, —O-aryl, —O-heteroalkyl, —O-heteroaryl, —SH, —S-alkyl, —S-aryl, —S-heteroalkyl, —S-heteroaryl, —NH$_2$, —NHR$^{14}$, —NR$^{14}$R$^{15}$, —NO$_2$, —S(O)NHR$^{10}$, —S(O)NR$^{10}$R$^{11}$, —S(O)R$^{10}$, —S(O)$_2$NHR$^{10}$, —S(O)$_2$NR$^{10}$R$^{11}$, and —S(O)$_2$R$^{10}$;

each R$^{10}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;

each R$^{11}$ is independently selected from alkyl, alkenyl, haloalkyl, heteroalkyl, heterohaloalkyl, —S(O)$_2$-alkyl, -alkyl-OH, —C(O)Oalkyl, —C(O)alkyl, —C(O)NHalkyl, —C(O)N(alkyl)$_2$, cycloalkyl, heterocycloalkyl, heterocycloalkenyl, aryl, and heteroaryl;

each R$^{14}$ is independently selected from alkyl, alkoxy, alkenyl, haloalkyl, heteroalkyl, heterohaloalkyl, alkylamino, alkylthio, heteroalkenyl, haloalkenyl, —S(O)$_2$-alkyl, -alkyl-OH, -alkyl-O-Acyl, —C(O)Oalkyl, —C(O)alkyl, cycloalkyl, cycloalkyl-alkyl-, heterocycloalkyl, heterocycloalkyl-alkyl-, heterocycloalkenyl, heterocycloalkenyl-alkyl-, aryl, arylalkyl-, heteroaryl, and heteroaryl-alkyl-, wherein each said alkyl, each said alkoxy, each said alkenyl, each said haloalkyl, each said heteroalkyl, each said heterohaloalkyl, each said alkylamino, each said alkylthio, each said heteroalkenyl, each said haloalkenyl, each said —S(O)$_2$-alkyl, each said -alkyl-OH, each said -alkyl-O-Acyl, each said —C(O)Oalkyl, each said —C(O)alkyl, each said cycloalkyl, each said cycloalkyl-alkyl-, each said heterocycloalkyl, each said heterocycloalkyl-alkyl-, each said heterocycloalkenyl, each said heterocycloalkenyl-alkyl-, each said aryl, each said arylalkyl-, each said heteroaryl, and each said heteroaryl-alkyl-, is unsubstituted or optionally independently substituted with from one to five substituent, which can be the same or different, each substituent being independently selected from —OH, halo, —NH$_2$, —NHR$^{10}$, —NR$^{10}$R$^{11}$, —C(O)OH, —C(O)OR$^{10}$, —C(O)NH$_2$, —C(O)NHR$^{10}$, —C(O)NR$^{10}$R$^{11}$, —S(O)$_2$alkyl, —S(O)$_2$aryl, alkyl, alkoxy, haloalkyl, haloalkoxy, heteroaryl, heteroalkyl, heterohaloalkyl, aryl, cycloalkyl, and heterocycloalkyl;

each R$^{15}$ is independently selected from alkyl, alkoxy, alkenyl, haloalkyl, heteroalkyl, heterohaloalkyl, alkylamino, alkylthio, heteroalkenyl, haloalkenyl, —S(O)$_2$-alkyl, -alkyl-OH, -alkyl-O-Acyl, —C(O)Oalkyl, —C(O)alkyl, cycloalkyl, cycloalkyl-alkyl-, heterocycloalkyl, heterocycloalkyl-alkyl-, heterocycloalkenyl, heterocycloalkenyl-alkyl-, aryl, arylalkyl-, heteroaryl, and heteroaryl-alkyl-, wherein each said alkyl, each said alkoxy, each said alkenyl, each said haloalkyl, each said heteroalkyl, each said heterohaloalkyl, each said alkylamino, each said alkylthio, each said heteroalkenyl, each said haloalkenyl, each said —S(O)$_2$-alkyl, each said -alkyl-OH, each said -alkyl-O-Acyl, each said —C(O)Oalkyl, each said —C(O)alkyl, each said cycloalkyl, each said cycloalkyl-alkyl-, each said heterocycloalkyl, each said heterocycloalkyl-alkyl-, each said heterocycloalkenyl, each said heterocycloalkenyl-alkyl-, each said aryl, each said aryl-alkyl-, each said heteroaryl, and each said heteroaryl-alkyl-, is unsubstituted or optionally independently substituted with from one to five substituent, which can be the same or different, each substitutent being independently selected from —OH, halo, —NH$_2$, —NHR$^{10}$, —NR$^{10}$R$^{11}$, —C(O)OH, —C(O)OR$^{10}$, —C(O)NH$_2$, —C(O)NHR$^{10}$, —C(O)NR$^{10}$R$^{11}$, —S(O)$_2$alkyl, —S(O)$_2$aryl, alkyl, alkoxy, haloalkyl, haloalkoxy, heteroaryl, heteroalkyl, heterohaloalkyl, aryl, cycloalkyl, and heterocycloalkyl;

or, alternatively, R$^{14}$ and R$^{15}$ are linked together with the nitrogen to which they are attached to form an unsubstituted or substituted 4- to 6-membered heterocycloalkyl.

5. A compound selected from the group consisting of:

-continued
| Compd # | Structure |
|---|---|
| 11 | 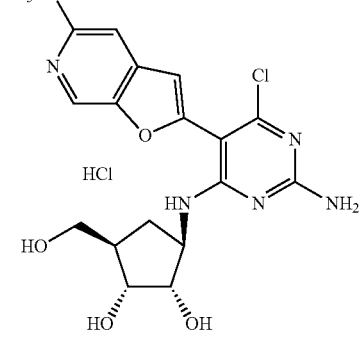 HCl |
| 12 | 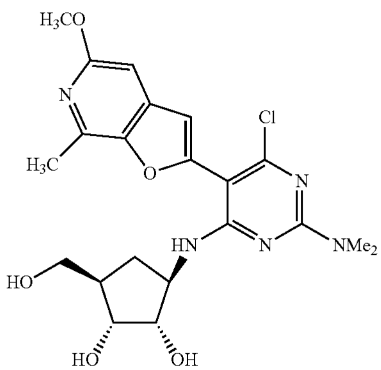 [SMILES: COc1cc2cc(-c3c(Cl)nc(N(C)C)nc3N[C@@H]3C[C@H](CO)[C@@H](O)[C@H]3O)oc2c(C)n1] |
| 13 | •HCl |
| 14 | CF₃CO₂H• |
-continued
| Compd # | Structure |
|---|---|
| 15 | 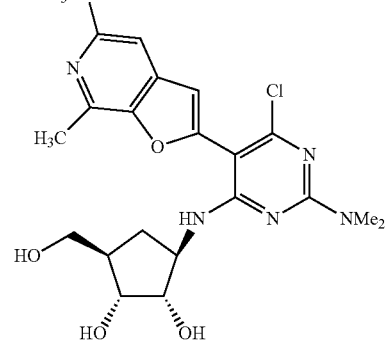 •CF₃CO₂H |
| 16 | 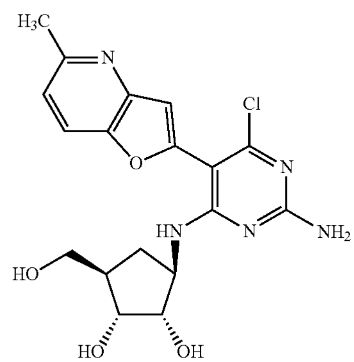 [SMILES: Cc1ccc2oc(-c3c(Cl)nc(N)nc3N[C@@H]3C[C@H](CO)[C@@H](O)[C@H]3O)cc2n1] |
| 17 | •HCl |
| 18 | •CF₃CO₂H |

-continued

| Compd # | Structure |
|---|---|
| 19 | (chloropyrimidine with trifluoroethylamino substituent, linked to methoxy-methyl-furopyridine and hydroxymethyl-dihydroxy-cyclopentylamino) · CF₃CO₂H |
| 20 | (chloropyrimidine with trifluoroethylamino, ethoxy-methyl-furopyridine, hydroxymethyl-dihydroxy-cyclopentylamino) · 1CF₃CO₂H · 1H₂O |
| 21 | (chloropyrimidine with methoxyethylamino, ethoxy-methyl-furopyridine, hydroxymethyl-dihydroxy-cyclopentylamino) · 1.6CF₃CO₂H |
| 22 | (chloropyrimidine with trifluoroethylamino, methoxy-furopyridine, hydroxymethyl-dihydroxy-cyclopentylamino) · HCl · H₂O |

-continued

| Compd # | Structure |
|---|---|
| 31 | (methyl-pyrimidine with methoxyethylamino, ethoxy-furopyridine, hydroxymethyl-dihydroxy-cyclopentylamino) · 0.5MeOH |
| 101 | (phenoxyphenyl-chloropyrimidine-amino with hydroxymethyl-dihydroxy-cyclopentylamino, NH₂) |
| 102 | (benzothiophene-chloropyrimidine-amino with hydroxymethyl-dihydroxy-cyclopentylamino, NH₂) |
| 103 | (phenoxyphenyl-chloropyrimidine with hydroxymethyl-dihydroxy-cyclopentylamino, NH₂) |
| 104 | (thiazole-chloropyrimidine with hydroxymethyl-dihydroxy-cyclopentylamino, NH₂) |

| Compd # | Structure |
|---|---|
| 105 | 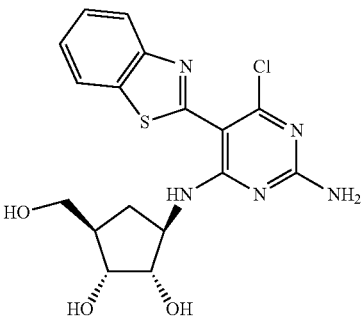 [SMILES: Nc1nc(Cl)c(-c2nc3ccccc3s2)c(N[C@@H]2C[C@H](CO)[C@@H](O)[C@H]2O)n1] |
| 106 | 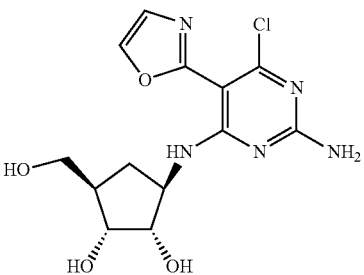 [SMILES: Nc1nc(Cl)c(-c2ncco2)c(N[C@@H]2C[C@H](CO)[C@@H](O)[C@H]2O)n1] |
| 107 | 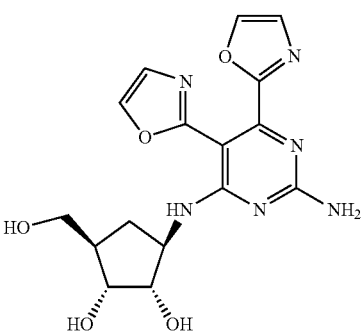 [SMILES: Nc1nc(N[C@@H]2C[C@H](CO)[C@@H](O)[C@H]2O)c(-c2ncco2)c(-c2ncco2)n1] |
| 108 | 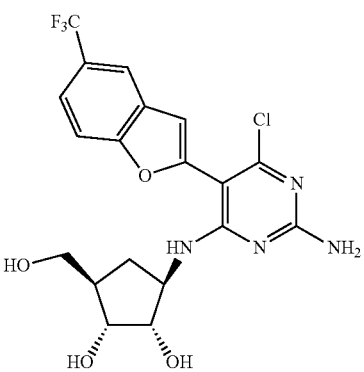 [SMILES: Nc1nc(Cl)c(-c2cc3cc(C(F)(F)F)ccc3o2)c(N[C@@H]2C[C@H](CO)[C@@H](O)[C@H]2O)n1] |
| Compd # | Structure |
|---|---|
| 109 | 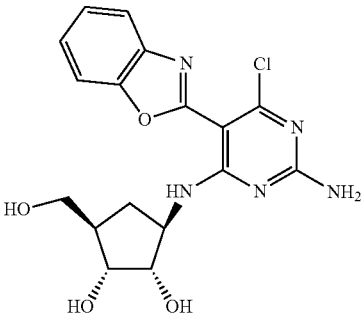 |
| 110 | 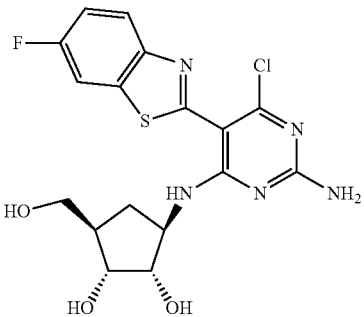 [SMILES: Nc1nc(Cl)c(-c2nc3ccc(F)cc3s2)c(N[C@@H]2C[C@H](CO)[C@@H](O)[C@H]2O)n1] |
| 111 | 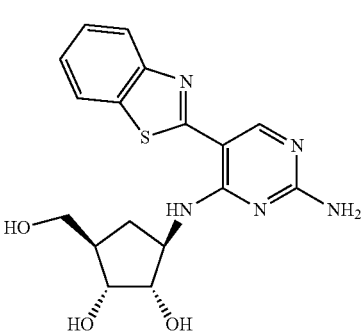 [SMILES: Nc1ncc(-c2nc3ccccc3s2)c(N[C@@H]2C[C@H](CO)[C@@H](O)[C@H]2O)n1] |
| 112 | 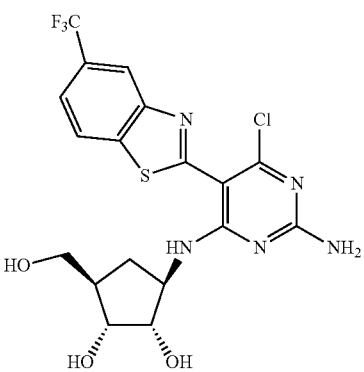 [SMILES: Nc1nc(Cl)c(-c2nc3cc(C(F)(F)F)ccc3s2)c(N[C@@H]2C[C@H](CO)[C@@H](O)[C@H]2O)n1] |

TABLE-continued
| Compd # | Structure |
|---|---|
| 113 | 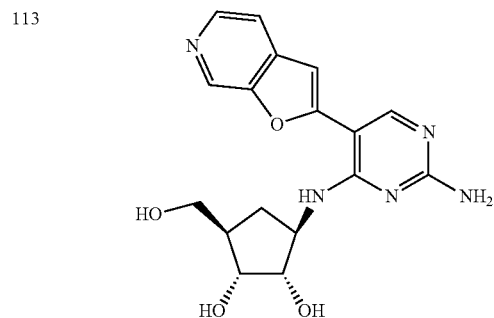 |
| 114 | 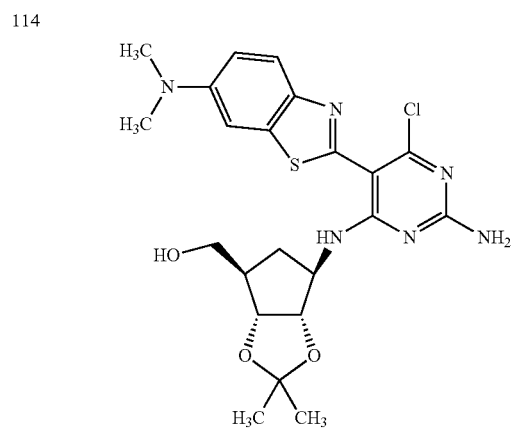 |
| 115 | 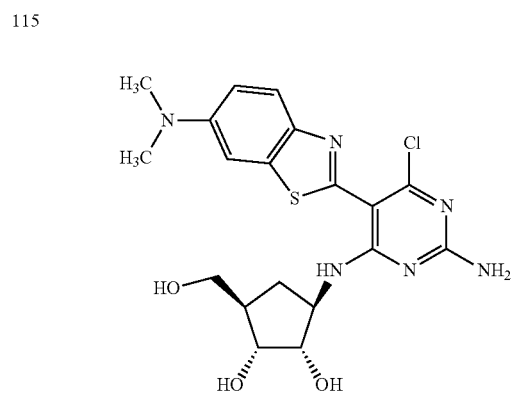 |
| 116 | 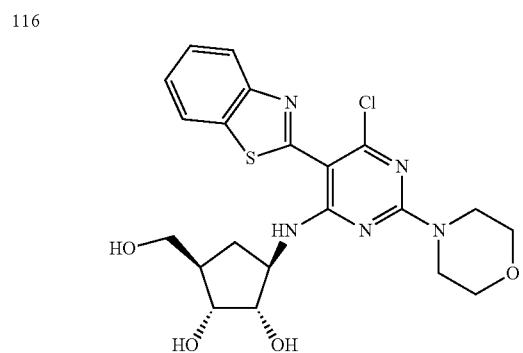 |
| 117 | 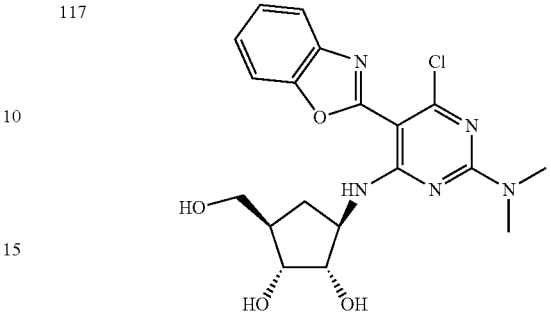 |
| 118 | 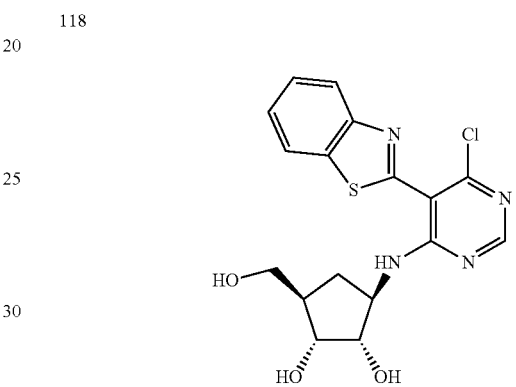 |
| 119 | 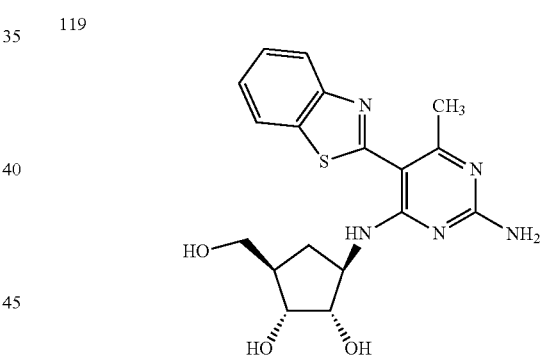 |
| 120 | 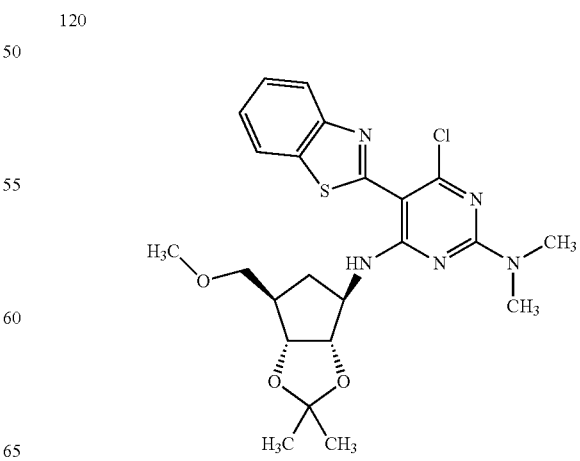 |

| Compd # | Structure |
|---|---|
| 121 | 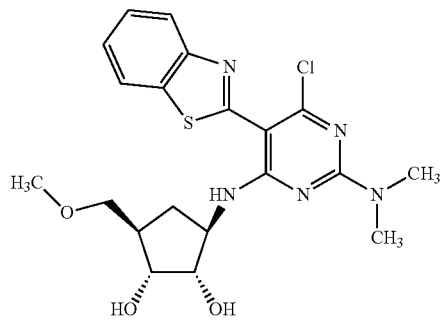 |
| 122 | 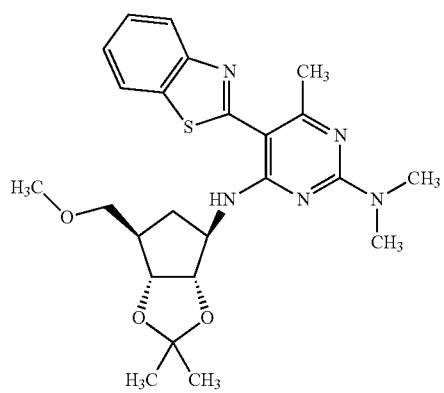 |
| 123 | 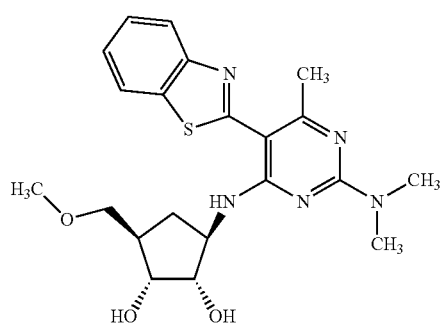 |
| 124 | 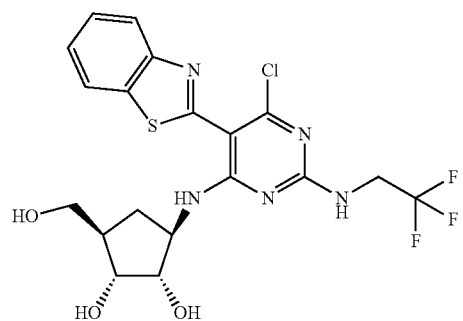 [SMILES: OC[C@H]1C[C@@H](Nc2nc(NCC(F)(F)F)nc(Cl)c2-c2nc3ccccc3s2)[C@H](O)[C@@H]1O] |
| Compd # | Structure |
|---|---|
| 125 | 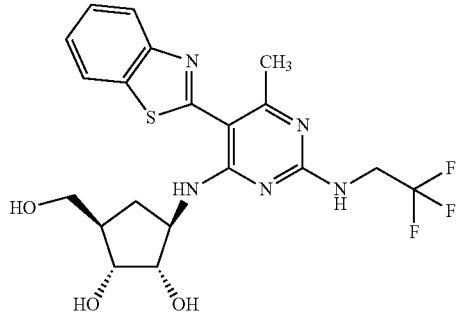 [SMILES: Cc1nc(NCC(F)(F)F)nc(N[C@@H]2C[C@H](CO)[C@@H](O)[C@H]2O)c1-c1nc2ccccc2s1] |
| 126 | 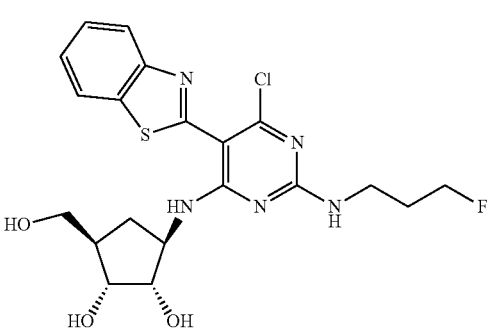 [SMILES: OC[C@H]1C[C@@H](Nc2nc(NCCCF)nc(Cl)c2-c2nc3ccccc3s2)[C@H](O)[C@@H]1O] |
| 127 | 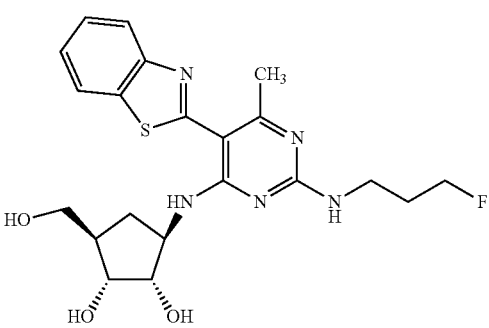 [SMILES: Cc1nc(NCCCF)nc(N[C@@H]2C[C@H](CO)[C@@H](O)[C@H]2O)c1-c1nc2ccccc2s1] |
| 151 | 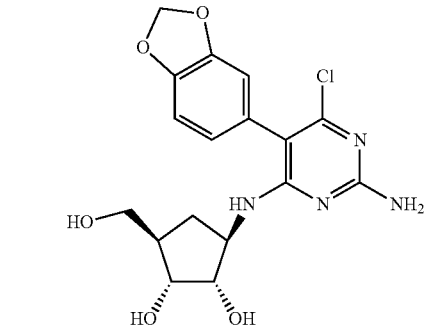 [SMILES: Nc1nc(Cl)c(-c2ccc3c(c2)OCO3)c(N[C@@H]2C[C@H](CO)[C@@H](O)[C@H]2O)n1] |
| 152 | 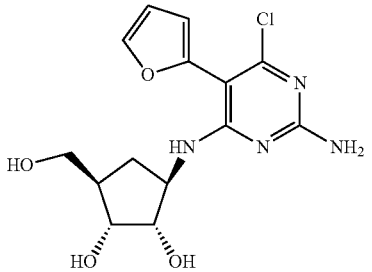 [SMILES: Nc1nc(Cl)c(-c2ccco2)c(N[C@@H]2C[C@H](CO)[C@@H](O)[C@H]2O)n1] |

-continued

| Compd # | Structure |
|---|---|
| 153 | 5-(thiophen-2-yl)-6-chloro-pyrimidine derivative |
| 154 | 5-(5-acetylthiophen-2-yl)-6-chloro-pyrimidine derivative |
| 155 | 5-(5-formylthiophen-2-yl)-6-chloro-pyrimidine derivative |
| 156 | 5-(5-formylfuran-2-yl)-6-chloro-pyrimidine derivative |
| 157 | 5-(pyridin-2-yl)-6-chloro-pyrimidine derivative |

-continued

| Compd # | Structure |
|---|---|
| 158 | 5-(6-morpholinopyridin-2-yl)-6-chloro-pyrimidine derivative |
| 159 | 5-(pyrazin-2-yl)-6-chloro-pyrimidine derivative |
| 160 | 5-(pyrimidin-2-yl)-6-(pyrimidin-2-yl)-pyrimidine derivative |
| 161 | 5-(thiazol-4-yl)-6-chloro-pyrimidine derivative |
| 162 | 5-(pyridin-2-yl)-6-(pyridin-2-yl)-pyrimidine derivative |

| Compd # | Structure |
|---|---|
| 163 | 5-(thiazol-5-yl)-4-chloro-6-amino pyrimidine with cyclopentane-diol-methanol aminolinker |
| 164 | 5-fluorobenzofuran-2-yl pyrimidine analog |
| 165 | 5-chlorobenzofuran-2-yl pyrimidine analog |
| 166 | 6-fluorobenzofuran-2-yl pyrimidine analog |
| 167 | methyl benzofuran-5-carboxylate pyrimidine analog |
| 168 | N,N-dimethylbenzofuran-5-carboxamide pyrimidine analog |
| 169 | 5,6-difluorobenzofuran-2-yl pyrimidine analog |
| 170 | 5,7-difluorobenzofuran-2-yl pyrimidine analog |

TABLE 681-continued
| Compd # | Structure |
|---|---|
| 171 | 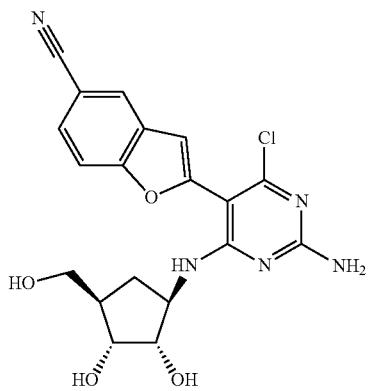 [SMILES: N#Cc1ccc2oc(-c3c(Cl)nc(N)nc3N[C@@H]3C[C@H](CO)[C@@H](O)[C@H]3O)cc2c1] |
| 172 | 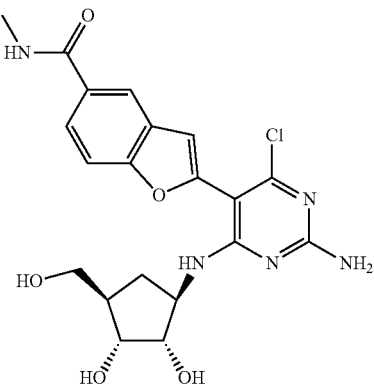 [SMILES: CNC(=O)c1ccc2oc(-c3c(Cl)nc(N)nc3N[C@@H]3C[C@H](CO)[C@@H](O)[C@H]3O)cc2c1] |
| 173 | 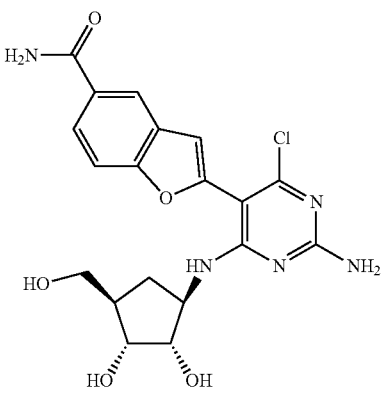 [SMILES: NC(=O)c1ccc2oc(-c3c(Cl)nc(N)nc3N[C@@H]3C[C@H](CO)[C@@H](O)[C@H]3O)cc2c1] |
TABLE 682-continued
| Compd # | Structure |
|---|---|
| 174 | 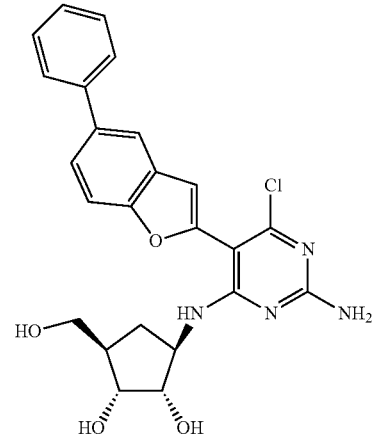 [SMILES: Nc1nc(Cl)c(-c2cc3cc(-c4ccccc4)ccc3o2)c(N[C@@H]2C[C@H](CO)[C@@H](O)[C@H]2O)n1] |
| 175 | 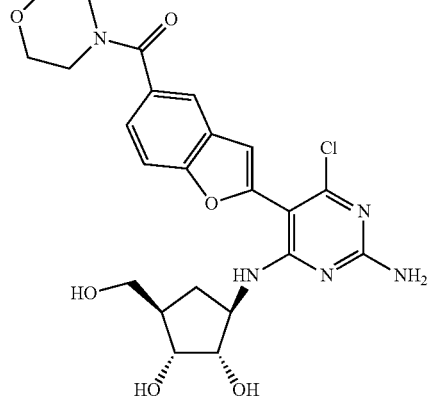 |
| 176 | 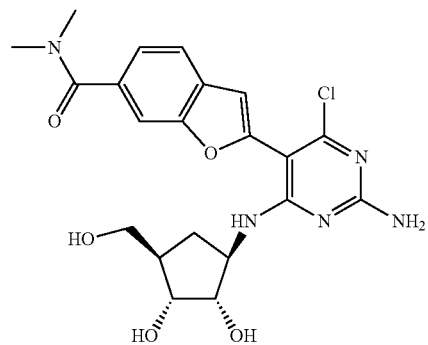 [SMILES: CN(C)C(=O)c1ccc2cc(-c3c(Cl)nc(N)nc3N[C@@H]3C[C@H](CO)[C@@H](O)[C@H]3O)oc2c1] |
| 177 | 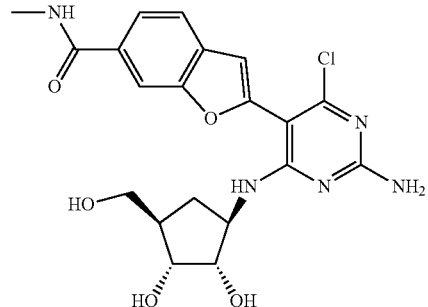 [SMILES: CNC(=O)c1ccc2cc(-c3c(Cl)nc(N)nc3N[C@@H]3C[C@H](CO)[C@@H](O)[C@H]3O)oc2c1] |

| Compd # | Structure |
|---|---|
| 178 | 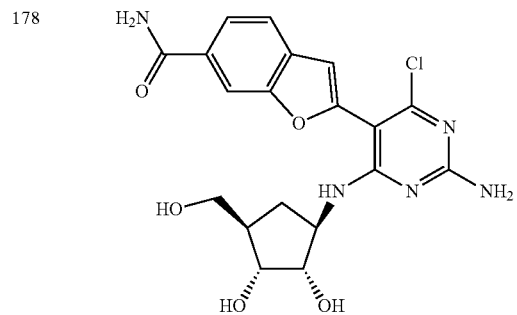 |
| 179 | 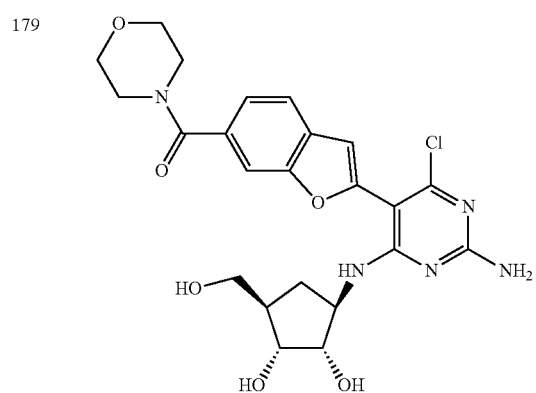 |
| 180 | 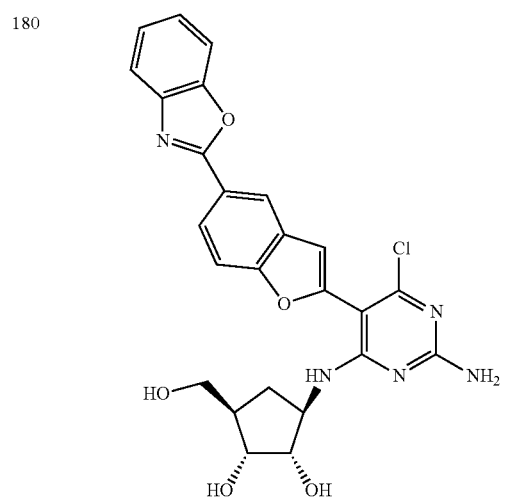 |
| 181 | 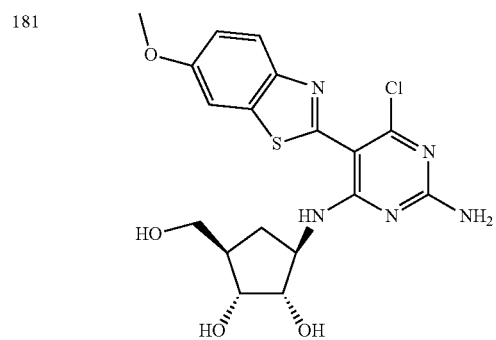 |
| Compd # | Structure |
|---|---|
| 182 | 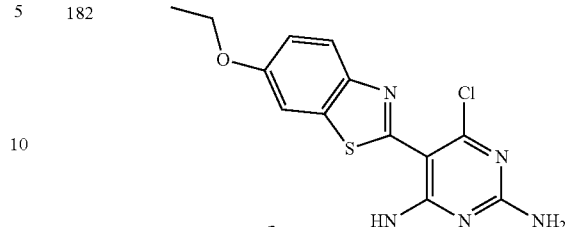 |
| 183 | 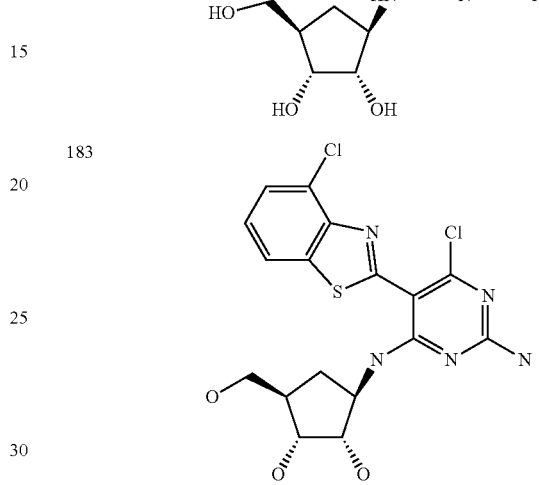 |
| 184 | 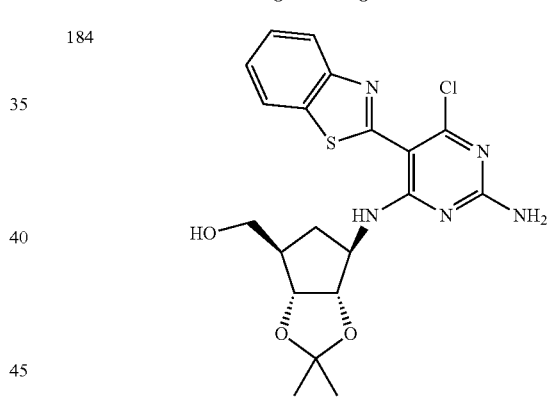 |
| 185 | 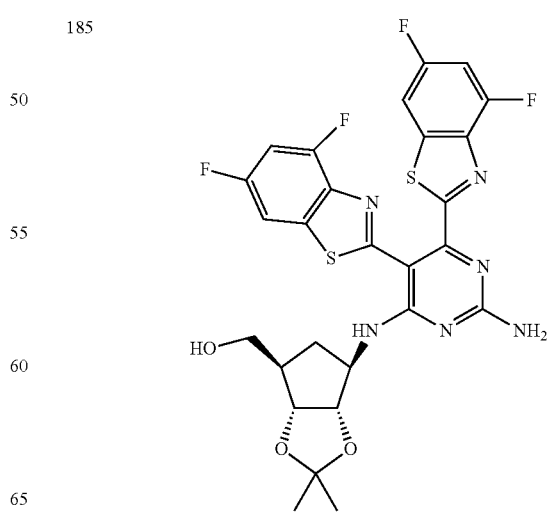 |

| Compd # | Structure |
|---|---|
| 186 | 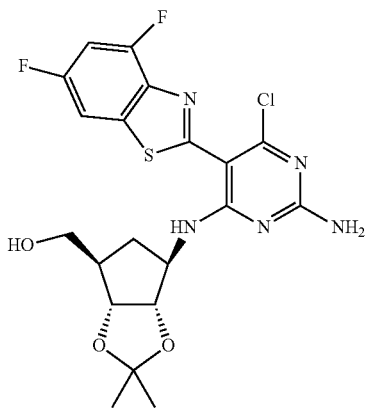 [SMILES: CC1(C)O[C@@H]2[C@@H](CO)C[C@@H](Nc3nc(N)nc(Cl)c3-c3nc4c(F)cc(F)cc4s3)[C@@H]2O1] |
| 187 | 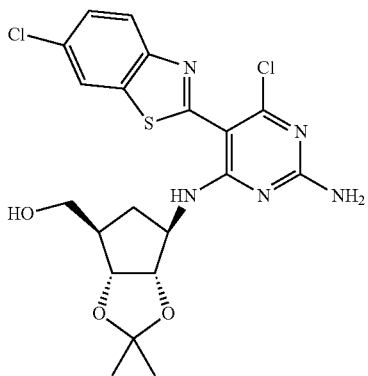 [SMILES: CC1(C)O[C@@H]2[C@@H](CO)C[C@@H](Nc3nc(N)nc(Cl)c3-c3nc4ccc(Cl)cc4s3)[C@@H]2O1] |
| 188 | 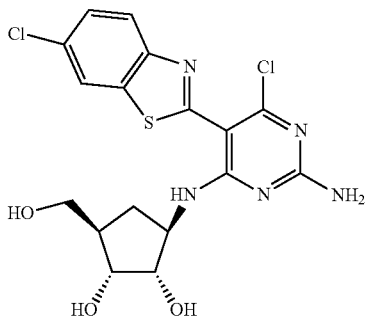 [SMILES: Nc1nc(Cl)c(-c2nc3ccc(Cl)cc3s2)c(N[C@@H]2C[C@H](CO)[C@@H](O)[C@H]2O)n1] |
| 189 | 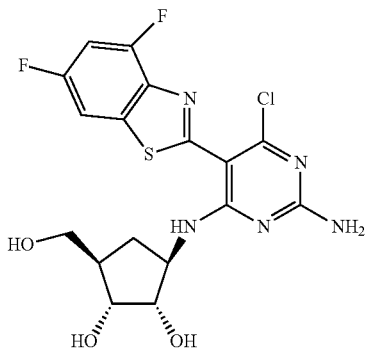 [SMILES: Nc1nc(Cl)c(-c2nc3c(F)cc(F)cc3s2)c(N[C@@H]2C[C@H](CO)[C@@H](O)[C@H]2O)n1] |
| Compd # | Structure |
|---|---|
| 190 | 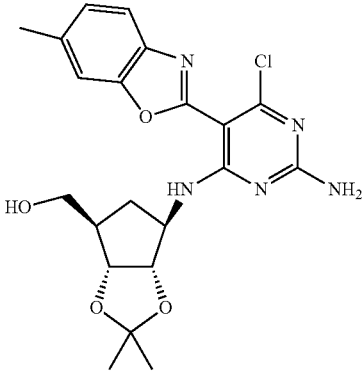 [SMILES: Cc1ccc2nc(-c3c(Cl)nc(N)nc3N[C@@H]3C[C@H](CO)[C@H]4OC(C)(C)O[C@H]43)oc2c1] |
| 191 | 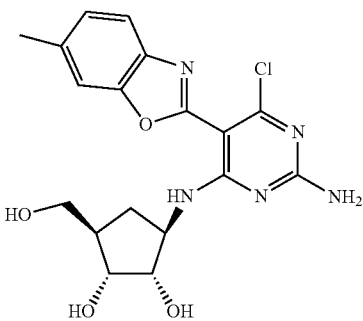 [SMILES: Cc1ccc2nc(-c3c(Cl)nc(N)nc3N[C@@H]3C[C@H](CO)[C@@H](O)[C@H]3O)oc2c1] |
| 192 | 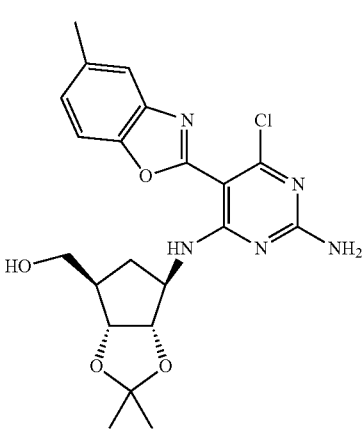 [SMILES: Cc1ccc2oc(-c3c(Cl)nc(N)nc3N[C@@H]3C[C@H](CO)[C@H]4OC(C)(C)O[C@H]43)nc2c1] |
| 193 | 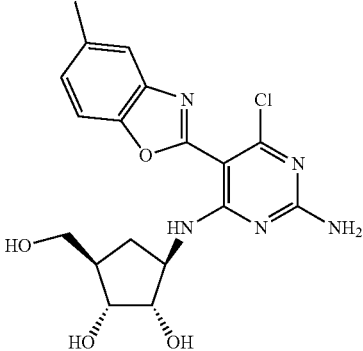 [SMILES: Cc1ccc2oc(-c3c(Cl)nc(N)nc3N[C@@H]3C[C@H](CO)[C@@H](O)[C@H]3O)nc2c1] |

687
-continued
| Compd # | Structure |
|---|---|
| 194 | 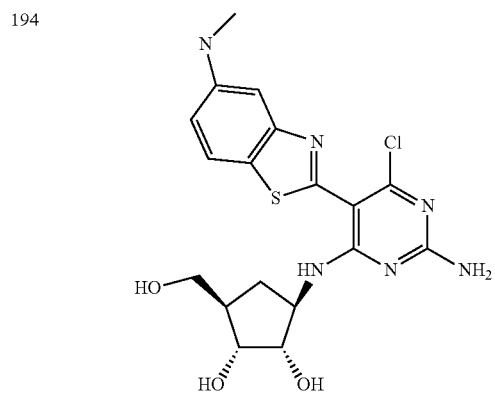 |
| 195 | 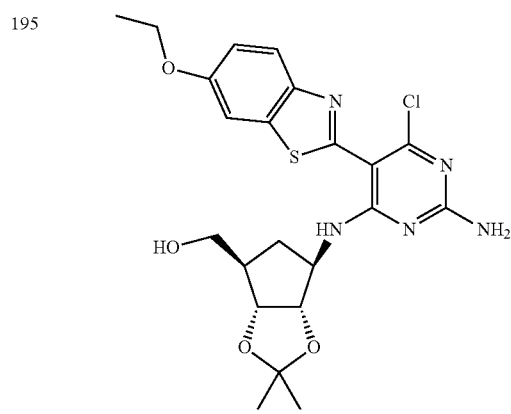 |
| 196 | 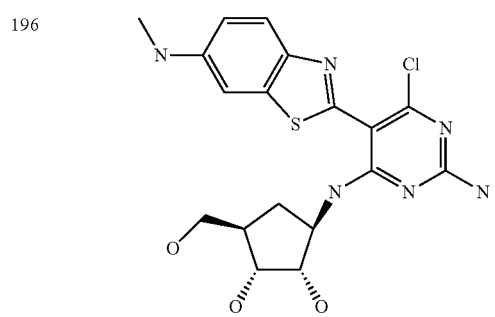 |
| 197 | 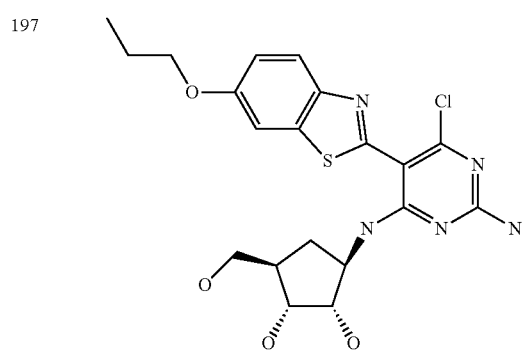 |
688
-continued
| Compd # | Structure |
|---|---|
| 198 | 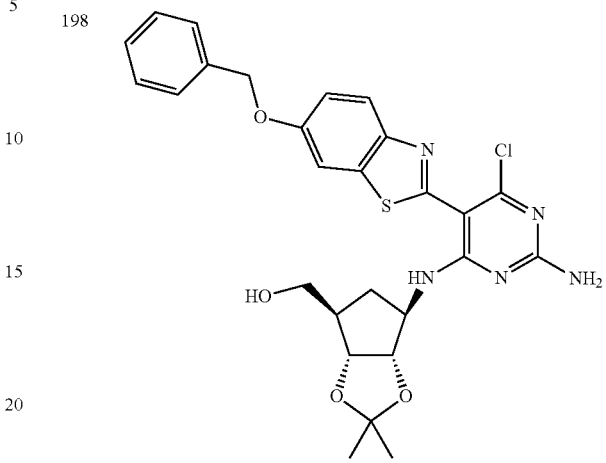 |
| 199 | 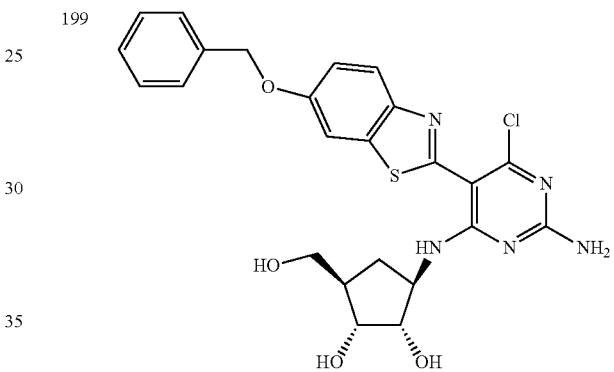 |
| 200 | 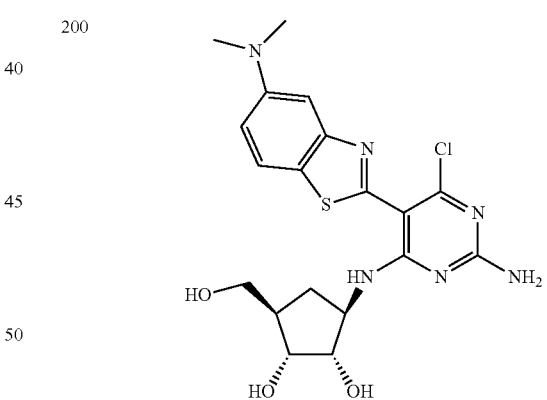 |
| 201 | 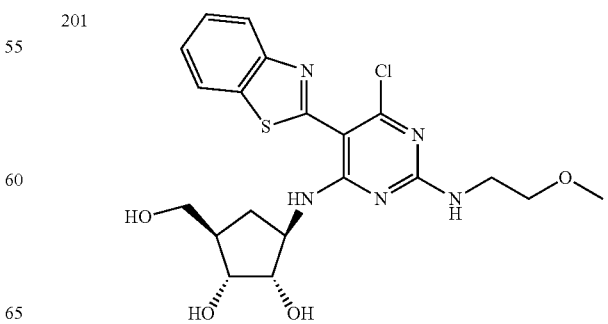 |

| 689 -continued | | 690 -continued | |
|---|---|---|---|
| Compd # | Structure | Compd # | Structure |
| 202 | 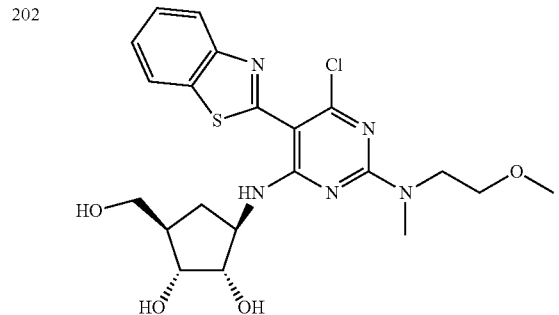 | 207 | 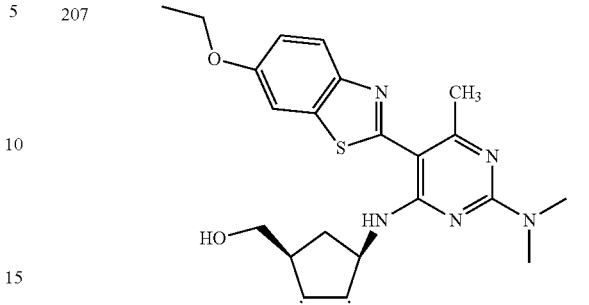 |
| 203 | 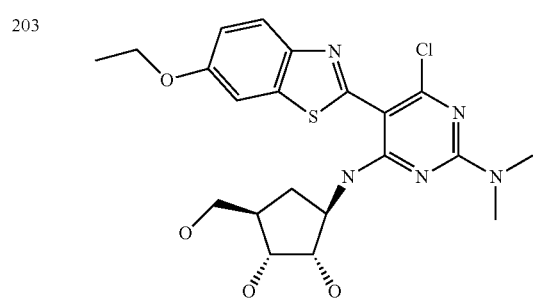 | 208 | 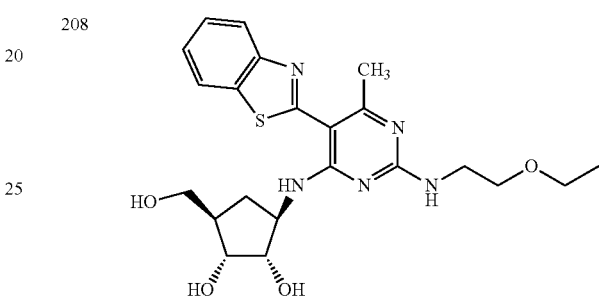 |
| 204 | 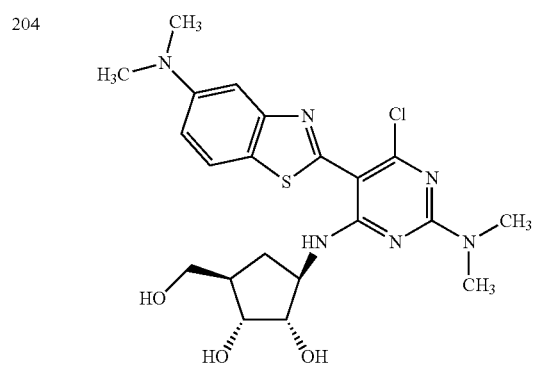 | 209 | 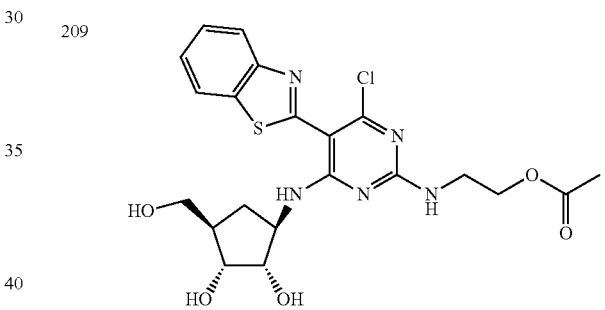 |
| 205 | 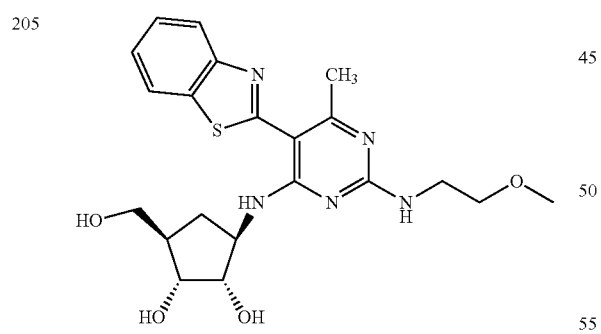 | 210 | 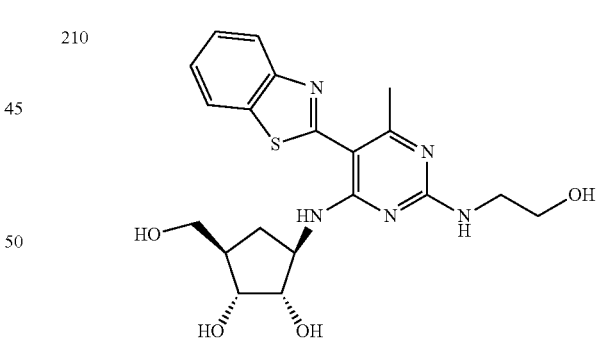 |
| 206 | 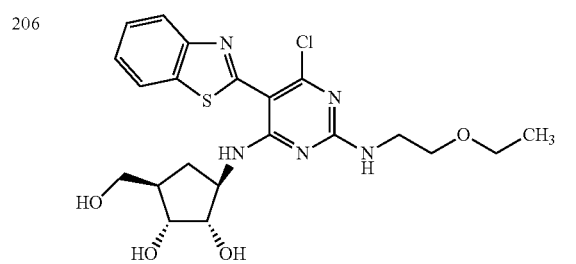 | 211 | 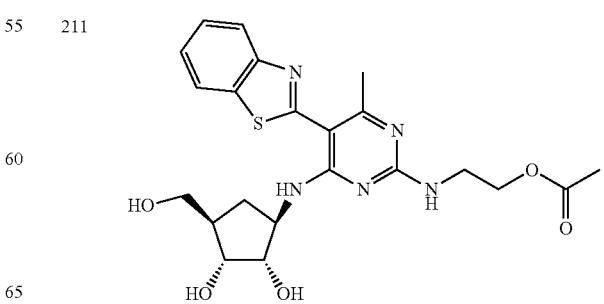 |

| Compd # | Structure |
|---|---|
| 212 | 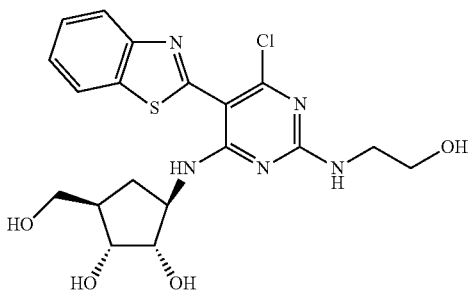 [SMILES: OCCNc1nc(Cl)c(-c2nc3ccccc3s2)c(N[C@@H]2C[C@H](CO)[C@@H](O)[C@H]2O)n1] |
| 213 | 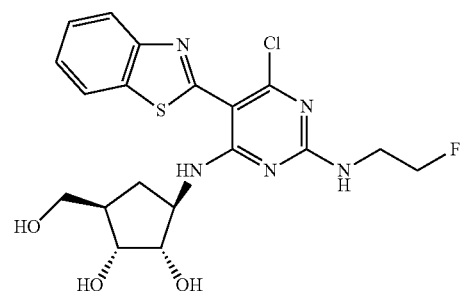 [SMILES: OC[C@H]1C[C@@H](Nc2nc(NCCF)nc(Cl)c2-c2nc3ccccc3s2)[C@H](O)[C@@H]1O] |
| 214 | 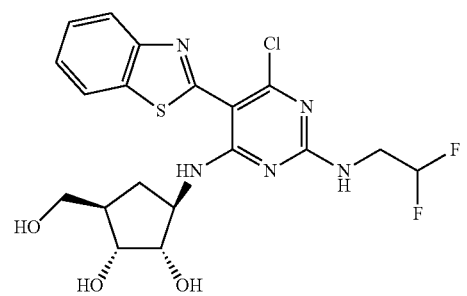 [SMILES: OC[C@H]1C[C@@H](Nc2nc(NCC(F)F)nc(Cl)c2-c2nc3ccccc3s2)[C@H](O)[C@@H]1O] |
| 215 | 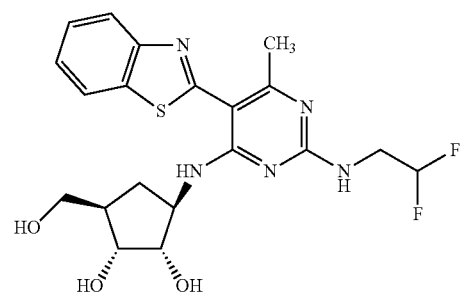 [SMILES: Cc1nc(NCC(F)F)nc(N[C@@H]2C[C@H](CO)[C@@H](O)[C@H]2O)c1-c1nc2ccccc2s1] |
| 216 | 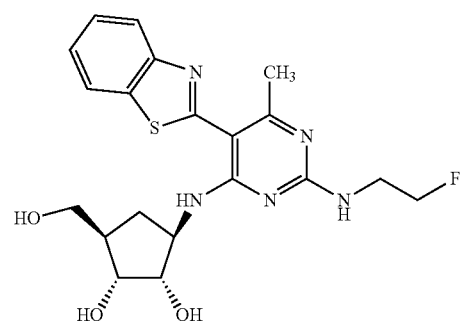 [SMILES: Cc1nc(NCCF)nc(N[C@@H]2C[C@H](CO)[C@@H](O)[C@H]2O)c1-c1nc2ccccc2s1] |
| Compd # | Structure |
|---|---|
| 217 | 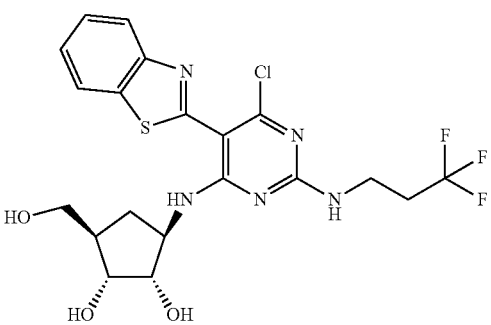 [SMILES: OC[C@H]1C[C@@H](Nc2nc(NCCC(F)(F)F)nc(Cl)c2-c2nc3ccccc3s2)[C@H](O)[C@@H]1O] |
| 218 | 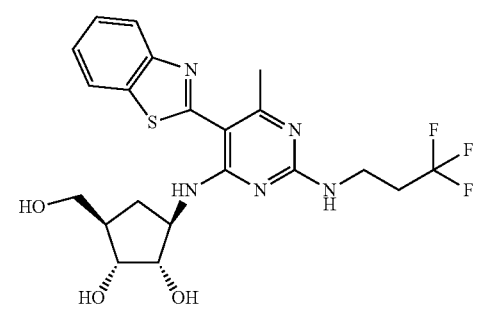 [SMILES: Cc1nc(NCCC(F)(F)F)nc(N[C@@H]2C[C@H](CO)[C@@H](O)[C@H]2O)c1-c1nc2ccccc2s1] |
| 219 | 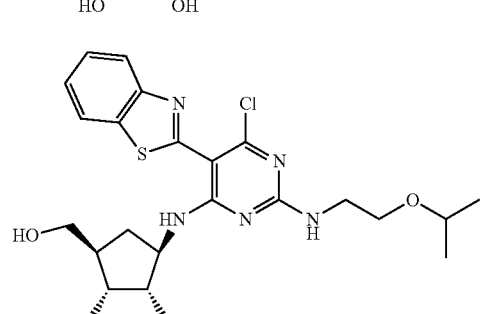 |
| 220 | 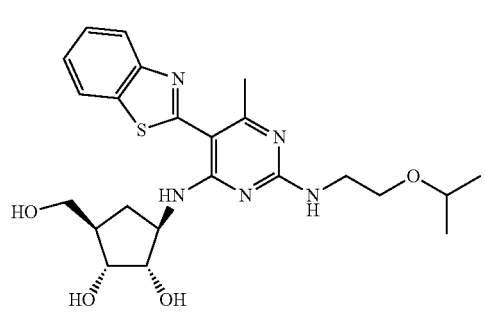 [SMILES: Cc1nc(NCCOC(C)C)nc(N[C@@H]2C[C@H](CO)[C@@H](O)[C@H]2O)c1-c1nc2ccccc2s1] |
| 222 | 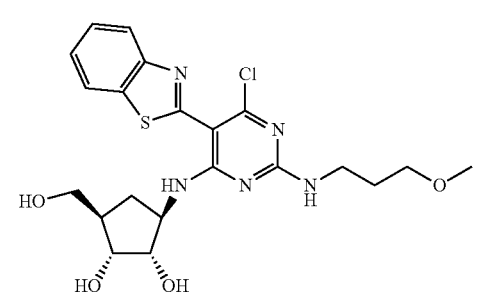 [SMILES: COCCCNc1nc(Cl)c(-c2nc3ccccc3s2)c(N[C@@H]2C[C@H](CO)[C@@H](O)[C@H]2O)n1] |

| Compd # | Structure |
|---|---|
| 223 | 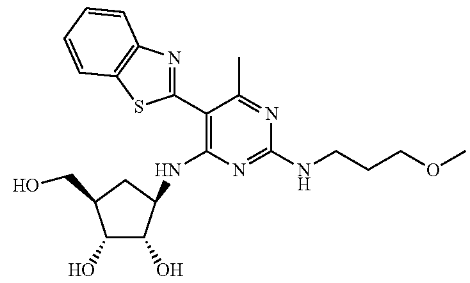 [SMILES: COCCCNc1nc(C)c(-c2nc3ccccc3s2)c(N[C@@H]2C[C@H](CO)[C@@H](O)[C@H]2O)n1] |
| 224 | 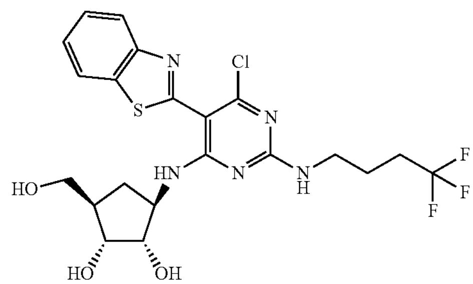 [SMILES: OC[C@H]1C[C@@H](Nc2nc(NCCCC(F)(F)F)nc(Cl)c2-c2nc3ccccc3s2)[C@H](O)[C@@H]1O] |
| 225 | 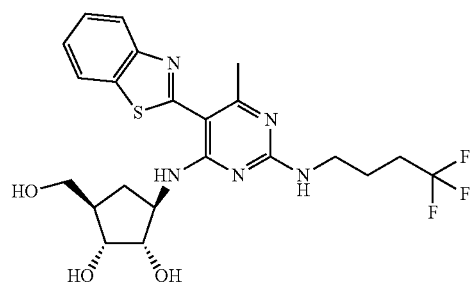 [SMILES: Cc1nc(NCCCC(F)(F)F)nc(N[C@@H]2C[C@H](CO)[C@@H](O)[C@H]2O)c1-c1nc2ccccc2s1] |
| 226 | 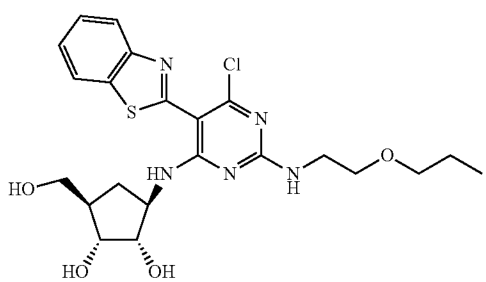 [SMILES: CCCOCCNc1nc(Cl)c(-c2nc3ccccc3s2)c(N[C@@H]2C[C@H](CO)[C@@H](O)[C@H]2O)n1] |
| 227 | 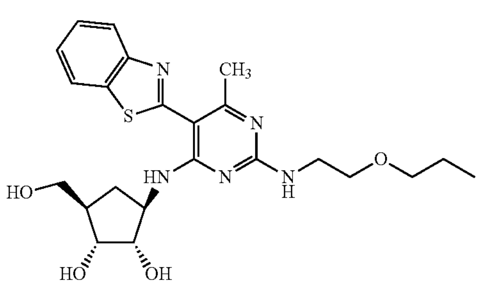 [SMILES: CCCOCCNc1nc(C)c(-c2nc3ccccc3s2)c(N[C@@H]2C[C@H](CO)[C@@H](O)[C@H]2O)n1] |

| Compd # | Structure |
|---|---|
| 228 | |
| 229 | |
| 302 | |
| 303 | |

695
-continued

| Compd # | Structure |
|---|---|
| 304 | 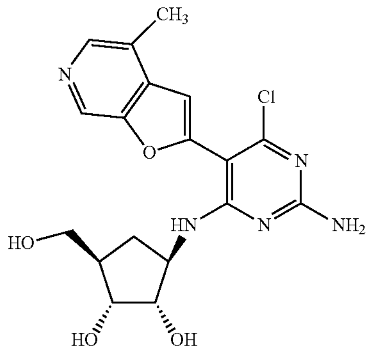 [SMILES: Cc1cncc2oc(-c3c(Cl)nc(N)nc3N[C@@H]3C[C@H](CO)[C@@H](O)[C@H]3O)cc12] |
| 306 | 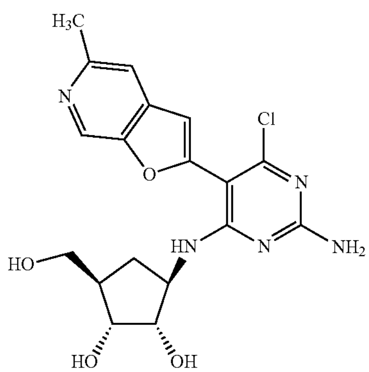 [SMILES: Cc1cc2cc(-c3c(Cl)nc(N)nc3N[C@@H]3C[C@H](CO)[C@@H](O)[C@H]3O)oc2cn1] |
| 305 | 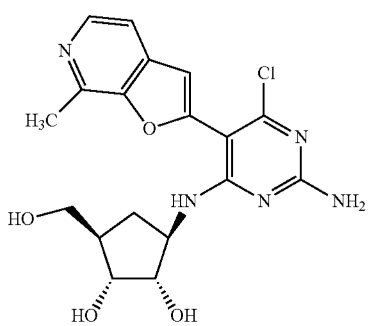 [SMILES: Cc1nccc2cc(-c3c(Cl)nc(N)nc3N[C@@H]3C[C@H](CO)[C@@H](O)[C@H]3O)oc12] |
| 307 | 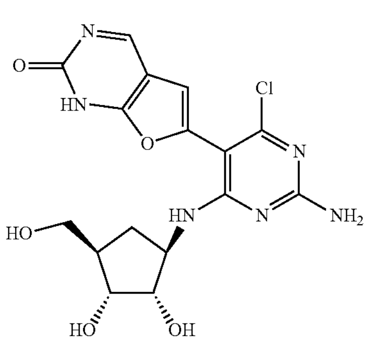 [SMILES: Nc1nc(Cl)c(-c2cc3cnc(=O)[nH]c3o2)c(N[C@@H]2C[C@H](CO)[C@@H](O)[C@H]2O)n1] |

696
-continued

| Compd # | Structure |
|---|---|
| 308 | 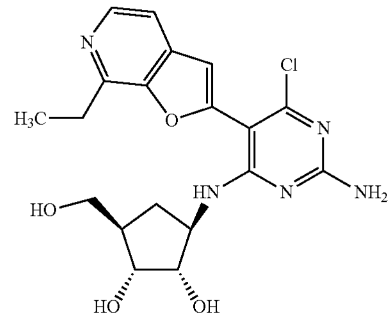 [SMILES: CCc1nccc2cc(-c3c(Cl)nc(N)nc3N[C@@H]3C[C@H](CO)[C@@H](O)[C@H]3O)oc12] |
| 309 | 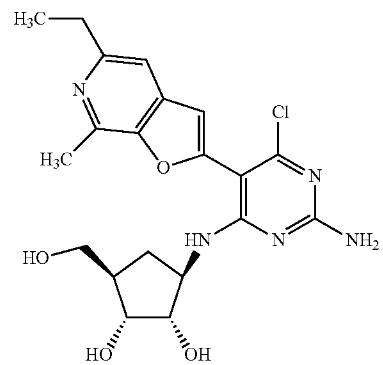 [SMILES: CCc1cc2cc(-c3c(Cl)nc(N)nc3N[C@@H]3C[C@H](CO)[C@@H](O)[C@H]3O)oc2c(C)n1] |
| 403 | 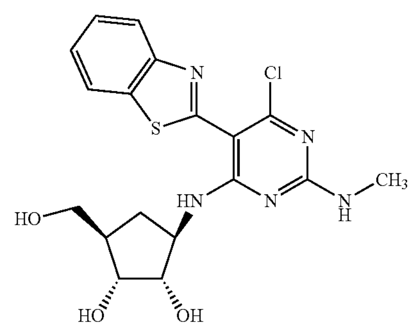 [SMILES: CNc1nc(Cl)c(-c2nc3ccccc3s2)c(N[C@@H]2C[C@H](CO)[C@@H](O)[C@H]2O)n1] |
| 310 | 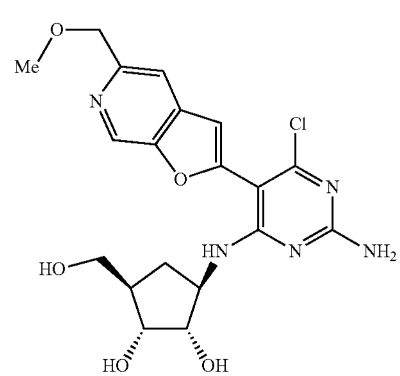 [SMILES: COCc1cc2cc(-c3c(Cl)nc(N)nc3N[C@@H]3C[C@H](CO)[C@@H](O)[C@H]3O)oc2cn1] |

US 8,697,694 B2
697
-continued
| Compd # | Structure |
|---|---|
| 311 | 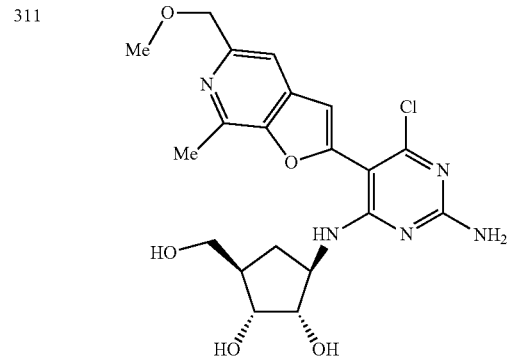 |
| 408 | 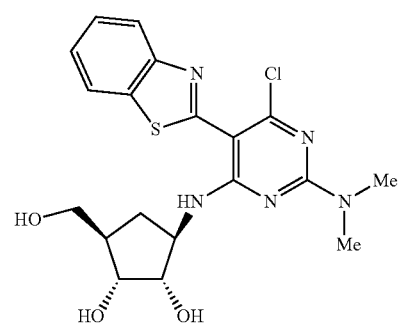 [SMILES: CN(C)c1nc(Cl)c(-c2nc3ccccc3s2)c(N[C@@H]2C[C@H](CO)[C@@H](O)[C@H]2O)n1] |
| 312 | 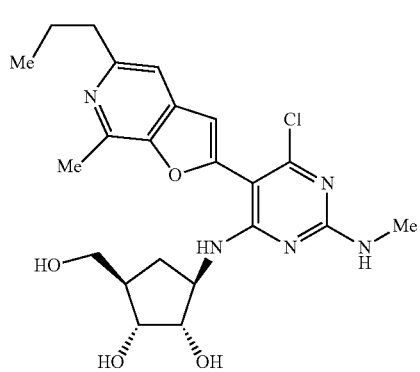 [SMILES: CCCc1cc2cc(-c3c(Cl)nc(NC)nc3N[C@@H]3C[C@H](CO)[C@@H](O)[C@H]3O)oc2c(C)n1] |
| 313 | 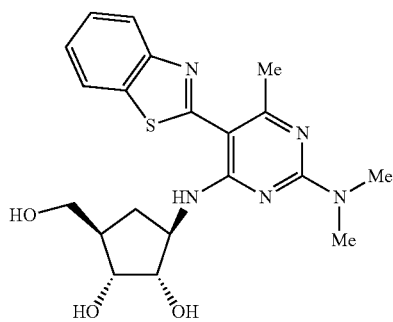 [SMILES: Cc1nc(N(C)C)nc(N[C@@H]2C[C@H](CO)[C@@H](O)[C@H]2O)c1-c1nc2ccccc2s1] |
698
-continued
| Compd # | Structure |
|---|---|
| 314 | 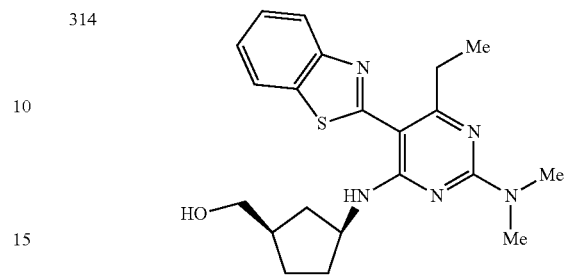 |
| 412 | 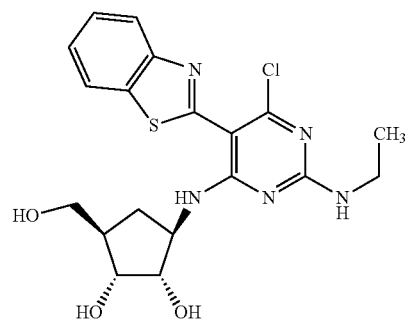 [SMILES: CCNc1nc(Cl)c(-c2nc3ccccc3s2)c(N[C@@H]2C[C@H](CO)[C@@H](O)[C@H]2O)n1] |
| 317 | 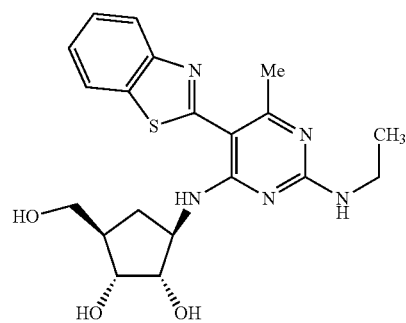 [SMILES: CCNc1nc(C)c(-c2nc3ccccc3s2)c(N[C@@H]2C[C@H](CO)[C@@H](O)[C@H]2O)n1] |
| 318 | 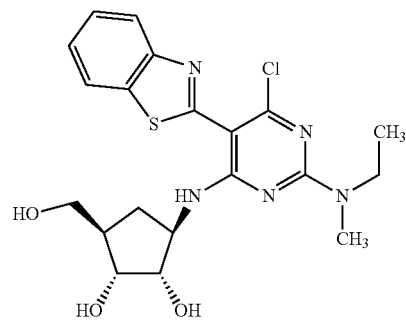 [SMILES: CCN(C)c1nc(Cl)c(-c2nc3ccccc3s2)c(N[C@@H]2C[C@H](CO)[C@@H](O)[C@H]2O)n1] |

-continued
| Compd # | Structure |
|---|---|
| 319 | 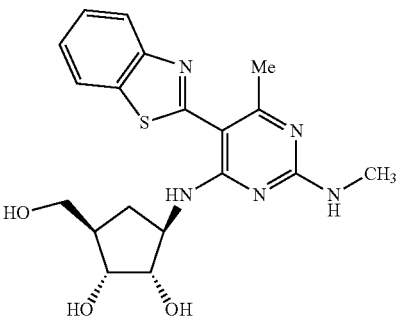 [SMILES: CNc1nc(C)c(-c2nc3ccccc3s2)c(N[C@@H]2C[C@H](CO)[C@@H](O)[C@H]2O)n1] |
| 321 | 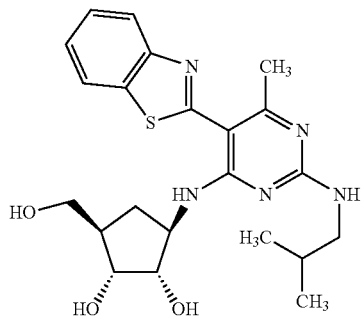 [SMILES: Cc1nc(NCC(C)C)nc(N[C@@H]2C[C@H](CO)[C@@H](O)[C@H]2O)c1-c1nc2ccccc2s1] |
| 320 | 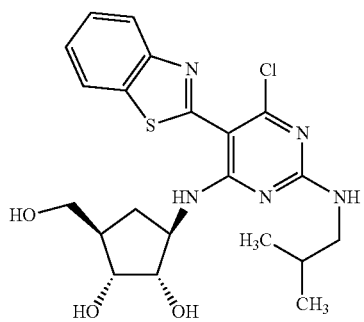 [SMILES: CC(C)CNc1nc(Cl)c(-c2nc3ccccc3s2)c(N[C@@H]2C[C@H](CO)[C@@H](O)[C@H]2O)n1] |
| 401 | 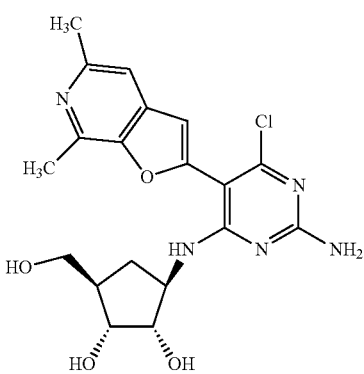 [SMILES: Cc1cc2cc(-c3c(Cl)nc(N)nc3N[C@@H]3C[C@H](CO)[C@@H](O)[C@H]3O)oc2c(C)n1] |
-continued
| Compd # | Structure |
|---|---|
| 402 | 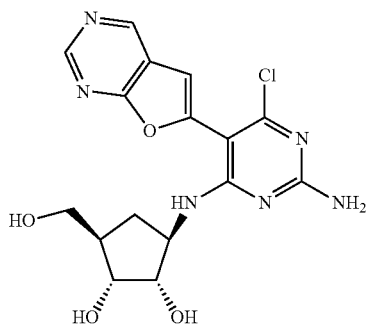 [SMILES: Nc1nc(Cl)c(-c2cc3cncnc3o2)c(N[C@@H]2C[C@H](CO)[C@@H](O)[C@H]2O)n1] |
| 404 | 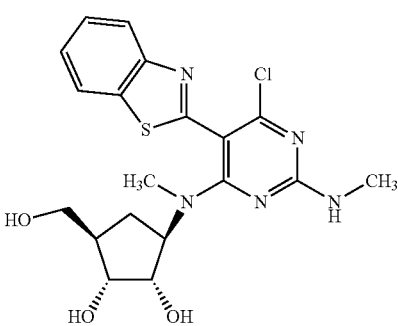 [SMILES: CNc1nc(Cl)c(-c2nc3ccccc3s2)c(N(C)[C@@H]2C[C@H](CO)[C@@H](O)[C@H]2O)n1] |
| 406 | 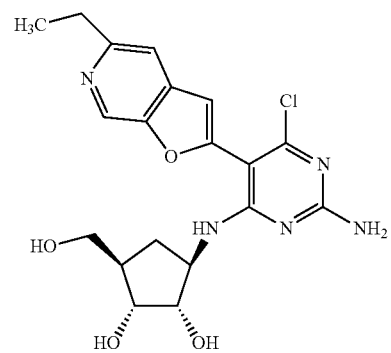 [SMILES: CCc1cc2cc(-c3c(Cl)nc(N)nc3N[C@@H]3C[C@H](CO)[C@@H](O)[C@H]3O)oc2cn1] |
| 407 | 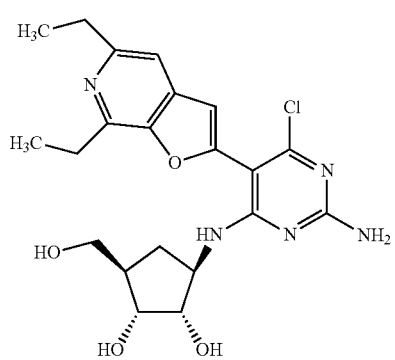 [SMILES: CCc1cc2cc(-c3c(Cl)nc(N)nc3N[C@@H]3C[C@H](CO)[C@@H](O)[C@H]3O)oc2c(CC)n1] |

TABLE 701-continued
| Compd # | Structure |
|---|---|
| 410 | 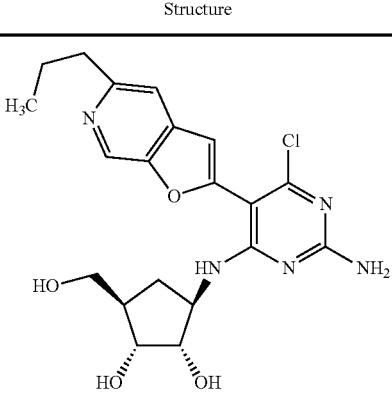 |
| 411 | 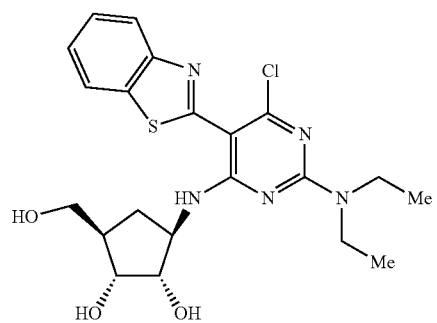 [SMILES: CCN(CC)c1nc(Cl)c(-c2nc3ccccc3s2)c(N[C@@H]2C[C@H](CO)[C@@H](O)[C@H]2O)n1] |
| 413 | 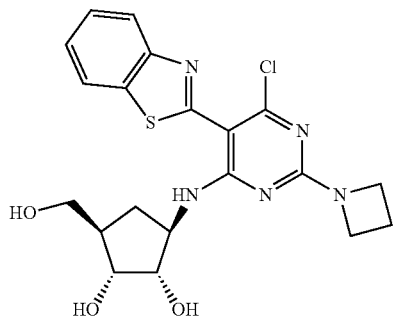 [SMILES: OC[C@H]1C[C@@H](Nc2nc(N3CCC3)nc(Cl)c2-c2nc3ccccc3s2)[C@H](O)[C@@H]1O] |
| 414 | 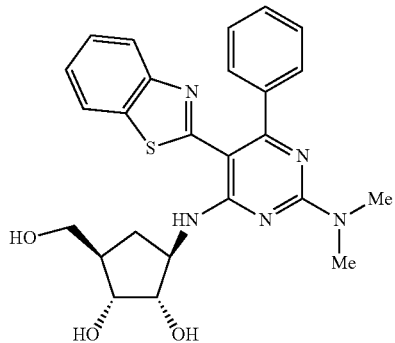 [SMILES: CN(C)c1nc(N[C@@H]2C[C@H](CO)[C@@H](O)[C@H]2O)c(-c2nc3ccccc3s2)c(-c2ccccc2)n1] |
TABLE 702-continued
| Compd # | Structure |
|---|---|
| 415 | 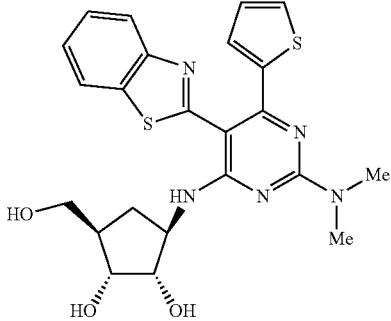 [SMILES: CN(C)c1nc(N[C@@H]2C[C@H](CO)[C@@H](O)[C@H]2O)c(-c2nc3ccccc3s2)c(-c2cccs2)n1] |
| 416 | 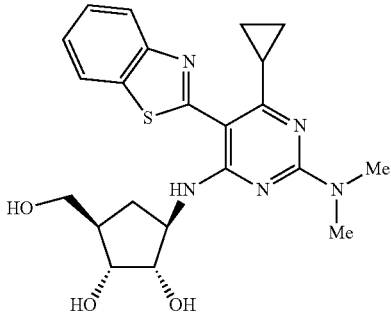 [SMILES: CN(C)c1nc(N[C@@H]2C[C@H](CO)[C@@H](O)[C@H]2O)c(-c2nc3ccccc3s2)c(C2CC2)n1] |
| 418 | 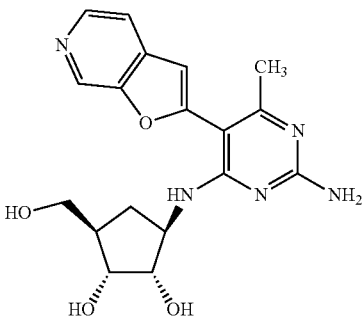 [SMILES: Cc1nc(N)nc(N[C@@H]2C[C@H](CO)[C@@H](O)[C@H]2O)c1-c1cc2ccncc2o1] |
| 420 | 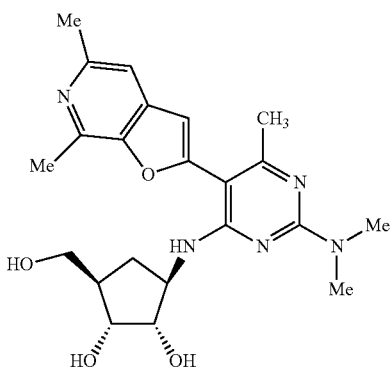 [SMILES: Cc1cc2cc(-c3c(C)nc(N(C)C)nc3N[C@@H]3C[C@H](CO)[C@@H](O)[C@H]3O)oc2c(C)n1] |

-continued
| Compd # | Structure |
|---|---|
| 419 | 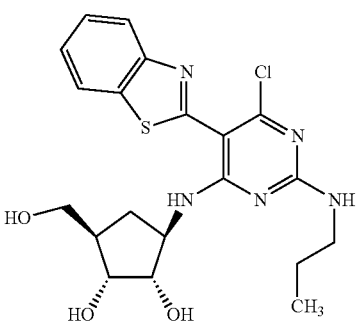 [SMILES: CCCNc1nc(Cl)c(-c2nc3ccccc3s2)c(N[C@@H]2C[C@H](CO)[C@@H](O)[C@H]2O)n1] |
| 422 | 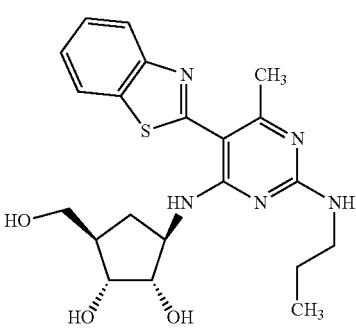 [SMILES: CCCNc1nc(C)c(-c2nc3ccccc3s2)c(N[C@@H]2C[C@H](CO)[C@@H](O)[C@H]2O)n1] |
| 423 | 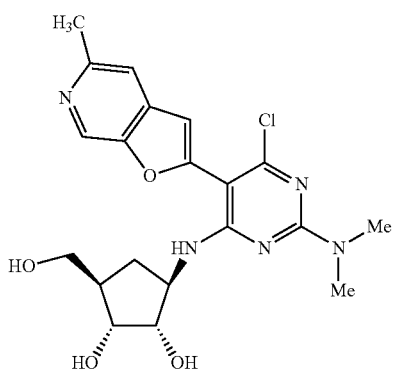 [SMILES: Cc1cc2cc(-c3c(Cl)nc(N(C)C)nc3N[C@@H]3C[C@H](CO)[C@@H](O)[C@H]3O)oc2cn1] |
| 424 | 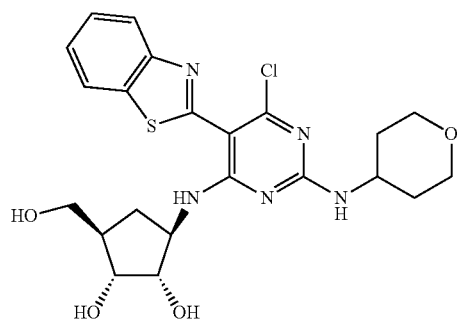 [SMILES: OC[C@H]1C[C@@H](Nc2nc(NC3CCOCC3)nc(Cl)c2-c2nc3ccccc3s2)[C@H](O)[C@@H]1O] |
-continued
| Compd # | Structure |
|---|---|
| 425 | 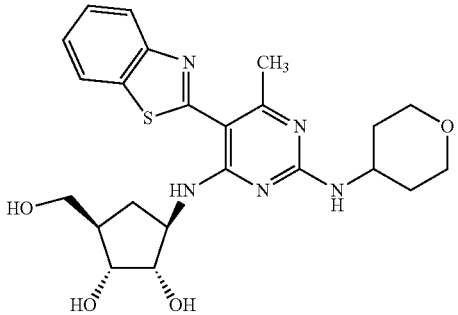 [SMILES: Cc1nc(NC2CCOCC2)nc(N[C@@H]2C[C@H](CO)[C@@H](O)[C@H]2O)c1-c1nc2ccccc2s1] |
| 426 | 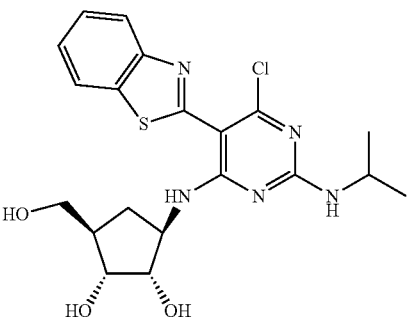 [SMILES: CC(C)Nc1nc(Cl)c(-c2nc3ccccc3s2)c(N[C@@H]2C[C@H](CO)[C@@H](O)[C@H]2O)n1] |
| 427 | 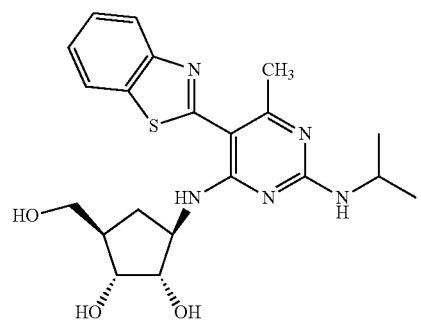 [SMILES: Cc1nc(NC(C)C)nc(N[C@@H]2C[C@H](CO)[C@@H](O)[C@H]2O)c1-c1nc2ccccc2s1] |
| 428 | 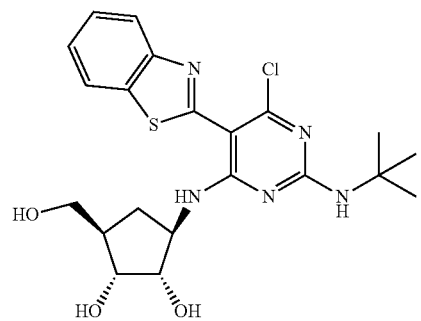 [SMILES: CC(C)(C)Nc1nc(Cl)c(-c2nc3ccccc3s2)c(N[C@@H]2C[C@H](CO)[C@@H](O)[C@H]2O)n1] |

| Compd # | Structure |
|---|---|
| 429 | |
| 430 | |
| 431 | |
| 432 | |
| 433 | 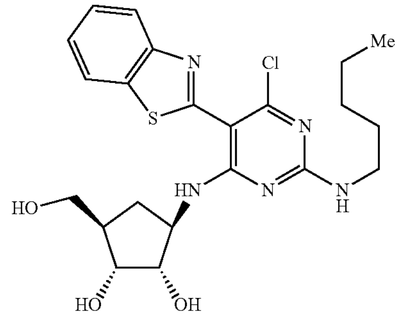 [SMILES: CCCCCNc1nc(Cl)c(-c2nc3ccccc3s2)c(N[C@@H]2C[C@H](CO)[C@@H](O)[C@H]2O)n1] |
| 434 | 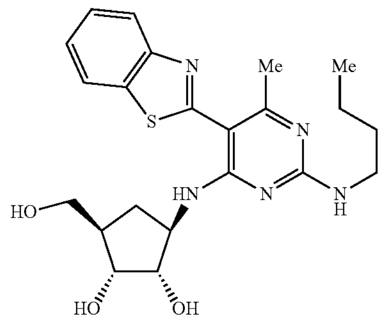 [SMILES: CCCCNc1nc(C)c(-c2nc3ccccc3s2)c(N[C@@H]2C[C@H](CO)[C@@H](O)[C@H]2O)n1] |
| 435 | 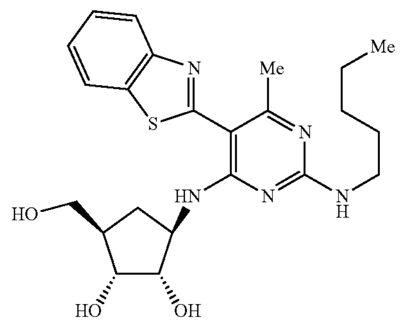 [SMILES: CCCCCNc1nc(C)c(-c2nc3ccccc3s2)c(N[C@@H]2C[C@H](CO)[C@@H](O)[C@H]2O)n1] |
| 436 | 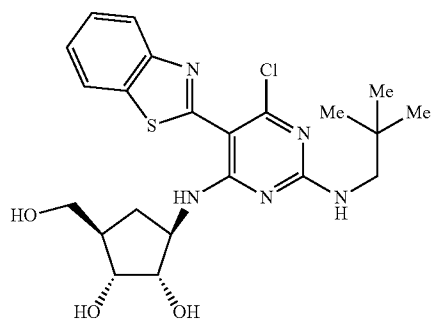 [SMILES: CC(C)(C)CNc1nc(Cl)c(-c2nc3ccccc3s2)c(N[C@@H]2C[C@H](CO)[C@@H](O)[C@H]2O)n1] |
| 437 | 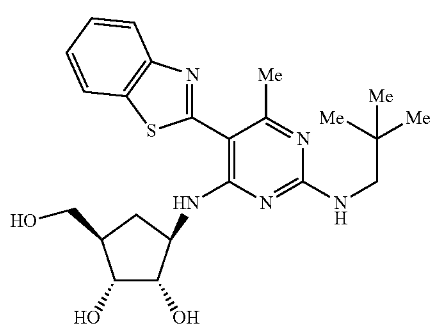 [SMILES: Cc1nc(NCC(C)(C)C)nc(N[C@@H]2C[C@H](CO)[C@@H](O)[C@H]2O)c1-c1nc2ccccc2s1] |

| Compd # | Structure |
|---|---|
| 438 | 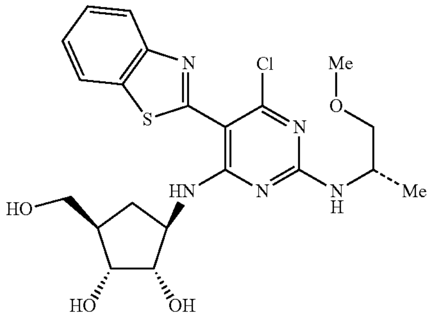 [SMILES: COC[C@H](C)Nc1nc(Cl)c(-c2nc3ccccc3s2)c(N[C@@H]2C[C@H](CO)[C@@H](O)[C@H]2O)n1] |
| 439 | 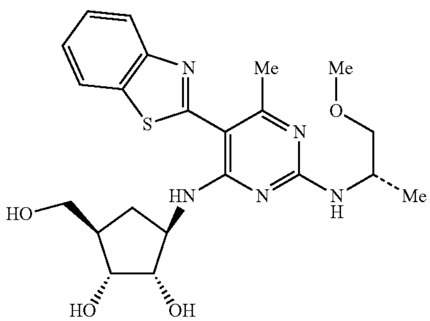 [SMILES: COC[C@H](C)Nc1nc(C)c(-c2nc3ccccc3s2)c(N[C@@H]2C[C@H](CO)[C@@H](O)[C@H]2O)n1] |
| 440 | 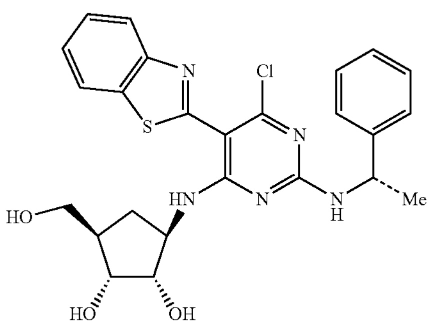 [SMILES: C[C@H](Nc1nc(Cl)c(-c2nc3ccccc3s2)c(N[C@@H]2C[C@H](CO)[C@@H](O)[C@H]2O)n1)c1ccccc1] |
| 441 | 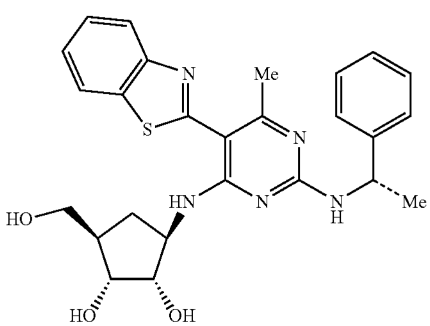 [SMILES: Cc1nc(N[C@@H](C)c2ccccc2)nc(N[C@@H]2C[C@H](CO)[C@@H](O)[C@H]2O)c1-c1nc2ccccc2s1] |

| Compd # | Structure |
|---|---|
| 501 | 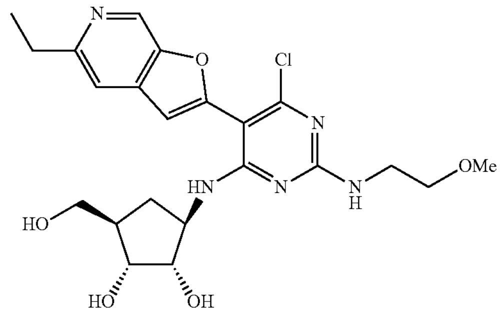 |
| 502 | 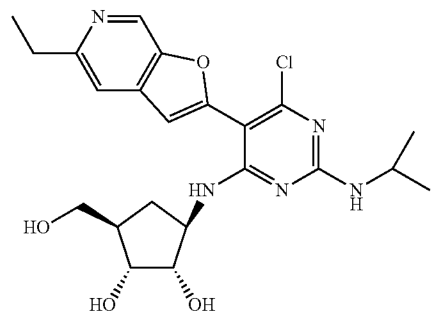 [SMILES: CCc1cc2cc(-c3c(Cl)nc(NC(C)C)nc3N[C@@H]3C[C@H](CO)[C@@H](O)[C@H]3O)oc2cn1] |
| 503 | 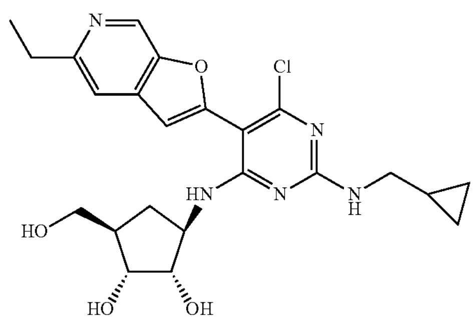 |
| 504 | 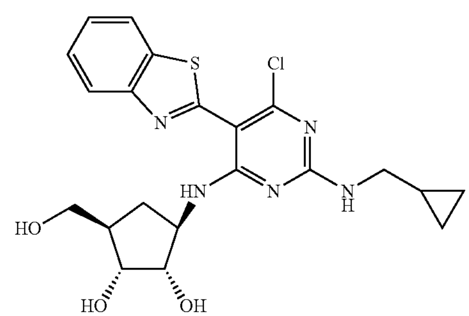 [SMILES: OC[C@H]1C[C@@H](Nc2nc(NCC3CC3)nc(Cl)c2-c2nc3ccccc3s2)[C@H](O)[C@@H]1O] |
| 505 | 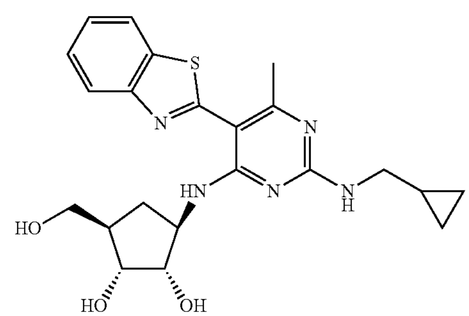 [SMILES: Cc1nc(NCC2CC2)nc(N[C@@H]2C[C@H](CO)[C@@H](O)[C@H]2O)c1-c1nc2ccccc2s1] |

| Compd # | Structure |
|---|---|
| 506 | (benzothiazole-pyrimidine with Cl, tert-amyl amine, aminocyclopentane triol) |
| 507 | (benzothiazole-pyrimidine with Cl, 1-acetylpiperidin-4-ylamine, aminocyclopentane triol) |
| 508 | (ethyl-furopyridine-pyrimidine with Me, 2-methoxyethylamine, aminocyclopentane triol) |
| 509 | (ethyl-furopyridine-pyrimidine with Me, cyclopropylmethylamine, aminocyclopentane triol) |
| 510 | (benzothiazole-pyrimidine with Cl, piperidin-4-ylamine, aminocyclopentane triol) |

| Compd # | Structure |
|---|---|
| 511 | (ethyl-furopyridine-pyrimidine with Cl, pentylamine, aminocyclopentane triol) |
| 512 | (ethyl-furopyridine-pyrimidine with Cl, 2-ethoxyethylamine, aminocyclopentane triol) |
| 513 | (benzothiazole-pyrimidine with Me, tert-amyl amine, aminocyclopentane triol) |
| 514 | (ethyl-furopyridine-pyrimidine with Me, pentylamine, aminocyclopentane triol) |
| 515 | (ethyl-furopyridine-pyrimidine with Me, 2-ethoxyethylamine, aminocyclopentane triol) |

US 8,697,694 B2
711
-continued
| Compd # | Structure |
|---|---|
| 516 | 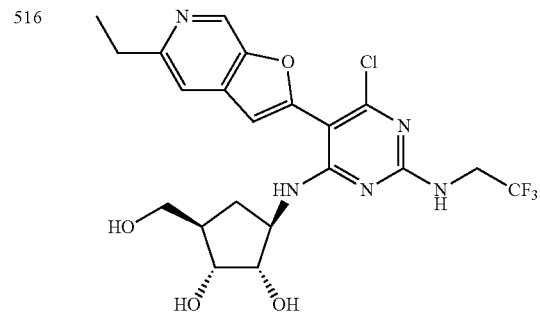 |
| 517 | 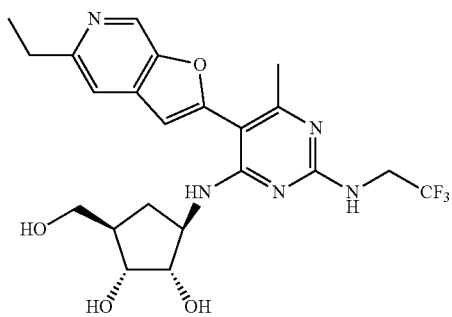 [SMILES: CCc1cc2cc(-c3c(C)nc(NCC(F)(F)F)nc3N[C@@H]3C[C@H](CO)[C@@H](O)[C@H]3O)oc2cn1] |
| 518 | 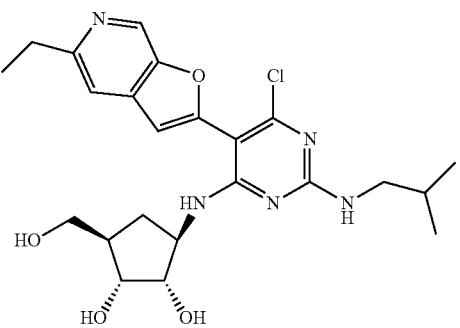 [SMILES: CCc1cc2cc(-c3c(Cl)nc(NCC(C)C)nc3N[C@@H]3C[C@H](CO)[C@@H](O)[C@H]3O)oc2cn1] |
| 519 | 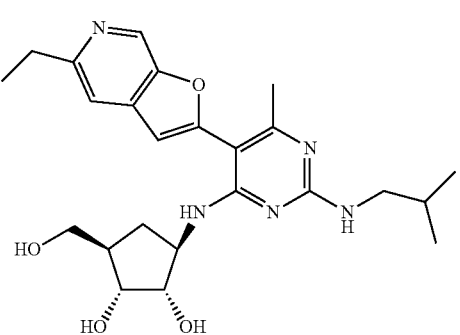 [SMILES: CCc1cc2cc(-c3c(C)nc(NCC(C)C)nc3N[C@@H]3C[C@H](CO)[C@@H](O)[C@H]3O)oc2cn1] |
712
-continued
| Compd # | Structure |
|---|---|
| 520 | 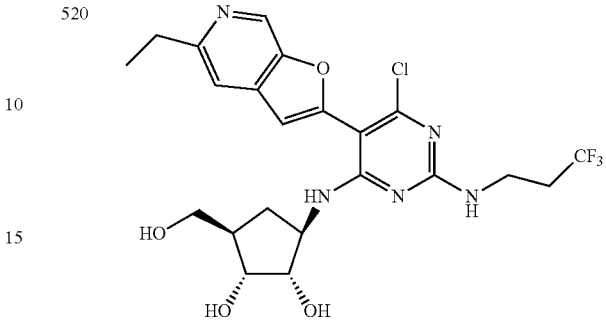 |
| 521 | 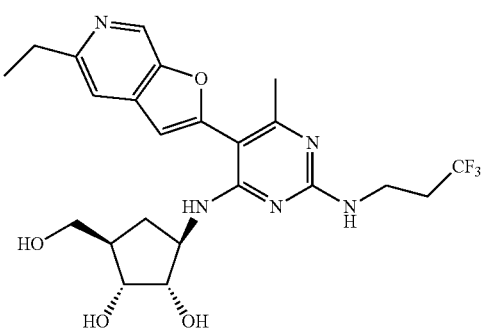 [SMILES: CCc1cc2cc(-c3c(C)nc(NCCC(F)(F)F)nc3N[C@@H]3C[C@H](CO)[C@@H](O)[C@H]3O)oc2cn1] |
| 128 | 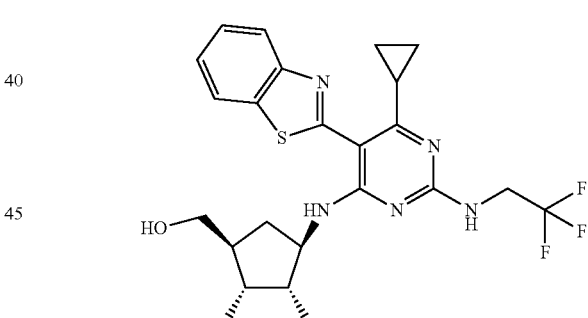 |
| 129 | 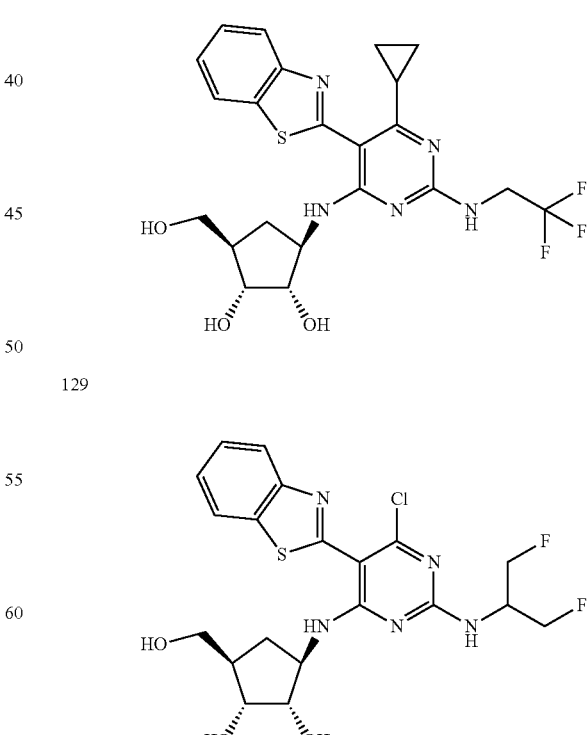 |

| Compd # | Structure |
|---|---|
| 130 | 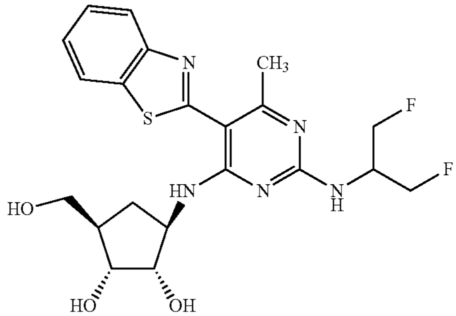 [SMILES: Cc1nc(NC(CF)CF)nc(N[C@@H]2C[C@H](CO)[C@@H](O)[C@H]2O)c1-c1nc2ccccc2s1] |
| 131 | 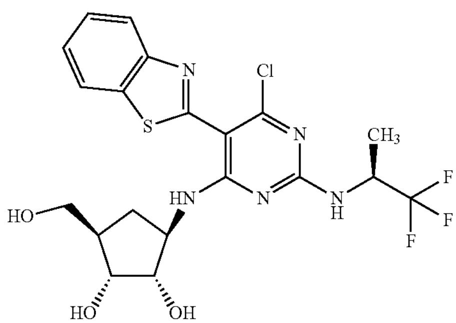 [SMILES: C[C@H](Nc1nc(Cl)c(-c2nc3ccccc3s2)c(N[C@@H]2C[C@H](CO)[C@@H](O)[C@H]2O)n1)C(F)(F)F] |
| 132 | 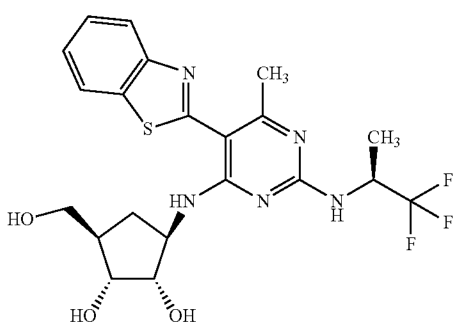 [SMILES: Cc1nc(N[C@@H](C)C(F)(F)F)nc(N[C@@H]2C[C@H](CO)[C@@H](O)[C@H]2O)c1-c1nc2ccccc2s1] |
| 133 | 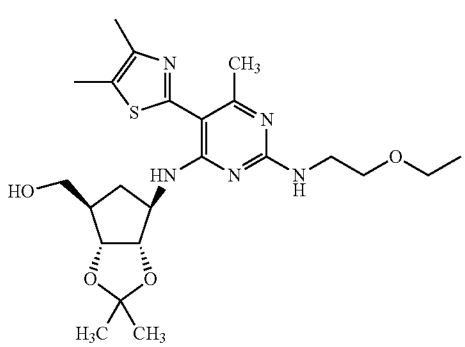 [SMILES: CCOCCNc1nc(C)c(-c2nc(C)c(C)s2)c(N[C@@H]2C[C@H](CO)[C@H]3OC(C)(C)O[C@H]32)n1] |
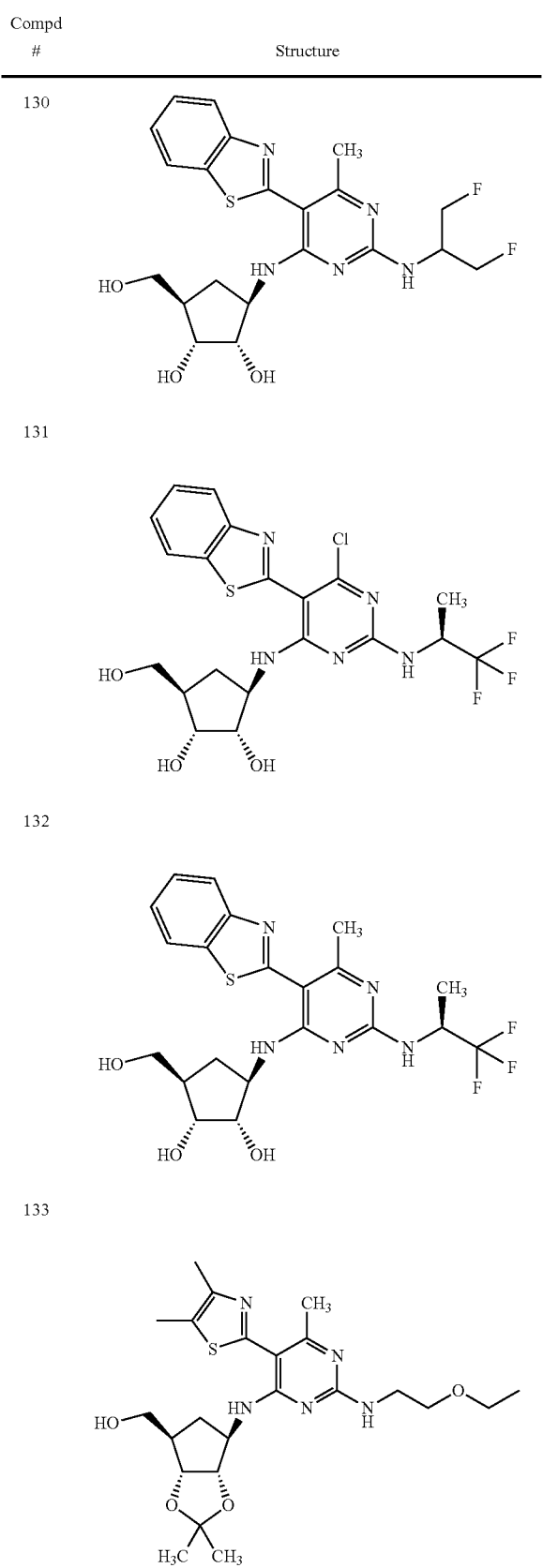
| Compd # | Structure |
|---|---|
| 134 | 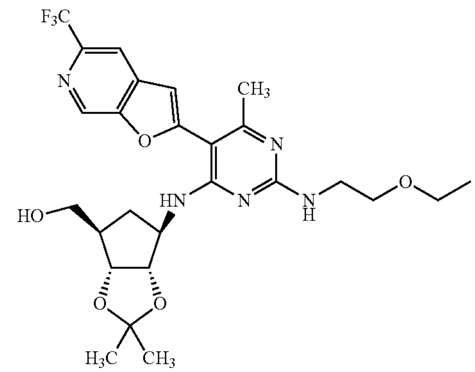 [SMILES: CCOCCNc1nc(C)c(-c2cc3cc(C(F)(F)F)ncc3o2)c(N[C@@H]2C[C@H](CO)[C@H]3OC(C)(C)O[C@H]32)n1] |
| 135 | 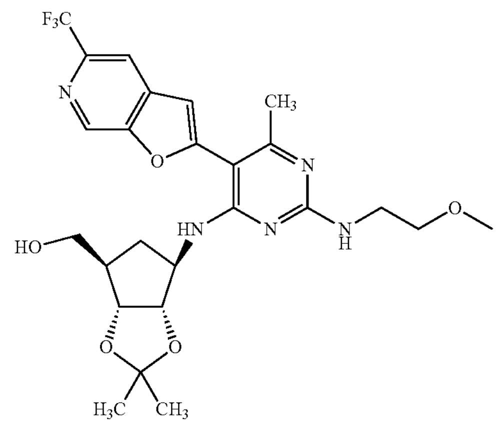 [SMILES: COCCNc1nc(C)c(-c2cc3cc(C(F)(F)F)ncc3o2)c(N[C@@H]2C[C@H](CO)[C@H]3OC(C)(C)O[C@H]32)n1] |
| 136 | 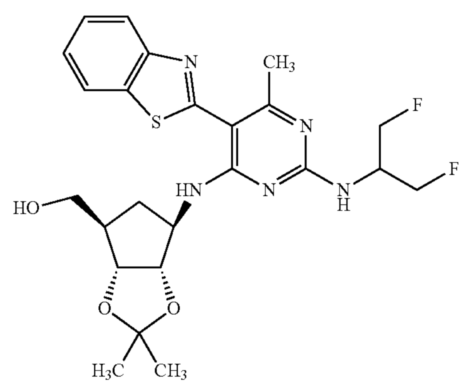 [SMILES: Cc1nc(NC(CF)CF)nc(N[C@@H]2C[C@H](CO)[C@H]3OC(C)(C)O[C@H]32)c1-c1nc2ccccc2s1] |
| 137 | 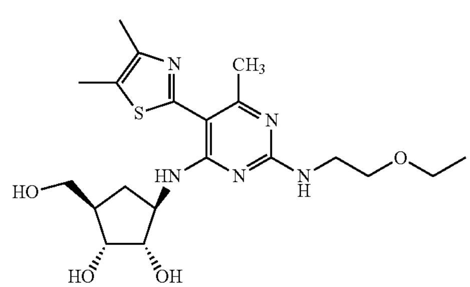 [SMILES: CCOCCNc1nc(C)c(-c2nc(C)c(C)s2)c(N[C@@H]2C[C@H](CO)[C@@H](O)[C@H]2O)n1] |
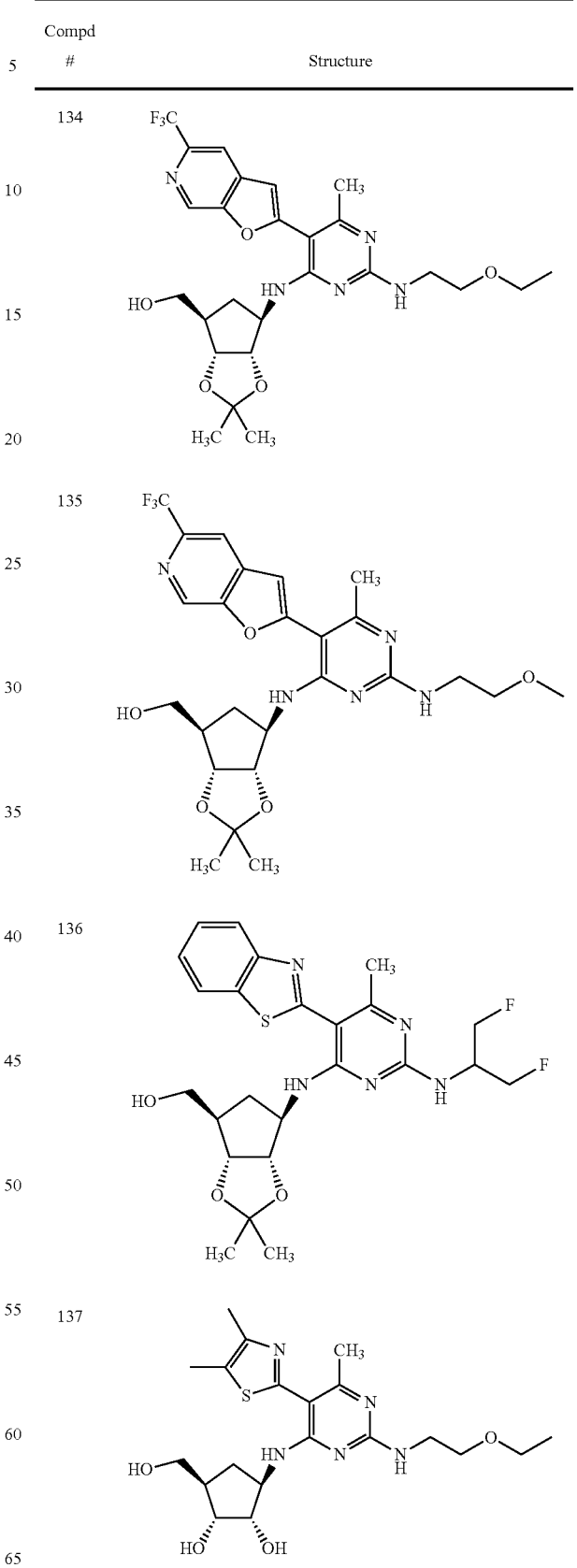

| 715 -continued | 716 -continued |
|---|---|
| Compd # 138 | Compd # 142 |
| Compd # 139 | Compd # 143 |
| Compd # 140 | Compd # 230 |
| Compd # 141 | Compd # 231 |

-continued

| Compd # | Structure |
|---|---|
| 232 | 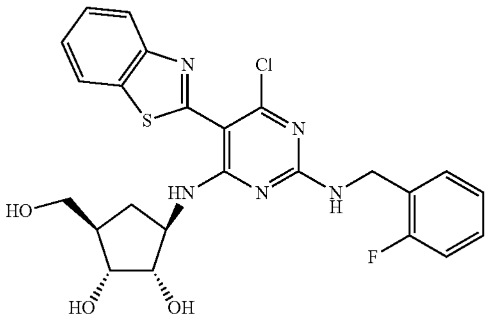 [SMILES: OC[C@H]1C[C@@H](Nc2nc(NCc3ccccc3F)nc(Cl)c2-c2nc3ccccc3s2)[C@H](O)[C@@H]1O] |
| 233 | 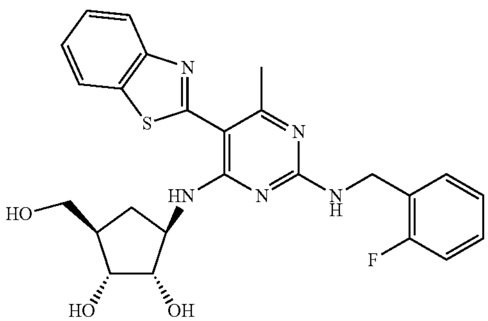 [SMILES: Cc1nc(NCc2ccccc2F)nc(N[C@@H]2C[C@H](CO)[C@@H](O)[C@H]2O)c1-c1nc2ccccc2s1] |
| 234 | 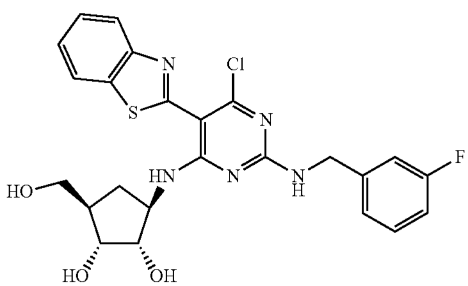 [SMILES: OC[C@H]1C[C@@H](Nc2nc(NCc3cccc(F)c3)nc(Cl)c2-c2nc3ccccc3s2)[C@H](O)[C@@H]1O] |
| 235 | 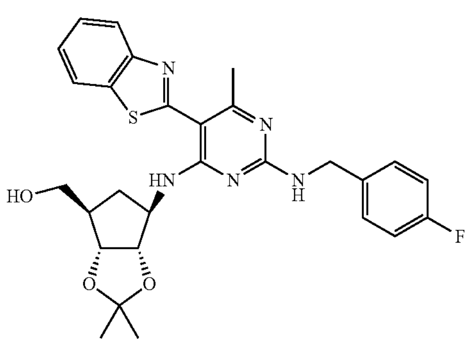 [SMILES: Cc1nc(NCc2ccc(F)cc2)nc(N[C@@H]2C[C@H](CO)[C@H]3OC(C)(C)O[C@H]32)c1-c1nc2ccccc2s1] |

-continued

| Compd # | Structure |
|---|---|
| 236 | 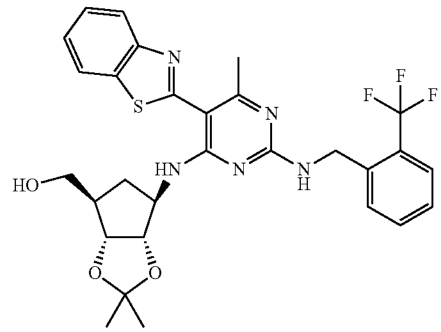 [SMILES: Cc1nc(NCc2ccccc2C(F)(F)F)nc(N[C@@H]2C[C@H](CO)[C@H]3OC(C)(C)O[C@H]32)c1-c1nc2ccccc2s1] |
| 237 | 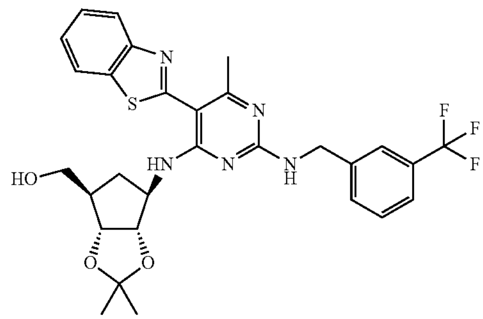 [SMILES: Cc1nc(NCc2cccc(C(F)(F)F)c2)nc(N[C@@H]2C[C@H](CO)[C@H]3OC(C)(C)O[C@H]32)c1-c1nc2ccccc2s1] |
| 238 | 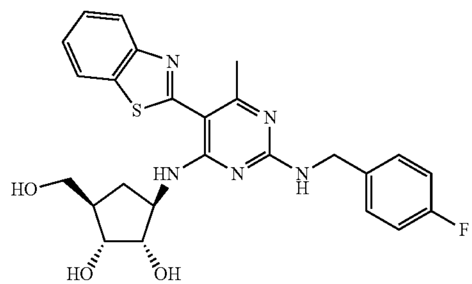 [SMILES: Cc1nc(NCc2ccc(F)cc2)nc(N[C@@H]2C[C@H](CO)[C@@H](O)[C@H]2O)c1-c1nc2ccccc2s1] |
| 239 | 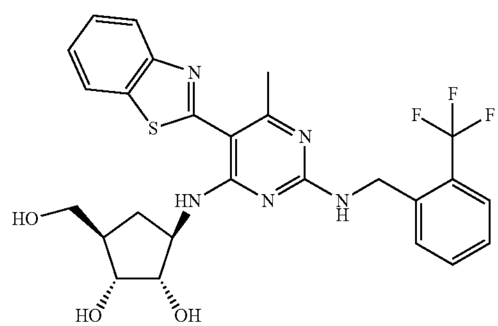 [SMILES: Cc1nc(NCc2ccccc2C(F)(F)F)nc(N[C@@H]2C[C@H](CO)[C@@H](O)[C@H]2O)c1-c1nc2ccccc2s1] |
| 240 | 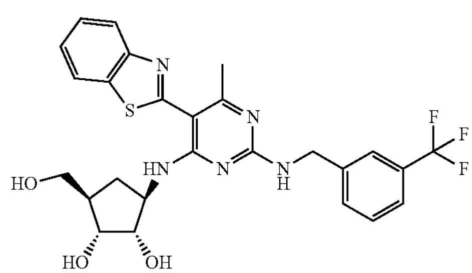 [SMILES: Cc1nc(NCc2cccc(C(F)(F)F)c2)nc(N[C@@H]2C[C@H](CO)[C@@H](O)[C@H]2O)c1-c1nc2ccccc2s1] |

| Compd # | Structure |
|---|---|
| 241 | 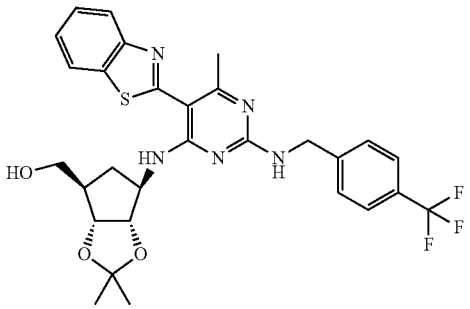 [SMILES: Cc1nc(NCc2ccc(C(F)(F)F)cc2)nc(N[C@@H]2C[C@H](CO)[C@H]3OC(C)(C)O[C@H]32)c1-c1nc2ccccc2s1] |
| 242 | 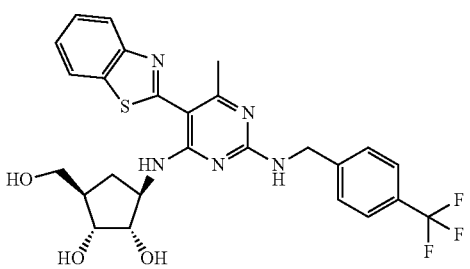 [SMILES: Cc1nc(NCc2ccc(C(F)(F)F)cc2)nc(N[C@@H]2C[C@H](CO)[C@@H](O)[C@H]2O)c1-c1nc2ccccc2s1] |
| 243 | 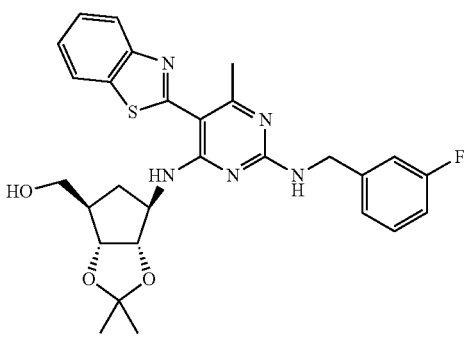 [SMILES: Cc1nc(NCc2cccc(F)c2)nc(N[C@@H]2C[C@H](CO)[C@H]3OC(C)(C)O[C@H]32)c1-c1nc2ccccc2s1] |
| 244 | 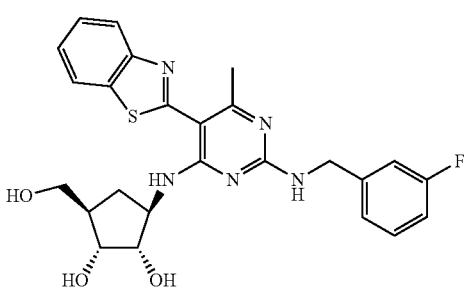 [SMILES: Cc1nc(NCc2cccc(F)c2)nc(N[C@@H]2C[C@H](CO)[C@@H](O)[C@H]2O)c1-c1nc2ccccc2s1] |
| 245 | 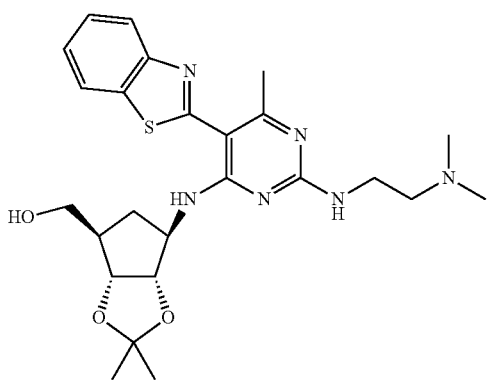 [SMILES: Cc1nc(NCCN(C)C)nc(N[C@@H]2C[C@H](CO)[C@H]3OC(C)(C)O[C@H]32)c1-c1nc2ccccc2s1] |
| Compd # | Structure |
|---|---|
| 246 | 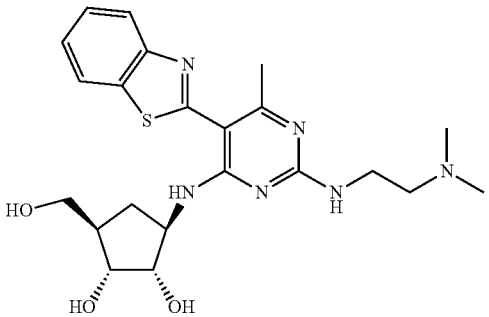 [SMILES: Cc1nc(NCCN(C)C)nc(N[C@@H]2C[C@H](CO)[C@@H](O)[C@H]2O)c1-c1nc2ccccc2s1] |
| 247 | 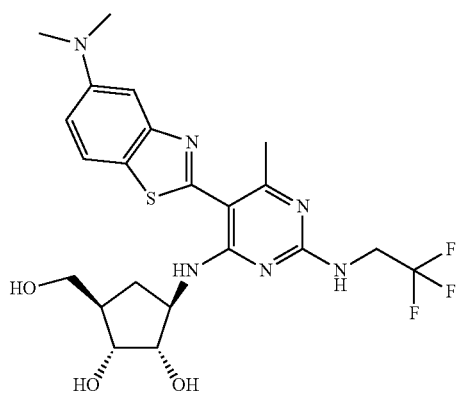 [SMILES: Cc1nc(NCC(F)(F)F)nc(N[C@@H]2C[C@H](CO)[C@@H](O)[C@H]2O)c1-c1nc2cc(N(C)C)ccc2s1] |
| 248 | 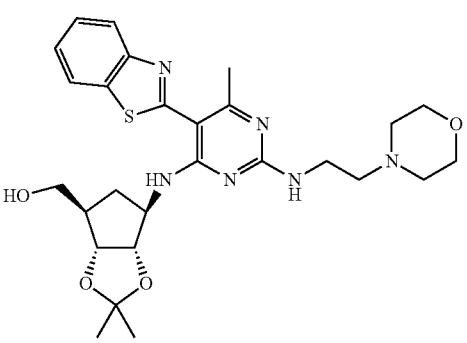 [SMILES: Cc1nc(NCCN2CCOCC2)nc(N[C@@H]2C[C@H](CO)[C@H]3OC(C)(C)O[C@H]32)c1-c1nc2ccccc2s1] |
| 249 | 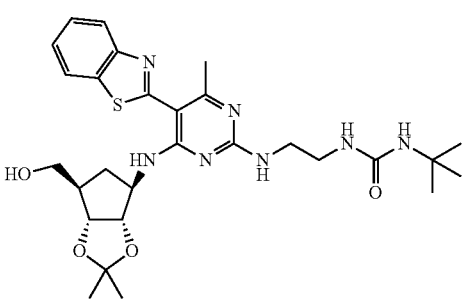 [SMILES: Cc1nc(NCCNC(=O)NC(C)(C)C)nc(N[C@@H]2C[C@H](CO)[C@H]3OC(C)(C)O[C@H]32)c1-c1nc2ccccc2s1] |

-continued

| Compd # | Structure |
|---|---|
| 250 | 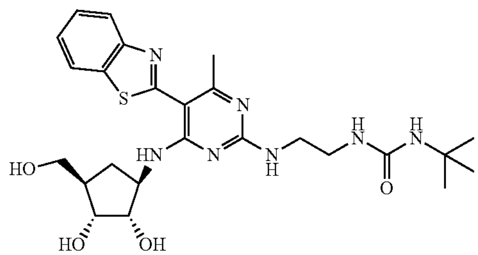 [SMILES: Cc1nc(NCCNC(=O)NC(C)(C)C)nc(N[C@@H]2C[C@H](CO)[C@@H](O)[C@H]2O)c1-c1nc2ccccc2s1] |
| 251 | 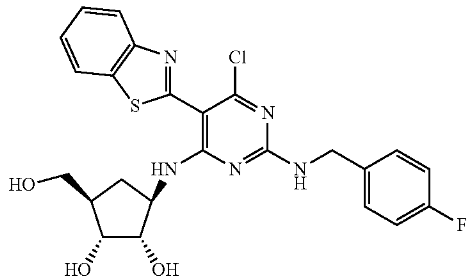 [SMILES: OC[C@H]1C[C@@H](Nc2nc(NCc3ccc(F)cc3)nc(Cl)c2-c2nc3ccccc3s2)[C@H](O)[C@@H]1O] |
| 252 | 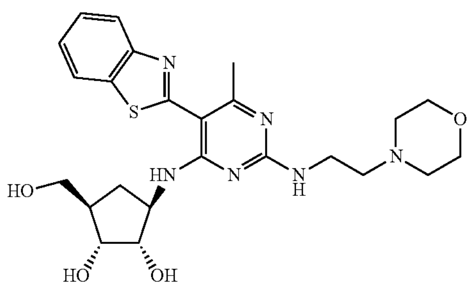 [SMILES: Cc1nc(NCCN2CCOCC2)nc(N[C@@H]2C[C@H](CO)[C@@H](O)[C@H]2O)c1-c1nc2ccccc2s1] |
| 253 | 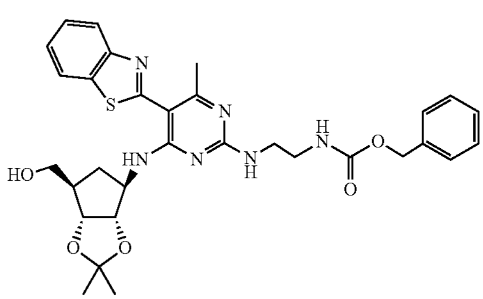 [SMILES: Cc1nc(NCCNC(=O)OCc2ccccc2)nc(N[C@@H]2C[C@H](CO)[C@H]3OC(C)(C)O[C@H]32)c1-c1nc2ccccc2s1] |
| 254 | 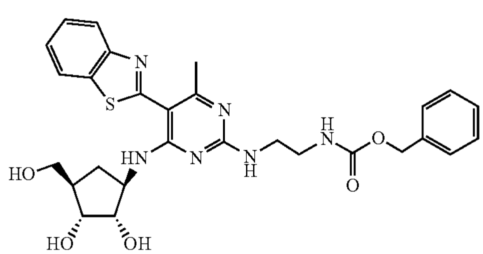 [SMILES: Cc1nc(NCCNC(=O)OCc2ccccc2)nc(N[C@@H]2C[C@H](CO)[C@@H](O)[C@H]2O)c1-c1nc2ccccc2s1] |

-continued

| Compd # | Structure |
|---|---|
| 255 | 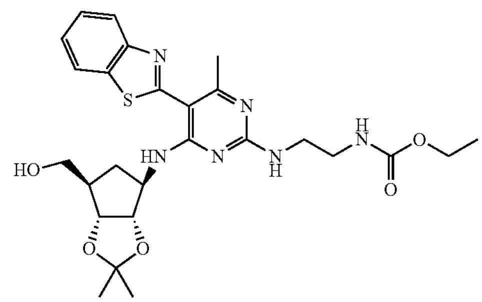 [SMILES: CCOC(=O)NCCNc1nc(C)c(-c2nc3ccccc3s2)c(N[C@@H]2C[C@H](CO)[C@H]3OC(C)(C)O[C@H]32)n1] |
| 256 | 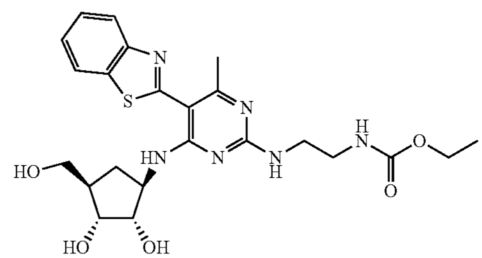 [SMILES: CCOC(=O)NCCNc1nc(C)c(-c2nc3ccccc3s2)c(N[C@@H]2C[C@H](CO)[C@@H](O)[C@H]2O)n1] |
| 257 | 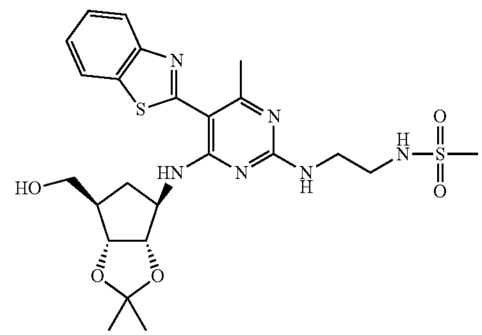 [SMILES: Cc1nc(NCCNS(C)(=O)=O)nc(N[C@@H]2C[C@H](CO)[C@H]3OC(C)(C)O[C@H]32)c1-c1nc2ccccc2s1] |
| 258 | 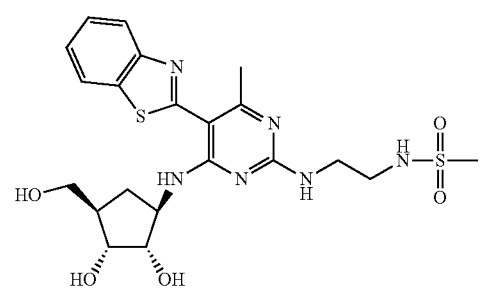 [SMILES: Cc1nc(NCCNS(C)(=O)=O)nc(N[C@@H]2C[C@H](CO)[C@@H](O)[C@H]2O)c1-c1nc2ccccc2s1] |
| 259 | 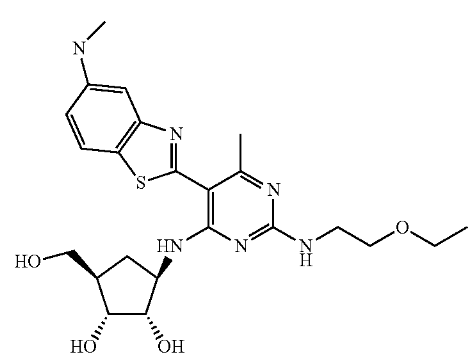 [SMILES: CCOCCNc1nc(C)c(-c2nc3cc(NC)ccc3s2)c(N[C@@H]2C[C@H](CO)[C@@H](O)[C@H]2O)n1] |

723
-continued
| Compd # | Structure |
|---|---|
| 260 | 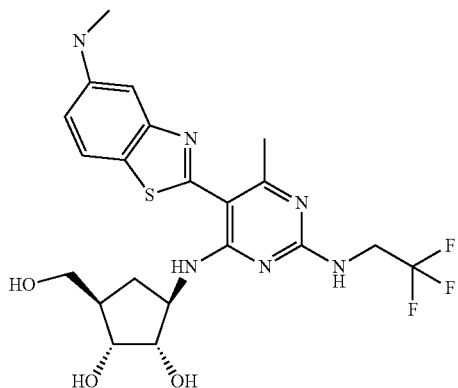 [SMILES: CNc1ccc2sc(-c3c(C)nc(NCC(F)(F)F)nc3N[C@@H]3C[C@H](CO)[C@@H](O)[C@H]3O)nc2c1] |
| 321 | 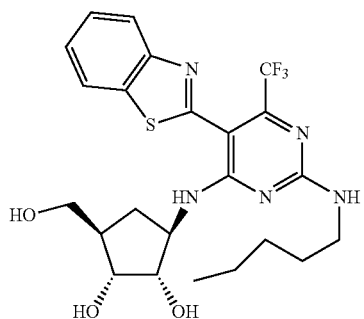 [SMILES: CCCCCNc1nc(N[C@@H]2C[C@H](CO)[C@@H](O)[C@H]2O)c(-c2nc3ccccc3s2)c(C(F)(F)F)n1] |
| 322 | 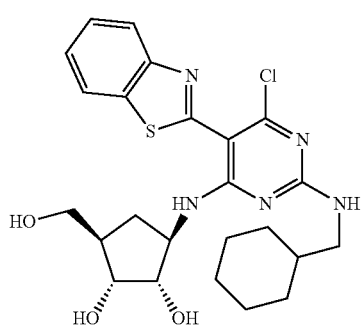 [SMILES: OC[C@H]1C[C@@H](Nc2nc(NCC3CCCCC3)nc(Cl)c2-c2nc3ccccc3s2)[C@H](O)[C@@H]1O] |
| 323 | 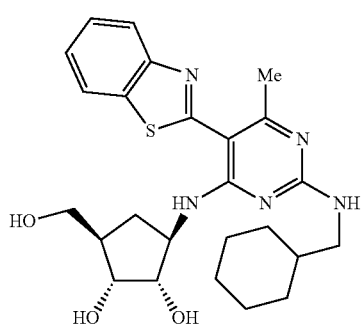 [SMILES: Cc1nc(NCC2CCCCC2)nc(N[C@@H]2C[C@H](CO)[C@@H](O)[C@H]2O)c1-c1nc2ccccc2s1] |
724
-continued
| Compd # | Structure |
|---|---|
| 324 | 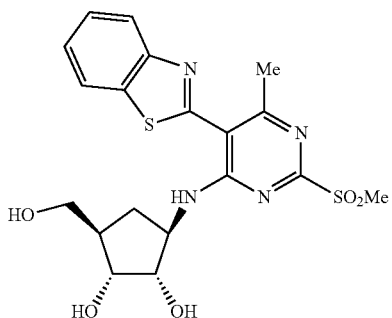 [SMILES: Cc1nc(S(C)(=O)=O)nc(N[C@@H]2C[C@H](CO)[C@@H](O)[C@H]2O)c1-c1nc2ccccc2s1] |
| 325 | 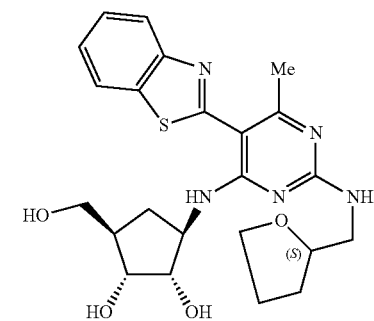 |
| 326 | 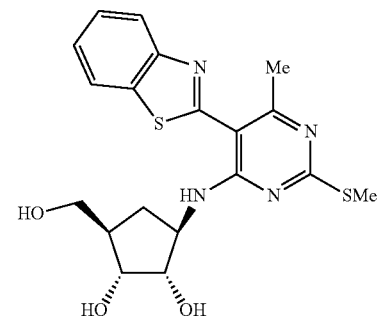 [SMILES: CSc1nc(C)c(-c2nc3ccccc3s2)c(N[C@@H]2C[C@H](CO)[C@@H](O)[C@H]2O)n1] |
| 327 | 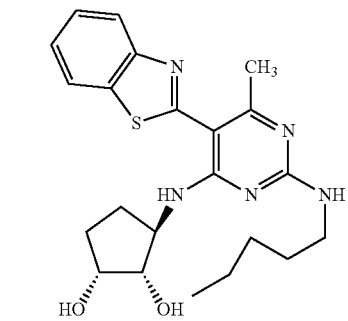 [SMILES: CCCCCNc1nc(C)c(-c2nc3ccccc3s2)c(N[C@@H]2CC[C@@H](O)[C@H]2O)n1] |

| Compd # | Structure |
|---|---|
| 328 | 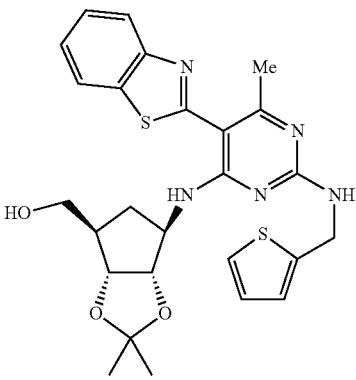 [SMILES: Cc1nc(NCc2cccs2)nc(N[C@@H]2C[C@H](CO)[C@H]3OC(C)(C)O[C@H]32)c1-c1nc2ccccc2s1] |
| 329 | 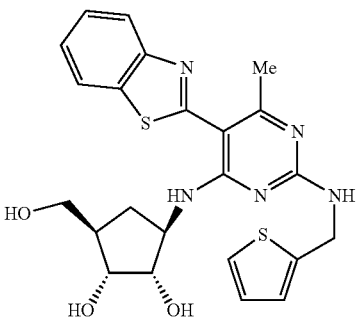 [SMILES: Cc1nc(NCc2cccs2)nc(N[C@@H]2C[C@H](CO)[C@@H](O)[C@H]2O)c1-c1nc2ccccc2s1] |
| 330 | 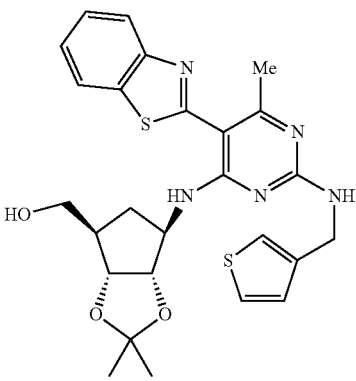 [SMILES: Cc1nc(NCc2ccsc2)nc(N[C@@H]2C[C@H](CO)[C@H]3OC(C)(C)O[C@H]32)c1-c1nc2ccccc2s1] |
| 331 | 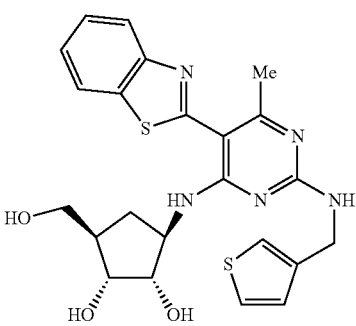 [SMILES: Cc1nc(NCc2ccsc2)nc(N[C@@H]2C[C@H](CO)[C@@H](O)[C@H]2O)c1-c1nc2ccccc2s1] |
| Compd # | Structure |
|---|---|
| 332 | 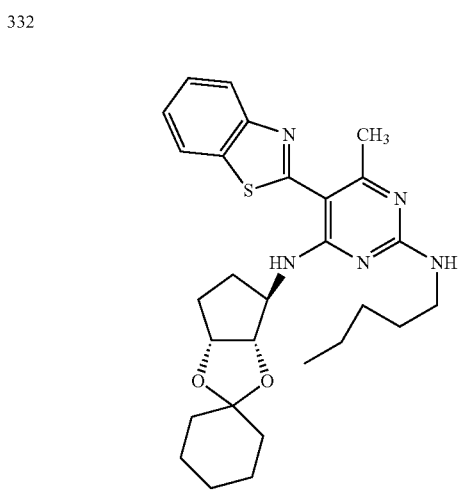 |
| 333 | 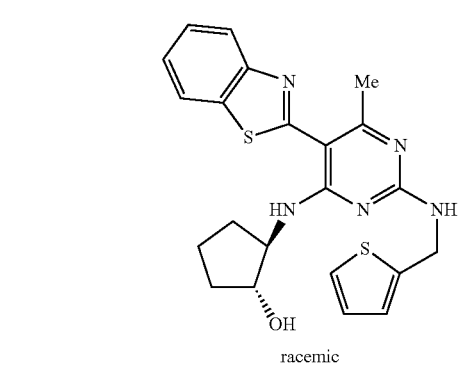 [SMILES: Cc1nc(NCc2cccs2)nc(N[C@@H]2CCC[C@H]2O)c1-c1nc2ccccc2s1]<br>racemic |
| 334 | 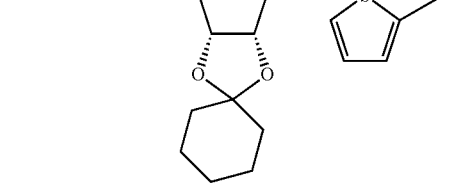 |

-continued

| Compd # | Structure |
|---|---|
| 335 | 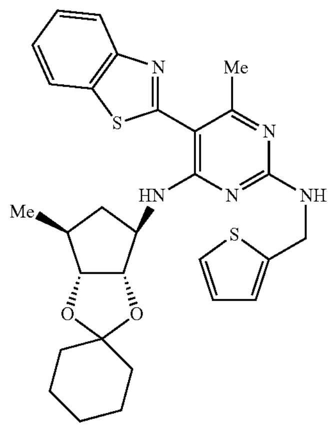 [SMILES: Cc1nc(NCc2cccs2)nc(N[C@@H]2C[C@H](C)[C@H]3OC4(CCCCC4)O[C@H]32)c1-c1nc2ccccc2s1] |
| 336 | 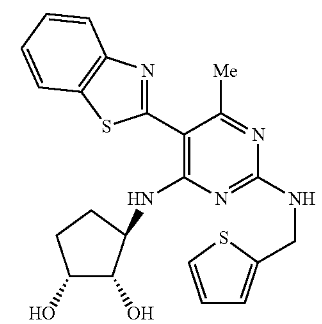 [SMILES: Cc1nc(NCc2cccs2)nc(N[C@@H]2CC[C@@H](O)[C@H]2O)c1-c1nc2ccccc2s1] |
| 337 | 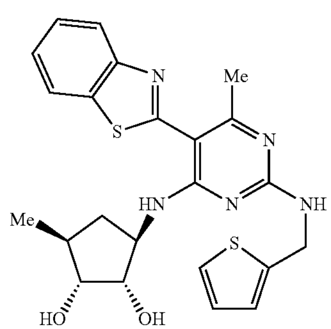 [SMILES: Cc1nc(NCc2cccs2)nc(N[C@@H]2C[C@H](C)[C@@H](O)[C@H]2O)c1-c1nc2ccccc2s1] |
| 338 | racemic |

-continued

| Compd # | Structure |
|---|---|
| 339 | 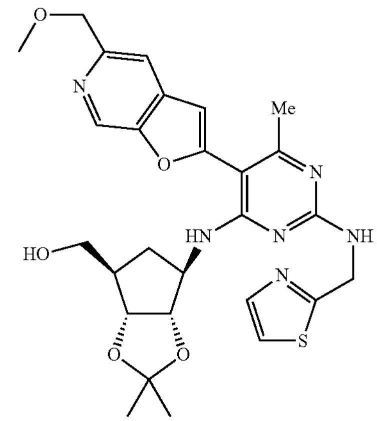 [SMILES: COCc1cc2cc(-c3c(C)nc(NCc4nccs4)nc3N[C@@H]3C[C@H](CO)[C@H]4OC(C)(C)O[C@H]43)oc2cn1] |
| 340 | 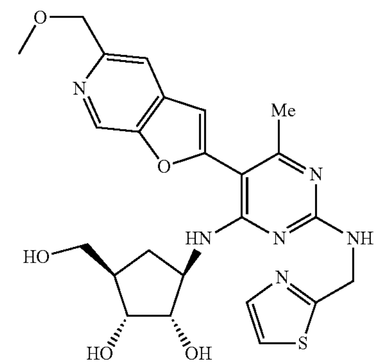 [SMILES: COCc1cc2cc(-c3c(C)nc(NCc4nccs4)nc3N[C@@H]3C[C@H](CO)[C@@H](O)[C@H]3O)oc2cn1] |
| 341 | 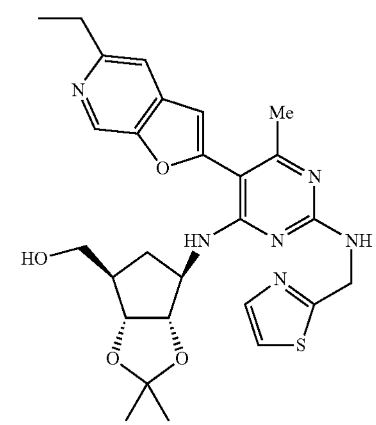 [SMILES: CCc1cc2cc(-c3c(C)nc(NCc4nccs4)nc3N[C@@H]3C[C@H](CO)[C@H]4OC(C)(C)O[C@H]43)oc2cn1] |
| 342 | 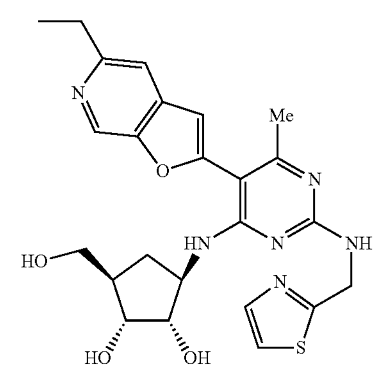 [SMILES: CCc1cc2cc(-c3c(C)nc(NCc4nccs4)nc3N[C@@H]3C[C@H](CO)[C@@H](O)[C@H]3O)oc2cn1] |

| 729 -continued | 730 -continued |
|---|---|
| Compd # Structure | Compd # Structure |
| 343 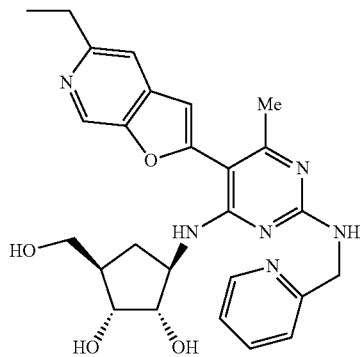 [SMILES: CCc1cc2cc(-c3c(C)nc(NCc4ccccn4)nc3N[C@@H]3C[C@H](CO)[C@@H](O)[C@H]3O)oc2cn1] | 347 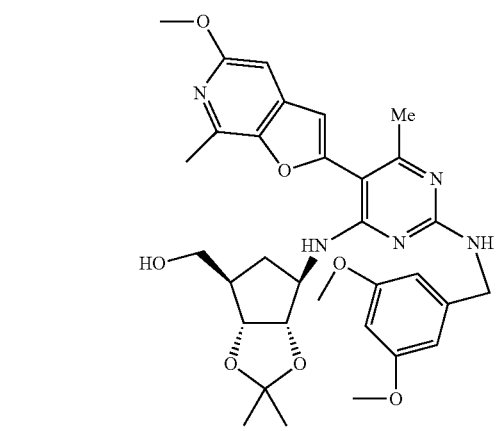 |
| 344 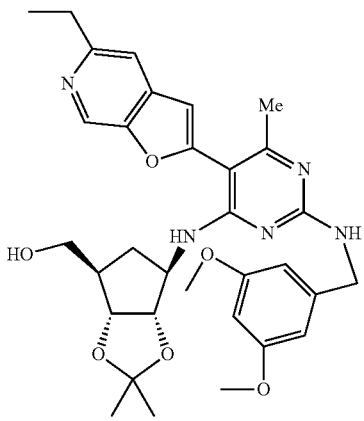 [SMILES: CCc1cc2cc(-c3c(C)nc(NCc4cc(OC)cc(OC)c4)nc3N[C@@H]3C[C@H](CO)[C@H]4OC(C)(C)O[C@H]43)oc2cn1] | 348 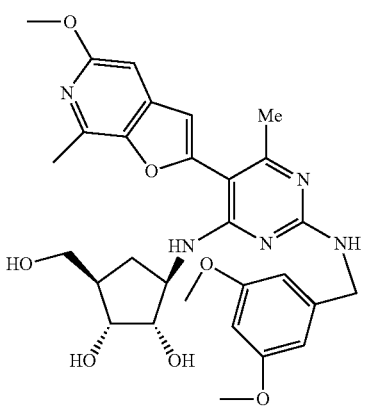 |
| 345 | |
| 346 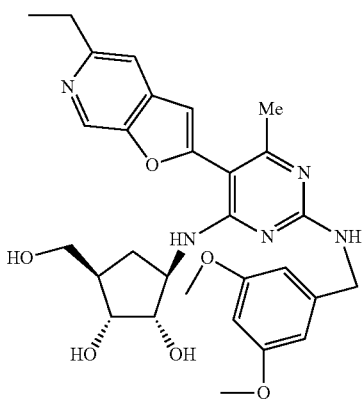 [SMILES: CCc1cc2cc(-c3c(C)nc(NCc4cc(OC)cc(OC)c4)nc3N[C@@H]3C[C@H](CO)[C@@H](O)[C@H]3O)oc2cn1] | 349 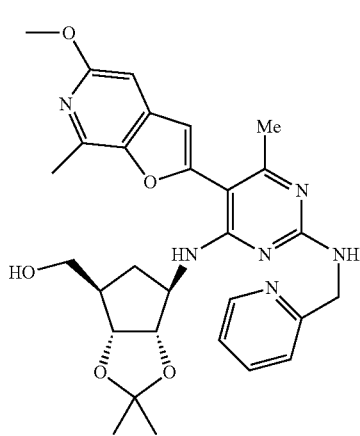 [SMILES: COc1cc2cc(-c3c(C)nc(NCc4ccccn4)nc3N[C@@H]3C[C@H](CO)[C@H]4OC(C)(C)O[C@H]43)oc2c(C)n1] |

-continued
| Compd # | Structure |
|---|---|
| 350 | 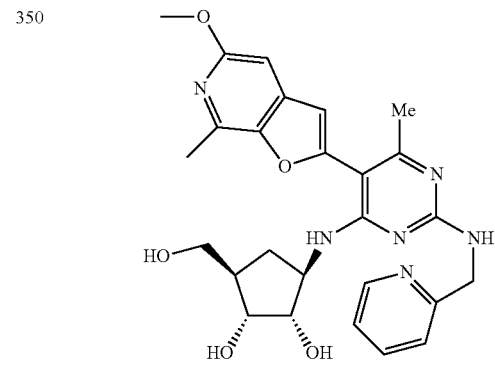 |
| 351 | 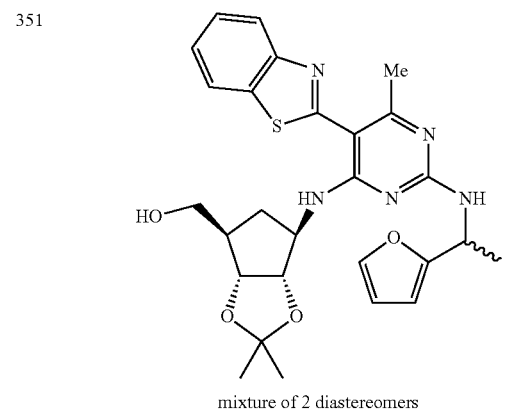
mixture of 2 diastereomers |
| 442 | 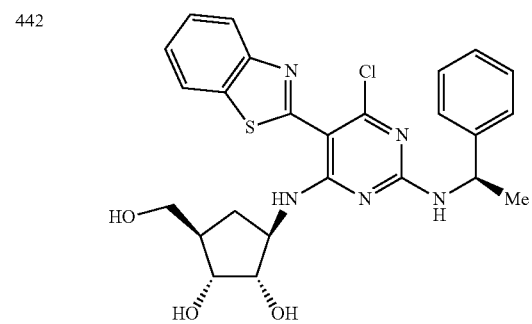 |
| 443 | 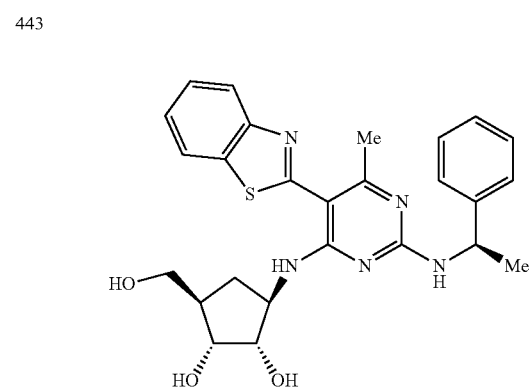 |
-continued
| Compd # | Structure |
|---|---|
| 444 | 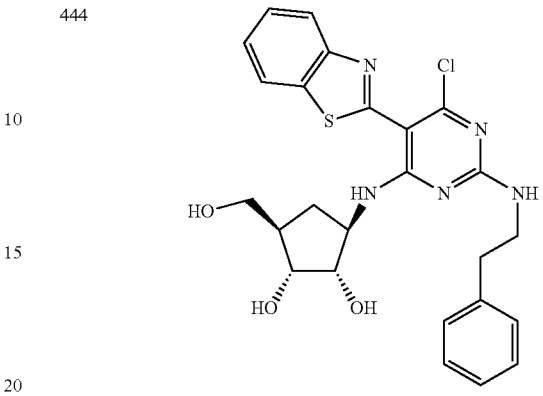 |
| 445 | 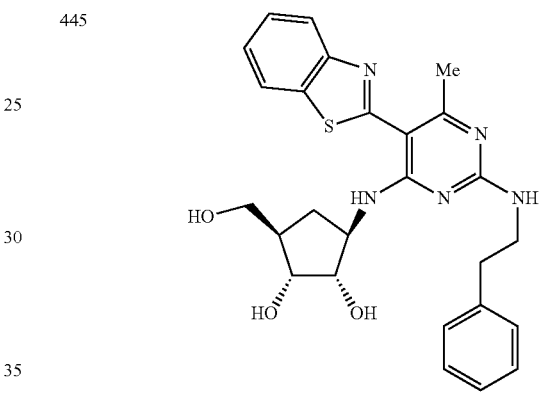 |
| 446 | 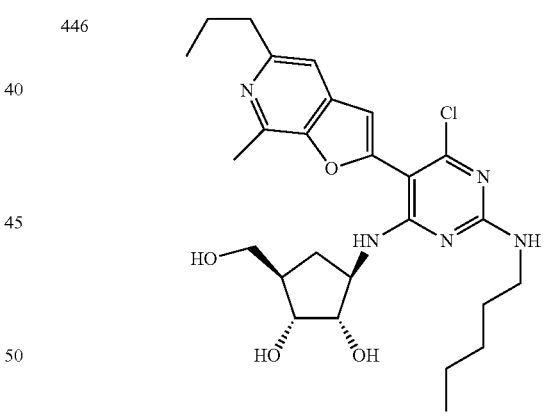 |
| 447 | 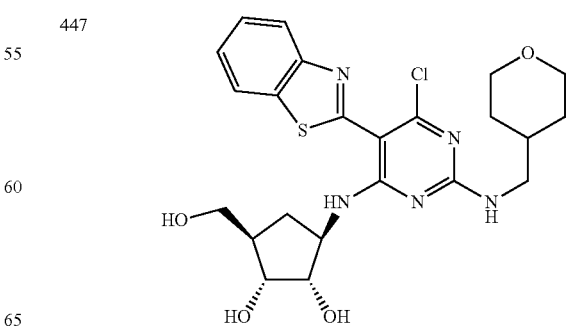 |

733
-continued
| Compd # | Structure |
|---|---|
| 448 | 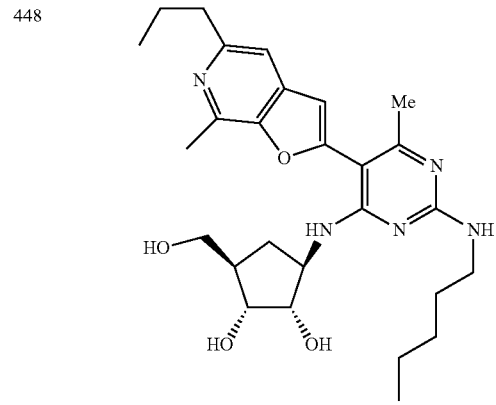 |
| 449 | 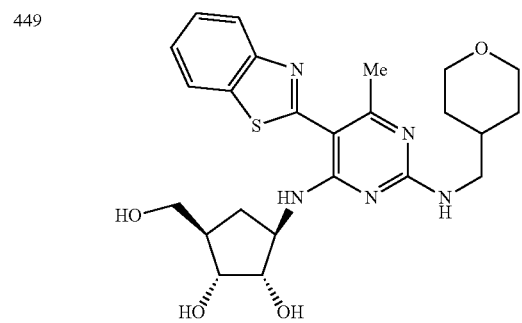 |
| 450 | 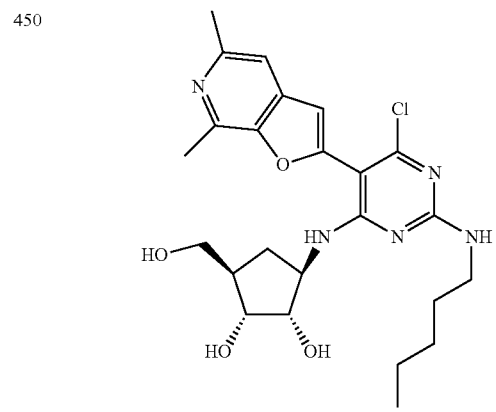 |
| 451 | 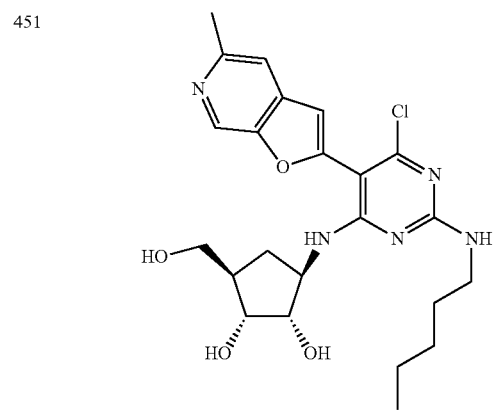 |
734
-continued
| Compd # | Structure |
|---|---|
| 452 | 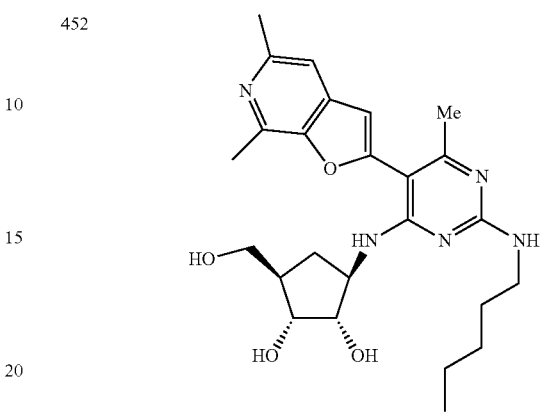 |
| 453 | 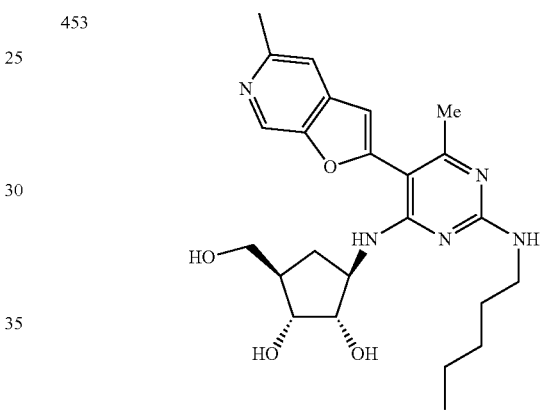 |
| 454 | 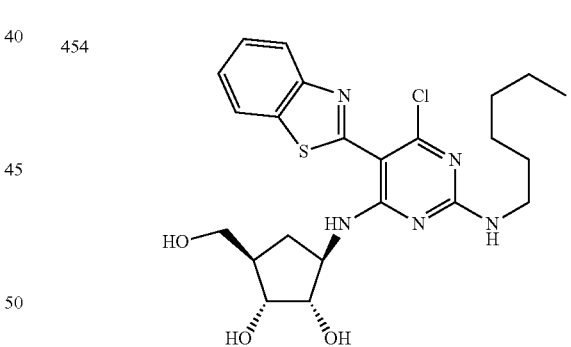 |
| 455 | 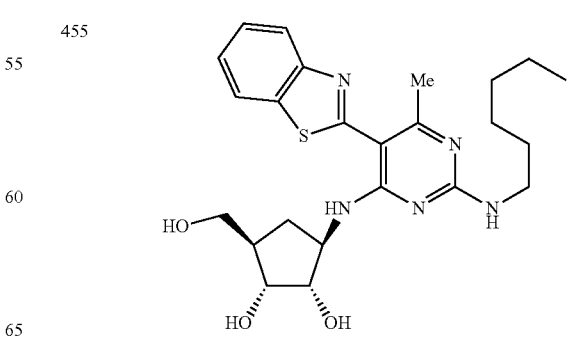 |

735
-continued

| Compd # | Structure |
|---|---|
| 456 | (structure) |
| 457 | (structure) |
| 458 | (structure) |
| 459 | (structure) |

736
-continued

| Compd # | Structure |
|---|---|
| 460 | (structure) |
| 461 | (structure) |
| 462 | (structure) |
| 463 | (structure) |

| Compd # | Structure |
|---|---|
| 464 | 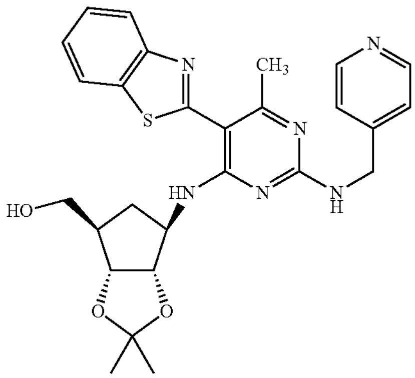 [SMILES: Cc1nc(NCc2ccncc2)nc(N[C@@H]2C[C@H](CO)[C@H]3OC(C)(C)O[C@H]32)c1-c1nc2ccccc2s1] |
| 465 | 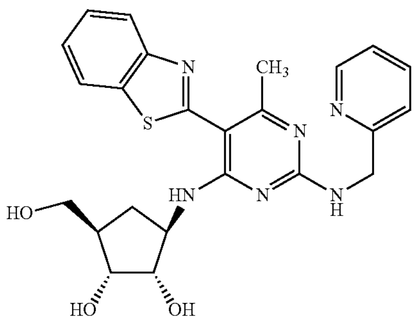 |
| 466 | 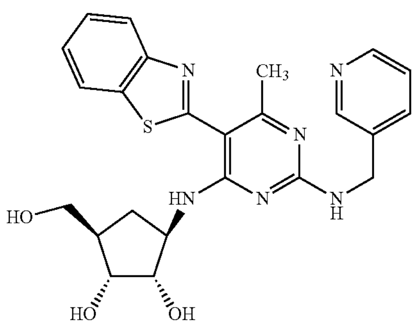 [SMILES: Cc1nc(NCc2cccnc2)nc(N[C@@H]2C[C@H](CO)[C@@H](O)[C@H]2O)c1-c1nc2ccccc2s1] |
| 467 | 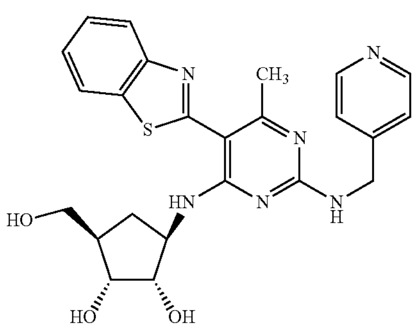 [SMILES: Cc1nc(NCc2ccncc2)nc(N[C@@H]2C[C@H](CO)[C@@H](O)[C@H]2O)c1-c1nc2ccccc2s1] |

| Compd # | Structure |
|---|---|
| 468 | 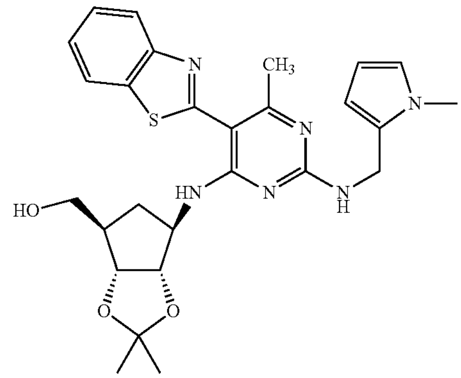 [SMILES: Cc1nc(NCc2cccn2C)nc(N[C@@H]2C[C@H](CO)[C@H]3OC(C)(C)O[C@H]32)c1-c1nc2ccccc2s1] |
| 469 | 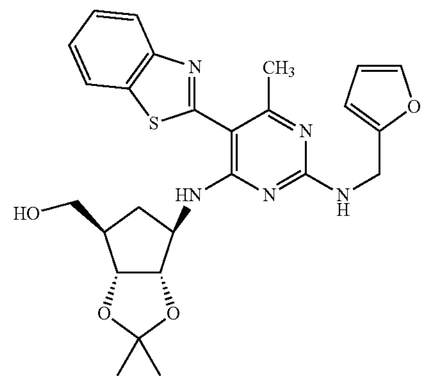 [SMILES: Cc1nc(NCc2ccco2)nc(N[C@@H]2C[C@H](CO)[C@H]3OC(C)(C)O[C@H]32)c1-c1nc2ccccc2s1] |
| 470 | 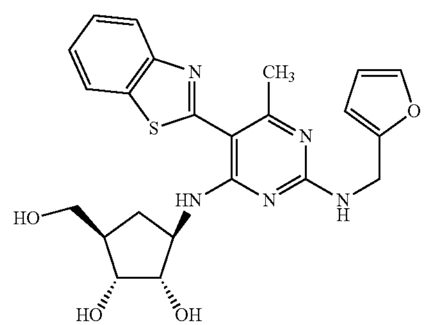 [SMILES: Cc1nc(NCc2ccco2)nc(N[C@@H]2C[C@H](CO)[C@@H](O)[C@H]2O)c1-c1nc2ccccc2s1] |
| 471 | 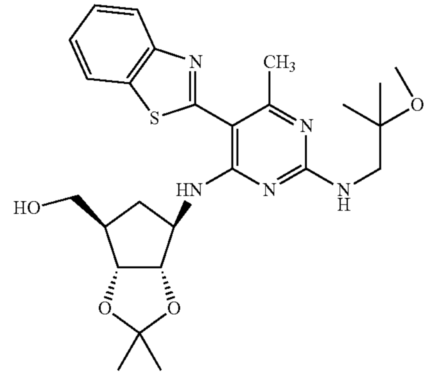 [SMILES: COC(C)(C)CNc1nc(C)c(-c2nc3ccccc3s2)c(N[C@@H]2C[C@H](CO)[C@H]3OC(C)(C)O[C@H]32)n1] |

| Compd # | Structure |
|---|---|
| 472 | 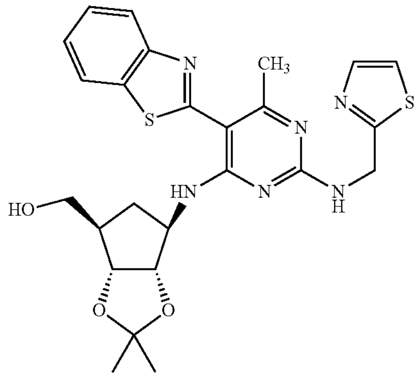 |
| 473 | 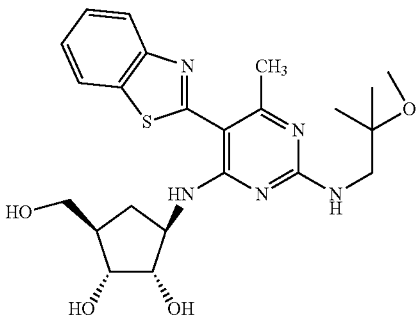 [SMILES: COC(C)(C)CNc1nc(C)c(-c2nc3ccccc3s2)c(N[C@@H]2C[C@H](CO)[C@@H](O)[C@H]2O)n1] |
| 474 | 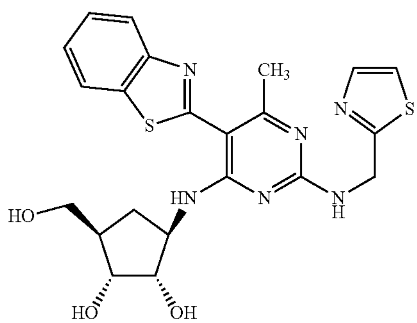 |
| 475 | 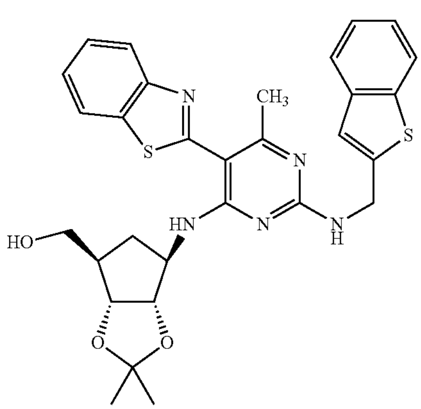 [SMILES: Cc1nc(NCc2cc3ccccc3s2)nc(N[C@@H]2C[C@H](CO)[C@H]3OC(C)(C)O[C@H]32)c1-c1nc2ccccc2s1] |
| 476 | |
| 477 | |
| 478 | |
| 479 | |

US 8,697,694 B2

| 741 -continued | 742 -continued |
|---|---|
| Compd # Structure | Compd # Structure |
| 480 | 484 |
| 481 | 485 |
| 482 | 486 |
| 483 | 487 |

743
-continued
| Compd # | Structure |
|---|---|
| 488 | 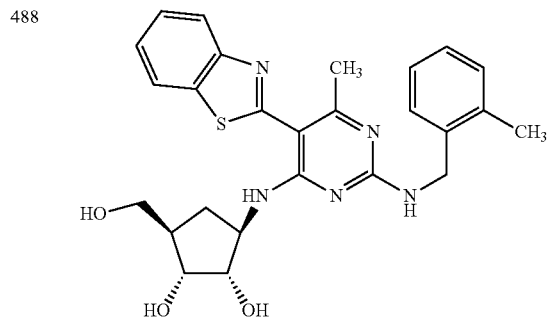 |
| 489 | 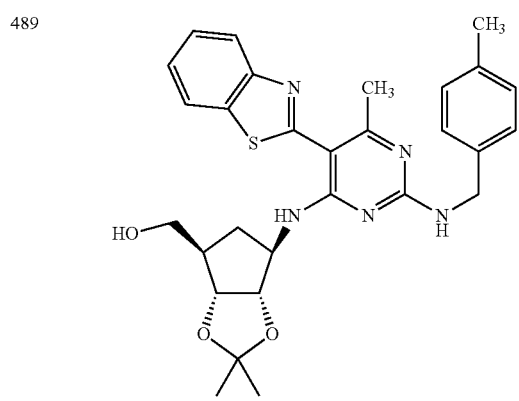 |
| 490 | 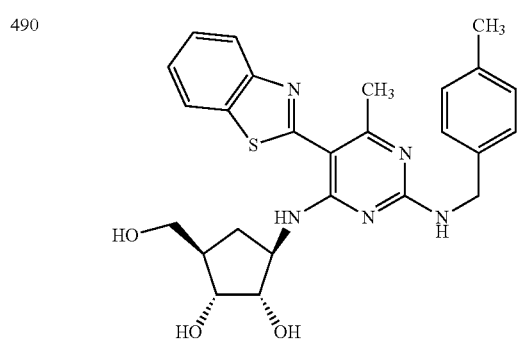 |
| 491 | 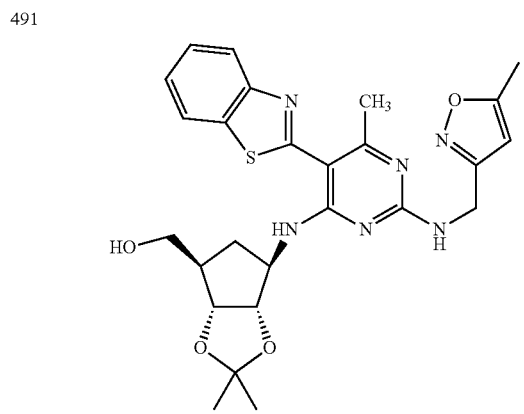 |
744
-continued
| Compd # | Structure |
|---|---|
| 492 | 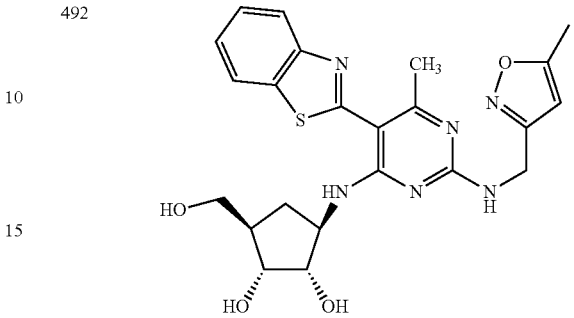 |
| 493 | 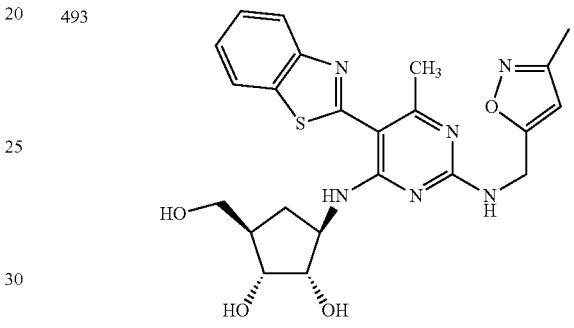 |
| 494 | 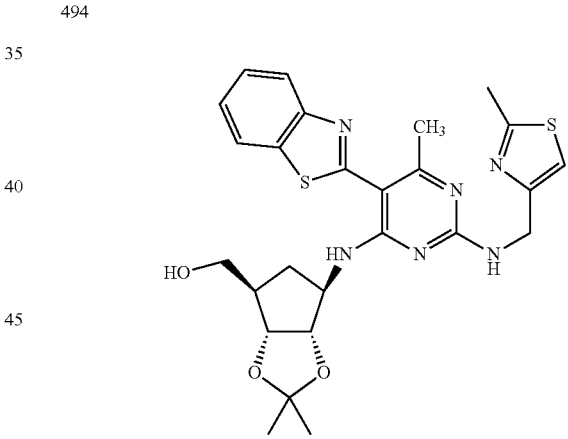 |
| 495 | 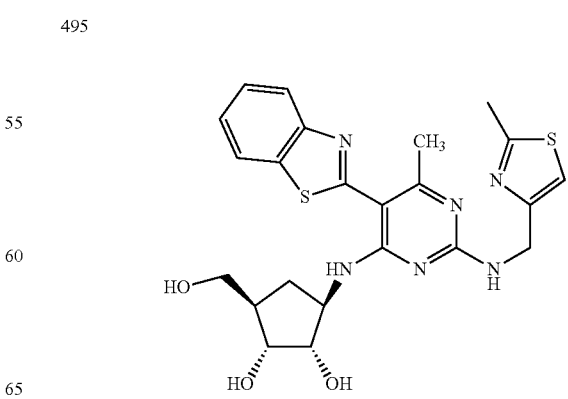 |

| Compd # | Structure |
|---|---|
| 496 | (structure) |
| 497 | (structure) |
| 498 | (structure) |
| 499 | (structure) |
| 500 | (structure) |
| 701 | (structure) |
| 702 | (structure) |
| 703 | (structure) |

| Compd # | Structure |
|---|---|
| 704 | 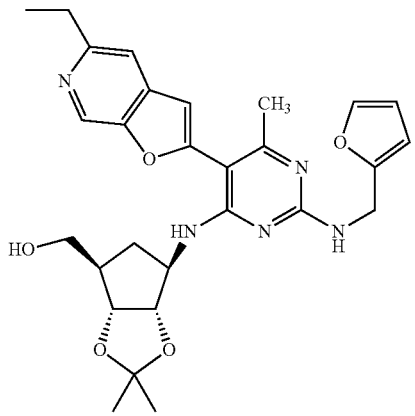 [SMILES: CCc1cc2cc(-c3c(C)nc(NCc4ccco4)nc3N[C@@H]3C[C@H](CO)[C@H]4OC(C)(C)O[C@H]43)oc2cn1] |
| 705 | 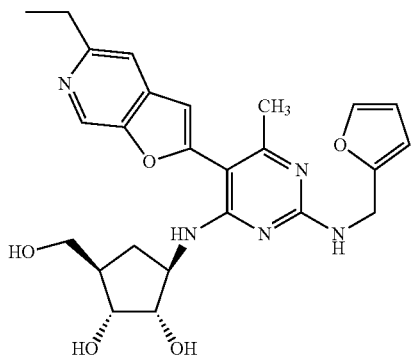 [SMILES: CCc1cc2cc(-c3c(C)nc(NCc4ccco4)nc3N[C@@H]3C[C@H](CO)[C@@H](O)[C@H]3O)oc2cn1] |
| 706 | 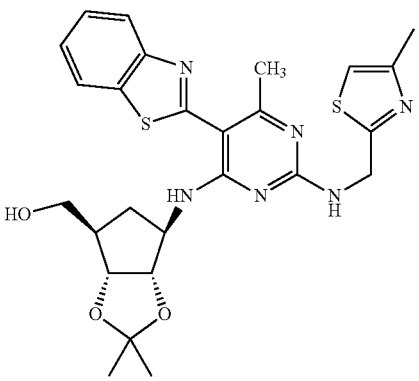 [SMILES: Cc1csc(CNc2nc(C)c(-c3nc4ccccc4s3)c(N[C@@H]3C[C@H](CO)[C@H]4OC(C)(C)O[C@H]43)n2)n1] |
| 707 | 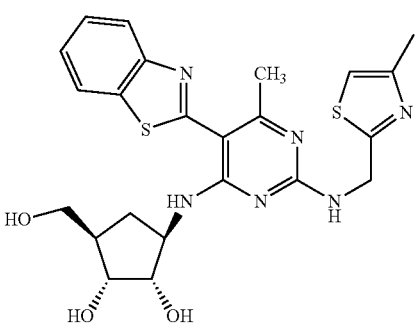 [SMILES: Cc1csc(CNc2nc(C)c(-c3nc4ccccc4s3)c(N[C@@H]3C[C@H](CO)[C@@H](O)[C@H]3O)n2)n1] |
| Compd # | Structure |
|---|---|
| 708 | 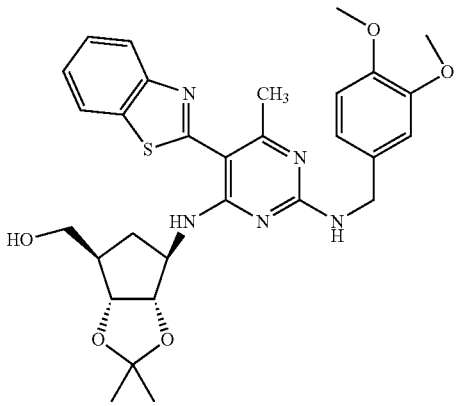 [SMILES: COc1ccc(CNc2nc(C)c(-c3nc4ccccc4s3)c(N[C@@H]3C[C@H](CO)[C@H]4OC(C)(C)O[C@H]43)n2)cc1OC] |
| 709 | 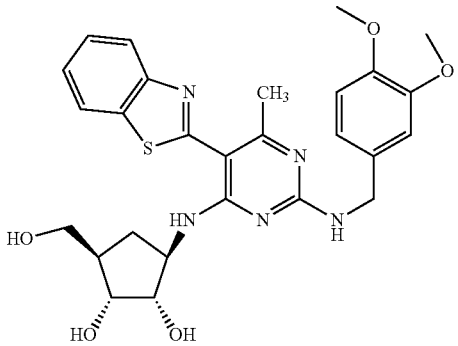 [SMILES: COc1ccc(CNc2nc(C)c(-c3nc4ccccc4s3)c(N[C@@H]3C[C@H](CO)[C@@H](O)[C@H]3O)n2)cc1OC] |
| 710 | 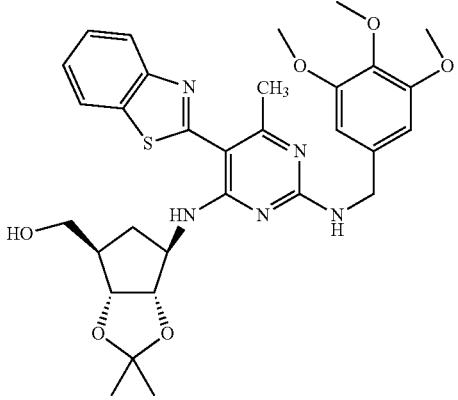 [SMILES: COc1cc(CNc2nc(C)c(-c3nc4ccccc4s3)c(N[C@@H]3C[C@H](CO)[C@H]4OC(C)(C)O[C@H]43)n2)cc(OC)c1OC] |
| 711 | 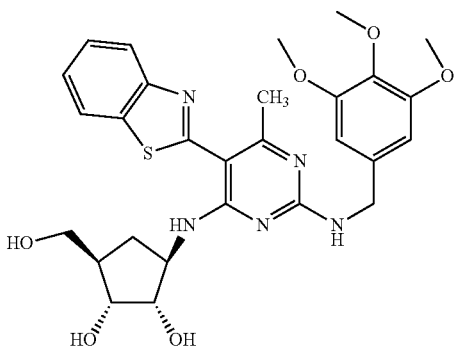 [SMILES: COc1cc(CNc2nc(C)c(-c3nc4ccccc4s3)c(N[C@@H]3C[C@H](CO)[C@@H](O)[C@H]3O)n2)cc(OC)c1OC] |

| Compd # | Structure |
|---------|-----------|
| 712 | 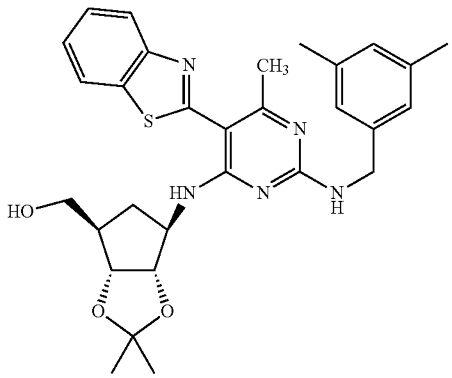 [SMILES: Cc1cc(C)cc(CNc2nc(C)c(-c3nc4ccccc4s3)c(N[C@@H]3C[C@H](CO)[C@H]4OC(C)(C)O[C@H]43)n2)c1] |
| 713 | 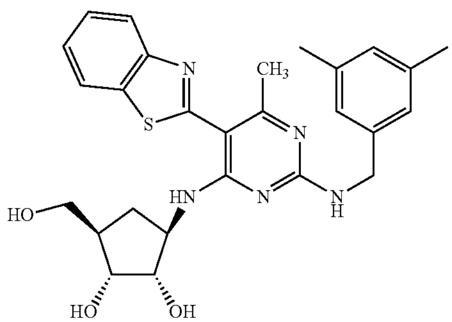 [SMILES: Cc1cc(C)cc(CNc2nc(C)c(-c3nc4ccccc4s3)c(N[C@@H]3C[C@H](CO)[C@@H](O)[C@H]3O)n2)c1] |
| 714 | 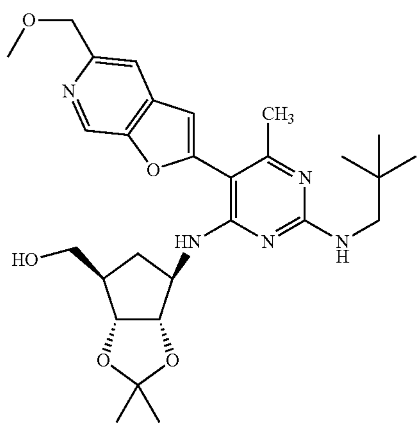 [SMILES: COCc1cc2cc(-c3c(C)nc(NCC(C)(C)C)nc3N[C@@H]3C[C@H](CO)[C@H]4OC(C)(C)O[C@H]43)oc2cn1] |
| 715 | 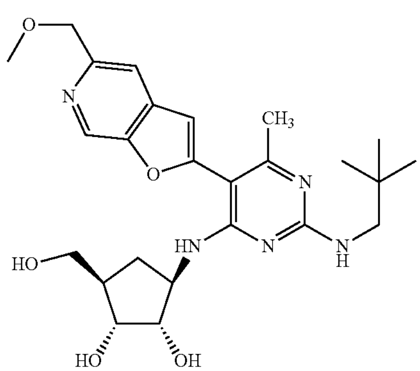 [SMILES: COCc1cc2cc(-c3c(C)nc(NCC(C)(C)C)nc3N[C@@H]3C[C@H](CO)[C@@H](O)[C@H]3O)oc2cn1] |
| 716 | |
| 717 | |
| 522 | |
| 523 | |

| Compd # | Structure |
|---|---|
| 524 | 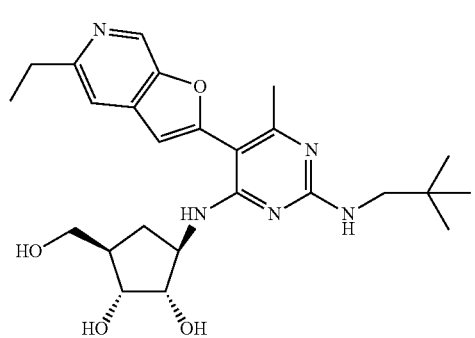 [SMILES: CCc1cc2cc(-c3c(C)nc(NCC(C)(C)C)nc3N[C@@H]3C[C@H](CO)[C@@H](O)[C@H]3O)oc2cn1] |
| 524 | 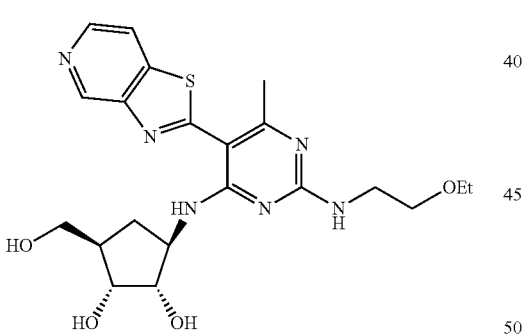 |
| 525 | 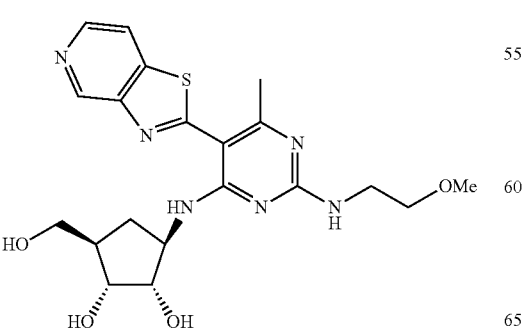 |
| Compd # | Structure |
|---|---|
| 527 | 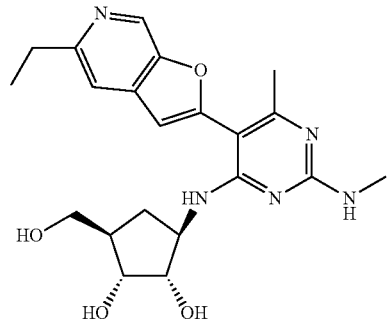 [SMILES: CCc1cc2cc(-c3c(C)nc(NC)nc3N[C@@H]3C[C@H](CO)[C@@H](O)[C@H]3O)oc2cn1] |
| 528 | 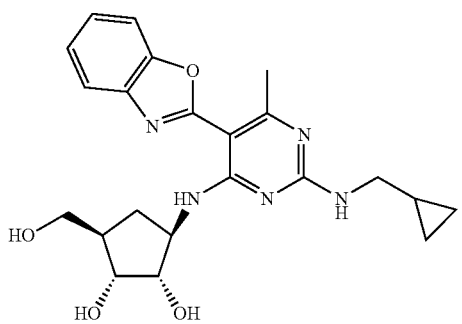 [SMILES: Cc1nc(NCC2CC2)nc(N[C@@H]2C[C@H](CO)[C@@H](O)[C@H]2O)c1-c1nc2ccccc2o1] |
| 529 | 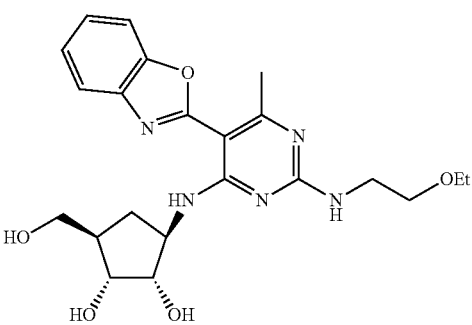 |
| 530 | 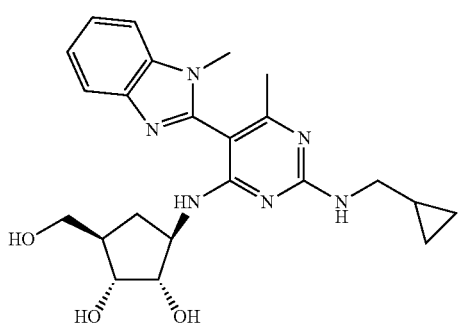 [SMILES: Cc1nc(NCC2CC2)nc(N[C@@H]2C[C@H](CO)[C@@H](O)[C@H]2O)c1-c1nc2ccccc2n1C] |
526

| Compd # | Structure |
|---|---|
| 531 | 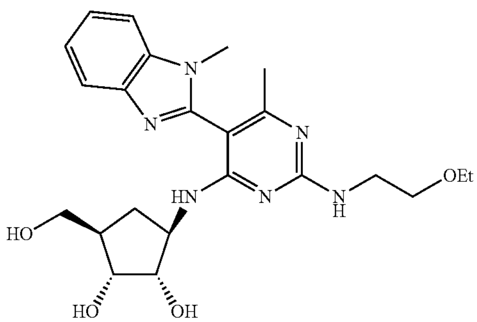 [SMILES: CCOCCNc1nc(C)c(-c2nc3ccccc3n2C)c(N[C@@H]2C[C@H](CO)[C@@H](O)[C@H]2O)n1] |
| 532 | 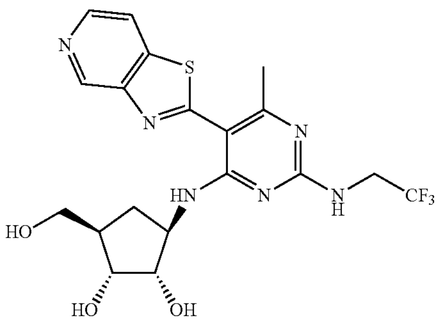 [SMILES: Cc1nc(NCC(F)(F)F)nc(N[C@@H]2C[C@H](CO)[C@@H](O)[C@H]2O)c1-c1nc2cnccc2s1] |
| 533 | 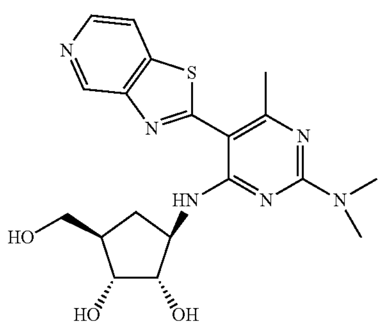 [SMILES: Cc1nc(N(C)C)nc(N[C@@H]2C[C@H](CO)[C@@H](O)[C@H]2O)c1-c1nc2cnccc2s1] |
| 534 | 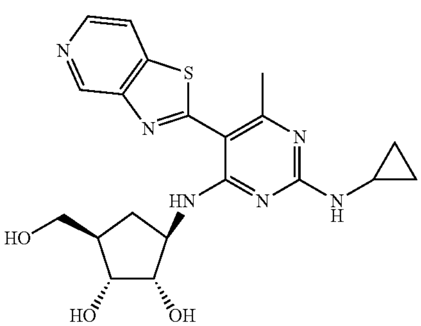 [SMILES: Cc1nc(NC2CC2)nc(N[C@@H]2C[C@H](CO)[C@@H](O)[C@H]2O)c1-c1nc2cnccc2s1] |
| 535 | 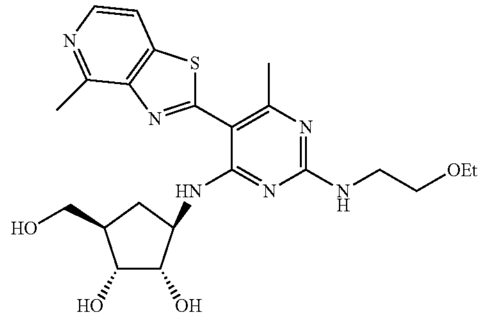 [SMILES: CCOCCNc1nc(C)c(-c2nc3c(C)nccc3s2)c(N[C@@H]2C[C@H](CO)[C@@H](O)[C@H]2O)n1] |
| 536 | 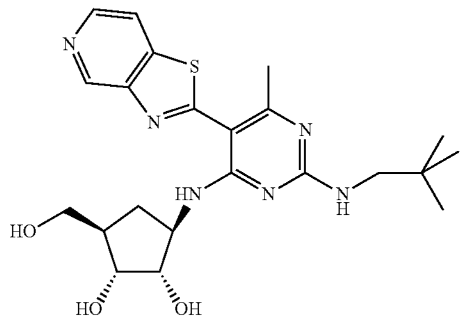 [SMILES: Cc1nc(NCC(C)(C)C)nc(N[C@@H]2C[C@H](CO)[C@@H](O)[C@H]2O)c1-c1nc2cnccc2s1] |
| 537 | 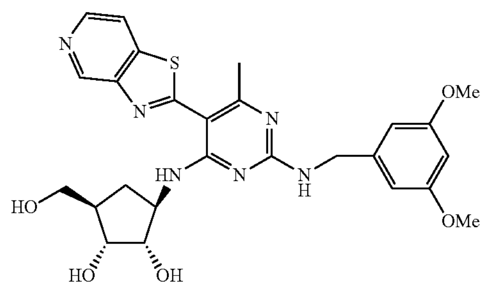 [SMILES: COc1cc(CNc2nc(C)c(-c3nc4cnccc4s3)c(N[C@@H]3C[C@H](CO)[C@@H](O)[C@H]3O)n2)cc(OC)c1] |
| 538 | 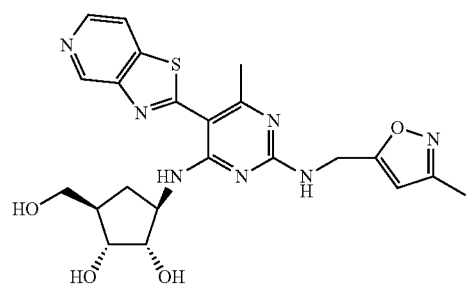 [SMILES: Cc1cc(CNc2nc(C)c(-c3nc4cnccc4s3)c(N[C@@H]3C[C@H](CO)[C@@H](O)[C@H]3O)n2)on1] |
| 539 | 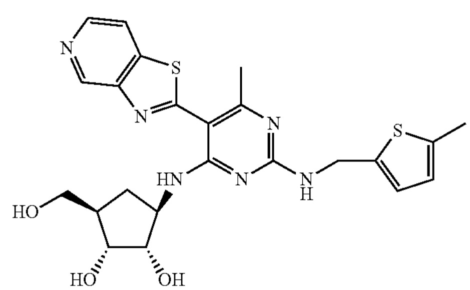 [SMILES: Cc1ccc(CNc2nc(C)c(-c3nc4cnccc4s3)c(N[C@@H]3C[C@H](CO)[C@@H](O)[C@H]3O)n2)s1] |

| Compd # | Structure |
|---|---|
| 540 | (structure) |
| 541 | (structure) |
| 542 | (structure) |
| 543 | (structure), and |
| 544 | (structure). |

| Compd # | Structure |
|---|---|
| 1001 | (structure) |
| 1002 | (structure) |
| 1003 | (structure) |
| 1004 | (structure) |

757
-continued
| Compd # | Structure |
|---|---|
| 1005 | 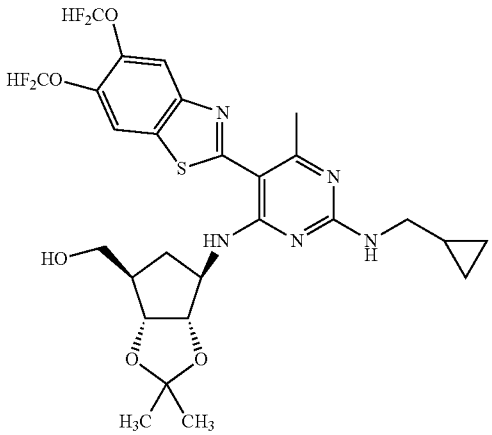 |
| 1006 | 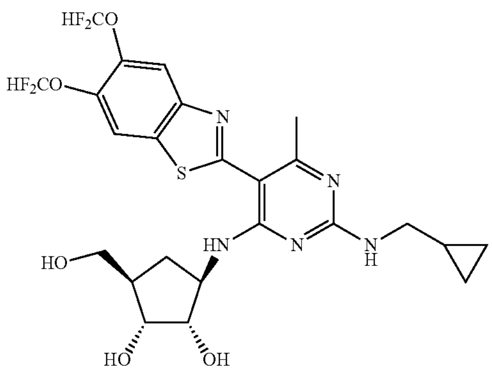 |
| 1007 | 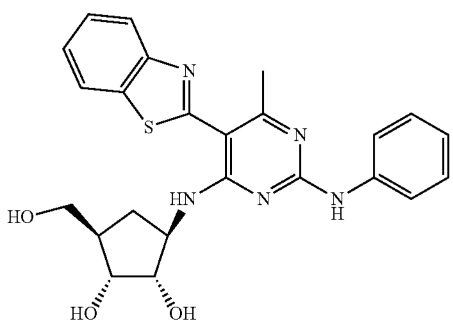 [SMILES: Cc1nc(Nc2ccccc2)nc(N[C@@H]2C[C@H](CO)[C@@H](O)[C@H]2O)c1-c1nc2ccccc2s1] |
| 1008 | 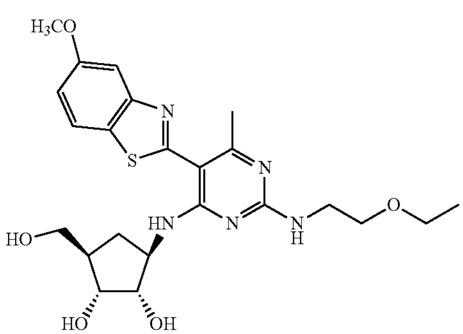 [SMILES: CCOCCNc1nc(C)c(-c2nc3cc(OC)ccc3s2)c(N[C@@H]2C[C@H](CO)[C@@H](O)[C@H]2O)n1] |
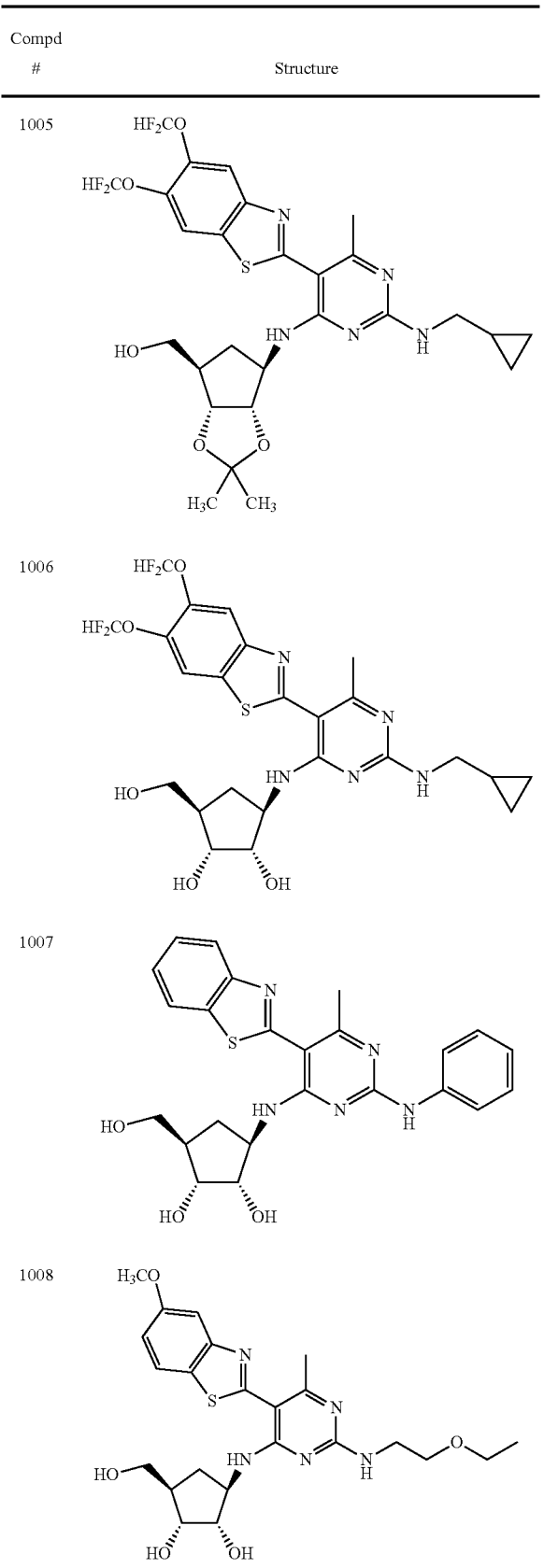
758
-continued
| Compd # | Structure |
|---|---|
| 1009 | 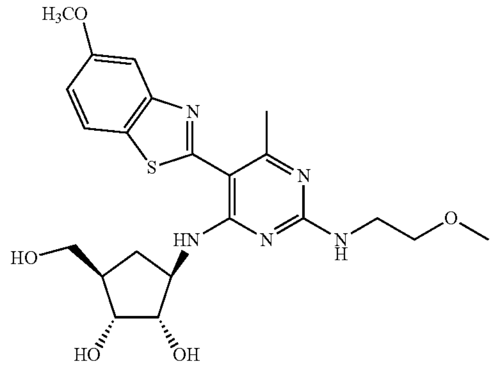 [SMILES: COCCNc1nc(C)c(-c2nc3cc(OC)ccc3s2)c(N[C@@H]2C[C@H](CO)[C@@H](O)[C@H]2O)n1] |
| 1010 | 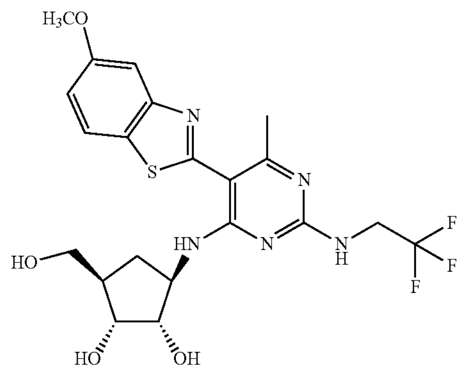 [SMILES: COc1ccc2sc(-c3c(C)nc(NCC(F)(F)F)nc3N[C@@H]3C[C@H](CO)[C@@H](O)[C@H]3O)nc2c1] |
| 1011 | 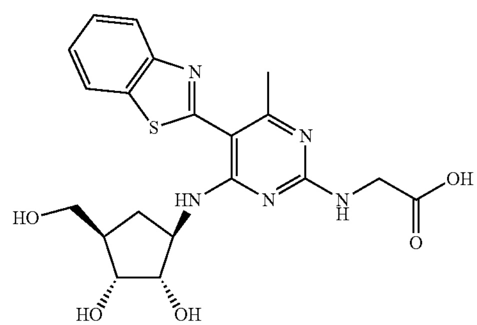 [SMILES: Cc1nc(NCC(=O)O)nc(N[C@@H]2C[C@H](CO)[C@@H](O)[C@H]2O)c1-c1nc2ccccc2s1] |
| 1012 | 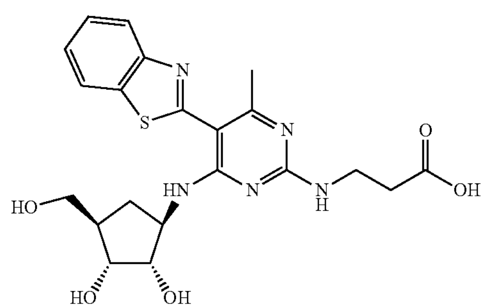 [SMILES: Cc1nc(NCCC(=O)O)nc(N[C@@H]2C[C@H](CO)[C@@H](O)[C@H]2O)c1-c1nc2ccccc2s1] |
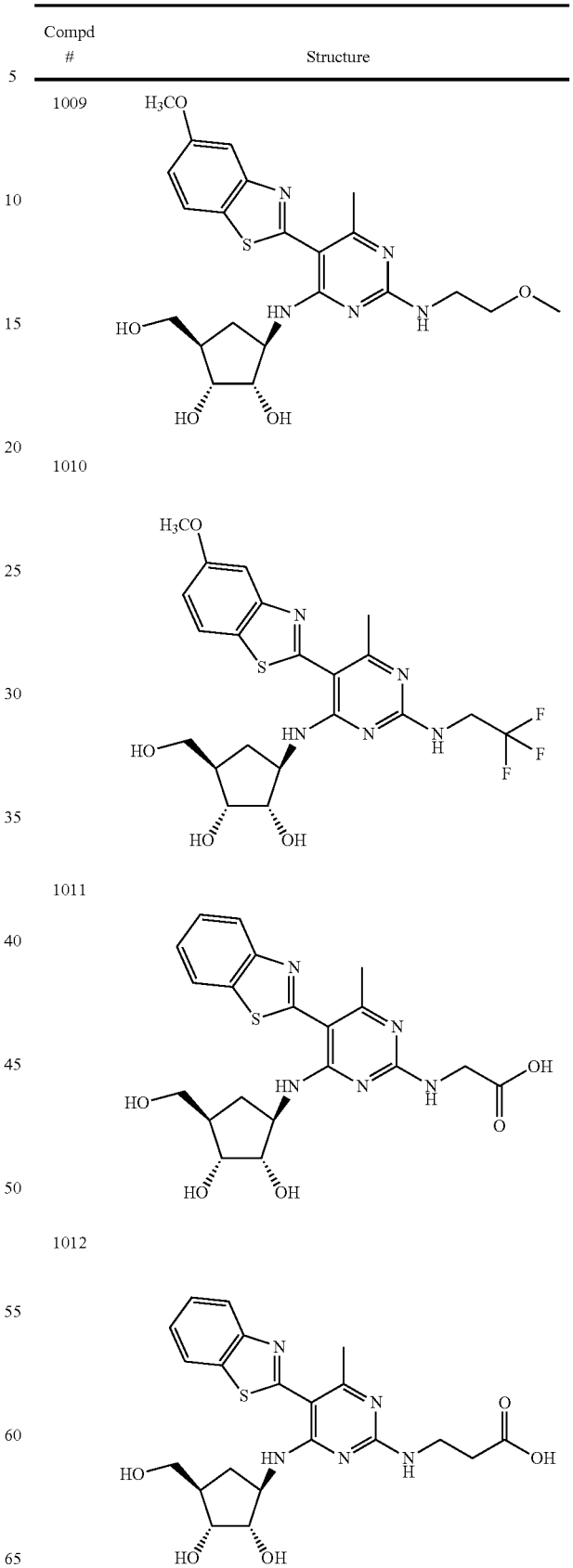

| 759 -continued | 760 -continued |
|---|---|
| Compd # 1013 | Compd # 1018 |
| 1014 | 1019 |
| 1015 | 1041 |
| 1016 | 1042 |
| 1017 | 1043 |

| Compd # | Structure |
|---|---|
| 1044 | 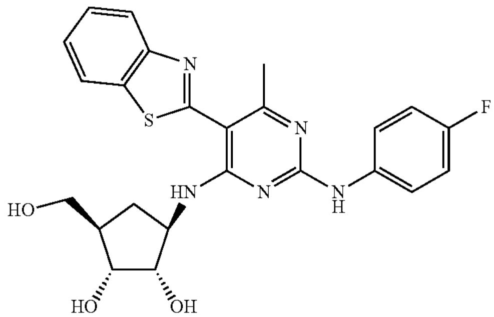 [SMILES: Cc1nc(Nc2ccc(F)cc2)nc(N[C@@H]2C[C@H](CO)[C@@H](O)[C@H]2O)c1-c1nc2ccccc2s1] |
| 1045 | 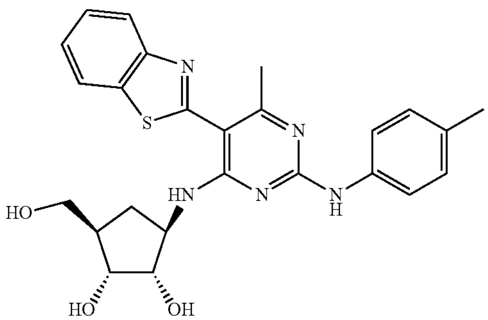 [SMILES: Cc1ccc(Nc2nc(C)c(-c3nc4ccccc4s3)c(N[C@@H]3C[C@H](CO)[C@@H](O)[C@H]3O)n2)cc1] |
| 1046 | 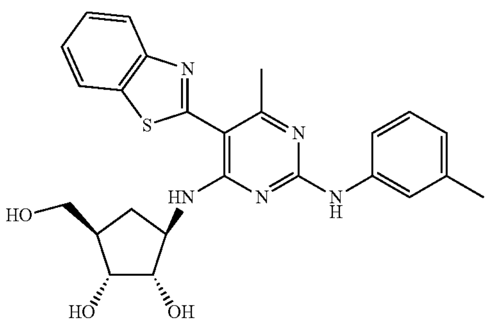 [SMILES: Cc1cccc(Nc2nc(C)c(-c3nc4ccccc4s3)c(N[C@@H]3C[C@H](CO)[C@@H](O)[C@H]3O)n2)c1] |
| 1047 | 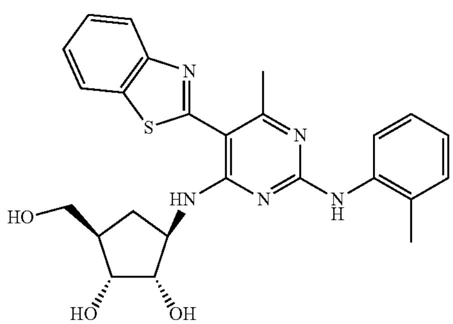 [SMILES: Cc1ccccc1Nc1nc(C)c(-c2nc3ccccc3s2)c(N[C@@H]2C[C@H](CO)[C@@H](O)[C@H]2O)n1] |
| 1048 | 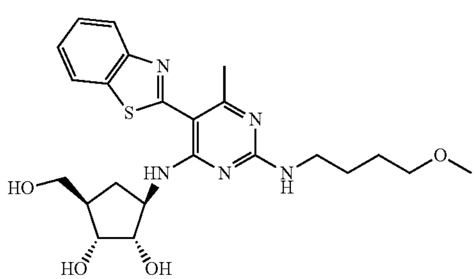 |
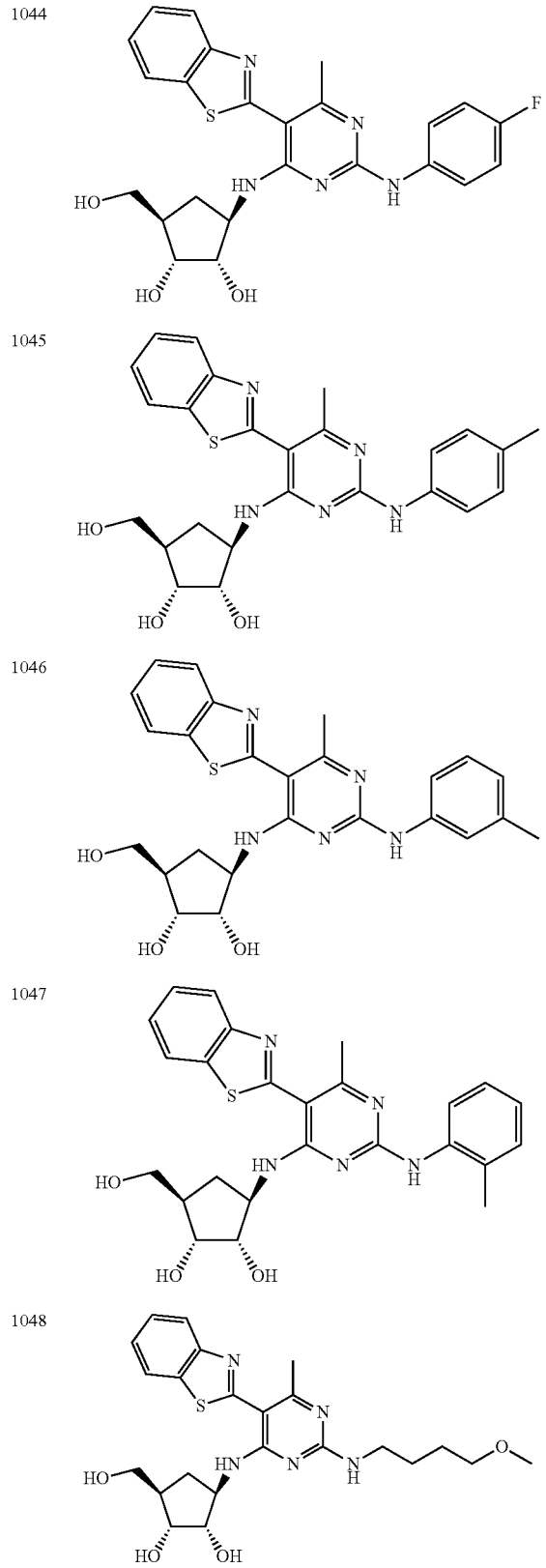
| Compd # | Structure |
|---|---|
| 1050 | 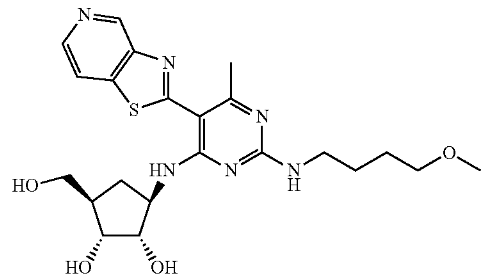 [SMILES: COCCCCNc1nc(C)c(-c2nc3cnccc3s2)c(N[C@@H]2C[C@H](CO)[C@@H](O)[C@H]2O)n1] |
| 1051 | 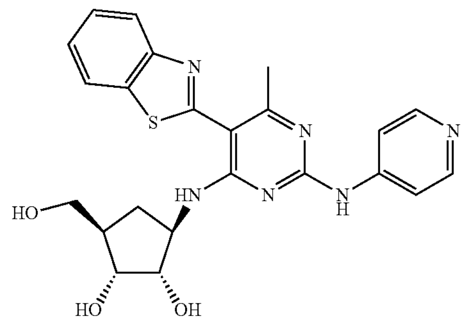 [SMILES: Cc1nc(Nc2ccncc2)nc(N[C@@H]2C[C@H](CO)[C@@H](O)[C@H]2O)c1-c1nc2ccccc2s1] |
| 1052 | 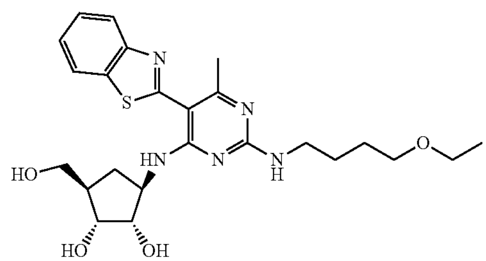 [SMILES: CCOCCCCNc1nc(C)c(-c2nc3ccccc3s2)c(N[C@@H]2C[C@H](CO)[C@@H](O)[C@H]2O)n1] |
| 1053 | 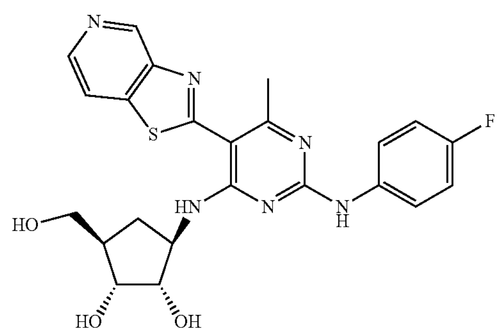 [SMILES: Cc1nc(Nc2ccc(F)cc2)nc(N[C@@H]2C[C@H](CO)[C@@H](O)[C@H]2O)c1-c1nc2cnccc2s1] |
| 1054 | 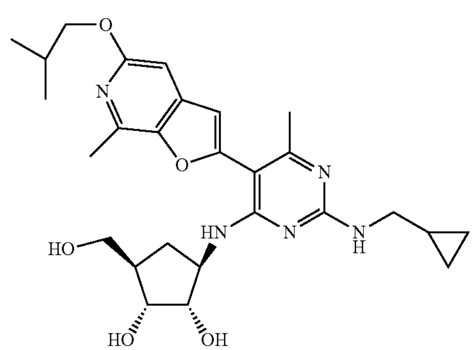 [SMILES: Cc1nc(NCC2CC2)nc(N[C@@H]2C[C@H](CO)[C@@H](O)[C@H]2O)c1-c1cc2cc(OCC(C)C)nc(C)c2o1] |
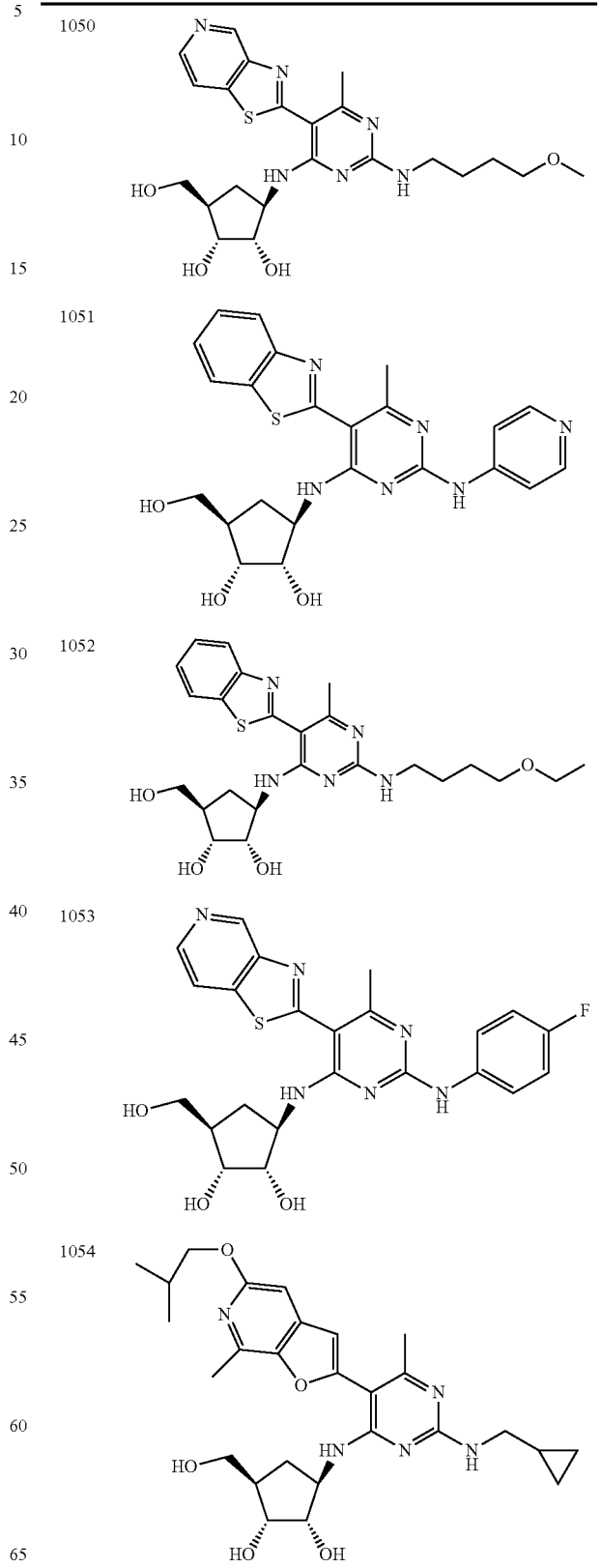

| 763 -continued | 764 -continued |
|---|---|
| Compd # Structure | Compd # Structure |
| 1055 | 1059 |
| 1056 | 1060 |
| 1057 | 1061 |
| 1058 | 1062 |
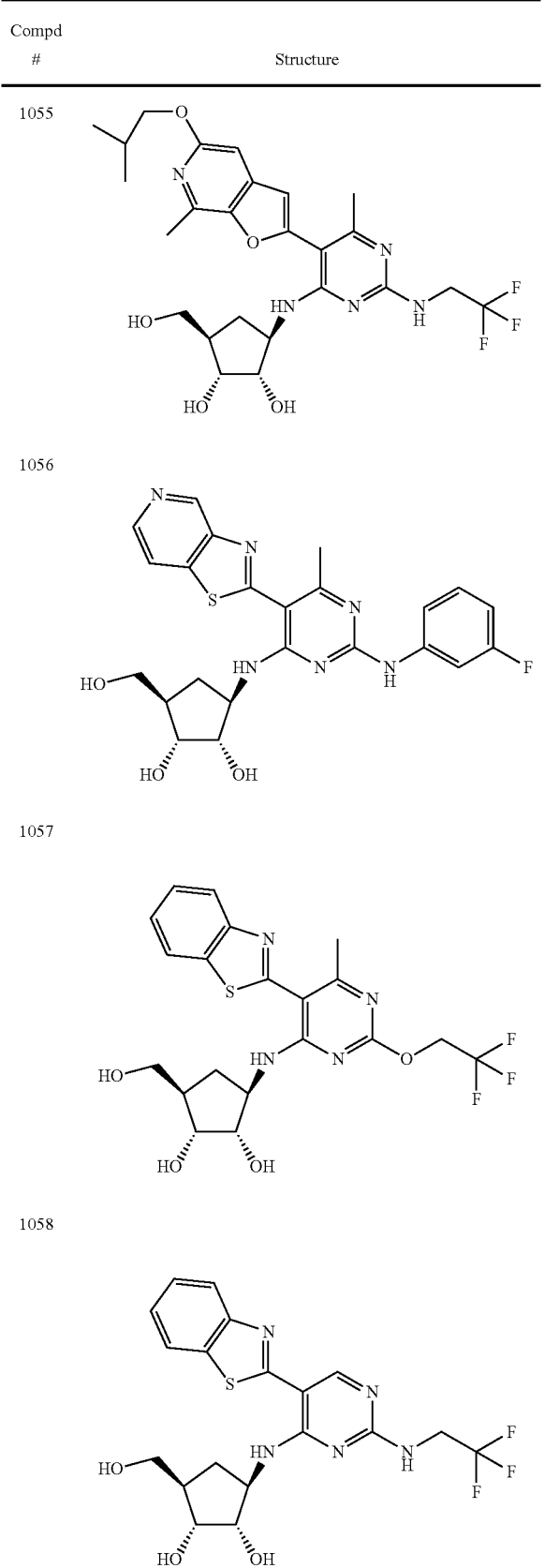
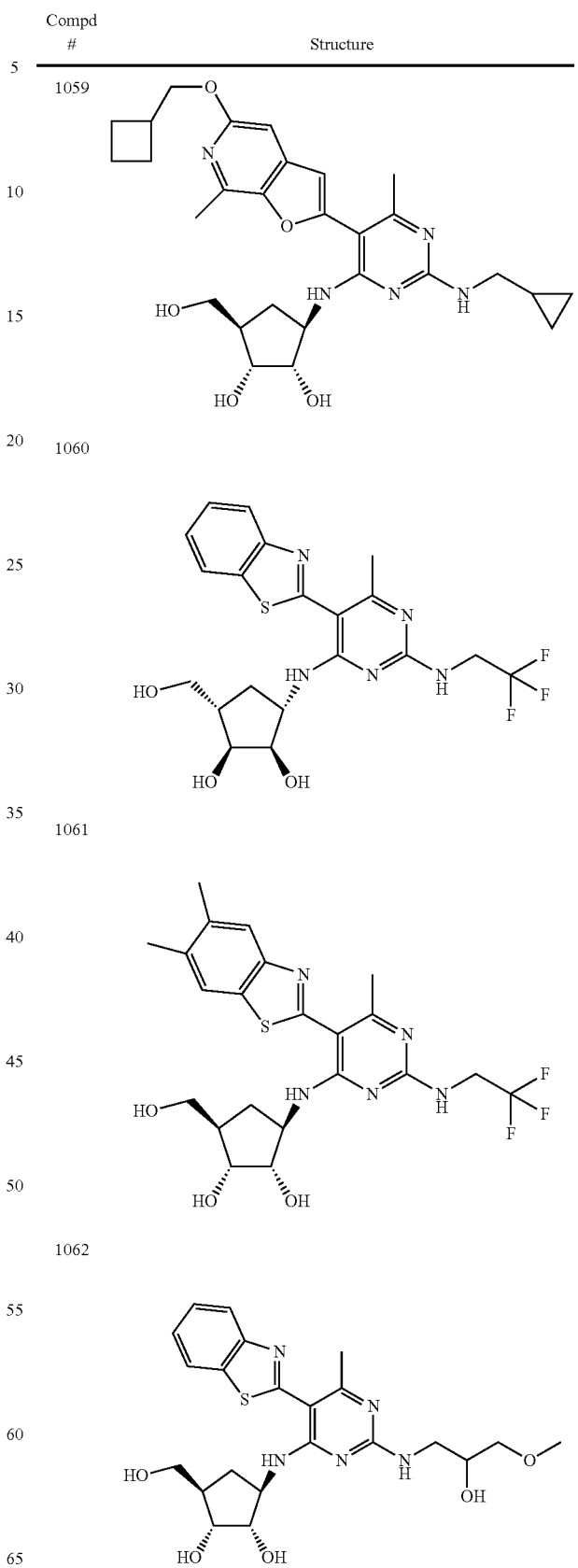

| Compd # | Structure |
|---|---|
| 1063 | 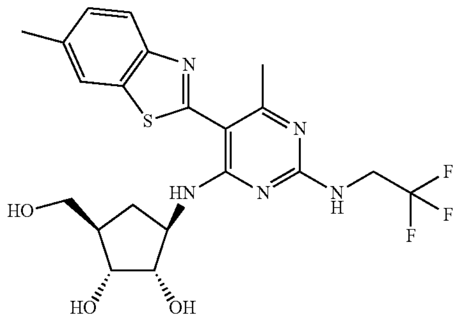 [SMILES: Cc1ccc2nc(-c3c(C)nc(NCC(F)(F)F)nc3N[C@@H]3C[C@H](CO)[C@@H](O)[C@H]3O)sc2c1] |
| 1064 | 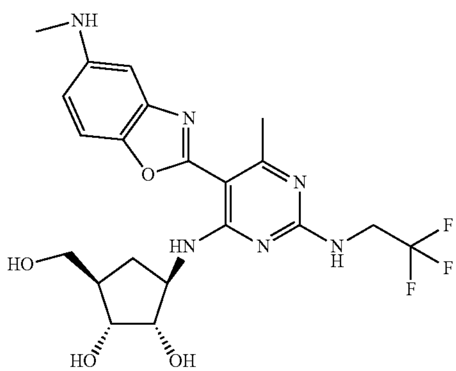 [SMILES: CNc1ccc2oc(-c3c(C)nc(NCC(F)(F)F)nc3N[C@@H]3C[C@H](CO)[C@@H](O)[C@H]3O)nc2c1] |
| 1065 | 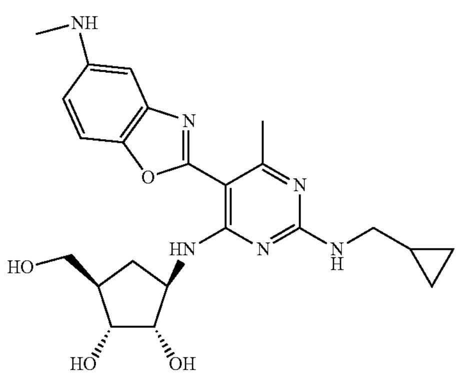 [SMILES: CNc1ccc2oc(-c3c(C)nc(NCC4CC4)nc3N[C@@H]3C[C@H](CO)[C@@H](O)[C@H]3O)nc2c1] |
| 1066 | 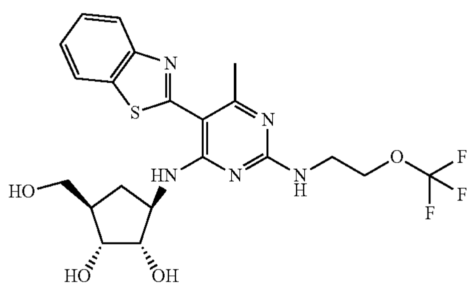 [SMILES: Cc1nc(NCCOC(F)(F)F)nc(N[C@@H]2C[C@H](CO)[C@@H](O)[C@H]2O)c1-c1nc2ccccc2s1] |

| Compd # | Structure |
|---|---|
| 1067 | 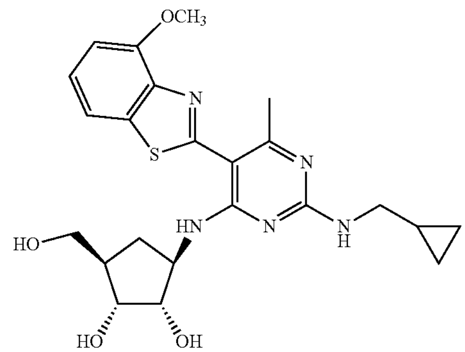 [SMILES: COc1cccc2sc(-c3c(C)nc(NCC4CC4)nc3N[C@@H]3C[C@H](CO)[C@@H](O)[C@H]3O)nc12] |
| 1068 | 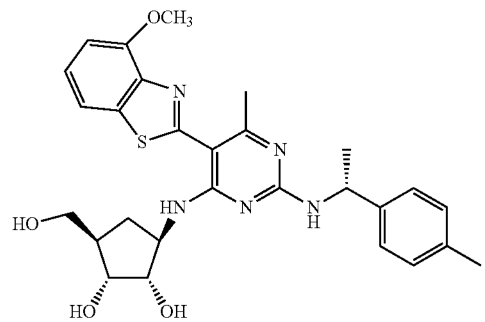 [SMILES: COc1cccc2sc(-c3c(C)nc(N[C@H](C)c4ccc(C)cc4)nc3N[C@@H]3C[C@H](CO)[C@@H](O)[C@H]3O)nc12] |
| 1069 | 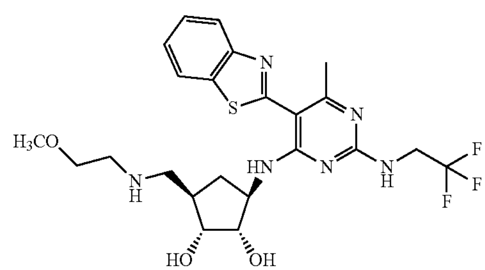 [SMILES: COCCNC[C@H]1C[C@@H](Nc2nc(NCC(F)(F)F)nc(C)c2-c2nc3ccccc3s2)[C@H](O)[C@@H]1O] |
| 1070 | 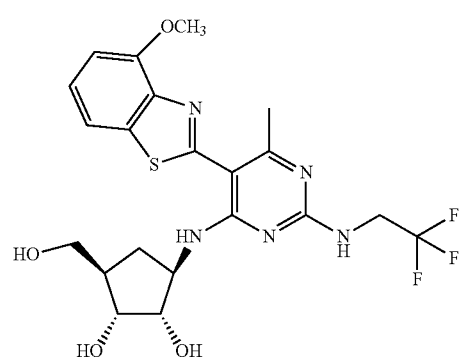 [SMILES: COc1cccc2sc(-c3c(C)nc(NCC(F)(F)F)nc3N[C@@H]3C[C@H](CO)[C@@H](O)[C@H]3O)nc12] |

767
-continued
| Compd # | Structure |
|---|---|
| 1071 | 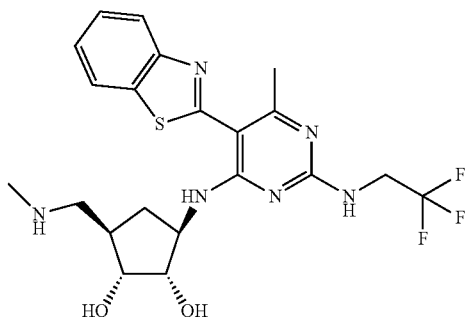 [SMILES: CNC[C@H]1C[C@@H](Nc2nc(NCC(F)(F)F)nc(C)c2-c2nc3ccccc3s2)[C@H](O)[C@@H]1O] |
| 1072 | 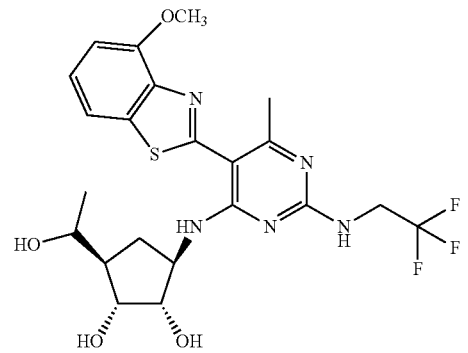 [SMILES: COc1cccc2sc(-c3c(C)nc(NCC(F)(F)F)nc3N[C@@H]3C[C@H](C(C)O)[C@@H](O)[C@H]3O)nc12] |
| 1073 | 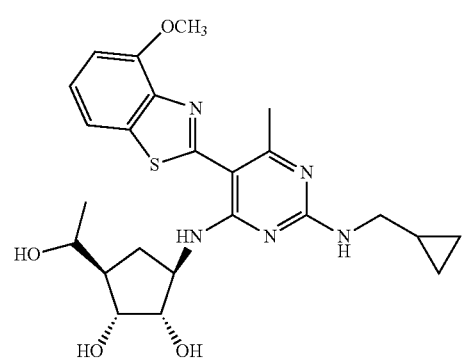 [SMILES: COc1cccc2sc(-c3c(C)nc(NCC4CC4)nc3N[C@@H]3C[C@H](C(C)O)[C@@H](O)[C@H]3O)nc12] |
| 1074 | 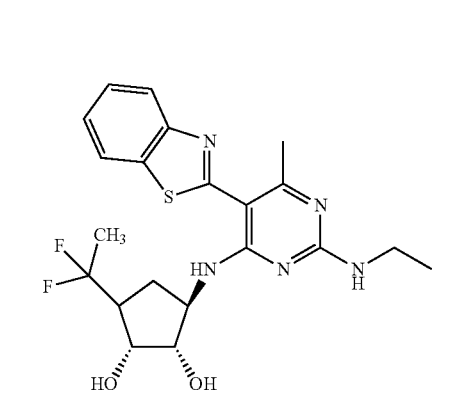 (isomer 1) |
768
-continued
| Compd # | Structure |
|---|---|
| 1101 | 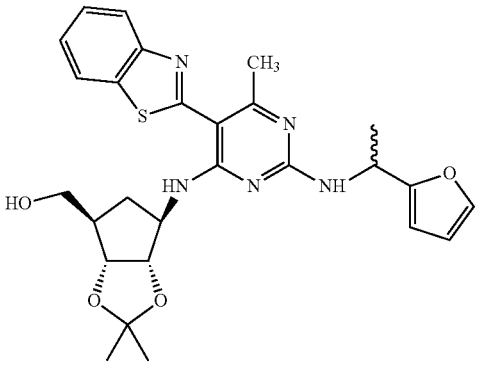 [SMILES: Cc1nc(NC(C)c2ccco2)nc(N[C@@H]2C[C@H](CO)[C@H]3OC(C)(C)O[C@H]32)c1-c1nc2ccccc2s1] |
| 1102 | 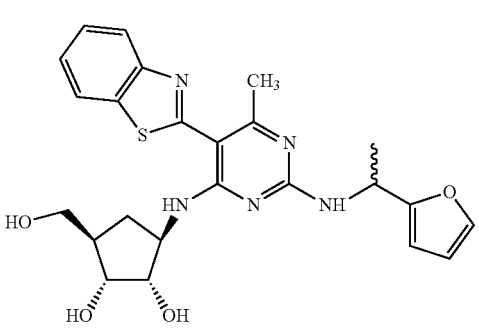 [SMILES: Cc1nc(NC(C)c2ccco2)nc(N[C@@H]2C[C@H](CO)[C@@H](O)[C@H]2O)c1-c1nc2ccccc2s1]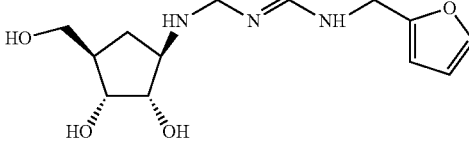 |
| 1103 | 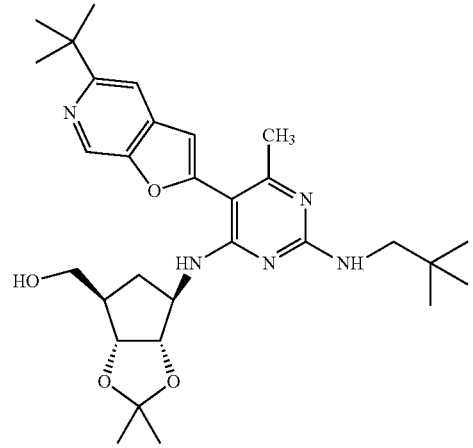 [SMILES: Cc1nc(NCC(C)(C)C)nc(N[C@@H]2C[C@H](CO)[C@H]3OC(C)(C)O[C@H]32)c1-c1cc2cc(C(C)(C)C)ncc2o1] |
| 1104 | 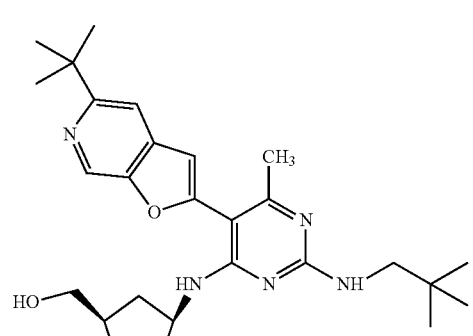 |

| 769 -continued | 770 -continued |
|---|---|
| Compd # Structure | Compd # Structure |
| 1105 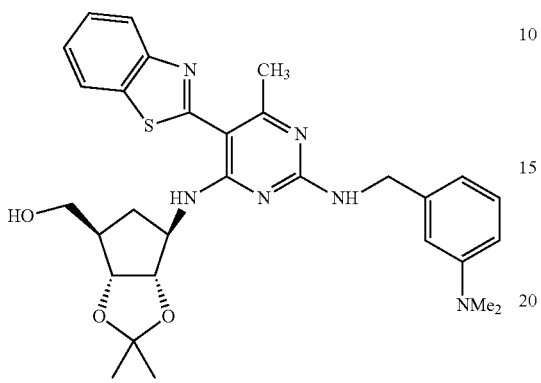 | 1108 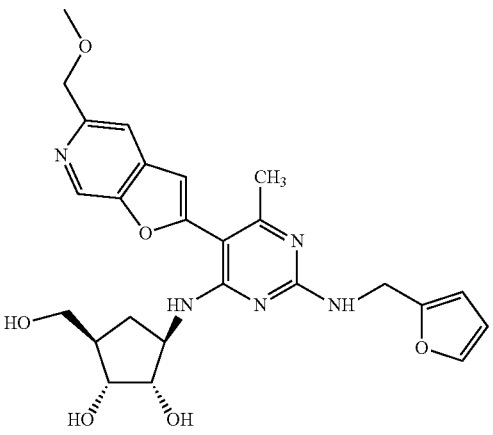 [SMILES: COCc1cc2cc(-c3c(C)nc(NCc4ccco4)nc3N[C@@H]3C[C@H](CO)[C@@H](O)[C@H]3O)oc2cn1] |
| 1106 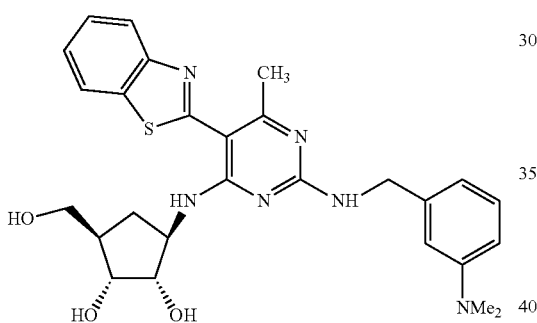 | 1109 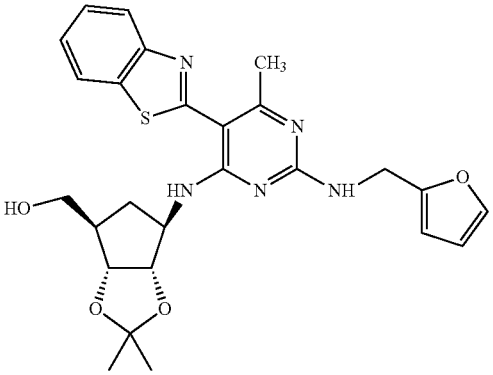 [SMILES: Cc1nc(NCc2ccco2)nc(N[C@@H]2C[C@H](CO)[C@H]3OC(C)(C)O[C@H]32)c1-c1nc2ccccc2s1] |
| 1107 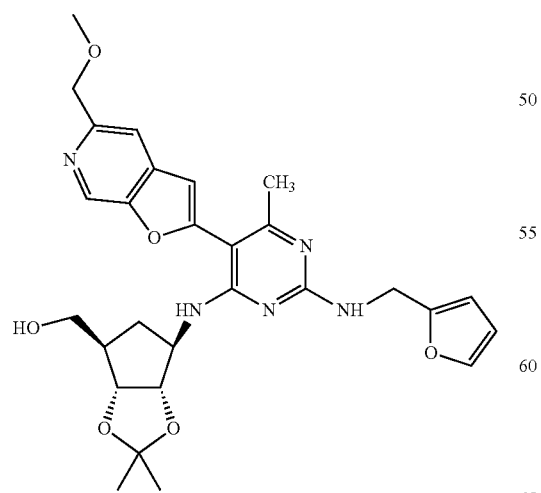 | 1110 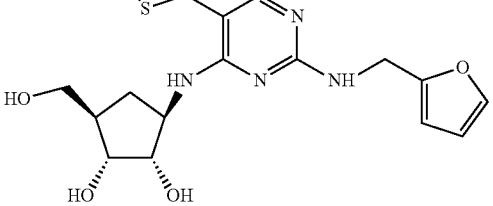 |
| | 1111 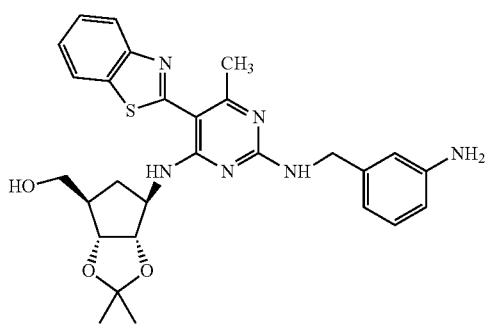 [SMILES: Cc1nc(NCc2cccc(N)c2)nc(N[C@@H]2C[C@H](CO)[C@H]3OC(C)(C)O[C@H]32)c1-c1nc2ccccc2s1] |

771
-continued
| Compd # | Structure |
|---|---|
| 1112 | 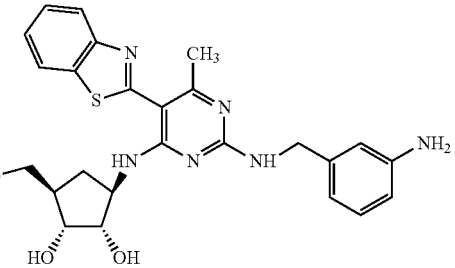 |
| 1113 | 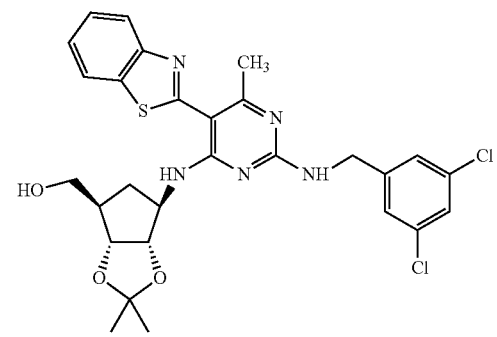 [SMILES: Cc1nc(NCc2cc(Cl)cc(Cl)c2)nc(N[C@@H]2C[C@H](CO)[C@H]3OC(C)(C)O[C@H]32)c1-c1nc2ccccc2s1] |
| 1114 | 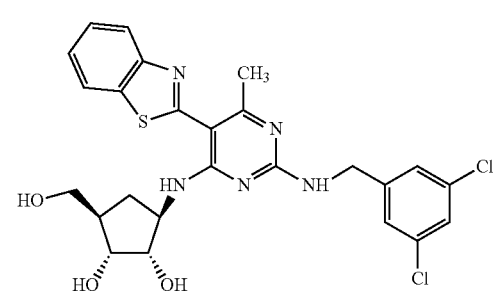 [SMILES: Cc1nc(NCc2cc(Cl)cc(Cl)c2)nc(N[C@@H]2C[C@H](CO)[C@@H](O)[C@H]2O)c1-c1nc2ccccc2s1] |
| 1115 | 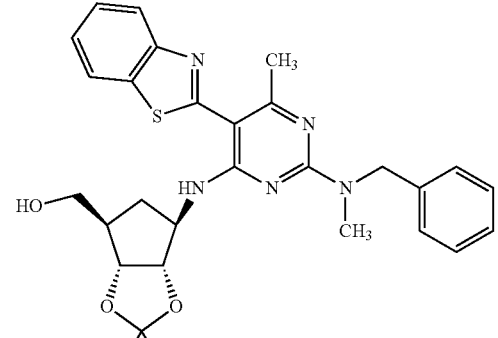 |
| 1116 | 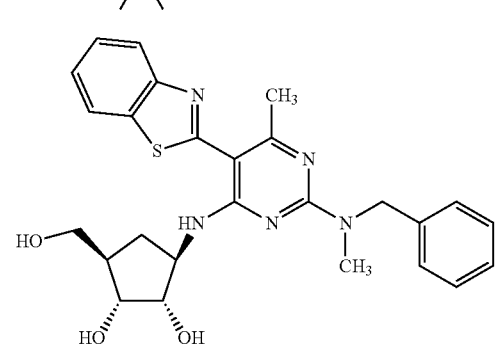 |
772
-continued
| Compd # | Structure |
|---|---|
| 1117 | 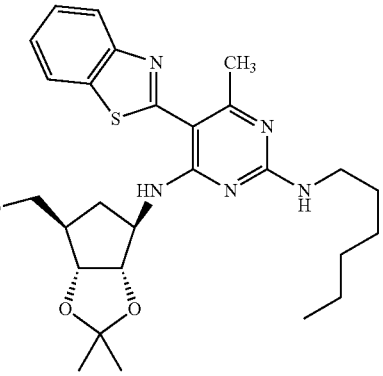 |
| 1118 | 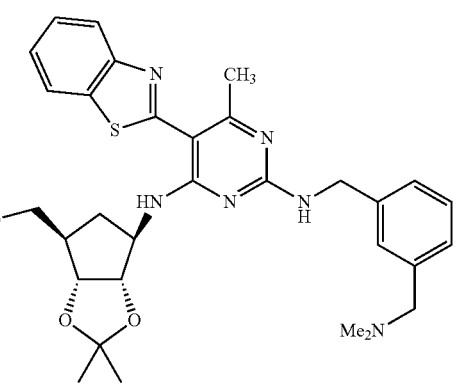 |
| 1119 | 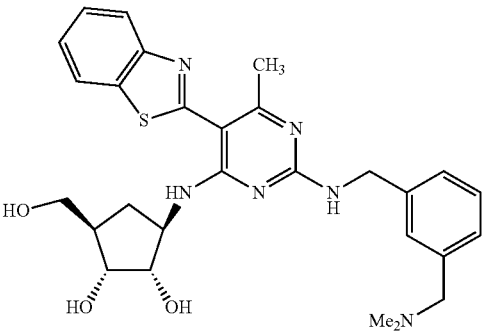 [SMILES: Cc1nc(NCc2cccc(CN(C)C)c2)nc(N[C@@H]2C[C@H](CO)[C@@H](O)[C@H]2O)c1-c1nc2ccccc2s1] |
| 1120 | 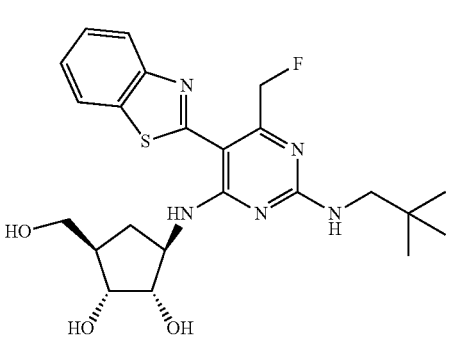 [SMILES: CC(C)(C)CNc1nc(CF)c(-c2nc3ccccc3s2)c(N[C@@H]2C[C@H](CO)[C@@H](O)[C@H]2O)n1] |

| Compd # | Structure |
|---|---|
| 1121 | 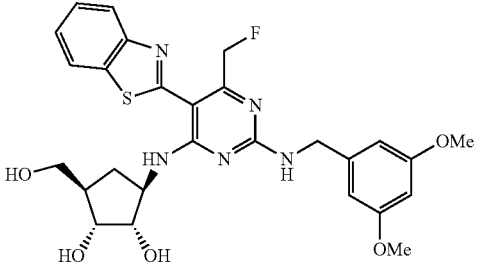 [SMILES: COc1cc(CNc2nc(CF)c(-c3nc4ccccc4s3)c(N[C@@H]3C[C@H](CO)[C@@H](O)[C@H]3O)n2)cc(OC)c1] |
| 1122 | 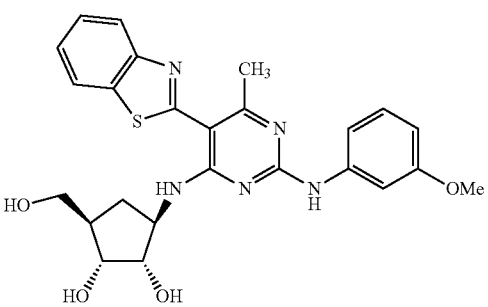 [SMILES: COc1cccc(Nc2nc(C)c(-c3nc4ccccc4s3)c(N[C@@H]3C[C@H](CO)[C@@H](O)[C@H]3O)n2)c1] |
| 1123 | 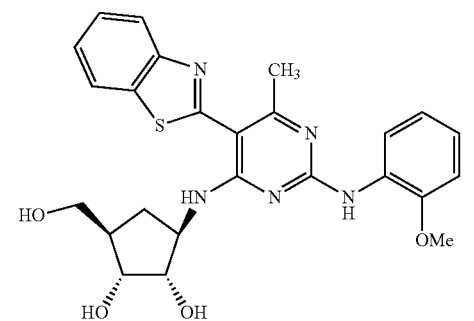 [SMILES: COc1ccccc1Nc1nc(C)c(-c2nc3ccccc3s2)c(N[C@@H]2C[C@H](CO)[C@@H](O)[C@H]2O)n1] |
| 1124 | 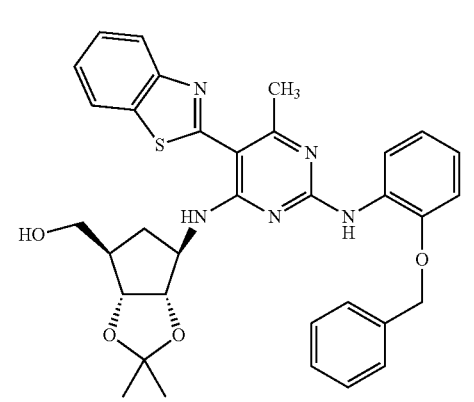 [SMILES: Cc1nc(Nc2ccccc2OCc2ccccc2)nc(N[C@@H]2C[C@H](CO)[C@H]3OC(C)(C)O[C@H]32)c1-c1nc2ccccc2s1] |
| Compd # | Structure |
|---|---|
| 1125 | 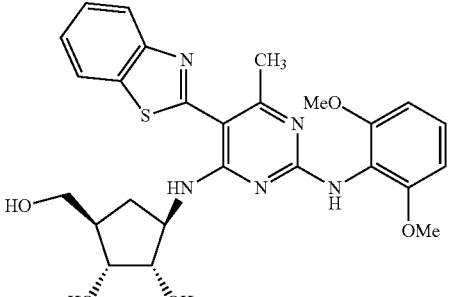 |
| 1126 | 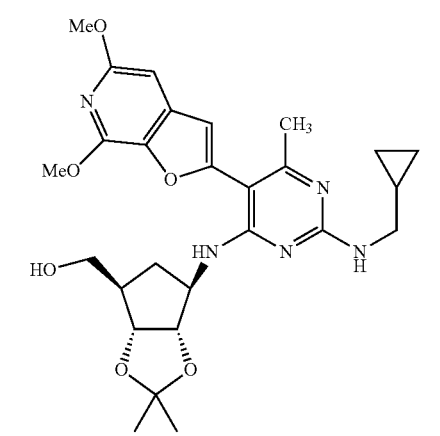 [SMILES: COc1cc2cc(-c3c(C)nc(NCC4CC4)nc3N[C@@H]3C[C@H](CO)[C@H]4OC(C)(C)O[C@H]43)oc2c(OC)n1] |
| 1127 | 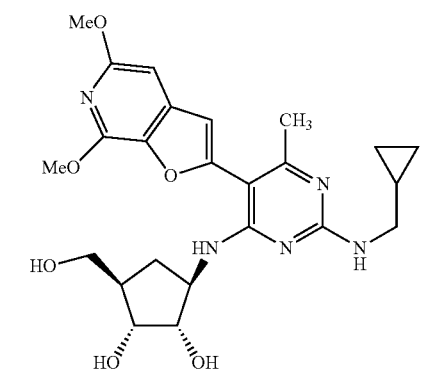 [SMILES: COc1cc2cc(-c3c(C)nc(NCC4CC4)nc3N[C@@H]3C[C@H](CO)[C@@H](O)[C@H]3O)oc2c(OC)n1] |
| 1128 | 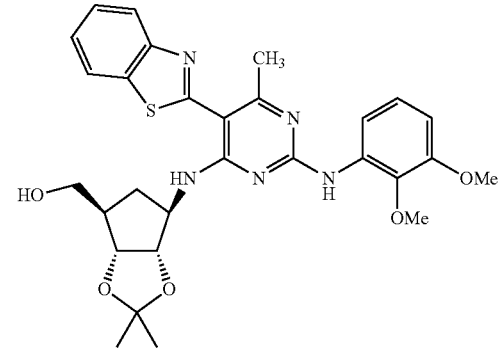 [SMILES: COc1cccc(Nc2nc(C)c(-c3nc4ccccc4s3)c(N[C@@H]3C[C@H](CO)[C@H]4OC(C)(C)O[C@H]43)n2)c1OC] |

-continued
| Compd # | Structure |
|---|---|
| 1129 | 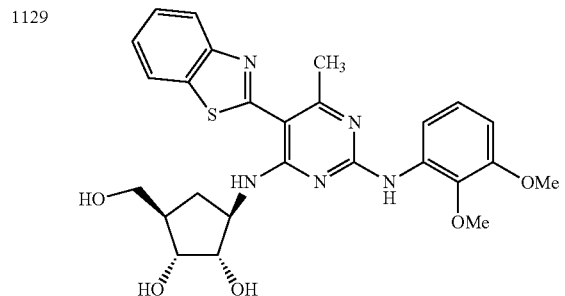 |
| 1130 | 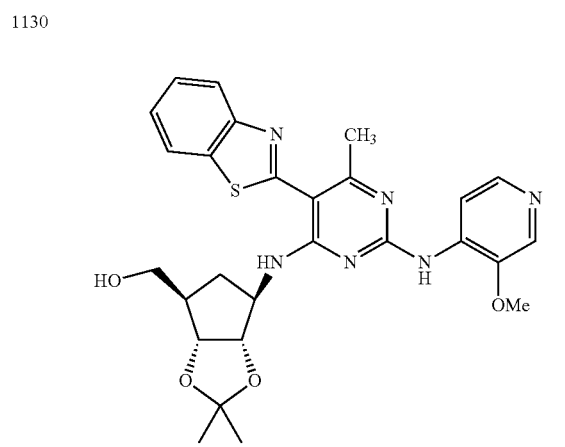 |
| 1131 | 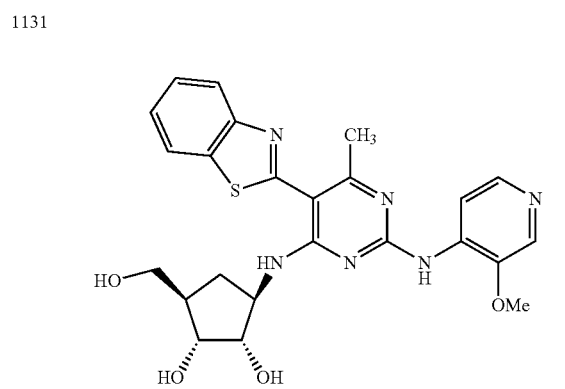 |
| 1132 | 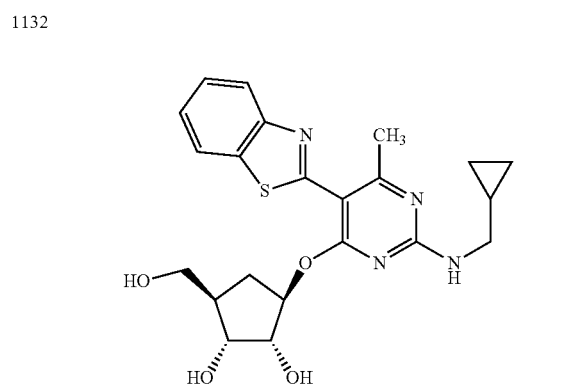 |
-continued
| Compd # | Structure |
|---|---|
| 1133 | 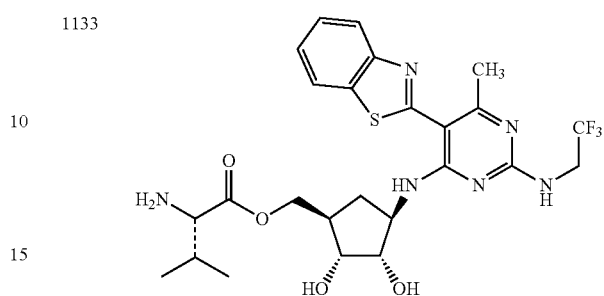 |
| 1134 | 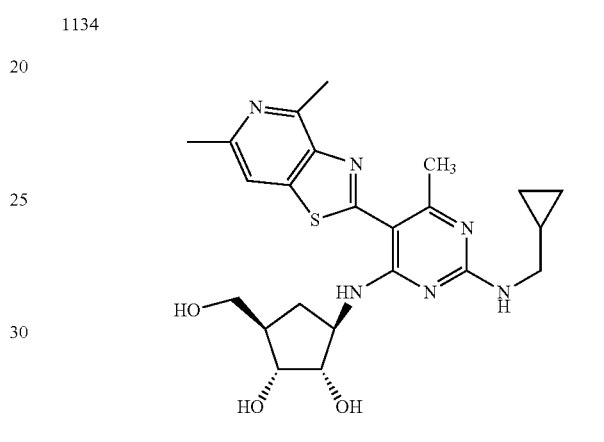 |
| 1135 | 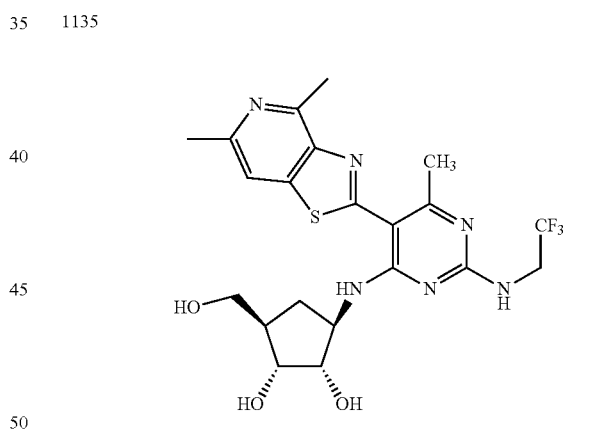 |
| 1136 | 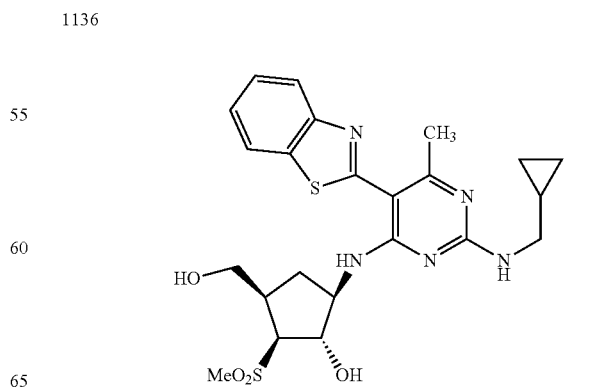 |

777
-continued

| Compd # | Structure |
|---|---|
| 1137 | 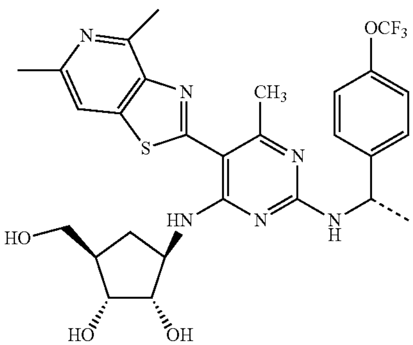 [SMILES: Cc1cc2sc(-c3c(C)nc(N[C@@H](C)c4ccc(OC(F)(F)F)cc4)nc3N[C@@H]3C[C@H](CO)[C@@H](O)[C@H]3O)nc2c(C)n1] |
| 1201 | 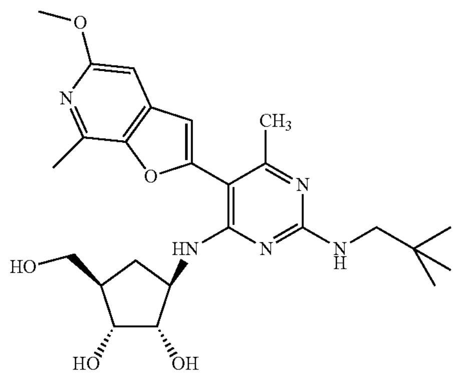 [SMILES: COc1cc2cc(-c3c(C)nc(NCC(C)(C)C)nc3N[C@@H]3C[C@H](CO)[C@@H](O)[C@H]3O)oc2c(C)n1] |
| 1202 | 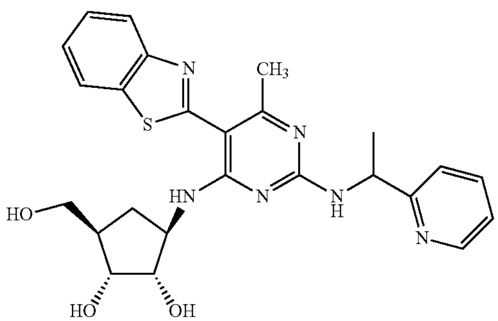 [SMILES: Cc1nc(NC(C)c2ccccn2)nc(N[C@@H]2C[C@H](CO)[C@@H](O)[C@H]2O)c1-c1nc2ccccc2s1] |
| 1203 | 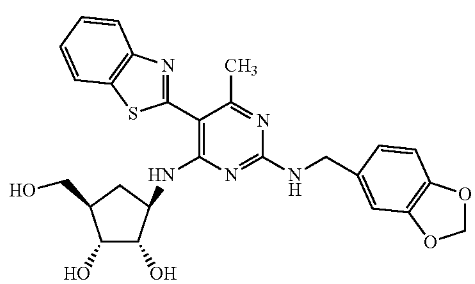 [SMILES: Cc1nc(NCc2ccc3c(c2)OCO3)nc(N[C@@H]2C[C@H](CO)[C@@H](O)[C@H]2O)c1-c1nc2ccccc2s1] |

778
-continued

| Compd # | Structure |
|---|---|
| 1204 | 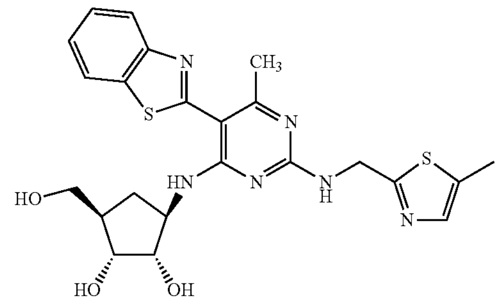 [SMILES: Cc1cnc(CNc2nc(C)c(-c3nc4ccccc4s3)c(N[C@@H]3C[C@H](CO)[C@@H](O)[C@H]3O)n2)s1] |
| 1205 | 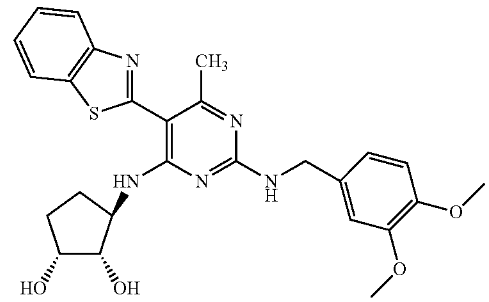 [SMILES: COc1ccc(CNc2nc(C)c(-c3nc4ccccc4s3)c(N[C@@H]3CC[C@@H](O)[C@H]3O)n2)cc1OC] |
| 1206 | 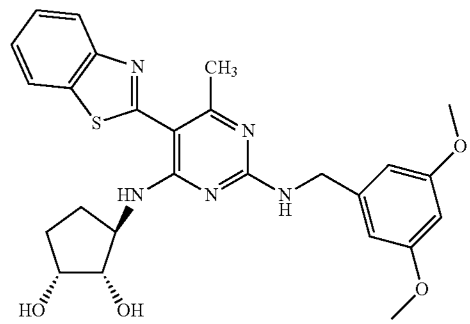 [SMILES: COc1cc(CNc2nc(C)c(-c3nc4ccccc4s3)c(N[C@@H]3CC[C@@H](O)[C@H]3O)n2)cc(OC)c1] |
| 1207 | 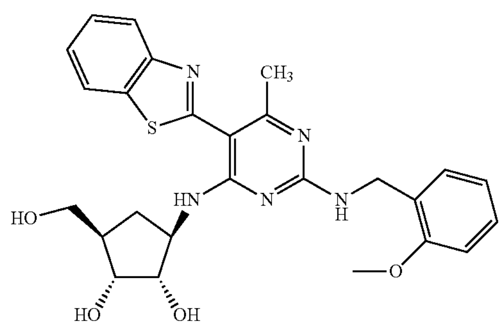 [SMILES: COc1ccccc1CNc1nc(C)c(-c2nc3ccccc3s2)c(N[C@@H]2C[C@H](CO)[C@@H](O)[C@H]2O)n1] |
| 1208 | 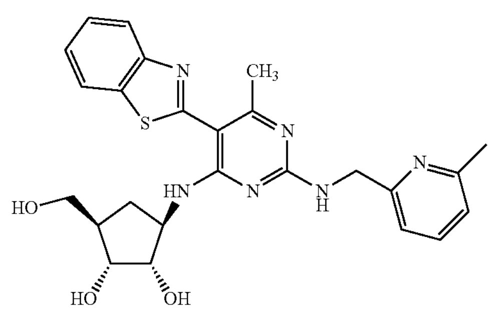 [SMILES: Cc1cccc(CNc2nc(C)c(-c3nc4ccccc4s3)c(N[C@@H]3C[C@H](CO)[C@@H](O)[C@H]3O)n2)n1] |

US 8,697,694 B2
| 779 -continued | | 780 -continued | |
|---|---|---|---|
| Compd # | Structure | Compd # | Structure |
| 1209 | 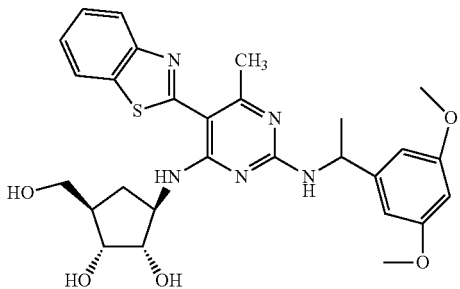 [SMILES: COc1cc(OC)cc(C(C)Nc2nc(C)c(-c3nc4ccccc4s3)c(N[C@@H]3C[C@H](CO)[C@@H](O)[C@H]3O)n2)c1] | 1214 | 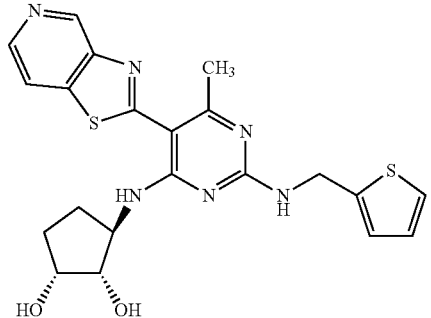 |
| 1210 | 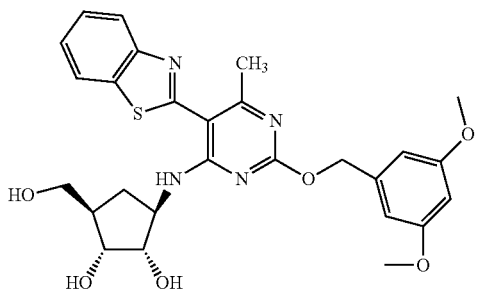 [SMILES: COc1cc(COc2nc(C)c(-c3nc4ccccc4s3)c(N[C@@H]3C[C@H](CO)[C@@H](O)[C@H]3O)n2)cc(OC)c1] | 1215 | 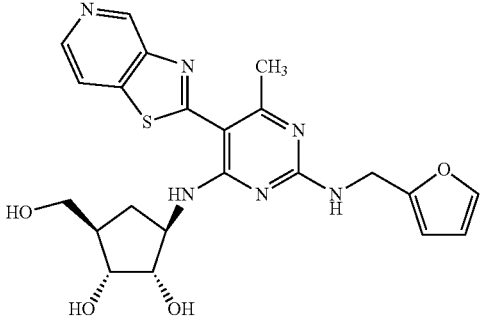 |
| 1211 | 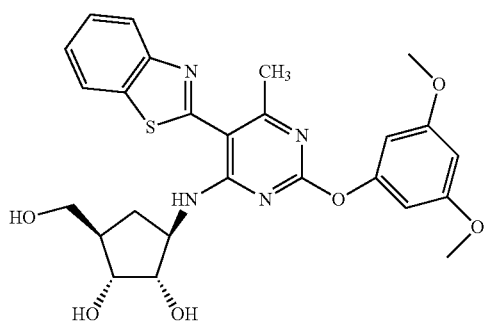 [SMILES: COc1cc(OC)cc(Oc2nc(C)c(-c3nc4ccccc4s3)c(N[C@@H]3C[C@H](CO)[C@@H](O)[C@H]3O)n2)c1] | 1216 | 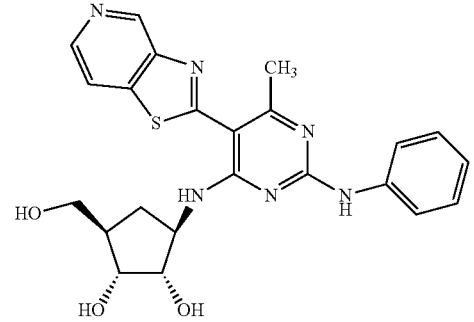 |
| 1212 | 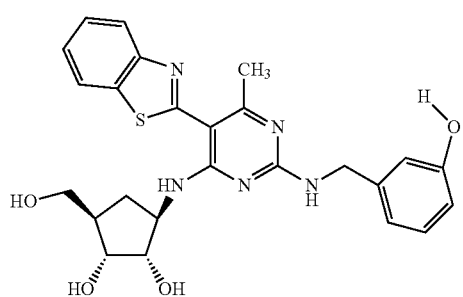 [SMILES: Cc1nc(NCc2cccc(O)c2)nc(N[C@@H]2C[C@H](CO)[C@@H](O)[C@H]2O)c1-c1nc2ccccc2s1] | 1217 | 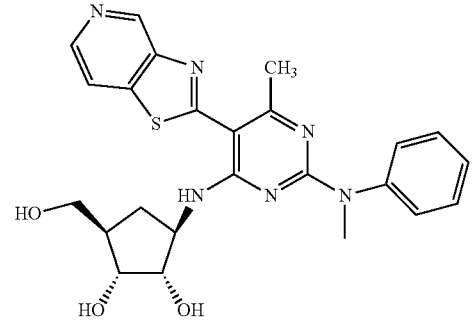 |
| 1213 | 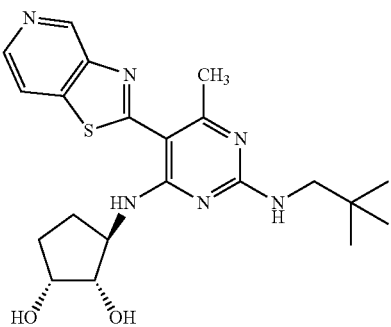 [SMILES: Cc1nc(NCC(C)(C)C)nc(N[C@@H]2CC[C@@H](O)[C@H]2O)c1-c1nc2cnccc2s1] | 1218 | 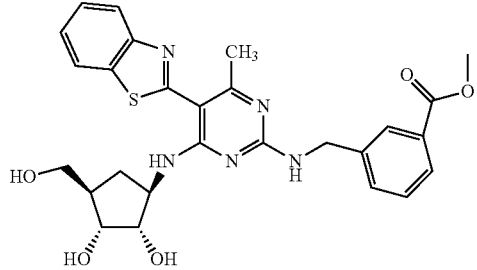 [SMILES: Cc1nc(NCc2cccc(C(=O)O)c2)nc(N[C@@H]2C[C@H](CO)[C@@H](O)[C@H]2O)c1-c1nc2ccccc2s1] |

781
-continued

| Compd # | Structure |
|---|---|
| 1219 | (structure) |
| 1220 | (structure) |
| 1221 | (structure) |
| 1222 | (structure) |
| 1223 | (structure) |

782
-continued

| Compd # | Structure |
|---|---|
| 1224 | (structure) |
| 1225 | (structure) |
| 1226 | (structure) |
| 1227 | (structure) |
| 1228 | (structure) |

US 8,697,694 B2
783
-continued
| Compd # | Structure |
|---|---|
| 1229 | 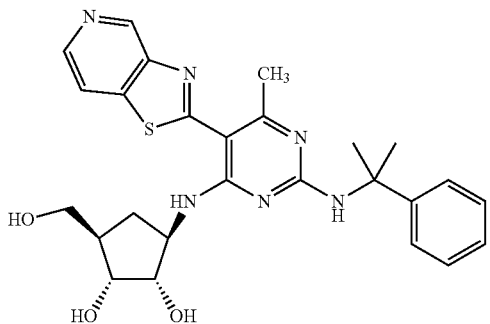 [SMILES: Cc1nc(NC(C)(C)c2ccccc2)nc(N[C@@H]2C[C@H](CO)[C@@H](O)[C@H]2O)c1-c1nc2cnccc2s1] |
| 1230 | 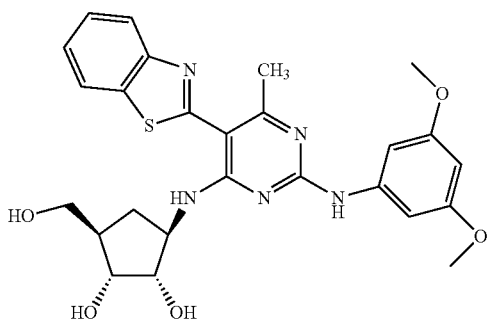 [SMILES: COc1cc(Nc2nc(C)c(-c3nc4ccccc4s3)c(N[C@@H]3C[C@H](CO)[C@@H](O)[C@H]3O)n2)cc(OC)c1] |
| 1231 | 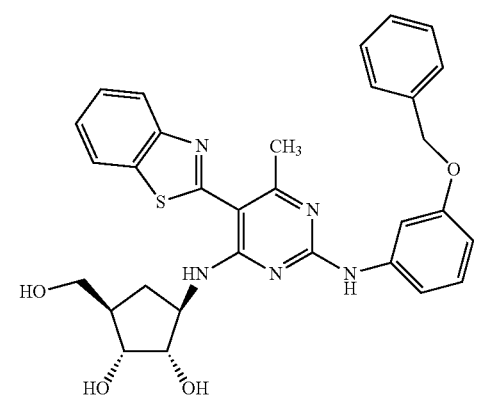 [SMILES: Cc1nc(Nc2cccc(OCc3ccccc3)c2)nc(N[C@@H]2C[C@H](CO)[C@@H](O)[C@H]2O)c1-c1nc2ccccc2s1] |
| 1232 | 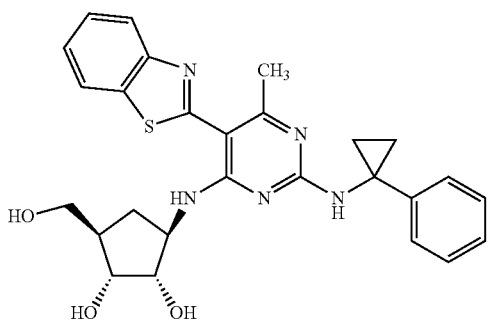 [SMILES: Cc1nc(NC2(c3ccccc3)CC2)nc(N[C@@H]2C[C@H](CO)[C@@H](O)[C@H]2O)c1-c1nc2ccccc2s1] |
784
-continued
| Compd # | Structure |
|---|---|
| 1233 | 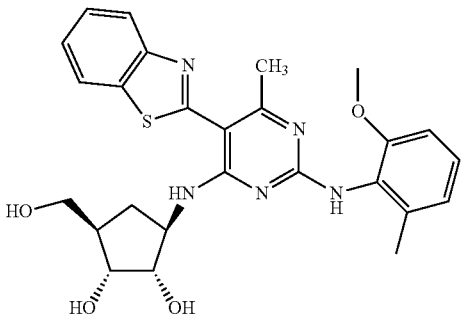 [SMILES: COc1cccc(C)c1Nc1nc(C)c(-c2nc3ccccc3s2)c(N[C@@H]2C[C@H](CO)[C@@H](O)[C@H]2O)n1] |
| 1234 | 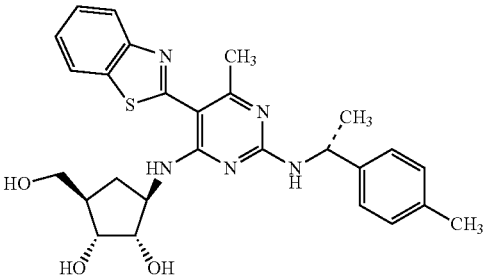 [SMILES: Cc1ccc([C@@H](C)Nc2nc(C)c(-c3nc4ccccc4s3)c(N[C@@H]3C[C@H](CO)[C@@H](O)[C@H]3O)n2)cc1] |
| 1235 | 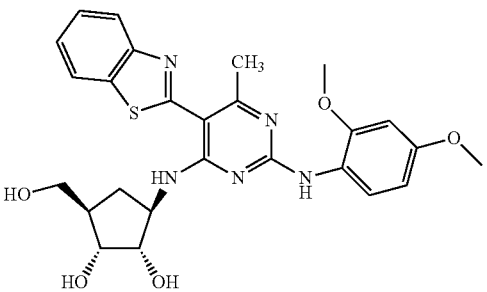 [SMILES: COc1ccc(Nc2nc(C)c(-c3nc4ccccc4s3)c(N[C@@H]3C[C@H](CO)[C@@H](O)[C@H]3O)n2)c(OC)c1] |
| 1236 | 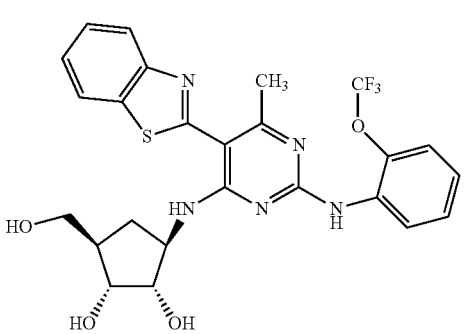 [SMILES: Cc1nc(Nc2ccccc2OC(F)(F)F)nc(N[C@@H]2C[C@H](CO)[C@@H](O)[C@H]2O)c1-c1nc2ccccc2s1] |
| 1237 | 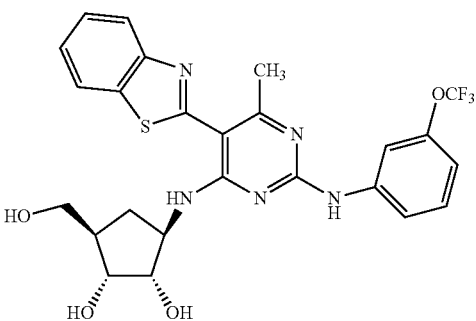 [SMILES: Cc1nc(Nc2cccc(OC(F)(F)F)c2)nc(N[C@@H]2C[C@H](CO)[C@@H](O)[C@H]2O)c1-c1nc2ccccc2s1] |

| Compd # | Structure |
|---|---|
| 1238 | 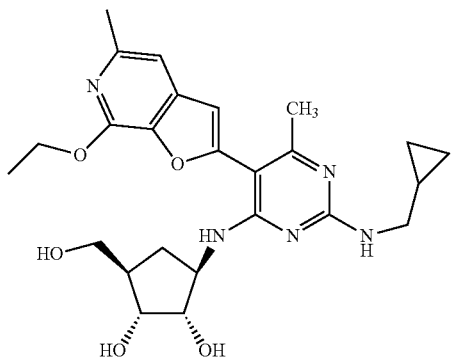 [SMILES: CCOc1nc(C)cc2cc(-c3c(C)nc(NCC4CC4)nc3N[C@@H]3C[C@H](CO)[C@@H](O)[C@H]3O)oc12] |
| 1239 | 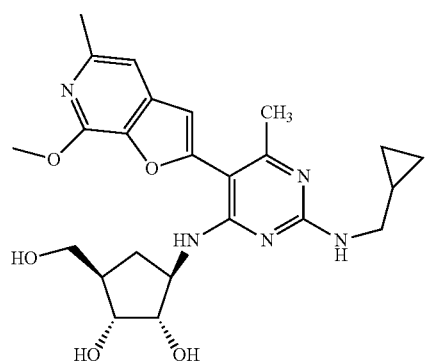 [SMILES: COc1nc(C)cc2cc(-c3c(C)nc(NCC4CC4)nc3N[C@@H]3C[C@H](CO)[C@@H](O)[C@H]3O)oc12] |
| 1240 | 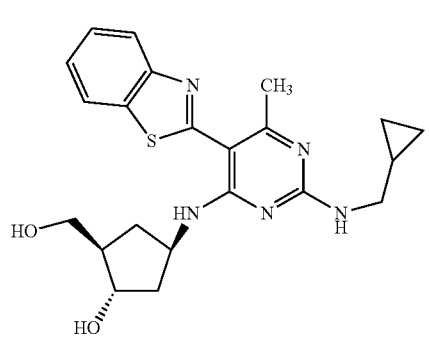 [SMILES: Cc1nc(NCC2CC2)nc(N[C@@H]2C[C@H](CO)[C@@H](O)C2)c1-c1nc2ccccc2s1] |
| 1241 | 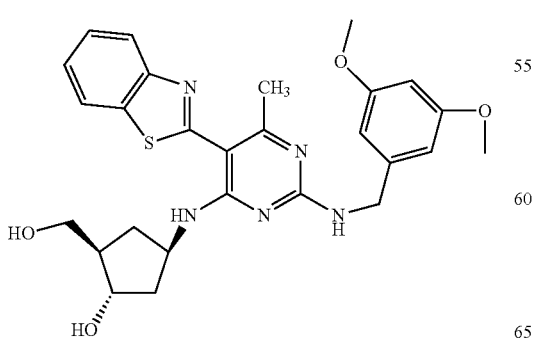 |
| Compd # | Structure |
|---|---|
| 1242 | 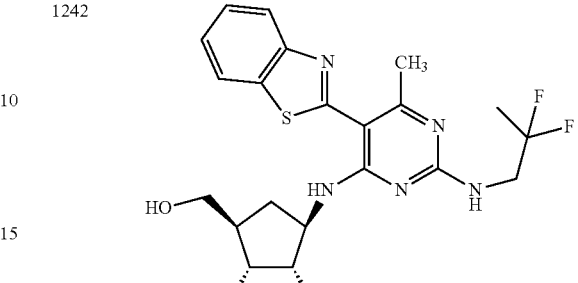 |
| 1243 | 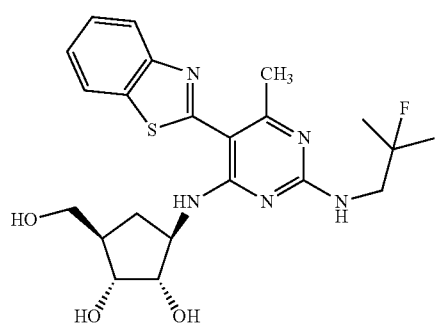 [SMILES: Cc1nc(NCC(C)(C)F)nc(N[C@@H]2C[C@H](CO)[C@@H](O)[C@H]2O)c1-c1nc2ccccc2s1] |
| 1244 | 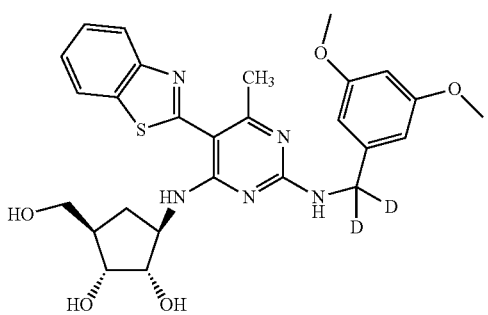 [SMILES: [2H]C([2H])(Nc1nc(C)c(-c2nc3ccccc3s2)c(N[C@@H]2C[C@H](CO)[C@@H](O)[C@H]2O)n1)c1cc(OC)cc(OC)c1] |
| 1245 | 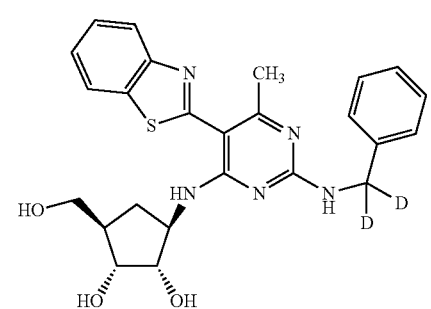 [SMILES: [2H]C([2H])(Nc1nc(C)c(-c2nc3ccccc3s2)c(N[C@@H]2C[C@H](CO)[C@@H](O)[C@H]2O)n1)c1ccccc1] |

787
-continued
| Compd # | Structure |
|---|---|
| 1246 | 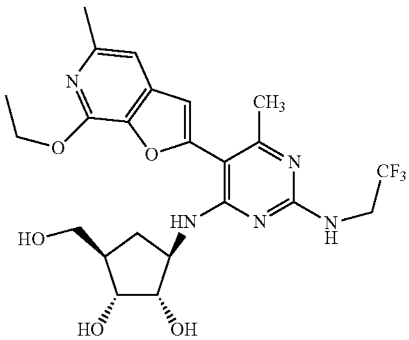 [SMILES: CCOc1nc(C)cc2cc(-c3c(C)nc(NCC(F)(F)F)nc3N[C@@H]3C[C@H](CO)[C@@H](O)[C@H]3O)oc12] |
| 1247 | 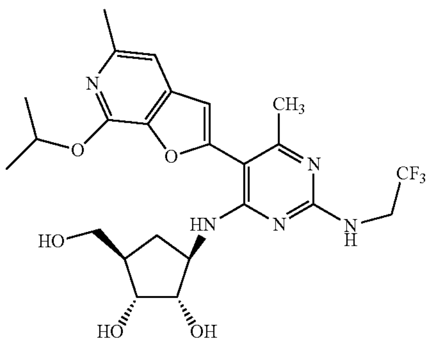 [SMILES: Cc1cc2cc(-c3c(C)nc(NCC(F)(F)F)nc3N[C@@H]3C[C@H](CO)[C@@H](O)[C@H]3O)oc2c(OC(C)C)n1] |
| 1248 | 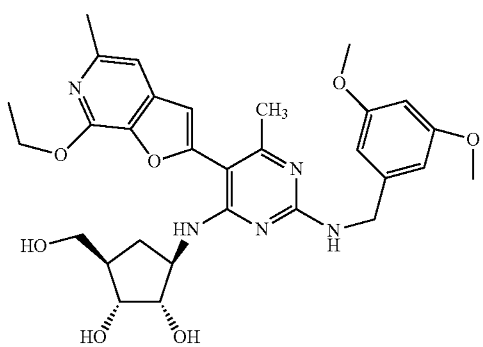 [SMILES: CCOc1nc(C)cc2cc(-c3c(C)nc(NCc4cc(OC)cc(OC)c4)nc3N[C@@H]3C[C@H](CO)[C@@H](O)[C@H]3O)oc12] |
| 1249 | 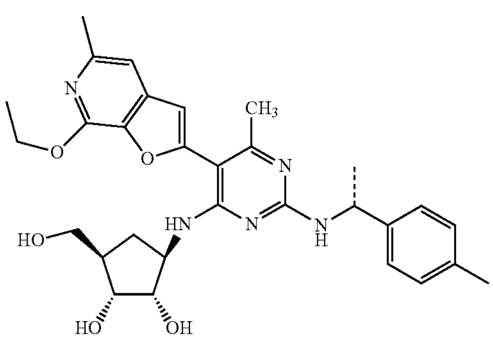 [SMILES: CCOc1nc(C)cc2cc(-c3c(C)nc(N[C@H](C)c4ccc(C)cc4)nc3N[C@@H]3C[C@H](CO)[C@@H](O)[C@H]3O)oc12] |
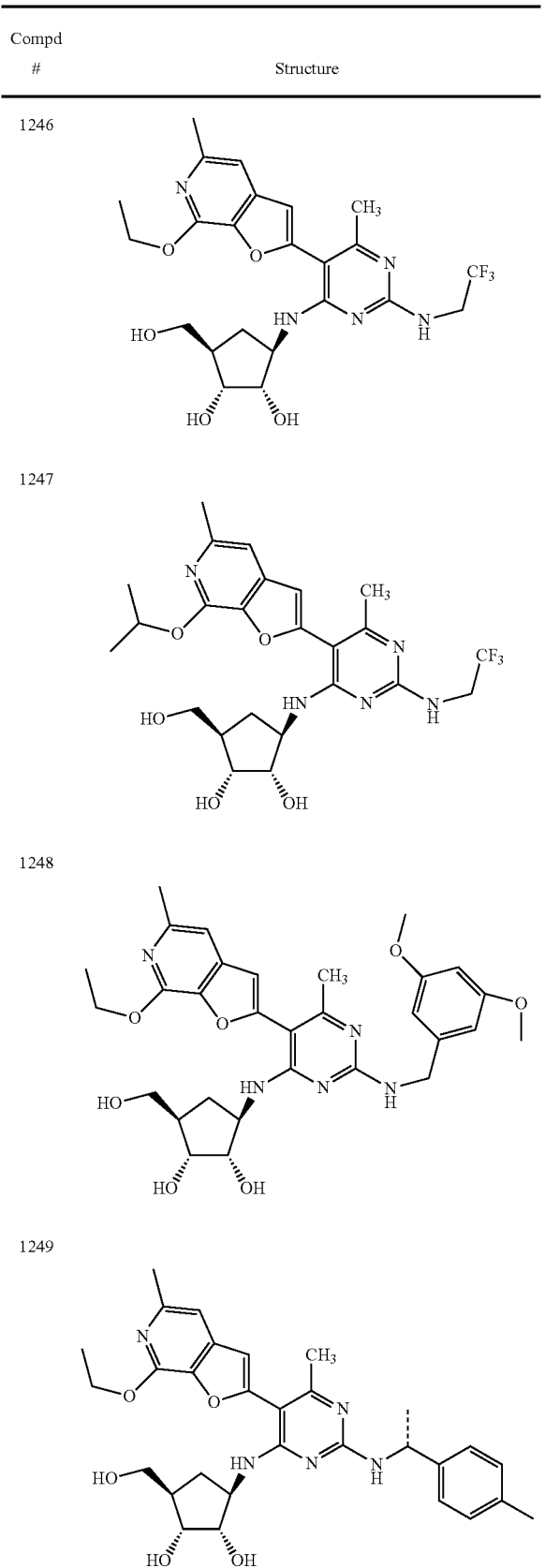
788
-continued
| Compd # | Structure |
|---|---|
| 1250 | 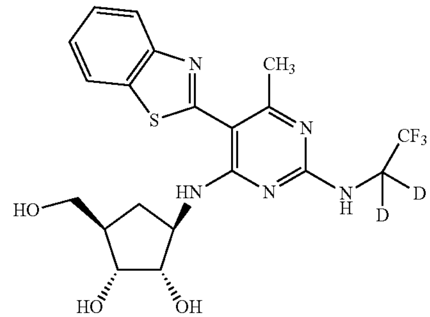 [SMILES: [2H]C([2H])(Nc1nc(C)c(-c2nc3ccccc3s2)c(N[C@@H]2C[C@H](CO)[C@@H](O)[C@H]2O)n1)C(F)(F)F] |
| 1251 | 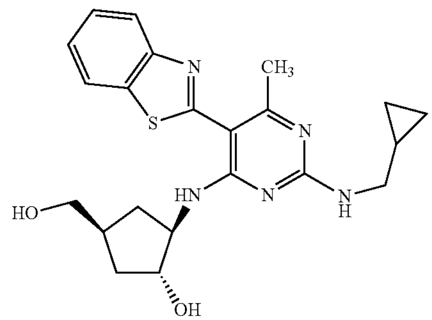 [SMILES: Cc1nc(NCC2CC2)nc(N[C@@H]2C[C@H](CO)C[C@H]2O)c1-c1nc2ccccc2s1] |
| 1252 | 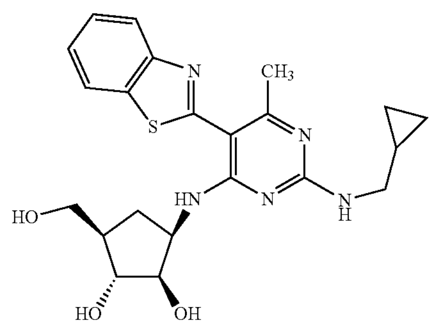 [SMILES: Cc1nc(NCC2CC2)nc(N[C@@H]2C[C@H](CO)[C@@H](O)[C@@H]2O)c1-c1nc2ccccc2s1] |
| 1253 | 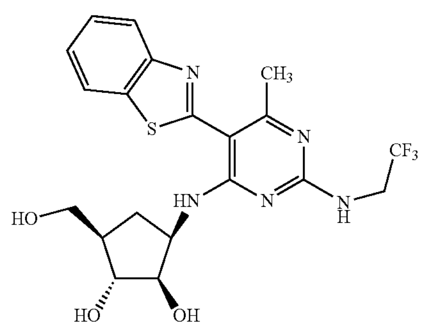 [SMILES: Cc1nc(NCC(F)(F)F)nc(N[C@@H]2C[C@H](CO)[C@@H](O)[C@@H]2O)c1-c1nc2ccccc2s1] |
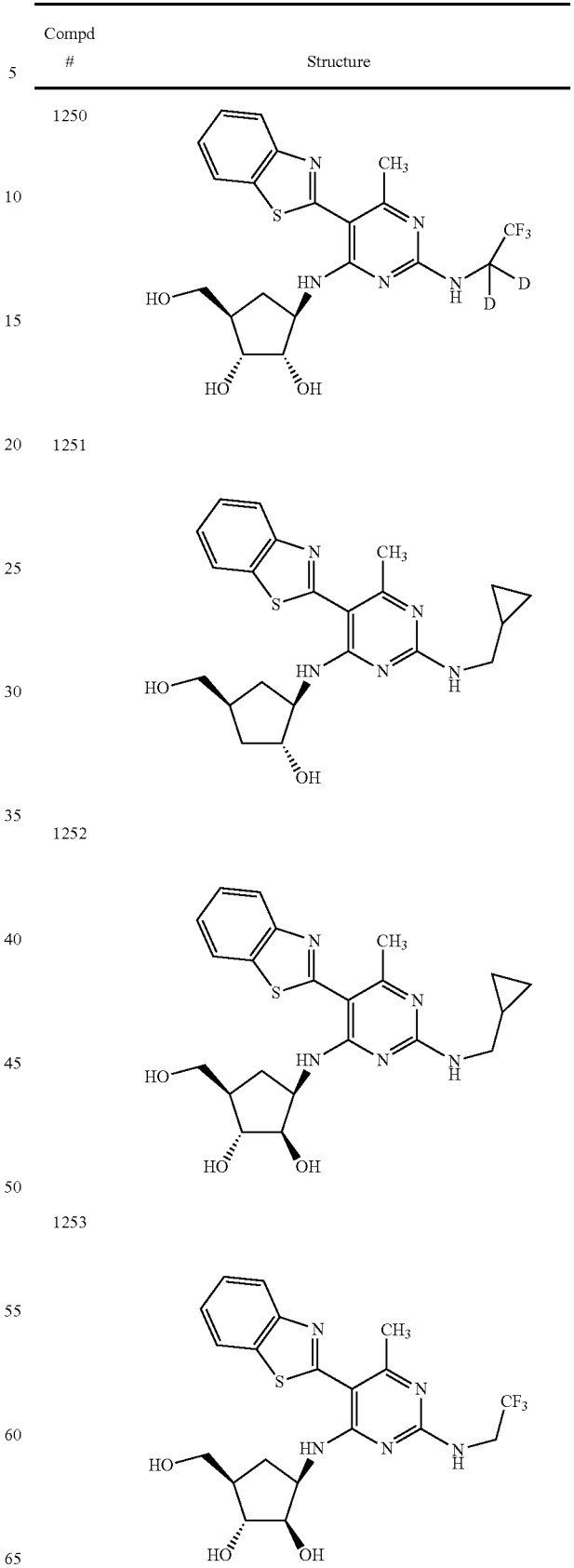

| Compd # | Structure |
|---|---|
| 1301 | 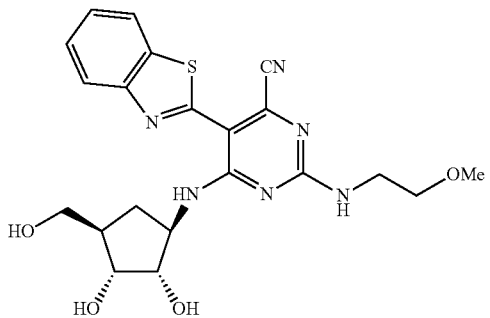 [SMILES: COCCNc1nc(C#N)c(-c2nc3ccccc3s2)c(N[C@@H]2C[C@H](CO)[C@@H](O)[C@H]2O)n1] |
| 1302 | 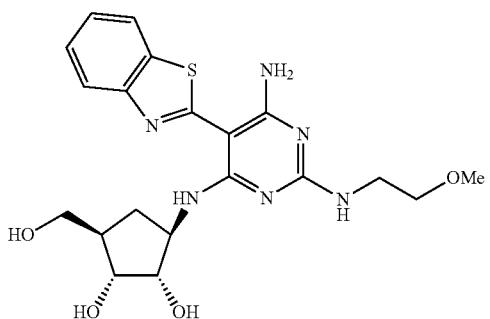 [SMILES: COCCNc1nc(N)c(-c2nc3ccccc3s2)c(N[C@@H]2C[C@H](CO)[C@@H](O)[C@H]2O)n1] |
| 1303 | 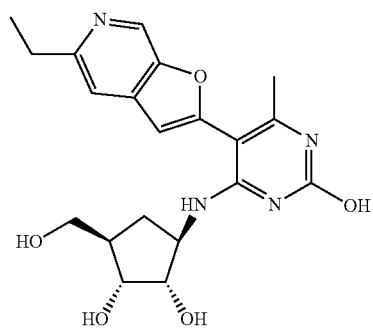 [SMILES: CCc1cc2cc(-c3c(C)nc(O)nc3N[C@@H]3C[C@H](CO)[C@@H](O)[C@H]3O)oc2cn1] |
| 1304 | 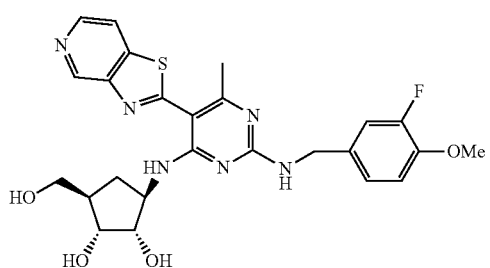 [SMILES: COc1ccc(CNc2nc(C)c(-c3nc4cnccc4s3)c(N[C@@H]3C[C@H](CO)[C@@H](O)[C@H]3O)n2)cc1F] |
| 1305 | 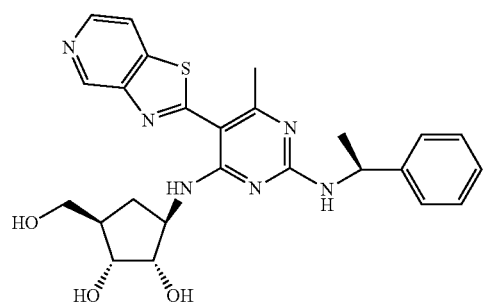 [SMILES: Cc1nc(N[C@@H](C)c2ccccc2)nc(N[C@@H]2C[C@H](CO)[C@@H](O)[C@H]2O)c1-c1nc2cnccc2s1] |
| Compd # | Structure |
|---|---|
| 1306 | 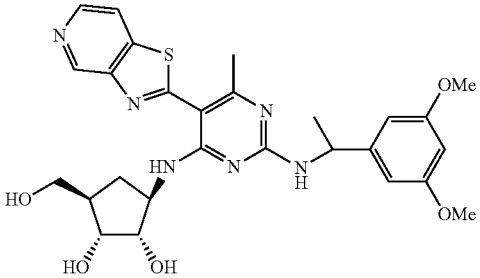 [SMILES: COc1cc(OC)cc(C(C)Nc2nc(C)c(-c3nc4cnccc4s3)c(N[C@@H]3C[C@H](CO)[C@@H](O)[C@H]3O)n2)c1] |
| 1307 | 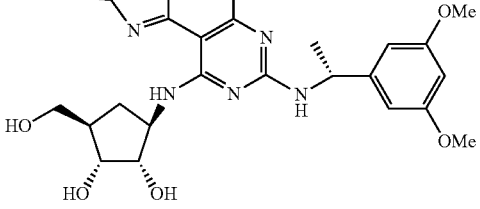 |
| 1308 | 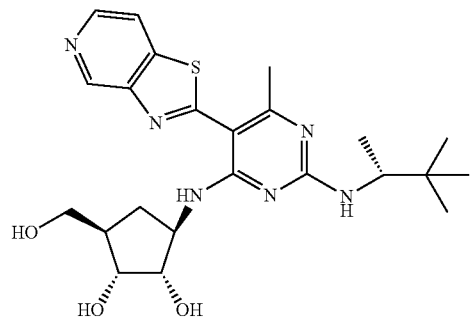 [SMILES: Cc1nc(N[C@H](C)C(C)(C)C)nc(N[C@@H]2C[C@H](CO)[C@@H](O)[C@H]2O)c1-c1nc2cnccc2s1] |
| 1309 | 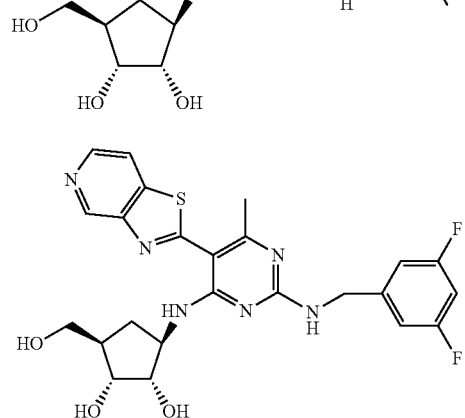 |
| 1310 | 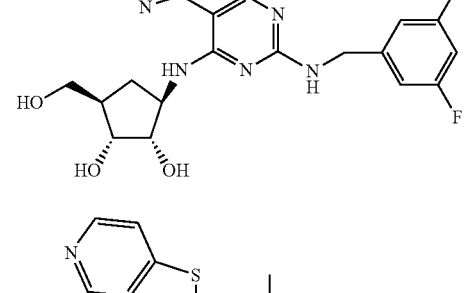 |

| Compd # | Structure |
|---|---|
| 1311 | 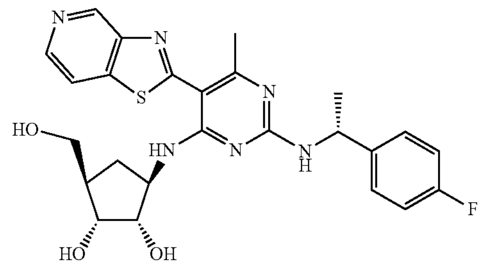 [SMILES: Cc1nc(N[C@H](C)c2ccc(F)cc2)nc(N[C@@H]2C[C@H](CO)[C@@H](O)[C@H]2O)c1-c1nc2cnccc2s1] |
| 1312 | 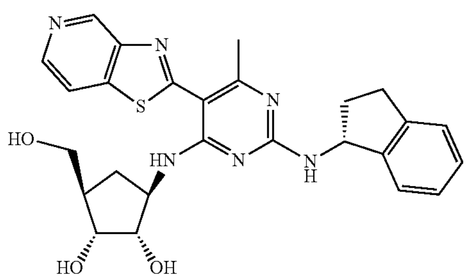 [SMILES: Cc1nc(N[C@@H]2CCc3ccccc32)nc(N[C@@H]2C[C@H](CO)[C@@H](O)[C@H]2O)c1-c1nc2cnccc2s1] |
| 1313 | 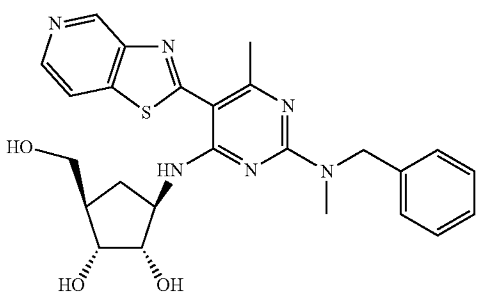 [SMILES: Cc1nc(N(C)Cc2ccccc2)nc(N[C@@H]2C[C@H](CO)[C@@H](O)[C@H]2O)c1-c1nc2cnccc2s1] |
| 1314 | 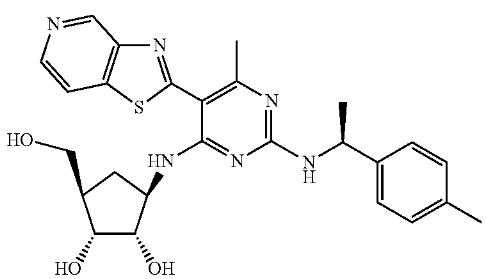 [SMILES: Cc1ccc([C@H](C)Nc2nc(C)c(-c3nc4cnccc4s3)c(N[C@@H]3C[C@H](CO)[C@@H](O)[C@H]3O)n2)cc1] |
| 1315 | 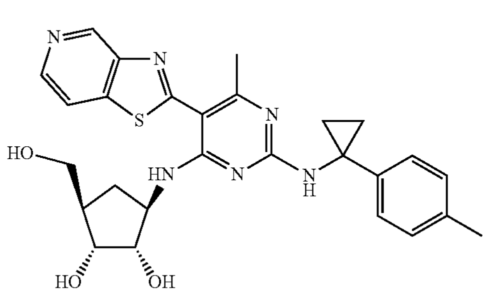 [SMILES: Cc1ccc(C2(Nc3nc(C)c(-c4nc5cnccc5s4)c(N[C@@H]4C[C@H](CO)[C@@H](O)[C@H]4O)n3)CC2)cc1] |
| 1316 | 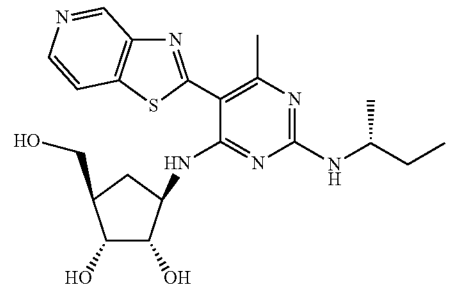 [SMILES: CC[C@@H](C)Nc1nc(C)c(-c2nc3cnccc3s2)c(N[C@@H]2C[C@H](CO)[C@@H](O)[C@H]2O)n1] |
| 1317 | 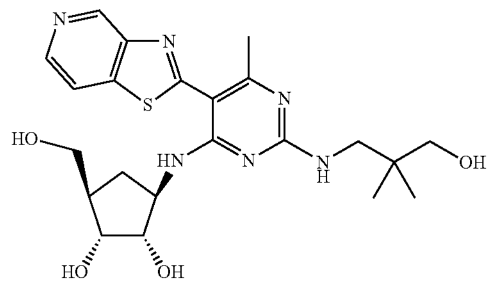 [SMILES: Cc1nc(NCC(C)(C)CO)nc(N[C@@H]2C[C@H](CO)[C@@H](O)[C@H]2O)c1-c1nc2cnccc2s1] |
| 1318 | 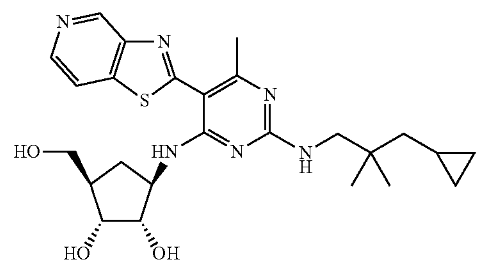 [SMILES: Cc1nc(NCC(C)(C)CC2CC2)nc(N[C@@H]2C[C@H](CO)[C@@H](O)[C@H]2O)c1-c1nc2cnccc2s1] |
| 1319 | 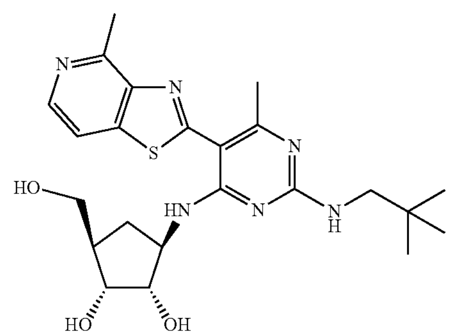 [SMILES: Cc1nc(NCC(C)(C)C)nc(N[C@@H]2C[C@H](CO)[C@@H](O)[C@H]2O)c1-c1nc2c(C)nccc2s1] |
| 1320 | 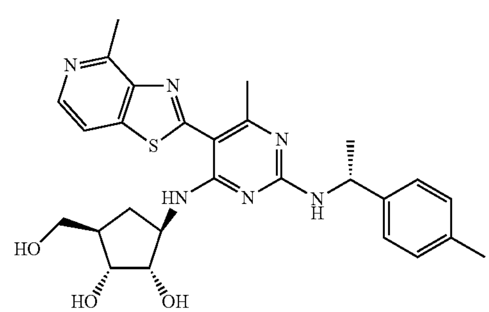 [SMILES: Cc1ccc([C@@H](C)Nc2nc(C)c(-c3nc4c(C)nccc4s3)c(N[C@@H]3C[C@H](CO)[C@@H](O)[C@H]3O)n2)cc1] |

| Compd # | Structure |
|---|---|
| 1321 | |
| 1322 | |
| 1323 | |
| 1324 | |
| 1325 | 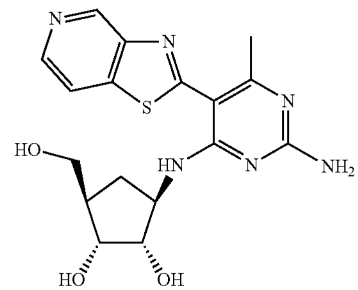 [SMILES: Cc1nc(N)nc(N[C@@H]2C[C@H](CO)[C@@H](O)[C@H]2O)c1-c1nc2cnccc2s1] |
| 1326 | 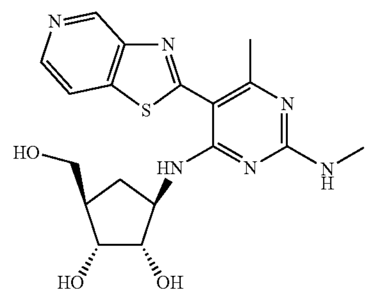 [SMILES: CNc1nc(C)c(-c2nc3cnccc3s2)c(N[C@@H]2C[C@H](CO)[C@@H](O)[C@H]2O)n1] |
| 1327 | 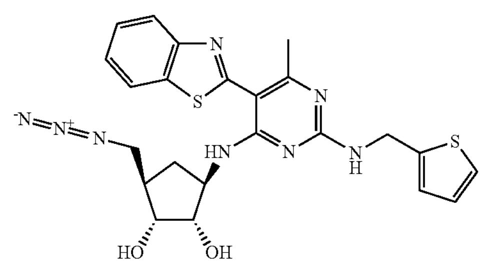 |
| 1328 | 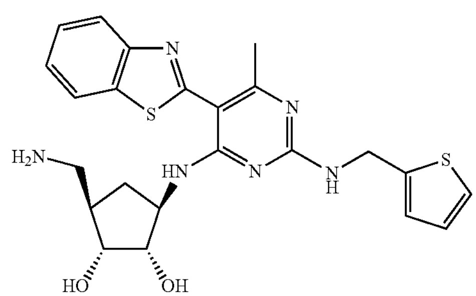 [SMILES: Cc1nc(NCc2cccs2)nc(N[C@@H]2C[C@H](CN)[C@@H](O)[C@H]2O)c1-c1nc2ccccc2s1] |
| 1330 | 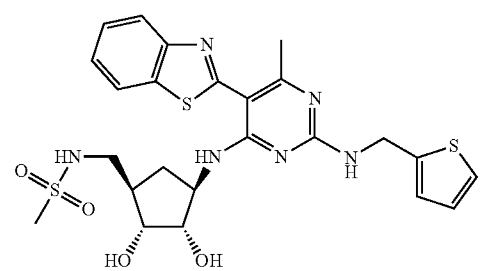 [SMILES: Cc1nc(NCc2cccs2)nc(N[C@@H]2C[C@H](CNS(C)(=O)=O)[C@@H](O)[C@H]2O)c1-c1nc2ccccc2s1] |

| Compd # | Structure |
|---|---|
| 1331 | 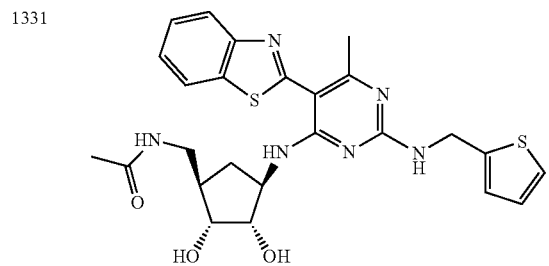 |
| 1333 | 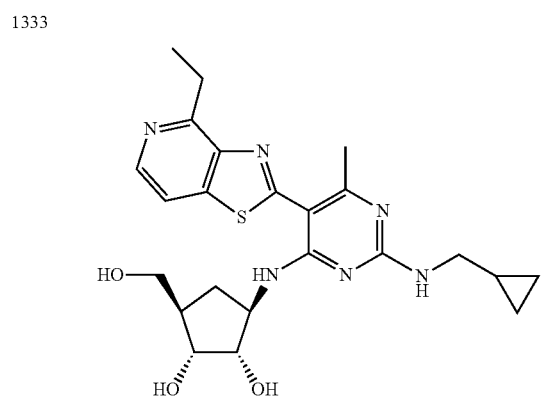 |
| 1334 | 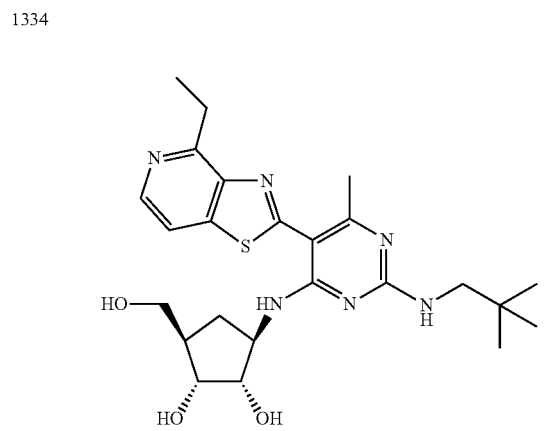 |
| 1335 | 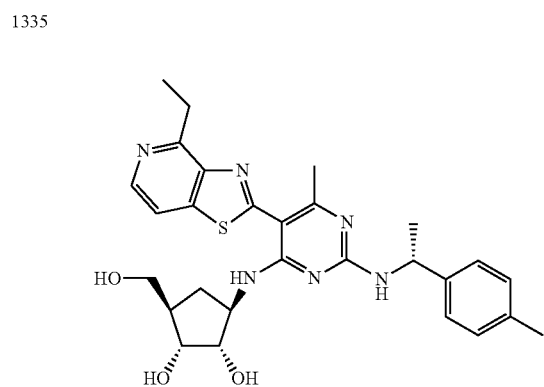 |
| Compd # | Structure |
|---|---|
| 1336 | 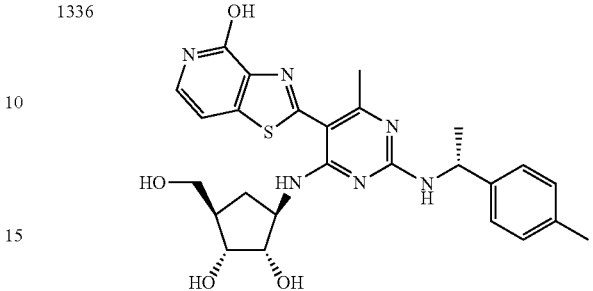 |
| 1337 | 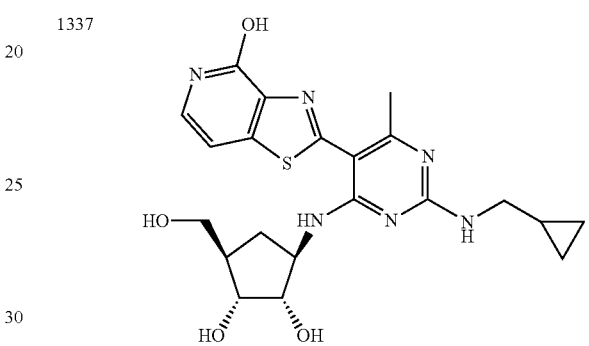 |
| 1338 | 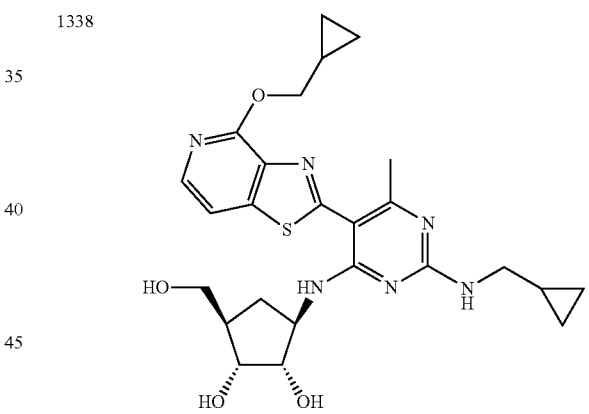 |
| 1339 | 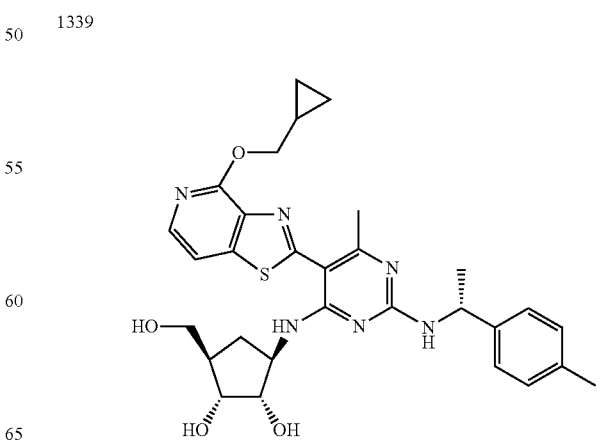 |

| Compd # | Structure |
|---|---|
| 1340 | 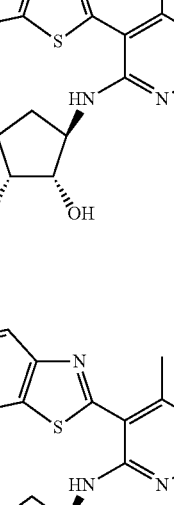 |
| 1341 | |
| 1342 | |
| 1343 | |
| Compd # | Structure |
|---|---|
| 1344 | 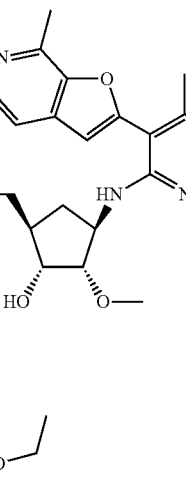 |
| 1347 | |
| 1348 | |
| 1349 | |

| Compd # | Structure |
|---|---|
| 1350 | 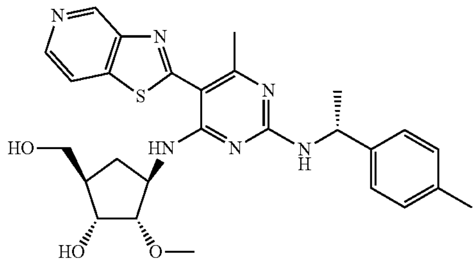 |
| 1351 | 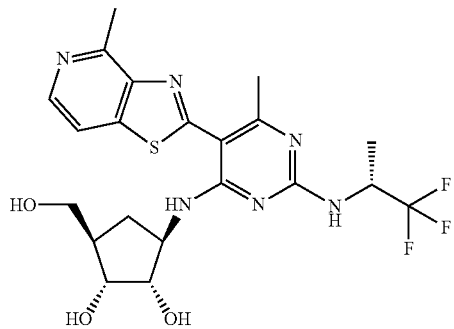 [SMILES: Cc1nc(N[C@H](C)C(F)(F)F)nc(N[C@@H]2C[C@H](CO)[C@@H](O)[C@H]2O)c1-c1nc2c(C)nccc2s1] |
| 1352 | 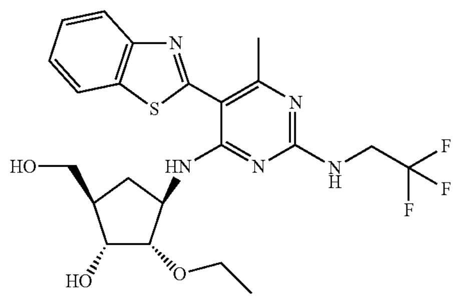 [SMILES: CCO[C@@H]1[C@H](O)[C@@H](CO)C[C@H]1Nc1nc(NCC(F)(F)F)nc(C)c1-c1nc2ccccc2s1] |
| 1353 | 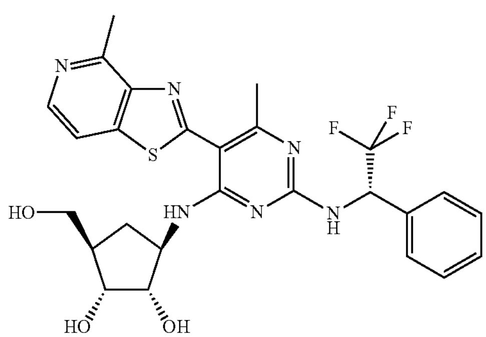 [SMILES: Cc1nc(N[C@@H](c2ccccc2)C(F)(F)F)nc(N[C@@H]2C[C@H](CO)[C@@H](O)[C@H]2O)c1-c1nc2c(C)nccc2s1] |
| 1354 | 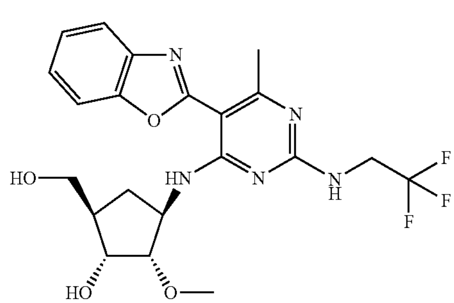 [SMILES: CO[C@@H]1[C@H](O)[C@@H](CO)C[C@H]1Nc1nc(NCC(F)(F)F)nc(C)c1-c1nc2ccccc2o1] |

| Compd # | Structure |
|---|---|
| 1355 | 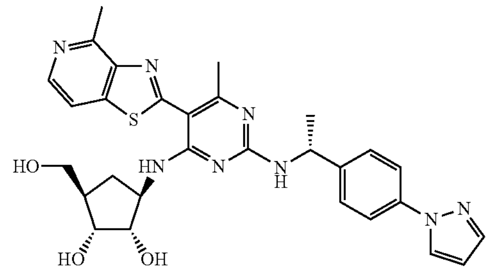 [SMILES: Cc1nc(N[C@H](C)c2ccc(-n3cccn3)cc2)nc(N[C@@H]2C[C@H](CO)[C@@H](O)[C@H]2O)c1-c1nc2c(C)nccc2s1] |
| 1356 | 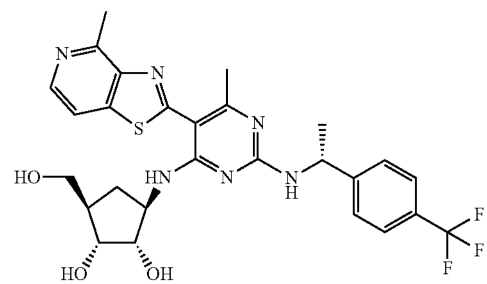 [SMILES: Cc1nc(N[C@H](C)c2ccc(C(F)(F)F)cc2)nc(N[C@@H]2C[C@H](CO)[C@@H](O)[C@H]2O)c1-c1nc2c(C)nccc2s1] |
| 1357 | 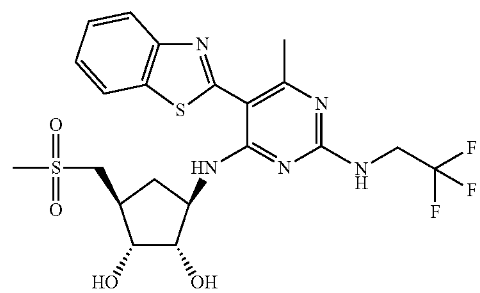 [SMILES: Cc1nc(NCC(F)(F)F)nc(N[C@@H]2C[C@H](CS(C)(=O)=O)[C@@H](O)[C@H]2O)c1-c1nc2ccccc2s1] |
| 1358 | 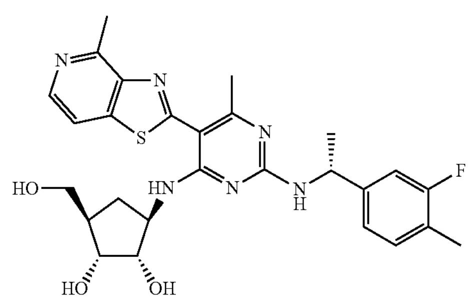 [SMILES: Cc1ccc([C@@H](C)Nc2nc(C)c(-c3nc4c(C)nccc4s3)c(N[C@@H]3C[C@H](CO)[C@@H](O)[C@H]3O)n2)cc1F] |
| 1359 | 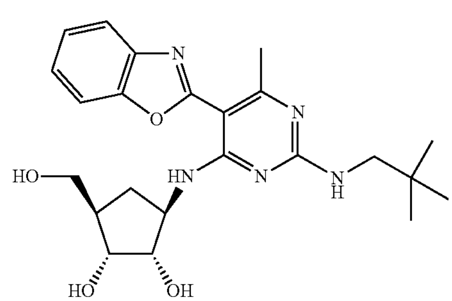 [SMILES: Cc1nc(NCC(C)(C)C)nc(N[C@@H]2C[C@H](CO)[C@@H](O)[C@H]2O)c1-c1nc2ccccc2o1] |

| Compd # | Structure |
|---|---|
| 1360 | 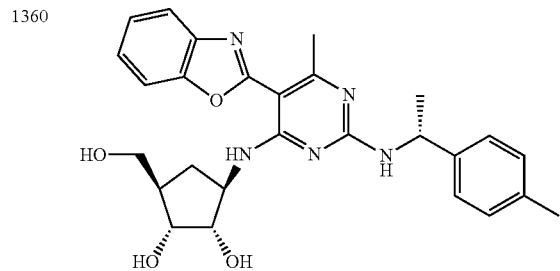 |
| 1361 | 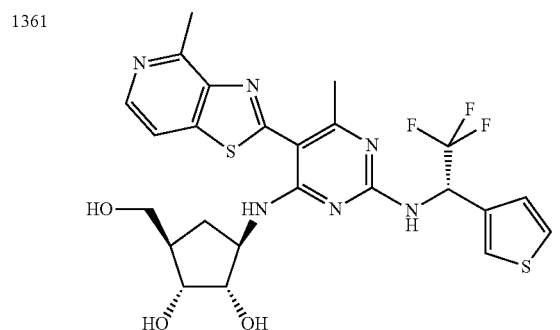 |
| 1362 | 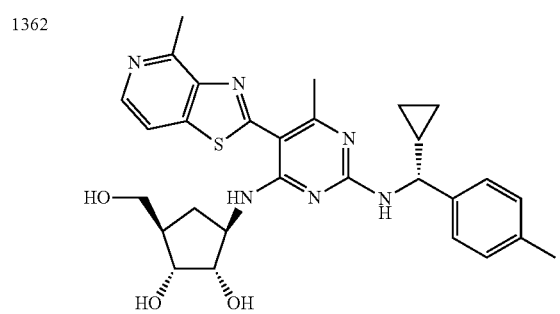 |
| 1363 | 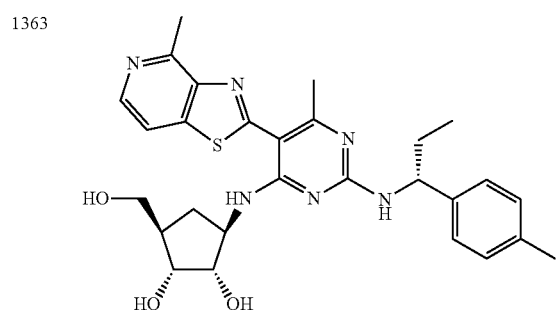 [SMILES: CCOc1cc2sc(-c3c(C)nc(N[C@H](C)c4ccc(C)cc4)nc3N[C@@H]3C[C@H](CO)[C@@H](O)[C@H]3O)nc2c(C)n1] |
| 1364 | 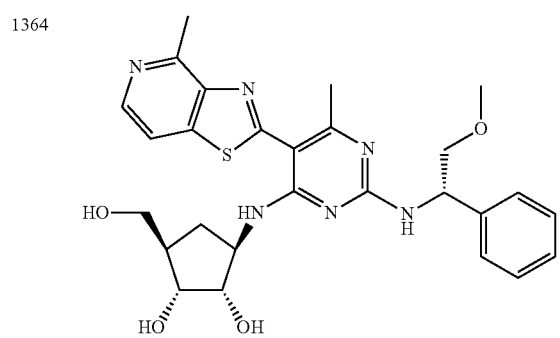 |
| Compd # | Structure |
|---|---|
| 1365 | 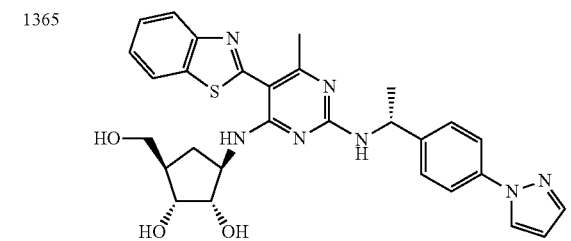 |
| 1366 | 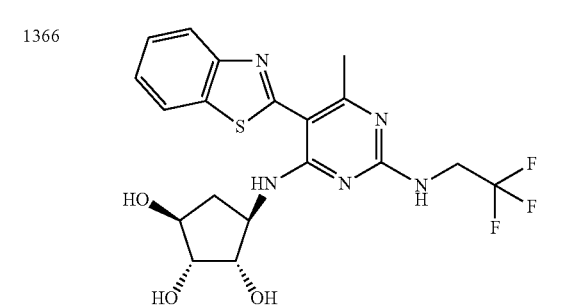 |
| 1367 | 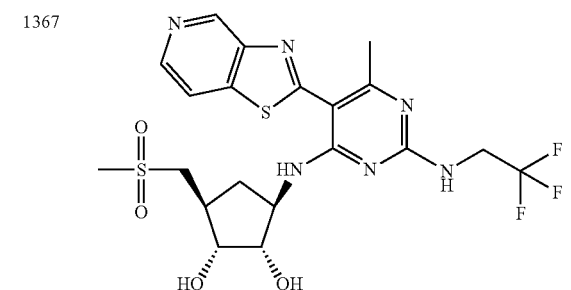 |
| 1368 | 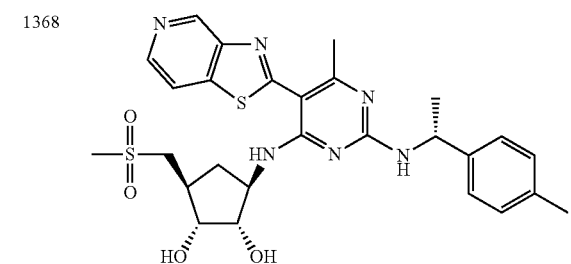 |
| 1369 | 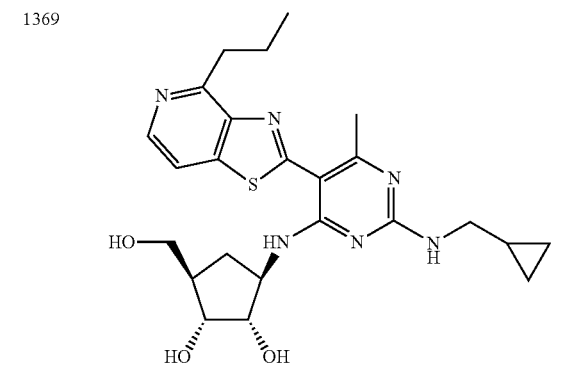 |

| 803 -continued | 804 -continued |
|---|---|
| Compd # / Structure | Compd # / Structure |
| 1370 | 1373 |
| 1371 | 1374 |
| 1346 | 1375 |
| 1372 | 1376 |
| | 1377 |

| Compd # | Structure |
|---|---|
| 1378 | 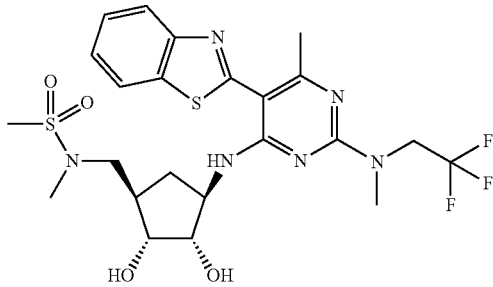 [SMILES: Cc1nc(N(C)CC(F)(F)F)nc(N[C@@H]2C[C@H](CN(C)S(C)(=O)=O)[C@@H](O)[C@H]2O)c1-c1nc2ccccc2s1] |
| 1379 | 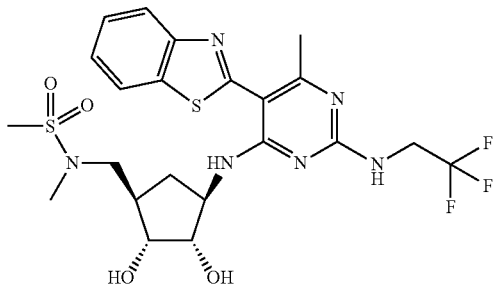 [SMILES: Cc1nc(NCC(F)(F)F)nc(N[C@@H]2C[C@H](CN(C)S(C)(=O)=O)[C@@H](O)[C@H]2O)c1-c1nc2ccccc2s1] |
| 1380 | 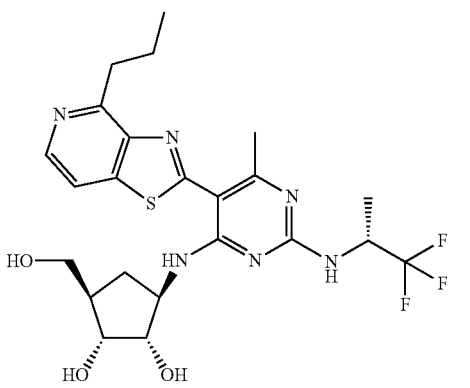 [SMILES: CCCc1nccc2sc(-c3c(C)nc(N[C@H](C)C(F)(F)F)nc3N[C@@H]3C[C@H](CO)[C@@H](O)[C@H]3O)nc12] |
| 1381 | 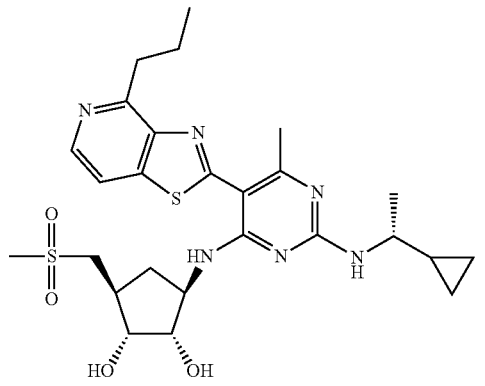 [SMILES: CCCc1nccc2sc(-c3c(C)nc(N[C@H](C)C4CC4)nc3N[C@@H]3C[C@H](CS(C)(=O)=O)[C@@H](O)[C@H]3O)nc12] |
| Compd # | Structure |
|---|---|
| 1382 | 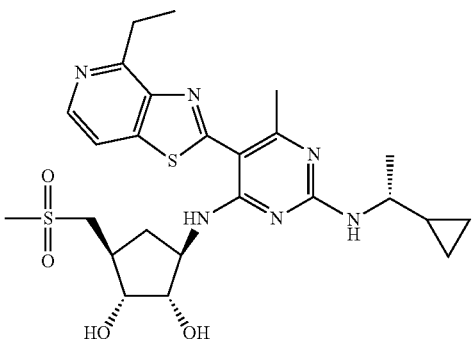 [SMILES: CCc1nccc2sc(-c3c(C)nc(N[C@H](C)C4CC4)nc3N[C@@H]3C[C@H](CS(C)(=O)=O)[C@@H](O)[C@H]3O)nc12] |
| 1383 | 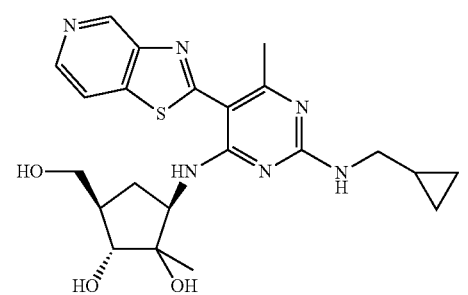 [SMILES: Cc1nc(NCC2CC2)nc(N[C@@H]2C[C@H](CO)[C@@H](O)C2(C)O)c1-c1nc2cnccc2s1] |
| 1384 | 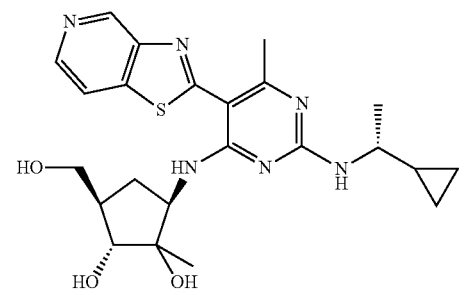 [SMILES: Cc1nc(N[C@H](C)C2CC2)nc(N[C@@H]2C[C@H](CO)[C@@H](O)C2(C)O)c1-c1nc2cnccc2s1] |
| 1385 | 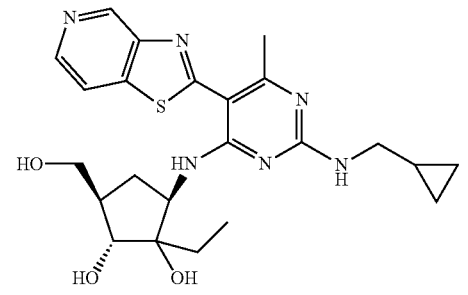 [SMILES: CCC1(O)[C@H](O)[C@@H](CO)C[C@H]1Nc1nc(NCC2CC2)nc(C)c1-c1nc2cnccc2s1] |

| Compd # | Structure |
|---|---|
| 1386 | 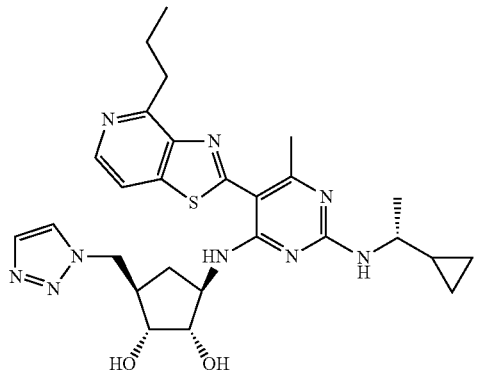 [SMILES: CCCc1nccc2sc(-c3c(C)nc(N[C@H](C)C4CC4)nc3N[C@@H]3C[C@H](Cn4ccnn4)[C@@H](O)[C@H]3O)nc12] |
| 1387 | 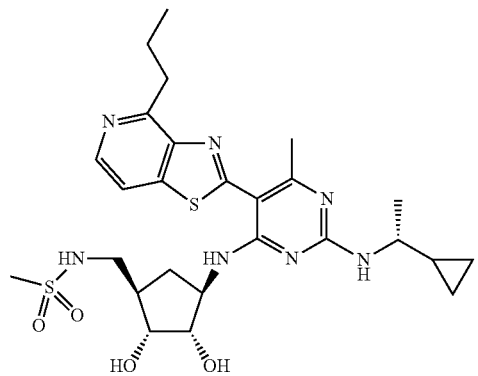 [SMILES: CCCc1nccc2sc(-c3c(C)nc(N[C@H](C)C4CC4)nc3N[C@@H]3C[C@H](CNS(C)(=O)=O)[C@@H](O)[C@H]3O)nc12] |
| 1388 | 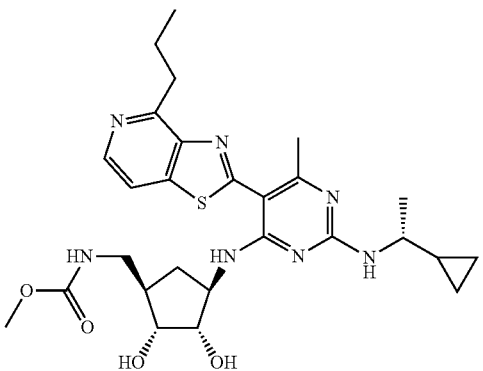 [SMILES: CCCc1nccc2sc(-c3c(C)nc(N[C@H](C)C4CC4)nc3N[C@@H]3C[C@H](CNC(=O)OC)[C@@H](O)[C@H]3O)nc12] |
| 1389 | 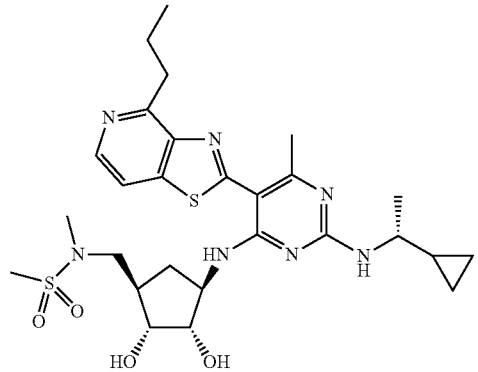 [SMILES: CCCc1nccc2sc(-c3c(C)nc(N[C@H](C)C4CC4)nc3N[C@@H]3C[C@H](CN(C)S(C)(=O)=O)[C@@H](O)[C@H]3O)nc12] |
| Compd # | Structure |
|---|---|
| 1390 | 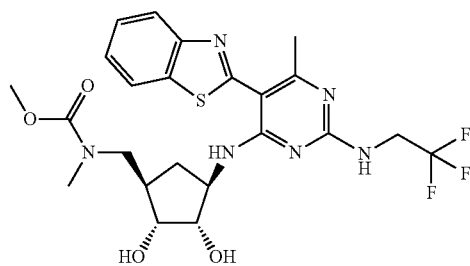 [SMILES: COC(=O)N(C)C[C@H]1C[C@@H](Nc2nc(NCC(F)(F)F)nc(C)c2-c2nc3ccccc3s2)[C@H](O)[C@@H]1O] |
| 1391 | 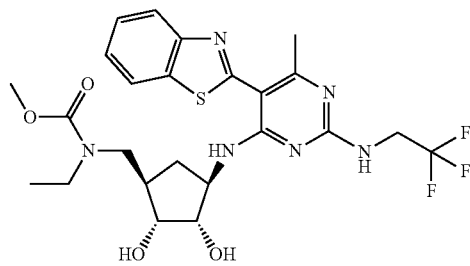 [SMILES: CCN(C[C@H]1C[C@@H](Nc2nc(NCC(F)(F)F)nc(C)c2-c2nc3ccccc3s2)[C@H](O)[C@@H]1O)C(=O)OC] |
| 1393 | 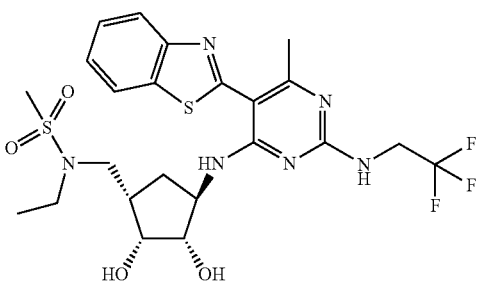 [SMILES: CCN(C[C@@H]1C[C@@H](Nc2nc(NCC(F)(F)F)nc(C)c2-c2nc3ccccc3s2)[C@H](O)[C@@H]1O)S(C)(=O)=O] |
| 1392 | 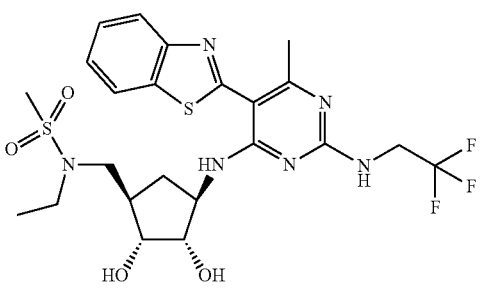 [SMILES: CCN(C[C@H]1C[C@@H](Nc2nc(NCC(F)(F)F)nc(C)c2-c2nc3ccccc3s2)[C@H](O)[C@@H]1O)S(C)(=O)=O] |
| 1394 | 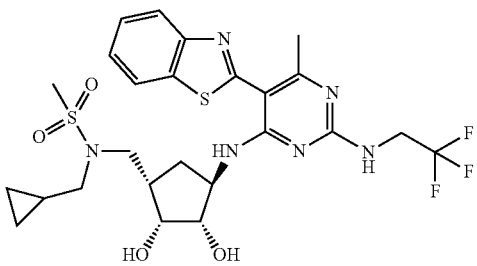 [SMILES: Cc1nc(NCC(F)(F)F)nc(N[C@@H]2C[C@@H](CN(CC3CC3)S(C)(=O)=O)[C@@H](O)[C@H]2O)c1-c1nc2ccccc2s1] |

| Compd # | Structure |
|---|---|
| 1395 | 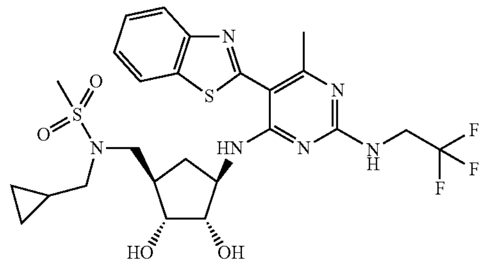 [SMILES: Cc1nc(NCC(F)(F)F)nc(N[C@@H]2C[C@H](CN(CC3CC3)S(C)(=O)=O)[C@@H](O)[C@H]2O)c1-c1nc2ccccc2s1] |
| 1396 | 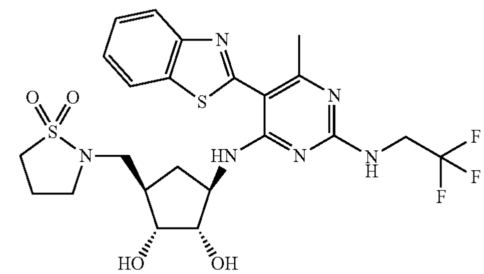 [SMILES: Cc1nc(NCC(F)(F)F)nc(N[C@@H]2C[C@H](CN3CCCS3(=O)=O)[C@@H](O)[C@H]2O)c1-c1nc2ccccc2s1] |
| 1397 | 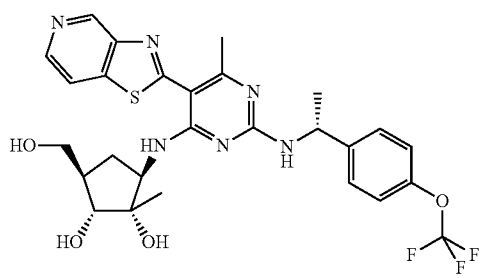 [SMILES: Cc1nc(N[C@H](C)c2ccc(OC(F)(F)F)cc2)nc(N[C@@H]2C[C@H](CO)[C@@H](O)[C@@]2(C)O)c1-c1nc2cnccc2s1] |
| 1398 | 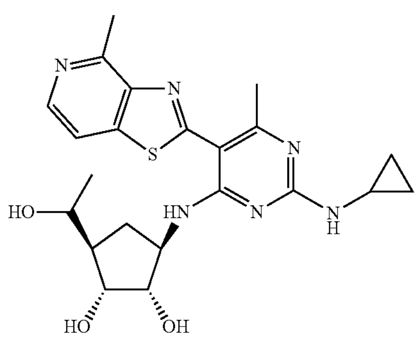 [SMILES: Cc1nc(NC2CC2)nc(N[C@@H]2C[C@H](C(C)O)[C@@H](O)[C@H]2O)c1-c1nc2c(C)nccc2s1] |
| 1399 | 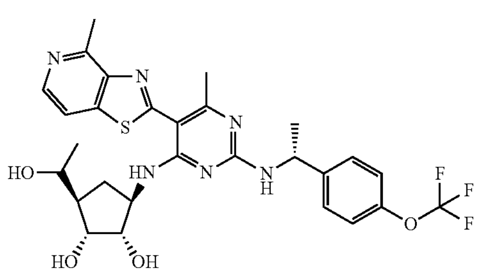 [SMILES: Cc1nc(N[C@H](C)c2ccc(OC(F)(F)F)cc2)nc(N[C@@H]2C[C@H](C(C)O)[C@@H](O)[C@H]2O)c1-c1nc2c(C)nccc2s1] |
| 1400 | |
| 1401 | |
| 1402 | |
| 1501 | |
| 1502 | |

| Compd # | Structure |
|---|---|
| 1503 | |
| 1504 | |
| 1505 | |
| 1506 | |
| 1507 | |
| 1508 | 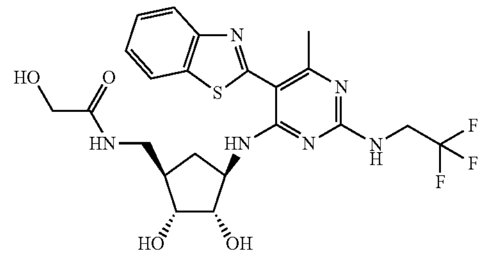 [SMILES: Cc1nc(NCC(F)(F)F)nc(N[C@@H]2C[C@H](CNC(=O)CO)[C@@H](O)[C@H]2O)c1-c1nc2ccccc2s1] |
| 1509 | 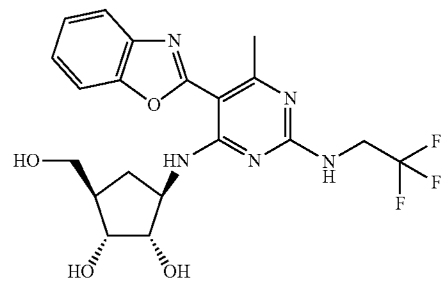 |
| 1510 | 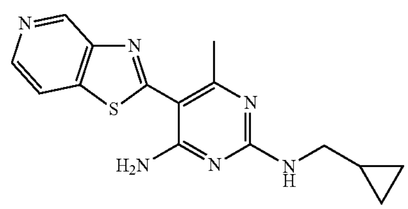 [SMILES: Cc1nc(NCC2CC2)nc(N)c1-c1nc2cnccc2s1] |
| 1511 | 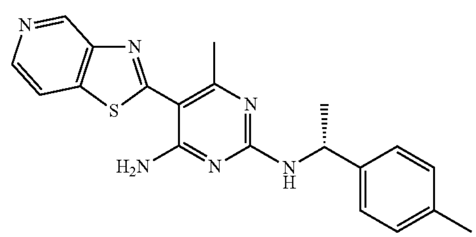 [SMILES: Cc1ccc([C@@H](C)Nc2nc(C)c(-c3nc4cnccc4s3)c(N)n2)cc1] |
| 1512 | 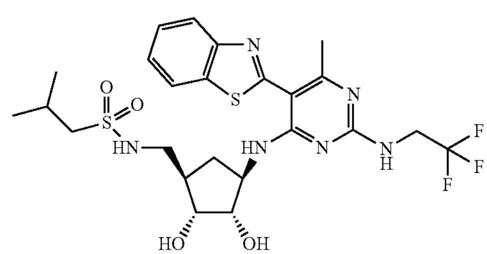 [SMILES: Cc1nc(NCC(F)(F)F)nc(N[C@@H]2C[C@H](CNS(=O)(=O)CC(C)C)[C@@H](O)[C@H]2O)c1-c1nc2ccccc2s1] |
| 1513 | 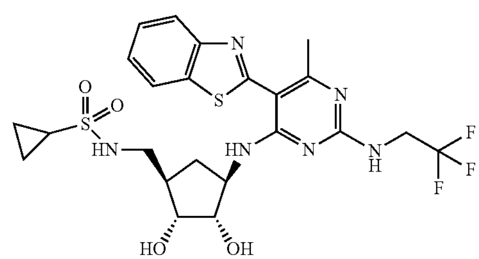 [SMILES: Cc1nc(NCC(F)(F)F)nc(N[C@@H]2C[C@H](CNS(=O)(=O)C3CC3)[C@@H](O)[C@H]2O)c1-c1nc2ccccc2s1] |

| Compd # | Structure |
|---|---|
| 1514 | 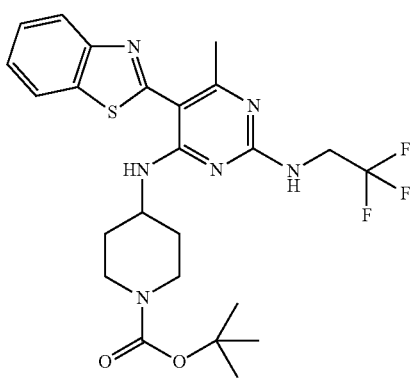 [SMILES: Cc1nc(NCC(F)(F)F)nc(NC2CCN(C(=O)OC(C)(C)C)CC2)c1-c1nc2ccccc2s1] |
| 1515 | 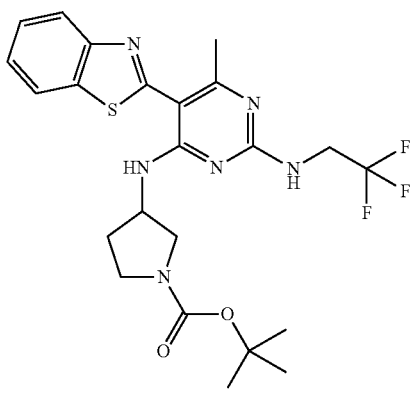 [SMILES: Cc1nc(NCC(F)(F)F)nc(NC2CCN(C(=O)OC(C)(C)C)C2)c1-c1nc2ccccc2s1] |
| 1516 | 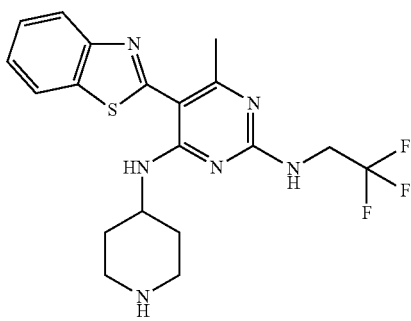 [SMILES: Cc1nc(NCC(F)(F)F)nc(NC2CCNCC2)c1-c1nc2ccccc2s1] |
| 1517 | 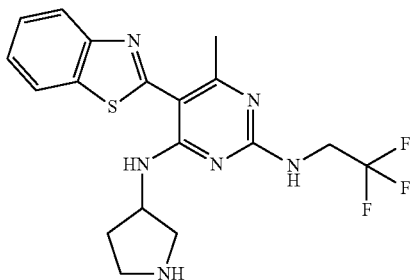 [SMILES: Cc1nc(NCC(F)(F)F)nc(NC2CCNC2)c1-c1nc2ccccc2s1] |
| 1518 | 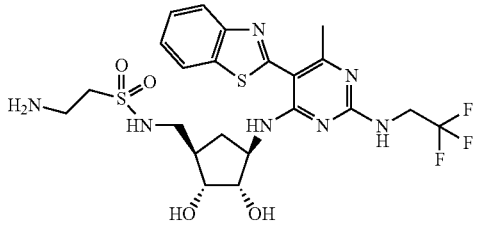 [SMILES: Cc1nc(NCC(F)(F)F)nc(N[C@@H]2C[C@H](CNS(=O)(=O)CCN)[C@@H](O)[C@H]2O)c1-c1nc2ccccc2s1] |
| 1519 | 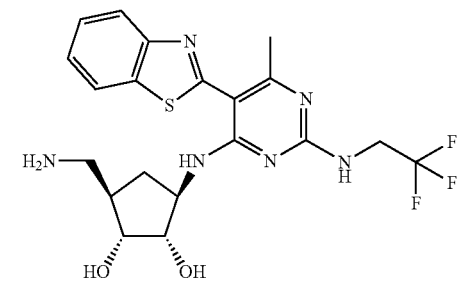 [SMILES: Cc1nc(NCC(F)(F)F)nc(N[C@@H]2C[C@H](CN)[C@@H](O)[C@H]2O)c1-c1nc2ccccc2s1] |
| 1520 | 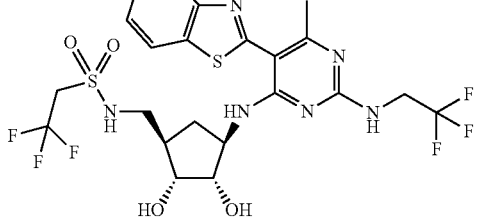 |
| 1521 | 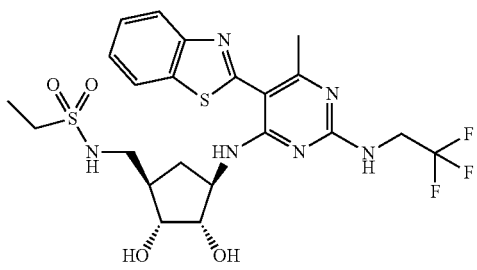 [SMILES: CCS(=O)(=O)NC[C@H]1C[C@@H](Nc2nc(NCC(F)(F)F)nc(C)c2-c2nc3ccccc3s2)[C@H](O)[C@@H]1O] |
| 1522 | 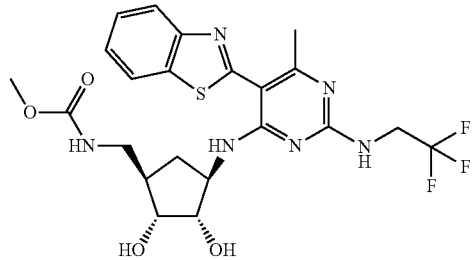 [SMILES: COC(=O)NC[C@H]1C[C@@H](Nc2nc(NCC(F)(F)F)nc(C)c2-c2nc3ccccc3s2)[C@H](O)[C@@H]1O] |
| 1523 | 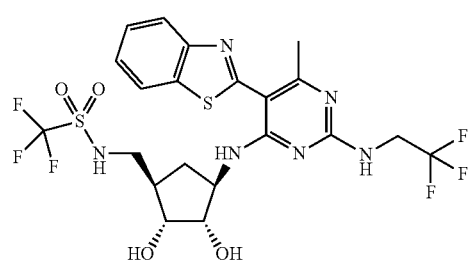 [SMILES: Cc1nc(NCC(F)(F)F)nc(N[C@@H]2C[C@H](CNS(=O)(=O)C(F)(F)F)[C@@H](O)[C@H]2O)c1-c1nc2ccccc2s1] |

TABLE-continued
| Compd # | Structure |
|---|---|
| 1524 | 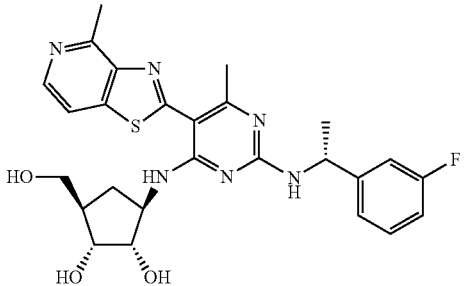 [SMILES: Cc1nc(N[C@H](C)c2cccc(F)c2)nc(N[C@@H]2C[C@H](CO)[C@@H](O)[C@H]2O)c1-c1nc2c(C)nccc2s1] |
| 1525 | 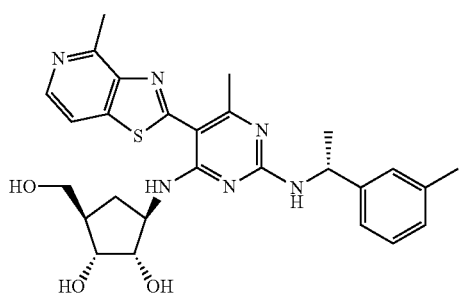 [SMILES: Cc1cccc([C@@H](C)Nc2nc(C)c(-c3nc4c(C)nccc4s3)c(N[C@@H]3C[C@H](CO)[C@@H](O)[C@H]3O)n2)c1] |
| 1526 | 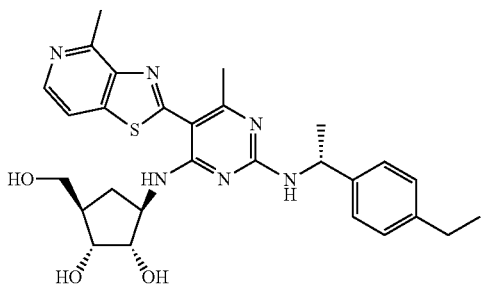 [SMILES: CCc1ccc([C@@H](C)Nc2nc(C)c(-c3nc4c(C)nccc4s3)c(N[C@@H]3C[C@H](CO)[C@@H](O)[C@H]3O)n2)cc1] |
| 1527 | 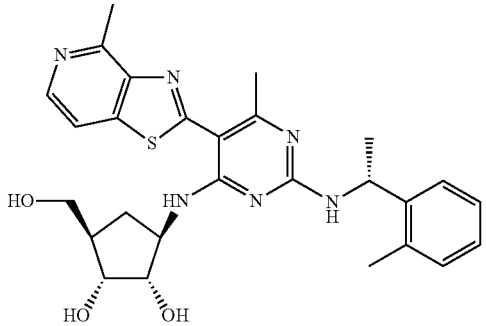 [SMILES: Cc1ccccc1[C@@H](C)Nc1nc(C)c(-c2nc3c(C)nccc3s2)c(N[C@@H]2C[C@H](CO)[C@@H](O)[C@H]2O)n1] |
| 1528 | 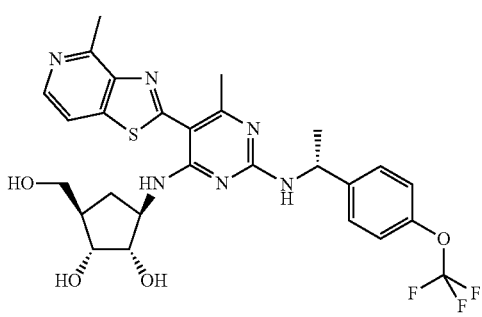 [SMILES: Cc1nc(N[C@H](C)c2ccc(OC(F)(F)F)cc2)nc(N[C@@H]2C[C@H](CO)[C@@H](O)[C@H]2O)c1-c1nc2c(C)nccc2s1] |
| 1529 | 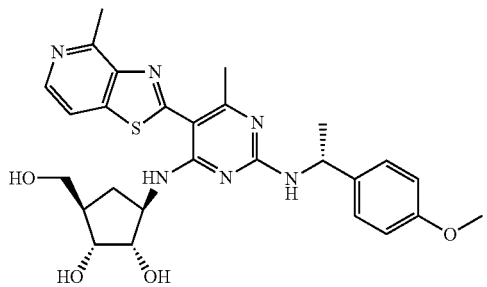 |
| 1530 | 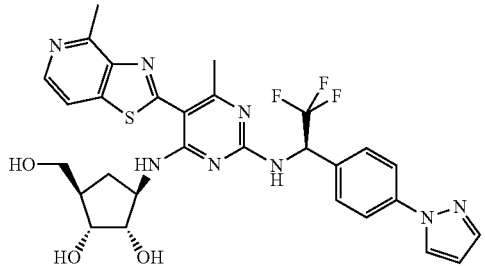 [SMILES: Cc1nc(N[C@H](c2ccc(-n3cccn3)cc2)C(F)(F)F)nc(N[C@@H]2C[C@H](CO)[C@@H](O)[C@H]2O)c1-c1nc2c(C)nccc2s1] |
| 1531 | 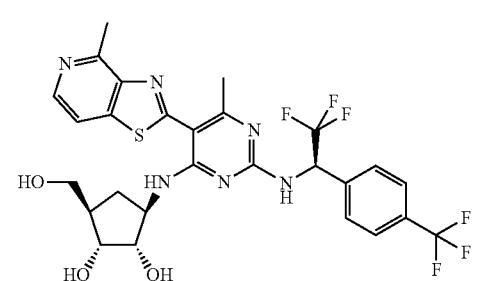 [SMILES: Cc1nc(N[C@H](c2ccc(C(F)(F)F)cc2)C(F)(F)F)nc(N[C@@H]2C[C@H](CO)[C@@H](O)[C@H]2O)c1-c1nc2c(C)nccc2s1] |
| 1532 | 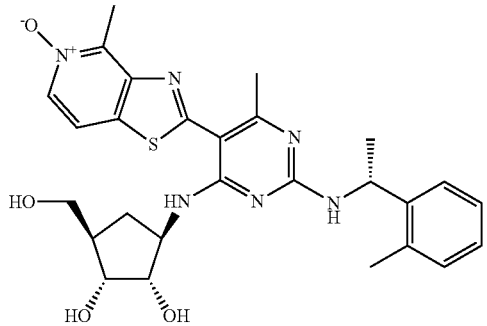 |
| 1533 | 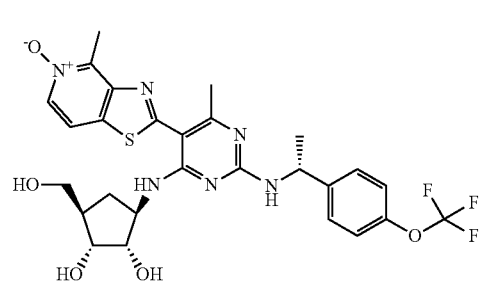 |

817
| Compd # | Structure |
|---|---|
| 1534 | 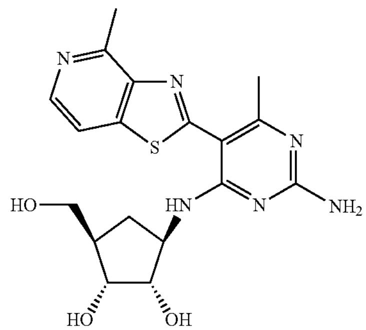 [SMILES: Cc1nc(N)nc(N[C@@H]2C[C@H](CO)[C@@H](O)[C@H]2O)c1-c1nc2c(C)nccc2s1] |
| 1535 | 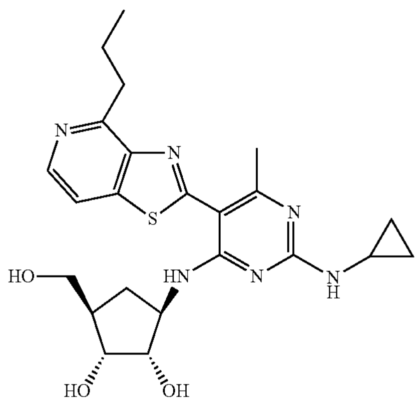 [SMILES: CCCc1nccc2sc(-c3c(C)nc(NC4CC4)nc3N[C@@H]3C[C@H](CO)[C@@H](O)[C@H]3O)nc12] |
| 1536 | 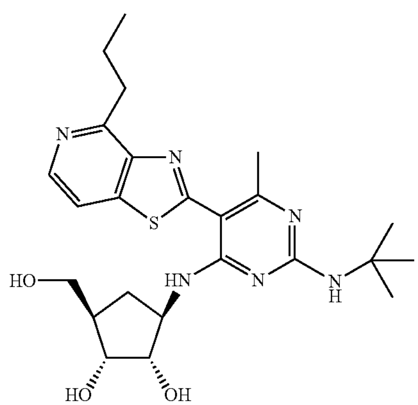 [SMILES: CCCc1nccc2sc(-c3c(C)nc(NC(C)(C)C)nc3N[C@@H]3C[C@H](CO)[C@@H](O)[C@H]3O)nc12] |
| 1537 | 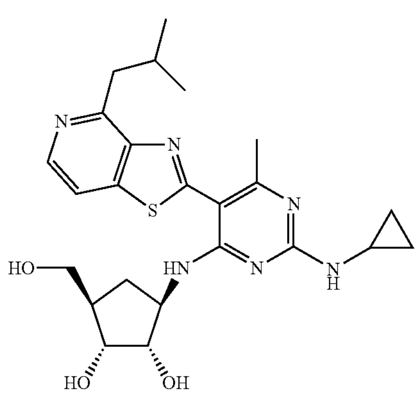 [SMILES: Cc1nc(NC2CC2)nc(N[C@@H]2C[C@H](CO)[C@@H](O)[C@H]2O)c1-c1nc2c(CC(C)C)nccc2s1] |
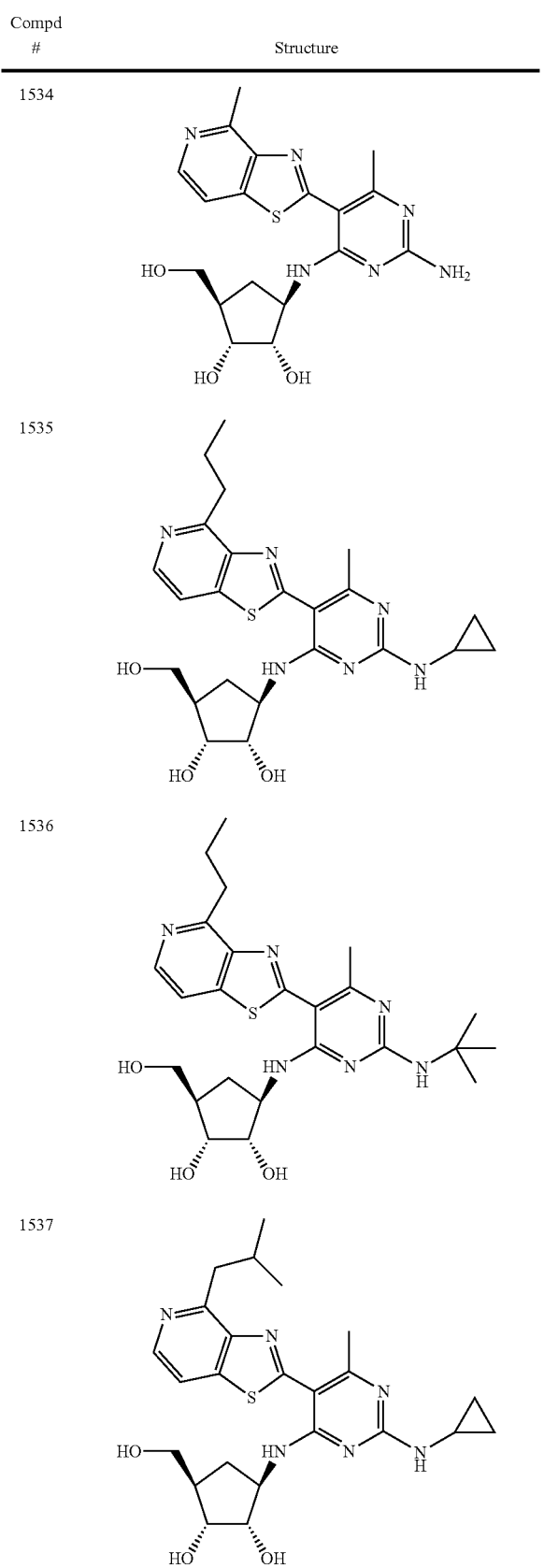
818
| Compd # | Structure |
|---|---|
| 1538 | 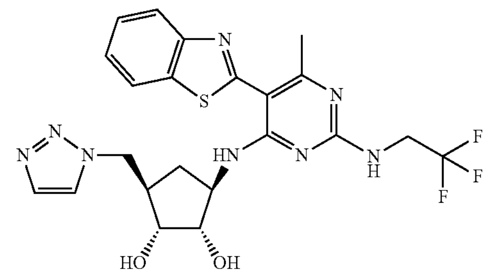 [SMILES: Cc1nc(NCC(F)(F)F)nc(N[C@@H]2C[C@H](Cn3ccnn3)[C@@H](O)[C@H]2O)c1-c1nc2ccccc2s1] |
| 1539 | 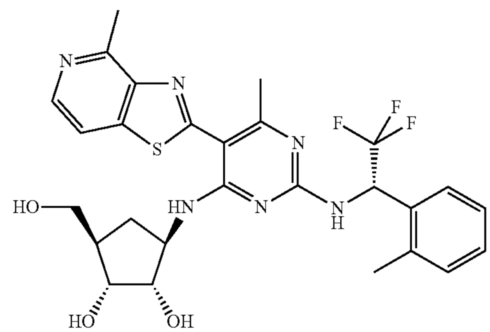 [SMILES: Cc1ccccc1[C@H](Nc1nc(C)c(-c2nc3c(C)nccc3s2)c(N[C@@H]2C[C@H](CO)[C@@H](O)[C@H]2O)n1)C(F)(F)F] |
| 1540 | 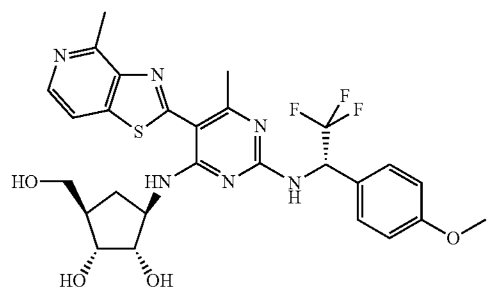 [SMILES: COc1ccc([C@H](Nc2nc(C)c(-c3nc4c(C)nccc4s3)c(N[C@@H]3C[C@H](CO)[C@@H](O)[C@H]3O)n2)C(F)(F)F)cc1] |
| 1541 | 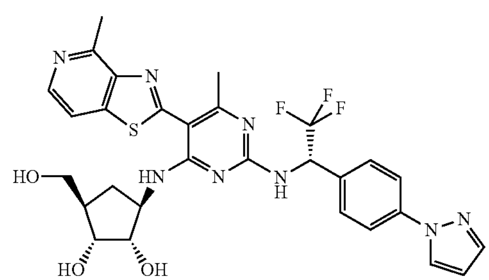 [SMILES: Cc1nc(N[C@@H](c2ccc(-n3cccn3)cc2)C(F)(F)F)nc(N[C@@H]2C[C@H](CO)[C@@H](O)[C@H]2O)c1-c1nc2c(C)nccc2s1] |
| 1542 | 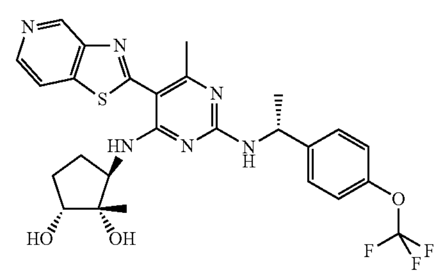 [SMILES: Cc1nc(N[C@H](C)c2ccc(OC(F)(F)F)cc2)nc(N[C@@H]2CC[C@@H](O)[C@@]2(C)O)c1-c1nc2cnccc2s1] |
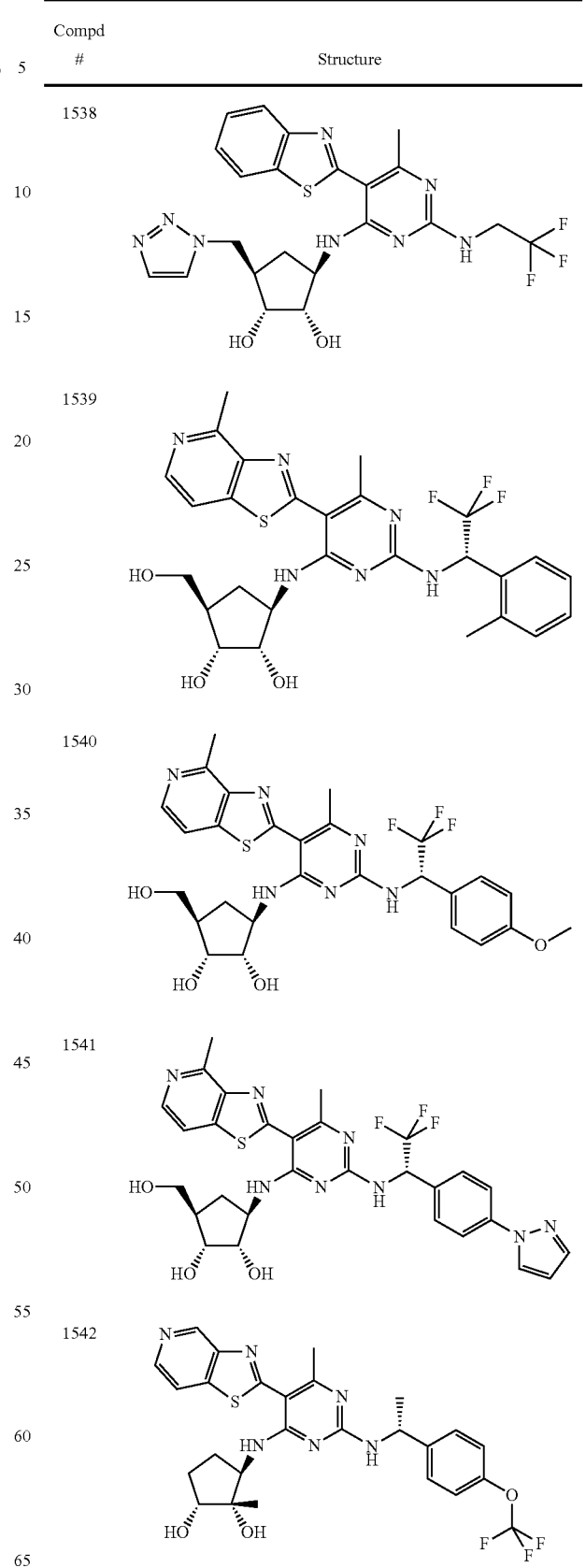

819
-continued
| Compd # | Structure |
|---|---|
| 1543 | 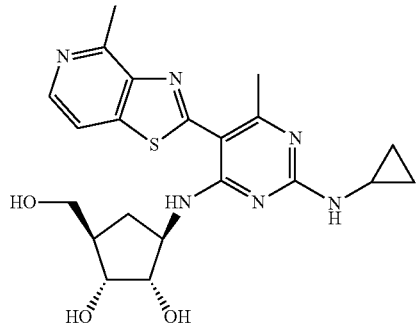 [SMILES: Cc1nc(NC2CC2)nc(N[C@@H]2C[C@H](CO)[C@@H](O)[C@H]2O)c1-c1nc2c(C)nccc2s1] |
| 1544 | 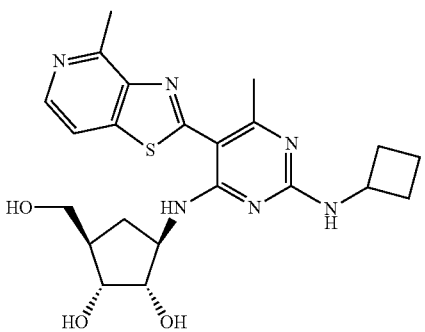 [SMILES: Cc1nc(NC2CCC2)nc(N[C@@H]2C[C@H](CO)[C@@H](O)[C@H]2O)c1-c1nc2c(C)nccc2s1] |
| 1545 | 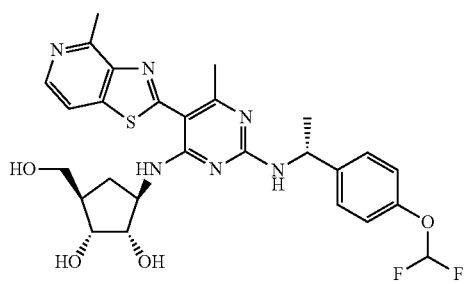 [SMILES: Cc1nc(N[C@H](C)c2ccc(OC(F)F)cc2)nc(N[C@@H]2C[C@H](CO)[C@@H](O)[C@H]2O)c1-c1nc2c(C)nccc2s1] |
| 1546 | 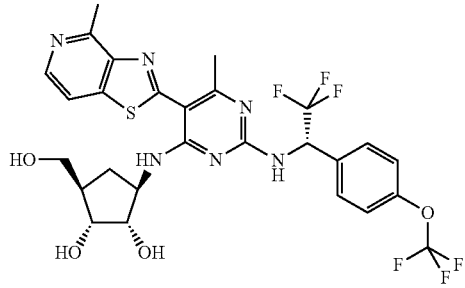 [SMILES: Cc1nc(N[C@@H](c2ccc(OC(F)(F)F)cc2)C(F)(F)F)nc(N[C@@H]2C[C@H](CO)[C@@H](O)[C@H]2O)c1-c1nc2c(C)nccc2s1] |
| 1601 | 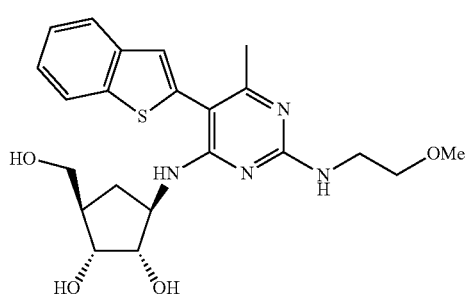 [SMILES: COCCNc1nc(C)c(-c2cc3ccccc3s2)c(N[C@@H]2C[C@H](CO)[C@@H](O)[C@H]2O)n1] |
820
-continued
| Compd # | Structure |
|---|---|
| 1602 | 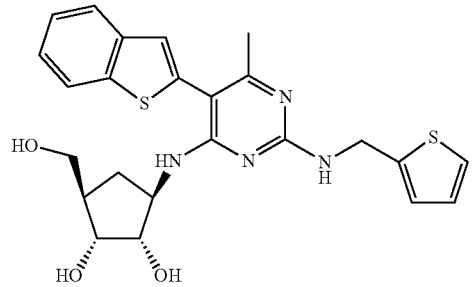 [SMILES: Cc1nc(NCc2cccs2)nc(N[C@@H]2C[C@H](CO)[C@@H](O)[C@H]2O)c1-c1cc2ccccc2s1] |
| 1603 | 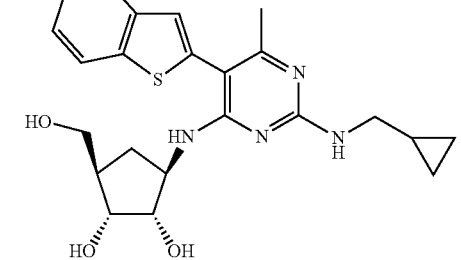 |
| 1604 | 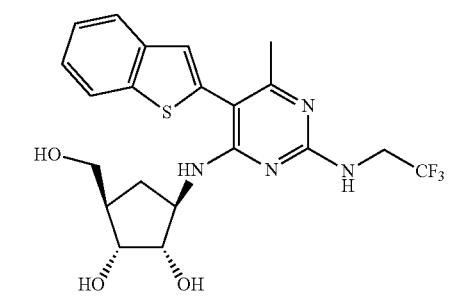 |
| 1605 | 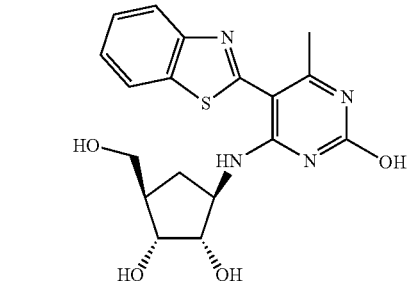 [SMILES: Cc1nc(O)nc(N[C@@H]2C[C@H](CO)[C@@H](O)[C@H]2O)c1-c1nc2ccccc2s1] |
| 1610 | 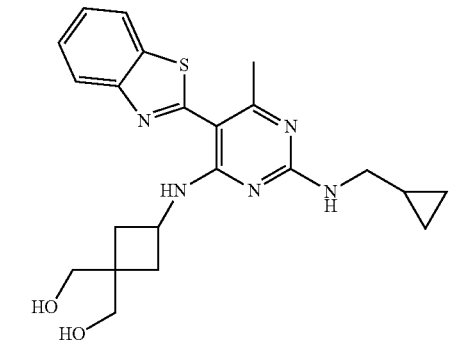 [SMILES: Cc1nc(NCC2CC2)nc(NC2CC(CO)(CO)C2)c1-c1nc2ccccc2s1] |

| Compd # | Structure |
|---|---|
| 1611 | |
| 1616 | |
| 1617 | |
| 1618 | |
| 1619 | 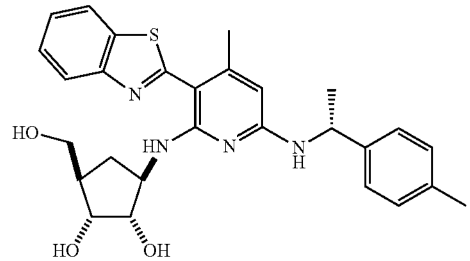 |
| 1620 | 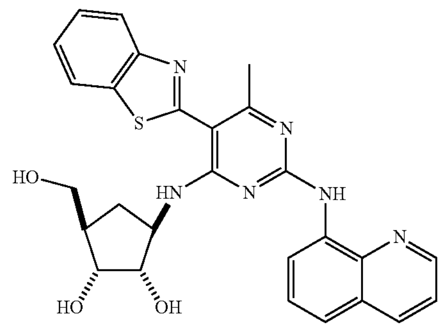 |
| 1623 | 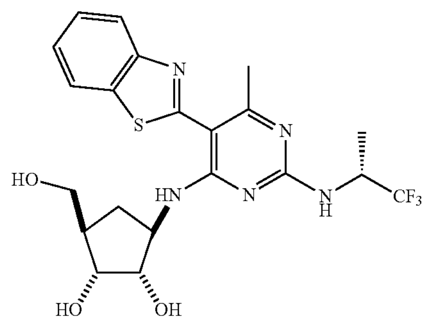 |
| 1625 | 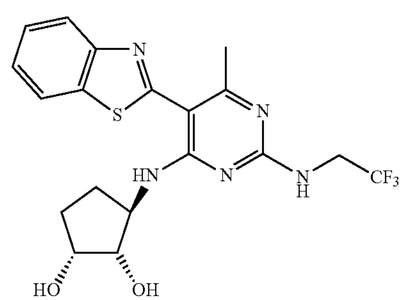 |
| 1626 | 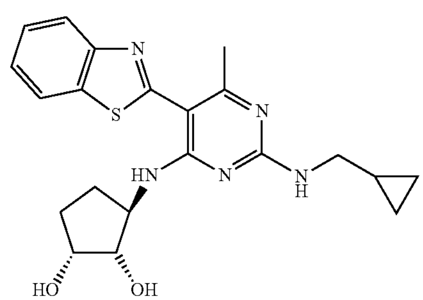 |

| Compd # | Structure |
|---|---|
| 1627 | 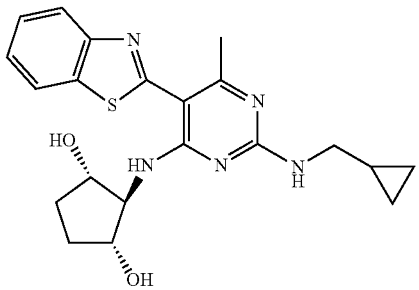 [SMILES: Cc1nc(NCC2CC2)nc(N[C@H]2[C@H](O)CC[C@@H]2O)c1-c1nc2ccccc2s1] |
| 1628 | 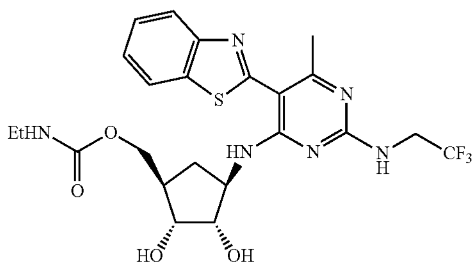 |
| 1629 | 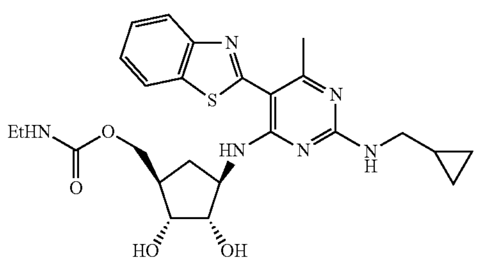 |
| 1630 | 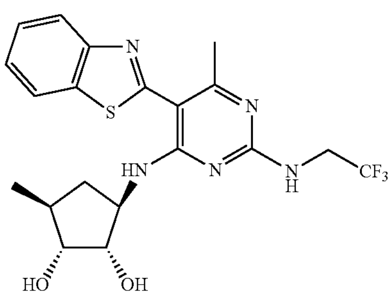 [SMILES: Cc1nc(NCC(F)(F)F)nc(N[C@@H]2C[C@H](C)[C@@H](O)[C@H]2O)c1-c1nc2ccccc2s1] |
| 1632 | 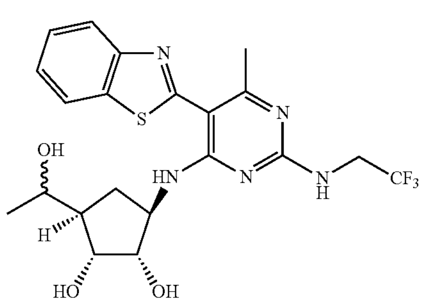 [SMILES: Cc1nc(NCC(F)(F)F)nc(N[C@@H]2C[C@H](C(C)O)[C@@H](O)[C@H]2O)c1-c1nc2ccccc2s1] |

| Compd # | Structure |
|---|---|
| 1633 | 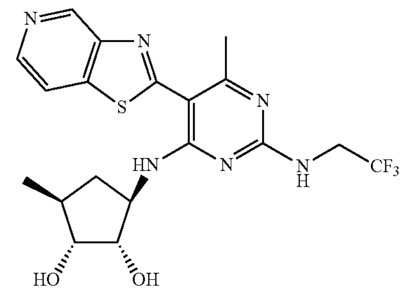 [SMILES: Cc1nc(NCC(F)(F)F)nc(N[C@@H]2C[C@H](C)[C@@H](O)[C@H]2O)c1-c1nc2cnccc2s1] |
| 1634 | 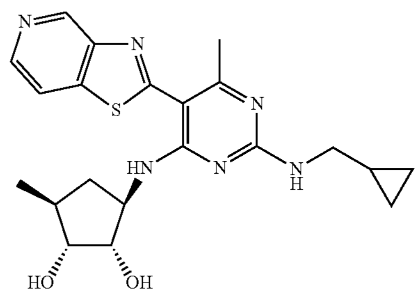 [SMILES: Cc1nc(NCC2CC2)nc(N[C@@H]2C[C@H](C)[C@@H](O)[C@H]2O)c1-c1nc2cnccc2s1] |
| 1635 | 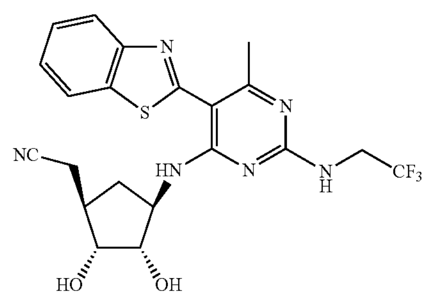 [SMILES: Cc1nc(NCC(F)(F)F)nc(N[C@@H]2C[C@H](CC#N)[C@@H](O)[C@H]2O)c1-c1nc2ccccc2s1] |
| 1636 | 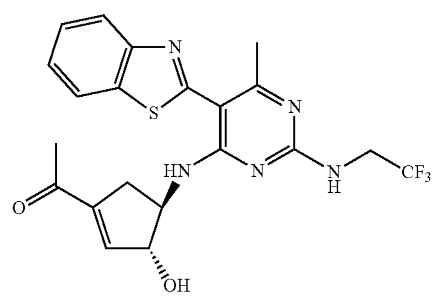 [SMILES: CC(=O)C1=C[C@@H](O)[C@H](Nc2nc(NCC(F)(F)F)nc(C)c2-c2nc3ccccc3s2)C1] |
| 1637 | 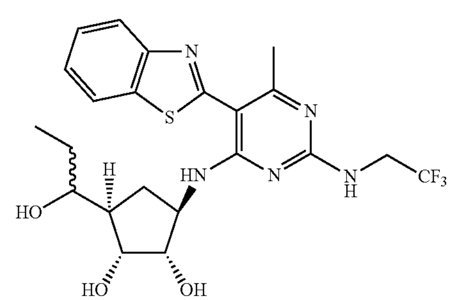 [SMILES: CCC(O)[C@H]1C[C@@H](Nc2nc(NCC(F)(F)F)nc(C)c2-c2nc3ccccc3s2)[C@H](O)[C@@H]1O] |

825
-continued
| Compd # | Structure |
|---|---|
| 1638 | 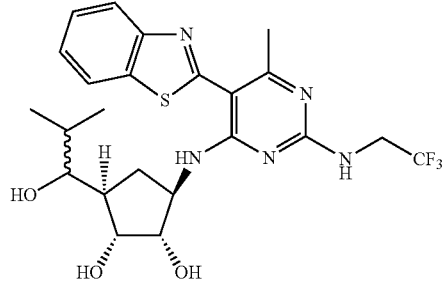 [SMILES: Cc1nc(NCC(F)(F)F)nc(N[C@@H]2C[C@H](C(O)C(C)C)[C@@H](O)[C@H]2O)c1-c1nc2ccccc2s1] |
| 1639 | 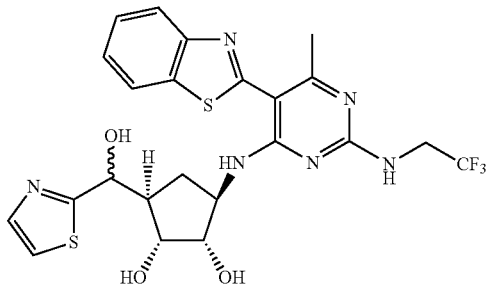 [SMILES: Cc1nc(NCC(F)(F)F)nc(N[C@@H]2C[C@H](C(O)c3nccs3)[C@@H](O)[C@H]2O)c1-c1nc2ccccc2s1] |
| 1640 | 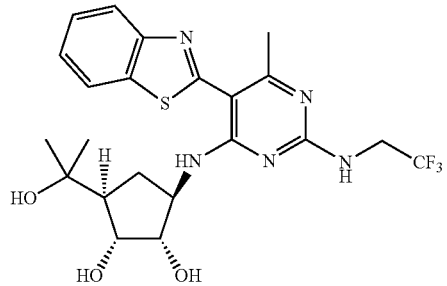 [SMILES: Cc1nc(NCC(F)(F)F)nc(N[C@@H]2C[C@H](C(C)(C)O)[C@@H](O)[C@H]2O)c1-c1nc2ccccc2s1] |
| 1641 | 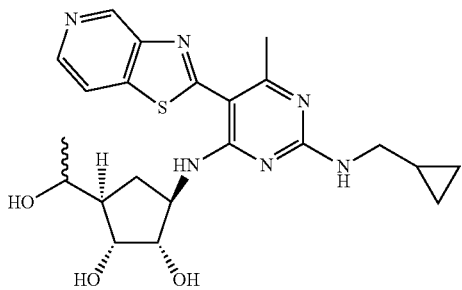 [SMILES: Cc1nc(NCC2CC2)nc(N[C@@H]2C[C@H](C(C)O)[C@@H](O)[C@H]2O)c1-c1nc2cnccc2s1] |
| 1642 | 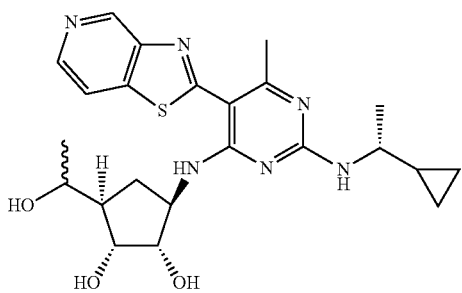 [SMILES: Cc1nc(N[C@H](C)C2CC2)nc(N[C@@H]2C[C@H](C(C)O)[C@@H](O)[C@H]2O)c1-c1nc2cnccc2s1] |
826
-continued
| Compd # | Structure |
|---|---|
| 1643 | 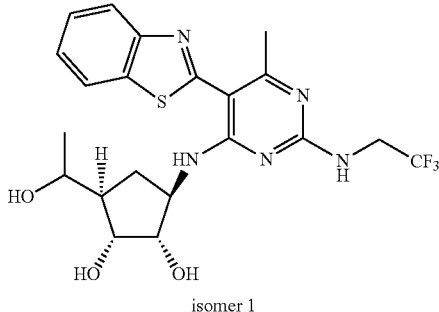 [SMILES: Cc1nc(NCC(F)(F)F)nc(N[C@@H]2C[C@H](C(C)O)[C@@H](O)[C@H]2O)c1-c1nc2ccccc2s1]<br>isomer 1 |
| 1644 | 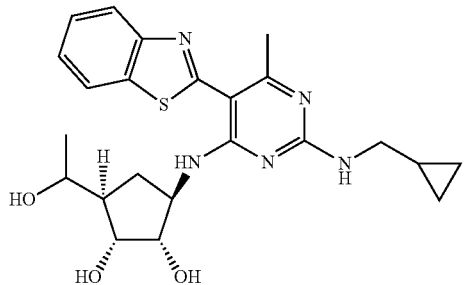<br>isomer 1 |
| 1645 | 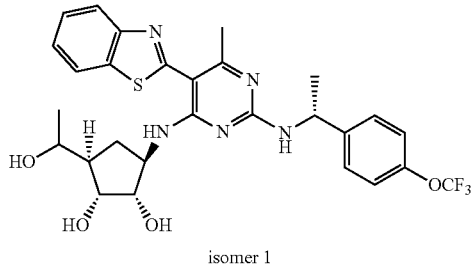 [SMILES: Cc1nc(N[C@H](C)c2ccc(OC(F)(F)F)cc2)nc(N[C@@H]2C[C@H](C(C)O)[C@@H](O)[C@H]2O)c1-c1nc2ccccc2s1]<br>isomer 1 |
| 1646 | 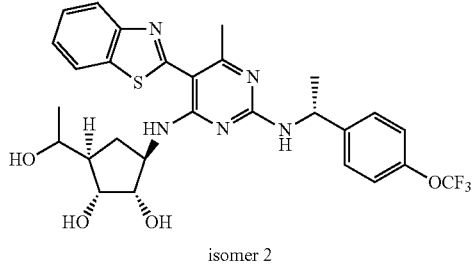 [SMILES: Cc1nc(N[C@H](C)c2ccc(OC(F)(F)F)cc2)nc(N[C@@H]2C[C@H](C(C)O)[C@@H](O)[C@H]2O)c1-c1nc2ccccc2s1]<br>isomer 2 |
| 1647 | 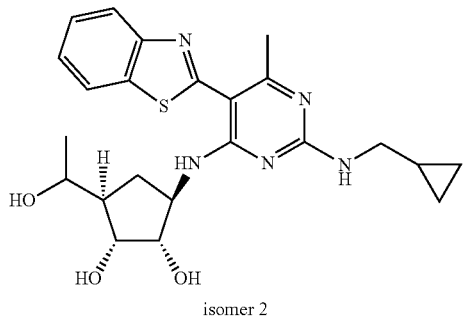 [SMILES: Cc1nc(NCC2CC2)nc(N[C@@H]2C[C@H](C(C)O)[C@@H](O)[C@H]2O)c1-c1nc2ccccc2s1]<br>isomer 2 |

| Compd # | Structure |
|---|---|
| 1648 | 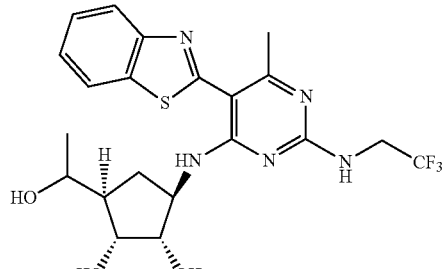 isomer 2 |
| 1649 | 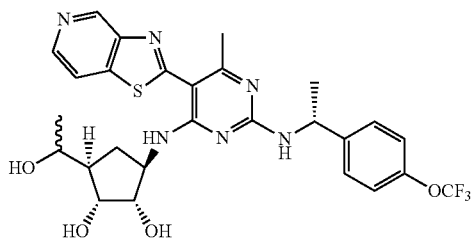 [SMILES: Cc1nc(N[C@H](C)c2ccc(OC(F)(F)F)cc2)nc(N[C@@H]2C[C@H](C(C)O)[C@@H](O)[C@H]2O)c1-c1nc2cnccc2s1] |
| 1650 | 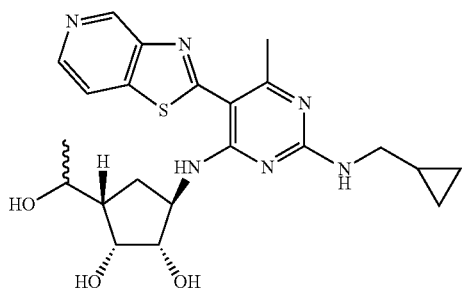 [SMILES: Cc1nc(NCC2CC2)nc(N[C@@H]2C[C@@H](C(C)O)[C@@H](O)[C@H]2O)c1-c1nc2cnccc2s1] |
| 1651 | 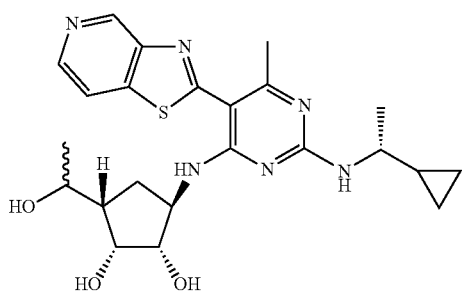 [SMILES: Cc1nc(N[C@H](C)C2CC2)nc(N[C@@H]2C[C@@H](C(C)O)[C@@H](O)[C@H]2O)c1-c1nc2cnccc2s1] |
| 1652 | 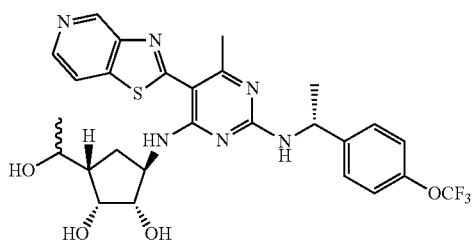 [SMILES: Cc1nc(N[C@H](C)c2ccc(OC(F)(F)F)cc2)nc(N[C@@H]2C[C@@H](C(C)O)[C@@H](O)[C@H]2O)c1-c1nc2cnccc2s1] |
| Compd # | Structure |
|---|---|
| 1653 | 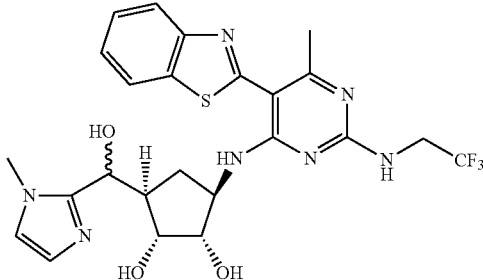 [SMILES: Cc1nc(NCC(F)(F)F)nc(N[C@@H]2C[C@H](C(O)c3nccn3C)[C@@H](O)[C@H]2O)c1-c1nc2ccccc2s1] |
| 1654 | 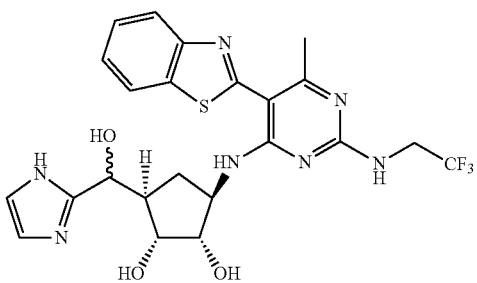 [SMILES: Cc1nc(NCC(F)(F)F)nc(N[C@@H]2C[C@H](C(O)c3ncc[nH]3)[C@@H](O)[C@H]2O)c1-c1nc2ccccc2s1] |
| 1701 | 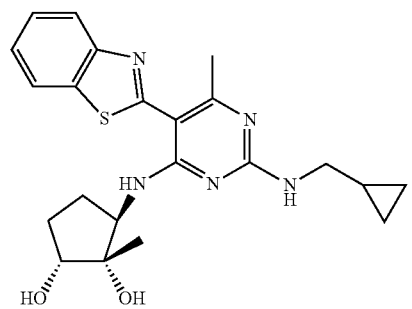 [SMILES: Cc1nc(NCC2CC2)nc(N[C@@H]2CC[C@@H](O)[C@@]2(C)O)c1-c1nc2ccccc2s1] |
| 1702 | 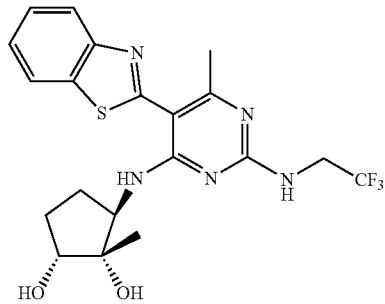 [SMILES: Cc1nc(NCC(F)(F)F)nc(N[C@@H]2CC[C@@H](O)[C@@]2(C)O)c1-c1nc2ccccc2s1] |
| 1703 | 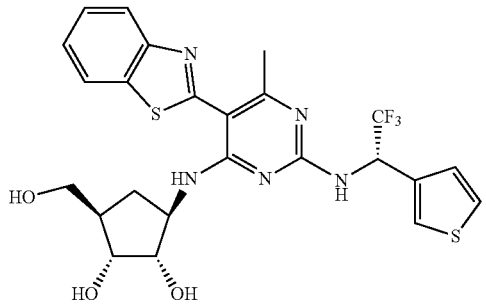 [SMILES: Cc1nc(N[C@@H](c2ccsc2)C(F)(F)F)nc(N[C@@H]2C[C@H](CO)[C@@H](O)[C@H]2O)c1-c1nc2ccccc2s1] |

829
-continued

| Compd # | Structure |
|---|---|
| 1704 | 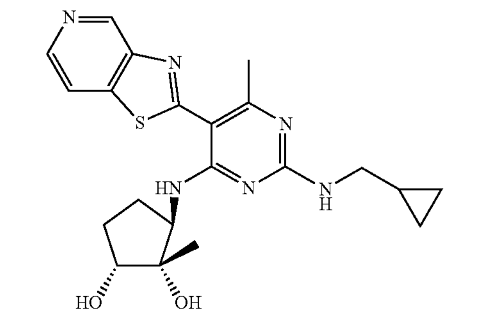 [SMILES: Cc1nc(NCC2CC2)nc(N[C@@H]2CC[C@@H](O)[C@@]2(C)O)c1-c1nc2cnccc2s1] |
| 1705 | 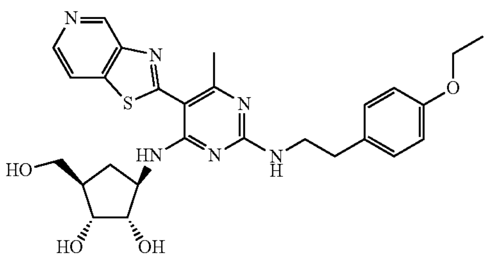 [SMILES: CCOc1ccc(CCNc2nc(C)c(-c3nc4cnccc4s3)c(N[C@@H]3C[C@H](CO)[C@@H](O)[C@H]3O)n2)cc1] |
| 1706 | 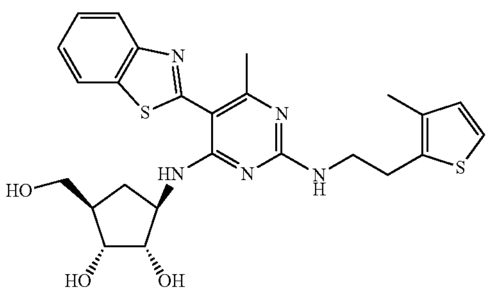 [SMILES: Cc1ccsc1CCNc1nc(C)c(-c2nc3ccccc3s2)c(N[C@@H]2C[C@H](CO)[C@@H](O)[C@H]2O)n1] |
| 1707 | 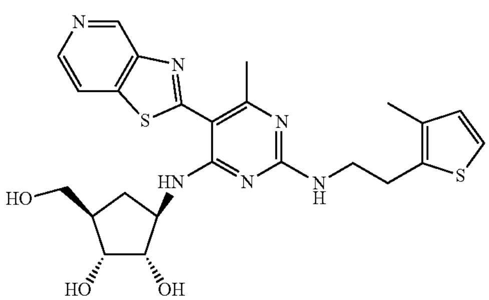 [SMILES: Cc1ccsc1CCNc1nc(C)c(-c2nc3cnccc3s2)c(N[C@@H]2C[C@H](CO)[C@@H](O)[C@H]2O)n1] |
| 1708 | 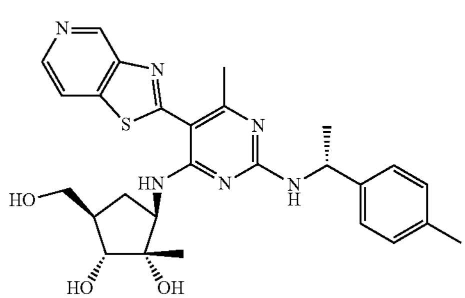 [SMILES: Cc1ccc([C@@H](C)Nc2nc(C)c(-c3nc4cnccc4s3)c(N[C@@H]3C[C@H](CO)[C@@H](O)[C@@]3(C)O)n2)cc1] |

830
-continued

| Compd # | Structure |
|---|---|
| 1709 | 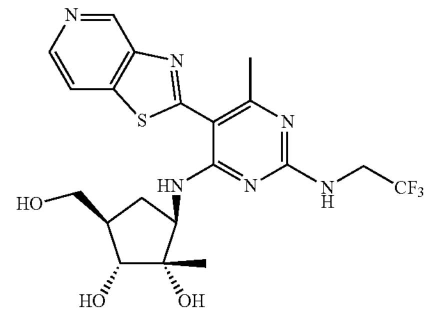 [SMILES: Cc1nc(NCC(F)(F)F)nc(N[C@@H]2C[C@H](CO)[C@@H](O)[C@@]2(C)O)c1-c1nc2cnccc2s1] |
| 1801 | 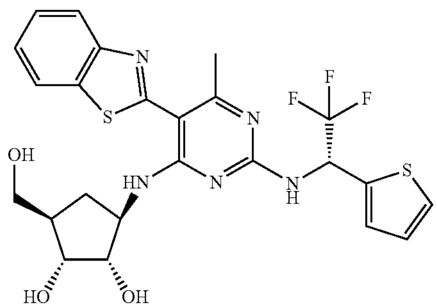 [SMILES: Cc1nc(N[C@@H](c2cccs2)C(F)(F)F)nc(N[C@@H]2C[C@H](CO)[C@@H](O)[C@H]2O)c1-c1nc2ccccc2s1] |
| 1802 | 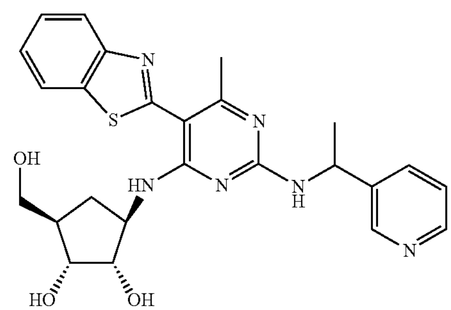 [SMILES: Cc1nc(NC(C)c2cccnc2)nc(N[C@@H]2C[C@H](CO)[C@@H](O)[C@H]2O)c1-c1nc2ccccc2s1] |
| 1803 | 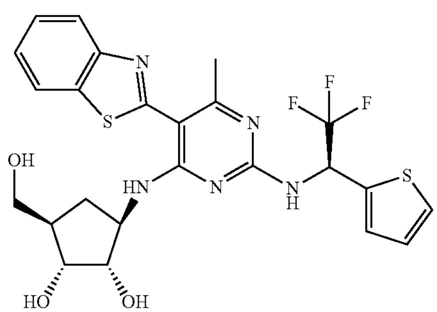 [SMILES: Cc1nc(N[C@H](c2cccs2)C(F)(F)F)nc(N[C@@H]2C[C@H](CO)[C@@H](O)[C@H]2O)c1-c1nc2ccccc2s1] |
| 1804 | 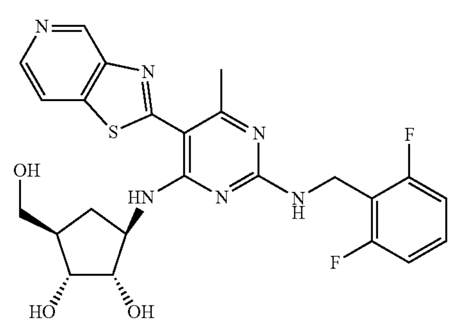 [SMILES: Cc1nc(NCc2c(F)cccc2F)nc(N[C@@H]2C[C@H](CO)[C@@H](O)[C@H]2O)c1-c1nc2cnccc2s1] |

| Compd # | Structure |
|---|---|
| 1805 | (structure) |
| 1806 | (structure) |
| 1808 | (structure) |
| 1809 | (structure) |
| 1810 | (structure) |
| 1811 | (structure) |
| 1812 | (structure) |
| 1813 | (structure) |
| 1814 | (structure) |
| 1815 | (structure) |

| Compd # | Structure |
|---|---|
| 1816 | 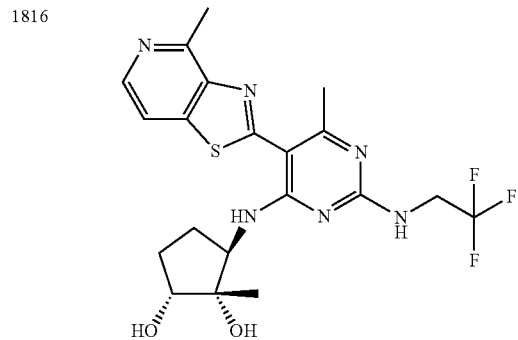 |
| 1817 | 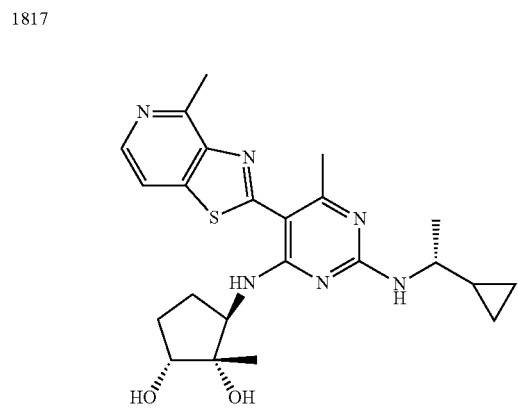 |
| 1818 | 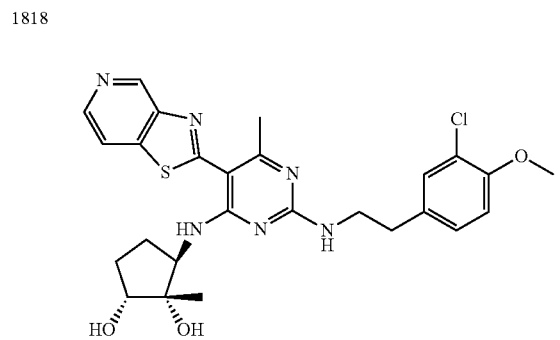 |
| 1819 | 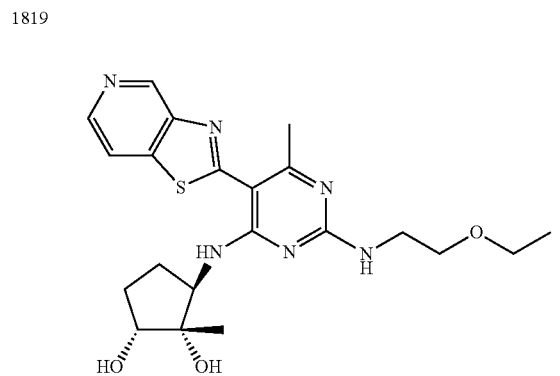 |
| Compd # | Structure |
|---|---|
| 1820 | |
| 1821 | |
| 1901 | |
| 1902 | |
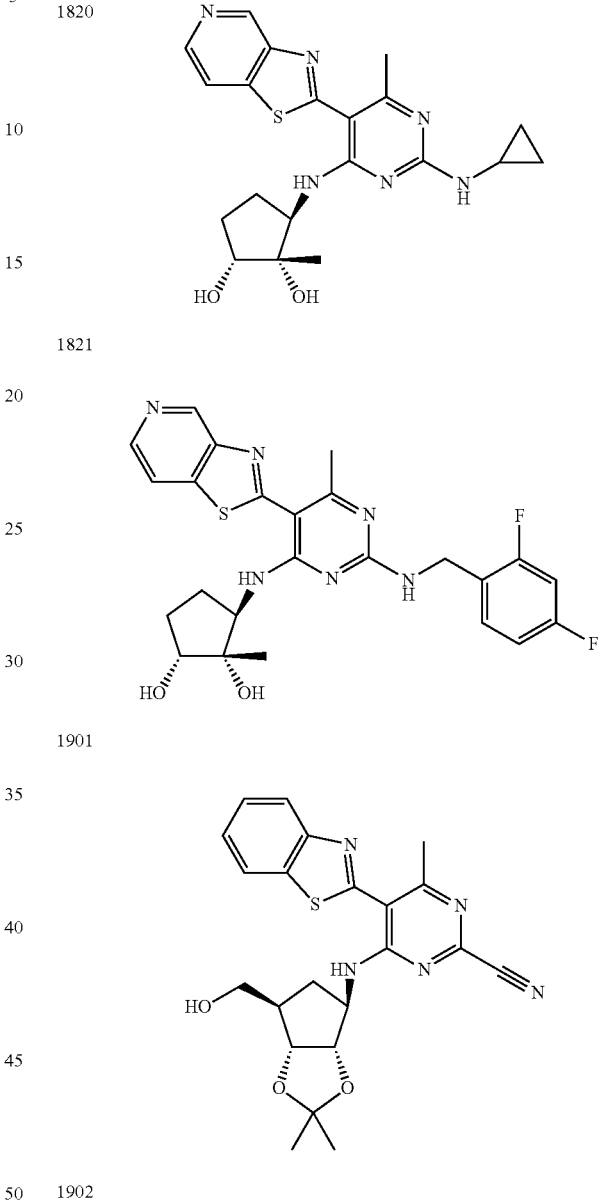

| Compd # | Structure |
|---|---|
| 1903 | |
| 1904 | |
| 1905 | |
| 1906 | |
| 1907 | |
| 1908 | 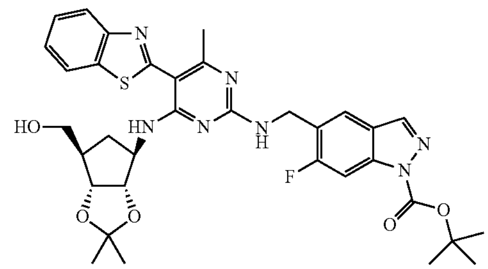 [SMILES: Cc1nc(NCc2cc3cnn(C(=O)OC(C)(C)C)c3cc2F)nc(N[C@@H]2C[C@H](CO)[C@H]3OC(C)(C)O[C@H]32)c1-c1nc2ccccc2s1] |
| 1909 | 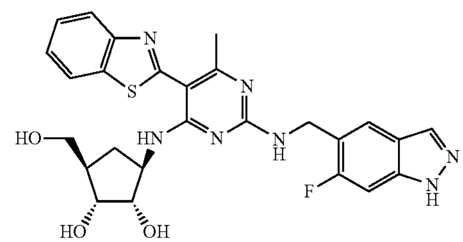 [SMILES: Cc1nc(NCc2cc3cn[nH]c3cc2F)nc(N[C@@H]2C[C@H](CO)[C@@H](O)[C@H]2O)c1-c1nc2ccccc2s1] |
| 1910 | 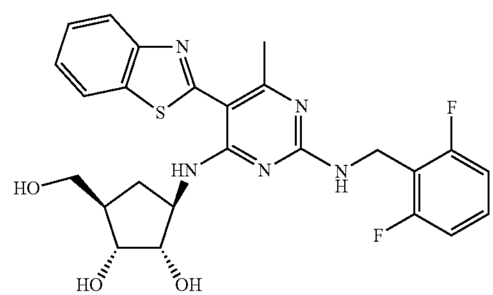 [SMILES: Cc1nc(NCc2c(F)cccc2F)nc(N[C@@H]2C[C@H](CO)[C@@H](O)[C@H]2O)c1-c1nc2ccccc2s1] |
| 1911 | 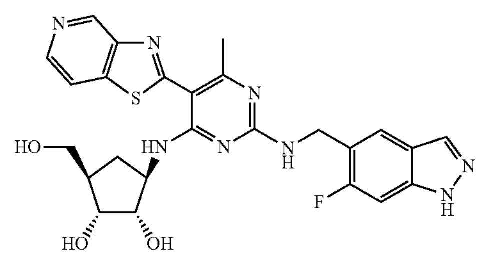 [SMILES: Cc1nc(NCc2cc3cn[nH]c3cc2F)nc(N[C@@H]2C[C@H](CO)[C@@H](O)[C@H]2O)c1-c1nc2cnccc2s1] |
| 1912 | 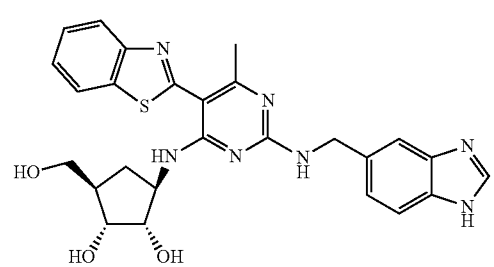 [SMILES: Cc1nc(NCc2ccc3[nH]cnc3c2)nc(N[C@@H]2C[C@H](CO)[C@@H](O)[C@H]2O)c1-c1nc2ccccc2s1] |
| 1913 | 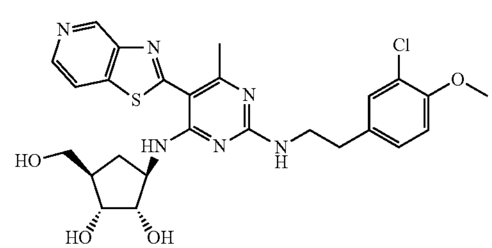 [SMILES: COc1ccc(CCNc2nc(C)c(-c3nc4cnccc4s3)c(N[C@@H]3C[C@H](CO)[C@@H](O)[C@H]3O)n2)cc1Cl] |

| Compd # | Structure |
|---|---|
| 1914 | 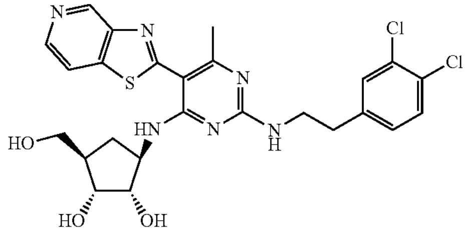 [SMILES: Cc1nc(NCCc2ccc(Cl)c(Cl)c2)nc(N[C@@H]2C[C@H](CO)[C@@H](O)[C@H]2O)c1-c1nc2cnccc2s1] |
| 1915 | 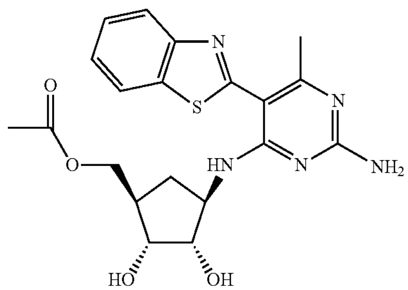 [SMILES: CC(=O)OC[C@H]1C[C@@H](Nc2nc(N)nc(C)c2-c2nc3ccccc3s2)[C@H](O)[C@@H]1O] |
| 1916 | 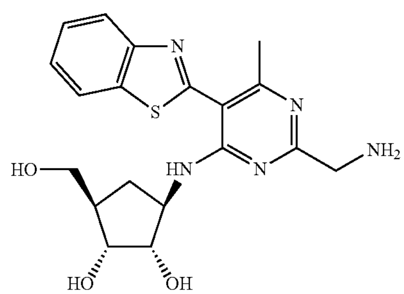 [SMILES: Cc1nc(CN)nc(N[C@@H]2C[C@H](CO)[C@@H](O)[C@H]2O)c1-c1nc2ccccc2s1] |
| 1917 | 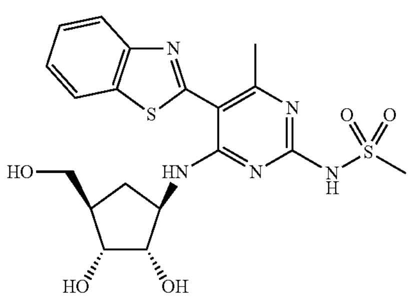 [SMILES: Cc1nc(NS(C)(=O)=O)nc(N[C@@H]2C[C@H](CO)[C@@H](O)[C@H]2O)c1-c1nc2ccccc2s1] |
| 1918 | 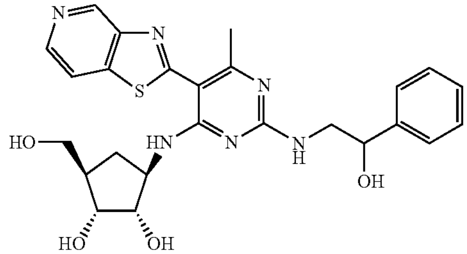 [SMILES: Cc1nc(NCC(O)c2ccccc2)nc(N[C@@H]2C[C@H](CO)[C@@H](O)[C@H]2O)c1-c1nc2cnccc2s1] |

| Compd # | Structure |
|---|---|
| 1919 | 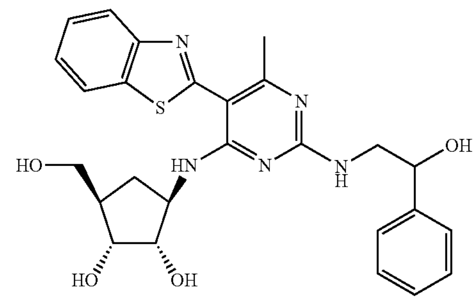 [SMILES: Cc1nc(NCC(O)c2ccccc2)nc(N[C@@H]2C[C@H](CO)[C@@H](O)[C@H]2O)c1-c1nc2ccccc2s1] |
| 2001 | 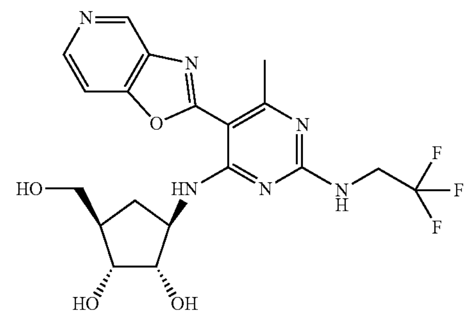 [SMILES: Cc1nc(NCC(F)(F)F)nc(N[C@@H]2C[C@H](CO)[C@@H](O)[C@H]2O)c1-c1nc2cnccc2o1] |
| 2002 | 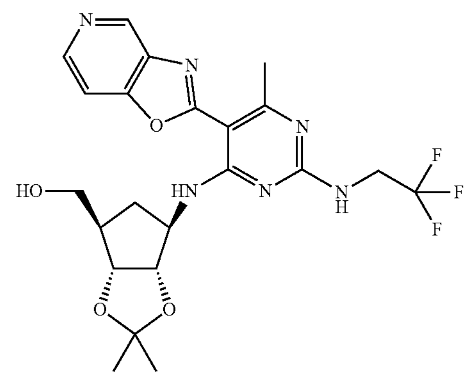 [SMILES: Cc1nc(NCC(F)(F)F)nc(N[C@@H]2C[C@H](CO)[C@H]3OC(C)(C)O[C@H]32)c1-c1nc2cnccc2o1] |
| 2003 | 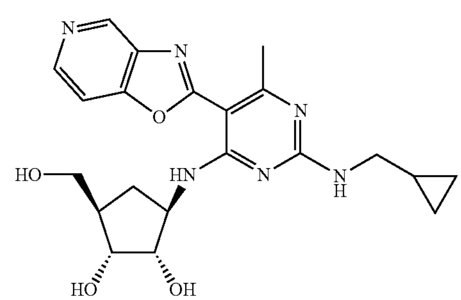 [SMILES: Cc1nc(NCC2CC2)nc(N[C@@H]2C[C@H](CO)[C@@H](O)[C@H]2O)c1-c1nc2cnccc2o1] |
| 2004 | 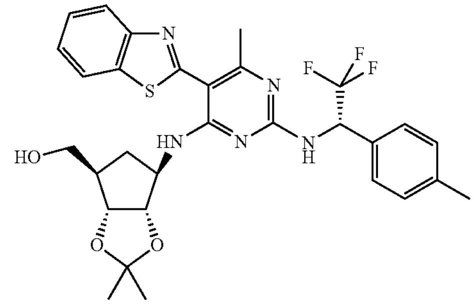 [SMILES: Cc1ccc([C@H](Nc2nc(C)c(-c3nc4ccccc4s3)c(N[C@@H]3C[C@H](CO)[C@H]4OC(C)(C)O[C@H]43)n2)C(F)(F)F)cc1] |

| Compd # | Structure |
|---|---|
| 2005 | |
| 2006 | |
| 2007 | |
| 2008 | |
| 2009 | |
| 2010 | |
| 2011 | |
| 2012 | |
| 2013 | | or a pharmaceutically acceptable salt thereof.

6. A pharmaceutical composition comprising at least one compound according to claim 1, 3 or 4, or a pharmaceutically acceptable salt thereof, and a pharmaceutically acceptable carrier.

7. A method, of treating a viral infection or a virus-related disorder comprising administering to a patient in need of such treatment a therapeutically effective amount of at least one compound according claim 1, 3 or 4, or a pharmaceutically acceptable salt thereof, wherein said viral infection or virus-related disorder is an HCV infection.

* * * * *

UNITED STATES PATENT AND TRADEMARK OFFICE
CERTIFICATE OF CORRECTION

PATENT NO. : 8,697,694 B2  Page 1 of 1
APPLICATION NO. : 13/059193
DATED : April 15, 2014
INVENTOR(S) : Arasappan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 423 days.

Signed and Sealed this

Twenty-ninth Day of September, 2015

Michelle K. Lee
*Director of the United States Patent and Trademark Office*

SEQUENCE LISTING

<160> NUMBER OF SEQ ID NOS: 3

<210> SEQ ID NO 1
<211> LENGTH: 17
<212> TYPE: DNA
<213> ORGANISM: Artificial Sequence
<220> FEATURE:
<223> OTHER INFORMATION: Chemically synthesized

<400> SEQUENCE: 1
atggacaggc gccctga                                                    17

<210> SEQ ID NO 2
<211> LENGTH: 20
<212> TYPE: DNA
<213> ORGANISM: Artificial Sequence
<220> FEATURE:
<223> OTHER INFORMATION: Chemically synthesized

<400> SEQUENCE: 2
ttgatgggca gcttggtttc                                                 20

```
<210> SEQ ID NO 3
<211> LENGTH: 17
<212> TYPE: DNA
<213> ORGANISM: Artificial Sequence
<220> FEATURE:
<223> OTHER INFORMATION: Chemically synthesized

<400> SEQUENCE: 3
cacgccatgc gctgcgg                                                17
```